(12) United States Patent
Philippsen et al.

(10) Patent No.: US 6,239,264 B1
(45) Date of Patent: *May 29, 2001

(54) **GENOMIC DNA SEQUENCES OF *ASHBYA GOSSYPII* AND USES THEREOF**

(75) Inventors: Peter Philippsen, Riehen (CH); Rainer Pöhlmann, Lörrach; Sabine Steiner-Lange, Bonn, both of (DE); Christine Mohr, Allschwil (CH); Jürgen Wendland, Lörrach (DE); Philipp Knechtle, Oberwil (CH); Corinne Rebischung, Saint-Louis (FR)

(73) Assignee: Syngenta Participations AG, Basel (CH)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/998,416

(22) Filed: Dec. 24, 1997

(51) Int. Cl.$^7$ ............................ C07H 21/04; C12N 15/11; C12N 15/63

(52) U.S. Cl. .................. 536/23.1; 435/320.1; 536/24.3; 536/24.32

(58) Field of Search ............................... 435/6, 440, 471, 435/490, 320.1; 536/23.1, 24.3, 24.32

(56) References Cited

U.S. PATENT DOCUMENTS 5,821,090   10/1998   Doval et al. ........................ 435/88

OTHER PUBLICATIONS

Johl and Philippsen, AgTHR4, a new selection marker for transformation of the filamentous fungus *Ashbya gossypii*, maps in a four–gene cluster that is conserved between *A. gossypii* and *Saccharomyces cerevisiae*, Mol. Gen. Genet., 250:69–80 (1986).

Steiner et al., Homologous Recombination as the Main Mechanism for DNA Integration and Cause of Rearrangements in the Filamentous Ascomycete *Ashbya gossypii*, Genetics, 140:973–987 (1995).

Steiner and Philippsen, Sequence and promoter analysis of the highly expressed TEF gene of the filamentous fingus *Ashbya gossypii*, Mol. Gen. Genet., 242:263–271 (1994).

Mohr and Philippsen, Establishment of a non–reverting auxotrophic *Ashbya gossypii* mutant by one step gene replacement, Fungal Conference—Wageningen, Apr. , 1994.

Wendland et al., A novel approach to identify centromeric of the filamentous fungal pathogen *Ashbya gossypii*, Institute of Applied microbilogy, Fungal Genetics Conference, Mar., 1997.

Steiner et al., The Gene for the Translation Elongation Factor EF–1a of the Filamentous Yeast *Ashbya gossypii* and the Use of its Promotor in Transformatin Experiments, $15^{th}$ Int. Conf. On Yeast Genetics and Molecular Biology.

Mohr et al., Gene Technology with the Filamentous Yeast *Ashbya Gossypii*, $16^{th}$ Int. Conf. On Yeast Genetics and Molecular Biology.

Johl and Philippsen, The Auxotrophic Marker thr4 in the Filamentous Yeast *Ashbya gossypii*, Applied Microbiology, $16^{th}$ Int. Conf. On Yeast Genetics and Molecular Biology.

Steiner et al., Early Steps in Establishing Gene Technology with *Ashbya gossypii*, EMBO Workshop, Molecular Biology of Filamentous Fungi, Berlin, Aug. 1991.

Steiner et al, Transformation, gene targeting, gene expression and genome mapping in the filamentous ascomycete *Ashbya gossypii*, Molekularbiologie der Pilze, 1993—Berlin.

Steiner et al., *Ashbya gossypii*—A Filamentous Fungus With a Genome of Less Than 10MB, $3^{rd}$ European Conference on Fungal Genetics, Germany, Mar. 12996.

Wright and Philippsen, Replicative transformation of the filamentous fungus *Ashbya gossypii* with plasmids containing *Saccharomyces cerevisiae* ARS elements, Gene, 109:99–105 (1991).

*Primary Examiner*—Scott D. Priebe
(74) *Attorney, Agent, or Firm*—J. Timothy Meigs

(57) ABSTRACT

The present invention relates to the terminal sequencing of random genomic fragments performed with the filamentous fungus *A.gossypii*, to the sequences obtained therewith and the use of the sequences for forensic identification, to characterize genes and gene organization of this ascomycete by inter-genomic comparison, to identify biosynthetic genes that can be used as selection markers, to isolate promotors and terminators for application in a homologous as well as heterologous context, to find putative centromere containing clones, chromosome mapping, chromosome identifying, general information about chromosome organization and in addition to identify ORF containing SRS sequences with no homology to *S. cerevisiae* or any other organism which allows the identification of *A. gossypii* specific genes.

2 Claims, No Drawings

US 6,239,264 B1

GENOMIC DNA SEQUENCES OF ASHBYA GOSSYPII AND USES THEREOF

Priority is claimed to Swiss App. No. 0016/97, filed Dec. 31, 1996, incorporated by reference.

FIELD OF THE INVENTION

The present invention relates to genomic DNA sequences obtained from terminal sequencing of random genomic fragments of the filamentous fungus Ashbya gossypii and uses thereof.

BACKGROUND OF THE INVENTION

The phytopathogenic fungus Ashbya gossypii is a filamentously growing ascomycete that was first isolated as a plant pathogen in tropical and subtropical regions. It infects the seed capsule of cotton plants (Ashby S. F. and Nowell W. (1926) Ann. Botany 40: 69–84) and has also been isolated from tomatoes and citrus fruits (Phaff H. J. and Starmer W. T. (1987) In "The Yeasts", Vol. I Rose A. H., Harrison, J. S. (eds), Academic Press, London, 123 ff; Dammer K. H. and Ravelo H. G. (1990). Arch. Phytopathol. Pflanzenschutz, Berlin 26: 71–78Dammer and Ravelo, 1990). The infection of the seed capsule is caused by transmission of A. gossypii mycelium pieces or spores by stinging-sucking insects and causes a disease called stigmatomycosis.

Studies characterising the karyotype of A. gossypii have been performed (Wright, 1990; Wendland, 1993; Gaudenz, 1994, "The small genome of the filamentous fungus Ashbya gossypii: Assessment of the karyotype", Diploma Thesis, Department of Applied Microbiology, Biocenter, University Basel). It has been found using yeast chromosomes of precisely known length as size markers that the genome of A. gossypii has a total nuclear genome size of 8.85 Mb. A. gossypii is systematically grouped to the endomycetales belonging to the family of spermophthoraceae (Lodder J (1970) General classification of the yeasts. In: "The Yeasts", Lodder J. (edt.), North Holland Publishing Company, Amsterdam-London, 1ff Lodder, 1970). This classification is based on the observation that the spores that develop in hyphal compartments called sporangia look like ascospores, which are defined as endproducts of meiosis (Müller E. und Löffler W. (1971) Mykologie. Grundriβ der Pilzkunde. DTV-Thieme, Stuttgart, 37 ff). However, in several respects, A. gossypii more closely resembles the budding yeast Saccharomyces cerevisiae than other filamentous fungi. For example, homologous recombination has been found to be the main mode of integration of transforming DNA (Steiner S. (1991). Diplomarbeit, Institut für Mikro- und Molekularbiologie der Justus Liebig Universität GießenSteiner et al., 1995), which is in contrast to findings made in many other filamentous fungi (reviewed by Fincham J. R. S (1989) Transformation in fungi. Microbiol. Rev. 53 (1): 148–170).

Additionally, sequence analysis of the A gossypii TEF, LEU2 and THR4 genes (Altmann-Jöhl and Philippsen, 1996; Mohr, May 1997; Steiner and Philippsen, 1994) has identified high sequence homology to their functional homologues in S. cerevisiae. In addition, for the latter genes, syntenic (positionally conserved) arrangement of adjacent homologous ORF's has been found. The growing number of completely sequenced reference genomes, such as for example S. cerevisiae, offers new prospects for rapid comparative gene and genome analysis of so far less characterized organisms, such as A. gossypii, in parallel or even before the application of genetic techniques.

SUMMARY OF THE INVENTION

In view of the above, the present invention provides genomic DNA sequences obtained from terminal sequencing of random genomic fragments of Ashbya gossypii. The present invention particularly relates to genomic A. gossypii DNA sequences that are obtainable from the series of clones listed in Table 1 and presented in the attached Sequence Listing. Some of these A. gossypii sequences are homologous to S. cerevisiae sequences and to sequences from other filamentous fungi, e.g. ORF's specifically required for growth in filamentous fungi. Others of these A. gossypii sequences, such as those set forth in Table 2, have no homology to S. cerevisiae sequences, including sequences which have no homology to known sequences from any other fungus. The sequences of the invention find particular use in forensic identification, chromosome mapping, chromosome identification, and tagging of genes of known and useful function. Procedures such as these can easily be carried out by those of ordinary skill in the art.

The present invention also concerns chimeric genes comprising the sequences of the invention, recombinant vectors comprising such chimeric genes, wherein the vectors are capable of being stably transformed into hosts, as well as hosts stably transformed with such vectors. Preferred hosts are fungi such as A. gossypii as well as bacteria.

Furthermore, the present invention relates to the identification and characterization of A. gossypii ORF's based on the high homology of primary structures in A. gossypii and S. cerevisiae and the sequences obtained therewith. The present invention also relates to the use of the A. gossypii sequences provided in the Sequence Listing to characterize genes and gene organization of this ascomycete by intergenomic comparison, to identify biosynthetic genes that can be used as selection markers, to isolate promoters and terminators for application in a homologous as well as heterologous context, to find putative centromere containing clones, general information about genome organization and in addition to identify ORF's containing single read sequences (SRS) with no homology to S. cerevisiae or any other organism, which allows the identification of A. gossypii-specific genes.

The present invention also concerns a method for the detection of Ashbya gossypii, comprising the steps of isolating DNA from an organism to be characterized; subjecting said DNA to polymerase chain reaction amplification using a primer derived from one of the A. gossypii sequences provided in the Sequence Listing; and visualizing the product or products of said polymerase chain reaction amplification, whereby detection of the product or products of said polymerase chain reaction amplification indicates that the organism to be characterized is Ashbya gossypii.

| ABBREVIATIONS | |
|---|---|
| LIPS - Linked Pairs of Sequences | SRS - Single Read Sequence |
| MCS - Multi Cloning Site | RP - Reversed Primer |
| ORF - Open Reading Frame | UP - Universal Primer |

DESCRIPTION OF THE INVENTION

Encompassed by the present invention is a method of sequencing the termini of randomly picked A. gossypii shotgun clones to obtain linked pairs of genomic sequences. Said linked pairs of genomic sequences can be used for identification of open reading frames (ORFs) showing or lacking homology to functionally characterized or uncharactezized genes from S cerevisiae, other fungi or other organisms. The sequence information provided herein in the attached Sequence Listing is sufficient to generate gene deletions in Ashbya by using, for example, by PCR-based gene targeting methods as described herein.

One of the main prerequisites for success in such an analysis is a relatively compact, organized genome. This is required to obtain a maximum of information from the limited length of single read sequence (SRS) analysis. *A. gossypii* represents such a compact genome. The presence within the Ashbya genome of short intergenic regions and rare occurrence of introns increases the probability of finding matches to open reading frames (ORF's) in the majority of SRS's.

Thus one embodiment of the present invention is a method to identify and characterize *A. gossypii* ORF's by sequence comparison of their *S. cerevisiae* homologues without the requirement of complete sequence information for the *A. gossypii* ORF'S.

Further encompassed by the invention is a method for characterization of an Ashbya gene, the knockout of which leads to a non-growth phenotype.

In a specific embodiment of the invention a method for characterization and validation of an Ashbya gene is provided comprising
 (a) inserting into Ashbya sequences of genomic pAG clones as provided herein in the attached Sequence Listing a chimeric gene construct comprising a selectable marker plus adjacent multiple cloning regions from a suitable cloning vector;
 (b) selecting clones carrying Ashbya sequences disrupted by the selection marker gene in a suitable host system;
 (c) transforming Ashbya with a disruption cassette according to (a);
 (d) revealing the disrupted open reading frame by DNA sequence analysis around the site of integration of the selection marker module and determining the orientation of the selection marker module;
 (e) determining whether deletion/insertion at the disruption site results in any phenotypic alterations.

A further embodiment of the invention relates to a method for characterization and validation of an Ashbya gene comprising
 (a) designing cassette for gene targeting comprising terminal Short Flanking Homology regions encompassing a selectable marker module;
 (b) transfecting the gene targeting cassette of (a) into *A. gossypii* and selecting transformants;
 (c) verifying correct gene targeting by applying suitable testing procedures;
 (e) determining whether deletion/insertion at the disruption site results in any phenotypic alterations.

Further comprised by the present invention is a method for characterization and validation of an Ashbya gene involving a triple selection marker module which method comprises
 (a) inserting of a reporter, a selectable marker and a strong promoter, which is preferably a regulatable promoter, in front of the start codon of a coding sequence of interest (promoter exchange mutant) within the Ashbya genome
 (b) applying potential antifungal agents for growth to the promoter exchange mutant of (a) and to a wild-type strain, respectively;
 (c) identifying a growth or non-growth phenotype of the strong promoter exchange mutant.

Within this novel process any DNA encoding a selectable marker can be used that, upon transformation, is capable of conferring a resistance phenotype to *A. gossypii* or any other advantage based on which the transformant can be separated from non-transformed clones such as, for example, ScLEU2, kanMX, kanSC or GEN3.

Promoters that can be suitably used as part of the triple selection marker module are those that are capable of functioning in Ashbya and in heterologous systems such as, for example, *S cerevisiae* or *K lactis*. Preferred within this invention is a heterologous promoter from *S cerevisiae* or *K lactis*, which is not only to be qualified as a strong promoter also within the Ashbya system but is also well regulatable in Ashbya.

A reporter that can be suitably used within the triple selection marker module is one that is easily detectable such as, for example, the green fluorescent protein.

If the activity or expression of the gene product is inhibited by one or more agents, the inhibitory effect for growth will be overcome in the strain overexpressing the gene product. If the reporter expression, controlled by the wild-type promoter, is not changed one can conclude that the agent inactivates the gene product and not a transcription factor or signaling factor for expression of the gene product. If the reporter expression is much lower, the agent most likely affects the expression of the gene product and not the gene product itself.

The present invention further relates to a DNA molecule comprising a DNA sequence selected from the attached Sequence Listing which molecule is validated as a potential target in a pesticide screen based on the use of said molecule in a gene disruption method as described herein.

Further encompassed by the present invention is the use of sequences selected from the attached Sequence Listing to identify substances having antifungal activity; the use of sequences selected from the attached Sequence Listing to identify substances having pesticidal activity; the use of sequences selected from the attached Sequence Listing to identify biosynthetic genes that can be used as selection markers; the use of sequences selected from the attached Sequence Listing to identify promoter and terminator regions including downstream non-translated regions and up-stream nontranslated regions, respectively; the use of sequences selected from the attached Sequence Listing to identify putative centromere-containing clones; the use of sequences selected from the attached Sequence Listing to identify ORF's containing SRS sequences with no homology to *S. cerevisiae*; the use of sequences selected from the attached Sequence Listing to identify ORF's containing SRS sequences with no homology to any other organism, which allows the identification of *A. gossypii*-specific genes; the use of sequences selected from the attached Sequence Listing to characterize genes and gene organization of this ascomycete by inter-genomic comparison; and the use of sequences selected from the attached Sequence Listing to identify and characterize the genome organization of *Ashbya gossypii*.

In particular, the present invention encompasses the use of a DNA sequence selected from the Sequence Listing to identify *Ashbya gossypii* promoter and terminator regions including downstream non-translated regions and up-stream nontranslated regions, respectively.

The invention further relates to the use of a DNA sequence selected from the Sequence Listing wherein a putative promoter region is identified by sequence alignments and the ORF of a genetic selection marker plus start codon and terminator is placed downstream of said putative promoter region.

Further comprised is the use of an a DNA sequence selected from the Sequence Listing and variants thereof in a screening method for identifying compounds capable of inducing broad spectrum disease resistance in plants.

The suitability of the DNA sequence to be used in such a screening assay is determined in gene disruptions in the Ashbya genome. For that purpose a disruption cassette may be used comprising a selectable marker plus adjacent multiple cloning regions from a suitable cloning vector.

In a further embodiment of the invention a DNA sequence selected from the Sequence Listing or parts thereof is used within a gene targeting procedure involving short target sequence homologies added to both ends of a DNA molecule encoding a selectable marker.

In a further embodiment according to the invention a DNA sequence selected from the Sequence Listing may also be used for distinguishing among different species of plant pathogenic fungi and for distinguishing fungal pathogens from other pathogens such as bacteria.

It is one embodiment of the present invention to use sequences selected from the attached Sequence Listing to identify promoter and terminator regions including downstream non-translated regions and up-stream nontranslated regions, respectively. In many cases, the attached sequences allow one to locate the precise boundaries between open reading frames and promoter or terminator regions either from the first single read or after additional sequencing. The promoter and terminator regions so obtained are also part of the present invention.

In particular, sequence alignments can reveal 5' ends of open reading frames plus adjacent sequences of their putative promoter regions. By placing the ORF of a genetic selection marker plus start codon and terminator downstream of this putative promoter sequence, one can identify and use novel *Ashbya gossypii* promoters.

The promoter and terminator regions so obtained are also part of the present invention.

The DNA sequences provided in this application are especially suitable to be used in gene disruptions in the Ashbya genome. This can be performed, for example, using classical procedures involving gene disruption cassettes.

Said gene disruption cassettes essentially consists of a selectable marker plus adjacent multiple cloning regions from a suitable cloning vector. This transformation selection module upon expression of the selection marker gene preferably leads to resistance in yeast and filamentous fungi and also in bacteria such as, for example, *E. coli*. This module is inserted into Ashbya sequences of genomic pAG clones as provided herein in the attached Sequence Listing. To this purpose the selectable marker is released from the cloning vector by cleavage with a suitable restriction enzyme such as, for example, BamHI, SalI or XhoI. It is ligated into cloned Ashbya DNA cleaved with a corresponding restriction enzyme that is, for example either BglII, XhoI (partial) or SalI (partial), respectively. Clones carrying Ashbya sequences disrupted by the selection marker gene are selected in a suitable host system such as, for example, *E. coli*. DNA sequence analysis around the site of integration of the selection marker module (i1 and i2sequences in the attached Ashbya data base) reveal the disrupted open reading frame and determine the orientation of the selection marker module.

A selection marker that is especially suited to be used within the scope of the present invention is kanMX0 expressing G418 resistance in yeast and filamentous fungi and kanamycin resistance in *E. coli* (International Patent Application No. PCT/EP 91/01116; Steiner et al, 1995).

Especially preferred within the scope of the present invention is a new PCR-based Ashbya gene targeting procedure provided herein. Gene targeting in Ashbya relies on homologous recombination in this fungus (Steiner et. al., (1995) Genetics (in press 1995)). Short target sequence homologies added to both ends of a DNA molecule endoding a selectable marker are sufficient to mediate sequence specific gene targeting in Ashbya. The length of the target sequence homologies is preferably in the range of between about 20 to 80 nt, more preferably between 35 and 60 nt, and most preferably is about 45 nt.

Within this novel process any DNA encoding a selectable marker can be used that, upon transformation, is capable of conferring a resistance phenotype to *A. gossypii* or any other advantage based on which the transformant can be separated from non-transformed clones.

The fragment designed for gene targeting thus carries terminal Short Flanking Homology regions encompassing the selectable marker module. These fragments are transfected into *A. gossypii* by a suitable method such as, for example, electroporation and transformants are selected. Verification of correct gene targeting is achieved by suitable testing procedures such as, for example, PCR testing the presence of the new junctions between target DNA and integrated marker using specific verification primers. Verification of the gene targeting can also be performed by DNA-hybridization experiments.

In using verification primers it proved advantageous to use specific primer pair combinations. One pair of verification primers, for example, may be derived from the open reading frame of the selectable marker gene. Whereas a second pair of primer sequences can be derived from the single read sequence and correspond to regions upstream and downstream, respectively, of the homology regions used for the targeting process. Using this PCR-based targeting approach sequences can be manipulated that are app. 150 nt in length. A criterium matched by all single read sequences of the attached Ashbya database. This is of major advantage considering classical methods of gene disruption that are laborious and require cloning steps to incorporate a selectable marker within rather large flanks of surrounding target sequence homology.

After clonal purification (spore isolation) it ican be easily determined whether deletion/insertion at the targeted locus results in any phenotypic alterations such as, for example, a reduction or abolition of fungal growth, decrease or loss of viability, etc. Once such a phenotypic alteration can be estabished for one of the Ashbya disruption or knockout mutants it is futher examined whether said mutant qualifies as a target to be used in a pesticide screen, preferably a fungicide screen.

Owing to the provision within the scope of this invention of a novel and powerful gene disruption process, there is no longer a need to know the exact biological function of the protein product encoded by a gene comprising or, in the alternative, being flanked by one of the *A. gossypii* DNA sequences provided herein.

Those sequences that have no homology neither to *S. cerevisiae* nor to any other organism and are thus *A. gossypii* specific are especially useful, as they are promising candidates to be used in a pesticide screen for identifying substances which have pesticidal and, preferably, fungicidal activity, but are non-toxic to other organisms especially mammals. Though nothing is known about the exact biological function of the genes comprising said DNA sequences or being flanked by said DNA sequences, they are nevertheless especially valuable owing to their being unique to the fungal pathogen. Thus, any pesticidally active substance being identified in a pesticide screen involving one or more of those sequences have a high potential of exhibiting a biological activity that only affects A. gossypii and possibly other pathogenic fungi having (yet unidentified) homolgous sequences, but do not interfere with any vital functions in other organisms such as, for example, mammals.

It is thus a further embodiment of the present invention to identify genes within the A. gossypii genome which are potential targets for the action of pesticidally active compounds, but especially fungicidally active compounds, by using those Ashbya sequences identified in the Sequence Listing corresponding to ORF's with 100 and more codons showing less than 20% homology to a yeast gene classified as 3 or 4.

DESCRIPTION OF TABLE 1, TABLE 3 AND THE SEQUENCE LISTING

The sequences in the Sequence Listing correspond to the PAG names in Table 1, and Table 3 correlates the SEQ ID NO's in the Sequence Listing to the PAG names in Table 1. Thus, Table 1 describes SEQ ID Nos: 16–1152 in the Sequence Listing in six columns: "PAG name", "Yeast", "Gene Name", Brief Description", "Homology Class", and "Additional Comments", the details of which are as follows:

PAG Name: Number of Ashbya gossypii plasmid clone (e.g. PAG1001) followed by RP (sequence obtained using the reverse primer) or by UP (sequence obtained using the universal primer) or I1 or I2 (internal sequences obtained after insertion of kanMX0 in the Ashbya DNA at a BglII, XhoI or BamHI site and sequencing in both directions from these sites using sequencing primers binding to the 5' and 3' region of kanMX0). CRP and CUP mark sequences from rare chimeric genomic clones, the ends of which map to different genomic regions. For a few clones, only RP or UP sequences are listed. 5% of the plasmid clones carry ribosomal DNA sequences, as concluded from high sequence homologies of their RP and UP sequences to ribosomal DNA of S. cerevisiae. These overlapping clones representing tandem copies of the 8.2 Kb Ashbya ribosomal DNA repeat are not listed in the Ashbya genome data base. The PAG name is set out above each individual sequence in the Sequence Listing.

Yeast name: Systematic name of S. cerevisiae gene with highest homology to the Ashbya sequence, as determined by the search algorithm. For some Ashbya sequences, two systematic names are listed because they carry information from two Ashbya ORF's with homology to S. cerevisiae genes. Sequences of high (significant) homology are distinguished from those with low (insignificant) homology by the classification in column 5 (Homology Class). If no systematic gene name is listed, the Ashbya sequence shows either no homology to S. cerevisiae genomic DNA or it is mitochondrial DNA (around 80% AT base pairs and homology to genes coded by the mitochondrial genome).

Gene name: S. cerevisiae gene name used in the literature.

Brief Description: Brief description of the S. cerevisiae gene showing highest homology to the Ashbya sequence.

Homology Class (HC): Significant homologies to S. cerevisiae genes are classified as 1. Intermediate homologies (about one quarter to one third identity on the amino acid level) are classified as 2. ORF's with 100 and more codons showing less than 20% homology to a yeast gene are classified as 3. Ashbya sequences lacking ORF's of 100 and more codons and showing less than 20% sequence homology to S. cerevisiae are classified as 4.

Additional Comments: Useful comments concerning (a) presence of promoter or terminator sequences as judged by the presence of 5' ends (N-terminus) and/or 3' ends (C-terminus) of ORF's and adjacent DNA, (b) identification of novel Ashbya ORF's (minimum size in nucleotides (nt) as only ORF in frames +1 to +3 or −1 to −3 and lacking significant homology to yeast and fungi, (c) synteny, (d) reason for changes of ORF classification, (e) matches to tRNA genes, (f) presence of intron, judged from interruption of regions of high level of protein homology and confirmed, in addition, by applying the S. cerevisiae intron-recognition rules, (g) high CAI (codon adaptation index) marking a well expressed gene and with that a strong promoter. Further abbreviations are explained in the MIPS yeast data base.

EXAMPLES

Standard recombinant DNA and molecular cloning techniques used here are well known in the art and are described by Sambrook, et al., *Molecular Cloning*, eds., Cold Spring Harbor Laboratory Press, Cold Spring Harbor, N.Y. (1989) and by T. J. Silhavy, M. L. Berman, and L. W. Enquist, *Experiments with Gene Fusions*, Cold Spring Harbor Laboratory, Cold Spring Harbor, N.Y. (1984) and by Ausubel, F. M. et al., *Current Protocols in Molecular Biology*, pub. by Greene Publishing Assoc. and Wiley-Interscience (1987).

Example 1

Construction of a Genomic Library

A.) Preparation of Partially Digested DNA

Genomic DNA of A. gossypii (strain ATCC10895) was partially digested with Sau3A and separated on a low melting agarose gel. Two regions were cut out off the gel: the first gel piece containing DNA fragments in the range of 3.5–6 kb in length and the second gel piece from containing DNA fragments in the range of 5–8 kb in length.

B.) Ligation and Cloning (Standard Procedures and Media as Described in Sambrook et al Cold Spring Harbor Press, 1989)

Sau3A fragments of different sizes, derived from the partial digestion of the genomic DNA, were cloned into the yeast shuttle vector pRS416 (Sikorski and Hieter, 1989, Genetics 122: 19–27). For this purpose pRS416 was cut with BamHI. The 5'-phosphate group of the linearized vector (4.8 kb) was removed with Calf Intestinal Phosphatase to minimize the recircularization of the vector during ligation. DNA of the two size fractions, one with fragments in the range of 3.5–6 kb and the other with fragments in the range of 5–8 kb were cloned separately into the vector. The ligation samples were separately transformed into the E. coli strain XL1-blue yielding together approximately 21,500 colonies on 55 plates. 80% of the colonies (17,000) were white indicating insertion of a A. gossypii DNA. The 21,500 colonies derived from the two size fractions were combined by washing each plate with 2 ml full medium (2*YT). Approximately 120 ml cell suspension were obtained. 100 ml of the cell suspension were used to inoculate once a 1 liter culture for the isolation of plasmid DNA. The remaining 20 ml cell suspension were mixed with 5 ml glycerol and stored divided into two aliquots at −70° C. The ratio of white to blue colonies stayed stable after growth in selective full medium ON. The isolated plasmid DNA was purified over a caesium chloride density gradient and separated on agarose gel. The total yield of plasmid DNA isolated from the 1 liter culture was approximately 5 mg.

All plasmids of the genomic library had a common structure based on plasmid pRS416. The average insert length was approximately 4 kb. The genomic library with 17,000 recombinant clones carrying an insert therefore covers 8 times the 9.7 Mb A. gossypii genome (Gaudenz, 1994).

Example 2

Sequence Determination

A.) Sequencing the Partial Sau3A Fragments at Both Ends

Approximately 350 to 450 ng of plasmid DNA was taken for cycle sequencing (T3 and KS primer or similarly binding primers) with the Perkin Elmer AmpliTaq FS PRISM™ Ready Reaction Dye Terminator Cycle Sequencing kit using the protocol of the manufacturer (addition of 1% DMSO to the sequencing reaction, 95° C. denaturing temperature) and the 373A automated sequencing system (Perkin Elmer) for electrophoresis and fragment detection. SRS's were named with the plasmid name and the suffix UP or RP was added to mark the side of the insert from which the sequence was derived regardless, of which primer present at this side of the multiple cloning site was actually used.

B.) Sequence Processing

Concerning the pAG1001 to pAG1000 and 1201 to 1700 series of clones, the vector part of the sequences was removed, obvious base-calling errors were edited and, depending on the quality of the sequence, an individual end point was determined. SRS of the pAG1001 to pAG1100 and 1201 to 1700 series were not further edited and were taken as provided. All sequences were transferred on a VAX system and put into GCG format. Query sequences were translated in all six reading frames and run in a BLAST search (Altschul et al., 1990) against MIPS data base on the world wide web at mips.biochem.mpg.de/mips/yeast/).

Alignment of sequences from mitochondrial or rDNA clones was performed with the SeqMan module of the Lasergene software package (DNASTAR, Ltd., London, UK) on a Macintosh Power PC.

Example 3

Classification of the BLAST Search Results

In the evaluation of the BLAST results, four different categories of homology class (HC) were used. HC 1 and 2 represent SRS's showing a significant hit to an S. cerevisiae ORF. The border between category 1 and 2 was made at approximately 40% identity in the aligned protein sequences. SRS's showing no convincing homology (around 20% identity and lower) but with an possible open reading frame (with or without ATG) of at least 300 nt length were assigned to HC 3. All SRS's with no significant homology and no possible open reading frame of at least 300 nt were put into HC 4. However, the described values for classification were not applied as strict rules. Factors such as length of homologous block, in cases of several blocks the overall homology, relation of scoring hit to possible open reading frames, position of homologous block within the S. cerevisiae protein sequence (for example very N- or C-terminus), a biased sequence, etc. were taken into account for classification.

Almost 30% of the clones listed in the attached Sequence Listing show synteny with S. cerevisiae. Thus, Ashbya genes of interest for antifungal screening assays (e.g. homologues of essential fungal or yeast genes) can be found due to positional conservations (synteny) when RP and/or UP sequences match adjacent S. cerevisiae homologues. Applying the rules of ancient synteny, the frequency of such predictions increases by a factor of 2 or even more.

Over 5% of RP and UP sequences identified open reading frames of 100 and more codons with no apparent homology to sequences in data bases. In Table 1, they are marked as class 3 or 4. These sequences are therefore candidates for novel lead target genes. Fungal pathogens (e.g. Candida albicans or phytopathogenic fungi) carrying homologues of these genes can be treated by compounds which were developed based on assays using the Ashbya lead target.

Example 4

Use of the Ashbya gossypii Sequences for Isolation of Ashbya gossypii Promoters

Sequence alignments can reveal 5' ends of open reading frames plus adjacent sequences of their promoter regions. By placing the ORF of a genetic selection marker plus start codon and terminator downstream of this promoter sequence, one can identify and use novel Ashbya gossypii promoters. For example, an ORF of 67 amino acids was identified on the SRS of pAG1245rp (SEQ ID NO:296). This ORF shows 98% homology to the S. cerevisiae Ribosomal Protein S28.e.12 in a BLAST search (Altschul et al. (1990) J. Mol. Biol. 215: 403–410). The ORF (AgRPS33B) for the putative A. gossypii Ribosomal Protein is located from 195 to 395 on the SRS with 700 bp, leaving 300 bp for the promoter. Based on these findings plasmid pAG1245 may be used for isolation of a novel promoter using the AgLEU2 marker in PCR-targeted gene exchange in S. cerevisiae.

A.) PCR synthesis of a DNA Fragment Carrying the AgLEU2 Marker

Two primers, RP5 and RP3, are selected for the amplification of the AgLEU2 gene. Both primers are 60 mers showing beside 20 bp homology to AgLEU2 in addition to 40 bp homology to pAG1245.

Primer RP5: 5' TTT TAC TAG ATA TTT TAT ATC CAA GAA GCA ATA GAT CAA AAT GGC TGC GGT AAA GAG AAT 3'(SEQ ID NO:1). The 40 bp at the 5' end of RP5 are homologous to 40 nucleotides in front of the ATG start codon of AgRPS33B. The 20 bp at the 3' end of RP5 are homologous to the first 20 nucleotides of the AgLEU2 ORF, including the ATG start codon.

Primer RP3: 5' CTG GAG CTC CAC CGC GGT GGC GGC CGC TCT AGA ACT AGT GCG CCA ACG TTG CGA GAT ATA 3'(SEQ ID NO:2). The 40 bp at the 5' end of RP3 are homologous to 40 nucleotides in the pBlISk+ multiple cloning site (Alting-Mess M. A. and Short J. M. (1989) Nuc. acids Res. 17(22): 9494) of pAG1245 covering the SacI, SacII, NotI, EagI XbaI and SpeI restriction sites. The 20 bp at the 3' end of RP3 are homologous to 20 nucleotides in the AgLEU2 terminator region (1261–1281).

Sequence carrying the AgLEU2 coding region and the AgLEU2 terminator sequence (the ATG start codon of AgLEU2 is written in bold letters and the stop codon (1117–1119) is underlined):

```
(1) ATGGCT GCGGTAAAGA GAATTGTGGT GCTTCCGGGC GACCACATCG GCCGCGAGGT CGTGGAGGAG

GCGGTGAAGG TGCTTGGCGC CGTGGAGCAG AGCCTGTCGG ACGTGCACTT TGACTTCCAG TACCACCTGG

TCGGCGGGGC GGCCATCGAC GCCACGGGGT CGGCGCTGCC GGACGAGGCG CTGGGCGCGG CGAAGGAGGC

GGACGCGGTA CTGCTGGGGG CAGTTGGCGG ACCGAAGTGG CAGGGCGGCG CGGTCAGGCC GGAGCAGGGC

CTGCTGAAAC TGAGACAGGA GTTGGGCGTG TACGCGAACC TGCGTCCCTG CAACTTTGCG GCGGACTCGC

TGCTCGAGCT GTCGCCGCTG CGCCCCGAGA TTGCCCGGGA TACCGATATT ATGGTGGTGC GGGAGCTGCT

GGGCGGGAGC TACTTCGGCG AGCGCCACGA GGACGAGGGC GACGGAGTCG CGTGGGACAC CGACAAGTAC

ACCGTGAAGG AGGTGCAGCG CATCGCGCGC ATGGCGGGGT TCCTGGCTCT GCAGCACGAC CCGCCGCTAC

CTGTGTGGTC GCTGGACAAG GCGAACGTCC TGGCCAGCTC CCGCCTGTGG CGCAAGACCG TGGAGGAAAC

CTTCCAGAGT GAGTTCCCAA ACGTGCAATT GCAACACCAG TTGATAGATT CAGCTGCAAT GATTTTGGTC

AAGAACCCGC GGGCGTTCAA CGGGGTCGTG GTGACGAGCA ACATGTTCGG GGACATTATC TCTGACGAAG

CGTCGGTGAT CCCAGGGTCC CTAGGGTTGC TGCCATCGGC CTCGCTCGCG TCTTTGCCGG ATAGCAAGAG

CGCCTTTGGC CTCTACGAGC CCTGCCACGG CTCTGCGCCC GATCTGCCCG CCGGGAAGGC GAACCCGATC

GGATGCATCC TCTCTGCTGC CATGATGCTG AAGTTGTCGT TGAACATGGT TGCTGCCGGC GAGGCGGTCG

AGCAGGCAGT GCAGGAGGTG TTGGACTCGG GAGTCAGAAC GGGCGACCTG CTCGGCTCGA GCTCCACTTC

GGAGGTTGGC GACGCCATTG CGCTTGCAGT TAAGGAAGCC TTGCGCAGGC AATCCGCAGC TGGTCTGAGC

TAGCCTCGAG GACCCTTCTC TTTAGACTAT TCTACTCTTA TGCACGTAAA AAATTCTAGG AAATATGTAT

TAACTAGGAG TAAAATAACC GGCTAGTGGC ATTCATATAG CCGTCTGTTT ACATCTACAT CACACATTTC

GAGTGTATAT CTCGCAACGT TGGCG (SEQ ID NOs:3-4)
```

The PCR reaction is performed in a Thermocycler from ams Biotechnology. As a template, the isolated 3.1 kb BamHI/SalI fragment from plasmid pAG150 (Mohr Ch. (1997) Ph.D. Thesis, Institute of Applied Microbiology, University of Basel) carrying the AgLEU2 gene is used. 100 ng template are added for a 50 µl reaction volume supplemented with 0.2 mM of dATP, dCTP, dGTP and dTTP. 5 µl of 10*Thermo Pol Buffer (Biolabs). The concentration of primer RP5 and primer RP3 in the reaction is 1 µM. After the hot start, 1 µl enzyme mixture (Taq Polymerase (Pharmacia) and Vent Polymerase (Biolabs) 5:1) is added. PCR is executed under the following conditions: hot start 2 min at 94° C., 30 cycles of 30 sec at 94° C., 30 sec at 55° C. and 2 min at 72° C. and finally 4 min at 72° C.

Analysis of the PCR reaction on a 1% agarose gel shows a concentration of 100 ng/µl for the 1.36 kb PCR product, which can be used to transform S. cerevisiae.

B.) Transformation of S. cerevisiae

For the direct exchange of the ORF of AgRPS33B on plasmid pAG1245 in S. cerevisiae with the AgLEU2 marker via homologous recombination a cotransformation is carried out. As a recipient strain, YP98 with the phenotype a, ura3-52, lys2-801$^{amber}$, ade2-101$^{ochre}$, trp1-Δ1, leu2-Δ1 (Sikorski R. S. and Hieter P. (1989) Genetics 122: 19–27) is used. Transformation is performed according to Gietz et al. (1992) Nuc. Acid Res. 20 (6): 1425.

2 µg plasmid DNA of pAG1245 and 2 µg PCR product are cotransformed into strain YP98. Plasmid pAG1245 carries the CEN6/ARSH4 cassette and the URA3 gene providing replication and selection in strain YP98. Recombination between the 40 bp at the ends of the PCR product, which are homologous to parts of the pAG1245rp SRS, leads to excision of the AgRPS33B open reading frame and integration of the AgLEU2 marker gene. Transformants are double selected for URA+ and LEU+ on SD-minimal medium supplemented with lysine, adenine, tryptophan and lacking uracil and leucine (Sikorski R. S. and Hieter P. (1989) Genetics 122: 19–27). As a positive control, 2 µg plasmid DNA of pRS415 and pRS416 (Sikorski R. S. and Hieter P. (1989) Genetics 122: 19–27) were cotransformed. Plasmid pRS416 carries the CEN6/ARSH4 cassette and the URA3 gene, and pRS415 carries the CEN6/ARSH4 cassette and the LEU2 gene for replication and selection. Transformants are also selected on SD-minimal medium supplemented with lysine, adenine, tryptophan and lacking uracil and leucine. As a negative control, 2 µg PCR product are transformed to exclude the possibility of genomic integration of the AgLEU2 marker gene. Selection for the negative control is carried out on SD-minimal medium plates supplemented with lysine, adenine, tryptophan, uracil and lacking leucine. After 2–3 days of incubation, the first transformants appear, and after 5 days the transformation efficiency is calculated. The negative control, only transformed PCR product; has no transformants. The positive control, pRS415 and pRS416, has a transformation efficiency of 300 transformants/µg DNA. The cotransformation of pAG1245 and the PCR product shows a transformation efficiency of 10 transformants/µg DNA. For verification of the integration of the AgLEU2 marker gene into pAG1245, the new plasmid, which is named pAG1245-1, is isolated from the transformants and further investigated.

C.) Verification of the Integration of the AgLEU2 Marker into pAG1245

Genomic DNA from several independent S. cerevisiae transformants harboring the newly generated plasmid pAG1245 is isolated according to Philippsen P. et al., (1991) Methods in Enzymology 194: 169–182, Guide to Yeast Genetics and Molecular Biology, Academic Press.

The genomic DNA is transformed into the *E. coli* strain XL1-blue (Bullock W. O. et al., (1987) Bio Techniques 5 (4): 376–378) using the protocol described by Dower J. W., (1988) Nuc. Acids Res. 16: 6127–6145). Plasmid DNA of pAG1245-1 is isolated and integration of the AgLEU2 marker gene is verified via analytical PCR. A primer pair with one primer located in the multiple cloning site and one primer in the promoter region of AgRPS33B indicates excision of the ORF of AgRPS33B and integration of the AgLEU2 marker gene. For this purpose, two primers RP1 and RP2 are selected. RP1 (5' CAT GAT TAC GCC AAG CGC GC 3') (SEQ ID NO:5) is homologous to 20 nucleotides in the pBIISk+ multiple cloning site (Alting-Mess M. A. and Short J. M. (1989) Nuc. acids Res. 17(22): 9494) in pAG1245 adjacent to the Reverse Primer binding site. RP2 (5' CCA AGC ACA TTT CAC CTG CG 3') pAG1245 SRS from 521–540. With this primer combination, the expected PCR product is 0.6 kb for pAG1245 and 1.5 kb for pAG1245. PCR reactions were performed using plasmid DNA from pAG1245 and from pAG1245-1, originated from two independent *S. cerevisiae* transformants, as templates. 100 ng template are added for a 50 μl reaction volume supplemented with 0.2 mM of dATP, dCTP, dGTP and dTTP. 5 μl of 10*Thermo Pol Buffer (Biolabs). The concentrations of primer RP1 and primer RP2 in the reaction is 1 μM. After the hot start, 1 μg enzyme mixture (Taq Polymerase (Pharmacia) and Vent Polymerase (Biolabs) 5:1) is added. PCR is executed under the following conditions: hot start 2 min at 94° C., 30 cycles of 30 sec at 94° C., 30 sec at 55° C. and 2 min at 72° C. and finally 4 min at 72° C.

Analysis of the PCR reaction on a 1% agarose gel shows a band at 0.6 kb for pAG1245 and a band at 1.5 kb for pAG1245-1. This result demonstrates the right integration of the AgLEU2 marker gene in pAG1245.

Example 5

Isolation of New Fungal DNA Elements Based on Synteny of Linked Sequence Pairs

With the initial bi-terminal SRS's of the DNA insert of plasmid PAG1489 (PAG1489RP and PAG1489UP), synteny is discovered to the centromeric region of *S. cerevisiae* CEN2. This synteny reveals homology to the yeast genes YBL003c and YBR001c. The complete double stranded insert sequence shows synteny to the yeast genes YBL003c (97% identity), YBL002w (94% identity), YBL001c (69% identity), and YBR001c (73% identity) as determined by BLAST searches to the Yeast Genome Database (Altschul, Stephen F., Gish, Warren, Miller, Webb, Myers, Eugene W., and David J. Lipman (1990). Basic local alignment search tool. J. Mol. Biol. 215:403–410).In yeast, the centromere of chromosome II is placed between YBL001c and YBR001c. Homologous sequences to the yeast centromere II are found in the *A. gossypii* DNA sequence of PAG1489 between positions 2900 to 3200. This homology comprises the essential Centromere DNA Elements CDEI, CDEII, and CDEIII. Making use of the synteny of RP and UP sequences of a single pAG-plasmid to a reference genome, the detection of potential antifungal drug targets can be inferred in the same way as the centromere on PAG1489. In addition, using *Ashbya gossypii* as a reference genome, potential antifungal drug targets of other pathogenic fungi can be isolated.

```
Sequence of pAG1489 insert DNA:
GATCGTAACATTGCCCAATAGCTTGTTTAGCTCGTCATCGTTTCTGATGGCTAGCTGTAGATGTCTTGGGATGATTCT

GGTCTTCTTGTTGTCTCTGGCGGCGTTACCGGCCAACTCTAGGATTTCGGCGGCCAAGTATTCTAGCACAGCGGTTAG

GTACACAGGCGCGCCCGACCCGATTCTCTGTGCGTAGTTGCCCTTTCTGAGCAATCTGTGGACTCTCAAGACAGGGAA

AGTCAAACCGGCCTTAGCCGATCTCGACTGCGAAGCCTTGGCGGCAGAACCAGCTTTACCTCCTTTACCAGACATTAT

TTGTGTTGTGTGTGTGTGTGTGTTTAGTGTGAACTGCGTGTGCTATGAGAAAACACTACGCTGAAACTGCTAAATA

ATCCAGACAGGTCCCCCACCGCAAAGGATCCACGCTATACTTCTCTCTACATATTTATACTTGTCCTTTTGCCTTCT

AATCCTCGATCGTACGCGTCTGACGCTTCAACAGACGCTTCACCTAGACGCTCGACCTGTGCGGCCTGGTTTTTTCGC

ATGACATGTCCGTGCTGGTTTTTTCGCGCTGAAAAGGAAAGCGCGTGGCTCCCAGCACCAGAGCCGTACTAGCTCTTT

CGCGTGCTGTCCTATGTGCACGCGAAATTTTCATACTGTAGAGTGTGCCATCAGCTTCACAGAGTACAAACGGTAGGC

GAGTGGATACGCGTCTTGTAGCCGGACGTGAATGGCAGAACTTTTTGGCAGTCGCGTAATCTTAGATTGAAAGTATTT

AAGTGGAACGTATAAAACAAAAGTTCGGGCTGAAGAGGACCTCTTTTGGCG[00a7]TCTGCTACTTCCCAGTTATCTGTTGG

ATACTAAGCATATCGAACTCTAATTGCAATTCTAAAGATGGCACCAAAGGCTGAGAAGAAACCTGCTTCCAAGGCCCC

AGCGGCAAAGAAGACCACTGCTTCTACCGACGCTTCTAAGAAGCGGACGAAGACTAGAAAGGAGACCTACTCCTCTTA

CATTTACAAGGTTCTTAAGCAGACTCACCCAGATACTGGTATCTCGCAGAAGTCTATGTCCATTTTGAACTCGTTTGT

GAACGATATCTTTGAGAGAATCGCGTCTGAGGCATCCAAGCTTGCGGCCTACAACAAGAAGTCTACGATCTCTGCTAG

AGAAATCCAGACTGCTGTCAGATTGATCTTGCCCGGTGAGCTAGCCAAGCACGCCGTGTCTGAGGGTACCAGAGCTGT

TACCAAGTACTCGTCTTCTACCCAAGCCTGAATGGAACTCATTCTTAGAATGAAAGAACTTCCTTCAAGAAGGTTCTC

GTCAGCTAGTGCTTGTGGGACCCGCCTCTTATTCCAGAGCAGCTGCGGCAGAGCGGTATGTGGTACGTTCCGTTTCAT
```

-continued

```
CATTTTGTATTATTAGTACATGTAGAAATAGGGTTTTCTGGTTTCATAATTCGGTATAAATTCCAACGTAATGTATAT
TAGATAAGTTTTAAACTAGTAATCGGAGAGCTTCTTTTCAACCACGTCTACCTTGTCTTGCGCAGTCTGCTGTTTGTC
TGTTCTAGTTCCGAGCCTCATTTCGGTGTGGATTCTAACGTATCCCAATTCGTGGCTGTATTCGTGCAACTGGCCGAT
GAGGCTCATGACCTCGTCCCAAGGGCCCTCAATCGTCGTTCCAAAGCTGTGCATAGTGCTTTTCAAGTGACTCTCCCT
AATTCGTTTCTCAATCTTGGTGACATAGTCTGAGACACTTGGTGAGCTAGTACCTAGCTATGATTCAAAAGTTTAGTA
TATTGTTTTATATATGCAGCTGGAGATGTGAACATACCGGCACCATGCAAATGTCCACTAATGTGTGCAGCTTCGACA
TTTTGATTTCTACCTTCAGAGTATTGGAATATGTTCTTGTATGTAACGTCTACTAATTTTCTGGTTTATATCGCTGAT
CTTAAGGGAGATAATTTCGTTCACCCATCACACAGAAGTTTTAAGTACAAAACTTGTCCCCAGATATAGCAAGTCATC
AATTCAGGTATAATTGGTGTGCATGCTAATTTGAAGGGCTGTTATATAGTTGAAGTTGTTCTTTTGGCATTGAGCCAA
ATTTGGATTCTATTCAGTAGTATTGAACATCAAGTCTCCAAAGCTGAAGTCTGAAGCAAAACATCTCAATAGCTATAG
AACTCTAGCAAACAACAGACCAGAGCTTATATCATGACACATTATAAGCTCAGCTATTACTCTGAGTGATAGAGTGAC
CCTCAATTAGTTGGTTCATTTTATATATAAAAATATAAAACTATAGCTATTTCAAATGACTACTAACTAATACGAGAG
AAGAAAACAAATTAAACACGATGGTCTACAGATAGCTTGAAAGAGACACTAAGAGAAATTTCAGGAAACAGTTCAGAA
AATAGCCATTCAGCTCTACAGCTCTCTTTATTATCAAGAGTACAGTTTCTTTCACTAATATCGCTTAATTAATTATAT
TTCTTGCCATTAAATGCGACGGTGACGGGATAACAATTTTTGGCAATTCTTCATATTTTGATTTAAAAAAAAAACAAT
TTACCAGAATTAGACGAAATAGTCGCTTACTACAAACAGGTTCAGCCACTGGATAAATCTCATAGTTTAAAATATTGA
GTTACAGAAATTGGCTTACAGAAAGCACTAGCGATTAGGCCATTTGCCATTGATTTAAACATGAACTAACGAACCTCC
ATGAATTACAATAACCACAAATTTAACCGGACAATTAATTTTATGTAGCAGGCTCTGCCATGGGAATAGCTTTACGTG
AACAGGATATTTAACGTATATCCTTGTTATGATAAAGACTTTGATAGGTGCTTATACTTGCAAGTTCATATTTTACAG
TTAAATATCTAAATTTAATATATTACGCAGTTCACGCAATGTAGCACGTGACATAAATATGAAATTTACTATGTGCTT
GCTTTATTTAAAATAAGTTTATAAAGTTAGTAAAAATATCAGAGTATATATATTTAATTAAATAATATCCTAAAATAT
ACTAATACAATTTATCAATTAAGCTTTATACACTTTATAAATAGTTATAATTATAGATGTGTATACGATTTCCGAAAC
ATAAAAATATTTCACTGCTTTCGTGAAAAATAATTTTTTTATTATAAAACAATCCCTAATATAGTATTACCTCCAATT
ATGAGTCTATCGTAATATATGAAGTACTACCAAAATTTACCACTGATTTTTCAAAAAAAAAACACCATTTTTCAAAAA
TATTTTATTAACTGAATTTTTTATAATTAAATTTTTTATATCTATATAGAATATCTATTATACGCAAGAAAAACCAAA
AAGTACCCTATAAGTAGGTACCGCTTGTCCACATTATAATAAAAAAAGTGAAGTACTCATCAATACTTTTATTTAGGA
TACCTGCAGTCTAATATCCCTTCACGTAAGTTACTTAGTGCACAATATTCACAGTGAGTTAGTAACCCGGTTCAGATC
AAGGCATACCGAGCTTTCTCTTCTGGCTTCATATGCTTAAAGAAAATATCAGGGACGGTGCAGTTAGCTAAAGCTCTC
TTAGCATAAGTATTCATAAATTTCAAACCTAAGATATAACTGGAATTGACCCAGCCAAATCCTTCAGTAGCAACACCT
TTAAAGTCTGCACCTTGGTTACCATATTCGGCATCAACTCTATGAGGATCTGTGCCTCTGGTAACGTCGTATTTCTCT
ACTACGATACCATTGTAGTCGACAAATGCCTTGGTCATTAAAAATAACCACCTATAGGCCAACCTTCTTGCAACTCCT
GTAAATCCGTAATTATCTAACCCGGTCCAAGCAAGCATTTGATGAGGGGCCCAACCATAAGGGTAATCCCATTGCCTG
CTTGGTCTATTCATTGTTATCTCACCCCGAGACTCCTCAGTACAGGCAACCAGGCCTCCTAGCATTTCAAGCCTTGGC
AATGCCTTCTCGACCATAGCGTTGGCTTGTTCCTGGGTTGCCAAGCCTGCCCACATGGCCCAAAATGTTGTTGCAGAA
TCGTAAGATGTTCTCTTTCCAATATGGACATTGTAGTCATAGAAAAAGCCTGTTTCCTCGTCCCACAAATATTTCGTG
ATTCTTTGCTTACGAATGTCTGCAAGTGCCTCCCAATGAGAAGAAGTGGTGGTTTCACCAGCATAATCAGTAATACTA
TCATCGAAGTACTTGGAAACCACATATGCAATATCTTTTTCGTACTTGTATAGTAACGAATTCAAATCAATCGTCGCT
AAGTAAGCACAGACGTTCTCTAGACGGTAAGAGGTGTCATGTCCACTCTCACGTACAGCACGATCATGCAAAAGAAC
TCATCTAGTTCGGGCTCGTGTACTTCGCCGGCATCGTACATGCACCTGAACTCCGGAATCGTTACATTGTGCTTTTCC
GCAAATTTCCGGCAAATTGCGTCAAAGTGGTCAGGCTCGGTTTCTGGTGGGAAACCGATACCATCTGGATGATAACAT
```

-continued

```
GAAAGACCCGTGGTTTTGTCGTACCGCGGTTCTGCCATCCATACACTCTTGTATTCCTTAATGGCTGCGATGAATGCT

CTTTTCAAGAAATCCACAGCGGTAGGATTTTGGTCACCACCGAACTTTTCGAAGACCTTCAAAGCCATGTCGGTTAGG

AACGGGGGTTGTGACCGACAGAGGTAGTAGCTCCTATTGGCGTTCAATATTTTACCGTAATGCTCTATCTCAAAGATG

AAATGCTCAACCATCCCACGTGCTATGTCCACTTTGTTACAGTCTAGAAGACCCAAAGCCATTAGGTATGAGTCCCAG

CCGTAAAGTTCATTAAAACGACCGCCCGGAACAACGTAGGGAAAACCAACCAATGTACTCTCACCGGTAATTGGGTCC

CTGTGACTCTCCATCGCCAAAGCAAGCAACCCCGGGCTTTCGTTCAATGATTGCACGTGCTCCGGCGTGATC(SEQ ID NO:7)
```

Example 6

Identification of Antifungal Drug Targets Represented in the Attached *Ashbya gossypii* Database A.) Principle of Gene Disruption using Short Flanking Homology (SFH)-PCR Mediated Transformation of *Ashbya gossypii*

Gene disruptions in the Ashbya genome represented by sequences provided in the Sequence Listing are performed using a new PCR-based Ashbya gene targeting procedure. Gene targeting in Ashbya relies on homologous recombination in this fungus (Steiner et. al., 1995). It has been found that short (approximately 45 bp) target sequence homologies added by PCR to both ends of a selectable marker (e.g. GEN3) are sufficient to mediate sequence-specific gene targeting in Ashbya. The PCR fragment for gene targeting thus carries terminal Short Flanking Homology regions encompassing the selectable marker module. These PCR fragments are transfected into *A. gossypii* (e.g. by electroporation) and transformants are selected for G418 resistance. Verification of correct gene targeting is achieved by PCR-testing the presence of the new junctions between target DNA and integrated marker using verification primer pairs G1-G2 and G3-G4 as described by Wach et al. (1997) P. Yeast 13: 1065–1075. Also, verification of the gene targeting can be performed by DNA-hybridization experiments. The verification primers (G2: 5' GTTTAGTCTGAC-CATCTCATCTG 3'(SEQ ID NO:8) and G3: 5' TCGCA-GACCGATACCAGGATC 3') (SEQ ID NO:9) are derived from the open reading frame of the selectable marker gene GEN3. G1 and G4 primer sequences are derived from the single read sequence and correspond to regions upstream and downstream, respectively, of the homology regions used for PCR-based targeting. Using this PCR-based targeting approach, sequences can be manipulated that are approximately 150 nt in length, a criterium matched by all single read sequences of the attached Ashbya database. This is of major advantage considering classical methods of gene disruption that are laborious and require cloning steps to incorporate a selectable marker within rather large flanks of surrounding target sequence homology.

After clonal purification (spore isolation) it is determined whether deletion/insertion at the targeted locus results in any phenotypic alterations (e.g. decrease or loss of viability) identifying a potential target for antifungal drugs.

B.) Protocol for Short Flanking Homology (SFH)-PCR Mediated Transformation of *Ashbya gossypii*

1.) Selection of S1 and S2 primers is done in order to link app. 45 nt specific of the target locus sequence to 20 nt homologous to pGEN3 in order to allow amplification of the selection marker GEN3. The standard sequence on the 5' side of GEN3 corresponds to 5' GCTAGGGATAACAGGG-TAAT 3'(SEQ ID NO:10), which includes the recognition site of the rare cutting endonuclease I-SCE1 to the PCR fragment. This restriction site is not found in the nuclear genome of *A. gossypii* and can be used to physically map the position of the *A. gossypii* insert DNA to a chromosomal location. The sequence on the 3' side of GEN3 corresponds to 5' AGGCATGCAAGCTTAGATCT 3'(SEQ ID NO:11). Put together, the S1 and S2 primers comprise a total of app 65 nt. Selection of verification primers G1 and G4 which are neither part nor overlap with S1 and S2 primer sequences is dependent on the target locus sequence.

2.) Generation of SFH-PCR fragment is achieved by using the S1 and S2 primers to amplify GEN3 to an amount of approximately 10 mg from linearized pGEN3 cleaved by the restriction endonucleases EcoRI and BamHI (Biolabs). To increase the fidelity of the PCR-product a mixture of Taq DNA Polymerase (Pharmacia) and Vent DNA Polymerase (Biolabs) is used in a ratio of 10: 1–2 units.

Standard PCR conditions are:

Step1: Initial denaturation: at 96° C. for 2 min.
Step2: Denaturation: at 96° C. for 30 s.
Step3: Primer annealing: at 50° C. for 30 s.
Step4: Elongation period: at 72° C. for 2.5 min.
  Steps 2–4 are repeated for 25–35 times.
Step5: Terminal elongation period: at 72° C. for 5 min.
Step6: Storage at 4° C. (optional).

3.) Transfection of the SFH-PCR product into *A. gossypii* is done by electroporation (Steiner et al.,1995 with modifications):

1.) Inoculate 100–200ml YPD or AFM (YPD: 2% casein peptone, 2% glucose, 1% yeast extract; AFM: 1% casein peptone, 2% glucose, 1% yeast extract, 0.1% myoinositol) with a spore suspension of app. $10^7$ spores.

2.) Incubate at 30° C. for a max. of 18 h under rotation of 200 rpm.

3.) Collect the mycelium by filtration and wash once with sterile $H_2O$.

4.) Resuspend 1 g of wet weight mycelium in 40 ml of 50 mM potassium phosphate buffer, pH 7.5 containing 25 mM DTT and incubate at 30° C. for 30 min with gentle shaking.

5.) Collect the mycelium by filtration and wash once with 50 ml cold STM buffer (STM: 275 mM sucrose, 10 mM Tris-HCl, pH 7.5, 2 mM $MgCl_2$.)

6.) Resuspend to a densely packed mixture of mycelium in STM buffer.

7.) Mix app. 150 ml of mycelium with max. 50 ml of SFH-PCR product in an Eppendorf tube and transfer the mixture into an electroporation cuvette (BioRad 4 mm).

8.) Apply an electric field pulse of 1.5 kV, 100½, 25 mF which will result in a pulse length of app 2.3 ms. Add 1 ml of YPD or AFM and spread equal amounts onto 3 pre-dried AFM plates.

9.) Incubate at 30° C. for a min. of 4 h.

10.) Overlay with 8 ml 0.5% agarose top layer containing Geneticin/G418 at a final concentration of 200 mg/ml.

11.) Incubate at 30° C. for a max. of 4 days.

C.) Examples of Gene Disruptions Revealing Potential Antifungal Drug Targets Using Short Flanking Homology (SFH)-PCR.

1.) Disruption of PAG1025RP

The amino-terminal part of the RHO 3 gene is located on PAG1025RP. The location of the homology region to the target locus of the four primers (S1, S2, G1, and G4) necessary to construct and verify the SFH-PCR transformants are indicated in section E.) below. Using the S1 and S2 primers (including the 20 nt homologous to pGEN3 at the 3' end of the homology region to the target locus as indicated in A) together with pGEN3, the plasmid carrying the selectable marker gene GEN3, (linearized by cutting with EcoRI and BamHI restriction nucleases [Biolabs]), a PCR fragment is generated that carries terminal Short Flanking Homology regions encompassing the selectable marker module. Primary transformants, which are heterokaryotic with respect to transformed and untransformed nuclei, are clonally purified by spore isolation using a micromanipulator. Germination of spores deleted for RHO 3 on selective medium is only obtained by adding osmotic stabilizers such as 1 M sorbitol. Verification of the set deletion is performed by PCR using the verification primers G1 and G4 that are unique to the target locus and are not used in the initial transformation event, as well as the primers G2 and G3 that are specific to the selectable marker. PCR products indicative of a homologous gene targeting event can be obtained by using the verification primers in the combination G1-G4 (which amplifies the entire locus in which integration of GEN3 is targeted), G1-G2 (which amplifies the 5' novel joint that is created by insertion of GEN3) and G3-G4 (which amplifies the 3' novel joint that is created by insertion of GEN3).

2.) Disruption of PAG1634RP

The amino-terminal part of the BAL 1 gene is located on PAG1634RP. The location of the homology region to the target locus of the four primers (S1, S2, G1, and G4) necessary to construct and verify the SFH-PCR transformants are indicated in section E.) below. Using the S1 and S2 primers (including the 20 nt homologous to pGEN3 at the 3' end of the homology region to the target locus as indicated in A) together with pGEN3, the plasmid carrying the selectable marker gene GEN3, (linearized by cutting with EcoRI and BamHI restriction nucleases [Biolabs]), a PCR fragment is generated that carries terminal Short Flanking Homology regions encompassing the selectable marker module. Primary transformants, which are heterokaryotic with respect to transformed and untransformed nuclei, are clonally purified by spore isolation using a micromanipulator. Germination of spores deleted for BAL1 on selective medium is only obtained by adding osmotic stabilizers such as 1 M sorbitol. Verification of the gene targeting event is done as described in C.1)

3.) Disruption of PAG1486RP

The aminoterminal part of the BUB1 open reading frame is located on PAG1486RP. The location of the homology region to the target locus of the four primers (S1, S2, G1, and G4) necessary to construct and verify the SFH-PCR transformants are indicated in section E.) below. Using the S1 and S2 primers (including the 20 nt homologous to pGEN3 at the 3' end of the homology region to the target locus as indicated in A) together with pGEN3, the plasmid carrying the selectable marker gene GEN3, (linearized by cutting with EcoRI and BamHI restriction nucleases [Biolabs]), a PCR fragment is generated that carries terminal Short Flanking Homology regions encompassing the selectable marker module. Primary transformants, which are heterokaryotic with respect to transformed and untransformed nuclei, are clonally purified by spore isolation using a micromanipulator. Germination of spores deleted for BUB 1 cannot be obtained indicating that this gene is essential in *A. gossypii*. Verification of the gene targeting event is done as described in C.1)

SFH-PCR mediated marker integration into the *A. gossypii* DNA can be applied to all RP and/or UP sequences of the attached data base. Further applications of SFH-PCR mediated gene targeting in *A. gossypii* are:

1.) Generation of antisense transcripts.

2.) Overproduction of mRNA and presumably overexpression of a protein.

3.) Addition of reporter genes to a target sequence (e.g. GFP, lacZ).

4.) Introduction of longer deletions using RP and UP sequences.

D.) Examples of Gene Disruptions Revealing Potential Antifungal Drug Targets by Classical Procedures 1.) Construction of Disruption Cassettes As a selectable marker, kanMX0 is used. This is a transformation selection module expressing G418 resistance in yeast and filamentous fungi and kanamycin resistance in *E. coli* (International Patent Applicatin No. PCT/EP 91/01116). This module is inserted into Ashbya sequences of genomic pAG clones. The module is a chimeric kanamycin gene plus adjacent multiple cloning regions from the cloning vector pAG-231 (Steiner, Wendland, Wright, and Philippsen, Genetics 1995: 140, 973–987) To this purpose the selectable marker is released from the cloning vector pAG-231 (by cleavage with either BamHI, SalI or XhoI. It is ligated into cloned Ashbya DNA cleaved with either BglII, XhoI (partial) or SalI (partial), respectively. Clones carrying Ashbya sequences disrupted by kanMX0 are selected in *E. coli* by kanamycin resistance. DNA sequence analysis around the site of integration of the kanMX0 module (i1 and i2sequences in the attached Ashbya data base) reveal the disrupted open reading frame and determine the orientation of the kanMX0 module.

2.) Disruption of PAG1010i1/i2, PAG1017i1/i2, PAG1021i1/i2, and PAG1044i1/i2

Disruption cassettes are released from the plasmids leaving several hundred base pairs of Ashbya DNA flanking kanMX0 (e.g. by cleavage with NotI and KpnI in the multi-cloning region). Transformation of Ashbya with the disruption cassettes induces homologous recombination into the target locus (Steiner et al., 1995). Primary transformants are selected on G418 containing plates and analyzed by DNA hybridization experiments or by PCR, followed by clonal purification (spore isolation). Chromosomal mapping of the target loci is achieved by I-SceI endonuclease mapping of chromosomal DNA separated by pulsed-field gel electrophoresis.

Primary transformants are heterokaryotic, carrying nuclei with a wild type allele and nuclei with a disrupted allele. Spores with single haploid nuclei develop in the older mycelium and allow clonal purification of transformants (e.g. by single spore isolation with a micromanipulator, Steiner et al., 1995). Spore isolation is followed by a growth assay. The disruption of Ashbya ORF's identified for example in sequences PAG1010i1/i2, PAG1017i1/i2, AG1021i1/i2, and PAG1044i1/i2 do not grow on reveals no growth of spores on G418 medium hereby classifying the products of these ORF's as essential for growth (novel antifungal targets).

One advantage of using Ashbya, a fungus with a small genome and apparently very few gene duplications, for novel drug target identification is demonstrated by the fact that the ORF represented by PAG1017i1/i2 is essential in Ashbya but the highly homologous ORF Yer082c of *S. cerevisiae* is not (Smith, Chou, Lashkari, Botstein, and Brown Science 1996: 274, 2069–2074).

Clonally purified disruptions of several other ORF's do grow on G418 medium, sometimes identifying mutants that display slow growth phenotypes (e.g. disruption of AgDHC1).

E.) Construction of pGEN3

The GEN3 selection module is designed specifically to allow homologous recombination in *Ashbya gossypii* using short flanks of DNA sequence homology to the desired target locus. GEN3 consists of the open reading frame of the kan$^R$-gene which is under the transcriptional control of the *S. cerevisiae* TEF2 promoter and terminator. GEN3, which confers resistance to the antibiotic drug geneticin, bears no sequence homology to the *A. gossypii* genome.

To construct pGEN3, the ORF of the kan-gene is amplified from pFA-kanMX4 (Wach, A., Brachat, A., Poehlmann, R., and Philippsen, P. (1994). New heterologous modules for classical or PCR-based gene disruptions in *Saccharomyces cerevisiae*. Yeast 10:1793–1808) using primers PTEF2-kan and TTEF2-kan (table 1) that contain an additional 40 bp of short flanks of homology to the *S. cerevisiae* TEF2 gene. The diploid yeast strain FY1679 is transformed with this SFH-PCR product (Wach et al., 1994). Genomic DNA of transformants resistant to G418 is checked for integration of the PCR product at the TEF2 locus by analytical PCR using primers TEF2-150RPG and TEF2-BglII. Because of the diploid background a wild-type band 2.26 kb and a replacement band of 1.7 kb is generated. This 1.7 kb fragment contains the kan-ORF flanked by 609 bp of the TEF2-promoter region and 274 bp including the TEF2-terminator. This gene is termed GEN3. The fragment is extracted out of an agarose gel and ligated as an BglII-fragment into the BglII site of pAF100 (Thierry A., Fairhead, C., and Dujon, B. (1990). The complete sequence of the 8.2 kb segment left of MAT on chromosome III reveals five ORF's, including a gene for a yeast ribokinase. Yeast 6:521–534) yielding pGEN3. The usefulness of GEN3 as a marker gene in *A. gossypii* is corroborated by recloning of the gene in an ARS containing vector (Sikorski, R. S. and Hieter, P. (1989). A system of shuttle vectors and yeast host strains designed for efficient manipulation of DNA in *Saccharomyces cerevisiae*. Genetics 122:19–27.) that allows free replication upon transformation in *A. gossypii*.

Example 7

Forensic Identification Using PCR-Based Diagnostic Techniques

The DNA sequences of the present invention are also useful for distinguishing among different species of plant pathogenic fungi and for distinguishing fungal pathogens from other pathogens such as bacteria. Particularly, the DNA sequences of the invention can be used as primers in PCR-based analysis for fungal identification, as well as primers derived from these DNA sequences. Alternately, primers of at least 10–20 contiguous nucleotides in length derived from the DNA sequences of the invention may be used in PCR-based diagnostic assays. Preferably, the primers should amplify a DNA sequence of at least 20–30 nucleotides in length, and preferably the primers define regions of DNA that are not highly conserved compared with other genomic databases. DNA sequences that vary among different pathogens can be used to identify and distinguish among those specific specific pathogens. For example, the presence of *Gaumannomyces graminis* in infected wheat has been detected using PCR of sequences specific to the pathogen mitochondrial genome (Schlesser et al., 1991; *Applied and Environ. Microbiol.* 57: 553–556), and random amplified polymorphic DNA (i.e. RAPD) markers have been able to distinguish numerous races of *Gremmeniella abietina*, the causal agent of scleroderris canker in conifers. U.S. Pat. No. 5,585,238 describes primers derived from the ITS sequences of the ribosomal RNA gene region of strains of Septoria, Pseudocercosporella, and Mycosphaerella and their use in the identification of these fungal isolates using PCR-based techniques.

Methods for the use of DNA sequences in PCR analysis are well known in the art, See, for example, see U.S. Pat. Nos. 4,683,195 and 4,683,202, as well as Schlesser et al. (1991) *Applied and Environ. Microbiol.* 57:553–556. See also, Nazar et al. (1991; Physiol. and Molec. Plant Pathol. 39: 1–11), which used PCR amplification to exploit differences in the ITS regions of *Verticillium albo-atrum* and *Verticillium dahliae* and therefore distinguish between the two species; and Johanson and Jeger (1993; *Mycol. Res.* 97: 670–674), who used similar techniques to distinguish the banana pathogens *Mycosphaerella fijiensis* and *Mycospharella musicola*. Similarly, the sequences of the present invention set forth in the Sequence Listing can be adapted for use in such PCR analysis.

```
Oligonucleotide primers[1]
PTEF2-kan    GTTTTTAGAATATACGGTCAACGAACTATAATTAACTAAACataaataaaaaaaaactca    (SEQ ID NO:12)
TTEF2-kan    GGTATATAAAAATATTATATGGAAGCAATAATTATTACTCttagaaaaactcatcgagca    (SEQ ID NO:12)
TEF2-150RPG  gcgagatctGGTGTATTTACCAATAAT                                  (SEQ ID NO:14)
TEF2-BglII   gcgagatctGATGAGGCCGTCTTTTGTTG
```
[1] Upper case letters correspond to S. cerevisiae DNA used as homology regions. Lower case letters correspond to homologies to pGEN3, pFA-kanMX4 (double underlined), or represent additional nucleotides containing the restriction site BglII (bold) used in the cloning of pGEN3.

TABLE 1

| pAG name | Yeast Name | Gene Name | Brief Description | HC | Additional Comments |
|---|---|---|---|---|---|
| PAG1001RP | YNR030w | | weak similarity to SMP3 protein | 1 | |
| PAG1001UP | YCR069w | SCC3 | peptidyl-prolyl cis-trans isomerase precursor | 1 | |
| PAG1002I1 | YIL014w | | similarity to Mnn1p (alpha-1,3-mannosyltransferase) | 2 | homology due to PAG1002I2-hit |
| PAG1002I2 | YIL0142 | | similarity to Mnn1p (alpha-1,3-mannosyltransferase) | 2 | |
| PAG1002RP | YIL105c | | similarity to hypothetical protein YNL047c | 3 | open frame > 450 nt in −2 |
| PAG1002UP | YBL009w | | homology to DNA damage responsive ALK1 protein | 4 | |
| PAG1003RP | YCR053w | THR4 | threonine synthase (o-p-homoserine p-lyase | 1 | Terminator, Syntenie, see PAG1003UP |
| PAG1003UP | YCR057c | PWP2 | periodic tryptophan protein | 1 | Syntenie, see PAG1003RP |
| PAG1004RP | YLR102c | | hypothetical protein | 2 | Syntenie, see PAG1004UP |
| PAG1004UP | YLR100w | | hypothetical protein | 1 | Syntenie, see PAG1004RP |
| PAG1005RP | YBR216c | | homology to hypothetical protein (chromosome VII) | 3 | open frame > 350 nt in −1 |
| PAG1005UP | YNL068c | FKH2 | homolog of Drosophila forkhead protein | 3 | open frame 300 nt in −3 |
| PAG1006RP | YDG432w | NPL3 | nucleolar protein | 3 | open frame > 450 nt in −3 |
| PAG1006UP | YOR290c | SNF2 | component of SWI/SNF global transcription activator complex | 3 | open frame > 350 nt in −1 |
| PAG1007RP | YER091c | MET6 | 5-methyltetrahydropteroyl triglutamate-homocysteine methyltransferase | 1 | Syntenie, see PAG1007UP |
| PAG1007UP | YER093c | | weak similarity to *Staphylococcus epidermidis* PepB protein | 1 | Syntenie, see PAG1007RP |
| PAG1008I1 | YHR196w | | hypothetical protein | 1 | does not fit in Syntenie of PAG1008RP, UP and I2 |
| PAG1008I2 | YJR133w | | similarity to hypothetical D9509.18p | 1 | Promotor + Terminator (the latter according to PAG1008I1), 279 nt.Syntenie, see PAG1008RP and UP |
| PAG1008RP | YJR132w | NMD5 | putative Upf1p-interacting protein | 2 | Terminator, Syntenie, see PAG1008I2 and UP |
| PAG1008UP | YJR134c | | unclear similarity to paramyosin, myosin | 1 | Terminator, Syntenie, see PAG1008I2 and RP |
| PAG1009RP | YNL218w | | homology to *C. burnetii* trxB, spoIIIE and serS genes | 1 | Syntenie, see PAG1109UP |
| PAG1009UP | YNL219c | | probably membrane protein | 2 | Syntenie, see PAG1109RP |
| PAG1010I1 | YLR337w | VRP1 | proline-rich protein verprolin | 3 | open frame 350 nt in +3 and −2 |
| PAG1010I2 | YLR332w | MID2 | serine-rich protein, multicopy suppressor of temperature sensitivity to htr1 null mutant. Open frame whole length in +3 and−3 | | |
| PAG1010RP | YOR240w | | weak similarity to unknown *S. pombe* protein | 1 | |
| PAG1010UP | YGR115c | | questionable ORF | 1 | |
| PAG1011I1 | YLR374c | | questionable ORF | 4 | |
| PAG1011I2 | YKR054c | DYN1 | dynein heavy chain, cytosolic | 1 | additional Hit see PAG1011RP and PAG1219RP |
| PAG1011RP | YKR054c | DYN1 | dynein heavy chain, cytosolic | 1 | additional Hit see PAG1011I2 and PAG1219RP |
| PAG1011UP | YJL133w | MRS3 | splicing protein and member of the mitochondrial carrier family | 1 | Terminator |
| PAG1012RP | YER074w | RP50A | ribosomal protein S24.e | 1 | Terminator, cannot be checked for Intron, not on sequence of PAG1012RP |
| PAG1012UP | YIL068c | SEC6 | component of a multiprotein complex involved in fusion of post-golgi vesicles to plasma membrane | 1 | |
| PAG1013I1 | YLR344w | RPL33 | ribosomal protein | 1 | Promotor, Syntenie, see PAG1013UP, RP and I2 2nd Hit, Intron in A.g. at the same position like in S.c. (CAI S.c. 0.63) |
| PAG1013I2 | YLR344w | RPL33 | ribosomal protein | 1 | Terminator, Syntenie, PAG1013UP, RP and I1 |
| PAG1013RP | YLR345w | | similarity to 6-phosphofructo-2-kinase (EC 2.7.1.105) | 1 | Syntenie, see PAG1013UP, I1 and I2 2nd Hit |
| PAG1013UP | YLR343w | | homology to *Candida albicans* pH responsive protein | 1 | Syntenie, see PAG1013RP, I1 and I2 2nd Hit |
| PAG1014RP | YDR376w | ARH1 | similarity to human adrenodoxin reductase | 1 | Syntenie, see PAG1014UP |
| PAG1014UP | YDR375c | BCS1 | MT protein of the CDC48/PAS1/SEC18 (AAA) family of ATPases | 1 | Terminator, Syntenie, see PAG1014RP |
| PAG1016RP | YIR002c | | similarity to ATP-dependent RNA helicases | 1 | |
| PAG1016UP | YJR078w | | indoleamine 2,3-dioxygenase homolog | 1 | |
| PAG1017I1 | YER082c | | hypothetical protein | 1 | |

TABLE 1-continued

| pAG name | Yeast Name | Gene Name | Brief Description | HC | Additional Comments |
|---|---|---|---|---|---|
| PAG1017I2 | YER082c | | hypothetical protein | 1 | |
| PAG1017RP | YIL075c | SEN3 | tRNA processing | 1 | |
| PAG1017UP | YKL216w | URA1 | dihydroorotate dehydrogenase (EC 1.3.99.11) | 2 | |
| PAG1018RP | YKL018w | | hypothetical protein | 1 | |
| PAG1018UP | YIR019c | STA1 | extracellular glycoamylase | 3 | open frame whole length in +1 and −3 |
| PAG1019RP | YKR084c | HSB1 | elongation factor 1 alpha-like protein | 2 | |
| PAG1019UP | YKR092c | SRP40 | weak suppressor of a mutant of the subunit AC40 of DNA dependent RNA POL I and III | 3 | open frame whole length in +1 |
| PAG1020RP | YOL130w | | strong homology to YFL050c (ALR2, aluminium resistance protein) | 1 | |
| PAG1020UP | YNL310c | | hypothetical protein | 1 | |
| PAG1021I1 | YIL019w | | hypothetical protein | 1 | Terminator, Syntenie |
| PAG1021I2 | YIL019w | | hypothetical protein | 1 | syntenie |
| PAG1021RP | YIL022w | TIM44 | MT inner membrane protein required in transport across the inner membrane | 1 | syntenie |
| PAG1021UP | YIL019w | | hypothetical protein | 1 | syntenie |
| PAG1022RP | | | | 3 | open frame whole length in −1 |
| PAG1022UP | YDR331w | | weak similarity to S. japonicum hemoglobinase | 3 | open frame > 350 in +1 |
| PAG1023I1 | YCR092c | MSH3 | DNA-repair protein | 2 | |
| PAG1023I2 | YCR092c | MSH3 | DNA-repair protein | 1 | |
| PAG1023RP | YCR092c | MSH3 | DNA-repair protein | 1 | |
| PAG1023UP | YNR047w | | similarity to microtubule-associated serine/theronine protein kinases | 1 | |
| PAG1024RP | YBR119w | MUD1 | U1 snRNP-specific A protein (snRNA-associated protein) | 2 | most likely Intron, no ATG in correct frame found slightly different position compared to S.c. |
| PAG1024UP | YER105c | NUP157 | nuclear pore protein (nucleoporin) | 3 | open frame whole length in +3 and −2 |
| PAG1025RP | YIL118w | RHO3 | similarity to RAS proteins; belongs to RHO sub-family | 1 | |
| PAG1025UP | YNL061w | NOP2 | homolog to human proliferation-associated nucleolar antigen, p120 | 1 | |
| PAG1026RP | YIL096c | | hypothetical protein | 1 | Terminator |
| PAG1026UP | YNL039w | TFC5 | transcription factor TFIIIB, B" component of RNA polymerase III | 2 | |
| PAG1027RP | YOL122c | SMF1 | suppressor of mitochondrial matrix protease (MAS1) mutant | 1 | |
| PAG1027UP | YOR359w | | hypothetical protein | 4 | |
| PAG1028RP | YNL308c | | similarity to unknown protein on S. pombe CHR I cosmid c22G7 | 1 | Syntenie, see PAG1028UP |
| PAG1028UP | YNL309w | STB1 | Sin3p-binding protein (transcription regulatory protein) | 2 | Syntenie, see PAG1028RP, (classification in Hom_Class 2 according to Syntenie) |
| PAG1029RP | YOR205c | | hypothetical protein | 2 | |
| PAG1029UP | YGL141w | | similarity with hypothetical protein 1 - human (A38919) | 2 | |
| PAG1030RP | YHR205w | SCH9 | cAMP-dependent protein kinase homolog | 1 | Syntenie, see PAG1030UP |
| PAG1030UP | YHR204w | | similarity to alpha-mannosidases | 1 | Syntenie, see PAG1030RP |
| PAG1031RP | YKL012w | | similarity to C. elegans hypothetical protein ZK1098.1 and to Myo2p | 1 | Promotor, Syntenie, see PAG1031UP |
| PAG1031UP | YKL011c | CCE1 | cruciform-cutting endonuclease 1 | 2 | Syntenie, see PAG1031RP, (classification in Hom_Class 2 according to Syntenie) |
| PAG1032RP | YKL209c | STE6 | ABC transporter responsible for export of A factor mating pheromone | 4 | |
| PAG1032UP | YDL133w | | putative membrane protein | 1 | Terminator |
| PAG1033RP | YBR274w | | probable serine/threonine-specific protein kinase (EC 2.7.1.-) | 1 | |
| PAG1033UP | YDL037c | | putative glucan 1,4-alpha-glucosidase (EC 3.2.1.3) | 3 | open frame whole length in −2 |
| PAG1034RP | YGL114w | | hypothetical protein | 1 | |
| PAG1034UP | YOR246c | | similarity to reductases | 4 | |
| PAG1035I1 | YLR337w | VRP1 | proline-rich protein verprolin | 3 | open frame 300 nt in −3 |
| PAG1035I2 | YNL281w | | hypothetical protein | 3 | open frame > 350 nt in −1 |
| PAG1035RP | YJR090c | GRR1 | required for glucose repression and for glucose and cation transport | 3 | open frames > 350 nt in −1 |
| PAG1035UP | YBL079w | NUP170 | nuclear pore (nucleoporin) | 1 | see PAG1035UP for additional Hit to YBL079w |
| PAG1036RP | YLR266c | | similarity to transcription factors | 3 | open frames 350 nt in −3, 300 nt in +2 |
| PAG1036UP | YDR370c | | hypothetical protein | 2 | |

TABLE 1-continued

| pAG name | Yeast Name | Gene Name | Brief Description | HC | Additional Comments |
|---|---|---|---|---|---|
| PAG1037RP | YLR430w | SEN1 | positive effector of tRNA-splicing endonuclease | 1 | |
| PAG1038RP | YNL068c | FKH2 | homolog of Drosophila forkhead protein | 3 | open frame whole length in −3 |
| PAG1038UP | YLR389c | STE23 | protease involved in a-factor processing | 1 | |
| PAG1039RP | YDR443c | STB9 | component of RNA-POL holoenzyme and kornberg's mediator (SRB) subcomplex | 1 | nearly whole gene on clone |
| PAG1039UP | YDR443c | SRB9 | component of rna polymerase holoenzyme and kornberg's mediator (SRB) subcomplex | 1 | Promotor, nearly whole gene on clone |
| PAG1040RP | YAL040c | CLN3 | G1/S-specific cyclin | 4 | tRNA (Val1), pos. 134–207, perfect match to S.c. tRNA(Val1A), 1 mismatch to tRNA(Val1B), no intron |
| PAG1040UP | YPR097w | | hypothetical protein | 2 | |
| PAG1041RP | YJL054w | | hypothetical protein | 2 | |
| PAG1041UP | YLR337w | VRP1 | proline-rich protein verprolin | 4 | |
| PAG1042RP | YGL035c | MIG1 | transcriptional repressor involved in glucose-repression | 3 | open frame > 300 nt in −2 |
| PAG1042UP | YKR075c | | weak similarity to negative regulator Srn1p/Hex2p | 3 | open frame 300 nt in +1 |
| PAG1043RP | YDR456w | | similarity to NA+-H+ antiporters | 2 | |
| PAG1043UP | YML029w | | putative membrane protein | 2 | |
| PAG1044I1 | YDL076c | | | | |
| PAG1044I2 | YDL076c | | | | |
| PAG1044RP | YDL077c | | hypothetical protein | 2 | syntenie |
| PAG1044UP | YDL075w | RPL34A | ribosomal protein L31.e.c12 | 1 | Promotor; Intron, in A.g. at same position compared to S.c. (CAI S.c. 0.60);syntenie |
| PAG1045RP | YBL096c | | hypothetical protein | 4 | |
| PAG1045UP | YDL195w | SEC31 | component of the COPII coat of ER-golgi vesicles | 4 | |
| PAG1046RP | YHR132c | | carboxypeptidase homolog | 1 | |
| PAG1046UP | YBR149w | | | 3 | open frame 350 nt in +1 |
| PAG1047RP | YLR377c | FBP1 | fructose-1,6-bisphosphatase, gluconeogenic enzyme | 1 | Syntenie, see PAG1047UP |
| PAG1047UP | YLR378c | SEC61 | member of the protein permease family of the major facilitator superfamily (MFS) | 1 | Promotor, has STOP (???) in Hom_Reg, Syntenie, see PAG1047RP (CAI S.c. 0.24) |
| | YLR379w | | questionable ORF | 1? | has STOP in Hom_Reg |
| PAG1048RP | YBL023c | MCM2 | member of the Mcm2p,Mcm3p,Cdc46p family | 1 | |
| PAG1048UP | YER139c | | similarity to YD9609.20 (similarity to amino acid permeases) | 1 | |
| PAG1049RP | YLR050c | | similarity to human MAC30 C-terminus | 2 | Terminator |
| PAG1049UP | YFL018c | LPD1 | dihydrolipoamide dehydrogenase precursor | 1 | |
| PAG1050RP | YGL139w | | similarity with hypothetical protein (chromosome XVI) YPL221w | 1 | |
| PAG1050UP | YIL090w | | hypothetical protein | 1 | |
| PAG1052I1 | YPL221w | | homology to hypothetical protein (CHR VII) and probable membrane protein YAL053w | 2 | |
| PAG1052I2 | YPL221w | | homology to hypothetical protein (CHR VII) and probable membrane protein YAL053w | 1 | |
| PAG1052RP | YGL139w | | similarity with hypothetical protein (chromosome XVI) YPL221w | 1 | Syntenie, see PAG1052UP |
| PAG1052UP | YGL137w | SEC27 | coatomer complex beta chain (beta'-cop) of secretory pathway vesicles | 1 | Promoter, Sytenie, see PAG1052RP, I1 and I2 (match all to YGL139w), Intron possible, same position like in S.c. (CAI S.c. 0.21) |
| PAG1053RP | YJL197w | UBP12 | ubiquitin specific protease | 3 | open frame whole length in −1 |
| PAG1053UP | YGR255c | | hypothetical protein | 1 | Terminator |
| PAG1054RP | YBL023c | MCM2 | contains N-term down to codon 106, Member of the CDC46p/ MCM2p/MCM3p family that acts as a complex at ARS's to initiate replication | 1 | former class III |
| PAG1054UP | YDL120w | | hypothetical protein | 3 | open frame 350 nt in +3, +2, and −2 |
| PAG1055RP | YBL023c | MCM2 | member of the Mcm2p,Mcm3p,Cdc46p family | 2 | |
| PAG1055UP | YDR065w | | hypothetical protein | 3 | open frame 350nt in +3 and −2 |
| PAG1056RP | YBR290w | BSD2 | metal homeostasis protein and probable metal ion transporter | 1 | |
| PAG1056UP | YNL228w | | questionable ORF | 4 | |

TABLE 1-continued

| pAG name | Yeast Name | Gene Name | Brief Description | HC | Additional Comments |
|---|---|---|---|---|---|
| PAG1057RP | YDR143c | SAN1 | protein that may antagonize the function of Cdc68p (general chromatin factor) and Sir4p | 2 | |
| PAG1057UP | YIL169c | | homology to glucan 1,4-alpha-glucosidase | 3 | open frame 400 nt in +3 |
| PAG1058I1 | YDR151c | CTH1 | protein of the inducible CCCH zinc-finger family | 1 | Syntenie, see PAG1058UP |
| PAG1058I2 | YOR306c | | similarity to human X-linked PEST-containing transporter | 4 | |
| PAG1058RP | YDR150w | NUM1 | nuclear migration protein | 4 | |
| PAG1058UP | YDR152w | | hypothetical protein | 1 | Syntenie, see PAG1058I1 |
| PAG1059RP | YLR289w | GUF1 | similarity to E. coli elongation factor-type GTP-binding protein lepa | 1 | Syntenie, see PAG1059UP 1st and 2nd Hit |
| PAG1059UP | YLR291c | GCD7 | translation initiation factor eif2b,43 KD (beta) subunit | 1 | Terminator + Promotor (300 nt, for Terminator see PAG1059UP 2nd Hit), Syntenie |
| | YLR292c | SEC72 | involved in recognition of signal peptides | 1 | Terminator + Promotor (300 nt, for Terminator see PAG1059UP 1st Hit), Syntenie |
| PAG1060RP | YER157w | | unknown function | 1 | syntenie same as PAG1637 |
| PAG1060UP | YER155c | BEM2 | GTPase-activating protein | 1 | same as PAG1637 |
| PAG1061RP | YGR276c | | weak similarity with GOR protein - Pan troglodytes | 1 | same as PAG1112 |
| PAG1062RP | YMR297w | PRC1 | carboxypeptidase y (CPY)(YSCY), serine-type protease | 1 | |
| PAG1062UP | | | ORF not regarded, homolog to Gly-X carboxypeptidase, pseudogene in S288C, three ORF's are seperated by two in-frame STOP-codons | 3 | open frame 300 nt in −1, many stops in other frames |
| PAG1063RP | YPL004c | | homology to hypothetical protein (chromosome VII) | 1 | |
| PAG1063UP | YFL002c | SPB4 | putative ATP-dependent RNA helicase | 1 | |
| PAG1064RP | YBR180w | | similarity to drug resistance proteins | 1 | |
| PAG1064UP | YNL185c | | similarity to ribosomal protein L11 | 4 | |
| PAG1065RP | YPL040c | ISM1 | mitochondrial isoleucine--tRNA ligase (EC 6.1.1.5) | 2 | Syntenie, see PAG1065UP |
| PAG1065UP | YPL037c | EGD1 | protein with a negative role in gal gene expression | 1 | Terminator, Syntenie, see PAG1065RP |
| PAG1069RP | YPL265w | DIP5 | dicarboxylic amino acid permease | 1 | former class III |
| PAG1069UP | YGR211w | | hypothetical protein | 1 | |
| PAG1071CRP | YLR405w | | similarity to Azospirillum brasilense nifR3 protein | 3 | (Chimera or) repated region, hybridizes to A.g. chr. II and III open frame> 350 nt in +2 and −3 |
| PAG1071CUP | YDL164c | CDC9 | DNA ligase | 3 | (Chimera or) repeated region (see pG1071CRP), hybridizes to A.g. chr. II and III , open frame whole length in −3 |
| PAG1073RP | | | | | Mito |
| PAG1073UP | | | | | Mito |
| PAG1074RP | | | | | Mito |
| PAG1074UP | | | | | Mito |
| PAG1075RP | | | | | Mito |
| PAG1075UP | | | | | Mito |
| PAG1076RP | | | | | Mito |
| PAG1076UP | | | | | Mito |
| PAG1077RP | | | | | Mito |
| PAG1077UP | | | | | Mito |
| PAG1078I1 | YJL024c | YKS7 | sigma-2 adaptin homolog | 1 | Intron possible, 5' splice site not found |
| PAG1078I2 | YJL024c | YKS7 | sigma-2 adaptin homolog | 1 | Terminator, for Intron see PAG1089I1 |
| PAG1078RP | YCR081w | SRB8 | component of RNA polymerase holoenzyme and SRB subcomplex | 4 | |
| PAG1078UP | YGR175c | ERG1 | squalene monooxygenase | 1 | Terminator |
| PAG1079RP | YNL133c | | hypothetical protein | 2 | tRNA (Phe), pos. 446–538, Syntenie of YNL133c and tRNA (Phe), 18 nt intron in S.c., anticodon (gene)=GAA, same as PAG1200 |
| PAG1079UP | YHR069c | | homology to unknown S. pombe and human proteins | 1 | same as PAG1200 |
| PAG1080UP | YLL009c | COX17 | interacts genetically with SCO1 and SCO2 in cytochrome oxidase assembly | 1 | Promotor, whole gene on clone, (CAI S.c. 0.09)) |
| PAG1081RP | YOR378w | | homology to aminotriazole resistance protein | 3 | open frame whole length in +3 |
| PAG1081UP | YCR075c | ERS1 | intracellular protein transport | 2 | |
| PAG1082RP | YGR055w | MUP1 | high affinity methionine permease | 1 | |

TABLE 1-continued

| pAG name | Yeast Name | Gene Name | Brief Description | HC | Additional Comments |
|---|---|---|---|---|---|
| PAG1082UP | YLR357w | | similarity to hypothetical protein (chromosome VII) | 2 | |
| PAG1083RP | YNL283c | | similarity to mammalian mucin and yeast chitinase | 3 | open frame whole lentgh in −2, many stops in other frames |
| PAG1083UP | YDR158w | HOM2 | aspartate-semialdehyde dehydrogenase (EC 1.2.1.11) | 1 | Promotor (CAI S.c. 0.43) |
| PAG1201RP | YDL140c | RPO21 | RNA polymerase II, largest subunit (B220) | 1 | Promotor (CAI S.c. 0.21) |
| PAG1201UP | YLR218c | | hypothetical protein | 2 | |
| PAG1202RP | YPR003c | | hypothetical protein | 2 | |
| PAG1202UP | YPL108w | | hypothetical protein | 1 | |
| PAG1203RP | YMR076c | | similarity to E. nidulans bimD protein,includes C-term + terminator | 1 | two genes covered by RP-SRS;syntenie |
| | YMR075w | | promoter terminator combination, | | |
| PAG1203UP | YMR076c | | similarity to Emericella nidulans bimD protein | 1 | syntenie;covers codons 170–372 |
| PAG1204RP | YGR282c | BGL2 | endo-beta-1,3-glucanase of the cell wall | 1 | Promotor, Syntenie, see PAG1204UP |
| PAG1204UP | YGR284c | | similarity with mouse Surf-4 protein | 1 | Syntenie, see PAG1204RP |
| PAG1205RP | YJR104c | SOD1 | superoxide dismutase (EC 1.15.1.1)(Cu—Zn) | 1 | divergent Terminator (123 nt) |
| | YBL039c | URA7 | CTP synthase 1;last step in pyrimidine biosynthesis pathway | 1 | divergent Terminator (123 nt) |
| PAG1205UP | YHR150w | | unknown function | 1 | former class III |
| PAG1206RP | YDR353w | | putative thioredoxin reductase (NADPH) | 1 | Promotor |
| PAG1206UP | YHR103w | | homology to hypothetical protein D9476.7 | 1 | |
| PAG1207RP | YPL072w | | hypothetical protein | 2 | Syntenie, see PAG1107UP.Classification in Hom_Class 2 according to Syntenie |
| PAG1207UP | YPL074w | YTA6 | probable regulatory subunit of 26S proteasome complex | 1 | Syntenie, see PAG1107RP |
| PAG1208RP | | | | | Mito |
| PAG1208UP | | | | | Mito |
| PAG1209RP | YDL073w | | putative mitochondrial protein | 2 | |
| PAG1210RP | YLR094c | | hypothetical protein | 1 | Terminator, Syntenie, see PAG1210UP |
| PAG1210UP | YLR095c | | hypothetical protein | 2 | Syntenie, see PAG1210RP |
| PAG1211RP | YHR072w | ERG7 | lanosterol synthase (EC 5.4.99.7) | 1 | |
| PAG1211UP | YDR317w | | hypothetical protein | 2 | |
| PAG1212RP | YBR180w | | similarity to drug resistance proteins | 1 | |
| PAG1212UP | YDL202w | | hypothetical protein | 2 | |
| PAG1213RP | YJR005w | YAP80 | clathrin-associated protein complex beta chain, large subunit | 2 | |
| PAG1213UP | YLR007w | | hypothetical protein | 1 | open frames whole length in +1 and −3,former class III |
| PAG1214RP | YIR008c | PRI1 | DNA polymerase alpha subunit 48KD (DNA primase) | 3 | open frame whole length in −2 |
| PAG1214UP | YLL031c | | similarity to YJL062p | 4 | |
| PAG1215RP | YIR035c | | similarity to YIR036p and YIL124p | 1 | Promotor, "Syntenie", see PAG1215UP. |
| | YIR036c | | similarity to short-chain alcohol dehydrogenase family, YIR035p and YIL124p | 1 | Promotor, "Syntenie", see PAG1215UP |
| PAG1215UP | YIR035c | | similarity to YIR036p and YIL124p | 1 | Promotor, "Syntenie", see PAG1215RP. |
| | YIR036c | | similarity to short-chain alcohol dehydrogenase family YIR035p and YIL124p | 1 | Promotor, "Syntenie", see PAG1215RP |
| PAG1216RP | YIL047c | SYG1 | protein for which truncation and overexpression can suppress $ lethality of G-alph protein deficiency | 3 | open frams >300 nt in +2 |
| PAG1216UP | YJR032w | | peptidylprolyl isomerase homolog | 4 | |
| PAG1218RP | YAL053w | | homology to hypothetical proteins on chromosomes VII, XV and XVI | 1 | |
| PAG1218UP | YOR367w | | homology to human SM22 homolog | 2 | Promotor |
| PAG1219RP | YKR054c | DYN1 | dynein heavy chain, cytosolic | 2 | Syntenie, see PAG1219UP, additional Hit see PAG1011I2 and RP |
| PAG1219UP | YKR056w | NUC2 | endo-exonuclease | 1 | Syntenie, see PAG1219RP |
| PAG1220RP | YBR062c | | unknown function | 2 | |
| PAG1220UP | YDR044w | HEM13 | coproporphyrinogen III oxidase | 1 | |
| PAG1221RP | YGL227w | | hypothetical protein | 2 | Terminator |
| PAG1221UP | YER043c | SAH1 | S-adenosyl-L-homocysteine hydrolase | 1 | |
| PAG1222RP | YLR403w | SFP1 | involved in nuclear protein localization | 1 | Terminator, Syntenie, see PAG1222UP |
| PAG1222UP | YLR401c | | hypothetical protein | 1 | Syntenie, see PAG1222RP |

TABLE 1-continued

| pAG name | Yeast Name | Gene Name | Brief Description | HC | Additional Comments |
| --- | --- | --- | --- | --- | --- |
| PAG1223RP | YGR002c | | hypothetical protein | 1 | syntenie |
| PAG1223UP | YGL003c | | unknown function, has MT-energy transfer proteins signature, has cytochrome c oxidase subunit I, copper B binding region signature | 1 | former class III.SYNTENIE |
| PAG1224RP | YML127w | | hypothetical protein | 1 | |
| PAG1224UP | YLL067c | | homology to other subtelomeric encoded proteins | 3 | open frame > 300 nt in −1 |
| PAG1225RP | YNL087w | | probably membrane protein | 1 | |
| PAG1225UP | YKR092c | SRP40 | weak suppressor of a mutant of the subunit AC40 of DNA dependent RNA polymerase I and III | 3 | open frames > 500 nt in +2 (S-rich) and >450 nt in −1 |
| PAG1226RP | YOR181w | LAS17 | proline-rich protein | 3 | open frame whole length in +2 |
| PAG1226UP | YFL049w | | weak similarity to Np16p (nuclear protein localization factor | 2 | |
| PAG1227RP | YDR262w | | hypothetical protein | 2 | |
| PAG1227UP | YGR160w | | questionable ORF | 4 | |
| PAG1228RP | YFL008w | SMC1 | chromosome segregation protein | 1 | Promotor (CAI S.c. 0.16) |
| PAG1228UP | YAL017w | FUN31 | probable serine/threonine protein kinase | 1 | |
| PAG1230RP | YNL317w | | similarity to *Arabidopsis thaliana* PRL1 protein | 1 | |
| PAG1230UP | YOL138c | | hypothetical protein | 1 | |
| PAG1231RP | YMR176w | | hypothetical protein | 3 | open frame > 350 nt in −1 |
| PAG1231UP | YPL027w | | hypothetical protein | 3 | open frams > 400 nt in +1 |
| PAG1232RP | YGL027c | CWH41 | involved in beta-1,6-glucan assembly | 1 | open frames 300 nt in +1 |
| PAG1232UP | YBL014c | RRN6 | component of a multiprotein complex essential for initiation of RNA-POL I | 2 | |
| PAG1233RP | YKR092c | SRP40 | weak suppressor of a mutant of the subunit AC40 of DNA dependent RNA polymerase I and III | 3 | open frames whole length in +2 and nearly whole lengthin −3 |
| PAG1233UP | YML102w | | similarity to human chromatin assembly factor I p60 chain | 2 | |
| PAG1235RP | YDL122w | UBP1 | ubiquitin-specific protease | 1 | |
| PAG1235UP | YGL156w | AMS1 | alpha-mannosidase | 1 | |
| PAG1236RP | YDR373w | | homology to human BDR-1 protein and other calcium binding proteins | 1 | Promotor |
| PAG1236UP | YOR124c | UBP2 | ubiquitin-specific proteinase (EC 3.4.-.-) | 1 | |
| PAG1238RP | YPL195w | YKS4 | putative alpha/gamma adaptin | 1 | |
| PAG1238UP | YGL080w | | similarity with R07E5.13 protein (clone R07E5) - *C. elegans* | 1 | Promotor |
| PAG1240RP | | | | | Mito |
| PAG1240UP | | | | | Mito |
| PAG1241RP | | | | | Mito |
| PAG1241UP | | | | | Mito |
| PAG1242RP | YKR014c | YPT52 | GTP-binding protein | 1 | Promotor (CAI S.c. 0.21) |
| PAG1242UP | YJL080c | SCP160 | histone-like protein involved in control of mitotic chromosome transmission | 1 | |
| PAG1243RP | YLR247c | | weak similarity to *S. pombe* RAD8 protein | 1 | Syntenie, see PAG1243UP |
| PAG1243UP | YLR248w | RCK2 | calcium/calmodulin-dependent SER/THR protein kinase (CAM kinase) | 1 | Syntenie, see PAG1243RP |
| PAG1244RP | YBL057c | | unknown function, non-essential | 1 | former class III, two genes covered by RP-SRS |
| | YER090w | TRP2 | Anthranilate synthase component I, first step in tryptophane biosynthesis pathway, non-essential | 1 | former class III, two genes covered by RP-SRS |
| PAG1244UP | YHR165c | PRP8 | U5 snRNP protein, pre-mRNA splicing factor | 1 | Terminator |
| PAG1245RP | YLR264w | RPS33B | ribosornal protein S28.e.c12 | 1 | Promotor, whole gene on sequence, Terminator |
| PAG1245UP | O3364 | TY1A | TY1A protein | 3 | open frams > 400 nt in −2 and > 300 nt in +1 |
| PAG1246RP | YDR531w | | hypothetical protein | 1 | Syntenie, see PAG1246UP |
| PAG1246UP | YDR527w | | hypothetical protein | 2 | Syntenie, see PAG1246RP |
| PAG1247RP | YNR044w | AGA1 | A-agglutinin anchor subunit | 3 | open frams whole length in -3,open frames > 400 in +3 and +2 |
| PAG1249RP | YOR244w | | similarity to SAS2 protein ( involved in silencing at HMR) | 1 | Syntenie, see PAG1249UP |
| PAG1249UP | YOR243c | | hypothetical protein | 1 | Syntenie, see PAG1249RP |
| PAG1250RP | | | | | Mito |
| PAG1250UP | | | | | Mito |
| PAG1251RP | YCR076c | | glycine-rich | 3 | open frames > 450 nt in +1 and > 400 nt in −3 |
| PAG1251UP | YMR259c | | hypothetical protein | 2 | Terminator |
| PAG1252RP | YFR015c | GSY1 | UDP glucose--starch glucosyltransferase 1 | 1 | |

TABLE 1-continued

| pAG name | Yeast Name | Gene Name | Brief Description | HC | Additional Comments |
|---|---|---|---|---|---|
| PAG1252UP | YFR014c | CMK1 | Ca2+/calmodulin-dependent serine/threonine protein kinase type I | 1 | |
| PAG1253RP | YGL122c | NAB2 | nuclear poly(A)-binding protein | 3 | open frame > 500 nt in +2 |
| PAG1253UP | YIL130w | | similarity to probable membrane protein YJL206c and Put3p | 1 | |
| PAG1254RP | YJR016c | ILV3 | dihydroxy-acid dehydratase (EC 4.2.1.9) | 1 | Terminator |
| PAG1254UP | M_D113 | | hypothetical protein | 4 | |
| PAG1255RP | YDR300c | PRO1 | glutamate 5-kinase | 1 | |
| PAG1256RP | YGL195w | GCN1 | component of a protein complex required for activation of Gcn2p protein kinase | 1 | Syntenie, see PAG1256UP |
| PAG1256UP | YGL194c | | high similarity with RPD3 protein (transcription modifier protein) | 1 | Syntenie, see PAG1256RP |
| PAG1257RP | YGL147c | RPL9A | ribosomal protein RPL9 | 1 | Terminator |
| PAG1257UP | YDL117w | | hypothetical protein | 2 | Terminator |
| PAG1258RP | YOL023w | IFM1 | mitochondrial translation initiation factor 2 | 1 | |
| PAG1258UP | YPL115c | BEM3 | GTPase-activating protein for Cdc42p and Rho1p | 1 | |
| PAG1259RP | YBR087w | RFC5 | replication factor C subunit 5 (40kDa) | 1 | Promotor (CM S.c. 0.15) |
| PAG1259UP | YBL036c | | similarity to *Caenorhabditis elegans* cosmid F09E5 | 1 | |
| PAG1260RP | YDR306c | | hypothetical protein | 2 | Promotor, Syntenie, see PAG1260UP, next to tRNA (Val) in S.c. |
| PAG1260UP | YDR304c | CPR5 | cyclophilin of the ER | 1 | Promotor, Syntenie, see PAG1260RP |
| PAG1261RP | YLR333c | RPS31B | ribosomal protein S25.e.c12 | 1 | Terminator |
| PAG1261UP | YLR336c | | hypothetical protein | 2 | Terminator |
| PAG1262RP | YER069w | ARG5,6 | acetylglutamate kinase | 1 | Syntenie, see PAG1262UP |
| PAG1262UP | YER068w | MOT2 | transcriptional repressor | 1 | Promotor, Syntenie, see PAG1262RP |
| PAG1263RP | YJR090c | GRR1 | required for glucose repression and for glucose and cation transport | 1 | |
| PAG1263UP | YIR019c | STA1 | extracellular glucoamylase | 3 | open frame >400 nt in −1 |
| PAG1264RP | YBL051c | | similarity to *Schizosaccharomyces pombe* protein Z66568_C | 4 1 | |
| PAG1264UP | YHR202w | | hypothetical protein | | |
| PAG1265RP | YHR143w | | similarity to a-agglutinin core protein AGA1 | 3 | open frame 450 nt in −1, same as PAG1176 |
| PAG1265UP | YNL083w | | hypothetical protein | 1 | same as PAG1176 |
| PAG1266RP | YGL163c | RAD54 | DNA-dependent ATPase of the Snf2p family | 1 | |
| PAG1266UP | YNL066w | SUN4 | homology to *Candida wickerhamii* beta-glucosidase (EC 3.2.1.21) | 3 | open frame >400 nt in +3, check Hom_Class, better 2 (25%/95 aa) |
| PAG1267RP | YLL040c | | hypothetical protein | 4 | |
| PAG1267UP | YGR054w | | hypothetical protein | 3 | open frame nearly whole length in +1 |
| PAG1268RP | YGL142c | | hypothetical protein | 1 | |
| PAG1268UP | YDL108w | KIN28 | cyclin-dependentSER/THR protein kinase component of transcription initiation factor TFIIH | 1 | Terminator + Promotor (177 nt, see 2nd Hit for Promotor), Syntenie |
| | YDL107w | MSS2 | serine/threonine protein kinase | 2 | Terminator + Promotor (177 nt, see 1st Hit for Terminator), ATG not inframe Syntenie |
| PAG1269RP | YCL057w | PRD1 | saccharolysin;proteinase yscD | 2 | Terminator |
| PAG1269UP | YPL101w | | hypothetical protein | 1 | |
| PAG1270RP | YLR106c | | putative membrane protein | 2 | longest yeast gene, only 1 gene on clone |
| PAG1270UP | YLR106c | | putative membrane protein | 1 | longest yeast gene, only 1 gene on clone |
| PAG1271RP | | | | | Mito |
| PAG1271UP | | | | | Mito |
| PAG1272RP | YDR083w | | hypothetical protein | 1 | Terminator |
| PAG1272UP | YIRO19c | STA1 | extracellular glucoamylase | 3 | open frame whole length in +3 (?) |
| PAG1273RP | YCR098c | | similarity to Pho84p, Itr1p, Itr2p (myo-inositol transporter) and to *E. coli* citrate transport protein | 1 | |
| PAG1273UP | YGR160w | | questionable ORF | 4 | |
| PAG1274RP | YOR338w | | similarity to FUN19 protein | 4 | |
| PAG1274UP | YOR347c | | similarity to pyruvate kinase Pyk1p | 1 | Terminator |
| PAG1275RP | YKL079w | SMY1 | member of the kinesin family that can interact with or substitute for Myo2p | 3 | open frame whole length in −3 |
| PAG1275UP | YKL081w | TEF4 | elongation factor eEF-1 gamma chain | 2 | Intron possible, same position like in S.c., unusual 5′-splice site |

TABLE 1-continued

| pAG name | Yeast Name | Gene Name | Brief Description | HC | Additional Comments |
|---|---|---|---|---|---|
| PAG1277RP | YKR043c | | similarity to phosphoglycerate mutase (EC 5.4.2.1) | 1 | |
| PAG1277UP | YNR044w | AGA1 | A-agglutinin anchor subunit | 3 | open frame >500 nt in −1 |
| PAG1278RP | YDL042c | SIR2 | protein involved in maintenance of silencing of HMR, HML and telomeres | 2 | Terminator |
| PAG1278UP | YOL067c | RTG1 | basic helix-loop-helix (BHLH) transcription factor see 2nd Hit (CAI S.c. 0.12) | 1 | Divergent Promotor of 215 nt, for 2nd Promotor |
| | YDL007w | YTA5 | similarity to human S4 component of 26S protease | 2 | divergent Promotor of 215 nt, for 1st Promotor see 1st Hit |
| PAG1279RP | YCR032w | | probable acetic acid export pump | 2 | only 1 gene on clone |
| PAG1279UP | YCR032w | | probabie acetic acid export pump | 2 | Terminator, only 1 gene on clone |
| PAG1280RP | YBR156c | | weak similarity to myosins | 3 | open frame whole length in −2, two separated short blocks with high homology |
| PAG1280UP | YPR026w | ATH1 | required for vacuolar acid trehalase activity | 1 | |
| PAG1281RP | YER172c | BRR2 | RNA helicase-related protein | 1 | Syntenie, see PAG1281UP |
| PAG1281UP | YER171w | RAD3 | DNA helicase/ATPase | 1 | Syntenie, see PAG1281RP |
| PAG1282RP | YBL019w | | hypothetical protein | 1 | Syntenie, see PAG1282UP |
| PAG1282UP | YBL022c | PIM1 | serine protease required for intramitochondrial proteolysis | 2 | Syntenie, see PAG1282RP |
| PAG1283RP | YPL217c | | hypothetical protein | 1 | Promotor, Syntenie, see PAG1283UP 2nd Hit |
| PAG1283UP | YPL219w | | similarity to hypothetical protein (chromosome VII) | 1 | Terminator, Syntenie, see PAG1283RP |
| PAG1284RP | YDL126c | CDC48 | microsomal protein of CDC48/PAS1/SEC18 (AAA) family of ATPases | 1 | |
| PAG1284UP | YOR348c | PUT4 | proline and gamma-aminobutyrate permease | 1 | |
| PAG1285RP | YGR068c | | with sim to ROD1(which is a protein that mediates resistance to o-dinitrobenzene) | 1 | former class III |
| PAG1285UP | YMR137c | PSO2 | DNA repair protein for interstrand crosslinks | 2 | Terminator |
| PAG1286RP | YBR204c | | similarity to peroxisomal serine-active lipase | 3 | open frame >400 nt in −3, |
| PAG1286UP | YIR019c | STA1 | extracellular glucoamylase | 3 | open frames >500 nt in +1 and −3 |
| PAG1287RP | YBL004w | | hypothetical protein | 1 | |
| PAG1287UP | YDL003w | RHC21 | similarity to S. pombe rad21 | 2 | |
| PAG1289UP | YKR072c | SIS2 | stimulates G1 cyclin expression | 1 | |
| PAG1289RP | YGR061c | ADE6 | 5′-phosphoribosylformyl glycinamidine synthetase | 4 | |
| PAG1291UP | YKL211c | TRP3 | contains anthranilate synthase (EC 4.1.3.27); glutamine amidotrans-ferase (EC 2.6.1.-); indole-3-glycerol-phosphate synthase(EC4.1.1.48) | 1 | |
| PAG1292RP | | | | | Mito |
| PAG1292UP | | | | | Mito |
| PAG1293RP | YGL062w | PYC1 | pyruvate carboxylase 1 | 1 | |
| PAG1293UP | YPL187w | | MFalpha1;mating pheromone alpha-1 precursor | 3 | open frams 300 nt in +2 and >400 nt in +1, check Hom__Class: mating pheromomone in S.c. is processed a lot |
| PAG1294RP | YLR147c | SMD3 | snRNA-associated protein of the SM class required for pre-mRNA splicing, sn RNP D3 homolog | 1 | open frame <300 nt in +3, former class III |
| PAG1294UP | YDR167w | TAF25 | similarity to human TBD-associated factor 30 | 1 | Promotor + Terminator (171 nt), for Promotor see 2nd Hit, Syntenie (CAI S.c. 0.10) |
| | YDR168w | CDC37 | cell cycle protein necessary for passage through START | 1 | Pormotor + Terminator (171 nt), for Terminator see 1st Hit, Syntenie |
| PAG1295RP | YJL172w | CPS1 | Gly-X carboxypeptidase (EC 3.4.17.4) precursor | 2 | |
| PAG1295UP | YMR298w | | hypothetical protein | 2 | |
| PAG1296RP | YGL246c | | hypothetical protein | 1 | |
| PAG1296UP | YFR050c | PRE4 | proteasome subunit | 1 | |
| PAG1297RP | YGL123w | SUP44 | ribosomal protein SUP44/RPS4 | 1 | Promotor (CAI S.c. 0.80) |
| PAG1297UP | YMR136w | | hypothetical protein | 2 | |
| PAG1299RP | YLR223c | IFH1 | controlling pre-rRNA processing machinery in conjunction with Fh11p | 3 | open frame >350 nt in −1 |
| PAG1299UP | YAL017w | FUN31 | probable serine/threonine protein kinase | 1 | |
| PAG1300RP | YOR104w | | hypothetical protein | 3 | open frames >350 nt in +1 and −2 |

TABLE 1-continued

| pAG name | Yeast Name | Gene Name | Brief Description | HC | Additional Comments |
|---|---|---|---|---|---|
| PAG1300UP | YNL097c | | similarity to YHR090p (similarity to human zinc finger/leucine zipper protein) and YM9916.14 (Chr. XV) | 1 | |
| PAG1301RP | YCL064c | CHA1 | L-serine/L-threonine deaminase | 1 | Syntenie, see PAG1301UP |
| PAG1301UP | YCL061c | | partial identity to hypothetical protein 1 (URK1 5' region) | 2 | Syntenie, see PAG1301RP |
| PAG1302RP | YGR058w | | weak similarity with calcium-binding protein (clone pMP41) - mouse | 1 | |
| PAG1302UP | YOR291w | | weak similarity to cation translocating ATPases | 1 | |
| PAG1303RP | YLR106c | | putative membrane protein | 3 | open frame >350 nt in +2 or ending frams >250 nt in −1 |
| PAG1303UP | YGR023w | | similarity with Mid2p and Kai1p | 3 | open frame whole length in −2 |
| PAG1304RP | YNL221c | POP1 | component of ribonuclease P and ribonuclease MRP | 1 | for continuation of Syntenie (also match to YNL221c) |
| PAG1305RP | YDR192c | NUP42 | nucleoporin | 3 | open frame whole length in −2 |
| PAG1305UP | YNL246w | | similarity to D. melangonaster SET protein | 2 | cannot be checked for Intron, not on sequence of PAG1305UP |
| PAG1306RP | YDL240w | LRG1 | GTPase-activating protein of the rho/rac family | 1 | |
| PAG1306UP | YGL133w | | similarity with hypothetical protein (chromosome XVI) P1770 | 3 | open frame whole length in +2 |
| PAG1307RP | YKL142w | MRP8 | ribosomal protein MRP8, mitochondrial | 1 | Syntenie, see PAG1307UP |
| PAG1307UP | YKL145w | CIM5 | tat-binding protein homolog; probable 26S protease subunit | 1 | Syntenie, see PAG1307RP |
| PAG1308RP | YLL034c | | similarity to mammalian valosin | 1 | divergent Terminator (100 nt), for 2nd Terminator see 2nd Hit, Syntenie, see PAG1308RP 2nd Hit |
| | YLL035w | | hypothetical protein | 2 | divergent Terminator (100 nt), for 1st Terminator see 1st Hit, Syntenie, see PAG1308RP 1st Hit |
| PAG1308UP | YHL027w | | single-stranded zinc-finger DNA binding protein required for replication in mitochondria | 2 | Homology due to zinc-finger? |
| PAG1309RP | YDR270w | CCC2 | copper-transporting P-type ATPase of the cation transport (E1–E2) ATPase family | 1 | Syntenie, see PAG1309UP, see PAG1165UP for additional Hit to YDR270w |
| PAG1309UP | YDR268w | MSW1 | mitochondrial tryptophanyl-tRNA synthetase | 1 | divergent Terminator (40 nt) -> see PAG1309UP 3rd Hit, Syntenie -> see PAG1309RP |
| | YOR038c | HIR2 | histone transcription regulator | 1 | divergent Terminator (40 nt) -> see PAG1309UP 1st Hit |
| PAG1310UP | YLR245c | | homology to cytidine deaminases (EC 3.5.4.5) | 1 | |
| PAG1311RP | YDR060w | | unknown function | 1 | former class III |
| PAG1311UP | YBR081c | SPT7 | probable transcription factor; suppressor of Ty transcription | 1 | open frame 500 nt in −2, former class III |
| PAG1312RP | YDRS23c | | Ser/Thr protein kinase; limited homology only | 2 | |
| PAG1312UP | YKL203c | TOR2 | phosphatidylinositol 3-kinase required for G1 progression | 3 | open frame whole length in +1 |
| PAG1313RP | YGL211w | | hypothetical protein | 1 | |
| PAG1313UP | YER033c | | weak similarity to human BRCA2 early onset breast cancer gene | 1 | former class III |
| PAG1314RP | YGR023w | | similarity with Mid2p and Kai1p | 3 | open frame >350 nt in −3 |
| PAG1314UP | YJR151c | | similar to proteins of the Srp1p/Tip1p family | 4 | |
| PAG1315RP | YPR181c | SEC23 | component of COPII coat of ER-golgi vesicles | 1 | Syntenie, see PAG1315UP |
| PAG1315UP | YPR184w | | protein with strong similarity to glycogen debranching enzyme (4-alpha-glucanotransferase) | 1 | Promotor, Syntenie, see PAG1315RP |
| PAG1316RP | YLR440c | | hypothetical protein | 2 | |
| PAG1316UP | YLR441c | RP10A | ribosomal protein S3a.e | 1 | Promotor |
| PAG1317RP | YJL085w | | hypothetical protein | 1 | Syntenie, see PAG1317up |
| PAG1317UP | YJL087c | TRL1 | tRNA ligase (EC 6.1.1.-) | 1 | Syntenie, see PAG1317RP |
| PAG1318RP | YIL159w | | similarity to BNI1 protein | 3 | open frames >300 nt in −2 |
| PAG1318UP | YER073w | | probable aldehyde dehydrogenase (NAD+) | 3 | open frames >450 nt in −3 and >600 nt in +2 |
| PAG1319RP | YMR277w | | hypothetical protein | 1 | Syntenie, see PAG1319UP |
| PAG1319UP | YMR276w | DSK2 | ubiquitin-like protein | 1 | Syntenie, see PAG1319RP |
| PAG1320RP | YOR207c | RPC128 | DNA-directed RNA polymerase (EC 2.7.7.6) III second-largest chain | 1 | |
| PAG1320UP | YMR147w | | hypothetical protein | 4 | |

TABLE 1-continued

| pAG name | Yeast Name | Gene Name | Brief Description | HC | Additional Comments |
|---|---|---|---|---|---|
| PAG1321RP | YBL020w | RFT1 | involved in nuclear division | 1 | Syntenie, see PAG1321UP 1st and 2nd Hit |
| PAG1321UP | YBL018c | | hypothetical protein | 1 | divergent Terminator (38 nt), Syntenie, see PAG1321RP and PAG1321UP 2nd Hit, cannot be checked for Intron, not on seq. of PAG1321UP |
| | YBL019w | | hypothetical protein | 1 | divergent Terminator (38 nt), Syntenie, see PAG1321UP 1st Hit and PAG1321RP |
| PAG1322RP | YIL033c | BCY1 | cAMP dependent protein kinase, regulatory subunit | 2 | Promotor(CAI S.c. 0.18) |
| PAG1322UP | YFR037c | | similarity to transcription factor SWI3 | 1 | |
| PAG1323RP | YNL011c | | probably membrane protein | 1 | |
| PAG1323UP | YHR165c | PRP8 | U5 snRNP protein, pre-mRNA splicing factor | 4 | |
| PAG1324RP | YDR129c | SAC6 | actin filament bundling protein | 1 | Terminator, cannot be checked for Intron, not on sequence of PAG1324RP |
| PAG1324UP | YLR102c | | hypothetical protein | 2 | |
| PAG1325RP | YDR049w | | putative DNA-binding protein | 1 | |
| PAG1325UP | YBR073w | | probable DNA repair protein | 1 | |
| PAG1326RP | YDR217c | RAD9 | DNA repair checkpoint protein | 2 | Terminator, Syntenie, see PAG1326UP |
| PAG1326UP | YDR216w | ADR1 | zinc-finger transcription factor | 2 | Syntenie, see PAG1326UP |
| PAG1327RP | YER011w | TIR1 | cold-shock induced protein of the Tir1p,Tip1p family | 4 | |
| PAG1327UP | YLR337w | VRP1 | proline-rich protein verprolin | 4 | |
| PAG1328RP | YNL201c | | involved in regulation of carbon metabolism | 2 | Syntenie, see PAG1328UP, Classification in Hom_Class 2 according to Syntenie |
| PAG1328UP | YNL200c | | hypothetical protein | 1 | Syntenie, see PAG1328RP |
| PAG1330RP | YLL039c | UBI4 | ubiquitin precursor | 1 | 100% identity on AA-level, 78.3% on DNA, Syntenie, see PAG1330UP |
| PAG1330UP | YLL036c | PRP19 | non-snRNP spliceosome component | 1 | Most probable Intron in A.g. but NOT in S.c. Syntenie, see PAG1330RP |
| PAG1331RP | YDR150w | NUM1 | nuclear migration protein | 2 | open frame >450 nt in −2, 30% ident./140 aa, check Hom_Class: better 3? |
| PAG1331UP | YNR044w | AGA1 | A-agglutrnin anchor subunit | 3 | open frames >400 nt in +2>350 nt in +3 and >350 nt in +3 |
| PAG1332RP | YKL014c | | hypothetical protein | 3 | open frame nearly whole length in +1 |
| PAG1332UP | YJL194w | CDC6 | involved in initiation of DNA replication and spindle function | 2 | Terminator |
| PAG1334RP | YHR217c | | similarity to hypothetical protein (chromosome IV) | 3 | open frame whole length in −2 and +2 |
| PAG1334UP | YMR038c | LYS7 | homocitrate dehydrogenase | 1 | |
| PAG1335RP | YKL129c | MYO3 | myosin type I | 3 | open frames whole length in −2 and 300 nt in +3 |
| PAG1335UP | YOR008c | SLG1 | similarity to N0583 | 4 | |
| PAG1336RP | YJR092w | BUD4 | required for formation of axial but not bipolar budding pattern | 1 | Terminator, Syntenie, see PAG1336UP |
| PAG1336UP | YJR095w | ACR1 | protein of the mitochondrial carrier (MCF) family | 1 | Promotor, Syntenie, see PAG1336RP |
| PAG1337RP | | | | | Mito |
| PAG1337UP | | | | | Mito |
| PAG1338RP | M_A394 | | hypothetical transmembrane protein | 4 | |
| PAG1338UP | YCR065w | HCM1 | transcription factor | 2 | |
| PAG1339RP | YDL244w | | nearly identical to Thi5p (involved in pyrimidine biosynthesis pathway),YJR156p,and YNL332w (nmt1 homolog to fission yeast and *Aspergillus parasiticus*) | 1 | Promotor, YNL332w near telomere |
| PAG1339UP | YKL213c | DOA1 | protein involved in ubiquitin proteolysis | 1 | Terminator |
| PAG1340RP | YMR004w | MVP1 | required for sorting proteins to the vacuole | 1 | Terminator, Syntenie (?), see PAG1340UP |
| PAG1340UP | YMR003w | | hypothetical protein | 2 | Terminator, Syntenie (?), see PAG1340RP |
| PAG1341RP | YPL242c | | hypothetical protein | 4 | |
| PAG1341UP | YFL036w | RP041 | mitochondrial DNA-directed RNA polymerase | 1 | |
| PAG1342RP | YNR030w | | weak similarity to SMP3 protein (functions in the protein kinase C pathway) | 2 | |

TABLE 1-continued

| pAG name | Yeast Name | Gene Name | Brief Description | HC | Additional Comments |
|---|---|---|---|---|---|
| PAG1342UP | YPR088c | SRP54 | signal recognition particle 54K protein homolog | 1 | |
| PAG1343RP | YKL134c | (MIP1) | mitochondrial intermediate peptidase (EC 3.4.24.-) precursor | 1 | |
| PAG1343UP | YLR109w | | similarity to *Candida boidinii* peroxisomal membrane protein 20K A | 4 | UGG tRNA (Pro), pos. 434–545, intron pos.470–509 (40 nt), intron in S.c. 32nt, w/o intron only 1 difference |
| PAG1344RP | | | | | Mito |
| PAG1344UP | | | | | Mito |
| PAG1345RP | YPL042c | SSN3 | cyclin-dependent serine/threonine protein kinase of the RNA polymerase II holoenzyme complex and kornberg's mediator (SRB) subcomplex | 1 | Syntenie, see PAG1345UP |
| PAG1345UP | YPL040c | ISM1 | mitochondrial isoleucine--tRNA ligase (EC 6.1.1.5) | 1 | Syntenie, see PAG1345RP |
| PAG1347RP | YBR221c | PDB1 | pyruvate dehydrogenase (lipoamide) beta chain precursor | 1 | Promotor (CAI S.c. 0.34) |
| PAG1347UP | YGL126w | SCS3 | probably involved in the synthesis of inositol phospholipids | 2 | |
| PAG1349RP | YEL011w | GLC3 | 1,4-glucan branching enzyme (glycogen branching enzyme) | 1 | Promotor (CAI S.c. 0.13) |
| PAG1349UP | YCR017c | | putative membrane protein | 1 | |
| PAG1350RP | YPR105c | | hypothetical protein | 2 | Promotor, Syntenie, see PAG1350UP |
| PAG1350UP | YPR106w | | similarity to protein kinases Gcn2p, galactosyltransferase-associated protein kinase P58/GTAP, and the raf proto-oncogene | 2 | Syntenie, see PAG1350RP |
| PAG1351RP | | | | | Mito |
| PAG1351UP | | | | | Mito |
| PAG1352RP | YPL033c | | similarity with to *S. pombe* CEK1 serine/threonine protein kinase | 2 | |
| PAG1353RP | YDR456w | | similarity to NA+-H+ antiporters | 2 | Terminator |
| | YML031w | NDC1 | component of the nuclear envelope | 2 | Terminator, Syntenie, see PAG1335UP 1st Hit |
| PAG1353UP | YML029w | | putative membrane protein | 2 | Terminator, Syntenie, see PAG1353RP 2nd Hit |
| PAG1354UP | YOR017w | PET127 | probable mitochondrial translation factor | 2 | |
| PAG1355RP | YCR092c | MSH3 | DNA-repair protein | 2 | Syntenie, see PAG1355UP, order wrong |
| PAG1355UP | YCR094w | | homology to hypothetical protein YNL323w and EST from rice | 2 | Syntenie, see PAG1355RP, order wrong |
| PAG1356RP | YKR092c | SRP40 | weak suppressor of a mutant of the subunit AC40 of DNA dependent RNA polymerase I and III | 3 | open frame whole length in −3 |
| PAG1356UP | | | SP entry: UAPC_EMENI purine permease | 2 | |
| PAG1357RP | YPL158c | | hypothetical protein | 3 | open frame whole length in −2 |
| PAG1357UP | YPL155c | KIP2 | kinesin-related protein | 1 | |
| PAG1359RP | YIL130w | | similarity to probable membrane protein YJL206c (probable regulatory zinc-finger protein) and Put3p (positive activator of the proline utilization pathway) | 4 | |
| PAG1359UP | YER163c | | hypothetical protein | 1 | |
| PAG1360RP | YCR0S7c | PWP2 | periodic tryptophan protein | 1 | |
| PAG1360UP | YLR342w | GLS1 | component of beta-1,3-glucan synthase | 1 | |
| PAG1362RP | YOR340c | RPA43 | essential subunit of RNA polymerase I | 1 | Terminator |
| PAG1362UP | YCR065w | HCM1 | transcription factor | 3 | Open frames >350 nt in +3 and >300 nt in −3 |
| PAG1363RP | YLR454w | | similarity to hypothetical protein YPR117w | 1 | |
| PAG1363UP | YDL037c | | putative glucan 1,4-alpha-glucosidase (EC 3.2.1.3) | 3 | open frame whole length in +2 |
| PAG1364RP | YDL108w | KIN28 | cyclin-dependent serine/threonine protein kinase component of transcription initiation factor TFIIH | 1 | Terminator, cannot be checked for Intron, not on sequence of PAG1363RP |
| PAG1364UP | YGL142c | | hypothetical protein | 1 | |
| PAG1365RP | YJL011w | | similarity to YIL176p,YIR041p and other members of the Srp1p/Tip1p family | 3 | open frame whole length in +3 (?) |
| PAG1365UP | YHR144c | DCD1 | deoxycytidylate deaminase (EC 3.5.4.12) | 1 | |
| PAG1366RP | YLR413w | | homology to hypothetical protein YKL187c | 3 | open frame whole length in +2 |
| PAG1366UP | YKL188c | | similarity to human adrenoleukodystrophy (ALD) protein and yeast peroxisomal protein Pa11p | 1 | |
| PAG1367RP | YHR089c | GAR1 | asscciated with snoRNA and involved in 35S rRNA processing | 1 | |
| PAG1367UP | YBR115c | LYS2 | L-aminoadipate-semialdehyde | 1 | |

TABLE 1-continued

| pAG name | Yeast Name | Gene Name | Brief Description | HC | Additional Comments |
|---|---|---|---|---|---|
| | | | dehydrogenase | | |
| PAG1368RP | YDL171c | | putative glutamate synthase | 1 | |
| PAG1368UP | YNR012w | URK1 | uridine kinase | 1 | |
| PAG1369RP | YPR175w | DPB2 | DNA-directed DNA polymerase II chain B | 1 | Terminator, Syntenie, see PAG1369UP, same as PAG1144 |
| PAG1369UP | YPR179c | | hypothetical protein | 1 | Syntenie, see PAG1369RP, same as PAG1144 |
| PAG1370RP | YJL102w | MEF2 | translation elongation factor | 2 | |
| PAG1370UP | YKR026c | GCN3 | translation initiation factor eIF2B (guanine nucleotide exchange factor), 34 KD, alpha subunit | 1 | Terminator |
| PAG1371RP | YFR050c | PRE4 | proteasome subunit | 1 | |
| PAG1371UP | YGL246c | | hypothetical protein | 1 | |
| PAG1372RP | | | | | Mito |
| PAG1372UP | | | | | Mito |
| PAG1373RP | | | | 4 | seems to be Mito but PAG1373UP is not, Chimera? strong homology to S.c. mitochondrial ATPase (72%/48aa) |
| PAG1374RP | YDL105w | QRI2 | function unknown | 2 | |
| PAG1374UP | YMR167w | MLH1 | mismatch repair protein | 1 | Terminator |
| PAG1375RP | | | | | Mito |
| PAG1378RP | | | | | Mito |
| PAG1378UP | | | | | Mito |
| PAG1379RP | YJL083w | | homology to hypothetical protein YKR019c | 1 | Syntenie, see PAG1379UP |
| PAG1379UP | YJL084c | | homology to hypothetical protein YKR021w | 1 | Syntenie, see PAG1379RP |
| PAG1380RP | YCL043c | PDI1 | protein disulfide-isomerase precursor | 1 | Syntenie, see PAG1380UP |
| PAG1380UP | YCL040w | GLK1 | aldohexose specific glucokinase | 1 | Syntenie, seePAG1380RP |
| PAG1381RP | | | | | Mito |
| PAG1381UP | | | | | Mito |
| PAG1382RP | YAL038w | PYK1 | pyruvate kinase, activity is regulated by glucose levels, inducer:glucose | 1 | CDC19 |
| PAG1382UP | YOR346w | REV1 | similarity with *E. coli* mutagenic repair protein umuC | 1 | |
| PAG1384RP | YAL042w | FUN9 | similarity to hypothetical *S. pombe* protein | 1 | Syntenie, see PAG1384UP |
| PAG1384UP | YAL043c | PTA1 | pre-tRNA processing protein | 1 | Syntenie, see PAG1384RP |
| PAG1385RP | YGR207c | ETF-b | electron-transferring flavoprotein, beta chain | 2 | Terminator, Syntenie, see PAG1385UP |
| PAG1385UP | YGR205w | | hypothetical protein | 1 | Terminator, Syntenie, see PAG1385RP |
| PAG1386RP | YIL093c | | hypothetical protein | 1 | |
| PAG1386UP | YNL023c | | similarity to *Drosophila melanogaster* shuttle craft protein probable transcription factor, has something to do with prolyl-isomerase? | 1 | |
| PAG1387RP | YDR371w | | similarity to chitinases | 2 | |
| PAG1387UP | YPL150w | | probable serine/threonine kinase | 3 | open frames >450 nt int −3, >350 nt in +1 and +2 |
| PAG1388RP | YFL013c | | hypothetical protein | 4 | |
| PAG1388UP | YPR160w | GPH1 | glycogen phosphorylase (EC 2.4.1.1) | 1 | Terminator |
| PAG1389RP | YDR327w | | homology to hypothetical protein YHR080c | 1 | Syntenie, see PAG1389UP |
| PAG1389UP | YDR328c | SKP1 | kinetochore protein complex CBF3, subunit D | 1 | Terminator, Syntenie, see PAG1389RP |
| PAG1390RP | | | | | Mito |
| PAG1390UP | | | | | Mito |
| PAG1391RP | YPR189w | SKI3 | antiviral protein | 1 | Syntenie, see PAG1391UP |
| PAG1391UP | YPR190c | RPC82 | DNA-directed RNA polymerase III chain | 1 | Syntenie, see PAG1391RP |
| PAG1392RP | YLR274w | CDC46 | acts in a complex at ARS's to initiate dna replication | 1 | |
| PAG1393RP | YGL240w | | hypothetical protein | 1 | Syntenie, see PAG1393UP |
| PAG1393UP | YGL241w | | similarity to Cse1p (probable kinetochore protein,17% identity over 1053 amino acids) | 1 | Syntenie, see PAG1393RP |
| PAG1394RP | YBR176w | | homology to *E. coli* 3-methyl-2-oxobutanoate hydroxymethyltransferase | 1 | |
| PAG1394UP | YPL101w | | hypothetical protein | 1 | |
| PAG1396RP | YNR023w | | similarity to YCR052p | 1 | Terminator, Syntenie, see PAG1396UP |
| PAG1396UP | YNR021w | | probable membrane protein | 2 | Syntenie, see PAG1396RP |
| PAG1397RP | YGR098c | ESP1 | required for normal spindle structure | 2 | only 1 gene on clone |
| PAG1397UP | YGR098c | ESP1 | required for normal spindle structure | 1 | only 1 gene on clone |
| PAG1398UP | YMR291w | | putative protein kinase | 2 | |
| PAG1399RP | YDR338c | | similarity to hypothetical protein YHR032w | 1 | |
| PAG1399UP | YJL158c | | member of the Pir1p/Hsp150p/Pir3p family | 1 | Terminator |

TABLE 1-continued

| pAG name | Yeast Name | Gene Name | Brief Description | HC | Additional Comments |
|---|---|---|---|---|---|
| | YKL163w | PIR3 | member of the Pir1p/Pir2p/Pir3p family | 1 | Terminator |
| PAG1399UP | YKL164c | PIR1 | required for tolerance to heat shock | 1 | Terminator |
| PAG1400RP | YDL167c | ARP1 | unknown function | 1 | |
| PAG1400UP | YLR200w | | similar to KE2 protein (Mus musculus), encoded in MHC region and expressed in embryo | 1 | |
| PAG1401RP | YDR406w | PDR15 | Member of ATP-binding cassette (ABC) protein family | 1 | very good homology to YOR153W |
| PAG1401UP | | | has 43/45bases identity to rDNA transcription end. the rest might be the promoter region of YDR406w which was hit with the RP-SRS | 2 | Chimeric plasmid? |
| PAG1402RP | YOR023c | | unknown function | 1 | |
| PAG1402UP | YOR161c | | unknown function | 1 | |
| PAG1403RP | YBR280c | | YBR280c:sim to SRM1p/PRP20p YJL068c:sim to human esterase D | 1 | Syntenie two genes covered by RP SRS;end of syntenie |
| PAG1403UP | YBR281c | | has beta-transducin (WD40) repeats | 1 | |
| PAG1404RP | YPL012w | Lpa5p | unknown function | 1 | syntenie |
| 1 | YPL014w | LPA3 | unknown function | | mito ribosomal S24 protein |
| PAG1405RP | | | | 4 | |
| PAG1405UP | YHR086W | NAM8 | protein essential for meiotic recombination and suppressor of MT- splicing defects, has 3 RNA recognition domains | 1 | |
| PAG1406RP | YHR007C | ERG11 | Cytochrome P450 L1 (14DM) (Lanosterol 14-alpha-demethylase) | 1 | |
| PAG1406UP | YPL026c | SHA3 | Ser/Thr-protein kinase, suppressor of Hta1p mutations that cause aberrant transcription | 1 | |
| PAG1408RP | MITO-DNA | | | | Chimeric Plasmid |
| PAG1408UP | YBR072w | HSP26 | YEAST HEAT SHOCK PROTEIN 26 expressed during entry to stationary phase and induced by osmostress | 1 | |
| PAG1409RP | YPR154W | | YPR153W:unknown fubtion, gene may be spliced;YPR154w:protein with sim to several SH3 domain-containing proteins includung myosin ID and IC heavy chains, human growth factor receptor-bound grb2 protein, C. elegans sex muscle abnormal protein 5 | 1 | syntenie, two genes covered by RP-SRS; YPR153W |
| PAG1409UP | YPR156c | | member of the major facilitator superfamily (MFS) mulitdrug resistance proteins family 1 | 1 | YPR155c:NCA2:protein required for CTRL of MT synthesis of ATP6 and ATP8;Hit no 1:YGR138C (putative drug transporter) neglegcted due to syntenie |
| PAG1410RP | YOR116c | | YOR116c: RPO31: RNA-POLIII largest subunit | 1 | syntenie |
| PAG1410UP | YOR117w: | | YOR117w: YTA1: Syntenie: subunit of 26S proteasome complex and member of the ATPase family | 1 | syntenie |
| PAG1412RP | YJR153w | | sim to polygalacturonases | 1 | |
| PAG1412UP | | | | 4 | |
| PAG1413RP | YDR150w | NUM1 | nuclear migration | 1 | syntenie ;should contain the N-term of NUM 1 |
| PAG1413UP | YDR152w | | unknown function | 1 | Syntenie YDR151c:CTH1:protein of the mammalian growth factor induced proteins, len 325 aa |
| PAG1414RP | YLR272c | | unknown function | 1 | |
| PAG1414UP | | | | 4 | |
| PAG1415RP | YGR271w | | seems to be an RNA-helicase related protein; | 1 | just one gene on this plasmid |
| PAG1415UP | YGR271w | | has sim to Yer172p; has A(P-loop) | 1 | UP-SRS covers 1917aa to 1676aa |
| PAG1416RP | YLR430w | SEN1 | positive effector of tRNA-splicing endonuclease, required for intron cleavage for all ten precursor tRNA families | 1 | codons 1790 up to 1971;C-term including terminator should be on this plasmid;syntenie |
| PAG1416UP | YLR432w | | protein highly similar to to PUR5p and inosine-5'-monophosphate of human and E. coli, has sim to YML056c (which was actually hit no 1) | 1 | syntenie |
| PAG1417RP | YPR183w | | Dolichol-phosphate mannosyltransferase | 1 | syntenie.SMX3:YPR182w: SnRNA associated protein |
| PAG1417UP | YPR181c | SEC23 | Protein transport protein | 1 | syntenie |
| PAG1418RP | YCL060c | | protein with sim to SDL1 L-serine dehydratase | 1 | syntenie |

TABLE 1-continued

| pAG name | Yeast Name | Gene Name | Brief Description | HC | Additional Comments |
|---|---|---|---|---|---|
| PAG1418UP | YCL061c | | unknown function | 1 | syntenie |
| PAG1419RP | YLR219w | | | 2 | |
| PAG1419UP | | | | 4 | |
| PAG1420RP | YJR107w | | sim to acylglycerol lipase | 1 | |
| PAG1420UP | YJR014w | | YJR014w: unknown functionYGR198w:unknown function | 1 | two genes covered by UP-SRS |
| PAG1421RP | YNL075w | | unknown function | 1 | |
| PAG1421UP | | | only sim with Ser/Thr rich sequences | 4 | |
| PAG1422RP | YGL091c | NBP35 | NBP35: nucleotide binding protein (ATP/GTP) | 1 | syntenie |
| | YGL092w | NUP145 | nuclear pore protein (nucleoporin) | 1 | |
| PAG1422UP | YGL092w | NUP145 | | 1 | Hit no 1 to YGL172w corresponds to NUP49 and was disregarded due to syntenie |
| PAG1423RP | YDR189w: | SLY1 | SLY1: YDR189w: member of the SEC1-family, involved in vesicle trafficking between the ER and Golgi | 1 | syntenie |
| PAG1423UP | YDR191W | HST4 | sim to SIR2 | 1 | has A(P-loop) |
| PAG1424RP | | | | 4 | |
| PAG1424UP | | | | 4 | |
| PAG1425RP | YLR187W | | YLR187W unknown function, sim to YNL278W | 1 | YNL278w was hit no 5;gives weak indication of syntenie or a probable homology region for chromosomal rearrangements |
| PAG1425UP | YNL279w | | probable membrane protein | 1 | weak syntenie |
| PAG1426RP | YDR196c | | unknown function, has A(P-loop) | 1 | two genes covered with RP-SRS |
| | YDR197c | CBS2 | CBS2:translational activator of COB mRNA, non-essential | | |
| PAG1426UP | YDR194c | MSS16 | MSS16:MT RNA helicase of the DEAD box family required for splicing of group II introns of COX1 and COB | 1 | syntenie; neighboring-clone to SLY1 |
| PAG1427RP | YLR214W | FRE1 | ferric (and cupric) reductase, acts on ferric iron chelates external to the cell | 1 | syntenie; two genes with RP-SRS |
| | YLR215c | | unknown function | 1 | syntenie |
| PAG1427UP | YDL143w | CCT4 | Component of chaperonin containing T-complex | 1 | end of syntenie |
| | YLR215C | | | 1 | same gene sequenced witb RP-SRS |
| PAG1428RP | YDL060w | | unknown function | 1 | syntenie,whole gene on plasmid |
| PAG1428UP | YDL060w | | unknown function | 1 | start of gene,syntenie. Two genes covered by UP-SRS |
| | YDL061c | YS29B | ribosomal protein | 1 | syntenie.Two genes covered by UP-SRS;identical to YLR388w |
| PAG1429RP | | | | 4 | |
| PAG1429UP | YBR260c | | protein with weak sim to human bcr (break point cluster) protein | 1 | |
| PAG1430RP | YLR213C | | YLR213C :unknown fnction, has WAP-type 'four disulfide core' domain signature | 1 | syntenie. End of syntenie |
| | YDL144C | | unknown function | 1 | syntenie |
| PAG1430UP | YDL145c | | YDL145c: RET1: N-Term has 4 WD-beta transducin repeats. Coatomer complex alpha chain | 1 | syntenie |
| PAG1431RP | YHR178W | | protein with sim to transcription factors, has Zn(2)-Cys(6) fungal-type binuclear cluster domain in the N-terminal region | 1 | |
| PAG1431UP | YMR270C | RRN9 | component of the upstream activaton factor (UAF)-complex, involved in activation of RNA polymerase I promoter; non-essential | 1 | |
| PAG1432RP | | | sim to proline rich sequences | 4 | |
| PAG1432UP | YDR330W | | Small region of similarity near C-terminus to Undulin extracellular matrix glycoprotein | 1 | |
| PAG1433RP | YBR141c | | unknown function | 1 | involved in maintenance of M dsRNA killer plasmid |
| PAG1433UP | YBR143c | SUP45 | SUP45:recessive omnipotent suppressor, translational release factor eRF1 | 1 | syntenie |
| PAG1434RP | | | | 4 | |
| PAG1434UP | YCR065w | HCM1 | HCM1 hom to forkhead. Has a transcriptional activation domain of Drosophila fkh homeotic gene | 1 | |
| PAG1435UP | | | | 4 | |
| PAG1436RP | YCR093w | CDC39 | nuclear protein that negatively affects basal transcription from many promoters, mutants activate the pheromone response pathway at the level of the G-proteins | 1 | N-term up to aa570 on plasmid |
| PAG1436UP | YKL215c | | protein with sim to Pseudomonas | 1 | |

TABLE 1-continued

| pAG name | Yeast Name | Gene Name | Brief Description | HC | Additional Comments |
|---|---|---|---|---|---|
| PAG1437RP | YOR224C | RPB8 | hydantoinases hyuA-hyuB RPB8:Shared subunit of RNA-POL I,II,III, essential | 1 | syntenie. Two genes with RP-SRS |
| | YOR226C | | protein with sim to nitrogen fixation proteins | 1 | Hit no3 was YPL135w:LPI10:protein with sim to *H. influenza* nitrogen fixation protein HIU32721-12 which was equally good as hit no 2. Taken this we reach syntenie to PAG1437UP |
| PAG1437UP | YPL133c | LPI12 | protein with sim to transcription factors, has Zn(2)-Cys(6) fungal type binuclear cluster domain in the N-terminal region | 1 | syntenie |
| PAG1438RP | YJR132w | NMD5 | Nam7p/Upf1p interacting protein. Nam7p: protein involved in decay of mRNA containing nonsense codons | 1 | |
| PAG1438UP | YBR079c | | protein homologous to surface antigens from trophoblast endothelial activated lymphocytes and *P. falciparum* | 1 | |
| PAG1439RP | YGR276c | | unknown function | 1 | |
| PAG1440RP | YGL137w | SEC27 | Coatomer complex beta chain of secretory pathway vesicles required for transport from ER to Golgi, member of beta-transducin WD40 repeat familiy | 1 | syntenie. Two genes with RP-SRS. C-term must be shorter in the AG-gene |
| | YGL136c | | protein with sim to *E. coli* ftsJ protein | 1 | syntenie. Dual terrninator |
| PAG1440UP | YGL134w | | unknown function | 1 | YGL134w-YGL137w Syntenie. YGL134w: unknown; 135w: SSM1B: ribosomal protein homologous to L1; 136c: protein with sim to *E. coli* ftsJ protein; 137w: SEC27 |
| PAG1442RP | YLR149c | | unknown function | 1 | syntenie |
| PAG1442UP | YLR150w | MPT4: | protein with specific affinity for guanine rich quadruplex nucleic acids and multicopy suppressor of pop2;G4 quadruplex nucleic acid binding protein; multicopy suppressor of tom1 and pop2 mutations | 1 | syntenie |
| PAG1443RP | YGL141w | | unknown function | 2 | |
| PAG1443UP | YMR171c | ALD2 | Aldehyde dehydrogenase2 | 1 | or rather YMR170c |
| PAG1444RP | YFR042W | | unknown function | 1 | |
| PAG1444UP | YGL232w | | protein with sim to dihydropteroate synthase | 1 | |
| PAG1445RP | | | | 4 | |
| PAG1445UP | YOR281c | | protein with weak sim to phosducins | 1 | |
| PAG1446RP | YHR077C | NMD2 | protein involved in decay of mRNA containing nonsense codons | 1 | syntenie. Two genes with RP-SRS |
| | YHR076w | | unknown | 1 | syntenie. Two genes with RP-SRS |
| PAG1446UP | YHR077c | NMD2 | | 1 | N-TERM OF GENE |
| | YDR323C | VAC1 | Required for vacuole segregation and vacuolar protein sorting | 1 | syntenie End of syntenie |
| PAG1447RP | YPR061c | | sim to *E. coli* DnaJ and other DnaJ-like proteins | 1 | YPR062w:len 158aa; protein with sim to members of the cytidine and deoxycytidylate deaminase family. YPR063c: len 140aa, unknown. YPR064w: unknown, len 139aa questionable ORF; SYNTENIE |
| PAG1447UP | YPR065w | ROX1 | Heme dependent transcriptional repressor of hypoxic genes including CYC7; N-terminal domain with sim to HMG-box proteins | 1 | syntenie |
| PAG1448RP | YKL025c | | unknown function | 1 | |
| PAG1448UP | YIR036C | | CHR IX: Short-chain alcohol dehydrogenase family signature;YIR036C and YIR035c: sim to human corticosteroid 11-beta-dehydrogenase and short-chain alcohol dehydrogenase family | 1 | |
| PAG1449RP | YPL041c | | unknown function | 1 | syntenie; YPL040c:ISM1:Isoleucyl-tRNA synthetase of mitochondria; YPL042c: SSN3: cyclin dependent Ser/Thr protein kinase of the RNA Pol II holoenzyme |
| PAG1449UP | YPL043w | NOP4 | nucleolar protein required for ribosome biogenesis | 1 | syntenie |

TABLE 1-continued

| pAG name | Yeast Name | Gene Name | Brief Description | HC | Additional Comments |
|---|---|---|---|---|---|
| PAG1450RP | YMR109w | | protein with sim to myosin heavy chain homolog YKL129 (76% id over 1090 AA) | 1 | syntenie |
| PAG1450UP | YMR108w | ILV2 | Acetolactate synthase, first step in the valine and isoleucine biosynthesis pathway | 1 | |
| PAG1452RP | YBR269c | | unknown function | 1 | syntenie |
| PAG1452UP | YBR268w | MRPL37 | Mito protein of the large ribosomal subunit | 1 | syntenie |
| | YJL062w | | unknown function | 1 | end of syntenie. Two genes with UP-SRS |
| PAG1453RP | MITO-DNA | | | 1 | |
| PAG1453UP | MITO-DNA | | | 1 | |
| PAG1454RP | YBR229c | | protein with sim to alpha 1,4 glucosidase. YBR225w-Ybr229c | 1 | syntenie |
| PAG1454UP | YBR225w | | Syntenie.YBR225w,YBR226c both of unknown function.227c: protein with sim to *E. coli* ATP-binding protein clpx | 1 | syntenie. Two genes with UP-SRS |
| | YBR226c | | | 1 | overlapping ORF to YBR225w. Syntenie |
| PAG1455RP | YMR131c | | unknown, member of the WD-40 family(?) | 1 | |
| PAG1455UP | YOL155c | | protein with hom to *S. cerevisiae* 1,4 alpha glucosidase | 2 | |
| PAG1456RP | YPR034w | | has 28% id to ACT1p over 66 aa | 1 | syntenie; YPR035w: GLN1: Glutamine synthetase, combines ammonia to glutamate in ATP-driven reaction |
| PAG1456UP | YPR036c | VMA13 | protein involved in Vacuolar H(+)-ATPase assembly or function | 1 | syntenie |
| PAG1457RP | YPR072w | | protein with sim to Not3p. has 44% id over 148 aa with Not3p, has sim to N-term of CDC36p, has potential coiled-coil domain at the N-term. | 1 | syntenie YPR073c: LTP1: protein tyrosine phosphatase with sim to a phospha- tase from bovine heart and human placenta homologous to *S. pombe* stpl+ which is a multicopy-suppressor of cdc25 |
| PAG1457UP | YPR074c | TKL1 | Transketolase1 | 1 | syntenie |
| PAG1458RP | | | | 4 | |
| PAG1458UP | YGR099w | | protein with sim to mannosyltransferase, has strong sim to Pmt3p; has 6 predicted transmembrane domain | 1 | |
| PAG1459RP | YJR088c | | unknown function | 1 | SYNTENIE YJR087w:len 116: unknown; YJR086W:len 107:STE18: Guanine nucleotide binding protein gamma subunit of the pheromone - pathway |
| PAG1459UP | YJR085c | | unknown function | 1 | syntenie |
| PAG1460RP | YFL049W | | sim to NPL6:Nuclear protein localization factor | 1 | syntenie |
| PAG1460UP | YFL047w | | unknown function | 1 | syntenie; YFL048c: EMP47: Golgi membrane protein with C-terminal KXKXX ER-retrieval motif, len 445aa |
| PAG1461RP | YIL017c | | with sim to adenylate cyclase | 1 | |
| PAG1461UP | YBR256c | RIB5 | Riboflavin Synthase, last step of riboflavin synthesis, converts 6,7-dimethyl-8-ribitylumazine to riboflavin | 1 | |
| PAG1462RP | MITO-DNA | | | 1 | |
| PAG1462UP | MITO-DNA | | | 1 | |
| PAG1463RP | YDR232w | HEM1 | 5-Aminolevulinate synthase, first step in heme biosynthesis pathway (pyridoxal-5'-phosphate is essential cofactor) | 1 | |
| PAG1463UP | YBR057c | MUM2 | protein with sim to ubiquitin C-terminal hydrolase | 1 | |
| PAG1464RP | YOL119c | | with weak sim to mammalian monocarboxylate transporter proteins | 1 | syntenie; YOL118c:unknown len 102 YOL117w: unknown, len 645 |
| PAG1464UP | YOL116w | MSN1 | transcriptional activator for genes regulated through SNF1p, multicopy suppressor of invertase defect in snf1 mutants | 2 | syntenie |
| PAG1465RP | YFL046W | | unknown function | 1 | syntenie |
| | YFL045c | SEC53 | Phosphomannomutase, involved in the synthesis of GDP-mannose and dolichol- | 1 | syntenie; end of syntenie defined; two genes covered by |

TABLE 1-continued

| pAG name | Yeast Name | Gene Name | Brief Description | HC | Additional Comments |
|---|---|---|---|---|---|
| PAG1465UP | YLR078c | BOS1 | phosphate-mannose Vesicular transport protein Synaptobrevin (-SNARE) homolog involved in ER to Golgi transport | 1 | RP-SRS |
| PAG1466RP | | | | 4 | |
| PAG1466UP | YMR196w | | unknown function | 1 | complete gene should be on this plasmid |
| PAG1467RP | YIL144w | | protein with sim to myosin heavy chain, possible coiled coil | 1 | syntenie; YIL145c: len 345aa: with sim to E. coli pantoate beta-alanine ligase (pantothenate synthetase) |
| PAG1467UP | YIL146C | | unknown function | 1 | syntenie |
| PAG1468RP | YER133w | GLC7n | protein SER/THR phosphatase PP1 required for glucose repression, probably functions antagonistically to SNF1p | 1 | |
| PAG1468UP | YGL200c | EMP24 | component of the COPII coat of certain ER derived vesicles | 1 | |
| PAG1469RP | YHR098c | | protein with unknown function | 1 | Syntenie |
| PAG1469UP | YHR097c | | unknown function | 1 | syntenie |
| PAG1470RP | YOR172w | | protein with sim to transcrition factors, has Zn(2)-Cys(6) fungal-type binuclear cluster domain in the N-terminal region | 1 | identical to 1155,1470,1527,1535,1546,1595 |
| PAG1470UP | YNR043w | ERG19 | Mevalonate kinase, generates mevalonate-5-phosphate from mevalonate, needed for ARS-CEN plasmid stability (regulation of autonomous replication) | 1 | identical to 1155,1470,1527,1535,1546,1595 |
| PAG1471RP | YHR096c | HXT5 | Highly similar to hexose transporters HXT2 and HXT4 (S. cerevisiae) | 1 | syntenie due to the transporter genes ; continued syntenie with plasmid PAG1469RP/UP |
| PAG1471UP | YHR094C | HXT1 | HEX1:Hexokinase II, converts hexoses to hexose phosphates in glycolysis and plays a regulatory role in glucose repression | 1 | chosen due to syntenie, the other hits(YJL214W:HXT8;YDR345C; YLR081W) had no higher sim. |
| PAG1472RP | YDR016c | | unknown function | 1 | weak case of syntenie |
| PAG1472UP | YDR014w | | hypothetical protein | 2 | weak syntenie |
| PAG1473RP | YMR097c | | has ATP/GTP-binding site motif | 1 | syntenie |
| PAG1473UP | YMR094w | CTF13 | kinetochore proteinCbf3, subunit c | 1 | syntenie; YMR096w: len 297aa, sim to YFL059p and YNL333p.YMR095c: len 224aa, sim to YML334p |
| PAG1474RP | YOR070c | | unknown | 1 | |
| PAG1474UP | YKR081c | | unknown | 1 | |
| PAG1475RP | | | | 4 | |
| PAG1475UP | YPR190c | RPC82 | RNA-POL III, third largest subunit | 1 | |
| | YGR049w | | Similar to Scm4p (SCM4_YEAST), possible Cdc4p-interacting protein. | 1 | |
| PAG1476RP | YML091c | RPM2 | Ribonuclease P of MT, generates mature tRNA molecules by cleaving their 5' ends | 1 | |
| PAG1476UP | YML126c | HMGS | 3-hydroxy-3-methylglutaryl coenzyme A synthase, functions in mevalonate synthesis | 1 | located near TUB3/YML124c |
| PAG1477RP | YER093c | | unknown function | 1 | syntenie |
| | YNL116w | | unknown | 1 | |
| PAG1477UP | YER091c | MET6 | Homocysteine methyltransferase, methionine synthase; 5-methyltetrahydropteroyl triglutamate--homocysteinemethyltransferase- | 1 | syntenie.YER092w:len 125:unknown |
| PAG1478RP | YER022w | SRB4 | component of RNA-POLII holoenzyme and Kornberg's mediator (SRB) subcomplex, required for basal transcription | 1 | syntenie |
| PAG1478UP | YER021w | SUN2 | Component of 26S proteasome complex | 1 | syntenie |
| PAG1479RP | | | | 4 | |
| PAG1479UP | YJR091c | JSN1 | protein that when overexpressed can suppress the hyperstable microtuble phenotype of tub2-150 | 1 | almost all of the ORF on this plasmid starting from codon 20 |
| PAG1480RP | YMR167w | MLH1 | Mismatch repair protein and homolog of E. coli MutL involved in repair of small insertions | 1 | syntenie; YMR168c:CBF3b, len 608aa YMR169c:ALD3, len 506aa |
| PAG1480UP | YMR170c | ALD2 | Aldehyde dehydrogenase | 1 | syntenie |
| PAG1482RP | YLR214w | FRE1 | Ferric (and cupric) reductase, acts on ferric iron chelates external to the cell | 1 | syntenie |
| PAG1482UP | YLR215c | | unknown function | 1 | syntenie |
| PAG1483RP | YDL171c | GLT1 | Glutamate synthase, involved with | 1 | |

TABLE 1-continued

| pAG name | Yeast Name | Gene Name | Brief Description | HC | Additional Comments |
|---|---|---|---|---|---|
| PAG1483UP | YNR013c | | glutamine synthase in glutamate biosynthesis protein with sim to Pho87p and YJL198p, member of the phosphate permease family, 12 TMD | 1 | |
| PAG1484RP | YNR006w | VPS27 | protein involved in vacuolar sorting | 1 | |
| PAG1484UP | YPL256c | CLN2 | G1/S-specific cyclin, interaczs with CDC28p protein kinase to control the events at START | 1 | |
| PAG1485RP | | tRNA | pre-tRNA-leu | 1 | redundant |
| PAG1485UP | YGL170c | | with sim to phosphoribulokinase precursor (phosphopentokinase) | 2 | |
| PAG1486RP | YNL161w | | SER/THR protein kinase of unknown function; related protein from *N. crassa* is required for hyphal elongation, has sim to DBF2, DBF20, YPK1, YPK2, and TPK2, strong sim to cAMP-dependent protein kinases like cot-1 and human myotonic dystrophy kinase MDK | 1 | |
| PAG1486UP | YHR142w | | unknown function, has 7 potential TMD | 1 | |
| PAG1487RP | YOR036w | PEP12 | PEP12:Syntaxin(t-SNARE) involved in Golgi to vacuole transport, len 288aa | 1 | disturbed syntenie. Two genes covered with RP-SRS |
| | YDR267C | | protein with sim to SEC13 and other proteins with WD-40 repeats; has sim to transcription factors | 1 | disturbed syntenie |
| PAG1487UP | YOR038c | HIR2 | HIR2:Histone transcription regulator, required for periodic repression of 3 of the 4 histone gene loci and for autogenous repression of HTA1-HTB1 locus by H2A and H2B | 1 | disturbed syntenie |
| PAG1488RP | YIR007W | YIB7 | sim to endoglucanases | 1 | |
| PAG1488UP | YOL027C | | unknown,sim to YPR125p | 1 | |
| PAG1489RP | YBR001c | NTH2 | alpha,alpha-trehalase, converts alpha,alpha-trehalose to glucose, promoter contains the stress-regulated CCCCT-elements (STRE) common to stress-induced genes, repressors: glucose | 1 | CEN-PLASMID,HISTONES:SYNTENIE |
| PAG1489UP | YBL003c | HTA2 | Histone H2a | 1 | syntenie |
| PAG1490RP | YMR167w | MLH1 | mismatch repair protein and homolog of *E. coli* MUTL | 1 | syntenie:YMR170c:ALD5.YMR169c:ALD3 YMR168c:CBF3B |
| PAG1490UP | YMR170c | ALD5 | Aldehyde dehydrogenase | 1 | syntenie |
| PAG1491RP | | | | 4 | |
| PAG1491UP | YNL082w | PMS1 | protein required for mismatch repair, homologous to MutL | 2 | |
| PAG1492RP | YKR070w | | unknown function | 1 | two genes covered by RP-SRS |
| | YOR052c | | unknown function | 1 | two genes covered by RP-SRS |
| PAG1492UP | YLR292c | SEC72 | SEC72:Component of ER protein-translocation complex that includes SEC61,62,66 and KAR2p | 1 | |
| PAG1493RP | YPL243w | SRP68 | signal recognition particle subunit | 1 | syntenie |
| PAG1493UP | YPL246c | | unknown function | 1 | syntenie.YPL245w: has A(P-loop), len 454 YPL224c:len 339 |
| PAG1494RP | YOL095c | HRE571 | sim to *S. aureus* helicase pcrA | 1 | syntenie.YOL094c:RFC4:len323 aa, replication factorC |
| PAG1494UP | YOL093w | | unknown function | 1 | syntenie. End of syntenie |
| | YJL007 | | unknown function | 1 | syntenie. End of syntenie |
| PAG1495RP | YGL227w | | with sim to Dictyostelium non-receptor tyrosine kinase U32174; contains WW(WWP) domain of about 40aa which is also found in dystrophin, Rsp5p, and Ess1p | 1 | |
| PAG1495UP | | | | 4 | |
| PAG1496RP | YER020w | GPA2 | guanine nucleotide binding protein alpha subunit involved in regulation of the cAMP pathway during mating | 1 | |
| PAG1496UP | YJR109c | CPA2 | Carbamoylphosphat synthase, arginine specific | 1 | |
| PAG1497RP | YPL022w | RAD1 | component of the nucleotide excision repairosome, homolog of human XPF xeroderma pigmentosum gene pRoduct and the mammalian ERCC-4 protein, required for double-strand-break induced recombination | 1 | |
| PAG1497UP | YPL016w | ADR6 | SWI1; Component of the SWI/SNF global transcription activator complex, acts to assist gene-specific activators | 1 | end of gene covered by RP-SRS |
| PAG1499RP | YOR021c | | unknown function | 1 | |

TABLE 1-continued

| pAG name | Yeast Name | Gene Name | Brief Description | HC | Additional Comments |
|---|---|---|---|---|---|
| PAG1499UP | YPR133c | | unknown function | 1 | |
| PAG1500RP | YOL094c | RFC4 | replication factor c | 1 | |
| PAG1500UP | | | | 4 | |
| PAG1501RP | MITO-DNA | | align | | |
| PAG1501UP | MITO-DNA | | align | | |
| PAG1502RP | YLR056w | ERG3 | ERG3:C-5 sterol desaturase, an iron non-heme oxygen-required enzyme of the ergosterol biosynthesis pathway, ER retention signal | 1 | syntenie; |
| PAG1502UP | YPL055c | SPT8 | member of the TBP class of SPT proteins that alter transcription start site selection, functionally relatet to SPT3p and TBP | 1 | syntenie |
| PAG1503RP | YNL297c | | unknown | 1 | syntenie |
| PAG1503UP | YNL294c | | unknown, has 6 potential TMD | 1 | YPL296w: q-ORF, len 104.YPL295w: len 524, unknown |
| PAG1504RP | MITO-DNA | | | | |
| PAG1504UP | MITO-DNA | | | | |
| PAG1505RP | YOR007c | | sim to protein phosphatases | 1 | |
| PAG1505UP | YML002W | | unknown function | 1 | syntenie. Two genes covered on UP-SRS |
| | YML003w | | unknown protein | 1 | syntenie with YML002w |
| PAG1506RP | YLR454W | | unknown function | 1 | |
| PAG1506UP | | | | 4 | |
| PAG1507RP | YBR053c | | protein with sim to glucan-1,3-beta-glucosidase | 1 | |
| PAG1507UP | YDR028c | SRN1 | REG1:regulatory subunit for protein phosphatase GLC7, required for glucose repression | 1 | |
| PAG1508RP | | | | 4 | |
| PAG1508UP | YKL211c | TRP3 | Anthranilate synthase component II, first and fourth steps in Tryptophan biosynthesis pathway | 1 | useful as TRP-selectable marker gene? |
| PAG1509RP | YOR166c | | unknown function | 1 | |
| PAG1509UP | | | | 4 | |
| PAG1510RP | YGR056w | | unknown function, has high sim to YLR357w | 1 | syntenie |
| PAG1510UP | YGR057c | | unknown function | 1 | syntenie |
| PAG1511RP | | | | 4 | |
| PAG1511UP | YBR274w | | protein kinase with sim to members of the growth factor and cytokine receptor family | 1 | |
| PAG1512RP | YML067c | | unknown function | 1 | syntenie |
| PAG1512UP | YML069w | | has sim to HMG1 proteins | 1 | syntenie |
| PAG1513RP | YDL136w | SOS2 | ribosomal protein homologius to rat L35 | 1 | syntenie YDL191w = SOS1 = L35 |
| PAG1513UP | YDL139w | | unknown ,but with sim to N. crassa protein | 1 | syntenie |
| PAG1514RP | YNL126w | | sim to YJL207p | 1 | same as PAG1699 |
| PAG1514UP | YHR121w | | unknown function | 1 | same as PAG1699 |
| PAG1515RP | YFR007W | | unknown function | 1 | |
| PAG1515UP | YGR021w | | unknown function | 1 | |
| PAG1516RP | YPL072w | LPF12 | unknown function | 1 | syntenie |
| PAG1516UP | YPL074w | YTA6 | strong sim to YTA4p, member of the CDC48/PAS1/SEC18(AAA) family of ATPases and probable regulatory subunit of the 26S proteasome complex | 1 | syntenie;there is no YPL073 |
| PAG1517RP | YPR190C | RPC82 | RNA-POL III. third largest subunit | 1 | syntenie |
| | YPR189W | SKI3 | end of gene on this SRS Antiviral protein with tetratricopeptide (TPR) repeats, part of a system to protect cells from dsRNA viruses | 1 | two genes covered by RP-SRS. Syntenie |
| PAG1517UP | YPR189W | SKI3 | sequence begins at codon 504 | 1 | syntenie |
| PAG1519RP | YBR112c | SSN6 | general repressor of trans- cription that is brought to target promoters by sequence specific DNA-binding proteins, has tetratricopeptide TPR repeats | 1 | |
| PAG1519UP | YPR070W | | unknown function | 1 | |
| PAG1520RP | YDL100c | | with sim to E. coli arsenical pump-driving ATPase, has amino- transferases class-V pyridoxalphosphateattachment site | 1 | |
| PAG1520UP | YMR157c | | unknown function | 1 | |
| PAG1521RP | YDL145c | RET1 | RPC128:RNA-POL III, secondlargest subunit | 1 | |

TABLE 1-continued

| pAG name | Yeast Name | Gene Name | Brief Description | HC | Additional Comments |
|---|---|---|---|---|---|
| PAG1521UP | YLR213c | | unknown:has WAP-type 'four-disulfide core' domain signature | 1 | |
| PAG1522RP | | | | 4 | |
| PAG1522UP | YPR015c | | YPR013c:with sim to mouse REX1 encoded transcription factor, contains C2H2-type zinc finger domain; YPR015c: same type of zinc finger | 1 | |
| PAG1523RP | YML006C | | unknown function, has prenyl group binding site (CAAX)-motif | 1 | |
| PAG1523UP | YDR421W | | unknown function, has a(P-loop) | 1 | |
| PAG1524RP | YPR049C | | unknown function, has a probable coiled coil | 1 | syntenie |
| PAG1524UP | YPR048W | | protein with sim to NAPDH-cytochrome P450 reductase, has a MT energy transfer proteins signature | 1 | syntenie. Two genes covered by UP-SRS |
| | YPR047w | MSF1 | also YLR168c:protein possibly involved in intra-mitochondrial sorting | 1 | syntenie overthree genes |
| PAG1525RP | | | | 4 | |
| PAG1525UP | YOR362c | PRE10 | proteasome subunit Y13 | 1 | two genes covered on UP-SRS |
| | YAL047c | FUN42 | unknown function | 1 | two genes covered by UP-SRS |
| PAG1526RP | YJL111w | CCT7 | component of chaperonin-containing T-complex | 1 | |
| PAG1526UP | YNL135c | FPR1 | (FKB1) FK506-binding protein, homolog of human FKBP12, human FKBP12 is functional in yeast, has peptidyl-proly isomerase activity; produces lethal complex with rapamycin | 1 | |
| PAG1527RP | YOR172w | | with sim to transcription factors | 1 | identical to 1155,1470,1527,1535,1546,1595 |
| PAG1527UP | YNR043w | ERG19 | Mevalonate diphosphate-decarboxylase, functions in the polyisoprene biosynthesis pathway | 1 | identical to 1155,1470,1527,1535,1546,1595 |
| PAG1528RP | YLR430w | SEN1 | positive effector of tRNA-splicing endonuclease, required for intron cleavage for all ten precursor tRNA families | 1 | one gene on plasmid; covering codons 1356 to1588 |
| PAG1528UP | YLR430w | SEN1 | | 1 | one gene on plasmid covering codons 132 to 365 |
| PAG1529RP | YLR187w | | unknown functionhas strong sim to YNL278w | 1 | syntenie |
| PAG1529UP | YLR188w | MDL1 | ATP-binding cassette (ABC)-transporter family member, equivalent to a "half molecule" ABC protein plus an ATP-binding domain, has sim to mammalian multidrug resistance protein and peptide transporter TAP | 1 | syntenie |
| PAG1530RP | YGR277c | | sim to CTR1 (cholin permease)=HNM1; has multiple membrane spanning domains | 1 | syntenie, same as PAG1538 |
| PAG1530UP | YGR279C | | unknown function | 1 | syntenie.YGR278w:unknown, same as PAG1538 |
| PAG1531RP | YCL057w | PRD1 | Proteinase yscD, saccharolysin, homologous to rat metallo-endopeptidase, contains zinc metallopeptidase motif HEXXH | 1 | |
| PAG1531UP | | | | 4 | |
| PAG1532RP | YIL144w | | protein with sim to myosin heavy chain, possibly coiled-coil | 1 | syntenie |
| PAG1532UP | YIL145c | | sim to E. coli PANTOATE-BETA-ALANINE LIGASE | 1 | syntenie |
| PAG1533RP | YJR052w | RAD7 | nucleotide excision repair protein involved in G2 repair of inactive genes | 1 | |
| PAG1533UP | YPR194c | | unknown, has sim to S. pombe C-terminal region of ips4 | 2 | |
| PAG1534RP | YOR165w | | unknown function | 1 | syntenie |
| PAG1534UP | YOR163w | | unknown function | 1 | syntenie.YOR164c:unknown function |
| PAG1535RP | YOR172w | | sim to ts factor | 1 | identical to 1155,1470,1527,1535,1546,1595 |
| PAG1535UP | YNR043w | ERG19 | | 1 | identical to 1155,1470,1527,1535,1546,1595 |
| PAG1536RP | YJR085c | | unknown function | 1 | |
| PAG1536UP | YPR040W | | unknown function, has sim to a C. elegans protein | 1 | |
| PAG1537RP | YER164w | | with sim to mouse chromodomain-helicase-DNA-binding protein, contains putative Myb DNA-binding domain | 1 | |

TABLE 1-continued

| pAG name | Yeast Name | Gene Name | Brief Description | HC | Additional Comments |
|---|---|---|---|---|---|
| PAG1537UP | | | | 4 | |
| PAG1538RP | YGR277c | | protein with sim to CTR1:copper transport protein, required for high-affinity uptake of copper (=HNM1) | 1 | YGR278w: unknown, len 577aa.syntenie same as PAG1530 |
| PAG1538UP | YGR279c | | unknown, but related to YMR305p | 1 | syntenie.same as PAG1530 |
| PAG1540RP | YML061C | PIF1 | single-stranded DNA-dependent ATPase and 5'-3' DNA helicase required for maintenance and repair of MT-DNA, also functions in nucleus to regulate telomere length | 1 | syntenie |
| PAG1540UP | YML060w | OGG1 | DNA glycosylase, excises 7,8-dihydro-8-oxoguanine and Fapy residues from DNA | 1 | syntenie |
| PAG1541RP | YDR035w | ARO3 | 2-dehydro-3-deoxyphosphoeptonate aldolase, phenylalanine inhibited | 1 | |
| PAG1541UP | tRNA-Asp | | closest to YDR035w is a copy at YDR058 | 1 | |
| PAG1542RP | YIR019c | STA1 | Glucoamylasel (alpha-1,4-glucan glucosidase), extracellular enzyme | 2 | weak similarity based on Ser/thr residues |
| PAG1542UP | YMR241W | | protein with sim to MT-carrier family proteins, has prokaryotic membrane lipoprotein lipid attachment site | 1 | |
| PAG1544RP | YDR316w | | unknown function; Weak similarity to *E. coli* hypothetical 28.1 kD protein in udp-rfah region to. accession number P27851) and *Lactococcus lactis* hypothe-tical protein 2 (pip 3'region) (PIRaccession number B48653) | 1 | |
| PAG1544UP | YHR070w | | unknown function | 1 | |
| PAG1545RP | | | | 4 | |
| PAG1545UP | YLR043c | TRX1 | Thioredoxin 1:required for vacuolar inheritance | 1 | |
| PAG1546RP | YOR172w | | protein with sim to transcription factors | 1 | identical to 1155,1470,1527,1535,1546,1595 |
| PAG1546UP | YNR043w | ERG19 | Mevalonate diphosphate decarboxylase, functions in polyisoprene biosynthesis | 1 | identical to 1155,1470,1527,1535,1546,1595 |
| PAG1547RP | YDR371w | | with sim to chitinases, has chitinases family 18 active site signature, has sim to Aphanocladium album chitinase | 1 | |
| PAG1547UP | YOR122c | PFY1 | Profilin, can act to prevent actin polymerization and to complex with monomeric actin; C-terminus is implicated in actin binding | 1 | two genes covered by UP-SRS. Syntenie |
| | YOR123c | LEO1 | unknown function, extremely hydrophilic | 1 | syntenie |
| PAG1548RP | YER056c | FCY2 | Cytosine/purine permease | 1 | syntenie;between 56c and 62c are 56cA(L34, len 121), 57c(unknown len 129), 58w (PET11, len87aa), 59w (sim to PHO80 and other cyclins, len420aa), 60w (FCYY, len 528aa), 60wA (FCYX, len530aa), 61c(CEM1, len 442aa); |
| PAG1548UP | YER062c | HOR2 | DL-glycerol phosphatase, strong sim to GPP1 | 1 | syntenie |
| PAG1549RP | YNL162w | RPL41A | | 1 | syntenie |
| PAG1549UP | YNL163c | EF4 | translation elongation factor EF4 | 1 | syntenie |
| PAG1550RP | YLR440C | | unknown function, has carbamoyl-phosphate snythase subdomain signatures | 1 | redundant clone? |
| PAG1550UP | YML060w | OGG1 | DNA-glycosylase | 1 | redundant? |
| PAG1551RP | | | | 4 | |
| PAG1551UP | YLR095c | | unknown function | 1 | |
| PAG1552RP | YDL008w | | unknown function | 1 | end of syntenie; two genes covered from RP-SRS |
| | YBR011c | IPP1 | Inorganic pyrophosphatase, cytoplasmic | 1 | syntenie |
| PAG1552UP | YBR009c | HHF1 | Histone H4 | 1 | syntenie; YBR010w=HHT1 which is Histone H3 |
| PAG1554RP | YGR277c | | | 1 | redundant? Syntenie |
| PAG1554UP | YGR279c | | | 1 | syntenie, redundant? |
| PAG1555RP | YDL060w | | unknown function | 1 | syntenie; redundant? |
| PAG1555UP | YDL061c | RPS29B | YEAST 40S RIBOSOMAL PROTEIN YS29B. | 1 | syntenie |
| PAG1556RP | YPR070w | | unknown | 1 | |
| PAG1556UP | YBR112c | SSN6 | | 1 | redundant? |
| PAG1557RP | | | | 4 | |
| PAG1557UP | YCL057w | PRD1 | =NCPR1:YHR042w: NADP-cytochrome P450 reductase | 1 | |
| PAG1559RP | YBR119w | MUD1 | U1snRNP A protein (snRNA -associated | 1 | two gened on RP-SRS; Syntenie |

TABLE 1-continued

| pAG name | Yeast Name | Gene Name | Brief Description | HC | Additional Comments |
|---|---|---|---|---|---|
| | YBR120c | CBP6 | protein with 2 RNA recognition (RRM) domains, helps to fold U1 RNA and maintain it in an active configuration translational activator of COB mRNA | 1 | syntenie |
| PAG1559UP | YPR082c | | Weak similarity to hypothetical *E. coli* protein (PIR accession number S47687) | 1 | |
| PAG1560RP | YDL185w | VMA1 | VMA1 Vacuolar H(+)-ATPase catalytic subunit, 69 kD subunit of V1 sector, self splicing protein | 1 | syntenie |
| PAG1560UP | YDL186w | | unknown | 1 | syntenie |
| PAG1561RP | YDL185w | VMA1 | vacuolar H(+)-ATPase catalytic subunit, self splicing protein | 1 | syntenie;whole gene |
| PAG1561UP | YDL186w | | unknown function | 1 | syntenie |
| PAG1562RP | YDR100w | | possible membrane protein | 1 | |
| PAG1562UP | YER176w | | protein with sim to UPF1, a putative helicase | 2 | weak homology to the C-terminal 21 aa |
| PAG1563RP | YGL120c | | protein with strong sim to PRP22; related to putative mRNA processing protein | 1 | Syntenie; YGL121c:unknown |
| PAG1563UP | YGL122c | NAB2 | Nuclear poly(A)-binding protein, required for proper polyadenylation of pre-mRNA and for mRNA export | 1 | syntenie |
| PAG1565RP | YJR156c | | YJR156c:protein with strong sim to THI5 and YNL332wYDL244w:has 99.7% identity to THI5;YNL332w:THI5: YFL058w: biosynthetic enzyme involved in pyrimidine biosynthesis pathway above the hydroxymethyl-pyrimidine precursor leading to the thiamine moiety. *S.pombe* homolog nmtl | 1 | |
| PAG1565UP | YJR107w | | protein with sim to acylglycerol lipase | 1 | |
| PAG1566RP | YMR202w | ERG2 | C-8 sterol isomerase, enzyme of the ergosterol biosynthesis pathway: null mutant is lethal in the absence of exogenous ergosterol | 1 | syntenie |
| PAG1566UP | YMR205c | PFK2 | Phosphofructokinase beta subunit, converts fructose -6-phosphat into fructose -1-6-bisphosphat: key regulatory step in glycolysis | 1 | syntenie; YMR203w: TOM40:MT integral membrane protein involved in protein import, forms the outer membrane import-channel.YMr204c: unknown, len 420 |
| PAG1568RP | YOR361c | PRT1 | subunit of eIF3 initiation complex, required for initiation of protein synthesis, has an RNA recognition domain | 1 | syntenie |
| PAG1568up | YOR362c | PRE10 | Proteasome subunit YC1 | 1 | syntenie |
| PAG1569RP | YDR238c | SEC26 | coatomer complex beta chain (beta-COP) of secretory pathway vesicles,required for transport from ER to Golgi | 1 | syntenie |
| PAG1569UP | YDR236c | | unknown | 1 | syntenie |
| PAG1570RP | YKL054c | | unknown function, glutamic acid rich | 1 | |
| PAG1570UP | YOL048c | | unknown function | 1 | |
| PAG1571RP | YLR077w | | unknown, has regulator of chromosome condensation signature (RCC1) | 1 | syntenie |
| PAG1571UP | YLR075w | GRC5 | ribosomal protein of the 60S subunit (rat L10), len221 | 1 | syntenie;YLR076c:unknown, len 140 overlapping ORF's anyway |
| PAG1572RP | MITO-DNA | | | | |
| PAG1572UP | MITO-DNA | | | | |
| PAG1573RP | YJR066w | TOR1 | Phosphatidylinositol kinase (PI kinase) homolog involved in cell growth and sensitivity to the immunosuppressant rapamycin, kinase domain is essentila for G1 cell cycle functions; depletion causes starvation response but not through RAS/cAMP pathway | 1 | hit no 1 (YKL203c: TOR2) neglected due to syntenie |
| PAG1573UP | YJR065c | ACT4 | actin related protein , essential, len 449 (=ACT3) | 1 | syntenie |
| PAG1574RP | YML070w | | unknown function, has sim to dihydroxyacetone kinase | 1 | syntenie |
| PAG1574UP | YML069w | | YML069w:has sim to HMG1 proteins | 1 | syntenie |
| PAG1575RP | YOR009w | | weak sim based on Ser-residues | 2 | |
| PAG1575UP | YNR044w | | weak sim based on Ser-residues | 2 | |
| PAG1576RP | YML125c | | protein with sim to NADH-cytochrome b5 | 1 | syntenie, same as PAG1688 |

TABLE 1-continued

| pAG name | Yeast Name | Gene Name | Brief Description | HC | Additional Comments |
|---|---|---|---|---|---|
| | | | reductase | | |
| PAG1576UP | YML124c | TUB3 | TUB 1:YML085c: tubulin alpha-1 chain, required for mitosis and karyogamyTUB3:YML124c: tubulin alpha-3 chain, non-essential, null mutant has poor spore viability; TUB 1 and TUB3 each have an intron in CODON 9 | 1 | syntenie.C-term of TUB3 on plasmid |
| PAG1577RP | YJR117w | | protein with weak sim to tetracycline resistance proteins | 1 | relaxed syntenie |
| PAG1577UP | YJR106w | | unknown function, with sim to a *C. elegans* protein | 1 | relaxed syntenie |
| PAG1578RP | YDL220c | CDC13 | protein proposed to regulate generation of single-stranded tails at telomers; required for passage through G2/M; required in meiosis after DNA replication but before chromosome synapsis or recombination mutants are arrested At the RAD9 checkpoint; | 1 | |
| PAG1578UP | YNL192w | CHS1 | Chitin synthase I, has a repair function during cell separation; major form of chitin synthase representing 90% of activity, null mutants resistant to calcofluor, and with lower mating and sporulation efficiency | 1 | |
| PAG1579RP | YMR160W | | unknown function | 1 | |
| PAG1579UP | YMR205c | PFK2 | see 1566UP | 1 | |
| PAG1580RP | YLR368W | | unknown function | 1 | syntenie |
| PAG1580UP | YLR370c | | unknown function | 1 | syntenie, two genes with UP-SRS |
| | YLR369w | | protein with strong sim to HSP | 1 | syntenie |
| PAG1581RP | MITO-DNA | | | | |
| PAG1581UP | MITO-DNA | | | | |
| PAG1582RP | YLL023c | | unknown function | 1 | syntenie; two genes on RP-SRS |
| | YLL024c | SSA2 | HSP70 family, cytoplasmic | 1 | syntenie |
| PAG1582UP | YLR314c | CDC3 | Septin:Component of 10 nm filaments of mother-bud neck | 1 | N-Term up to codon 240 on the plasmid |
| PAG1583RP | YCL039w | | unknown, probably a member of the beta-transducin (WD-40) repeat family | 1 | syntenie |
| PAG1583UP | YCL040w | GLK1 | Glucokinase, specific for aldohexoses, sim to YDR516p | 1 | syntenie |
| PAG1584RP | YKL062w | MSN4 | Zinc-finger transcriptional activator for genes regulated through Snf1p homologous to MSN2 | 1 | |
| PAG1584UP | YMR035w | IMP2 | Inner membrane protease of MT, acts in complex with Imp1p but has a different substrate specificity for removal of signal peptidase | 1 | |
| PAG158SRP | YGL162w | SUT1 | protein involved in sterol uptake; expressed only in anaerobic conditions | 1 | syntenie |
| PAG1585UP | YGL163c | RAD54 | DNA-dependent ATPase of the Snf2p family, required for recombination and repair of X-ray damage; required for an early step of mating-type switching; mutant cells die if mating-type switching is attempted, mutants are unable to repair double-strand breaks | 1 | syntenie |
| PAG1586RP | tRNA-Val | | | 1 | |
| PAG1586UP | YDR420w | HKR1 | *Hansenula mrakii* K9 killer toxin-resistance protein | 2 | |
| PAG1587RP | YAL036c | FUN11 | YAL036c:unknown, has GTP-binding motif | 1 | |
| PAG1587UP | YOR346w | REV1 | protein required for mutagenesis by physical and chemical agents, has some sim with *E. coli* mutagenic repair protein umuC | 1 | |
| PAG1589RP | | | | 4 | |
| PAG1589UP | | | | 4 | |
| PAG1590RP | MITO-DNA | | | | |
| PAG1590UP | MITO-DNA | | | | |
| PAG1591RP | Leu-tRNA | | | 1 | |
| | YKR036c | | WD-40 repeat protein | 1 | syntenie,not overlapping with tRNA |
| PAG1591UP | YKR038c | | sim to Qri7p and *Pasteurella haemolytica* | 1 | syntenie.YKR037c:unknown, |

TABLE 1-continued

| pAG name | Yeast Name | Gene Name | Brief Description | HC | Additional Comments |
|---|---|---|---|---|---|
| | | | glycoproteinase | | len 295 |
| PAG1592RP | YNL244c | SUI1 | translation initiation factor, 16kD subunit | 1 | |
| PAG1592UP | YJR107w | | protein with sim to acylglycerol lipase | 1 | |
| PAG1593RP | YLR422w | | protein of unknown function | 1 | one gene on plasmid. Codons 1107–1327 |
| PAG1593UP | YLR422w | | protein of unknown function | 1 | one gene on plasmid. Codons 1–109;incl. promoter |
| PAG1594RP | YDR176c | SEC7 | component of non-clathrin vesicle coat required for traffic within the Golgi | 1 | just one gene on the plasmid; RP-SRS down to codon 1703 |
| PAG1594UP | YDR170c | SEC7 | | 1 | up to codon 318; so N-term as well as C-term are missing |
| PAG1595RP | YOR172w | | | | identical to 1155,1470,1527,1535,1546,1595 |
| PAG1595UP | YNR043w | ERG19 | | | identical to 1155,1470,1527,1535,1546,1595 |
| PAG1596RP | YNL294c | | SyntenieYNL294c: unknown, 6 potential TMD | 1 | syntenie |
| PAG1596UP | YNL297c | | YNL297c: unknown, 6 potential TMD | 1 | syntenie. YNL296w: len 104aa questionable ORF YNL295w: unknown, len 524aa |
| PAG1597RP | | | | 4 | |
| PAG1597UP | | | | 4 | |
| PAG1598RP | MITO-DNA | | | | |
| PAG1598UP | MITO-DNA | | | | |
| PAG1600RP | YEL023c | | unknown function | 1 | |
| PAG1600UP | YJR035w | RAD26 | putative helicase homologous to Cockayne syndrome B gene ERCC-6, involved in transcription-coupled repair, has putative NLS | 1 | |
| PAG1601RP | YBR041w | | protein of unknown function, probable ATP-binding protein, with 4 potential TMD | 1 | syntenie |
| PAG1601UP | YBR043c | | member of major facilitator superfamily (MFS), multidrug-resistance proteins family 1 | 1 | syntenie |
| PAG1602RP | YPL059W | | protein with sim to Legionella pneumophilia LPNTSAA_1 glutaredoxin-like protein | 1 | |
| PAG1602UP | YBR162c | | protein with sim to AGA1 | 1 | |
| PAG1603RP | YJL190c | RPS24A | ribosomal protein | 1 | syntenie. Same as PAG1670 |
| | YJL191w | CRY2 | ribosomal protein | 1 | same as PAG1670 |
| PAG1603UP | YJL069c | | unknown function | 1 | same as PAG1670 |
| PAG1604RP | YGL123w | SUP44 | ribosomal protein, E. coli S5, rat S2 | 1 | |
| PAG1604UP | YDR172w | SUP35 | =SUP2; omnipotent suppressor with sim to EF1-alpha, protein responsible for the (psi+) phenotype probably through a prion mechanism, required for G1/S-transition; has EF-TU homology domain, C-terminal 2/3 homologous to EF-1alpha, N-terminal domain has tandem oligopeptide repeats and has structural sim to mammalian prion protein | 1 | |
| PAG1605RP | YDR170c | SEC7 | data on length vary, but it should be larger than 1800aa | 1 | this clone contains the N-terminus down to codon 432 syntenie with upstream genes |
| PAG1605UP | YDR172w | SUP2 | =SUP35; | 1 | syntenie YDR171w:HSP42 |
| PAG1606RP | | | | 4 | |
| PAG1606UP | YNL254e | | unknown function | 1 | |
| PAG1607RP | YBR214w | | protein with sim to moc1 protein of S. pombe | 1 | |
| PAG1607UP | | | | 4 | |
| PAG1608RP | YNL287w | SEC21 | Coatomer complex gamma chain (gamma-COP)of secretory pathway vesicles; primary role in retrograde transport, essential | 1 | |
| PAG1608UP | YBR025c | | unknown, probable purine nucleotide-binding protein | 1 | |
| PAG1609RP | YJL041w | NSP1 | TFS1:suppressor of CDC25: has affect on the phosphorylation state of two proteins whose phosphorylation varies with the cell cycle | 1 | |
| PAG1609UP | | | | 4 | |
| PAG1610RP | YNL267w | PIK1 | PIK1:Phosphatidylinositol4-kinase, | 1 | syntenie |

TABLE 1-continued

| pAG name | Yeast Name | Gene Name | Brief Description | HC | Additional Comments |
|---|---|---|---|---|---|
| | | | generates PtdIns4-P; overproduction causes increased sensitivity to growth arrest by alpha factor | | |
| PAG1610UP | YNL268w | LYP1 | Lysine specific permease | 1 | syntenie |
| PAG1611RP | YMR061w | RNA14 | component of pre-mRNA 3'-end processing factor involved in poly(A)-site choice | 1 | same as PAG1667 |
| PAG1611UP | YKL075c | | protein with sim to HEX2, histidine-rich protein | 1 | same as PAG1667 |
| PAG1612RP | YJL004c | | protein of unknown function, probable membrane protein | | |
| PAG1613UP | YJR019c | | unknown function | 1 | overlapping ORF's no 2 has two stop codons in alignment region |
| | YJR020w | | unknown function | 1 | stop codons make this hypothetical ORF very questionable even in yeast |
| PAG1614RP | YLR368w | | unknown function | 1 | syntenie |
| PAG1614UP | YLR370c | | unknown function | 1 | syntenie, two genes covered by UP-SRS |
| | YLR369w | | strong sim to HSP70 | 1 | syntenie |
| PAG1615RP | YJL044c | GYP6 | GTPase-activating protein GAP for YPT6 | 1 | same as PAG1191 |
| PAG1615UP | YKL151c | | unknown function | 1 | same as PAG1191 1 |
| PAG1616RP | YMR079w | SEC14 | Phosphatidylinositol/phosphatidylcholine transfer-protein, required for transport of secretory proteins from Golgi | | |
| PAG1616UP | | | | 4 | |
| PAG1617RP | YPL235w | | unknown function | 1 | syntenie |
| PAG1617UP | YPL239w | YAR1 | protein with two ankyrin repeats | 1 | divergent promoter, two genes covered by UP-SRS. Syntenie and one end of syntenie |
| | YMR185w | | unknown function | 1 | divergent promoter; two genes covered by UP-SRS. Syntenie and one end of syntenie |
| PAG1618RP | | | | 4 | |
| PAG1619RP | YOR085w | OST3 | Oligosaccharyltransferase gamma subunit, member of a complex of 6 ER proteins that transfer core oligosaccharide from dolichol carrier to Asn-X-Ser/Thr motif | 1 | syntenie |
| PAG1619UP | YOR86c | | unknown function | 1 | syntenie |
| PAG1620RP | YKL217w | JEN1 | protein with sim to E. coli osmoregulatory proP proline/betaine transporter and KgtP alpha-ketoglutarate transporter, member of the major facilitator superfamily | 1 | CHIMERIC-PLASMID |
| PAG1620UP | MITO-DNA | | | | CHIMERIC-PLASMID |
| PAG1622RP | MITO-DNA | | | | |
| PAG1622UP | MITO-DNA | | | | |
| PAG1623RP | YDR150w | NUM1 | | 1 | syntenie |
| PAG1623UP | YDR152w | | unknown function | 1 | syntenie, YDR151c:CTH1:len 325: protein of the inducible CCCH zinc-finger family |
| PAG1624RP | YIL093c | | unknown function | 1 | |
| PAG1624UP | YNL023c | | protein with sim to human DNA binding protein tenascin and Drosophila shuttle craft protein | 1 | |
| PAG1625RP | YLR180w | SAM1 | S-adenosylmethionine synthetase 1;repressors: methionine | 1 | high degree of identity to SAM2 (YDR502c), which is induced by methionine actually Sam2p is first hitwhole gene on this plasmid SYNTENIE |
| PAG1625UP | YLR178c | TFS1 | CDC25-dependent nutrient- and ammonia-response cell-cycle regulator, suppressor of CDC25 mutations | 1 | YLR178c and YLR179c are overlapping ORF's, whole gene on this plasmid. Additionally there are two genes covered by UP-SRS, second gene ends one kind of syntenie. |
| | YDR505c | GIN5 | high copy-number suppressor of ts mutations in DNA-POL alpha | 1 | |
| PAG1626RP | | | | 4 | |
| PAG1626UP | YGR274c | TAF145 | component of the TAF(II) complex (TBP-associated protein complex) required for activated transcription by RNA-POL II | 1 | two genes covered by UP-SRS |
| | YMR298w | | unknown function | 1 | |

TABLE 1-continued

| pAG name | Yeast Name | Gene Name | Brief Description | HC | Additional Comments |
|---|---|---|---|---|---|
| PAG1627RP | YCL031c | | unknown function | 1 | syntenie |
| PAG1627UP | YCL030c | HIS4 | Phosphoribosyl-AMP cyclohydrolase . . . ; second, third and tenth step of histidine biosynthesis pathway | 1 | syntenie |
| PAG1628RP | YKR092c | SRP40 | suppressor of mutant AC40 subunit of RNA-POL I and III, overproduction is lethal | 2 | |
| PAG1629RP | YNL257c | SIP3 | interacts with SNF1, contains PH-domain | 1 | |
| PAG1629UP | YGR255c | | protein with sim to E. coli ubiH protein | 1 | |
| PAG1630RP | YLR424w | | protein with sim to retrovirus-related proteases | 2 | |
| PAG1630UP | | | | 4 | |
| PAG1631RP | MITO-DNA | | align | | |
| PAG1631UP | MITO-DNA | | align | | |
| PAG1632RP | YNL068c | FKH2 | Homolog of Drosophila forkhead protein | 1 | |
| PAG1632UP | | | | 4 | |
| PAG1633RP | MITO-DNA | | | | |
| PAG1633UP | MITO-DNA | | | | |
| PAG1634RP | YBL085w | BOI1 | BEM1p-binding protein, has a SH3 domain and a PH domain; involved in bud formation redundant with BOI2p | 1 | |
| PAG1634UP | | | | 4 | |
| PAG1635RP | YDL052c | SLC1 | Fatty acyltransferase | 1 | two genes covered by RP-SRS,same as PAG1664 |
| | YLR377c | FBP1 | Fructose-1,6-bisphophatase | 1 | two genes covered by RP-SRS,same as PAG1664 |
| PAG1635UP | YDL054c | | putative transmembrane protein | 1 | same as PAG1664 |
| PAG1636RP | YLL055w | | protein with sim to DAL5 and members of the allantoate perinease family of the major facilitator superfamily (MFS) | 1 | |
| PAG1636UP | YKL215c | | protein with sim to Pseudomonas hydantoinases hyuA-hyuB | 1 | |
| PAG1637RP | YER157w | | unknown function | 2 | syntenie,same as PAG1060 |
| PAG1637UP | YER155c | BEM2 | bud-emergence protein | 1 | codons 403 to 218 including N-term+promoter(?)syntenie YER156c:unknown function,same as PAG1060 |
| PAG1638RP | YCL037c | | with sim to SLF1, has a motif in common with conserved sequence in LHP1 but does not contain a RNA recognition motif | 1 | syntenie.YCL038C:unknown function, len 528aa37c:is SRO9 |
| PAG1638UP | YCL039w | | probably a member of the WD-40 family | 1 | syntenie |
| PAG1639RP | YKL046c | | unknown function, has 2 predicted TMDs | 1 | |
| PAG1639UP | YMR020w | FMS1 | sim to corticosteroid-binding protein | 1 | |
| PAG1640RP | | | | 4 | |
| PAG1640UP | YLR196w | PWP1 | member of WD-40 repeat family | 1 | |
| PAG1642RP | YKR023w | | unknown function | 1 | syntenie |
| PAG1642UP | YKR024c | | unknown function, probable purine nucleotide-binding protein | 1 | syntenie |
| PAG1643RP | YMR179w | SPT21 | protein that amplifies the magnitude of transcriptional regulation at various loci | 1 | syntenie; YMR180c:len 320, unknown |
| PAG1643UP | YMR181c | | unknown function | 1 | syntenie |
| PAG1644RP | | | | 4 | |
| PAG1645RP | YDR089w | | unknown function ; with leucine zipper pattern | 1 | syntenie, two genes covered by RP-SRS ending syntenie |
| | YER161c | SPT2 | HMG-like chromatin protein that interacts with SNF1p through a conserved domain | 1 | syntenie, two genes covered by RP-SRS ending syntenie |
| PAG1645UP | YDR088c | SLU7 | pre-mRNA splicing factor affecting 3' splice site choice, required only for the second catalytic step | 1 | syntenie |
| PAG1646RP | YML120c | NDI1 | NADH-ubiquinone oxidoreductase | 1 | |
| PAG1646UP | YHR190w | ERG9 | Squalene synthtase(farnesyl-diphosphate farnesyltransferase), branch point for isoprenoid biosynthesis pathway | 1 | |
| PAG1647RP | YML004c | GLO1 | sim to glyoxalases | 1 | |
| PAG1647UP | YNR011c | PRP2 | RNA-dependent ATPase of DEAD box family required for first catalytic event of pre-mRNA splicing | 1 | |
| PAG1648RP | | | | 4 | |
| PAG1648UP | YNR016c | FAS3 | first and rate limiting step in fatty acid biosynthesis pathway | 1 | |

TABLE 1-continued

| pAG name | Yeast Gene Name | Gene Name | Brief Description | HC | Additional Comments |
|---|---|---|---|---|---|
| PAG1649RP | YHR206W | SKN7 | Transcription factor with homology toresponse regulator proteins of bacterial two-component systems and DNA-binding region of Hsf1p, may be involved in the response to oxidative stress. May act in parallel to PKC1-MAP kinase pathway to regulate growth at the cell surface, but is not in the sane pathway as PKC1, null mutant w/O phenotype, high level of overexpression is lethal: Has a potential coiled-coil domain | 1 | |
| PAG1649UP | YER183c | | unknown function | 1 | syntenie; two genes covered by UP-SRS |
| | YER182c | | unknown, but essential | 1 | syntenie, two genes covered by UP-SRS |
| PAG1650RP | YOR317w | FAA1 | :long-chain fatty acid CoA ligase (fatty acid activator 1), can incorporate exogenous myristate into myristoyl-CoA and other fatty acids to the CoA derivatives | 1 | |
| PAG1650UP | YMR100W | | unknown function | 1 | |
| PAG1651RP | YNL121c | TOM70 | MT specilized import receptor of the outer membrane, has tetratricopeptide repeats | 1 | syntenie |
| PAG1651UP | YNL123w | | unknown function | 1 | syntenie, two genes covered by UP-SRS |
| | YNL122c | | unknown function | 1 | syntenie; two genes covered by UP-SRS |
| PAG1652RP | YOL095c | | sim to DNA helicase pcrA | 1 | syntenie |
| PAG1652UP | YOL094c | RFC4 | Replication Factor C , 37kD subunit | 1 | syntenie |
| PAG1653RP | YHR047c | AAP1 | see ATP8,ORC6;Highly similar to aminopeptidase yscII (*S. cerevisiae*), AMPE_MOUSE, and several other zinc metalloproteases | 1 | |
| PAG1653UP | YHR074w | | Weak similarity to spore outgrowth factor B (sporulation protein OUTB, *B. subtilis*) | 1 | |
| PAG1654RP | YMR196w | | unknown function | 1 | very end of the gene |
| PAG1654UP | YMR196w | | unknown function | 1 | very start of gene, w/o promoter |
| PAG1655RP | YNL202w | SPS19 | sporulation specific protein, probably peroxisomal, ends in SKL* | 1 | syntenie |
| PAG1655UP | YNL200c | | contains a possible signal-peptide, predicted to be extracellular | 1 | syntenie; two genes covered by UP-SRS |
| | YNL201c | | protein involved in the regulation of carbon metabolism | 1 | syntenie; two genes covered by UP-SRS |
| PAG1656RP | YHR201c | PPX1 | degrades polyphosphate, converting ADP to ATP | 1 | |
| PAG1656UP | YJR141w | | unknown protein | 1 | |
| PAG1657RP | YJL130c | URA2 | multifunctional pyrimidine biosynthesis protein | 1 | from codon 1781 to the C-terminus |
| PAG1657UP | YKR051w | | unknown protein | 1 | |
| PAG1659RP | YBR038w | CHS2 | Chitin Synthase II, responsible for primary septum disk; Mutants resistant to calcofluor white, 8 TMD, | 1 | syntenie |
| PAG1659UP | YBR037c | SCO1 | mutant is unable to grow on non-fermentable c-sources Membrane location is altered in an rho0 strain | 1 | syntenie |
| PAG1660RP | YBL004w | | unknown function; has 12 TMD | 1 | codons 800–1033 |
| PAG1660UP | YBL004w | | | 1 | codons 2167–1951; C-terminus missing |
| PAG1664RP | YDL052c | SLC1 | | 1 | syntenie, same as PAG1635 |
| PAG1664UP | YDL054c | | unknown function, putative transmembrane protein | 1 | syntenie; same as PAG1635 |
| PAG1666RP | MITO-DNA | | | | |
| PAG1666UP | MITO-DNA | | | | |
| PAG1667RP | YMR061w | RNA14 | component of pre-mRNA 3' end processing factor involved in poly(A) site choice, interacts with Rna15p, Fip1p, and Pap1p | 1 | same as PAG1611 |
| PAG1667UP | YKL075c | | unknown protein | 1 | same as PAG1611 |
| PAG1669RP | YLR277C | BRR5 | protein required for processing of mRNA 3' end | 1 | syntenie |
| PAG1669UP | YLR281c | | unknown, however there are other overlapping ORF's | 1 | syntenie; YLR278c:protein with sim to transcription factors, has Zn(2)- Cys(6) fungal- type binuclear cluster domain in the |

TABLE 1-continued

| pAG name | Yeast Name | Gene Name | Brief Description | HC | Additional Comments |
|---|---|---|---|---|---|
| PAG1670RP | YJL191w | CRY2 | ribosomal protein rp59 (*E. coli* S11, rat and human S14) | 1 | N-terminal region, len 1341aa syntenie; two genes covered by RP-SRS, same as PAG1603 |
|  | YJL190c | RPS24A | RPS24A:ribosomal protein RPS24 (*E. coli* S8, mammalian S24) | 1 | syntenie, same as PAG1603 |
| PAG1670UP | YJL069c |  | unknown protein | 1 | same as PAG1603 |
| PAG1671RP | YBR112c | SSN6 | has 10 TPR repeats (TPR-Tetratricopeptide) | 2 |  |
| PAG1671UP | YML042w | CAT2 | Carnitine-o-acetyltransferase, peroxisomal and mitichondrial, not required for growth on fatty acids,Catalytic activity: undetected in cells grown on glucose, increased on glycerol or acetate, very high on oleate | 1 | codons 442 to 655 promoter and terminator missing; regulatable promoter? |
| PAG1672RP |  |  |  | 4 | sp\|P24197\|YGID_ECOLI HYPOTHETICAL 28.3 KD PROTEIN IN T . . . -3 73 1.2e-10 5 |
| PAG1672UP | YDL203c |  | unknown, has weak sim to SKT5 | 1 |  |
| PAG1673RP | YDL104c | QRI7 | sim to *E. coli* orfX gene; may be in a cold spot for recombination | 1 | syntenie |
|  | YDL105w | QRI2 | unknown | 1 | syntenie; two genes covered by RP-SRS |
| PAG1673UP | YMR166c |  | sim to members of the MCF MT carrier protein family | 1 | not in syntenie to RP-SRS |
| PAG1674RP | YPL072w | LPF12 | unknown function | 1 | syntenie |
| PAG1674UP | YPL075w | GCR1 | required for expression of glycolytic genes. binds to DNA with high affinity but low specificity, motif CTTCC, contains a leucine zipper that is necessary and sufficient for homodimerization | 1 | syntenie; YPL074w:YTA6:CDC48-ATPase- family |
| PAG1675RP | YMR259C |  | unknown, has sim to YGR273p | 1 |  |
| PAG1675UP | YML100w | TSL1 | alternate third subunit of the trehalose-6-phosphate synthase complex, probably regulatory | 1 |  |
| PAG1676RP | YLR429W |  | unknown, with WD-40 repeats | 1 | syntenie |
| PAG1676UP | YLR426w |  | rotein with sim to FOX2p, *E. coli* 3-oxoacyl-reductase and insect-type alcohol dehydrogenase/ribitol dehydrogenase family | 1 | syntenie, YLR427w:len 670aa,unknown function |
| PAG1677RP | YNL116w |  | unknown function | 1 |  |
| PAG1677UP | YNR044w |  | sim relies on Ser-residues | 2 |  |
| PAG1678RP | YLR347c | KAP95 | karyopherin-beta, acts to target proteins with nuclear localization signals (NLS) to the nuclear pore complex | 1 | syntenie; YLR345w: len 509: sim to rat fructose-2,6-bisphosphatase;YLR346c :len 101: unknown |
| PAG1678UP | YLR344w | RPL33A |  | 1 | syntenie |
| PAG1680RP | YLR107w |  | Similar to *S. pombe* hypothetical protein C22G7.04p | 1 | syntenie; YLR108c: unknown, len485aa; YLR109w: sim to *C. boidinii* peroxisomal membrane proteins A and B |
| PAG1680UP | YLR110c |  | cell wall protein, probably highly O-glycosylated, null mutant fails to flocculate; repeat domains account for 70% of the protein FLO1 homolog | 1 | complete gene |
| PAG1681RP | YER172C | BRR2 | RNA-helicase reoated protein required for pre-mRNA splicing | 1 | syntenie |
| PAG1681UP | YER171w | RAD3 | DNA-helicase component of RNA polymerase transcription initiation factor TFIIH(factor b) and the nucleotide excision repairosome | 1 | syntenie |
| PAG1682RP | YKL214C |  | unknown function | 1 | syntenie; two genes covered byRP-SRS |
|  | YKL213c | DOA1 | DOA1:Protein involved in ubiquitin proteolysis, has WD-40 repeats | 1 | syntenie |
| PAG1682UP | YKL212w | SAC1 | Protein involved in Golgi function and actin cytoskeletal organization, required for growth only at low temperature; mutants are inositol auxotrophs; Sac1p is not associated with actin cytoslkeleton | 1 | syntenie |
| PAG1683RP | YDL077c |  | unknown protein | 1 | start of gene to codon 164, same as PAG1133 |
| PAG1683UP | YDL077c |  |  | 1 | very end of gene; maybe including terminator, same as PAG1133 |
| PAG1684RP | YLR425W |  | unknown function | 1 | syntenie |
| PAG1684UP | YLR424w |  | protein with sim to retrovirus-related | 1 | syntenie; somehow disturbed by |

TABLE 1-continued

| pAG name | Yeast Name | Gene Name | Brief Description | HC | Additional Comments |
|---|---|---|---|---|---|
| | | | protease (only in a short region near the N-terminus | | overlapping hitno 1 |
| PAG1685RP | YNL330c | RPD3 | Transcription modifier required for full repression or full activation of many genes including PHO5, STE6, SPO13, HO, TRK2, and TY2 | 1 | |
| PAG1686RP | YLR129w | DIP2 | DOM34p interacting protein, with WD-40 repeats. | 1 | |
| PAG1687RP | | | | 4 | |
| PAG1687UP | YOR240w | | unknown function | 1 | |
| PAG1688RP | YML125c | | sim to NADH-cytochrome b5 reductase | 1 | syntenie; same as PAG1576 |
| PAQ1688UP | YML124c | TUB3 | TUB3 rather than TUB1 due to syntenie | 1 | same as PAG1576 |
| PAG1689RP | YKR059w | TIF1 | Translation initiation factor 4a eIF4A of the DEAD-box family | 1 | |
| PAG1689UP | YJL140w | RPB4 | RNA-POLII, fourth largest subunit | 1 | syntenie, two genes covered by UP-SRS |
| | YJL139c | YUR1 | Mannosyltransferase of KRE2/KTR1/YUR1 family | 1 | syntenie, almost overlapping genes |
| PAG1690RP | YDL033c | | sim to *H. influenza* protein HI0174 | 1 | syntenie |
| PAG1690UP | YDL035c | | unknown function; putative transmembrane protein | 1 | syntenie; YDL034w: unknown, len 114; overlapping with YDL035c |
| PAG1691RP | YHR023w | MYO1 | Myosin heavy chain (myosin II), involved in septation and cell wall organization; null mutant has abnormal nuclear migration and cytokinesis, has delocalized chitin deposition , are defective in cell division, are osmosensitive,, and have an altered budding pattern, mutants show wild-type movement of actin cortical patches. Molecule is a dimer with two heads and a long coiled coil tail | 1 | N-Term down to codon 198 |
| PAG1691UP | | | | 4 | |
| PAG1692RP | MITO-DNA | | | | |
| PAG1692UP | MITO-DNA | | | | |
| PAG1694RP | YBR280c | | sim to SRM1/PRP20 | 1 | syntenie |
| PAG1694UP | YBR281c | | unknown, with WD40 repeats | 1 | syntenie |
| PAG1695RP | YPR194C | | unknown function | 1 | |
| PAG1695UP | YPL010c | | unknown function | 1 | |
| PA01696RP | YCL036w | | unknown function | 1 | syntenie. Hit no1: YDR514C:unknown has sim to YCL036w |
| PAG1696UP | YCL035c | | sim to thioltransferase | 1 | syntenie |
| PAG1698RP | YHL002w | | has one SH3-domain;Similar to several proteins with SH3 domains | 1 | syntenie |
| PAG1698UP | YHL004w | MRP4 | MT ribosomal protein of the small subunit | 1 | YHL003c:LAG1:Longevity assurance protein, has sim to YKL008p and mammalian UOG-1 protein; has 7 TMD |
| PAG1699RP | YNL126w | | unknown function, has weak sim to YJL207p | 1 | same as PAG1514 |
| PAG1699UP | YHR121w | | unknown protein | 1 | same as PAG1514 |
| PAG1700RP | | | AG-TEF | 1 | 481 out of 491 bases are identical |
| PAG1700UP | | | | 4 | |

TABLE 2

*Ashbya gossypii* sequences with (>100 codons) ORF's that show no homology to *S. cerevisae*

| | |
|---|---|
| PAG1002RP | open frame > 450 nt in −2 |
| PAG1005RP | open frame > 350 nt in −1 |
| PAG1005UP | open frame 300 nt in −3 |
| PAG1006RP | open frame > 450 nt in −3 |
| PAG1006UP | open frame > 350 nt in −1 |
| PAG1010I1 | open frame 350 nt in +3 and −2 |
| PAG1010I2 | open frames whole length in +3 and −3 |
| PAG1018UP | open frames whole length in +1 and −3 |
| PAG1019UP | open frame whole length in +1 |
| PAG1022RP | open frame whole length in −1 |
| PAG1022UP | open frame > 350 in +1 |

TABLE 2-continued

*Ashbya gossypii* sequences with (>100 codons) ORF's that show no homology to *S. cerevisae*

| | |
|---|---|
| PAG1024UP | open frames whole length in +3 and −2 |
| PAG1033UP | open frames whole length in −2 |
| PAG1035I1 | open frame 300 nt in −3 |
| PAG1035I2 | open frame > 350 nt in −1 |
| PAG1035RP | open frames > 350 nt in −1 |
| PAG1036RP | open frames 350 nt in −3, 300 nt in +2 |
| PAG1038RP | open frame whole length in −3 |
| PAG1042RP | open frame > 300 nt in −2 |
| PAG1042UP | open frame 300 nt in +1 |
| PAG1046UP | open frame 350 nt in +1 |
| PAG1053RP | open frame whole length in −1 |
| PAG1054RP | open frame whole length in −2, 350 nt in +1 |
| PAG1054UP | open frames 350 nt in +3, +2, and −2 |
| PAG1055UP | open frames 350nt in +3 and −2 |
| PAG1057UP | open frame 400 nt in +3 |
| PAG1062UP | open frame 300 nt in −1, many stops in other frames |
| PAG1071CRP | open frame > 350 nt in +2 and −3, possible chimeric plasmid, hybridizes to A.g. chr. II and III |
| PAG1071CUP | open frame whole length in −3, possible chimeric plasmid, hybridizes to A.g. chr. II and III |
| PAG1081RP | open frame whole length in +3 |
| PAG1083RP | open frame whole length in −2, many stops in other frames |
| PAG1214RP | open frame whole length in −2 |
| PAG1216RP | open frame > 300 nt in +2 |
| PAG1220RP | open frame 350 nt in +2 (S-rich) |
| PAG1223UP | open frame whole length in −2, open frames > 350 nt in +2 and −3 |
| PAG1224UP | open frame > 300 nt in −1 |
| PAG1225UP | open frames > 500 nt in +2 (S-rich) and > 450 nt in −1 |
| PAG1226RP | open frame whole length in +2 |
| PAG1231RP | open frame > 350 nt in −1 |
| PAG1231UP | open frames > 400 nt in +1 |
| PAG1233RP | open frames whole length in +2 and nearly whole length in −3 |
| PAG1245UP | open frames > 400 nt in −2 and > 300 nt in +1 |
| PAG1247RP | open frames whole length in −3, open frames > 400 in +3 and +2 |
| PAG1251RP | open frames > 450 nt in +1 and > 400 nt in −3 |
| PAG1253RP | open frame > 500 nt in +2 |
| PAG1263UP | open frame > 400 nt in −1 |
| PAG1265RP | open frame 450 nt in −1 |
| PAG1266UP | open frame > 400 nt in |
| PAG1267UP | open frame nearly whole length in +1 |
| PAG1272UP | open frame whole length in +3 |
| PAG1275RP | open frame whole length in −3 |
| PAG1277UP | open frame > 500 nt in −1 |
| PAG1280RP | open frame whole length in −2, two separated short blocks with high homology −> funct. domain? |
| PAG1286RP | open frame > 400 nt in −3, |
| PAG1286UP | open frames > 500 nt in +1 and −3 |
| PAG1293UP | open frames 300 nt in +2 and > 400 nt in +1 |
| PAG1294RP | open frame > 300 nt in +3 |
| PAG1299RP | open frame > 350 nt in −1 |
| PAG1300RP | open frames > 350 nt in +1 and −2 |
| PAG1303RP | open frame > 350 nt in +2 or ending frame > 250 nt in −1 |
| PAG1303UP | open frame whole length in −2 |
| PAG1305RP | open frame whole length in −2 |
| PAG1306UP | open frame whole length in +2 |
| PAG1311UP | open frame 500 nt in −2 |
| PAG1312UP | open frame whole length in +1 |
| PAG1314RP | open frame > 350 nt in −3 |
| PAG1318RP | open frame > 300 nt in −2 |
| PAG1318UP | open frames > 450 nt in −3 and > 600 nt in +2 |
| PAG1331UP | open frames > 400 nt in +2 > 350 nt in +3 and > 350 nt in +3 |
| PAG1332RP | open frame nearly whole length in +1 |
| PAG1334RP | open frame whole length in −2 and +2 |
| PAG1335RP | open frames whole length in −2 and 300 nt in +3 |
| PAG1356RP | open frame whole length in −3 |
| PAG1357RP | open frame whole length in −2 |
| PAG1362UP | open frames > 350 nt in +3 and > 300 nt in −3 |
| PAG1363UP | open frame whole length in +2 |
| PAG1365RP | open frame whole length in +3 |
| PAG1366RP | open frame whole length in +2 |
| PAG1387UP | open frames > 450 nt int −3, > 350 nt in +1 and +2 |

SEQUENCE LISTING (1) GENERAL INFORMATION:

(iii) NUMBER OF SEQUENCES: 1152

(2) INFORMATION FOR SEQ ID NO:1:

(i) SEQUENCE CHARACTERISTICS:
       (A) LENGTH: 60 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "primer"

(xi) SEQUENCE DESCRIPTION: SEQ ID NO:1:

TTTTACTAGA TATTTTATAT CCAAGAAGCA ATAGATCAAA ATGGCTGCGG TAAAGAGAAT        60

(2) INFORMATION FOR SEQ ID NO:2:

(i) SEQUENCE CHARACTERISTICS:
       (A) LENGTH: 60 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "primer"

(xi) SEQUENCE DESCRIPTION: SEQ ID NO:2:

CTGGAGCTCC ACCGCGGTGG CGGCCGCTCT AGAACTAGTG CGCCAACGTT GCGAGATATA        60

(2) INFORMATION FOR SEQ ID NO:3:

(i) SEQUENCE CHARACTERISTICS:
       (A) LENGTH: 1281 base pairs
       (B) TYPE: nucleic acid
       (C) STRANDEDNESS: single
       (D) TOPOLOGY: linear (ii) MOLECULE TYPE: cDNA (vi) ORIGINAL SOURCE:
       (A) ORGANISM: AgLEU2

(ix) FEATURE:
       (A) NAME/KEY: CDS
       (B) LOCATION: 1..1116

(xi) SEQUENCE DESCRIPTION: SEQ ID NO:3:

```
ATG GCT GCG GTA AAG AGA ATT GTG GTG CTT CCG GGC GAC CAC ATC GGC         48
Met Ala Ala Val Lys Arg Ile Val Val Leu Pro Gly Asp His Ile Gly
 1               5                  10                  15

CGC GAG GTC GTG GAG GAG GCG GTG AAG GTG CTT GGC GCC GTG GAG CAG         96
Arg Glu Val Val Glu Glu Ala Val Lys Val Leu Gly Ala Val Glu Gln
            20                  25                  30

AGC CTG TCG GAC GTG CAC TTT GAC TTC CAG TAC CAC CTG GTC GGC GGG        144
Ser Leu Ser Asp Val His Phe Asp Phe Gln Tyr His Leu Val Gly Gly
        35                  40                  45

GCG GCC ATC GAC GCC ACG GGG TCG GCG CTG CCG GAC GAG GCG CTG GGC        192
Ala Ala Ile Asp Ala Thr Gly Ser Ala Leu Pro Asp Glu Ala Leu Gly
    50                  55                  60

GCG GCG AAG GAG GCG GAC GCG GTA CTG CTG GGG GCA GTT GGC GGA CCG        240
Ala Ala Lys Glu Ala Asp Ala Val Leu Leu Gly Ala Val Gly Gly Pro
65                  70                  75                  80
```

```
AAG TGG CAG GGC GGC GCG GTC AGG CCG GAG CAG GGC CTG CTG AAA CTG        288
Lys Trp Gln Gly Gly Ala Val Arg Pro Glu Gln Gly Leu Leu Lys Leu
             85                  90                  95

AGA CAG GAG TTG GGC GTG TAC GCG AAC CTG CGT CCC TGC AAC TTT GCG        336
Arg Gln Glu Leu Gly Val Tyr Ala Asn Leu Arg Pro Cys Asn Phe Ala
            100                 105                 110

GCG GAC TCG CTG CTC GAG CTG TCG CCG CTG CGC CCC GAG ATT GCC CGG        384
Ala Asp Ser Leu Leu Glu Leu Ser Pro Leu Arg Pro Glu Ile Ala Arg
            115                 120                 125

GAT ACC GAT ATT ATG GTG GTG CGG GAG CTG CTG GGC GGG AGC TAC TTC        432
Asp Thr Asp Ile Met Val Val Arg Glu Leu Leu Gly Gly Ser Tyr Phe
            130                 135                 140

GGC GAG CGC CAC GAG GAC GAG GGC GAC GGA GTC GCG TGG GAC ACC GAC        480
Gly Glu Arg His Glu Asp Glu Gly Asp Gly Val Ala Trp Asp Thr Asp
145                 150                 155                 160

AAG TAC ACC GTG AAG GAG GTG CAG CGC ATC GCG CGC ATG GCG GGG TTC        528
Lys Tyr Thr Val Lys Glu Val Gln Arg Ile Ala Arg Met Ala Gly Phe
                165                 170                 175

CTG GCT CTG CAG CAC GAC CCG CCG CTA CCT GTG TGG TCG CTG GAC AAG        576
Leu Ala Leu Gln His Asp Pro Pro Leu Pro Val Trp Ser Leu Asp Lys
            180                 185                 190

GCG AAC GTC CTG GCC AGC TCC CGC CTG TGG CGC AAG ACC GTG GAG GAA        624
Ala Asn Val Leu Ala Ser Ser Arg Leu Trp Arg Lys Thr Val Glu Glu
            195                 200                 205

ACC TTC CAG AGT GAG TTC CCA AAC GTG CAA TTG CAA CAC CAG TTG ATA        672
Thr Phe Gln Ser Glu Phe Pro Asn Val Gln Leu Gln His Gln Leu Ile
            210                 215                 220

GAT TCA GCT GCA ATG ATT TTG GTC AAG AAC CCG CGG GCG TTC AAC GGG        720
Asp Ser Ala Ala Met Ile Leu Val Lys Asn Pro Arg Ala Phe Asn Gly
225                 230                 235                 240

GTC GTG GTG ACG AGC AAC ATG TTC GGG GAC ATT ATC TCT GAC GAA GCG        768
Val Val Val Thr Ser Asn Met Phe Gly Asp Ile Ile Ser Asp Glu Ala
                245                 250                 255

TCG GTG ATC CCA GGG TCC CTA GGG TTG CTG CCA TCG GCC TCG CTC GCG        816
Ser Val Ile Pro Gly Ser Leu Gly Leu Leu Pro Ser Ala Ser Leu Ala
            260                 265                 270

TCT TTG CCG GAT AGC AAG AGC GCC TTT GGC CTC TAC GAG CCC TGC CAC        864
Ser Leu Pro Asp Ser Lys Ser Ala Phe Gly Leu Tyr Glu Pro Cys His
            275                 280                 285

GGC TCT GCG CCC GAT CTG CCC GCC GGG AAG GCG AAC CCG ATC GGA TGC        912
Gly Ser Ala Pro Asp Leu Pro Ala Gly Lys Ala Asn Pro Ile Gly Cys
290                 295                 300

ATC CTC TCT GCT GCC ATG ATG CTG AAG TTG TCG TTG AAC ATG GTT GCT        960
Ile Leu Ser Ala Ala Met Met Leu Lys Leu Ser Leu Asn Met Val Ala
305                 310                 315                 320

GCC GGC GAG GCG GTC GAG CAG GCA GTG CAG GAG GTG TTG GAC TCG GGA       1008
Ala Gly Glu Ala Val Glu Gln Ala Val Gln Glu Val Leu Asp Ser Gly
                325                 330                 335

GTC AGA ACG GGC GAC CTG CTC GGC TCG AGC TCC ACT TCG GAG GTT GGC       1056
Val Arg Thr Gly Asp Leu Leu Gly Ser Ser Ser Thr Ser Glu Val Gly
            340                 345                 350

GAC GAA ATT GCG CTT GCA GTT AAG GAA GCC TTG CGC AGG CAA TCC GCA       1104
Asp Glu Ile Ala Leu Ala Val Lys Glu Ala Leu Arg Arg Gln Ser Ala
            355                 360                 365

GCT GGT CTG AGC TAGCCTCGAG GACCCTTCTC TTTAGACTAT TCTACTCTTA           1156
Ala Gly Leu Ser
            370

TGCACGTAAA AAATTCTAGG AAATATGTAT TAACTAGGAG TAAAATAACC GGCTAGTGGC     1216

ATTCATATAG CCGTCTGTTT ACATCTACAT CACACATTTC GAGTGTATAT CTCGCAACGT     1276
```

TGGCG                                                                        1281

(2) INFORMATION FOR SEQ ID NO:4:

(i) SEQUENCE CHARACTERISTICS:
        (A) LENGTH: 372 amino acids
        (B) TYPE: amino acid
        (D) TOPOLOGY: linear (ii) MOLECULE TYPE: protein (xi) SEQUENCE DESCRIPTION: SEQ ID NO:4:

```
Met Ala Ala Val Lys Arg Ile Val Val Leu Pro Gly Asp His Ile Gly
 1               5                  10                  15

Arg Glu Val Val Glu Glu Ala Val Lys Val Leu Gly Ala Val Glu Gln
                20                  25                  30

Ser Leu Ser Asp Val His Phe Asp Phe Gln Tyr His Leu Val Gly Gly
            35                  40                  45

Ala Ala Ile Asp Ala Thr Gly Ser Ala Leu Pro Asp Glu Ala Leu Gly
        50                  55                  60

Ala Ala Lys Glu Ala Asp Ala Val Leu Leu Gly Ala Val Gly Gly Pro
65                  70                  75                  80

Lys Trp Gln Gly Gly Ala Val Arg Pro Glu Gln Gly Leu Leu Lys Leu
                85                  90                  95

Arg Gln Glu Leu Gly Val Tyr Ala Asn Leu Arg Pro Cys Asn Phe Ala
                100                 105                 110

Ala Asp Ser Leu Leu Glu Leu Ser Pro Leu Arg Pro Glu Ile Ala Arg
            115                 120                 125

Asp Thr Asp Ile Met Val Val Arg Glu Leu Leu Gly Gly Ser Tyr Phe
        130                 135                 140

Gly Glu Arg His Glu Asp Glu Gly Asp Gly Val Ala Trp Asp Thr Asp
145                 150                 155                 160

Lys Tyr Thr Val Lys Glu Val Gln Arg Ile Ala Arg Met Ala Gly Phe
                165                 170                 175

Leu Ala Leu Gln His Asp Pro Pro Leu Pro Val Trp Ser Leu Asp Lys
                180                 185                 190

Ala Asn Val Leu Ala Ser Ser Arg Leu Trp Arg Lys Thr Val Glu Glu
            195                 200                 205

Thr Phe Gln Ser Glu Phe Pro Asn Val Gln Leu Gln His Gln Leu Ile
        210                 215                 220

Asp Ser Ala Ala Met Ile Leu Val Lys Asn Pro Arg Ala Phe Asn Gly
225                 230                 235                 240

Val Val Val Thr Ser Asn Met Phe Gly Asp Ile Ile Ser Asp Glu Ala
                245                 250                 255

Ser Val Ile Pro Gly Ser Leu Gly Leu Leu Pro Ser Ala Ser Leu Ala
                260                 265                 270

Ser Leu Pro Asp Ser Lys Ser Ala Phe Gly Leu Tyr Glu Pro Cys His
            275                 280                 285

Gly Ser Ala Pro Asp Leu Pro Ala Gly Lys Ala Asn Pro Ile Gly Cys
        290                 295                 300

Ile Leu Ser Ala Ala Met Met Leu Lys Leu Ser Leu Asn Met Val Ala
305                 310                 315                 320

Ala Gly Glu Ala Val Glu Gln Ala Val Gln Glu Val Leu Asp Ser Gly
                325                 330                 335

Val Arg Thr Gly Asp Leu Leu Gly Ser Ser Ser Thr Ser Glu Val Gly
```

```
                340                 345                 350
Asp Ala Ile Ala Leu Ala Val Lys Glu Ala Leu Arg Arg Gln Ser Ala
                355                 360                 365
Ala Gly Leu Ser
    370
```

(2) INFORMATION FOR SEQ ID NO:5:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:5:

```
CATGATTACG CCAAGCGCGC                                              20
```

(2) INFORMATION FOR SEQ ID NO:6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:6:

```
CCAAGCACAT TTCACCTGCG                                              20
```

(2) INFORMATION FOR SEQ ID NO:7:

(i) SEQUENCE CHARACTERISTICS:
        (A) LENGTH: 4985 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1489

(xi) SEQUENCE DESCRIPTION: SEQ ID NO:7:

```
GATCGTAACA TTGCCCAATA GCTTGTTTAG CTCGTCATCG TTTCTGATGG CTAGCTGTAG    60
ATGTCTTGGG ATGATTCTGG TCTTCTTGTT GTCTCTGGCG GCGTTACCGG CCAACTCTAG   120
GATTTCGGCG GCCAAGTATT CTAGCACAGC GGTTAGGTAC ACAGGCGCGC CCGACCCGAT   180
TCTCTGTGCG TAGTTGCCCT TTCTGAGCAA TCTGTGGACT CTACCGACAG GGAAAGTCAA   240
ACCGGCCTTA GCCGATCTCG ACTGCGAAGC CTTGGCGGCA GAACCAGCTT TACCTCCTTT   300
ACCAGACATT ATTTGTGTTG TGTGTGTGTG TGTGTGTTTA GTGTGAACTG CGTGTGCTAT   360
GAGAAAACAC TACGCTGAAA CTGCTAAATA ATCCAGACAG GTCCCCCCAC CGCAAAGGAT   420
CCACGCTATA CTTCTCTCTA CATATTTATA CTTGTCCTTT TGCCTTCTAA TCCTCGATCG   480
TACGCGTCTG ACGCTTCAAC AGACGCTTCA CCTAGACGCT CGACCTGTGC GGCCTGGTTT   540
TTTCGCATGA CATGTCCGTG CTGGTTTTTT CGCGCTGAAA AGGAAAGCGC GTGGCTCCCA   600
GCACCAGAGC CGTACTAGCT CTTTCGCGTG CTGTCCTATG TGCACGCGAA ATTTTCATAC   660
TGTAGAGTGT GCCATCAGCT TCACAGAGTA CAAACGGTAG GCGAGTGGAT ACGCGTCTTG   720
```

-continued

```
TAGCCGGACG TGAATGGCAG AACTTTTTGG CAGTCGCGTA ATCTTAGATT GAAAGTATTT      780
AAGTGGAACG TATAAAACAA AAGTTCGGGC TGAAGAGGAC CTCTTTTGGC GTCTGCTACT      840
TCCCAGTTAT CTGTTGGATA CTAAGCATAT CGAACTCTAA TTGCAATTCT AAAGATGGCA      900
CCAAAGGCTG AGAAGAAACC TGCTTCCAAG GCCCCAGCGG CAAAGAAGAC CACTGCTTCT      960
ACCGACGCTT CTAAGAAGCG GACGAAGACT AGAAAGGAGA CCTACTCCTC TTACATTTAC     1020
AAGGTTCTTA AGCAGACTCA CCCAGATACT GGTATCTCGC AGAAGTCTAT GTCCATTTTG     1080
AACTCGTTTG TGAACGATAT CTTTGAGAGA ATCGCGTCTG AGGCATCCAA GCTTGCGGCC     1140
TACAACAAGA AGTCTACGAT CTCTGCTAGA GAAATCCAGA CTGCTGTCAG ATTGATCTTG     1200
CCCGGTGAGC TAGCCAAGCA CGCCGTGTCT GAGGGTACCA GAGCTGTTAC CAAGTACTCG     1260
TCTTCTACCC AAGCCTGAAT GGAACTCATT CTTAGAATGA AGAACTTCC TTCAAGAAGG      1320
TTCTCGTCAG CTAGTGCTTG TGGGACCCGC CTCTTATTCC AGAGCAGCTG CGGCAGAGCG     1380
GTATGTGGTA CGTTCCGTTT CATCATTTTG TATTATTAGT ACATGTAGAA ATAGGGTTTT     1440
CTGGTTTCAT AATTCGGTAT AAATTCCAAC GTAATGTATA TTAGATAAGT TTTAAACTAG     1500
TAATCGGAGA GCTTCTTTTC AACCACGTCT ACCTTGTCTT GCGCAGTCTG CTGTTTGTCT     1560
GTTCTAGTTC CGAGCCTCAT TTCGGTGTGG ATTCTAACGT ATCCCAATTC GTGGCTGTAT     1620
TCGTGCAACT GGCCGATGAG GCTCATGACC TCGTCCCAAG GGCCCTCAAT CGTCGTTCCA     1680
AAGCTGTGCA TAGTGCTTTT CAAGTGACTC TCCCTAATTC GTTTCTCAAT CTTGGTGACA     1740
TAGTCTGAGA CACTTGGTGA GCTAGTACCT AGCTATGATT CAAAAGTTTA GTATATTGTT     1800
TTATATATGC AGCTGGAGAT GTGAACATAC CGGCACCATG CAAATGTCCA CTAATGTGTG     1860
CAGCTTCGAC ATTTTGATTT CTACCTTCAG AGTATTGGAA TATGTTCTTG TATGTAACGT     1920
CTACTAATTT TCTGGTTTAT ATCGCTGATC TTAAGGGAGA TAATTTCGTT CACCCATCAC     1980
ACAGAAGTTT TAAGTACAAA ACTTGTCCCC AGATATAGCA AGTCATCAAT TCAGGTATAA     2040
TTGGTGTGCA TGCTAATTTG AAGGGCTGTT ATATAGTTGA AGTTGTTCTT TTGGCATTGA     2100
GCCAAATTTG GATTCTATTC AGTAGTATTG AACATCAAGT CTCCAAAGCT GAAGTCTGAA     2160
GCAAAACATC TCAATAGCTA TAGAACTCTA GCAAACAACA GACCAGAGCT TATATCATGA     2220
CACATTATAA GCTCAGCTAT TACTCTGAGT GATAGAGTGA CCCTCAATTA GTTGGTTCAT     2280
TTTATATATA AAAATATAAA ACTATAGCTA TTTCAAATGA CTACTAACTA ATACGAGAGA     2340
AGAAAACAAA TTAAACACGA TGGTCTACAG ATAGCTTGAA AGAGACACTA AGAGAAATTT     2400
CAGGAAACAG TTCAGAAAAT AGCCATTCAG CTCTACAGCT CTCTTTATTA TCAAGAGTAC     2460
AGTTTCTTTC ACTAATATCG CTTAATTAAT TATATTTCTT GCCATTAAAT GCGACGGTGA     2520
CGGGATAACA ATTTTTGGCA ATTCTTCATA TTTTGATTTA AAAAAAAAAC AATTTACCAG     2580
AATTAGACGA AATAGTCGCT TACTACAAAC AGGTTCAGCC ACTGGATAAA TCTCATAGTT     2640
TAAAATATTG AGTTACAGAA ATTGGCTTAC AGAAAGCACT AGCGATTAGG CCATTTGCCA     2700
TTGATTTAAA CATGAACTAA CGAACCTCCA TGAATTACAA TAACCACAAA TTTAACCGGA     2760
CAATTAATTT TATGTAGCAG GCTCTGCCAT GGGAATAGCT TTACGTGAAC AGGATATTTA     2820
ACGTATATCC TTGTTATGAT AAAGACTTTG ATAGGTGCTT ATACTTGCAA GTTCATATTT     2880
TACAGTTAAA TATCTAAATT TAATATATTA CGCAGTTCAC GCAATGTAGC ACGTGACATA     2940
AATATGAAAT TTACTATGTG CTTGCTTTAT TTAAATAAG TTTATAAAGT TAGTAAAAAT      3000
ATCAGAGTAT ATATATTTAA TTAAATAATA TCCTAAAATA TACTAATACA ATTTATCAAT     3060
```

```
TAAGCTTTAT ACACTTTATA AATAGTTATA ATTATAGATG TGTATACGAT TTCCGAAACA      3120

TAAAAATATT TCACTGCTTT CGTGAAAAAT AATTTTTTTA TTATAAAACA ATCCCTAATA      3180

TAGTATTACC TCCAATTATG AGTCTATCGT AATATATGAA GTACTACCAA AATTTACCAC      3240

TGATTTTTCA AAAAAAAAAC ACCATTTTTC AAAAATATTT TATTAACTGA ATTTTTTATA      3300

ATTAAATTTT TTATATCTAT ATAGAATATC TATTATACGC AAGAAAAACC AAAAAGTACC      3360

CTATAAGTAG GTACCGCTTG TCCACATTAT AATAAAAAAA GTGAAGTACT CATCAATACT      3420

TTTATTTAGG ATACCTGCAG TCTAATATCC CTTCACGTAA GTTACTTAGT GCACAATATT      3480

CACAGTGAGT TAGTAACCCG GTTCAGATCA AGGCATACCG AGCTTTCTCT TCTGGCTTCA      3540

TATGCTTAAA GAAAATATCA GGGACGGTGC AGTTAGCTAA AGCTCTCTTA GCATAAGTAT      3600

TCATAAATTT CAAACCTAAG ATATAACTGG AATTGACCCA GCCAAATCCT TCAGTAGCAA      3660

CACCTTTAAA GTCTGCACCT TGGTTACCAT ATTCGGCATC AACTCTATGA GGATCTGTGC      3720

CTCTGGTAAC GTCGTATTTC TCTACTACGA TACCATTGTA GTCGACAAAT GCCTTGGTCA      3780

TTAAAAATAA CCACCTATAG GCCAACCTTC TTGCAACTCC TGTAAATCCG TAATTATCTA      3840

ACCCGGTCCA AGCAAGCATT TGATGAGGGG CCCAACCATA AGGGTAATCC CATTGCCTGC      3900

TTGGTCTATT CATTGTTATC TCACCCCGAG ACTCCTCAGT ACAGGCAACC AGGCCTCCTA      3960

GCATTTCAAG CCTTGGCAAT GCCTTCTCGA CCATAGCGTT GGCTTGTTCC TGGGTTGCCA      4020

AGCCTGCCCA CATGGCCCAA AATGTTGTTG CAGAATCGTA AGATGTTCTC TTTCCAATAT      4080

GGACATTGTA GTCATAGAAA AAGCCTGTTT CCTCGTCCCA CAAATATTTC GTGATTCTTT      4140

GCTTACGAAT GTCTGCAAGT GCCTCCCAAT GAGAAGAAGT GGTGGTTTCA CCAGCATAAT      4200

CAGTAATACT ATCATCGAAG TACTTGGAAA CCACATATGC AATATCTTTT TCGTACTTGT      4260

ATAGTAACGA ATTCAAATCA ATCGTCGCTA AGTAAGCACA GACGTTCTCT AGACGGTAAG      4320

AGGTGTCATG TCCACTCTCA CGTACAGCAC GATCATGCAA AAAGAACTCA TCTAGTTCGG      4380

GCTCGTGTAC TTCGCCGGCA TCGTACATGC ACCTGAACTC CGGAATCGTT ACATTGTGCT      4440

TTTCCGCAAA TTTCCGGCAA ATTGCGTCAA AGTGGTCAGG CTCGGTTTCT GGTGGGAAAC      4500

CGATACCATC TGGATGATAA CATGAAAGAC CCGTGGTTTT GTCGTACCGC GGTTCTGCCA      4560

TCCATACACT CTTGTATTCC TTAATGGCTG CGATGAATGC TCTTTTCAAG AAATCCACAG      4620

CGGTAGGATT TTGGTCACCA CCGAACTTTT CGAAGACCTT CAAAGCCATG TCGGTTAGGA      4680

ACGGGGGTTG TGACCGACAG AGGTAGTAGC TCCTATTGGC GTTCAATATT TTACCGTAAT      4740

GCTCTATCTC AAAGATGAAA TGCTCAACCA TCCCACGTGC TATGTCCACT TTGTTACAGT      4800

CTAGAAGACC CAAAGCCATT AGGTATGAGT CCCAGCCGTA AAGTTCATTA AAACGACCGC      4860

CCGGAACAAC GTAGGGAAAA CCAACCAATG TACTCTCACC GGTAATTGGG TCCCTGTGAC      4920

TCTCCATCGC CAAAGCAAGC AACCCCGGGC TTTCGTTCAA TGATTGCACG TGCTCCGGCG      4980

TGATC                                                                 4985

(2) INFORMATION FOR SEQ ID NO:8:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:8:
```

GTTTAGTCTG ACCATCTCAT CTG                                          23

(2) INFORMATION FOR SEQ ID NO:9:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:9:

TCGCAGACCG ATACCAGGAT C                                            21

(2) INFORMATION FOR SEQ ID NO:10:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:10:

GCTAGGGATA ACAGGGTAAT                                              20

(2) INFORMATION FOR SEQ ID NO:11:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:11:

AGGCATGCAA GCTTAGATCT                                              20

(2) INFORMATION FOR SEQ ID NO:12:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:12:

GTTTTTAGAA TATACGGTCA ACGAACTATA ATTAACTAAA CATGGGTAAG GAAAAGACTC  60
A                                                                  61

(2) INFORMATION FOR SEQ ID NO:13:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: other nucleic acid (A) DESCRIPTION: /desc = "primer"

(xi) SEQUENCE DESCRIPTION: SEQ ID NO:13:

GGTATATAAA AATATTATAT GGAAGCAATA ATTATTACTC TTAGAAAAAC TCATCGAGCA        60

(2) INFORMATION FOR SEQ ID NO:14:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:14:

GCGAGATCTG GTGTATTTAC CAATAAT                                           27

(2) INFORMATION FOR SEQ ID NO:15:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:15:

GCGAGATCTG ATGAGGCCGT CTTTTGTTG                                         29

(2) INFORMATION FOR SEQ ID NO:16:

(i) SEQUENCE CHARACTERISTICS:
        (A) LENGTH: 508 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1001RP (xi) SEQUENCE DESCRIPTION: SEQ ID NO:16:

GTGATTCGTC CGAGATTGAA AAGTCCCTAA CAATCAAAAA CAACGGGAAG GCGTACGAGG        60

AATGGCTGGA CCTGGGTAAT GGGTGCCTAT GTTGCAGTCT GAAGGACGTA GGGGTGAAGG       120

CCATCGAGGC GATGGTTTCG CGGTCGCCAG GTAAAATCGA CTACATCATA CTTGAGACAA       180

GCGGGATAGC GGACCCAGTG CCGATCGTGA AGATGTTCTG GCAGGATGAG GGTCTCAATA       240

GCTGCATCTA CATTGATGGG ATTGTGACGG TGCTGGACGC AGAGCATGTG ATGACATTGC       300

TCGACGAGGT GGCCCTCCCG CGCCAATTGC GCGGCGACCA GGTGCTGATG GAAAACCAGA       360

TGACCCNNGG GNATCTTCAG GTTGCCATGG GGNGCGGGG GNGTTGATTA AATCNACCCC       420

TGNAGGCTGN NTAAAAATCT TGGNNGGGAA AANGGTGANT ATAAGCGGCC TTTTTCGGCN       480

AATNCGGGAN TTTNGNTANN AAAGNTNT                                         508

(2) INFORMATION FOR SEQ ID NO:17:

(i) SEQUENCE CHARACTERISTICS:
        (A) LENGTH: 490 base pairs
        (B) TYPE: nucleic acid
        (C) STRANDEDNESS: single (D) TOPOLOGY: linear (ii) MOLECULE TYPE: DNA (genomic)

(vi) ORIGINAL SOURCE:
        (A) ORGANISM: PAG1001UP (xi) SEQUENCE DESCRIPTION: SEQ ID NO:17:

```
TGATCCGACC AAGAGCAGGG CTTTGGTGCG GTGAATCTCG AACTCCTGCC CCTGTGTCAG      60

CTCACCCCGG CCGAAGTCCT TCCAAAGAAG AGCTTGTAGA AAGTGTTCTT CGAACCACTC     120

GAGCTCAGCC TTGTCGCGCA GCGGCCGGCA GGTCAAGGTG ACCGTGGACA GCCGCGGATC     180

ATGGTAAGCC ACGTGGGCAT CGGGAATGTC AGAGGCACCA AAAGCATGGA GATTCAAGTA     240

CCTTGTTTAT CTCCAGATCG CCGAACTTGG TCCCGATAGA TGGGCGCGAC TGCATTAATG     300

CTACGCACTT TTTCCTCCAA CCACAGCGAT TCGTCATCAA NGCCTCCCAG CCNGTCGGAT     360

TTATCAAAAC AACCNNGTCC GCCATGGCNA GTTGNAGATG GCANGGCACT TTNTTTCCAC     420

AGACTGGNGG CCGGCAATGG GGGGGGCACC CGCGACATTA NAATTNTGTC AGACCNAAAC     480

CNCAATTGNN                                                            490
```

(2) INFORMATION FOR SEQ ID NO:18:

(i) SEQUENCE CHARACTERISTICS:
        (A) LENGTH: 571 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1002I1

(xi) SEQUENCE DESCRIPTION: SEQ ID NO:18:

```
GATCTCCGCA AATTCTCCCA AAATGGTAAG TCGTTATCCA CCTTAAATGC TTGCTCGGGT      60

AGCTTGTTCC CCAATAAATA ACGTGACCCA TCATTGAGAT CCAATACCTG GGGGAGCAGT     120

TCGCTCCAAT CGCGTACTTT CTTTAAAAAC GGAAATAGTT CATGATGGAG AGAGTACAAG     180

TTTATGTCCT CACCAAAAAC CTCACGAAGA CCTATATCTC CTTGCATGAA ACAAGTGTCG     240

AACACTCGTA GTCGTTCCAG CATGGCAGCT GTCACCGAGG CATCCTTCAT GCGACCACGC     300

GACCTTTCGA TAATTTCGTT CAGCCATTGT TGTCTCTTTT TCTTTCGCAA AGTACCACTG     360

GCATTCTTTT CCAGGGGGCA TCTCCCGAAC TGGGTTGGTC AACAGAATGT ACTGTNTGGG     420

GNGGGGTTTG GTGTTGGACG ACNTTTNGTG AAGATGGGGC ACAGTTNTGC CGTTTTTGAG     480

GNCAGGCAGA TNTGAAACAA ATTNNCGNNA ANTTCGNTTT CCCNACGCAC GGGGCCCGAN     540

TTCAGGCAAC CTNGACATTN TCGAAGTACC N                                    571
```

(2) INFORMATION FOR SEQ ID NO:19:

(i) SEQUENCE CHARACTERISTICS:
        (A) LENGTH: 521 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1002I2

(xi) SEQUENCE DESCRIPTION: SEQ ID NO:19:

| GATCTTCGAG TGGGCGAGGG ATAGTAGCGA CCGTGGCAGA CATTCATCTT GATCAATTGA | 60 |
| AGCGCCTGCT CCATGTCCTT GATGAACTGG GGAATAAATT GCCTATAGAG TTGGTGTACA | 120 |
| AGGGTAACGA CTTCTCTCGA TTGCCTATCA AAAGACTGAA AAGGTACGTT CGGCAGCACA | 180 |
| CAAAACAGCG AGTTCGGCTG GTGGACTGTT CGCGTGTACT ACGCAGTACA CATATACCTA | 240 |
| AGATAAAGAG GTTCATGAAT AAGTGGTTAG CCACTATATT CAATTCATTT GGAGGAAATA | 300 |
| ATACTACTAG ACGTGGATTG TTGGTGCCAC TGGGTTCCAA TCGATAGCTA CTTCAAACTT | 360 |
| CCCGGCTACA CTAAAAACGG GCGCTCTTGT CCTTCAAGGA TAGAACGCTT CCGGAGTACC | 420 |
| TCCCTGTTTC ATGCACAAAA GCGAACTACT CTTGGCACCA CCGCCGGAGG AGACAAACTT | 480 |
| TGGGGCAATC CTTTGAGATT TCGACACCAN TGNAAAAGNT N | 521 |

(2) INFORMATION FOR SEQ ID NO:20:

(i) SEQUENCE CHARACTERISTICS:
        (A) LENGTH: 518 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1002RP (xi) SEQUENCE DESCRIPTION: SEQ ID NO:20:

| GATCTACTAA GGAATTATGG GAATCGTGTC TTTTCTTCTT AGAAATGAAT TTGTTTGCAG | 60 |
| TCGAAGACGA GGTGGAAGAC GAGCGCGACT GTTTACTCTT GGGGAAGTTA GTCAAACAAT | 120 |
| CGCTAGATTG TATCCGCATG GTATCACCTG AGTTTCTATC TATAGGAATG CTACTATYAC | 180 |
| GGAAGTTGCG ATGCTGATGG GCATGGTTGT CATGAAAAAT AGGATGTTGG CTCCGGTTAG | 240 |
| ATGACTGMCC GAATACCTCT TCTATGATTA ATTCCTWCAA GCGGGTATTG ATTAATGTCG | 300 |
| ATCCTGTGGC GTATGATGAA ATGACTGCCG CGTCATTGCC GGTACGCCCT TGGAGTGTTT | 360 |
| GGANTTGACA AGAANNCGCT CTTAGGTGCC NGGATTCCCN GGGTTGGAAA GATGATNGCG | 420 |
| AATNCCAATT TNGGTCCAAT AGGGAATCTG GNATTATTTG TTATTGCAAT NAGGATNCCC | 480 |
| GGGAGGGGGT TNCNCTACGA AGAAGGATTA GGTTTNNC | 518 |

(2) INFORMATION FOR SEQ ID NO:21:

(i) SEQUENCE CHARACTERISTICS:
        (A) LENGTH: 441 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1002UP (xi) SEQUENCE DESCRIPTION: SEQ ID NO:21:

| GATCCACGKG AGTCGCAGCG CCAAAGGCCG CTGGGCGTCA CGATGCAGGT TATGCTGTCG | 60 |
| CGTCGACAGA GTGCGCCCCG CTGGATGAAG CCCATAAGAC TATTGAGCCA CTATATAATA | 120 |
| CCAGCTGGTT ACATGATACT ATATGGTCAT AGCATCAATT GTAGTAGCCA GGGCAGTGAG | 180 |
| GCTATAGCAG CTGGAAAGGC GACTCTGAAA AGGGATTTAT GCCAAGAGCT TCAGAAGTGG | 240 |
| ACTCAGGCCA CGCATCCAAC GGATTCTTCC TCAATTCCTC TATATTGAGC CAGAGCTCCA | 300 |
| TCTTGACCGA GGTCCCTCAT TCATATTCAT ACGAGTTACT TGAACATCCA ACAGGTGCCA | 360 |

```
TATTTAGKTT GGGGGGGTAA GTACAATANC GNTGNNGGCC GTGGAACCCC GGTCCGTTCC    420

CNGGGTTTTG GAATTTTTNG G                                              441

(2) INFORMATION FOR SEQ ID NO:22:

(i) SEQUENCE CHARACTERISTICS:
        (A) LENGTH: 513 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1003RP (xi) SEQUENCE DESCRIPTION: SEQ ID NO:22:

GATCGCTCAT GACCAAAACA ACGAAATCCA CTACATTTCG CTTGCCACTG CTCACCCAGC     60

GAAGTTTGCG GACGCTGTGA ACGAAGCTCT CTCCTCTTAC GATGACTACA ACTTCGATGA    120

CGTTCTTCCA GACCGTCTAA GACGTCTAGG TGACCTTGAG AAGAGAATTA AGTACGTGGA    180

CAACACCGAC GTTGATGTTA TCAAATCTAT CATTGAGGAG GAACTGATTA ACATGGGCAT    240

TTACAATCCA TAGATGATCT GAACTCTAGA TGATTTATAG ACTATCTAGT TAGCCTTCTA    300

GTCCTATATA CCTAATTCCA ATAGGCAGGG GGGCCTATGT CAAGTTTAAA TCCATTTTGC    360

CTTCTACTGC CGCAACGTGG TTTTTTGCAA AGCCAATTTT GCCGTCGGGG CCAACTTCAC    420

CTCANTACCC AGNTCTGNGA GTCATCANCA TTCCCCGCTN TAGGCCCCAG TGANTAGAAG    480

TGGTCTAGGT CGTTTCAAGA GGAACATNAA TNT                                 513

(2) INFORMATION FOR SEQ ID NO:23:

(i) SEQUENCE CHARACTERISTICS:
        (A) LENGTH: 504 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1003UP (xi) SEQUENCE DESCRIPTION: SEQ ID NO:23:

GATCTTTAGA CAATTATGAC ATCCAAGTTT GGTCCGTTCA GACTGGTCAG TTGCTTGACA     60

CACTCTCTGG TCACGAAGGC CCAGTCTCTT GCTTGTCTTT CAGCCGGGAA AATAGCATAC    120

TAGCCTCTGC CTCTTGGGAC AAAACTATAA GAGTGTGGCC GATATTTGGG CGGCCCCAGC    180

AAGTCGAGCC TATAGAAGCA TACTCTGATG TGCTGGATAT TTCCATGAGA CCTGATGGTA    240

AGCAGGTCGC TGTCTCCACG CTGAATGGTC AGCTGTCATT CTTCGACGTT TGAAACCTCA    300

CGGCAGGTTG GCAACAATTG CTTGCAAGAG GGACATCATA TCAGGACGCC ATTTAGAGGA    360

CCGGTTTACT CAAAGAACTT CGGCAACGGC CCAAATATTC ACAACAATCC ACTACAGTTC    420

GGCGGCTTTC AATGNTGGAG NTGGGANAAA ATCTNTTGGT NTAGAATCCN ATAAGGGTAT    480

AANCGTCATG TTCCANAAAT NATC                                           504

(2) INFORMATION FOR SEQ ID NO:24:

(i) SEQUENCE CHARACTERISTICS:
        (A) LENGTH: 530 base pairs
        (B) TYPE: nucleic acid
```

(C) STRANDEDNESS: single
            (D) TOPOLOGY: linear (ii) MOLECULE TYPE: DNA (genomic)

(vi) ORIGINAL SOURCE:
            (A) ORGANISM: PAG1004RP (xi) SEQUENCE DESCRIPTION: SEQ ID NO:24:

```
GATCTTAAAG AGGCTCAGTA TGCAGAGGCA GTTTCCAGAA GAAGACAGGC TGGGCTTCGA       60

AATCCCTCAG CTCCCGCCGT GGAAGAGTCC GCAGATGAAG CAACACACAC AACAGGGCCA      120

GCAAACGCCG CTGCGGCGGC CGCGCTGCAT CCTCGGTGCC CCTTATGAAC CGAGCAGGGC      180

GTCGTCCACT GGTGCAGGCC AAAAGCGCGA CTACGACTAC TCCGTGTTCA ATGAGAGCAG      240

GCTCCTCACT GAGAGCAAGA TAGACCAGTA CTTGAAGAGC GAGGCCGCAA CGCACAAACG      300

CGTATTCCAC CCGCGACCGC CCCCACGACG ACAGCTACCC GCCCCGACTT TGCAGCCCGC      360

TCTGCTTGCG ACAAGCTTCG GACGANGAGG GAGAGCCCCN CCCCCCTCNC AGAGNGCGCN      420

TTNGNGACCC CCCNTGGNTG TTCATCATCC CCCCANTCCT CCAGGAGAGT TTTNGAAAGG      480

GCGCCCCCNA NACNCCNTAG GATTCGTGGA GGATGGAGTN GGGCCCTTTT                 530
```

(2) INFORMATION FOR SEQ ID NO:25:

(i) SEQUENCE CHARACTERISTICS:
            (A) LENGTH: 494 base pairs
            (B) TYPE: nucleic acid
            (C) STRANDEDNESS: single
            (D) TOPOLOGY: linear (ii) MOLECULE TYPE: DNA (genomic)

(vi) ORIGINAL SOURCE:
            (A) ORGANISM: PAG1004UP (xi) SEQUENCE DESCRIPTION: SEQ ID NO:25:

```
GATCACCGAG CCTAATGAGT GGTGCTAGGG TAGCGGTTAT TACCGGTACT AATAGGTATG       60

TTAATATGCC ATCAGTGTCT GAGCTCACGA CTGACATATA TTAGCAATCT TGGCCTGAAT      120

ATCGCATACA GGTTGATTGA GCAGTTTACT GATGACAGCA AGTTGGTTAT CGTGGTAACA      180

TCGCGTACGC TGCCAAGAGT AAGGGAGGTG GTAGACCTAA TCAAAACATA CGCCGAGAAA      240

TGTGGYAAGT CTGGAGCAGT AGATTTCGAC TACCTGCTGG TGGATTTCAC CGACATGGTT      300

AGTGTGCTGG GCGCGGCATA CGAATTAGAA AAACGATATG ACGCTATACA TTACTTCTAC      360

GCTAACGCTG GCAGGGTGTG TATTCCCCGA ATTGATTGGT TGGGTGCACC NGGTGTTTAC      420

GGGATCCNCG GGTGTGTGAT ATCCNCGTTA GNCNGGGTGG ANNAATCAGG ATGGTNGGTT      480

AGTTTCAAGC ANTC                                                        494
```

(2) INFORMATION FOR SEQ ID NO:26:

(i) SEQUENCE CHARACTERISTICS:
            (A) LENGTH: 529 base pairs
            (B) TYPE: nucleic acid
            (C) STRANDEDNESS: single
            (D) TOPOLOGY: linear (ii) MOLECULE TYPE: DNA (genomic)

(vi) ORIGINAL SOURCE:
            (A) ORGANISM: PAG1005RP (xi) SEQUENCE DESCRIPTION: SEQ ID NO:26:

```
GATCTCCCCC AGGAACCGCG ACGGGTACGC AGTCGTCGTT CTTCCCAGCG TGGTCGTCAC       60
```

```
GAATTCCATC AGCATGTGGA ACTTCAGCGC GAACATCTCC TCACGCAGGA TCCGCGTCTT      120

CCTCCTCCTC TGCGGCCACC GAGAGCTCCG CCAGCTGCTG GCACCCGGTC AGGAAGCACT      180

CCCGCGCGTT CCCCTCGCGC CCCACCTCCC TGAAGCAGCC CACCAGGAGC CGCCACACCA      240

TATCATCCCC GAGCCCTTCG TTGAGGTTGA AGTTGTCTGC CCTAATGCAC CGCACAAGCA      300

CCTTCGGGAT ATCCCAACCC AAATCTCCCA CGAGTGCAGG GTGCTCCCGG AGCTGCTCCC      360

ACAGCGCCTC CAGGAAGCTC GCCAGCCGCC CCGCGTTACC GCTCGCAAGC GCCTGCTCCG      420

CGCACAACTC GATCCCCGCT GCGAGCGAGA TCTCGTCCCC GCCTGCTCCG CGAATAGCAC      480

GCCCAGACTC TCACCTTCCG TATTGCGTGG CGTTTCATAG AATCACTCT                  529

(2) INFORMATION FOR SEQ ID NO:27:

(i) SEQUENCE CHARACTERISTICS:
        (A) LENGTH: 523 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1005UP (xi) SEQUENCE DESCRIPTION: SEQ ID NO:27:

GATCTTGCAG TTAACGGTTC TTCCATCAAG GGACAAATGG GCGTACCGAA GCTCTTAGCC       60

CAGCCAAGTA TCCCACAGCT GCACAATGCT AAGGGTGAGG TAATTGATGT TCAGTCCCAG      120

CCCCCCGCGG GCTGGCGGCA GGTGCTACTA NAGCATGGCC CAGAAGTATT TGCGAAGAAG      180

GTGCGTGAAT TCGATGGAAC ATTGCTTACA GACACTACAT GGAGAGATGC CCATCAATCA      240

TTGTTGGCAA CTAGGGTGCG TACTTATGAC CTAGCTGCTA TTGCACCTAC CACTGCACAT      300

GCATTAGCAG GAGCCTTTGC ATTAGAGTGT TGGGGTGGCG CTACGTTTGA CGTTGCCATG      360

CGGTTTTTGC ACGAAGACCC ATGGGAGCGC TTGAGGACAC TGCGGAAATT GGTGCCAAAC      420

ATCCCATTCC AGATGTTGCT TCGTGGTGCC AACGGTGTTG CTTACTCCTC TCTGCCTGAT      480

AATGCGAATG ACATTCGTCA AACAAGCAAA GGAGAATGGT GTC                        523

(2) INFORMATION FOR SEQ ID NO:28:

(i) SEQUENCE CHARACTERISTICS:
        (A) LENGTH: 567 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1006RP (xi) SEQUENCE DESCRIPTION: SEQ ID NO:28:

NNNNNGNNNN NNNNTGTGGG GCGTGGTAGA NTAGTGGGTC TCGTAGACAA TGGATGCCTG       60

TAAGCATGTG TAACGGGTAT CGTGGAGGGG TCCCTTCCCG CCTCCGAAGC CTTCTTCGGT      120

TTCTCAATTT CCCATAGCAA TGGCGACTCG CACCAGTAAA TCCTCCTCTG GGTAGGCTCC      180

GCTCATTAGT CGAACGGTTC TCCGTAGCCC ATCCTCGTCC AGTTGCGGCG CCGCGAAAAC      240

AAACAAACAC TGGCCGCCCG GATAACGTCA GTAGCTATGT TTCAGCAGAT TCCGCGGAAA      300

CCGTCCAACA GATCGTCTGT AACCGGTGCA GATACGTCTG GGCAGCGGGT TTTAACTGCA      360
```

```
GCCAGTGCAG ATTTAACGTG CGATGGAAGC CTGCGCGCGG TTCTGGCTGC CCGCCGGTGG      420

CTCCAGCGGA GCGAGCGCGC GCGTCGCGAT GCGCGGCGTA AGTCTGTGAT CGCCGGGAGC      480

TGAGTAGCGC TAGCGAAGGT CACACGGACG CCGGATAGTA GATGGAGCAA GGGGCCTCTT      540

TGGACGGTTT GGTTACGAAA TNCCGGG                                         567

(2) INFORMATION FOR SEQ ID NO:29:

(i) SEQUENCE CHARACTERISTICS:
        (A) LENGTH: 471 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1006UP (xi) SEQUENCE DESCRIPTION: SEQ ID NO:29:

GATCTCTGTT CTTTTTTTAC CTCTGAAGGT GCCGAATGTG TGCGCGTGAA ACCACTCTTT       60

CGCGATGGGA TGTTTCCTGA TCTCCCTCGC GAGCTGTTTC ATGTATTACT TCCTTGTAAG      120

GCAATCGCCA CGCAGGACAG ACCGAGCTGG TGCCAACGGT TTCTCCGGCG TGCCTTTGCT      180

GAGATGCGTT CGCATGTTTT GACCCCAGCT CTGGAATATG CGCGCGGTGC GATGCTGCGT      240

GTGGTACGAT GCAACGTCAG CGATCCCGCA GGGCGGGGGT GCAGGGGTGT ACTTCGATCG      300

TAGGCCGCTG TAAATGCTCC TCTGGGACGC CGCTCCCGCC GATCTTACTG TCCGCCATGA      360

ACGATGGGAC AGAGTAGCCG GGATGGTTCC CTTTGCAGAT AGGAAATCTG GAAGAATTTG      420

GTCCCGCTCC GCCTGATTTG TTTATACAAA AAATTGGCCA TACATTCCTT G              471

(2) INFORMATION FOR SEQ ID NO:30:

(i) SEQUENCE CHARACTERISTICS:
        (A) LENGTH: 518 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1007RP (xi) SEQUENCE DESCRIPTION: SEQ ID NO:30:

GATCTTCTCG CCGAAGTACT GCACCATGTC ATTTCTCTCC GGTTCACCAT GAACAAGGAC       60

ATCTAGGCCG ACCTCCTCCT GGAAGCGGAT GACTTCCTCA ATCTGAGAAT TGATGAAGTT      120

GGTGTACTCC TCCGTGGAAA TCGCCCCCTT TGCATGCTTG TTTCTGTTGA TCCGAATGTC      180

CTTAGTCTGT GGGAAGGAAC CGATGGTGGT GGTTGGGAAT AGCGGGAGCT TGAAAATTGG      240

CTGCTGCTCC TTGAGACGCT CCCCGAATGG TGCGGCTCTC GTGGATAGCT TCTCGTTCAA      300

ACCAGCAACA CGTTCCTGGA CAGAAGGATC GTTGGGTGAT CGCAGAGGCG GGACGCGCAG      360

CAATCGAGTC TGCATTTGGC TCCAACTCAG AGGAAAAGTC TTCGCCAGAG CGTCCTTAGC      420

GAGGAAACAA ACTCATGCAG TTCTTGGTTG AAAAGAGAAC CAGCCTGGCT TNTTGTCCAA      480

GGAGATCGTT TCCAAGTAAC TGGNNTTGAA NAAGGAGC                             518

(2) INFORMATION FOR SEQ ID NO:31:

(i) SEQUENCE CHARACTERISTICS:
        (A) LENGTH: 492 base pairs
```

(B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1007UP (xi) SEQUENCE DESCRIPTION: SEQ ID NO:31:

```
GATCTTGTCG AGCTCGCCAT GACAGATGAG AATCCGACAG CACGTTTCAC GGCATTTTAT       60

GCGCTGGGGC TAATTAGTAA AACGGAGGAA GGCTGTGAAC TATTGGACGA GTTGGGCTGG      120

GACTGTTGCA TCGATGTTCG TCGCCAGCCA GTTGGTATTT GGGTACCAAA TAACATCACC      180

ACCTTTCTCA GTTATCCTCA AGAGAGCGTC GAGAAAACAA CCGTTTCGGA AGGTATCGAC      240

CAATTTGGAC CACGGAATTT CGGGAGGAGG GACTTCCCCC CACTGGAGGG TATCACAAAT      300

ACAAGTTGAT ACAATACTCT GAAAAGGTAG GAAAGGGATG TCCTGACAGA CAACCAAGAG      360

CTTAAATCCA TCCTCGCACA CAGGGGTAGA CAAGTGANTG NAAGCGGNGA TTGATCTTCC      420

CATGGAGNTC CAGGATGACC AGCTCCCCAA GATTTCCGTT CGTGGGAANC GGAATCATTT      480

NTACACAGNG GA                                                          492
```

(2) INFORMATION FOR SEQ ID NO:32:

(i) SEQUENCE CHARACTERISTICS:
        (A) LENGTH: 595 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1008I1

(xi) SEQUENCE DESCRIPTION: SEQ ID NO:32:

```
TCGAGTCATT TCTTGTAGTC CAGTGCATCG ACAAAGTCGT CTGCTTCGCC GTTGGCATAC       60

GTTATTTCGC TTCCATACTC GGCATCATCA GCGTCCTCAA GCGCGACCTG AGACAACTCC      120

TGGCGCAACT TTGTCTGGGC GCGAAGCATC TCCAGGGGAC CCCTGCATTG ATAACAGGAT      180

CGGGAGCGAG TCGGAACTGG CCTTGAGGTT CGCGCGAAGA GCCTTGATTT CCTTGTTACC      240

CCGCGGCTGC AAGGAATCTA GGTGAGGAGC ACGCAGTCGA AGCAACCACT TAAACCACCA      300

ACGGATCGCT GAGCTTTCTG TCCAAACGTC AGAGGCCACC CGCTGGCTCA CGATGACAAA      360

ACAGTTCATT GNANCGCNAT GGAAGGNGAT NCATGTCGCN NANATTCTTT NNTTCTTTCC      420

TCGGACCANG NGTNANAACT NACAGTCCCT GACGANTTCC TCACCTANGT CNCCGCAGGG      480

GATNNTTTCA ACGCCGCNCC GTCTNNCCCC CTCNCCNTCG NNNACCTTCT TTGTTNNNGG      540

TTTTCCTTTN CCNNCNCCCC TNNTNCNCAC TTNGGTTTTT NNACNCCNTC NNNAC           595
```

(2) INFORMATION FOR SEQ ID NO:33:

(i) SEQUENCE CHARACTERISTICS:
        (A) LENGTH: 680 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1008I2

(xi) SEQUENCE DESCRIPTION: SEQ ID NO:33:

| | | | | | |
|---|---|---|---|---|---|
| TCGAGACCGC | ATCAAATATC | TGTCATTATG | TAAATGTGCA | TATTATAGAC | TTCCTATTTC | 60 |
| AGTACCAGGC | AATTGTGTCC | GATAAATGAG | GTGCAATGAG | CACCCGTCAT | CACCGGACGC | 120 |
| GATAAATTTT | TTTTTGGGGG | TCAACCATTA | AATCTACGTG | CATCTAACGC | AAGGAGCAAT | 180 |
| TTAGCTAACA | ACTCTTCTTA | TCTTAAGAAT | CGGGTATACC | TCCTCTTCGC | ACATCTTCGC | 240 |
| CTTCTTTAGT | CTCGAGTCTT | AACTACGTTC | AACAATGTCA | GCCTCCGATA | AGATGTACAT | 300 |
| GTCGTATAAC | AACATACACA | AACTGTGTCA | GCAGGTAGCT | GGCCAAATTA | TGGAGCGTGG | 360 |
| TGACAGACCG | GACGTGATTA | TCGCCATTAC | CGGCGGCGGC | ATGATTCCTG | CAAGAATCAT | 420 |
| CCGGTCGTTC | CTCAAGGTCA | AGGGCCAGAA | AAACATCCCC | ATCCAGGCGA | TTGGGTCTTT | 480 |
| CTTTGGTACG | AGGACTTGGG | TTTGGAAGAC | GGGACGGAAA | GCATCGGCAA | GGAAGTTATC | 540 |
| CGGATCAAGT | GGCTAGACTT | TGGGGGCCTT | GGGCAAACAC | TTTGGACTCA | ACTGATTGGA | 600 |
| AGAAGGTGTT | GGATTGGCGC | CGAGTTGGNC | GANACCCNGA | CACGTCCCTA | CGGTTGTNAC | 660 |
| CGANTTGGGG | AGGGGGNCAN | | | | | 680 |

(2) INFORMATION FOR SEQ ID NO:34:

(i) SEQUENCE CHARACTERISTICS:
        (A) LENGTH: 509 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1008RP (xi) SEQUENCE DESCRIPTION: SEQ ID NO:34:

| | | | | | |
|---|---|---|---|---|---|
| GATCTGTCTT | GGACGATATC | AACGTCTATG | CCATCTTCCA | AACCGTCTTT | TCCACATTGC | 60 |
| AACAAAATGA | CTCTACAAAA | TACCAGTTAG | TCCTAGAAAA | TATGTCACAG | GACGAACAGA | 120 |
| TGCACCTAGC | ACATATTACA | TCGTTATGAG | CACCATAAAT | CTCATAGTCT | TCCTACTTTA | 180 |
| TCTTTAATAT | TAATAGTATG | TGTATGCCAA | TCGGCGCGTT | ATGCCCGGGT | AACAGTAGTT | 240 |
| TCTTTTTCTN | GAACATCTGA | AAAATTTCAC | CCGATGAGCT | CTCTTGTTGC | AATGGCGCAT | 300 |
| CGAGCTACAA | GTGCAGGTGT | ACCATTCACA | TCCCTATCGG | NATTCGGCTG | TTGNTAGAGC | 360 |
| TGTTAAAATG | ATTGCTTCAG | AAGATACGAG | GTCCTTGGGA | GTTTTCGGCC | CGATGAACGN | 420 |
| GGTCGCATTC | CAAGCCAATG | CGTGGAAAGG | ACTCATTGAA | TTTTCANNGA | CCNGNAGAAT | 480 |
| TAANGGNAAA | GTCANCNGTA | ACCNATTGT | | | | 509 |

(2) INFORMATION FOR SEQ ID NO:35:

(i) SEQUENCE CHARACTERISTICS:
        (A) LENGTH: 500 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1008UP (xi) SEQUENCE DESCRIPTION: SEQ ID NO:35:

| | | | | | |
|---|---|---|---|---|---|
| GATCAAGCGG | GAATTTCGGC | GCAAATGCAC | GTTAATGCTC | ATATTGTTAA | CAAGCTCGGG | 60 |
| GCAGAAGTCC | GCCGTTTGGA | GCTAGAAATT | TCCACATTGA | AAGCGTTCAA | TAACACATTA | 120 |

```
GAGGAAGAGA AAGCTCGTGC AGAAGATGAT ATTTTGAAGC TGCTAGAGGA AAATCACACT      180

GTGCATCATT TGAAGACTAC CAACGAAGCG TTGACTACCA AGGTAGCCGA CTATAGCAAT      240

AGACAAGATA CGATTCTCCA GCTGTTGGGC GAAAAGACGG AACGTGTAGA GGAACTTGGA      300

AAATGACGTC GAGGACCTCA AGCAGATGCT GCGGATGCAA GCACAGCAAC TTGGCCGACA      360

TGCAAGAGAG GTTAAGAATT TAGATTCCCA TATCTTATTA ACATTATTNA TNCAANCGGC      420

TTGGGTTNGT TAATCAACTT CNCCAGATGC NTAGATTTGG GTAGTTAGNC ANTTTTTCGA      480

NGTGGNTCAA ATGGNGGCCC                                                  500

(2) INFORMATION FOR SEQ ID NO:36:

(i) SEQUENCE CHARACTERISTICS:
        (A) LENGTH: 506 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1009RP (xi) SEQUENCE DESCRIPTION: SEQ ID NO:36:

GATCTTCGCT TGGGGCCGTG CGTTCACGGT CTTAGAAAGC AAGCGTGCAA GCGATGTCTT       60

GCCTACCCCT GGGGGGGCCC ATAGTATCAT CGAAGGTATT GTTCCCTGGC TCACATATTT      120

GTATAGTGCC CCGCTTTCCT GGGAGAGAAT ATGCTGTTGC CCCACGTACT CCCGCAGCTC      180

GCGGGGACGA AGTTTCTCAC TTAAGGGCAA ATGTGCCATT TTCTGCAGCT CACGCTGATC      240

TGAGTTCACC GCCCCTGTTG GACGTGCCCG CTTCCGTTGG GGAGAGTCGT CCATCTCTAT      300

CACCTCACTA TCCTCCATAT TAACGTCCGA GATCACAGAC ACGCTATCCT CATCCTCCAG      360

CTTATGCTTG CGCCCCAGCA TCTCAGATAC GGACGTGGTC CTCGCTCCTT TCGGCTCCTC      420

CTGCAGGGAT GCATCTAGAT GGTATGGATG TGATGAATGG AAAGCCTGCA ATCTGGNAAT      480

GGTAAGTCTC CCCCCCGTAT CATTTN                                           506

(2) INFORMATION FOR SEQ ID NO:37:

(i) SEQUENCE CHARACTERISTICS:
        (A) LENGTH: 500 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1009UP (xi) SEQUENCE DESCRIPTION: SEQ ID NO:37:

GATCATGCTA GTTCTGCAGC TGAGTTTTTA AAAACGCAGT ACTGGAGATG TTTCGCTTTA       60

TGGTATCGCT CCACTAGCGC ACGGACTGAC TTTGGTAAAC GGCTTAGCAC TGATGCCGGT      120

ATTTGGAACG CCCGTCCTAA GAAGCTTGAG TTCGCACCAT CAATGAAGGG AGCGCAAGTC      180

GAAATTTCCC AGCCTAGAGG CATGTCAGTA GGGTCAAATA CGTCTTGTTC TGGATCGCTC      240

TGCATCATGA TATCGACATA GTAGTCGCAC ATATCGATGG AGACGACCTT GCCGGGGTCA      300

AATTTGTTAA ATTGGTTCAA TCCCTCAGGC ACTTGGGTGA TAACCTCAAG TAGCGGCATT      360

TCTTCAGGGA AATCGCCCGG TAGGAGGGCA TCGAAGNCAG AGTTNGACGA ACCNCAGGCG      420
```

```
GGGGGANTCT TTGAAGGGAG AAAGAGGCCG GGAANTGGTA CCACTCCGCT CCCCNTCANA      480

AGTTGGCCCC AGCCTCAATN                                                 500
```

(2) INFORMATION FOR SEQ ID NO:38:

(i) SEQUENCE CHARACTERISTICS:
        (A) LENGTH: 627 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1010I1

(xi) SEQUENCE DESCRIPTION: SEQ ID NO:38:

```
TCGAGGCGCT TACGTGGGTC CACCTGAAGA TGCGGCAGAC GGCGCACGCG GAGCTGGTGC       60

GGGCGAACCC CACCGTGTTC CCCCTGCTGC TGGCGAACTT TCTCAGAAAC GATCTGTCGC      120

TGACCGGGGC TGCGATGGAG GGCCAGGAAG CGAAGTGCAG CGACGTGCAC GTGCTAGTAC      180

CGAAAACACA CGCCGCGCTG GCGTCTCTCC TGCTTGCACA TAGTCCCGTG GCGCGGGGTG      240

GCGATCTTGG CATCACCCTT GGCGACATTT TATCGTTGTC CCTGCAGGAT GCACTAGACG      300

CGGGCCAGTT AACGACAGCT GAACCCAAAG GAAAGTTAGA GGGTGACCTA GTAAGCGCTC      360

TGGTACATAC AAAACAGCTA GAGCGCCCGG TGGAGTTCTC TACGACTGAA TTAATACGGA      420

GGTACCGACT TGCGGACAAA GAGGCGTCTA TGGATGCCTT GGCCTGTCGC TGGAGATTTC      480

CTGACAGATT TAAAGATGAC GATGAGGTAG AATGACATTT CTTGTCAGGG TCTCAAGTGG      540

GATGAGAGGT CGGCATTTTC GAAGGAGNNT GGTTTATNAN NANATCTTGG ATTTTCTGAG      600

GGGGCTNAGN TNCAAGAAAG TCANATN                                         627
```

(2) INFORMATION FOR SEQ ID NO:39:

(i) SEQUENCE CHARACTERISTICS:
        (A) LENGTH: 628 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1010I2

(xi) SEQUENCE DESCRIPTION: SEQ ID NO:39:

```
TCGAGGTGGC GGGCGGGAAA CCCCTGCGCA ATCCTGGCCT CCAGCGCCCG GCTGACTGCG       60

GGTACCGTCA AGCACTTGAA GTGGCTCCGC TCAAGATAAT CCACCGCCTC GTTCGCCCGC      120

AGCCCGCGAC TCCCGTGCAC ATCCCGCGGG ATCAGCTTGA ACTCCCCCGC GCTCAGCCAG      180

AGTCGGTTGT TGCCCACCGG GTAGTCGTAC TCCTCTGGCA GCGCCTCGCT GCTCATCATC      240

AGCAGAAAGT CGCCCTCTGT GTCGCACATC TTGATGAAAA CCTCCGCGCC CTGAGCCCGG      300

GAGAATCGCT GCAGCACCCC TGCCACCAGC GCCTCCTCCT CCTCGGGTTG TCCGCGACTT      360

CCACTCCGCC AAGCACCATC GCCTGCCCTC CCGCGCCCCG CACCGCCCGC AGGTGCACCC      420

GCTGTACCCC TGNCACGGGT AGTGGTCATT CCACGGCCGG AACACTCCTC AAGCTGAGCA      480

TGTTCTTGGG ATCTTTGTTT GGACGTCATC AAAATTGTCG ATTTGAAAAA CGATACAATA      540

NAGNGGCTCN GGGGTNGAAA GTCACACCNA TCACTCTGGT TCAAAGCATG TCTCAATNTG      600

CGGGGCATAA CCAATTGCNC GGTANGCA                                        628
```

(2) INFORMATION FOR SEQ ID NO:40:

(i) SEQUENCE CHARACTERISTICS:
        (A) LENGTH: 517 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1010RP (xi) SEQUENCE DESCRIPTION: SEQ ID NO:40:

```
GATCCGGCTC GCAAAGGAGA AGATAGAAGA GCAGAAAGAA TACCCGGTGC AGGAGTTTGA      60

CAAAAAGCTG TATCATAGCA ACCCCGCAAG GTACTGGGAT ATATTCTATA AAAATAACAA     120

AGAAAACTTC TTCAAAGACA GGAAGTGGTT GCAGATTGAG TTTCCCTCTC TATACGAAGC     180

TACCAAGAAA GATGCTGGTT CAGTGACTAT CTTCGAGATT GGGTGTGGTG CGGGCAATAC     240

CATGTTCCCG ATCTTATCTG CAAACGAAAA CGAACACTTA CGCGTTGTGG GTGCGGACTT     300

CTCCCCGAAG GCCGTGGGAA TTGGTAAAGA CGTCGCAAAA CTTTAACCCC TCGAATGCCC     360

ACGCGACGGT ATGGGACTTT AGCCAACCCT GATGGTCTTT TGGCCGATGG TGTCGAGCCG     420

CATTCGGTCG ANATCGNAGN AATGATTTTN GTTTTAGTGC CTNGGNGCCC ACAGGGGCC      480

AGGNTNTGGT TATTGGANAA AGTCTTNANC AGNGGGT                             517
```

(2) INFORMATION FOR SEQ ID NO:41:

(i) SEQUENCE CHARACTERISTICS:
        (A) LENGTH: 492 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1010UP (xi) SEQUENCE DESCRIPTION: SEQ ID NO:41:

```
GATCAGGACA GTAGCAGCTT GACTGAGTAT CAGCAGGAAA AGCCTAGCTA ATTGGCGCGA      60

GTACAATTAC AAGTACCTGT CTGACTACTT CTTTGGGTGG GATGCCATAT TTTTTAGGAT     120

GGCCTGCAAC GGGCCGGTGG GGGCGCCATC CAAATTTATG GAGTTGAAGA GCTGTTCAAT     180

GCCCTTTATC CCATCTGCAC CGTCTTTATC GCCGAACATG GCATGCAACT CTTCAAGCAT     240

GATATCTTCT TCCTCGTGCT CTGATCCGGC GTTGGTCGTC GTTTGGGCAG TCTTCGTAGG     300

CGCCATTTCT GTAATGTTGA AGCTGGTCTT TGGTCATCTT CAGACCCTCC CGTCAGGAAA     360

TATCAAAGAA ATCGGCTTCA CTAATATCTA CGCCTCACTC TCGAAAAATG TCCGAGGCTC     420

TTCATCCCCA GCTGAAGGAC CCTGACCAGA AAAATGTCAA TGGTACTCAA CGCAACTTTA     480

ATNTTNCAAG AN                                                        492
```

(2) INFORMATION FOR SEQ ID NO:42:

(i) SEQUENCE CHARACTERISTICS:
        (A) LENGTH: 620 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
    (A) ORGANISM: PAG1011I1

(xi) SEQUENCE DESCRIPTION: SEQ ID NO:42:

| | | | | | |
|---|---|---|---|---|---|
| GATCTGCGCG | GCGGATGTTC | AGCAGCGACG | CGTATCTAAA | CAATTTCGAA | GTTGTCCAAG | 60 |
| GCCTGACCGT | TCCAATAGAC | CGCTCTAGCT | ATTCCCAGTA | TGACAAATGG | TTTAAATCGC | 120 |
| TAGATGCAGC | TGCAGAACGT | ACAACTGCCT | GGTTAGAGCT | GTCGGATGCT | TCGGCCCTGC | 180 |
| AAAACTTCTA | CGCTCACGAG | GCCAGGATGA | TCTGCAAAAA | AATCATCCAG | ACCAATGGCC | 240 |
| CCACATCTTT | AATTCACTGA | GTGTAATGTC | CATACCTCCA | GTACTCACCA | GTCTTTTGGT | 300 |
| TTTCTGGATG | TCAGATACCA | GACTATGTAC | TGAATAGCGA | CAACATTAGA | TATCTAAAAA | 360 |
| GTCTGTCGGT | TTACAATCTT | AAGGTCGGCT | GAAAGAAGAG | AAACAATCTT | CGAAAACAAT | 420 |
| ACTAAGGCGA | ATATATCAAC | GTAATATGAC | CGCTCAGGCT | TCGGATAACA | TTCCGATATC | 480 |
| AGAGGGAGAA | GACTCCGCNG | GNGTCTTGNC | NNTCNGGCGN | AAAATTGCNCA | GTNTTNATCC | 540 |
| CGGNAGCCNC | CCACNGGTTC | TCANACCCCT | TTTTNGGNGT | TCNCGNCAAT | NAAGGGNGNC | 600 |
| CTCCTGCANT | TACCCTANNA | | | | | 620 |

(2) INFORMATION FOR SEQ ID NO:43:

(i) SEQUENCE CHARACTERISTICS:
    (A) LENGTH: 420 base pairs
    (B) TYPE: nucleic acid
    (C) STRANDEDNESS: single
    (D) TOPOLOGY: linear (ii) MOLECULE TYPE: DNA (genomic)

(vi) ORIGINAL SOURCE:
    (A) ORGANISM: PAG1011I2

(xi) SEQUENCE DESCRIPTION: SEQ ID NO:43:

| | | | | | |
|---|---|---|---|---|---|
| GATCTCTTGC | ACCAGTCCAA | ATCAGCGGGG | TCGTCCACCT | TTCCTCCATA | TATGATTTTG | 60 |
| CCGATGGTGT | CGCTGACAAG | CTTCCAGGGC | ACCAAATCGG | GGTCGACATG | CTCCTTGCCG | 120 |
| TTACTGCTCT | GTTCAAATAT | GTGGTCCAAA | AACTTGCTAC | CTGCGTGGAA | GTCACCATCG | 180 |
| TGGAAGTCGT | ACTTCTTGGT | GAATCCAATA | GGCGCGAGAG | GGCACCTGGC | CATGATAATA | 240 |
| GAGTGGAACC | ACACGAGGAT | GAACTTGCTA | TGAAGTTTTT | CTACTGGTTT | GACATTCTTC | 300 |
| AGTTCCTCTG | ACTGAGTCCG | CCACAGCTCG | CAGACTGTGT | TTAGAACGCC | GGGCTCACCC | 360 |
| TCGTACGCTA | TCTTATAGTT | CTGCTGAGCA | AAGGAACCAC | TAGAGGCTTG | CTTTGGGATC | 420 |

(2) INFORMATION FOR SEQ ID NO:44:

(i) SEQUENCE CHARACTERISTICS:
    (A) LENGTH: 732 base pairs
    (B) TYPE: nucleic acid
    (C) STRANDEDNESS: single
    (D) TOPOLOGY: linear (ii) MOLECULE TYPE: DNA (genomic)

(vi) ORIGINAL SOURCE:
    (A) ORGANISM: PAG1011RP (xi) SEQUENCE DESCRIPTION: SEQ ID NO:44:

| | | | | | |
|---|---|---|---|---|---|
| GATCCAAAGC | AAGCCTCTAG | TGGTTCCTTT | GCTCAGCAGA | AGCTATAAGA | TAGCGTACGA | 60 |
| GGGTGAGCCC | GGCGTTCTAA | ACACAGTCTG | CGAGCTGTGG | CGGACTCAGT | CAGAGGAACT | 120 |
| GAAGAATGTC | AAACCAGTAG | AAAAACTTCA | TAGCAAGTTC | ATCCTCGTGT | GGTTCCACTC | 180 |

```
TATTATCATG GCCAGGTGCC GTCTCGCGCC TATTGGATTC ACCAAGAAGT ACGACTTCCA      240

CGATGGTGAC TTCCACGCAG GTAGCAAGTT TTTGGACCAC ATATTTGAAC AGAGCAGTAA      300

CGGCAAGGAG CATGTCGACC CCGATTTGGT GCCCTGGAAA GCTTGTCAGC GACACCATCG      360

GCAAAATCAT ATATGGGAGG AAAGGTGGAC GACCCCGCTG ATTTGGACTG GTGCAAGANA      420

TCTGCGCGGC GGATGTTCAG CAGCGACGCG TATCTAAACA ATTCGAAGTT GTCCAAGGGC      480

TGACCGTTCC ATAAACCGCT CTANCTATTC CCAGTATGAC AAATGGGTTA AATCNCTAAA      540

NGCANCTGCA GAACGTACAA CTGCCCTGNT TANANCTGTC GGATGCTCGG CCTGCAAACT      600

TCTACNNCNC GAGGCCAGNA NGATNGGCAA AAAAATCTNC AGANCNANGG CCCCCTCCTT      660

TAATCCCTNG ANTNTNATNT CCAACCNCCN TTNCCCCATC TTTTGNNTTT TGTTNTTAAA      720

AACCAAATTN TC                                                         732

(2) INFORMATION FOR SEQ ID NO:45:

(i) SEQUENCE CHARACTERISTICS:
        (A) LENGTH: 641 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: 1011UP (xi) SEQUENCE DESCRIPTION: SEQ ID NO:45:

GATCTTCACA CGCACTATTT GTCCAAGGGG CTTCAATCGT CATTGCATTA CACGAAGAAA       60

CAATACTTAC ATGAGAATGG AACAATAATA AACTAAGCGT ATGGTGCCTA ATGATTGTCC      120

AGATGGGCGT TGCTGTTCGT GAACAGTAAA TGCTTGGCAA ACTCATAAGA TGTCCACGAT      180

ATAGCAGTTG CAGGCATGTT GCTGATAATT CTGGGTTTTA GGCCCCGAAA GAAACCGGAC      240

CAACCATATG TTTTGTGGAT TGCAGATGCA GCCTTGCGGA ATGTGTCAGC CTCCTTGAAC      300

AGCTGACTTT GAACAGAATC TGCACCGCGA ATCTGCAATA CTGTCTTCAC GCAGTCTAGC      360

GGTGTGGGTT ATGGCGGCAC ATGTTGGCGC CCGGATATCC CACCGCACAG ACAATGTATC      420

CAGGGGTTTG TAGCTGGTTA CTCGGATTGA TTATTTTGGT GGATGATTCA ATAAATTACA      480

AAAATTCAAC GCTGCGACGG ATTGTTCATA GCAATAGTTG TCCGGTTATG ATTAGAAAAA      540

CGCTTGAAAT GCCCCTCGTG GGTCAATCCG CACGGGGCAT CCCGCAATGG ANCANTGGGG      600

TGAANTGAAC TCTTTGGTGG GNGNNANCGG TCCNNAGGGA C                         641

(2) INFORMATION FOR SEQ ID NO:46:

(i) SEQUENCE CHARACTERISTICS:
        (A) LENGTH: 653 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1012RP (xi) SEQUENCE DESCRIPTION: SEQ ID NO:46:

GATCCTAACC CAACTGCACA AAATTGTCAG TCATATGTTG GGAGGCAGTT TACCCTTCCG       60

CCGCAAAATA CATACTTCTC CTTAGGAAAC GCTCCTCGCT CAGGACTGCA ACTGCATTGA      120
```

```
CGAGCAGCAG AATAACGTAG AATAGCTTTC CCAGGCCAAA TATCATCCCT CCACGTACAG      180

TCTATCAGCA GTGTACTGCG CTGTGCGAGA AGTGGCATTC ACAAGATAAG CAGAAGTAGT      240

TCTAAAAATC AGTGGTCACC AACGCGAGGC TGCAAAATCG TGTTGTTCAT TCCCATCTCA      300

AAGCATCGCC TGAAAACAAA GGCTCACAGT TGCAGGTGCC CCCGCGTGAT AACAGATGAT      360

AATTTATATT TTAAGTTATA TTAACACACA TATACAAAAA GATTTGGTAG TGGATTAATG      420

ATGATTTGCT TAATCAGCGT TACGTCTTGC GGCCTTCTTA GCCAATCTCT TACCGGTACC      480

AAAGACCTTC TTACCTCTGT TCTTTCTTTG CTTTCTCTGT TGTCTGGAAG CCTTCTCAGC      540

CTTCTCAGCC ATGCCGTATC TGACCAATCT GTANGTTGGC TCGAACTTCT TGGCGTCNGC      600

AACAGAGTTG TAGATCAAAC CGAAACCGGT GGACTTGCCA CCACCAAACT GGG             653
```

(2) INFORMATION FOR SEQ ID NO:47:

(i) SEQUENCE CHARACTERISTICS:
        (A) LENGTH: 650 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1012UP (xi) SEQUENCE DESCRIPTION: SEQ ID NO:47:

```
GATCTTCCTC GAGCGCACCA CGCCGCCCCA CACAGACTCC GAGAACCTGC TCTTCCTGGA       60

GGGCACCAAA ACATGCTTCC AGATGTTCAC GCAGCAGGTG GAGGTCGCCG CAGGCTCGGG      120

CCAGGCGAAG ATCCTGGTCG GCGTCGTCGA GCGCTTCTGC AAGCTCCTGT TCGAGCGCCA      180

AAGCCACTGG ATGCAGGCCA TTTCGTCCGA GGTCAAGAAG TGCCTCCAGT ACAACCACAA      240

GTATGAGAAA GACCCCGACA CATCGCGCA GGAGGAGGAG TGCGCCGGCG GCCTCGTCGA      300

GTACCTCGTC GCGGTCGCCA ACGACCAGAT GAAGGCCGCA GACTACGCCG TCGCCATCTC      360

GCAGAAGTAC GGCTCCATGG TCTCCAAGGT GCACGAGCGC ACCATCACGA ACCGCATCGA      420

GGAAGACCCT CGACGGCTTC GCAGAGGTCG CCAAGTGCAG CAACAGCGGC CTCGTCGCCC      480

TGATCTTCGA CGACCTGCGC CGCCCCTACG CCGAGATCTT CAGCAAGGCC TGGTACTCCG      540

GCAACCAGGC GCAGCAGATC GCAGACACCC TCTACGAGTA CCTCGCCGAC ATCCGCAGCC      600

AGATGAACCC TTCGTCTACT CCACCCTCGT CGAGTCCGTC ATCGAAGAGA                 650
```

(2) INFORMATION FOR SEQ ID NO:48:

(i) SEQUENCE CHARACTERISTICS:
        (A) LENGTH: 727 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1013I1

(xi) SEQUENCE DESCRIPTION: SEQ ID NO:48:

```
TCGACGCGGA CAGCGTACTT CAATCTGTAG ACAGAAGAAA CCTTGCCCTC TTGGCCCTTC       60

TTGGAGCCAC GCACAACCAT AATCTCGTCG TCCTTTCTGA TTGGTAGAGA CTTGATGTTG      120

TACTGCTCTC TCAACTCCTT GGATAGAGGA GCAGACATGA TCACGCGGCG CTCGGAAGAT      180

GGCGCGTTGA AGTACGCCTT TCTGGCCTTT CTTCTGTCGG AGGAAACGTC TGCAGACATG      240
```

```
TTAGTACTGT GCCGGGCCAC CAACTTGTTC CACGCACTGG ATTATGCTAG GTCCGCCTGC      300

GCGCTGGGCC GTATGCCCAG GTTACCACGG ATCGCAGCGC CAGAGACGCT CATTCCCAAT      360

GTTTCGGGAG CCACCATCGT TCTGTCACAT ACCTAGAGAT TGCTTAGCCA TTGCTGATTC      420

GCCTGGTGCT GTGTAAGAAC CTCTGTTTCA NNATGTGNAN AATCTCAATN GTCGNAACTT      480

TTTCANNTTG TCCCGNCTAC GCTGNACCCN CTNNCNNTCG TNAANCNCCN NNNNNNNNCN      540

CAANCGTTTC GCTANNTNNN TCCTANANAC NNANANNNNT CNNCNNNAAN NCCCNNCNNN      600

CACNNTNTTC NACCNCCNNN CAANNNNNNN NNCNNNNNNN NANCCCNNNN NATNCNTCAT      660

NCCCCCTTNC NNNACTNNNN ANCCNNNNNC TNNNNNNANN NTNNNCNNNC ATNNNAACNA      720

NAACNCC                                                                 727

(2) INFORMATION FOR SEQ ID NO:49:

(i) SEQUENCE CHARACTERISTICS:
        (A) LENGTH: 635 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1013I2

(xi) SEQUENCE DESCRIPTION: SEQ ID NO:49:

TCGACAAGGT GACCAAGGAG AAGTCCAACG GTGCCTCCGT GCCATTGGAC GTCCACCCAT       60

CCAAGGTTGT CATCACCAAG TTGCACTTGG ACAAGGACAG AAAGGCCTTG ATCGAGAGAA      120

AGGGTGGCAA GTTGGAGTAA ATGCATTCCA CAGGTCAGCC AGCATATTAT AAGTAATTAT      180

GTTCTACCAA CTCTCCTCGA TATATAGTAA GTTCAGAAAG TCGTGTTTCA CTAGTGTTTA      240

TCAGTGGGCA TAATGACTGC TCTGGTGCTC CGCTCGTGCG CAGCCATTCT TGGCGGACAG      300

CCATGACTCC CGCGGACCAG TGAACAGGCG CGAAATTCCG TTCTCCGGGC CGACCACCNT      360

TGGACTCTTA TTGATTTCCT TCCGCCCTAA GAAAGTAGAC AGCGCCTACA TATATGACAC      420

ATCCCTGTCT GGGTGTTTAA GGAGCACCGC TCTGAAGAGC AGGGAAAACA CGGAGTCACT      480

AGGCTCTGCT ACGGCTCGAG GTTTTGGAAG TGAGTTTGNA ATTATTCGTC CNNTGAGAAN      540

TGANAGGGGT GGAGGCCGTC ACCCGATCAA CAGACNANCA GGCAATGGTN TGAGTNGNAA      600

CACAGCNCGG CGAGAACGTG GCAANCNTCN ANGNA                                 635

(2) INFORMATION FOR SEQ ID NO:50:

(i) SEQUENCE CHARACTERISTICS:
        (A) LENGTH: 669 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1013RP (xi) SEQUENCE DESCRIPTION: SEQ ID NO:50:

ANAATGGCTG GTAGTTATTG TTAACCACTA GTTTCTCCCC GAAGTTGAAG TACTTCACAT       60

AACTCAGCCC CTCCGAGGGA CTCATCTCCT CGTACAGAGG CCTATTCAAC TCAATGCGCT      120

GCTTGTAGTC CTCCAATGCA TCCTGCCTAT TCCAACCCTT GTNGTCTGCA GAGGCTGCTG      180
```

```
CCATCTCCAC TGTGCGCGCC CTCAGAATTG ACTCGCTCAC GACAGACTCA ACGAAGAATA     240

CTTTTACATT AAGAGCAGCA AACTCCTCGG CGAGCATTCT GCGCTCCTCG CGCATGATGT     300

TCATCCCATC ATAGACAGNA AGCTGTCCCT GCTCGAAGAA CTTCTTCATG TCCGCCTGGA     360

TCTCGGCTAT CAGCGTGCGC CGCAGTCTGA TCCCTTCCGG CGTAACTGGT CTGGTAGAGA     420

AGTAGTCCAG CGGTAGNTTC ACCATCCCCT GCGGGACCCG NGNCCNNCGA TACTCGGACA     480

CANTGAAGGA TTGTGTGNGC ACCCCNAGCC ACCCCCGTAT TGCGTGTATT GNCACCGNAA     540

CAANNNTTTT GGGTGNTCGT TGNAGGCCAC CCAGGACGNA CCAAAATTTT TCCCGCNTTG     600

GAAANCCCCC CAGNTCCCAN NNNGNAAATT GGNCCCCGGG AATTTTTTNG CCCTNGGCNC     660

CNCCGNCNG                                                            669
```

(2) INFORMATION FOR SEQ ID NO:51:

(i) SEQUENCE CHARACTERISTICS:
        (A) LENGTH: 632 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1013UP (xi) SEQUENCE DESCRIPTION: SEQ ID NO:51:

```
GATCGCTTAC CAGCCCAGTA GTGCGCCACA GGAACTTGAG GTTGGCTATC CGGCTGACAC      60

GAAGTATATC GACCCTTTGG CAGAAGTTGA CATATGTAAA CGGGATTTGC CGCATTTGAA     120

AAAGCTCGGA GTCAATACCA TTCGTGTTTA CTCCATTGAT CCAACCAAGC CACATGACGT     180

TTGCATGGAG GAGTTGAGCA AGCTGGGAAT CTACGTTCTC ATCGATTTAT CAGAACCAGA     240

CACCTCTATA ATTAGGGAAA CACCAACATG GGATGTAAAA GTATTCCAGC GGTACAAAGA     300

CGTAGTAGAC TCCATGCAGA AATACAATAA TGTTCTGGGC TTTTCTGCTG GTAACGAGGT     360

CACTAATGAC CGCACGAACA CAGACGCATC GTCTTTTGTG ACGGCGGCTA TCAGAGATGT     420

CAAAAACTAC ATCAAGCAAA TGGGATACAG AACTCTTCCG GTTGGTTACT CACCATCGAT     480

GACCAGGAGA CGAGGGATCA CTGGCCTGAT ACTCCCCTTC GGTNGCGTAT CTNCAGANNC     540

TTTTGGCATA ANTTTGTCCG ATTGGGCCGG CATCCACCTN CNGACGANCG TTCAAGAGAG     600

NGGCTTNCNA TTCNNGAACT CCCCTTGCCG CC                                  632
```

(2) INFORMATION FOR SEQ ID NO:52:

(i) SEQUENCE CHARACTERISTICS:
        (A) LENGTH: 602 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1014RP (xi) SEQUENCE DESCRIPTION: SEQ ID NO:52:

```
GATCAAACTG CCGTCTTGGC GCAGCACGCG GCCGCGCGAG TTGGATACGC GGTCCGCGTC      60

AAAGGCCACG CCGAGCGCGC CAAACTCCGG GAGGGGCTGG CCGCGGTAGC CCAGTGACGT     120

GATAAGCACG TCCAATTCGT AATCCAATTG CTCGTCCAGG TGACGTACAA CCTTGTTTTC     180

AGGGGTCAGG GAGTTTTTGC AGACGGTCAG CGCAGATATC GCGCCGGCGC CGTCCCTGCG     240
```

```
GATGTAGAGC GGCGTCTTGA GATAGTCGGA CACCCAGGCC TTGGAGTAGC CTTCCGCCGG       300

AGGAGGGTAT TTACTCGCGG ACTTGCTGCC GCGGGCGGCG TACGGCAGCA GGTACTGCTG       360

GCACATGTCA ATGCGGCGTT TCGTCGCGCG GTCGAGCGGC AGCGCCGCCC ACGCCTCGGG       420

CGTGAAGTGC TCGGGCGCGA TGTGGCCGCG CACGCCGCAG CGCTCGAGCT CCCACATCTC       480

GCGCAACTCC TTGNTCGTGA ACTTGCTGCC GAGGAAGTCC CGGCGCCCGA TGAGACGCAC       540

CTCCTCGAGC GGCGCGCGCC GCAACGCCTG CAGCGCGTGC GGGTTTGATG TCGGTCTGGC       600

CC                                                                     602

(2) INFORMATION FOR SEQ ID NO:53:

(i) SEQUENCE CHARACTERISTICS:
        (A) LENGTH: 627 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
         (A) ORGANISM: PAG1014UP (xi) SEQUENCE DESCRIPTION: SEQ ID NO:53:

GATCAGTGTT CGGGGCGAGC CGGAGAGCAT ACTGCTGTCA TGTCTATACC AGGAGCTGCT        60

CTCGCGGGTC ATTGAGGAGT CCAAGCGTTT TGCAGACAGG GACAGCACCA AGCACATCAC       120

AGCCGAGCAC CTAGATGAGG CGGTGGAGGC GTTGCTGGGA GATGTAGACC GAGGCGCGGA       180

CGGGGCATGG CCTTGATGTA AGTCTATGTA CAGGATATTA GCTTTCAAAA TGCATGGTTG       240

GGGTACTTCA GCGTTTCCAC CATGGAAAGG GCGCTGGCGG CGTCGTTTTT GTTGAGCACG       300

AAGAGGCCCT GGAGCTGCGC GGTCGACACT GGGACGCCTA GCGCGACGGC CTTGGCGACA       360

AACTCCGCGC AGAGCGCCGA GTCGTCCGGG TAGAAGCGCA GGAACATCTG CTCGATCTGG       420

TGCGGCGTTG CGTTCCCCAC AAGGACCTTG TAGTCGATGC GGCCCGGGCG CAGCACGGCG       480

GGGTCGAGGA CCTCGGGATG GTTGGTGGTC ATAAAGGTGA TCATCTTCTC ACTGGAGGCG       540

ACGCCGTCCA GGGCGTTGAG CAGCCCGCTG AACGTGACGC CGTTGGTGTA ACCGTCGTCG       600

TTCTTCTTGC GCTTGACAAA GGCGCGT                                          627

(2) INFORMATION FOR SEQ ID NO:54:

(i) SEQUENCE CHARACTERISTICS:
        (A) LENGTH: 698 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
         (A) ORGANISM: PAG1015RP (xi) SEQUENCE DESCRIPTION: SEQ ID NO:54:

GATCCAATTC CAAACGTAAT AACCATGGAG ACTGATGCTT CAAAGACGCC TCGGTCTCTT        60

CATCCATCAA AGAAAAGTGC AATTGTATAA TTTCCTCATC CTCTTCAATC ACAGTAGAGC       120

TAGGATCCCC CGGGCTGCAG GAATTCGATA TCAAGCTTAT CGATACCGTC GACCTCGAGG       180

GGGGGCCCGG TACCCAATTC GCCCTATAGT GAGTCGTATT ACGCGCGCTC ACTGGCCGTC       240

GTTTTACAAC GTCGTGACTG GGAAAACCCT GGCGTTACCC AACTTAATCG CCTTGCAGCA       300
```

```
CATCCCCCTT TCGCCAGCTG GCGTAATAGC GAAGAGGCCC GCACCGATCG CCCTTCCCAA      360

CAGTTGCGCA GCCTGAATGG CGAATGGACG CGCCCTGTAG CGGCGCATTA AGCGCGGCGG      420

GTGTGGTGGT TACGCGCAGC GTGACCGCTA CACTTGCCAG CGCCCTAGCG CCCGCTCCTT      480

TCGCTTTCTT CCCTTCCTTT CTCGCCACGT TCGCCGGCTT TCCCCGTCAA GCTCTAAATC      540

GGGGGCTCCC TTTAGGGTTC CGATTTAGTG CTTTACGGCA CCTCGACCCC AAAAAACTTG      600

ATTAGGGTGA TGGTTCACGT AGTGGGCCAT CGCCTGATAG ACGGTTTTTC GCCTTGACGT      660

TGAGTCACGT TCTTTAATAG TGGACTCTTG TCCAACTG                             698

(2) INFORMATION FOR SEQ ID NO:55:

(i) SEQUENCE CHARACTERISTICS:
        (A) LENGTH: 716 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1015UP (xi) SEQUENCE DESCRIPTION: SEQ ID NO:55:

GATCCTAGCT CTACTGTGAT TGAAGAGGAT GAGGAAATTA TACAATTGCA CTTTTCTTTG       60

ATGGATGAAG AGACCGAGGC GTCTTTGAAG CATCAGTCTC CATGGTTATT ACGTTTGGAA      120

TTGGATCCAC TAGTTCTAGA GCGGCCGCCA CCGCGGTGGA GCTCCAGCTT TGTTCCCTT      180

TAGTGAGGGT TAATTGCGCG CTTGGCGTAA TCATGGTCAT AGCTGTTTCC TGTGTGAAAT     240

TGTTATCCGC TCACAATTCC ACACAACATA CGAGCCGGAA GCATAAAGTG TAAAGCCTGG     300

GGTGCCTAAT GAGTGAGCTA ACTCACATTA ATTGCGTTGC GCTCACTGCC CGCTTTCCAG     360

TCGGGAAACC TGTCGTGCCA GCTGCATTAA TGAATCGGCC AACGCGCGGG GAGAGGCGGT     420

TTGCGTATTG GGCGCTCTTC CGCTTCCTCG CTCACTGACT CGCTGCGCTC GGTCGTTCGG     480

CTGCGGCGAG CGGTATCAGC TCACTCAAAG GCGGTAATAC GGTTATCCAC AGAATCAGGG     540

GATAACGCAG GAAAGAACAT GTGAGCAAAA GGCCAGCAAA AGGCCAGGAA CCGTAAAAAG     600

GCCGCGTTGC TGGCGTTTTT CCATAGGCTC CGCCCCCTGA CGAGCATCAC AAAAATCGAC     660

GCTCAAGTCA GAGGTGGCGA AACCCGACAG GACTATAAAG ATCCAGCGTT TCCCCT         716

(2) INFORMATION FOR SEQ ID NO:56:

(i) SEQUENCE CHARACTERISTICS:
        (A) LENGTH: 656 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1016RP (xi) SEQUENCE DESCRIPTION: SEQ ID NO:56:

GATGTGAATC GATGTGTGGA GACGAGTGTA ACTAGACACA AGCTGGCGAT GCAGCGAGAT       60

CTAACAGGAA AGGTGCTGGT TGGGAGAAA AGGTACTACG AAGAGGTAGT CACTAGTGTC      120

ACCTACAAGC CTACACACCA CCAACTGCGT TACGAAAATC TAAATACGTA CCTCTATCCT     180

ACAAACTACG AGGTGCGCGA ATTCCAATTC AATTTTGTCC ATCGTGCGTT ATTCGAAAAT     240

GTGCTCTGTG CGATTCCCAC AGGTATTGGT AAGACCTTCA TTGCCAGTAC GGGGATGCTC     300
```

```
AATTACTATT GGTGGACAGG GGGCACAAAA ATTATTTTTA CTGGTCCCAC ACGACCACTT      360

GTTGGGCAGG AAATTAAAGC ATTCCTGGGG ATTACTGGTT TTCCCCNTTA TGATACGGGA      420

ATNCTTCTTT GACAAGAGCC NNNNGCACAG GGNACAGATT TGGGNCAAAA GAAAACGTTT      480

TTTTTTTCGN NAACGCCCCC CANTGGGGGG GNAANTTTCC CCNNCGAGAG GGGGGACTTN      540

NNTCCCCNNA GANNNTNGGN TTTTCTNGGG NNTNNGNNGA NGGNTCCACC CCNGNCNNGG      600

GGGGCCCACN NCCCCCNCNN NNGGNNTTTT NNGNNNNTTN TTTTNACAAA ANTTNC          656

(2) INFORMATION FOR SEQ ID NO:57:

(i) SEQUENCE CHARACTERISTICS:
        (A) LENGTH: 435 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1016UP (xi) SEQUENCE DESCRIPTION: SEQ ID NO:57:

GATCCATCGA ACGTCCATTT TATACGACGA CATTTTTATA CAATTTTTAT TTAATAATGA       60

GGATTTGGCA TTCCCTCAAA CTCGCTGACT AGAAGTTAGC TGGTGCTAGT AGTGTAGCTG      120

GGCTAATGTC GACTGAATTG CCGTTGCCGG TGCTGGAGGA TTATTTTGTG TCCGCAGCTA      180

ATGCCTTCCT GCCAGATGAA TTCCCAGTGA AAGAATTGCA AGATGAATAC TATCGACCTT      240

GGGAAACGAT TGTGAGTAAT CTACCCGCGC TATTGTTGGC GCGACAGCTG CGGGATGTGG      300

TGGACCAGCT GAAGGTGCTG GAGGTGAAGA AGGAGCTGTT CGACGATATT TCGGCAGGTT      360

CGGCGCGCAT ATTCGGCGTT GGGCTTCAAC GTCAATGCGT ATGTGTCGAG CTACGACGAC      420

GCGTTCGACA CGATT                                                      435

(2) INFORMATION FOR SEQ ID NO:58:

(i) SEQUENCE CHARACTERISTICS:
        (A) LENGTH: 347 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1017I1

(xi) SEQUENCE DESCRIPTION: SEQ ID NO:58:

GATCTTCAAA TGGGACAAAT GCAAGGCTAT TGATCTTATT CCCAGCAAAC AAGTGCGACA       60

TGTATGGTGT ATTTTTGTTG GGCAACCGAC TGCTGGTGAA AACGGGCTTA AAATCTGAGC      120

TAGTTTTAAA GGCATCCTTC CAAAGTGTCA CATGTGGTCC TCTCGACACT GCAAGCAAGC      180

CCATGTCAGA GATTTTCACA TTGCTTGCTG GTATAGGCAG GTTTTCAACG GAATGTAACT      240

CCTTGAAGTT CCTGATATCC CACAGTCTCA TGGACTTATC TGCTCCGGTN TGTAGCCATA      300

TAGTAACCTT GCCTATCTAC CGCGACACCA GTGACGGGCC CGGTACC                   347

(2) INFORMATION FOR SEQ ID NO:59:

(i) SEQUENCE CHARACTERISTICS:
        (A) LENGTH: 673 base pairs
        (B) TYPE: nucleic acid
```

```
        (C) STRANDEDNESS: single
        (D) TOPOLOGY: linear (ii) MOLECULE TYPE: DNA (genomic)

(vi) ORIGINAL SOURCE:
        (A) ORGANISM: PAG1017I2

(xi) SEQUENCE DESCRIPTION: SEQ ID NO:59:

GATCTTCTTG GCGTCGGGCA TCAGACAGGC GTAACTAATT TGATCATTCC TGGTGCGGGT      60

GAGGCTAACT ATGATGCATT GGAAGTTAAT CCTTACGAGA CGACGAAGCA AAGGAAAGAG     120

CAGGAGGTTA GATCGCTACT GAACAAATTA CCTGCTGATT CTATTGCATT AGATCCAAAT     180

GTGATTGGTA CGGTCGACAA GCGTTCTGCG CAGATTAGAT TGACCGCCAA AGACCTGACC     240

CAAATCGCAA CTGATGAAGA CATGAAATCT AAGGAGAATA GAGACATTCC AAAAGCAAAC     300

CCTGCTGTGA AGAGTAAGAA ATTCAGGTCT GCGTACATTC CTCCGTAAGA AGACGCAGAA     360

TGTTGTAGAT GAGAGGAAGT TGAGAGTACA GAAGCAGTTA GAAAACGAAA AGGNNGCCCN     420

CTTGCGGAAG CANCANGCTG CTGAGGNGAG CTANCAGNAG ATNCGANCTN CCCTGNCGAN     480

GCGTCAGCNA GTCCACTCGC NNTNNNCTCA CCCNNNATTC TTCGTTNNCN GANTTCACNC     540

CANNNCNCCT CCCGNNCTNN NNCTTNCCCN NCCTNCNNTC ACCNCNNCNC TCCCNNTTCC     600

NANCCCACNC CCCCNCCNCC NNCCCCNNCN CCNNNNNNAN NCNNNCCCCC CTCTNCCCCN     660

NCCCCCCCNT NCC                                                       673

(2) INFORMATION FOR SEQ ID NO:60:

(i) SEQUENCE CHARACTERISTICS:
        (A) LENGTH: 523 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1017RP (xi) SEQUENCE DESCRIPTION: SEQ ID NO:60:

GATCAAGGTT GAAAACGAGC AGCGTGATAA AAAAGAGCAT GACGCCGATG TCCCTGAAGA      60

GGAATTTAAG ATTAAATATA CCTCGACCTA CTATAAGGTT GAGAATATGA CGCGTGTAGT     120

ACCACAGCAA TTAAAATATA TTGCATTTCC AAAGGATGAG AGATTTACTC CCGCTCGCAA     180

GTTTAAGGGT AGCAATGGCG TTATAGTGCT ATCGGACAAA ACTCCTGACG AGCCGGTCGA     240

AGTAATCAAA ACCGCTAGAC AGGAAAAAGA GACGGATGCT CCTCTGCCTG CTCCCTTCAA     300

GGTTCAGGAT GACTTAGAAT TCTGAACTGA TAATTAGGAA GCGTCGATTA TGTTCATTAG     360

GAAAAAGGGT ATTTTTTCTA GAAACGAAAG AACTTACTGA TTGCAGCTCT CTCTAAACAA     420

GTATATTATG AGGTGATTTA TTTCAACTGA ATCTGGCTAA CGCCCGGCAA CTAGGTCTTA     480

TCTTCTTGTA GTCACCCTAG AGGTGGTGGT CCCCAANCGG CNC                       523

(2) INFORMATION FOR SEQ ID NO:61:

(i) SEQUENCE CHARACTERISTICS:
        (A) LENGTH: 493 base pairs
        (B) TYPE: nucleic acid
        (C) STRANDEDNESS: single
        (D) TOPOLOGY: linear (ii) MOLECULE TYPE: DNA (genomic)
```

(vi) ORIGINAL SOURCE:
            (A) ORGANISM: PAG1017UP (xi) SEQUENCE DESCRIPTION: SEQ ID NO:61:

GATCTCCATC CACGTTTTGG CCTCGTTCCT GAGCTCCTCT GTGACTTCAT CCTTGATACG      60

CGCAATTAAG CCAGGGCCTC TGTATGCGTA CGCAGTGTAG AGTTGCACAA AGTGCGCCCC     120

CGCTTTGGCA AACTCGATGG CATCCTGGCC ACTACTGATA CCACCACATC CAACCAAAAC     180

CAGGTTCGTG TCCTTTGTGT ATTGGTGTAT CGTGCGCAAA GCTTTTAGCG CAAATGGTTT     240

CACGGGCTTG GCGGACAAGC CGCCTGCCTG GTTTTTCAGC TCCTCATCGA CAGTGTACAG     300

CGAGTCTGGC CTTTGGATAG TAGTGTTTGG AAACGATGAT ACCCCCAATA CTCGATTTTC     360

TTGGGCCGCC TCTGCGATCG ATTGGAATCC TGGCTCGGTC AAATCCGGTG CGATTTTAAC     420

AGGAAAGTTG GTTATGGTTA CTGGACCAAG AAAATGCCNC CGTGGNCAAA GATTGGGTTA     480

GCANAACAAG NTN                                                        493

(2) INFORMATION FOR SEQ ID NO:62:

(i) SEQUENCE CHARACTERISTICS:
        (A) LENGTH: 523 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1018RP (xi) SEQUENCE DESCRIPTION: SEQ ID NO:62:

GATCATCGTC GAGGAGTACA CGCACTCGCT CTGCGCGTGC GTGAACTTCG CCGCGTGACA      60

CCCGTACTTC TTCGACGCCA CCGTGTTCAG GAACCGGCAC CCGGCCGCGT CGTACAGGTG     120

CATGTTGTCG CACGCCGTTG CGCTCAGAAG GTACTGTCCA TGGTCGTCGA ACGACAGCGA     180

CGTGATCGGG CCCTGTTCCT TCTGCGCCAC CTTGAAAGAC TTGACCGCCC GGAACCCCGC     240

CAATGTGTCT TTGTTGATCC CGATACTCAT CCCGCTCGTC TTGCAGCTTC CGGTCCTTGG     300

CCCTCTCGCC GCTGCTCTGC ACTGCTGGCT AGCAGAGCTC ACCAAAATTT TTATAGCCAT     360

GGCCAGGCCA AACTTCACTA ACTGGGGAAC CACACGACCA CAGCAAGCAA TGCCCTCAGT     420

ATGTCGGTCG GTCGCACCGT CCTGGGATCG CTACTAACCC GCACAGCTCA AGCAGATGGT     480

GCACTTCAGC GCCGACCTCG CGCTGGTGGC GATGGTGCTG GCC                       523

(2) INFORMATION FOR SEQ ID NO:63:

(i) SEQUENCE CHARACTERISTICS:
        (A) LENGTH: 770 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1018UP (xi) SEQUENCE DESCRIPTION: SEQ ID NO:63:

GATCGCGTGT ACGACTTCAT GCGGATGCAC TACGTTATCA CCCAGATGGT GGTGCGGCGC      60

GACTTTCGGT TCATGCGCGA CTACCTGGAG GTCCTGGCGC GCCGGCTCGA GCAACACGAG     120

TTGTGCGATG CCCGCATGTC TGCCGCTGTG CAACGGGACC ACATTGCCCG ATACACCGAG     180

```
CTGCTGATGC TGTATGCGCG GAAGTCTGGG GATGAGAAAA TGCTGGCGGA GCTCTTTGCC      240

TCCTTGGTCG ATAGTCTGCC TCGCGGGATG GGCGGAGCCA CTCTTCGTCA GCCATTGCAT      300

GAAGTCATGA CGTACCTGAT CAGCGAAAAC CAGCCGCAAC AGGTGCTGAA ACTGGTGGCG      360

GGCATGCGCA AGGCGGAGCC CAATCGGCGG CCGGGCAAAT CCTCCGTTCC AGGCACCTTG      420

GCGCTGGTTG TTTCGGCGTT GCGACAGTTC AACAATCCTA ATCTCGTCGT GAGCTTTATT      480

GTGCAGGCAT ACAGAAAGAC GCAAACGAGA GTGCTGCTGG GACAACTCGG GCTATGGTCT      540

CTGGCATTTT ATGGCCGCGC TGTTGCGCTC TCTCCCGAGG CGGCGAAGTC GCCGCAGGAG      600

CTGGCGCAGA TATCGCCTGT GGACCTGCCG AAGGAGCTAA TACTGAAGTC CGTACCTGAC      660

AGCTGATAAT GTGCGAGCTC TATCAGCGAA TCTATCCGAG AAGCGATCGC AGGTGCCCGC      720

GGAGGAGTAC CGCGAGATTT AATCCAGCTA TTTGCGCTTT ACCAGGACTT                 770
```

(2) INFORMATION FOR SEQ ID NO:64:

(i) SEQUENCE CHARACTERISTICS:
        (A) LENGTH: 735 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1019RP (xi) SEQUENCE DESCRIPTION: SEQ ID NO:64:

```
GATCCATGAC CCATGCTAGG TGGAAGGAGC CCTTACCCGC TAACTCGGAC TCCCTCTTCA      60

ATTGCCTTAT CAGTTTGGTA TCCACAGCAC CCACGTCGTA CAACAACCGC CCCATCAGCG      120

TAGACTTGCC CGCATCCACA TGGCCTAGAA CAACAAACGA CATATGGGGC TTCTTCTCAC      180

GTACATATGC AGGGATGTCG AATGGGTTCC GCGGGTTAGT GGGCTGCACA ACCTTCTTGG      240

CCGACGGCTG TTCGCCCTCC TTCGGCCGCG AATCCTCCTC CTCGTCCTCG TAGTTCTTCG      300

GGGCCGCGTC CTTGTTGTTG AATTTCAGAT CGGCCACCTT CTCGGCCACC TGCTTAATCT      360

CAAAGGCTCG CTTCTGGGAT TCCAACACCA CGTCATCCGG CGAGGGCTTC ATGAAATTGG      420

CACTGGCCTG CTTCTTAGCT GCTTTATAGT TGTTAGGATA AAAAACTGAG AACACCTCCT      480

CCACTCGCCT CTTGAGCTGG GTTTTGCGTG GTTCTGCGCA TCCTGTCTGT CTCGAGAGGA      540

GCACGCTCGA CAGCTGCAGT GCAGGGCGCG CTGCAGGCTT GAAGGACGGC TGACGCTGCA      600

GAAGAGCCCC CAGGGCCATC CACTGGTCTT GCCGTGCCTC CGTCCTTGCG GGGCGCGCTG      660

CAACAGGCTT TGCCTCAGCG TCGCCGCGCG ACTGCTTCGC AGAGACGACA GCGTCTGCAT      720

CAGCGACGCG CCCGG                                                      735
```

(2) INFORMATION FOR SEQ ID NO:65:

(i) SEQUENCE CHARACTERISTICS:
        (A) LENGTH: 740 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1019UP (xi) SEQUENCE DESCRIPTION: SEQ ID NO:65:

```
GATCGCAGAT TCATCATCGC TGTTATACCA GGCTCTATCT TCCTCGAGGT CCTCGGGACC      60
```

```
AAACGCGGCG CTCTCTTGTG TGCCAAGAGG TGCAGGACCC TCGGCGCGAT CCTCGGCCAG    120

CAGAGTGGCA ATCTGGTCTT CATCCGCTAT CGCTGTCAGC TTAGGCACAA AAGCCAGTTT    180

TTCCGTTTTG TCGCCGTGAT CATCCTGCTC GAGCGTGCTC TTCTGATCTC TGCGACCCTC    240

TGCAAACTCT TTGAGCTGCC TTGCTGCTGC CTTGTCAAGT CGCTTAAATC TCAGCGGTTT    300

CTGTTTCTGG CCACCGCTCC CCAAGCTCTG GTCCGGCTCC AGTGCTGTTT CCAGTTCGTC    360

GTCCGAATCT TCGAAGCTCA GCGCGACCAA GTTTCTGGAT GTGTTTCCCT TCACGCGCTC    420

CCCGTCAAGG ACAGCCTTCA CCGTGGTGTT TGTGCGCTCC TCCTGCGTAC TCCGCAGGGA    480

TACTAGCAGC TCATGCAGGA ACTTCTCCTC CCCTTAAACT TGCCAAGCGC CATGCAGCTC    540

TTAGTGAACT TCACTGGATC GTATGCATGC ACGCGCGCTA TATTGCATAT CGGCTGCACA    600

AACTTTCTGT GACATTGGAT GCGGATGTTG GTGGATCACT CCTTCAGCCG GGTCATCGT     660

CTTAGCTCCT ACCGTACTTG CTCTCTCAGA TGCATGATGT GTACCATCGC ATCTTCAGCT    720

TGACAGACTT CCATATACGT                                                740

(2) INFORMATION FOR SEQ ID NO:66:

(i) SEQUENCE CHARACTERISTICS:
        (A) LENGTH: 537 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1020RP (xi) SEQUENCE DESCRIPTION: SEQ ID NO:66:

GATCGTTCCT GTTTCTGCGG GCAAAGTTCA GAATTGACCT AGTGCCAGAC ATGACAGTAT     60

CGTTCAAACT CCTCGGAGAG TTAGCCTTGG ATATCCACCA TGAAGACAAA AACCAGAGAC    120

CAACAGCGGA TCCTACCAAA ATGGCCAGAA TACCGAAAAA CCAGTGCAAT TCTCCGGTTG    180

CTTCACCTGG GACAGTGACG TTCATCCCAA ATAGACCCGT AACAAGATTC AAAGGAACTA    240

ACATTGTTCC AATCATAGTG ACCTTTCCCA ACATTTCAGT AACACGATTG TTACACCGGA    300

AGGACTCAAC TTGCAATTGT GCCAAGTAGT TACCATGTGA ACGGGAGAAA ATCTTCTCAT    360

AGGACAGTAA ATTTTGAAAC ATCGGGAGGA CATGGTCCTG AATATCTCCC AAATAGAGCG    420

CTATATCAGC TCTTGGTTGA GTGCGCTGGA CATGATGATG TTGTATGTTC GAGCCTAGCC    480

TGGCAGACAG AGGGTCGTGT CCGCTAGCCT GCAAGTTCGC AATGTTTATC TCGAGGT       537

(2) INFORMATION FOR SEQ ID NO:67:

(i) SEQUENCE CHARACTERISTICS:
        (A) LENGTH: 563 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1020UP (xi) SEQUENCE DESCRIPTION: SEQ ID NO:67:

GATCAGCACC GTGCCCTTCG TGTACGCCTG CTTGGACATG GTGTGCGACG ACCGTGTGTC     60

GCATTTCTTA CACGTGAAAG CAATCATCAT CATCGGCTTG TCCACCTTTA TAGACCCGAT    120
```

-continued

```
ATGCCGAAAC TCATCTGCAA TAGGCGGTTT CTGGCTGTTT TGCAGCTGCG GCGAACCGCT    180

GTGGAACCGA TGAGCTACCA AATGCCCCCC AAACACCGGA CCCAGCACGT ACTGCATGCA    240

GTTACGGCTT GGGCGGAGTA AACCAGCAAT CCTGAGAGGC CCCATCGAAC GTCTAAGCAT    300

TTTAAACAGT TATACGTAGT CAGCGGTTTT CCTAAAACAG GACATGAGAG TGCGTCGAAA    360

GAAGGCGTCA TCTCAAATTT TTCAACTTTA GAAGCGCTGC CCGAAAAAGC ACCGTCACCA    420

TTTATCTATT ACAAGATGAA CAGTTAGTGG TGCCGGCAAT TGTGTCAGAT ATATGTCTCT    480

GGACATGGAT ACAAGACACT CTCGCCACAG AAGGAGCAGG AGATAGCATC GAAAATCTTG    540

CAGAAGGCTG AGCTGGCTCA GAT                                           563
```

(2) INFORMATION FOR SEQ ID NO:68:

(i) SEQUENCE CHARACTERISTICS:
        (A) LENGTH: 346 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1021I1

(xi) SEQUENCE DESCRIPTION: SEQ ID NO:68:

```
GATCTCACCC TGCGCACCAT CGACAACCCT GCATACGCCG GCGGTGAGGT CATCGGCAAG     60

GCCCGTGCCC GCACACTCGA GATGCGCCTC AATGCCCTGT CCGCTACCAA TGGCGCGGCA    120

CGAACCCTCG AAACCGTGCC TATGAACATA CGCAAAGGCA TGGTTTCCAA GCACCGCAGT    180

CGCATCCGGG AGCACGAGCA GCTGGCCCGG GACTCCGGCA CCGTCCTCGC CAAGGTCCGT    240

CGCGGAGAGT TCCGGAAGAT AGACGCAACC TACAAAAAAG ACATCGAGCG TCGCATTGGC    300

ACGACCATCA AGGCTGCAGA CCGTGCCCGC AAGAAACACC GCGATC                   346
```

(2) INFORMATION FOR SEQ ID NO:69:

(i) SEQUENCE CHARACTERISTICS:
        (A) LENGTH: 562 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1021I2

(xi) SEQUENCE DESCRIPTION: SEQ ID NO:69:

```
GATCTGCGCC GGATGGCTGC GAGTTGAGCG CGGCGAAGAT GTGTGACTCC TGCAGAAAAC     60

GCTGGAGCTC GATGTCCTGT TCCAGCAGCT GCTTCTCGTC GCGGTCGGCC GCGGCAGATT    120

TCGGCGCGGG CTCGGTCTCT AGGCCCGGCG CCTTGCCGCT GCGGATGCGG CGCAGTTCTC    180

GTGGAGAAGG CCCGCTGTAG GCATCTGACG GCGCGCGGAA CGAGATCACG CGCGGCGTAT    240

GGGCCGCCTC GTCGTCGGAG CTGGCTGAGG CGCCGTCCAT TTCGGACTGC TCGTCGGATT    300

CAGACTGTCC GGAGCGCGCG TCGCCCTCGC TCTCCGGGTC ACTGTCGCTC TCGGAGGCGC    360

TGGTGCTTGT GTCGCTGCTT TGTGCAGCAC GGGTCTTGTC TACATATCCC ATATCCTCTA    420

GGGAGCCAAA CTGGGCCTCG AAGGCCCTCC CCTGGGNCCC GACNTGCTTG NATTTATCTT    480

CAATTGTCGG TCATCCNGGG GGGTTCTTGG GCCCCANGAA GTNTNTNANC AGGAANCCCT    540

AGNANNANGG TTTTCAAATT CC                                             562
```

(2) INFORMATION FOR SEQ ID NO:70:

(i) SEQUENCE CHARACTERISTICS:
        (A) LENGTH: 611 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1021RP (xi) SEQUENCE DESCRIPTION: SEQ ID NO:70:

```
GATCCTCGAG TTTGTGCGCG GCGGGTCCCG CTCATTTACC TAATCCTGTC TATAGTAAAC      60
ACGTTGTTGT ATCTACATAG CGCACCTGTT GTAACTTACG CTGCACGCAT GCGCGGGCGC     120
ACGTCCCCCA CCAGCGCCCG GTAGAACGCC TGGCCCGCGC GCCGCCCGCC CAGCATGCAC     180
AGGCGCAGCC ACGGTTTCAT CGTGATCAGC AGGCCAGTCC ACAGCGGGCC CTGCACCAGC     240
GGGATCAGCA GGACGTCCCG CACCACCACC TTGGCGACGA CCAGTGCGCT GATCCCCGTC     300
TCGCCGTCCG CCGTCGCCTC GCCCTCCTTC TGTGCCCGCA GGTGTCGCTG GCGCGCGCTT     360
TCCTTCGCCA GCGCTGCGCG GAACGTCTTT TTCGAACCTG ACGTCGGGTA TCGTTATTGC     420
TTGGGGTCCA TTGGAACGGC TGTTCGGGGT CAGAGGGAGG ATTCCTGCGC TGGTTTGGTT     480
TTTACGAAGA CGACCCTCGG TGAGAATGTC AGTTTGGCCA CTGGGCAGCC CCAGGAAGGA     540
CCGNGAATTC AAACCACCTG AGTNGGGCGN CGGNGTAAAA ACGCTAAGTT AGTGCNNTGC     600
ANACCCNCCT C                                                         611
```

(2) INFORMATION FOR SEQ ID NO:71:

(i) SEQUENCE CHARACTERISTICS:
        (A) LENGTH: 346 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1021UP (xi) SEQUENCE DESCRIPTION: SEQ ID NO:71:

```
GATCGCGGTG TTTCTTGCGG GCACGGTCTG CAGCCTTGAT GGTCGTGCCA ATGCGACGCT      60
CGATGTCTTT TTTGTAGGTT GCGTCTATCT TCCGGAACTC TCCGCGACGG ACCTTGGCGA     120
GGACGGTGCC GGAGTCCCGG GCCAGCTGCT CGTGCTCCCG GATGCGACTG CGGTGCTTGG     180
AAACCATGCC TTTGCGTATG TTCATAGGCA CGGTTTCGAG GGTTCGTGCC GCGCCATTGG     240
TAGCGGACAG GGCATTGAGG CGCATCTCGA GTGTGCGGGC ACGGGCCTTG CCGATGACCT     300
CACCGCCGGC GTATGCAGGG TTGTCGATGG TGCGCAGGGT GAGATC                    346
```

(2) INFORMATION FOR SEQ ID NO:72:

(i) SEQUENCE CHARACTERISTICS:
        (A) LENGTH: 438 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:

(A) ORGANISM: PAG1022RP (xi) SEQUENCE DESCRIPTION: SEQ ID NO:72:

ANNNNNGNNN NNNANGGTGG GGCGTGGTNG AATAGTGGGT CTTTCTGCCG GGGTCTGTGC        60

AGAAAACGAG ATTCTGGGGA GTATCTGAAA TTCTTTGTTG CGCCGAGCCG TCTGGGTCTG       120

CGTCAAGCGA CAGCGAGTTT GCGACAGGAA CTGAAGCTAA TTTCGTTGCT GGAGGTGTTT       180

TGGGGCTTCG CGTTTTCAGC CTTTCAGGAA ATCTAGAGGG GCTGTGTGCT TTGAGGCTGA       240

AATCAGGGGA ATAGCCTGAA TTTGCGAGCG TGAATTGAGC GGTTATATGG AACTGTGGTA       300

CATCGNCACA CTGTACCACG AGGACAGCGA ATATCTGACA GTAGGGCGTC CTTCGTAAGA       360

ACACAGTGTA TCGCGTGAGA TAGGTGTTGA TTGAGTCTAG CGTGCTAGGT ACTCTTTAAC       420

TTTCAGTCGG TGTTTTTT                                                    438

(2) INFORMATION FOR SEQ ID NO:73:

(i) SEQUENCE CHARACTERISTICS:
        (A) LENGTH: 461 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1022UP (xi) SEQUENCE DESCRIPTION: SEQ ID NO:73:

GATCCAGCAG ACGTTTTAAT CACCGATTTT TTCGGTAACA TTCAAAATAT AATTCTCGAT        60

GACAGTGAGA TAGATGGTGA AACTCCAGCT GGACTTACGG AATCTGGCCG GACTCGCAAT       120

CTGCTAGAAT TCGCAAAAGC GAAATTTTTT GGCANTGTAG ACGCAGAGAC TAATGGCACG       180

CATAAAAACG TGATTCCAAG CTATCCAGTG GTAAATGAGG ATTTACTAAG TGGGNANCA        240

AATGCATCCA CAAACAAAAT GATAAAATTG TGGGGGATTA TCATCTTCCT GGCACTAACG       300

TCATTAATGA TGAAGTACGC CAACACTGAA AACATATCGG GTAGTCGAGC ACTATTATGT       360

TTCTCTTAGA AAAATGCTTC ATGCTTCATG GAATTAAGGC GGCAACAAGT GCAAGGTTAA       420

GAACGGAATT TTACTATAGG CGCGAAATTT GTATATATTA T                          461

(2) INFORMATION FOR SEQ ID NO:74:

(i) SEQUENCE CHARACTERISTICS:
        (A) LENGTH: 213 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1023I1

(xi) SEQUENCE DESCRIPTION: SEQ ID NO:74:

GTCGAGAAAA CAGAGCTTGA GGTCCCACTG TTCTTTTTCA CTGCGGATGT CTCTGTCTGC        60

TCCACGACCC CCACTTTCAG ATTGTGGTGC ATCAAGCGCT GCAAGTGGAC TTCGAGACGG       120

GTGTCTGGGA TGGTGCAGTA CGCAAACTTC TTGTGCTTGT GATCAGCGGG GTCTGTCTCG       180

TGTACCGTAA GCTTGCCGGG CACCAGCTTG ATC                                   213

(2) INFORMATION FOR SEQ ID NO:75:

(i) SEQUENCE CHARACTERISTICS:
    (A) LENGTH: 725 base pairs
    (B) TYPE: nucleic acid
    (C) STRANDEDNESS: single
    (D) TOPOLOGY: linear (ii) MOLECULE TYPE: DNA (genomic)

(vi) ORIGINAL SOURCE:
    (A) ORGANISM: PAG1023I2

(xi) SEQUENCE DESCRIPTION: SEQ ID NO:75:

```
GTCGAGGGAA GTAACCAATA TATTCACGAG GGCTACCTAT GGCATCAATG AGACGTTCGG      60

AACCAAAGAT CGTCGGGTCC TGGGTGATAG CGCTTCTGTG TGGGGTCTTG TGTGCAAGCG     120

ACAACCTTCA TACACGCGAT ACTTCCTGGT TAGTGTTAAT CTCAACAGCG GTGAAGTTAT     180

CTTCGATGAC TTCAAAGAGG AGCGTTTTCT GACGGAGGCT TTGGAGACGC GAATAAAATA     240

CACAAACCCG AGTGAAGTTG TGGTCGGAGA TGGCCTTGGC TCAGAAATCG AAAAGGTGTT     300

TCATACTTCA GATTCCGATA TCACTCTAAA TAGGATCGAG CTCGTCGGGT TGTATGAAGA     360

AATCTTCAGT GAGCCGCACC CAGCCTTTAG GGGCAACGTT CCTCTGCAAA CAGCGCTCAT     420

GCTGGTGCAT GGCTACCTAA CAAACTTCAA AAATGAGAGT TTACTCTTCT TCAAGGAAAA     480

CTTTAAACCA TTCTGCTCGA AGACGCACAT GATTCTTCCC TTCTAGCGCT ATTGGAAGCT     540

TAGATATTTT GGGGACAGTA CAGATAGGAG CAGTAAAGGT CCCCTGTTAT GGGTNTTAGG     600

TCAANCTAGA ANAACTAGGG TTAAGGACTT GGAGGACTGG NTTGAAAGGC CTTNTAATTT     660

GGTCAAGTCA ANAGAGTTGN GGNNGCCAAN GATTCACNAG GNGGGNATTN TCATGGCTCG     720

GAATT                                                                725
```

(2) INFORMATION FOR SEQ ID NO:76:

(i) SEQUENCE CHARACTERISTICS:
        (A) LENGTH: 659 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1023RP (xi) SEQUENCE DESCRIPTION: SEQ ID NO:76:

```
TGCCCGGCAA GCTTACGGTA CACGAGACAG ACCCCGCTGA TCACAAGCAC AAGAAGTTTG      60

NGTACTGCAC CATCCCAGAC ACCCGTCTCG AAGTCCACTT GCAGCGCTTG ATGCACCACA     120

ATCTGAAAGT GGGGGTCGTG GAGCAGACAG AGACATCCGC AGTGAAAAAG AACAGTGGGA     180

CCTCAAGCTC TGTTTTCTCG ACGCTAGGGA TAACAGGGTA ATACAGATAT CAGATCTAAG     240

CTTGCCTCGT CCCCGCCGGG TCACCCGGCC AGCGACATGG AGGCCCAGAA TACCCTCCTT     300

GACAGTCTTG ACGTGCGCAG CTCAGGGGCA TGATGTGACT GTCGCCCCGT ACATTTAGCC     360

CATACATCCC CATGTATAAT CATTTGCATC CATACATTTT GGATGGNCGC ACGGCGCGAA     420

GCAAAAATTA CGGGTCCTCG CTGNAGACCT GCGAGCAGGG AAACGCTCCC CTCACAGACG     480

CGTTNGATTC TTCCCCACGG CGNGCCCNTG TNGAGAATNT AAAGGTTAGG ATTNGCAATG     540

AGGTNCTCCT TTCANTTNCT CCCTTTTNAA ATCNTTGTNG GTCAAGTCNT CANATCAAAT     600

TCCCAACATT AACACCNTGG TTAGGGAAGT TCANNTTTCN GGGGCCNNGA TTANTTCCN     659
```

(2) INFORMATION FOR SEQ ID NO:77:

(i) SEQUENCE CHARACTERISTICS:
    (A) LENGTH: 646 base pairs
    (B) TYPE: nucleic acid
    (C) STRANDEDNESS: single
    (D) TOPOLOGY: linear (ii) MOLECULE TYPE: DNA (genomic)

(vi) ORIGINAL SOURCE:
    (A) ORGANISM: PAG1023UP (xi) SEQUENCE DESCRIPTION: SEQ ID NO:77:

| | | | | | |
|---|---|---|---|---|---|
| GATCTCAAAC | CTGAGAATAT | TCTACTTCAT | CAATCTGGTC | ACGTTATGCT | TTCTGATTTT | 60 |
| GACCTGTCAG | TACAGGCAAA | AGGAACCAGA | AATCCTCAGG | TTAAGGGAAA | TGCCCAGTCT | 120 |
| TCGCTTGTCG | ACACAAAAGT | TTGTTCTGAT | GGCTTCAGGA | CTAATTCTTT | TGTTGGAACG | 180 |
| GAAGAGTACA | TTGCACCTGA | GGTCATCAGG | GGAAATGGCC | ATACAGCATC | CGTGGATTGG | 240 |
| TGGACATTGG | GTATACTTAC | TTACGAAATG | CTCTTTGGGT | TCACTCCTTT | CAAGGGCGAC | 300 |
| AACACAAATC | AAACGTTCTC | CAATATTTTG | GAAGAATGAC | GTTTATTTCC | CAAACAATAA | 360 |
| CGATATATCT | CGCACTTGCA | AGGACTTGGA | TTAAAAAGTT | ATTGGGTCAA | GAAAGAGAGT | 420 |
| AAGCGACTTG | GTCAAAGTTT | GGCGCCAAGT | GAGATTAAAA | AAGCATCCCT | TTCTTTTAAG | 480 |
| ACCCGTCCAG | TGGGCGGTTA | TTGGAGGGAA | CCAGGAACCT | CCCTTTTATC | CCCGTATTGA | 540 |
| CGGGAGATGG | GTACGACTTT | GGAAAGNTAT | CACATTAAAG | GATGTTAAAA | AGGCCGGGAA | 600 |
| TCCGGCCCAC | CCGGGTTAGT | CTCATATTCA | AAGGCGNGGT | TCNNCN | | 646 |

(2) INFORMATION FOR SEQ ID NO:78:

(i) SEQUENCE CHARACTERISTICS:
        (A) LENGTH: 557 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1024RP (xi) SEQUENCE DESCRIPTION: SEQ ID NO:78:

| | | | | | |
|---|---|---|---|---|---|
| ATNNNNNGNN | CANNNGTGGG | GCGGAGCGAN | TAGTGGGTCA | GCANGGTGCG | CTCGGTGTGT | 60 |
| GCGCAGCCGT | TGGCATGCTC | GCGGATCCTC | GCGTCCAATA | TACCGAATG | CATCATGCTT | 120 |
| CGCTGGCTCT | ATATTGACCT | GGTGGCCATA | TATGAAAAGG | CGGTCCTTGA | AGTTTTGTAG | 180 |
| AAACTCGTCT | GCCTGAGATG | GCGTAGCGAA | CCCAAGGAAG | CATTTATTGC | GGCATTTACG | 240 |
| AGGCCTGGAA | ACACTAACTA | CCCCGTACTT | CTCATCTAGC | AGTGGAAGGG | GCACGTCTGC | 300 |
| GGAAGGAAGC | GGCTCTGGCA | ACGTTTTCTC | CGCCGATAGA | GCATATGGGT | TATCCTTGTT | 360 |
| GATGGACTTC | AACAGTTGTC | GAGCATATTC | TATCCTGGAG | GCATTTGACG | CTGGCAAATT | 420 |
| TGACAGGTAG | ACACTGGATG | GCGGCGTTAG | TATCGAATCG | ACAGCAGTAT | AGTGACCAGC | 480 |
| ATTCACATAC | GACCGGACGC | ATGATATTAC | TTCCTTGNGN | ACTTAANTTN | CCCAATCTTN | 540 |
| NGCCAGATTN | ATTTTCG | | | | | 557 |

(2) INFORMATION FOR SEQ ID NO:79:

(i) SEQUENCE CHARACTERISTICS:
        (A) LENGTH: 334 base pairs
        (B) TYPE: nucleic acid
        (C) STRANDEDNESS: single (D) TOPOLOGY: linear (ii) MOLECULE TYPE: DNA (genomic)

(vi) ORIGINAL SOURCE:
    (A) ORGANISM: PAG1024UP (xi) SEQUENCE DESCRIPTION: SEQ ID NO:79:

```
GATCTAAATT CCCACGCCGC TGCGGCGGTT TCTCTGCGAG TCTTTGCCGT GAAGCACGAC        60

ATAATCGAGC CCAAACACAG CAAGATCGCA GAGAATCAAG CTTATGTAAG TCTCACGTGA       120

CTCGANGCGT GCAGAACGGT ACGGGTGTGC ACTGCAGGTG CCACGCCATG TCTCACATGG       180

TTGTAACACG GCGCGACCGC GGTTCGGAAT ATCAAACAAA CATATGTTTG CCGCAAAAGG       240

GACTGGTTCC CGCAGCTGCC ACCCGCAGGG GCACAGCGCG GCAATGCAGA GTCGCGTTAG       300

GGTGCCGTCG CCCCGATGGG GCAGTGTCGC CGCC                                   334
```

(2) INFORMATION FOR SEQ ID NO:80:

(i) SEQUENCE CHARACTERISTICS:
        (A) LENGTH: 621 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1025RP (xi) SEQUENCE DESCRIPTION: SEQ ID NO:80:

```
GATCAGCCCG TTGCCGCCGC CGCCGTTGTA CTTCTGGTTC TGGATGGACC CCGGCGTGAT        60

GGCGCTCTCG TTGCCGTACT CGTCGCTGCT GCGCAAGTCG CACTTCAGCG CCACTAGCAC       120

CAGCTTCACG CCCTCGCAGT GGTCCGCAAT TTCGCTCACC CACTTGTTCT TGACGTTCTC       180

CAGCGAGTCC CGCGAGTCCA CCGAGAAACA CAGCATAATC GTGTGTGTGT CCGAGTACGA       240

CAGCGATCGC AACCGGTCAA ACTCCTCCTG CCCAGCAGTG TCCCACAGGC TCAGCGTGAT       300

GTGCTGGTTG TCCACGAAGA TGTCATGGAT GTAGTTTTCG AATACCGTGG GCTCGTACAC       360

CTTCGGAAAG TACCTCGCGT GAACACGTTC AACAGCGACG TCTTCCCGCA AGCACCGTCT       420

CCGAGGATGA CGATCTTGCG CTCGATAGGA TGCTTCGACG ACGAGCTCGA CCACACAGAG       480

GCATCTTGTG TTTGTAGAGC TGGTGGTGGG AGCTCCTCTG ATGCCAGTCC ACGCTACAAA       540

TACAGCGTTT GAGACGAAAT ACTAGCTGCT ACTGTCCTTT CTCTCTGACG AGGTGCACGG       600

CGCATCCCCG TTATAACTGT C                                                 621
```

(2) INFORMATION FOR SEQ ID NO:81:

(i) SEQUENCE CHARACTERISTICS:
        (A) LENGTH: 522 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1025UP (xi) SEQUENCE DESCRIPTION: SEQ ID NO:81:

```
GATCCCCATG AGAATGAGCG CATCTTGGAT ATGGCGGCGG CACCCGGTGG TAAAACCACC        60

TATATATCTG CCATGATGAA GAACACTGGT TGTGTCTTTG CAAATGACGC CAACAAGGCA       120
```

```
AGAACGAAGT CCTTGATTGC GAATATTCAC CGTCTCGGCT GCACGAATAC AATTGTCTGC    180

AACTACGACG CCCGCGAATT CCCTAAGGTT ATCGGTGGAT TTGACAGAAT TCTACTTGAT    240

GCCCCTTGCT CAGGTACAGG TGTTATCGGC AAAGATCAAT CTGTGAAAGT AAATCGTACT    300

GAGAAGGACT TTATGCAAAT TCCACACCTG CAAAAGCAAC TGATATTATC TGCAATTGAC    360

TCTGTTGACA GCAACTCCAA GCACGGCGGT GTCATTGTCT ACTCTACTTG TTCCGTTGCG    420

GTTGAAGAAA ACGAGGCCGT GGTCGAATAC GCCTACGGAA GAGACCTAAT GTCAGCTGTT    480

GAAACCGGCT GGCTATTGGT AAGGAAGGCT CACTAGCTAC GA                      522
```

(2) INFORMATION FOR SEQ ID NO:82:

(i) SEQUENCE CHARACTERISTICS:
        (A) LENGTH: 508 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1026RP (xi) SEQUENCE DESCRIPTION: SEQ ID NO:82:

```
GATCCAATTG CTGGTCATAC ATACGCATTA ACAGATTTTA TTACTATGTA TCCAACGTGA     60

ATTGCTATAT GTACCTTATT ATCGGTTTCA TAAAGATGCT TTAATTTCTT ATTCTGAATC    120

GGAGTCGTTT GACCGGCGCT TAGACTGGTT ATGCCTCTTG CCATCGTTTT TCTCGAAAAT    180

GAAAATTCTA GCTTCACGCT CGGCTGCAGG CTTAGTCGTA TCCTGCTCAT TGTTAGTTCT    240

CCTATGACGG TATCCTGGGA AGGTATCCCA CTGGAATTTG TGCGACCTCT CAAGCTTTAA    300

ACCATGCTCC TTGGCAAGTA CCTTAGGCTG CCAAGAATCG TATGGATCAC CGGCAAATAG    360

GGACAAAATG ATCCTCCCCA TATCATCAGA TGATTGTTCT TTTTCCTACT TCATATCCGG    420

AAAGATGGGC AACAACTACC TTCTTATTCG CCAGCTTGAT AGTTGTTTAC AGCTATCAAA    480

AATATCCCGA TAGAGCTCTG AGCTCTCT                                      508
```

(2) INFORMATION FOR SEQ ID NO:83:

(i) SEQUENCE CHARACTERISTICS:
        (A) LENGTH: 594 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1026UP (xi) SEQUENCE DESCRIPTION: SEQ ID NO:83:

```
GATCTAGCAG ACTAGACTCT CTATCGCATC AAGTTTCTGT TTTCAAGTCT GGGTTTCTTG     60

AGCAACCTGG TGCCCCTATA CCTGTGTCAG ACGCACAGCG AAGCAGACGT CTATCGACGA    120

TGTCGAACTT ACAGACGAAA AAACAGCGCC CGCCAGCTAT TCCAGAGGCA GACGTATCAC    180

TCCAGGCTAT CAAGAAGCGG CGCATGTCCG CCAGGTCTTC TACCTCCCGT AAGTCGGGTT    240

CTGCCCAGCG TATTAGTGTT GTGCCACGGG CCGCAGCTTC AGAGTCATAT GTGGTTCCAC    300

CTGCTGGTGC TCCTCTGAAG AAAGAGTCTG CGGATGACTT ATTTCAAACG ACTGCTTCCT    360

TTTATGAACG TTACACTATT TCCACACTGA AAGAAATACC GAAAAACATT GCAGATGAGG    420

ACTCTGCCCG ATATACCGTT AACGAGGATA GCATCACTAT GGCTGACCTT TGCAAACCTC    480
```

TATTCCCGAT AGGTGAAGTA TCTGATAATT TCACCGGGCG AAAGAAGCTG CAAAAGCCAA     540

GATGGAAGCT CGGAAGAAGC GCCGCGAACT CCGACAGATG GCTAAGCGTC AATC          594

(2) INFORMATION FOR SEQ ID NO:84:

(i) SEQUENCE CHARACTERISTICS:
        (A) LENGTH: 454 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1027RP (xi) SEQUENCE DESCRIPTION: SEQ ID NO:84:

CATATCGACG TACTCTGGCG TTTGTTCTTC TTCGTCAGCA GGAACGCCGT CCGGCATAGG     60

CTTACTGACT TTCACAGACA TGATTCTTTT GCTGCAAGTA AAGTATATTA ATGGCGCTGT    120

CAAAAATGGT AATAGTACGG AAAGAGCAAC CTGAGAAGCG TCCAGGGCCT GCGATAAGCC    180

GTTTTTACCT AGAGCAGTGG ATACAGCTAA TGTTGGAATC AATGCAATGG CTCGTGTCAG    240

AATTCTCCGT TTCCATGGGG TTATAGTCCA GCGTATATGG CCTCCGCATA CTATTTGTCC    300

AGCTATGGTA CAGACAATNC CTGCCGATTG GCCCGAGATT AAGAGTGCGA GCATGAATAT    360

GGTACCTGCC GCTGGTGCCA AAGTGTTGGA TAATAGGTGG TGTATCGTGT ATAGATCCGC    420

ATCGATGGCT TCCGGGGTAT CATACAGTGC GCTA                               454

(2) INFORMATION FOR SEQ ID NO:85:

(i) SEQUENCE CHARACTERISTICS:
        (A) LENGTH: 446 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1027UP (xi) SEQUENCE DESCRIPTION: SEQ ID NO:85:

GATCAACGAG TAAAAATGCC AGGTGTTTCC GTTAGGTACG TGTCATGAGT GCTAGTTTAT     60

GGTTTGGTAC GGCTGCTGGG GGGCGCTTTC TGGGAGGTTC CAGCGCTCAT ACGTTATGTG    120

AAGATGCTTC GATCGNGAGG GTTGCGAGAA GGAATGGGAA TGTGCCAAGC AGGACTTGGT    180

GATTGGTTCC AGAACGTCGC TGACTGTGTC AAATATGAAA TCATTGGGCG AAACTTAGCT    240

TGCTACGGAG TCCAGCATGC AGAACGTGCG GCCGAAGCTA GCTGAGGCTC GATGAGACGG    300

TGGCGGAAAT CCTTCGATCC CAGGCCAAAG CAGACGTACC TACCAGCTTT TAATGTGCCC    360

GCCTACTAAC ATGATATACA GAGACGTTCC AGCTCAAGAG TTCATCAACG CTTACGCTTC    420

TTTTCTTGCA AGACAAGGT AAGTTG                                         446

(2) INFORMATION FOR SEQ ID NO:86:

(i) SEQUENCE CHARACTERISTICS:
        (A) LENGTH: 551 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
    (A) ORGANISM: PAG1028RP (xi) SEQUENCE DESCRIPTION: SEQ ID NO:86:

```
GATCATGCAA ACGGAGAGAA GGAGAAGAAG TCTAAGAAAG AGGGCACTAA AGAGAAGAAA      60

GCCAAAAAGC AGGAGAAAAA GGAACTGAGA AACATCATTG AGGAGTCCGT TGAGCAAAAT     120

AAGCTAGCAC TGATAGAAAA GGTGGAGGAA GAAAGAGGCC GCACGAAGGA GAAAGACCTT     180

GACATCAAGT TCAGGTATCG GGAAGTTTCG CCAGAAAGTT TTGGCTTGAC CACCCGTGAG     240

ATATTTATGG CTGACGACGC TGCCTTGAAT GAGTATATTG GCCTCAAGAA ATTTGCACCA     300

TATAGAGCAA AGGAGTTGCG CAACAAAGAT AAAAGGAAGG TCATGAAGGC TAAGCGTCTA     360

AAAGAATGGA GGAAAAAGGT GTTCAATAAC GAAAATGGGT TGGCCGATGA GGATGAGGCC     420

CTTGATACCC AGGCGGCTCC TAAAAAGGAG AAAAGCCGTT CTAAGCACAA GACAAGTAAG     480

TAATATTACC GTCTTTATGT ACGTTCTGCC GTAATTATAT TTTGCTATAC ATATATATTA     540

ATTTAAACTT T                                                          551
```

(2) INFORMATION FOR SEQ ID NO:87:

(i) SEQUENCE CHARACTERISTICS:
        (A) LENGTH: 628 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1028UP (xi) SEQUENCE DESCRIPTION: SEQ ID NO:87:

```
GATCCGCGCC CGGCACAGGC CTGGCAGCAC CCATCGCCGC ATGCTGTGCC TAAGATGTCT      60

CAGAATTACG CGGCCGCTCA GGCGGGCGCC AGCCCCTCCA TGCTTTTGGG CCAGGAAGCC     120

TTCCACGAGC TGGGCGACTC GCCTGGCATG TCAATGTACA TGTCGCCCCA GACCCATAGG     180

CTCAAGGGCA ATGGCGGGTA CCTGTTGCCG ACCGCTTCTA TCTCCGACCC TTCGGTGCTC     240

GGTGACACCG GCCGCCCTCC GTCTTCTCAG TCATTGACAT CGCACCTTCT GCGTACCCCG     300

AACTTTAACA TGAATGACTA TGTGCATAAC CTTTTCAGCC CCTCACCAAG AATAGACCCG     360

CCAGGTAGCT CTGGGAATAT ATAGGGCCTC GCACACATTT AGCGCACAGT ATACTAGCTA     420

ATCCTACATT CTCTGTCATA GTAATGCCTA TGTCAGCACA CCTGCCGTAT AATTTCATTA     480

TTTCCTGTTT CATAAATGCT GACATATGTC ACGTGGCTGG ATCAGCACGT GATGGCAAAA     540

TTCTTATGAA TGAGCCTGTT CATCTCGTCA GACAATACAT TATACACGCA TCCATCTCTC     600

GGTATGATAC GGACTCTCTC ACACTGGA                                        628
```

(2) INFORMATION FOR SEQ ID NO:88:

(i) SEQUENCE CHARACTERISTICS:
        (A) LENGTH: 655 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1029RP (xi) SEQUENCE DESCRIPTION: SEQ ID NO:88:

```
GATCGTAACA CTCTGGAGAA GTGGAAAGAG CTAGTCCCTC CGAGCTGTAA ACGATGCATG        60

GATGCGCTTC ATCACAACCG GTACGACACC GCCGAGTTTC CGGAGCACAC GCTCGAGGAT       120

GTGGGAAAAG GGGTTCCGCG CGATGCAGTG GTATACCATA TTGCGCCACT GTGGCAATTT       180

CCGATGGGAC TGGATCGGCG CGTGCTGCAG AGCTCAAAGA AGGTTTGTGT GCTATTCTCG       240

AAGATCGATA TGGTGGTGCA GAGACCGTCG CACATGCCGC AGGACGTAGG TGCATTTTTT       300

CAGAGCTTGC TTTATCATGA CCTGCATGTC AAGATCACGA ACTTCCGCTT CTTTTCTGCG       360

CTGAAGCAAT GGAACATCCA GACGGTGCGG AACGCTCTGA GTAAAGAAAG TTACTTACTT       420

GGCGGGCCAA ACGCGGGCAA GTCGTCATTG ATCAATGCCC TGATGAAGAC TGTTGTTTAC       480

GAAAGTCGGC GTCTCGTATC CTCAAAGCAG TCCTCTGCGA CCCCTGCCGA CCTGCCTCCA       540

AAAGCGCATT TGGACATCCA TTCTGCGGGT GTGAGCACAA TACCGAACTT CACTCGCCAA       600

CCCAGCAATA CGATATAAAG GGCAAGATCT CCACGATTTC CAGGCTACCG CACAT           655

(2) INFORMATION FOR SEQ ID NO:89:

(i) SEQUENCE CHARACTERISTICS:
         (A) LENGTH: 638 base pairs
         (B) TYPE: nucleic acid
         (C) STRANDEDNESS: single
         (D) TOPOLOGY: linear (ii) MOLECULE TYPE: DNA (genomic)

(vi) ORIGINAL SOURCE:
         (A) ORGANISM: PAG1029UP (xi) SEQUENCE DESCRIPTION: SEQ ID NO:89:

GATCTCGTGG TGTTTTGCAA CTTGGTGCGT GACGCGATAT CTCAGGCTTT GCGTGCTGAG        60

CATGATTATG AGGTGAACAA GATGCGCCGC GCGCTCTCCT TACTCCAAAA GCTGTATATT       120

AGGGATAGAA GGACCAATTT CCTCTCCGCG GCCAAGGGGG ACGACTTCTG GGTCATTGCG       180

GATACCACGG TGAAAAACTG CGACATTACA TCTCTCCTTC TTTACTTTGA TGAGTTCTAC       240

AGAGAACAGT TGGATTTGTT CCTGGCGCAG GGCCGTGCTC GGCACGAGGT CCCCAGCGGC       300

GATCTCGTAG CGTGGGAAAA CGATATAAAA GTAAAGTTCT TTAGCGAGAA GTCATCGAAG       360

CACGCTTCGT GGGGTTCCCT TGCCCTGCGG AAATTCGAAC TCGTACTGCG CGCTCCGTTT       420

CTGTTGCCCT TTCGCGAGCG GGTCGCCTAC TTTGAAACGC TGATACACCA CGACCGACGG       480

CGGTTGCAGG GACGCCACAC AGGACCAGCC TTGCGCCTGC CCGACCTGTA CTTCCCGTCG       540

TCGCGGCGGC AGCGTGCGAT TATCTCCAGG AACAACATCC TGGAAGATGC ATACSAGGCG       600

TATTATCCGC TGGGCGAAGA CTTTAAGGAC CAGCTGGC                              638

(2) INFORMATION FOR SEQ ID NO:90:

(i) SEQUENCE CHARACTERISTICS:
         (A) LENGTH: 688 base pairs
         (B) TYPE: nucleic acid
         (C) STRANDEDNESS: single
         (D) TOPOLOGY: linear (ii) MOLECULE TYPE: DNA (genomic)

(vi) ORIGINAL SOURCE:
         (A) ORGANISM: PAG1030RP (xi) SEQUENCE DESCRIPTION: SEQ ID NO:90:

GATCTGCTTG TTGCGCAACG CTTCCCAATC GATGTCGCTG AGAAAGGGGT GGGCGCGGAC        60
```

-continued

| | |
|---|---|
| CTCTGCGCCG TCGTTGACCG CACCGAGGCG GTGCTTGGGA TTGCGGTTCA AAAGGCCCTT | 120 |
| GACAAAGGAG CGACCTTCCG GCGATAGCAC GTCCCTGGGG AATTTGACCT TGCCAAACGC | 180 |
| AATCTTCTGG TACATCTTCT GGTTGTCCTC TGCAAAAAAA GGCGACCAGC CACAGCACAT | 240 |
| CTCGAATATC AAGACGCCCA GCGACCAGAA GTCAACCATT TTCGTGTAGC CGGTCTCATC | 300 |
| GAGCAGCAGC TCGGGCGCTA GATACTCGGT GGTACCGCAG AACGTATTGG TGCGATCCTT | 360 |
| TAGGTCCGCT TTTGAGAGGC CGAAGTCACA TAGTGCGATA TTGCCGTTGG CGTCTAAAAG | 420 |
| GATGTTTTCT GGCTTGAGGT CGCGGTACAC GATATCATTA TCGTGAAGGT ATTCCAACGC | 480 |
| AAGCACCAAC TCGGCAATGT AGAACTTTGC CCGCTCCTCC GCGAACCGAC CTTCTTTCTG | 540 |
| AAGGTGCCAG AAAAGCTCAC CACCGNTCAG GAAGTCAGTC ACCAAGTATA AGTCTGTGGG | 600 |
| CGTTTGAAAA GAAAATTTCA ACCAACAATG AAGGGACACG ACTTTGAGCA GTACGAACGA | 660 |
| GATGTTGCGC TCACCAATAG TATGTGCA | 688 |

(2) INFORMATION FOR SEQ ID NO:91:

(i) SEQUENCE CHARACTERISTICS:
        (A) LENGTH: 751 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1030UP (xi) SEQUENCE DESCRIPTION: SEQ ID NO:91:

| | |
|---|---|
| GATCGATTCC CTGAGCATGT TTTTCCCTAT GCTGCAGGTT TTACATGGTG ACATTGCGGA | 60 |
| TGCCGAACTA AAGAACCTTA TGTCTTTGAA ACTCTGGAAC ACTTACGGCG GAATTCCTGA | 120 |
| ACGCTGGCTA TTCACTACTC TCTACAAGAA ACAGCAAGTT ACCGTAAATG ATACCGTGCA | 180 |
| GCTCGAGTGG TATCCTTTAC GGCCAGAGTT TGTAGAATCA ACCTATTCCC TTTACAGGGC | 240 |
| CACTAAAGAC GCATTTTATC TGAATATCGG ACGAAGCATC CTCCAGGCTC TATCAACGCG | 300 |
| CTTTAAAACG AAATGTGGGT TTGCGGGCAT ACAAAACGTC ATAACGGGAG AGCCACATGA | 360 |
| TAGGATGGAA TCGTTCGTTT TGGGCGAGAC CTTAAAATAT CTCTATCTCC TCTTTGACGT | 420 |
| ATCCAATGAA TTGCATACAC AAAAACGCAC TAACCAAATA TTTAGCACTG AGGCGCATCC | 480 |
| ACTGTGGTTG ACTGCCTCGA TGAAGGCTCG CTACGAAAAA AACAAGTACT GTGAAAACGA | 540 |
| CGTGTATATA CAGAACTTGC GTCGCCTACA GGAGCTTGAC CAGCTGAAAA GCCGTGCCAA | 600 |
| TTCATTCACT GCAGAGGAAG CCATGATACC AGCTTCAGAT TTCAAAACAG AAGACTCCGA | 660 |
| GGAGTCTTTG AAGGACCGCG TTGCAGCGCC ATACTAGAGG CCTACACGTA GATACGACAC | 720 |
| GTTCGTGGAA CATGCAGACC TTTCGCGACA A | 751 |

(2) INFORMATION FOR SEQ ID NO:92:

(i) SEQUENCE CHARACTERISTICS:
        (A) LENGTH: 646 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1031RP (xi) SEQUENCE DESCRIPTION: SEQ ID NO:92:

```
GATCTTAGTA ATGATCACGT GATTGGATTA CCGCTTGTGC GTTTTGCTCT CCGCAAAGCG        60

ACATTTACAC GGGAAAAGCG GTGAACTCCC GCCGAAACCC AAATACTCGT ACACTATGAC       120

TATAGACGAC AATGTCGATG ACGTGAGCAC AGTTTAACTC TAGTGTACAA TCACGTGCAC       180

ATACCTTCTC TGCCACCCAC ACATTAACCA TTTATTTGTG GTCACGTGAA ATGAATCGAT       240

GCATTTTATA ACTGCAGGTT AGTTGAGCCA TCTCGCCAAC GATGTCCTGC GACAGCATTC       300

GGGGCACGGC GCGTCATGAG TGATTGGAAG GAGGCACAGG ACTCCACGGG GCGTGTTTAC       360

TACTATAATT CGAAGGGGGA AACGTCATGG AATAAGCCCA ACGACACGCC AGTTGAGCTG       420

GAACCGCGAC TCGAAGAATG TGGCTGGAAA GTGGCAACGA CGGAGGACGG TAACGTGTAC       480

TATTACAACA GGGAAACTGG CGAAAGCAGG TGGGAGAAGC CGGAGTTGGA GCCAGCCGAG       540

GAAGTGCCCC GGGAAGARGA CGAACGCGCG CCGGAGGARG AGAAGAACGA GCCGTCCGCT       600

GCTGARGAGC CCGGGGTCCG GATCGAACTG CTGCTCAACT CAAACC                     646

(2) INFORMATION FOR SEQ ID NO:93:

(i) SEQUENCE CHARACTERISTICS:
        (A) LENGTH: 386 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1031UP (xi) SEQUENCE DESCRIPTION: SEQ ID NO:93:

GATCANCGAN CAGCACGGAC AAATATAACA GCAGCACGGG CATTTGTCTA GTCGGCTGGT        60

GYYYTGTGTC CACCGTGACG CTGGCGCTGG GCTGGAGTGC AAAAACCGGA GCCACAAGCG       120

TGCGCGTCCG ACGGGGAAAG CTGCGATCGT GGCAGCAGCA GAGAATGGGT GCGGGAGTGC       180

YAGAGCGGTG CTGGGAGCGC GCGGACGCGC GCACGCTGCG CGCGGCCGCG CTGATGCTGG       240

GCGCGGCATA CCGAATCAAG AAGGCACACG CGCGGGCGCA GCTGGCGATG CAGGTGGCGC       300

GGCTGCSCCG CCTGCGTGAC GTGCGGCTGC GCCGCGGGCG CGTCCCGCTG CTGGCKGTAC       360

ACCCCGGTCT GGTGAACTTC GCGTAC                                            386

(2) INFORMATION FOR SEQ ID NO:94:

(i) SEQUENCE CHARACTERISTICS:
        (A) LENGTH: 775 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1032RP (xi) SEQUENCE DESCRIPTION: SEQ ID NO:94:

GATCTTTAAC CTCTGGACTT CAATCTTCTG GGTAAAAGCA CAAGTTTAGA GATGTATGAT        60

CCAAGCACCA AACTACAGTC TCGAGACAGC AAAATAATCC TACTTATATA AACTGAACGT       120

TGCAATTCTT TAAAAAATTT ACTAACTTCG ATTAATGCGG CGCCGGTGAG CGCCTCTGTT       180

ATTAGCTGAG TCATGCTGAG GGTTTGGCTA GGAAGCATCC GCTCTTACTA CGTATTTACC       240

AAGGCACAGG AAAATGTGGT GGTATTCTTG ATTTCGGCGG CGTTTTGTAC ATTACTCCAT       300
```

-continued

```
AGCTCATGGT CAGCAATCCC GTTCAATGGA CATTTGCTCA ATCGTGAGTC TTCCACTGGA        360

CTTGAAATCC CGCAGGGATT TTCGGCTCCT GGCTCAACCA GGTCGCCCGG ACACCTACAG        420

CCGAAAAAAT TGCTGCTTGG ACTAGGTCCG CTGACGTGGA CATGCGAGAT GACTTTAAAG        480

TGATACATTA AAACCAGGGC TGTATGAACT CAGCAAAGGT CTCTTTTATA CAGTGTGCAT        540

ATAATATTTC GGGCGCTTGC AATTACCTCA TGCCAGGTAC TCGTAAGATT CGCCGTCCGC        600

GAGCGCTGTA GGTATTCCTT GCTAATTAAG TTGTCGATGG CCTTCTTGAT AGAGATACCT        660

TTGCATTTGA CCGTTGTGAG ATTCGGCTAT GCATTCGTCA CCAAAGTGGC ATGAGAGACG        720

ACCCGTTTGC TTTCATAATT CTGACGATAC AAGCTTCAGA ACAATTGCTT TCTTG            775
```

(2) INFORMATION FOR SEQ ID NO:95:

(i) SEQUENCE CHARACTERISTICS:
        (A) LENGTH: 720 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1032UP (xi) SEQUENCE DESCRIPTION: SEQ ID NO:95:

```
GATCCCGAAA ATAGACTACA TCTGCCGCAA GCAGCGCGCC CTATCTGCAT TTCTCTTCTT         60

GGTGGTTGTC ATGTGGGTCA TCACGTTCAC CATTAGCATT CTAAGGGTAG TGGAACGGGT        120

GAGTTCACTT TCACCCAGAT AAAAGTTAAC AGGACAAGTG AAAAAAAACG GGATAAAGG         180

CATCAGTTAT GTAATAAAGA GCTATACGGC AATAAACATT TAAGTAACTA CCATGGTATC        240

TCCAGGGTAT TACTAGGTTT CCCTGAAGTT TCGAATGTGC CTTCGTTACC CGGTGTTCAT        300

GCAGGCTAGC GCGACAAGAA AAATGCGGTC CCACCCATTC CACGATTAGC GGTGGCAAAA        360

GTCCTAAAAG TTAGGCAAAT AAACACATAA CCATCCCTCA AAAGCGCTT GAGCAAGGCT         420

ATCGGGGTC AGAGCAGGTG TAATATACAT TAGAAGTGAG CGATGAACGA TAAATTGCCG         480

AGAGCAGATG ACTTGGAAGC CACTTGGAAC TTTGTGGAGC CCGGTATCGG GCAGATCCTG        540

GGCCGGGATG GGTCGCCCCA TGCAGGGCGA GTGCAGAAAC TGCTGTCAGC TGCGATGTAC        600

ATGGATGTCT ACACGGCTAT CTACAACTAC TGCGTCAACA AGTCGCGGTC CACCGGGCAT        660

TTTCAGTCGG ACTCGGCGCA ACGGCAGTCG AACCAGTCAT CGATCCTGGT CGGAGGGAGA        720
```

(2) INFORMATION FOR SEQ ID NO:96:

(i) SEQUENCE CHARACTERISTICS:
        (A) LENGTH: 602 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1033RP (xi) SEQUENCE DESCRIPTION: SEQ ID NO:96:

```
GATCTTGTCG AACAGGTCGC CCCCGTCCGC CAGCTCCATC GCGATCCATA GGTACTCACG         60

TGACACATTG CAGTCCAGCA CCCTCACCAC ATGTCGGTGC CCCGCGCACC GCGTCTGCAG        120

CACCACCTCG CGCGTCAGAT CCTCGTCCGT CATCCCTCGC GCTTTGCAGC GCTCGACGTG        180

CACGAACTTC ACAGCCACTA TCGTCTGCGG GTCTGCGCGC AGCGAGGCGG TTTTGACGAA        240
```

```
CGCGAACGTG CCCTGCCCAA TCGTCTCCCC GAGCTCTAGT TCCTTAATCT CCGGCAGGCA      300

TTCAGCCTGC GACGACTCCA TAGTAGCCCA AAGTCGTTGG ACGGCCTTCC AGGTGGCCTC      360

TAAGTGCTGG TGATGGTTGG TTGAAAAGTG ATGCCCCAAC AATAGTGTGA AAAACGGCAA      420

AGTGGGCCTT ACGGGGGGAA CAAAACAAGT GCTAACTACA CGGAAGCAGG AATTAATTTG      480

GGAAGTGGGC TTGGAGCACG GTATAGGAGT ACCGGAGGTG GATATGAGTG TCGAACAGGT      540

GTCTGGTGCG CACGCGTGCG AAGAACAGGT GGCACGGTTT GAACGCAATG TGGAGGCGCG      600

GA                                                                    602
```

(2) INFORMATION FOR SEQ ID NO:97:

(i) SEQUENCE CHARACTERISTICS:
        (A) LENGTH: 683 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1033UP (xi) SEQUENCE DESCRIPTION: SEQ ID NO:97:

```
GATCCGCGTC GTCGAAAACA GGTCCTTGGG GTGCGATACC GCCAGCACCT TGCACGACGT       60

CCGCACCAGC TGGTCGTCGC TCTCCAGCGC CGTGATGATG TCCTCCACCG AAAACACCTC      120

CAGCACCGTC TCAAACGGCG CAAGCTTCAC CACTGTGTCC AGCAGCGACA GAAGCCCGCT      180

ATAGTCCAGC CCACTCATCT CCCCTGCCGT GAGCACCTTT TTCATCGCCG AGAGTAGTGG      240

CCGTGCGTCT GCGTCGAGAC GCACCATCAC CCCCAGGTCG AGCTGCAGCA TGTCCACCAG      300

CCCGTTCACC GACCCCACGC CGTGCTCCTC GGGCGCCTCC AGCACATCCG CCAGCTGGCT      360

CATTCGGTCC TGGATCCTCC ATTCCTCCAT CGCGATATCG ACTCTTCCGA AGTAGCGTTT      420

TGGGGTTTGT AAAAGTAAAG GGCACTTTTC CAGCACTTCG CCACTTAATG TCGTGAGGCA      480

CAGAACCGGG GCCCTATGTT GCCGGAGTCA AGGCTTGCCT CGCTATATTC CGACTTCAGG      540

AAGCTGCAAG AGCTCAATCC AGATGGGTTC CAGGCTAACG TTCTAACATG GAAAGACCAC      600

CTGATGAACA CAGTGTGGCG GGACGAGCTT CTGATAGAAG GGGGCGACAA GCTGCTGGAG      660

CGATTGAGCA CCAAGGAGAC GGG                                             683
```

(2) INFORMATION FOR SEQ ID NO:98:

(i) SEQUENCE CHARACTERISTICS:
        (A) LENGTH: 653 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1034RP (xi) SEQUENCE DESCRIPTION: SEQ ID NO:98:

```
GATCATATTG GTCTTGGCGC CAGCATCGCC TCTTCTGGTT CTGAGCCAGT AGTATGATAG       60

CATGCCGCCG ATGAACCTGG CAATGGAGAA ACTAGGTGAG TTGTACATCC CGACGCCAAG      120

GGCAACGCCT GAGGGTAACC ACTGCGCCCA TCTGTACTTG TCCTTATCAA TACAATTCTT      180

TACGAGGGAT ATGACTGCAA AGATGCTTCC TAGGATGATC GAACATTCCA GTGCGTATGG      240
```

| | |
|---|---|
| TGGGAGTGCC ATACCCATGA CCAGACGTGC GCAGTCTATC CATACGAACG CAGTTGGGAT | 300 |
| CCGGAATTGC TGGCTGGGGA TTTCGTAGAC CTTGTTGTAA AAAATGTACA TTACGCTAGA | 360 |
| CAACACGATC GACCAGCTGG CGCCGATAAT CTGCGCGGTA AACTGAGCCC TAGGAGAAGC | 420 |
| ACCGATTAAA TGCCCTGTCT AAGATCTTG CATTAAATCG CCCGCTTGCT GAGCGCCCGC | 480 |
| CTCAGCTATA CTTCCGGCAA CCAAATTTAT TAATACAGCG GCCTTGTGAT CCCTGGGTAC | 540 |
| ACAAGAGCGA AAATGATTTG AGCCAGCTTT CCGATGCCGC TGAACGGGTT GAGATCGGTT | 600 |
| TCCCCAAGAC CCGGACGCCC AAAATCGATA GAAAGATGCT ATAAGGAGAG CCA | 653 |

(2) INFORMATION FOR SEQ ID NO:99:

(i) SEQUENCE CHARACTERISTICS:
        (A) LENGTH: 670 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1034UP (xi) SEQUENCE DESCRIPTION: SEQ ID NO:99:

| | |
|---|---|
| GATCACGCAC AGCGGACACC ACCAAAGCAG AACCACGGTA CCATATCTCT CACACACGGC | 60 |
| TCCCACTAGC ACAGCGCCTC CACCTGGCCG CCCTGGGCTC GGCCCCCCGT CGGCATAAGC | 120 |
| ACGTCGGGGG ACCTATTTAG TTCCAAAAAT ATTGTTGTAA CAGTAATAAT ATCCTCATTG | 180 |
| AGGACATTTC AGTTGTTACA CTGAAAAGAA CAGATACTAC ACTTGATCTA AGCCAAAAGG | 240 |
| CAAAGAGATT TGGTTTCTAA AAGAAAGAGA ACATGCCTG TAAGAGGGAG GGCCATCGCA | 300 |
| CATTTTTTCT CTCCTTATAT ACCAAGTAAA ATTTAGAAAA AGAAACGACG CGGCTGCTTG | 360 |
| GTCGGCGCCG TCTGCCTGGG ACTCCAGAGG GGCTCACGCA GGAATCCTGC ATCCAGGGCG | 420 |
| ATGCGATCAA GCTCTGAACG CCCATAGCTG CCGCCATACA CGCCGCCATT CGCGAGCTTT | 480 |
| CGTTGAGTTC GTAAGCCATG AAATCACAGT ATACGATTCT CGAGCGCAAG TTAAAGAGAG | 540 |
| CCCACTGGGC ATACTGCTAG GGCTACAACT GCGCACCAGC TGCGAAAGCG AACTCCAAT | 600 |
| AGTTAAGGGC GGGTGGCAAT AGTATCTGCT GCAAGCAGCT TCTAGAATTT GGTAGATGAG | 660 |
| TGCGTTCATG | 670 |

(2) INFORMATION FOR SEQ ID NO:100:

(i) SEQUENCE CHARACTERISTICS:
        (A) LENGTH: 558 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1035I1

(xi) SEQUENCE DESCRIPTION: SEQ ID NO:100:

| | |
|---|---|
| GATCTTTTGT GGAACCAAGA TCACCACACA CGAATATGCG ACGCCAAGCG CCGGAACGAG | 60 |
| CCACACATGG GCCGCGGCGG TAGCGGTGGG CCCAAGCAAG CGTATTTTGA GGACCTGACG | 120 |
| TGCTGTGGGT GAGCAATCCA GGGCATACTA GGCCCAGGTT GTCAGCTGAA AGTGTGTTAC | 180 |
| CCGGTATCGG TATTACCCGG CTCGTATAAA TGTTACCCGG ATATGGTGAA GCCAAAATTT | 240 |
| TCCACGGCGT AAACAACAGG AGAGTGTACG TGCATATGGC GGCAGCAGCT AGTGTAGCCT | 300 |

```
AGTGAGAAGA AGGNCTGTGA GCTAAGACTA GCGAGGAGAC GAGGATTGGG CACTGATTGC      360

GCGATGTCGA TATTCTCTAC GCCGCTGAAG AGCAATGTNG NATATNNGGN CGCGCTNGTN      420

GGCAACCNGN GGNCCNGNGG AGAGNACCGA GNTTGNTTNA NGGNGNGGCG CNCANAACCA      480

ANNNNTNCCN CAATCNCTTA CNATCAANNC CAANTTNCCN CNNNCANCCC CNNNGNNNAT      540

NNNNATTCNN NCNNCNCN                                                   558

(2) INFORMATION FOR SEQ ID NO:101:

(i) SEQUENCE CHARACTERISTICS:
        (A) LENGTH: 604 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1035I2

(xi) SEQUENCE DESCRIPTION: SEQ ID NO:101:

GATCCTTAAA AGCTGGCCTC CGCAGATAGA CCTTCTGCGC AGAGGCTGGA AACCTCAACT       60

AGCAAGTCGC CACCCGAATC AGATAAGCAC TAGAGTCGTT CCAGTAACAG AGGAAGCGAT      120

CAAGGAAGAT AGTAGAAGAG GACACTGCTG CCAGGCTTGA TCGGACAGAG GGTTTAGCTT      180

TCTGTTGAAT TTCAGAGTTT CGGCGCTTTG TTTACTTCGC TTCATTCTTT CGTGTAAAGA      240

AGCTGTTTGC AGGATGTCAT CATTTGCCAG TCGCCAGGTA GGGTATTGCA GGGCCGACGG      300

AGTCGGTGAA ACAGAGTCAG GACCGAGAAC GCCGATAGAC AGGCGTTTGG TTTGTAAGCG      360

GTGAGAGCTG AAGCAGCTCA AGAGGCCCGC CTTGGTCAGG TTGTGCGGTG GCGGTAGAGC      420

ACAGCAGGGC ATCCCTCGTC GGTGGAGCGT NCGGNCAGNA GCCCAGGCGC NTCGAACAGG      480

GGGTGTTTAT NANGANCNAC CGACCACAAA CACGCTNTNA TTCGNACCGG CGGCCAGTTN      540

CCTCANCNTG GTTCCCGNGA CTTGTTTTNN GAGCCNATCC TTGGCNCTCC GCCNNAGNAA      600

AAAA                                                                  604

(2) INFORMATION FOR SEQ ID NO:102:

(i) SEQUENCE CHARACTERISTICS:
        (A) LENGTH: 480 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1035RP (xi) SEQUENCE DESCRIPTION: SEQ ID NO:102:

GATCTTAAAT TGTTGCATTG TGACCTGAAA GTTGCCCCGT AGACGCTGCA TATTCAAGGT       60

TTCCATTTCC ACGGGACGTA ACCTAATCCG CTGCACTTTC GACAAACGAC TAATGTATCT      120

GTTCTCGGAC TCTGGGTCAT TCGCATCCCC ACTCCACTGT ACTTGTCCTG ACTGTAGTTG      180

TTGAAGCTTG AGGTTATCTG CCTCGAATGA CTGCAGTAGT AGTGATTTTC GTCTCCCAAT      240

CGTTTCTATG GACCGCCTGA ACACCGAACG TGCCTCCGCC TGGAAGGACT CGAAAAGCCG      300

CCGCTCCTCT GCAGAAGGCG GGAAATAAGA CATAACTTGC TCATCGCGTA GGTAAATCTA      360

CGTCATTATC CGCGTCCACC ATGTTCGGCT GGGATAAAAT GGTGTTTCCT CCAGGGGGCG      420
```

```
GGGAATACCA CCCACTCTCC AATCCTGCCC CCGTTANTGA ATNGNTTTNT TNATGGGGNN      480
```

(2) INFORMATION FOR SEQ ID NO:103:

(i) SEQUENCE CHARACTERISTICS:
        (A) LENGTH: 482 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1035UP (xi) SEQUENCE DESCRIPTION: SEQ ID NO:103:

```
GATCTGGCGT ACGGTACCGA TATATTTCAA CTGAGGTATT CGTTAGAACA GCTACCTTCA       60
GTGGTTCCAC GCTATATTGC GTTGCAAATA TGTTTGCGTA CCCTTCTGGC TTATCAGTGG      120
CATTAAAGAG CGCGCTAATG GGACTATCT CTTTTACTGG GCCAGTGGTC TCCAAGAAGG       180
AAGCATTCTC AATATATTTT CCGTGGTTTT TCAGGATGCC ATAATCTGGT ACACTCACAA      240
ACAATTTATG TTGCACTGGG TGAGATGCAG GGGTATTAGT ATTTGGAATC ATGTGGGTGA      300
TTGTCCCGGA TGGGGTGCGC TTCACAACCG CAGAGGAAAA AATATCCCCA GGGGATATT       360
ATTNGTCGAA GCAAGAATCG CTTCGAGTAG GGATTGAAGA TTTCTTCTTG ATACTTAAAG      420
CTGAATTGGT TCANATGGGG TCCAACGAAN GANTAGGNTG GATGGNCCCT TNGGGGGGGG      480
CC                                                                    482
```

(2) INFORMATION FOR SEQ ID NO:104:

(i) SEQUENCE CHARACTERISTICS:
        (A) LENGTH: 645 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1036RP (xi) SEQUENCE DESCRIPTION: SEQ ID NO:104:

```
GATCATATTT CAATGCAAGA GCTCCATTAA TAGGTATTGT CTTGAGACAT GCGCTCAAGT       60
CATTAATGTC ATGGGAAAAA TGCACCGTTC CACCTCCTAT CTCCAATGTA TATTTTAGCA      120
TTTCAAAATC ATGTTTTCTG TTTACTATAA AGTGCAACCC ATTCAGGTCT GCGGCTTTCT      180
TAGTAAAGCC TCTAAAGGCG TAATGCTGCT CTTGTATACT GCGTAGCTGT GGGTCAAAAT      240
CGGTAACAGG CTGTCGAAGA AGAGCGGTAA ATTGTTTCAG AAATTCGAGA TGCAATATTG      300
GTATGCCTTT AACAAGTGCA AAACAAATAC TTTTTCGGAA TCTTGGTCAT CTTCATGGGG      360
TCTTAATAAT ATGATGTGTA GTGGGCCTCC GAAAAAGAGG TCACCACTCG TATTCCTAAC      420
CCTTAATTAC CTCAAGCAAA GCAGGGCTTC TTGTAACAAA GTTTCGGGAC CTGGACTCCC      480
CATGGGCCCC TCCAATNTGA TTGGNCGGAT NTGNNCCCCT TCCNGATANA GGNCTGGATG      540
GCCANCGGAA NCCNTCCTAG TGATNTCCCN CCCCTTCAGT GNNNCCNCTN GAGGTTTGGA      600
NGGCNNNTTT TCCNNTNGCG GGNNTNTCTG GNAACCNCCC CCTNT                     645
```

(2) INFORMATION FOR SEQ ID NO:105:

(i) SEQUENCE CHARACTERISTICS:
        (A) LENGTH: 613 base pairs (B) TYPE: nucleic acid
(C) STRANDEDNESS: single
(D) TOPOLOGY: linear (ii) MOLECULE TYPE: DNA (genomic)

(vi) ORIGINAL SOURCE:
(A) ORGANISM: PAG1036UP (xi) SEQUENCE DESCRIPTION: SEQ ID NO:105:

```
GATCCCCTTT GGTAACGAGA GGTGTCGGCT TGTATTCACC GCACATCGTG GGCTATTTGT      60

CATTACTCTG GCCCCGTCCC AGAGACCTAC AGGTATAAAT TCCCCATCAA GTGCCACCAG     120

AAAGATATGC TATACTGGTT TTGAGCTTGA GCGACTGTTA ACTGCAACCA GCGGGACCGA     180

ACGGGGTAGC TTTTACTCAT TTATTGAGGC TAAATTGGAA CCAGACATCA CAATTCTGCT     240

TCAGTGCGAA ATGGACGCAT ACAATCCAAA ACGCCAGAAG TATACTGAAA TAAAATCCTC     300

TGTGGACTTC AATGTACGAA ATGTCCGGCA CCTGAGCAAA CTGCTTAAAA TATGGGAACA     360

AACAGGGGTG GTCCCATCCA CTGATATCTT GTAGGGGTCA GAGACCCATC AACCCATGTG     420

TTGAAACAGN CGGCCCTTAT GGGTGGTCAA ATCGNAGGAA AATCTTTTTA GGGTCGNCGN     480

NAGGCANCAC TTNTTTTANT TATCCGAGTG CAANATGGAA ATAANCATCG TNAATTTGGA     540

AGGTATTTCC CGGGGNGAAC CANCGGNCNC AANNNTTTTN NGGGGTNGAA AGANTCAAAT     600

TAAATNGGCC NGT                                                       613
```

(2) INFORMATION FOR SEQ ID NO:106:

(i) SEQUENCE CHARACTERISTICS:
(A) LENGTH: 606 base pairs
(B) TYPE: nucleic acid
(C) STRANDEDNESS: single
(D) TOPOLOGY: linear (ii) MOLECULE TYPE: DNA (genomic)

(vi) ORIGINAL SOURCE:
(A) ORGANISM: PAG1037RP (xi) SEQUENCE DESCRIPTION: SEQ ID NO:106:

```
GATCATCATT ATTTCCTGCG TTCGTGCCGA CGATTCGAAG GGCGGGGTCG GTTTCTTGAA      60

GGATTTCAGG CGTATGAATG TTGCTCTCAC CAGAGCAAAG GCCAGTCTCT GGATCCTGGG     120

TCACCATAAA TCTTTATACA AGAACAAGCT ATGGATGCAT TTGATTTCAG ATGCGAAAGG     180

GCGTGACTGC CTCCAAATGG CATGTCCGGG CTTCCTTGAT CCACGGAACA GAGCCGCCCA     240

GGATGCTCTT CATAGGTTCA AAAATCACCA TAATTATATC GAGAACGCAG ATGATTATGG     300

GCCTGAACCG GTGATGACTA AATCAAGAGG ACGCAATAGA TCATCCAGAA AACGCAAACA     360

TATGGAAGAT AATCCAGATG ATAACTACGA TCCCGTTGCT GAATTCAAGA AGGAAAATCA     420

AAGAGAAAGC AACACAGGCA CCGGTGGTTA CCGTGCGGAT ACATCTAACC ACAGATTGGC     480

ACCTGCTAGG AACGATAGCA AGAAGGCCAA GACGTGCTCC AATGCCGCCG GTATTTCCGA     540

GGCTACTTCA NARGATGGTG ATCGAAGTCA GAAAGGACAT GGAACTAAGA AGARTCTTCC     600

ATATTC                                                               606
```

(2) INFORMATION FOR SEQ ID NO:107:

(i) SEQUENCE CHARACTERISTICS:
(A) LENGTH: 653 base pairs
(B) TYPE: nucleic acid
(C) STRANDEDNESS: single
(D) TOPOLOGY: linear (ii) MOLECULE TYPE: DNA (genomic)

(vi) ORIGINAL SOURCE:
    (A) ORGANISM: PAG1038RP (xi) SEQUENCE DESCRIPTION: SEQ ID NO:107:

```
GATCAAAAAA AGAAATTACA ATTGACTGTT GCACCCACAC ATTCAACGGT TGCACCCACA        60
CATTATGAGA TGCTTGATTT GGCGCGAACT GCGCTTTCCA ACTACAGTCC CGAGACTTTG       120
GGTGCCAACC GAAGCAGACT TCAACAGTGG TGATAACCAT AGTGTCGAAG TCTAGCGAAT       180
CTAAGGATAA TACCAAGAGA CAAAGCATAA TCGTATGTGC ACAGGATGGG GCGAAGTGTG       240
GTCTAGAGCT GTCGGTGCGA GCAGAATACG GTGCGGGCAA TGAGGACGCC GCAGACGCCG       300
AGCGTGTGGG CAGCTCACGA GGGCCGGAGC GCTTCCAAGC GGTCAGACAG AGTACTAACG       360
CATTGCAGAC AAGATGGCTC ACGAAAACGT TTGGGGTCTC CCACCCNNAN AAACTACGGT       420
AAGGGGTCCC CCAGTGCGCG TGTGCGCTTC GNCTCTTGTT GGTCANAAAG TACGGGTTGG       480
ACATCTTCCC CAATGGTTCA NAGAGAAGGC CACGACATTG GTTCCCAAAT CCCCTAAGAG       540
GGGGGGGGCC CTTCCCCTCT TNCNAAATCC GGGGGGGGTT TGGTTTCNCG GAGGTTTTNT       600
TATTTTTCNA NACCCCNTTT TTTANTTTNA NNCNCGGTNC CCAGNNGTTT GGN             653
```

(2) INFORMATION FOR SEQ ID NO:108:

(i) SEQUENCE CHARACTERISTICS:
        (A) LENGTH: 609 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1038UP (xi) SEQUENCE DESCRIPTION: SEQ ID NO:108:

```
GATCGGTTCT CGGGCTTCTT TAGCTGCCCG TTATTCAACG AGTCATCGAC TGAGAAAGAG        60
ATAAAAGCGG TCGATAGCGA AAATAAGAAA AATCTCCAAA ATGATATGTG GCGCCTTTAC       120
CAGCTGGGTA AGTCGCTGAC CAACCCCATT CACCCGTACC ACAAATTCTC TACTGGAAAC       180
TTTGAGACTT TATGGAGCAT TCCGAGATCG AAAGGCGTCA ACGTCCGTGA TGAGCTGCTG       240
AAGTTCTACA AACGGTCATA TTCTGCAAAT CTCATGAAAT TAGTGATCTT GGGCCGCGAA       300
GATCTAGATA CCTTGGGTCA GTGGGCATAT GAGCTGTTCA AAGACGTCCC TAACCATGGG       360
ACCAAAGTGG CTGAGTATCA CGGCCAGGGA TTCACGGCCG AGACCTGATG AAGGTAATTA       420
AAGTGAAGCG GNTAAAATCT TAAGAGTGTG GAATTCATNC GNGGGGCAGA TTTGGTTAGN       480
ATGGAGGCAG CAGTCGTATG NGGATTTATC GCCAGAGGAA GGTCCTCCCG NTCTGGAGAA       540
AAAGTGGAAN CGNCNNCCGT NGGNNTCCCC TTNAAAGGAA AATNCCCCNC AANNGGCTTN       600
ANNAAGGNT                                                              609
```

(2) INFORMATION FOR SEQ ID NO:109:

(i) SEQUENCE CHARACTERISTICS:
        (A) LENGTH: 643 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1039RP (xi) SEQUENCE DESCRIPTION: SEQ ID NO:109:

GATCATTTCT CTTCAATCCC ATTGACGTGA ATGATGAACC GCATTATCTT TTTAACAGCG      60

ACAACATGCC ACGGTATATA ATTGTCCTTA CCTCGTGATA TGCAGAACCA GGTGTTTAGA     120

CTGGCAATAT CCCTAAACTG GTGTAATATG GTCTTCAAAA GTTTTGTGCT GTCCGAATGA     180

GGGCAATTTA GTAAATTAAC CTCGAATTTG TCTAAAGTAT CGCCACCGGC ACATCTTTTA     240

AACCGCACCA GCGCGCCGCT TTTTATTGCG CATCGGCGCT GTGAATTAGC AAGTTGTAAA     300

GGGCTACTGA ATACGACGCC ATGCAGCTCT TCATCGATAT TCACAACCTC GTAATCATCC     360

AATTGGTTAG CTTGGATTTT GGNGGGCATA TCTCTTATCC CTAAAAAGTG GGTTGGATGA     420

TGGATAAAAC TGATCTTCAT CATATAGAGA AATTTGGGCT CGCCCCAACG CAGACACAGN     480

CAATGTAGTT TCTTGTGGCA NAGTTNGCTN CGCAGGNATT ACTCGCANCC GGGGAGGTNT     540

CACCCCGGAG ACAAAAATTC CCCCTTTTCT NTGGAAATCG TNGTAGNNCC TANCAAGGAT     600

GGGTCAAGGA CCTGGTTGCC ATTCCANTTT ACCATTTTTN CCC                      643

(2) INFORMATION FOR SEQ ID NO:110:

(i) SEQUENCE CHARACTERISTICS:
        (A) LENGTH: 635 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1039UP (xi) SEQUENCE DESCRIPTION: SEQ ID NO:110:

GATCCTTCCA ATAACGGCTA AACATCCATG TGCTGGTTTT AACTATGAGG GAGTTGGAGT      60

AATTTCGCGG TCTCGCAAAG TAAATTGACA GAAAACCCTC AGATCGGTAA CGAAACAGCT     120

GAACGACGGA GATTAAAAGG AAGAGGCAAA TAAGCTATAG ATAAGATCGA TAAATATTGA     180

GGGGGGGATG GATATATTAG AAACTAGCTT TAGACTTGAA GATGTGCTTT CACGCTATTA     240

TAGAGTTGAA AAGGTGGTGC GAGTCAATTA TCAACAGTTC GTACCGAGGA CTCCAGATGA     300

TCAATGGTGT ATCCAATCCG AGCTTCTTAA TCCGCAAGAA GGATCCGAAA GCGCTGGTGG     360

CGCTTTTTTC GCGGGAACTC TGGTGCTTTT AGCATCAATG ACCAGGACTT ACCCATTCCC     420

GGGGTTGGAA GGGATAGGCG AACCCCCCNC CTCGGAGAAG AAGGGCCACT TTACGGCAGG     480

GTTTTCCAAG GCNAACCTGC AACGCCNNTG GATCTTTTTA AAGCNTGGGG GGATGNTCAA     540

TAANAATTCN GAGGCGNAGA ACCTTTGGCA ATTGGAAAAN NNNTTTCCCC GNAAGAAAGC     600

NNAGGGANCC CCCCGGGNCN NATTTTTGGA ATGNC                                635

(2) INFORMATION FOR SEQ ID NO:111:

(i) SEQUENCE CHARACTERISTICS:
        (A) LENGTH: 648 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1040RP (xi) SEQUENCE DESCRIPTION: SEQ ID NO:111:

```
GATCCAGTGT ACCAGGTAGC GTCAGGCACT TCTAGCGCAA GGGCCGCCGT AAACCTTGGC      60

CTCTCACAGC ATTTGGGATG AGTATGGGCC ATCTTTAGGG CACGTGAGTG ATCATGATGG     120

GTACAAAAAG AAATGATTTC GCCCAGGATC GAACTGGGGA CGTTCTGCGT GTTAAGCAGA     180

TGCCATAACC GACTAGACCA CGAAACCACT TTCTGCAGGC TCTTATTGGA CAGGTGATGT     240

TAGCGCAGAA GAACATGAAC GTGATAATAA TTCAGAAACC TCTTATGCTA AAGTGAATTA     300

CTATTGCTTA ATAACCTGAA GGGAATAGGC ATTGCCAGTA TTGAAAATCG GCTTTGGGT      360

TTATTGGCTA ATTATATTAT TNNCANTATA TATATATACC AACAAGGTGA AGAATGGNTG     420

TCGNTGGTTT GGGGGCGATA CCCNAGAACC AAAGTAGAAG TTGACAAGTT GGTGGNAGNG     480

GTTCAATTCA GNACTTCATG GCAACNTTTA CNATNNTTTN NTNAGAACCC CCNATTANTC     540

TTTNNCTTCG GGGGGTCTCN NCNAACCGGA AACAATNTTN CNGAACTGAG TTNGGGGGAN     600

GTTCNTCGGT NTTTTCNNCC TTTGGGTCCA AATTGGGCCG GAANCCCT                  648
```

(2) INFORMATION FOR SEQ ID NO:112:

(i) SEQUENCE CHARACTERISTICS:
        (A) LENGTH: 613 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1040UP (xi) SEQUENCE DESCRIPTION: SEQ ID NO:112:

```
GATCAGCAAC CTTCTCCGCC GTCTGTGTCC TCGCTTTACC GAGGATACGA AAATAGCCGC      60

GGCTCTGTTT CAAATGGCGA TGCTGACGAG CAAACCACGT CTTCTGATGC AAGCAGTACT     120

AGTTACATTA TTCTAGAGAT GGAGGCAATG CGGACAGCTC TGCGTCAGTA TTTGAGGGCA     180

ATCTGCCAAG ATGCAGAGGT ATCCGCCAGT CTGTCCCTAA CGAAATTCCT ATTCAAGAGG     240

ACGATAGACA AGCGTGCTTT TACGCCAGAA ATCCTGGAAG ATATTGAATC TCGGGAGCTT     300

ATGGATGTAT ACAACCTCGA AAATCAAGTT AAATTCCAAA AAATGGCGGT TTGGATAGAA     360

CTGTGAAGCT ACAAGTCCTC GCTAAAGTCC CTAAAAGAAA AAATCTTGCA AGATATGACT     420

ACATTATGAG GTTTTCCNCC AATTTAAGGA GAGGAGGATC CCAGNGACNA TTTAGCTCTC     480

AGAGATTCTT GGNTGGGGAA AATTTTTTAG GTACCNATNC AGGTTCCCGG AATNAATGTN     540

NATTNTTTAC ANTCGCGCNG AAATATGCTC ANAGNNNAAG TTTGGGCACC CCCCCCNCCT     600

ATGANGTTTT GTC                                                       613
```

(2) INFORMATION FOR SEQ ID NO:113:

(i) SEQUENCE CHARACTERISTICS:
        (A) LENGTH: 649 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1041RP (xi) SEQUENCE DESCRIPTION: SEQ ID NO:113:

```
GATCCTCCAC CAGAGCGTCG GCGTCCCATA CCTTCTGTTC ACGCAGTGGC GCGTTCTTGT      60
```

```
AGAAAACGCC CAACAGTTGT TTGTAGGTGA ACTCGTCGCG GAATTTCTGG GCGCGAATTC      120

GCTCCAGCTC CTCTTCGGAA AGCTTTTCAC GGCGCCACCA GCTTCTCATC CGGTTCAACC      180

AGCGCTTTTC GTCGAGTGCC CGCTGTTCCG CCGCTTCTGC CGCAGCAATA TCTCGGCGCA      240

GATGCCGTAC GCGCTCCGCC ACTTCATGAC GGATGACGCC CTGCCGCTCT TCTGTGAAGA      300

ACTCGTAGTC CAACCCAGCT TCGAACAAAC AACTGCTTCA CGTATCGCCG CCATACTTTC      360

ATCGACGTCT CGAGATAGTC GGCCGGAGGA GGGGCAACAA ACAACGCGAG CCGCCGCGGT      420

TTGGGGCATG TGTCANGTNG GCTGCGCCTG GGCCTTCACC AACGACGAAT AATGTTGGAT      480

TTNGCCCTNG TCCCNTGGCG GNTNCAATCA GAATGCCGGN TCAACCNAAN CAAAAGGGAC      540

AATNNGCCGG AACCAAGGCG GTTCCANGCC GAAAGTGTTT ATTNNCCNAC TNTTCCGGTA      600

NAATTTTTNT TTNTCNCTGG GGNTGTGNNT NACCNCCACC CCNAAATAA                 649
```

(2) INFORMATION FOR SEQ ID NO:114:

(i) SEQUENCE CHARACTERISTICS:
        (A) LENGTH: 645 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1041UP (xi) SEQUENCE DESCRIPTION: SEQ ID NO:114:

```
GATCTGCTTC CTGAAAAATG GCGTCTCTGT CTTACTGGTA CTCTCAAATA GCTACGTCTA       60

GGTACAGGGC CATTTCCGGA TCCCAGCCAC GGGTCCACTG CAGGAGGTAC AACAGGATAT      120

CGCACGTCTC GCCCTGCGCA CGTCACTTGG AGCCTCCCGT TCTCGTCCTG ACGTCTCAAT      180

AAGGTACGCC GTTTCTCTTC GCCGATGGAC TGCGCTAACT GTATGGCCTG GCTACAAGTC      240

TGTTGGTTTC GAGCAGCCCA CTTCTTTATC CACCCTCAAG GTTACCGCA ATCCAGCAAT       300

TTTGGGTCCT GGCACAGCCG GATATCATGT GACTTAATTA CGTCAACGTT CAAGAGTTGG      360

GGGCGGCGGC AGCAAATTTA ACGGGGGCGN CGGTCGTCCC CCCCGATCGG GGGGGGGGA       420

GGGNATTANC ANTCCANTGC CGGCCAAATC TTNGTTTACA NAAAGCAAGC ANANTCATAG      480

TGATTTGGGG GAANANCCCA AGGTTNNGGC CNCCANGGNT CAAANTCNCC CNTTNNTTTT      540

TGGGTTCCCG NCGGAAAANN CCATTCNCCG AGGGGCCNAG GNCCGGGAAT TTTCCCCNGT      600

TNNAGGGGAG TCNNTTNGGG GGGGANNCNG CCANAGGAAG GNGGT                     645
```

(2) INFORMATION FOR SEQ ID NO:115:

(i) SEQUENCE CHARACTERISTICS:
        (A) LENGTH: 682 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1042RP (xi) SEQUENCE DESCRIPTION: SEQ ID NO:115:

```
GATCCGTGCT GCGGACAACC GCCAGAGCTC GCCTACAGCC CGTATATATA CGCCGGCTGC       60

CGGCCTGCCG CATGCGATTT GTCCCACCTC GCTCTGCTTC GTCCCGCCTG CCGTTGCTCC      120
```

-continued

```
ATGGGACCTT TCATTTAGTG TCTCGCGAAC GTTTCGAATG TACCCTATCG TGGTACCACG    180

TTGCCTGCCG TGCCGTTACT ACATCTTCTA GCGCGGACTG AGTCACATGT CTCGCCGCGC    240

ACTCCTTTTC TGTAGATAGT CAGACGACAG ATAGTCGATA GTTGGAGATT TGGGCAACAA    300

TAGCGGTGGC CATTACGCCT GCCCATTGTT CCCATGTCAT TGGGAGGCTG GGNCCCACCC    360

ACGGGAACTC TTNCCCGTTT AANCCTNANA GNCCCNGGGA ATGNAAAACN CTTTCTTTNG    420

NCNGCNGCAA ACGGGCCTNN AGGNGATTTC TTTGNCGATT NGGGANGCAC TGAGAATCCA    480

AGTNGGAAGG GGGCTNNAAA AATNGCTCCG GGCCANNCCT NCCCAAAGGT TTNAAAANCN    540

GCNTAAATNA GCCNCAGAAG AACCNCGGGA GGAANCANAC ANAAANTNGG CCCCNCCTGA    600

AGGAAAGGGG CNGNNNTGGG GNCGAANCCC CNGNAACGNT NTTTCTTAAA GGANAACAAA    660

NGGTNCAAAA AAAATGGGGG NC                                              682
```

(2) INFORMATION FOR SEQ ID NO:116:

(i) SEQUENCE CHARACTERISTICS:
        (A) LENGTH: 649 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1042UP (xi) SEQUENCE DESCRIPTION: SEQ ID NO:116:

```
GATCGCGTCC TCGAGCGACT TGTGAGGGTG AAGCTCGATA CGGTGATGGT GGTGGTGATG     60

GTGGTGGTGA TGGTGGTGTG CTCTGCCCTG CGGTATGACC TGGGCTGTTG GCGTTGGGCT    120

GTTGCTGCCG ACAGCAGCAC CTGTATCCGC AATGCCCGAT ATGCTAGAAT GGAGCAAATT    180

AATGGACTGG TCTGCATTCT TGCAGAGCGG AGCCTCGCAC ATGCTGGATA TGCTTACGAG    240

ATCGCCGGAG GATCTTTATG TCTGTTTCGC TATTCACCAC GTGGTCGTGG CAGTGCTGTT    300

GTTTCATGAC CAGCCCGTAT CTTCANAGGA GTCGTAGTTC ACGCATTGTT GGGCAAAGCC    360

AGTCGAAGGA GGCCATCCTC CACGGTCGGG GAGTCCCCGG GGGACGTTTC CACAAGCCAA    420

GGTACCTAGA AGATGAATCT TTTTTGANTC ANCNGTTGGG CCNCTNGGCA ATTTNAAGTC    480

GNAANTGNTG AACTTCGGAA AGTTGGAAAT TGGNCCNAGG NCTTCTTCCC CCCNCCNCNT    540

TNGGNAAGCA AAAANAAAANA ATTAATTGGN CCCCCCCCCG CAAATTTGNG GTCNGAGAAA    600

TTTCCAAACC TTGGGTTAAT AGTAAGGNCC CCGNTGNCTG GGCCCNCCC                 649
```

(2) INFORMATION FOR SEQ ID NO:117:

(i) SEQUENCE CHARACTERISTICS:
        (A) LENGTH: 648 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1043RP (xi) SEQUENCE DESCRIPTION: SEQ ID NO:117:

```
GGATCGGCGA TGGCGATAAA AGAATTGCTC CCTGATTGAT TGTTGTTCGA AGGAGATGCA     60

GATGGATTGT CCAGAAAAAC CGGTTTTAAG ACTCGTTCAT CAAACTTGTT AAACCATTGC    120

CCATCGGCTT GCAGTATATT GCCCAAGGTT TCGCGGATAT TTCTTCTGTC TAATGATAAT    180
```

```
CGCCCCACAG GCTGGTCAGC GCCTGATGCA GAGCGCGAAG AGGGTCGGTC TATCATAGGA        240

GGAAAGCTTT CTTGATCCGG GGAGCCGGTC GGGCTGTCGG TTAAAAATGG AGGTGCGTCT        300

AATGAAGACA TTAGCTGGAC AGGTCTAGGG GCTTCAATAT CAAATTCATC ATCCGTTTCC        360

TCCTGTTCTT CTACGCACCC TGTCTTTATG TTTAAGATCT CAAGCATACC CGCAGGAGTA        420

CCTCCAAATA TGATAACGGT GAGAACCACA ACTACCAGCA CAGTGGCCAG AAGAGGGGAA        480

CTTGGANCTC GCCCNNNNGA CCCNTAGCCA GNGNCACTCC AANAGNAACC CCNAANCCCG        540

NCCNNNNNGG NAACNNCCTN NNTTTNGNNT TGGATNTCCC CNANNANTNN AAAACCCCCC        600

CCCCGGGNTN TTNNNGGGNC CCNNNNNCCC NNNAANGGGN AAAANNNC                     648

(2) INFORMATION FOR SEQ ID NO:118:

(i) SEQUENCE CHARACTERISTICS:
        (A) LENGTH: 419 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: 1043UP (xi) SEQUENCE DESCRIPTION: SEQ ID NO:118:

GATCAGATTG TCTTGTGATG GAGAAGCTGG CGCATCAGTA GAGTGCAGAG AAGACCCATG         60

CGGAACAACT GTACCACCCA GGGACTGCCG TCTTCCCGGA ATGTTGGGAA AAACAACAGC        120

ACGGCCTGAG TCACTTACAG TCGCAGTGGG TTGCGAGCGC GACAGATTAA AAGAAAAGCG        180

CTCGGGGTTT GTGAACAGNT CAGACCAAAA CCCAGGTCCT GGCTCGCGGA ATTCCTCGCT        240

TACCTTCACA TNCAACTTAG TGTGTTCGCT GTCCNAAATA TACTCCAAAA TCTTGATCGG        300

CGCACCTCTG TGGTTCATGT CCTGCACAAG TTGACCACTG TATTCCAGTT TGACATCAGA        360

GGGCGAAATC ATCAGTGTGT GGCGTTCACA GAGCAAATAA ACTCCTTTAC TTCCTGCAC         419

(2) INFORMATION FOR SEQ ID NO:119:

(i) SEQUENCE CHARACTERISTICS:
        (A) LENGTH: 606 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1044I1

(xi) SEQUENCE DESCRIPTION: SEQ ID NO:119:

GATCTCCGAC TGCCGCCGTC TGTACCCGTC ATCGCCCTCT GTAGTCGCCG TCATGCTCAT         60

CCTACCCAGC CGCACCAACC AATGCTCGAT GCAAGCTCAA TGCTCGCAGC CGGCGACTGC        120

TGTATACGTG CTGGCTTAGG GTGGGGACGT CCCTTCACGG CCCGGCCGCC ATTGGAGTCC        180

AGCAAGCGGG GAATGCTGTT GTGACTGTAA CACCCATACA TTGCAGGCCG TACATTTCAA        240

CGATGGGACG CGAGTGCGTG GGGAGCTGGA CGGAGACCGA ACGGGGGGAG CCAGGCGGGC        300

GGGCGGCAAT CCGCAGGCCG ACCCAGCGGC CGACCACGCG GGCGCTAGGC CGAGGGCAGC        360

AGGCCAGAGC CGCGGGCGCG GTTTTTCATG AAAAATATAG TGGCTACAAG AGGGATAGGT        420

TGGATATACC AGAACTCACT CGTAAGAGAT AATTAAGCAG ACGAAATGGT TGTTTGGAGG        480
```

```
ACGTTGGTAT CGCGAATCAC AATAATTTGA CAAAAGGTTT TTGANTCGGG GAGGTCGNTG       540

TTGTTGNGGG NGCNAGACCG CCNTATTANA NGAAGNGANG GNAACNCAAG ANNGGGGCAN      600

GGGGTC                                                                606

(2) INFORMATION FOR SEQ ID NO:120:

(i) SEQUENCE CHARACTERISTICS:
        (A) LENGTH: 632 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1044I2

(xi) SEQUENCE DESCRIPTION: SEQ ID NO:120:

GATCTACAGA ATGCAGGAGA CGCTGCTTGA CACAACACAA ACGGCTGAGA CGGCAGGCGC       60

GGCCGAGCGC GTGCAGGAGG CGGACCCGGA CGGACAGGGG GCGGGCGTCG ACTCGGGCGA      120

GCTGCTGGAG GTTGTGGAGC GCCACTACGG GGCGCGGCGG TGCGCGCTGG GGACGATACG      180

GTACGAGGCC GCGCGCGCGG GCCGGCTGAC GGGCGGCGCG GGCGCGGCCC TGCCGTTTCC      240

GTACGAGGTG GGGCAGCAGA CCGTGCCGGT GCCGCTTGCT GCCGCGCATG GGCACGGCAG      300

CGATCCAACA GGCTCGTGAC GGTGGAGCTG AGCGCGGAGG ACCTTGAGAG CGCGCTCGCG      360

ACGGGCGAGA ACGCACGGGT TGCGCAACCC GGAGCTTTTG TGGGTAGNCG TGTTCAACTN      420

AGANTCGGGA CCCNNTTNCT NNTGCTNNNG NACTNNNGNG TGNTNNACGN NGAGCTGAGN      480

TGCAGGNCAN GNNAGNNNNC CNNNCNNCGN ACGCCCNCCA ACCCNNNGAN CCCNNTTTTT      540

TAGNNNGNTT TAANNCCNNC CCCNNNNTNN GNGNGGGNNT CCCCCTTGNT NTNNNNNNNN      600

ANTTNTCATT TTCCCCCCTT CGNAGGNTTN NT                                   632

(2) INFORMATION FOR SEQ ID NO:121:

(i) SEQUENCE CHARACTERISTICS:
        (A) LENGTH: 626 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1044RP (xi) SEQUENCE DESCRIPTION: SEQ ID NO:121:

GATCGCGTGC CTAGTGCGAC CTCATGCACC GCTTGGAACT GCCGCCCCAC CCATGTCAGC       60

ATCTTTATCT TGCTCGACCC TGTGACCGAG TAAACAAGCA CCGTCATCCA CGTCTCAGCC      120

TTCCCACATG GATGTTCAAA CAGCCAGGCA TGGTCAATGC CTCGTTTGTC AACTATCTTG      180

TCGTAATGTT GTAAGTTGCT CGAATGAAGT AGCAGTAAGC ACTTGGTCGT GCGGACGAAT      240

ATTGTCCGCA GCCGTTCGGA GTACAGCAGC TCTTCTACAC CATAATTCGG GCCAAGCAAT      300

TCTGTATATG TCTGAACTAG ACGCAGGCCT CTCTCGTCCA TACTGGAGTA CACCAAGAAG      360

TCCCTATTAT TTCGGACCAC CACAAGTTGT CGAACGGCAT CAACCACAGG GACACACTGA      420

GCACCTTGGG ACGAATGGGA ATTTACTAGC TCAGCCCTAA GCATCTTATG ATGAGGGCTG      480

CCCTTAGCTT GCTGAGTGCT TCGGGCTGCC TGCTTGTGGT TGGTGGGTCC TTTCTTAGAA      540

CGATTGTTCA AAACCATGAT GATGGGGTTT GGTCCGGCCN GGTGATTTGA AGATTTAAAC      600
```

CGGTNCCAAG GAATTGACCN TGGGGG                                          626

(2) INFORMATION FOR SEQ ID NO:122:

(i) SEQUENCE CHARACTERISTICS:
        (A) LENGTH: 545 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1044UP (xi) SEQUENCE DESCRIPTION: SEQ ID NO:122:

GATCTCCTTG ACCGCGCGTG GCGCTCTCTT CTTGAAGGTG ACACCGTGCA ACTGCTACTG       60

TTAGTATCGG TCCGGTCTGC GGCTCCGCTC CACGCAGCAG GGAGCCCTGC TCCGCACTCA      120

ACATACCCTC TTGTGCAAGT TAATGGTGTA CTCGCGAGTA ACAACGTCCT TCAAACCAGC      180

CATTTCGGCT GCTTAATTAT CTCTTACGAG TGAGTTCTGG TATATCCAAC CTATCCCTCT      240

TGTAGCCACT ATATTTTTCA TGAAAAACCG CGCCCGCGGC TCTGGCCTGC TGCCCTCGGC      300

CTAGCGCCCG CGTGGTCGGC CGCTGGGTCG GGCTGCGGAT TGCCGCCGCC CGCCTGGNTC      360

CCCCCNNCGG CTCCNNCCAG NTCCCCACGA NTCGNGNCCA TNGNNGAAAT GTACGGNTTG      420

AANGNTTGNT GTNAAAGGCA NAAAAGAATC CCCNNTTGGT GGNTTNNAAN NNNGGCNNNN      480

NNNNAGGGAN GNCCCACCNN ANNNAGAANT TTAANAAGNG NNNNTNNANA TNNNTNGATN      540

NANAA                                                                 545

(2) INFORMATION FOR SEQ ID NO:123:

(i) SEQUENCE CHARACTERISTICS:
        (A) LENGTH: 723 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1045RP (xi) SEQUENCE DESCRIPTION: SEQ ID NO:123:

GTGGATCCGT AATGTGGGTT TGTAGGCCAG AGGGGATTCG ACGGTGGCTG GGGGCCATTC       60

TGCCCGTTAA TTAGATGCCA CCCAATTGTT TTCACATCCC AGGCGAAGGT TCGCATACCG      120

CCCACATACT TGGGTAATTG ATAATGCCGC CACATGACGG GATACTAAAC AAAGCAAAGT      180

GTCACATTCT TATTTCTGT TGTGGTCAAA AATCGGGGGG TAGGCGATCA ATTTGCATAT      240

ACAACACGAA AGGGGATCGG AGATTTCTAG GTCACAGGAC AGTTTGGGGT TTTTATTGGG      300

TGTCTTTGTG AAACCATAGG CACTTGACAT AGGAGCCCTC TTTAGAGTAC AATAAGCAAC      360

TGGCAGCAGC CCTACAGCTT GGGCTAAACT TCTCCATTAT GTGAAACGGG AAAGACGACA      420

ATGCCTCTGA ACGCTTTCAC GCCACTTTTG GTGGCCCAAT TGCATNGNTT CCGNAANTAN      480

NNTTTTNTNN TNGGGNTTTT TTGGNNNAAA AAAACCNNNA AAAAAGGGGG GGGGGGNTNA      540

AAACCANGNA TNNTTTTTTT NGGGNNGGGG GGGGCCCCCT TTTNTAAAAN CCNNNCCCCC      600

CNNNNAAAAN GGNNNTTNNN GGNNNAAAAA TTNNNNNTNN NTTTTTNGGN NNCCNNNNTT      660

NCCCCCCCNA NNGNCCNNNC CCNNNNTTTT TTTTNTNNNA NNAAANCNCC CNNGGGNNGG      720

CCC                                                                    723

(2) INFORMATION FOR SEQ ID NO:124:

(i) SEQUENCE CHARACTERISTICS:
        (A) LENGTH: 502 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1045UP (xi) SEQUENCE DESCRIPTION: SEQ ID NO:124:

```
GATCTAATAA CCACCCGTTG TATATTTGGG CGGTTAACTA TATATGGGAA TCATATAAGT      60

GCTTAAAAAC ACCTCACCCG CAAGGGGGTC ATCTATAAAC AAGCCATAGT GTGTGTATCT     120

TTGCCTACAT AGCATCATGA CTATGTTGCG CACGCGTCAT TTGCACTGTT TTAGCATGTA     180

ACTGGCAGAG CCAGCAACGA ACAGAGCTAA TTTTGGAGGC TTACCATACT GTTGTCGCTG     240

GATGTTGAAG CACGGCTGTT GTGGATAAGT TTAGAACCCG TCGCCAGCAC ATTCATACCC     300

TGAAACTACC AGTTCCAGGG GACATGTTCT TCGTGGCTTT GACAGAATTA TTATTGTAGT     360

CCAGTTAGAT GTACTACCAT TGTTGCGCTA ACATAATCAC CATTGTCATC TCTGGAATCA     420

CGTGTCGCCA AGCATATTAA TGTTTGTACT TAAACTCGGT ACTCCCTTTA TCGAAAGGCA     480

TCACGGAATC GCCCTTCACT AT                                              502
```

(2) INFORMATION FOR SEQ ID NO:125:

(i) SEQUENCE CHARACTERISTICS:
        (A) LENGTH: 515 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1046RP (xi) SEQUENCE DESCRIPTION: SEQ ID NO:125:

```
GATCGCGCGC GCAAGCCCGT GCGCGAGCTC GAGCAGGTTC TCGAGGTCGC GGGGCAGCGC      60

GTCACACGAG TAGGCGTAGG GATAGAGGAT CTCCTCCGAG TACGAGTGCA GGTCCAGGTA     120

GGCGTAGATG TCCAGCTCGG CCTTCGTCTT GTTCACGTAG TCGTTCCAGC TGCGCGCCTC     180

CACGGCCTCG AACGGCTGCT GGCCGCTATA GTCGCCCGAG CAGGGGTAGG CGTGCTGGCC     240

GGTCCAGTGG TAGTCGAACG AGTGGTCAAT GTCGACGCCA TCGCAGCCGG GCATGTACGT     300

GGGCTGCCGG TTCTTGCGCC ACAGGCGGTC GTGCGTCCAC GTGTACGCGT AGCCGTCTGG     360

GTTGAACACA GGGATCACCA GGAAGTCGAG CGCGTCCAGG TAGCGCGTCT CCTTGGGCGC     420

CCGCCCATAC CGCGAGAGCA GACGCTCCAC GACAAAGCAC GCCGTGCTCA CGCCAATCCA     480

CTCGCGAGCA TGCACGCCGT CCGTAATTAC CACCG                                515
```

(2) INFORMATION FOR SEQ ID NO:126:

(i) SEQUENCE CHARACTERISTICS:
        (A) LENGTH: 561 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
            (A) ORGANISM: PAG1046UP (xi) SEQUENCE DESCRIPTION: SEQ ID NO:126:

| | | | | | |
|---|---|---|---|---|---|
| GATCCGGGAG | CTCCATCATT | AGAGGGTCTG | GACTTCGGGA | AGACACGCAG | TGGTATGTCT | 60 |
| GTAACTTTGC | AATTTCAAAT | TAATTCTCCT | TTCATCGTAG | TTCGGGCTGC | TGGGCGATCT | 120 |
| CCGACACAAA | CGGCTGAGTC | GCTGACACAA | ACAAAAACTC | GACTACGAAA | AACGACTAAG | 180 |
| CGTCGCAGAT | GCTATATATA | TACAACTTGG | TTCCTAATTA | GGGTTAGATC | CTTGCGAGAA | 240 |
| ACAGACGTTG | AGCTTGTGCA | CTTCACAATT | TTAGTCCCGT | CTCCGAAGTT | TCCAGGCAAC | 300 |
| ACGAATAACA | ACACATATTG | CCATGGCATC | GGTAACGTTT | AAAGACAATG | CGGAAGTGAT | 360 |
| AATGATAGGT | GAGCAGGATC | GGAGAAGAGA | GCAAGGTATG | GCCAGGCCCT | GGATAACGGG | 420 |
| ATTCATCGAC | GCGGATATCA | TGTGGCAAAA | GGACGGTCCG | TAACTCATAG | TAGACATCGC | 480 |
| CAAAGAGAAC | TTCGACAGCT | TATATTGACA | TTCGTCCTCT | TGCTCTACAT | TGTTGAGGCA | 540 |
| AAGATATAAG | AGAGTATGGT | G | | | | 561 |

(2) INFORMATION FOR SEQ ID NO:127:

(i) SEQUENCE CHARACTERISTICS:
            (A) LENGTH: 685 base pairs
            (B) TYPE: nucleic acid
            (C) STRANDEDNESS: single
            (D) TOPOLOGY: linear (ii) MOLECULE TYPE: DNA (genomic)

(vi) ORIGINAL SOURCE:
            (A) ORGANISM: PAG1047RP (xi) SEQUENCE DESCRIPTION: SEQ ID NO:127:

| | | | | | |
|---|---|---|---|---|---|
| GATCGAGTAG | ATGTTCCGCA | GCGCTGGCAT | CTTCAGGTCC | CGGTACGTCA | GGATGAACTC | 60 |
| GCCAATGCTG | GTATCCAGCG | TGAACCCGTT | GACGCCCTGC | CCCGTCGTTA | GCATGACGTG | 120 |
| CGTGGACGCG | CCGTACATCG | CGTAACACGC | TGCCACGATC | TCCCGGCCCG | ACCGCAGCAC | 180 |
| ATCCTTGATT | GTCCCGCTCG | AGTCCGGAGT | CAGCTTGAAA | ATCGAAACGA | TCGTGCCCAC | 240 |
| CGACACACCG | GCGTCCAGGT | TCGACGACCC | GTCAATCGGG | TCGCAGCACA | CCGCATACGT | 300 |
| CCCACCGGTC | TCCGGGAACA | CGATCAGGTC | CTCCTGCTCC | TCCGACACCA | GCACCTTGAC | 360 |
| GTTCCCGCTG | GCCTTCATCG | CATTGATGAA | GATCTCATCG | CCCAGCACAT | CCAACTTTTT | 420 |
| CTGCTGGTCC | CCAGTCGCGT | TAGACGCGCC | GGAGAGCCCA | ATCAGGTTCA | CCAGCTCCGC | 480 |
| GCGTCTGATC | GTCTGCGAGA | TGAACTTGAA | CGCAAACGAC | AGTGAGTTGA | GCAGCAGGTT | 540 |
| GAACTCGCCC | GTCGCGTTTT | TGGCCGAGCT | GCGCTGCGAC | TCCAGGATGA | AACGCGCCAG | 600 |
| CGTAATGATA | TCCGTGTCGA | TAGCCTCTGC | GGAGTCGCGT | CTCTGTGGGT | TCACGGTAGC | 660 |
| CATTTCTGCT | TGAGTGCGCT | GTGGT | | | | 685 |

(2) INFORMATION FOR SEQ ID NO:128:

(i) SEQUENCE CHARACTERISTICS:
            (A) LENGTH: 678 base pairs
            (B) TYPE: nucleic acid
            (C) STRANDEDNESS: single
            (D) TOPOLOGY: linear (ii) MOLECULE TYPE: DNA (genomic)

(vi) ORIGINAL SOURCE:

(A) ORGANISM: PAG1047UP (xi) SEQUENCE DESCRIPTION: SEQ ID NO:128:

```
GATCACTCCC CTCGCTTGAA ACAATGCCGT ATAGCGGAAT CTGGCCGAGC ACCAAGAAGA      60

TCAGCAGCGA GACGGCTGTC CAGATCAACT TCTGGTTGTA TGGCACTTTG CGCTCGGGCG     120

CGATCACCTC GGGCAAAAAA GCCTCGAAGG GTTTGAATAG ATCCAACAGA CGCCCACTCA     180

TTTCAGGCTC ACAATGTTTG TAGGTAGCTT GCTGGGCTTG GATTGGCTAC ACAGTTGGAA     240

CCACACAAAG TCACTATTGG GCGAGATGGT ACTCTAAATG ACTGCAAGGA GAACTGGTCG     300

GTTTCGTTTC CTGAACAGCT TAATTGGACT GAGTTGCAGT AGCTGTACTG AAAGGAACAC     360

GTATCTTGAA AAAATTATAA ATCTCAGTAC CACGTGACCG GATACGAGGT GCTATTCCAT     420

CTCGCTAGAG GAGCTATATG CCTAGTCGGC GTACCCTTGG TGAGTAAGAA TAGCTCTCTT     480

GGACAATAAT CCGTGATGAC CTTATTATGC TATAAAGCTA TTTTACATAG CAATGGATCT     540

CCGTGTTTAG ACCTTTGCGC CGCCAAAAGA CCAAGTACAT CAGCACCGAG AACAGCAGGC     600

AATCGCCAGG CGCTTGTGGA GCTCCAGAAG ACATGCTGGA TGCAAACCGG AAGAACGCCG     660

NTCGGAGTAC AGTTGGCG                                                  678
```

(2) INFORMATION FOR SEQ ID NO:129:

(i) SEQUENCE CHARACTERISTICS:
        (A) LENGTH: 638 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1048RP (xi) SEQUENCE DESCRIPTION: SEQ ID NO:129:

```
GATCGTCATA GTCCGCCTCG TCGTATTGGT TCCTTCTGCG CCGGCGCTGC ACCGGCATAC      60

CCATCGCGTC CACCTGCATC TTGTCATCCG CGTCCATCTC GTCGTCCAGA AACACCTGGC     120

TATCGTGGAG CATCCTGTCC CGCGCATTGA GCTGCGCGTC GATCCGTCGC CGGTCCGCCA     180

ACGACAGCTC CTCGTGCTCC GCGTCGTCCA CGCCCTCATT TTCATAGAAG TCCTTGTTGC     240

GATTGGCGGT ATAGTCCGCG TACATGTCGT CGCCCACCAG GTCGACCTCG TCTATGCGCT     300

CTTCTGCGTC ATCCAGGTCG TCTTGCAAAC TCGATGCGCT CGTCGCCGTC GGTAATCGGG     360

GTTCTCGAAG TCGATCTTCG TCCCGGGGAC CCCAGGGGGG ATTATTCCCC CATACGGGAA     420

GCGGGGCCCG CTCCCAACTT GTGGGAAGAT AGTGGGTGCT CCGAGGTTCT TTTGACCTGC     480

TGTAATANTC CNCTGTCTTT TTCGGTTCAA CTNTAGCCCT CNGGGCCNGG TTNACCCCCC     540

ATCCCGTATG GAAGCANCCA ATAACAAATG CCTCCGAAAA NTTTGTTNTT TTCCNATTTT     600

GGAANAAGNA AGTTCTNANA ANGAATTTTN NANTTNNN                             638
```

(2) INFORMATION FOR SEQ ID NO:130:

(i) SEQUENCE CHARACTERISTICS:
        (A) LENGTH: 621 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1048UP (xi) SEQUENCE DESCRIPTION: SEQ ID NO:130:

```
GATCGCGCTC CTCAGCCATG GCTTCCTCTA ATAGTAACAC ACGCCCTGCT TCGTAGTCGT        60

CGAGGTGCAC ACCTACCCGC GCAAATAATG CCTCATCTGA CAGCTGCACC TGGTAGAACT       120

GTGAGCACCG GAAGTGCAGC TTGCTGCAGA AGCTTGTGAG ATATTTGTAG GGGTTGTTCT       180

GTGTCAGAAA GTTGCTCACC CGTCGATTCT CGTAGGGATC ACGGATACGA CCTTGGCTCT       240

GCCCGCACAG CGGGTACCCG CATAGCTTGT TTAGATTGCG CTCATCTATC AAGTCTGAAT       300

ATGTCGGCTT GGGGAAAGAA CCTTCCCACG TATTTTAGTG TCTCGGGTGT GCATTCTTGT       360

CTTGCGAAGA GCAGTTCGGA GCAATTCGAC CGTCAGAAGG TCCCCCTCCT TTAGTGAAAG       420

NNGCGATGTT GGTGATAGGA ACTTAAAACC CGTTTTGGNT TNTCNCAATA GNAGCCANNA       480

CCTTANGTAC GGTNTNCCGT TCTTAACCCC GCCGGGTCCC NGGGNGGTTT CAAGTTCTTG       540

GNGGGANAAG GTNCCGNTNC CCGGGGGTNC GCCTACTTAA GNGANGCCAN AAGGNAAAAG       600

NCCCCCNGAA AAGTGGNTTT T                                                621
```

(2) INFORMATION FOR SEQ ID NO:131:

(i) SEQUENCE CHARACTERISTICS:
        (A) LENGTH: 480 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG149RP (xi) SEQUENCE DESCRIPTION: SEQ ID NO:131:

```
GATCTTTCAG CTTTGGCGTG CTATGGCAGG CAGCCTGCGC CTTTATGGCC TCAATGCCTC        60

GCTGACGACT CTCATGTGCC TGTGGGCAAT CTGGTCACGT GGGTACTATC CAGCGACGGG       120

ACTCCCTATG GCTGTTGCAG ACAAAGCGAA ACTCAGCATG CTCTACGTGC CCTACTTCCT       180

GATTCCTCTG CGCCTCGTCT TTGTGTGAGG TCTGGAGCAA TGCAGAAGTG CAACACTCTA       240

TATATAATCA CCTGACTATG TACCTATTTC TGGCATAGCA CGTTACGTTT TGTCACGATT       300

CCAGTCAGTT AGCTGCCTCG AGCAACCGGT GAGCTCCGAA AAGGGAATTC GCTACAAGGT       360

CTTAGCGCAT AGNCCTGCAA CTGGCTTTGG CTAGGTCAAT TGGTTTTCTT GGAACCANTC       420

TTGGTATAGA CTCTTGCGTA TTGATCGGGC TGAGGAGTGT TTTNGNGGNA GNCAAACACC       480
```

(2) INFORMATION FOR SEQ ID NO:132:

(i) SEQUENCE CHARACTERISTICS:
        (A) LENGTH: 477 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1049UP (xi) SEQUENCE DESCRIPTION: SEQ ID NO:132:

```
GATCGTCTCC TCGGCGACAG CGCCTTCTAG ACCCTCGACG GGCGACACCT TGATGCTGCT        60

CTCGCTCTCA AACGTACCCA GACCCTTGTA GTAGGTGACG CCGTTTTTCT TGAAGAGCAT       120

CTCAATACCG CCAGTCAATT GCTTCACAAC GGTGTCCTTG GCCTTTTGGA ACTGGGGCAT       180
```

```
GTTCACAGTG ACCTCGCCCT TGACGTCGAT ACCGCGCTGC TTGGCATCGA GTTGCATCTG      240

GTGCAGCAGG TGCGAGTTGT TTAGCAGCGC CTTGGATGGG ATACACCCCA CGTTCAAACA      300

GGTGTCACCT AGACGGGCGG GCTTCTCCAC ACACGCGGGG TCGAAAACCA GTTTGTTGCA      360

GCCTTCGATG GCCGCCACNN TTAACCACCG GGGACCNCCA CCCATCAACC ACAACGTCGG      420

GGTTTTCTTT TGTTGGGAAT TCAACCAGGC CCNCTTTNNT GGGACGACCN CTTANNC        477
```

(2) INFORMATION FOR SEQ ID NO:133:

(i) SEQUENCE CHARACTERISTICS:
        (A) LENGTH: 443 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1050RP (xi) SEQUENCE DESCRIPTION: SEQ ID NO:133:

```
NNNTTTNTGG TGGGGCGTGT AGANTAGTGG TCGGGGNGCC GCTCCACATT CTCCATGCTC       60

ACCACCACGA CAGACTGGAA GTACAGGAAA AGCGACATTG TCGTCGCAGA GATGTGCGAC      120

GCGGCGTTCG AGTTCCCAAA AGCAGACAGC GTTGCGGACG CCAGCAGTCC AAGCCCCGCA      180

ATTGTCGCCG TCGCCCACTT CACAGGTGTT TGGGCCACGG TGCGGCCGTT CGTGAAGTGC      240

GTCTGGATGC ACGACACCTG GTCGTTCGAC TGGGTTTCGT GTACCATCAC CTTGAGGTAG      300

GCGTCATTGT CCGGCACCTG GTACGTCACG CCGGGAATCT TNTTTGTGTT CTCCGCGCTC      360

ACATACTGCA CGGCCTGGAT CTGAATGTCA CCGGGTGTCA CAGGACAAAA CTGCTTCTAG      420

CCGATCCCAT ACATGTCCTT CGC                                              443
```

(2) INFORMATION FOR SEQ ID NO:134:

(i) SEQUENCE CHARACTERISTICS:
        (A) LENGTH: 400 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1050UP (xi) SEQUENCE DESCRIPTION: SEQ ID NO:134:

```
GATCCTTTCG TATGAAGTAT GCAGCTGTCG ATATGCTTAG TTAACTTCTG CCCAGCTATT       60

TAAGCTGCAA TTGAATCGGC GGTGACTCAG CTTGCAAAGG GTAGCAGAGA GGACGCGATG      120

GGTTTATTCG GAAAGGATAG AGGTGAACGG ATAGCTGAGT TTCCGTGTTA CCTGCTAGAG      180

ACCNGAACGC ATCTGGTGCC GNTGNCAGGG GATTCTATAC AACCTTGTGA TCGAGCGGAC      240

ATATNGCGAG CGGATACTAG GGCAGNTCCC TGGGATAGGT GAGGCTNTAG ACGGGGCGCT      300

GACGGGCGCT TTTGAGGCCG CAGAGGTACC CCCGCGGGTT GCGGAGGTGA TGAAGGCGTT      360

CCAGGAGCGG TACGACTCCC GGGGACAAAA ACGCAGGCCC                            400
```

(2) INFORMATION FOR SEQ ID NO:135:

(i) SEQUENCE CHARACTERISTICS:
        (A) LENGTH: 713 base pairs
        (B) TYPE: nucleic acid
        (C) STRANDEDNESS: single (D) TOPOLOGY: linear (ii) MOLECULE TYPE: DNA (genomic)

(vi) ORIGINAL SOURCE:
         (A) ORGANISM: PAG1051RP (xi) SEQUENCE DESCRIPTION: SEQ ID NO:135:

```
GATCAAATTT GACATGTAAT TAATATATTG AGGTAAAATC TAGATAATAA ATACTGCCAG      60

CAGTGCTGAC CAACTTCCAT TAGCAAGCAT ATAAGAGGTC TTAAATCAGC CGAAGGTATA     120

TGCGAGGGAA GATAGATCCC CCGGGCTGCA GGAATTCGAT ATCAAGCTTA TCGATACCGT     180

CGACCTCGAG GGGGGGCCCG GTACCCAATT CGCCCTATAG TGAGTCGTAT TACGCGCGCT     240

CACTGGCCGT CGTTTTACAA CGTCGTGACT GGGAAAACCC TGGCGTTACC CAACTTAATC     300

GCCTTGCAGC ACATCCCCCT TTCGCCAGCT GGCGTAATAG CGAAGAGGCC CGCACCGATC     360

GCCCTTCCCA ACAGTTGCGC AGCCTGAATG GCGAATGGAC GCGCCCTGTA GCGGCGCATT     420

AAGCGCGGCG GGTGTGGTGG TTACGCGCAG CGTGACCGCT ACACTTGCCA GCGCCCTAGC     480

GCCCGCTCCT TTCGCTTTCT TCCCTTCCTT TCTCGCCACG TTCGCCGGCT TTCCCCGTCA     540

AGCTCTAAAT CGGGGGCTCC CTTTAGGGTT CCGATTTAGT GCTTTACGGC ACCTCGACCC     600

CAAAAACTTG ATTAGGGTGA TGGTCACGTA GTGGGCCATC GCCCTGATAG ACGGTTTTCG     660

CCCTTTGACG TTGAGTCCAC GTTCTTTAAT AGTGGACTCT TGTTCCAAAC TGG           713
```

(2) INFORMATION FOR SEQ ID NO:136:

(i) SEQUENCE CHARACTERISTICS:
        (A) LENGTH: 703 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
         (A) ORGANISM: PAG1051UP (xi) SEQUENCE DESCRIPTION: SEQ ID NO:136:

```
GATCTATCTT CCCTCGCATA TACCTTCGGC TGATTTAAGA CCTCTTATAT GCTTGCTAAT      60

GGAAGTTGGT CAGCACTGCT GGCAGTATTT ATTATCTAGA TTTTACCTCA ATATATTAAT     120

TACATGTCAA ATTTGATCCA CTAGTTCTAG AGCGGCCGCC ACCGCGGTGG AGCTCCAGCT     180

TTTGTTCCCT TTAGTGAGGG TTAATTGCGC GCTTGGCGTA ATCATGGTCA TAGCTGTTTC     240

CTGTGTGAAA TTGTTATCCG CTCACAATTC CACACAACAT ACGAGCCGGA AGCATAAAGT     300

GTAAAGCCTG GGGTGCCTAA TGAGTGAGCT AACTCACATT AATTGCGTTG CGCTCACTGC     360

CCGCTTTCCA GTCGGGAAAC CTGTCGTGCC AGCTGCATTA ATGAATCGGC CAACGCGCGG     420

GGAGAGGCGG TTTGCGTATT GGGCGCTCTT CCGCTTCTCG CTCACTGACT CGCTGCGCTC     480

GGTCGTTCGG CTGCGGCGAG CGGTATCAGC TCACTCAAAG GCGGTAATAC CGGTATCCAC     540

AGAATCAGGG GATAACGCAG GAAAGAACAT GTGAGCAAAA GGCCAGCAAA AGGCCAGGAA     600

CCGTAAAAAG GCCGCGTTGC TGCGTTTTTC ATAGGCTCCG CCCCTGACGA GCATTACAAA     660

AATCGACGCT CAAGTCAGAA GTGGCGAAAC CCGACAGGAC TAT                      703
```

(2) INFORMATION FOR SEQ ID NO:137:

(i) SEQUENCE CHARACTERISTICS:
        (A) LENGTH: 595 base pairs
        (B) TYPE: nucleic acid

```
        (C) STRANDEDNESS: single
        (D) TOPOLOGY: linear (ii) MOLECULE TYPE: DNA (genomic)

(vi) ORIGINAL SOURCE:
        (A) ORGANISM: PAG1052I1

(xi) SEQUENCE DESCRIPTION: SEQ ID NO:137:

GATCTCCGCT TCAAACCAGC TAGGGACGAC CGGAGGTCGT TCCAGAGAAA GTCAACAATC      60

AATATCCTGG GTAAAGCTAG CACCGCCGAA CTACTTGCTC TTGGCACCAC CGCAAAGGCA     120

CACAACGAAA ACTGGGAAGA TGAACTGAAG AAACAACAAA CGGTCACCGT TGATGACCAG     180

GTTGTTTCGC CAGAAGATTC GCCCTTTGCA GAGCCAGTGC AGGAACCAAA GACCTCAGTG     240

TCCGGCTACA TCAAGAGGAA ACTATCCCTC AAGCGTGATA AATCCACAAG ATCCAATCGT     300

TCGCAATATG ATAGGTTACA GGACTAGATA TGGATGTTAA GTATAGAAAA ACTGTATATT     360

ATTTGACGTG CTGGGCGTTA CGGAAACATA TAAAGATTTA ATTACTCATG GCGGATGGT     420

ATTTTTTCAT GGGCCCCACT GGACTCCATT TGGGCAGTTG GAGGACGAAG TAGGAACCCA     480

ATTGCTGGTT ACAAGCGCTC GGTTTCATGT ACCCTATACA CAAGTATCCA TTATTNGGGC     540

TTATTGATTT GTGTCTNTGG GCCGGACTTT TANCTTTCTC ACTGGGGGAN GTCCT          595

(2) INFORMATION FOR SEQ ID NO:138:

(i) SEQUENCE CHARACTERISTICS:
        (A) LENGTH: 625 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1052I2

(xi) SEQUENCE DESCRIPTION: SEQ ID NO:138:

GATCTGGGTT GCGCGTGAAG ACCACCAATG CGATGCACAC GAGTATCATG ATCAGCAAGA      60

TTAAAGAAAA GACAGCGTTC AAAATAAAAA ATACCCATGC CATAATGGAG CTGACGCTTG     120

CAGGCTGTCC AAAGAGCCCT GAGAAAAATA AGAAGAGGAA CGAATTAACA AGAGTAACAC     180

TGGATATCAT AATGTTCAGG ATGTTAGTCG CGCGGTCGAG GTACGGCCTG CATTTAGCCA     240

GAGCTGCGAG GTATATTATT TCAATGACAA ATAGAGCGAC GGCCTGGGTT TTACCGGAAT     300

TGTGGGCAAA TGCAATAAAT ACCGCTTTCA ACAAAATATG CGCGAGGATC ATGCAGGACC     360

ACCAGTAGTG TGTCGCACTG TACATTGTGT AGAAGAAGCC GTATTTGTGT AGCACATTTT     420

CATTGCCGCA TAGAATGGCA GCTGGGTTCG AGTGCACACC AATGGAAGCC CTTCCACNGT     480

AGATAGTGCG GCAGGCAGCC CANCCCATAA TTGACAAGAT AAANGTNGAG CTAAGNCTGC     540

CAGAACGACC NCCGCCGGGG ATCANCGTTC ANTGATTCCC CACCAGCAGA GATCGCNATT     600

GANTGACCCC GGCAGTTNTN CGCAA                                           625

(2) INFORMATION FOR SEQ ID NO:139:

(i) SEQUENCE CHARACTERISTICS:
        (A) LENGTH: 486 base pairs
        (B) TYPE: nucleic acid
        (C) STRANDEDNESS: single
        (D) TOPOLOGY: linear (ii) MOLECULE TYPE: DNA (genomic)
```

(vi) ORIGINAL SOURCE:
    (A) ORGANISM: PAG1052RP (xi) SEQUENCE DESCRIPTION: SEQ ID NO:139:

```
GATCGCGGAC GCGTGGGCGC AGAACCTGGC GTGGAGCATG GGGCTGATCC GAGTGGAATT      60

CATGCAACGC ATCTTCCGGT GGTACGTCCA GGCGAGCGGC GGCGAGCCGT CGCTGCATTT     120

GACGTCAACG ACCACGTCTG TGCTTGCCCA ACGCTCACTG GATGCGCTAG TGGGCCGGCC     180

CGTGAGCAAG GCGACACAGT CGCTATTTGC CAGCACACAC ACGATGATCT TCAGAGGGAT     240

CCGTAGACTG GCCTACCGTG CGAACATAGA GAGCTCATCG GTTGTGTGTA CCGGGCTAAC     300

GTTCTTCCTT CTGTTCGGCT ATTTGGATTG GCGTGGCGGT TTACATTTGT TCAAGCGGGG     360

CTACTCGGAG CTGCTTATCC CGCATGAAGG TCAATGAACC CAGGTCCGGG TCCCTAGACT     420

TCCAAGAAAA ACGTGGGTGA TTGNGCTCAA AGGTGTTCTT TTGGGGTANA TCTTCCCCCG     480

NGTTCA                                                                486
```

(2) INFORMATION FOR SEQ ID NO:140:

(i) SEQUENCE CHARACTERISTICS:
        (A) LENGTH: 468 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1052UP (xi) SEQUENCE DESCRIPTION: SEQ ID NO:140:

```
GATCCAGCTC TTGCGCGGTA TGAACTTTCC CGCCCGCACC GGCGCCTCGC ACACCGAAAT      60

CGACCGCACC TCCGTCTGCG TCTCGTAGTT CCAAATTTCC GCGCGCCCCG AGTACAGCGT     120

GATCAGCACC CACGGCTCGC TCGGGTGAAA GTCAATGCCC TTCACCCTGT CTGTCCTCGA     180

GACAAACGTT TTCTACTCAC GTTAGTACTT GCTCCGCGCC CTGGATAGCA TGGTCGAGCT     240

CTGCGGGTCC GCCCCCTCCG TGGGTGGCAA AGATGGTCTT CAAACACACC GTAATAGGCC     300

GTGCGCGACC ATGCAGGCCC CATTCGTCCT CGGACACACA CATACCTTCG TTTCCAAACT     360

TCATTGGTCC CCACTTGGGA TTCCTAGTAG CTGTTCAACT CGGCTTTTTG GGTTCTTGTG     420

GAAAANTAAT ATTCCCNTGG ATTATTTAAA TAGGGGTCCN TTTTNTTT                  468
```

(2) INFORMATION FOR SEQ ID NO:141:

(i) SEQUENCE CHARACTERISTICS:
        (A) LENGTH: 672 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1053RP (xi) SEQUENCE DESCRIPTION: SEQ ID NO:141:

```
GATCATAGTG ATTGATATCG GGAGAGGGTT TCGTATGTGA CAGCCTGTAT TCACGTATCT      60

GGTCCTTCAC TTCATATATT TCTTGTGGGA GCTGTGAATA TATCTCCATG CGTTCTCTGT     120

TCCATTTTTC GTGCATTTTG TGGAATGCAG CCCACTTCTC GTACGTTGAA GTAGGCTTGG     180

GTACTAACGA TCCCTGAACA GGGAGGAGGC ATGTTGCGAG GGAGAATATT AAGGAATCAT     240
```

```
ATCTCATTTT TACGTCTGAG ATAACTAGTA CTAACTGCAA TGCGGCGTCC AAATACCCGT      300

CGTAGTAATC GTATAGGAGC AAAGCTTCAT CTCTTATACG ATGTGGAGTT GATTCAGTCC      360

ACTGCAGCCC TTGGTATTTA GCCAGCATTC CATCATATTT GGACTGATAA TATTCGAAGT      420

TCTTCCACGC GTCCTTATAC GGATCAATTA CTGATTTTAC AACATCGAGT AATATGGAAA      480

GATATAACTC TGGATTGCCC TGTATGACTT CCAGCACGCC ATGGAACATA TCCCGAATGC      540

CGTCGCGGCA CTTGGAGACT AACTTTGGCG TGTATATCTG CTCTTCGACT GTCCCATGGT      600

TGAGGTAGGT ATCTTCAGGT AGAATGAAGT CAATGAGCGA TAAACTGACT TGCTTGAATC      660

GTCCCAAAGA GT                                                         672

(2) INFORMATION FOR SEQ ID NO:142:

(i) SEQUENCE CHARACTERISTICS:
        (A) LENGTH: 609 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1053UP (xi) SEQUENCE DESCRIPTION: SEQ ID NO:142:

GATCTCGGCT CGCTGCTCGC GCTCGAGCCC TACTGGGCAG AGCGCTACCC AATAAACAAC       60

GCCCTAATCG GCGGTGCAGA TAAATTGCAC AAGCTCTACT CAACCGATTT TGCGCCCATC      120

GTCGCCGCCA GGACTTTCGG CTTGAACCTC GTCGACAAGC TTGGACCGCT GAAAGACCTC      180

ATAATGGCAA AGGTCAGCGG CCCAAATTAA TAGTCACGTG TACATAAAGG TTTTCCTAAT      240

AGCTATACAG CTTGCCCGCG TCCTCAGCTT GCAGCGCGCA ACCGGCGTGC AGCCATGAGC      300

GTCCTACTGG AAACTACCAT TGGCGACCTT GTAGTAGACC TGGACTACAA GACATGCAGC      360

GCCGAGAGCT ACAACTTCCT CAAACTCTGC AAAACTCGCT TCTACGACTG TCAGTGCATC      420

TACCGACCTC CATCCTGAAG GCTCAGCACG CCCTCGGCGA TCCACAGGTG GGCTTTGCAT      480

TCCGCACGGA TTTGCCTGTA CACAATACCT CGATCGAAGG CCTGCGCGAC ACACGGGCGG      540

TCACCCCGAA GCTCATTGAA GCCTCCGTTG CCGCTCAACC CGCAGAGCGC TTCGGACAGG      600

TCGCCTTTG                                                             609

(2) INFORMATION FOR SEQ ID NO:143:

(i) SEQUENCE CHARACTERISTICS:
        (A) LENGTH: 594 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1054RP (xi) SEQUENCE DESCRIPTION: SEQ ID NO:143:

GATCCGTCGC CGGTCCGCCA ACGACAGCTC CTCGTGCTCC GCGTCGTCCA CGCCCTCATT       60

TTCATAGAAG TCCTTGTTGC GATTGGCGGT ATAGTCCGCG TACATGTCGT CGCCCACCAG      120

GTCGACCTCG TCTATGCGCT CTTCTGCGTC ATCCAGGTCG TCTGCAAACT CGATGCGCTC      180

GTCGCCGTCG TTATCGGGGT TCTCGAAGTC GATCTCGTCC GGCGACCCCA GCGGCGAATT      240

ATTCCCCATA CGCGAGCCGC GCCCGCTCCC AACTTGTGGC GACGATGGTG GGTGCTCGTA      300
```

```
GCTCTGTGAC CTGCTGTCAC TACTCCGCTG CTCTGTATCG TTTTCATCTC TAGCCCTTCT      360

GCGCCCGTGT GAACCCTCCA TTCCGTTATG CGAAGCCATA CCCAAATTAC CAAATTGCCC      420

TTCCTGAGAT CTTGAATACT ATCTCCCAGA TGTTTGACAG ACGCGCAGCT TCTCACGATA      480

CGAAATATCG TGATTTTACG TGACTTTCAA TACCTCATTT GGATTGGATT GGTGAAGCAT      540

AGATTTTCAG TCATATTGAA AAATTATTTC CAAACAGGGC AATTGGATGA GCTG           594
```

(2) INFORMATION FOR SEQ ID NO:144:

(i) SEQUENCE CHARACTERISTICS:
        (A) LENGTH: 545 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1054UP (xi) SEQUENCE DESCRIPTION: SEQ ID NO:144:

```
GATCGTCGCG TTGCGCAGGG CTGCCCAACG AAGCCTTGAC ATGTCAAACC GCTTGAAAGA       60

AGAGGTGATA TGGGCCACCC ACGAGGCCAA GTGGGAGCAA CTGCTCGCTA CTGGGACCCT      120

TCCCCCAGAT GGGGCCAAAA GCGACTGGAA GCCTGGCCGA GCATGGCTGG AACCATATGA      180

GGCCGCGTTT CGGAACCAGC TTGCAAATCG CAAGCGCACG AGCCAGAAGC TCAAGCGCTA      240

TAGTGCCCAA ATCAGCAAGG TACACCTCCC GTATTACATT AAGTGCAGTG CTGCTATGCA      300

TACCCGTCGC GCCAAACGCT TCGAGTGTTT CCAGAAAGAG CTCCACACCG TTAATCCATT      360

CGTTCCAGGC AGAGATCTCG GTTCCCTACT CTCCAAGTGG CGAATGGTGA ACGGAAAAAA      420

CTACTATCGC TGAATGTATA TAGTTTATAG TCCTATTCCT TCATCAGGTC TCCCAGCAGA      480

GGCGGCCGCT CGGTCTCAAC TATGCGCACC TCGCTCAGCC ATTCGCTGAG GTCCTTCTGA      540

GTTCG                                                                  545
```

(2) INFORMATION FOR SEQ ID NO:145:

(i) SEQUENCE CHARACTERISTICS:
        (A) LENGTH: 532 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1055RP (xi) SEQUENCE DESCRIPTION: SEQ ID NO:145:

```
GATCCGTCGC CGGTCCGCCA ACGACAGCTC CTCGTGCTCC GCGTCGTCCA CGCCCTCATT       60

TTCATAGAAG TCCTTGTTGC GATTGGCGGT ATAGTCCGCG TACATGTCGT CGCCCACCAG      120

GTCGACCTCG TCTATGCGCT CTTCTGCGTC ATCCAGGTCT CTGCAAACT CGATGCGCTC       180

GTCGCCGTCG TTATCGGGGT TCTCGAAGTC GATCTCGTCC GGCGACCCCA GCGGCGAATT      240

ATTCCCCATA CGCGAGCCGC GCCCGCTCCC AACTTGTGGC GACGATGGTG GGTGCTCGTA      300

GCTCTGTGAC CTGCTGTCAC TACTCCGCTG CTCTGTATCG TTTTCATCTC TAGCCCTTCT      360

GCGCCCGTGT GAACCCTCCA TTCCGTTATG CGAAGCCATA CCCAAATTAC CAAATTGCCC      420

TTCCTGAGAT CTTGAATACT ATCTCCCAGA TGTTTGACAG ACGCGCAGCT TCTCACGATA      480
```

```
CGAAATATCG TGATTTTACG TGACTTTCAA TACCTCATTT TGGATTGGAT TG            532
```

(2) INFORMATION FOR SEQ ID NO:146:

(i) SEQUENCE CHARACTERISTICS:
        (A) LENGTH: 553 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1055UP (xi) SEQUENCE DESCRIPTION: SEQ ID NO:146:

```
GATCGTCGCG TTGCGCAGGG CTGCCCAACG AAGCCTTGAC ATGTCAAACC GCTTGAAAGA    60
AGAGGTGATA TGGGCCACCC ACGAGGCCAA GTGGGAGCAA CTGCTCGCTA CTGGGACCCT   120
TCCCCCAGAT GGGGCCAAAA GCGACTGGAA GCCTGGCCGA GCATGGCTGG AACCATATGA   180
GGCCGCGTTT CGGAACCAGC TTGCAAATCG CAAGCGCACG AGCCAGAAGC TCAAGCGCTA   240
TAGTGCCCAA ATCAGCAAGG TACACCTCCC GTATTACATT AAGTGCAGTG CTGCTATGCA   300
TACCCGTCGC GCCAAACGCT TCGAGTGTTT CCAGAAAGAG CTCCACACCG TTAATCCATT   360
CGTTCCAGGC AGAGATCTCG GTTCCCTACT CTCCAAGTGG CGAATGGTGA ACGGTAAAAA   420
CTACTATCGC TGAATGTATA TAGGTTATAG TCCTATTCCT TCATCAGGTC TCCCAGCAGA   480
GGCGGCCGCT CGTTCTCAAC TATGCGCACC TCGCTCAGCC ATTCGCTGAG GTCCTTCTGT   540
AGTTCGTCAC CCG                                                      553
```

(2) INFORMATION FOR SEQ ID NO:147:

(i) SEQUENCE CHARACTERISTICS:
        (A) LENGTH: 556 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1056RP (xi) SEQUENCE DESCRIPTION: SEQ ID NO:147:

```
GATCATCAGC GCGAGCTTCC AATTTGTGGG CTTTCTGTTG ACATACATCC TCCACACCTC    60
GCATGCGGCG CGCCAGGGCT CGCGCTTTGG CCTCGGCCTG ACCTTCACGG GATACGGGTA   120
CAGCATGATT CCTAGCGACG TGACGAGCAA GGTCGGCAAG GACCGCGACA TCGCGCGCGT   180
GGAGCTGGAC GACCCCAACG AATTCGAAGA TTCGCACCTG TACTCGCCGC TGGCGCAGCC   240
GGCGCAGGAC CGCTTCGAAT CACAGCTCTC GCACGGGCTG ATGGAAAAAC GGCGCAGAAT   300
TCCGGCGCTC GCGATCGTGC TAGAGATTTT GGGGCTTGCA ATTATGTGCA AAAGCGTGTA   360
CGACTACATT GTGGTCAAGC GCATGGAGCG CCGCATCTTT ACTGCGAGCG ACAGCGAGAG   420
CCCCGCATAG ATGTTCATAT AACTTATATA TCCCTCATTG ATCTTCGCTT GGGCCCCGTC   480
TAGGGAGCAG ACCAGCAGTT TCTTCGTTCG CCCTNAAGTC GATGCCGCCA GAGAGACCAG   540
ACGCCCCAGC GCGGTA                                                   556
```

(2) INFORMATION FOR SEQ ID NO:148:

(i) SEQUENCE CHARACTERISTICS:
        (A) LENGTH: 550 base pairs (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1056UP (xi) SEQUENCE DESCRIPTION: SEQ ID NO:148:

```
GATCCAACCC AGGACTTCTC GAAAGATAGA ACTCCGAACA CAGCCACCGG CACGAACTTC      60
TCATCAGCTA GCAGCAATAC TAAGCAGACC TTCAGCGAAA ATGAAGAAGA ATCTGATGCT     120
GAGTTCGAAG ATGTATAGTT GTACCCGTAT ATTGCATTTT TTTTTTTTTT TTTTTTTTTT     180
TTTTTTTGGA GATGTCAAAA GCTCATCTCA ACTCCATGAC CAGCCAGTAG TGACTAAAGC     240
AGTGTGTCTA GTTCTTCTAA GTGATTTTAA GGACTATGAG CTTTAATGAG AAGGTGAAGT     300
GGGTACTAGG CACTGCTGTT GCGACTCTAG TTACGATAAA GTCTGTCGAA GCCGTATATC     360
GCCTCTATGC AGCTAAGCAG AACACTAGCA GGAGCATTTC TGGGGAGGAG AAGGACGTAA     420
GACTGGCCAA ACGGATTCGT GAGTCTAGGG CGTACGATGA GGAATTATAT CGGGAGCAGT     480
TAGCTCGGAA CTACGCATTT TGGGCGAAGA CGGTATGGCA CGACTACAGG AACAGTACTC     540
ATATGGTGGG                                                            550
```

(2) INFORMATION FOR SEQ ID NO:149:

(i) SEQUENCE CHARACTERISTICS:
        (A) LENGTH: 653 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1057RP (xi) SEQUENCE DESCRIPTION: SEQ ID NO:149:

```
GATCAGGGCC AAATCACTGC TAAGTACAAA CACAAAGGGC CAAGTATTAA GGTGAGAGAG      60
CGTTACAGGT GCATTGATAA TACCGCAGGT ATATATCAAG GCGCACAGTG AACACATTCT     120
GCAGACGATA GATATGTCTG AGACGAAGTA GGTTGAGATA TTTACGCACA AGCCTCATTT     180
GTAAGATAAA TGGTCATTAC TAACGTTTTT GGGTTTAGCA GCAGCAGGCG GAGCAACAAC     240
GAGGGGCAGG AGCACGGTGG TGGTGGACAG GGTCCAGGAG TCGAGGATGG CGGGGAGCCA     300
CGGGCCAGGG CGAACACGCG CAATGTGACT GTGGCAATCC AGTACTCGTG GCTCCACGAC     360
ATGAGGAATG TCGGGGGAGA GGGCGAGGAA CGGGACAGGG CCCGGGGGAG AACGGAGATA     420
CGTTCGTGAT GAGCTTCACG GACGTGCCGG ACTCGACGTC GAACGATCGG TTTCAGGAAG     480
TGATCGGCAT TGCGGCGCAG TTTGCATTGA GCCGCGTGGC GCGGCGGATC AGCCTCCTGC     540
GGGGGCTCTC GAAGGAGTCC TTTGAAAACT CCCTCTCAGG AAGCTCAGCG AGCTGGACAG     600
CGAGCTGTGC AGTATATGCT ACGACGACTT TGAAGACGAC ACGTCGATCG GGT           653
```

(2) INFORMATION FOR SEQ ID NO:150:

(i) SEQUENCE CHARACTERISTICS:
        (A) LENGTH: 668 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
            (A) ORGANISM: PAG1057UP (xi) SEQUENCE DESCRIPTION: SEQ ID NO:150:

GATCTAGGGG TTCTTCTTGC CGCGCTACGG GCGCCCCTCG CAGCCTCGCG CTGGCTCCCG        60

CGCGAGAGGG GATCGGCAAG GCTCCTCGCA GCCGCACACT GCGTCTATGC CTGGACCGTC       120

CGGCGAGCCG GACAGCCGAG GAGCAGCCCC GCGATGTCTG TCTCCCCGGC GGCGCTTACT       180

CTGGGGCTGG TGTTGAATTT TCCTAAAACT GGTGAAATTG TACGGGCTCG CTGGAGCCCG       240

CGCCTGTCGA TTGTACACGG GAATAGCGGA TCAATTGGAT GGGGACGCCA GTGTTACCCC       300

CGAAACCGTG CGCAGCGGCT GGCGGGCCGA GGGCTGAGGT GCCGCTGCCG CGCAAGGCGC       360

ATTTGCTGTC GACTGCAGAG CTGCAGGAGC TGTTGAAGGC GCAGGACAAG TTGCAGCTGT       420

ACGTGGCGGG GTTGTGCGAG AGCGAGGAGA CGCAGAAGCG GGTGGAGCAG CAACGAAAAC       480

AGCTGGCTGA AATACGGGAA ACGTTTGCGG GGCTGGAAGG GGAACGACAG CGCGTGCAGG       540

AGCGGCTGGA CGGGTATCAG AGGCTAATGT TCCGGTACCA TGAAGCGTGG CAGGCGGTAR       600

ACGGGCGTGC CGGGCCCGTT ACAACGACGG GTTCTGCCGG CGCGGCTGCA CAAGAAATGC       660

GCGCTGCG                                                                668

(2) INFORMATION FOR SEQ ID NO:151:

(i) SEQUENCE CHARACTERISTICS:
        (A) LENGTH: 614 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1058I1

(xi) SEQUENCE DESCRIPTION: SEQ ID NO:151:

GATCTTCACA TTCGCATGCA GGTTCTTCTT GTTTTTAGTA GCACCCTCCG GCGCCTTGTT        60

GGCCTTCAAC TTGAGTTCAT CCGCACTTGG CTTGATAAGA CCAGCTTTCA AGTACACCAT       120

GATGTCGTCG TCATCACCGT GCTTAAAGCA ACAGCGCTTG CCATAGCGGC AGTAGCCTGT       180

CTTACTCCAA TTGATACATG GCTTCGTGCG GAATTTGTCC GACCGCTCCT TGAACTTTAA       240

CTCGTGGAGA CCATGGGCAA ATTGGCACTT GTTATCGTAC TTGCAGGCCC CCGTAGTCGC       300

AAATGATTCG CATAACTCTG TCTTGTAAAG CATCTTGTTG ACCTTCTCCT GCGATGGCTG       360

TGGCTGCTGC TGTGGGGTGG CGGGGCGGG GACTGAACCC GGCAAAAGTT CGGCTCCGGC        420

TGTGCGCCTG CTCGCCCTGG GCGCTCGGGT CCTCCCGACG GATGCTGCAG GAGCGCAGGT       480

TTTCGGGCGT CAGGGTAGTA TCCCATTGGT AGGCCGNTAA TGAGAGTTTA TCGCCACCTC       540

NAAGGTAGGT TCCCCGTTCC GNAGGGCCAA GGGNAATCAN TNGCCGCCCA AACCGTNAAC       600

CNCCCCCNCC CNGC                                                        614

(2) INFORMATION FOR SEQ ID NO:152:

(i) SEQUENCE CHARACTERISTICS:
        (A) LENGTH: 634 base pairs
        (B) TYPE: nucleic acid
        (C) STRANDEDNESS: single
        (D) TOPOLOGY: linear (ii) MOLECULE TYPE: DNA (genomic)

-continued (vi) ORIGINAL SOURCE:
    (A) ORGANISM: PAG1058I2

(xi) SEQUENCE DESCRIPTION: SEQ ID NO:152:

```
AAGCTTGCAT GCCTGCAGGT CGACTCTAGA GGATCTTGCA AAGTATGGCT TGGTAGTGTG    60
GTGATGGTTA TCTGCAGTTT CAATTGCTTT GTTAGTTAGT GTATCACATT CTTCTGGCTT   120
TGGCCGATTA GAGTGCTGGG CCTCATGGAT GGGGATCTCC GGTGTATACA CGTATATTTA   180
TTCTCTTCGC CCAAGTGGCG GAGTACAATT TTCCTCTAGC TGGACCTATT TCGGTTGTAT   240
TTCAGTAGTG AAATAAAACT ATCAATTAAG TACAGCTTTC GTATGACTCT GCCACAGGAT   300
GAGAGCAGAC ACTCTGCAAA GTACCGGATT TCAAATAAAT GTTAGGAAT AAAATCAAAG    360
GCGTACAATT ACATAATTAT AAAATGCTCT CGTAGCTATG TCTTTCGGGT CTTTTTTTA    420
TCTTAAAGTG AACATCGAGT CTTGTCCTTC TTAGGTGTTT AGATGACAAG CTTACATGCC   480
TGCNGNNGNN AAACAGTTNG TCGAATCCCT CGGATCCTCN CCANGTAGNA AGGNANTACG   540
NNCAGCAGAG TCATTACCNC NACCCACCGG CTTGCCANCC NANTTNCTTN GGNNGNAGNG   600
GGNNGGNGNT TGNACCNANN TTTGNNCCNT NGCC                               634
```

(2) INFORMATION FOR SEQ ID NO:153:

(i) SEQUENCE CHARACTERISTICS:
        (A) LENGTH: 475 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1058RP (xi) SEQUENCE DESCRIPTION: SEQ ID NO:153:

```
GATCATTCTT GAGAATGCTC ATAGTTATGG TTTAACGGTT CTTCAAACGG AAGAGTATCT    60
TCAATTACAG AGTAGTTTGG AGAGAGAACA GGTAACGTCC TACAACATTG CCGAGAAAGC   120
AACTACAATT GGCTACGTTG CACTTCCAAG AACCGAGTAC GATGAACTTG TAGCTTCGCA   180
AGCTTCTACG AAAGAACAGA ATTTTGAGGT ATACGCGGCG GAAAATGGCA AGGTCATAGT   240
GGATAAATCT GAGTATCACG ATTTGAAGAT CAAAGCTATC CCAGTGATTT CACCATTGCC   300
TCAAATGAGC AAAGAGCAGA TGGTTGAAAA GGCCAAGGAA CTTGGAATGG TAGCTTTGCT   360
CCATTGACGA GTATGAGAAG TTAAAGAGCC CTATTTCCCG ATAACGCTTT GGATTGCAAC   420
AGCGAAGGAC CGCGGAAAGG TTGGTCTCCT AAAGGAGGAG TACAACCCCT TATTG        475
```

(2) INFORMATION FOR SEQ ID NO:154:

(i) SEQUENCE CHARACTERISTICS:
        (A) LENGTH: 476 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1058UP (xi) SEQUENCE DESCRIPTION: SEQ ID NO:154:

```
GATCTGGCGC CCCGACAGCC TGCCCAGGTG CGCCTGCATC CGCCGCTCCT GGTCGCGCTC    60
GTCGAGCCCC AGCTCCTGCC GGAAGCTAGC CCTCCAGCTC ATGTACGACT CATGCGTTAC   120
```

| | |
|---|---|
| CTTCGTTCCG CGGAATTTCT TCTGCTCTTC GAGCTCGCGT TCGCGTAGCT GCCGCTCGTG | 180 |
| CTCCTTCTCT CGGCGCTCAA GCTCCTTCTG AAACCACGAC TCCGCGTCCT CCTTTATTGA | 240 |
| CGAGATCAGC GCAAAACACA TCTGTATTCC CAGCAGGATG TCCTCCTCCA CCTGTCGCAT | 300 |
| GGACTGGCTT GGAAAGACCG TCCACCTCGC CGGTCAAAAT GAAATGCTTG TCCGGAATAT | 360 |
| TCTCCAGTTT CGCAACACAA GGGTTCCCCC GTGCTCGTCC GGACTTCCTN GTTCCTCAAT | 420 |
| CCCNCCTCAA CCTGCTCGGN TTTCGGCGGG GAAGGTNCCA NCGGGCTTAA TGTCAC | 476 |

(2) INFORMATION FOR SEQ ID NO:155:

(i) SEQUENCE CHARACTERISTICS:
        (A) LENGTH: 644 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1059RP (xi) SEQUENCE DESCRIPTION: SEQ ID NO:155:

| | |
|---|---|
| GATCTGTTAC GCTGCAGCGC GAAACCTCCA ATGCTCTGGG CCAAGGTTGG CGGCTGGGAT | 60 |
| TCTTGGGCTC ACTGCATGCT TCGGTTTTCA AGGAACGACT GGAGAATGAA TACGGCTCGA | 120 |
| AACTCATTAT CACACAACCC ACTGTTCCAT ATGTCGTGGA GTACTCCGAT GGGACCCAGA | 180 |
| TAACAGTAAC AAATCCAGAT GACTTTCCTG ACCTGACACT TCGGCGAACC AAGATAAAGA | 240 |
| ATTTCCAGGA GCCATATGTA GAAGCTATAA TGACTCTTCC ACAGGATTAT CTCGGAAGGG | 300 |
| TTATCACTCT CTGCGACGAC AACCGTGGCA TACAGAAAGA GATAACGTAC ATTAACACCA | 360 |
| CGGGGCAAGT GATGCTGAAA TATGATATCC CATTGGCACA TCTAGTAGAC GACTTTTTTG | 420 |
| GTAAGCTCAA GTCTGTCACG CATGGTTATG CTTCCCTAGA CTACGANGAT GCAGGCTATA | 480 |
| AGCCGTCTGA CATTGTCAAG ATGGAGTTGC TTGTAAATGG AAAAGGTGTG GATGCACTTG | 540 |
| CACAAGTGAT GCATCGCTCC CAAACCGAAC GARTGGCCAA AGAATGGGTT ANGAAGTTCA | 600 |
| AGCAATATGT CAAATCCCAG TTATACGAAG TGGTTATCCA GGCC | 644 |

(2) INFORMATION FOR SEQ ID NO:156:

(i) SEQUENCE CHARACTERISTICS:
        (A) LENGTH: 649 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1059UP (xi) SEQUENCE DESCRIPTION: SEQ ID NO:156:

| | |
|---|---|
| GATCGTGGCG GACGTGTTTG TGCGCACCGC GGACGTGCTG CTGAAGATGT CGCGGTACGA | 60 |
| RGAAGCCAAG GCGGCGGCGG ARCGCGGCCT GAGCCTGGAG CCGGACCACA TGAAGCTGAA | 120 |
| GGCGCTGCAC CTGGAGTCTG TGCGCAAGTT GGCCGACTAT AACGGCGACA TCTAGTCCGC | 180 |
| GCGCGCGGCC CGCGCGGGCA CCACGGGTAT ATATACACAG CCGGTCTCCG CGCGCCATGC | 240 |
| CGCCCGCCGG GACCGCAGAC ACAGGCCCCG ATCTTGGCGC GCGGCGGGCG ATGAGCTGGT | 300 |
| GCAACCCTCT TGGCCCGTAC CCTGCTAAGG AGGGTAATCT CCCACCTCAG TACTATAAAA | 360 |
| AATTTTTAAG TTAGCCACTT TCGAGTTACA ACTCCCCGCC TGTCGGGTAA CGGATCTCAA | 420 |

```
CTTGTGAAGC CCCTAACGCT GCTCTACTCC TTTTGCGCTA AGGCAATATC CCGCCATGTC         480

TTCGTCGGAT ATCAATGTCA CGGTTGATTC GTTTATTGAT AGGTTGAAGC GGAAGCAGAT         540

TACTGGCACG TACAATGTGT CGCTGGAGAC GTTACAAATT CTGATGCGTT ACGTATCTGC         600

CATCCGGTGG TCGACGAAGG ACGARCTCAT TGAACAGATC CGTCTACTC                     649

(2) INFORMATION FOR SEQ ID NO:157:

(i) SEQUENCE CHARACTERISTICS:
        (A) LENGTH: 641 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1060RP (xi) SEQUENCE DESCRIPTION: SEQ ID NO:157:

GATCTGCTCA TACTGAGCGG CCAACTGGTC GTACTCCGTA TGCAAAACAT CTGTGGTTTC          60

CTGGAAGTGC GCCACCTTGA GCGATATCTC ATTAAACTTG GTAACCAGCT CTCCCAACTG         120

ATGATTGACT GCACTGGTTT CCGTCAGCAG GTCCTCCAGT TCGCCAGTTC TGGTGTCCAC         180

TTCCGCCACG TATCCGCTGT ACAATGTATA CTCGTCGTTC GCAGACCCCA GARCAGAAGC         240

TCGCCGCCAC TCTGGCGCCA GCAGCTCAAT TACCTGAGGT TCAATCTCTG TTTCAACCGT         300

TGCCAACAGA GTGTCTACTT TTTGGCGTAA CGAACTATCC CCAAAAAGCG GAGGCAGCTC         360

ATCGTGAGAR GARGCACCGG GATTTGCCGC TACATCCTGT ATGACTGART TCTTCCGGCT         420

CCTAAGCATG GTGCAGTTGC TGCCTCAACG GCTTTCTTCC TGGTGCARGT CTGCAGTGGT         480

TCGTGCTTAT GCGCAAGCAG AATACCATGT TGAGCCGGCG AAATCTCATC ACGTGATCAT         540

CATCTTGCAA CGGCTCGGAR GACRCTGATG CACTGTTCCA TAGGCTTAGG GCGCAATTAT         600

ACGCTAGCTA GTTATATTGA TAATATGTAC ATGATGCCTT C                            641

(2) INFORMATION FOR SEQ ID NO:158:

(i) SEQUENCE CHARACTERISTICS:
        (A) LENGTH: 649 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1060UP (xi) SEQUENCE DESCRIPTION: SEQ ID NO:158:

GATCTTGCCG TCCTTCTTGT CCAGCTGTAG GTCCGGATGA GGGTACGCCT CGCTCAGGTA          60

CTCCAGCCGC AGCTCGCCGC TCTCCATGGA CGCCTCCAGG ATCGAAGGCG CCGGCACAGC         120

CTCGGAGGGG AGGGGCGGCT GCAGGAGGGG CATCTCCTGT CGCTCCTGGT GCATCTGCAG         180

CGCCGCAGCG CTCGGCTCCA GCGCCGGGTC GAAGTACTTC ACATTCGTCA GGCCCGACTT         240

GTACAGATTC AGGATGCAGC CCTTGAGCTG CGCACGGTGC AACCGGTACG CAGTCGCGAC         300

ATACTGGTAC CCGCTCGTCC CCCCTCCCGT GAAGTGCGGC CGCTCCGATC CGATCGAAGA         360

CAGTGACGCT GTTGGCTGGT GGCTGTATCG CCCCTCGCGC GCCGGCGCTG CGCCCTGCGC         420

CTTGTTCACC CACCCGAGCC GAAACACAGT CCCGTCGTAC GTCTCCCCGT TCAGCCCGCC         480
```

```
TCCACGTCGC ACCGGCGARC CCGCCGGCTG CGARCAAGGC GACACCTGCT CCTCGCAGCG      540

CGCACCCGCC TTCATGTCCT CACATGTCAG CGTCCGCTTG TGCGCTTGCC CCGTCNGCAC      600

CTGTTAACTG CATCCGCGTC TGTTGGCTGC TGCTGCTTGC TGCTTGCTT                  649
```

(2) INFORMATION FOR SEQ ID NO:159:

(i) SEQUENCE CHARACTERISTICS:
        (A) LENGTH: 570 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1061RP (xi) SEQUENCE DESCRIPTION: SEQ ID NO:159:

```
GATCTGCTTT TGTAAGTATT CATCAGCTAA ATACCGTAAA GCTGGTTTGA ACGGAGGTCC       60

TGCCTTGTGC TCATATATTA TAGAAGTATC AATGACGAGG GGATGCCGCA TTTTCAAGAC      120

GTTCAAGTCG GCCTGCAATG AATGGCCGAT AAGCACATCT GTTGCGCTTA TCATCCGCAA      180

GAGATCCTGT TGGACGTCTT GCAAAGTCGT GGTCACCCCG ACCAACTTCT CCTCTGTAAT      240

ACCGCTGTAC TTCGTCAAGT AGTCCACAAT GGGCTCATCT GGCTTGACAA ACTTGTCATA      300

AACTAAGTTA CAATCAAAAT CGACGACGCT CACACGCGTC AACACGTATC CGTTTTTAGA      360

AAGGCACATC TCACAGTCGA TGGCAAACGT GTGAGAACCG TCGTGTTGGA AACTGACAGT      420

GTCCACCCAC CCACTGCACT TCTCCTTATT CTGATACTTT AGCAACAAAG CCTTTTGGGT      480

ACTCCTCCGA TAAGCCAGGT GTGTTTAGAT GGATGGGGTA CTCATTATGC AATAAGTCAA      540

CAACGGGCAT AGCAAATCAA GCAAGTGATT                                       570
```

(2) INFORMATION FOR SEQ ID NO:160:

(i) SEQUENCE CHARACTERISTICS:
        (A) LENGTH: 522 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1062RP (xi) SEQUENCE DESCRIPTION: SEQ ID NO:160:

```
GATCTCGGTG ACGTGGCGCT GGTATGGCTT CATCCAGTCG CCGTTCAACA AGAAGTTTCT       60

GTTAACGTCG AAGTTACAGC TGGTGAAGGA ATCAACCTCT GCGCCCACGG CCTTGATCAC      120

CTCTGGTGTG TTCAAATACT CCTCACTGTA CTTCATGTCA TCGTAGCAGA GCTGGCCCTC      180

ACACTCCTTG CGAACGTCGT AGACGTTCTT ACCAGTTCTC TGGAACGGCG TCAACTGGTT      240

GCCATTACAG TACAGAGAGG CTGGAACACA CGACCACACG TTCTGCAGGG TGTAGCATGT      300

GCGGATCAAA CGCAAGCACC GTGGCAAGGT CTCGTTCATT GCCGAGCATT GCTCTGGGCC      360

AAGAATGGCG GGTTCGCCGC CACCACCGCA GGCCATACGC TCGTAGTAGG GGTACTGTGT      420

CAATGGGTCT GTCAACCCGT TCCCAATTAG CACAGAGCTC AACTTAAACG AGCGCTCCTC      480

GCCTGGGTGC GACAAGATCT CGGCAGCAAT AGCAGGAATG TG                         522
```

(2) INFORMATION FOR SEQ ID NO:161:

(i) SEQUENCE CHARACTERISTICS:
        (A) LENGTH: 633 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1062UP (xi) SEQUENCE DESCRIPTION: SEQ ID NO:161:

GATCCTGGTT GTATCATAGA GAATGAACAT ATTGATAAAA AAATGCTACT GTGTACAGTA      60

ATGTCTGAAC ACCAACATGC TCTTTTCTTG TATTAAATGA TGGGATAACG AAGTCTTGGA     120

AGAATCCTGG GCGGAAATAG TAGACATGTT TAGAGAGATT TTTGTAATGG CTAGAGTCGG     180

TTTTGATGGC CGAAAAAGAA GTGCCAACAT TTAATTTCGA AGGTTTATCA GGTAGGTCAG     240

GGAATATACT ATCCTCGTAT AAACCCTTGA TTGTACTTGC AAGGAGCTCC AAGTCGTCTG     300

AGTTAGGCGA TGGTTCATCT TTAGTGTCAG CATCGACGAG GACCTCACAT GTGATTCCTG     360

AGTCAATTGC ATCTATGACC TCTCCATTCA CAATCAAGCC CATGGGTCCA ACCTCCTTGA     420

GAGCCGCCTT GATAAGCTCA GTACGCAGCT CGACCGAAGT ATCCAACGTA AGTGACTCCT     480

TTATTTCGAA TTGCAGATAT TCGGGCCGCA CTGCATGTAT AGATCCCCCA TGAATAAAGG     540

AGAATTGCTG CACAGTAGTA AACGCAAATC CCGCGTAATT AGTTGGTTGG CTTCTTAGGA     600

AGTCAGTGAA CCGATTATTT GCGTCCTGAT CCT                                  633

(2) INFORMATION FOR SEQ ID NO:162:

(i) SEQUENCE CHARACTERISTICS:
        (A) LENGTH: 505 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1063RP (xi) SEQUENCE DESCRIPTION: SEQ ID NO:162:

GATCGACTTG ACCGTCACCC GGTACTGGTC GTACTTGTCG ATGAACTGGT CCTGTAGTTC      60

CCCCAGTTCG TAGATGAGCA CGCCCAGTTT GTCGGTCACG TCGGACACAT CGTCGTCGTT     120

GTCCATGCCC CACATCGACA GCTGCCGCGC AGCGGCGCGC CGCTCATTGG CCACCACTTC     180

CAGCGCACGT AGCACCCCCT TTTCCGTCTT CACGAACGAA GACAGCTTCC GTGCCAACTC     240

GGGGCCAAAG TTTCCCGCTG CATTCTTGCG GAACGAGGAA GCAATCCCGG CACGCCCAAA     300

GAACTTGGAA CGTGTGGAAG AGGGTGGGGG AGGGGGTGAC TGGAGGTCTG ACGCAGTAGG     360

CGCCTTCTGG TTTCTCAAAG AGTATGTTCT GTGCATATTC TCGTGCTTAG ACTGGTCTGG     420

CAGTCGGTAT TTGTAGGTCC GATAAGATTC TCAGACGACA GCAAGTAAAG TACAACGGTG     480

GTCGGTGCCC CTCCAACGTC TTTTT                                          505

(2) INFORMATION FOR SEQ ID NO:163:

(i) SEQUENCE CHARACTERISTICS:
        (A) LENGTH: 631 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
              (A) ORGANISM: PAG1063UP (xi) SEQUENCE DESCRIPTION: SEQ ID NO:163:

GATCTTAATA GCAATAGTCG ACTACAGGAA ACACAAGCTT TCATAATGTC GAAATCTTTA      60

TCATGGGATA CACTAGACTA TACTCTACAA CCATGGATTC GTACTGCTGT TGATGCCATG     120

GGTTATGAGA CCATGACACC TGTACAGGCA TCGACGATCC CGCTATTTGC CAGAAACAAA     180

GATGTGGTTG TAGAATCTGT GACCGGTTCG GGGAAGACCG TGGCATTTGT CATACCTGTA     240

TTGGAGAGAG TGATACAGGA TGATGCCAAT AGTTCAAAGC TCAAAAAAGG CCACTTCCAC     300

ACCATAATAA TCTCCCCTAC GCGGGAGCTT GCATCACAGA TACAGGGCGT GATTGAAGCG     360

TTTCTGACAT ACTATCCAGA TGGAGAATAT CCTATAAAAT CACAGTTGCT TATCGGTAGC     420

AATACCAGTA GTGTCAGAGA TGATGTTGCA GCGTTTTTGG AACATAGACC GCAAATTTTA     480

GTTGGTACGC CTGGAAGGCT ATTAGACTTT CTTAAGATGC CAAACATCAA GACGTCTTCA     540

TGTGGCGCAG CTATTCTTGA TGAGGCCGAC AAGTATTGGA TATGAATTTG AGAAGGATGT     600

CCAGACAATA CTGGAGATGC TACCAAGCCA A                                   631

(2) INFORMATION FOR SEQ ID NO:164:

(i) SEQUENCE CHARACTERISTICS:
              (A) LENGTH: 626 base pairs
              (B) TYPE: nucleic acid
              (C) STRANDEDNESS: single
              (D) TOPOLOGY: linear (ii) MOLECULE TYPE: DNA (genomic)

(vi) ORIGINAL SOURCE:
              (A) ORGANISM: PAG0164I1

(xi) SEQUENCE DESCRIPTION: SEQ ID NO:164:

GCAGGAANTG GGTAGCCAAG AACCCGGCAA GACCTTCCCG AGCTACAACC GCCTCATCTC      60

GCAGGTGTTT GGCATCTGCG TCAGCATGGC CGGCTGTATC GGGTACGGCT GGGGAATTCA     120

ATTTCACTAT CACATCGCTA TCGTGCTATT CTTTTCTTTC CTAATGGCGT TGGGTATGAC     180

CTGGTGCTCT AACTCCACCA TGACCTTCCT TACGGAGTCC AACCCAAAAA GAGCTGCCGG     240

TACCATTGCC GTAAGCAACA GCTTCCGCAA TATCGCTGCC GCCATCAGCT CCGCCATTAT     300

TTTCAAACTA TGCAACGCCA TGGGCGTTGG ATGGTGTNTT ACAGGCTTGG GTCTAATCGA     360

CTTGCTATCC ATGTTGAGCG TCTATTACTT GATCCGTAAT GGGCGCGAGA TTACAAGGAT     420

AGCTGCTGAG CTATGATATC ATAACACATC CGCATTTTTA CGGATTTAGA TAACCAAAAC     480

AGCATANTTA GCATGTTTAG AATCTATCAG AAGAACCTCC CTTGTTCCTT TAATGATTAA     540

TTTGAACAGT CATTGATTCC GTCTTTCGAC CAAGAAGTTA GCACGTGATA TCCGCTGACG     600

CCGAAACGGC GTGCCTTGTC TTTCAC                                         626

(2) INFORMATION FOR SEQ ID NO:165:

(i) SEQUENCE CHARACTERISTICS:
              (A) LENGTH: 394 base pairs
              (B) TYPE: nucleic acid
              (C) STRANDEDNESS: single
              (D) TOPOLOGY: linear (ii) MOLECULE TYPE: DNA (genomic)

(vi) ORIGINAL SOURCE:
              (A) ORGANISM: PAG1064I2

(xi) SEQUENCE DESCRIPTION: SEQ ID NO:165:

| | | | | | |
|---|---|---|---|---|---|
| AAAAATCATT | TTTATCACCA | CTCAAGATGC | AGTCTGATTG | AAGTGTAAAG | CTGCAGTAGA | 60 |
| AGAGACAAGT | AAGCCATCAT | GAAGGTATGT | TATAGGTGCT | AAGTTCCCGA | TACNAGCACA | 120 |
| GTGGGCATGC | TAGGGCTGCA | GAGACAGGGC | ATGGGCGTGT | TACGATAGCC | GGAGACTCCG | 180 |
| ATTGGCGGGC | TAGCGGGAGG | TTAGCGCGGC | GTTGAAACGA | TAATGGGTGC | CAGGACGCGG | 240 |
| GCCACGGCGG | CACTGATGCT | TGTATTGTTT | GGCATGAATC | TGATACTAAC | ATTCCTGTAG | 300 |
| TTGAACATTT | CTTACCCAGT | TAATGGTACG | CNAAAGACCA | TTGAGGTCGA | TGACGAACAC | 360 |
| CGTGTCCGTG | TCTTCTACGA | CAAGAGAATT | GGCC | | | 394 |

(2) INFORMATION FOR SEQ ID NO:166:

(i) SEQUENCE CHARACTERISTICS:
        (A) LENGTH: 559 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1064RP (xi) SEQUENCE DESCRIPTION: SEQ ID NO:166:

| | | | | | |
|---|---|---|---|---|---|
| TAGTGGATCC | AGCATCCCGT | CTCGACCAGT | CCTGAGTTCC | GCCGGCTCTA | TCCTAGACCG | 60 |
| CCAAAGCCCA | GCTTGAAGAC | GTACTGGGAG | ATCGTGAAGG | AACCAAACCT | CACTATATGT | 120 |
| TCCCTGAGCA | CAGCGCTAAT | GTTCGCCACC | TACTATGGGT | TCAGCGTCAC | GTTCGCCCAC | 180 |
| TACTTGAAAC | TTGACTATGG | CTTCAGTAAC | CTTGCGATCG | GCGCGTGCTA | TGCCTGTCCA | 240 |
| GGCGTGGCCC | TAATGATGGG | CTCCCTCTTG | GGCGGTCACA | TTTCCGACCG | CTTCCGCAGG | 300 |
| AAGTGGGTAG | CCAAGAACCC | CGGNAAGACC | TTCCCGAGCT | ACAACCGCCT | CATCTCGCAG | 360 |
| GTGTTTGGCA | TCTGCGTCAG | CATGGCCGGC | TGTATCGGGT | ACGGCTGGGG | AATTCAATTT | 420 |
| CACTATCACA | TCGCTATCGC | GCTATTCTTT | TCTTTCCTAA | TGGCGTTGGG | TATGACCTGG | 480 |
| TGCTCTAACT | CCACCATGAC | CTTCCTTACG | GAGTCCAACC | CAAAAGAGC | TGCCGGTACC | 540 |
| ATTGCGTAAG | CAACAGCTT | | | | | 559 |

(2) INFORMATION FOR SEQ ID NO:167:

(i) SEQUENCE CHARACTERISTICS:
        (A) LENGTH: 611 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1064UP (xi) SEQUENCE DESCRIPTION: SEQ ID NO:167:

| | | | | | |
|---|---|---|---|---|---|
| GATCTGTTCT | CGCCCGCCTA | TGGGCCCTGC | CTGCGGGCAG | AGGGAGATCG | TCCTGGTCGG | 60 |
| CCTAGGCTAG | GCACGGCCCT | AGGCGGAGCT | TGTCCTGCGG | AGGCGCGGCC | GGCTGAGCCC | 120 |
| CGCTGCGCAG | GCGCGCAGCC | CGTGAGACGG | TAGCGGCCCG | CCTAATGCCT | CCTACGCAGC | 180 |
| GACCGCGCAG | CGGACCTGCA | CGTTAGTAAA | AAATCATTTT | TATCACCACT | CAAGATGCAG | 240 |
| TCTGATTGAA | GTGTAAAGCT | GCAGTAGAAG | AGACAAGTAA | GCCATCATGA | AGGTATTTTA | 300 |

```
TAGGTGCTAA GTTCCCGATA CAAAGCACAG GTGGGCATTC TAGGGCTGCA GAGACAGGGC      360

ATGGGCGTTT TACGGATAGC CCGGAGACTC CCCATTGGGC GGGCTTAGCG GGAGGGTTAG      420

CGCGGNGTTT GGAAACGAAT AATGGGNTGC CANGACGCGG GCCACGGNGG GACTGATGCT      480

TGTTTTTGTT TGGGAATNAA TCTTNATACT AACAATCCCN GTNGGNNGGA CAATTCTTAC      540

CCCNGTTAAT NGGTACGCAA AAGACCATGN AGGTCGGNTG ANGACAACCN NNTCCCNNNT      600

TTCTTNCGAN A                                                          611
```

(2) INFORMATION FOR SEQ ID NO:168:

(i) SEQUENCE CHARACTERISTICS:
        (A) LENGTH: 615 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1065RP (xi) SEQUENCE DESCRIPTION: SEQ ID NO:168:

```
GATCTGTAGT TTCGCAGTCC CTGATGCGGT CCGCCAGAGC AGGCAGCGCG GGCCAGGGTC       60

TGCGCAAGGC AGGCGTTGTG TCACCGCGGA GCCACTCTCT GGGCAGGCAG TTCCACGCCT      120

CCTGAACGAG CGCGGGCATG ATGGGGCCCA GAATGCTGCG ATAGGCATCC AGAATGTGGA      180

ACAGGGTCGT CTTTATGGCC AGACGCCTCT TATTATGTGG GGGTTCCATG TAAAGCGTGT      240

CCTTCGAAGC ATCAAAGTAG AGGGACAGGT CGTTGCTCAT GTGGTACAGA ACAAAGACTG      300

ATGACATTGG AGTAGGTCTG GGATTCCGCA CAGACCCTGA CACTTGGGGG GCAAAATTCT      360

TTGTCTTGTC GAGGGNTTTT CCCNTCANTC CCCNGGCAGG TGGGGCAGN CTTCCCCNGG      420

GCAAAAAAGG CTNTTCCCCA CCNAGATNAA CCCCTGGGAA ANCCCGAAGG TGNCANNAAT      480

TNAGNGGAAG TNNCCTNACC NCTCCACCNA ATCGGAAAAA TTGGGGANNA ANGCCCCANC      540

CCAACNCCCA AANTTTTCTT GGAAAAAAAA AGGGGNGCCC CACCCNGGNG GANTNANTTT      600

TNTCCCCCCC NATCC                                                      615
```

(2) INFORMATION FOR SEQ ID NO:169:

(i) SEQUENCE CHARACTERISTICS:
        (A) LENGTH: 604 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1065UP (xi) SEQUENCE DESCRIPTION: SEQ ID NO:169:

```
GATCTCTTCC CTTCGATCAT CCCTCAGTTG GGTTCTGAGT CCATCGATGC GTTGACGCAG       60

TTGGCCACAC AGTTGCAGAA CGCACAGGCT GCAGCTCCAG CAACCGAGGG CCATGAGGCA      120

GGCGAGAAGA AGGACAACGA CATCCCAGAG TTGATTGAGG GCCAGTCTTT CGACGCGGAT      180

GTTGAATAAG TGCGCTGTGC GAGGACTGTG TTCTCGCCGC CCATCTCAGA ATTTGTCTAT      240

TTCTGCAGGG AATATACATA TATTGAGTGC ACATATGGAT ATTATGTATA TATATGTACA      300

TACACTATAC CCGCCCCGTC TTAGTCGGAC CACATAAACC TACGGGTCGG CGCCCCTATA      360

TCGTTTTACA ATAAACGCGC CGNNCTTGCG GGNNTNCTTC GANAATCTCN TTGGGGGGCC      420
```

```
CNCCNNCCNT TANNAGGTNC TTCTNCCGGG TNGGAAGTNA AAAAGCNNNN GTTCNGTTGN      480

NAGNGTCCCC GGGGGAAANC CNNCCCCGNG GNGGATTTTC NCCCAAACCG NAGAANACNN      540

CNTTGCNCCA AGTTGCCCGT GGGAGAAAAA AANCCNATGN NGAAGNAAAA TTGCCCCCTG      600

CCCN                                                                   604

(2) INFORMATION FOR SEQ ID NO:170:

(i) SEQUENCE CHARACTERISTICS:
        (A) LENGTH: 653 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1066RP (xi) SEQUENCE DESCRIPTION: SEQ ID NO:170:

GATCCTGAGG CCTCACTAAG CCATTCAATC GGTACTAGCG ACGGGCGGTG TGTACAAAGG       60

GCAGGGACGT AATCAACGCA AGCTGATGAC TTGCGCTTAC TAGGAATTCC TCGTTGAAGA      120

GCAATAATTG CAATGCTCTA TCCCCAGCAC GACGGAGTTT CACAAGATTA CCCAGACCTC      180

TCGGCCAAGG TTATACTCGC TGGCTCCGTC AGTGTAGCGC GCGTGCGGCC CAGAACGTCT      240

AAGGGCATCA CAGACCTGTT ATTGCCTCAA ACTTCCATCG GCTTGAAACC GATAGTCCCT      300

CTAAGAAGTG CGCAACCAGC AAATGCTAGC AGCACTATTT AGTAGGTTAA GGTCTCGTTC      360

GTTATCGCAA TTAAGCAGAC AAATCACTCC ACCAACTAAG AACGGCCATG CACCACCACC      420

CACAAAATCA AGAAAGAGCT CTCAATCTGT CAATCCTTAT TGTGTCTGGA CCTGGTGAGT      480

TTCCCCGTGT TGAGTCAAAT TAAGCCGCAG GCTCCACTCC TGGTGGTGCC CTTCCGTCAA      540

TTCCTTTAAG TTTCAGCCTT GCGAACATAC TCCCCCAGA ACCCAAAGAC TTTGATTTCT       600

CGTAAGGTGC CGAGTGGGTC ATAAGAAAAC ACCACCCGAT CCCTAATCGG CAT            653

(2) INFORMATION FOR SEQ ID NO:171:

(i) SEQUENCE CHARACTERISTICS:
        (A) LENGTH: 669 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1066UP (xi) SEQUENCE DESCRIPTION: SEQ ID NO:171:

GATCTGGAGG ACCTATATAT ACCATTTCGC TGCACCTTTC TTTTTGTGCC TGATGTTTTA       60

TAAGTAGACG ATCTCTGATT ATTATCGCGA GGTCGTTAAA GTCCCATGCG AGCACACTGT      120

TTGCAATGAT GGCCATCGCC CACCAGACCA GTCAGAAGTA GATATCTGAA TTGCATGTGA      180

GCCATACTAG GGTGACCTGT GTTGGCGGCC AGCTTGCAGG AGGAGGAAAA AAAAAAGATT      240

GCAGCACCTG AGTTTCGCGT ATGGTCACCC ACTACACTAC TCGGTCAGGC TCTTACCAGC      300

TTAACTACAG TTGATCGGAC GGGAAACGGT GCTTTCTGGT AGATATGGCC GCAACCGAAA      360

TATATAGCCT AGAGCAGACA TGATATCAGA TGGTGGATGC ACGTGAGGGC GTAGACATGT      420

AATAACGATA TCGAGTACAT TTGGTGCCAG ATGGCTGGGG CTATGGCGCA GATGTGTGGT      480
```

```
AATTGGCACA TCGGGGTAAG TCACGGGGTA AGAAGAGTTT GTCGGCATTG GAGTGCCATT      540

CCGTACCGAA TGTCACGTAG TGATCTGAAA AGTGATATGC TATGTGAAGT GCAAAGTATG      600

GGAAGTCTGG CTGGGGTTAR GAAGAAGATG TCRACTGCAA GGCAACGGAA CGTCCGARCA      660

ATGCTTTGA                                                              669
```

(2) INFORMATION FOR SEQ ID NO:172:

(i) SEQUENCE CHARACTERISTICS:
        (A) LENGTH: 652 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1067RP (xi) SEQUENCE DESCRIPTION: SEQ ID NO:172:

```
GATCCCCTAA CTTTCGTTCT TGATTAATGA AAACGTCCTT GGCAAATGCT TTCGCAGTAG       60

TTAGTCTTCA ATAAATCCAA GAATTTCACC TCTGACAATT GAATACTGAT GCCCCCGACC      120

GTCCCTATTA ATCATTACGA TGGTCCTAGA ACCAACAAA ATAGAACCAA ACGTCCTATT       180

CCATTATTCC ATGCTAATAT ATTCGAGCTT GCGCCTGCTT TGAACACTCT AATTTTTTCA      240

AAGTAAAAGT CCTGGTTCGC CTAGAGTACA AGTACCCTAG GTTAGCCAGA AGGAAAGGTT      300

CGGTTGGATC CCGTACACGA AGAAAATCGG ACGGGCCAAC CAAACCCAAA GTTCAACTAC      360

GAGCTTTTTA ACTGCAACAA CTTTAATATA CGCTATTGGA GCTGGAATTA CCGCGGCTGC      420

TGGCACCAGA CTTGCCCTCC AATTGTTCCT CGTTAAGGTA TTTACATTGT ACTCATTCCA      480

ATTACAAGAC CCGTATGGGC CCTGTATCGT TATTTATTGT CACTACCTCC CTGAATTAGG      540

ATTGGGTAAT TTGCGCGCCT GCTGCCTTCC TTGGATGTGG TAGCCGTTTC TCAGGCTCCC      600

TCTCCGGAAT CGAACCTTAT TCCCCGTTAC CCGTTGAAAC CATGGTAGGC CA             652
```

(2) INFORMATION FOR SEQ ID NO:173:

(i) SEQUENCE CHARACTERISTICS:
        (A) LENGTH: 669 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1067UP (xi) SEQUENCE DESCRIPTION: SEQ ID NO:173:

```
GATCGGGTAG TGAGGGCCTT GGTCAGACGC GGCAAGTGTG CTTGTGGTCT GTCCTCGGGG       60

GCTTGCTCCT GGGGACGGAC TGCTTGCGTG CTCTGTCGTA GACGGCCTTG GTAGACCATC      120

TCTGGTCGTC GCTTGCTACA ATTAACGATC AACTTAGAAC TGGTACGGAC AAGGGGAATC      180

TGACTGTCTA ATTAAAACAT AGCATTGCGA TGGTCAGAAA GTGATGTTGA CGCAATGTGA      240

TTTCTGCCCA GTGCTCTGAA TGTCAAAGTG AAGAAATTCA ACCAAGCGCG GGTAAACGGC      300

GGGAGTAACT ATGACTCTCT TAAGGTAGCC AAATGCCTCG TCATCTAATT AGTGACGCGC      360

ATGAATGGAT TAACGAGATT CCCACTGTCC CTATCTACTA TCTAGCGAAA CCACAGCCAA      420

GGGAACGGGC TTGGCAGAAT CAGCGGGGAA AGAAGACCTG TTGAGCTTGA CTCTAGTTTG      480

ACATTGTGAA GAGACATAGA AGGTGTAGAA TAAGTGGGAG CTTCGGCGCC AGTGAAATAC      540
```

```
CACTACCTTT ATAGTTTCTT TACTTATTCA ATTAAGCGGA GCTGGAATTC ATTTTCCACC       600

TTCTAGCATT TAAAGTCCTA TACGGGCTGA TCCGGGTTGA ARACATTGTC AGGTGGGGAG       660

TTTGGCTGG                                                               669
```

(2) INFORMATION FOR SEQ ID NO:174:

(i) SEQUENCE CHARACTERISTICS:
        (A) LENGTH: 596 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1068RP (xi) SEQUENCE DESCRIPTION: SEQ ID NO:174:

```
GATCCACCNC TNNCCCATTC AATCGGTACN ACTCGACGGG CGGNNTGTNN AANCGGNCCG        60

GACCTAATCA ACGANAGCTG ATGACTAGAC GCTTACTAGG AATNCGTCCT TCAAGANCAA       120

TGATTTGCTC TGTNTCTATC CCCAGTCATT ACNGNCTANC AGACATGATC CTCCATGATC       180

TGTCGGTGCT GTGTGGTATN CCGCAGGACN CCGNCNCTGT ACCGCGCGTG CGGCCCAGAA       240

NNTCTANGGG CCTCCCAGAC NTGTTATNGC CTCTAACTTN CATCGGNTCN ANACCGANAN       300

TCCTNCTAAG ANGTGCGCNA CCAGCANNTG CNNCCNGCNC TATTTACTAG GTTAAGGTCT       360

CGTTCGTTAT CNCCNTTANT CAGACAAATC ACTCCANCNN CTAANAACGG CNNTGCCCCN       420

NCNNCCNGAA NNTNNNGAAA CANCTCTCAT CTGTCAATCC TTATCGTGTC TGGACCCGCT       480

GAGTTTCCCG TGTTGAATCT AANTAANCCG CAGGCTCNAC TCCTNNTGGT GCCTTCCGTC       540

NATTCCTTTA AGTTTCAACC CTGCGACATA NTCCCCCAGA ACTCANAGAC TNTGAT          596
```

(2) INFORMATION FOR SEQ ID NO:175:

(i) SEQUENCE CHARACTERISTICS:
        (A) LENGTH: 641 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1068UP (xi) SEQUENCE DESCRIPTION: SEQ ID NO:175:

```
GATCTGGAGG ACCTATATAT ACCATTTCGC TGCACCTTTC TTTTTGTGCC TGATGTTTTA        60

TAAGTAGACG ATCTCTGATT ATTATCGCGA GGTCGTTAAA GTCCCATGCG AGCACACTGT       120

TTGCAATGAT GGCCATCGCC CACCAGACCA GTCAGAAGTA GATATCTGAA TTGCATGTGA       180

GCCATACTAG GGTGACCTGT GTTGGCGGCC AGCTTGCAGG AGGAGGAAAA AAAAAAGATT       240

GCAGCACCTG AGTTTCGCGT ATGGTCACCC ACTACACTAC TCGGTCAGGC TCTTACCAGC       300

TTAACTACAG TTGATCGGAC GGGAAACGGT GCTTTCTGGT AGATATGGCC GCAACCGAAA       360

TATATAGCCT AGAGCAGACA TGATATCAGA TGGTGGATGC ACGTGAGGGC GTAGACATGT       420

AATAACGATA TCGAGTACAT TTGGTGCCAG ATGGCTGGGG CTATGCGCA GATGTGTGGT       480

AGTTGGCACA TCGGGGTAAG TCACGGGGTA RGAAGARGTT TGTCGGCATT GGAGTGCCAT       540

TCCGTACCGA ATGTCACGTA GTGATCTGAA AAGTGATATG CTATGTGAAG TGCAAAGTAT       600
```

```
GGGAAGTCTG GCTGGGGTTA AGAAGARGAT GTCACTGCAA G                641
```

(2) INFORMATION FOR SEQ ID NO:176:

(i) SEQUENCE CHARACTERISTICS:
        (A) LENGTH: 654 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1069RP (xi) SEQUENCE DESCRIPTION: SEQ ID NO:176:

```
GATCGACCCC GGTCCCGCTC GCATCAGCGA GCTGCCCGTG CCGATCAGCA GCCCGGTCCC     60
TAGCGACCCG CCGATGGCTA TCATCGACAC ATGACGTGCC TGCAGGTCCT TCTTGAGCCG    120
GATGCCCTCG TGCTTGCCAT CGTAGTTCCA GTCTACGGAC TGCGCCTCCT GGTCTGTGCT    180
GCTGTGGGTA TGCCGCAGAC CGCGGCCCTC ACCAGCGGCG GCCAGCTTGG GGCCTTTCAA    240
CTCGTCCAGC GTGGACGCCT CTGATGCCTG TGCGAACTTC TCTTCCGCCA TAAGTGCGGA    300
GCTGTTATCT ATGCTACTCA AGCTCCCGCC GTATAGCCTT GCTATATATA CTTACGCTGC    360
GACGCCCTAT TCCGGACACA GCTATATATT GGCCCGCCGT CTCGCGCGCT GCTTGGGGAG    420
CCGACTGACC CCACCCTGAT AGTGCCGTTG CACTTCTGCT GGGCCGCCTC AGCCCGTTCA    480
GCGTCCGACT GTGACATCGG GCTGCGCGAG CGCGATTAAT CACCCGACTG GCTGCATGC     540
CGCACTAAAC CTCCCCTCGC GGCGCAGGGC GCCCTTATCG CCTCCGTGAT GACGTACGTA    600
TGTTTATCAA AGATCCGGAG AMCTGTTCCA GGCTCCTACG TTGCGATAAG AGGC          654
```

(2) INFORMATION FOR SEQ ID NO:177:

(i) SEQUENCE CHARACTERISTICS:
        (A) LENGTH: 708 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1069UP (xi) SEQUENCE DESCRIPTION: SEQ ID NO:177:

```
GATCTTTCTG CCCTTATCAG GGATGGCACC ACCGGTCTTC ACCTCGTTTG ACTTGTAGCC     60
ACAGTGCTCG CAGACCGTGG ACATGATGAT GACCTCTTTG AAGTGTGGGA TGTTGACCGG    120
CTTCATATGC GTGTCACATG GGTGAACACA TGATGGGCAC GTGGCAGTGA AGGTCTGCAC    180
CTCGTTGTGG AAGTTCTCGA TATCCGTAGC GTCAGATAAG AGACCGGCCT GTGCCGCTTG    240
CGATTTGTTG CGCTCGCGCT GCGACAGCTC CGCGCGCTTC TCTTGACGCC GTTGCTCCAA    300
TTGGTCGCGC GTAATGATGC CCACCTGGAC GTTTTGCTCA TCTGAACGCA GGTACTCGGT    360
TTTGGACCAT TTTGGCGCAG CTTCGCCTGG CTTGTATTCG ATCCAGGAAT TGCCAGCAGG    420
GTCGTCCAGC GTAAAAGTCA GCGGTAGAGT GCCCGGCTCG CACGACAGCG CAGCGCGGAC    480
CTTGGCAATG AACTGCGCAA TCTGATCGTA CAGGTTCTCG TCCACTTCCT TCCGCGCCGC    540
CTGGTCGGCG TCCAAGTCCT CGATCATCTC GGTCAGCAGG CCCTCCACAG TCGTCAGCTG    600
GCCGCGCTTG GGAAGAATCT CCAGGTCCAA TTCAACGAAG CGGGAAGCCG CAGTTTCGGC    660
CTTGATGACT GCCTGTCAAA ATCGGCCTTC TCCTCAACCT TCAGCTGA                 708
```

(2) INFORMATION FOR SEQ ID NO:178:

(i) SEQUENCE CHARACTERISTICS:
        (A) LENGTH: 703 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1070RP (xi) SEQUENCE DESCRIPTION: SEQ ID NO:178:

```
GATCCCGTAC ACGAAGAAAA TCGGACGGGC CAACCAAACC CAAAGTTCAA CTACGAGCTT        60

TTTAACTGCA ACAACTTTAA TATACGCTAT TGGAGCTGGA ATTACCGCGG CTGCTGGCAC       120

CAGACTTGCC CTCCAATTGT TCCTCGTTAA GGTATTTACA TTGTACTCAT TCCAATTACA       180

AGWCCCGTAT GGGCCCTGTA TCGTTATTTA TTGTCACTAC CTCCCTGAAT TAGGWTTGGG       240

TAATTTGCGC GCCTGCTGCC TTCCTTGGAT GTGGTAGCCG TTTCTCAGGC TCCCTCTCCG       300

GAATCGAACC CTTATTCCCC GTTACCCGTT GAAACCATGG TAGGCCACTA TCCTACCATC       360

GAAAGTTGAT AGGGCAGAAA TTTGAATGAA CCATCGCCAG CACAAGGCCA TGCGATTCGA       420

AAAGTTATTA TGAATCATCA AAGAGTCCGA AGACATTGAT TTTTTATCTA ATAAATACAT       480

CTCTTCCAAA AGGTCGAGAT TTTAAGCATG TATTAGCTCT AGAATTACCA CAGATATCCA       540

TGTAGTAAAG GAACTATCAA ATAAACGATA ACTGATTTAA TGAGCCATTC GCAGTTTCAC       600

TGTATAAATT GCTTATACTT AGACATGCAT GGCTTAATCT TTGAGACAAG CATATGACTA       660

CTGGCAGGAT CAACCAGATA ACTATCTTAA AGAACAACCC GAA                        703
```

(2) INFORMATION FOR SEQ ID NO:179:

(i) SEQUENCE CHARACTERISTICS:
        (A) LENGTH: 675 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1070UP (xi) SEQUENCE DESCRIPTION: SEQ ID NO:179:

```
GATCCTTTAG TTCCTCGGAG TTTGAGGCTA GAGGTGCCAG AAAAGTTACC ACAGGGATAA        60

CTGGCTTGTG GCAGTCAAGC GTTCATAGCG ACATTGCTTT TTGATTCTTC GATGTCGGCT       120

CTTCCTATCA TACCGAAGCA GAATTCGGTA AGCGTTGGAT TGTTCACCCA CTAATAGGGA       180

ACGTGAGCTG GGTTTAGACC GTCGTGAGAC AGGTTAGTTT TACCCTACTG ATGAATGTTA       240

TCGCAATAGT AATTGAACTT AGTACGAGAG GAACAGTTCA TTCGGATAAT TGGTTTTTGC       300

GGCTGTCCGA CCGGGCATTG CCGCGAAGCT ACCATCCGCT GGATTATGGC TGAACGCCTC       360

TAAGTCAGAA TCCATGCTAG AACGCGATGA TTCTTTTTCT CGCACATTAT AGATGGATAC       420

GAATAAGGTG CTTTTAGCAT CGCTGAACCA TAGCAGGCCG GCAACTGGTG TTCANACGGA       480

AAGGTCTGGG CGCGTGCCGG CGGATTGCAA TGTCATACTG CGCGAGAGTA AATCATTTGT       540

ACACGACTTA RATGTACAAC AGGGTATTGT AAGCAGTARA GTAGCCTTGT TGTTACGATC       600

TGCTGAGATT AAGCCTTCGT TGTCTGATTT GTTTTCTATT TGGAAGTCTG CAGGAGCAGG       660
```

(2) INFORMATION FOR SEQ ID NO:180:

(i) SEQUENCE CHARACTERISTICS:
    (A) LENGTH: 498 base pairs
    (B) TYPE: nucleic acid
    (C) STRANDEDNESS: single
    (D) TOPOLOGY: linear (ii) MOLECULE TYPE: DNA (genomic)

(vi) ORIGINAL SOURCE:
    (A) ORGANISM: PAG1071RP (xi) SEQUENCE DESCRIPTION: SEQ ID NO:180:

```
GATCTGNGGG GGAAACNCAG CATTCACCGT TGTGCAAAAA GATTTGACTG GTAACATCAC      60

CAAGCTTCGC AACAGACAAT TGTCGCACCC CGGTGAGTCT GCAACCCTGC AGGAGCTTGT     120

GATTGCAGAG CGTGCACAGG GCAGCAAGAC TGCTTCGGAA GGGCTGCTGT GGCTCACCAG     180

AGGCCTGCAA TTCACCGCGC AAGCTCTTAG AGAAACGCTA GACCATCCAG AGCTCGAATT     240

GTCTAAGACA TTCACAGATG CGTATTGGAA GACGTTGACG AAGCACCATG GTATGCTTGT     300

ACGTCCGGTT TTCAAAGCTG GCCATGAAAG CTTGCCCCTA CAGGAAGGAC TTTTTTGCAG     360

AAACTAGGCA GCGACCAAGA GAAGGTTGAC ACGCAACTTT AAGCAGTGGC TGGCTGCACT     420

TGAAAAGATC GTAGAGATTC TGCTTCAAAT CCCTTGGGGG AAACGTGCAA AGGATTTATG     480

AGTATTATTA TAGAAGCC                                                   498
```

(2) INFORMATION FOR SEQ ID NO:181:

(i) SEQUENCE CHARACTERISTICS:
    (A) LENGTH: 625 base pairs
    (B) TYPE: nucleic acid
    (C) STRANDEDNESS: single
    (D) TOPOLOGY: linear (ii) MOLECULE TYPE: DNA (genomic)

(vi) ORIGINAL SOURCE:
    (A) ORGANISM: PAG1071UP (xi) SEQUENCE DESCRIPTION: SEQ ID NO:181:

```
GATCGACAGC CTCGAAGAAG TAGCCTCCAC AGCTTCAAAC ACAGCGCACA GGTCTGCATA      60

CATCACGCTG GTGCTTGCTG CAGGCTTAAC CGGAGAACTT TGTGCGCGTG GCACGGCGCT     120

GGCAGACTGT GGCAGCACCC CCCCCGGCGC GGGCTTATCT GCAAGCTCGG GGAGGATGTT     180

CTTCACCTCG GCGTCCTGTT CATGGGCTGC CGGTGCCGCT AGGCACTCGG GAGACTCTAC     240

CTTCGATTTC TTGACCCTCG CTGTTGACGT CGCTCCATCT TGAGGCCTCT TCAGCGCAGC     300

GAAGAATCGG ACCAATGTGG CCTGCTTCTT TGGAGTAGAC ATTGGCCTGA AGTAAAACCC     360

TACTGACCTG CCAAATAGCT CCACTTTGGT CTCGCGACAG GAGCTTCCNA AGANTGACAT     420

TNNNTGTNGN NAAGGCCNNN NNNTNNCAAA GACGAANCTN NTATCAAGGN CCTNNTTNCC     480

CCAGNCNNNA NAAGNAANAA NNNNATTNNN GGNATTNNNN AAATTANGGT TNNNNNATNN     540

NCTTNGNAAA TTNNTNNGNN TTNNTNATTC CCNNNGGNTT TCNNNTTNCC NCNCNCCTNN     600

GGNTTTTTTN NANNNTNAAN NNNCC                                           625
```

(2) INFORMATION FOR SEQ ID NO:182:

(i) SEQUENCE CHARACTERISTICS:
    (A) LENGTH: 491 base pairs

CTTTGAAATA RAGTT  675

(B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1072RP (xi) SEQUENCE DESCRIPTION: SEQ ID NO:182:

```
GAGCAACTAT TATTAGGCGC CCCCCACCCC AGTCTGCAGC ATTCGAAAGC CTTCCTAGCC      60
TTTGTGCGAT GTCCCAAGGT ACAATTTTCT CGCAGNTGAA AATACGAAAG AAGCGCCAAG     120
AAGTGGCCTT CTTTGAATCC AACGCCGACG CCAATGATGT CGAGGCGGGC GAACATTTTA     180
TAACAGAGCT CGATAAGGGC GATAAGCGGC TCGGCCTGTT TTCTTCGATC GGCTTGATAT     240
GCAATAGAAT GCTCGGGACA GGTATCTTTG TCGGTCCCGC GAAGATCTTC CAGTCCGACT     300
GGCTCAGTAT ACTTTGCGCT AGGGTTATGG GTACTAGGAG CTTTAATTGC TCTAGCAGGT     360
CTTTATGTTT ACATGGAATT TGGTAACTGC AATACCGCCG AACGGTGGCG AGAAGAACTA     420
CCTTGAGTGC ATCTCCAATG AAACCGAACT TCTTCACTTA CAGTCAAGTG TACTCAGCAT     480
ATGATCATCT T                                                          491
```

(2) INFORMATION FOR SEQ ID NO:183:

(i) SEQUENCE CHARACTERISTICS:
        (A) LENGTH: 726 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1072UP (xi) SEQUENCE DESCRIPTION: SEQ ID NO:183:

```
GATCCGCAGC TTCGGCAAGC GCCGCTTCTC CTCCGTGTAC TCCTCGTCGT CGTCGTACTC      60
CGGCACCATC GACGCCTCCG GCTCCTCCTC ATCCGCCGTC GCGTCCTTCT CCTCGTCCAC     120
CGTCTCCGGC AGAAGAGAGT CGGCCTTCGC CCCCGTCTCG TCGTCGTCGC GCTCCAGCAG     180
AGCGCCCGGA AGCGGCTGCT CGTCCGGGAG CGGCCCGAGG TACGGGTACT TCACCGGACC     240
CATCTCCCGC TCAATCCGCG GGATCAACAC CTCCCGCACG TACCGGTCCA TGATCTGCGC     300
ATAGTGGTAA GATTACCTAA TTCATACGTG TAGATCATCC CATGCTTACC ATGTTGAACC     360
GTCACCATGT AAATTTCCAA TAATTCTCTA GTCTCTCATT TGTAGANATT AGNANCTTTC     420
CTTTATATTA ATNCTTTTAC TNAATAATTN ATNNANNTTT TNNTTTGANC ANTTCTCCAT     480
ATTGTATTAA ANTNATATAT AATATTATTN TCTACTAATC TAACAAATTA NNNTCTNTAT     540
TATATATTTA NNNANCATAT NATNATATTA AATTATTTAT AATNATNCTN TCCTCTTNTA     600
ATNTTTAAAT NNNANNTNTT TNTNCNTANN CTAATNNATT TTTNGATATT TTNTTTNNTA     660
NTNNNNTAAA AAATATNNNN TTTATCNANT ATCTTCCATT TATNAATCNN NTTTTTATCA     720
AACCCC                                                                726
```

(2) INFORMATION FOR SEQ ID NO:184:

(i) SEQUENCE CHARACTERISTICS:
        (A) LENGTH: 641 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
            (A) ORGANISM: PAG1073RP (xi) SEQUENCE DESCRIPTION: SEQ ID NO:184:

GATCAATTAA TAAATGGTTT AACTAATAAA GTTAATAATA AATCTATTAA TTATATAAAA      60

CTACCTGATT TTATTGAATC AAATAATATT TTCTTAATGA ATACTACTAA ATCATCATCT     120

ATTGAGTTTA TATTAAATTC ACCACCTCTT ATTCATTCAT TTAATACTCC TCTAATTCAA     180

TCTTAAAATA TTCTTAATTA TTAAATTATA TAATAAAAGT TAGTGGATAT AGTTTAATTG     240

GTAAAACATA TGTTTTAGGG ACATATATCT TCAGTTCAAA ACTGAATATC TACATATTAT     300

ATCATTAATA TAATAACTCT TTAATTAGAG TGGTACCACA AGAATGCTGA AAGCATTAGG     360

GGTGTGTACC TTAGCTCTCT AATTAAAGTT ATAAAATTAT CTTAACTAAT AAAAATAATT     420

AATTAAATAA ATAAATAATT AATTAAATTT AAAATGTTTA AAAAAAGAAA TAAATAATAT     480

GTTATATTTA AATAGATCAA AATTTCAACA ATTTCCATTT CATTTAGTAC TACCATCACC     540

ATGACCAATT GTTACATCAT TTAGTTTATT AGGTTTACTA TTAACTTTAG CTTTTACTAT     600

ACATGGTATT ATTGGTAATA TTTATCCTTT ATTATTATCT T                        641

(2) INFORMATION FOR SEQ ID NO:185:

(i) SEQUENCE CHARACTERISTICS:
            (A) LENGTH: 662 base pairs
            (B) TYPE: nucleic acid
            (C) STRANDEDNESS: single
            (D) TOPOLOGY: linear (ii) MOLECULE TYPE: DNA (genomic)

(vi) ORIGINAL SOURCE:
            (A) ORGANISM: PAG1073UP (xi) SEQUENCE DESCRIPTION: SEQ ID NO:185:

GATCTTAATT TAAAATTTTA ATTAACTATT TATAATTTAG AAATATATAA TCTAGAGATA      60

TATAATCTTA AAATCATAGG TAAAAATACA TAAGATAGTA AGAATAAAAT TAGTAAAATA     120

AATAGAAAAC CATAAGTTAA TTGATTCATA AAGAAAAATG GAATTATTTG TGGCATCTTA     180

ATTTTTATTA TTTAATTGAT TATTATCTAT TTAACATAAA ACATTTTAAA ATGTTATAAA     240

ATAAATAAGA AATTACTTAT AGAATATTTA TTAAATAGTA TTTAATTTAA TTTTAATATT     300

AAATATACCA TTTTTATTAA TAAATAGATT ATTAAGTTTA TTAATATTAA GTGATATATA     360

ATTTAATTTA TATAAATTAT TTAATTTACT TCATTGATAT ATATAATTAT TAAATGTACC     420

TTTCATAATA TTTATTTTTA TTAGTCTAGT AATATTTCTA TTTAATAGTC TACCCTTTAA     480

TTGGATATTA CTACCTACTA AATATTTACC TAATAATATA TTATTAAGAA TACTTAAATC     540

TAATAATTTA TTATCTAAAG TATATAAATT AATTAAATCN TTTTTTATTA TTATTTAAAT     600

TATTATTAAT TAGTAAATTA TATTTATTTA TTTTATTAAC ATAATTTTTT GNATAATAAT     660

AT                                                                   662

(2) INFORMATION FOR SEQ ID NO:186:

(i) SEQUENCE CHARACTERISTICS:
            (A) LENGTH: 615 base pairs
            (B) TYPE: nucleic acid
            (C) STRANDEDNESS: single
            (D) TOPOLOGY: linear (ii) MOLECULE TYPE: DNA (genomic)

(vi) ORIGINAL SOURCE:
            (A) ORGANISM: PAG1074RP (xi) SEQUENCE DESCRIPTION: SEQ ID NO:186:

| | | | | | |
|---|---|---|---|---|---|
| GATCTAAATA | TATATAATTT | AATTTATAAA | GATTAATATA | AACTTTTTTA | TTATAATATT | 60 |
| TAAGTATTAA | ATTATTTAAA | CTATTATTAT | CATTATTTAA | TAAATTAATT | ATTTGATTAT | 120 |
| TAATACTTAT | TATATAATTA | TTATATAATT | TACTTAATTC | ATCATTATTA | ATATTTATAT | 180 |
| AATTATAAAA | ATAATATTTA | ATATGAATAC | TATTTAGTCT | ATGTTCAAAT | TTTAAATTAG | 240 |
| TTATTAAAAT | ATTATTAGAT | ATTATTATTT | TCTTTAATAA | ATTATTAAAT | AGATTATCAA | 300 |
| TAATTAATAT | ATTATTTATT | AATTGTTTAT | TAAAATAATA | TATTTTATTA | TTATAAAGAT | 360 |
| TTAATTTATT | TAAATATTGT | AAATTATTAT | TTTTATTATA | ATATCTATTT | TTATAAATAT | 420 |
| TATGTTGATT | TATATTATTT | AACTTTTTAT | AAGAATTATT | ATTAAAATTA | ATTTTAACTT | 480 |
| TAATTTCTTA | TTATTAATTT | TTATATTATT | TAATAAATTA | TATTCATTTT | ATTTATTTAT | 540 |
| TTATTTAATT | AAATTAATTA | TTTAATTAAT | ATTTATCAT | TATTTAATTA | ATTAATAAAA | 600 |
| TATTATAAAG | AATGT | | | | | 615 |

(2) INFORMATION FOR SEQ ID NO:187:

(i) SEQUENCE CHARACTERISTICS:
            (A) LENGTH: 663 base pairs
            (B) TYPE: nucleic acid
            (C) STRANDEDNESS: single
            (D) TOPOLOGY: linear (ii) MOLECULE TYPE: DNA (genomic)

(vi) ORIGINAL SOURCE:
            (A) ORGANISM: PAG1074UP (xi) SEQUENCE DESCRIPTION: SEQ ID NO:187:

| | | | | | |
|---|---|---|---|---|---|
| GATCTTGATA | CTAGAGCTTA | TTTTACTTCA | GCTACTATAA | TTATTCTTAT | TCCTACTAGT | 60 |
| ATTAAAGTAT | TTAGTTGATT | ACTAACTATT | TATGGTGGTT | CATTAAGATT | ACTAACACCA | 120 |
| ATATTATATC | TATTATCATT | TTTATTTTTA | TTTACTGTAG | GTGGTTTAAC | TGGTGTAGTA | 180 |
| TTAGCTAATC | TATCATTAGA | TGTAGCATTC | CATGATACTT | ATTATGTAGT | ACTACATTTC | 240 |
| CATTATGTAT | TAAGTTTAGG | TGCTGTATTC | TCTATGTTTG | CTGGTTATTA | TTATTGAAGT | 300 |
| CCTCTTGTTT | TAGGTTTAAA | TTATAATGAA | AAATTATCAC | AAATTCAATT | CTGATTAATT | 360 |
| TTCTTAGGTC | TTAATATTAT | TTTCTTCCCT | ATGCATTTCT | TAGGTATTAA | TGGTATACCA | 420 |
| AGAAGAATTC | CTGATTATCC | TGATCTATTC | CTAGGTTGAA | ATTTAGTATC | TTCATTTGGT | 480 |
| TCTATAATAA | CTATTATATC | ATTAATGTTA | TTCCTTTATA | TTATTTATGA | TCAATTAATA | 540 |
| AATGGTTTAA | CTAATAAAGT | TAATAATAAA | TCTATTAATT | ATATAAAACT | ACCTGATTTT | 600 |
| ATTGAATCAA | ATAATATTTT | CTTAATGAAT | ACTACTAAAT | CATCATCTAT | TGAGTTTATA | 660 |
| TTA | | | | | | 663 |

(2) INFORMATION FOR SEQ ID NO:188:

(i) SEQUENCE CHARACTERISTICS:
            (A) LENGTH: 639 base pairs
            (B) TYPE: nucleic acid
            (C) STRANDEDNESS: single
            (D) TOPOLOGY: linear (ii) MOLECULE TYPE: DNA (genomic)

(vi) ORIGINAL SOURCE:
             (A) ORGANISM: PAG1075RP (xi) SEQUENCE DESCRIPTION: SEQ ID NO:188:

GATCTATCTA ATTACAGTAA AGCTGCAAAG GGTCTTTTCG TCTTTCTACA AATACTTAGC      60

ATCTTCACTA AGATTTCAAT TTCACTTAGA TTAAAGGAGA GACAGTTGTT GTATCATTAC     120

GTCATTCATG CAGGACCATA ATTAGTGGAC AATGAATTTC GCTACATTAT AACCCTCATA     180

ATAAGGCTGC TATTTAATAA AATTTATTAT TATTATCTTT ATTAAAATAT TAATTTTTAT     240

ATTTTATCAT GGAGCAGAGT TCACACTTTA TACTTTAACT TACGTTTCTG CAAAGTGTTG     300

TGTTTTTAGT AAACAGTTGT ACAACTTTGT TCTTATTATT AATTATTATT TTAATTAATA     360

TCTCTTTATT GACTAACGTC AGAGCTATTT TTGCCGAGTT CCTTTCCTTT AATTATCTAA     420

TTCACCTTCA TATACTCTAC TAACATACCT GAGTCGGTCT ACATTACGGT ATTTTATACA     480

TAAATATTTC TTGAACTTAA TAAATTTATA AAGACATTAT TTAAGTTAAT TTATATATTA     540

GATTATTTCT ATCATATTAT ATTTTTTAAT ATATTACTTA AGAACCGCTT TTATTGTTAA     600

ACCTTATGCT TTAGGTGATA AGGATTATAC CTTATTTTC                           639

(2) INFORMATION FOR SEQ ID NO:189:

(i) SEQUENCE CHARACTERISTICS:
             (A) LENGTH: 663 base pairs
             (B) TYPE: nucleic acid
             (C) STRANDEDNESS: single
             (D) TOPOLOGY: linear (ii) MOLECULE TYPE: DNA (genomic)

(vi) ORIGINAL SOURCE:
             (A) ORGANISM: PAG1075UP (xi) SEQUENCE DESCRIPTION: SEQ ID NO:189:

GATCCAGTTA CTTAGTAGAA TGATAAAATT AATAAATATT ATTTATTAAT ATTTGGTTAA      60

CAATAAAATT CAATAATTTA TTTAAATAAT GATTAAATAA TCTCAATATA AAATTATTAA     120

TATAATGAGA TATATATTTT TAAAAAGAAT ATATAATTAA ATAATCCCAA CCAAAATTTG     180

TGCCAGCAGC TGCGGTAAGA CAANGGGGGT TAGCGTTAAT CGTAATGGCT TANAGGGTTC     240

GTAGAATGAT TATTTAAAAT AATAATTAGA ATTAATAAAA ATAATTTAAG AATTATTCAA     300

GTAAAGATGA AATAATAATT ATATGAATAA GACTTATAAA GTGAAAATTT AAATTATATA     360

TTAATTGACA TTGAGGAACG AAGGCTAAAG TAGCAAATCG GATTCGATAC CCGAGTAGTT     420

TTAGCAGTAA ACAATGAATA CCTATTTATT TTTTATTAAT TAAAGAATAA ATTAAATGAA     480

AATTAAAGTA TTCCGCCTGA TGACTACGTT AGCAATAATA AAAATCAAAA CAATAGACGG     540

TTACAGACTT AAGCAGTGGA ACATGTTATT TAATTCCGAT AATCCTCCGA TAAATCTTAC     600

CATTTTTTGA ATATTTAATT ATAATAATTT ATAATTAATT ACAGGCGTTA CATAGTTGTC     660

TTC                                                                 663

(2) INFORMATION FOR SEQ ID NO:190:

(i) SEQUENCE CHARACTERISTICS:
             (A) LENGTH: 650 base pairs
             (B) TYPE: nucleic acid
             (C) STRANDEDNESS: single
             (D) TOPOLOGY: linear (ii) MOLECULE TYPE: DNA (genomic)

-continued (vi) ORIGINAL SOURCE:
        (A) ORGANISM: PAG1076RP (xi) SEQUENCE DESCRIPTION: SEQ ID NO:190:

GATCTTAAAA TAAGATAGAA TGGTAATAAA TATCATTCAG GTACAATAGA TGCTGGTGTT        60

ACTAAAGGAT TACCTGGAAT ATAATTATCA GGATGTCCTA AAGTATTAGG TGAAAAGAAT       120

ACAAATAATG AAAAGAAAAT TATAAATACA AATACTGTTA CTAAATCTTT AAAAATAAAA      180

TAACCATGCA TTGGTAATCT ATCTAAATTA CCTGTAATAC CTAATGGATT TGATGAACCA      240

TGTACATGTA ATAGCATTAA ATGCATAATT ACTATTGCTG CAATAATAAA TGGTACTAAA      300

TAATGAAATA GAAAGAATCT TATAATAGTA GGATTACTAA CACTAAATGA TCCTCATAAT     360

CATAGTACAA TATCATTTCC AATAAATGGA ATAGCACTAA ATAAATTAGT AATAACAGTA     420

GCACCTCAAT GTGACATTTG TCCATATACT AAACAATAAC CTAAGAAAGC TGCTGCTATA     480

GTTAAAATAA AGATAATAAC ACCAACTGTT CATACAATAA CTCTAGGTGA TTTATAAGAA     540

CCATAATATA AACCTTTACC AATATGAATA TACATACCAA TAAAGAAGAA TGAAGCACCA     600

TTAAGATGCA TATATCTAAT TAATCAACCT AGTTGTTCAT CTCTCATAAT                 650

(2) INFORMATION FOR SEQ ID NO:191:

(i) SEQUENCE CHARACTERISTICS:
        (A) LENGTH: 663 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1076UP (xi) SEQUENCE DESCRIPTION: SEQ ID NO:191:

GATCTAGAAT TATTAAGTCA ACTATTAACT AATATCTATA ATAATAATGG TTTATCATTA        60

AAATCATTAA AGATAATTAT TAATAAATTA CCATTTAATA ATGATATATT ATTATCAAAA      120

AATTATGTTA ATAAAATAAA TAAATATAAT TTACTAATTA ATAATAATTT AAATAATAAT      180

AAAAAAGATT TAATTAATTT ATATACTTTA GATAATAAAT TATTAGATTT AAGTATTCTT      240

AATAATATAT TATTAGGTAA ATATTTAGTA GGTAGTAATA TCCAATTARR GGGTAGACTA      300

TTAAATAGAA ATATTACTAG ACTAATAAAA ATAAATATTA TGAAAGGTAC ATTTAATAAT      360

TATATATATC AATGAAGTAA ATTAAATAAT TTATATAAAT TAAATTATAT ATCACTTAAT     420

ATTAATAAAC TTAATAATCT ATTTATTAAT AAAAATGGTA TATTTAATAT TAAAATTAAA     480

TTAAATACTA TTTAATAAAT ATTCTATAAG TAATTTCTTA TTTATTTTAT AACATTTTAA     540

AATGTTTTAT GTTAAATAGA TAATAATCAA TTAAATAATA AAAATTAAGA TGCCACAAAT     600

AATCCATTTT CCTTTATGAA TCAATTAACT TATGGTTTNC TATTTATTTT ACTAATTTTA     660

TCT                                                                    663

(2) INFORMATION FOR SEQ ID NO:192:

(i) SEQUENCE CHARACTERISTICS:
        (A) LENGTH: 642 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:

(A) ORGANISM: PAG1077RP (xi) SEQUENCE DESCRIPTION: SEQ ID NO:192:

GATCCAGTTA CTTAGTAGAA TGATAAAATT AATAAATATT ATTTATTAAT ATTTGGTTAA      60

CAATAAAATT CAATAATTTA TTTAAATAAT GATTAAATAA TCTCAATATA AAATTATTAA     120

TATAATGAGA TATATATTTT TAAAAAGAAT ATATAATTAA ATAATCCCAA CCAAAATTTG     180

TGCCAGCAGC TGCGGTAAGA CAAAGGGGGT TAGCGTTAAT CGTAATGGCT TAAAGGGTTC     240

GTAGAATGAT TATTTAAAAT AATAATTAGA ATTAATAAAA ATAATTTAAG AATTATTCAA     300

GTAAAGATGA ATAATAATT ATATGAATAA GACTTATAAA GTGAAAATTT AAATTATATA      360

TTAATTGACA TTGAGGAACG AAGGCTAAAG TAGCAAATCG GATTCGATAC CCGAGTAGTT     420

TTAGCAGTAA ACAATGAATA CCTATTTATT TTTTATTAAT TAAAGAATAA ATTAAATGAA     480

AATTAAAGTA TTCCGCCTGA TGACTACGTT AGCAATAATA AAAATCAAAA CAATAGACGG     540

TTACAGACTT AAGCAGTGGA ACATGTTATT TAATTCGATA ATCCTCGATA AATCTTACCA     600

TTTTTTGAAT ATTTAATTAT AATAATTTAT AATTAATTAC AG                        642

(2) INFORMATION FOR SEQ ID NO:193:

(i) SEQUENCE CHARACTERISTICS:
            (A) LENGTH: 658 base pairs
            (B) TYPE: nucleic acid
            (C) STRANDEDNESS: single
            (D) TOPOLOGY: linear (ii) MOLECULE TYPE: DNA (genomic)

(vi) ORIGINAL SOURCE:
            (A) ORGANISM: PAG1077UP (xi) SEQUENCE DESCRIPTION: SEQ ID NO:193:

GATCCGTGTA TTTTTTATTT ACATTATTTA ATTAAAAATA ATGATTTAAA TAAATATTTT      60

TTATAAAAAA TAATTAGTGC ATTGTTACAT GTTCATTAAA GAATGATTAT TATCAAAACC     120

ATCAACTAAT TGTTATATAT TTATTAAATA TTAATTTCAC TTAATTAAGA ATTAGGAACT     180

TTATCTATTA GTCTGGGCTG TTTCCCTTTT GATTATTAAC CTTATCGCTA ATAATCTGAA     240

ATATTTAATT TTAGATTAAT AATATATTCT GAGATTAAT ATTTTTAATA AAATAAATAA      300

TTATTCCCTA ATAATATTA ATAACTATAC CATATATATC TAATATTTAA ATAATCATAC      360

TAACATATGT TTCGTAGAAA ACCAGCTATT TGCAAATCAG ATTTGACTTT CTCTACTTAC     420

CATTATTCAT CAGATAATAT TGCTACATTA ACCTGTTCAA TCGTTTTTAT ATTTTATTAT     480

ATTTAAATA TAATAAATAT ATATTTAAT CATTTGATAA TAGTAAGATC ATCTGCTTTC       540

GGGTTAATTA ATATTAACTA AATTTAATTT ATTTTAATTA ATTTAACAT TGTTAAATAT      600

TTATATTATT TTTAATATCA TTTTTTATTT TAATATTATG CTAATATTAA TTACTTGC      658

(2) INFORMATION FOR SEQ ID NO:194:

(i) SEQUENCE CHARACTERISTICS:
            (A) LENGTH: 445 base pairs
            (B) TYPE: nucleic acid
            (C) STRANDEDNESS: single
            (D) TOPOLOGY: linear (ii) MOLECULE TYPE: DNA (genomic)

(vi) ORIGINAL SOURCE:
            (A) ORGANISM: PAG1078I1

(xi) SEQUENCE DESCRIPTION: SEQ ID NO:194:

```
GATCTAGTTC GTTAACTTCC GCAAAACACC TGTCAAGCGC TTCAACAAAC GTCTGGATCA      60

GATCCAAGAT GGCCAGTTCT GACTCCTGGT CGTCGACAAT GAAAGTAAAA TAGAGTGTTG     120

CATAGTTCTT GTAGATTATT TGGATATCTT CGTTAATGGT TTCACTACCA CTCGATAGTA     180

GCGAGGGCGG CGTAATTAAG AATGAAGACT GAATTGAACT GTTGCGCTGG CTGATCAGCT     240

CGTAAACCTG CTCCAGTAGT AGCTTCTGCT TCGGGAGATC GACAGGAGTA TAGTACTTTA     300

CAAGCCTAGG TTGGCACTTC TTGTTAACTT CATGTGTTAG TAGGATAATT TAAGTACTGC     360

GGCTGCGCGG TGGCAAAGGG GTTCACCCAT ATCAGGACGG CGNCGNNTCA TCCNCNGTCC     420

CCACCACGGN TACNCGCCNC NCCCA                                          445

(2) INFORMATION FOR SEQ ID NO:195:

(i) SEQUENCE CHARACTERISTICS:
        (A) LENGTH: 443 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1078I2

(xi) SEQUENCE DESCRIPTION: SEQ ID NO:195:

GATCTAATAT TCAATTGGCA AACTCTTGAG AGTGTCTTGG AGGAAATTAT TCAAGGGGGT      60

ATGGTAATTG AAACGAACGT GAAGAAAATT GTGGAGACCG TCGACGAGCT CAATAGAACT     120

TCTAACCAGG AAGCCAGGTT TGGGAATGGA CTAGGAAACG CTTTTCAGGC CATCACCATG     180

GGTGGCTTTT CAAATTGGGG TGCGCGGCAG TGAATATTAG CACACACTGT CTTGAAACCC     240

CATAATAAAT GAAATAAATA CTCCTTGCTA GTGTCTAAGT ACGAAACAAC GCCAAGGCTT     300

TTGGATCATC TATGTACGCA TTCAGTTCGG CAGCACTCAC CATGGGCACC AACTCTTCTT     360

ACTTGCTATT TCCTGTGTCT TCATTTGCGC TTCGGCTGCC TGATGGTCTC AAAGCTCCTC     420

CCTAATCCTC TGTAATTCTC CTG                                            443

(2) INFORMATION FOR SEQ ID NO:196:

(i) SEQUENCE CHARACTERISTICS:
        (A) LENGTH: 451 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1078RP (xi) SEQUENCE DESCRIPTION: SEQ ID NO:196:

GATCAGGATG GCGATGAGAT ACTACCTTGA AGCAGCAGCC TTGACCTCAG CTAACTCCGC      60

AAATTCCTTT CATTTTTCGA AAGCAGATTA TAATTGCTTC TAAGCCATTC AATTGCTTTA     120

CTTTTCCGTT AATCAATGCT CTATTTTACC ATCATTCGAA GTAAGAGTAT GTCGATATGT     180

CTGACCTAAG CTACAGATTA TCTAATCACA TAGTTATGTA CGAACCAATA AGATTATCGA     240

ATTTCGTTGA AAAACTCAGG CGAACGGCAC AGCGTTGCTT GCGCCTATTA GATGCTTTGG     300

CCATAGCATA TCACGAAGTG ACCTCACAGT TTTTAAGTAA CCGGAATAGT CTGTAGATAT     360

GGTATTGTGA AAAGTTTATT NGCTGGTTTC ACCCCCTGGG AATCTNGGNG CTGGNCTGGG     420
```

```
TTCTTAGGTG GGGAATCCGG NCCCCCCNNT C                                    451
```

(2) INFORMATION FOR SEQ ID NO:197:

(i) SEQUENCE CHARACTERISTICS:
        (A) LENGTH: 480 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1078UP (xi) SEQUENCE DESCRIPTION: SEQ ID NO:197:

```
GATCTCCTTC CTTTCTGGTG TCTTGCCAAG CCCTTATTTG TTGACCAAAG TATTCTTCAC      60
CGTTGCCCTG TACTCTGTTC TCATAAATTT CCGCGGTAGG ACACCTCTGG GCTTTCTCTT     120
GGCGATCTAT GAGGGCTTTG CAATCATCTT CACCGCCGCT AAAGTTTTCA CACCATTTTT     180
GTATGAGCAG CTACTTCAGT AAGCCCCCGT ATTAGGATTG TTAAAAGAAG TAGGATCGAT     240
ACCCTTCAAT TCCAGATGAT CGTTGCGGTG GGCTATTAAT TTGTTAGCCA CCTAATACTG     300
AAATTTACAT ATTATTGCAC TAGTTAATTA ATATTTATGA TGCAATGGGA ATCTATATCG     360
GTTCTCCGTT CCATCTTCTC GTAATTAGAT CACGTCGGAT ATNGTNGCCC CGTACCGAGG     420
AGGGACCCGA TTGGGNTTAT CTTTATGGTC CCGAGAANTN ATAGAGNGCC NNAANATAGA     480
```

(2) INFORMATION FOR SEQ ID NO:198:

(i) SEQUENCE CHARACTERISTICS:
        (A) LENGTH: 703 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1079RP (xi) SEQUENCE DESCRIPTION: SEQ ID NO:198:

```
GATCGCTCAT TATTTTTGGT CGGAGCCTGG GCCCTCTTCT GCTTCTTCTC AAATACCTTC      60
AAATTTTCGT CTATATAGGT CTGCAGCTCT TCCTTCTTCG AACATTCCGC CTTGTGAAGC     120
TGGTTGAAAT ACTGCAGGGC CTCTGCACTC ATGCGATTCA CCATTGAATT GCGCTCTTGT     180
ATCTCTTGCT GGAACTGTTC TTGTTTGCGA ATGGCGTTTT GCCGCAGTTG AGCTTGCAAA     240
CTGGTTGTAT CAGACTCGTC CACTTCATCT TCCACGTCCA GTGGATCCAT CCCTGCAGCT     300
AGTCTAGGTG GAGTGGTCTA TGTACAGTGC TGCTGTGCGT GTTAGCGCGC TCACCTTCTG     360
CGACTGTTCA AAGATGTGCG TTTCCAGCAA GAAAAGAGAC AACCGGAAGT ATAAGTACAG     420
CACGCGAGCC TAATTTTGTC AGCTTGCGGA TTTAGCTCAG TTGGGAGAGC GCCAGACTGA     480
AGAGAAACTT CGGTCAATCG TAATCTGGAA GTCCTGTGTT CGATCACAG AATTCGCATA      540
TTTTTTGCTC ACGTCACCCA CCGGGTANGA ACTGGCATTG CCTACCTAAT GGCCAGCAGT     600
GGAAAGCGCT CTTGTGATAT ATATATATCA AGTAACACAT CTATGTAACC TTTTGACACA     660
GTCCCAAGGT GAATCTTGCC TCGGATCTGC CTCATCTGAR TCC                       703
```

(2) INFORMATION FOR SEQ ID NO:199:

(i) SEQUENCE CHARACTERISTICS:
        (A) LENGTH: 673 base pairs

```
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1079UP (xi) SEQUENCE DESCRIPTION: SEQ ID NO:199:

GATCAGCGAG CTAGGTACCC GGACGAACAT GCCGTTGCGC AGCTTCCCAT ACTTCAGCGA      60

CCGTGTGTGT AGCGCAGAGC TTCCGTCCTG GAATAGCGAC TGCACCTCTG CGTTCAGCAG     120

ATCGCCCTCT TTCAGAAAGC TGCGCATCTG CAGCTCATCG CTCTCAGACT TCCGCCGCAG     180

CACGCCGCCG GGCAGGTTCA CAGAACCCAG CATGAGCACT GCGTGCTGCT TTCCGCCAAT     240

ATCCACCTTC CATCGTTTGT TGCCGACCTC CACGATCCTG CCGACAATGT GGTCGCCCGT     300

CTCTGGCGTG TACCGCCCGC GCCAAGGAAT CACCGACAGG AGTCGGTTCA CCCTGGAAAC     360

GGTGCCCGCC ACCGACGAGT ACGTTTTGTT CTCCAGGAAG TATGTGCCGT GGCCTCGCAT     420

CCACACAGGA TCATCTGTAA TCAGCTCTCC TGGCGTCATA ATCACCGACG AATCCGCTCC     480

TTCCATCTCC ACGTCCAAAT CAAACTCTTC TTCCTCATCG TCCAGGTACT GGCTCCGATG     540

GAACTGAAAC CCACGCCGCT TGCGGATCGT TATTACCTCG CTCATTACTG CTGAGACGAC     600

ACGTTTCARA ACTTCAGAGG CTCGCTAGGC CAGGCGAAAC AGTGTTGARG ATACGCTTTG     660

TTACTTCTTG AAG                                                       673

(2) INFORMATION FOR SEQ ID NO:200:

(i) SEQUENCE CHARACTERISTICS:
        (A) LENGTH: 441 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1080UP (xi) SEQUENCE DESCRIPTION: SEQ ID NO:200:

GATCCGGCCA CGCATGTATT CCACTATGTA CGCTATATCG CGGCCTCGCC TCCGTGCGGG      60

GCACCGCCTT ACACCTCAAA GCCGCAGCCT TTCATGCAGC CCTTGTACTT TTGCACCAGT     120

TCCTGGCACT TGACCGCATC CACGCCGTTG AACAGCAGAC AGCTGTCTCT CGCTTCCTTC     180

TCGGGCTTGC ACACACAGCA TGGCTTTGGC TTGTCGGTAC TACTACCTTG TGAAACACCT     240

GGCACAGAAG AGGATTCAGG CATGATTAAT GCTACAGTTC TTGGAGATCT TCCAACACCG     300

CCCGCTCCTT GGGGTTTTTC TCACTTTATT TTTGCTTCAA CGCGCAAAAA TTGTTGTCGA     360

ATTACAATAT ACAGAGGCGC AGTAACCCCT TTAGTGGCTT TTTGGCTTCT TGGGCTGGAA     420

ANTTNGACCC CCCAACNTNC C                                              441

(2) INFORMATION FOR SEQ ID NO:201:

(i) SEQUENCE CHARACTERISTICS:
        (A) LENGTH: 644 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
```

(A) ORGANISM: PAG1081RP (xi) SEQUENCE DESCRIPTION: SEQ ID NO:201:

GATCTTTCGC AGTGACTAGT GCATGCGGCT ATTTAAAAAG TATCGAGTTA CCCTTGGAAA      60

TTTCAGCATT TATAGTACTG ACGGAGCCGC TACAAAGCCA AGGCTTTGAA GGTACTAGGA     120

GACATATTCA GGCGCATAAA TCACCGCAAG CTGGATTGAG CGATGTTTTG GGTTGTGTTT     180

ACAGGAGCCA GCGCGGTGGC ATGCGTTTTT GCGTATGGGA TGGTGGACCG ATATCTCTCC     240

TTCAAGCTGC ACAGGCATAC GCACCCGTTT GTGTTGGTAA CACTTTTCGC AAATATGACA     300

CTGTTGCTCT CGATCACATA CCTGCTTCCA CTCGATGTGT TTTACTCAAA CCAGACAAGC     360

GGGCGGGAAG ACGAGCGGCC AGAGCTGCCG AACCTCGCGT TGTTCTGGGC GGTGATCTAC     420

TGGGCGGAGT TTGTGATATG CTGGTTGGTG TTCCCGGTGC TGATTTCGTA CGTGGATCTC     480

AAGTACTTGT ATCCGCGCGA GCCACAGGAG CCGGGGCGGC GCAGCGTGCT TCGGCGACTG     540

CGANGCGCCG TTATATGCAA TCTCAAGTTC TATGGTCTTT GTCTACTGGG GGTGATCTGC     600

NGGCTGGTAT ATCTCAAGAC GACGACCGAT CGCGGGCGTC AGAC                      644

(2) INFORMATION FOR SEQ ID NO:202:

(i) SEQUENCE CHARACTERISTICS:
        (A) LENGTH: 669 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1081UP (xi) SEQUENCE DESCRIPTION: SEQ ID NO:202:

GATCCAAGAC GAGCTGCGCC AGGGGAGAAA ACCCCCCCAC ATATGTCCAG CGATACGCTC      60

AGCATGGAAA ACCCAACCGT GGACTTGCGC TCGTAGTTGT GCTTGGCCTG TGCGATATAC     120

TTCAGCACAG ACATGATGAT TTTTATAAAG TACAGCACAT GGCAGTAGAA CAGTGTCGAC     180

TGATTGTTCA ACCCTGTTTG CGTAATGCTA ACCACATATT GCACTGTGCC AATGCAAAAA     240

AGCCCGATGA ACAACTGCAT CATCTTCCGG TGCGCTGTGC TCATCCTATT CGCCGGCTCT     300

CCGGTGAAGC CCCATAGTCT GGTGCCCCAT AGCACCTGCG ACGCCAGCAG TCCGTTAAGA     360

AGCCAGCTAT GCATGGCATA CCAGTAGTCC GACCACCCTA CCGACGGCCT CACCGCGCTG     420

GACGTGTCGC CTTCATTCTG CCAGAGCACG TCTGCACAAC CAGCGAGAGT ACTAGCGCTG     480

TATACCCGAT GCAATTAAAC ACCACGTAGC CTTTCGACAA TGCTCTTGCG CTCTGCCGCT     540

TCCAGTTGAT CCATAGTGGC GGATACATCG ACACCGACCA ACATGTCGCG TACAAGTATC     600

CGAGCAACTG TCTCTTCCTC ATTCCAGCCT CGTTCCAAGT GCTTCTACGC CGGTCTTCTG     660

GCGTCAGAT                                                             669

(2) INFORMATION FOR SEQ ID NO:203:

(i) SEQUENCE CHARACTERISTICS:
        (A) LENGTH: 654 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1082RP (xi) SEQUENCE DESCRIPTION: SEQ ID NO:203:

```
GATCCACGAG CAAACTATTA TTAGGCGCCC CCCACCCCAG TCTGCAGCAT TCGAAAGCCT      60

TCCTAGCCTT TGTGCGATGT CCCAAGGTAC AATTTTCTCG CAGCTGAAAA TACGAAAGAA     120

GCGCCAAGAA GTGGCCTTCT TTGAATCCAA CGCCGACGCC AATGATGTCG AGGCGGGCGA     180

ACATTTTATA ACAGAGCTCG ATAAGGGCGA TAAGCGGCTC GGCCTGTTTT CTTCGATCGG     240

CTTGATATGC AATANAATGC TCGGGACAGG TATCTTTGTC GTTCCCGCGA ANATCTTCCA     300

GTTGACTGGC TCAGTATACT TTGCGCTAGG GTTATGGGTA CTAGGAGCTT TAATTGCTCT     360

AGCAGGTCTT TATGTTTACA TGGAATTTGG AACTGCAATA CCGCGGAACG GTGGCGAGAA     420

GAACTACCTT GAGTTCATCT TCAAGAAACC GAAATTCTTC ATTACGTCAA TGTACTCAGC     480

ATATGTCATC TTTTTAGGCT GGGCCGCAGG TAACTCTGTG ATGGCAGCTG CAATGTTCCT     540

TGATGCTGGA AAGGTCGAAG CAACACGTTG GCGTTGAACG CCGTCTTGGA GTTGCGGTCA     600

TTTTCTTCTG CTTCCTTGTC AACTCTCTCA GTGTCAAAGC TGGGTTGTTA CTTC          654
```

(2) INFORMATION FOR SEQ ID NO:204:

(i) SEQUENCE CHARACTERISTICS:
        (A) LENGTH: 680 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1082UP (xi) SEQUENCE DESCRIPTION: SEQ ID NO:204:

```
GATCCGCAGC TTCGGCAAGC GCCGCTTCTC CTCCGTGTAC TCCTCGTCGT CGTCGTACTC      60

CGGCACCATC GACGCCTCCG GCTCCTCCTC ATCCGCCGTC GCGTCCTTCT CCTCGTCCAC     120

CGTCTCCGGC AGCAGCGAGT CGTCCTTCGC CCCCGTCTCG TCGTCGTCGC GCTCCAGCAG     180

TGCGCCCGGA AGCGGCTGCT CGTCCGGGAG CGGCCCGAGG TACGGGTACT TCACCGGCCC     240

CATCTCCCGC TCAATCCGCG GGATCACCAC CTCCCGCACG TACCGGTCCA TGATCTGCGC     300

ATAGTGGTAG ATTTCCGACT CCTTCGTGTT GTACATCCGC GCGTTCCACG TGATCCGCAC     360

CAAGTCGTTC ACGAACTCCT GGGCCCGCTT GTAGTGGTTG AGCTTCTTTT TCACCGTCGC     420

GAGGCTGAGC GGCTTCTTGA TGATCCGGTA GTAGTCGGGA TAATCCTTCC TCAGCGGCAA     480

AGTGTAGAAA ATCGGCAAAA TCTCAATACC ATTTTCCTCC TTTAAGTCAA ACACGCCATC     540

CAACAAAACT TTGAGCTGGT CCCGTAGCAA CATCGTTAGC CCTCGCCACC TGAAAAGCTG     600

AAGACTTTGG TAGTGTACTA TGTGTTCCGA ACAACATCC CACGCGTCGT TTCTGCCCGT      660

TCACAGCCTT GCTTCAAGTT                                                 680
```

(2) INFORMATION FOR SEQ ID NO:205:

(i) SEQUENCE CHARACTERISTICS:
        (A) LENGTH: 613 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1083RP (xi) SEQUENCE DESCRIPTION: SEQ ID NO:205:

```
GATCATCAAT TTCTTTTTGG CTGTTTTCTT ATTTACAGCC TCTATTTCTG AGCGAACATG      60
CGACGCCACA GCAGTCCTAA TGAGCTCATC TGTTAGTTCG GTTGCAACCG CGTTACGCAG     120
TTCATTCCCT TCTATTGCTT TGGAGCCAGA ATCTCTAGCT TCATCTTGAG CGCTAGCTTC     180
AGTTTGGGCT CCCAGTTTTA AAGCTGTTTG GTTAAAATGA AAAGTATTTT CCTCTTTTAG     240
CTGGGAATTG CCAGCAAATG GTTTTCTGTG CGATGACTCA AACGGTACAT CTTTTTTAGT     300
TTTTGTTTCC TCTAAAATAT GCGGTGAGGT TGTAGAGCCG ACACTAGACA TAAATGGTGC     360
CGTAAACTGT TTCGTGGACT GCAGATCAGA CTGTTGCTGT GGCTTGAACT GCATGCTAGA     420
TTTCACTTCA CTTCCAGCGC GGGATTGGGT AGTGGGTTCG GTAGTCTTAT AATCTCCACT     480
ATCGAAGTTG AAAGTTTTAG ATATATCCTG GTGTTCTCCG TGCAAGGAAG ACCCCTGCTC     540
AATGATGCTT TCCGAATATG TGGGTAGATT TGAATCATTG CTCCCTAGNA GCAGCATCAT     600
CCTCCGAAAG AGA                                                       613
```

(2) INFORMATION FOR SEQ ID NO:206:

(i) SEQUENCE CHARACTERISTICS:
        (A) LENGTH: 656 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1083UP (xi) SEQUENCE DESCRIPTION: SEQ ID NO:206:

```
GATCCTGAGC GGTGCGGACG AGGAGGAGCG CGAGGAGGAG CCGGAGGCGG TTGTGGGGA      60
AACCGTGAGC CGCAGCGCGA CGGGCGGGAC GAAGCGGCGC TTTGCGGATG AGGAGGCGGA    120
GAAGGCGGAA GAGGCGGCGA CGGCCGCCTC GGACGACGAG GAGGCGCCCA AGAAGGCGCG    180
GAAGTAGCGT AGATAGAAGG ATATAACTGT ACAGTACCAT GCAAGACGAA TCTGAGGCCG    240
GCGGACGCGC GCTGGCGCGG CGCCGCGGTA GCTGCGGAGG GCAGAAAAAA TCGCCGTCGA    300
CAATCTCTGC GTCATCATCC CGGCCAGAGG ACAAGATGGC TGGCAAGAAG ATTGCGGGTG    360
TGCTAGGCGC GACGGGCTCC GTGGGGCAGC GGTTTATCCT GCTGTTGGCG GACCACCCTG    420
ACTTTGAGCT GAAGGTGCTT GGGGCATCGC CGCGATCCGC TGGCAAGCGG TATGCGGACG    480
CGGTGAATTG GAAGCAGACC GAGCTGATGC CGGCGTTTGC CGAAGACATC GTGGTGAGCG    540
AGTGCAAGGC TGAAGCATTT TGCGGCTGCG ACGTTGTGTT CTCTGGGCTC GATGCGGACT    600
ACGCAGGCCC CATCCAAGCG GGAATTTGCC GACGCCSGAC TGGCTGTTGT CTCGAA        656
```

(2) INFORMATION FOR SEQ ID NO:207:

(i) SEQUENCE CHARACTERISTICS:
        (A) LENGTH: 453 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1200RP (xi) SEQUENCE DESCRIPTION: SEQ ID NO:207:

```
GATCGCTCAT TATTTTTGGT CGGAGCCTGG GCCCTCTTCT GCTTCTTCTC AAATACCTTC      60
```

```
AAATTTTCGT CTATATAGGT CTGCAGCTCT TCCTTCTTCG AACATTCCGC CTTGTGAAGC      120

TGGTTGAAAT ACTGCAGGGC CTCTGCACTC ATGCGATTCA CCATTGAATT GCGCTCTTGT      180

ATCTCTTGCT GGAACTGTTC TTGTTTGCGA ATGGCGTTTT GCCGCAGTTG AGCTTGCAAA      240

CTGGTTGTAT CAGACTCGTC CACTTCATCT TCCACGTCCA GTGGATCCAT CCCTGCAGCT      300

AGTCTAGGTG GAGTGGTCTA TGTACAGTGC TGCTGTGCGT GTTAGCGCGC TCACCTTCTG      360

CGACTGTTCA AAGATGTGCG TTTCCAGCAA GAAAAGAGAC AACCGGAAGT ATAAGTACAG      420

CACGCGAGCC TAATTTTGTC AGCTTGCGGA TTT                                   453

(2) INFORMATION FOR SEQ ID NO:208:

(i) SEQUENCE CHARACTERISTICS:
        (A) LENGTH: 590 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1200UP (xi) SEQUENCE DESCRIPTION: SEQ ID NO:208:

GATCAGCGAG CTAGGTACCC GGACGAACAT GCCGTTGSGC AGCTTCCCAT ACTTCAGCGA       60

CCGTGTGTGT AGCGCAGAGC TTCCGTCCTG GAATAGCGAC TGCACCTCTG CGTTCAGCAG      120

ATCGCCCTCT TTCAGAAAGC TGCGCATCTG CAGCTCATCG CTCTCAGACT TCCGCCGCAG      180

CACGCCGCCG GGCAGGTTCA CAGAACCCAG CATGAGCACT GYGTGCTGCT TTCCGYCAAT      240

ATCCACCTTC CATCGYTTGT TGGCGACCTC CACGATCCTG CCGACAATGT GGTCGCCCGT      300

CTCTGGCGTG TACCGCCCGC GCCAAGGAAT CACCGACAGG AGTCGGTTCA CCCTGGAAAC      360

GGTGYCCGCC ACCCACGAGT ACGTTTTGTT CTCCAGGAAG TATGTGCCGT GGCCTCGCAT      420

CCACACAGGA TCATCTGTAA TCAGCTCTCC TGGCGTCATA ATCACCGACG AATCCGCTCC      480

TTCCATCTCC ACGTCCAAAT CAAACTCTTC TTCCTCATCG TCCAGGTACT GGCTCCGATG      540

GAACTGAAAC CCACGCCGCT TGGGGATCGT TTTTACCTCG CTCATTACTG                 590

(2) INFORMATION FOR SEQ ID NO:209:

(i) SEQUENCE CHARACTERISTICS:
        (A) LENGTH: 754 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1201RP (xi) SEQUENCE DESCRIPTION: SEQ ID NO:209:

GATCTTCGAG ATGAACCCAA TATGGAACAC GGGCTTCGCC AGCTCGATGT GCCCGAAGTG       60

GCCCGGGCAG TCGTTCATGC CCTCGCCACA CGTCTGACAC TTGAAGTTCC GGTCGATGGA      120

GCCCAGCCGG GGGTCGTTCA GCCCTCCCAC CTTTGCGCGC ATCTGCGTCT CGTCCATCGT      180

CTCTGGAAAC TCAATCTTGG CCACCGAAAT CGCCCGCACC TCCTCGGGCG AGAACAGCCC      240

AAACTGCACC TCCTTGATGG TCCGCAGAGG CGCGCTCGAA TACGGAAAGT CCACCATCGC      300

TGTGTCGTAC TACCGCTCCC GGAGATACAC CCGTTTGCAA GTTCGTGTGT GCACCTGACG      360
```

```
CCCAGCCGCC ACTCGCAATC CTCGTTTACG CCGACCGCTT TGTTTCGCTC CCTTGCCGCA      420

ACAACGAAGC TCTGTTATAT GTGCCCGCTC GAGACCCTAA GCCTGCTCCT GTCGAACACA      480

CGCTCACGCC CAGAAACTCG TGTCTTTACC TTGCAGCTCT GGAATTGGTN CGCGCCAAAC      540

CNGCTTATTG CTTGGGCGAA CNCCTATGCT CCGTGTNATC TCAGCTGGAA TNCACCANAA      600

ACNGACCCCC CACCTACCCC NCAACTCTGG TTATTGGATT TTGCCGGGAA TAAACNCANT      660

GTTNCCAATC CTTNCACCCC CAACTGTTGT NTCCNCTGTT CNGTNCNCTN TTACTCNTNA      720

CCCTCCNACN CCAATTTTTT TTNCCCGTTG CCCT                                  754
```

(2) INFORMATION FOR SEQ ID NO:210:

(i) SEQUENCE CHARACTERISTICS:
        (A) LENGTH: 643 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1201UP (xi) SEQUENCE DESCRIPTION: SEQ ID NO:210:

```
GATCCTCCGA TTAGCCTCGT CTTAAAACTC AACCAAGCTG CTCTGAAACA AACAACACGT       60

ACCACTTCTG TGTTGTTCCT CTGCGCTTGT TGACCGTCCC GCAACTACTA TGTCGTTACG      120

TGTGTTTTTT CGGGAAACTT GCCACCGTCT CAGAATCAGA GGCTGTGAGA TTCTTCTGTC      180

GAATATCGCT CTGGACGTTC GCTTACGTGC GCCCCGCCAG TGCTCTTAAC CGGCGCCGTA      240

GCCCCCGGCC CTGGCCGGTA CCAACAAGCA TGGCAGGAGA CACAGAGTAC TACAAGCAGG      300

CGGTGGAGGA GTACGCGGCG CTCAAGCAGG ACACGGACCC GGAGGAGTGG GACAGGCGGA      360

TCGCGCAGAC GGGCTGCTAA GTCGAGAATA TGGCGCTGCA GCTGTGCCAC GCGGAGACCG      420

GGGACTGGCG GCGTGCGCG GCGGACATGG CGCGGTTCAA GGCGTGCTGG GCGGCGCAGG       480

CAACCGCGAG CGCGTGACGC ACCGTGGACG GTGAGCTGCG GGCTGTAAAT AGGTGTATCT      540

GGAGGCGTGT CACGTTGACA CTGGACACGT TACGAANCAT TNTCNGGNTN GGCCNCCGGA      600

ATGGCCANCC CCNATCTNAN NACCCAAACN GGGGTATGAT NTN                        643
```

(2) INFORMATION FOR SEQ ID NO:211:

(i) SEQUENCE CHARACTERISTICS:
        (A) LENGTH: 735 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1202RP (xi) SEQUENCE DESCRIPTION: SEQ ID NO:211:

```
GATCGAAAAC GCTGCCACCG AAAGCTTGAC ACTGAAGGGA TTTGAGTATT CTCTTGCATT       60

TTCCAAGGCG AATACCAGCT TGTCCCAGGC TGCCGATCCA ACCTTCCCCT CCTTCAGGGC      120

CTGCTTGTAC CTGTCGTCTA TCTGCAGCTG AGGTAGCAGC TCTGTGATCA GCATGACGAC      180

GGCCAGCGCA GAGGTAAAAC CTTTCAGAAA GGCCTTTGAG ATTGCATTGT CGATGAAACC      240

GAGCCTGAAG ATGCCCATGG CGAACACCAG GACCCCTGAT ATGCATCCGA TAACCGCAAC      300

GGTCATCAAC GGTTCAAGCG ACTTGTGCGC CCATGCATCG CAGCTCTGGC CCACCACAAG      360
```

```
GGACGCAACC GTCTGCGGCC CTACAACCAT CGTCGGGACG CTGCCGAAGA CTGCATATAT      420

CAGTGGGGGG ATCACCAGTG CGTACAGCCC TGCGTATGGT GACACATGTG CCATAGTGGT      480

CAGCGAAATG CCAGCGGTA TCTGGAATGA CGTCAGCGTC AGCCCAGCAA GCATGTCCTT       540

CGCATTTCCC CAGAATACTC TGGCAGCCAG CGTATAATGG GCCGTAGTAA GACNCATAAA      600

ATTTNTTTCC TNCCTACCGT TGTCNNTTTA TNGNCTGTAC CCCNTACGAC TTGTCANAAG      660

CAGNTNCCCC CCGCCCGGAG ACTTCCANCC CNTCCCTACT CCCAATTTGG ACCANGACCC      720

GGTTCCTGGT GCTTN                                                      735
```

(2) INFORMATION FOR SEQ ID NO:212:

(i) SEQUENCE CHARACTERISTICS:
        (A) LENGTH: 777 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1202UP (xi) SEQUENCE DESCRIPTION: SEQ ID NO:212:

```
GATCGCCGCC GCGCCCCAGG ACTACGTCGA CTTTCTCTCG CTCACACACG TACTGGACGA       60

CCCGCAGCAG CCCGAAGCGG ACTGCGTCGA GCACAGCTAC ACGCCCGATC CGCTGCAGCT      120

CGCCGTCTAC GCGCACGCCC AATGAGAGCT CATCGCTCCC GCGCAGTGCG ATTTTTTTGC      180

CGGCCGCCCG CAGCGCTCCG CCTGGCCGTC ACCGAAGCCC CAGCGATGAC AGCCAGCGTC      240

CAGGATATCG TGGTGCCCAC CGCCGGCGAC AGCGCCGGCG GGCGCGACGG GCGCCCCAAC      300

CAGGCGGTCA CCCTCCCCGT CGCGCTCGAC AGCGCGACCG GCGAGGTGCT CGTGCGCAAG      360

GCCACCGGCA AGACCCGCGT GCGCAAGGGC CAGACAGAAG AGCAGTACTG CGAGCAGCTG      420

CAGCAGTACT TCGAGCGTGA CGGCGGTCCC GAGTGCACGG ACGAGGGCTG GCTCGACCGC      480

GCGGCGCCCG CGGCCGCCGC GCGCACCAAG CAGGAGCGCC AGCGCCTCGC CCGCCGTCTA      540

CCAACGCCTC TACTTCCTCG GCCGCCGTCG CGAANCCGCC GCNNTCGCCC GCCACTGCTG      600

TATACGTTCC CNGNTCNGGG CNCCTNCCNA TTNGCGCCCG AANTNCTCNA NCTCNNNNCT      660

NNTNCTNNCN GACCCNNNNN CCCTTAATTT TTCNTTTNNN NNTTTNTCTT TTCCCCTCCC      720

NCTGTTACCC TCNCTNCNTC CNTGGTNNTT CCNTTTGGTG NGCTNTCTTC CNTNCTC        777
```

(2) INFORMATION FOR SEQ ID NO:213:

(i) SEQUENCE CHARACTERISTICS:
        (A) LENGTH: 756 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1203RP (xi) SEQUENCE DESCRIPTION: SEQ ID NO:213:

```
GATCAAACAG CTGCAGTTGT TGAAAAGGTT GCTTGAATCC AAACCAAGGA AGGACGTATT       60

TTCGTTTCTA GGCCTGGATA ACTAATCTCT TCTCCACTCT AGCTGGGGAT AACACCTGCA      120

GGACGTGAAC TAACAAGTTG ACTACTATAC AGCAAAATAA CTCGAACAAG TTATACAGAA      180
```

| | |
|---|---|
| TTTTGTAAAT ATATTATAGC AGCCCTATTA CTATAATTCC ATCATTTGTT AACGCTTTAG | 240 |
| CCTTCGTTCT CAGACTCGTC GTCATTTTCT TCATGATAGT TGATATTTTT GCGTTGCCTT | 300 |
| GAGCTTTTCC TTACTGGGCC TGCATTGAGG CTCCTACTCT TTGGCCTGTA GTCACCTGCA | 360 |
| GAGCTTGGTG TATCTTCGTC CTCGCTTCCC TCATCGACAA CTTTGCGCTT CTTCTTAGTT | 420 |
| TTAGATGAGG CTGATGATGG CCGTTGCGCT TCTTGAATTC TCTTCCTCTG CCCTTGGCGA | 480 |
| TGTTGAATTG GCGCGATTAG AGAAGCGCGA TACTTTGGCC CTTATATTTA CTGTCAGTGT | 540 |
| TTCAACATGC TGGTCTGATA TATAGCTCAT GAACGCGTTT CTTTGCGCCT CTTCCCATAT | 600 |
| TGGGGAATGG CTGATAAAGT TCAGAAGGCA GATTAGCTCC CAGGTAGACT GGTAGATTCC | 660 |
| ACCCCCGTTG GTTTTAGCTC AAANATNATC AATTGGCAAC CNGCTAGANA TAATNTNTGA | 720 |
| ACATATGCTC CGTGTNGGAT CCGNTGCGAT CTCCCC | 756 |

(2) INFORMATION FOR SEQ ID NO:214:

(i) SEQUENCE CHARACTERISTICS:
        (A) LENGTH: 781 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1203UP (xi) SEQUENCE DESCRIPTION: SEQ ID NO:214:

| | |
|---|---|
| GATCATTGGC TCGCTGCTCG GGGAGACCAT CTCGGAATGC GACACTGTGT CGATGTCTGT | 60 |
| GCTGCGGAAG ATCTTCAACA AGTTTCTGAC ACACGATTTT GGCCCGCTGC GCTCCCTGCA | 120 |
| GGCCTCCGCG CGCGACCCGG CCTTTGATTT TTCTCTGACG ATCTGCCAGT CGTACAGTAA | 180 |
| CCGACTCGGG CGGCAATTCA CGAAGTTCTA CTCCGAGATC CTGTACGGGA TTACGAACCC | 240 |
| TGGCTCGGCC GGCTCAGGCG AGACCGCGGG CCTGCAGTCG ACACTTGACT CGGAGTTCAA | 300 |
| GACTCTTCTG AAACTGCATA AACTTACGGC CAACATATGG GAGCATGTGC CGGAACTGCT | 360 |
| GGGCTCCGTC GTCGGATTTG TGCATCAGGA GTTATGCTCA GACAATGTGC CGCTGCGAAT | 420 |
| TGGGGCTACG CGACTTGTAG GTGATTTGTT AGCCGCACCC TCCGCTGCCA ACTTCGTCAC | 480 |
| GATGCATACG GACACATATA ATGCCTGGAT GTCGAAGATA GCGGACATAG ACGCCACGGT | 540 |
| GAGGCGCGAA TGGGTGAAAG CCATACCTAA GATACTGGAT AACAGTCTGA TTTGGCAACA | 600 |
| GATATCTGCA AAGGCTCAAC AAGACACTAA TGGATACCGA CGATGTGGTT AGACTATGCA | 660 |
| GCTTAGAAGC GCCTGAAAGA ACTACAGTCC CCACGATTCT GGGANATCTC AAAATTCCAC | 720 |
| TTNTTCCNAA TTGTTGCGCC TACCCAAANA AAACNAANCT TAGGAACTTT TCATTTGTAC | 780 |
| C | 781 |

(2) INFORMATION FOR SEQ ID NO:215:

(i) SEQUENCE CHARACTERISTICS:
        (A) LENGTH: 765 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1204RP (xi) SEQUENCE DESCRIPTION: SEQ ID NO:215:

```
GATCCGCTTG GCTAGGTCCT CAGCCGGCAT GTCGTCACGG TATAGGGCCT CGGAGCCAAC      60

TAGGAAGCCG CGCACCGTGT CCGACTTGAT CCATGGCAAG TAGGTCTTGA GCGCATCCTT     120

CTCCATCGAA AAGTGAGCGT CGTCGTCTGG CCAGACACCG ACCCATAGCT TGAAGCCAGC     180

ACGGTCCGCA GCAGGACCCA AGAACTGCAA CGTGTTGCAG TCAGAGGTAG AGTAGACTTT     240

GACCGTGTCC GTGTAGGGGC GCAAGGCCTC GAAGTCGTCG AGGTAGTCCT GAGTGTACTT     300

GCAGGTACCG TCGTGCTTCT TCACACCTAG GTTGAAGGCC AAATCGCCCA TAGCGTGTAC     360

AGACGAGGCA CCAAGCAGAG CTGCGGAAAC AGTGGCAGAG AAACGCATAG CTAACGAATT     420

GATGGTGAGT TAGTCTGGCT AAAGTGGCTT GTACTGGAGA AACGACAGAG AGGGACAAAT     480

ATATGTTAAT ACCAGGTCAG CGCCATCTGC CGGAGGAAAA AGAAATGTGC CGCGTGTTCC     540

CGGCACCTTC CTTAATTTAG AAGCATTATC TATCACGTGA ATATCACGTG AAACACGTTA     600

AGCCTACAGA GAGCTATTGA CGGTGGCTCG AACACGTTA GCACTGAGTT ATGTACTAAG     660

GTGGCCACGC ACCATGCAGC TGTCCTCGAT GCAATATAAC CCCCCGGGCC CCGGCAGTCA     720

ACCGCCATCA AAAGTNCTGN CCCCGAGNNC CCTCAAATGT CCNTG                    765

(2) INFORMATION FOR SEQ ID NO:216:

(i) SEQUENCE CHARACTERISTICS:
         (A) LENGTH: 776 base pairs
         (B) TYPE: nucleic acid
         (C) STRANDEDNESS: single
         (D) TOPOLOGY: linear (ii) MOLECULE TYPE: DNA (genomic)

(vi) ORIGINAL SOURCE:
         (A) ORGANISM: PAG1024UP (xi) SEQUENCE DESCRIPTION: SEQ ID NO:216:

GATCAGGAAG CAATAGGTAC TCAATTGCGG AAGATTCAGA GACAGCAAAG GTCAAGTGCA      60

GTTCAGCAAC ATCGAATCCA CACAAGTTAT GTCGTACAGA GGCCATAACT ACAACGCAAT     120

GGCACCCGGG GGGCAGACGT TCTCCAACAG TCCATATACG AGCAATATGG GGTCCACGGG     180

GGCTCGCGGG CGCAGCTCAG AGCTGTTCCA GAAGTTCGAG CGATTTGCGA AGCGCATAGA     240

GGACGTGACG GACCACCCGC TGGTGCAGCG GTTCGTGCCG TACACACCGC TGATTGCGCG     300

GTTTTTTATT GTGGCCACGT TCTACGAAGA CTCGATCCGG ATTCTGTCGC AATGGCCGGA     360

GCAGGTGTCG TTTCTATCCT ACTACCGGCG CTACCCCCGA GTTTTCGTAG TGCTGTTTTT     420

GATGGTGGTC GCGGTGCTGA TGATGGTGGG GGCCACGATG ATCCTGCTGC GCAAGCAGCA     480

GCTGTATGCG ACTGCGATCC TATGCGCGTG TATCATCTCC CAGGATTTGT GTACGGGCTG     540

TTCTCCGGCA CTCCTTCGTG TTTGCGGAAT TTCAGCGTAA TCGGCGGTTG CTGATTACTT     600

CCGTGACTCC ATCCGTGCAG AAGCGCATCA CATTCGGCAT GCTGCCGGAG CTAACAGCAG     660

GAAGGCGCAC CAAGGCTACA TCCTGCTTGC GGCCGCATAT CATAGTCTTA GTTTGTGACT     720

TTACCTCCGC AAACTGGTGA CGNTTCCTCN CCTCGCGNAC GGTNCTCCCC TCGGTN        776

(2) INFORMATION FOR SEQ ID NO:217:

(i) SEQUENCE CHARACTERISTICS:
         (A) LENGTH: 747 base pairs
         (B) TYPE: nucleic acid
         (C) STRANDEDNESS: single
         (D) TOPOLOGY: linear (ii) MOLECULE TYPE: DNA (genomic)
```

(vi) ORIGINAL SOURCE:
     (A) ORGANISM: PAG1205RP (xi) SEQUENCE DESCRIPTION: SEQ ID NO:217:

```
GATCGCACTT CAACCCATTC AAGAAGACGC ACGGCAGTCC GGAGGACGAG AACCGTCACG      60
TGGGCGACAT GGGCAACGTG CTCGCGGACG CAAACGGCGT GGCCGTAGGA TCGGCGAAGG     120
ACCCTCTAAT CAAGATTTTT GGTCCTACGT CGATTCTGGG CCGTACGGTC GTTGTCCACG     180
CCGGCAAGGA CGACTTAGGC CGCGGCGGCA ACGAGGAGTC GCTAAAGACG GGCAATGCGG     240
GCCCCAGACC TGCTTGCGGC GTGATTGGCA TTGCCAACTG AGCTGGCTGC TGCCGCGTGC     300
CGGAAGCTCT GGAAGGTTGC CAACTAGAAG CTCTGATGAC TATGTTAGCA GAATAAACGT     360
TTTATGGTTC GCTGTGTTGG CGCTGTATGT TACAATTGCA GCAATTAGAA GTCTGCTCTC     420
GCGCCCGACG GCACGCTCGG CAGCGAGTAG CTTGGTAGGA TGTTTGCGGC CGCCAGCAAC     480
AAGCCGAGGA AGGGCTGCGA AGGGTTCTAG CACCTTGGAC ATGTTACTCT GGTTGGTACT     540
GCGTGGCGAC GTTAGTAGGG TTGGTCGACG AGCTCGAGAA TCTCGCACCG GTGCCGTCTC     600
GTCTCTGCCC CCNAATTCAG CCAGCNCCCG ATTTCTGCNC ACTTTGGTTG ATCCCNTACN     660
ATGAAATNTT CCNCCCAAAG AGCCTGCCGT TATTTCTNAN ATGACATCGG TTCCCCCGAA     720
AAGTGTCTAA ACATCCCTGT CCCCCCN                                        747
```

(2) INFORMATION FOR SEQ ID NO:218:

(i) SEQUENCE CHARACTERISTICS:
        (A) LENGTH: 777 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
         (A) ORGANISM: PAG1205UP (xi) SEQUENCE DESCRIPTION: SEQ ID NO:218:

```
GATCTTCAGG TTCCGCGACA TGATTATCAG CGAGATGGGG TGGCTGCGCC GGCGCCCCGG      60
CTCCTGCACA CGCTGCGTGA ACTGCTCCCG CTCCGGCAGG TCCTCGGGCA GCACCGCAGA     120
GATCATCTTG TCCAGCAGGA TGTCAATGAA GTGCTCCTGC TCCTGTACCT GAGACACCGC     180
GCGCAACTTG GCCGCGCGCT GCTCCTCCGT ATCCTCCTCG TCCGACATAC CGGCGCCATT     240
GTCGCTGGTC TCCTCCTGCC AGAAGCTGTC CGCGCTGCTC TCCAGCTCGT GCCGCAACGC     300
GAACTCGTCG AAGTCGTCGT CGATTGTTTT GCGCTGCTGG TCTTTGCCCG TCCGCAGCCG     360
CTCCCATGTC GCGTCGAACA GTGAGCACGC GATGTTGGTC ACCAGCTCCC GGTTCGTGAC     420
GCACGGCCGC GCCTTTTCAT CGTCTGCCAC CCTCTCCTCT GCCTCCATGA TGCGTTCATA     480
CTTGCGCGCC AGGAATTCCC CCAGCAGCGA ACGCCGCTTC TTGCTGCCAA TTGCAACGCT     540
CTCAAGCGCC TTGGTCTATC GTCCTCCTTC ATCGGTCCTC CGCCCCACG TCATATAGAT     600
TGCGGCTCGC GGTAGCACAC TGGCGAAGGC TGCCTTGGTT ATATGCCGCT AGAAGCAGTC     660
TCGGCGGTCA GTTAGTCCTT TCGTGATGAT GACGTGTTCA CGATGACTCG GATATAGAAC     720
AGTCATCTAT CGATTGAGAA CATAGCTATA TAGAAATGAT TTACTGTAAT ATATCGA       777
```

(2) INFORMATION FOR SEQ ID NO:219:

(i) SEQUENCE CHARACTERISTICS:
        (A) LENGTH: 751 base pairs (B) TYPE: nucleic acid
            (C) STRANDEDNESS: single
            (D) TOPOLOGY: linear (ii) MOLECULE TYPE: DNA (genomic)

(vi) ORIGINAL SOURCE:
         (A) ORGANISM: PAG1206RP (xi) SEQUENCE DESCRIPTION: SEQ ID NO:219:

```
GATCGCGTCC GTCGTCGTCG GCTCCTCGTC CTCGTTGAAC TCCGTCCACA GCTTGAACGG      60
CCGCGCCGAC AGGTCCACCT TCGCCACCGT CTCCGTCACC ACCTCGGTTC CGAACTTCAC     120
GGACTGCGCC TTCATCCGCT CCATGAGGTC GCTGCCCGTT AGCCCGTCGG GGAACCCCGG     180
GAAGTTCTCA ATCTCCGTCG TTGTCGTCAG TTGCCCGCCT GCAGCCACTC CGTTCGCGAA     240
CATGCCCTCG TACAGCGTCG GCTTGATCTC CGCGCGCGCT AGGTAAATGG CCGCAGTGTG     300
TGCGGCAGGG CCGGAGCCAA TGATCGTAAC TTTGTGATGC ACCATTCGTG TCTGCAAAGC     360
TTGTCCCAAC CGGTATCTTG TTGCTGCTGC TAGCATCAAC TGTGCACCGC TAAGTTTCGC     420
TCGCGCTTGC TGGTTTTATA CCTCTGGGCT TCACCATCGG TGAACCTTGA TCGCCGTTAC     480
TATTTCCGAC GCTTATGTCC GCACCTGACA AATTCGGCTT CGCGGGTGCG CGACTGCGGT     540
CAGTGGGGGG TGCAGTACAA GATACGCACC GCGGGCCTNT NGNNNTCNNC GGCCCTCTCN     600
GNGGCCCGCC GNCCCTTCNC AGGATCNTTN CCTCANCTAN AACNGGCCC GGNGNNNTCT      660
TTTTTTTGTN CNGCNAACGA AGGCAATNNA ATNTTTNNTN GGNCNTNNGT TNGAANTGTC     720
CNNCNGTGGG CATCGCNGCT TATNAACACN C                                   751
```

(2) INFORMATION FOR SEQ ID NO:220:

(i) SEQUENCE CHARACTERISTICS:
        (A) LENGTH: 778 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
         (A) ORGANISM: PAG1206UP (xi) SEQUENCE DESCRIPTION: SEQ ID NO:220:

```
GATCCGCTGC TCGTGCACCA CCTGCTGCAG GTAGGTTGCT ACTCCACGCG CGAGATATGG      60
GTCCTGGTCA ACATCCTACA GCTGACCTGC TTTAACGAGA CAACCAAGGA CAAGTACGAC     120
CGCCGCATCA TCAGTTCGCG CGGAACGGTT TCGACGGCCC TGTCTGCAGA TAAGACCTTC     180
GCTCAGGAGT TTAACTCCAA ATGTCTCAAC TTTACGACCT GGTGGCACCT CATGGCCCGC     240
CTAGACCACG CTGTTTTCAT GTGGTGTCTA GACATTATCG TGGCCGAGAA CTCACAACCC     300
TTCAAAAGCA ACCCCATCAT CCGCGATAAG CTCAACGGCA AGGACTGGGA CTACTACCGT     360
GATCTACACG TTGTTGTCAN CTATAGGATT ATCTGCGCCC TGACTCTTAC AGTGCTTCTC     420
AGCTATCATT TTGGCTTCAA TAATCTCTAC GACCTCTCTT TTGTCGACCC AGCCTTCCAG     480
ATAATAGGGC CCGAACAAGC GACTTGGGGG ACGTGCATGC AACCTTTATC AAGAAATGGC     540
ATCACAACTA TAAAAGTTC TAGTTGCTCG ACTTGTAATC TCATCTCTAA ACATAATATT      600
CTTTTATATG CTTGTATTAC TTANCCTCAA CATGATNACN TATGCCTGGA AGATTTCCNC     660
GNTGGCCGTN AGAACNGATT TGTGTCAACT TNTATAAAAC TGACCCGTGC GCCCCTCCCG     720
TAACCCGANA TTTCCTGATN CNTGATCCTA TGANGATGCC GGCNCATTNN CANTATTC      778
```

(2) INFORMATION FOR SEQ ID NO:221:

(i) SEQUENCE CHARACTERISTICS:
        (A) LENGTH: 756 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1207RP (xi) SEQUENCE DESCRIPTION: SEQ ID NO:221:

```
GATCTGTTTC AAAAATTGGA AACGCTTACC ACCTCACCAA CACACCAGGA CTTTATTTCG      60

TAGAAACAGG CGATCGGCCT GAACAACAGT CACTAGAAAC GGTGCACCAA GGCAGCTTGG     120

CAACGAGGAG GCACCCTAGG GCTCAATGCG TTGATAGTAA AGCATGTACA CGAGCTTTGT     180

CTCCGAGAGA AGGAACGACG TCTTGCACTC CGACACGTAC GAGTCTGAGA TACACCACCA     240

CGGGTGCGTA GTGGTGCGAC GTAAAGCCTT CAGTTTGCGG GGACGGCCCT GGGGACGGGG     300

GAGTACCTTC GTGGCAGCCG AAGATACGCC CGATGAGCTC GCAGAGCTGG CTCCGGAGCT     360

GTCCTGCTCG GCTGACGCGT CGGGCTTGGA GACGGGTTCT TCCGTTAGTA GTGACTGTTG     420

ATGGAAGCTC CCCAGTAACG GTCTTGAGCA AGCGGCCATC GGCCCAGGCG GAAGGCTTCC     480

AGCTGGCGTA GGGCACAGGC ATTCGAGGGG CTGGCTGCGG GACGGCGTCC GACGAGATCA     540

CATCTGAGCG AATGATATCT CGCCCGTCCT TGGTCCTTCC TAAGTCAGTT TGTTGGCGAA     600

CATGCGTTAT GCCCTGAGAA TGGTTGCCAT GTGCTTGATT CATGCGCCAA CAGCTTATAG     660

CGAATGCCAA ACCCCCACCA TTGTTNTCCC CNACACTGCT CNTGAGACAC CCCCCCCGGA     720

AANTNAATGC GGTTTNTTTG TTAAAACCCN TNAAAA                               756
```

(2) INFORMATION FOR SEQ ID NO:222:

(i) SEQUENCE CHARACTERISTICS:
        (A) LENGTH: 771 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1207UP (xi) SEQUENCE DESCRIPTION: SEQ ID NO:222:

```
GATCTAATGA GCGATAAGTC ACCGGTTATA GAAAGTTCGC CGAATCCTAC AACTGACTCC      60

AACTCGCCAC AGGAGATATC TCTATTAGAA AAGAATATCA AGGATGTCAT GCGTTCACTA     120

AAGGGCGTTG ACACGCACTC ATGTGAACAG ATCATTAACG AAATTCTTGT GGTTGATTAC     180

GATGTTCGAT GGGAAGATAT AGCTGGTCTT ACAATAGCAA AGAAGTGTTT GAAGGAAACA     240

GTTGTTTACC CATTTTTGCG GCCAGACCTT TTTCGGGGTC TCCGGAACC TATCTCCGGG      300

ATGTTGTTAT TTGGACCTCC AGGAACAGGT AAAACGATGA TTGCCAGGGC CGTTGCGACT     360

GAATCGAATT CAACTTTCTT TTGCATCAGT GCTTCCTCTT TGTTATCGAA ATACTTGGGT     420

GAGTCGGAAA AACTTGTCAA GGCCTTATTT TACCTAGCCA AACGGCTTTC CCCCTCAATT     480

ATATTCATTG ACGAAATCGA CTCTCTACTA ACTACCGTTC AGATAATGAG AACGAATCAT     540

CCAGAAGATT AGACGAGCTC TTGGTCCAAT GTCCTCCCTA ACGAGCGCCA CGGCTAGGAA     600

CAGAGAGGCG AAGAGGCCAG ACGCGTACTG TCTTGGCCGC AACCACTTAC CGTGGGCAAN     660
```

```
AANGANGCTG CNATAAACTT TTTCACGGGT CTATNATCCC TTGCCGGAAT ACAACNAAAT        720

GTTCTTTGAA AACTTNTGGC CTCCAAAAAG AATTTCGAAC TNATTCNNCN T                771

(2) INFORMATION FOR SEQ ID NO:223:

(i) SEQUENCE CHARACTERISTICS:
        (A) LENGTH: 740 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1208RP (xi) SEQUENCE DESCRIPTION: SEQ ID NO:223:

GATCAATTAA TAAATGGTTT AACTAATAAA GTTAATAATA AATCTATTAA TTATATAAAA         60

CTACCTGATT TTATTGAATC AAATAATATT TTCTTAATGA ATACTACTAA ATCATCATCT        120

ATTGAGTTTA TATTAAATTC ACCACCTCTT ATTCATTCAT TTAATACTCC TCTAATTCAA        180

TCTTAAAATA TTCTTAATTA TTAAATTATA TAATAAAAGT TAGTGGATAT AGTTTAATTG        240

GTAAAACATA TGTTTTAGGG ACATATATCT TCAGTTCAAA ACTGAATATC TACATATTAT        300

ATCATTAATA TAATAACTCT TTAATTAGAG TTGGTACCAC AAGAATGCTG AAAGCATTAG        360

GGGTGTGTAC CTTAGCTCTC CTAATTAAAG TTTATAAAAT TATCCTTAAC TAATAAAAAT        420

AATTAATTAA ATAAATAAAT AATTAATTAA ATTTAAAATG TTTTAAAAAA AGAAATAAAT        480

AATATGTTTA TATTTAAATA GATTCAAATT TCCAACAATT CCCATTCATT TAGTACTACC        540

ATCACCATGA ACAATTGTTA CATCATTAGT TTATAGTTTA CTATACTTAG CTTACTAACA        600

TGGTATATGG TATAATANCC CTAATAAACC TTATANANTT TTTACCNAAC TTNGATTAAA        660

AAAAGGGCGA NCNNCTTTGG NGGACCCCTA CCCNTAAAAG GNGTAATGGT TCCCCAATTG        720

GTGGCCGAAA TAANTTGGCC                                                   740

(2) INFORMATION FOR SEQ ID NO:224:

(i) SEQUENCE CHARACTERISTICS:
        (A) LENGTH: 782 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1208UP (xi) SEQUENCE DESCRIPTION: SEQ ID NO:224:

GATCTTAATT TAAAATTTTA ATTAACTATT TATAATTTAG AAATATATAA TCTAGAGATA         60

TATAATCTTA AAATCATAGG TAAAAATACA TAAGATAGTA AGAATAAAAT TAGTAAAATA        120

AATAGAAAAC CATAAGTTAA TTGATTCATA AAGAAAAATG GAATTATTTG TGGCATCTTA        180

ATTTTTATTA TTTAATTGAT TATTATCTAT TTAACATAAA ACATTTTAAA ATGTTATAAA        240

ATAAATAAGA AATTACTTAT AGAATATTTA TTAAATAGTA TTTAATTTAA TTTTAATATT        300

AAATATACCA TTTTTATTAA TAAAATAGATT ATTAAGTTTA TTAATATTAA GTGATATATA      360

ATTTAATTTA TATAAATTAT TTAATTTACT TCCCCTGATA TATATAATTA TTAAATGTTC       420

CTTTCATAAT ATTTATTTTT ATTAGTCTAG TAATATTTCT ATTTAATAGT CTACCCCTTT       480
```

```
AATTGGATAT TACTACCTAC TAAATATTTA CCCTAATAAT ATATTATTAA GAATACTTAA        540

TCCTAATAAT TTATTATCCT AAGTTATATA AATTAATTAA TCCTTTTTAT TATTATTTAA        600

ATTATTATTA ATTAGTAATT ATATTTATTA TTTTATTAAC ATAATTTTTG ATAATATATA        660

TCCATATAAT GGTATTTATT ATATACCNTN ATGAATTAAT GANAACCCTA TATATGANAT        720

TAGTTATAGT GACTTAATCC CNATCTCAAT ATATATAATT ATTATAGAAN ANATACTTTT        780

TC                                                                      782

(2) INFORMATION FOR SEQ ID NO:225:

(i) SEQUENCE CHARACTERISTICS:
        (A) LENGTH: 533 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1209RP (xi) SEQUENCE DESCRIPTION: SEQ ID NO:225:

GATCAGCCTA TGTAGCAACT GATCGGCGCT GGTCCGTGTC AAACGCCGAA AACACCCCAC         60

CAGATTACGC AGACACTCCC ATATTTTGAC CGACTGGAAC TTTGTGTACA CAAAGCTATT        120

CAGCTTGTCA CTGGCCACCG TCAGCGGCAT GTTGTTCAGC CGAGTCGCTA GCGCCGCACT        180

GCTGTTGCCC TGCGCCAGCG ATGGCTCCTT AAGATCCTGC GTTCGCATAT ATTGCGCAAA        240

CTTCGATAGG TCTCGACTGA GCGAATTACC GACATGGTCC AGTAATAACA ACACCCCAGG        300

GCAGCCCCCC CAGCTGTAAT TCACCGTTTT GACCAGCAGA AAGTGCAATT GTAAAAGAAT        360

GTACCAGTAA TGCCAGTAAA ATGTGGAAAA GACCTGGTCG TTCTGAAGAT ACGAAATCAT        420

CACCTGAAGA TTCTTCAGTC TTCTCCGTCC CGAACATCTT GGAAAAATCT GCNGNTCGTC        480

GCTTCTCTTC CACTCGAACC GCAGGGCTTC CAAGGACACT CCTTGCAATT GAA              533

(2) INFORMATION FOR SEQ ID NO:226:

(i) SEQUENCE CHARACTERISTICS:
        (A) LENGTH: 534 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1209UP (xi) SEQUENCE DESCRIPTION: SEQ ID NO:226:

GGAGGATCGT CGAACTTGAT TATTTTCTTC TGGTACGACG ACAGCTCGTC CGCGTTCCGC         60

TTTAACGCCA CCAGCACCAC GTACTTGTTC GACCGCAGCC CGACTGTGGC GCTCCCCTGC        120

TTGATGGCCT CTAGCGCGTA CTCCACCTGG AACAGTCTCC CAGTCGGGGA AAACGTCACA        180

GTATCACCGT CGTAGTTATT TCTGAACATC ACTAACTCAC AGNGCCCCAA TTGNTCGTGC        240

ACACCGCCCT CTTTACTGGT GCTAGTTAAC TGGACAGGAG CTGTGTTTGC CACCCGGCCG        300

CGGGAAGTAG CTCTGGTATT GTCATTTGAT ACGGAGATTT GATATTCGTG GAAAGGTATA        360

TAGATGATTC CGTCTCCGCG ATTGATTGGA GGCTCGGTCG CATACTGGAG TCGTCCGANG        420

TGTCGNATCT TCTACATAAC CGTTGNAGGN CAGGGGAGAG GTTTGNNNGC GCAGTTGTCG        480

CGGAGTACCA TATTAGGCGA TGTGCGGTGA AGAGGTATCT ACTGGTGGTG TTAT             534
```

(2) INFORMATION FOR SEQ ID NO:227:

(i) SEQUENCE CHARACTERISTICS:
        (A) LENGTH: 547 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1210RP (xi) SEQUENCE DESCRIPTION: SEQ ID NO:227:

```
GATCTAAATT TATCAGCCCA TGGACGGATG GATTTACGGC AGCGTGTCGC CGCAGCACGG      60

GGCACGCCAG ACTGCGAGGT GGCAAATAAT TCACATAGCA ACCTGCATTA TAAACATCCC     120

AAGTCATTAA ACTTACTAAA TATTGTTGCG TAACCAAAAG CACCGTGTAT CATCATCTTC     180

ATAGTCTTAG CTGAACCTAC TGTCGCACCA GCCCTTTACT ACGTATTGTA TCTCCCTTTT     240

ACAATGCTTG CCCACTGCCA GTTTTCCGCA CGGGCGTTAG CATGAAGTCT TTGCCGCCTT     300

TGTACCACGG CTTGACGTCT GACTCTACGC GGACCAACGA GGTTAGACGG AGTGCACCCG     360

GGACCGAGTC ATCCTCGCTC GCGTGTTCCC AGAGACAATT TGAGGTTCCA CGGAGCATCC     420

ACGCCCATGC AATCCTGCCC GTAAAAGTTT GCACANTTCA TCCCACACTT GGGGGGTTNT     480

TATCACNCCA NCCTGATCTG GTACGNAAAA NTTTTCCNTN TTTGGTGAGG AAATCAGGTT     540

CCCAATA                                                                547
```

(2) INFORMATION FOR SEQ ID NO:228:

(i) SEQUENCE CHARACTERISTICS:
        (A) LENGTH: 600 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1210UP (xi) SEQUENCE DESCRIPTION: SEQ ID NO:228:

```
GATCGAGAAG ATGCGGCGCC GCAACGAGGC CGCCACGCCC GAGGCGGGCG GCNACGAGCT      60

CCTGACGCCG GCGGAGCGCT ACGCGCTGGA GCAGGGGCAG GGCTTCCTGG CGCCTGTCGT     120

CCCTGTCGCN GAGCCGGCNC GGCCCCTGGC CGTGCCCTGC AACGAGCTTC CCGATGAATA     180

CTGCATCACC AAGACTGACT TCGACCGGCT CGCTAGCCAC GGCATCCCGG TCGAGGACGT     240

CCACGAGGAC AGCAAGGACT GGTACTTCCA GTGCCCCTGT GGAGTAGAGG AGGTTAGCCC     300

GGGCCTAGAG AGCCCCGCGC TGCAGCAGGC CCTGGTCTGC TGCGACCAAT GCCTCCGCGT     360

GGCAGCAGCT GGGACTGCCA GCACCCCGCA GCGATTGAGC TTGCTGGCCN GCGGGCAAGA     420

CTCCTCACTA TTTTGCCCTC CNTGCCCCCT TGGCCTGCCC CACGCGCCCG CGCCCTCACG     480

GGCGGGNGCG GCGCNAAAC CCCTACCAGA ACCAAANNAA CNACGCCNCC GCCGCCCNTC     540

GGTGAAGCGA ACCCTTTTTN NCTCCTGTCT TCCCNCCCTG AAAGACCTAN TTCTCCTTCA     600
```

(2) INFORMATION FOR SEQ ID NO:229:

(i) SEQUENCE CHARACTERISTICS:
        (A) LENGTH: 539 base pairs
        (B) TYPE: nucleic acid (C) STRANDEDNESS: single
        (D) TOPOLOGY: linear (ii) MOLECULE TYPE: DNA (genomic)

(vi) ORIGINAL SOURCE:
        (A) ORGANISM: PAG1211RP (xi) SEQUENCE DESCRIPTION: SEQ ID NO:229:

```
GATCTCCTCC AGTAATGGCG TCAGAGCACA CTGGTAGCGG ACCCCTGCCA GGTAGCTCAT      60

CGGCAAAAAG ATAGCACGCG TATGTACCCA CCAGCGAGCC GGGTGATAAG GAAACTGGTA     120

CGGCAGCAGC CATAGCTCTG GTGGCGCTGG GTTCACGCCC TCCCACTTGT ATAAATTGAG     180

CACGGAAAGC CACACTTTAC CCCAGTACGG CGAGCCAATA GCACCCCCCA TGCGCAGCAG     240

GGTCTTCCGC GCCCGCTGCA TCACGATGTG TTCGCGCTCC ATCCCTAAGA GCCGCAGCAG     300

AACGTAGTTC AGCGCGGTGC CCATCGACAG TCGACTTGTC CTCCGAATGC AATCCCCACC     360

CGCCGTCGAC AGGTGTGCCG TGTTCACCAC GTTAGCGCAC TAGCTCCCGC CGCTGAGGCT     420

CAGGAATACC ACCCCGCCCA CATGCATCGC CACCACATAC CCATATCATN ACATCNGGCC     480

CCCTGTTACA ACAGGAAANT GCCCNAACCT CCTCCTGCAG ANGGCCCAAA CCGCCCCCG     539
```

(2) INFORMATION FOR SEQ ID NO:230:

(i) SEQUENCE CHARACTERISTICS:
        (A) LENGTH: 593 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1211UP (xi) SEQUENCE DESCRIPTION: SEQ ID NO:230:

```
GATCTACATC ATGGGAGGCT AGGAAGAGCA AGGCACCGCG TGCATTTGTA GACTACACGC      60

TATAATATGC AAATGGCCAA TACCTTTGCC CCGGATCCAA AGAAGGGCAC TGTCAAGCAT     120

ATGGTTATCG AGACGAGCTT CAACCACTTG GCTCTAGGCA TGGTCAGCCA GATATTTCCG     180

CACTAAACAA CGTCTAGAAA ATGACTTGAC CTATGACGTG CCGGGCTTGA CTCATCTTAC     240

TATCCTCAGG CCCGGCCCTC TTCTTGGCGA GCATGGCTCT AAACCCGTAA TAAGCCCTAC     300

CAACCCTGAT ACAGGAAACA TGCTTACGCG CTGTTACACT TATAAGAAGA ATGTTATGCG     360

CACGCAATTT AATTGGCTTG CGCCAGTTTA AGAAGTTGGG CCAACACTAA GTCACCCGAA     420

CTATCCGCGA AGGCTACCTA TCATTTACCC TGGAACTGGA TTGTTTGGCT ACTCANTCCC     480

CAGCNTGAAA ATTGCCCCNA ATTGCCGCTC CAGAANCGCT ATCCAACGGA ACTACTCGAC     540

CAAATCTAAT TTCCCCTATA ATGTGAATTA CACTGTNAAT TCAGAANTGA ACN           593
```

(2) INFORMATION FOR SEQ ID NO:231:

(i) SEQUENCE CHARACTERISTICS:
        (A) LENGTH: 536 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1212RP (xi) SEQUENCE DESCRIPTION: SEQ ID NO:231:

```
GAGATCTCCC AGTACGTCTT CAAGCTGGGC TTTGGCGGTC TAGGATAGAG CCGGCGGAAC      60

TCAGGACTGG TCGAGACGGG ATGCTGGATC CCGAAGCTCT TCATAAGCAA CAACCGCGGT     120

TGCCGCGTGT AGTCATCGAA CCGTCCCTCA GCGAATCCTG CGAGTCTCCA CCTGACATCA     180

CCATTGCCCA CGATGCACCG AAGCGTTTCT GGAAGGAACA CGCAAACTAG CAAGAAGCCG     240

ATGCCGGCCA TGATGCTAGT GAAACCAAAC AACCATCTCC AACGGTCATT ATCGAATAGG     300

ATCAAGCCAG CAATAATGGG CGCCCAAAAT CGGGCCCACN TTTAGGGCCC CAACATNAAT     360

TACGCAATTG CCTTGCCGGG GTTTTTCGGN GGTGTTGATT TCNCTTACCG TACGGGCCCC     420

TGAGAAAACG AGAACTCNGA GGAAATGCTG CNCCCCTNTT AAAAAAATAC NCCCATCGNG     480

CAGGNTGAAA GCANTTACNC TTGACTATAA ATCANCCCCC GANAANNTTA NACTCG        536

(2) INFORMATION FOR SEQ ID NO:232:

(i) SEQUENCE CHARACTERISTICS:
        (A) LENGTH: 586 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1212UP (xi) SEQUENCE DESCRIPTION: SEQ ID NO:232:

GATCAGCAGT GTCTTCCGGG ACGTCAACGG CTTGACGGTC TTGCGTACCG TGGCCAGCGT      60

CCGCACGCCA TGAAATGCCT GCACTGCCTG CCGCAGTCCA CAGTTGCGCA GCGATGCCAG     120

ACACGAAAAC ATCCTCGTTA ATGCAGCTTG GGTCCTTCCG TCGTCACTGT GCGTCTCGAT     180

TAAGCCCAGG TTATCAGTAA CATCAAAATT TTACATAACT GCCACGTGAT ATACACGTGA     240

TAAAGATCTA CACCCATGCC CCTGATTGT GTAAAAAAGC AACTTTTGAA AAATTTTCTA     300

CGGTTCCATC CGATGAGATG AGCTTAGCCT AGTGCGAGTC CAATATCAGT GCACTAAGTT     360

TATCCAGTGA TACTTGTTCT CGAGCTTTCA GCAACAGCAT CAGTTTACAA ATCGCACCAG     420

CAGTTATCCC TGGAAAGAAA TCCTACGGTC CGAACTCCCA TGATAGTTTG ATACGGCCCT     480

TACAGACGCC AGCGAAAATC CCACATCTCC NGGNGGCTTC AAATNNNCTT CCGNGGTTCT     540

AAAGCTTAGG GGNATTCCCA TGCANGGGTT TATNAAATTT GANAAT                   586

(2) INFORMATION FOR SEQ ID NO:233:

(i) SEQUENCE CHARACTERISTICS:
        (A) LENGTH: 535 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1213RP (xi) SEQUENCE DESCRIPTION: SEQ ID NO:233:

GATCTTTTTT AGAGAGTTCA GTGTCGCGAC CAACACGGTC GGAGGCCCTT CAGCTACTTC      60

CAGAAGGTCG TAAAGAGTCT CCAGTAGCCC CAGGGTGCGC TCGTGGTCAT AACAGTCCAT     120

CTGAGGTAGC GTGTTAATAA CCGCTTTCAG CATGCTCGTA GAGGACTTCT TTACTAGGGC     180

AGAACTTATA AACTTAAATG TCTCGTCTAT GCATTCAGGG GTACGAAGAG CTGCCAGTGT     240
```

-continued

| | | |
|---|---|---|
| CCGAATGTCA TCAGCCGATC TGCTCGTTTT ACTTTGCTCA GAATCGCGCC ATAGTTTAAC | 300 |
| TNCNGTTCCC AAATTAACCC GGTTTCCCNG GACCCTTTTN AACAAAAAGG AAAAAAAATT | 360 |
| CCGTTTCCCC CCCNCTNCCC NNNNTGGGCN AAAAATTTTT TNCCNCGGGN AAAATTTANC | 420 |
| CCCCCCNCTT AAGNCCCATT AAAAAAAAAN NNNNNNTTTT TTTTTTTTNT NGGNGCCCNN | 480 |
| NAAAAANNTN CCCCNNTTTN NAAAANNGNG NGGNTTNNNG NNNNANANNN NANNN | 535 |

(2) INFORMATION FOR SEQ ID NO:234:

(i) SEQUENCE CHARACTERISTICS:
        (A) LENGTH: 603 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1213UP (xi) SEQUENCE DESCRIPTION: SEQ ID NO:234:

| | | |
|---|---|---|
| GATCGCCCAC TTCACGAACT CCAGCTCCGC AGGCCGAAAC GTCGTCGCCA GCTCCGCCTC | 60 |
| GCGCGACGCC CCCACGTTCA CATACACGTA GAAGCGCCCG CCCTCCGCGC CTGCCTGCTC | 120 |
| CCCCGCGTAC CGCCGCCCCA GCGCGTGAGT CACCCGCTTC ACCTGGTACC CCAGCCCCCG | 180 |
| CAACCGCACG TTCATCTCCG TTACGTATGT CCCCAGCTCT CCCCCGTCGC CGCCCAGCGC | 240 |
| GCCCAGGCAC TGTGCCAGCA CTTGCTCGTG CACCGCCCCC CGCGCCCGCA GGATGCACTG | 300 |
| CAGCAGCAGC CGCCGTCTAT CGTCGCGCGT CGTCTCCGTC ATTGCTCTCC TGCGCCCCCG | 360 |
| ATGCACGCAA ATCCGCTCTC GAATGCCTTT GGCCTGCCCC GGCTTGCGGT GTCTGGGGTT | 420 |
| GATTGCCACG AATGCTGAAC CAAACTGACA CATTTTGCCA AAAGAAACGC CAATGTCTCT | 480 |
| CGAACGAATT TCNCGNTCTC GTTGAACTAA CCGCCGCGCC CAGTTGGGTG AAGCCGCTGC | 540 |
| TGTTCCCACC TATCCGGTAG GGTTCAGCCT TCCTGTGNTT CCACTANTGG NAAACNCCTG | 600 |
| CTT | 603 |

(2) INFORMATION FOR SEQ ID NO:235:

(i) SEQUENCE CHARACTERISTICS:
        (A) LENGTH: 527 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1214RP (xi) SEQUENCE DESCRIPTION: SEQ ID NO:235:

| | | |
|---|---|---|
| GATCGTTCAC GTCAGCCAAT TCTGTGTCGT AGCCCACTAC ATTGTAGAGC TTATAGATTA | 60 |
| AACCTCGAAT GCAATCATTG GGGTAAGCCA CAGCTTCTGT AGTCTGCCTA TAGCAGAACT | 120 |
| TTTCATCTTC AAGGGTATGT CTTGAAGGCG GCTTTAAGGA ACCCTTCATC GAAGTACTGG | 180 |
| GTCTTTCTAC CCCTCCGCGG GAGCAGGATG TTAGCCGGAG CTTCTGAATC AAACTCTTGC | 240 |
| ACTTCAAACT CTTGTCGTGG ACCGAACGCA ACTTTAGCTG CGCCTTCAGG TTTTGTTTCT | 300 |
| TTACTGCCAG AACTTGTGGG CGGTGATGGT AGGAATTTTC TCCCATCTGG GTTAAGTTCC | 360 |
| TTCCATATCN ATTGACACTG CACGCCCCAA CATTCNAATT TCCANANCCC CTACCCCCCC | 420 |
| NANATGTTAA TTTTTCNGGT TTAAAGGACT TATCNNCCCT NTCAATTTTT CTTNAATNAA | 480 |

CTCCATTTGT CCCNAACNAA CAATTNAATT CCCCTGTTCC TTCCCNA                527

(2) INFORMATION FOR SEQ ID NO:236:

(i) SEQUENCE CHARACTERISTICS:
        (A) LENGTH: 597 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1214UP (xi) SEQUENCE DESCRIPTION: SEQ ID NO:236:

GATCAAGACC TGACGGCTTC CTAAAATCGC TAAGTTTAGT ACATAAATTG CGGCAAGAAT     60

TACCCAAATC ACCTGCTGTG GAGATACGAG GCAAGCTGAG CGGGTGGATG TGCCCATTCC    120

ACACCAGTAA CTCTTTGGTG TGTGGCTGTC ATGGTACTGC TCGCTACCGC CGTGTTCACG    180

GCCTTGTCTA ACGGGAAGCG ATGCCGGTAA AGCCAAATCA TGTAACACCC AGCGATAAGT    240

CCACGAGCAG ATGCTGAGAG GCTCGACCAG AACGACGTCG CATGGGTGAT GCTACAGATG    300

CCTATGCGTG TGACAGGTCG AAGCAACTGT GTTCTGCTTC AAGTAATAGC CAAACTTGGC    360

GCGGTAGAGA ATGACACTGC GGTGTCTGTG CATATGTTGG CACTATGCAA GGTTACAGAT    420

TCGCAAGCTG CCCGAATGTT GGCCCAAATT CGAACAACCA GCCAGCTATT GGTATGGAAT    480

TATATACAAC TTGGTNGGGG AGGAATTCCG GTGAAAAACG GCGCACCAGG NAACTTTACT    540

GGAACGGGAA NCGGGNAATT TCCCCCCCNC CCCGGGTTTT TGGAACCGGC CCCNTTG       597

(2) INFORMATION FOR SEQ ID NO:237:

(i) SEQUENCE CHARACTERISTICS:
        (A) LENGTH: 754 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1215RP (xi) SEQUENCE DESCRIPTION: SEQ ID NO:237:

GATCAGAGCA AAGTGATTCA AAGCGATTTT GGACGACGCG TAAGCTGCCA GCGCAGGATG     60

GCCCATCTGA CTGAGCCCCG AGGTTACGGC AATGAAAGCG CCCTGCGACT TACGTAGCAG    120

TGGAAGCGCC TTGCTGGCCA GATTCACGAC GCTAAACAGA TTAATCTCGA ATAGGCGTCT    180

CCATTCCTTG ATGTCCGCCT CCGCGATGCG TTGTTGGTAC GAGACACCCG CGTTCGCTAC    240

GACAGCGTCT AGCCGCCCAT ACTCCGAGGA CACCTTATCG ATCACGGCCT GCACCACACG    300

CTCGTCAGTG ACGTCTCCGA CAACATAGTC GAATTTCTTG CCATGTCTCG CCTTCAGCTC    360

CTGCAATTTG GTTTCCGCCC GTGCAACCCC TACTACAACC ACGTCGGGGG TTGAGCACAA    420

TCTGTCAACG GTTGCCGCGC CAATGCCACG CGATGCACCT GTCACAATTA TAACCTTCAT    480

TCTTGCTTGG TACTTTATCT TCAATGGGCC ACGAACGCTC CCGCTGTTAG TTTATATATG    540

ACTTCAGGGG CTGTTGGCAC AGCTCACTAG CACACTACCC TTCACATGTC ACACCAGTTC    600

GAGAATGAAT GGCACAGTTC CATTTGTAAT CATGATTATC AATACAATAT GTGTTGTAAT    660

TATTGATTTG TAATATGCAT AATATAGATG GTTATGATTT GTAATACAGT AAATATACGG    720

TAAATATAAA GTATTTTAAG GAATATTTAT AATT                                           754

(2) INFORMATION FOR SEQ ID NO:238:

(i) SEQUENCE CHARACTERISTICS:
        (A) LENGTH: 776 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1215UP (xi) SEQUENCE DESCRIPTION: SEQ ID NO:238:

```
GATCGCCCGG GGCCTACGTC ACTGCAGATT GGCGCAAGCC AGGAACAAGA CGGACACTAA      60
GTCATTCTGT TTATGTAGAT TGGGTGCGCA GCAGCGCACG CGGCGCCGCT GATCTAGCCG     120
TACCGCACCA ACGGCGGGAC GCATGCGGGC CCGGCGCGCT AAACCACGAC CGTCGTGCCC     180
GGTGCCAATG GACCGCGCGG TCATCCACCC CGCTCAGCCG GAATGTAGAC CAAAAAAGA      240
GTGTGGTTCC AGCTCTCAAA TTGGGCTGGT CTCAAGGGGT CGCGGCCCCG CAATCGCCTA     300
TATAAACGGA CAGCGGAGAC AGTCCGTGCA CTGTCGAGGA CAGGCACACC GATGGTGAGG     360
GTTATCATTG TGACAGGCGC GTCGCGCGGC ATCGGTGAGG CAACCGTTGA AAAGTTGTGC     420
ACAGCCCCCG ACGTTGTGGT GGTGGGAGTT GCGCGGGCGG AAAAGACTTG AAGGTGCTGA     480
AAGAGAGATA TGGCAGTAAA TTCGACTACG TTGCTGGAGA CGTCACCGAT GAAAGCGTGG     540
TGCAGGCGGT GCTCGACAAG GTGTCCTCGG ATTATGGGCG GCTAGACGCC ATCATAGCGA     600
ACGCAGGCGT CTCGCGCTTC GAACGCATCG CCGAGGCAGA CATCCAGCAG TGGAAGCGCA     660
CGTTTGAGAT CAATTGTTTA GCGCGGTAAG CCTGGTGAGC AAGGCGCTCC GATGCTAANG     720
AATCCCAGGG TTACGGTGAN TGTGGTTACC TCNNGANTCA ACNAGGTAGN TANCCG         776
```

(2) INFORMATION FOR SEQ ID NO:239:

(i) SEQUENCE CHARACTERISTICS:
        (A) LENGTH: 546 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1216RP (xi) SEQUENCE DESCRIPTION: SEQ ID NO:239:

```
GATCAAGTCT TTTATCACTA CAAATGAGCA GCGCTTAAAT TTCCAGAATC GTTTACAGCT      60
GGGTACGCTT GCAAGCAAAT TTGGCCTTTT TGAGCTAGCG GAGGAACAGT TCGCTCACGC     120
CAAGCGCCTC ATGCGGCCTA CAGAGCGCCG CGAGCTTTAC ATGTATTACA AATCTCTCAG     180
CGCGTTCTAT TCCTTAGCCA AAATGCCGAC CTGCTTAATA GATACTCTGC GTGCCTTTAA     240
TAACGAGCCG CACTCGTCCC TCCGTAACAC ACTACTGGCT GCGCTCTATC CGAACACATA     300
TCCACTGGCT CCGCCGCAAT AATGCAGAAG AAGAGGTCCA TAGATGAGCT GAACCAGCCA     360
GCGCCANCAG AATGTACTCC CACTTATGCG AACTCCNANA NTGGAAGGCC CTGCATACAT     420
TTCCGGTCCC ACCNACTTCT GCGTTCCTTG GCTTACCACT CTTGTGAACC GAATNGTGCG     480
GCATGCCTTG CCCAAAAACC CCTGGAAATC CATAAATACC TCNCGGGGGT TANCTGCGCT     540
CCCCCG                                                                546
```

(2) INFORMATION FOR SEQ ID NO:240:

(i) SEQUENCE CHARACTERISTICS:
        (A) LENGTH: 593 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1216UP (xi) SEQUENCE DESCRIPTION: SEQ ID NO:240:

```
GATCTGTGAA TATATGCTTG GGGTCGATTG GTTTGCCAGT GCTATAGAGA GCGGTCACCG     60

GCGTACGCAC GGCAACTCTT CGAGTTGTCA GCCCAAGTAG CCTGATCATA TACAGGTGAT    120

GGATGGCTCC TGTATACCTT CCCACACTGC AAGCCCCTGA GTTGCTCAGG TGTTACTGCG    180

GCAGATGGTC ACATCGCTTC GGAGTATATA GTCTGCGCTT TGAGCCACTT AAAAGGGGCT    240

CGCCGGCTAG CCCGGCCGCG TGGTCACGTG ATTGCCATCT GCCCCGAACG GAAACGTAAC    300

AGGCCGTTGT AACGTGGTGC TCATCCGTCA GCAGGCCGGT CTCCCAATGT ACTTCGCATA    360

TGTTATTTTA CGTTTATGTT ACCTATCGAG GGTCGCTCAG GGTTATGCCC GCGGTGCTGC    420

CCTGCCACGG AACCCGCAGC CTGCAANCCT CCCTAATTGC CCATGGTGAA TTGAACTCNC    480

AAGCTTATAT CTCCTTGCCT GATCCCCCAT NATGCATTTG AAGTTCNCCA NAGGACAAGA    540

AACANACNCA AAAAACNAAA TGGTTAAGTA AAATTGATTT GGTGTTCCCN CCT           593
```

(2) INFORMATION FOR SEQ ID NO:241:

(i) SEQUENCE CHARACTERISTICS:
        (A) LENGTH: 592 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1217UP (xi) SEQUENCE DESCRIPTION: SEQ ID NO:241:

```
GATCTCGTTT CTGGGGATTT TTATTGGGTT GGAAGAGGAC CTTGGGCCTA CACCACTGAA     60

GGTGTGCGAG TTCTCCAGTT GAGGCCTATT GAAGTGCATA TCTGATGATA GAGCGCTCAA    120

ATGTTCTGAT CCTGACATCG AATAGAGCGC ATTTTTCTGT ATCGTAGCCG CTGGGTTCTC    180

GCGTGGGATA TCTTTGATGT TTGGAGTGGT GTTGTGCATC ATGTACACCA TATTTGATGT    240

AATCGGTTGA ATACCATGAG GAAGTGGACT CATTTGATTG GCTGGTGGCT GCGGATGTGT    300

TACCATTGGC GTAGAGGTTA GAAAATTGGT GAGTTTGCCA AAGGAAGAGC TGGCTGGCTA    360

GCAGAATGAT GGACTGGCGT TCAAGCGCCA TGTTTCNTCC TTTCGAGGTT AAAAATTAGG    420

AAGGGGACAA GGACTCCCCT GAATCCTACT ANCCCCTTCT AAAACTTGGC AATATTGGTC    480

CCCTGAACAG ATGCNCCCNC CACATCCCCC TATTAAATTT TTTAACAACC ATATTTGTGG    540

ANACCTNGAA NTTGAACTTG CCNGCNAANN GATTCCCCTN CCTCCCCAGA TN            592
```

(2) INFORMATION FOR SEQ ID NO:242:

(i) SEQUENCE CHARACTERISTICS:
        (A) LENGTH: 558 base pairs
        (B) TYPE: nucleic acid

```
      (C) STRANDEDNESS: single
      (D) TOPOLOGY: linear (ii) MOLECULE TYPE: DNA (genomic)

(vi) ORIGINAL SOURCE:
      (A) ORGANISM: PAG1218RP (xi) SEQUENCE DESCRIPTION: SEQ ID NO:242:

GATCTTTGTG GGCCACGACG ACCACCGGAG TACCGCCCGT GGCTTGGACG TACCACTGAA      60

AAATGTTCTG CATGAATCCC ACCTTGATAA TACCCATGGA CCACTGGAAG TTCTGCGACC     120

ACGCAGCAGC GATGGGTGGC ACACGAGCCA CTCCCATCAT AGACGTGATC GCCAAATTTT     180

GGAAGTACGA GAAAAGAGAG ATCGAGTTCG AAGCGATGTG CGCGGCAGTG GTTGAGTGCC     240

CGATCACAGA CACAAACCCG GAAGTCCAGG ACACCCACAC CAGCTATCGC GGCGAATCGG     300

CCACGAATGC ATACTTCGTC TGCACCGTCT TGCCGTGCCG ACAGCACCCG CCCTGCAACA     360

CAGGCCCATT GGATGCTCCG TACTGGTGTT TCAGCTTTCC GCNAAGGCCT TTACACCATC     420

CGTGCTTCCC AGTTCCCNGG AAAATATACC CCNCCTTGGT ATCTTCCCNT GAAAAATCAC     480

CGCCGAAATT TCCCAGTTGA ANCCTCTTTG ATTCCCCCCC CNTGCCCTCC CCCAGNNCGG     540

GANATTCACA ACNAATNC                                                   558

(2) INFORMATION FOR SEQ ID NO:243:

(i) SEQUENCE CHARACTERISTICS:
        (A) LENGTH: 604 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1218UP (xi) SEQUENCE DESCRIPTION: SEQ ID NO:243:

GATCCACAGT TTCCGCACTG AACTTACTAT CCCTCAGCAA CCGCAGGTCA TCGTCAAGCG      60

TTGTGACATC AGGCTTCACC CCGTAGCTCA TAATGCCTGG GACGGATGCC TTGGTAGAGT     120

AACAACCAAA AAGGCATGTT GGATCAGCTG CATAAGCTAG TAAAAAAGAG CAGACGCCGC     180

CTGAGCCACT AAAGGCAACG ACCCGCCAAT ATATGATAAA TAGAGAATAT AGAATGTTGC     240

CACTAGGCCA AGATGACCTG CATTGAGATC CAGCGACAAA GTGCCAGGAA TTAAGGGATC     300

TTCAACATTC CTGATCATAT GAGAAGAGCA ATACAGGGTT AAAACGGCGG CGTTTAAAAT     360

TTCACAGACT CAATCAAATG TTTCACAATA CCTGGTTTGG ACAAGTCCGA GACATCCCCC     420

TAACTGATCT GCCTCCCCCA GCCAAGGATT TTGCGCCATA TACGGGCCAT ATTTTGCCTG     480

ACGATTCTTT TGCATTCCTC CCCGAACCAC AAANACCTTA GGGGCACNAA CGGCCCCATT     540

CCCNANNGAA AAAAAAATA GGTGCTTTGN ATNNCCCGNA CCCCCCCCCC CCCCTNTTTC      600

CCNG                                                                  604

(2) INFORMATION FOR SEQ ID NO:244:

(i) SEQUENCE CHARACTERISTICS:
        (A) LENGTH: 550 base pairs
        (B) TYPE: nucleic acid
        (C) STRANDEDNESS: single
        (D) TOPOLOGY: linear (ii) MOLECULE TYPE: DNA (genomic)
```

(vi) ORIGINAL SOURCE:
    (A) ORGANISM: PAG1219RP (xi) SEQUENCE DESCRIPTION: SEQ ID NO:244:

| | | | | | |
|---|---|---|---|---|---|
| GATCCTGATA | TTGTACCGGC | TCATAAATAC | TTTGGATATC | TTCGGACAAT | GTATCGTACC | 60 |
| CGATACCTTT | CAGCACATGG | ATCAGTATAT | CATGCTTCTT | CCTAAATGCA | GCAACAGTAT | 120 |
| TGAGGACTTC | CTTCAGACTG | TCCGTCTGAG | TATCTATCTT | CATAAAGATG | AACTTTTCGG | 180 |
| ACCTCTTCCT | CATCAGCTCT | CTGATGAGTG | ACGTTGAATT | CTTTTAATAG | CGCTTCCCAC | 240 |
| TGGTTTGATA | ATCTTGATAC | AGTGGTCCAT | AGTCCTCCCT | GGAAAGAAAT | GAAGTCGGAA | 300 |
| GAAATCAGTT | TTGGCAGCAC | TCTCTCAGTT | TCTGATTCAA | CTCCCGTTAG | ATATTTCCTC | 360 |
| CCACAAATGT | TTACGGCCCT | ACAGTTGGTT | TCTTTTGANA | CCTTCACTTC | CNTCCNAAGC | 420 |
| CATGAAAATG | ANTCCATCNC | CNCCCCCCCA | CTTTGTNAAA | NTTCCCATTC | GCAAATTNCN | 480 |
| CAGTTGAATT | CCCCCANCCG | GGTGTTCCCC | GCGTTCCCCC | NAAAAAANAC | NGAGGGGGGT | 540 |
| TTTAAAAAAN | | | | | | 550 |

(2) INFORMATION FOR SEQ ID NO:245:

(i) SEQUENCE CHARACTERISTICS:
      (A) LENGTH: 598 base pairs
      (B) TYPE: nucleic acid
      (C) STRANDEDNESS: single
      (D) TOPOLOGY: linear (ii) MOLECULE TYPE: DNA (genomic)

(vi) ORIGINAL SOURCE:
      (A) ORGANISM: PAG1219UP (xi) SEQUENCE DESCRIPTION: SEQ ID NO:245:

| | | | | | |
|---|---|---|---|---|---|
| GATCGCGGCG | CTGCCGCCGG | CGTCGGAGTG | GCGCCACGTG | GGCCGGCCCT | TTTGGCCAAA | 60 |
| TCCCAGCGGT | GGGCGGGTTT | CGAGCTGCTT | GACCTTCCGC | GGCATGTCAA | AGTGCGGCGT | 120 |
| TAGTTTGGTC | CTGTAGGCGA | ACTGTAGCGG | CGATGCGACC | GTCTCGCCGA | CGGTGGGGAG | 180 |
| CAGGCCCTCG | GCCAGCAGCT | GGGGAGCAAA | GAACTTGAAC | GCATTTGACA | CGGTTCGCTG | 240 |
| TTTGAGCTGC | AGCTGCTGGT | CATACGTCAG | GAACTGATAC | TGGCAACCGG | AGCACTTCCC | 300 |
| GAAGTACTTG | CAGTTGATGA | GGTCGTCGTG | GCGCATTTCA | GCAGAGGTCT | GCACCTCCAG | 360 |
| CAGAGACGCT | TCGGCGTAGT | GCGGTGTGTC | TTGTGCACTT | GGATGGTGAC | CACGTCGCCC | 420 |
| TGGCCAGCCC | AAATTGGCAC | CCAGCACTAC | TGTTTCCTTG | TTTGCTATCC | TCCCGGGCTG | 480 |
| TCCAACAANA | CCCATCCCTC | CCCATCCACT | TTACNTCCAC | ACATCACTTT | CATCAGCNCC | 540 |
| GGTTGTTCTT | CTGCTGCATC | GCCCCCCGAA | TTTNTTCAGA | ATGATTACTC | CTCCNCNG | 598 |

(2) INFORMATION FOR SEQ ID NO:246:

(i) SEQUENCE CHARACTERISTICS:
      (A) LENGTH: 747 base pairs
      (B) TYPE: nucleic acid
      (C) STRANDEDNESS: single
      (D) TOPOLOGY: linear (ii) MOLECULE TYPE: DNA (genomic)

(vi) ORIGINAL SOURCE:
      (A) ORGANISM: PAG1220RP (xi) SEQUENCE DESCRIPTION: SEQ ID NO:246:

| | | | | | |
|---|---|---|---|---|---|
| GATCGCGCAG | TTGTCGCCCT | CAGCCAGCCG | CTTTTTGGGC | ACGCGCGGGA | GCGTGTCCAT | 60 |

```
GTACCCGTCG GGCACGCCCC CGTCGCCCTC GCCGATCAGC TGCAAGTGCT GCTGTAGCTC      120

CTCCGGCATC AGTCTCACGA TCACATTTAG TAGCGCGGTG CTGTGCGCAT CTGCCTCCTG      180

GAACATGTCA GCCAGCTGCC TGCGAAGTTC GGACCGTGTC CCCTGGTCGT CTGTGAGAGT      240

TAGTATTCTT GGCCGCAGTC GGTCGCACAT TGGCATCACT TACTATTGTC GCTGGGCATT      300

CACCTCCCTG GATCACTGGT GCTCCCGGTG GCGGTAAGGG GCAACAGACA GGCTTTTTTT      360

ATTTTCCTCT ATAATACGCT GCTCTATGTA GCGTATACTA TACAAGTCTT AACTAAGGTG      420

AAGTGAGAAG TCATTATTTA GCTGCGTTTC GGCCGGTCAT GCAGCCGGCT ACCATATTAG      480

CATGCCGCTG GCCTTGACGG CTTTGGACGT GGGGGAATTG TTGATGCCCA AGGACCTTAT      540

GGAGTTCAAC CTCACGGAGA GGTTTCCGAG ATCGAAAATG TCACTTTCGG CAAATTGCGA      600

CACACCGTAA TACTCGGCAA ACGAGTTCTC GACACCGCTG AGCTCGTCGT CGACGTCGTC      660

GACATAGGAC AGAAGAGGCT TCGTTCGGGC TGGCGGGCGC GCGCGCGCAA CCGGAAGNGC      720

CCCCCCANAG CTGGCGCCNG GCCGCCC                                          747

(2) INFORMATION FOR SEQ ID NO:247:

(i) SEQUENCE CHARACTERISTICS:
        (A) LENGTH: 777 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1220UP (xi) SEQUENCE DESCRIPTION: SEQ ID NO:247:

GATCCAGAAT ACTCGTCGCA CCACTTCTTG AACCGCGGGT ACAGCGCGGG GTCCGTGCGG       60

TCCAGCGCGG CCTTGTGCGC CGCGTGGAAC AGCCGCGCGT CCTCCTCGTA CAGGTAGCTT      120

GGCGTCAGGT CCGAGCCGCC GCCGAACCAC CACGTCTGCG GCTTGCCCGC CGCGTCCCAC      180

GTCTCAAAGT AGCGGTAGTT GAGGTGCACG GTCGGCGCGT GGGGGTTCAC GGGGTGCATC      240

ACCAGAGAAA TGCCGCAGGC GAAGAAGCGC ACGCCGGCCG CCGGCTGCCC GGTCACGGGG      300

TCCGTGGGGA GGTGCAGGTT TTTGTGCTCG GCCCGCATGG CACTGACGGC TGCCGGCGAC      360

AGCTCGCCGT GGACTACCGA GACGTTAACG CCGGCCTTTT CGAACGTGGT GCCGTGCTGC      420

AGCACGCACG ACGTGCCGCC GCCACCCTCC TTGCGCTCCC AGGAGTCGGC CTTGAACTTG      480

ACCGTGTCGA TCGCCTCGAA CGCGGCTGTA ATCTCGCGCT GCTTGCGGCG CACGAGCTCT      540

TCCATGCGCT CGCGCATGTG GGGGTGTGG GCGGATGCCA TTGCTGGGGC GCCGCAAGAG      600

GCGAAATNAN CNGTGCGCCC GGCGGCTTAT ATAAAAGCGT GGCACGGGTG TTTTGCCCAC      660

GNCACCANGG GCTGCNAACG TCCGCGCCAA NANANCCAGG GTCCCGGCCA NAACACNTCG      720

GCGGGCGGCC NAACGCCGCC NCNCACAATC ACNCCGACAA TCGCGCNCNG GGATTCC        777

(2) INFORMATION FOR SEQ ID NO:248:

(i) SEQUENCE CHARACTERISTICS:
        (A) LENGTH: 537 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1221RP
```

(xi) SEQUENCE DESCRIPTION: SEQ ID NO:248:

| | | | | | |
|---|---|---|---|---|---|
| GATCTCTGCT | GTTTGGGCTT | GCAAGCATCT | TCCTCGCTAA | CTCGTTCGGC | GTTTACGTTT | 60
| GAGGTTGCGG | GGACGTATGC | TANACCGAGG | GCATTGCGGG | GTTGAGGGGA | AGAGGTTGAG | 120
| ATTATGAATG | ATATATACTG | TTATACCGGC | TGCGGGTGGC | TGTGCGCGTC | ATCACGAGGG | 180
| ACTTACAAGT | TCAAAAGGTC | TTCATCGATA | TTTACCAACT | TGTAATAACG | CTCTTGTGAG | 240
| TCTGAGTTGG | AGGAGCCGGG | CTGGTCGCCA | TACTCCATCA | ACGTGTTTAC | CATTGCGCGT | 300
| GTATAGCTGA | TCAGGTTTTC | GAGGGATGAC | TCGCTCTCCT | CCTTTAGGAA | CATCAAAATG | 360
| GTGGTGTTCC | ACAANCNGGA | AAACCTATCC | TGTTAGTNNA | GAAGGGTTGA | GAACACCGCT | 420
| AATCCCTTAG | GCACTCCACC | ATGGTTTTAT | CCGTACCCCA | TTACCCAAAT | TTCCCCCAAG | 480
| TGCCCTTNAA | CTTTGNCGAA | CCCCCGCNAA | ATNCCCGTTT | TTAAAACCCN | AAAAANG | 537

(2) INFORMATION FOR SEQ ID NO:249:

(i) SEQUENCE CHARACTERISTICS:
       (A) LENGTH: 584 base pairs
       (B) TYPE: nucleic acid
       (C) STRANDEDNESS: single
       (D) TOPOLOGY: linear (ii) MOLECULE TYPE: DNA (genomic)

(vi) ORIGINAL SOURCE:
        (A) ORGANISM: PAG1221UP (xi) SEQUENCE DESCRIPTION: SEQ ID NO:249:

| | | | | | |
|---|---|---|---|---|---|
| GATCGACCCT | ATCAACGCCT | TGCAGGCTGC | TATGGAGGGC | TATCAGGTCA | CCACTATGGA | 60
| CCAGTGCGCC | AGCTACGGCC | AGGTTTTTGT | CACCACCACC | GGCTGCAGAN | ACATCATCAA | 120
| GAAGGAGCAC | TTCTTGGCCA | TGCCTGAGGA | CGCCATTGTG | TGCAACATCG | GCCACTTCGA | 180
| CATCGAGATC | GACGTCGCCT | GGCTAAAGGC | CAACGCCGTC | GANGCCGTCA | ACATTAAGCC | 240
| ACAAGTCGAC | CGCTACTTGC | TTTCCTCCGG | CAGACACGTC | ATCCTGCTTG | CCGATGGTTA | 300
| GACTAGTCAA | CCTAAGCTGT | GCCACTGGCC | ACTCCTCCGT | TTGTCATGTC | TTGCTCTTTC | 360
| TCCAACCAGT | CTTTGGCACA | GATGGTCTCN | TTCAAGGGCA | ATNAAAAGGC | CTTCAAANAA | 420
| ATTNNTTNNT | TTCCCAAAAA | ACGGCCNTCA | AANCGGGNTT | CATTTCTNNC | CNAAAATTGN | 480
| AAAGGCGCNC | CCATTTCCCC | CTAAATTTGG | GTTTTNTTTT | AAAACATTCC | CCCCCCCCA | 540
| TTTCCGGGTT | CCCAAAAGGG | TNTTTNGGGG | NCCCTTAAAT | NTTA | | 584

(2) INFORMATION FOR SEQ ID NO:250:

(i) SEQUENCE CHARACTERISTICS:
       (A) LENGTH: 535 base pairs
       (B) TYPE: nucleic acid
       (C) STRANDEDNESS: single
       (D) TOPOLOGY: linear (ii) MOLECULE TYPE: DNA (genomic)

(vi) ORIGINAL SOURCE:
        (A) ORGANISM: PAG1222RP (xi) SEQUENCE DESCRIPTION: SEQ ID NO:250:

| | | | | | |
|---|---|---|---|---|---|
| GATCGAATAA | TAAAAGTGGC | TAATACTTGG | TAATAATATA | ATAGAAAGGG | AAATAGAAGA | 60
| GAAGTCAAAT | GGGAAATAGT | CAACGGCGTA | CTAGGTGAGT | GTTCAGTTGC | ATGGAATCGT | 120
| AGTCAGAGAG | GTTTATCAAA | AACGGCAGTC | GTCTGATGAT | AGCAGTATCA | CGAAGTGCTC | 180

| | | |
|---|---|---|
| ATGCGCCCTG | CATACAATGG CAGGCTCAGC GCAGGATCAA ATGGATAGCA GCGGGCGTAC | 240 |
| CCGCGAACGG | ACTCAGTGGG TGGAGTGGCC CCGGTGGTAC TTGAGGCCGT TGAGGTTCTT | 300 |
| GTAACGTTTG | CCACAGACCT CGCACCGGTA AGGCTTGTCC TTCTCGAACC CATGCCCGTC | 360 |
| TGGATAGGGC | TCGTTGGACT CCGGGTCCAT GATGCTAAAA GTGCCCGTCT GGGTTTTCAT | 420 |
| GAAGCTTTTG | ATTCTGGTGG CCGTGGTTTT ATGGTACTTG AGTCCCGTTT GATCCTGGTT | 480 |
| AGTCTTATCG | CAGCCCATGA GGGACNNTTG AAGGCTTNTC CCCNCCTTGT CCNCN | 535 |

(2) INFORMATION FOR SEQ ID NO:251:

(i) SEQUENCE CHARACTERISTICS:
        (A) LENGTH: 581 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1222UP (xi) SEQUENCE DESCRIPTION: SEQ ID NO:251:

| | | |
|---|---|---|
| GATCTCGCTC | AGACCGTCAC CCACGTTGTC TGCAAGGGCC TCCGCCGCTT TANCTGCCTG | 60 |
| CCACGGCTTG | GAGCACGCTA GCTGCACGCC AAACCCGGGC AGCTCCGAGC AGTGCGCCTT | 120 |
| GGGCAGCGCC | CACTCCGAGT TGGTGCCCTG GATCAGCGGC ACAGCGAGCG CCATCTCACT | 180 |
| GTACGTCACG | TCGGCGCCCA ATTGGCGCAT CAGGCGCCGG AACGGCAGGT TCCCGACGGT | 240 |
| GGTCAGCGGA | GAAACGATCT TCTTGTGATG CAGGTCCAGC GGCTTCTTCT CCTGTGCAAA | 300 |
| GTAGCGTGTC | TCGTGATACT GGGCGTACAG CTCGCGCTGC CGGGCGCGCT TGTTGCTCAA | 360 |
| TTGCTCCTCC | CGCTGCTGCA CCTGCGGCAC CTCTGCGACC GCGCCTCCGG GGCCGCCGCG | 420 |
| GCCCCCTGCA | TCTCGTCGCC GGAACTCCTG CTGGATGGCT CAAAATTCC ACNATTTCTC | 480 |
| CCTGCNCNGG | AAGGGCCCAA NTTTTCCCCA ATNANCNCCA ATGAACCATT GNTNCCCCCN | 540 |
| TGGTTNCAAA | ACNAATTTTG CCCCCCCCG AGATTNTCCC A | 581 |

(2) INFORMATION FOR SEQ ID NO:252:

(i) SEQUENCE CHARACTERISTICS:
        (A) LENGTH: 544 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1223RP (xi) SEQUENCE DESCRIPTION: SEQ ID NO:252:

| | | |
|---|---|---|
| GATCGGTTTT | CACCTCAATT CGTTTCTGGT CGCGCAGTTG GTGATGCTGC TGATGCTGAA | 60 |
| GCTGTAATTG | CTGTTTCTGC TGAGCAAACT GCTGCTGCTG TTTCATCCAG GGATTCTCCG | 120 |
| GAGGAGCTGA | GTCCGGTTTG CGCCGTCTCT GCTTGTCGTT CAACAAGTTG TTATATAGCT | 180 |
| GGTTCATACC | TTGGGAGGTC AGGAACTGAC TGACATTCGC GTCGCCCTGC GGGTGGTCTA | 240 |
| GCAAACGGAG | CATGGCCTCT CTCTCCTGTA GAGTTTTCTT TGCCGCCATC TCAAACTTCC | 300 |
| TAGATTCCAT | TATCAGCGCT TCTTCCTCAG CAATCTCAGC CGCCGACCTC GAAAGCAGCC | 360 |
| TCCGTCAAAT | ACTTCTTCCG CTGTATTTCC CTGGTCTTTG GAATACGCTA GGATGGTAGT | 420 |
| AGCGGTTTCC | CCGGGTCTTT CGCCCTGAAA TTATTTTTGG CATACGNGGT TAAAAATCTC | 480 |

```
CCCGTANTTC CTCCAACGGT CCTNNANNCG NCNTAAANAN ACNGGTCNGT AAATNATAGC      540

NNCC                                                                   544

(2) INFORMATION FOR SEQ ID NO:253:

(i) SEQUENCE CHARACTERISTICS:
        (A) LENGTH: 608 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1223UP (xi) SEQUENCE DESCRIPTION: SEQ ID NO:253:

GATCGCGCGC TTGAACATGG ACGTGGACAC GGCGAAGTGG CGCTGGAGCG CGCGCACCGC       60

TGCGTCCTGG AGCTCTGTGT GTGCCATGGT GCGCTCTGTC TTGAGCTGGC GCACAACCGC      120

GGCGGATATG GCCTGGACCC TACTGGCGGC GAGGACATCT GGTAGCGCGG CCGCCTGCTC      180

GGACTTGACC ACGACAGTGG CGACGCGGAC CTTGGTGGTC GGCGCCGTGA ACGCCGTGTT      240

GACTGCAAAG TGGTCCGAGG GCGCGATGGT GCCGGGAGGG AGGGGTTTTG GTGAGGATGC      300

GTGTGCGCGG CGCGACGGCG AGCGAGATGA GCTGGCGCTG CAGCTCGGCA TCTGGATTGC      360

GGTCAGGTCC TGAATCTGCT CGGTGGTCAG TTCTGCGTAG TCTCCGGAAA ACAGGAAAA      420

ATGGTTGGCG GCATNGTTCA ACATCCTTGG CNCCCTGGGT TAAAAATGGC CGAACTGGNN      480

GCCGATTTCC CCGAGAACCC ATTTTGTTAT CCCCCTTCCT TCTGCNTNCC GATTTTTTTG      540

CAAAANTNAA AACCCCCCCT AAGAAGANNN CGGGGNNGCC CCNCGGCGGN TTTTTTTTTC      600

CNCCCCCA                                                               608

(2) INFORMATION FOR SEQ ID NO:254:

(i) SEQUENCE CHARACTERISTICS:
        (A) LENGTH: 731 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1224RP (xi) SEQUENCE DESCRIPTION: SEQ ID NO:254:

GATCAGTAAC AACCATAGCA GCCGCACCTA CGAAAGCATT CGATACATTT TTAATAAATT       60

CGACAGCAGG TAGTAGTCTT CTTCCGGATT GCTTTACAGG CTCGCTAAAG ATGTGTTCGT      120

AGCTCTTCCA AAGAGAAATT TGTGTAACTT CAGAGTCAGC AGCGGACTCA AAACAGCACC      180

TCAACCAAGC GGTTGACCGC ATAGGTTCAT TCAAGCCCAA TAGTTTTTGG AATAGATCAG      240

GGGGAAGAGT TGGAACATGC GTAGGGGGTC TCGGTTTTAC TCGCCTAACT AGTTTTATCT      300

CTACTTTTGA AAGATAGTCG TAGTCGGGAA GCTCAACATT GTAAGTCAAC AAGCTAGGCA      360

AAACTGTAGT CAAGATTGAG TTCCGCTCAG GGTTTTGACA ACAGAGTAGT TATTCTCTCA      420

CTCCCCAGGC AAGATGTACT GGTATAGAAA ATCCAGTTGA AGCCATAACC AGCTCGTTGT      480

CACAGTCCAC CAGAAGATAG GANACATCAG GTTGAAGAAT TCCTCATCTA GGTTATCTGC      540

TGCCTTTCCT GTTCTGCTTT GGACCAACCC ACAACCCNAA AACCAACGCN AAATCAAANA      600
```

```
CCNGGTTCCT TCCTTGNTCC CCCCNAATGA AANAGGTTTT GAAANGGTTN TCCCTCTTGC        660

CGGGCCAANT AAAAAAAAGG CCCNCAGGNT CNACNATATT ANCANTCCCC NAAAAAGGCC        720

TTCTGNTCTA A                                                             731

(2) INFORMATION FOR SEQ ID NO:255:

(i) SEQUENCE CHARACTERISTICS:
        (A) LENGTH: 762 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1224UP (xi) SEQUENCE DESCRIPTION: SEQ ID NO:255:

GATCGGGTGC GGCACATGCC TCATCGGGCA GGTGGGGTGG CGGAGGCATA AACCCACCCC         60

TGGTTGTTGC AGTGAATAGG TATGGGTACA GCCTTGGCGG CCACGAATGT GCGGAGACGT        120

TTCAGCTGCC AGAGGGACCC GACCGCACCG GTGGACTGTT GGCTTGGTTG GACGCTCCAG        180

GGTTACGAGC CGGCGCCCTG CGGAGCACAT GATGTCGAGC TGTGCATTGG TCCAGGTGCG        240

CACTAACCAT GCCAAGGGCA TCCGGCCAAG GCGGATGGGG CTGGACGGCG CCAGGGCGGG        300

ACGACTATCA CTAAGAAATC ATCGATTAAA ATATAAACTA CATAAAGTAA AGGGCGGACT        360

GAGTGCACTC TCAGCGCACT AGCAGCGAGT AGCCGTAGTT GAACCACTTG CNTGCGATCC        420

GTGGCACGAA GCGGAAGTAA CCGGAACTCC GATAGTTCAG AACGAAGAAC CGAAAAAGCC        480

TTAAAATGGC TTCACNCCTA GGTCCCCCAA CNGGTCCTCC TGTTTGGAAT TAGGGTGGGC        540

GGAAACCCAA ACTGCCCANT TGTTNTCCAA TTCCCCGGNG GCCCAATTT NAATTTCCAA        600

ACCNATCNCN ATCTCGGCTG NATCCCCCCC NTTGCCCCCC TCAATGGCCC CGAACCTTTT        660

NTGNCCCCCC CCCAAGGGCC CTTGNGNATT TTTTTCCCNG CCCNCCCGNT TNTCTTAAAA        720

NAAAGCNGCA TTTTTCAATT CCCCNGGAAC NCTTTTTTGT TT                           762

(2) INFORMATION FOR SEQ ID NO:256:

(i) SEQUENCE CHARACTERISTICS:
        (A) LENGTH: 710 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1225RP (xi) SEQUENCE DESCRIPTION: SEQ ID NO:256:

GATCCTTTTC TTTCTTCTTC CCTCCTCCGA GGATTCCCTT TTTGAGCTTG CCCACTGCGC         60

CCAACCCACC GCCTATGACA CTAGTACCGG CGGACAGACC AGCGGATAAG CCCTTATTGG        120

CAAAATCGCC AACCTTTGTC TCCACCTTGG TAACAGAGAC AGTGTACCTA GGAGAAAATT        180

TGAAGTTCAA GTAAAGAATA CCACCGTCCT CGCCGTTAGG ACCAGTTAGC TGGACTTCCA        240

TTGGGGTTTC ACTGTCTGGG TCCACCTCAG CTAGAGCGAT GGTTGCGGTG CCAATGAGAT        300

CGTCACTGTT TCCGGCATCC CAGTCCATGA CCTTGATGCG CAGGTAGTTG TTAATCCGGT        360

TATTCAACTG CAGGGATGTG TTCTCGTTCC AAACAGGTTC AAGCGTCTTC TTCTGGGTTC        420

TTGGTCTTGT ATATTACCTC ATCTGAATTG TCGAGGTTAG AATTTGACAT AAGGTCGGAC        480
```

```
TTGCCGTTCC GGTCAGCAGG TAGAGCCTGA CTGCATTTAG AACCTCCAGT GTTAGGTCGC      540

AGTGTTCGTA TCAGTTTGCT TGTNGCATCT CNAACCCAAA AAGGAACCAC AACCGTTANN      600

TCCTTTTGNG ACCCAACCTT NTTTACAANN AGGTTTAAAT TACANTTTCN ATTTNTTTGN      660

TGGAANGAAC CCCNAAGNGT CCNCCTGTTT TACTGANCNT NNTCCCNAAT                 710

(2) INFORMATION FOR SEQ ID NO:257:

(i) SEQUENCE CHARACTERISTICS:
         (A) LENGTH: 750 base pairs
         (B) TYPE: nucleic acid
         (C) STRANDEDNESS: single
         (D) TOPOLOGY: linear (ii) MOLECULE TYPE: DNA (genomic)

(vi) ORIGINAL SOURCE:
         (A) ORGANISM: PAG1225UP (xi) SEQUENCE DESCRIPTION: SEQ ID NO:257:

GATCCTACTG GAACCACCCA CTCAGGAGCA GGTTAAAAAA CCAGCCAAAG TAAAGACAGA       60

GACAAACGTA AGCATCCCAA AGCAGACCCC TACTCCAAAG TCTAAGTCGG CTTCAGCTTC      120

GTCTTCTAAA GTGCCTACAC CCCTGTCAAA GCAGGAGCCC GAAGCGCCGT CTACCATTTT      180

TGACGCTCCT TCTTCTTCCT CCTCCACTCC GGTGCCTGGG CACTTGGATA TCTTTAGCAA      240

ATTTAGGAAA GCATCCAGTG ACTTTGACAA GCCCTTTGTG GCCGAGTCGA ATGAAGTTGC      300

CGAGAAGCCG TCCGGGAAGG CCAAACGGCA AACTACTCCC GCTGCCAGCA AATTAAAGCC      360

CGCTGCAAAG AAAATAAAGA CGCCCGCGCT CGATGAAAGC GAATCTGATT TTGACCTTGA      420

CCTCAGCGAC TCCCAGCCCG CCATCGCCCC TAGAAGTAGA GCCTCGCGAG CTGTCGCCAA      480

AAAGCCAACC TACGTAGTTG ACCTTTCCGA TGACAGTTTT GTTGATGGAG ACGCCCAGAG      540

ATGTTGAGGA ACCGATACTG ACGAATCCTT CCAGCTCTGA CTAGCACTCT AGCTCGCGCA      600

TTGACAGTNC NCTACCTTAT GGAGGNTTCC GAAATCCNTT GAATACCCCC CGTTTTTTAC      660

TAAAACCCCC NCTTTCCTTT TCACCCCCCA ACCCCCAGGG GACGAATACT TTTTTCTTTA      720

CTTTCTATCA NGGGGTTCGT CNCCNCCCNT                                      750

(2) INFORMATION FOR SEQ ID NO:258:

(i) SEQUENCE CHARACTERISTICS:
         (A) LENGTH: 729 base pairs
         (B) TYPE: nucleic acid
         (C) STRANDEDNESS: single
         (D) TOPOLOGY: linear (ii) MOLECULE TYPE: DNA (genomic)

(vi) ORIGINAL SOURCE:
         (A) ORGANISM: PAG1226RP (xi) SEQUENCE DESCRIPTION: SEQ ID NO:258:

GATCGTCCTC GCATGGGAGC ATCAGATGTC ATATCGGCGA AGCCTTTCCA TATGGCGGCT       60

ACGAACGATA CGAGTTCCGC TCCTGCTTGC GCTGTTGGGG TCTGTGAGCG TGCTGCTATT      120

GCTGTCGCTG ACGCCACACA TGTGGCCTGG ATGGCCATCT CCGGCAGCAC GGGAGGTCCC      180

GGCTTCACCA GAGTCACAGG CCCCGGCTTC ACCAGAGTTA CAGGCCCCGG CTTCAACACA      240

GCCACAGTCC CCAGCAGGGT CTAAGACGCT ACTGCAAGAC TTACTGCTAG ATAGCAAAAA      300

ACCGGAGGGG GCCTCTACGC CACAGATGCA GTGCAAGCGC TACTTTGAGG GCACATATCT      360
```

-continued

```
CCGGGAGCCT TCCTGGGCAA ATAGCGTGTT GCGCATGGCA GACGACTTTC TTACGGCTAC      420

GCAATACACA GCGAGGCTGT TGGAGCGGTG GCGCATATTT GCTGATTGTT TCGTTATTCA      480

GATTTCCGAT TTTCAAATAC NCTATCCAAA CAAAAAAAAC TGCCCAANTT CCATCAGCGA      540

ANTTCCCCTT TCNTNGGCAA AAAAAAAAAN NGAGGANATT TTGCCTNTCC CCNGAATTTC      600

NCCCGGGAAA ATTTTTAAGG NGGNTTTTTT GNAAANGGGC CCCACCAAAA NANAAAAGGN      660

GCCTTTTTTG GAAAACGGGC CCTTTTCCCC GGNGNGAACA AATTNNTNNN GGGGACGCCC     720

NGAATTTTC                                                              729
```

(2) INFORMATION FOR SEQ ID NO:259:

(i) SEQUENCE CHARACTERISTICS:
        (A) LENGTH: 742 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1226UP (xi) SEQUENCE DESCRIPTION: SEQ ID NO:259:

```
GATCGCTTCA AATTTCCAGC CGTTGATATT CAAAGAGTGG TCACGTTCCG AAAGATGGTC       60

CTTCTGTTCG TCTGTACGTT TGGAGGGCCG GCCTACCGGG GCGTTCGGCG TTGTCTCCAC      120

GGTGCGGTGC TGTCCTATGG GGACATCCTG GATGTTGTTC TGCAACGCAT TAGCAAATGA      180

GTTTTTGTAG TGGTACTTAG GAAGTTTATA ATTTAGGCTC AGTTCTATAC TGCCGCTAAT      240

ACTTTGACCT GGAACAATCA TCGTTATGTG CTCACCTCTG GCGTGTTCTC TAGCGTATTC      300

CCGCCGTGCT TCAGCATTTG GTTGTTCCTG GATCGTTGGG TATGGATCCT CCCACTTCTG      360

TAGCCAGTTG GTATCCAGCT TCTCACCCTG CTGATGCGAT TCTGGACGCG GGGGTTTCAG      420

CAGGCGTTAG CAATGAAGTT GGCGTTGCCG GTTCAAAAAA AAANACCGGN GGGGGCNTGG      480

TAANCCCGNC CCTTTAAGGG CGGCCCCATA TTCNCNATNA CCNNNACCGC NCCCCCCATN      540

ACGCCCCCAA AANATNTTTG AAAAAATTGC CNTACCTTTT TGNGGGAGCC CACNCNCTTA      600

NATAACCCAT TTTTTGAAAN ANGCCNNTCT TTTNTTTAAC NCCNCGGTTC NCNANTATGC      660

NGGGGCAAAA TTAAACCNCC CCCCCNAAAT GNAATCNNTT TCCCCTCNAA NACAAAAAAT      720

ATTTTNNTTT NGGGCNGGGA AT                                               742
```

(2) INFORMATION FOR SEQ ID NO:260:

(i) SEQUENCE CHARACTERISTICS:
        (A) LENGTH: 744 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1227RP (xi) SEQUENCE DESCRIPTION: SEQ ID NO:260:

```
GATCGATGAA CAGACTGGAG AACAGAGAAA GGTGGTGCCC CTCGAACTCG AACGGTTTTT       60

CCCGCTCGAT TTTGATGAGA TATTACTCCG GGATACGATG CAGAGGAACG CAGCTATGGA      120

AGAGGAGGAC TACAGGGAGC TGGGGAAAAG AGATATTGAG GTGGCGTTCC AGAACACCGG      180

CGTGACGCTG GATGACAGGC TCCAGTCGTT GCCGGCCATA TCGCTCTTCG GGAGGTATGT      240
```

```
ACGGGATATC GACGGGATGT CGGAAGCGCT TGCGGACGGG GACAGGCACA TCATGGTGTT      300

TGCGCCGACA AATGACGCCA TTACGGCGAT GCCCAAGAAG CCGTGGGAGT ATCCACGGAA      360

CATCGACAAG TTGGAGCAGG CAGGCGCGTC TGCGAGCGAA ATCCACGACG CCATCCAGGC      420

GAATGTGAGA CGCTTTGTGC TAACCCACGT GGTTTCCGAC ATCGACCTCT CTAAGGTGGT      480

TCGGGAAGAT TGCTCCAGCC GTGTTTGACA AGCGACTTCA TCCCAAGAGC ATGCAGGGGA      540

TATTCTTTTG CGCCCAGGAT GGCAANGGTT TTACAGTNTC NTCCAANANN GGGCGGACCT      600

TGCCGTTNAG ANGTTACCCC CCGCTCTAAC GGTTTATTTT GGTTNTCACN CCCCCTTGGN      660

TGCGAATTNG AAAACCCTCC NCCTGNCCCN NCCCAATNAN TCNCTTGAAT CCCCNTTTNG      720

GAACCNNCNN TTNCCCCCAN CNCC                                            744

(2) INFORMATION FOR SEQ ID NO:261:

(i) SEQUENCE CHARACTERISTICS:
        (A) LENGTH: 768 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1227UP (xi) SEQUENCE DESCRIPTION: SEQ ID NO:261:

GATCATTTGC CGGACCAAGA AATATTTTCA CTCCTCGAAG AGCTGGCCAC TAAACTTCGT       60

GTCTGGTTAG GTTCCGCTCC AGCTGATGTG CTAGATATCG AGGTGAGAGG TAAGCTTATT      120

GAATACTGCA TGAATACTGC ACTTTATTGC GGTGGGAAAA TAGAACATCC TACATCGACG      180

ACTTTGATGA CTGACCATGA TGAAGACGAA TCTGAAAGCT CTGATTCGGA ATAGTCCAGG      240

CAAGTTAATA CCCAATGCTC GGCTTTAGCC TCAAGGGAGA TATCGGTAAC AGCTCTATCT      300

ATGCTGCCAG CACGTACGAG TTTTTACTAA ATTTGGCATA CAGTTCATGG TATTTGACAT      360

AAGCTTAATG TTTCATTCGC AACACAAGGC TTGCCGATGT GTAAAGTGCG CCGCGTCTCT      420

GCATTCAAGA CAGCATACAT GAACTTTCAG TTTTATACGC CGATCATGTT GATTTCTAAT      480

AGGGCTAGTC CATGGCCCCT ACCTATAATA TACTACCATC CAGCCCNCCG AACCGNAACN      540

NNATTTTTTA TTTTAATNAA ATTTTGGGGG NATNCCACAC NNNCCCTANC NNGGANTTCC      600

AATGTTTATT TAANTNAAAA ANCAGTTTGA AGGGTATTCC NNCNCCCCNC CCCACCNGNT      660

TCAAAACCAA ACNANACCGT GAAGCNNGTN NTCCCCCNCA AGGAGNGCCC CCCCGCTTCN      720

AAAAACGGTN NCCTTTNCCN CCCTTGCNCA ANATTCCCCC CGCTGCCC                   768

(2) INFORMATION FOR SEQ ID NO:262:

(i) SEQUENCE CHARACTERISTICS:
        (A) LENGTH: 738 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1228RP (xi) SEQUENCE DESCRIPTION: SEQ ID NO:262:

GATCCATTGG GCCCAACGAT GCTAATGAAG TTCTTGCCTC CAAAACCCAC ATTGTGCACA       60
```

```
CCCTTGTACG ACTTGAAGTT CTTCACCTCT AAGCCAATCA GCCTCCCCAT CTTTTTGAGA      120

CACTGAAGCT CAGTCTAACT GCTCTCGATG TTGTTAGTGC GCTGTTAATA TGTCCAAACA      180

AACGCGATCA TGGTTGTGAA GAACTGCGCG TTCGCATACA GCGTCAGCAC GTAGCCCAGC      240

GGCCCCGCGG GCCCGAAGAT CACTGAGATC GGCAGGAACA GCGGCGTCCA CAACAGCACC      300

AGAAATACCA AAATCGCCGC AAACGTTATG ATGTACAGGA TCACCAGAGT CACCGCCTGA      360

ACCCAGATCT GCCCGTGGCC CATCCCGACC ACCATCGACT GCCTGAATTA GTATATTCCG      420

TCCCACCTGC TGTTTCATAC ATACCACCCC AGGGCACACC AGGCGGTAAC AACCCCAAAG      480

GNGTCCCTAG GGAGCGCATG CAAAATATCC ACNCTCCGCA TGGCATCTCC CNNTTGGAAA      540

GGGGNCCCCC NAAATTTGGG CCNAAANCCC TTAAAAGGNC CCTGTGNCCN CAANNACTTC      600

NAATTTCCCG NTTNGGCCCC CCCCCCCCTC CAACGGGATT TAAAACAGGN GGGNGNGGGA      660

AAAACCCNCG AGGGGNTTTT TTTNGCCCCT TTCCGAAANA ANCCNCCCCC CCNGGGAAAA      720

AAATATTTTT TTTTNGGG                                                   738
```

(2) INFORMATION FOR SEQ ID NO:263:

(i) SEQUENCE CHARACTERISTICS:
        (A) LENGTH: 748 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1228UP (xi) SEQUENCE DESCRIPTION: SEQ ID NO:263:

```
GATCATGCCA TTCTTACGCT TTGCCCACAT GGACGCCCAA ATGAATTTCT GTGTATGCGA       60

GGATGCTGAC GATGCAGCTG AAGCAGGAGA CGACAGCGAT GTGACGCCTG GTTGTATGAC      120

GCCTACTATT TCACCTGTGA ATACTTGTTC TTGGCCCTCT GTAGACATAA TCTTGTTAAG      180

GACAAAGCTC CTGCTGTCGG TGTGTATCAG GTCAAGTAAA GTAAGCGCCT TAAATGCCAA      240

TTTGGAGATA CCGAAGATTA AGCATGCCAA ATCGTTAGCC GCCCTAAACT GCCATGGGTG      300

ATGCTGGGAA CAGGTAAATA TGGCCTGAGG TGCTGTGTAC TTACCTGATA TAAAAGTATG      360

CAGTATGCGG GGCGCTTCGT ACGTTCTGCT GTAGTCTATC GGATCCTGGA TAGATGTTAG      420

TTCATCGGTA AATGGTTGGA GATAATTTTC GTCCTGCGAG GCCTGTATAG TAGTTTCCTG      480

TGTTTGAATA TTCATGAAAT GGTTGGGCTA GCTTTCAGCA GCTGCTTCTT TAGTTCTTGC      540

TCATACTGAC TTCTTCGCAG ATCTACNCCA CCGCNTTGGG GCTGACCCCA GCACACTTAT      600

GATTTTTANA AGGAATCCCC GTAATCCAAN GCCCTTNCNT ACCCNGTCCC AATNGTTNCA      660

TCAAAANGTC ANNCCCTCNA TTTCCNCTTT TCTCNCCAAA ACNCCCACNT TAATTGAANA      720

NGNCCNTTTC ACCGCGAGAG GTGGCGNC                                        748
```

(2) INFORMATION FOR SEQ ID NO:264:

(i) SEQUENCE CHARACTERISTICS:
        (A) LENGTH: 653 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1229RP (xi) SEQUENCE DESCRIPTION: SEQ ID NO:264:

```
GATCGTAACA ACAAGGCTAC TCTACTGCTT ACAATACCCT GTTGTACATC TAAGTCGTGT      60
ACAAATGATT TACTCTCGCG CAGTATGACA TTGCAATCCG CCGGCACGCG CCCAGACCTT     120
TCCGTCTGAA CACCAGTTGC CGGCCTGCTA TGGTTCAGCG ATGCTAAAAG CACCTTATTC     180
GTATCCATCT ATAATGTGCG AGAAAAAGAA TCATCGCGTT CTAGCATGGA TTCTGACTTA     240
GAGGCGTTCA GCCATAATCC AGCGGATGGT AGCTTCGCGG CAATGCCCGG TCGGACAGCC     300
GCAAAAACCA ATTATCCGAA TGAACTGTTC CTCTCGTACT AAGTTCAATT ACTATTGCGA     360
TAACATTCAT CAGTAGGGTA AAACTAACCT GTCTCACGAC GGTCTAAACC CAGCTCACGT     420
TCCCTATTAG TGGGTGAACA ATCCAACGCT TACCGAATTC TGCTTCGGTA TGATAGAAGA     480
GCCGACATCG AAGAATCAAA AAGCAATGTT CGCTATGAAC GCTTGACTGC CACAAGCCAG     540
TTATCCCTGT GGTACTTTCT GCACCTCTAG CCTCCACTCC CGAGAACTAA GATTCGATAG     600
CACACTTTCA TGTTTGTATC ACACTGAATC AATCAGGACT TTACCTTGTC TAC           653
```

(2) INFORMATION FOR SEQ ID NO:265:

(i) SEQUENCE CHARACTERISTICS:
        (A) LENGTH: 528 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1229UP (xi) SEQUENCE DESCRIPTION: SEQ ID NO:265:

```
GATCAGATAC CGTCGTAGTC TTGGCCATAA ACTATGCCGA CTAGGGATCG GGTGGTGTTT      60
TCTTATGACC CACTCGGCAC CTTACGAGAA ATCAAAGTCT TTGGGTTCTG GGGGGAGTAT     120
GGTCGCAAGG CTGAAACTTA AAGGAATTGA CGGAAGGGCA CCACCAGGAG TGGAGCCTGC     180
GGCTTAATTT GACTCAACAC GGGGGAAACT CACCAGGTCC AGACACAATA AGGATTGACA     240
GATTGAGAGC TCTTTCTTGA TTTTGTGGGT GGTGGTGCAT GGCCGTTCTT AGTTGGTGGA     300
GTGATTTGTC TGCTTAATTG CGATAACGAA CGAGACCTTA ACCTACTAAA TAGTGCTGCT     360
AGCATTTGCT GGTTGCGCAC TTCTTAGAGG GACTATCGGT TTCAAGCCGA TGGAAGTTTG     420
AGGCAATAAC AGGTCTGTGA TGCCCTTAGA CGTTCTGGGC CGCACGCGCG CTACACTGAC     480
GGAGCCAGCG AGTTATACCT TGGCCGAGAG TCTGGTATCT GTGAACTC                528
```

(2) INFORMATION FOR SEQ ID NO:266:

(i) SEQUENCE CHARACTERISTICS:
        (A) LENGTH: 756 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1230RP (xi) SEQUENCE DESCRIPTION: SEQ ID NO:266:

```
GATCCCGGTA GGCGTCTGGC GGCATAATGT CTGCCGTATA GGTGGACTCT GGCTGTATTG      60
TCCGCAGGGG AATGGCATGC TTCTTGTAGA AATACAACCG ATCATAGGGC GAGCTCATAT     120
```

| | |
|---|---:|
| CCACCGTACG TCGCTGGGAC ACGTACTTTT TGACTGAGCC ATCATTCGCG CTGTTCATTG | 180 |
| CGACTCTAAT CTGATTCAGA ACCCTGACCT CTAGTGCTAT AGCGCAGGGC GTACCTGTCT | 240 |
| GATGATGCGC TTTTCAATGC TCGAGCGTGC GCAGTGTTAC ATCGATCGTC GCGGACGATG | 300 |
| TTTAAGCAGG ATGCTGAGCT AATATGTATC GGTATAGGCT ATTGGCAGTA GACCTGGGTA | 360 |
| TATACGCCTA GATATGGACA AGATGCTGCG CCTAGACATC CAGAACTTAA CCAGGCTCGG | 420 |
| GTTAAAGCCA CCCAGATAAC ATTTGAACAT TAGAACAATT ACCACCGCGA ATGGAGGGGA | 480 |
| ACCCAGTCGA AACCCCACGG CATCCAATAG TTTCCCCCAA CNGCGAAANG GCAGAATGCA | 540 |
| CCGCCCAATG CTGCCCCAAC GCCCACGGCC ACCCTGACCC CATTGACCTN GAAGCCCTGG | 600 |
| GGCNAAACTG CATTTTACCC CCCCCCATTN GGAAAAANTG ACCGAATAAA ANNCCCCCCN | 660 |
| AAAAANAAAN GGCCNCCCCC AATTACTTTT TNNCCNNGGG CCCCNAACCC CNGGGCNNAA | 720 |
| AAAANNANTG GGGGGGGGTT TCCGNNNTTT AAAAGG | 756 |

(2) INFORMATION FOR SEQ ID NO:267:

(i) SEQUENCE CHARACTERISTICS:
        (A) LENGTH: 784 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1220UP (xi) SEQUENCE DESCRIPTION: SEQ ID NO:267:

| | |
|---|---:|
| GATCTTCCGC TCCACTTGGT TGGGCTGGCG CATGTCAAAG GTTAGTAAAA GCCCCGAATC | 60 |
| GTGTACTGAC GCGAACTTGT TGGATCTTCC GGAAGAACAC AAGGACGTAT CCGCGCCCAA | 120 |
| GGACGCGAAA TCATAGGTCG GCATCCACTT TACATCACGG ACGGAATCTG AGCCTGAATT | 180 |
| GAAATTCAGG TCGCTGCGGT TCACCTTGTA AGAGTGCGAC CGCAAGTCCC ACACCTTGAT | 240 |
| GCAGCCGTCC TGGCCACCGC TGATAAGGAG ATGCGTCTGG CCCATGTTGA AGTCCACGCT | 300 |
| GTTGATGGAA CGCGAGTGCT CCGACAGGGT CCGTGATCAG CGGCGAATCC TTTGCCGACG | 360 |
| CGCGGTTGAT ATCGTAGATG GAAACCGAGG TCGACGTCCC GCATATGGCG ATGTAATTCT | 420 |
| TGTGGTGGTG GAACCCCGCC CTTGACGTCC CGAAATCCGT GCTAATCTTG CGCCATGTTC | 480 |
| CCGGCGCCAT GCTGCTCGAA GAACTTCGTC CCGCCCGCC AAGGNTCCCC NGTTGTTCNT | 540 |
| GTTATTCCGT GCACCCTGCT GCTCCCTGTA CCCTCCGTCN AACTTGTTCA GCCCAAATGG | 600 |
| TCTTCCCCCN CCCCCNCAAC CATGCCCCCT ANCTTCTTTG ATTTTTTTCC AACCCTGCCA | 660 |
| CCCCCGGTTG CCTGGAGGGG GGGTACCCCC CCCAAAACCC CNCGCCCCCC CAATTNTCCC | 720 |
| ACGCCCNCCC GAATTTGGTT TNCCTNNGGG NCCCCCNNGG GNCCNNAAAA CCTCCCCTAA | 780 |
| AGNA | 784 |

(2) INFORMATION FOR SEQ ID NO:268:

(i) SEQUENCE CHARACTERISTICS:
        (A) LENGTH: 751 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1231RP (xi) SEQUENCE DESCRIPTION: SEQ ID NO:268:

```
GATCATCTGC GTGAAGGGCG ACAGAAGCCT GGCGATGGAA ACATTGGAAT TGATGCATTA      60
ACGCAAACAC ATGGGTCATT TCCTCAAACT CAACAGAAAG GGGACGAAGC TGCGCACACA     120
GTCGCTGCAA ATCTTTAGCC GAGTTCTGAA AATTCAAAGT CGGTAGTTCT CGTATGTTGA     180
AGCCAGATCC ATAAACTATC TTCTCACTCG CCGGATGCAA AGTATCAAGG AATAGGCGAC     240
AATCGGTAAT GATTGGCTCG AGCTCACGCA GATATTGGCG CACTTCTGAT ATCCGTGGGT     300
TGTTCGATGC ATGATGCACA TGAATAAAAG GAAGAAGCTT CGAAAGAGGT ACACGGCCCG     360
GGTAGCCGTG TGATGAGAGC TGTTAGTTCG GCTTCAACAT CAGCAAGTTT CTCTATAGGG     420
GACGCAGGGT CGTCAACATC ATTTATTAGA CACTCCCAGC ATTTGTTCTT GAAAAAAAGT     480
NGTGCATGNA CAATNGCNCC CCCCCCTTTT GAAANGCCGG AGAAAATTTC CCTNNAANAC     540
NAATNTCTNG GTNNAANTGC TTNNAAANCC CCTTNAATTA AACCCTTNNN GCCNCAAAAA     600
AATTNTTTAA ANCCTTTTNA ACNCCCCGGG AAACANAAAC CCCCCCCCCA AAAAAAACA     660
NGTTTTNTCC NCCCCCCCCC CCCCCGANNT TTTNAAAACC TTTNNAAAAT CCCCCCCCCC     720
CNAAAAANCC CNCNAATTTT TTTTTTAANC C                                   751
```

(2) INFORMATION FOR SEQ ID NO:269:

(i) SEQUENCE CHARACTERISTICS:
        (A) LENGTH: 762 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1231UP (xi) SEQUENCE DESCRIPTION: SEQ ID NO:269:

```
GATCGTCAGC GTGCATCGAC TTGGCATTGC AAAGGGATGT GATCCCTGAG GGGAGGCTTG      60
CAGCAGGCGC GCTCCTTGTT TCACATCATA GGCTGTCGAG GCCGGACTGA TTCAGCTCTC     120
AAGGCGAGCA CCCTCCCAAC GCCCAATAGG GGCCCCCTCC TGGGCTGTGC ACGGGAATAC     180
CTCAGACACT GCGTTAAGAT ATATGTATTT AAGAGGGCAC CAGCTGGCTA TCAATTGCCC     240
TCTCTGCTCT TGTTCCAACA CCAGGCAAGT ATCATGATGT CTGCTGCAGG AAAAATGTTC     300
AAGAACAACG GCCAGAAGGA TGAGCGGAAG AATGCGGGCC AGAGAGAGGA GCGCCAGTAC     360
AGGGTCGGCG ATGAGCAGGG CTTGGGCCGC CAACAGCAGG CTGACTTGGG CGCCCCAGTA     420
CCAGCAGGCG CCACGCTCGC AGCAGTTCGA CGACACTTGG NGCTTCCCNA CATTTGGGCC     480
CCCCACCAAT TGGGNCCCCA GCAAAATGGG CCCCNCNNCT TTNATTTTNG GGGCGAATGG     540
GCCNAAACCT ATCCCCAANT TGNGGGNAAC TCCCCCCCCA GNANGAGAAC NCATTTTTGC     600
ATTGGAAAAC NCACCTTNNN TTTGNNAACG CCCCCCCCNA AAAGCCANGG GACTGTTNTT     660
TTTNGAAAAC GNCCCCCTTT NTGTCNCNNN ANAAATTTTT CTANAATTTG CGNGGATTCC     720
TCCCTTGGGG CCATTCCNTT TTTACCCTTT TAACCCCCCC CC                        762
```

(2) INFORMATION FOR SEQ ID NO:270:

(i) SEQUENCE CHARACTERISTICS:
        (A) LENGTH: 746 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
         (A) ORGANISM: PAG1232RP (xi) SEQUENCE DESCRIPTION: SEQ ID NO:270:

| | | | | | |
|---|---|---|---|---|---|
| GATCTTATTA | ATGAATTTTT | CCCCACGAAG | CTTGTCGAAT | TTTGATTCTA | TGCTTTGCAA | 60 |
| GCACTCAACT | TGGGCTGTGG | TCATGCGAAA | CTAACACGCC | GCGAAACAGA | TACTGCCCAA | 120 |
| GCGTTAGCAC | TCGCTCTTTG | CGGTGCTACA | AACAAGTGTC | GAGCATTAGC | GTGTGACTTA | 180 |
| TTTAGGGTTG | GAATATACAA | AAGTAAGGCG | TACATGCCGA | TATCTCTCTT | GTGTTGCTCT | 240 |
| CTCTTACCTA | CATCTAGATG | TATTCAGGGA | ACTTCCCCGC | GAGATTCACG | GCCAAGGCCG | 300 |
| TCCAGCCCGT | AAAGTGCTGC | ACCCGTTGAC | CTTTCCATCG | TTCTGGTTGT | ATTGTTCGGT | 360 |
| AACAAAAACC | ACCTTTCCCC | AAANTCNAAT | AATTGNTTCA | ACAGGTTGTT | CCCCCCATTG | 420 |
| AAAGGGATAN | NCGTTTAAAC | CCGGNCNAAA | CAANNAANGG | GNNGNTTTTT | TTGGGCANAA | 480 |
| ACCCCCCCCC | NAATTNAACC | GCGTGGGGCC | CTNCNCAAAA | TTNTTTTTTT | CCCCCCNTGG | 540 |
| GGNCCCCNCC | NAANAACCCC | CGNNGTTNNA | ATATATCCCN | CTTTTNCCAG | AAGNGANTCC | 600 |
| CCCNNAACCC | GNGGNGATNT | TTTTGTGNTT | TAAAAANNCC | CCCCCCCCCC | CCNGGGAGGG | 660 |
| NNTTCCNCNC | CCCANCATTT | NNACCNAGGN | GAGTTTTTTT | TCCCTCCCGG | GGGAAAAAAC | 720 |
| ANTGTTNNTT | TTNNNNCCNA | AAAAAA | | | | 746 |

(2) INFORMATION FOR SEQ ID NO:271:

(i) SEQUENCE CHARACTERISTICS:
        (A) LENGTH: 777 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
         (A) ORGANISM: PAG1232UP (xi) SEQUENCE DESCRIPTION: SEQ ID NO:271:

| | | | | | |
|---|---|---|---|---|---|
| GATCAGTTTG | CCGTAATTGA | TACAAAAGGC | AACTGGTGCG | TGGGCGACGT | TGCGAGGAGT | 60 |
| AAAAAGAAGT | CCCGGCGACT | GCGCTTGTTA | AGGAAGTTTA | GCGGGACTAT | TTTTGACCCA | 120 |
| GAGGAGTACT | CCAATTGGAA | TATGATAGAA | TGGTCACATA | TTCACACAAG | ATTGCTTGTG | 180 |
| ATGAATAGGT | CAACTTTCAT | GGAAATTGAC | TTTGTAGACG | GATGGCAGCA | GGAAATTGTC | 240 |
| CAAGCAAAGA | CGTGGTCTAA | CTTGCGCGAT | TTTAAACGCC | TTTCCGATGA | GAGCAGTGTC | 300 |
| CTACTCACCT | GCAAAGAGAT | TATATTCCTA | GACCACAAGC | AGCAGGGAAC | AAAGAGGGCG | 360 |
| CTATCCTGGA | AACACAATTG | GGATAGCAAA | GATTCATCTC | TAAAGCTTGC | TATACACATT | 420 |
| TCTGGCAGCC | ATATGAAACA | ATATTTACAT | GCATTCCTAT | TTCCACCATG | ACTCCCTGCA | 480 |
| GTGCTTATGT | GTCCTTCTTC | CCGGTCCGAA | ACACTTTCC | ATTTTTCCAG | CCATCCCCCC | 540 |
| GCTGNTTGTT | TTTTNCCATT | TACACNCCNG | NTTTTACCGA | AATTACCTCC | CCCNTGTNCC | 600 |
| NAGAAACCGA | GTTTNANAGA | ACCACACCCC | CTTTCATTTC | CCTANNTGTG | CCCGCCCCCC | 660 |
| CCAGGGCGAG | AGTTTTGGGN | CCCCCNTTTT | NTGNACCATN | TTNCCCCNCC | CCNCNAGGGT | 720 |
| TCCCCACCNT | AAAANCCCTG | AAACCCCTTT | TCCCCCCCAC | ATTTTNGGTN | GGGGATN | 777 |

(2) INFORMATION FOR SEQ ID NO:272:

(i) SEQUENCE CHARACTERISTICS:
        (A) LENGTH: 734 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1233RP (xi) SEQUENCE DESCRIPTION: SEQ ID NO:272:

```
GATCACAGTG CTGTGGGCAT TGCTGCTCGT CGTGCTCTTG TGCCCCTCAA GCGCCGAAGT      60

AGACAAGCTG CCAGCAAGCA CTGATTGGTA CAGGAGCTTT TTGTTCACGT TCTTAAGCAG     120

GTTCGCGGTC GAGTCCGCGT TGTTCAAAAC AGCGCCCGGC TGCACGCTCG AGCTCGACTC     180

CCCCGCCGGC GACGACGCCG TGGAATACAC CTCTGATCCC GGGTCGGCAT CCCTCGCTCT     240

CGCAGTCCCC CCGGAAGCAA AAAATTCCTC CACGGATGTA TTCCCGTGGT TGCCCAGCTG     300

CGCACCGGGC GTACCCGCAG CGCTGTTGAC ATTGGACGTG ATATTCTCCA TCAGCAGCTG     360

CGAGCTGATG CCCCCTCGGG CGCCTGTCTT GCTCGCATCT GTAACGTCGT CAGACCCCGA     420

GTTTTGTTCT GTCGTCCACG AACGAGACGT TCAACCATGT GACGACGCAG GCGCGTTTGG     480

CCTTCACCAC CNNATTTGGG CCTTTCTGCT GGAACNCCAA CCCCGGGAAT TTCCCAACCT     540

NTGATTCCCN AANTGCCCGG CCNCCNTCCC AAATTANAAT CCCCAATTGN GNTTGAAATN     600

GNCNAAATNA AACCCCNTTT TCCCCTNNTN CNNNNCCCNG GCCCNAANGA GCCGNTGGGG     660

GNTTAAANNC CCCNACCCCC AAANTTATAC CCTTTTTTTG NNCCCNCCCC CCNNCCCTNT     720

TTTTTTNCCC NTCN                                                      734
```

(2) INFORMATION FOR SEQ ID NO:273:

(i) SEQUENCE CHARACTERISTICS:
        (A) LENGTH: 761 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1233UP (xi) SEQUENCE DESCRIPTION: SEQ ID NO:273:

```
GATCCAGCTT CCATATAAGC TCGTGTTTGC GGTCGCGACC TCTACAGAAG TGGTGATATA      60

TGATACTGTT ACCACGAAAC CCATTGCAGT GGTGGGAAAT TTGCATTACA CCCCGCTAAC     120

GGACCTCAGC TGGTCTGACA GCGGCCACCT ACTCGTCGTG TCATCAACAG ACGGTTTCTG     180

CTCCTATATC TCAATGGAGG ACAGCCTATT TGGCGAGCCA TACAGTTCCG AGGCACAGCG     240

GACGGATTCT CTCATACCTT CGACTCCAAA AAGCAACATC TTCAGGAACA CCCTGCGGTC     300

CAACCCGGTC AACGTAAAGC GGAAGCACTC TGTAGGCGGC CACAACGACT CACCCATAAA     360

GCGCGCTGCC AAAAAATGTC GCCGCTTTCC CCTGTGGTCG TCGATGAGGG ATCTGCGCCG     420

GCACACAACC GCCTACTCCT AGCAAAGATC TCAAGCCTCC GAAGGCGCAT CCAACCCGTC     480

CTTGTTTAAT GACAACAACG GCGGCACCTA GTATCCCCNC ACGCCATCCT ANAAGTTTNG     540

ATTCCNNTAT ACTNAAATAC AAACCCGANA ANCNNTTTTC TTGTTNACAA ACTTTTTTTT     600

GACCTGCATC ACACTATCCC GGNGNGGTCA TTCTTGCCGA ATGCCCCTC CCCCTTANAA     660

CNCCCNTACN TAAACCTTCC CNCNTCCATA TTTACTCATG AATCNCNGCG AANTCNCTGC     720
```

```
GGATCNNCCA NCTTTTGCGT AGTNTTCCCC TTTTTGTTCC C                        761
```

(2) INFORMATION FOR SEQ ID NO:274:

(i) SEQUENCE CHARACTERISTICS:
        (A) LENGTH: 728 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1234RP (xi) SEQUENCE DESCRIPTION: SEQ ID NO:274:

```
GATCACAGTG CTGTGGGCAT TGCTGCTCGT CGTGCTCTTG TGCCCCTCAA GCGCCGAAGT    60
AGACAAGCTG CCAGCAAGCA CTGATTGGTA CAGGAGCTTT TTGTTCACGT TCTTAAGCAG   120
GTTCGCGGTC GAGTCCGCGT TGTTCAAAAC AGCGCCCGGC TGCACGCTCG AGCTCGACTC   180
CCCCGCCGGC GACGACGCCG TGGAATACAC CTCTGATCCC GGGTCGGCAT CCCTCGCTCT   240
CGCAGTCCCC CCGGAAGCAA AAAATTCCTC CACGGATGTA TTCCCGTGGT TGCCCAGCTG   300
CGCACCGGGC GTACCCGCAG CGCTGTTGAC ATTGGACGTG ATATTCTCCA TCAGCAGCTG   360
CGAGCTGATG CCCCCTCGGG CGCCTGTCTT GCTCGCATCC TGTAACGTCG TCAGACCCGA   420
GTTTTTGTTC TGTCGGTCCC ACGAACGGAG ACGTCCAACC ATGTGTACAA CAAGNCGTTT   480
TTGGCCTTCA CACCCATTTG CNCTTTTCTG GTNGAACGCC AACCCCGGAT TTCNCAACNG   540
GNATTTCCNT ATNGCCCGCC CCCNCCNNA AATANAACCC CAATGTNGNN TGAAANGGNA    600
NAAAANAACC CCCTTTTCCC CCTTTTCAAA CCCCGGCCCN AAAGGCCNNT GNGTGNNTAA   660
ANCCCCCCCC CCCAATTTAA TCCCTTTTAA TTGCCCCACC CCCACCCCTT TTNTTTNNTC   720
CCTNNNCN                                                            728
```

(2) INFORMATION FOR SEQ ID NO:275:

(i) SEQUENCE CHARACTERISTICS:
        (A) LENGTH: 782 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1234UP (xi) SEQUENCE DESCRIPTION: SEQ ID NO:275:

```
GATCCAGCTT CCATATAAGC TCGTGTTTGC GGTCGCGACC TCTACAGAAG TGGTGATATA    60
TGATACTGTT ACCACGAAAC CCATTGCAGT GGTGGGAAAT TTGCATTACA CCCCGCTAAC   120
GGACCTCAGC TGGTCTGACA GCGGCCACCT ACTCGTCGTG TCATCAACAG ACGGTTTCTG   180
CTCCTATATC TCAATGGAGG ACAGCCTATT TGGCGAGCCA TACAGTTCCG AGGCACAGCG   240
GACGGATTCT CTCATACCTT CGACTCCAAA AAGCAACATC TTCAGGAACA CCCTGCGGTC   300
CAACCCGGTC AACGTAAAGC GGAAGCACTC TGTAGGCGGC CACAACGACT CACCCATAAA   360
GCGCGCTGCC AAAAAGTGTC GCCGCTTTCC CCTGTGGTCG TCAANAAGGN ATTTGGGCCC   420
GGACCACNAA CGCCTACTCC TTANCAAAAA ATTTTTCAAA NCCCCAAAG GGGTCCCAA     480
CCCGNCCCTT GTTTTTTTGA AAAAAAAANG GGGGNCCTCA TTTTTTNCCC CNCCCCCNCC   540
CCAAAATTTT GGGGATCCCN NTNCCNAAAA AACAACCCCC AAAANCCTTT TTCCGGTTAN   600
```

```
NAAANNTTNN CNNTNGACCC CCNCCCCCCC TTCCGGGNGG TCATTTNTNC NAATNGCTCC    660

NCCCCCTTNA AAGNNCCCNN CNAAAAANCN CCCCCCCCCC NTTTTTCCCC NNNAACCCCC    720

GGGAAAATTC CCNCNGGGAN NNNCNANTTT TTCTTGGTCT CCCCCTNTTT NTTCCCTTNA    780

GG                                                                  782
```

(2) INFORMATION FOR SEQ ID NO:276:

(i) SEQUENCE CHARACTERISTICS:
        (A) LENGTH: 747 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1235RP (xi) SEQUENCE DESCRIPTION: SEQ ID NO:276:

```
GATCCTTGAG AAGCCAGATA ACGACGAGGA CGAGGAGCCC AGTGACGATG AGGATGCCGA    60

CGACTACGAC TCGGATTCTC CCCGGCCCGG CGACAGCGGC AGCGAACTCA GAGACCCTCC    120

TGCGCCGGCG ACATTCGCTA CGGAACTGCA CGGATCCAGC GTCCTGGCCT CCCCGTTGAC    180

CTATTCCTTG CGCTCCGTCA TCGTCCACTA TGGCACACAC AACTACGGAC ACTACATTGC    240

CTTCCGCAAG TTCCGTGGTG TGTGGTGGCG CATCAGCGAC GAAACAGCGT ACATCGTCGA    300

TGAAGCTGAG GTCTTGTCCA CACCGGGCGT TTTCATGTTG TTCTACGATA TGACTATGAC    360

GAGGCGACCG GGCAGTTGCG TGACGACTTG GGCTGCCTAC AGGAGCCCAG TCCGTGCTGT    420

CAGATGGGGA CGGAAGAATA CGACTCATTG ACCGGGTCCA CCAAGACCTC GATTCAACGA    480

NCCAGCTGTT GCTCCCGCCA ATAAACTTTG TTTGGGGCTG GCCGGCCATA TNTNCTCCAT    540

GCATGTTCAT GCCCCCACCG GACATGTTTG ATCCANATAC TTTTTGTTTN GTTNCCCCCT    600

TTCAGNGNTT CCCCCNAAGC AAGATTCTTA NNCTACTTGC CTNGTTGTTC CCNCCTGGTT    660

TGGNACCCCA AATTCCTNTT NNCCNTTTNT GGCCCANCCC NNGGNAAACC CNCCCTTTTT    720

TTTCAAACCA GGNTTNCCCT TTTNGCN                                       747
```

(2) INFORMATION FOR SEQ ID NO:277:

(i) SEQUENCE CHARACTERISTICS:
        (A) LENGTH: 776 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1235UP (xi) SEQUENCE DESCRIPTION: SEQ ID NO:277:

```
GATCACACCC GTGTTCTTTT CAAAGGTGAC CTGCAACTTC TTGTTATTCA AGATGATAGT    60

CTCACTGTCC TTTGACACGC TAGCAGGGTA AAATACCGAC TCCTGCGCGT CAGCGTTTTC    120

TGCAGCCATG TTATCCCATT GCAAGGTGCC TATTGGGACC AAACTTTCCC CTCCTGTGTT    180

CAAGGCCTCC AAAGCTCTCT CTATGAACCG ATCTGCTAGC TGCACGACCT TGTTAAGCAT    240

TGGTATTGCT TCATATTTGT ATACCATTTC TATACATGTC CCGGGAAGGA CATCGTGGAA    300

CTGGCATAAC AAGATATCTT CCCATAGAGC GTTAATATCA TTAACAGGGT ACGTGTACTT    360
```

```
GTTAGGCGCT AGTAGCGAAA CCTTTGTGGC AATCCACTCC AAATCATGGA TCTTAACCTC      420

AGATAGTCTC ATCAACCGTT TAACGTCTGC CTGTGTCGTA TACGTGCCTC CTATGGAAAT      480

CAAAGTTACA ATCCGCCCAT CCAAGTTGGC CAATGNGTTC CCANTGTCTG NCTTCNGCAT      540

AATATCACCG TAAAAACCGT TTANGGAATC CCCNACCCCC NACCTTNGGG AANAACATTG      600

CATTCCCGGT TAAAATTGAA CCGANACCCC CCATTTGTTC CACCNCCCCC TGTTTGAACC      660

CCNCCCCCGN CNCCGNACCC NNAAAAANAA CCGTTGCCNA ANGTTCATTN AAAGTTTTGT      720

TCCCCCCGGG TTTAAAANCC NAATTTTNAN AAGCGTTCTT TTTCCCGGGG GGGTTG         776

(2) INFORMATION FOR SEQ ID NO:278:

(i) SEQUENCE CHARACTERISTICS:
        (A) LENGTH: 722 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1236RP (xi) SEQUENCE DESCRIPTION: SEQ ID NO:278:

GATCTCCCTC CGGTCGAAGT ACGTCGACTG TTTGAGACTC TGCAGGTCGT CTTTTGATAG       60

CTTCGATGCC TTAGCTCCCA TGTCTACTAT AACGCTGTCC CGGGCCTCAG CTATGTGCGG      120

GCTGCCTATC TTACTGCCTA ACTCTTGGAA GCGTGAGAGG CCATAAGCCA CGATCGGCGA      180

GCTGCTCAAA TTATGTCCTC TGAAAGCGGT GTGTGGGTCC ACTTTCCCAG ACCCAAGGCT      240

ATGCCGGTTA CCTGACCTCC GGTCCGGATG TGACGCTGGG AGGCGGTGCG ATGCCGGCCC      300

TCATGGCTGT CGGTCGCGAA GGACTATCTA CCAGGGACTT GGCTGCCTGC GCAATTTGCA      360

CTGCAGCTTG CAGTGGAGGT CTTGGCGAAG CTCACCGGCA GCGGCAGGCA GTTACAGCCA      420

TGGCACAGGC CAAGCCCCGC GAGTTGACCG GAGTTGGTTG CCAGATATTG GGCCGTCCAA      480

ATTCTGANTA GCCCTTTATA TNAGANCCCC NCCGTTGAAC CCCAAGNTTT TTTATGCGGA      540

TGGTTCGAAT TCNGCCCCCT GCGTTAACCC CCCCCGAACC CCTNCCCCCG GCAAAANCAA      600

ATCCTNCCCC NGTTCNAAAA ANCCGAACNC NNAAAATTTT AAAAGAGACA AATCANNNCA      660

CCCGNGAAAA AGAGCCCTNT CTTTTGAGAA TTCCCGGGGG GGGGNGTAAA TTNAACCTTT      720

GA                                                                    722

(2) INFORMATION FOR SEQ ID NO:279:

(i) SEQUENCE CHARACTERISTICS:
        (A) LENGTH: 789 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1236UP (xi) SEQUENCE DESCRIPTION: SEQ ID NO:279:

GATCTTCGTC CGCTTGCGGT CAGGAAATTC AAGCGGGATG AGCTCTTGTT TCAGTTTACC       60

ATAAAAGAGC TGTTTTACAA GGTCGAATTG CTCGCCCTCT TCATCCAAGC TGAGCGGGAC      120

GGACGCACTC TCAATTTGGT AGAGGACGTT CCCAATGCAT TCCGTCACAT CTTGCTGTCT      180

GCCAATCTCC AATGTGTTTT CTAGCTGGTC GGAACTAATT TTCGCAACAT AGGTGGAAGT      240
```

```
TTCAGGGCCT TCGGCCTCTG GACTCCCGAC CATGGTGATA TCTTTACCTG AGTCATCATT    300

CTCAACAGCC TGCCTATCCT CAAGCGGACC TGCGCTGGTG TTTTCACCCN TTGGGNGGNN    360

GAANTCCAAT ANNCCCCCTT TCTGGGGTTC TTGGAAAGNA TTNGGANAAT TTNNTGGCCC    420

GGTTNTTACC NTTTTNGANA GAGACCCTTG GNNTNTCNAN ACCNAAATNN TCCCNNGGGG    480

CNCCCGCNCG AATNTTTTTN TNTCCAAANT TTCCNAAANN CCNCTTTTNT GCTTTTCCCC    540

NTTTNGGNGG NAGCGCCCCA GGGGGNCCCC CGAANTAATC NGGGGGNTGG AAAAANAAAA    600

NAATTTCCCA NAGGGGTNTT TNTTTTTCCN TCNGAGAAGG GNGGTTANAA AAACCCATTT    660

TTTCCCCCCN NTAGANAACC CCTTTTNCNC CGGGGGNTCC NGCCGGGGGG ATTNTTGNGG    720

GNGCNTTGNN NACCTCCCTT CCCCNCTATA NAAATNCCCC CGGGGGGGGG TTTNNTTTTC    780

CCCNNAAAN                                                            789

(2) INFORMATION FOR SEQ ID NO:280:

(i) SEQUENCE CHARACTERISTICS:
        (A) LENGTH: 676 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1237RP (xi) SEQUENCE DESCRIPTION: SEQ ID NO:280:

GATCCGGGTT GAAGACATTG TCAGGTGGGG AGTTTGGCTG GGGCGGCACA TCTGTTAAAC     60

GATAACGCAG ATGTCCTAAG GGGGACTCAT GGAGAACAGA AATCTCCAGT AGAACAAAAG    120

GGTAAAAGTC CCCTTGATTT TGATTTTCAG TGTGAATACA AACCATGAAA GTGTGGCCTA    180

TCGATCCTTT AGTTCCTCGG AGTTTGAGGC TAGAGGTGCC AGAAAAGTTA CCACAGGGAT    240

AACTGGCTTG TGGCAGTCAA GCGTTCATAG CGACATTGCT TTTTGATTCT TCGATGTCGG    300

CTCTTCCTAT CATACCGAAG CAGAATTCGG TAAGCGTTGG ATTGTTCACC CACTAATAGG    360

GAACGTTGAG CTGGGTTTAG ACCGTCCGTG AGACAGGTTA GTTTTACCCT ACTGATGAAT    420

GTTATCGCAA TAGTAATTGA ACTTAGTACG AGAGGAACAG TTCATTCGGA TAATTGGTTT    480

TTGCGGCTGT CCGACCGGGC ATTGCCGCGA ACTACCATCC GCTGGATTAT GGCTGAACGC    540

CTCTAAGTCA GAATCCATGC TAGAACGCGA TGATTCTTTT CTCGCACATT ATAGATGATA    600

CGAATAGTTG CTTTTANCAT CGCTGAACCA TACAGCCGCA CTGTGTTCAA CGAAGTCTGG    660

CCCTTCCGCG ATTGCA                                                    676

(2) INFORMATION FOR SEQ ID NO:281:

(i) SEQUENCE CHARACTERISTICS:
        (A) LENGTH: 709 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1237UP (xi) SEQUENCE DESCRIPTION: SEQ ID NO:281:

GATCCCGTAC ACGAAGAAAA TCGGACGGGC CAACCAAACC CAAAGTTCAA CTACGAGCTT     60
```

| | |
|---|---|
| TTTAACTGCA ACAACTTTAA TATACGCTAT TGGAGCTGGA ATTACCGCGG CTGCTGGCAC | 120 |
| CAGACTTGCC CTCCAATTGT TCCTCGTTAA GGTATTTACA TTGTACTCAT TCCAATTACA | 180 |
| AGACCCGTAT GGGCCCTGTA TCGTTATTTA TTGTCACTAC CTCCCTGAAT TAGGATTGGG | 240 |
| TAATTTGCGC GCCTGCTGCC TTCCTTGGAT GTGGTAGCCG TTTCTCAGGC TCCCTCTCCG | 300 |
| GAATCGAACC CTTATTCCCC GTTACCCGTT GAAACCATGG TAGGCCACTA TCCTACCATC | 360 |
| GAAAGTTGAT AGGGCAGAAA TTTGAATGAA CCATCGCCAG CACAAGGCCA TGCGATTCCG | 420 |
| AAAAGTTATT ATGAATCATC AAAGAGTCCG AAGACATTGA TTTTTTATCT AATAAATACA | 480 |
| TCTCTTCCAA AAGTCGAGAT TTTAAGCATG TATTAGCTCT AGAATTACCA CAGATATCCA | 540 |
| TGTTAGTTAA AGAACTATCA AATAAACGAT AACTGATTTA TGAGCCATTC CGCAGTTTCA | 600 |
| CTGTATAAAT TGCTTATACT TAGACATGCA TGCTTATCTT TGAGACCAGC ATATGACTAC | 660 |
| TGGCAGATTC AACCAGATAC TATCTTTAAG ACACCCGAAA TGCGCAACA | 709 |

(2) INFORMATION FOR SEQ ID NO:282:

(i) SEQUENCE CHARACTERISTICS:
        (A) LENGTH: 820 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1238RP (xi) SEQUENCE DESCRIPTION: SEQ ID NO:282:

| | |
|---|---|
| GATCACGGCA ATGAAAAACT ACGCAAACGT TACAGACTTT GAGTGGTACA TCGCCCTGCT | 60 |
| TTCGGATCTC TGCATAGTCT CCCAGGACCT GCAAGACAAG ACCCTCGCGC AGAAACTGGG | 120 |
| TGAGCAAATT AGAAACATCA TGGTGAAGGT TCCTGACCTG CGGGATCGCA CTTTGGCGCA | 180 |
| GATTGTGCAG CTGGTGAAGA GCGAGGACAT CACGGCCCGG CTGCCCGGTG TTCTGAAGGA | 240 |
| GTGCATCTGG TGCCTGGGCG AGTATTCGTC GTTGCTCGAC AATAAGGATG AGTATATTCT | 300 |
| GCTATTGGCA GAAAATTCGA ATTATATGA GCCTGAACTA CAGCAAACTT TGATCCCTGC | 360 |
| CATTTTGAAG ATTTATAGCA ATTGGTGTAA CGAGTCGGTG GTCGACACGG GTCCGTATTA | 420 |
| AATGGGTTAC CGAGCGGATA ATCACCCCAC TAGAAGATCT AATAATCTCG AAGAACTTCG | 480 |
| AAGTCCAGGA GCGGTCTTCC GAGGCTCTCG AATTCTACCC TTNTTTCTGG ACNCCCCTC | 540 |
| CNAAATNNTC TGNATCCCTA NCNGCTGGCA NCTTACNAAT TCCTNGCCCA NTTCTNCAAC | 600 |
| CCTTTGAATT NACCNCNNTN CCNTCGGGCC CCCAAAAANC TCNNNNNAAA CTNTTNTTCN | 660 |
| ATGGGAACCC CCTTTNCCCN AAANGAAGCC ANANNNNACC GNAAAACNCN CTTGAAGNGA | 720 |
| TTTCCCCGAG TTTTGANAAC ATTTCNNCCN AATTTTCCGG GACGGCCAAA AAGGGTTTTN | 780 |
| CAAATTANTT CGGGGGGGGA AGGGGAAGGG GGGGGNGNNA | 820 |

(2) INFORMATION FOR SEQ ID NO:283:

(i) SEQUENCE CHARACTERISTICS:
        (A) LENGTH: 875 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1238UP (xi) SEQUENCE DESCRIPTION: SEQ ID NO:283:

```
GATCAGAAAC GGCCGGCTGC AAGAATGGAT GGCGATGAGC TTCGAGCAGT TGAGGCATCG      60

CTTATGCAAA AAAGAAATT  CCTCAGATCA CGTGACAAAG TTTCGTCATC TCTAAATGTC     120

GACGGTTGGG CGAAATGTGC CGTCCTCTGC TATAAAATAT AAACTAGTTT CTCTACCACT     180

AGACTGATTG GGAATATCTA AGCTTTCACT TGATAGCAGC AGGAGCACTT CATAATCCAG     240

TACCTTCTTT GGCTTATCCA CACTAGTCAT CTCATCGAAA ATGTCACAGC CAGTGCAGAG     300

AGCCGCCGCT CAATCCTTGA TATCCAAATA TGTCAATAAG GAAACGCTAA AATACATGCT     360

TACAACGCAC TTCTGGGGCC CCGTATCGAA CTTTGGTATT CCGATTGCTG CGATTTATGA     420

CTTGAAGAAG GACCCTGAGT TGATTTCCGG CCCCATGACG TTGGCGCTCG TGGTATACTC     480

AGGTATTTTC ATGCGTTACT CGATGGCCGT CACTCCCAAG AACTACCTCT TGTTTGGGTG     540

CCCACTTTAT AAACGAGTCC CGCGCAACTC GGACAGCGTT CCCGCTGGCT CAAGTTTCAA     600

TTACTTCGGC GAGAGCCCTG CTGTCAAGGC ACCCGAGAGA CCCGCATAGG TGCGTTTGCG     660

TCCGCACACG TTGCATTACA GCGTCGACCA CTACATAGAA TATTATTAAG CCGACTATCC     720

TACACGTTTC TAGAGCTAGT CGAGATGCCT TTGGCTGATA CTGCTGCGTT GGGCCAGGCC     780

GTATCTTGCT CCTCCTGGCT TTGCTGCGTT GCGCAGCTCC CANTTGNCCG TTCNCGATNN     840

TCCTGTGTCC CGTATCCATT GNCTAAATGT CTCCC                                875
```

(2) INFORMATION FOR SEQ ID NO:284:

(i) SEQUENCE CHARACTERISTICS:
        (A) LENGTH: 716 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1239RP (xi) SEQUENCE DESCRIPTION: SEQ ID NO:284:

```
GATCAACTTA GAACTGGTAC GGACAAGGGG AATCTGACTG TCTAATTAAA ACATAGCATT      60

GCGATGGTCA GAAAGTGATG TTGACGCAAT GTGATTTCTG CCCAGTGCTC TGAATGTCAA     120

AGTGAAGAAA TTCAACCAAG CGCGGGTAAA CGGCGGGAGT AACTATGACT CTCTTAAGGT     180

AGCCAAATGC CTCGTCATCT AATTAGTGAC GCGCATGAAT GGATTAACGA GATTCCCACT     240

GTCCCTATCT ACTATCTAGC GAAACCACAG CCAAGGGAAC GGGCTTGGCA GAATCAGCGG     300

GGAAAGAAGA CCCTGTTGAG CTTGACTCTA GTTTGACATT GTGAAGAGAC ATAGAGGGTG     360

TAGAATAAGT GGGAGCTTCG GCGCCAGTGA AATACCACTA CCTTTATAGT TTCTTTACTT     420

ATTCAATTAA GCGGAGCTGG AATTCATTTT CCACCTTCTA GCATTTAAAG TCCTATACGG     480

GCTGATCCGG GTTGAAGACA TTGTCAGGTG GGGAGTTTGG CTGGGCGGC  ACATCTGTTA     540

AACGATAACG CAGATGTCCT AAGGGGACT  CCATGGAGAA CAGAATCTCC CAGTAGAACA     600

AAGGGTAAAG TCCCCTTGAT TGATTTCAG  TGTGAATACA ACCATGAAGT GTGGCCTATC     660

GATCCTTAGT TCCTCGAGTT TGAGCTAGAG TGCCAGAAAT TACACAGGAT ACTGCT        716
```

(2) INFORMATION FOR SEQ ID NO:285:

(i) SEQUENCE CHARACTERISTICS:
        (A) LENGTH: 793 base pairs
        (B) TYPE: nucleic acid

```
        (C) STRANDEDNESS: single
        (D) TOPOLOGY: linear (ii) MOLECULE TYPE: DNA (genomic)

(vi) ORIGINAL SOURCE:
        (A) ORGANISM: PAG1239UP (xi) SEQUENCE DESCRIPTION: SEQ ID NO:285:

GATCATCTTC GATCCCCTAA CTTTCGTTCT TGATTAATGA AAACGTCCTT GGCAAATGCT       60

TTCGCAGTAG TTAGTCTTCA ATAAATCCAA GAATTTCACC TCTGACAATT GAATACTGAT      120

GCCCCCGACC GTCCCTATTA ATCATTACGA TGGTCCTAGA AACCAACAAA ATAGAACCAA      180

ACGTCCTATT CCATTATTCC ATGCTAATAT ATTCGAGCTT GCGCCTGCTT TGAACACTCT      240

AATTTTTTCA AAGTAAAAGT CCTGGTTCGC CTAGAGTACA AGTACCCTAG GTTAGCCAGA      300

AGGAAAGGTT CGGTTGGATC CCGTACACGA AGAAAATCGG ACGGGCCAAC CAAACCCAAA      360

GTTCAACTAC GAGCTTTTTA ACTGCAACAA CTTTAATATA CGCTATTGGA GCTGGAATTA      420

CCGCGGCTGC TGGCACCAGA CTTGCCCTCC AATTGTTCCT CGTTAAGGTA TTTACATTGT      480

ACTCATTCCA ATTACAAGAC CCGTATGGGC CCTGTATCGT TATTTATTGT CACTACCTCC      540

CTGAATTAGG ATTGGGTAAT TTGCGCGCCT GCTGCCTTCC TTGGATGTGG TAGCCGTTTC      600

TCAGGCTCCC TCTCCGGAAT CGAACCCTTA TCCCCGTTAC CCGTTGAACC ATGGTAGCCA      660

CTATCCTACC ATCGAAAGTT GATAGGGCAG AAATTTGAAT GAACCATCGC CAGCACAAGG      720

CCATGCGATC CGAAAGTTTA TATGAATCAT CAGAGTCCGA GAACTTGATT TTTATCNATA      780

ATNCNCTCTC CAA                                                        793

(2) INFORMATION FOR SEQ ID NO:286:

(i) SEQUENCE CHARACTERISTICS:
        (A) LENGTH: 836 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1240RP (xi) SEQUENCE DESCRIPTION: SEQ ID NO:286:

GATCTTAAAA TAAGATAGAA TGGTAATAAA TATCATTCAG GTACAATAGA TGCTGGTGTT       60

ACTAAAGGAT TACCTGGAAT ATAATTATCA GGATGTCCTA AAGTATTAGG TGAAAAGAAT      120

ACAAATAATG AAAAGAAAAT TATAAATACA AATACTGTTA CTAAATCTTT AAAAATAAAA      180

TAACCATGCA TTGGTAATCT ATCTAAATTA CCTGTAATAC CTAATGGATT TGATGAACCA      240

TGTACATGTA ATAGCATTAA ATGCATAATT ACTATTGCTG CAATAATAAA TGGTACTAAA      300

TAATGAAATA GAAAGAATCT TATAATAGTA GGATTACTAA CACTAAATGA TCCTCATAAT      360

CATAGTACAA TATCATTTCC AATAAATGGA ATAGCACTAA ATAAATTAGT AATAACAGTA      420

GCACCTCAAT GTGACATTTG TCCATATACT AAACAATAAC CTAAGAAAGC TGCTGCTATA      480

GTTAAAATAA AGATAATAAC ACCAACTGTT CCATACAATA ACTCTAGGTG ATTTATAAGA      540

ACCATAATAT AAACCTTTAC CAATATGAAT ATACATACAA ATAAAGAAGA ATGAAGCACC      600

ATTAAGAATG CATATATCTA ATTATCCACC TATTGTACTC TCTCANAATA GTTCCTACCT      660

GATGANAAGC TATCCATATT ANAAGAATAT GCATACCTTA AAAATACCGT TANAATTGAA      720

TACTAACATA ACCTATAANA CCNAATTCAC CATAATAATG AGAGGGTGAG GNGAACCATA      780
```

```
CNTACNATAC TAATTTAATT ATTGATTTCT TTCCCNTTTT ATTATTAAAT TTTAAT          836
```

(2) INFORMATION FOR SEQ ID NO:287:

(i) SEQUENCE CHARACTERISTICS:
        (A) LENGTH: 860 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1240UP (xi) SEQUENCE DESCRIPTION: SEQ ID NO:287:

```
GATCTAGAAT TATTAAGTCA ACTATTAACT AATATCTATA ATAATAATGG TTTATCATTA       60
AAATCATTAA AGATAATTAT TAATAAATTA CCATTTAATA ATGATATATT ATTATCAAAA      120
AATTATGTTA ATAAAATAAA TAAATATAAT TTACTAATTA ATAATAATTT AAATAATAAT      180
AAAAAAGATT TAATTAATTT ATATACTTTA GATAATAAAT TATTAGATTT AAGTATTCTT      240
AATAATATAT TATTAGGTAA ATATTTAGTA GGTAGTAATA TCCAATTAAA GGGTAGACTA      300
TTAAATAGAA ATATTACTAG ACTAATAAAA ATAAATATTA TGAAAGGTAC ATTTAATAAT      360
TATATATATC AATGAAGTAA ATTAAATAAT TTATATAAAT TAAATTATAT ATCACTTAAT      420
ATTAATAAAC TTAATAATCT ATTTATTAAT AAAAATGGTA TATTTAATAT TAAAATTAAA      480
TTAAATACTA TTTAATAAAT ATCTATAAGT AATTTCTTAT TTATTTTATA ACATTTTAAA      540
ATGTTTTATG TTTAAATAGA TAATAACAAT TAAAATAATAA AAATTAAGAT GCCACAAATA     600
TTCCCATTTT CCTTTATGAA TCAATTACTT ATGGTTTCCT ATTTATTTTA CTATTTTATC      660
CTTCTATCTT ATGTNTTTTA CCTAAGAATT TAANAATATA TACTCCTAAA TATATATTCC      720
NAAATTATAA TAGTTATTAA ATTTTAATTA ATCCANTATG ATCCNTATTT ATAAATATAT      780
AAGAANATTT TAATATATAT ATATGAATNT TATATCNCCN TGAACCATTG NAATNNATTA      840
TAGTTTACAC CCCCTANATC                                                  860
```

(2) INFORMATION FOR SEQ ID NO:288:

(i) SEQUENCE CHARACTERISTICS:
        (A) LENGTH: 837 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1241RP (xi) SEQUENCE DESCRIPTION: SEQ ID NO:288:

```
GATCTAAATA TATATAATTT AATTTATAAA GATTAATATA AACTTTTTTA TTATAATATT       60
TAAGTATTAA ATTATTTAAA CTATTATTAT CATTATTTAA TAAATTAATT ATTTGATTAT      120
TAATACTTAT TATATAATTA TTATATAATT TACTTAATTC ATCATTATTA ATATTTATAT      180
AATTATAAAA ATAATATTTA ATATGAATAC TATTTAGTCT ATGTTCAAAT TTAAATTAG       240
TTATTAAAAT ATTATTAGAT ATTATTATTT TCTTTAATAA ATTATTAAAT AGATTATCAA      300
TAATTAATAT ATTATTTATT AATTGTTTAT TAAAATAATA TATTTTATTA TTATAAAGAT      360
TTAATTTATT TAAATATTGT AAATTATTAT TTTTATTATA ATATCTATTT TTATAAATAT      420
```

```
TATGTTGATT TATATTATTT AATCTTTTTA TAAGAATTAT TATTAAAATT AATTTTAACT        480

TTAATTTCTT ATTATTAATT TTTATATTAT TTAATAAATT ATATTTCATT TTATTTATTT        540

ATTTATTTAA TTAAATTAAT TATTTAATTA ATATTTTATC ATTATTTAAT TAATTAATAA        600

AATATTATAA AGAATGTAGT TAAAAATACT TATAAAAGGA TCCGAACCTA TATTATTGTT        660

TATGAGACAA ATGCTTTAGC CCATAAGCTA TATAGTTTGA CTATCATTTG AGANTTGGGT        720

NCNCCCCCTA TGCTNNCATC CTGNTGTCCC CNCTAAANGA ATTTNTTTNT TNANANATGA        780

AAAANTTATT TATCAAAGAA TTATAATTTT TTAANAAGGG GNANAAGGAA AGACCCG          837
```

(2) INFORMATION FOR SEQ ID NO:289:

(i) SEQUENCE CHARACTERISTICS:
        (A) LENGTH: 856 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1241UP (xi) SEQUENCE DESCRIPTION: SEQ ID NO:289:

```
GATCTGTATA CTAGAGCTTA TTTTACTTCA GCTACTATAA TTATTCTTAT TCCTACTAGT         60

ATTAAAGTAT TTAGTTGATT ACTAACTATT TATGGTGGTT CATTAAGATT ACTAACACCA        120

ATATTATATC TATTATCATT TTTATTTTTA TTTACTGTAG GTGGTTTAAC TGGTGTAGTA        180

TTAGCTAATC TATCATTAGA TGTAGCATTC CATGATACTT ATTATGTAGT ACTACATTTC        240

CATTATGTAT TAAGTTTAGG TGCTGTATTC TCTATGTTTG CTGGTTATTA TTATTGAAGT        300

CCTCTTGTTT TAGGTTTAAA TTATAATGAA AAATTATCAC AAATTCAATT CTGATTAATT        360

TTCTTAGGTC TTAATATTAT TTTCTTCCCT ATGCATTTCT TAGGTATTAA TGGTATACCA        420

AGAAGAATTC CTGATTATCC TGATCTATTC CTAGGTTGAA ATTTAGTATC TTCATTTGGT        480

TCTATAATAA CTATTATATC ATTAATGTTA TTCCTTTATA TTATTTATGA TCAATTAATA        540

AATGGTTTAA CTAATAAAGT TAATAATAAA TCTATTAATT ATATAAAACT ACCCTGATTT        600

TATTGAATCA AATAATATTT TCTTAATGAA TACTACTAAA TCACATCTAT GATTTATATG        660

AATCACCACT CTTAATCNAT CAATTAAACC CTCTAATCCA ACTTTAAATA NNCTTAATTA        720

TAAATTANNA ATAAATTTAG TGGAANAATT AATNGTAANC AATNTTTTNA NGGANTTTAT        780

CTCNNTCCAA CCGAAACTAC TTTTATCCTT AANNAAAACC TTTAATNAAT GGACCNCANA        840

NTCNNAACNN GTTTTC                                                        856
```

(2) INFORMATION FOR SEQ ID NO:290:

(i) SEQUENCE CHARACTERISTICS:
        (A) LENGTH: 831 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1242RP (xi) SEQUENCE DESCRIPTION: SEQ ID NO:290:

```
GATCACGTGC TAAATGTCCG GGTACATTAG TGCACCCGTA CACCGCATTA CGACATTACG         60

ACGCTTCTTG ACTAACCAGG TTATCACGTG TATATAGTTA CATACGAACG TCTGGTACAA       120
```

```
GGAAGAGCCG GCCGGAAGTC CACTTCACCC TTAAATTGCC ACATTTCATG AGCATTTACA       180

ACAGAAGCAC AGCTGTAAAC GTTTCTCGAA CTCGTGAAGT TTCATATTGT TCCTTAAGGG       240

CCCTTGATGT TGCAGTTCAA GCTAGTTCTG TTGGGAGACT CGTCGGTCGG TAAGTCGTCA       300

ATTGTTCATC GCTTCGTGAA GGATTCGTTC GATGAGTTCC GGGAAAGCAC AATCGGCGCC       360

GCATTTCTGT CCCGTACCAT CAAGCTGGCG GACCACGACG ACGCAATGAT CAATTTGAGA       420

TCTGGGACAC CGCGGGACAG GAGCGGTACA AATCGCTGGC TCCGATGTAT TACAGGAATG       480

CGAACGCCGC GTTGGTGGTG TTATGACGTT GACACAGGAG GATTCTCTAG CAAAGGCACA       540

GAGCTGGGTT GAACGAATTA AGAGCAGGTT GGTGACGAGA ATTCTGGTAT CTTCCCTGTT       600

GGGCATAATT GATTNGGGGA NGAGGANCGG AACCNAGGTG ATTGACNCGA GAACNCAGGC       660

TCCCCAAACC CNGGGTGANT TCCCCNAGGT TTNNNCCAAA CCGGCCGGTT NCCGGATTTN       720

TTCCNGGGAT TGGGGGAANN CTAAAACNGG GCNATTCCNT NGGGGCCCCC CCGCNTCCCC       780

ANTTTCCNTT CAAGNCCCCC CAAAGAACAC CCTGGGGNTT ACCCCCTCCC N               831

(2) INFORMATION FOR SEQ ID NO:291:

(i) SEQUENCE CHARACTERISTICS:
        (A) LENGTH: 878 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1242UP (xi) SEQUENCE DESCRIPTION: SEQ ID NO:291:

GATCTTGTCG ATTGTGAAGG AGGAGACGAA AAACGCTACC ATCAGTGTTG CCGTCGAGAA        60

CAAGCAGCTC ATCCCATTCA TTTCGCTGGC GGACGTGGAG ATTTCCGAGG ACGTGACTGT       120

GAAGGCCTTC CCTAACGGCT CTGAGAAGAT CGTTCTTATG GGGCCACGCG ATGAAGCGAA       180

GGAAGCAAAG GTGAATGTTC AGAATTACTT GAACACTTTA GCAAGCAAGG TATCTGAGAA       240

AAAGATTTCG ATTCCTCGCA AGTTCCAGCC TCTGATCGAT GCAGAGGATG TCAGGGAGAA       300

ATACAAGGTC TCCGTTATCT TCCCAACCGC CCTTGGTGAT GATACTGTGT CGTTCTACGG       360

ACTGTCCGCT AATCTTGATG ACGCGATCGC ATATGCTCGC CAGTCGTCTA AGCAGTACAT       420

GGTAGAATCT TTGGAGGTAT CCAAGGCTCA CGGAAAGAAT GTCGCTCATG CAAAGAATTT       480

AATGTTCTAC TTCGCCAGTT ACGAACTCCT CCAAGGATAT TAAGGAATTC GTTCCAAGGG       540

ANTTGAANTT TTGTNCTACC CACTCCCGGA GGGATTTGCC CGNTTTAAAN AAGNTTTTNA       600

ATNCACANTT TTTCCAAAGG GNGAATTTTG GGGNACAAAA AAAANTGTNT TCCCCGNCNA       660

TNCCTTATTT NTTAACNACC CCCCCTCCCC NGTTTCCNCC GNTGAANACC NAANTATNAC       720

CCTTTCCCCC AGNGATTTAC CNGGGCCNTN CAGGGGANTC CNCTTTTTTN CTCCGGANTC       780

AANAAGGGA AANACCNGNN GCTTTTGCCA GGNTGANAAA AAATCCNCCC CCCCCAGAGG       840

TAAGANCCNN GNAAGGNGNG CCCNTTTGGA GAATNCCC                              878

(2) INFORMATION FOR SEQ ID NO:292:

(i) SEQUENCE CHARACTERISTICS:
        (A) LENGTH: 844 base pairs
        (B) TYPE: nucleic acid
        (C) STRANDEDNESS: single
        (D) TOPOLOGY: linear
```

(ii) MOLECULE TYPE: DNA (genomic)

(vi) ORIGINAL SOURCE:
            (A) ORGANISM: PAG1243RP (xi) SEQUENCE DESCRIPTION: SEQ ID NO:292:

```
GATCGCTAAT CCCGAGGTTT GTTTTGAAGT CTGTGATCAG TTGGTTCTCC ACATCTTTGA      60
GAATTCTAAT AGCCTCCGAT GGCAGTTCCT CCAATTCCAT TCGCACCTGG GCAGACTGTA     120
TCTTTAGAGA GTAATTTTCC ACACACAAAG AGTCAATCTT GTCTTGAACA TCGTCAATCA     180
TATACTTCAG TACATCGTTC ATGTTTGGTA GATTCACTGA GCTTTTGAGT GCGCCTTTTC     240
CTAGCGCCGA AAGGTTCCCC GCTTCATTCG ATGAGAAGCC TAGAACTGAC ATCATGGCGT     300
GGCAGCATGT CTTCCGCAAC TGTGACAACC AATAATTCAA GACTGCGGGG CCTAGATAAC     360
AGGGCCCTTG CCCGTCTGAG TCATAGCCTG AAGCCTCCAA GAAGGATTTC CATAGGTTAA     420
CATAATTATC ACGCTCTATC GGTGAGAATT GAAGTTGGAT TAAGTAATGA TGCTGCTTTG     480
GGATTTTAAT CTGATATTCG ACATCATTCT TTGTATGACG GATACAAAGG TTGAAACGTG     540
GGATGATATC AAGAAGTTCT CTTGCGGTGA AAGTCACACC GTTGACACGT TGGAGCTTTG     600
CGAATTTGTT GCGGGATCTA GATGCATCCG ATTGTTGCCC AGTTCCCTGG TATTCTGGCA     660
GACTGTGTTC GATATACTTT GGAGATCCCT TGAAGGGATG CACTGCCATT AGAAATACAC     720
CTTGAATCCN CTAGTGAATG ATAGGTNTAC CCGAACCCCC ANTTTTGATA CCCNGCAGAG     780
TTTGTNCATC GGCCCCTTCN NCTTCCTGCC CACATTGCCT CCCNATTTTA TCCTGAAATG     840
CTTA                                                                  844
```

(2) INFORMATION FOR SEQ ID NO:293:

(i) SEQUENCE CHARACTERISTICS:
            (A) LENGTH: 865 base pairs
            (B) TYPE: nucleic acid
            (C) STRANDEDNESS: single
            (D) TOPOLOGY: linear (ii) MOLECULE TYPE: DNA (genomic)

(vi) ORIGINAL SOURCE:
            (A) ORGANISM: PAG1243UP (xi) SEQUENCE DESCRIPTION: SEQ ID NO:293:

```
GATCTCGTCC CACCACGGGC GCAGGAACGT GTACTGGCCT TTTGAGATCA ACTCTGTCAG      60
GACGTCGATC TTTTCGTCGT AAAAAGGCGG GAAGCCGCAC AACACGGTGT ATAGGACGCA     120
GCCGATCCCC CACATGTCGA CCTTCATGGA GTAGCGTTCG TCCTTCACCA CCTCGGGCGC     180
GGTGTACCCG ACAGTCCCGC ACGGCGTCGT GGTGTTGGTA GCATAAATTT GCTTCGAGAG     240
TCCGAAGTCT GCGAGCTTTA TCACACCGAT CCCGCCGCCC CCGATGCCAG GTCGGAACAG     300
GCCCTCGTCT TGTTTTGTCT TTGGGTCGTC CGACTGTCTC AGCTGCTGGC GCTTGCTGGG     360
TATAAAATCA ATTGGGGAGA ACAGCAAGTT TTCTGGCTTG ATATCCCGGT GGACAATGCC     420
AAGCGAGTGC ATGTGTTTTA CCGCGAGTGC CAGCTGCCTG ATTACATGTC TAGAAAGGTC     480
CTCCGAAAAA TAAGTGAGTC GCACGATTTC TCCAAAAATC TCCCCCCCGG GCAAGCAGCT     540
CCTGGACTAT GAAGTAGTAT GACTCGGTCT CCCTGGAAGT CGATAAACGT CACAATGTTT     600
TCGCCCGAGG ACACCGCCTT GTGGATGGTG ATCTCCTTCA GAACTGCTCT CGCGATGTCG     660
CCTGTTTCGC CGGCTCCNCC CNCTTNTNNC GGGCCCCCCC NCGTGCCCCC ATCGTTAANA     720
GGNNCCTTTT GCTGATCNCC TTGACGGCNC CGTTTNNTAC NGNCNAAGTN CCCTTTCGGN     780
```

```
CGNCCTTCAG CGGNCCNNCG ANNCCCNCGN AAACCCCNCC CNATTTNCCC NAACTTNTCC    840

CNCAANCCAA GNNCCGAANC CCCCC                                          865

(2) INFORMATION FOR SEQ ID NO:294:

(i) SEQUENCE CHARACTERISTICS:
        (A) LENGTH: 851 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1244RP (xi) SEQUENCE DESCRIPTION: SEQ ID NO:294:

GATCCTGCCT TATCACGAGC GCCATCCGAA CTTCCCCCGG GATGTCGTTG AGAGGTAGCG     60

AGCTCACCTC CACAACTTCC TCATCTGAAT CGTCTTCGTA TGTACTATCT AGCTCTTCAG    120

CGTCGCGCGA TGCAGATTCC GCCCTGTCTT TCACCTGTTT CAGCACCGCC TGTGCGTTAA    180

GCTCAGAGAG GCAGGCATGT GTCGCACCCC CGTATATCTG GCCCAGGTAA TACCCCGTGG    240

CCAGCGAAGC CATCGTAACG CTCAGTATGA ACGGTAAGTT GATACCTGCC ATCCTAGTTT    300

CTGTTTGGTA TTCTGCATGC TGAGTGCGCA AGCCAAGTTG GTTGAAAATT CCTTCAAGCT    360

GACAATCGCT GGTCCTGCGC GCAGTTCAAC ACAGCAAAAC TCAGAGAGAG GTATAAACGC    420

CATATATAGG AGGAGACTAC TCTATTCACT GCCTATCTTT TCAGCCCACA GTTCCTCTGC    480

CTGCAGAATT GTGTTGTGAT TCCGCCAGCA TTTTGTTCAT CGTCTCGACA TATTCGTCCG    540

TTATGATTCG GAATCCGTGG AACATTCCGC CGCCAGCCTG TTAGATTAGG CCACACCGCC    600

CTTGTTAGAC CATAGTGCGC GAGTGCGATT ACAGGTTATC CNTCGAACAC CATCCGTAGA    660

ACCAGTGGCT ACNCTCCGGN GTTAAACCCC TACGCTNCCC TTCCACTNTC CGATAGTCCA    720

TACGCGGAAT TTGGGGGGCC AAAAAAGTGC CCNGCAGGAA CNCAAACGAA GNNTCAACGC    780

CNTGTNTTGG GCNGGTGCCN TTTCCNCAAA NCAGTGCGTA NTTNTAANCC NGCCNCTTAT    840

TNTCCCCCAT T                                                         851

(2) INFORMATION FOR SEQ ID NO:295:

(i) SEQUENCE CHARACTERISTICS:
        (A) LENGTH: 859 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1244UP (xi) SEQUENCE DESCRIPTION: SEQ ID NO:295:

GATCAATCTG ACAGTTGGAT TGATACCAGG TGCTATCTCC TTATCAGCCT TTACAGTGAC     60

GAAGGAGGGA TTGGATTGGG GAATGGAGAA TAAAGATATT TTTGATCCAT CACCAGAAGG    120

ATTTGATCCC TCTTTCAGTG AGCATGCCCA ACTTTTACTC TCGGAACGTA TAATGGGAAA    180

CTTTCTCGTT CCAAAGTCTG GCATCTGGAA TTATGCATTT ATGGGTGCTG GATTTAACAG    240

AGAGCTACGT TACGAGCTAT CTCTCGACAT ACCACTCGGA TTTTATGATG AACAGCACCG    300

TGCAACGCAT TTTCTACAAT TCAACGAAGT GGCAGCTGAC GATACTTTGG AAGCAGAACA    360
```

-continued

```
GGAAGATTTA TTCTCCTAAG TACATATTAA GGATAGAGCC AAACTTGCAA CTAGCTTCAG      420

TTGCGTATGA ATCCCATATA TGTATATATC AATACACGGG CCACTCATGG CTGGTGACCC      480

ATTTAAGCAA ATACCATATT TTTTAATGTT GCGGTGATTT TATAATCTCG ATATCATGAT      540

TTTATTTATA GGAGATGACT TTTCCCTCTA CAACGCCACA TTATAGAAGA CCGTCAATGC      600

AGCACCCAGG CTGAAGCCAG AACGGAAATG TTGGAACCAG AACAGGCAGG TTTGAATAGC      660

TCGACATATG AACCTCCCCA GAACATGTTT TTTTTGAACA TCNAATGANT TTCTGCCAAA      720

AACANGAAAA TGGACNCCNN GCATCATTCA AAAAAAACCN TCCTTGAACC TGACAAAAAA      780

TATGCACCCN GATTTTTTGA TCACGGANNG TTTTCTTTAC NCCAATTAAA TAGGNCCCCC      840

NGAGATTTTT ACACCCNCC                                                    859
```

(2) INFORMATION FOR SEQ ID NO:296:

(i) SEQUENCE CHARACTERISTICS:
        (A) LENGTH: 833 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1245RP (xi) SEQUENCE DESCRIPTION: SEQ ID NO:296:

```
GATCAAAAAC AGAGTACCCT CCGCACGAAC TTCCCATATG AGGCCCAGAG AGAACAACAT       60

CGCCGATCAC CTATATCAAC AACGGAGACC TTGGTCTGCC GAGAACGTCA CAGCTTATCT      120

TATTATCGAT CGAATGGATG TTGGAAAGAA GATACAAAAT AACGCATAAT TGCTGAATAT      180

ATTGCACGCT TCTAACGCAA ACGACGAGCC TCACGCTCAG ATTCCATCAA GACCAAGATG      240

TCGTTCTCTC TAACTGGGCC CTTGACGTTT CTGACAATGG TTCTGGAAGT GTCGTCCAAG      300

AACTCAACGC GGACCTGGGT GACACCACCA CGAGAACCGG TTCTACCTAG AACCTTGATA      360

ACCTTAGCTA GAGTGACTGG GGTCTTGGAG TCCATTTTGA TCTATTGCTT CTTGGATATA      420

AAATATCTAG TAAAAGTGC TGAATAGGTG AGAGGAAGAT ATCATGAACA GGCGGTTTTT       480

TTTGATGCCC CGAAAATTT TTCAGGTCTG CGATGCCCAT CGCAGGTGAA ATGTGCTTGG       540

GTTCTTGAAA AATCACATCA TACGATAACT ATGCGTGCAC CCAAAGGCCT TGGCAGCAGC      600

GAAGTGCGCG AAGGTTAGCC AGCCCAGAAC GAAACCTGAG AACAGGTTAA GCTCAGGTGA      660

ATTGTTTGCT TCTATTGCCT TACAGTTCAT CTTCCGGTAA TTGCAGTATC CGTTGATTCC      720

CCNCAGCTGA CCAGCCGTTN ATTCCCGTTT GAACTTTCAG AGNTCNTGAA ACCCTNGTNT      780

TTTCAACCCN TGACACNTAT ATCNCCCCCT TATATGACTT CCGTCNATNC CCG             833
```

(2) INFORMATION FOR SEQ ID NO:297:

(i) SEQUENCE CHARACTERISTICS:
        (A) LENGTH: 864 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1245UP (xi) SEQUENCE DESCRIPTION: SEQ ID NO:297:

```
GATCCGGGTA ATACAACGCC TCGGACCCCT CGGCGGCTAA CGAGAAAATC GCGCTAAGCT       60
```

| | |
|---|---|
| TCCAGCCTAA TCATAATAAA AGGGGCATTG GTGGAAGCTT TCTGGTACTT ACGCGAGTAA | 120 |
| ACAAAAGGCG CAAGGACGTT TCAGAAGAAG CCAGAAGCAG CAATGAGCGA GATCAACTCG | 180 |
| ATCATTCACA GAGTGAATGT ACTGGTCTCA AAACTGCCCA AAGAGAAGGA TGCAGGCCTG | 240 |
| GAGAAAGAGT GCGCGCTGAT CAAGTTCGGC GGCATGGTAT CTAACCGCGA ATCGGGCCTG | 300 |
| TTGTTTGGAG AACTGGCGCA GCAGATGGAT CGCACAGCGG TGCTACGGCA GCCATGGATT | 360 |
| GTCGAGTTTG TTGTGCGCTT GGGCAACGAG CTATGCCGGC GTGGCGAGGT GGGCGAGAGC | 420 |
| TTCTGGGGCA AGATATTGGT TCCGTTGGAT GGACAGACCC CGTTATTGAC AGTTACTAAC | 480 |
| AAGAATCCAG GGTGCGAAGT TTTCGCGTAA TGTTGCGGTC CATGGCCGGT TGGTGGAGGC | 540 |
| GCTGCTGGAC GGCGCCTTGT CGCGTACGGC TCCCTGTGCG TGGCAGAATA TGGCGTTGTT | 600 |
| GCTCCAGCTG TCCTATNNAC CNNCCGGATT NTCCGGAAGT TGNTGNCCCC CCTTTACCCC | 660 |
| CCCCCTNNCN AGNATGGTTG GNGACCNTTT GNNCGNTTNC CAACTTCCTT NTNCCCCNCT | 720 |
| TTTTTTGNAC NTTGAANCNA TTTTTCCCCC TTNAANTCAA CCNACCNGTT NTNNCAACCC | 780 |
| CCCCCCCCTT TGGGAAAANN AGNAAAAAAN ACCTTTTCCA CCCNGGATNC CCTTTGGNCA | 840 |
| NCTGGAACNG NNNTNTTCNC CCTC | 864 |

(2) INFORMATION FOR SEQ ID NO:298:

(i) SEQUENCE CHARACTERISTICS:
        (A) LENGTH: 830 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1246RP (xi) SEQUENCE DESCRIPTION: SEQ ID NO:298:

| | |
|---|---|
| GATCAACAAT GATTGTGGCG ACGGGCGGCG GGGCGTTCAA ATTCTACGAC GTGCTGCTGT | 60 |
| CGGAATTTCC GGGCGTGTCA GATATCCTCC GGCTGGACGA GATGGACTGC CTGACGAAGG | 120 |
| GGTTGGACTT CTTCATCCAC AAGGTGCCCT ACGAGGTGTT CACATACAAC GACCTGGACG | 180 |
| GCGAAGGCAC GGTGGATGCG GTGGCGGATG ATGAGATGTA CCCGTACATG CTAGTGAACA | 240 |
| TAGGATCCGG GGTCTCGATT CTGAAGGTGG AGTCGCCCAA CGAGTGCATG CGTGTGGGCG | 300 |
| GCTCGTCATT GGGCGGCGGC ACGTTGTGGG GACTACTGTC GCTAATTACT GGGGCGAAGA | 360 |
| CGTACGACGA GATGCTGGCC TGGGCAAACC AGGGCAATAA CGCGAACGTG GACATGTTGG | 420 |
| TAGGCGACAT ATACGGCACC GACTATGCGA AGATCGGCCT GAAATCCAGT AATATTGCAT | 480 |
| CGTCGTTCGG GAAGGTCTTC CAACGGGAGA GCGTCACCGC GCCCCTCGGC GGGCCTGACT | 540 |
| TCGGCGTCTG CGACCTCGAC GTGTGAGATC CGAGATTCGA AATGAGAAAT CCNNCACGCC | 600 |
| GAATNTTCCC ATCCCTCNTG TACCCATCTC CAACAAATCG GCCAAATGCT TNCTGCAGCC | 660 |
| AAATCCCCAA CTCAAAAAAA NNTCTTTGCG GTCNTTATNT CCCCGCCTTT TACCCCCTGA | 720 |
| CCCTTTACCC CCCCCTAACT CNGGTCNAAN GNTTTTAACA NCCCNCCCCC TNAGGNTTAA | 780 |
| GGTNNTGGCC CCNNGGCCCT TNTTGCCCCA AAAATTTCCC NNCGNTTCTN | 830 |

(2) INFORMATION FOR SEQ ID NO:299:

(i) SEQUENCE CHARACTERISTICS:
        (A) LENGTH: 861 base pairs
        (B) TYPE: nucleic acid (C) STRANDEDNESS: single
        (D) TOPOLOGY: linear (ii) MOLECULE TYPE: DNA (genomic)

(vi) ORIGINAL SOURCE:
        (A) ORGANISM: PAG1246UP (xi) SEQUENCE DESCRIPTION: SEQ ID NO:299:

```
GATCGTAGAG CGTGAGACGG CACCGGCGGA GGCGCCAGCG CCGGACGGTG TGCAGCCACG      60
GGGGTTTCCT GAGCTGTACC GCCCGGCAGC GATATCTAGC TGGCGCCAAC GGCTGCAGAA     120
GAAGAATGGG CAGCGCAGGC CGCCCGCGGC GGCCCTCGCC GCAAGCGAGG CGGAGAAGAT     180
CCACAAGGAA AACATGGCGT ACATCGAGGG GCTGTCGGAG GAGCAGCGGA CGGCAGAGCG     240
CCGCGAGCTG TTAGAGAGCC TGGACCCCAA GGTCGTGCAG GCGTTGTACC GTCGGTTGGA     300
TGCACGTGCA GCAGCGGACG GAACGGCGCC CTTAGTGGCG GAAGTCGAGG GAGCGGCAGG     360
CACGTGGGTG GGCGGCACCC GCGAGGAGCC GATGATGCCG CGCCTGGATG ACGCGACCGT     420
CGACGCCGCG CTAGGCGCGC CACAGGCTTC GATGCCAGAG GCCGCGCCCA CGTACGACCT     480
GCCAGCGCCG CTGGAGGATG CGGACGACAT CGCGCCCCAG GAATACCAGT TCATCAGCAG     540
ATGGACCATA TGAAGGACAG GACTTGCTAC GAGATATCCA CTTCCTCCGC AATGAGACTG     600
TGGCGCCCAG ACTGGACATC AACGACCCCA ACTTTATGAG CAGCTGCACG AGAATACTTC     660
CGGATNTTCC GAAAGAAANA AATAACTNGA ATGGATGAAG GCCACTGAAC CCTGACACTC     720
TTCTNCTAAC TCNCCGATTT TGCCGAATGC CCTCCAACTT AGGGCCCATG TCCCCCCCCC     780
CCGGAATTTN NTCCCCNNAA CNGCCTCNNC CCTTCGAAAA CCCCCCTTTN CCGGCNTTCC     840
TCCCATTTGC ACNTTCCCCA C                                               861
```

(2) INFORMATION FOR SEQ ID NO:300:

(i) SEQUENCE CHARACTERISTICS:
        (A) LENGTH: 810 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1247RP (xi) SEQUENCE DESCRIPTION: SEQ ID NO:300:

```
GATCTGGCCG CGCAGCTGCG GCCTCGTATT GCTCCCCTGC GTTACTGTGG CGCCGCCGGC      60
GTGTCTTATT CGGCATCGCG TACGCGTCAC TAAGCCCCTC CAGGACGGGC ACAAAAAGCG     120
CAGGGCGCTC ATAGAGCACC ACAGCGTCTG GGTCGGGAAG CACGTGCATC CGCGGCGTGT     180
GCTTGCTCAC CGCCTCGTGC GCCTTGCCCC GCTCTGCCAC CGGCGCAGCC GTTGCAGCCC     240
CGCGGGCCGC GGGCGCCCTG TGCACTGTAG CGGCACGGCC GCGGCGGACG CTCCGCTTGC     300
GGACCGCCTT GATGACCCGC TTTGCGCCCG GCCCGCGCGC GCTCGCCCGA GCGAGCGCCA     360
GCCCCCGCTG CACACGCATC AGCATCCCAT CCACCGCTTT CCTGTCGTCT TCCACCACGC     420
TGTCGCCTGA AGCAGACTCT GCGCTATCTC CTCCGCCTCG GACGAAAGGC CTCGTCGCTG     480
CTCGACTCGC TCTGCCCGTA CTTCCGTCGA AGTACGCGCG CAGTGCCGCC GCGCGCTTCG     540
CCTCCGCGGC CGCCGGCGGC GCGAAGGGCA CGTTAGGGCG CCGAGCCGCC GTCAGACCCT     600
CCTCATCGAA TCCGAACCGC TCGCGCCGTC GCGCCAATCG CCCACGGAAC CANCCCCCCG     660
GGGGGTTNCG NGGCCCGGCC GGCCCCCTCC TTTTNAAAAC GACNACCNCT TGNAAANCCG     720
```

```
TTACCCCNCN CNNTTCAAAC NCCNGGAAAA ATTTTCGNCN ANNNNNNNNN CCCCCCCCCT    780

NTNCTNNGAA ANAANGNCCN GGCCCTNNGG                                    810

(2) INFORMATION FOR SEQ ID NO:301:

(i) SEQUENCE CHARACTERISTICS:
        (A) LENGTH: 630 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
         (A) ORGANISM: PAG1248RP (xi) SEQUENCE DESCRIPTION: SEQ ID NO:301:

GATCAGATAC CGTCGTAGTC TTAACCATAA ACTATGCCGA CTAGGGATCG GGTGGTGTTT     60

TCTTATGACC CACTCGGCAC CTTACGAGAA ATCAAAGTCT TTGGGTTCTG GGGGGAGTAT    120

GGTCGCAAGG CTGAAACTTA AAGGAATTGA CGGAAGGGCA CCACCAGGAG TGGAGCCTGC    180

GGCTTAATTT GACTCAACAC GGGGAAACTC ACCAGGTCCA GACACAATAA GGATTGACAG    240

ATTGAGAGCT CTTTCTTGAT TTTGTGGGTG GTGGTGCATG GCCGTTCTTA GTTGGTGGAG    300

TGATTTGTCT GCTTAATTGC GATAACGAAC GAGACCTTAA CCTACTAAAT AGTGCTGCTA    360

GCATTTGCTG GTTGCGCACT TCTTAGAGGG ACTATCGGTT TCAAGCCGAT GGAAGTTTGA    420

GGCAATAACA GGTCTGTGAT GCCCTTAGAC GTTCTGGGCC GCACGCGCGC TACACTGACG    480

GAGCCAGCGA GTATAACCTT GGCCGAGAGT CTGGGTAATC TTGTGAACTC GTCCCGTGCT    540

GGGGATAGAG CATTGCAATT ATTGCTCTTC CACGAAGAAT CCCTAATAGC GCAGTCATCA    600

CTTGCGTTGA TACTTCCCCT GCCCTTGTAC                                    630

(2) INFORMATION FOR SEQ ID NO:302:

(i) SEQUENCE CHARACTERISTICS:
        (A) LENGTH: 700 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
         (A) ORGANISM: PAG1248UP (xi) SEQUENCE DESCRIPTION: SEQ ID NO:302:

GATCGCTAGA TGCCCAGGAT GAGACTGTTC AGGTTAGGCA GGTGTTGTAT GCGCCGCCAG     60

AGGGAAACCC AATGACTTTG CATAGAACAA ACCCGCCATC ACCCATGTCT TGCGCTGTAT    120

AGAGACTAAG GTATCTGACG ATCCCTTAGC GACTCTCTCC ACCGCTCGAC GAGGCCATTG    180

AGCTCTTACG AACTGCACAA ACCTACTCGA ACTCTGTTTC CAGACTTCTT TCTGTTTGTC    240

TTCAACTGCT TTCGCATGAA GTACCCCCCA GGCTATTTTT CTTACCCGCC TGGTGTTTGT    300

CTATATACCC GGTTGTATTT TTGATAAAAA ACTCAGCTCT TCCTCTACGG CAGAAATATA    360

TATCCAGTCC TTAGCGCCAT GCGAAAATCT GCCTTTTTAC CGCTGTTTCT CCCAGTCTTA    420

GCACTGGCAG AAAAAAGATG TATGGCGTAT AGGCGCTGGC CCCGCGGAAA AAAAAAAAA    480

ATAGAAAAAT AGAAAAATAA AAAGACGTGG GCCGCCCCGC GGGCAGACGA AGAAAAAATA    540

GGCGCCCACC CCTCCCAAGC AGACGAACAG GCGAGACATA ATAAATCCCA CACCAGGGAA    600
```

| | |
|---|---|
| GAAAGTCTTG TGCACGCTCC CGGCTCATAC GCTGCCATCT GTTCCATCCG GNTTGCAACC | 660 |
| AGTATGGATG TTCAAGCATG TCCGANGCTC CGCTGCCTTG | 700 |

(2) INFORMATION FOR SEQ ID NO:303:

(i) SEQUENCE CHARACTERISTICS:
  (A) LENGTH: 837 base pairs
  (B) TYPE: nucleic acid
  (C) STRANDEDNESS: single
  (D) TOPOLOGY: linear (ii) MOLECULE TYPE: DNA (genomic)

(vi) ORIGINAL SOURCE:
  (A) ORGANISM: PAG1249RP (xi) SEQUENCE DESCRIPTION: SEQ ID NO:303:

| | |
|---|---|
| GATCATGCAA CATTTCTTCT TTTCCCGCTT TCTGCCTGTG CCGGACGGTG TGTCCCCGCC | 60 |
| CCGCACCTCT GAGGAAGAGC TTGCGGACTG CAGCGAGCAT GCCCACAGTA CCTGGGGCGA | 120 |
| CTGCTGCGGC ATTCCGATAC CCAGCGCGGT GGCCGCCTCC GAGGCCACTC GCAAGCATTC | 180 |
| TAAACCACTT CCATTCGATT GAATCAAATT ATATATACCA TTAAGTAGAG CTACCATGCG | 240 |
| AACCTTAGCT GGGACGCAGT AAAGATTGGC GGTTTCCAGA TCAGCTTCTC GGGGTCGATC | 300 |
| GATCGCCTTT TCTTCGCTAT CAGCTTCTCG TACCTTAGCA GCACGTCCTC GTTCAGGTAC | 360 |
| AAGATGTGCT GGCCCTTGTA ATATCGCAGT ATGTTAAGAG CCTTGGCTGT GTGCAGTATG | 420 |
| TCTGTAGTCG TGAGCGATGT CATGCTACTG ATTTCATCGA TCGTGATCTC GGTGCCGTTT | 480 |
| TCGACTAGCA GCTTGATCAG GGTATCGGAC CAATAGGCTC TGTAGAGAGC AGCCCAAGAT | 540 |
| CAGAGAGCGG CTTCTCCGGC ACCCAACTTG TTCTCCTTCT TAGAGAGCTC CATACGAAAC | 600 |
| TCAATCAGCA GCCTGCCGTA CCCCATCCGC TGGTACTGAG GGAGCGTCCA GAATACACGC | 660 |
| CACATTGTAC CCGTCCGCCA NTCCTTTCCN TTGGANAATN CCCACCAAGT NGGTGCCCCA | 720 |
| CTCACTCCCC TGTGTTCTTG CANTAAAAAA AAGGTCAANT TCCTATNACT CNTGTGNTCC | 780 |
| AAAAAACTTT GANAAAGNTN GTTGCGNACC ACTTCCTNNT NCCCCGTCAA TTCAAAT | 837 |

(2) INFORMATION FOR SEQ ID NO:304:

(i) SEQUENCE CHARACTERISTICS:
  (A) LENGTH: 853 base pairs
  (B) TYPE: nucleic acid
  (C) STRANDEDNESS: single
  (D) TOPOLOGY: linear (ii) MOLECULE TYPE: DNA (genomic)

(vi) ORIGINAL SOURCE:
  (A) ORGANISM: PAG1249UP (xi) SEQUENCE DESCRIPTION: SEQ ID NO:304:

| | |
|---|---|
| GACCTGCCGA TGGACNGCCG TTGGCAGGTG ACTGCCCTAC GGTCTTTAGT CCCCGCAAAG | 60 |
| CGGATGGCCT TTGTCGGCAC ACGCAAGAAC TTGGCAATGA TGTTGACCAC GTCCATGGTG | 120 |
| TCCTTATTCT CCTTGTACAT TGTGAAGTGC ACGCAGTTCT TGGAGGGGCC GTACCCCAG | 180 |
| TTAATGACAC CGTTCTCGTC TCTTGTCTGC TCCACATAGT CCTCTTTGCT GACTCTGGTT | 240 |
| TTACGGTTGG CCAGGGCAAT CTGGAATGTG TTGGACGCCG AAGTGACCGA TTCAAGCTCA | 300 |
| TTGTTGAACG CCTTTCGTAG CAGCTGGTGG ATCTTCGTCC GTGCAGCTTT GTCGTCAAAG | 360 |
| CTCCTGGTGG TTTCCATTTT CGTGACGTTC CTGTACACGG CCTCAATCTG CTGCATGTCC | 420 |
| TCCTCGCCCA GTAGCTCTAC CAGCTGGTTC CGCAGCTCTG CCTCCACCGC GTGGTTGTGG | 480 |

```
CGCCGTTCGC GCTCTTCAGC CTGCTGTGCC TTCACCTGGT CGGCAGAGGT TTGGGTTTAG      540

CAGGCATTTT GAACCCATTG TCCCGCAAGT ACACCACTGT TCCATCCTTC TGGATCTCAT      600

TGACCATGAA GTCGGAATAG CGCTGCTTGA TCTGCCCGCT AAACCCTGGT ACTCTGCTGA      660

GAGGTACTCT GTGATCCAAC GTCGATTCCT TGAGTCCATC GGTCTCCGNT TTGGCCCCTT      720

NCCNCAAAAG TTCCTGGCTG CTCCNNANCC GCTCTNTAAT CCCCCGAAAN TCTGTACNNT      780

TCNCNATTTC CNNTNTNNCC TACCTNAACC CTTGTTNAAC CTTCCACCCN ANAANTCATA      840

AATATTCCCC NCC                                                        853
```

(2) INFORMATION FOR SEQ ID NO:305:

(i) SEQUENCE CHARACTERISTICS:
        (A) LENGTH: 834 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1250RP (xi) SEQUENCE DESCRIPTION: SEQ ID NO:305:

```
ATCTTAATTT AAAATTTTAA TTAACTATTT ATAATTTAGA AATATATAAT CTAGAGATAT       60

ATAATCTTAA AATCATAGGT AAAAATACAT AAGATAGTAA GAATAAAATT AGTAAAATAA      120

ATAGAAAACC ATAAGTTAAT TGATTCATAA AGAAAAATGG AATTATTTGT GGCATCTTAA      180

TTTTTATTAT TTAATTGATT ATTATCTATT TAACATAAAA CATTTTAAAA TGTTATAAAA      240

TAAATAAGAA ATTACTTATA GAATATTTAT TAAATAGTAT TTAATTTAAT TTTAATATTA      300

AATATACCAT TTTTATTAAT AAATAGATTA TTAAGTTTAT TAATATTAAG TGATATATAA      360

TTTAATTTAT ATAAATTATT TAATTTACTT CATTGATATA TATAATTATT AAATGTACCT      420

TTCATAATAT TTATTTTTAT TAGTCTAGTA ATATTTCTAT TTAATAGTCT ACCCTTTAAT      480

TGGATATTAC TACCTACTAA ATATTTACCT AATAATATAT TATTAAGAAT ACTTAAATCT      540

AATAATTTAT TATCTAAAGT ATATAAATTA ATTAAATCCT TTTTTATTAT TATTTAATTA      600

TTATTAATTA GTAAATTATA TTTATTATTT TATTAACATA ATTTTTTGAT AATAATATAT      660

CCATATTAAA TGGTAATTTA TTAATAATAT CCTTTAATGA TTTNATGATA ACCNTATTAT      720

TATGANATTA GTTAATAGTG ACCTTAATAT CCCNATCCNA ATATATNTAT TTATTTNTAA      780

NAACANANAA CTTCTTATNN CATATTTANT TTNANTATTN ACCNTTNCCN NNNT            834
```

(2) INFORMATION FOR SEQ ID NO:306:

(i) SEQUENCE CHARACTERISTICS:
        (A) LENGTH: 847 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1250UP (xi) SEQUENCE DESCRIPTION: SEQ ID NO:306:

```
GATCAAAATT TCAACAATTT CCATTTCATT TAGTACTACC ATCACCATGA CCAATTGTTA       60

CATCATTTAG TTTATTAGGT TTACTATTAA CTTTAGCTTT TACTATACAT GGTATTATTG      120
```

-continued

| | |
|---|---|
| GTAATATTTA TCCTTTATTA TTATCTTTAT TAGTAGTTTT ATTACTAATA ACTTTATGAT | 180 |
| TTAGAGATAT TGTAGCTGAA CTTACTTATT TAGGTGATCA TACTTTAGCT GTAAGAAAAG | 240 |
| GTATTAACTT AGGTTTCCTA TTATTTGTTG TATCTGAAGT ATTAATTTTT GCTTCTTTAT | 300 |
| TTTGAGCTTA CTTCCATTCA GCTATAAGTC CTGATATTCT ATTAGGTAAT GTTTGACCAC | 360 |
| CAGTAGGTAT TGAAGCAGTT CAACCAACAG AATTACCATT ATTAAATACT ATTATTTTAT | 420 |
| TAGCATCAGG TCTAACTATT ACATATAGTC ATCATGGTTT AATTGAAGGT AATAGAAAAC | 480 |
| ATGCTTTATC AGGTTTACTT ATTACTTTCT GATTAATTGT TACATTTGTA TTATGTCAAT | 540 |
| ATATTGAATA TAGTAATACA TCATTTACAA TTACAGATGG TATTTATGGG TCCAGTATTT | 600 |
| TTGCTGGTAC TGGTTACATT CTTACNTATG GTTAGTTTAC TAATTAGGTA GGTNCTATTA | 660 |
| NGAANAACAA GAAATTNCCT TTAACNCCCN CCCCTCCGTT NGANATNNAA CCNCACCTAT | 720 |
| TATTACNNTT TTTNAAAATA NTGAANACCC CANNATTGTT NTAANGAAAG GNNTAACGTN | 780 |
| NACNCACCCN TAGNNTTTNG GTCCCCCCCC NTGCTACCCC ATTTTGNCCC CCCCCACAAN | 840 |
| AACCCCC | 847 |

(2) INFORMATION FOR SEQ ID NO:307:

(i) SEQUENCE CHARACTERISTICS:
        (A) LENGTH: 825 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1251RP (xi) SEQUENCE DESCRIPTION: SEQ ID NO:307:

| | |
|---|---|
| GATCAGGAGG GTTTTGCGGT GCTGCGCGAC GGCGGGTTAG AGGTAATGCT CCTGCGAGAG | 60 |
| GATGACAAGA CTGTCGCTGT GTACCGGAA GTGGCAGAAT AGTGTATACT ACATAGTCAT | 120 |
| AGTTATAATA AACAAGCCGC GGCGGGCTCT AACGAAATGG GGAGTTGCCC ATGCCACCGG | 180 |
| GGCCGCCGGG GCCGCCGGGG CCGCCAAAGG GCGCGTTCCA GCGCGCACCG GGGAGGAAAC | 240 |
| CGGGCGGCCT GCGCGGGTCC GCGGGGTCCG CGGGGTCGAA CTGGCCGCCG TAGGGCAGCG | 300 |
| GGGCGGTGGG CCGTTGTAGC CGCGGATCGA ATATCATGCC GCCCTGCGGG TTGGGCGCGG | 360 |
| GAAAGGGGTC AAACGGGTTT GGCCGCTTCT GGCCGCCTGG ATACAGGTCG CTGTCGCCGT | 420 |
| AGCCTGCAGG GCTGCCAGGC AGCGGCTGCG CGGCGCCGGC CGGGGGGGAG AGAACCTCGT | 480 |
| ACTCGTCCTC GAAGCCAGGC ATGTCTGCTG GCAGCCTGCG TGCAGGAACC TGCGCGCGGA | 540 |
| TTGGCGGAGG CGCGCCTCCG CTGAGGGCGT CNTAATCACC GGGCTGTGCT TTTGCGCNGG | 600 |
| GCTTCTCNTC CGCCCACCAG GGNAATTTCC CTNGNAAACT TNCCGAACTC CNCCCCCTTA | 660 |
| AAACTGGCCN CNCCCTTTTN CCTNNCNGCT NTCCTCCTGC NNCCCCNTTT CCCCCTCAAN | 720 |
| ACCCNCCTAC CCNTNTCTNT NGNTTCNNNC CCTACANCCT TTCNNCCTNC TCCCCCCNCC | 780 |
| ATNTCCTCNT TNTATCNNAA AATTTCNTTN CTTTTTACCC CCCCC | 825 |

(2) INFORMATION FOR SEQ ID NO:308:

(i) SEQUENCE CHARACTERISTICS:
        (A) LENGTH: 856 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
(A) ORGANISM: PAG1251UP (xi) SEQUENCE DESCRIPTION: SEQ ID NO:308:

| | | | | | |
|---|---|---|---|---|---|
| GACTGTTCGC | TGTTGAGGAA | GATAATCAAT | ACCGGAATCC | TCTGAGCTTT | GCTTCGGCCT | 60 |
| CCATTCGCCT | ATTACGAAAT | TCGCGTGCTG | CTCCTAACGA | TGTTGTACCG | TTTATACAAC | 120 |
| CGCTTGTTGA | TCGCTTTTTA | GCAGAAGCCC | GTTTTTGCAC | CGACAGAGAT | GACAACCTTT | 180 |
| GCTACTTCTC | CGATCCAGTA | TTGTTCAGTG | CTGTAGTCAT | CTTGCGATCG | TTGGTAAACA | 240 |
| CATATACCCC | ATCGCAGTTG | GAGAAGATCG | ATACCACGTT | GCTTTCGCTC | TCATTTCACC | 300 |
| CATTAATTTC | GCGCCTTTTA | TTGTAAAGGT | GCAGCACCAC | AGAAATACTT | GATAAAATCT | 360 |
| TAGGCAATGG | CCATATTGGG | AAGTTTATAT | TACTAGCACG | ATGGTTGCTC | ATCCCGGCCT | 420 |
| TGTGCTGTTC | GTTCTAGGGG | GCGCTGTTAC | TACCTTTAGT | CCTGTGTTAC | TCACAGCTTG | 480 |
| TTACCGGCCC | GGGCTTCTAT | GCAACTATTA | TATTTGCTTC | TAATATATAA | GTACTGACAT | 540 |
| TTTCATACGC | GCCTAGCTAC | CGCTGCTTTG | TCTTCGGTGA | CTCTCTTCAG | AACAGCTTCT | 600 |
| TGGAATTATC | TTGTACTATC | AACCATGGAG | ACACTGTTAC | GCCACACCCC | GACCAAAAGG | 660 |
| AGAACCGAAG | GACAATTTTG | ANCCTCCCTT | TCCCCCGAAT | TANGGNTTNT | GAANATATNA | 720 |
| ACCGGGACCG | GGTTCCCTNN | TCCCCCGGGT | ANTTNCCCNT | TAAATTCGTN | TAAANTTANN | 780 |
| AANGGTNTAT | GGGGNGAANG | AACCCCANCT | GACCCNAAAN | GTTNGNTGGG | GTTTAACCTN | 840 |
| CTNNTNCGCC | GTNCCG | | | | | 856 |

(2) INFORMATION FOR SEQ ID NO:309:

(i) SEQUENCE CHARACTERISTICS:
(A) LENGTH: 834 base pairs
(B) TYPE: nucleic acid
(C) STRANDEDNESS: single
(D) TOPOLOGY: linear (ii) MOLECULE TYPE: DNA (genomic)

(vi) ORIGINAL SOURCE:
(A) ORGANISM: PAG1252RP (xi) SEQUENCE DESCRIPTION: SEQ ID NO:309:

| | | | | | |
|---|---|---|---|---|---|
| GATCTCCTAT | TAGTGGGTAG | CTAGCTAGTC | GGCCCGGCTG | GCCGGGCCCG | AACTGGTACC | 60 |
| GGGTGCGAGG | CCGAGTGACT | AACACTCCGG | GTTCTTCTGT | CTCTTGCCAT | GCCGAACATA | 120 |
| ACCATGGCGA | CTTATATAAG | TTCGGGCGGC | GTGCAGTCGT | ATGAGCCCGT | ACGAGCAAGA | 180 |
| CGTCCAGCAG | TTTGCAGCGC | GGTAGTCGGG | GCGTTGCAGT | TGTGTATATA | TTGCCACCCT | 240 |
| TGCGAACTTG | GACAGCCGTA | TGCTGGAGGC | GGTCAGTAGT | AAGCAGGAGC | CGGTGACTCA | 300 |
| AAGTAGAAGT | CGGATTGTAA | AGGACAACAG | ACCAGTGGCG | GTACGGACAG | CAGCGGGCCA | 360 |
| ACGTAGTAAT | AAAATATGAC | GAGAGATATA | CAGAACCACC | TACTCTTCGA | GACGGCCACG | 420 |
| GAGGTAGCGA | ACAAGGTCGG | GGGCATCTAC | TCGGTGCTGA | AGTCGAAGGC | ACCGGTGACC | 480 |
| TGCGCTCAGT | ACAAGGACCA | CTACCACTGT | ATTGGGCCCC | TGAATCCAGA | CTCGGTGCAG | 540 |
| ATAGAAGTGG | AGGCGCTGGA | CTGGGAGGAT | GACAGCGTGT | TGGACCCGGG | AGATTGCTGC | 600 |
| CCGGTAAAAC | GTCCCCTGCA | GCACATGCGG | AACCCCGCGT | TGAACTCCGT | ATATGCCGGT | 660 |
| GGTTNGTGAA | GGTNCCCCCG | GTTATCTTGT | TCAACCTGTT | CCCGTACCCC | CCTCCTCCAC | 720 |
| AATTGAAGCC | ACCTGTTGAA | CACTGCGGAT | CCCCCCCCCC | CAAANAACCA | NAAACAAAAC | 780 |

CCATCCGTTA GGTNCCCCNG NCTGTCCCCG AAATTAANGC CGANCCNCNC TCAN        834

(2) INFORMATION FOR SEQ ID NO:310:

(i) SEQUENCE CHARACTERISTICS:
        (A) LENGTH: 858 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1252UP (xi) SEQUENCE DESCRIPTION: SEQ ID NO:310:

GATCTTTATC GCAACNTTTT GGTTCTGTTT CGAGTTACGG GCCTGGCGGA CCACACCGAA        60

AGCGCCAGCT CCGAGTGTTT TGCCGAATAT GTAGTCGGCT TTGTTCACAT ACGAGGCTGG       120

TTGACCTGTC ACCTTGTGGA AGAACTTCGT CAACATGTTG GCCTGAGACG GAGGACGATC       180

CTGGGGCTTC GATGCGTCTT CGTCGTGCTC CCCTACACCC TTACCGAGTT TTCCGGTGGA       240

ACTAGTGAAC ACTGCCATAG CCTCGCAGTT AAAGTGATGT GGCAATATTA TATTGTAGTT       300

TTGTTCTTTT CTTGATTGTT TTAGGCTGCC GATAGCCCAC GAGGTGAAGT TTTGTACACT       360

TCACACATCC CAGCACTGCC ATCACGACAG ATGTTGAAGA TCAAATTTCG CAGCTACATG       420

CTGCATTGTG GTGCTTGGGT TAGCAGTAGC GGCTAAGTTG CAACTACATT GTCCCCATTC       480

ACTCAGAAGT ACCTCGGTTA AGCTCACTAT GCGCTTATTG CCGAGCGAAG CCGAGCATTG       540

TTACAGCAAT GATGAGAAGA GGCTATTGGT ATGTTAACAT AACGCCAGTA GTGTTATATT       600

TACCACTAAC CATAGAAAAA GTACAGAATA TCCGTAGCCT ACGAACTGAA TGAATATNTT       660

GCTTCCCCNC CCCGNCCNTA TACCAATGAA TAATAAATTG GATTTGCTAA TATCTNCCCC       720

ATATCCNGCC GGGCCCCCGA NNCCCTNCAA CTTATTGGTN CACNCNCCCN TGCCNCCNCN       780

TTTTNTTTTN TCNNGGAACC CCCCCCCCGT CATCNTCGNN TGNNTNAANA TGANTACCCT       840

CCCTTGNTCC CCCNCCCT        858

(2) INFORMATION FOR SEQ ID NO:311:

(i) SEQUENCE CHARACTERISTICS:
        (A) LENGTH: 841 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1253UP (xi) SEQUENCE DESCRIPTION: SEQ ID NO:311:

GATCCTAACC AAGCTGATTG ACTCCAACTT TCCACTTGGC ACATTCGACA AGCTGTTGCA        60

GAGCTCGACG GCCGTGGGGG GTGGTGGCTC CATATTGGGA TCAGATGGTG GGTGTACAGA       120

CACGGAGGCA TTGGGACATG ACCGAAAACG CAAGAAGTTG GAGCCCCGCT TCCCGGCGCC       180

TCCGCCGAGC GTGGCACTCG GCCCGCGCCA TCGCCGATAT AATTCTGAAT TGGGCCTCAA       240

CTACTTGCGC GAGAGCAACG CGCAGCCCAG CGTGATGCTC CCGCAGGTGC AGCAGCGCTG       300

GAACACAGCT CCTCGACAAC AACCCAGACA ACAGCATAGA CAACATGGGC AGGCCGAGGA       360

AACGGGTTCA CCACCAATGG CTCTTCGCTA TCCCCCTCCA ATGTTAATGA ACAGCAATTA       420

TACATTCCCT GCCGGCCCCC AGCAGCCGCT CGGCCCGCAT CCACAATCGC GTGCCTCGAC       480

```
GCAGCAATCT GATGTCCCAG CTACCCTCCC CGGAATATCG GCGTAGCACC ATCGTCCCAA      540

CTTCCCACAG CCCCCACCGC TGACTAGTCT TTTGTCTAAA CATCAGCCTC ATCACTCGCA      600

GCCTAATGAG CTGCCTACCT CCCATGCATA TGTACAACAG ATTTGCCTAC TCCAATAGCC      660

CAGTTCTGAA GTCTGCTTGC TTACGTTGCG CCCTCTCCCC TTGGCCAATN TATCCTTGTN      720

NNNAAAACCN AACCCNNGTT CCCCTGTGCC NGAATTTCTA CTTTTACCGT CCGTTATTCC      780

NTAAATCATA ACCCGGTTCA ANAACCCTTT CCTTGACNAT ATCNCATTGN GCNANCCCNT      840

C                                                                      841

(2) INFORMATION FOR SEQ ID NO:312:

(i) SEQUENCE CHARACTERISTICS:
        (A) LENGTH: 842 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1253UP (xi) SEQUENCE DESCRIPTION: SEQ ID NO:312:

GATCGACGAG TTCGATGTTG AGACGTTCAA GAAGCTGTTT GCGAACTGCA TTCGCAAGGA       60

TGTGGATGTG CGCGAGGTTG TCGCGGAGTA CCGACTGATA GTGCCGTGTG AGGAGCCGGG      120

TGGGGTGCGG CGCGCGGCGG CCGGTGACGC GGCGGAGGCG GAAACGGAAC CGTTTTCGCA      180

GGAAGAGAGC AAAGAGATTA GGATCATTCT GCCTCCAAAG CCAATTGCGA TTGAGTTTGT      240

AAAGAATGTG TGGGAGAACT GCTGTGTGCT GTACCGTTTC TATCACCGCC CGACTTTCAT      300

CAGGAAGCTG GACGACCTGT ATGAGACAGA CCCGCGTGAG TACACGCACG AGCAGCTACG      360

CTTCTTGCCG TTGTGCTACG CTGTCATGGC AGTGGGTGCG CTGTTCTCTA GCTCCATGCT      420

CCCTGGTCGG GGAAGCGAAG ATGCGGGCTC TGCAGGCAGA ATAACAGCGG CTACATTGGC      480

GGATACGGAC ACACGGCACG CTTATCTGCA CGACGAGGGC TACCGGTACT ATGTGGCTGC      540

GAAAAAGCTA GTGATCTCAC GAACGCCCGT GACACCGAGG CGAATCAAAC CTTGTTCCCG      600

TTTGTGTTCT CCCAAGTTCC GCGCGGTCNC CCCGGCATCC GTTTTTCTGC CCNGCTATNA      660

ATTCCNCCCN CCTNNAGANT CCACCCACCC CCCCCCGANA ANTAAAAAAA TTTCCCCCCC      720

CAACCGGAAN TCCCNCCCCG NTTTACCCCC CTTANAAANG AGGTTTTTTA AACAAANCGG      780

GGNGCCCCNC NCCCCCGGNN CNNNACATCC CCCCCCTAAA TCGGAANATT NNCCGAAACC      840

GC                                                                     842

(2) INFORMATION FOR SEQ ID NO:313:

(i) SEQUENCE CHARACTERISTICS:
        (A) LENGTH: 836 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1254RP (xi) SEQUENCE DESCRIPTION: SEQ ID NO:313:

GATCGGCCAC ATTGTCCCTG AGGCCTATGA AGGCGGCCCA ATTGCGCTCG TGCAAGACGG       60
```

-continued

```
TGACGACATT GTCATCGACG CCGAGAACAA TGCCATCAAC CTCCTTGTGC CAAAAGAAGA        120

AATTGAGTCG CGCCGCGCTC GCTGGACCCA GCCGGCTCCA CGCTACAAGA GGGGCACGCT        180

CGCCACCTAT TCTAAGTTAG TCTCCAACGC CTCCAAGGGT TGTGTCTTGG ACAGCGACGA        240

CTAGCACCTC GACGCAAGTC ACTATTTATT AACAAGATTA TGTATATAAG CACCCCGCCA        300

TGTCCATTGA ATGGACCGCA TATGTAACAA AAATCGAGGA TGCTTCCCTA TCGTCTACAA        360

ATCTCAGGAT GTTGAGTACC TTTCAGGTGT CTGACTGAAA TAAATGTTGA ACTTTGATAG        420

TACTTTTATG TTTGAAAAAT TTTAAAATTT TATTGTATGG CTGTCACCAC GAGTACTCAT        480

CTTCACCCGA CATTACGGGT ACCTGAAGAG CTTATCTATC GATAACATGG CGACTCAGGA        540

GGCGGTATTT ATCGGGCGCA ATAGGCAGAC GAAGGTTGCG GACTTCTATT TGCCGACCAA        600

GACTGTCCAT TCGACTGGAA AGTGCATCCT CTATGGAATC CGTTGGACGA ACNCATGCNG        660

GNGTTTNNGC CATTGAAGGC CNCAACCCGA GNTACTCGGN AATTTATGGG GCNAAAAACT       720

TTTGGTCACN CTCNNCGAAG CACAATNCTT CGGCAAGNAA NAAAAANGGA ATTGNCCNAT       780

TTGGAGCCCN AAACCTNTAC NTNGCNTGGN GNNGGGTANC TCCNNTTCCN ANGTCN          836

(2) INFORMATION FOR SEQ ID NO:314:

(i) SEQUENCE CHARACTERISTICS:
        (A) LENGTH: 850 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1254UP (xi) SEQUENCE DESCRIPTION: SEQ ID NO:314:

GATCTCTGGT ACCCCAGCAG CCCTGGCGGG GACGTGGCAT TGGTGACTTC TCCCCCAGGT         60

AACCGGGTGT GCTCTCAGCC CCTTCCCCAC ATTGAAGTTA AGCTTGTTAG CGGTACTCCG        120

CTTCATTTTC TGTGCCCGGT CGACCGGTAG CGTCATAGTC CCGCCGTGTG GCCGACCGCG        180

GGCCGCCATC ACAGGTATCT ACAGTTCAAC GGCCGCGTCG CGATCCCAAG CGCAGTCTGG       240

AATCTCGAAC GGTGCTACAA AGAACGGATG CGTGGCAGAT CGAAGCTATC GAGAAGGTGG       300

TGGGGGAATT GAGTGAAAGT ACACGAAGGC AGGGTGTCAG ATCTCGTACC TCTCGCATAC       360

AGTACGAGAA GGAGTCGGCG ACGGTGTTCA GAAATCAGCG CAGTGTCCAG TGCGGGGAAG       420

CGTGCAAACG GAACTCGGAA ACAATCCGAC GGACCTACTG CCAGGTCCAA GCCCTTTCCA       480

CGGTGTCACA GCTAAGATGG TGACTGGCCA ATAATTTGTC ATGCTGGTAT TCGTGTGTCG       540

ACGATTATCT ATTCGGTTCA GCCGTTCATA TTTAGGTGCG CTGCAAACGT GGTGACATCA       600

CGATTGCACT GTATATATGA TGGAGTAATT CGCATACACT GAAAATCNTA ATAATCAATA       660

ACCCATGCCN CNACTCGNCA ACTTCNCCNC TTCNGCTCCN GGTGAAATCC CCTTCACTAN       720

TTTTTTTCAT TGCCCATTNN ACCGAACTTT ACNAATNATG CAATGANAAC CNCCCCTCCC       780

AAACCTANAT CCTTTTNTTN NGGGTCCCNN ACNGTTNCCN TTCCNGNCNA NCCCNCTTTN      840

ATTCCAANAC                                                              850

(2) INFORMATION FOR SEQ ID NO:315:

(i) SEQUENCE CHARACTERISTICS:
        (A) LENGTH: 827 base pairs
        (B) TYPE: nucleic acid
        (C) STRANDEDNESS: single
```

```
            (D) TOPOLOGY: linear (ii) MOLECULE TYPE: DNA (genomic)

(vi) ORIGINAL SOURCE:
          (A) ORGANISM: PAG1255RP (xi) SEQUENCE DESCRIPTION: SEQ ID NO:315:

GATCGTGTCG TCAGGGTGCA TTGCAGTGGG CCTGAAGACG GTGGGGACTG ATCGGCGGCC      60

GAAGAAGCTG TCGCAGCTAC AGGCGATTGC GGCTGTGGGT CAGGGCCGGC TTATTGCGCG     120

GTGGGACTCC CTCTTCAGAC CGTTCAACGA GAAGATTGCG CAGATTTTGT TGACACGGAA     180

CGACATAGTT GACTGGTCGC AGTATAAGAA CGCGCAGAAT ACGTTCCACG AACTGCTGGC     240

GATGGGCGTG ACGCCGATTG TGAACGAGAA CGACACGCTC TCAATCAGCG GAGTGAAGTT     300

TGGGGACAAC GACACGCTGA GTGCGATCAC AGCGGGGCTG ATCGGCGCAG ACTACCTGTT     360

CCTGATGACG GACGTGGACT GCCTATACAC CGACAACCCG CGGACGAACC CGGATGCAAA     420

GCCGATCTTG GTGGTGCCGG ATCTGTCACA GGGACTGCCC GGCGTGAACA CCTCTAGTGG     480

GTCCGGTTCA GGTGTGGGCA CCGGCGGCAT GGCGACGAAG ATCCTTGCTG CAGACCTGGC     540

AACGAACGCC GGGTGCATAC GATTATTATG AAGAGTGAGC GGCCGTCGAC ATGGTGCGGA     600

TCGTGGAGTT CATGGAATGG CGCAGCAGTG CACTGCAGTT TCTGCTGACG CGAGACTTGC     660

AGACGGACGA GCTGAATTTG TTGCAGAGCA CGGCGTCCCA CTACACACGC NCTTCNTGCA     720

ACTTTGCACC TCCTGAACNA CNGATTCNTG ATCCCNCGTC TGTGACNCGG NCGTATCTAA     780

CAGGGGCTNA GGCCCCCCCA AACAACTGNT CCCACGTTNT CCGTCAG                   827

(2) INFORMATION FOR SEQ ID NO:316:

(i) SEQUENCE CHARACTERISTICS:
          (A) LENGTH: 836 base pairs
          (B) TYPE: nucleic acid
          (C) STRANDEDNESS: single
          (D) TOPOLOGY: linear (ii) MOLECULE TYPE: DNA (genomic)

(vi) ORIGINAL SOURCE:
          (A) ORGANISM: 1256RP (xi) SEQUENCE DESCRIPTION: SEQ ID NO:316:

GATCTAATGG CATTCTCCCT ACCAAATGGG CCCAATTGTA TATTGCCGAT CTTCCTACAG      60

GGNACTGGTT TACGGATCCA GCGAAGATCG GGAGAGTTCA GCTCTTGGTA TTGCCGACAT     120

TGTGTCGAAA ACACCAGCTG CAAACTTGAG GCCATATGTC ACTGTCATCA CAGGTCCACT     180

TATCCGTGTT GTTGGCGAAA GGTCTAGCAG TGATATTAAG GCTGCTATCC TATATGCCCT     240

AAATGTTCTC TTTTCGAAGG TTCCACAATT CCTGCGGCCA TTCATACCTC AACTACAGAG     300

AACATTTGTT AAATCTCTTT CCGACTCAAC CAATGAGACC TTAAGATTGC GGGCCGCGAA     360

GGCACTAGGT ACTTTGATAC AATATCAACC AAGAATTGAC CCTCTGGTGG TGGAGCTAGT     420

AACAGGCGCT CAGCAGGCCA CTGAAAGGGG AGTAAGGACG GCTATCTTGA AGGCATTGTT     480

GGAAGTTGTC TCCAAAGCTG GCAGCAAGAT AAGCGAAGCT TCCAAAGCTA ACATCATTAG     540

ACTTGTGGAG CAAGAGATGG CATCCACAGA CAGCAAGTTT GCAGTCGCTT ACGCCAAGCT     600

TCTAGGTGCA CTTTCTGAAA TCATGTCTCC GGAGGAGGCG CAGACCATAC TTCACGAAAA     660

GTGCTTGATC CAATTTTGAA GANGCACNGT AAATTGCCGT CNGACCCCAC TCTATCCTNC     720

TACCCCTGTA CNTTCTCCCG CCATNCACCN ATNTTGACTN TTNGTGGTGC ACGGATCNCN     780
```

```
ATCCTTCCNN CACACGTTTN CCCNTNGNAT TCCCCCCNAA NGAAAGTNAN CCCCCC            836
```

(2) INFORMATION FOR SEQ ID NO:317:

(i) SEQUENCE CHARACTERISTICS:
        (A) LENGTH: 841 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1256UP (xi) SEQUENCE DESCRIPTION: SEQ ID NO:317:

```
GATCAACTGG TCGGGCGGGC TGCACCACGC CAAGAAGAGC AATCCTTCGG GGTTCTGTTA         60
CGTGAACGAC ATTGTTCTGG CGATTCTGAA TCTGCTGCGC TACCACCCAC GCGTTCTGTA        120
CATTGACATT GATCTGCACC ACGGAGACGG TGTCCAAGAA GCATTCTACA CTACTGACCG        180
CGTGTTCACG GTCTCGTTCC ACAAGTACAA TGGTGAGTTT TTTCCGGGAA CGGGGGATTT        240
GGATGAGATC GGATGCTCGC GCGGCAAGCA CTTTTCGCTG AATGTGCCGC TCAATGACGG        300
CATCGATGAT GATTCGTACA TCAACTTATT TAAGAGCATC ATAGACCCGC TAGTTACATC        360
ATACAAGCCA ACAGTAATTA TTCAGCAATG TGGAGCAGAC TCTTTGGGGC ATGACAGACT        420
GGGGTGTTTC AATCTAAATA TCAGAGCCCA CGGCGAGTGC GTCAATTTGT GAAGTCGTTC        480
GGGATACCTA TGCTATGTGT CGGTGGTGGA GGTTACACCC CCAGGAATGT GTCGCGGCTA        540
TGGACGTACG AGACAGGCAT CCTTAATGAT GTGCTCTTAC CTTCAGATAT CCCAGAAGAT        600
ATTCCGTTCC GCGAATGGTT CGGTCCAGAC TATCTCTGCA CCCGGTCCTT GGATGANTTN        660
TCCAAAATAA ACNCCCAAAT TACTGGANAA NATACGTNCG GNTTTAAAAN NTAAATTNTG        720
CNGGGGCCAT TTTGNCNTGA NNCGAATATC CTCCAGATTT CCGTTTAACN AAAAAAAAAT        780
GATCGGAANA ACCAAAANAT NCCTTGNTAA CANTNAAGAA NTTTGCCGNN ACTTNTTANT        840
C                                                                       841
```

(2) INFORMATION FOR SEQ ID NO:318:

(i) SEQUENCE CHARACTERISTICS:
        (A) LENGTH: 841 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1257RP (xi) SEQUENCE DESCRIPTION: SEQ ID NO:318:

```
GATCACTGGT GTCACCAAGG GCTACAAGTA CAAGATGAGA TATGTGTACG CGCATTTTCC         60
CATCAACGTC AACGTTGTCG AGAAGGACGG CGAGAAGTTC ATTGAGATCA GAAACTACTT        120
GGGTGACAAG AGAGTTAGAG CTGTGCCTGT CAGAGAGGGC GTCAGCGTCG AGTTCTCCAC        180
CAACCAGAAG GACGAGATTG TTTTGTCCGG TACCTCCATC GAAAACGTTT CTCAGAACGC        240
TGCTGACATC CAGCAAATCT GCCGTGCCAG AAACAAGGAT ATCAGAAAGT TCTTGGACGG        300
TATCTACGTT TCTGAGAAGG GTGTCATTGC CGAGGAAGCC TAAGTGCCTT ACTGACCGTA        360
TCTTGATAAA TAATATGAGT ATTATGTAAT CAAAGAACTC ACTGCTTTTT ATTGGTGGTG        420
TTTTCGTCAA ACGCTCTTAT TAGCGCCGGG GTTAGAGTGT GGGAATACTG GCGTTATATG        480
```

| | |
|---|---|
| CTTTAGAAGT TATGTTAAGT AAATTTAATG TCCTATCAGG GCCACAGCCT TAGCAACTAG | 540 |
| GTGCAGGTAC TCCTTTAGCT TGCCACTGTT CTGGAACAGA AGATATATTT TATCTGTCTC | 600 |
| GTTGGCACCA TCGTAGACAG GTTCACCGCT TCCTTGCAGG AACGATGGAA CGCCAGCTTT | 660 |
| CCGCGGTGGA AGTTATAGGA ATTATGGATT CCAATGACAG TTGGTGTGTT AACNANCCTG | 720 |
| ATTTGTCCAN TTTCCCGTCT CNGAAGCTNC ANTGNTTCCN TGACCNANCA AACCCGGGAN | 780 |
| ACCCCTAGGG CTGNNAGGCT TGAATGCNTT AAAANANTTT CNTTGANAAA NCATTGNTAA | 840 |
| T | 841 |

(2) INFORMATION FOR SEQ ID NO:319:

(i) SEQUENCE CHARACTERISTICS:
        (A) LENGTH: 856 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1257UP (xi) SEQUENCE DESCRIPTION: SEQ ID NO:319:

| | |
|---|---|
| GATCGGGCCG CTCACACACT CAGGTACCTC AAAGGAATAC GAGTTTGTCG CACGCTTCCC | 60 |
| GTGTCCAGAT GCACAGAAAA TCGATATGTA CATCAAGGAG CCGCAAAACA AGTACCTCTT | 120 |
| TTCGGGAACA GAGTACACTT TCCAAATCAT CTGCAGCCCT GCAGACGGCC TCACTCACGA | 180 |
| TCCATACGAC GCGCAAGCCG CTGCGCCAAA TGTGATAGTC GTCCAGTCCC CATCCGGCAA | 240 |
| GATCTACCGT CTGAAAAAGG CGGAATCCGA TGTCGAATTT GGCGTATGCG AAGCTAGGCT | 300 |
| AAAAGTGCAC GAGCCAGGCG TCTGGCTGGC CCTAATTACC TCTGAGGCAG GTGCTGGTTG | 360 |
| GTGCACTTTC GCGAAGTGGA TCTGTGTTTA ACACCTAGAT GCTACACAGT CATCCACCCC | 420 |
| ACGAAATTAA TAGATAGTAC GGGTACATAC AAGCCCTATA GTTTCTTAAT ACACTTGCCC | 480 |
| TATATTGAAT ATGTCTACGA AGTATATGGG CGAGGCACTT TCAAAATCGG TGAAAAAAAA | 540 |
| TGCACCACTT CGAAATCCAT GTTTTATGAG CTTAAACAAC AGTGGTTGTT GAAGAACAAT | 600 |
| ACCCTGCCAA GGAAATGTCA GGTACTCGAA CCAGCTCTCA ACAGATTCTT AAAGATTGCC | 660 |
| AGTGTTGTAA CCGAATCCAC GTTCGCTGAA TGCTGGGACC GACATCAGAC CCTTGCATTG | 720 |
| GTACAAAATC AGTCTATACG GNGAGCGCCT GTNTGCCCNA AAAANAAANA CCACGGAAGG | 780 |
| ACNCATTGTC ACTTGAACNG AGNCAATGTG TNCNGTGACG CGGNTNTTTC GNTTCAAGCC | 840 |
| CCAAGGACAA NAACGC | 856 |

(2) INFORMATION FOR SEQ ID NO:320:

(i) SEQUENCE CHARACTERISTICS:
        (A) LENGTH: 724 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1258RP (xi) SEQUENCE DESCRIPTION: SEQ ID NO:320:

| | |
|---|---|
| GATCCAACCT TCTACTAGGG TATTTTTCCC TACCTCAGCC TGCAATTCCA TGCCATCGCT | 60 |

-continued

```
AACCAAGATA ATATTCTCCT CCAGTAGATC CATATTCTCT CCCGACTTCG CACTAATCGG      120

GATGACTGGC ACGTTTCCAC CCAGATCTTC AGCATGTATT TCATGCTGTA GCAAATCATT      180

CATTATTTTG TTGATCACAG TTTCCTTTTC TTTTGCCGAC CGGAGTTTGT CCACCTTGGT      240

TATGGCGACA ATCAGCTCAT TCCCTGATTT TTTGACATGC TTAATCGCTT CAATGGTCTG      300

GGGTTTAATT GAGTCTTCGG CAGATACTAC CAAGACAACG ATATCGGTAA TATTCGCGCC      360

CCGTTCCCTC ATCTTCAAAA ATGCTTCGTG CCCGGGCGTA TCCAAAAACG TGATCTTCCG      420

CTTCGAAACA GGTGTGACAA CCTGGAACGC ACCAATGTGT TGTGTAATGC CACCAAACTC      480

CTGCGAAACG ATGCTCGACT TCCGCAGATA GTCCAATATG GTGGTTTTGC CGTGATCAAC      540

GTGACCCATA ATCGTCACAA CAGGTGGCCG GTCCTTCAGG GCCTTCGGGT CTGCAGGCTG      600

CTTCAATTCA TCGTAAACGT TCTCCGGAGT GACAATTCCC TGCCGGAGGG CAGTTGGTAG      660

CTATCTCCTC CCAATATAGC TCGATGTAGT CTCCTGGAAA TATGTAGTCC GCCTGGCTTT      720

TCAA                                                                   724

(2) INFORMATION FOR SEQ ID NO:321:

(i) SEQUENCE CHARACTERISTICS:
        (A) LENGTH: 853 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1258UP (xi) SEQUENCE DESCRIPTION: SEQ ID NO:321:

GATCCTGTTT ACAACTAAGT TCGCATCCCT ACCAGGGGAA AATATGAAAT ACCAAGTGTT       60

GTATTCCGAA CGCTAGAATT CTTGTACAAA AACCGCGGCA TTCAGGAAGA AGGTATATTT      120

AGGTTAAGCG GATCCAGTTC TCTCATAAAA TCTTTGCAGG AGCAATTTGA CAAAGAATAT      180

GACGTGGATT TGTGCAATTA CAACGATAAA GTTTCTGTCA CACCAGGAAA CGAAAATCAG      240

GGCGGTCTCT ACGTCGATGT GAATACCGTT TCAGGTTTAT TAAAACTATA CCTAAGAAAG      300

CTTCCTCATA TGATCTTTGG GGATGCTGCA TATATGGATT TTAAGAGAAT CGTGGAAAGA      360

AACGGAGATG ATAGCAAACT AATAGCACTC GAGTTCAGGG CATTGGTTAA TTCCGGACGA      420

ATTGCCAAAG AATATGTCGC CTTAATGTAT GCATTGTTCG AGTTATTGGT GAAGATCACC      480

GAGAACAGCA AATATAACAA GATGAATCTG CGGAATTTGT GTATCGTATT TTCGCCAACG      540

TTGAACATAC CCGTGAATAT ACTACATCCG TTTATCACTG ACTTTGGCTG TATATTCCAA      600

GATAAGGCGC CGATGGAGAA CGGACACGGT CAACATACAC ATCCCGCAAT TTAGTTCATA      660

CTAAGTAAAA TACTATTAAC TTAGAATATG TGATAAGTGT TTTAATTACN TAACTTGGTA      720

TTAGTCCNAT TGTNTAATAA TTGAATATGA ATGCNTTATT NTCTCTNANT CAATNTGTCA      780

CGATTGGATT TACACCNGCG TCTGTAANGA CNTCTAGCTT GGTCATCCCA NTTCTCANTT      840

NCTCCCGCTT NCA                                                         853

(2) INFORMATION FOR SEQ ID NO:322:

(i) SEQUENCE CHARACTERISTICS:
        (A) LENGTH: 836 base pairs
        (B) TYPE: nucleic acid
        (C) STRANDEDNESS: single
        (D) TOPOLOGY: linear
```

(ii) MOLECULE TYPE: DNA (genomic)

(vi) ORIGINAL SOURCE:
     (A) ORGANISM: PAG1259RP (xi) SEQUENCE DESCRIPTION: SEQ ID NO:322:

| | | | | | |
|---|---|---|---|---|---|
| GATCACACGA | ATATTGCGGG | AGTATTTCTC | CATCGTTCGC | CGCAACGCGG | CCTGCGCATC | 60 |
| GCGCGTGAGC | GATTCGGCCT | CGTTGATGAT | CACACTCTTG | TACCTCCGCG | CTAGCCCCTC | 120 |
| CGATCCGCTC | TGGAAATCCA | CCTGCTCCAT | CTGCGCAATC | TCCTTCAACA | ACTCCTGAAT | 180 |
| CACGATCCGG | TCATTGTGCC | CCATGTCGCT | CGGCGTGATC | TCGATGTGGT | ATGGGCTGCT | 240 |
| GACGACGTTG | AGCTCGAGCT | TCTTGTTAGA | TGGCGTAACA | AATTGCCGCA | CATCAATCTT | 300 |
| TAATTTGTAT | ACACCTGCTC | CAAAGATACT | TGCAAGGAGC | CCCATGCACC | GTGTCTTCTT | 360 |
| CCCACTTCCA | TTGGGCCCGT | AAAGTAAAAT | ATGCGGCAGG | TCCTTCGCAG | AACCTGCTAA | 420 |
| AGCCTCGAGC | TGCTTGGTAA | GCGATGCCGT | ATGTGAAAGG | CTGGTCAACG | ACTTCGGTCT | 480 |
| ATGCTTGTCA | ACCCAAAGTG | ACATATTCCT | GTGTATCCTG | AGATGGGCTT | TTGTGTGTTG | 540 |
| TAGGGAAGGT | GAGCAATTCA | GTCGCAATTA | AATTCATTTA | GATTCGCGTT | TTAGCACAAA | 600 |
| ACGATATGCC | CTCAGTAAGG | CCAGAATACA | TACACGTACT | TCGCCTACTA | CTTTTGACAG | 660 |
| AAGTAAAGCT | CTCACGAGAT | CGCTCGAGGA | GATGGCATGT | ATATAACCCN | CAATTACTCT | 720 |
| GATGCNAAAA | ATGTTGCACC | CNTGCCTTTT | TANTTCNGTC | GACAACTANN | AGAGCCTNTA | 780 |
| TCNAGTCCAA | ATTTTNCCAA | ANCTGGAAA | ACCTTNTNCC | GTGGTNTATN | AACACA | 836 |

(2) INFORMATION FOR SEQ ID NO:323:

(i) SEQUENCE CHARACTERISTICS:
       (A) LENGTH: 851 base pairs
       (B) TYPE: nucleic acid
       (C) STRANDEDNESS: single
       (D) TOPOLOGY: linear (ii) MOLECULE TYPE: DNA (genomic)

(vi) ORIGINAL SOURCE:
        (A) ORGANISM: PAG1259UP (xi) SEQUENCE DESCRIPTION: SEQ ID NO:323:

| | | | | | |
|---|---|---|---|---|---|
| GATCACCCCC | CAAATCAGCA | ATAACTCGAA | AACTGTGCCC | AGTACCTTTC | AACGCGCATG | 60 |
| AACCTAACGG | CGCGCAGCGG | TCATGGGTAC | TCGACTGCCT | TTGTATCCCT | CACACTGCGC | 120 |
| CTCTTCGTGT | GCCGCACGTG | CTTGTTGATG | GTAGCGGCGC | GGCCCGGTGG | ATCTAAGCGC | 180 |
| ACGTCTCTTT | GTACGTGGGT | CTCACGTGCA | CATCGTCATC | CATCCGCTTG | CGAATGAGTA | 240 |
| GATCAGCACG | GAGACCATGC | TAGGCAGGGC | CGTTGGGCGA | GGTGGAAAGG | TTGCAGCATT | 300 |
| GAGGTGGAGC | AGCAAGATGA | CATCACAGGA | TAGTAGTCGG | AAGAAAGAGC | TATGTGCAGC | 360 |
| GTACAGCGTA | GTGGATGAGC | GGGTTTCGCG | CAGCATGGAA | GAATGCGGAC | GTAGAAGGTC | 420 |
| GGAGGTTCTA | TTGCTTGCCG | TTTCTAAACT | GAAACCTGCG | TCGGATGTGG | CGATACTGTA | 480 |
| CGAAGAAATG | GGGCTGCGGC | ACTTTGGAGA | GAACTACGTG | CAGGAGCTGG | TGGGGAAGGC | 540 |
| AGCAGAGCTG | CCGGGCGATA | TCCAGTGGCA | CTTTATCGGG | GCGCTGCAGA | GTAACAAGTG | 600 |
| CAAGGACCTG | GCGAAGGTAG | TGAACTGCAT | GCGGTGGAGA | CCATCGACTC | GCTAAGAAGG | 660 |
| CGCGGAAGCT | GAGGAGGCCG | TGCGAAGTTC | CAGCCGAGCC | CCCGCATCTG | TGTTACATTG | 720 |
| AGTGAACNCT | CTGGCAACNC | AAAGNNGTTN | CNCGATGAGC | NACNGTGCAC | TGTGATTCTT | 780 |
| CTNCCAAAAC | AAACCTTCCC | TGCCCGACGA | TAAATGGTCC | TGGACCCTCC | CCGCGAAGGG | 840 |

```
AACCGATCCC C                                                         851
```

(2) INFORMATION FOR SEQ ID NO:324:

(i) SEQUENCE CHARACTERISTICS:
        (A) LENGTH: 832 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1260RP (xi) SEQUENCE DESCRIPTION: SEQ ID NO:324:

```
GATCCTCAGA GGGCCCGCAA GAAGCTTCGG CCGAGACAGT AACGATGTTT GGCGAGGTTG    60
TGCTGTATCA CAGTTGAGCT CTAGGTTGCA CTTTCGGAAA GAGCGCTACC GTAGCTGCAT   120
GAAAAAAAG TAAGGCTCAT CAGTTTATGC AGAGGCAAGA ATAAGTTTGG TAGAGCCTTA    180
CTTCACAAGC GTCGCTCTAG CGAGCCATAT TATTCTATGG CCGGCAAGAG AAGACCGAAG   240
AAGGCCAGAG CTCCATATCG AAAGTACGTG GCGGGTCAAG GGTTTGTGCA TACCTACGGG   300
GTTTCCAGTA CTGAGAGTTC AGCACACGAT GAAAGCGGTT TGTTCCCCGC AGACAGTGGG   360
GTGCAGGTAT CTGACGATGA TATTGCGAGA CGACTTGTTG ATATGACACT TTCCGCAAGC   420
GCAGCGTTTG CCGGTGGAGC GGCACCCATA CCGTATCCCG ACACTCAAT GGTGCTTCCC    480
TGGGAGCTGC AGTTTTTGGT TCTGTCCAAA TGCAAAACTA TTGAAACACA CTTCATGCAA   540
GTGTGCAGGC GGTGGTATAT CATGTGTCTG CCATTGATCT ACCGAGCACC AAGGCTCTCC   600
AGCAAGACTT CTACAAGTTT GTGGAGACAC TGGTGGCAGC CCGTAAACAG AATTACCGGC   660
AATATTCCTC GATCTCGACC GTCCATGAAT ACCNNANCGC AAACCTTTTC CAAGGTCCTC   720
CCGTTGCTCC CACCCTTGAC ATTCCGGCCC CAAACACTCG TATCCCNTG AATCTTACGG    780
CNNCCCNNTT GCAACCGATT TGTCTNTTCC CAACGTTANC GAACNCNTTG AG           832
```

(2) INFORMATION FOR SEQ ID NO:325:

(i) SEQUENCE CHARACTERISTICS:
        (A) LENGTH: 846 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1060UP (xi) SEQUENCE DESCRIPTION: SEQ ID NO:325:

```
GATCGACCGG CCGCCCACGC CGGTGCCGTG GGTGAAGTCG CCGCCCTGGA TCATGAAGTT    60
GGGGATGACG CGGTGGAACG TGGAGTTGAT GTAGCCCGCG GAGGCGTCCT GGCTCTTTGC   120
GAGCGTGACG AAGTTGGCGA CGGTGCGCGG AGCGACGTCG CCGAACAGCC CGAGCACGAC   180
ACGGCCCAGT GGCTCGTCGC CGTGCTGCAG ATCGAAGAAG ACACGGTGTG TGACGGTGGG   240
GTCTGCGAGC GCGAACGCGC AGAGCAGCGC CTGTGCGAGA ACGAAGAGGA CCTGCATTGG   300
GGGTGGCTGC GGGAGGCGCG GGACGCCGCG GGAAAACGCC CGCTTTTATA CGCGAAAAAG   360
CTGCTTCGGC TACGTAGCTA GAGATACAGA GGCGTGGACT TGAGGCTCTG CAGCATCAGG   420
CGGTCCATCA TCTCGGGCGT CAGCACGTCC GAGTAGCCCG CGGTCGCGCC GTCCAGCGCC   480
GCGGTCAGCG CTGGCGCAGT GGCGCTAGAC GCGGTCGTGC CACTGGCCGG CTGCACGGAG   540
```

```
TTCTGCTCCA CGGGCACGAA GGCCGCGCCC TGGCCAGGCT GGAAGCGCGC CAGACGCTGA    600

TCGCGCCCAG CGCGGCCGAC AGGTGGAAGC CGGTCGACAG CAGGCCGTTC TGCACCACGC    660

TGTACGCCGT GGCGCCTGTA CCTTCCCCNA ANANGTNTAT CTTGACGCAT CACCGTTCCG    720

CCCCCGCTGC TTCCGAACCA AATCCGTCCC NCTTAACCAC CNTTTCANGC CNTCACTTGC    780

ACNCTGNCCA CACNCTTCNC GGTTACGTCC CAATGCCGTC TCCCCNGGGC GCTTAGCNCG    840

GCTCGT                                                              846
```

(2) INFORMATION FOR SEQ ID NO:326:

(i) SEQUENCE CHARACTERISTICS:
        (A) LENGTH: 835 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1261RP (xi) SEQUENCE DESCRIPTION: SEQ ID NO:326:

```
GATCATAAAC GAAGAATTCC TAATTAACAA TTTGTCCTGC ATGTACTTCC TCAGTGAGAA     60

ATAGCGATAT AATCATTAGA AAGCTTCCCC GAGCACTTTA GCAGCACCGC ATGCCAGCAT    120

AACCCCCTGG ACTCAGGGCA GTATGCCGGC TGGCACCTCG GCACCTCATC GCAGGCGAGA    180

CAGTCCACCA CTGCGAGCAC CGTAGTATTT ATACTTTTCC AGGTTGAAAA ATTTTCGACC    240

GCCCCACGCC GCAGAGGGCT GGACGCGCAT TAGGGCTCAC AGCGGTCGAC TGCCACTGCT    300

GCCCCAACAG CGCCGCGCAT GTAACGTGAA ATGATATATT ATACCTTCTG ACTACAATGT    360

GAAATATACA AAGGTGGCTC ATAGGCGCAT TGCATTTATT CAGACGCAGT AGCTCTGGTG    420

TAGATAGCCT GCTTGGAGTG CTTGGAGATT GGCTTGATGA TGCCCTCGGT CTCCAAGTGT    480

CTCAAAGCAA CTCTGGCCAT GGAACCGCCG ATCTTCAATC TGTCGACCAA CACGGACACA    540

GAGACGTATC TGTAGGTTGG GACCTCCTTT AGGATTCTGT CAAGCTTGTC CTGGTCCAAG    600

ATGACGGCGT GCTGGGCCTT GTCCTTGTGG GACTTCTTGG ACCACTTCTC TTGGACTTCT    660

TACCACCGGC CATGGCGCGC GCGCCTTCTG GGCCTTAAAN ATNTTGTTTT TGGTGCATAT    720

ACNGTGTGCC CNTATACTGT CCGCACCACT GGCNTCTCTG CGNAGGGTGG TGAGCTTCCG    780

TACTCCNCCC CCTACCCNCC CCCCCNNGNT TGTCCNTTTC NNCNNNCCTA ANTCT         835
```

(2) INFORMATION FOR SEQ ID NO:327:

(i) SEQUENCE CHARACTERISTICS:
        (A) LENGTH: 852 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1261UP (xi) SEQUENCE DESCRIPTION: SEQ ID NO:327:

```
GATCTGCAAC AACACCATTC CATCGCGAAG TCTTTCCAAT TTCTGTTCTG GAATATTATG     60

AGGAAGTTTG AGAACGATAT TGGGAGCGAT GATGAGGAAG ATCCCTTCCA GATCAACGAT    120

TTGGACGAGG AGAAGACCTT GCGCATGCTT TCTAACCAAG CCTGTTTCTT CGGCTACCTG    180
```

-continued

```
ATGGCCGAAG GTCAGGTAAA GTTAGATGTT TTAAAACATG TATCCATTAT GGGGTTGAAC      240

TCTGACGGGA GACTTTTCCT AGAGAATCTT CTATTTCAGT TTCTGTTGGC CTCAGCCAAA      300

AAAGCAGAAA CTAAAAAGAA GGTGGGGAAT ATCAAGGAAT GGTCTTACAG AGATGACTTG      360

TTGCAGGGCG CCCTGTCGCA TGGGATCCAG GCCGAAAATA AAAGATAAT CTGCAAATCG       420

CTCAGGATGT TTATGAGGAA TTTTAGATAC ACGAACTATA TTCGTGGTCA GCCTGGCTCG      480

AAGGAGTATC AACGTGACAT GAGAAGGTTG GACTGGGCCG TTAAGCGTTT TTTGGAACTT     540

ATAGATGAAG AACTGGATAG TGCAGATTGT GAAGAGCTTC TTGTCACTAG TCTGAATGCA      600

TATTACGTGT AACATTGAAC ATACGTACTC TATATTAAAG TGGTGAAAGT GATGAGAGTA     660

TGACGTCCNT GCTTTTATTG CATACCACTT NTGAATTACA GTTATTCGGT GAATGACNAC     720

AAACANGTTC CATTACTTAC TTGTTGACNT CGCCNCGACC ACCACCCGCG CCACACCTTT     780

GTTTACCTTA TAAAAATCTC CACNTCCGNC GTATANAGCC TNAANAATTC NTTCGCTCAT     840

GCGGTTTTGA CN                                                          852
```

(2) INFORMATION FOR SEQ ID NO:328:

(i) SEQUENCE CHARACTERISTICS:
        (A) LENGTH: 831 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1262RP (xi) SEQUENCE DESCRIPTION: SEQ ID NO:328:

```
GATCTTTGCA CACGCTGGTA ATGTTTCCCA CTAACTGGTA TTTTTCCTTG TCTAGATAGT       60

CTGCCGTAAA GACTCCCGAC GTGATCGGCC GGGCACGGAC GCCCATCTGC TCCAAGGCCG      120

TCACAAGTTT CAGGTTCTGT TCCAGAAAGC ACTCGCGAAC TACTGTCATG GTCACAGGAT      180

CAGTTACGCG AATTCCTTCT ATATATGAAG CTCGATACCC TGAGCCTCC AATTTGTTAT       240

TCACCTGCGG ACCCGTGCCA TGCAGCACAA TCGGATAGAG CCCCACATGG TACAGGAACG      300

CCAGGCATGA AGCCAGTTCC GGCAAGTTGT CGCTGATGAT GGCACCTCCA ACTTTGATAA      360

CCGCGAATTG CTGCTCCGAG ACGGAAGTAA AGTACTTCAG GTACTGTTCT ACTTCACGCT      420

TAGAGCCAAT ACTGTTGAGA AGCTGGATCA CGGTGGACCG TGTCTGCAGA GACCCAACGC      480

CCTCGTTGTT CCCGGTTCTT GCATAGTTCA GCTTCTTTAT AGCGGCAGTG CTGAACAATT      540

CGCGCTTGTA TGCGGCACGG ACAGCCCATG GCGTCCGGTT TTAGATCCTG CTACCAGCGA      600

AGCTCTACTA ACAGTAGAG AGTGCTCGCA AGCATCTTGG TACTCCGTTT ATCCCAGTCG       660

CGCGAGTTCT AGCTCTCGAA AGCAGTCCGT GTGGCTTATA GCCTAANTTC TCTTCGGTTC      720

CATAACCACA AACCGTCTCN TTGNCNTTCC TGANTTTCAA GACCCCNANA TTTTCACAAT     780

TTNTGCATTT NTCCNGNGNA AGGGTGCNAT TTATTNTTGC ATNCNTTTAA A               831
```

(2) INFORMATION FOR SEQ ID NO:329:

(i) SEQUENCE CHARACTERISTICS:
        (A) LENGTH: 865 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
    (A) ORGANISM: PAG1262UP (xi) SEQUENCE DESCRIPTION: SEQ ID NO:329:

```
GATCACAAGC TTGTTGAAGC CAACTGCTGA AAATGTCTCC TACGAGAAGA AACGATTCCT      60

TCCACTAGGA GACGTGTGGC AAATTTTAAA AGGAGCCAGT AAGACGCAGA CTAGCCCCAG     120

CAGAAGCGCC AGTAGTTGTT AGGAAGCATT CCAGAGCGTA TACGACACTT TGAAGACGGA     180

CAGCGTTCAG AGAAGACAGA GACAATCAAC ACCAAACAAA CATGGAGAAT CCTCACGTAC     240

ATGATAATTT ACAACACATC CAGGCGGTGT TATCGAACTA CGACACATCG TTTCTCTCGG     300

ACGATGAAGA GGACTACTGT CCGCTCTGCA TGGAGCCTTT GGACATCACC GATAAGAACT     360

TTAAGCCGTG TCCGTGCGGG TATCAAATCT GTCAGTTCTG CTACAACAAC ATCAGACAGA     420

ACCCGGAGCT AAATGGGCGG TGTCCTGCGT GTCGGCGAAA TATGATGATG AGTCGGTGGA     480

GTACATTGTT TTGAGCCCCG AGGAGCTGAA ACTTGAGCGA GCGAAGCAGG CGCCGAAGGA     540

GCGCGAGCGC AAGCAGCGCG AGAAGGAGCG AAAGGAAAAC GAATATGCCA CCGCAACATC     600

TCGCCGGCAT GCGCGTTATC CAGAAGATTG GTATACGTTA TTGGCCTGAA CCACCCGTAC     660

CGTACGAGGA GGTTGGTGCG CTGTTGCGCT CGGACAGTTA CTTTGGCNGT TNCGGGANAT     720

TTACNNATCN TCCGTGAACC GCAAAAGGCC CCATGACCCC NACGGTNTGG ATNTNTTTCC     780

TTCCCNGAAA AAGAGCGGCC CNNTTNCGGC GTGGATGTNT TTTNTGANGG CGNGGTGAGG     840

GGGTACGACC NATNTGCCTN TTTTG                                          865
```

(2) INFORMATION FOR SEQ ID NO:330:

(i) SEQUENCE CHARACTERISTICS:
        (A) LENGTH: 832 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1263RP (xi) SEQUENCE DESCRIPTION: SEQ ID NO:330:

```
GATCGCGCCA TTCGCTTCTG AATGGTTCCT CACAGAAGGA TTCGTCTACC AATGGCATTA      60

GTTCAGCGAG GTCCTCGCTA CTAACAGAAT CGTCTTGTGG AACTCTCTTT AGGAAGGTGA     120

ACAGTTCATC TATCCTTTCA AAATTGATAC TCTGAAAGGG TTCATTTGCG GCGTTAAACA     180

TACTAGATGC AGTCATTAGG GCGGCACTTT CTTGGTTAAT ATCGTCAGCT ATCCTTTTTA     240

GTGCTTCTTC CTCATTTTCA TTGGGCTTGA ATAAACCTCT AGCTATCAAA AACTCAATTA     300

GTATCTTCCT GACCTTAGTA GTTGGTCCGT CTGTGGGCCT AGTCATACTC ATTAAGTGAT     360

GACGGAGCTT TTGCACACCT TTGCCAGAAA ACACACAAAA TATTTGACGT TGGTTAACGG     420

TAAATTCACT AGGAGGAGGT CTGCAAAATT GTGTGATATC TGGCCTGAGA AAAGAAGTAC     480

CGCAGTCAAT GACAAATGAG AGAGCTTTGG ACAAGCCATT ACCAACTCAT ATATTGGATA     540

AATAGTCAAA TTAGTACAAT ATGATAGGTG AACTCTTTCC AATGTGTCAT TCCTACCACG     600

CAAAGCAATC ATATTTAATA ACCTCATCTG TCATCTGAGA ACATTCACCA ACCCTATCTT     660

TTTAGTTTGT TAATTCCCCA ATCATATAAG TATGAATTGT CCATTTTGTA CACAACNATC     720

CNCTTCTGAT CNNGGANATC CTGATTCAAC CTTATCCCCN CCCNGAATGA ACNTGGCCAA     780

NGANATTNTN GTTTTTCCCN CTTGAAANCT CNAAATNCAT ACCCCGCTTA CC            832
```

(2) INFORMATION FOR SEQ ID NO:331:

(i) SEQUENCE CHARACTERISTICS:
        (A) LENGTH: 851 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1263UP (xi) SEQUENCE DESCRIPTION: SEQ ID NO:331:

```
GATCTTAAAA GCTGGCCTCC GCAGATAGAC CTTCTGCGCA GAGGCTGGAA ACCTCAACTA      60

GCAAGTCGCC ACCCGAATCA GATAAGCACT AGAGTCGTTC CAGTAACAGA GGAAGCGATC     120

AAGGAAGATA GTAGAAGAGG ACACTGCTGC CAGGCTTGAT CGGACAGAGG GTTTAGCTTT     180

CTGTTGAATT TTAGAGTTTC GGGGCTTTGT TTACTTCGTT TCATTCTTTC GTGTAAAGAA     240

GCTGTTTGCA GGCTGCCATC ATTTGCCAGT CGCCAGGTAG GGTATTGCAG GGCGACGGAG     300

TCGGTGAAAC AGAGCAGGAC CGAGAACGCC GATAGACAGG CGTTTGTTTG TAAGCGGTGA     360

GAGCTGAAGC AGGTCAAGAG GCCGGCTTGG GCAGGTTGTG CGGCGGCGGC AGAGCACAGC     420

AGGGCATCCG AAGAAGGCGG AGCGTGCGGA CAGGAGCGCA GGCGCGCGAA CAGGGGGGTG     480

TGATGACGAG CGAGACGAAC AACAACAACG CGGCGAGCTC GAACGGCGGG CAGCTACCGC     540

CATCGGGGCT TCCGGCGAGC TGGTTTACGA CGCCATTCCT GCGCGCTCGA CCACAGACAG     600

ACAGCAGTAC TCCCAGAAGT TTCGCGAGCG TGTTTCGCGG TGACGCCAGC GCGCCAGAAC     660

TATTTTTCCA CTTACCAACC GGCCGNAATG CCCCCCACTT TNTTGNCCAA ANACCATTTT     720

TCCNCCAGCN CCCNCCCTNC TAAAACCATT TCTTACNGGG NCGAATGAAA TGGGTTGNTT     780

TTCCCGCCCC NGAGAACACA TTTTTCCNCA CTGTGACCCG ANTNNTTANT CTCCCNAACA     840

TTATTTTTTC C                                                         851
```

(2) INFORMATION FOR SEQ ID NO:332:

(i) SEQUENCE CHARACTERISTICS:
        (A) LENGTH: 801 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1364RP (xi) SEQUENCE DESCRIPTION: SEQ ID NO:332:

```
GATCTCGTTT TTGTAATGCT CTAGCTCATA TTTGTTGAAG GAGAAGGGTG AAAACAGCTC      60

CGAGGCTGCA ACTACTGCAA AGAATAAAGA GCAAAATATG GCACATAAGA TGTCTTCCCA     120

ATTCATTTGG TACAGCTCTA ATACTGTGAA CCCTTAATCT CGGGTAGGCG CAACAGTTAT     180

GCGGCCAACC ACGTTAACGT GATAATGATG TAGGTACCCC GGTGAAAAAA AGAGTATGTG     240

GAACCGCCCA GCTGAACCAA GCGGATGAGA CATGCCAACC ATATCCAAGC ATACTTGACC     300

ATGATGACGC AAAACTATCT AGCATAGTTA GTCTTGCAGC TGAGACAGGC TTCAATCGTA     360

AACCTCCCAC CTTCACTATT GTCACGTGAG AGGCAACATA ATTGATCTTG TGACTACCAC     420

CCATACATTT TGCTACCACC CATACATACT AATTAATGGG GAAAATAGCG GCTGGTACAG     480

ATTCTTGCAT CTCCCTGCCC CAGAGGGCCG CGGGCCTCTC GTTCCCCAGC GCGCGCAGGC     540
```

```
GGCCGCAGGC CGACTGTCCT ACTACGCTCT CCCTGTTGGC CCGTGGTTAC CGCGCCTCAA        600

ATTACCAANC CTCCAATTTT TGANATTCCC CGACAGTTNT GTNCCTNTTT TTTACCCCAA        660

TTCCGGAATT TCCCTATTAA ANGGTAAGAC CCNNNTTTAC TTTTGTGGAN TAACCTNNGG        720

CGTNCTTNNG GGNNTNCCTT TTNTTACNGG CCCCNTTCNA GGCCTTTTGG TTCCCTAAAA        780

CCGGTNAAAA AAAAAAGAT T                                                  801

(2) INFORMATION FOR SEQ ID NO:333:

(i) SEQUENCE CHARACTERISTICS:
        (A) LENGTH: 832 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1264UP (xi) SEQUENCE DESCRIPTION: SEQ ID NO:333:

GATCTCATGT ATCACAACCA GACTATGATG CGACTTGGGG TGACTATGTC TCCTTTGCCC         60

AGCGGTTCAG AGAACGAGTG AAAGACAAGG ACCTTATTTT GATCGACTCT GGTGACAAAC        120

GTACCGGTAA TGGTCTCAGT GATCTCACTA GTCCGATGGG TTTGAAGTCA AGCGGTATCT        180

TTAACCTTCA GAAACTTGAC TTGTTAACTC TCGGTAATCA TGAACTGTAT ACGGAAGATG        240

TGGTTCGCTT GGAATACTAT GGAACAGCAA TGGAGCCTGA GCTAAGTGAT AAATATGTCA        300

CAAGCAATGT GGAATTTATC ACAGAAGATG GGGACGTTGT ATCCGTTCGG CAATAAATAT        360

AGGTACTTTG AAACGCCAAA CCAGAATCTA CGTGTATTGG CGTTCGCATT CATGTTCGAT        420

TTTCCCGTGG GCTGCTAAAA ATGTTAGGTT AACCCCTCTG GCCGAAGAGG TTAAAAAGGA        480

CTGGTTCACC CAAACTGTGG AAAAGTACCC GCTGACAAGC TTGATATTAT AGTTGTCTTC        540

CGTCATTTAC CAGTCACCCG TGGCGAAACG AGAGCTTCTG CAGTTACACC AACGACTAAG        600

GGAATCTTAC CCCGACACTA TTATCCCGTA CTTCCGAGTG NNTACTCAGT CNGAAANTCC        660

CTNGTTTTNG ANAAAACGAN TGCTTTACCA ACGGCGAAAT TCCTGAAACA TGGAATCCNA        720

TCAANANNNG TTTCNCAAGA AACCAAATTT TCCATTCNAT ATGACTTACC CAATTCCTTT        780

TCCCCTCCNG NTTNANACTC CAAATTCCNT CCAAGGAAGA ANANTNACNC CC                832

(2) INFORMATION FOR SEQ ID NO:334:

(i) SEQUENCE CHARACTERISTICS:
        (A) LENGTH: 800 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1265RP (xi) SEQUENCE DESCRIPTION: SEQ ID NO:334:

GATCTTGCTC AGAAATAACT TGCATTGTCT CCACTATTTT CTCAAGATTA GCATTTATGC         60

ATGTCACTAG GCATTGCGTT TCAGGTAATG CATTCCCAAC AAGTGGCTTA CGATCTGGAA        120

CAGATTGTGT TCTTTGTGAT TCTGGTGGAG CCGTACCTCC AAAAGTTGAA TCTTCGTTTT        180

CCGCCGAGCA GGAATTGCAT GGACGAGACT TCTTGTCAGA CATAAACTCA AGTGGCGCCG        240
```

```
CTCTATCTGA CATATCTTCC TGACTCTCTT CTGCATACGT GCGGTTACCT GGCTCTAGTT        300

CGTCCTCAGT CCCTACGTCT CTTCTTGCAT GCATATCCCT TGTCGTCAGA TATGTTTCTC        360

TCTTCGGGCT AGAAGGGTCC TCATTTGTAG GATCTTGAAC AAAAAGTAGT TTGTTATTCT        420

CCAGCTGCGC AGTCTCTTCC AGGTTTTACT TCCGATGCTT ATTAATACTG GTTCTTTAGA        480

TGGTTCCCTG ACTTTGGCTA TAGGCCATTG GTTCCGGCGA CTTGTGAAGG TATGCATTGA        540

GAGTCCTCCT GGTTAAACGT GTNGTCCCCC CGTTATTTTA NCACGGCTTG GCCGGAATGG        600

TACACNGNTG AGTTAATCNC NGCGGGTTGC NGTTCCATCC TGTGGGGGC CCACCCAGAA         660

CCCNAACTTN GGCGCCACNA TTTCCCNTCN CCAAACNNTT TGGCCNAAAA AANAATTNTT        720

CCCCCAAGGN NGGANNACGC ATACCCCGAN ATGNNGTATN TTGTGGGGN AACCCCCNNA         780

ANCCCCNCCC CCCNGNGGAA                                                   800

(2) INFORMATION FOR SEQ ID NO:335:

(i) SEQUENCE CHARACTERISTICS:
        (A) LENGTH: 820 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1265UP (xi) SEQUENCE DESCRIPTION: SEQ ID NO:335:

GATCCGGTCG CCGCTGGTGA AGGCAGCGAC GTCGTTGTAC CGGCAAGGCG GCCTGCGCGC         60

GTTCTACCTG GGCAACGGGC TCAACGTCAT CAAGGTGTTC CCGGAGTCGG CGATGAAGTT        120

CGGCTCGTTC GAGCTGGCGA AGCGCGTGCT GGCGGGCTTG GAGGGCTGCG GCGAGACGGG        180

CGAGCTCTCG CGCCTGTCGA CGTACGTTGC GGGGGGGCTT GGCGGCATCA TGGCGCAGTT        240

CTCGGTCTAC CCAATCGACA CCTTGAAGTT TCGCATACAG TGTGCGCCCC TGGATACGCG        300

CTGCCGGGGT CTGCCGCTGC TAATCAAGAC GGCGAAGGAC ATGTACCGCG AGGGGGGTCT        360

GCGACTCTTC TACCGCGGCC TTGGCGTTGG CATTTTGGGC GTGTTCCCCG TACGCGGCGC        420

TCGACCTCGG CACCTTCTCG GCCCTCAAAC GCTGGTACAT TACCCGTCGC GCAAATGCGC        480

TGGGCATCTC CCGAGAACGA AGTGGTCATG AGCATCTCCG TGTGCTGCCG AATGGCGCCT        540

TCAGCCGTAC GTCCGCGCCA CGTGTCTACC CTATCAACCT TCTACNGANG CGNTCCCAGC        600

CCCAGGNAGT TNTCNCNCCC CCCTCCTACA ANGNTTCAAN TNTTTCCGAA AACACCNCNN        660

AGGCCCCCCC GCTTTTACAA GGTTGGTTCC NACATTGCCA GGTNNCCCNC ATCCCACNCT        720

NTTTTTTTNC NAAANTTAAA NNCCANCCCC CCNAATAAAG GCCCCTTNTC CCCCCNACCC        780

CNGGAATAAN GGTTCGGNCT NNAAAACCAA NACNCCCCCC                             820

(2) INFORMATION FOR SEQ ID NO:336:

(i) SEQUENCE CHARACTERISTICS:
        (A) LENGTH: 819 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: 1266RP (xi) SEQUENCE DESCRIPTION: SEQ ID NO:336:
```

```
GATCTTATCT GGAACACCCA TTCAGAACGA TTTATCTGAA TATTTCGCCT TACTAAATTT      60

TAGTAACCCT GGGCTTCTCG GTACGCGGGC ACAATTTAGG AAAAATTTCG AAATACCCAT     120

TCTACGGGGT CGGGATGCTG ATGCTACTGA CAAGGAGATC GCTGCTGGTG AGGTGAAGTT     180

ACATGAGTTA TCCCAGATTG TGTCGAAATT CATTATCCGG AGAACCAATG ATATCCTATC     240

GAAGTACTTA CCTTGTAAGT ACGAACATAT TCTATTCGTC AATCTCTCTC CGATGCAAAA     300

GGCAATTTAC GAACACTTCG TGAGGTCACG AGAGGTTGCC AAGTTAATGA AAGGTACAGG     360

GTCGCAGCCA CTGAAGGCGA TAGGTTTGCT GAAAAAGTTA TGTTACCACC CTGACCTGCT     420

AGATCTCCCG GATGAGATCG CCGGTTCTAC AAATTTAATT CCAGATGACT ACCAGAAGTG     480

CTAGTGACAC ACACTCCGCC GCCGAAGAAN TTCCCCTTTT GNATTCCAAC GANACATTCC     540

ATCNAATTTC GCNATTCCTA GAACGTTTTC NGTTTTAGAA TCCAGCCNTG ATTCNAATGA     600

AAAAAATGTC CCNGATTTCT ACNNCCCCCC ACCTTGGATT TTNTCCAAAA AATNTNNCCN     660

CCCNCCCCCN GGTTTNTTCC CANCTGAANG NNCCCNGNAA ATTAANNANC TTTNAACCTT     720

TTGAAAATTC CAAAACCCCC GGGAGAATTT NTCNTTTNTT TCCCCCNGGN CNGGGNNGGG     780

NTCCCCCTTT NGGCCCCCCG NGAANTTTGA CCCCAAAGN                           819

(2) INFORMATION FOR SEQ ID NO:337:

(i) SEQUENCE CHARACTERISTICS:
        (A) LENGTH: 807 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1266UP (xi) SEQUENCE DESCRIPTION: SEQ ID NO:337:

GATCTGTCAG CATTCACAGA AACCATCGCT ACGAAAAGTT TCCTACAAGT AATCCCAGCC      60

AGCCGAAGGA CTCCCCGTTG GGTCCTGTAG CCGTCTTGGC AGCGCACAGT TTCCAGGACT     120

TGTCTTCTGT TGGTCAGAGT ACTAGGCAGG ATGCGTTTGC TTATTCCAAT CACAGTGTTG     180

TGGCTAATGA TCGCCAGCCC TCTTTACCGC GAAACCCTGC CCCAGACTCC ACGTTCACTG     240

CGGAGTTTAA CCAGCTGCTA TCTGAATCCA GCAACTGCCT TGAGCTTGAT TCTATATTCT     300

CAGGCAACTC AGTTCTCTGG AATGGCGAGA CCTTAACCTC TGAAGCAAGA GCTACCCTCG     360

AGGGCGATGT GCCATCTGTC TCGGAAGATG CCCGCGACGA CAGCCAGGCA AATTCTGCAC     420

AGAATGGCCT GAAGTATTGA GTCTAGCGGA CACTGAGTAT GCGGACCTGG ATAGTTTGAT     480

CACTAATTTG TACTTCTACC ATGCGAGGGT TCGTCCCGCG GGTCTGAACG TTTTGTTATA     540

ATGATCGATT TTAGAAAATA TAAGAACCCC CTTGAATATG AATACNGNCN NTTAACCCCC     600

GGGGGTTGCT GATACCCCCC CTNTCCCCCN CTNGGNTGAA TTNTTACCCC NCGGNGGGGN     660

GANAAANAAT TCCTGCCNNC TTGGGTTCCN AANCCCCATT CCCTTTNNAA TNAAAANTGC     720

TTCCNNGNCN TNTTAAAAAA AAAACCGTGT TGCCCCNAT AACCAAATCC CCNCGCANGN     780

AATTTCCTGG GTTCAACANC CGCTCAC                                       807

(2) INFORMATION FOR SEQ ID NO:338:

(i) SEQUENCE CHARACTERISTICS:
        (A) LENGTH: 792 base pairs
        (B) TYPE: nucleic acid
```

(C) STRANDEDNESS: single
        (D) TOPOLOGY: linear (ii) MOLECULE TYPE: DNA (genomic)

(vi) ORIGINAL SOURCE:
        (A) ORGANISM: PAG1267RP (xi) SEQUENCE DESCRIPTION: SEQ ID NO:338:

| | | | | | |
|---|---|---|---|---|---|
| GATCCATTCC | ACCGGATTGC | AGCAGCTAGT | GCATTTGGCC | ATACGCCCGA | TTGCCCTTTC | 60 |
| TTATAATGAA | TCCCGGCTTG | TAGAGCATCA | TCCGGCACTT | CACGTGGTAT | TGAATAGCTC | 120 |
| CTCATAACCG | CACCGGAAGA | TTTCAGGAAT | ATATCTGGTT | GTGTAGTGTA | GAGGTTATCA | 180 |
| CTGTGGATTC | TGATATGGCT | GTTGCAGCTT | GAACATTCCA | CTAACCTCGG | TTCGAATCCG | 240 |
| AGCACGAACA | ATTTTTTGNC | TNAANCCCNA | NATTTTNNCC | CCTANAATAN | TGGNCTNNCC | 300 |
| AAAATCNTCN | NNTTTNAATT | TTTTCCAAAA | CTTTGTCCGT | GACCGGANTN | GAAATGNGGG | 360 |
| NAAGTGGAAT | GTCCAAGNCG | GGNNCGCNAA | ATTAGAATTC | CAGGGAAAAT | TCCTACANTA | 420 |
| NANAGGTGNC | ACCCNCGGNA | ACCCCGGGGN | GGGNNNACTG | GNCCCTTTNA | ACCTGNGAAT | 480 |
| GCGGTTNTCC | AACCTTTTNC | CGGGNGGCTT | GGCCCCCCNN | TTAATNCNAT | TACCCNCCCC | 540 |
| TNCTTTTCCC | NAAANNGATN | CCCCCCCNCG | GAAAGGTTCN | TTNNNNANCN | TAGGAGGCCC | 600 |
| CTTNGGTCCG | GAATTNGNNN | CCTTTCTNNC | TCCCCCCCCA | AATCCNGGAC | CCTGNAANNC | 660 |
| CCTTNTNCCC | CCCNTTTTAC | NNTTTTCCNN | GNAANTNCTT | CCCTTGGCCC | ATCCCCGGAC | 720 |
| NNNAATTGGG | GNTTTAANGG | CCCCCCGGNC | CCCCNCNTGN | AAAAAGNTNN | GGNNCCCCCC | 780 |
| CCCCCCCTTN | GN | | | | | 792 |

(2) INFORMATION FOR SEQ ID NO:339:

(i) SEQUENCE CHARACTERISTICS:
        (A) LENGTH: 824 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1267UP (xi) SEQUENCE DESCRIPTION: SEQ ID NO:339:

| | | | | | |
|---|---|---|---|---|---|
| GATCCGCATC | GTTTTGTTGA | GTCATACTAC | CTGGACGCCA | TGTTCGCCGA | GCTGGCGCCG | 60 |
| CCGGCGAGTC | TCGGGTCACT | GGTCGGCTTG | TGCAACGCGG | ACTGTGCCCC | CTCCTACTGG | 120 |
| TTGGAGCTAC | CCAAGGACCG | TATCCTGTTC | CTATGTGCGA | TTGCGAACCT | CGTAATCACG | 180 |
| CACCTCGTGA | ATGTAGACCC | AGCAGCAAGG | GACATGCACG | CCTTCTGGGA | GAAGGTGAAT | 240 |
| GCGCTCTTCT | TGGAGAACGG | CTCAGGGCGG | ATGCTGCAGA | AGGAGGCTTT | GGTGCCGCAA | 300 |
| CCGAAGAGCT | GCGAGAACGA | TGGCGGCGAG | GCGAACGTTC | CTGCGTCCCC | GATTTCCCGT | 360 |
| TCGCAGACAC | AATACACATC | GGACCAGGGC | AGCAATTACA | TGAACCCGCA | CGCATTCGGC | 420 |
| ACGGCGGCCC | ATGCGGCCGG | CACAGGCGCC | TCGTCTGTTG | CGCCTAACAG | CGACACCCTC | 480 |
| TCTGTGCGAC | TGGCTTCACA | CAACGCCTGC | GCCCCAGAAG | CGTCGCGCAG | ATTCCATACC | 540 |
| AGACTTGCTG | ACGCAGCGTC | GAGGACGCCA | TCAGACAGGG | AGCTTGCTGC | TTTGACCAGA | 600 |
| AGGGCTTGAG | CAGGATTCCC | AGGACGACAC | GACCGCNCTG | TAATGCAACT | GTTGTCCTTC | 660 |
| CNATTTGCGC | CCTATCCCCC | AATGGAACGC | CACTCCCCNG | AAAAAAAAAA | AATTTTCCGN | 720 |
| TGGATATTTG | ATGAATTGAA | TTAGAAAAAT | TACNTTTCTN | NNATTCTTGC | GGTGCCACAA | 780 |

| | |
|---|---|
| CAATTGCGAN TNCTAGACCC GCGNCCTGGC NTTNGGTTTT AAAT | 824 |

(2) INFORMATION FOR SEQ ID NO:340:

(i) SEQUENCE CHARACTERISTICS:
        (A) LENGTH: 787 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1268RP (xi) SEQUENCE DESCRIPTION: SEQ ID NO:340:

| | |
|---|---|
| GATCCTGAGA ACACTTTTTC TGTGGAGGCT TATCAATGCT CTTTCTATCC GCAGCTTCTT | 60 |
| CCAGGCAGAT GAATACTGGC AGTCGCTGGA GCCTGCGCAT GTTAAGGCGT TTGGATATGG | 120 |
| TGGGCTGACT TGGGAGTGGC AGCATGGGCT GCGCAGCTAT GCATTCCCGA TGCTCTTTGA | 180 |
| AATGTCGTAC TATGTGGCGT GGATACTGGG TGTGGCCACC CGGATGGCGC TGCAGGGGTT | 240 |
| GGCACATGCG ACGGCGCTGT GTGGGCGGT GGTGCCGAGC GGCGCGGCGG GCGTGGCCGC | 300 |
| GATGAAGGCC GTCTGGGAGC TGCCGGAGGC AGCGCAGGAA CTGGTGGAGT ACTACGGGGT | 360 |
| TATTGTACGG GCCGCGAAGT GGTGATGGCG GCGGTAGCAG CGTTCGGGGA GTTCTACAGC | 420 |
| GTGCTGCTGG TTGCGCAAGC TGTATCTGCG AGTCGCGGAT AAGGGGGACA CCAGAAGGGC | 480 |
| GACGCGCGCC GTCAGCCGTT GCGCTGATGC TGACCATGAC AACTTCTTCA ACTGTTTCTT | 540 |
| CGCGACGCGA ACGTTCATCA CTCCTTCGAG ATGACGCTCA CGCGTCGCGC TCTACCATTG | 600 |
| ATTGAACGGG CCTCACTTGG TTCTCTNGCT TCNCCCAACT TGCGGTGGCT CTTTTGCCTG | 660 |
| CCTCACGCCA NTACTTTTTA TCTGGCNCCC TGCTNTTCTT GGTGNGANCC TGTTCCCCCN | 720 |
| ANNGTGCNCN CCTTTTAACC CGNCCCAAGT TGCCCCGAGC CCCTGCGGTN TTTCAATCCA | 780 |
| ANNANNC | 787 |

(2) INFORMATION FOR SEQ ID NO:341:

(i) SEQUENCE CHARACTERISTICS:
        (A) LENGTH: 840 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1268UP (xi) SEQUENCE DESCRIPTION: SEQ ID NO:341:

| | |
|---|---|
| GATCCAGGTA TACCCGCCTC CGTCGCGCAG CGAGCTGCGC AGCCGCTTCA TCGCTGCAAC | 60 |
| TGAGAATGCC CTCGACCTGA TGTGCGGTAT GCTGACGATG GACCCGCACA AACGGTGGGA | 120 |
| CACGACTCGT TGCCTGCTCA GTCAGTATTT TGTAGAGCTT CCGGAGGCGA CACCTCCTAC | 180 |
| GGAACTTCCA AAACTAAATA AGTAATGACT ATGATAACCT AGATGGTATA CTCGGACGTT | 240 |
| TTGTGTTTGT GCTTTGAGGC GATGACATTG GCTTTTATGG TATCGCAGAC GTTGCCTGAA | 300 |
| AAAGATTCAA CGTCTCGGTA ACAGATTTGC GCAGACTACT TGTTGAAAGA ACAAAGACCA | 360 |
| GAGCGCTGGG ATGCTCACCC CAATGACGAA CCCACTCCGC CTTATTGGCG CTGGCTGCAG | 420 |
| GTTCCTTAGC ACCAACAATA GGCCGCCACT GCACAAGATC TTTCCCTCCC AAGAAGCTGG | 480 |

-continued

| | | |
|---|---|---|
| TGAACAGGAT GCTGTTCGAC CTTGATAGCC GACTGACCTT CCCGGAAATT ACTGCCTGTA | 540 |
| TACGAGCAGT TGTACACCCC AATTAGACAG TAGTACGGCG ATTTGTAGTA CCCCGCGCGT | 600 |
| TGAGGGCGCC ACGACGTTTA TGATTCATGA AAAGGTGCTG AGAAGACTCG CCCGCCAGAA | 660 |
| CGAGAGCTCC CATCGCCNTC TACTTGCNCC GGANAACAAC TGCTTTACTT GCTGCCCANT | 720 |
| GGANACNAAA ATGCACGNGC NCTNCCCTTG ANCCCGTGCA CCGNTTCGCC NAAGGNNCGA | 780 |
| AATGAATTTG CAATTTAGNT CNGATTTTAC NCTCTGGNTC CCCCCCCCCA CTGANNGANC | 840 |

(2) INFORMATION FOR SEQ ID NO:342:

(i) SEQUENCE CHARACTERISTICS:
      (A) LENGTH: 787 base pairs
      (B) TYPE: nucleic acid
      (C) STRANDEDNESS: single
      (D) TOPOLOGY: linear (ii) MOLECULE TYPE: DNA (genomic)

(vi) ORIGINAL SOURCE:
       (A) ORGANISM: PAG1269RP (xi) SEQUENCE DESCRIPTION: SEQ ID NO:342:

| | | |
|---|---|---|
| GATCCCACTC TTGGCAAGCT ATACGGTGAC ACTATCATAG CTCGCGGTGG CCTCTACGAG | 60 |
| ATGGAAGACA ACCTGGGCGA GTTCTTGGAC AGAGAACCCA ATAACGAGGC GTACCTCAGA | 120 |
| GATCAGGGCC TAGCCTAAAT GCTCCTTCTT TTCGCGGCCT TCCTGCCCTC CTATGTATAT | 180 |
| TCCAGCTAGA GAATCGCAAG CAAGCCATAC TTAGAAATAG GATATTGTTC CGGGAACACT | 240 |
| GATTTACTGT GCGTTACTGC TCCGGAAACT CACCTGTTCG GTATCGAATA ATTAGCGTTC | 300 |
| GACTACCGCC AGTGTGATGC TTTCTTTATA CCGGCATACT AAAACAGGGT CCTCAGTCGA | 360 |
| ATCGTGTGTC ACTGAATATG AGCCCCTCCA TGAGTTCCCA TCGCGTAGAG CGTCCTATGT | 420 |
| GCAGACCATA TCAACACCCT CTGTACACGC GTGGAGTTCA ATATACGCGT ACGACGCACA | 480 |
| TACAATAGTA CGTGTCGCCA ACCGTTATAC GAAGAGCTGC GTTCTGATTG CAGCATTTCC | 540 |
| CAAGCCCCGG AAATACAAAA CCGCATTTTT AGCCCAGTGC GATAGATGTC CTGAACCANG | 600 |
| GAATTACANC GAAGGNCGAT TGCTACTACN ANCATCANCC AGGGCTCGNG TATTTCTCAT | 660 |
| CCATCCCCCT CNAACNAAAA ATCCGGANTT TTTAAATTTC CATGCAAACC ATNCANATCC | 720 |
| CCNTTTNGAT ATTCNCCCAC TGGCCCCCCC NCCCCCANNT ANCNGTCGGG ATCCNGNATT | 780 |
| CCCCGGT | 787 |

(2) INFORMATION FOR SEQ ID NO:343:

(i) SEQUENCE CHARACTERISTICS:
      (A) LENGTH: 820 base pairs
      (B) TYPE: nucleic acid
      (C) STRANDEDNESS: single
      (D) TOPOLOGY: linear (ii) MOLECULE TYPE: DNA (genomic)

(vi) ORIGINAL SOURCE:
       (A) ORGANISM: PAG1269UP (xi) SEQUENCE DESCRIPTION: SEQ ID NO:343:

| | | |
|---|---|---|
| GATCGAACTC CATGAAGGAG CGTAATGGCC TCGTGGAGCT GCACCGCACT GGGTGCGTAC | 60 |
| ATAGCGGGAT GTAGGAATGC GGGGATAACG ATTCGGAAAA GCTGACTGGG CTGCGCCTCT | 120 |
| AGCTTCAGCT CAAGCTGGCG CAGCAGCGTT GCTATAGGCT GTTGTGGCGA CAAGGTCGAC | 180 |
| ACTTCAGTTG CAGTAGGAGC AGGTAGCATA CGACTAGTTA TATCGAACTG GTGCCGGTAA | 240 |

```
TGAGGATGAG GGTCAATTTC TGGCTCCGAG CGCTGGCTAG CACCACAATT ATCACCAAGT    300

CCATACCTCC ATGCAATTCT GAGATCTTGG CTACGTGCGA CCGGTTTTGC ACCCCCTCCG    360

GCTAAGTTTT GCACCGTGAC CTTCGATTCC TCCTGGGAAA TGCGAGATTT CTTTACCTCT    420

TTACGTGTGC CCTGGAATAT CCCCGGCAGC TCCTTCGCAT ACTGAGTGTT GAGCGTGATG    480

ACCACCACAT GCGTTATCCC CCCCCCCTGN GGGCCCCNAN TTTCCCCCCC GGTTATTTCT    540

GTCCCTGCGC CTGCAANAAC TTCCANTTAC GANGCAATCT GGTCCCCCTG TTCTTCCCCC    600

AAAACATCTG GCCCATTGGA NCCCATATGC CCTAGAACCN ATCCAATCTG CANCCCGNGA    660

NTTTTTGGAA ANNAATTACC GGNAAGGANC AACCCGGAAG NAAAGCCCGC CCCCCCTGTG    720

GAGCCNACTT CCCCCCCCCC NAAAACCNGA ANTTNNTTTT TNNTTTGGCC CNANCGNCCN    780

TTTTCNGCCC NGCCGGGANG GCCTTAAAAN TTCNTCCCCC                          820

(2) INFORMATION FOR SEQ ID NO:344:

(i) SEQUENCE CHARACTERISTICS:
        (A) LENGTH: 806 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1270RP (xi) SEQUENCE DESCRIPTION: SEQ ID NO:344:

GATCATATGG TGAACTTGGC ACATACAGTT GAATCATCCC AATAGCAAAG AGAACGTAAG     60

ATTTACCTAG CGCGGCATCA CCTGGAATAT CTAGCATTTG CAGCGCAGGT GAAAAGAATT    120

TCTCATGAAT TGATTGGAAA TGTGGTTCCG TGTGTTCCAT TGCTAAGCCC GCTAGTACAC    180

GATAATCATC ATTAGACTCA CAGGTTAGAT GGGCCTTCAC TGTTGCCTTA TACCAGTCTA    240

ATAGAACCTG CCTGTAACGA GCATATTGAT CCTGAAGAAT AACCACCGAT GCGTCAACCA    300

TCGAATTGAG CAACAATGTC GCGTCATTCA CGGTTTGAGT GATGTGACTT CCGGTGAAAT    360

TCTCAAAGGA ATTTAATTTC GGTATCAACC CCTTCAACAA GGAAGCTGTG AAGATATCAT    420

CAACATGCGA TTTGTAAGCT AAACCTTCCC GCATCCATAG GAAATCAAAA GTGGCTGGGA    480

AAGCATAGTT TGCGCTATTG GCTTTGACTA ACTGCGAAGT TAGAATACTA CTTGTGGGCG    540

CCAGTTTGAA TAGCAGAGTT AGACATTCAA CGGATTCTNA GAATATAATC CTNGCGAATT    600

TATCCATCCN CCTANAAAAT TNTTTCCNCC TTGATCCANA ACNANAAAAT TCCGTTGACC    660

NCTGAAGACC TATTCCTNCC TTTNAAAGAC CTGCNCATTC TTCNATTTCC CNAANGNNTC    720

CCGTTCTACC NAGAAANTTC TTGCATGCCN NCATGGTTTN AACCNAAACN TCCTTTGANG    780

NTANTNACTT CCCCCNNCCC AATTTA                                         806

(2) INFORMATION FOR SEQ ID NO:345:

(i) SEQUENCE CHARACTERISTICS:
        (A) LENGTH: 832 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1270UP
```

(xi) SEQUENCE DESCRIPTION: SEQ ID NO:345:

```
GATCCGATTG TCAAATTTTC TGAATGGTAT GGTAAGAAGT TTGGGGCTGG AAAGGCTAAC      60

AGTGGTGTTA TATCTTTGCG TGATATTTTA GCTTGGGTCG AGTTCATTAA TAGTACCTAT     120

AAGGCATTGG CTTGCCCTTA TGCTTCATTA ATCCATGGGG CGGCAATGGT ATTCATTGAC     180

GCCCTTGGAA CCAACAACAC AGCGTACCTT GCCGAGAGTG AGGAACGATT AGAACACCAG     240

AAGCAAGAAT GTCTCAAATA TCTGTCTGAA CTAGCAGGAA AGGATTTAAA CAAATACATG     300

TCTGGTCCAT TCGATGTTAA GATTGACGAT GAAACTCTCC AATCCGGGCT TTTTAGCCTA     360

CCCAGAGTTT CTTCCTCATC TGTCCAACCG GTTTTCAATC TTGGCGCACT ACTACAGCCT     420

ACAATCTCAT GAAAGTTGTC AGAGCAATGC AAGTACAAAA GCCATCTTAC TGGAAGGATC     480

ACCTGGTGTT GGTAAAACCA CATTAATTTC CGCATTGGCT GACTGTACCG TTACGAATTA     540

CCCNTTTTAA TTATCCGAAC CAACTGATTT GAATGAATTA TTTGGATCCG AAGCNCCCCG     600

AAAAAAAAAN GGNAATTTNT TTTGNGTTGA TGCCCCCNTT TTTNAAACTA TGCCAAAGTG     660

GATGGTTTTN TTTAAATAAA ANNANATTGC NCCCCANCCN TTTTTAAGGN CNNACCCTGT     720

TTGTNNCCNT GGNGAACCCA NTCCCAAATT TAANAAAATT TNTCGCCCCC ATCCGCTTTT     780

TTGNTNCCCA AACCCANACA GGGGNGGTGA AAAGGGNTGC CAANCTTCCC TC             832
```

(2) INFORMATION FOR SEQ ID NO:346:

(i) SEQUENCE CHARACTERISTICS:
        (A) LENGTH: 791 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1271RP (xi) SEQUENCE DESCRIPTION: SEQ ID NO:346:

```
GATCATTATA TTATAAAATA TAATAAAGAA TATATTTAAA TAATAATAAT AATATGAAAT      60

ATTATATTAA TTCTCCATTG GAGCAATTTG AGATTAGAGA TTTATTAGGT TTAACATCAC     120

CAATAATAGA TTTTAGTTTT ATTAATATTA CTAATTTTGG TTTATATCTT ATAATTCTTT     180

TATTAGTAAT TTTACTAATG AATTTAATAA CTAATAATTA TAATAAATTA GTAGGTTCTA     240

ATTGATATTT AAGTCAAGAA ATAATTTATG ATACTATTAT AAATATAGTT AAGACACAGA     300

TTGGTGGTAA AGTTATGAGG TTATTATTTT CCATTAGTTT ATACATTTTT TATTCTTATT     360

TTTACTATAA ATTTAATTAG TATAATCCTT ATTCATTTGC TATAACTTCA CATGTAGTAT     420

TTGTAGTATC AATAAGTATA ATTATTTGAT TAGGTCTAAC TATTATTGGT TTTTATACTC     480

ATGTTTAAAT CTTTGTTTAT TTTACCACTA GGTACACCAT TAATTTAGTA CCATTATTAG     540

TATCCATTGA ATTATATCCT ATTTGCTNNA ACTTATTCCA TAGGTTTTTA AAATACACTA     600

ATATATACCG GTCCATTTAT AATGGTTATT TAGNNGGTTT AATATTNAAT TNAAAACCAN     660

AATATTTACA TTTTATGGTN NCCNCCCAAN AAGGCATTGG TTTGGTTNTT TAAAAAGGCN     720

ACCTATATCN CCTANTTGAT NTTTTTTATN CCCCCTTTTA AANANCNATT TTNNCCTTAT     780

TAAANTAAAT C                                                          791
```

(2) INFORMATION FOR SEQ ID NO:347:

(i) SEQUENCE CHARACTERISTICS:
        (A) LENGTH: 834 base pairs (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1271UP (xi) SEQUENCE DESCRIPTION: SEQ ID NO:347:

```
GATCAATCTT TCGATCATTG TCCAATATTC CCCACTGCTG TATCATATAG ATATTGATTA      60

TAATTTCTAA ATCAACGTGA TTGTTCTAAC TTTAATTAAC AATTATGAAT TTTTGGCTAG     120

TTATTATTTT TTAATTAACT AATACCTAAA TCATTATAAG CTTGACTTAA AACAAATAAT     180

TATTACATTA TTCTTTATTT ATTATTTAAT ATTTAGTTAA ATTTTAAGTT CATTATTCTT     240

AATTTTTACT CACGAGTACA CCACTTATTA ATACTATTAA TTAATAATAT TAACGTTTGA     300

TTCGCATGTG TAATGTCCTT AGTTAGCGCT TAATCTGAAC CAACATCATG TTCTCATTAT     360

TATTAACTAT TTTTAATTAT TTTAAATAAT TATTTAATAC GAAAGTTATA GGATTCGAAC     420

CTATGAAATC ATAAAGATTT ATAATAGCTC AAATATTACA CTTTAAACCA CTCAGTCAAA     480

CTTTCTTAAT ATATATACCT TATATATGGT TTGATAATTT ACTTATAATA TATAGTATAT     540

AATTTAATGA TAACTCTTAT CATTTAGGTG CGTAGGGTTC ACCCCCCTAT TGCTAGTCAG     600

CATATGAGGT ACCTCCCCCC AATGATAAAA GTTATAATAT ATAATATTAT ATTAAGTATT     660

TAAAGAANAT AATATAATTA TTTAATAATA TTTTTATTTA GGNNAATAAA AAAAANTTTC     720

ANNTTTGAAA NANGGTGCNG AGAATTANAA AAAGCNAATA ATATGTTCAA TTTGACCCAT     780

TAANAATGTA GTNCNCTGAC ATCNCCTATT TCCTATANAA ANTTTANAAN AANA           834
```

(2) INFORMATION FOR SEQ ID NO:348:

(i) SEQUENCE CHARACTERISTICS:
        (A) LENGTH: 813 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1272RP (xi) SEQUENCE DESCRIPTION: SEQ ID NO:348:

```
GATCAAATCT AGGTTCTCCG ACGGCAACGG TGACGAGTTC GTGAACGCGC TCAAGCTCTG      60

TGGCTTTTTC CATAAACACA CAGACAACAG CAATAAAATG TTCACGAAGT TTGAGTTCTT     120

CAAGCCTCCA AAGGAGATCC TAGAAGAACG CAAAGCCAAG CTCGAGCGTA AGCAGAAGTT     180

CATCGAAGTG GAAACAGAGA AGGAAGCTCT AGAGTCTAAG CGGTCGGAAA ATCCAGAAGG     240

AAACTGGCTA CTAAAGCCAT GTATATATAA ACGGAGGTGA TTGCCTAGTC TCTTCTCAGC     300

ATGCGATCAT ACCTTATTCG TGTAATCTTA TCAAACTATA TATAGGGCGA CCGACAGCTT     360

CAACCGTTCC TAAAAAAGGT TTGGAAGGTG AACAGCCGCT GGATGTTCTC CACATTCGTG     420

AATGTAGGCA TTTGTGGCCA TATGCTGCTT GTCTCCGAGC TTTTCTTGTT GGGCTCCCAT     480

CTGTCGCCAG GAGCGGAATC CCGTACGCAT TGTACCTGTT ACCCTGCTGC GAACAGCACC     540

AGAAGAGGCT GATAATTGTA GTCNCAGCAC ACCATAGACG CCGAACAATG CCCCAAGCGC     600

AGTGCTGCGT TAGTTTGAAA TCCCAAAACA CTTCGAATCA TCGGTTCCCC GGAGGCCCAA     660

TTATCCGAAN TTGGCTTTTA AANTCCNAAT ACAANGANTG CGCCCCNTGT CCCCTGTACA     720
```

```
TTGTGCCCCN CCTAGGNNGC CCACTCCCNN CNCGAANTTT TTATTCATTT AATTCTNCNG        780

NCCCCNCTTT GTGANAATNG AATTCANTTT TTN                                    813

(2) INFORMATION FOR SEQ ID NO:349:

(i) SEQUENCE CHARACTERISTICS:
        (A) LENGTH: 844 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1272UP (xi) SEQUENCE DESCRIPTION: SEQ ID NO:349:

GATCGACCCC GCGCGCATCG GGCCCTCCGG CCTGCTGCGC CCCTCGCGCC TCGGCTGGCA         60

GCTCGTCTAC ATCCTCACCG TCGCCATCTT CACCAACGAC TTCTTCATGT CCGGCTTCTG        120

GCTGCGCACC TTCGCCGCGC GCTCCAACCG CGACCTGCTG CTCGGCTGCT CGCTGGCCGC        180

CGTGCTGCTC GCCGTCGTGC TGCTGCTCGT CGGCGTCACC GGCCTGCTCG CCGTGTGGGC        240

CGGCTACGCG CCGGTCGCAG ACCTCGACAG CGCCAGTTTC TTCCTGCTGC TCGCCGCGCT        300

GCCCGCCTGG GCCAACGGCG TCGTGCTCGC CCTCGTCGTC GTGCTATCCA CCTGCACGCT        360

CGACTCCTTC CAGAGCGCAC TCGTCTCCAC CATTTCCAAC GACCTCTTCC CGCAACCGCC        420

TGCCCCCGCT CTACGCGCGC GCCGCCGTCG CCGTCGTCAT GGTCCCCGTC GTCGTCGTCG        480

GCCTGCTGGC CACCCGACAT CCTGGCCATC TACCTCATCG TCGACCTGCT GTCCGCCGCC        540

GTCGTCCCCG TCATGCTGCT GGCTTCTGGC CGCGCGCCCG CGCGCCCTGT TCTGCCTTGG        600

AGCTGATCGG CGGCGGCTCC GGNGGGCTGT CTGCGTTCTC NTCTTTCCGG CCATCTATAA        660

CGCTNTNCCN CNANGGGGNC GCNTGCTATT TATTGNAANG NCCCTACTTN AATAANGGGG        720

NNCTTNNGGN GCCTNGTCNT TCCCCCCNTN GGGAACTGTT TTTCCCGGNA NAANTTCNGC        780

CTGGGNNCCC GTTGGNCCCN CCCGGANANT CANGNTAACC NCAGGGGAAN TCCAAANCTT        840

CTNC                                                                    844

(2) INFORMATION FOR SEQ ID NO:350:

(i) SEQUENCE CHARACTERISTICS:
        (A) LENGTH: 792 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1273RP (xi) SEQUENCE DESCRIPTION: SEQ ID NO:350:

GATCCCAATA CAAGCAATAT TGTCGCTACC AGAATGCCCC ATTTGCGACC CATATAATCA         60

CAAGCGAATC CCATCCCCAC CTGCCCTATG ATAGTCCCTA TGAGTGATGC ATTTGAAACC        120

CTTGTAGATA CATCTGCACT ATATTCTATC TCACCGTACT GATTTCTGAA TACACGGTTT        180

AACATCGACA TGACATTATT TTGGTAACCA TCTGAAATAA GCGCAAATCC TGCCGCCAGG        240

ATACTGAATA GATGTAGCCA TTTGCCCTTC TTCCCCACAG CAAAACGTGC TTTGCGAGCC        300

TCCGCGTCAT ACTTTAGTAA CCCTGTCGTG GACATCGTAT TTCTGCAAGC CCCGGCTATC        360

CGAATAATAT CTAGCGGGTC AAGCGTTAGG TTGCTGCATT CTATATTATA TATTTCCTCT        420
```

```
CTCTACCACG TGCAAATTTA CCTGTATGAT TATGCTGCAA TCTCCGCGTT CTACTTCCTT      480

TCTTGGAGAC CGCTACCGAC TGTCTTATGA TTATCGGTGC ACCATATGGC GTCAAGCAGC      540

ACTAGCTTTT ACCTGTGATA CCTTCCTTTA CTAACTGNAT TCCGAACTAN TTTGNNCCCA      600

TACTATATCC TTCCCCTAGA GTGAAATAAC CTTCCATTTA GGTTNNTCCC ATTCCCNGAA      660

ACAGTTTTTA AANAAANACA ACCTTTATCC TTNAACCCCA AACGCCCCAA AAANAAAATT      720

TCCCCATTTN CTAGGTTTTT TGNGCCNGGA GGGAAGAAAC CCCCCCTAAC CCCCTAAANA      780

ATTCCTCTNC CC                                                         792

(2) INFORMATION FOR SEQ ID NO:351:

(i) SEQUENCE CHARACTERISTICS:
        (A) LENGTH: 833 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1273UP (xi) SEQUENCE DESCRIPTION: SEQ ID NO:351:

GATCGGCGTA TAAAACTGAA AGTTCATGTA TGCTGTCTTG AATGCAGAGA CGCGGCGCAC       60

TTTACACATC GGCAAGCCTT GTGTTGCGAA TGAAACATTA AGCTTATGTC AAATACCATG      120

AACTGTATGC CAAATTTAGT AAAACTCGTA CGTGCTGGCA GCATAGATAG AGCTGTTACC      180

GATATCTCCC TTGAGGCTAA AGCCGAGCAT TGGGTATTAA CTTGCCTGGA CTATTCCGAA      240

TCAGAGCTTT CAGATTCGTC TTCATCATGG TCAGTCATCA AAGTCGTCGA TGTAGGATGT      300

TCTATTTTCC CACCGCAATA AAGTGCAGTA TTCATGCAGT ATTCAATAAG CTTACCTCTC      360

ACCTCGATAT CTAGCACATC AGCTGGAGCG GAACCTAACC AGACACGAAG TTTAGTGGCC      420

AGCTCTTCGA GGAGTGAAAA TATTTCTTGG TCCGGCAATG ATCCTCATGC GCCATTATAT      480

GGCGTAACGT TAGGTACATA CCTGTGACAC CCAACAAAGT ACAGTTGCTA ACGTCCCAAT      540

ATCTTAAAGG ANCCGTTTAA ACCNCATATT AAGGTGAAGT TTATGAACCT TTGANAGTAA      600

CTGNNTCNTT ATAGCGGAAT ACCANANNAA TAACGNCCTT GTTANGGNAT CTATCGAAGG      660

NTTACTTCCN NTTCGANCAT TTTATAGTTC NTNCTATTAC CCCCGANAAA TTTGAACAAC      720

CNTGAGAAAA GTTNTNNCCN CNGGGAAANG AAAANTNTNC TTNTGANTCC CCCCGTTTAC      780

CTTGAAGNTT CTCCATTCNC GAGATTCAAA TTTTTNTAAN AAGGANTTTN TAA            833

(2) INFORMATION FOR SEQ ID NO:352:

(i) SEQUENCE CHARACTERISTICS:
        (A) LENGTH: 803 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1274RP (xi) SEQUENCE DESCRIPTION: SEQ ID NO:352:

GATCAGAACC AAAAAGCAGT TCGAGTATAT CAGTAAGCAC TGGGAAGTTT GGGAAATAGC       60

AGTGCTGAGA GTTACGGGAC AGATTGGCAA AGACACATTT GCGATGGAAT TTAATTCGCC      120
```

-continued

```
GCAGCCAGAG CACGCACAAT TACACATTCA CCCTAAAGGT GCAGCCCGGC TGCTGGGAAA    180

ACTGCACGCG GAGGGTCGCG TGATGCACCA CGAAGATAAC CAAGAAAACC GGGGCCGGGA    240

AGGACCGCTG ATTCCGTCAC CGCCGCTGTC ACCACGAATC GGGCCGGGAG AGAACCGGGG    300

CGCCGTNGGA ACGGAATCCC CGAACCCTTT TTNTTACCCC AACTTGGNTC CCNGCCTTAN    360

TTTCAAACCG NTTNCAAACC CCNNCCCTGG GTTTNTTNGC CCNNTNCCCA NTANTTGGGC    420

TNCGGGGGG GGGGCCCNGN CCAAAAAAAA ANGGGGTNTN CCNGGGNGGC CCCCNGTTTT    480

ANCAAAANAT TTNCCCCCGG GGTTCNCCCC CNNAAAAGGT TTTTCCCCCC CCCGGGGTTT    540

ACCAAAAANC CNGCCCCCCC TTTGGANGGT TTCCCNNTCC CCATGGGGGG TTTTCNCGGG    600

GCTCCCCCCN GGGGAACCCC AAAAAAGGGC CCCCCCTTTT NTGGGCCCCC NAAANNCCCC    660

CNTNNTTTTC CAGANGGGTT NCCNCCCCCC TTTTTTTTCC CCATTANNCG GGAANTCCCN    720

NTNTTCCCCC CTTTNNCCCC CCCCCCAAAA ANNAATTTTT TNNATTAAAA GAGGGCCCCN    780

NGAAAAANAA NACCCNNCCC CAC                                            803
```

(2) INFORMATION FOR SEQ ID NO:353:

(i) SEQUENCE CHARACTERISTICS:
  (A) LENGTH: 814 base pairs
  (B) TYPE: nucleic acid
  (C) STRANDEDNESS: single
  (D) TOPOLOGY: linear (ii) MOLECULE TYPE: DNA (genomic)

(vi) ORIGINAL SOURCE:
  (A) ORGANISM: PAG1274UP (xi) SEQUENCE DESCRIPTION: SEQ ID NO:353:

```
GATCAATTGC GGATACACGA GGCACAGGGC GATAGGCCAA GCTTCCAAGA ATGGGAAGAG     60

TACCTAGTCA GGGTCGTCCT GGTAAGACTG AACCGCTGCA AGCAGCTCTA TACACAAAAT    120

GTAGAGATTC TATTCGATAT ATATCCGCAG ATAGACCGCC CATAAACACT AATGATACGC    180

TAATTCATAC ACCTACAGCG TGTACATCAA ACACACACAC AAGTTTGATG CACACGCTTT    240

ATTTGTTCCT TGCACACACT TGATTTAGAC GGTCAACACC CTCAAGGTGT TAGAGTGGCC    300

AACACCAGAC GCGAAACCCT GAATAGTGAC AATAGTGTCA CCCTCGCTCA GGATACCAAG    360

CTCCTTGGAC TTCTCCACAC CGAAGTTCAA TCTGGCCTCG ACGTCATCGG TCCACTCATC    420

AGCTGCCTCC TGTTCGTAGA CGAATGGAAA GACACCTCTG TGCAAGTGGC AGTATCTGGC    480

CGCTCCTTGG TTTCTGGTCA CCATAACGAT TGGAACGTTT GGCTTGTACT TGGAGACCAT    540

CTGTGGTGTT CACCCGAGGT TGATACACGA ANATGCCTTG GCTTCTGCTC GAANTNCCGC    600

GAAAGCAGCA CACAAGNCCC CGAGGTTGAA TTGGCTTGNT CATTTCCTGA GTCACCGTAT    660

TTGAACGTTT GGAAGGCCTG CNCCACNATC AAAATCTCGC CAGNCNTAAA CGTNAATGGT    720

TGANACCCTG GGGNTCCCCN AAAAATAANA TCNCCCGCCN GAAAAGTTCC ACTTCGAACN    780

CCCCNGTNGT CTGGTTTTGN TGGTANCCCA ACCG                                814
```

(2) INFORMATION FOR SEQ ID NO:354:

(i) SEQUENCE CHARACTERISTICS:
  (A) LENGTH: 754 base pairs
  (B) TYPE: nucleic acid
  (C) STRANDEDNESS: single
  (D) TOPOLOGY: linear (ii) MOLECULE TYPE: DNA (genomic)

(vi) ORIGINAL SOURCE:
        (A) ORGANISM: PAG1275RP (xi) SEQUENCE DESCRIPTION: SEQ ID NO:354:

| | | | | | |
|---|---|---|---|---|---|
| TGACTCGGCT | TCGTGAGGAA | CTGACGCTTT | TACTACATGT | AGATTGAAAC | CCGTTTTCCT | 60 |
| GGATCGCCTC | GTCTCGTTGC | TTGGTATCTT | TGCCAATCCT | CCTGAGTGGA | CGCTGCCTGT | 120 |
| AGAGGATCTT | CGCGATGGGC | CAAACACGCC | CCACCAGCCC | AAAGACGTTG | GAGAGAGGGC | 180 |
| TGAAGAAGGT | TCATTGACCT | CCTTTATGGC | TTCAAATGCT | GACGGAAGTG | ACAAATCGTT | 240 |
| CCCAAGACGC | ATGTCCGACA | ATTCTCTGAC | GGTGGACTCC | AAGACCTGGA | TGCGCTCTGC | 300 |
| CCTGGTCTTT | GATATTCTAT | GGATAGTGGC | AATGTCCTTT | GAGAGTGTCA | TGTTCTCGTT | 360 |
| TGTGAGGTTT | AGGTTATCAA | GTTGGGCAAT | AGCGAGCTGC | TCTGCAAGTT | GGTGGTTTTC | 420 |
| TCCACCAGCT | GTGCCTCTGT | GTGTTTCAGG | TCTGTCATCA | GTTTCTTTAA | GCCTCTCCTT | 480 |
| ATCGGCCGAT | CGTCCACCTG | GACTGNTATN | TTTTTNCCAC | NCCCATTNNN | CCATAATTTG | 540 |
| NTNAAGNAGG | TNCCCCNCCG | GAATTTNGNT | CCCGTTTCCA | NAGNTCGGNC | CGGGGATAAT | 600 |
| TTAAACNTTT | AAAAATTANC | CCCGGCCCTA | NTTCCTTTTN | CCNAATNNNN | GNNCCCCCCN | 660 |
| GNAANNTTTT | NCAANNCTTN | TGNNCCNTAN | CCTTTTTNNC | CCCACGGTTT | TTNNTCCCCC | 720 |
| CCCNTCCCCN | ATTNNGGANT | TCCCCCNTTN | CCCC | | | 754 |

(2) INFORMATION FOR SEQ ID NO:355:

(i) SEQUENCE CHARACTERISTICS:
        (A) LENGTH: 842 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1275UP (xi) SEQUENCE DESCRIPTION: SEQ ID NO:355:

| | | | | | |
|---|---|---|---|---|---|
| GATCGCCCAC | ATTATGTCTC | AGGGTACTTT | GTACGTTAAG | AAGACCTGCC | GCTCGATGCT | 60 |
| GCCTCAGAGC | ATCGTCGAGC | ACTACAACTT | GGACGTCTCT | ATTGTCGATG | CCGACAAGAA | 120 |
| CGAGGAGTTC | GAGAAGAAGT | TCCCATTGAA | GCGCGCTCCA | GCGTTTTCCT | GTGCGGCTGG | 180 |
| AAATCTAACT | GAGACCATGG | CCATCACCTA | TTACTGTAAG | TTGCCACCGA | CTACACACCG | 240 |
| AAGCATGGAG | CCCTAGTGTG | ATGAGAAAAC | CTTTCGAAAA | AACAGTTATC | CCTGTCTGAA | 300 |
| TGGGCATAAT | ATCTGGTTGC | ACATGTGTCG | AGAGACCATA | CTCTGATTTA | GAGCTACATG | 360 |
| CGAGGTTCCG | AGGAACACGT | ACTAACCGAA | CAACAGTGGT | CAACCTAATC | CAGGACGAGA | 420 |
| AGGCCAAGGC | TGCTCTGCTT | GGCTCCACGC | TAGAGGAGCA | GGCACAGGTG | TTGCGCTGGG | 480 |
| AGTCTTTGAC | CAACACCAAC | TTCATTGACG | ACGTTGGCTC | TGCCTCCTAT | ACCTAGAGAG | 540 |
| GGTGTGGTCC | CNTTNCACCA | ANNCNACATG | GAAAACGNCN | TTCCCNGNGG | CGAAACNTTN | 600 |
| CCCNAGNGTT | TTNNAAAAAA | GAAATAACCN | CTTCCCTCCC | TTACCCCCGG | AAANTTTTNT | 660 |
| TTNCCGGGAN | NCCNTGNCNN | TNGGGGGGTT | GAACNNANTT | CCCCACANTT | NGGGGNGNNN | 720 |
| NTGGGNCCNG | GCCCCCCCCC | CCCNNNNANG | GTTACCCCTT | GGGTANCCCC | NNNTAAAAA | 780 |
| CNNCCNCCCC | CCCTTNGGTC | GGACCNAAAG | GGGGGGNCCC | CAAANGAAAA | AAAAAAAAAA | 840 |
| AA | | | | | | 842 |

(2) INFORMATION FOR SEQ ID NO:356:

(i) SEQUENCE CHARACTERISTICS:
        (A) LENGTH: 77 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1276RP (xi) SEQUENCE DESCRIPTION: SEQ ID NO:356:

GATCGTATTT GTTGTTGACC AGTAGCACTT TTTTCATCTT CCCTTCGACG ACCACCTCCG    60

CCACGTTACC GAGGATC                                                  77

(2) INFORMATION FOR SEQ ID NO:357:

(i) SEQUENCE CHARACTERISTICS:
        (A) LENGTH: 77 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1276UP (xi) SEQUENCE DESCRIPTION: SEQ ID NO:357:

GATCCTCGGT AACGTGGCGG AGGTGGTCGT CGAAGGGAAG ATGAAAAAAG TGCTACTGGT    60

CAACAACAAA TACGATC                                                  77

(2) INFORMATION FOR SEQ ID NO:358:

(i) SEQUENCE CHARACTERISTICS:
        (A) LENGTH: 822 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1277RP (xi) SEQUENCE DESCRIPTION: SEQ ID NO:358:

GATCCGTCAC GGACAGACTG AATGGTCAAA ATCAGGTCAA TACACAGGCT TGACAGACCT    60

TCCGCTGACC GAATATGGTG TCGGCCAGAT GCGGCGCACT GGTGCTGCGA TATTTAGCGC   120

AAAATACATT GATCCTGCGC ACATAACATA CGTATTTACT TCTCCACGCC AACGCGCGCG   180

GAAGACTGTG GACCTGGTTT TGGAAAGCCT CAGTGAAGAT GAACGTGCAC GCATCCAGGT   240

GGTGGTCGAC GAGGACCTAC GGGAGTGGGA GTACGGTGAC TACGAAGGTC TGCTGACAAG   300

CCAGATTATC GAATTGCGTC GTAGCCGTGG CTTGGACTGC AAGCGCCCAT GGAATATATG   360

GCGCGACGGC TGCGAGAACG GCGAGAGCAC CCAGCAGGTG GGCCTGAGGC TATCACGAGT   420

GATTGCCCGG ATCCAGGCAT TACACCGGCA GCACCAAGCT GAGGGACGGC CGAGCGATAT   480

TCTGGTGTTT GCGCATGGCC ATGCTCTCCG TTATTTTTCT GCGCTCTGGA TGAAGATGGG   540

CGTCGAAGCG CCGACGCCAG ACTGCGCCAT GCCCTCGAGT AACCGGAATG ACGATCCGTG   600

CCCTTGGTGC GGCTGGAGCA ATCCGTACCT GCAGGACACC CCACTTCTTG CTAGACGCAG   660

GTGGCATCGG TGTGTTGTCC TACCCCCNCN ATTTGAGACC ANTCTACTCN CCTGGCCNTT   720

CNTTGCCCCC CCGAGATCCC CCCACGGTNA GTCCCACCGA AAATTTTTAT ATCTACAAGN   780

```
GNGTCCCCCC ATGAATATAC CNTATCTTCT TAATCGTCCN CN                822
```

(2) INFORMATION FOR SEQ ID NO:359:

(i) SEQUENCE CHARACTERISTICS:
        (A) LENGTH: 818 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1277UP (xi) SEQUENCE DESCRIPTION: SEQ ID NO:359:

```
GCCGTCCTTC TGCGGCCAGC GCGAGTCCAG GTGCCGCAGC ACGCCCCACG AGCGCGACCT    60
GCGCAGGCGA TAGTACGCGT ATGCGACCAG GCCCGCCGCC AGCACGTTGC TTGCGCCGAA   120
GAACCAGAGG AACCGCGAGC GGCTAACCAG CTGCACCAGC TGTCCGTAAT CGTGCCGCAG   180
CGCGTCCCCG GACGCCAGCC CCATGCGTGT GCCCACAGTC CCCAGCATCA CGCCGCCCCC   240
GCAGATCAGC ACCGTCCCGA CGCACGTAAG CATACAAAAC GGCTCTGCGA GCAGCCAACA   300
CGAAAACCAG CTGTTGAACA GCAGTCCGCA CGCCTGCAGC GGGGCCAGCA TCACCAGTGG   360
TAGCGTGGCA ATCTGCATCG TGCTTCCGAA CACGTTCGCT AGAATGAATA GCGTCAGACC   420
CATCTGCCAT AGGCGGCTAC GGTACACCAC CTGCACAGTT CCCCGTGCCA CTTGCAGCGC   480
AGCCTTGCGC TGAAAGTACC AGGCCCAAAA GACTGCATAC GCTTGAAACT ACCGCCACCA   540
CGACCCATAA TAACCAGTTG ATCGACCATT CGCTTGGATA CCCTGCACCC TTCGCTGCAG   600
AGTACTCTAC TGTGGGCGCC TTTTGGCTCT AGGTCTCTAC GCTATGCCAA ACATACTGGC   660
TCCGGTGCGT CATGTTCGAT GCTGTATGTC ACGTGACCGA TGACAGGGTA CCTGTCGGTT   720
CTCTTCCGGT TCCAGGGNAT GATACCGAAA NCCGAAATTA NCCGGATGAA TTTCCCGACC   780
CTGCGANTAC GACNCCAACN GGAGACGCNG TTTTNTGT                          818
```

(2) INFORMATION FOR SEQ ID NO:360:

(i) SEQUENCE CHARACTERISTICS:
        (A) LENGTH: 828 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1278RP (xi) SEQUENCE DESCRIPTION: SEQ ID NO:360:

```
GATCTTCAAC CTGCTTCCGC CTATGAACAT TCTGTTGTGA TTGAGAGGCG ATACCGCCTC    60
CACCTTTCTT CGAGCCTGCC CGGTTTTGGT AATCCATACG TTCTTCCCCA TTCTTTTGGT   120
ATTGGTATAA GCGATGCAAA TGAAAACAGC CTCTTGAATA CAAATCGACT TGCCTACGTA   180
TAAAATTATA TTTTTATCAG AAACTTGGCG AGCATCAAGC TCGGCTTCAT TGATTCATAT   240
ACTAAACAGA ATACACTACA TGCTACCGTC CGAAAACGAA TAATCTATTT CCAATATATA   300
TATATATATA TATATATATA TTATAGTTGT ACTTTATAAA TCTGAACTAG GTCATACAAC   360
TCTCAAATCA AACGATATTT ATTCTACATA TAGCACGGGC GACGCACCAA TTGAAGACTC   420
TAGGGCGCCT GAACTTGGCG CTGCCCTGTA TCTTTAGCCT GTTCCTTTAC AGGGTCATAA   480
```

| | | |
|---|---|---|
| ACATAGTACA TACCGCGCTC TAGTTCGTCA TACTGGATGT TCCTCTGTTT CAGCTGCGGC | 540 | |
| CAATTTTCGT GAGGGATATC CCACCCACAT TTCTGAGCTA TGAAAGCTGC AACGTCGTCG | 600 | |
| CACAGCCCCA GTAACTTAGG TCAATTCGCG TGCTTAACGG GTCTCCTATG ATAGTACTTG | 660 | |
| TGGTACGTGA GCTGGACCNT GTTTACATCN CGGAAACTGC GCNCCTTCAN CTNTTCNATC | 720 | |
| ANCNCAATCG CATNCANNTT CTGGCNANTT TTTTTGANTC CATGACCCCC CCNAAANTNT | 780 | |
| TTCCGGTNNG ACCCACACCC CCTTGAAATN NCTGATNTGN AGANGCNC | 828 | |

(2) INFORMATION FOR SEQ ID NO:361:

(i) SEQUENCE CHARACTERISTICS:
        (A) LENGTH: 855 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1278UP (xi) SEQUENCE DESCRIPTION: SEQ ID NO:361:

| | |
|---|---|
| GATCTTGGAT GTACTGGGGG CTCATACTTC GGCTTCTGTT TCTTGTCCTT TTTGCCCTTC | 60 |
| TGGCCCTTGC CATACGTCGA TGCTCCTTGG CCCATCTTAG AGATATCTGC TGTGCCGCTA | 120 |
| TGGAGTAACG CTTCTGCTTG CGAACTCTAA GTAGTGTTAT CAACTTGTGT GTATCATTTT | 180 |
| TGCCACCTGG AATCCATCAA TTTCACCTAG CCCAACCCAA GCTGCGACCT ATCAAAAAAC | 240 |
| AGGAGCAGGA AGCTGCCTGA GAAGCGCTC CAGGGGTCTA CCGACGGGAA AAACTACGAG | 300 |
| GACTGGTGCT ATGACATCCT TCCCGGGATC CATCCCGAGT TCAGTGCTTT CGAGCTGTAC | 360 |
| AATTGCGTCC GAGCGGTCGG AGCGCAAGCG TCGTGACAAC ATCAACGACC GTATCCAGGA | 420 |
| GCTGCTCAAC GTGATTCCAG AGGAGTTCTT CCAGGACTAC TACCAGAAGA AGAAGGACCA | 480 |
| GGAGTCCGAG AGCGGGACGC CGGGCGCTCT GCCCAAAAAC AAGGGAACTG GGACGCGCGA | 540 |
| CGGCAAGCCC AACAAAGGCA GATTCTCACG CAGGCCGTCG AATATGTGAC CTATCTGCAA | 600 |
| ACCAGTGGAT CTGCGCACCG CGAAGAGGTG GAGCTGATCC TGAAGGTCAG GAGCTGTGTC | 660 |
| GGCAGACGGG CAGCATCGTG AACGACGTGA ACTAGAAACA CCATTGCCGA CTCGCGCTGG | 720 |
| GAAATCGCGT TGGGCNCTGC AGCGTGCTCC GGAATTNTGC GGCCNCAGGG CAGCACACCC | 780 |
| NGGCAGCACA CCGCCCCAGA CCACACACTC ATTTGGGTCC CATTCGGACG CNTAGATTTT | 840 |
| CNCCTGGNCT GTTTT | 855 |

(2) INFORMATION FOR SEQ ID NO:362:

(i) SEQUENCE CHARACTERISTICS:
        (A) LENGTH: 831 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1279RP (xi) SEQUENCE DESCRIPTION: SEQ ID NO:362:

| | |
|---|---|
| GATCCTTCTG GATGCTGGTA GCTCCGATGA GGAAGTCGTA CTTTTGGTAA TGTCACTGCT | 60 |
| GCTTAAGCAT CTACTTTCAA AGCGTGATAT ACAGAGAGCG TTTGCTAAAA GTGGTGGATA | 120 |
| TACGTTACTG TTCTCCATAT TAAAGATAT CCAATCCGGG CTTACAGGAA AAGTCACGAA | 180 |

```
TCTATTGTGC ACCTATGCAT TTGGAAATCA TATTGTCCCA ACACACAGCG AAAGCACGTC        240

CCTTCTTATT AGACCGCAAG GCGATGGGCT ACAAAGGATA GTTTTCGAAC TTCATTATTT        300

GGCAATTGCA TTGTTAGAGA TAGCGGTGAT AAAAGCCCCA AAGGAGGATC AACAAGAGTT        360

GAGTAAAAAC ATTATTACGT ATATCAACGA GTTGGCGTTA CTTCATAGTA CTCACTCTCG        420

AATATCGCTT TTTGATCCAA GCGTATGCCA ACTTCATGAG AGATTGTTAA CTTTGTTATT        480

AACTTTGACA GATCCCAAAT ATCAGGGTTT CTATATACAG GCTATTCTGG ACATTGAACT        540

TCTATTGAGT AACAACATAT CTTTCACTTA AGAATGATG ATCCACCACC TTTTCGAACT         600

ACTTGCAAAA TATTTTGGTA ATGAAAGGGA CATCCGATTA GTCCTAGCAG ATTACAGTTA        660

GTAACAAAGG TCCAATTATA TTGAGACCAC TATATTNTAA AATTGTCCCC NTGTTATTGA        720

AAACTTNTGC CCNGGGTACA CTTATTGCTN TTCNACACCG TCCTGNAAAA ANTGTGNTTT        780

GTTACGATTA ACTCGTTTCC TTGATTGAGC AACTTTTGNT TTTTATCATA G                831

(2) INFORMATION FOR SEQ ID NO:363:

(i) SEQUENCE CHARACTERISTICS:
        (A) LENGTH: 841 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1279UP (xi) SEQUENCE DESCRIPTION: SEQ ID NO:363:

GATCAAGAGT ACAGTTGATG AAAAGGAGTT CCATGATGAA ATATGTAAGA TGGACTTGCT         60

TAAGAAATTG ATAATATAAA AGGCTACGAG CTTCAATATT ATAATACGCA TTGCATAATT        120

TATTACATTA AATTGATATA GGTATATTTT TCTTCGAAGA ATTAATTCTA ATCATTTCCA        180

TGTGAAGATA TCGCCCTCTG TGTTACCTGC GGATATTTCG ACTCTTAGTA TATCTACATA        240

TTTTGGCGAG CCATTATTTA AACTCGCCAG CTTGACTCTG GACCCAAGAG CCGTAATGGC        300

AGCAGCTCTT CCTGAGCGCA ATTTCTTCAA GCAATTGAGG CACCATGTGC CGTTCTTTAA        360

TTCAAGCACA TATAAACAGA CCGTCCCGTC AATAAACCCT AGCACAATTA TATCCTTTTC        420

TTTCCAATAC ATGTGCCGAT ACCTGGACAT TTCCTGAGAT GCAAAGTTAA CAAAGCTTAT        480

AGCAGTGATA TCTTGCGTTA GAGACATGCT TGCAAATTTC GAACCGTTGA GGTCATAAAC        540

ATGAACGTTA TTTGAGAATA TCAACCACCC ATTAAATGAA CTGTACCTGT TTGAAACCGC        600

AATGCACTGG NNTNNCTNGA AATATTCNCC AACCCNCCCT TAAAAGNGTC CCCCTTTATT        660

NNGNCCTNGC TATTCCCAAA AACNTACCCG NTTCNTTGTG NCNCCAAGGN NTTTTNNCNT        720

TNTTGGCAGC CTTTTAGAGN TTTAAANATN TTCCAANCCC CAAATCCANT TTTTAAAGGN        780

CTCCCCTNAA AANNTCNTGA ATGANCAGGN GAATTCGTTT GCCNTTTAAC TTCCCAGTNA        840

G                                                                       841

(2) INFORMATION FOR SEQ ID NO:364:

(i) SEQUENCE CHARACTERISTICS:
        (A) LENGTH: 826 base pairs
        (B) TYPE: nucleic acid
        (C) STRANDEDNESS: single
        (D) TOPOLOGY: linear (ii) MOLECULE TYPE: DNA (genomic)
```

(vi) ORIGINAL SOURCE:
             (A) ORGANISM: PAG1280RP (xi) SEQUENCE DESCRIPTION: SEQ ID NO:364:

```
GATCATCAGA CCTGTCGGAG GGTTCCGTAG TGGAACCTCT TCGTAGGGGG GAGCCGCTGT      60

TGTGAGCCTT GAGCCGCTCT GGAGACGGCG GCCTCGAGTG AAACGGAGCT CGTATCGGGG     120

ATCGCGAGAT GTACTGGGGC GACCTTAATG CAATTTTCTT CTCGAAGGAC TTTGTGGGGA     180

CGGAGGAAAG TCTTTCAAAT ATTGACGCAG AGCGGCCCTT TGAGATTTGG CTCTGGAAAG     240

ACGGTCTTTC CAAGGCCGCC GGCAGCTTTT CTCCCGTGCT TGCAGCGCTT GCCGCAGGTG     300

CAAGCACGGC CGCCTTCGCA AGAACGGGAC TCTGCTTCAG TAGGCTTGTC TTGGTCATCA     360

TCGGCTGCAC CACCAGCGGA TCTTTGTTCG GCAGCGGCAC AAACATGTTG GACCGCCGGA     420

GGGTGCGGTC ACGGCTCGGC GGAATCACGG CTGCCGTCCG AAACGTGAAC GTGTTCTCGG     480

GGCTCTTCGA CATCGAAACC TTCGTCTCGT TGATGCGACT TCTCCGAGTC CACCTCCTGT     540

ACCGTCGTCT GCTCCCGCTC CTGCGTGCGC TCCGGCTCCN GNCCNCCNGT TCCTGCCTCC     600

CTGACTNTTC CCCCCCCTTT AGGGGAACAC GGGAAGAAAA NAANTNCCCT TTCTNNCCCG     660

GCCCCTTGTG TCGCCCCCNN NNNNCCCCCN CCCTNNNNNN NNNNCNNNNN NNCCNNCNNN     720

NNNNNAAAAT NTAGGGGNGG GAAAAATGNG GTTAGNGTCC CCCACCNGAA CCCCAAAAAA     780

AACCNCCCAT GTNTCCAGGG NCTTNATGAN CANCTTCNCN NTGGGA                    826
```

(2) INFORMATION FOR SEQ ID NO:365:

(i) SEQUENCE CHARACTERISTICS:
        (A) LENGTH: 840 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
         (A) ORGANISM: PAG1280UP (xi) SEQUENCE DESCRIPTION: SEQ ID NO:365:

```
GATCATAATG CGACTATCGC CCATAAGCAG GGCAATACGC CTATCCACAT CAAAGTCCCT      60

GACCGTTCCA TTCTCCGCGA CCGTGACGTG CCTGTGTACA AAGGCTCAGC GCTCCAGGCG     120

CGCGATGTCA TCCCGTATCA CGAACTATCA AACTCGAACT ATTTCACTGT GAATCCTGGT     180

GAAACACTAA CACTTCCTGT GTATGAACCG GAGTTAAACA TCCAAGGCAA CATTGTCGAG     240

GGGCGGCAGA TTACCAATTT AACTCAGGGT GTACCAGGCG ATGTCCCGAT TTCTATTCTA     300

GACGGGAACA ACTATACCCA CTGGCAGCCG TTCGACAAGT CTGAGAGGGC ACTCTTGTTG     360

ATTGATTTGG GTTCCGAAGA GGAGTACGAG ATCACAACGG GTTAAAATTT TGTGGGCGC      420

TCGTCCCGCG AAGAACTTCT CCATCTCTAT TCTCCCCAAC TCAAAGCACA TCACAGAGAT     480

ATTGACAAAA CTGACGGCCA TGATGGACGG CCGGAATACG GACTTGTCTC CTGCTCAAAG     540

TGCCACGCCG TCTCTTCCTC GCAGCATCTG CTCGGCGGGC TGGCGAATGT CACCGATTCC     600

AGGGAACTCG CGGCCATTGA TGAAAACGTG GANNTGTTTT TAAAAAATTT CNGTTGGACT     660

TTCANCTCCN NCNNTTCACN TTTCCCNAGG CGCCAATNCN GANCTCCTNA GGCCCTGNAA     720

CACCATTNAN CNTCGACCTA CTCAAAAGTN TTCTATCCCC CAATNTCNTT TCCAACACAA     780

CGATCTGCTA ATTGNGCGNC CAACCATCAC TTNNTGCATC ATTTTGCCAC AACAATGNGA     840
```

(2) INFORMATION FOR SEQ ID NO:366:

(i) SEQUENCE CHARACTERISTICS:
        (A) LENGTH: 833 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1281RP (xi) SEQUENCE DESCRIPTION: SEQ ID NO:366:

```
GATCCGACGT TCAGTGGACT CTTCCCATTT AAGGTTTTCA ACAAATTCCA AACTCATGTG      60
TTTAATGCCT TGTACCATAC CGATGAAAAT GTATTTATTG GAGCTTGTAA GGGCTCGGGT     120
AAAACTGCAA TGGCAGAATT AGCTTTATTG AGTCACTGGA GAGATGGTAA GGGACGTGCC     180
GTCTATATAT GTCCATCTCA GGAGAAAATT GATTTTCTGG TGAAGGATTG GCGAAACAGA     240
TTTTTAAATG TGGCAGGTGG AAAGGTTATT AATAAACTCA CATTGGAATT AACTAACAAT     300
CTTCGAACGC TAGCCCAGTC GCATTTAATC TTAGCGACTC CAGAGCAGTT TGACCTGCTT     360
TCTCGTCGCT GGAAAAGAAG AAAAAACATT CAGACATTAG AGCTGTTGAT TCTAGATGAT     420
CTTCATATGA TCAGTAGTGA CTTGCCTGGC GCAAGGTATG AAAATATAAT ATCCAGAATG     480
CTGTTCATTC GGGGTCAACT TGAAACGGCC TTGCGTATAG TCGGTTTATC TACCTCCCTC     540
GCTAATGGTC GCGACTTTGG AGAGTTGGCT CCGAGCTAAA AAGCTACATT TTTATTTCTC     600
CTTTCACGAA GGGTTATGCC CTTACAGATC CNCTTACATC CGTTCCTAGA NGCATGAAAN     660
TCTTTAATTG AACTATGGCC AATCGCTTCC TGACGNACAA CTCTGTGATA CTGCCANTNT     720
TANCTTTTGT TCCATTAGAA ATGTTTCAAT TCTGTCNCTG CACGCCGCGC GGANGAAATC     780
CTGGTCNCCN ATTAGTTGGA ACCATTCTAG GNNAAAAGAC TCTTATCCTA ACN            833
```

(2) INFORMATION FOR SEQ ID NO:367:

(i) SEQUENCE CHARACTERISTICS:
        (A) LENGTH: 853 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1281UP (xi) SEQUENCE DESCRIPTION: SEQ ID NO:367:

```
GATCTGAACG TATGAGAGCG GGTTTTTACT AATTATAGAA CCATATGAGA TAGAAAATGC      60
GGCAGTTCCA AATCCAATAA TGCGATTCAC GTGCCTTGAT GCCTCCATTG CAATCAAACC     120
AGTGTTTGAG AAGTTTTCGT CAGTTATTAT TACATCGGGG ACCATTTCTC CGCTTGACAT     180
GTACCCTCGA ATGCTGAATT TTGAGACAGT TCTTCAAAAA TCTTACTCCA TGACGCTGGC     240
GCAGAAGTCC TTCCTCCCAA TGATTATAAC CAAGGGGTCA GACCAGGTAG CCATCTCTTC     300
TCGGTTTGAG ATCAGGAATG ATCCCTCAAT TGTCAGGAAT TATGGTTCCA TATTGGTTGA     360
ATTTGCCAAG ATTACTCCTG ATGGTATGGT AGTGTTCTTC CCCTCATATT TATATATGGA     420
ATCCATTATT TCAACTTGGC AGACAATGGG GATCTAGACG AGGTTTGGAA ATACAAGCTC     480
ATCCCTCGTG GAAACACCAG ACGCCACAGG AAACCTCCTC TACCTTTAAA AACTNACCNA     540
AGGCCNGCCC NNAATGGGNC GGGCCANTTA ATTTCNGTGG CCGNGGGAAA ATTCTNAGGA     600
```

```
ATGGATTTNG ACNCCCTCGG NGGGAGTGTT TGAAAATGGA TCCCTCCCTT NACCGANAAC      660

GTTTNTTTAG GGAGGGTTNT NTCCNTNANA AAANATCCAA ACCGGGAATA CTTTTTCCTT      720

NNAGCATGAA NCCCCCCCCT TTTGGGAAAA TTCAGGGGTG AGGAANATAT GGTTAATGTN      780

CCCCCCANCN GNNNCCNNAA AAAAANCACT CCCAATGTCC CAGGNCCTTN NGNACCACTT      840

CTNNNNATTG GAT                                                        853
```

(2) INFORMATION FOR SEQ ID NO:368:

(i) SEQUENCE CHARACTERISTICS:
        (A) LENGTH: 598 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1282RP (xi) SEQUENCE DESCRIPTION: SEQ ID NO:368:

```
GATCCGGAAT TATAGAATCG ATGAGCATTT CATTTAGCAA CCTTCTTCCA ATTCGTAATG       60

GTTCATATAT AAACTCCCTA GCTTCCTCTT GATAAATCCT TTCAAGAACA GCACCGTCGC      120

AGTCTGGGTT TATCTTTATA TTATTTCTTG TTATGCAACT CGCATGGTCT ATGAGGTCCC      180

TACATACATT TAGGTCGCCC ATCAGTACCA CCCTCTTCCC CAGATTCTCT ATGTTCCTCA      240

CACGTTTGAA TAGAGTTTTC AGGAAACGCA GCCTAAAAAC TTCACCCTCC TCAGTGTTCA      300

TAGAATTAGC AGGGCAGTAT ACGGAAATGA CCACCACCTT ACAGGCCAAT TCGACTAGAA      360

GGCATCTCCC CTCACTGTCT AGTTCCTGTG CATTAGCATC ACTCCCATAG GGCAAGCCAT      420

CATAACCACC AATACCAATG GTCGGGTCCT CGCAATATGC TACCAAGGCG CCATCCTTTT      480

TTAATTTTTT AGTCTGCCTG TAATACCTCC TCCCGCCTTC AATACTTGTA ATGATTATCG      540

CAACGATCGG CTGCTTCAGG GATTCTGTTC CACNCCCACN CCNATACCCT TCTCCTGN       598
```

(2) INFORMATION FOR SEQ ID NO:369:

(i) SEQUENCE CHARACTERISTICS:
        (A) LENGTH: 622 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1282UP (xi) SEQUENCE DESCRIPTION: SEQ ID NO:369:

```
GATCTGCGCA ACACCCCCA CTCTGTGTAC CTCCTCGATG CTGTCAATCG AGTCCTTGTC       60

CATGCTTCTA TCCTTCAGCA GGAACGCGCC TAGGTACGGG ATGTTCCGCC GCAGCAGCCC     120

GCAGATAGCT TCGATGACCG CGGGGTCGTA CACGGTCACC GACTTGTAGT ACCCGGGGAA     180

GAGCGGCCGG TTGCTCATCG GTAGCACCAT CAGCTCCTCG TACTTGCGCG GCACCTCGCC     240

CTCGCTCGGC GGGTTCGACC GGCCGCCGCC GCCCGCCGAA GACGCCGAAC CGCCGCTGCC     300

CCGCGAAGAA CTAGCCTCCG ACGACCGATT CGCCTGCTCT TCCCGTGGCT GCCGCTCCGC     360

CTCCTCGTCG CGCACCGCTT CCTCGTCGCG CCCCTCCTCC GCGCGCGGCG GCACCTTTTT     420

GTCGTCGCTC TGGTCCGGCT CCCCGGTCCT GCTTCAGTAT GCAACTGCCC GCCGCGTGTA     480

TCCCCGACTG CTGCCGCAAG GCCACTCTTT TTGGGGGGGG GGGGGGNNNG NNNNCCCCNC     540
```

```
CCCCCGCCGG GCGGCGTTGN CCGCCCGCGC CCGTTTGTGC TNTTCACGCC GGCGCNTTGG    600

CCATCCCCCC CTNNTTTTTC CT                                            622
```

(2) INFORMATION FOR SEQ ID NO:370:

(i) SEQUENCE CHARACTERISTICS:
        (A) LENGTH: 798 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1283RP (xi) SEQUENCE DESCRIPTION: SEQ ID NO:370:

```
GATCAGGAAA TCGACGGGAC TGGCTGATTG TCTTTATAGT CAAGCATATT AAACACACGT    60

GACTTAAACT AGATTTACAC GTGACATGCA ATTGTGTCGT TTCTTTTTTA TTTGAAAAAC   120

CTGCATCGAG CTATTAGATG CTCATCGACA CTAGTGTACA AACCAGTCAA GGCTTAAAAG   180

CTCTGCAGCA TGGACCAGTC GAATAAGGAG CATCGTCCTA AAAGGAGAA GGCGACAGCT    240

AAAAGAAGC TGCACTCCCA GGGCCACAAT GCGAAGGCAT TCGCGGTGGC CGCTCCGGGA    300

AAGATGGCCA AGCAGATGCA GCGCAGCAGC GATAAGCGGG AGCGCGCGCT GCACGTTCCG   360

ATGGTGGACC GGACGCCGGA CGACGACCCG CCGCCACTCA TTGTTGCCGT TGTAGGTCCC   420

CCGGGGACGG GTAAGACAAC NCTGATCAAT CGCTGGTGCG GCGGTTGACC AAGACGACCC   480

TCGGCGAGAT TAACGGTCCG ATCACGGTCG TCTCCGGCAA GCGCCGCCGT CTGACGTTCA   540

TTGAGACGCC CGCGGACGAT CTGAACTCCG ATGTGGACAT TGCGAAGGTT GCAGATTTGG   600

TGCTGCTGCT GATGGACGGT ACTTTGGTTC GAGATGAGAC ATGAGTTCCC TGACCTGGCN   660

CACNCCACGG ATNCCCTTTT NCTGGATTAC AANCNCNCAT TTTTCATTNC NAGGCCNCTC   720

CNGCTCNAAA ACTTTTNACC TCGTTCTGAC NATTTTNCCN GGGGNNCNNT CCCCTTCGTN   780

TTTTTTATGN NGNNCCNT                                                 798
```

(2) INFORMATION FOR SEQ ID NO:371:

(i) SEQUENCE CHARACTERISTICS:
        (A) LENGTH: 829 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1283UP (xi) SEQUENCE DESCRIPTION: SEQ ID NO:371:

```
GATCCGCTGG CCCATCGCCG AGAGCTATGT GCATCGCCTC ATAGTGGCCT TGATACGTGT    60

CTCAACCAAG ATTGTGGAAG ACACCGTGCA CTCCCACGAG TATTTCAGCA AGGTCTGCGG   120

CATATCGAAG AAGCTCTTGA TGCGCCTCGA GCTAGCCCTC ATACTCGTCC TCCGCGGCGA   180

GGGTTTGATG GTCACGGCTG CAGCTCTAAA CGCTGCCTCA AACGCACGTG CTCGGCTTCG   240

CGAGCAGTCT GCGCTGCCAG CCGCTGCTGC TCAGTGATAA TCGCCACTTC TAGGCCCACA   300

ATTCGGTTAT TTAATAAGCA ATAAATACTC CAACACTAAT AGTATACACC GTTTGCGAGA   360

GTAAGCACGC AGCAGGAGGT GGCAGCTTTT CTGGTACCAC CTCAAGCCCC TTGCCATTGC   420
```

```
TGCCTATCTG GTTTAGGCAT GAGCAACCTT AGTCAGTTTC GAACCCGTGA TATATGTTTC      480

GAACACGTTA CCTTTTCGGT GAAAAGAAAA AGCCTAAAGG CGAAATGTTT TCCATGTTAA      540

CACAGCAGAT TAGAGGTACC TTGTACTGGA TATTCTGTAG GATCACGGGC TACGAGCATT      600

CATCCAGAAG CTTTGAACTT ANGGTGTTTC NGGATGGCAG TTNGGGACTT ATNCCGTGGN      660

TNTAAAANAA TACTTCGTCC TAGTCTTTGG AACAAACNTG CATTTGTTGT TCTTNGTTTG      720

GANNATCGGN AAGACANCCT TTGCCCTGCT AANAAGACNG TTGGGAACNG NNGCCNNTGN      780

CCCNCTCCGA GNCNNGAACN GGCCCCNTTN CNNTTCNNCN GGGGNNNNC                  829

(2) INFORMATION FOR SEQ ID NO:372:

(i) SEQUENCE CHARACTERISTICS:
        (A) LENGTH: 817 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
         (A) ORGANISM: PAG1284RP (xi) SEQUENCE DESCRIPTION: SEQ ID NO:372:

GATCGATCTG GTCAGGTCTA TTTGTGGCAC CGATGACAAA AACATTTTTC TTTGCATTCA       60

TACCATCCAT TTCAGTTAAC AATTGGTTAA CGACTCTATC AGAGGCGCCA CCAGCATCAC      120

CCATTGAGCC ACCTCTAGCC TTTGCAATGG AATCTAGTTC ATCCAAAAAG ACAACGGTTG      180

GCGCTGCGGC TCTAGCTTTA TCAAAAATAT CACGAATGTT GGACTCAGAC TCACCATACC      240

ACATGCTTAG CAACTCTGGA CCCTTCACAG AAATGAAATT AGCAGATACT TCAGTTGCGA      300

CTGCCTTTGC CAACAACGTC TTACCAGTAC CTGGAGGACC GTAAAACAAC ACACCTTTCG      360

ATGGCGATAG ACCAAACTTA ATGTATTGGT CAGGATGCAA GACGGGATAC TCAACGGTTT      420

CCTTCAACTC CCGCTTTATG TCATCCAACC CACCAACATC GTCCCAAGTA ACGTTAACCG      480

ATTCAACCAC GGTTTCACGT AGCGCGGATG GATTGGAGTT CCCAAGTGCG AATCTAAAGT      540

TATCCATTGT AACTCCTAAG GAATCCAAGC ACTTCAGCGT CGATTTCATC CCTCGTCCCA      600

ATCAATTAGA CTCATCTTCT CTCTAATCTG TTGCATTGCA GCCTCTGAAC ACAAAGAGGC      660

ATATCAGCAC CCACATACCA TGGTTTCAGC AGCTAGCACT TCCAATCACG TCATCAGCCA      720

TCTCANTTCT TGNTGTGGAT GTTTAAATTC CCACCCTCCA GTGCTCTGGA NACCANTTTA      780

TTNNNGTCAA TTTACCAACT TTTAGNCGGN TNNATGG                              817

(2) INFORMATION FOR SEQ ID NO:373:

(i) SEQUENCE CHARACTERISTICS:
        (A) LENGTH: 831 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
         (A) ORGANISM: PAG1284UP (xi) SEQUENCE DESCRIPTION: SEQ ID NO:373:

GATCAAGCTG ATATGTATTC TCGGGCTACT GGTCGTATCC GTGGTAATCT TCTTCGGCGG       60

CGCTCCCAAC CACGACCGTA CTGGCTTCCG CTACTGGAAG AACCCGGGGC CCTTTGCGAT      120

GAGCCTCGCG CCAGGAAGCA CGGGCCGTTT CTTGGACGTG TGGCGCGCCG TGATCAAGTC      180
```

```
GGCCTTCGCC TTCATCCTAT CACCAGAACT TATAGGCATT GCATGCGTCG AGGCGCAGGA      240

CACCCGGCGG AACACTGAGA AGGCATCGAG ACGTTTCATA TACCGTATTA TCTTTTTCTA      300

TGTGAGCTGC GCGCTCATGA TCGGCGTCAT CTTATCAAGA ACTGATCCGA AACTCATAGA      360

GGCGCTGGAG ACAGGCGCGC CAGGCGCTGC CTCTTCTCCG TTCGTGCAGG GGATTGCCAA      420

CGCAGGGATT CCCGTGCTCG ACCACGTCAT CAACGTCGCG ATCTTGTCTT CTGCGTGGTC      480

GGCAGGCAAC TCCTTCATGT ATGCATCCAC GCGCATGGTG CTAGCGCTTG CGCGCGAGGG      540

AAATGCGCCA AAGTTCCTCA CCAAGATCAA CAGATATGTG TGCCCTACAA CGCGGTCATC      600

GTCTGCACGC TCGTCGCCTG TCTTGCCTAC CTGAACGTCA AGACGACTCC GCAATGTGTT      660

CCAGTGGCTG TCGAACATAT GCACCATCTC CGCTTCATCC GCTTGTTCGC CATGGCTCCC      720

TTATATCCGT TCCCNGGCGT TCTTTTCACA CTCCNANCCN TNCCCTNCCA GTTCCCTGCA      780

CCNTTTCNCC ACTATTCCNT TNTAATGTNT CTTTTTNGAC AATGTTCCCT C              831

(2) INFORMATION FOR SEQ ID NO:374:

(i) SEQUENCE CHARACTERISTICS:
        (A) LENGTH: 817 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1285RP (xi) SEQUENCE DESCRIPTION: SEQ ID NO:374:

GATCCGGGTC CGCCACAAGC TGCTGGTCCA CATCGTGCTG CTGCGCGGCC CCCCCGACGC       60

GCCCGGAAAG AAAACCGAAA TCAAGGCCAG CATTCCGGTT ATGCTCTACA TATCGCCGCT      120

CGTACCTGTG CAGGGCCGCA CCGTCCTGGT TGATAACGCT GGCCGCTTCC ACATCCGTCC      180

CGGCGTGCTG ACAGACCTAT TCCGGACGCG GAGCGCGGAC TCACTTCCGA GCTGGGACGC      240

GCCGCCGTCC TACGAGTCGC GCGTGCACGA TCGGCTGTAC GATGGCGACG TAGGCTCGCT      300

TGCTTCCGGC AGGGGGGCCC CGCCCGATTC GGCGGCGCCC CGCCCCCCGC CCCGAGATTC      360

GCCACTGGGT CTCCTTCCGC CCCTTCACGC CTTGTCGTTG GATGATCTAA GCAGGGTCCC      420

CACGTACCAA CAGCAGCACG ATGGACACTC CCTGCCATTG CATCACCTCT CCCCGGCGTA      480

TGCCGCCACC GCGCCACCNG CCGGGGGGCA ACAGCGCACN TGACAATCAC TTNTGCGGTC      540

CGTCGCGGCC CCCCGGACCC CCTTGCGCCC TTATTCTGCC CCCCCAAAC CNACCNTGCN      600

CCCAATAGGG TCAAACCGCG GNGTTGGNAA TTTNCTTGNT CNGNNNNCNG NNCNGGTTTT      660

GGGCCCCCCC GGTTNCCCCC CNNANTTNGC CCAANCGGAA NCCGGGGAGG GTTNNNGTGN      720

NNCNGTAAAA ACTTNTACCC CCCCNCTTTG GGTNCCNGGC CGGNGGGTTT TTTTTTTCCC      780

CGGGGNGCCC CCCCCNNGGG ACCNTTNGGG NACNATT                              817

(2) INFORMATION FOR SEQ ID NO:375:

(i) SEQUENCE CHARACTERISTICS:
        (A) LENGTH: 831 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
```

(A) ORGANISM: PAG1285UP (xi) SEQUENCE DESCRIPTION: SEQ ID NO:375:

```
GATCTTCTTC ATGACGCTAC TGTAGACAGT TTCACAACCG ATAGCCTGAA GACACAGTAC      60

AACCAGAGCA AAAGATATCA ACTGTTTCGG ATTCCGTATT CGGAGCATTC CAGCTTTAAG     120

GACCTAAGTA TTTTCGCAAC CACGATCCAG ATGAACGCCA TTCGATCTAC AGTGAACCTG     180

GCCTCTTTGG AGATGCATCG CATGTGGTTC GACACTTGGT CTCGTATTAG AAACGAAAAA     240

TACCTGCGTA AATTATGATT ACATGTTATA TATAGTAAAA GATAACACGC CACTCAGTGT     300

TAAATGGTCC ATCATGCCTC TAGGACTCGT TGTCGTTGCT CGACAGAACT GCAGTCCCCA     360

TTTGCCTGGT AGGTTTTTGT GAGGCTTTTT TCTAATTGTC TAATTTAAAG TCCTGAATAT     420

TATCCTCCAA TTGTGGAATG AAAGACACAT GTACCACTAG AGGTTCAGCC CGATGGCTGC     480

AAAACGGCAT ATTTGTCATC CAAATCATGC CGCTGGTCCA ACAGTTTAAT AATGTCTCTG     540

GAACTTCGAC TACGTCCGGA ACTCGTCTAT CATCTGGAAT ACCNCCTCCT GTTATGCNTT     600

ACCATANTCC CCTCCCTTGG TGGCCNAATT CTTAANCAAT TTTTGNTTAA ATNCCCCCNT     660

GCTTNNCTAA GGTNAATTCC NNTTGGCCCC CCCCTTCGGG TTTNTCCGTT CTTTGGAATG     720

GAGGAAGCCC AGGCTTGNCC CCCAATACNC GCCCTCCGGG AAGNGTCCTC CTTNGCCTTN     780

CCCANTGGGN TNCTTGGGTT NGNNGCAAAN CNACNNCNGG CCCTCCTNCN C              831
```

(2) INFORMATION FOR SEQ ID NO:376:

(i) SEQUENCE CHARACTERISTICS:
        (A) LENGTH: 802 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1286RP (xi) SEQUENCE DESCRIPTION: SEQ ID NO:376:

```
GATCGCACCT ATAATGAAGA CCGGTTTTTT TTTATGAGAA ATAGCAGCCC TCCAGGGGTT      60

ACTTATTAAA TAGCTACAGT AAGATTAGGT TATTCGTTTG CAAATTCATT GGTAGATCAA     120

CTTGTACACT TCAAATAATG CTTCGCTGGC ACCGTCATAA AACATGTTAT GCCCGGTGTT     180

GACAACTACT CTGAAGCTAT AGTCAGGGTA GTGCGTGGCA TTAGCTGGAC ACACCTTATC     240

TTCACTGCCG ACCAAGACAT GCCCTGTGCA CCCGCTGTCG AGCAAAGGTG GGCCGTTAAT     300

TAGGTCTTGC CAGCCTAGAA GATACTCAGT GATGGATTTG GTCGAAACTG CTACACCGTC     360

GTAGAAGTGA TTTAGCTTCC TGTACTTGTT CCCCATGTTG GAGAAAAAGA ACTTAATTCC     420

GGAGCTGTTC AACCCTTCAT CTGGTCGAAA TTGGTCCTTA TGAATTTGAG AAGCATGATC     480

AAGAAGGGCT TGAAGAATGT TAGTGAAAGG TTTAGATATG GCTCGACGAT ATCCAACTTT     540

GATTTGAGAG TTCTAGGTGG CGGCGGCGCC AATAGAATGA TCTTTCTGCG TTCAATTGTT     600

GACGCCGTAT CCTGAAGGCT AATGCCAAGC CAAATGCACC CCATCNATTG CCCAAAACTC     660

CCACNGACAT TATTATGGTT GGCNCGTAGA CCATGAATCT AAACCCCCTA TCACNCACCC     720

CCCCCACANG GTTACCATCG CCCATGTCCC TTCCCCANCC TGAGNTCNAC CCCATTNTCC     780

CCCTATTTNC CACATATCNT CC                                             802
```

(2) INFORMATION FOR SEQ ID NO:377:

(i) SEQUENCE CHARACTERISTICS:
    (A) LENGTH: 835 base pairs
    (B) TYPE: nucleic acid
    (C) STRANDEDNESS: single
    (D) TOPOLOGY: linear (ii) MOLECULE TYPE: DNA (genomic)

(vi) ORIGINAL SOURCE:
    (A) ORGANISM: PAG1286UP (xi) SEQUENCE DESCRIPTION: SEQ ID NO:377:

```
GATCTTCGCA GCCAGCGCGT AGTCCACCGG CGTCAGTCCC TCGCAGAACG CCCCGCCGTG      60

CACGTACAGC ACCACCGGGT CGTCTGGGTG CCGCTTGTCG GGCCGCGACA CATACACCGC     120

GCGCGCAGTC CGCTCCGCCG CCGCAGCCGC CGGCCCCCCG AGCTCGAACA GGTCGCTATC     180

CTGCACAACG TACGTCTCCT CCAGCACCTC GCCGCCGCGC TCGAACGACC GCCGCGCGTG     240

CCACCACGGC ACGCACGTCC CGACCGACGC CCGCAGCGCG GCCGCCGCCG CCGGGTCCGC     300

GTGCCGCGCG GCCTCTACGC CCAGCAGTCC CAGCAGCGTG CGCCGCCCCG CGCGCCGCAC     360

CACCGAGTAT ACCAGGCGCG CCAGCGCTGC CGGCACGCCC AACCCATAGA ACTTCAGCAG     420

AAACGCGAGT ACGCTCCACG TTTTGTTTGG AGATCCCATG ATGCCGGCCC GAGGGACGTC     480

GACGCCCGCC ACCTGACGGG GCGGCTACTT ATACACCACA AGATTCTATA GAAAAGGAAT     540

GCGACCAACG ACGAACGGTG TATCGTTTGG GAAAAAAAGG AGTCCCCCAA CTAAAGCTTG     600

CTTGCTGGCT ACGAGTTTGT GTTTCAGGTT TCTTCATAGC ATCCCAGTTG TTTTGTTTGT     660

TTGGCAAATC GCATATGAAC CATAAAAANAT CAAANNTTGT ACAATTGCTG CCGACCGTTG     720

CCCCATCCNC CGGCGAAANA TCCAGAAATC GAGANAATTT CAGACGCCGG GTTTGCCAAA     780

NTCCCGAAAC CCCAAANTCC CAACATTCCT GNCACATTTG ATTCTGNNNC NNNCA          835
```

(2) INFORMATION FOR SEQ ID NO:378:

(i) SEQUENCE CHARACTERISTICS:
        (A) LENGTH: 799 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1287RP (xi) SEQUENCE DESCRIPTION: SEQ ID NO:378:

```
GATCCCACTG GTATTAGGTG TCTGAACACG GCCAAATAAA ATACGCAAAA TGAAGGGCAT      60

TAATAATCTT TCATCAGTGT TGACAATAAC CCTTGACTCA TTCTGAGCAA ATAACTTTGT     120

TACTTCGTCG TTGAATAACG TGTCATCTAA TAAGTTCTTC AGATTGTCCC TATATTTCAC     180

AGCTACTGGA TCCTTGTATG CTAACAACGC ATCTAGGGCC AGTTTCTGCA CTTCCAGCGT     240

TCGACTACCC AATAATTCCA TCAACCTTTG GCGGACATCT TCGGATTTGT AAATAGCTTT     300

GATATTCTTG AACTTGCCCA ATAATTTCAA AATTAGATTC CTATCCGTCT CAGACCATGT     360

ATCCGCAGAG TGCACTGCTA ACTCACCCAG ATGGTCTTCA TCTTGGTTGG CATCGAATTG     420

ATCATTGCGT TTTAAGACAA AAGGTACAAT GAATCTGCTA TTTTGCTCCC GCGAGCTGTN     480

GCAGCGCGAT TAATATCTTC AATGCTTGTT TCTAATCATA CCGGATATCC GAGTGAACCG     540

CGANCCCCTT TAAGGTTTTC CAACCAAGGA TTTTTCGAAA NCAACATNCN TTTGAACNT      600

TCCNAANNCA AATAATTNAT CCTAAAAAAT TTNTGCCCNA NTCCAAAAAN TCCCNAGGG     660
```

```
GTNNAAAGAG TGGCCCCAAA TTCNAAATNA GNGNTTTTTN GGGNTTTTCC NAAAAAAAAT    720

CCCNCCCNAC CNCGNNTTTA ANAATTTTTG GGAANCCCAT TCCCCCCCCA AGGGGAAAAA    780

AGNGTGNNCC CNATTTTNA                                                 799
```

(2) INFORMATION FOR SEQ ID NO:379:

(i) SEQUENCE CHARACTERISTICS:
        (A) LENGTH: 817 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1287UP (xi) SEQUENCE DESCRIPTION: SEQ ID NO:379:

```
GATCAGGTGG TGTTGGCCGA TACCGTGACG GAAATGGATG TCCTGGCCAT GCCCGAGATA     60

GATTTCCTCG ACACAACGTC CTCCTCGAAG GGCCTGATGC GGCGAGAGCG CTCAATGGAG    120

AGGCACGTAC AGGGCGCGAA CACGGTCACA GACCCATGGG ACATGTCTTT GGAAGTGGGG    180

AGAAGATACG CCCCTGACGA CGACCTGGAG CAACAGACGT CGCTACTGGA CCTCAACTTT    240

GAACTCAGTG ACATGCAGAA CTCCAAATCT TGGGGTGAAG GGACGCACAA TTCCGAAGAG    300

ATCAGTGCCA ATGTGCTTGC AGAGTCGCAA CGCCAGGAGC TGCCCGGGAA CGAGGGCATT    360

GAGCGTGAAG AGGATCTTGA TTGGAATCTG GGATTCACGG AACCAGCAAT TGTAGTCCCT    420

TCAAGCGATT TTGAACACGA TAACAGCATA GAAGTGGGCC GGAGAGCAGT CCCCGAATGC    480

GGACCTTCAG GAAACTGTGG ATTTGGGATT CGACTTGGAT ATTGCCAGGG TTGACATTGA    540

GGCTACAGCC GGCGAGCAGA TGCTGGCAGT TTGCATCTGA GCTTTCCGGA AGTATAGTAC    600

GTCTTCCTGG AACACTGTNC ACANCCAAAA CAAGAAAGGC ACCTGGTTAT CAATTCTACA    660

TTCACCCCCA CCGGATTACT GAAAGGTGNT CNAAAACCCC CCCNACANTG CTCCNTGANT    720

ACCCATCCCN NCCCCATTCN NCCCNAAAAC GGNTNTCGAC CCTTTNAAAT GATCCTNCAA    780

TTTTGCNTGA CATCCTGCTC NTTTCCAACG AGNCCCA                             817
```

(2) INFORMATION FOR SEQ ID NO:380:

(i) SEQUENCE CHARACTERISTICS:
        (A) LENGTH: 787 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1289RP (xi) SEQUENCE DESCRIPTION: SEQ ID NO:380:

```
GATCGGGATT GACCGTAATA TTTCAGCTTT TGATGTGAA TTGCCAAGAG GACCAGCGAT      60

TTGAATCTCG CTGACTCTGT TGTGAGTAAT TAGTACAAGA ACCTGTGGCC TGTCACAATT    120

AAGCCCTGGG AATAGGACTT CAACTTCAGA AGCCCACGAT CGTCAAGCGA TGATACAAGT    180

GCCTACCAAC ATTGACTTAA CATGAAAATT GATAGCATTT TTATAACAAT GGAAGCAAAG    240

GACTAAGTCC TTCACGTGGT CGCCAATGCA GCCTGTTAGC AGGTTTCGGC ATATTCCTGG    300

AAGATGTCAA CCTTCCAAAA ATATTCCTCA GAGCATTAAT TATCATTACA CAAGCCCTTG    360

GTGTGAGACA GAATCTTGAG AGGTGCTGCG ATAAAACTCA AAATCGCAGT GCTTGGATTA    420
```

```
TAGGGCTTAT ATACTGATTT AAGTGGTGGT GGTTATCTAT TCAGGGTTGT ATAAATTAAA        480

ATATCACAGT CGGTATACTC TTACACACTA ATTATAATCA CGTGATATTT GACTATTTAT        540

TACACCAGGA CACCTCGCTA TGAAAATAGC AACAGGCTGA TGGTATTAAC ATCTGAAGAT        600

ATCGCCAACA TTAGAACACA CTACTGACAC AACGGCCAGC CATTCGAGAC TATGGCTCGT        660

ACTACTGCAN TACTGTCATG CTTATCTGAC NCCTGACCNC TGATTGTTGC GGAAATCCNT        720

TTGATCNGCA AAATCATNTC GNTGACCNCA ANTTCTACTN TATTAACCCC CCCACCGCCA        780

ACCTTTG                                                                 787

(2) INFORMATION FOR SEQ ID NO:381:

(i) SEQUENCE CHARACTERISTICS:
        (A) LENGTH: 788 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1289UP (xi) SEQUENCE DESCRIPTION: SEQ ID NO:381:

GATCCCAGGC TGCCCCAGGA TGACGGAAAG TTGCATGTTC TTTTCGGCGC TACAGGCTCG         60

CTTTCCGTAC TGAAGATTAA ATCGATGATC AAAAAACTCG AAGAGATTTA TGGTTGGGAC        120

CATATATCCA TTCAAGTCAT ATTAACTCAA GCCGCTGCGC AATTCTTTGC TAATAAAAAC        180

CCCAAGAAGA AGAACCTTTA CGTGTCTAGC GAAACAAACT CATTCTCAAA CTCCGTGGCT        240

CACCAGGGGA AACTTGCAAC AGAACAACTC AGACGCATCC TACACTGCGG TAAATAGCGT        300

CTCCAATACC CCTGCAGTTG GGGGCGCAC ACCAACGCCA GCAGATCTTC TCCAGGGCGC         360

AGCGCCGCAA GGCGCGGGCT CCGGTCTAAG CCAGGGCGCA GCTGCGGCGA AGATTGAGCT        420

CCCTCCACAC ATACAAGTCT GGACGGATCA AGACGAGTGG GACGTGTGGA AGCAAAGAAC        480

AGATCCGTAC TGCATATTGA ATTACGCAGG TGGGCGATAT CCTTGTCGTC GCGCCACTTA        540

CGCGAATACA CTTCCAAATT GCCCTGGGCC TTGTTAAAAC CCGCGAACAT GTTCNTCGGG        600

NNTGNAACCA NTTTTCCAAT TCTNCNCCCA NCCGNGTTTN GNGNTNTTNA ACCCCCCCCC        660

TACCCCCCNA AAAANAANAA NAAAAACCCC GTTNTCNGTG TTTCACCNCC CANAAAANAG        720

GGTNCCCCGG GAAAACGAAC TGGGGGGAGA GAGAGGNANN AAATTNCNAN AATCCTTTTA        780

NCCCNGGG                                                                788

(2) INFORMATION FOR SEQ ID NO:382:

(i) SEQUENCE CHARACTERISTICS:
        (A) LENGTH: 761 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1290RP (xi) SEQUENCE DESCRIPTION: SEQ ID NO:382:

GATCGCTAGA TGCCCAGGAT GAGACTGTTC AGGTTAGGCA GGTGTTGTAT GCGCCGCCAG         60

AGGGAAACCC AATGACTTTG CATAGAACAA ACCCGCCATC ACCCATGTCT TGCGCTGTAT        120
```

```
AGAGACTAAG GTATCTGACG ATCCCTTAGC GACTCTCTCC ACCGCTCGAC GAGGCCATTG       180

AGCTCTTACG AACTGCACAA ACCTACTCGA ACTCTGTTTC CAGACTTCTT TCTGTTTGTC       240

TTCAACTGCT TTCGCATGAA GTACCCCCCA GGCTATTTTT CTTACCCGCC TGGTGTTTGT       300

CTATATACCC GGTTGTATTT TTGATAAAAA ACTCAGCTCT TCCTCTACGG CAGAAATATA       360

TATCCAGTCC TTAGCGCCAT GCGAAAATCT GCCTTTTTAC CGCTGTTTCT CCCAGTCTTA       420

GCACTGGCAG AAAAAGATG TATGGCGTAT AGGCGCTGGC CCCGCGGAAA AAAAAAAAA        480

ATAGAAAAAT AGAAAAATAA AAAGACGTGG GCCGCCCCGC GGGCAGACGA AGAAAAAATA      540

GGCGCCCACC CCTCCAAGCA GACGACAGGC GAGACATAAT AAATCCCACA CCAAGGGAAG     600

AAGTCTTGTG CACGCTCCCG GCTCATACGC CTGCCATTCT GTTCCATCCC GCTTGCAACC    660

CAGTATGCAT GTCAAGCATG NTCCGAGCTC CGCTGCTTGG AGTCGAATCT CTTCCTACCC    720

AGCCGAATCC CATACTTGCC TTCACATACA TACCTTTCAT T                        761

(2) INFORMATION FOR SEQ ID NO:383:

(i) SEQUENCE CHARACTERISTICS:
        (A) LENGTH: 639 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1290UP (xi) SEQUENCE DESCRIPTION: SEQ ID NO:383:

GATCAGACAT GGTGTTTTGC GGCCCTCGCT CCTTGTGGGT GGGGTCACCG CAGTTCACTG       60

GGCCAGCATC AGTTTTGGTG GCAGCAGAAA CCCTTAGGAA TGTGACTTTC TCTTCGGAGG      120

AAGTGTTATA GCCTAAGGTT ATACTGCCAA CCGGGACTGA GGACTGCGGC TTCGGCCAAG     180

GATGCTGGCA TAATGGTTAA ATGCCGCCCG TCTTGAAACA CGGACCAAGG AGTCTAACGT    240

CTATGCGAGT GTTTGGGTGT AAAACCCGTA CGCGTAATGA AAGTGAACGT AGGTGAGGGC    300

CTCTTTAGAG GTGCATCATC GACCGATCCT GATGTCTTCG GATGGATTTG AGTAAGAGCA    360

TAGCTGTTGG GACCCGAAAG ATGGTGAACT ATGCCTGAAT AGGGTGAAGC CCNANGAAAC    420

TCTGGTGGAG GCTCGTAGCG GTTCTGACGT GCAAATCGAT CGTCGAATTT GGGTATAGGG   480

GCGAAAGACT AATCGAACCA TCTAGTAGCT GGTCCTGCCG AAGTTCCCTC CAGATACAGA   540

ACTCCTATCA TTTTATGAGT TAAACNAATG ATAAGTTACC GGGTTGAAAT GACCTGACTA  600

TCCCCACTTT AATAGTTAGA ATCCCTGTTG CTTATTGAC                          639

(2) INFORMATION FOR SEQ ID NO:384:

(i) SEQUENCE CHARACTERISTICS:
        (A) LENGTH: 813 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1291UP (xi) SEQUENCE DESCRIPTION: SEQ ID NO:384:

GATCGTGCAC GGCAAGACGT CGGAGCTGCG TCACGACGGG CGCGGGCTCT TCCAGGGGGT       60

ACCCCAGGCC GTGGCAGTGA CACGGTACCA CTCGCTGGCT GGACTGGCGT CAACGTTGCC     120
```

```
GGCGGAGCTG GAGGTGACGG CGCGCACGGA GACAGGCGTG GTTATGGGCG TGCGGCACCG       180

CAAGTACACC GTGGAGGGTG TGCAGTTCCA CCCGGAGTCG ATTCTGACGG ACCACGGGCA       240

GCTAATGGTG CGCAACATGC TAGCGCTGGA AGGCGGTACG TGGGCTGAGA ACGACAAGCT       300

CCAGCTGCGG GCAGGCGCGG GCTCTGTGCT GAGCGAGATA TACGCTCAAC GACAGGAGGA       360

CATGGCAGCG CAGATGGCTA TGCCGGGAAC TGGTATGGCG GACCTGGAGG CGAGCTTTCG       420

ATTGGGGGTT CTGCCGGGCG TGGTGGACTT CCATGAGCGG CTGGCGCGGG ACGCCCGCGG       480

CTGGCTGTGG TAGCCGAGAT AAAAGTGCGT CTCCGTCGCG TGGCAATATT AGCGAGGCGC       540

TTGGCNCCAN AANANGCGCT TNCNTNTTGC CGAAGGCGGA ATTTTCCGCC ATCTCCGGTG       600

CTTTACCGAA CCCACTGTTC TAAAGGGACC CGCNAGANCN NAATTATTNC CCGACCCNCC       660

CTTTGANAAA AACNANACTG CCCAAANACC GCCGCGTTTG CTNCTTTANG ANATCTTTAT       720

TNTCCNTTCC AATNTTTGAA GCCCGNTTNC GGCCNACAAT TTCCCTTATT TTNAAATTTT       780

NAACCACCCC CCCCCAGACC NTTTTTTTTN CCC                                    813

(2) INFORMATION FOR SEQ ID NO:385:

(i) SEQUENCE CHARACTERISTICS:
        (A) LENGTH: 773 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1292RP (xi) SEQUENCE DESCRIPTION: SEQ ID NO:385:

GATCCGTGTA TTTTTATTT ACATTATTTA ATTAAAAATA ATGATTTAAA TAAATATTTT         60

TTATAAAAAA TAATTAGTGC ATTGTTACAT GTTCATTAAA GAATGATTAT TATCAAAACC      120

ATCAACTAAT TGTTATATAT TTATTAAATA TTAATTTCAC TTAATTAAGA ATTAGGAACT      180

TTATCTATTA GTCTGGGCTG TTTCCCTTTT GATTATTAAC CTTATCGCTA ATAATCTGAA      240

ATATTTAATT TTAGATTAAT AATATATTCT GAGATTTAAT ATTTTTAATA AAATAAATAA      300

TTATTCCCTA AATAATATTA ATAACTATAC CATATATATC TAATATTTAA ATAATCATAC      360

TAACATATGT TTCGTAGAAA ACCAGCTATT TGCAAATCAG ATTTGACTTT CTCTACTTAC      420

CATTATTCAT CAGATAATAT TGCTACATTA ACCTGTTCAA TCGTTTTTAT ATTTTATTAT      480

ATTTTAAATA TAATAAATAT ATATTTAAT CATTTGATAA TAGTAAGATC ATCTGCTTTC       540

GGTTTAATTA ATATTAACTA AATTTAATTT ATTTTAATTA ATTTTACATN GTTAAANATT      600

TAAATTAATT TTAAAACCAN TTTTATTTTN AAATTTTGNC AAATTAATAC TGGGGGNCCC      660

CTTTCCAAGG GGCCTNNNTN NATTTTTTNA AAAAAATAAA AAAGGGCNNN ANAAACCTTT      720

TAAAANTTCC CCNGGGCCCC NNAANANTNA AANATTTNAC CCNAAAGGTC CCN             773

(2) INFORMATION FOR SEQ ID NO:386:

(i) SEQUENCE CHARACTERISTICS:
        (A) LENGTH: 798 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
```

(A) ORGANISM: PAG1292UP (xi) SEQUENCE DESCRIPTION: SEQ ID NO:386:

```
GATCCAGTTA CTTAGTAGAA TGATAAAATT AATAAATATT ATTTATTAAT ATTTGGTTAA      60

CAATAAAATT CAATAATTTA TTTAAATAAT GATTAAATAA TCTCAATATA AAATTATTAA     120

TATAATGAGA TATATATTTT TAAAAAGAAT ATATAATTAA ATAATCCCAA CCAAAATTTG     180

TGCCAGCAGC TGCGGTAAGA CAAAGGGGGT TAGCGTTAAT CGTAATGGCT TAAAGGGTTC     240

GTAGAATGAT TATTTAAAAT AATAATTAGA ATTAATAAAA ATAATTTAAG AATTATTCAA     300

GTAAAGATGA ATAATAATT  ATATGAATAA GACTTATAAA GTGAAAATTT AAATTATATA     360

TTAATTGACA TTGAGGAACG AAGGCTAAAG TAGCAAATCG GATTCGATAC CCGAGTAGTT     420

TTAGCAGTAA ACAATGAATA CCTATTTATT TTTTATTAAT TAAAGAATAA ATTAAATGAA     480

AATTAAAGTA TTCCGCCTGA TGACTACGTT TGCAATAATA AAAATCAAAA CAATAGACGG     540

TTCCGACTTA AGCAGTGGAA CATGTTTTTT AATTCGATAA CCNCCCANAA ACCTTACCAN     600

TTTTNGAATA TTTAATTATA ATAATTTNTA ATTATTACGG NGTGCATATT NTCTTCCCTC     660

CGGCCGGCNA GTTTTTNAAT TATCNTNAAC GAACAAACNC CCATTTTTTT TTTNANAAAA     720

ATTATTTATT TTTTGAATAT TNAAAAAAAA TAAANATCCT TTNTCCTTTT TAATGGNNGA     780

GTNTTTTTTT TTNTTCNN                                                   798
```

(2) INFORMATION FOR SEQ ID NO:387:

(i) SEQUENCE CHARACTERISTICS:
        (A) LENGTH: 762 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1293RP (xi) SEQUENCE DESCRIPTION: SEQ ID NO:387:

```
GATCACCGAG CAGCTGGTTG GCCTCGGCAT AAGCGCGCTT GGTCTCTGCC CACTGTTCTC      60

CAAGACCAAG CTGCTGTGCC TGGAACAACA GGTTTGTGAG CTGACCACCA GGAATTTCAT     120

GTTTGTACAC CTCTGGGTCG GGGCCCTTGA GGTCCGCTTC GAAGCATGAG TACAACAGTC     180

TCATCTCCGC CCAGTATGCG TCTAGTTCGA TCGCATGATC GGGGTCTACA CCCGTCGCGA     240

TATCGCCACC CAATGAGGCC TGCAAAGCCG TAATGGAGGG CTGGGACGTT AAGCCAGACA     300

TCGAGTTGGT GGCGACGTCC ACAACATCGG CGCCAGAGAT GGCGCATTGG ACCATTGATG     360

CGACACCTGT GCCTGCAGAA TCATGTGTAT GCACATGAAT TGGGAGGTCT GGATACTTTG     420

CCCTGATCGA GCCAATCAGT AGCTTTGCTG CACCGGGCTT CATGGTGCCG GCCATATCTT     480

TAATACCCAA GATATGTGTG CCCCATGGCA ACAATCTTTT CAGTCAATCC AGTAGTAATC     540

AAGGTTGTAC TTCTTGCCTG CTGTAGCATA TCACCTGAGT TACAGATAGT GCTCAACCAC     600

CCTCCCGCTT TCTTCACGGG TNNAAACCCA CTTCACTGTT CTAGTCNTCA CCCNTCNAAN     660

CTCTGAAATN TCANNCATCC CCTTGCTGTT TGACAAATGT CATCCCNTTT CCGCNAAAGA     720

ATTAACACCC GTGGCCCCAA CNCCCTGAAN GATTTTGCCC NG                        762
```

(2) INFORMATION FOR SEQ ID NO:388:

(i) SEQUENCE CHARACTERISTICS:
        (A) LENGTH: 805 base pairs (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1293UP (xi) SEQUENCE DESCRIPTION: SEQ ID NO:388:

```
GATCTTACAT CTGACAACAA TACGCTGGCG GCAGATGAGC TGCATTGATG GAAATTTTAA        60

CACAGCTCGG GCAACCAGCT ACACGGGATA TATAAACTCA ATGCACGCCG CTCTTTACTG       120

ACACAGTCCA TCAGCATCAG CACCACCCCC AAAAATGAAG ACTACACACA TCCTATCCCT       180

AGCAACACTT GCCGCCTGCG CACCTGTTCA GCCCGCACCT GTTCAGCCCA CGGACCTCGC       240

CGCAGCGGCA AACGTCCCCG AGAAAGCTGT TCTCGGCTTC TTCCAACTGT ACAATGTGGG       300

CGATGTGGAG CTGCTCCCAG TGGACGACGG CGCACACTCC GGGATCCTTT TCGTGAACCG       360

CACACTAGCG GACGTGGACT ACTCCTCCGA GCATGTGGTT CAAAAATGGT TCCGTCTGTC       420

TCTCCACCAT GGGCAAAGTA TGTAAGGCCG GACCAGAGAC AGTTTGCGTT GAGATATGTA       480

AGTTTACTTG GTGTCCTACA CCATGCATTA TGACACGGGC TTACGTACCT GCTTCTATAA       540

GCTAGTTTAA ATGTTTTCTA TGCGTATTAT ATGGTTTACC CGCGCCGATA GTTCGCAGAG       600

GCTGCTGTNT TAAGGCCNAA CTTTATTCCT AANANGGTGG ATTACCCGGT NGAAANAATG       660

AATCTGAATT GGCGAAATTC CCGCTGGNCT ATTANCTCCC CNNCCCGTCC NAATAAATGG       720

AANATGGTGG GGTTTAATAC AAAANGGNCC GNTGCCGGCA ATGNACTGGA TTAATTTCAA       780

AAACCTCCAA NTACCCCCAA NTGGN                                            805
```

(2) INFORMATION FOR SEQ ID NO:389:

(i) SEQUENCE CHARACTERISTICS:
        (A) LENGTH: 764 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1294RP (xi) SEQUENCE DESCRIPTION: SEQ ID NO:389:

```
GATCCGGAAT GTCGCTCAAG CTCCGCTGCT TTCGGCTGGC CTCGCTGTTC TCTGTGGAAT        60

CGTTTCTGGT GGTCTCCTTC TCCCATGTTG ACCTTGGGTT CAGCGTCTTC AGCTGGTACA       120

CCTCGAGAAG CTTCGAGTTA TCGAATGCAA ATGGGTTTAG CATCTCGACC ATATTCGCTG       180

CGCCACCTGC CTGCCCCTTT GGCCTTACAT CGGGAGTCCA ACTTCAACGT AATGCTATAG       240

AAAACGCCAT TGGCCTCGCC GTCTTATCAC GTGACTGTTC ATTCAGCTCG ACAGCTACTC       300

GACTAGCACT GCTGCTGCTT TAACTGGGCT ATACACTTTA TATCGTTACA TTACTTTCTC       360

CGTGGTCCGC GGATGGGTGG TGGTGGCTTG TGTGCAGACT CACTCTTGAA CAGAGGAGCG       420

TTCTTAAACA TGTCTGGTAC GACAAAGAAC CTTACGTGCG AGCCTCCGCA CGAATACATG       480

GTCCATATGT GTCACCTGGC CGTTCCGTGC CGTCGCTGTC ACGTCTCTTA GCTGGCAGTC       540

ATGTTGTCCT CGCTGCCCAC CAACTTGCCC CGATAGTTTC GCCGGTCGTT ACTCCAGCAN       600

ACCGTGTNGC TTNGGCTTCC TTCACACTTA CAGGAATCCG GAANTGCCAG ATCNTACTTT       660

TTGGTTTGGC CGTTTCCNTT CCTGACANAA ANTGGTTTAT ATTTTGCCGG AAAAGNTTTA       720
```

```
ATTTTACATT TTCNAAACAA CATANGTTGC NTTTTTACNN AACC              764
```

(2) INFORMATION FOR SEQ ID NO:390:

(i) SEQUENCE CHARACTERISTICS:
        (A) LENGTH: 800 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1294UP (xi) SEQUENCE DESCRIPTION: SEQ ID NO:390:

```
GATCTGGAAC TCCAAGTTCC TGATGTCCTG CTTACGCTTC TCTCGCTGCT CATGAATCGA   60
CTGCTGCTTC CACCGAATGA ACGACCGCTT GTCCACATTA GGATGTACCT CGATGTCCGA  120
GTCATCCGAG ATTTCTATCT TGTCCCACTT TGAGTAATCG ATTGCCATTG CACTACCTTG  180
TTTCGTTCTG GCTTCACTAC TGTTGTCCTT AGATCTTCTG GATCCACCAA TAACTGATAT  240
CAAAGATTCA TATATGCAAA CGTCCAACTA AATAATGTTA CACATAAGGA AGGACCAAGG  300
CAACGCCTGC CCAGTTCTAG CAACTTCTGT GTGTCACTCT CAACGATAGA AGTCTGGTCT  360
CGAGATGTTG AGACCGTACT CGGCCACAGC GCTGCTGAGG TCGTTGACGG TCAAGGTGAC  420
CTTGTTCGCA TTGGTCTTTT CGTTTTGTTG GTGCTGCTGC TGGCTGATCT GCTGTGTGCC  480
GGGCTGCTGC TGACCGAGCA TCAGTTGTCG GGCGCGGGCC TGGCCGTTGT TGGAGTTATG  540
GACGCGAATG AGGAGCGGAT ACGGAATACT CGTAGGCGTT CGGCCGCNAT GTCGCTAACG  600
AACTCTGGTT GCCAACGCGA AGAAGGCCTT GACCCGANAT CNGTGCACNC CGAACCGTCC  660
TGGTCANTTA TTATCCATCA CACNTCGGGA AAAGGGGGG GGTTCCTCCT AAGTCNAAAA  720
CNCTTGANGT CTGTCCTTGC GGTGAATCGG ATTTCCAAAA CTTCTTTNCT NGGGTTTGCC  780
CCNGCGGCCC CCNGGGGNGA                                              800
```

(2) INFORMATION FOR SEQ ID NO:391:

(i) SEQUENCE CHARACTERISTICS:
        (A) LENGTH: 796 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1295RP (xi) SEQUENCE DESCRIPTION: SEQ ID NO:391:

```
GATCTTTCCT TCAAATTGGG ACGAGGTGCT TAAGTCATCC TGATCCTGCA CAATCACGTC   60
CATATTGGCG GAGATCAGTG CCGGTTTGGC ACCAGAATCG CTGCCCGGCC AGGTGACTAG  120
CAATCCGAGC TCGTTGACAG TTTCCACCTT TAGCTTACAC CAAACCAGAG GAAAGTCCCG  180
CGACAGCTGC TCGTGCAACC GTTTGAACTG CTTGTATGTC TCCGTGTCGG ACTTCACCGC  240
TGTGCAGCAG TCCGCTGCAT CCACCACCCA TGCCGAGGGG ATCTGCACTG CACGCTGTAG  300
CTTCTCGACA GTGAGATTGC TGAGCGTCGA GTTGTGCAGA ATTTGCTGGA GGTGGTCTCC  360
AAAGCCCCCC TGAGGTTTGG ACACGTCCCA GCACGATGGC AGTGACGCCC CAGTCACCTC  420
CGAAGAAACA ACAGCACTCC GCGCTGTCTG AGCAGAAAAG CAGGCCAGCA ACGCCAGCGC  480
CGTTGCAAAG GATATCGGTT GCCCCAAAGG CCAAGCTGCA AACATCATTC TGGTGGTCAG  540
```

```
CGACTGCTTT TCCCACGAGA TCCGTGGGGA CCATGCGCCA GATGGCGCCC TTAATATAAG      600

CCCCTCCTCG CCAGCATGAC TTCTGCCAAC TCCCGAACAT TCTAAATGGC CAGCTGCTGC      660

TTTGATGGTA CCTNCCGCNG CTNGCGCCAA AATTNATATA CCATAATCCC CNTCCTAAAT      720

ATNCTTACAT ACCACGCCCC AAAGCGCTCC CCGNAGCNCN CCCGAGCCCC CACTTTCNCC      780

NNAAGNANCC GNTGNG                                                     796
```

(2) INFORMATION FOR SEQ ID NO:392:

(i) SEQUENCE CHARACTERISTICS:
        (A) LENGTH: 808 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1295UP (xi) SEQUENCE DESCRIPTION: SEQ ID NO:392:

```
GATCAACTTC AGTTCTGCGC GTTTGTCGCA TGGAGGCCCG CCAACGGCAG ATAGCTTCTC       60

AACTGTGGCG GTACCCTGCA CGGGCTCCAC GACCGCTGTG CAGTGGAAAC GCTCGTAATT      120

GTTCTTGGTG TAGTGCTTGA AGTACTCCAA AGACCACACG AATGCGAGGC CTGCGAGGAT      180

ATAGAAAACC AGCGTCCCGT ACCTACCGAT TGCCATGGTT GAAGCAAGGA TTCCACTGCC      240

GTAAGTACTC AATTATTGAG TGCTAGCAAG CTGATGTTGA TTGTGTGATA TCAACGGTAA      300

TCGGTCGTTA AGGAACCTTT TCAAGAAACG CAAAAGAAAT GCGTGCGTAG GTCGAGCAGG      360

TGACAACCTC ATATTACTCA TAACAGTTAT CTATCTAAGA AGCGGCACTA TCGATATACT      420

ATCAGCTTCG TATACACATA TATATCGGAG GTTTATAATC GCAAGTTAGC TATAATTGCC      480

ATCGAGGTGT AATACATCGA AGATTGTCTA CGAAACTACT CTGTCACCAA CACATCAGCG      540

TATGAACAAT AACAGCAATA TTATGACAGG CAATTGCATA AAAGTATTCA AAGAGGGTTA      600

AACAGTTAAA TTCCGTAAAG GTTCAGNGAN TATTCCCTGA CACCCCATAC CGAATCGCCC      660

TGCACCAATT GTTCACATGT TCANAGATTC TCCGGGACTT CATATGNACC ATGTTGCCGC      720

CCCNAACTCN CATTATGTNA ATGCTTGTNT TCCTGACTCC CCCGCTTGTC CCAAATGCCA      780

TCCCAGGGTG ANAGGTGCTC GTGATCTC                                        808
```

(2) INFORMATION FOR SEQ ID NO:393:

(i) SEQUENCE CHARACTERISTICS:
        (A) LENGTH: 779 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1296RP (xi) SEQUENCE DESCRIPTION: SEQ ID NO:393:

```
GATCCATTGT GCGTTTGGAG GTCACGCCAC GGACGTGGAC ATGTACGTGA TGAGCTTCGA       60

CGGGCAGCTC TTCATTCGTG CGGCACGCAA GAAGCTTGAG TTCCCGACGT CTCCGCGGGA      120

GAGTTGGGCG TACTTGCGT ATTACAGCGG ATACAAATTC GAGCGCATGG CGCTCCTGGA       180

CCGTCCGGTG GCCGAAACTC CGCGCGAGGT TCTGGAGAGC CGCGGCAAAC AGGTCGTCCG      240
```

```
CAACGGTCCG CAATACAGGA CTGTGATGAG AACCGGCGTC GGGGAGCACA AGCTGGTGCT      300

CGGAGCTGAG ATCGACGGCA TCATTGACTT CCGCGAGCCT ACGGGCGACA ACCTGAAGCA      360

CTACGTGGAG CTGAAGGTGT GTCAGAAGAA CCGGAACTTC TCAGAGAAAC TTTTCTCTTC      420

TTGGCTGCAA TGCTTTCTGG TGGGCATAAA CAGGGTTATT ATTGGATTCC GGGATGAGAA      480

ATTCCTCCTG AAGAGCGTCG AGGAGTTCAG TACGTCAGAG ATCCCACACC TGTTTAAAGG      540

GCACGGAATA TTCCATGTAT GTTGTGGACG CCATAGATTG TATGGTGCTC CTTACAAATT      600

GCTATNTGAC TCCCCCGGGC CCTGAAAANA NTTCAACTGT TACAGTCTCC TGCNNCATGG      660

TGCTTACTTT TGCCCCACTG CCCAACAAAA ACCCCCAATG GGANAAATTN TCCCTNGTTG      720

GTCCCCAATT GGNGNGNCCC CCANATANAA AATTCCGNAT TATTCCCTTG TTTCCTTAN      779

(2) INFORMATION FOR SEQ ID NO:394:

(i) SEQUENCE CHARACTERISTICS:
        (A) LENGTH: 815 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
         (A) ORGANISM: PAG1296UP (xi) SEQUENCE DESCRIPTION: SEQ ID NO:394:

GATCGTACGG TTCGCTGCTG CGGTTTACCG ATATGGATCG GTTGTTTGCA GTTGGCGAGA       60

GCACGGTGGT CGGTGTCTCT GGCGACGTCT CGGACATGCA ATACCTACAG CGCCTGCTCC      120

AGGACATGGA GATCGAGAAC AACTACGACA ACAGCCACGC AGACGGCGCG GAAGCGCTCA      180

AGCCGAGCTA TATTTTTGAG TACCTTGCCT CGCTCATGTA CCAGCGCCGC TCAAAGCTGA      240

ACCCGCTCTG GAACGCCATC ATCGTCGCCG GCGTCGAGGA CGGCCAGGCC TTCCTGCGTT      300

ATGTGGACCT CAAGGGCGTC AAGTACTCCG CCCCAAGCTT GGCTACTGGC TTTGGCGCCC      360

ATATGGCCAT TCCTCTCATG CGTAAAGTCG CAGATGCCGA AAAAGACTCG CCGGCGTCGA      420

CCTCTCAATT GCGCGAGCGA CTATCCTGGA GTCCATGAAG GTGTTATTCT ACCGCGATGC      480

GCGTAGTTCC CGTCGCTTCT CGCTTGCCAT CATCGACAAT GATGCCGGTG TTCAGCATGG      540

AGCAACTGGA AGTGGAAAAC ATGACCTGGG GTTTCGCCCA AGGATATTCC GGGCTATGGC      600

NCCCAAATNT TTTGAATTAC CNGGGCCGCA ACGCCGCACC CTGTTTACTA TCTTGTTCGC      660

GGNTGTCNCC CAACCGCTNG GNTATCCCAT ACNTTCAAAA NGCNTAATCA TCTGCCCTGA      720

ACCCCNCTGT TTTNGTNGAN ACCTTCNCCC CTTTTCCNGA TTTCCCGGAT TGNCAAAAAC      780

CCTTTGAAAA AACATTNCCC NTTGGNAAAT CGATG                                 815

(2) INFORMATION FOR SEQ ID NO:395:

(i) SEQUENCE CHARACTERISTICS:
        (A) LENGTH: 766 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
         (A) ORGANISM: PAG1297RP (xi) SEQUENCE DESCRIPTION: SEQ ID NO:395:

GATCTCCTCG ACGCTGGTGA CCTTGCCGGC CTTCACAAGA CGGCCCAACT TGGTCACTGG       60
```

```
CACCCAGCCC TTCTCCTCGA CCTCTCTTCT GCCCTTGCGG CCCTGACGGC CCTTGTTTCT    120

GGCGCCGAAG CCGCCTCTTC TTTGTTCTGG AGCTGACATC TTGCTATCGT CGGAATGGAA    180

CACGGAAAGC TGGGGGAGTA ACTTTCGATC GACGCTGCTG ATGTAGTTAC GATACAGCTC    240

CGGCCGCGCG CTTGCGTGCT GAAAACCTGC CCACGGTCTG CGTCACCAGA AAGGAGGTCT    300

GGGTGCTACC GCTGTTTCCG GCCTCACGAC GTGTCTGGGT TTCACACTGA AACCCACACA    360

TCAGACAAAC GCAGTCCCGG ACGGCTCGAA AGCAAAACCC GCGTGAAGGA GCAACGCGGA    420

AGCTGCGGCG TCCGTGCCGA ATCTCGTCAA AAACAGGGGT CACAAAGGGA TTGGCGCTGG    480

CGCCAGGACT GCTACGGGGG CATTGGCCCC GGCGGCAGCC CCGAGCAATG GAGCAACCCC    540

CTTCGCGAGG TACGGCTCAC ACTGCGGTAT AAAGGCGGGC AGAGCGGTGG AAGCAGACAG    600

TGACACACAG GAGAGGACAG ATGTCGGACN NCAAAATGAC AATCCTATCA ANAGGNGCGT    660

CGGGGCCAAA CTATCAANAG NTTCGAAGTT CCAAACTNGC CAGATCAAAA GGCCCCAAAG    720

GGAAAAAACT TCCCCCCCAC GACCCTTTGN CATTTTTAAC CGCCNG                  766

(2) INFORMATION FOR SEQ ID NO:396:

(i) SEQUENCE CHARACTERISTICS:
        (A) LENGTH: 795 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1297UP (xi) SEQUENCE DESCRIPTION: SEQ ID NO:396:

GATCCAAAAA CAATGAACTG TTTACAATGT GGAAGCCGTG ACACAAGTGA ATGGCGCTCA     60

GGACCGCTAG GAAGGAAGTC TATGTGCAAT GCATGCGGTA TCTGGTACAT GAAATTAAAG    120

CAGCGGTTTG GGGAGGAGGA TGCTGCGGTG ATTATGGAAT ACCGGAGATT AACTAATAGG    180

CACGATGATC GCAGGGTGCC CAAGAAATTT GAGGTCCCAT TGCCTGAGGT CGAAAAAGTG    240

AAGAGAGCCA TAAGAGCTCG TGTTGTGGAG TATTTGAATG ATGTTGAAAT CCCGGTTAAA    300

ACGAGGAGGC GGGCGTTATT ACATAAAGGC AAGCCGGGCA GTGCGTTAAA AACAGAGATG    360

AAAACCCCTG CCGCATGAAG CACTGGAAGG ATGAAACCAG TTTGTCAGCC GGAAGGACAA    420

TACCGGCGGG TAGGAAGGTA GAGACTATGC TGTGGCATGT AAGGAACGTA CTTTTATTTA    480

TCTAACATAA CTAGGGTTCT TTTGACCTGN TACCTTTGTA TTATCCTTTG AANAACTGAA    540

CCCCCNCCTT TTAAAAANTT TTCNNNTTGN AAATAAATCC CCTTTAAAGA ACCCCCCCCN    600

NAANCAAACC CTTNTNCCCT TNGCCCAAAC CCACCCAGAA ATTTTCCCNC CNTTNCCGAN    660

ACANCNGTTN CGAGATTCCC CCNTTTNCGC CNAAAAAANC TCCCCCCGAN TNTNTNCCAN    720

AGNGCCCTTT TNCNCTCCCC NCCNANAATC CCCAAATTAG AAGGGGTNTT CNCCCNNGCT    780

CCCCGAGATC CAAAA                                                   795

(2) INFORMATION FOR SEQ ID NO:397:

(i) SEQUENCE CHARACTERISTICS:
        (A) LENGTH: 601 base pairs
        (B) TYPE: nucleic acid
        (C) STRANDEDNESS: single
        (D) TOPOLOGY: linear (ii) MOLECULE TYPE: DNA (genomic)
```

```
    (vi) ORIGINAL SOURCE:
         (A) ORGANISM: PAG1298UP (xi) SEQUENCE DESCRIPTION: SEQ ID NO:397:

GATCTTCCTA CTGGACTGGC TGCTAGACGA TAAACGATTA TGGCTACGTC AACTGCGGAA      60

CTCGTGGGCC GCCTTGGAGG AAGCGCAGGT GGCACCCTTT CCAGGTGGCG CTGTGGTGGT     120

GGTCCTCAAC CCGAGTCACG TGACACAACT GGAGCGAAAC ACGATGGTTT GGAACTCCCG     180

CCGTCTGGAC CTGGTACACC AGACACTGCG AGCTGCATGC CTCAACACCG GCTCGGCGCT     240

AGTTACACTT GATCCTAATA CTGCGCGCGA AGACGTCATG CACATATGTG CGCTGCTTGC     300

GGGGCTGCCT ACATCCCGTC CCGTCGCGAT GCTAAGCCTG CAAAGTCTAT TCATCCCCCA     360

CGGTGCAGAT TCCATCGGCA AGATCTGCAC CATCGCGCCC GAGTTCCCTG TTTGCTACGG     420

TGTTCGACAA CGATTTTGTT GAGCTCGACA TTCGAGGCCG CAATTGCTCC AGAACTTACT     480

CCAAGAACAC TTGTGCCATC TGACCACCCC ATGGCTAACA GACCTACCAA CCCCCCTTCN     540

GAAGCAACCG CTTGNATTTC NATCTCCNAG GTCNCTCCCT ACCTATACCG CTCTTGTGAN     600

A                                                                    601

(2) INFORMATION FOR SEQ ID NO:398:

(i) SEQUENCE CHARACTERISTICS:
        (A) LENGTH: 753 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
         (A) ORGANISM: PAG1299RP (xi) SEQUENCE DESCRIPTION: SEQ ID NO:398:

GATCTCCCAC ATTGAGACGG TAGCAGCCCA CATATTGCGC TTGAACGCCA TTAAACGGCG      60

CCATTGCTCC CATAGAGCTT TCAGATTTCC TGTTAGGCTC CAACTCAACG TCATACTGGA     120

GTTTAAATCG AGTGGGTGCT GTTGATATCC AACTTGGAGG CGTTCTTTTT GTCCTCGTAT     180

CGCTTGAATA GCCGCCCAGG TCCCGTGGCG AAAATCCATA TATATCCATA TTGGCCACCC     240

AGCTTGTCAC ACATAGAGGC AATAGTGCCA GTAATGCCTC GAGCCGAAAC CATGCAGCTC     300

CCCGCGGAGG AGGCGCCCCG CAGCGTCGCG TTCCATAGAC GGCAAGCCCG GCGAGTGCGG     360

CGCACGCTCA GCACGCAGTT CCTCCCTGTC ACGGTATGTC CCCAGCCGGC GGTGCGCACA     420

CCCAGATACT AACACAGCAC AGACGCTGTA TCAGCTGATT GTCCAACCGG CGTACTATTT     480

CACGTTTCTG GCGAATGTGC TAGTGCACGC GTTCGCGCAG GGCGCGGCAG TCGCCATAGC     540

AGTGGCGTTC TGGATGTCGA CGGTGGGCCT GGGCATTCCC GCCCGCGCTG CCATTTGTGC     600

TGCCGCACGC GGTGTGGCAG GGTTGTCTGG TGGGTGCGGT GTGCTGCCGC AACTACCACC     660

TGGAGTACAT GGAGACCTAC ATTGCGAGCC TGCTCGTGAC GGGAGAGGGG GAGTCCTGTT     720

TTCNCCGATG GGCTCCCGGC GGTGGGCGGT TCC                                 753

(2) INFORMATION FOR SEQ ID NO:399:

(i) SEQUENCE CHARACTERISTICS:
        (A) LENGTH: 751 base pairs
        (B) TYPE: nucleic acid
        (C) STRANDEDNESS: single
        (D) TOPOLOGY: linear
```

(ii) MOLECULE TYPE: DNA (genomic)

(vi) ORIGINAL SOURCE:
    (A) ORGANISM: PAG1299UP (xi) SEQUENCE DESCRIPTION: SEQ ID NO:399:

| | | | | | |
|---|---|---|---|---|---|
| ACGCTTTTGG | TTTTCGGCGT | GATGGTGGGT | GGTGGTATAG | ACGATGTGAT | CTCCGGCTGC | 60 |
| AATTGTAAGC | CTTCTCCTCC | GGAGATATCC | CGCACGGAGA | AGTCGTCTAA | ATTTAACATT | 120 |
| ACGTTCATGT | AATCACAGGG | CACCTTTTCA | AAGACACAGA | CGATCATGCC | ATTCTTACGC | 180 |
| TTTGCCCACA | TGGACGCCCA | AATGAATTTC | TGTGTATGCG | AGGATGCTGA | CGATGCAGCT | 240 |
| GAAGCAGGAG | ACGACAGCGA | TGTGACGCCT | GGTTGTATGA | CGCCTACTAT | TTCACCTGTG | 300 |
| AATACTTGTT | CTTGGCCCTC | TGTAGACATA | ATCTTGTTAA | GGACAAAGCT | CCTGCTGTCG | 360 |
| GTGTGTATCA | GGTCAAGTAA | AGTAAGCGCC | TTAAATGCCA | ATTTGGAGAT | ACCGAAGATT | 420 |
| AAGCATGCCN | AATCGTTAGC | CGCCCTAAAC | TGCCATGGGT | GATGCTGGGA | ACAGGTAAAT | 480 |
| ATGGCCTGAG | GTGCTGTGTA | CTTACCTGAT | ATAAAAGTAT | GCAGTATGCG | GGGCGCTTCG | 540 |
| TACGTTCTGC | TGTAGTCTAT | CGGATCCTGG | ATAGATGTTA | GTTCATCGGT | AAATGGTTGG | 600 |
| AGATAATTTT | CGTCCTGCGA | GGCCTGTATA | GTAGTTTCTG | TGTTGAATAT | TCATGAAATG | 660 |
| GTTGGGCTAA | GCTTTCAAGC | AGCTGCTTCT | TTAGTTCTTG | CTCATTACTG | ACTTTCTTCG | 720 |
| CAGGATCTAC | GCCATCCGCG | TTGGTGCTGA | C | | | 751 |

(2) INFORMATION FOR SEQ ID NO:400:

(i) SEQUENCE CHARACTERISTICS:
        (A) LENGTH: 777 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1300RP (xi) SEQUENCE DESCRIPTION: SEQ ID NO:400:

| | | | | | |
|---|---|---|---|---|---|
| GATCTCTCTG | CGCGGTGCAC | AAATGACGCA | GAAACAGGCA | TTCACGGAAT | TGAAGAGGCC | 60 |
| TCAACTGCCG | CCGATCGCTA | CAGGCGCAGT | GGGACGACAT | CCTTTCTTTG | GTGCGTATGA | 120 |
| GGATACCTAA | ATAAGCACAT | ACAAAACGTT | AAATATGCAT | AAGGAGATAT | ATGCGAAAGT | 180 |
| TAAAGTGTTT | TTAGTGGCCC | TCGGCCACAG | TTGCGTGTTT | CAGCGATAAT | GGGAGACCAG | 240 |
| CCCGGCACGT | GATCAGATAC | GGTTGTAGTG | GCCATACGGG | CTTGCGGACG | AATCTACGGG | 300 |
| GTATGGTGCC | TGACGCTGCG | CCGGCGGCGT | CTTACGCTGA | GTTCCCCACA | GCCGTTCCTC | 360 |
| GTACTGGTTG | ACGTCTTCGT | CGTGCACAGC | CCCTCGTTTG | CCGTAGCGGC | CCCGACTGCC | 420 |
| CCCCGCCTTC | TGCGCCTCGA | GATCGTAAGA | CTCGTTGCTG | CTGCTCGAAA | AGCCCTTCTT | 480 |
| GCGCTCGCTG | TAGTACTCGT | CCTTGCCGTA | GTACCGCGCG | GCCTCCGGCG | TTACTACGGG | 540 |
| CTGGTATACC | ACTTGTGGCG | CGGAGCATAT | ACTTGTGCAC | GCTGCTTCTC | CTCGCGCCCG | 600 |
| CCGCTGGCGG | TGCCGTCTAT | AGCAGCAGCA | CGGCCAGCAC | AAGAGTCGCA | GATTCCNCTC | 660 |
| ACCCCCCCAT | AAACNCCGAN | TTACACCCCC | TATCCNATAC | CCAATTGACG | CTACNCATCC | 720 |
| CNCTATACCC | CATCNTTGCA | CNCGGTACCT | ACTTTTCCCN | AANTGACCCC | CACNTNC | 777 |

(2) INFORMATION FOR SEQ ID NO:401:

(i) SEQUENCE CHARACTERISTICS:

(A) LENGTH: 812 base pairs
(B) TYPE: nucleic acid
(C) STRANDEDNESS: single
(D) TOPOLOGY: linear (ii) MOLECULE TYPE: DNA (genomic)

(vi) ORIGINAL SOURCE:
(A) ORGANISM: PAG1300UP (xi) SEQUENCE DESCRIPTION: SEQ ID NO:401:

```
GATCGAGGAG TTTCCACTGG AGGTGGCGCG CTACATGACG CTGCTGCGCG AGATAGACGC        60

CAAGTGCGTG CACACGGTGC CGGAGCTTAA CGCGCAGATA GGGCGCTTCC TGGCTGGCTC       120

GCGGCAGCCG GGAAGCCCGC AGCTGCAGAC CATCAACCGG CTCTTCCAGG ACCTGATGCC       180

GTCGCTGGAG GAGAAGATGC ACGTCTCGTC CATTGCGTTC GAGACGCTCG ACCGGCTCGT       240

CGCGCGCGTC GAGCTCGCGT ACGAGGTCGC GCTCAAGAAC CAGGAGATCC CCGACAAGCT       300

GCGCCTGGGC AACGACAACC ACCCTGCCAT GCACCTGCAC CACGAGCTTA TGAAGAAGAT       360

CGAGTCCAAG CAGCAGAGCA AGTCGCAGCA GGCGCTGCGC TCCGAGTCCC GCCGCGAGGC       420

GATGGCGGCC AAGAAAATGC ACGTGGACCC GCCGGCGCCG CGCCTGCTCT CAAAGGCCCC       480

CGCTCCCGNT GGCCCCCGGG CGCCCCTTGG CCGCCAAGCG CCCGCGCAAA CTTTCCCCCC       540

CGCCCGCCGC GCNAGCGCAA GAAGCCCAGG AACAANTACT CCGCCCGCCC CCNAAACAAC       600

AATTTCGGGA AGGCCTCTTA CTGCTACTGC AACCATTCNC CCTACGGGAA AATGTCGGTT       660

GCGAANGGGA AAAATGCCNC TCNATGGTCC CTCCCCTGGA TCACTCNAAA CCTTACCGAN       720

GGGAAATGTT CTGCAANAAT GCAAAAAAAC CCTACATACA GNCCGGTTAC TANNTCCCCC       780

CCCNCCTNCN TGCCTTNCAA TGGGTTCCNC NT                                    812
```

(2) INFORMATION FOR SEQ ID NO:402:

(i) SEQUENCE CHARACTERISTICS:
(A) LENGTH: 786 base pairs
(B) TYPE: nucleic acid
(C) STRANDEDNESS: single
(D) TOPOLOGY: linear (ii) MOLECULE TYPE: DNA (genomic)

(vi) ORIGINAL SOURCE:
(A) ORGANISM: PAG1301RP (xi) SEQUENCE DESCRIPTION: SEQ ID NO:402:

```
GATCCGCGAG ATTCATCGTG GACCCGCCAC AGGCAATTAC TATAACAACA TCCTGCGGTG        60

TTAAAGGACC TAACTCACGC TCAAGTATTT CAGGATGATA TCCTAGATGA AGAGCTGCGC       120

CACACGCTGG TTCGGTTACA ATATTGCTCT CTTCCGCAAA ATTTAAACAT GTCTGTACTA       180

CAGCGAGCTG GTCAAGCACA ACAGATTTTG TCCTGTATTT TTGGGCGTAA CTCAGAGTAA       240

GATCCGTCAC GAAAGATGTG CATAAAGAAG TAGCAACGCT TTTAGGATTC ATCGAAACGT       300

TCCTGCCCAG CAGCAAAGAT CTGTGCAAAA CCTCGCACCC CTCTGTTTCC ACTGCTACAA       360

CAGGGATAGA GTCTGCCAAA CCATGTTTCT CCAGCCCATA TACAATCCCA TTATATAACC       420

CCCCGCCACC TACGCTGCAG ACGATACCTT TCACGCTCTC CAATTGCACG CCTTGGAGAT       480

GCAGTGCTTC TACTACTTCA TCTACCATTG TTGCATGCCC TTCCCAGATG AGTGGTTGTC       540

GAATGGATGT GCATATATCG GAGCGACTTT TTCTAATTCA CATTCCCCAT CAACTCCGGA       600

CCGTAAGTTA TCATCGCTCT CTTTCAATAC ACTTCCCATT GANATCACAT CNGCCCCCGT       660

TGANCGGTTC CGCTCTACCT CCNCCGCCAA TTNTTTCNGN CCTACNCGGG CAGGTNTCCT       720
```

```
NTTNNCGTGA CCCGTGGTGC TGCACCCNTG CNTGCNCCGA CTCCCNAAAC NTTTGGNTGC    780

GNGAAG                                                                786

(2) INFORMATION FOR SEQ ID NO:403:

(i) SEQUENCE CHARACTERISTICS:
        (A) LENGTH: 782 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1301UP (xi) SEQUENCE DESCRIPTION: SEQ ID NO:403:

GATCATCTGC GTGCGATACT GGCAAAAAAT GAGAGACAGC ATGATGAAAA TATAGTTAAT     60

AAGATATTGC ATGATATAAG CACAGGCGGG TTTCGTCGAA GAGGAAAGGG TGCACTTGAT    120

CTGGAAATGA GTGAAAATGA AGACCAAGAG TTACAACAGT TTAGACAGAA AGACGAGAA    180

CTTTTGAAAC AAAAGATATT GGAAAATGGT GATACTAGCA AGCTCGTATC TAACCCCAAG    240

TCATACGCCT TTTTTCAGAC GATGGTGGAC GATGTTACTG AAGCATCATT TGGAAATACA    300

TTTGATGCCA ATATAGATGA AAAAACAGAT CCATCTGCTG CAGGTCGGAA AATTGTCATA    360

TCAGAACAAT TTGTAAAGGA AACCCTGTCA TTCTTGTCGA GCAAGAGTGG CGACTCAGAA    420

ATCCCTGCAG AAACTAAATC TATTTCATCC AGCACAGTTG AACGTGAAGA AATTCAAGAC    480

TTCATACATT GAAGCAAAAT AGTAACATTA ACATTTGAAA GGAGTCTAGA CTTCCTGCTC    540

AGATGGCTGA CTCAGCAGTG AGATAGAGGT GATTACNGCT TTCTTTANAT ANATTCCNCN    600

GCCGCNAAAT TTTTATATGA ACTACTTCAC AANANTTTTA AAGTTGGCCC CAGGGGGGCN    660

ATCTTAAGGG AATAAANATN GCGTCCAAGC CCAATACTTT TNTNGGAAAN NGTNGNGGTC    720

CCCCCNAAAG GATTTAAATT CNACCAACTT NTCCNCCANN ACCCCCCCCC TTNTTTTCNG    780

NG                                                                  782

(2) INFORMATION FOR SEQ ID NO:404:

(i) SEQUENCE CHARACTERISTICS:
        (A) LENGTH: 785 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1302RP (xi) SEQUENCE DESCRIPTION: SEQ ID NO:404:

GATCGAAGAG CTTCTCGCTG ACTTCGAACG GCACAAGGTA CCCAAGCTCC TGTAAAGAGT     60

TATGAAACTC CGTAGCGGAA AGCGTGAACG AACCGTTAAT ATCATTGTCC ACATATATCA    120

TGCGCCACTT CTTCACGCGC TTGTATAACG AAGTAAACTC AGACAAGTTT ACGGTACCAA    180

AGCGCGTCGC GCCAAACAGG CTAATTAGCG CGTCCACCGA ACTCATGCAG AACTGCGAAT    240

TGTCATCATT CTGTAGCAGA TGCTGTAGCT CCTCTGCTGT GAGACGCTCC ATCTTCCGGA    300

CGTCGTGATT CATGAATAAT TTCTTTGCTG TTATAGCATC GGGGTCTTCA TTAGGAACGG    360

TGGCGGGCTT GGCTTGGGTA TGGTTCGGGT GAGGCTGCTG AGCTGGCTGC GGCCTTGCAG    420
```

```
GCAAATTATA GCTCTGTGCG CTCGGTGGTA TTGGCTTCCC GTGGCCCGGC AGGCCAGGCG      480

GGCCTGTGGA ACGCGAGGAG GATTTCCCTG AAGCTGCCCA ACGCCATGCG CAGGCAACTA      540

CTATGTGTAC AAAAATTGCC GTGNTCCTGC AAAACCTTTG GTCTGTACAG AACCCANCCC      600

ATGGCCCATG GAACGGNNTG GNTTTTTGCC CCAAATTAAN CCCTGGANAA NTGGGNAATT      660

TTTGGCCATN TTTTCCNATT AAAAANGGNG GGGTNNAAGT GCNAGGGNGC CCATNTNGGG      720

GGGNAAANTC CGCGCCTTTT TNTTTTNCAT AANGGNCCNC NTTGANNNCC GCCCCNNNNC      780

CCCAC                                                                 785

(2) INFORMATION FOR SEQ ID NO:405:

(i) SEQUENCE CHARACTERISTICS:
        (A) LENGTH: 803 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1302UP (xi) SEQUENCE DESCRIPTION: SEQ ID NO:405:

GATCAACAAC ATACTTCTAA AGACATCAAT ATACGCCCGC ATGTCTCCGG ATGAAAAACA       60

TGAATTGGTT GAGAGGTTGC AGTCCATTGG ATACCAGGTT GGCTTCTGCG GCGATGGTGC      120

GAATGACTGT GGTGCCCTTA AAGCGGCCGA CATTGGTATA TCTCTATCCG AAGCGGAGGC      180

ATCTGTTGCT GCGCCATTTA CATCCCGCTT GTTTGAAATC AGCTGTGTTT TGGACGTAAT      240

GAAAGAAGGC CGTGCCGCGT TGGTCACGTC CTTCGCCTGT TTCCAATACA TGAGCTTATA      300

TTCTGCCACA CAGTTTGTTA CAATATTGAT CTTGTACAGC CGTGGATCTA ACTTAGGGGA      360

CTTCCAGTTT TTGTACATCG ACCTCTTCTT GATCGTGCCG CTAGCGGTGT TCATGTCCTG      420

GTCGAAGCCC TATGAAGTAT TGGCCAAAAA GCGGCCAACG CCAATTTGGT TTCTCCGAAG      480

ATATTGATTC CTTTGCTCGT GCACATCGTG ATTTGTTCGT GTTTCAGCTT GTCCCGTGGC      540

TCGCAGTCCA GCATATGAAG TGGTACCGGC AGCCAGTCGT CGCGACGACG AACATGTTGC      600

TTCCCANGAN NACNCAACCC TTTCTTNGTC TCCACTTCCA TAAACCCTGG TCCCAATCNT      660

GCTTCCGGTN GTCCNCCCCN NCCNCNAACC NAANTTCGAA AATTTTGGTT TATGGCANTT      720

CCCCCTTCCC TGNCCCTCCC GGTGGANNAT TTCCCCCCCC CGAAACAACT TGGCNNCTTT      780

CNCTCCCGAA GTTNCTCCAT NTC                                             803

(2) INFORMATION FOR SEQ ID NO:406:

(i) SEQUENCE CHARACTERISTICS:
        (A) LENGTH: 773 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1303RP (xi) SEQUENCE DESCRIPTION: SEQ ID NO:406:

GATCAGGTCG CCTTTATGGC CATACTTGTT GGACTCATAG TATATCTCGG CGACTGCACT       60

ATTACTGGAC TGCTTGTCAA GATCTTGCGC ACCCATCACG CCGACTATAC TACATGTCTC      120

GTTGGGCTTT GCGTCGCTAA CCGGCAGAAA AGATACCTTT ATACTTTATA ATACCAGTGA      180
```

```
GGCGGCCATA CCACGTAATC CATCTTTGTT GCCAAATAAT TACAATATTC CTTTTAGCTA      240

CTGGAATTGG GCTTATCCTT ACAGTGTCAC ATCAATTTTC TATCGTAATT CGCTATCTCC      300

GCTCGCAATC ACTGCACTGC AAACCATTAT CGTCCTGATA GATAAAGATT ATAGGGTAGC      360

GATCAATAGT ACCGGTAAAG GCGTGACCAA TATTCTGCTG GGCGTGTTTA GATGGCCGAG      420

ACGCTAGAAT GTGGGAGCAT GCTGGTTTAG CGATATGGGA AGCCTTCACT AGAACCCTGC      480

CACTAGTAGA GCACAGAACG TTGAGACTTA CAGCTGTTCG AAGTATAAGT TGTAAATTTC      540

CAAGGGTGGC AAGTAATATC AATTGATTCN AAATGACTTA CCCCTACGTT GAACTGCTTA      600

CTTTAANTTG GGTCGGGCCC ATCAAGCCCT GACACTCTTG ACTTTCCCCC ATGAAAAAAC      660

TCCCGGGTGG GTTCNANCCC CATTNCCCAA ATACANTCCA TANGTCCTGG CCCTTAACCA      720

CTTGNTCCGG AGGATTTTTT TNCCAANAAG ANNNNACTTT TNAATTTNGC CAC             773
```

(2) INFORMATION FOR SEQ ID NO:407:

(i) SEQUENCE CHARACTERISTICS:
        (A) LENGTH: 807 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1303UP (xi) SEQUENCE DESCRIPTION: SEQ ID NO:407:

```
GATCTAAGTC CTCTCCCCCA AGCGGTGACG CAAGTGGACT GTCTGTCGCT CGGTTAATAA       60

AGTTATCGAG ATGGTCCACA AGCTCATCCA CCTCGGATAT ATGTCGCCTG TGAGTAGGCG      120

CAGAGTCACG TGCGGTGTCG AACGTGACAT CAGACTTTCG GGACGGGCTT CCTAGCTCAG      180

GGTCCAAATC AATGGACACC TTTTCCAGCT CTGCCAGCGA GCGCAAGAAC TTTTTGTCTA      240

ATATATAGTC GTTAGTTTGG ACCACGCAAG AAACCGGTCG TTCGTGGCCT CCTGACGCTC      300

TCCCGTGTAC CTCGGCTGCG CTGATGACTT TGCCAGTGGA TGGGTCAGCG CTCTTGGAGA      360

TGACTTGATC GGGCGACTGC CACTTTGCCA ATCGAGGATC GTCTACAGTT GTAAACGGGC      420

GCACTTTCTT TTCTGTAGGT GCTCGCGCTG CTGGTACTGG ACTCCTCCTG GACTGTCTGG      480

GCCTTACTGG ACCTGCTGCT GCTGCTGTTA CTGGAACCGA AAAAGAAAAA TGACTTCCCC      540

TCTTTTCATA TGACATTCCC NGTTGTGANA CNTACTATTG GCCCCNAGAA AATAANTTAG      600

GGNGAAATAC ACTCNCTATG TTTGCCTATA TTTCCCNTAC CATATACAGC CTGCTGATTC      660

CCAGTTTTAN AANTTTAAGT GCGTTACCTT ATATGTTGAA NCCCGTTATA TGAAGAATAA      720

CCCCCCAANT TTGCAANGAA CCCCGNAGGC ATTGNCTCCT TCANCANNAT TAAGNACATT      780

TTGTCCTTTC AAGNACTTTA TAAGNCC                                          807
```

(2) INFORMATION FOR SEQ ID NO:408:

(i) SEQUENCE CHARACTERISTICS:
        (A) LENGTH: 778 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1304RP (xi) SEQUENCE DESCRIPTION: SEQ ID NO:408:

```
GATCAATGAG CGTGGCTACT ACTGATGCTT ACTGCAGTGC TGTGTCAATA TTACATATCG      60
GTGGATAGCT AGATAAAAAT GCTATACATA TATCTGTCGC CATTGTGCCA ATCTATATCT     120
ATTTGTGCCG ACGTTGCGGA CCAGTAGGAG GTTGTGTTCC GCGCGGTGCG CAAATTCCGC     180
TGAGATCAAG CCATTGCCTG TGCTCTTGCC CTCCCCTAGA TGGTAGGTGC CACTTGTAAT     240
AAAACCGACG AGATCTTGTA CGCGCGGCAG AGGCTGATCG GCGTCATGGG TCCGTTTGCC     300
CGCAGCATTG TATTTCCTGG AAGCGACTGC CTGCCAATGG GCGAGATGCT TGACAGGCAC     360
TGCATACAAG CGGGCATTGT CCCTGAAATG GCCGCGTTCG AGGGCTGTAC AGACAACGGC     420
GATCACGGGA AGTTGGGTGG TCACAACAGC CAGTTGGACG GGCAAGCCTG TGTCCATAGG     480
AGGTTTTGGA AAAAGAGACA ACTGGCTTAT TGTNAAGGTC CCGGGGANCT NCNAAAANAA     540
TCTTGGTGGC AATACCAACN CCTAAGGATT TCANCGNGTT CCCCAACTTN ATTNTNTTTN     600
TNGCNCCCGT TTCAAATTCA TATNGGTGGG TTGCNGGCGN GAATNTTCTT TTCNATTTCA     660
AACCAACGNG GGGGNGCCNT TTGAGATTTG GANACNCCCC TCNAAANANA NTTGTCCCCT     720
TTCNCCNNAA AACAAAATTN NGGAGGAAGA GGTTTTANCC CNNTATATNC CCCCNCCN      778
```

(2) INFORMATION FOR SEQ ID NO:409:

(i) SEQUENCE CHARACTERISTICS:
  (A) LENGTH: 792 base pairs
  (B) TYPE: nucleic acid
  (C) STRANDEDNESS: single
  (D) TOPOLOGY: linear (ii) MOLECULE TYPE: DNA (genomic)

(vi) ORIGINAL SOURCE:
  (A) ORGANISM: PAG1305RP (xi) SEQUENCE DESCRIPTION: SEQ ID NO:409:

```
GATCAATGTA TCCATTATAC CCAGCTTTCG CAGCGACATA ATATATTGAC TTGATTTTAA      60
AGCGGTAGAA CTTTACGGGG CTAGGGCCGC TAGGTATCCA AGGTTTAGCA TCAGGATGCA     120
CGTCTGCAAA GCACTTCTGC AAGGCTGGAA TGGGCTGGAG TACTTCGAGC TCACCCGCGA     180
AGTTTGCACG AGGTGCTTTC ATGGGGTCTT CAATCGATAT AGACGCAACT GAGAAAGACA     240
CGTTGTTATT GTTTTTAGCG TTTACTTGTT GTAGTGTCGT GTCGACCATC AAAAAAATGG     300
GCTGGCCGTC ATGCTCTACT CCCTCACATC TGTCGGGAGA AATATAGTAC ATTCTAATAC     360
CATATGGAGT ACCGTTTTGA TTGATTGTTG TCAACTGGAA AGAACTTTCG TCTTTAATTA     420
ATTTCCTGAG TTGCACTGCT GCTTGTTGTT CCTCCTGCGA CGCTTGCGCG AAAGCCGAAG     480
TAACTAGTGC CAAAAAACAT GTAACTAATG AAAAAATCGA CTTCATTGTT GCTATTGAGT     540
GCCAATAGGC GAGACTCATC CATATGTNAT GAAAGCGTTT ATANATCNTT GTTNTGGCTT     600
GAAAGAATTA TTATACTTTT CCNGGCGGTT ACATTATCTT CCAACCAAAT TGTTTCCTTT     660
TNGANAGGNA ATCCCCAAAA TTTTTNAAAT TAATTNGTCN NCGCANCGGT TTTTTCCCCG     720
GNGGGGAAAA NAAAGCNGGN NACCCGCCAA ANCCGAATAA AGGATTTCCA TNAAAACCCA     780
ATTNTCCNAA AC                                                         792
```

(2) INFORMATION FOR SEQ ID NO:410:

(i) SEQUENCE CHARACTERISTICS:
  (A) LENGTH: 812 base pairs
  (B) TYPE: nucleic acid
  (C) STRANDEDNESS: single (D) TOPOLOGY: linear (ii) MOLECULE TYPE: DNA (genomic)

(vi) ORIGINAL SOURCE:
         (A) ORGANISM: PAG1305UP (xi) SEQUENCE DESCRIPTION: SEQ ID NO:410:

```
GATCCCCAAG AAGAACATCA AGATCCACGG GTTCTAGGCG CTATGTACTT TGTGTAACTC      60
AATACATATC CTCCTCCTCC TCCACCACCA CCACCTCCTC CTCCACGTCC CTCTGCGCCT     120
CCGCATAGTA CCTCACACAG TACGGGAACA GCTCCTCGCT GAACAGCCTG GCCAGCTCGT     180
CGCCGTTGGC AAACTCCTCG CCCGGCCGCT CGCCTGTCCA CCGGAACCAC GCAAAGAACG     240
TCCCGTCGTA GCGCTTCGGC CACTCCATCT CCACCGCCGC GCTCCGCACT TCCCCGTCCT     300
CCCCCACCGT GAACTGCTTC CTCACGCTCT GCGCCCGCAG CCTGCCCTCC ACCTCCCCGA     360
ACTCCACCGT GATCGCAAAG TCCCACGCCC CGGCCCCCGC CCACTCCACC TCCACCCGCC     420
GGATCGCCTC CACGTACCGC CAGTCCGCCG CCCGCACGTA GTTCGCGAAA ATCCCCGTGC     480
TGCGTCAGCA CGAATCCCCC AGAACCCCGC GATCCCCTCG ATCGCCTTGC TGCGCCGCGC     540
GTATACCGGC CCCAGCGCCG CTGCCGCTCC ACCTCCAGCG CCCGGTCCTC CCGCTCCCGC     600
NCCGCTNGGA NTCCGGAAGN GCTCCACGNG CGGGCCTGCN CCCGTTAGTC CCCTGCCCGC     660
CATTTAGGNG GGGNNGCGCC TTNNTTGTTT NNNGAAGGNA GNGTCCCGNT TCCNGGGCCG     720
GNTNNGTTTT TGGGNNGGAG NACGGNGTTT TTGGANCNCC CANTCNCGGA NTCCTGGNGC     780
GAANGGNNGT TNCCNCCNNN TTGAGCCCCC CT                                  812
```

(2) INFORMATION FOR SEQ ID NO:411:

(i) SEQUENCE CHARACTERISTICS:
         (A) LENGTH: 778 base pairs
         (B) TYPE: nucleic acid
         (C) STRANDEDNESS: single
         (D) TOPOLOGY: linear (ii) MOLECULE TYPE: DNA (genomic)

(vi) ORIGINAL SOURCE:
         (A) ORGANISM: PAG1306RP (xi) SEQUENCE DESCRIPTION: SEQ ID NO:411:

```
GATCTGATAT TGGGTAATTG CAACCTTTGC ACCGCTTTGA AAAGTACTTT AGGAAGTGGT      60
ATTTGCAATA TAGTTCATCA TTGTAGTGGA AGCACGAGGA TACCTTACAC TTGGTACCGC     120
AAACCGTGCA GCAGAAGTGT TCCTCGTCAT ATAGCTTACC AAATGTATTG TAATACACGC     180
CGCTCAGTGG CTTATTGCAC ACATAACACA ATAGCTTGTT CCGCGTGAAA TAATCCTGCT     240
GGCATAGCAG TACCACTTCA GACGTATCCG GGAGCTCATA AGGGAAGAAC TTCGGGCGAC     300
ACAAAGCTCC ACAATCGTGA CAAACCAGAC AGTTTTCATG GTAGTAATCA CCAAGCGCCT     360
TCAGGGAGTT CTGCGTGATA ACCCCCTTGC ATTGTTTACA GATTTGGCC GTTTTTTGAG     420
ATGAGGTGGC GGTTTATGCT CCGCAGACGT TCGCATTACT TGCTCCGACG CACTGTGTCT     480
ATGGTTGATA TGGTCACTAT ACGTCCAGCA ATAGCTGTGC TTCTGTATAT TAGTCATGAA     540
AAACAGTAGC ACTCCCTATC TTACCCTTGC NGATCGTATT GGTACCGCCA AATNGTTAAC     600
CCATTTTCCA AGAACATTCN ACCNCTTCCG TTTTTGCCCA AAGAGAGGTN TGCTATATTT     660
GCCAACAAAA GCCCAACTGA AATTNAANAA ACCCTTTTTT CCCCCTTTTN TTTCTCCCGA     720
GGAACCTTTT CGGCAANTTT CNCCCTAAAT TGTNTGGGGG NTGANANCCN AGAAAANC      778
```

(2) INFORMATION FOR SEQ ID NO:412:

(i) SEQUENCE CHARACTERISTICS:
        (A) LENGTH: 806 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1306UP (xi) SEQUENCE DESCRIPTION: SEQ ID NO:412:

```
GATCATTTCA GTGGATGGCG ACATTCATAT GGATATCAGT TCGACTTTTG TTTCCAGTCT      60
TATTCCACTG ATTTTCAGGT TACAAGAATT GGGAAGGGGT CTCCATTTTG TAGGGACGAA     120
CAATTGTAAG ATGTCTCAGG AATTCAAGAC TCAGGTTGAA ACGAAAACTA TTATCTTATC     180
CCTTCCTGTA GGGGACGATA CCCTACAGAT GATTATCCAA CCCATCTCTT ACGAACTGTC     240
ACTACATACA GTTTTCACTG ATTTTATTTC CATATCTAAG GTACAAAGCT CGGAAACTAG     300
GGATATCGCA ATTATTCGGG AAATTAAAAT TGGATATCAA ACAGCCAATT TTCAAGTGAA     360
ATCGTACAAC TTGAAATTGT CGGAGACGCT GCTAACATCA AAGCTACGGG GGAGTTGTTC     420
TCGAGCCGTT GAACTTTATT GTTCTGATAG TGACATCAAG TTGCTTTTTG ACGAATGTCC     480
CCCCCCCCGA AATGAATACC CGCNATNTNC ATTCCTNAAC CGAATTCCCA AAACCCNTTN     540
TNAANTAATC CCTTTAAAAA TTNATTTTTC CCNAAGNTTT ACNCCCGCNA ATTTTTTTCC     600
CAAATGGGCC CCTTANATGA AAAAANACTN CACCCCCCCN NCGAAAANAA ATTTCNCTTT     660
GGAAANTNNN AAACGAATTA TTCNCNCCCT TTNTCCCCCC CCCGAAANAC ANTNTTTCCT     720
CCCCCCCTTT AGGAAAANTG TTTTCCCCNA TTTNANANTN TCCNCCCNCC CCCNNAACNA     780
AAATNTTAAA NCACCCCNTN TTNTNG                                          806
```

(2) INFORMATION FOR SEQ ID NO:413:

(i) SEQUENCE CHARACTERISTICS:
        (A) LENGTH: 753 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1307RP (xi) SEQUENCE DESCRIPTION: SEQ ID NO:413:

```
GATCCCTTTA TCTCATATTA TAGTCCATAG TACCCCGTGG ATGCCTACCA CACAGAGGTC      60
CCTCTTCTGG ACCTGAGACC TAGATATCTT GCGATATCAT TGAAAATATC GTTCAATTGC     120
TCCTCCGTGA GCCGCTTAAC TTCCGCCTCG ATATCAGCAT CGGGTGTTTC CGAGATGTGG     180
AAGTTCTCAA CTTTGCCCTC CAAAAACTCC TCAAACTTCT CTTGTTCTCT CAGTGTCGGT     240
GGCAACAACT CATAAAATTT CGCAAGCTTA TACAGCTTCA CATTGTCTAG ACTTTCGAAG     300
TCGCCCAACG TGAGAGGGAA TACGCCGTCC TTCACGTCCG GAATCTCACC GTCCGCGTTC     360
GGCAATGGAG CCAAGAAGTC CTTCTCCTCC GACTTCGTCG AATTCACTAA GCGCCGCACC     420
GACCGCTCTT CCATCGTGTC AAGCTGGCCC TGAAGCTCCC CCACTAGCTG CACTAAGTCC     480
TCATTCGTGG CGAAATCCGT TGTATCAAAC TTGCCGGCGC CCCCTTTAGG AAGGAACTTT     540
TCGTCTAAGT TGCCATGTC ATGCTTTTGC TTGCTGACCT GTAGCTCCAG CACCGACTGT     600
```

```
CCTGTCTTGG TGATTAGGAC GCTCTGCCGT TTAACTAGCG CCTGTAGCTC CTCAACTGTT    660

TCTTCAATGC CTCGTCTGAC ATAACGCACT TCAAATTTAG TAGAACGCTT CTGAATATTC    720

CTACACCAAA CGCCGCAGAG AGAATGGTAA AGA                                 753
```

(2) INFORMATION FOR SEQ ID NO:414:

(i) SEQUENCE CHARACTERISTICS:
        (A) LENGTH: 811 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1307UP (xi) SEQUENCE DESCRIPTION: SEQ ID NO:414:

```
GATCCACCAA AGGGTATTTT ACTATATGGG CCTCCGGGGA CAGGTAAGAC ACTTTGTGCC     60

CGTGCCGTGG CCAACAGGAC CGATGCTACA TTTATCAGAG TCATTGGCTC CGAATTAGTA    120

CAGAAGTACG TCGGTGAAGG TGCTAGAATG GTTAGAGAGT TGTTTGAAAT GGCCAGAACA    180

AAAAAGGCAT GTATTATTTT CTTCGACGAA GTGGACGCAA TTGGCGGTGC TCGTTTTGAC    240

GATGGAGCGG GTGGTGACAA TGAGGTCCAA AGAACTATGT TGGAACTCAT TACGCAACTA    300

GACGGATTCG ATCCACGTGG TAATATCAAG GTGATGTTTG CTACCAATAG GCCGAACACC    360

TTAGACCCAG CATTGTTGAG ACCCGGTAGA ATAGACCGTA AGGTTAGAAT TCTCTCTTCC    420

GGATTTGGAA GGCCGTGCCA ATATTTTCCC GCATTCACAC AAAGTCCATG AGTGTTGAGC    480

GTGGTATTAG ATGGAATTGA TTCCCAGTTG GTGTCCAACT CCACCGGCGC TGACTANATC    540

TNGTTTGGCC CGAGGCTGGC ATTTTTGCAA TCCAATTCCC GACCCAGGTT ACCTACAGAA    600

ANGACTTCCT TAAACCNGTG GATAGGTCCT CCACGGCTAT AAAAATTCAC NCCCCTTCCC    660

CGTTTTNTGC AAACCCNAAN CNNTCNCCCC CCTTGNGGCG TTTTTTTAAA GGNTTATTTA    720

TCCCAAANNG TNTTCCTTTT ACNATACTAN TGTTCCAATT TCTATNAAAT NTTNTCCCCC    780

CCGTGAAANC CTNCCCCGTT NGCACCCCTA T                                   811
```

(2) INFORMATION FOR SEQ ID NO:415:

(i) SEQUENCE CHARACTERISTICS:
        (A) LENGTH: 791 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1308RP (xi) SEQUENCE DESCRIPTION: SEQ ID NO:415:

```
GATCTGTCTG CTGGTACACC GATGAACGAA ATAATTGTGA CCGTCACGGA CTTCGAGAAT     60

GCACTTCGGA AGATAAAGCC TTCGGTCAGC GATAAAGATA GAATGAAATA CAATAAGCTA    120

AACAAAAAAA TGGGCTGGAA TGACGAAGCA GGCGTGCAAG TCGAAGAAGA AGCATAGAGC    180

AGCAAGTTAA ATAGGCACAG CTATGTACAA ATAACCAATT TCAACTTGTT CAAAGTCGTC    240

CGCGTCTTAC AGATTTCACA CATGGAGACG GCGGAATTTA CTTGTTATAA TGCCCTCTCC    300

TGCGAACGTT TTTTCGAATC TTCCAGACAT ATTCCGTATT TCTTCCTTTT CGAGAAAGAA    360
```

```
ACATATGGTA TTTCTCTATT CCTGTAACTT GAGCTTAGCA ATTTCTGTGG ATATAGTTCC     420

GCAAAGAGGT AGATCCGTGG CACCTCTGAC AAGAACGAAG TTATTCTTCA GAGAATGAAC     480

ACGGCCGGAT ACATGCCCAG AATGTATATG TTCATAAACT TGCGCTCCAA CATCAATGGA     540

ATGGATAAGA GCCAGCGTAA CAAGTCCCAT ACTAGTATAG TCCAGCGGAA TGCTTCAACA     600

TTGGAATACC CGCACATGTC ATATCCGGAG CTCTTTGATT GATATAACAA CCCCCNCCCT     660

NTTNTGCCNC AAAATTCCCC CTGATGGTAC CCCTAANGGT TCTTGCAAAA GCGGAACCCT     720

ATCCCCTGGG AGCCNAAACC CTTTACGAGN AACNNATTAT GGCCCGGTNT TTNACGTCCC     780

TNNCCTGTCN N                                                         791

(2) INFORMATION FOR SEQ ID NO:416:

(i) SEQUENCE CHARACTERISTICS:
        (A) LENGTH: 817 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
         (A) ORGANISM: PAG1308UP (xi) SEQUENCE DESCRIPTION: SEQ ID NO:416:

GATCACGTGG GCCGTAAGTC GCAGAGAAAC TTGCAACTGA ACTGCCACTG GGGCTCATGC      60

ACCACCAAGA CGGTTAAGCG CGACCATATC ACCTCCCACC TGCGTGTGCA TGTTCCCCTG     120

AAACCCTTCA GCTGCTCCAC ATGCAGCCGT AAGTTTAAAC GCCCGCAAGA CTTGAAGAAA     180

CACCTGAAAG TGCACATGGA GGACACCATG AAAGAGCGTT CGCGTGCGGC GCCGGGCTCG     240

CGTGGTGTTC GCAAGACAGG CGTTAACAAG GGCTCTGCGC TACAAGAGAA GGCGCGCACG     300

TTACCCAACC TGACTGTGGA GAGCTTTGTC AGCCAGGAGA TGCAAAATTA CTACCCCTAC     360

TACAAAAGCA GACAGCACCT AGACGAAACA CTGTCGCACA TTATTCTCCC GCCCCCCAGC     420

CGCTCTAGGT TGGTACTTTG GCGTCCGAAC CGCCAAGCTA CACACGGAAA GCAGTGTCTT     480

CTTCACGACG CTGTCGCAGG ACATGTCTCG TCGCTTGCCT TCTCTTGCTC CTTGCAACAG     540

CCCCCGGCCT GCGGTTAAGA TGGTAATGCT TCCCCCGCCC CAGAACAGCA ATATGCACGC     600

CGTGCCCTAG ATATCCCAGC GATGCCCGGA CTCCCTCCCT TTGGTGACTC TCCNGGANCG     660

AATCCCANCC TTTGCCCGAG ANACACTTCC GACCCNCTCC ATATCCCTGC TCTANCTGCC     720

CNCCTCACCG CTTTCTCATA AAATCGCATT GTTGCCGCAN CCTATCCTCA TCAAGCCCCC     780

TGATANACCC TGNAAAAGAC TGANTCCCCC CCAAACC                              817

(2) INFORMATION FOR SEQ ID NO:417:

(i) SEQUENCE CHARACTERISTICS:
        (A) LENGTH: 795 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
         (A) ORGANISM: PAG1309RP (xi) SEQUENCE DESCRIPTION: SEQ ID NO:417:

GATCAATTAT TAGAGGCAAT ATCAAAGAAG TCCCATATTA CTGAGGAGAA CAGGGAACAG      60

CCTGGAGAAA GAATGCCGCA GACGTACAGA TACACGCTGG AAAATCAGCT TGCCCAGTGA     120
```

```
GTGCTCGAAC AGCCGATAAG AGTATTGACA GTGGTAGCGT GCAAGAGTCA ACGACAAAAT      180

GAACAGAACA TCATACTTCG GGCGCGAGAT GTTGAAGCTC GACTTGGTCC GCCCGTGGAC      240

CTTTTTTGAA GAAGTTGCGC CAGGATCCCA CGGCGGCCTT GCGCGACGCA GCAGGGACTG      300

GTCTCCAGCG CGCCAGCAGC AGGGAGCTTG TCACCACGCT CACAGAGCTC ATCGCCATAC      360

CCGCGGCGGC AGCCATGGGC GGCAATTGTA TGCCCCACGG AATGAGGACG CCCATGCTGA      420

CTTGGGAGCC ATGAGAGAAT TGTACAGGAC TGCCCAGAAA ATGTTCAGCT TGACGCGGTT      480

AACGTGGCGC GCGCGAGATT CGATGGCATA CAGAATGCGG TTTAGCGGCG GCGCCCGAGG      540

AATGTCCCAA ACCACGATTC CCGCGCGTTC CGCACGAAGT CACTGTTGCC GGACAGCGAA      600

ATACCGAGTT CNCTTTCACA ATTGCCACAA TTTCTTTGAN GCCGTCTCCC GATAAGGCAC      660

ATATTNGTTN TTTTTGCCGC ACTGCCGCAA NGTNCCACTT GCCCCCCTGG TACTTTCCCT      720

GAACATTTTG ACGGATNCCC AANCGTGCAA ACTCTCCCNC CCCGTGTTNN CCCATACCAT      780

CCANTTTTTG GCCNC                                                      795

(2) INFORMATION FOR SEQ ID NO:418:

(i) SEQUENCE CHARACTERISTICS:
        (A) LENGTH: 797 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1309UP (xi) SEQUENCE DESCRIPTION: SEQ ID NO:418:

GATCAGGACC GCGGTCNCTG ATTCGATTGG CCATGAGTTT AAGTATGACC CAGAGGGCCG       60

CCCTGGTGTA TCTAATCTGA TTAACATCGT AGCTGGCATC CAGAAGAAGA CTATCGCGGC      120

GGTGGAGGCA GATATTGCTG GATTAAGGA CCACGCAACT TTTAAAAACT ATGTTACAGA       180

CATCCTAGTA GCTGAGCTGA GGGGGCCCAG AGAGGAGTTT GCCCGCTATA TGAATGATAA      240

ATCATACATA TACGAGGTTG AGCGCAATGG GGCTGAGCGA GCAGGTGCCA TAGCTGCTAA      300

AACCCTGGCA GAAGTCAGAG CGATAATGGG TTATTAGTTA TATTCAGATT CCAACTTTGT      360

CTATAGACTA GCAATAATTA TAAAGATACA TCAAGAAGAC CAAGAGCAGA TGCGTAACTG      420

GTTGTCACTC TTTGGACCTG CCGGATATCA GCACATGCAA CCAATATCTG CTTCAGCAGT      480

CCTCCCGCTT CTCGTTAGCT ATTGTGCCAC CTTGTATTCT CCATCCGTTA TACAGCCAGC      540

TCAGCACATC ATCCATCTAT TTTGAGCCCA TTCTGCTAGG CTGATGCAAT AGACTTCCAT      600

ATTTGGTAAT CATTGTCCCN TTATTTTTTA GGNTACCACC ATCTNTTTTC CNATGAAAAN      660

CGTGACAATC CNCCNGTTTT TCNACCCTCC CTCCATNAAA TNTCTTTCAT CGTGGGTTTC      720

GGATCAANCC CTNNGGNTCN TCCCCTNCGC CTCCATCCNG GNATTTACAC CCNTTNTTTT      780

CTCCCCCCTC ATNAANC                                                    797

(2) INFORMATION FOR SEQ ID NO:419:

(i) SEQUENCE CHARACTERISTICS:
        (A) LENGTH: 830 base pairs
        (B) TYPE: nucleic acid
        (C) STRANDEDNESS: single
        (D) TOPOLOGY: linear (ii) MOLECULE TYPE: DNA (genomic)
```

(vi) ORIGINAL SOURCE:
    (A) ORGANISM: PAG1310UP (xi) SEQUENCE DESCRIPTION: SEQ ID NO:419:

```
GATCCAAAAA AATTTTAATA CTGAAAAAGA AATGCCACAA CTAAGCTCAG CTACCTTAAA        60

GAATCGGGAC CAAAGCTGTA AGGCAACAGC TCTTCCAATG TTCGCTGCAG AACCTTGGAC       120

CCGTCGGCGT TCATCATAAT CACCGTGAGC TTCTTCGGAT CAACGAACTC GCGCAGGACC       180

TGCCGGCAAA TCCCACACGG GGTCACGACG TCGGACGAGT CCCCACTCAA TGCGATGCAG       240

ACCCAATTCG TATGCCCGGC TGTTACCGCC TTTACGACCG CTGTGCGTTC CGCGCAAATA       300

CCGGCTGGGT AACTGGCATT CTCGACGTTA GCGCCGACAA TATACTCGCC TGACGCTGTC       360

AAGATGCAGC AGCCCACGCG GAACTTGGAG TTATGGGCTG TACGAGAGCT CCTTCGCGGC       420

TAGTGCTCGA GCAACCGCGC CCTGATATGG CTCTCCCTGT GTGCTTGGCA TTGGCTTCCG       480

TGGCGTCGCC TCCTAGGTAT TGGGGTTCCC CTAAGTACTG GCTGCGAACC CTTATGTTTT       540

TTGCAGGGGA ACGAATTGCG CCCGAACCGG GTGAATCCCG GAACATNCA ANTACCCNCT        600

TTTGGNTNNC GGGNAAAGGG NNANNTTCCN NNCCTTNGCNC CGGCNGGAAN AAANAATGTT      660

AACCATGTGG ANTAAACCTT TAANATGANN CCTATGGCCN GTTTAACTTT ATCCCCCCNC       720

CCCCCCTTTT AAANGTNNNA NCCCCGCCNT TNTACCTCTA NNCCNGCGGG GGNGCNNANC       780

CCACAAATNN TNTGTTGNGC GCNGNGCGTN NCTAATATGG AGCCTNGGGN                  830
```

(2) INFORMATION FOR SEQ ID NO:420:

(i) SEQUENCE CHARACTERISTICS:
       (A) LENGTH: 799 base pairs
       (B) TYPE: nucleic acid
       (C) STRANDEDNESS: single
       (D) TOPOLOGY: linear (ii) MOLECULE TYPE: DNA (genomic)

(vi) ORIGINAL SOURCE:
       (A) ORGANISM: PAG1311RP (xi) SEQUENCE DESCRIPTION: SEQ ID NO:420:

```
GATCTTATCG TTCAGCGTAC CGTCTGCAAG AATCTGAGAC ATAAACTTGC GCTGCGACGA        60

GTTCTTGGTA AATTCTTCGT AGTACTGTGC GTTGTCCGCT TCCAACGCTT CCTTCCCCCG       120

CTTGTACAGC AGCTCCACCT TTTCGGTGGA GAGCGGCTCT TGCTCGCGAG AAGCCTCCGC       180

GTCTAGCGGC ACCTCGTGCC AGGGCATGTC CGCAGGCACC AGAAGGTTGC CGCTGCGAAC       240

CGAGCGCAGG TCATCGACCA TGCCGCGCGC AGGTTCCTCC CCGGCGGACT CGGCATCGAA       300

CCCCGCATCG GACTCGCCCG CCTCTCCGGC GGACTCGGCG GCATCGCTGT CCTCCTCGGC       360

TTGCTCTTCG GCTTGCTCCT CGGCTTGCTC CTCGGCTTGC TCCTCTGCTT GCTCCTCGGC       420

TTGCTCCTCC AGCGAATCCT CCGGCTCGCT GCTCTCTGCT GCTGCCGCTG CCGCTGCTGC       480

CGCCGGCAGC CCATGTTCGC AGCAGCCCGC TGACGTCGTT CTGCAGCCCG GCATCGCCGT       540

CTCCTTCGTC GCCGCTGAAT GCCTGTTCGC TGAGCTCGTC TGCGTTCGCT CAGCCCTTCC       600

ACAGCGCCAA GTTGTTCTTT CTNAACCCCC CANNGCCAAT NGTTCNCGGG CNTCATCCCC       660

CNTTNTTTCC CTGGTTTCCC CTTTGGTNGN CCCCNGGNAN ACTTTTTCCC TGGCTTNCNN       720

CAATTCCTTT TTCATTTGGT TTTCCCCCCA AAATTTTNAN ANNGGGTTAN CTNNTCANNN       780

NGGCNGNNNA GAGAAACCT                                                    799
```

(2) INFORMATION FOR SEQ ID NO:421:

(i) SEQUENCE CHARACTERISTICS:
        (A) LENGTH: 790 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1311UP (xi) SEQUENCE DESCRIPTION: SEQ ID NO:421:

```
GATCTTCTGA TGCATATTTC CGCTCTCACC TTCGCCGTTA AGTTTTTCCA TGTAGATAGC      60

TCAAAGTCAT CATCCCCGTC ATCTTTTTCA GTGTATAGAT TCTGTGATAC TTCTCCTTCT     120

TCCTCTTCCT CTTCTTCCTC TTCTTCCTCG TCTATATGAT CTTCGCCTGT CAGTTCATTG     180

TCTATTCCAT AATTGGGTTC AACTTTCGGC TTGGGCTCCT TTTGCTGGCT ATGATCTTCC     240

TGGATACGTT TCTGTCCATC TGCCAATCCC GTTTTCTCAT CAGTAGCTTG CGAACCGGGC     300

ACAGTATGGA TTTGTTTTGA GCTAATTGCA TTACTACCGT CACGATCTTC AAGAGGTCCT     360

TTGCCAGCAT GACTTTCCGA AGATTTCGAG CGTTTACCTG CAGGCGCACT CTTACCCCGT     420

TTATCTGCAG GAATGTAGTC CTCATCGTCT TCATCTTCCT GTATCGTCTG TATGCCTCTC     480

CTCACGATGC CGCCCTTACG CTGTCCCTAC ACTCTTCATC ATCCTCCTCC TCATATCTAC     540

CTCTTTTCCA GTCTTCTCCA CTCATACTAT CTCTACCACA TATCAGGATA ACGTATAATG     600

GTGTGACTTT TTTGGATAGC ATCNCTGGCC CTAGGAANGC TNGGGTTCGG AATATAATTT     660

AACATCTTCC CAATCACAAA TTNCTCAGTA ACNGTGGTAA ATTNAAACGN AANTTTTTAA     720

CTTTCCATAC GGTTTANGNC CCATGGCTCT TGAAANCGGA AAAATCCGGG GCCCCCCTTN     780

GAACTTGTTT                                                           790
```

(2) INFORMATION FOR SEQ ID NO:422:

(i) SEQUENCE CHARACTERISTICS:
        (A) LENGTH: 788 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1312RP (xi) SEQUENCE DESCRIPTION: SEQ ID NO:422:

```
GATCATTCTC ACCAGTACAA ATGTATATTT ATATGTAATT GTCTCTCTCT GCTTTTGCCA      60

TATTTTTTTA TTTTTTGTGG TGACAGCGTG CACTGACGCT GACGCGCAAG CCGCAGGCGC     120

GATTCTTCGC AACTTTTCGT CAACGCGCGA CAGACAGTCA GAAAGTAATA GGAAACAATT     180

AAATACGTTG TTATGTTATA TGAAGTTATA CATAAGTGGC TGCCATCAGG TTATATATTG     240

CTTTAAATAA CCCATTCGTC TGGAAACCTC CTCTGTGAAT GCCTCGCTCA AACCGGGATG     300

GTTCTGTTCG ATCTCGGGCA AATATTACTG ATAATTGATC TACAGCGTCT TTTGTCTCTT     360

GAGTCCGTGC TCTATCACGG ACGCGTCGTA ACTGTAGCGG ATAACATGTT TAAAGAAGTT     420

TAGTTCCTTC TGTGAAGGAG CAGCAGCTTT GAGTGCCTTT TCATCATAAT ATTGTTCAAG     480

GTAGGAGAGG AGGTAATGTT TGTCTCTGGG TTCTTTGAAG GGCTGGATAA TAATGACTTG     540

ATTGTGACTC CTGGTGATGG TACATTTAAC ATGCCAATCC CAGTTCCCAA GTTAGATTCT     600
```

| | |
|---|---|
| TACCGGTTTT GTTATACCTT GTTTNATAAG GGTTACTTTG CNCCCCNACT TGCCAAGAAA | 660 |
| TCATCTTATC CCTTTGANAG GTCACCTGTC CCTTAATTGT AAACCTACNC CCTTTACAAT | 720 |
| CTATGCTTAT ACCCNGCCAT TGTCCCTGAA GGATTTTNTT ATTAACCCTG CNCACATCCC | 780 |
| TTGGCTGG | 788 |

(2) INFORMATION FOR SEQ ID NO:423:

(i) SEQUENCE CHARACTERISTICS:
        (A) LENGTH: 769 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1312UP (xi) SEQUENCE DESCRIPTION: SEQ ID NO:423:

| | |
|---|---|
| GATCAGGCAA AGGATTTCTA CTCGTATGTT GGCAAGAACC TGTCACAGAA ATCCGACAGC | 60 |
| AAGTTGCTTC CTCGGAGGAT TCAATTTGAA CTTCAGAGGT TTGACTATTT TCACTCTCTA | 120 |
| CTCCAGTATG TTGTAGGATG TAACGCTCGT GATTTTGCTG TGTCACTTGC GAGGTTTCAA | 180 |
| TCTTCGATCG ACCCTAATAA TAAAAATACA AACATGCACC TCGTGAAGAA GTATCGTTCC | 240 |
| CATTTCTTAC CATTTAACAA GATAAAGAGC CAACAGCGCA TAAGGCTTTC TAAAGTGTCC | 300 |
| AACTATTCTG ACTTGAATGA CTTCTACCAA CTTGCATCAG CTACCTCAGA ACCAAATAAG | 360 |
| CCCCTCAAAG AAGGACTCTT ATGGTCCTAC AGGAATAATG GATGGCATAA ACAGTGGGTG | 420 |
| GTACTACAAG GATCACAGCT CTCAGAATAT TCCGATTGGA AGACGAAAGC TAAGGTGCTC | 480 |
| AGCCGACCGG CCATTAATTT GACGTTTGTG TGTGTTAAAC GTTCGGAGAA AAAGCCTAAC | 540 |
| GGATTTGATA TCATAACTAC CGACGGCGAG GCTCGTTCTT TCCAAGCAGA GTCAGAGGAT | 600 |
| GAAATGAAGC AGTGGCTGTA TGCGCTTCAC TCTGCTGTCG GGATAATAGC CATTGAGGAG | 660 |
| ACAGATGAGA ACAAAGATCC ATTGTCTATT GTCCGTAATG CGGATCCGTC AAATAGTGCA | 720 |
| TGCTGTGACT GTCGGAGCGA TAAGCAAGTG AATGGATATC TCTGAATAT | 769 |

(2) INFORMATION FOR SEQ ID NO:424:

(i) SEQUENCE CHARACTERISTICS:
        (A) LENGTH: 799 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1313RP (xi) SEQUENCE DESCRIPTION: SEQ ID NO:424:

| | |
|---|---|
| GATCGTGTCT TGCTGACTTG CATGTCTAGC TCAGTTCTTT ATTACCCGCC TCATGTTGAA | 60 |
| ATTTTCCAGG AACCATCGCA CCAAATGTAC CGATGATATA GATTACATCT ACCCTTCCGC | 120 |
| AAGCCTGGAA GGAAGCTAGA CCTCTAATCT AGTAGCTTGC CATGTACATC CCGCCATCCG | 180 |
| ACCCGCGAAG ACCAGCCAAG GTGACGGCCG GCCAGCTCTG CGAGCTGTGC CACGCGCGCA | 240 |
| AGGCGCTGGT AAAGCGCCCC AAGAACTTGC AGAAAGTCTG TAAACTGTGC TTCTTCCATG | 300 |
| TATTCGAAAC CGAAATCCAC AATACCATTA TGGAGAACAA GCTATTCCAG CGCGGGGAGC | 360 |
| GGGTGGCAGT TGGCGCGTCC GGTGGGAAAG ACTCCACGGT GCTTGCGTAC ATATTGAAGC | 420 |

```
TGCTCAACGA AAGACACGAC TATGGTCTCG AGATTGTGCT TCCTGAGCAT CGACGAAGGG      480

CATTGTGGCT ACCGAGACGA TTCCGCTAGC TACTGTGAAG CGCAACCCAG AGCAATACGG      540

TTTGCCCCTG AGATTGTGTT CCTACAGGAC CTCTACGAAC TGGACGAATG ACGAATAGTG      600

CCTGCGCCCN GGAATGCNCA ACACTGCNCC TTACTGCGGG TTTTTTCGAC CCAGCGCCTG      660

ATTCCGGGGG GGNAATGCTT GAATCCACCN NTTTGTTAAN GGCCATACCC GAAAAAATGC      720

CNAAAGNGCC CANAAATCCT GGCCGGGAAA TTTGGCNAAT CNAAATAACN CTTTTCCCCA      780

AANAGGTCCC GNTAANNTT                                                   799

(2) INFORMATION FOR SEQ ID NO:425:

(i) SEQUENCE CHARACTERISTICS:
        (A) LENGTH: 819 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1313UP (xi) SEQUENCE DESCRIPTION: SEQ ID NO:425:

GATCAAAAAA GATACGGATG TTATGCTTGT TAAAATATTA TATGCTATAG TACAACGTAT      60

CGCGTCAAAC ATAACGCATG AGGACTATAT TTTTAATTCA CTAACTTCGG CGAAGCATCT      120

CCGGAAGAAA TAGCCTCCTG TATGGGGCTA AGTCCATAGG CGTCGGTTCG GCTCATCTCT      180

GGAGACTTTA AAGAATTAAG TCCGAAGGCT AGGCTCCCAT ACCCCAAAGG CGAGTGGGCA      240

CTTTGTTCGA GAGATCCTTC TGACATAGCC TTTCTTAGTG ACAGTGGCGG AACATGGGCG      300

CGGGAAGGAA TACTTTGTCC GTGCAATGAA CCCTCGGATA AAGGCCTACT TAGCCCGTTT      360

TTGAAAAATG TGACAGTCTT GTTCTTGATA TCTAGCTTGT ACCTCGTTGG AGTGGGTTCC      420

TTTGCAAGAC CAGTGGGTTT TTCGGAAAAG CTTCGCGTCT TCCCGGAATG AATTCTGAGT      480

CCTGGTAGGG AACATCCGAG ACTTCCCAAA AACCNTTTCN CTNTCCATTT TCNAAAAAAT      540

GGAAATCNNC CCGGCCATTA TNGATCTCTT CCCAAATTAC NNCNCCNCCC TCACTTTGNG      600

ACTTGGGNAT ANAGANCCCC NTCNNACCCC TCCAAANAAA AAAAATTCTC NTNGTGCCCC      660

NTNATTCCCC CCCGGGGCCN NNTTTTAATT CNGGGGAATT AAATTTTGTA TCCNNGCNGG      720

TNGAAGCANG TTATNGCCCC CCCTTGACCC ATNTTTNACT TNTTAATTTT TCCCCNNNCG      780

GNTGGAAACT TTGCCNAAAG GCANGCTTTT TGAACCAGT                            819

(2) INFORMATION FOR SEQ ID NO:426:

(i) SEQUENCE CHARACTERISTICS:
        (A) LENGTH: 791 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1314RP (xi) SEQUENCE DESCRIPTION: SEQ ID NO:426:

GATCCATAAA CTATCTTCTC ACTCGCCGGA TGCAAAGTAT CAAGGAATAG GCGACAATCG      60

GTAATGATTG GCTCGAGCTC ACGCAGATAT TGGCGCACTT CTGATATCCG TGGGTTGTTC      120
```

```
GATGCATGAT GCACATGAAT AAAAGGAAGA AGCTTCGAAA GAGGTACACG GCCCGGGTAG    180

CGTGTGATGA GAGCTGTTAG TTCGGCTTCA ACATCAGCAA GTTTCTCTAT AGGGGACGCA    240

GGGTCGTCAA CATCATTTAT TAGACACTCC AGCAGTTTGT CTGAAAAAAA GGTGTGCATG    300

GACAAGTGCA CCTCATCCTT TGAGATGCCG CGGATAACGT CCCTCAGCGA CGCCAGTCTC    360

ATCGTGCAAC TGCGTCAGAA AACTCTTGAT TGATAGCGTA ATGCAGTCAG AAGAAGTCGT    420

TAAAAGCACT TTCGATGCCC CAGTGAAACC TAATCCTCGT CCGATATAAA ATCGAACGTG    480

TTAGCAACAA TCTTCCATAT CCGGAAAGTG TTTTACAAGC TTCTTACGAT TTTCCACTCC    540

TCGATTGAAT ACTCCGGCCN AATTCTTTTA CCATATACAC CCNNTNCGGG GCTTTTGCAC    600

GAATTCNTTA TTTGTTGAAG AACTGGACAC TTTGAAACTT TGCACATTGC NGANTCCGAA    660

ACNCTTTTCN CNCCGAACTA ATNTNAACCC CAATCCTGAC CCAATACACT CCCCCCCAAA    720

CATGACCCCG CACANGATTN TTTTTTCCCN AGAATTTNTT NAACTNTTTG CCCCCTNANA    780

CATTNTAAAT C                                                        791

(2) INFORMATION FOR SEQ ID NO:427:

(i) SEQUENCE CHARACTERISTICS:
        (A) LENGTH: 833 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1314UP (xi) SEQUENCE DESCRIPTION: SEQ ID NO:427:

GATCTTGCTG CAGACAGATG CCGCGGAGCT ACCCTTTCGA ATCCTTATAT AAACCCTTTT     60

CCAGCTGTAC CGCAGTAAAC TCCCCTTGCT TCAGGAGCTC CAGGCTGCCA CGCACACTCG    120

AGGCCTACAC GCGTGACTGC ATTGGCTTCT GTGCGCACAC GGAAGTCTTA AACGAACCTC    180

AATCCCATCC AACCAGTTCT GCTAACGTAG CTACTTCTGG CCAATCGCTC AGCCCCATAC    240

CGTCGAGGCA ATCTTTCCAA GCCACATAAA CGAAACCTAC ACAGTTACTG CGCAAGGCAA    300

GTGCCAAAAG ACCACAGGTT CCGCAGTACC AGAGCAAAAA GCTTACCTGT CAACACTTCG    360

AACATTCGCG TGGCCTTAAC CATATGCCAC ATGAAGCAAT AGACCCCTAA AATAGAAAGC    420

GATTGGCGCG GAACAGACAT TCCTGGTGTT GTACTTGGAA CTCACATAGG GGCTGCACAC    480

GTGCTTAAGT CCTCGCTTGC AGCTGAGGCC ATGTGCCCCT CATTAGTGAC CCACGTTGAT    540

CTCGAGCCCG CAAATGATCG TCAGCGTGCA TCCGACTTGG CATTGCAAGG GATGTTGATC    600

CCCTGANGGG AGGCTTGCAA CAGCGCCNCC CTTGTTTCNC ATCCATAGGC TGTCGAGGCC    660

GGAATGATCC NCTCTCCAGG GGAACNCCCT CCCCAACGCC CCATAGGGCC CNCCCTGGGN    720

TNTTGCCCGG ANACTCCNAA NCNNGGTTTA AANNTTTTTT TTAAANGNCC CAGTGGTNTC    780

AAGGCCCCCN NGCCTTTTTC CANCCCGCAN TTNCTNAATT TTTGNCNGCG GNA           833

(2) INFORMATION FOR SEQ ID NO:428:

(i) SEQUENCE CHARACTERISTICS:
        (A) LENGTH: 839 base pairs
        (B) TYPE: nucleic acid
        (C) STRANDEDNESS: single
        (D) TOPOLOGY: linear (ii) MOLECULE TYPE: DNA (genomic)
```

(vi) ORIGINAL SOURCE:
    (A) ORGANISM: PAG1315RP (xi) SEQUENCE DESCRIPTION: SEQ ID NO:428:

| | | | | | |
|---|---|---|---|---|---|
| GCGGCCGCTC | NNCCAACTAG | TGGATCTTCA | TTTGTGGCCC | GGCCGACAGG | TTACCACCGC | 60 |
| TTTTCTCTCC | CGTCAGCATC | TCAACTAGCT | GCTGTAGCTG | GTACTCCCTG | TCGCCGCGGA | 120 |
| ACACGTTGCA | CTTGTCTATT | GCTGTGCATG | AAAGATCGTG | CAGCTGAACT | ACATTACCGT | 180 |
| AAGTGATCAG | CCCAACAAGC | GCGTTGGGGG | GCAGCAACGA | CAGAGAGGTG | ATGATCGAAT | 240 |
| CCTTCAGCGC | CTGGAGGTTC | TCCTCCTCCG | CGGTTACGTC | CACGACGTAG | AAGAAGATCG | 300 |
| GCGCCACCTG | CACCGGCCGA | TTTGTGATGT | ACTCAACCGT | CGTGGAGTTC | AGTTCCGCGG | 360 |
| GCATCGCCTC | CTGAGACATG | TTCGCATAGT | GCTGCGGAAG | ATGGTTCCGC | GTCCCCGCAC | 420 |
| AGAGGGCACG | CCCACACGTT | CGACCGCACG | TCGATCTCGC | AGTACGGGTT | CAGCACCCGC | 480 |
| CTTACAGTGT | TGGCCCCACC | CACACACCAC | CCGGTTTGTT | ACGAAAACCA | CCGCCCAGCT | 540 |
| CCCTCCAATC | TCCTTCCACC | GCGTTGTTAC | AGCATCCCCN | CCGGCNCCAC | GTTCCTTGTT | 600 |
| CNCGTTCCCG | TCCGGGAAGC | CCGGGAAAAC | ATTCCCACGA | NAACCGCACC | CCNTTTAGTT | 660 |
| CTTCCTTCCT | NTTTCGAANC | CACCCTTGAA | CCGNGANCCA | CTTTTANNCC | CCTTTACCCC | 720 |
| CTTTGATCCC | CNCCGAACCC | CCNAAATGGA | ACCAANNAGC | CCNTAACNNN | TGCNAAAACC | 780 |
| GANTTGCCCN | TTTCAAGGTC | CCATCCTTTG | CCCCCCGNGA | ANAAAANTNC | NCCGCCCNA | 839 |

(2) INFORMATION FOR SEQ ID NO:429:

(i) SEQUENCE CHARACTERISTICS:
        (A) LENGTH: 818 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1315UP (xi) SEQUENCE DESCRIPTION: SEQ ID NO:429:

| | | | | | |
|---|---|---|---|---|---|
| GATCTTGCGG | AATATCGGCT | CCCAATCCGT | ACCCATCCAC | TTCGACACTA | CCGACTGCAC | 60 |
| CGCCAGCGTG | TTCATCGGCA | CAAGCTGCTC | TCCTAGGCTC | AGCACCGGCG | GCACCACAAA | 120 |
| GTAGAACCGC | CGCGTGGTCT | CCAGCTGCTC | CCGCTCGTTG | CGGAACGACA | CGTAGTAGCA | 180 |
| ATACGAGCCC | GGTACGTACA | CATCCACATC | CACGCAGCTG | TCCTCCAAGA | AACCTGCGCT | 240 |
| CAGCAGATGC | TTGTAAAACT | TGTTCCGCTG | GAACTTCGTA | TTCCTTTCCG | GCGGGCAGTT | 300 |
| GGTCCACACT | AGCCCGTCCC | GTGTCACAGG | CGATCCGGCG | GCTACCACCA | ACCGCACCCG | 360 |
| CAGCCCGCTG | TCCTCCCCAG | CGTCTCGGCC | AACAGGTAAA | CATGGCAACG | TGAGCACACC | 420 |
| CTTTCCAACC | TCTCCTCTCA | CCGGCTCCCC | GTTGTCGTCT | AATCTCAACA | GCACGGTTTT | 480 |
| CATCGCTGTT | TGCGCCCTTT | GCTGCGATCT | AAAGGAAGCT | TCGCTTGTCA | TGCAGCTGCT | 540 |
| AGCCTTGGGA | ACTGCCATAG | TCCTTTGACC | TTGACGCCGT | GTTAAATAGT | GCATTTCAGT | 600 |
| ATACACAATT | TGACTTACGN | NCTCCCNCNG | TGCTAACTGA | GGGANATTAC | CCNAAACCCG | 660 |
| GANGGGANNA | TAACNGNTNA | NAATTTNCCC | GGTNGCACNC | NTGCCNTATG | NTTCCNTTTT | 720 |
| TGGAAANAAA | CCCTNGGGNN | GGTNGGTTGN | NAAAAATTGA | AAACCCNGGN | TNAATACTNC | 780 |
| NTTNACNTTN | TCGGAAAACA | AAANTNCGGC | CCCCCCGN | | | 818 |

(2) INFORMATION FOR SEQ ID NO:430:

(i) SEQUENCE CHARACTERISTICS:
    (A) LENGTH: 798 base pairs
    (B) TYPE: nucleic acid
    (C) STRANDEDNESS: single
    (D) TOPOLOGY: linear (ii) MOLECULE TYPE: DNA (genomic)

(vi) ORIGINAL SOURCE:
    (A) ORGANISM: PAG1316RP (xi) SEQUENCE DESCRIPTION: SEQ ID NO:430:

| | | | | | |
|---|---|---|---|---|---|
| GATCCAATAT | ATGCGATGGT | CTGAAGGGTT | GTCCACGTGA | GTAGCTTAGC | GAATACTTTG | 60
| CCAAGGCGTC | TGCGACATCA | AGAAGAGTCT | CAAGATAATA | ATAGTCCTTT | TTGGGCAGTA | 120
| AGCGAAGATT | GTTCCTCGCC | TTTGTCATTT | CTGGCCGGTC | CCTGGACCCA | TTTGGTGCGC | 180
| TGTTGAAAAA | GCGCCAAAAG | TACTTCAAAA | TGACCGATTT | TTCGACCTGG | AAACCTGCCT | 240
| GGAGAGAGAA | GTCGTGCAGC | AACGTAAATT | CACTGAGAGA | CAGCAGTGTT | TCGATAATTG | 300
| CAGATTCTTG | ATTCTCCTTC | GTTAATTTTG | GGTACAATTT | AGATGAGCTT | AATAAAAATT | 360
| GTAGTGTCTG | GACAGATGGC | GATTCAGCCA | ATAAATAATG | GCTGATGGAT | TAAATGATGC | 420
| CAGCTGCGCC | AACTCATCTG | CATTCGCTAA | GGAACGCATT | GATTTCAGAC | TATAGTTATT | 480
| GGCAGCATCC | ATGTACTTTG | TTGTACTCGA | TCAGGTCCTT | CACTGAGACA | CCGTCAGAAA | 540
| GCGTCACCGT | CTCGTCAATG | AGTTAGAGCC | ATCCATAGAT | TTCCCCGAGG | CAGTTCCCGC | 600
| CATGAATTTC | CACCCACTTC | CCCCCCGGTC | CATACCGCAA | TTTGAACATT | CCCGGTCAAT | 660
| ACCTTCTTCC | TCCCCCGGNT | NTTCCNCAAN | AGGGAAGTTA | NATTCCTGNC | CTTTTTTTTN | 720
| AAAACCCAAT | TCNCACCTTT | TCNGGGAANT | TTTCCGGGTT | GAGNAAAANT | CCNACNCCCG | 780
| GTNGCCGGTT | TAATTNCC | | | | | 798

(2) INFORMATION FOR SEQ ID NO:431:

(i) SEQUENCE CHARACTERISTICS:
        (A) LENGTH: 820 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1316UP (xi) SEQUENCE DESCRIPTION: SEQ ID NO:431:

| | | | | | |
|---|---|---|---|---|---|
| GATCAACACT | CGTACAAACG | AATATAGTCA | CATGACCAGA | TAATCGTCGT | GACTGGCACC | 60
| CATACATCGG | CACCCATGCA | CCCACATGAT | GGTTTTCTTG | GCGGGTGGGC | CGTGCTGGGC | 120
| GGGCTCCCCG | GTCTACGCTG | GCGGTGTAG | CGGCCGGCT | GGGCGGCCAG | GCGGAGCAAT | 180
| GGGCGGAGGA | ACAGCGAGCG | CGCCAGCAGC | GGTGCGCAGC | TGGAGCGTCC | GGCATGTGTG | 240
| GAAAATTTGT | AGAATATAGC | ACTGTTATAC | TGAACAGTAT | ATAGAAAGAG | CACTTCCTGT | 300
| AGGTTTGAAC | ATACTATACA | AGCTCCCAAT | CATCGACGAT | GGCTGTTGGT | AAGAACAAGA | 360
| GATTGTCAAA | GGGCAAGAAG | GGTTTGAAGA | AGAAGGTCGT | TGACCCATTC | ACCAGAAAGG | 420
| AATGGTACGA | CATTAAGGCC | CATCCACCTT | CGAGAACAGA | AACGTCGGTA | AGACCTTGTC | 480
| AACAGTCCAC | CGTTTGAAGA | ACGCAGCTNA | CTTCTTGGAA | GGGCNNTTTC | TTCAAGGTNT | 540
| NGCNTTGGCC | AACCANCNGG | TTCNTAGGAT | TNNCNCTTCC | NAAAGGTTCA | ATTANAAATT | 600
| TACAGGTCCC | NGGGCAAAAC | CCTTTNGACA | CCTTCCCCGG | TTTGGGATTC | CCCCCCCCNA | 660

```
CATTTTAATT CAAAGGNCCA AAATTTGGCN ACCTTAATTA NGGNATNTCC TNTTNAAACC        720

NGNAAAAANN TNTNTAATTN TTTNNCCTTG CNTNCCCAAA AAAATTTNCC CATTTNAAAA        780

ACNTTTTNNC CNTCCCCTCN NTTNAACNCC NAAGGTTTTN                              820
```

(2) INFORMATION FOR SEQ ID NO:432:

(i) SEQUENCE CHARACTERISTICS:
        (A) LENGTH: 807 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1317RP (xi) SEQUENCE DESCRIPTION: SEQ ID NO:432:

```
GATCTTTATC TTTCGATGAT ATCTTTCCTG AAGAATCGAC AAACACCTGG TCCAGCAAAT         60

TGGAAGCTAA GTCTCTCCAA TCGGATGCAA AATAGTTGAC ATACCGCGCA TTTAACTTCA        120

CTAACCGGGC GGCACCAATA TCCTCCAGAA CTGTATTTAT TTCGCTACGC TGAACGATTT        180

GTTCAATCAG CGTAATATTC GTCAATACAA AGAACCCAAT TCTCTGCATC TGAGGTATCC        240

TTTTATGTGG AGCTCCGACT TCGGGCTCTA AGTTTGGATT TAGAATCTTT TGGGCCTTGC        300

GCTCTAGAGA TATGGTTAAG TAATCTATAG CATCGCTGAA GAAGCAAGAG AGCAATTGCT        360

GTGCATTCTT CGGTGTCATA GATATCGTCC AAACATTTTT TGATTCATTG GGCAGCCATG        420

ATTCGCGAGT CATCGATTGT ATAGTAGCAA GGCAACCAGA CTTGTATTCA CTAAACTTGC        480

GTAGTCTGGA CATAACATCA ACTGTGGCCT CCAGTTACAC CATTATCAGT GGTAACTGAG        540

CCCAGAGAAG CGGTTTTTGA CCGATGTACT TGTNTCNATC TTTTTGAACA NGGACNCGGA        600

AATTTCATTT CANGTCNGGC TNCNCNCTCC CAAAACNGTT CCNTGGTTCT NGTAAAGGTT        660

TNNCCCTAAA AATNGGGNTT CCCNNGTNAG NTTCCCCCCC AATTCNAACN NAANACCCNA        720

TTTTTNTAAT TCCCCCNCCA AAATTCAATT ATACCCCCCN TTTTNGGTAT TNTAAATTTN        780

GGGGGNCNCN NTTCCAAAAA GGNGCNG                                           807
```

(2) INFORMATION FOR SEQ ID NO:433:

(i) SEQUENCE CHARACTERISTICS:
        (A) LENGTH: 835 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1317UP (xi) SEQUENCE DESCRIPTION: SEQ ID NO:433:

```
GATCGTTCTT ATATTTGTTA AAGAAGAGTT TTCTTCAAGC ACTTTGAGCT GAATAATCTT         60

GTCAAACATA TTGTCAGGGC TCCGCTGGTC GTTAACGCG CGAAACCTCT TGAGGAACCC         120

ATCTAAGATC ATAATTGCCT TTTCTGGCTC CGATAAAGCT TTAATAGATT GATGGTTGTC        180

GCCTCTTTCT GCAACGCGGG ATTTAGTTAT TTCTCTAACG GATTCCACAT CCTTGTAAGT        240

CAAAAATGAT AAACACACGA CTTTGACTGC ACTGTTGTAC GGAATATAAT TCTCCTTCAT        300

CTTTTCCAAC CATTCGAAAA GTTGTTTCCG CTCGAACGGC ATATGATTGT TTCTGTCCAC        360
```

```
AATTACAGCT CTTGAAGTAT CCTTTTGTAG AAACTCTAGC GCGTCACGCA TCAATTTGCT        420

CTTATCCTTA GTAACAATAT TATCATTCTG TATGTGGCCC CAGGACTCTC CAAAAATATT        480

CTTCAATGCC AGCGCGACTG TCGTCTTTCC ACAACCAACC GTGGCCACAG GGAATGAAAA        540

TGAACTTGGT ATCTCGTCCT ACCTTATCGA GCTCCAGATG CATACTGGTC CCCCCNAGCT        600

CCTTTATATC CTCCGAATTT CCATAATATC CAATCCCAAA ATCCCAAAT CNTTCCTAGG        660

AANATTTTCC NNNACTNGAA ATCCCCTTAC CTTGTNTATA CCCCCTGNAA ATTTNGGATN        720

TTGATTCCNG CCAGGGANTA CNATTCCCNA TTTTTNTTTG TGANNAACAA NGCTTTTGAA        780

TTTTTGTCCC CNCCCNCTGT GNANTACCCN CCCTCCTCCC CCCCTNTTTN TTACN            835

(2) INFORMATION FOR SEQ ID NO:434:

(i) SEQUENCE CHARACTERISTICS:
        (A) LENGTH: 748 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1318RP (xi) SEQUENCE DESCRIPTION: SEQ ID NO:434:

GATCGCCTCG TCGTTCGCCC GGCTCGTCAG GCTCTGCGCA AGGAACTGCC CGAACCGACC         60

AACCAAATCT GGCATGTCCT TCGCGTAGAT GAAACCCTGC TGCTTGCTGT CCACCGCATC        120

CCACACGTTG TTCAGAATAC CCTCTGCCTC CGTCATGACT CCTGAGCCGT GAGTGCAGTT        180

CCCAAGGCTT TTGTTGTGCT TGGCAGTTGA AACGACGCTC GCAGCGGCAA AACAACACCG        240

GCCCCGCCGC AATTGCTCAC GTGCCTCCTC GCGCCACATA AGCACGCACA CCCTGACCGC        300

ACACGCACCC TGCAAAGTAG GTCATCACCA AAGGGGCACC CCGCCTGACC GTTGCCTGCG        360

TCGAGCAGCC GCCCGCCACG CGCCAACGGC CACCAGCATG CGCGTTCTCC GTAGCCGCCG        420

GCGCCGTTGG CCATCGCCGA AAATACCTCG GTTTGGCCCA CTGATGCCGT CTGCCGTCCG        480

CCGCGCCCGC CCGGCGCCCA GGCACCGGTG CCTGGTCAGG GCGCCCGGGC GGGCGGGGTC        540

GGTCACGTGT GCGGTTACCC GGGCGTCGTT TAGATCGAAG GTTCTAGGTC TGTGCCGTGC        600

TGCCCCTTGT TGTGCTACCG CCAACAGTGG GCGCGGCGTA CGCGGCAGGC ACCACGTGGC        660

AGTGGCTATC ACGTGAAAAG AGGGCGGGTA ACGGTGGTTC GCCGCTGAGA CACATCGCAA        720

CTATTTACAG GGCACTTAGG NGTTGACC                                          748

(2) INFORMATION FOR SEQ ID NO:435:

(i) SEQUENCE CHARACTERISTICS:
        (A) LENGTH: 758 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1318UP (xi) SEQUENCE DESCRIPTION: SEQ ID NO:435:

GCAAAAAATG AGGTCCGCCA TGCGCGGCGG CTCGCGCCCG TCCGCGACCA AGCTCCGCCG         60

CCCGTCCGCG CCCCACAGGC ACCAGCTCGC GCCTGCGCGG TAGCTCGCGC CCATCGCGCA        120

GTCGCGCACC GCGCCCGCGC GCCGCAACGT CCACATGTCG CGCACCACCT TCTCGTCGAG        180
```

| | |
|---|---|
| CACACCGCCC CCGCACGTGG CCGGCGCTGG CGCCGCCCGC GGCACCTGGC GCTCGTGCGC | 240 |
| AGCCAACTCG CCTGTCATGA ACAACGCTGT AGGAATGCCC ATCTTTGCCC TTTCCGCTCG | 300 |
| CTGCCGCTGT GTGTGTGCTA TACGCTGCCT TATATACCTG CCAGGAGAAA TGTCTGCTAC | 360 |
| TATCCCCGCG AAAATATCCA TCCGATGCGA ACGGCGGAAC TCGCCGGAAA CCTGGAGCCC | 420 |
| CGCCTCTGTC GATCGTATGG AGAAACAGCT AAAATCGCTC AGCTACTCAT CTCTGGCGCT | 480 |
| GTGGTTCACG GTCGCCGCAA TGCGGCGCAT GCCCAAGTCC GTTTTTTCTC TGTGGCGGGG | 540 |
| CCAGGGAGAG CGGGGCGCAG ACGGCCAGAT TTTGTGCACG GCAGACCGCG TTGGCTGTGG | 600 |
| TAACGCGTAT GAAATACGGG GAAGCGGCGA TTACCAGTGG GTTTCGCTGT CAGGGGTGCC | 660 |
| TGGGGCGCGG AACGCGGTT ATGGTCTATA TTACAGAATG TGTACAAAGG AGTCACGTGG | 720 |
| GGGGGGTCGC GGGCNGGACA GCTGCCTCTG TTTCTTCC | 758 |

(2) INFORMATION FOR SEQ ID NO:436:

(i) SEQUENCE CHARACTERISTICS:
        (A) LENGTH: 801 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1319RP (xi) SEQUENCE DESCRIPTION: SEQ ID NO:436:

| | |
|---|---|
| GATCTTCCTG CCTTTTGACC TCTTCATTAA TCTTCTCCTT TAACTTCTTT TCCGTGTCAA | 60 |
| GAATGTCTGT TAGCAGTTCC TCTTCCTGTT TCGGTTTCTT CCTGTTCCTC CTGCCAAGAT | 120 |
| GCAGCATCGA GTTTTGCTGG ATGGGCAAGA AATTAGAATT GATATCGCCG ATCCCTACGA | 180 |
| AGAAATCGTA CGGCACAACC TTAATGAGAT TCTCGCACCA GTTCCAGACA TCACCTCTAT | 240 |
| CGTCAATGAC TACGACCATC GACTGGTCCA TCGGGAACAG ACGCTCGAGT GATTTTTGCG | 300 |
| TCAGCGAACC GTTTTCATCG CGTGACAAAA TTCTATCGCC AAAGAGCTTC CCATCCGGGT | 360 |
| CAATTATCTT GGCAATCTCT AGCGCATAGG CTCGAGTAGC CATGGTGTAT ATATGCAGCT | 420 |
| CGAAATGCGG CGCGATCTTC GCAAAGAATT CCTTCAGGCC TGGCCGTAAT TTCACGTTAG | 480 |
| TACCAACACT TGCGCCGTTG GTTGGCTTTT GGCCCCCATA TAGAACGGCG GCAGCACAGC | 540 |
| TCCTCCATCC GANAGANAAA AACTGCNCAT CCTTAGCGCC CCGTATTCGG GTTTGTTTNG | 600 |
| GTTCCCTTTG ACCACTCCCC CATGGTGGGT TCACACCCGC NATNGATTCN CCGTCTGGTT | 660 |
| CAATTTTACC CCCAGCATNG CTTGCGCNCN TCCNNNCAAC TTTGACTGCN CCNCTGACCA | 720 |
| AAATCCAACT TGCNTTGGAC CCGATTTGTT TTTTTNTTTG AAACGNNANT TCCTNGTCNN | 780 |
| CTTGGGNCCC CNCTTTCCCN A | 801 |

(2) INFORMATION FOR SEQ ID NO:437:

(i) SEQUENCE CHARACTERISTICS:
        (A) LENGTH: 834 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1319UP (xi) SEQUENCE DESCRIPTION: SEQ ID NO:437:

```
GATCATCGGC ATGCTGGAGA ACCCAATTTT CCAGTCTCAG ATGAACGAAA TGCTCAACAA      60
CCCGCAGATG ATCGACTTCT TGATACAGCA GCACCCGCAC CTGCAGGCAA TGGGCCCGGC     120
GGCGCGCGAA ATGCTCCAGA GCCCCTTTTT CCGCCAGATG CTCACCAACC CCGACATCAT     180
TCGCCAGATG TCTCGCCTGC AGATGGGCAT GGGCGGTGCG GGCGCCGAGC AGGGCACCGA     240
CTTTCCAGCC CCCGGCTCCG CCGCCACACC CGACGCCGCC GCCCCTGCGC CGAACCCGTT     300
GGCTGCCATC CTAGGCTTGC AGCCCGGCGC TGCTAACCCG CTGGGCGCTG CGCCCGCAGA     360
CCGCGGCCTT GCAATGCCCC CTCTAGACCC GGCTATGCTC TCTTCCCTCT TCGGCGCTGG     420
GCGCTGCCAG CCCTGCGCCC GCCGAATAAC AGGGCTNCCC AAGNANGNGN TANCAAACAA     480
ANATTCGCCC ANGCTNAATN AATTNGGGCN TCTCCAACTT GAANAAANAT TTCCGGGCTT     540
NAAGCGCNCG AAGATGTTCT NTCNNGGGCG CCCTTNTATT CTTTNNTAAA GGNAAANTTN     600
TAGGTGNNGA NTTNTCTGCT NCNNGGGGCG NCGTCGCCGT TTTTNTTTAT TCCCCNTTNT     660
TTGTNTTCTC CNTNCTGNTT TGCNACCCCA CNCAATTTTT TTTNGGTGGG GGCTNCCNTN     720
TTTTCATNNN TTNCNANNAC GNCGNTAATT ATANTTGTNT ATCACGTCCT NTTTNTTTTT     780
NNCCNACNGN TTGGGTTGCC CCTTTNANNT GAGGNTGGTG TAGGGAAAGA AAAT           834
```

(2) INFORMATION FOR SEQ ID NO:438:

(i) SEQUENCE CHARACTERISTICS:
        (A) LENGTH: 791 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1320RP (xi) SEQUENCE DESCRIPTION: SEQ ID NO:438:

```
GATCTTTTCA AGAAGTTTAA CAATGACTTT AAAGCTAGCA TTGATAAAGT ACTCAAGAAA      60
CCTAACAGAG CGGAGATGTA TGATGCTCTT TTGTCAATTA ACGTCCATTC TAACAATATC     120
ACCTCGGGAT TGAATAGAGC TATCTCCACT GGTAATTGGT CGTTAAAGAG ATTTAAGATG     180
GAACGTGCTG GTGTTACCCA TGTCTTGAGT AGGCTTTCTT ATATTTCTGC TCTGGGTATG     240
ATGACAAGAA TTTCTTCGCA GTTCGAAAAA TCTAGAAAGG TTTCTGGTCC TAGAGCTTTG     300
CAACCCTCGC AGTTCGGTAT GTTGTGTACA TCCGATACGC CGGAAGGTGA GGCCTGTGGT     360
TGGTTAAGAA CTTAGCATTG ATGACACATA TTACCACGGA TGATGAAGAG GAGCCCAATA     420
AGAATCTTTG CTACTTACTG GGCGTTGGAG AACATTACAT TGGCTAAANA ANGGCNCCCT     480
TCCTTTTAAA TNNNGGGGGT TTTATTTGGA AAGGGTACTA CCCCCGGTNC ACAAAATCCC     540
CCCCGNGTTT TTGTTCCCCC TTTTAAACTN TANAAAAAAC GNGTAAATTT CCNNATTTCT     600
TTTCCCNNTN TCCCAANNNC CTCAAAACTT NTTCTTTTGC AAGGAGGGGG GAAATTTNTN     660
ACCCCTTTNT TTTNTNGGAA GAGAATTTTT GTCCCGGNGG CCCCCAAAAA TTTTTAAGGG     720
GAANTCNTTA NATTCCCNAN NGGGGNTNNT AATTTTTGGN TTTTANAAAA AAANCCCCCC     780
CCNCCGNNAA A                                                         791
```

(2) INFORMATION FOR SEQ ID NO:439:

(i) SEQUENCE CHARACTERISTICS:
        (A) LENGTH: 844 base pairs (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1320UP (xi) SEQUENCE DESCRIPTION: SEQ ID NO:439:

```
GATCATGAGG GAATCCTTGG AAGAGGATGA CAAGAAGTCC GACGATGAAG GTGACCTGTC      60
TATTCCAGAT GCGCCTTCCT CTGAGGAGGA TTAGGCATAT AATGGGTCGT TTATATGTAC     120
ATTAATTAAC ATTCCGCTTT AGCTTTTTTA CTCTTATCCT TACGGTAGCT CACCCATATC     180
TGTAGCCCTG CTCAGTTATC ACTAAAACGA GTGCCAGGCC CTAGTACTAT ATAATCCCGA     240
GTTCGAGCTG AGAAACAATG TCTGATTCGG CTGGTTTGCA TGGGAGTACC GCGATGCAAG     300
ATCCAGATAG CACTTTAGTC GAGGAAAGGT TGGCGGCTAC GCCAAAAGTT ATCAACAAGG     360
TCAGCAAGAA AGGTTCAAGC CCCCTTTCAG TGTTTAAGTT TAAAGAGGGG AGCCTATCCT     420
GCCNAAANTG CGCCAGGGTN CNTGAATTTN GGAGAAAAAA NTGCGTTTTT TCCGGAAAAG     480
CGCCCCNTGA NNCCAAAATT TATTNGGGAC CCNCACACC  NCGAGAAATT TNNTTNAAGN     540
GCGCCCTTTA AAATNCCCAA TNTCTTCNAA ANNATTTGAG GNGGAAAGAC ANTTTNTTTN     600
AATTNCGCGG GGGGTNTTTT TTGCCGCCCC GGNGNTCNTC CCNCCTCCAC NANTTTNAAA     660
NATAGGAGGA ANGGGNGGNG GCCANATTTC CACCTTTCNN AGTTNGANNG CCNGNAAANA     720
GNNTGGATGN CCACCAATNC GGGTGNTNGA AAANANTNCN NACTGCTTGT ACACAAATTT     780
TTTTGTGCCG CNGGTGACAG AAAAAAAGAN GGATTTTTTN ACAACCNNAA AAANAAAAAA     840
AAAA                                                                 844
```

(2) INFORMATION FOR SEQ ID NO:440:

(i) SEQUENCE CHARACTERISTICS:
        (A) LENGTH: 788 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1321RP (xi) SEQUENCE DESCRIPTION: SEQ ID NO:440:

```
GATCACGTCG TTCCTGGACT TTCTATCGTC GACGGTGCTG TTCTTCAGCC GGGAGGCGAT      60
ACGGCTGGCG ACGCTGCGCA TCAAGACGGG CGGGGACGGC GGGCGCGGCG GCGAGATGTC     120
TGCGGAGCTG CAGACGGCGG TGAATTTTGC AAACATACCG ATGTGCATCG GGGCGCCGCT     180
GGCGGTGGTG CTGGCGGTGT GGCAGTACTC GAACCTCAAC AGCTACTTCA CGCAGCTGCC     240
GTTCTTCTCG TGGTCGATCT ACCTTGTGCT GCTGTCGATC CTGGCGGAGC TCGCGAGCGA     300
GCCGCTGTAC GTGGTGAACC AGTTCATGCT GAACTACCGC AAGCGGTCGC AGTTCGAGGG     360
TGCGGCGGTA GCAGCGTCCT GCCTGGTGAA CTTCGCGGTG ATCTACTGGT ACGAGAACTG     420
GTTGAATGGG CGCGGCAGAC GTGCACGACA GCTACAGCCA GGAGGCATCG CGGTGCTTGC     480
TTTTNCCCCG GGGAAGGTTG CCCCCNCCAA AACTTTNCCT GGCCCGNTCT ACTTGAANAA     540
CTTGCGNCTC TGGGCCCCCA AAAACTTTTT TCCCTTTNTT TNACAAGTTC CTTTTCCGGN     600
NATTTTTTAC GGGNTTNTTC CNCCCGNAAT TTNTTGCCCC TTCCNAAGGT TTTTTCCCCC     660
```

```
TNTTTNTTTA NCCCNCCTTN NCAAGGGGGA AANNTTTTTN CTTCCCCCNC CCCGGGAGAA    720

ANNGGGGANT TTCCTTTTTT TTAAAANGGN NCCCCCCCGN ANGNNTTTNN CCCCCNAGAA    780

NATTTTTT                                                             788

(2) INFORMATION FOR SEQ ID NO:441:

(i) SEQUENCE CHARACTERISTICS:
        (A) LENGTH: 815 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1321UP (xi) SEQUENCE DESCRIPTION: SEQ ID NO:441:

GATCGAATTC GATTTCCTTT CGGTGCAAGG AAACAGAGCC TTCGTTAAAG TGGGATACGA     60

AGACCGTGCC CAATTTTCGT CGGCCCTTTC TACATACATC TCAAGCGAGG AACTTATCGG    120

CGTGCCATTA GTGGTCCATA TATTGCAAGA ATGTACAAAG TTAGAGAGGA TGAAGGTTGG    180

GGAGGACGAT GAGCTATGGT TCAAAAGGAG TTTGGAGGAA NAAGTANCGG ATTCCAGTTG    240

TAATTAGCTA CAAAAGCGGA ACGGGTCACA CTAAAATTCC ATGCGCTAAC TTTTCCACTG    300

AAAGAAGCCA CATGAAGCTT TTATATCTTC TGGGGCTCCT CTGGGACGCT TACACGTCCA    360

GAACTGTTTC CCAAAATTCC TCGACGTTTT CGAGGTTTTA AGAACCGATC GGTCTCCGTG    420

CTTGCAGAGA GGTGCATTTG ATGGGGCGAA AAATGGTTTT TCAACCGCCG AGGGTCGTTG    480

TTCAGGAGCT TTGTTAGTTC GAAGTTGGAG CGCCATTCCA TTGATTGCCC CTTGCTCTTC    540

CTCCCTNGCA CTTGCCGCTT GCTGCTATGT TTACTTACTA NAAGCACCGA NCCACACTTA    600

TCTGGTTTTT TTTTCCTATC CTGANACTCC CTTGAATTAT TGCCTCCTTT TGACTTTCCC    660

CCTGTTCCAC GTTNGTTACA CNTTTGCTTT GAATATCTTT CCTTTCCGAA GCACCCATNT    720

TTATAATTAG TCCTATTGAC CCCCCCCACC TGGTTTTTGT TTTCCTCCCA ACANGTTCTC    780

TTCTCCACTN AGNTTTGTAT ACNGAATGTC NACCC                               815

(2) INFORMATION FOR SEQ ID NO:442:

(i) SEQUENCE CHARACTERISTICS:
        (A) LENGTH: 773 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1322RP (xi) SEQUENCE DESCRIPTION: SEQ ID NO:442:

GATCCAGGAA ATAGTACAAC GCCCTTGGAT AATGCCAGGG ATTCCTGACT CCTAACGAAA     60

AGCCTCTCCT CTTCTAATTT CTTATTAAAG TAGTTAGCTG CAAACTGTAA CAAATCCCCC    120

GGCCGTCTTT GCTCCACTTC TTTCTGGAAT GCGTCCAGTA GGTCACGGTG TTCCTGTGAT    180

AAAACCATCG AGTAGTTTGT TGTGTGATGC AGAAAACCTG CCTATAGCGG AACCAAAATG    240

CTCTAGTAGT GTGACGGCAC CGTTTTATCC AGTTTGCTAA GCAGCTGCCC TAGGTTAGGG    300

AGAGTAGAAA GTGTCATTGG ACCCGAATTT CCTTCTGCGC GCGGCGAACG ACGTTAAATG    360

TGATTCACGT GATCACGCTA CTGGGGCTAA CTACCAATTG AGACAGGCTA GTTGTCGAAG    420
```

```
CCTGAGGAGG TCTCCGAAAA GCTTGATGTG AGGATACTCG TGTTCAGTTA TCTTGTATGC        480

CTGTATTGAT CTGTCCGTGA GACCTCGAGC TCTTCGTCCG TCAATGCCCC GCGCCTAGAG        540

AGCTAGGTTG ACTCCGAGTT CTACAAAATT TCNAAACNCC TTGAAAATTC NCAACATTGT        600

TNTGGACCAT CNANTTCCCC NCCTTCGGAA NNAAGCCCTC CANCCTTTTT TNACGTTGCT        660

NACTTNCCCN CTGAAAAAAC GTTCNATTTA CCCTNTTNTA CNCGGCAGGA AACCCCCCAN        720

TTCTTTTTCC ATNAACCGGT ANCTNAAAGA ATTTTCNNGC CATGNGGTTT ANG              773
```

(2) INFORMATION FOR SEQ ID NO:443:

(i) SEQUENCE CHARACTERISTICS:
        (A) LENGTH: 817 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1322UP (xi) SEQUENCE DESCRIPTION: SEQ ID NO:443:

```
GATCTTCACA ATCGACGCCA CGTCCATCGC GATGTTCCGC CGCACTGCCG TCACTGTGAG         60

ATATTCGTAC GGAGAGAGCC GGTACGTGTT GATCATGAAG TTGCGCACAT CCTTGTACGC        120

TTTGGCCGTC TTGAACCGCA CCGAGTCGTT GAAAAAGTCG GCAACGCGC  GACGCTCCAG        180

CTCATGGATC TCGTTGAACT GGAACCACGA GGCAAACGAC GGCACGATCA CCGGGTGCGC        240

CTGCTTCGCT AAGAAGCGCG CCGCCTTGTC CTCCAATTTT TGCGCCTCCT GCTCGTAATC        300

GATCTTGGGT TGTTCCTGCT GCTGCTGCTG CTGTTGCAGA TGTGGCAGCA CAGGTACAGA        360

TGGATTCACG CTGCCCGTGT TGCCCGACGA AAGCGTTCCA TCGCCAGCGT TGTCAATATT        420

GCCATCCTGG ACATCCATTG GCTCGCTCAT CGTTATAAAG AGTATGCCAC GCTACTTTCC        480

CCGTTTAATA GCTTTCAAAC GCGTCTTCGC TCTGCTACCC CGCTTAANTC CACACTGGTT        540

TNTGTTTTCC NCCATACCCA AANTTTTAAA ACCCATTTTT CCACATCAGC CCCATATCCT        600

CCGTTTGGTN GNGGAAATTT GAAACCCANC CCTCGCCTGG CGGAAAANNC TNCTTATGGA        660

CCCCCTTCCC NTCTTTCAAT CGGTCCCCTT NACCAAGNNT TTAGCCCCCC GGNANANGAC        720

CAATTNGGTC CTTCCGTCNC TTTCCCTTNT TAAATTGAAA AAGGTTNCCC TTTGAAAATT        780

AACCCNGCCC NCNTCCCCCC GANAAATGGT TTTTTGT                                817
```

(2) INFORMATION FOR SEQ ID NO:444:

(i) SEQUENCE CHARACTERISTICS:
        (A) LENGTH: 759 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1323RP (xi) SEQUENCE DESCRIPTION: SEQ ID NO:444:

```
GATCAGTTTG CAGGGACCAT GAGCAGGGCG GGCGACGAAA GCAGCTCTCC TTCGTACACC         60

TCCGTGCAGG GGCTCAACAC GCCCTCGCAG GCGGACGACG ACGAGGAAGA GGAAGATGCG        120

GCACCGTTTT ACATCCATCC AGATTTGAGG ACATCACAGC TCTACTTTGA GAAGATGATC        180
```

```
GATGAAGAGC CCCTCCCGGC GCCTGTTAAG CGGGTGTTCT ACATTAATCC GTATGGAGAG        240

GAAATTTTCC CTGTCGCGAA CTCTCGGTCT ATCCACCAGC TGAAGCGATG CGATATGCTT        300

GTGTATTCCA TCGGGTCCTT AATTACCACC TATTGCCATG GTGATCCTCC GGTACTTGCG        360

AGGTGGTCGT CCAAGGGAAG ATGAAAAAAT GCTACTGGTC NCNCCAATCA ATNNCNAACC        420

TCCGATTAGG GGGGGGGGNT TNTTTTTTTA ATTTTAACCC CCCTTTGGGG TGACCCGNNC        480

NAAAAAAAAG GGGGCTTTGN NNNTTTTTTT TNGNCCCCGC CNCCTNTTCG GNAGNTTTTT        540

TTTTCTGGNG GGGGGGCCCC CCNNNCGGAA AATNTTNTNC AAAAGGAAGN ATTTNCCCCN        600

NANGGGGANT TTTTTNTTA NNAAATNNAA AAAAAATTNN TTCCATTCCC NNAATTTNNN        660

NTTTTTNNNN CTNTTNCGGN TTTGNAANTT NACCCCCCNC NANAANTTTN NTTTTTTCCC        720

CCCCCCCCCC CCCGGGNNNN TNCNTTTTTT TTNNNGATN                              759

(2) INFORMATION FOR SEQ ID NO:445:

(i) SEQUENCE CHARACTERISTICS:
        (A) LENGTH: 834 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1323UP (xi) SEQUENCE DESCRIPTION: SEQ ID NO:445:

GATCCGTTTT TCCAATATTT CACCGTCCTG TAAATCAACA GTTGAAAAAC AATGGCGTGC         60

TTAATCGACG AACGCAGCAC AACCAGCAAT AGGCTTCGAA GCCGTTCCAG AGGTGATATC        120

GCAAAGTTGC TCGAGCACTA GAACGGACTG GGTCATTATA TAGGTGGTAG TAAGAAGTGG        180

GTAGAAGGAA GGGGACTATG GTACAGCGCG GGCGTGGAGG CAGGGACGCC GCAGTGGGTG        240

CCGCTCATGG GCATGGGCAT ATGCGGCAGT TGTACGAGTT GGTTTACAAC CGGGGGGCGG        300

TGGGGACGTA GACGTTTACT GCCGGACCTG CCGCGGCACG GGACGCTTGA CCCGAGCAAT        360

GTTGTGTGCA CGCTAGTGGA GCTGTACCAC TCGATTCCGG GCGACATCCC GCTGATTAAG        420

ACGCATTCNA TCGCCGGTGG GTGTNTCTGA NCNAAGTTGG ACCNGGAAC CTGATTGTTT         480

TGTGGCNAGA ACACATNCCC TTGTTGGTGG ACCCACCCGA NAATTAAACC GCCCCNCCAA        540

GACNAGCCGC CCTCCCCCCN GNGCGTTTGG GTTNNNGCCA TTNGTCCGGA CNTCCAAGAA        600

NTTTACTNGC ACCGNCGGNG GCACCGCCGN CGGGGCACTT NTTTCAACNC CNTTCCCCCC        660

CNTGGGGGGG NCCCCCCCTT TGAAAAANNG TGGGGGGGAC CGGTTCGGGT CCCNTTCCCC        720

CCATTCNATT TTTNTTTANA NANNACCAAC CCGCCTCCCT TNNCCCCACN CAAANNTNGT        780

TNGTTAANCT NCCCCNTTAT TCTNCCCCCC CGNCNCNTAT TCCNACCCGN CNGT             834

(2) INFORMATION FOR SEQ ID NO:446:

(i) SEQUENCE CHARACTERISTICS:
        (A) LENGTH: 785 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1324RP (xi) SEQUENCE DESCRIPTION: SEQ ID NO:446:
```

```
GATCCTACCG GGATGCACGA CGCATACAAG TATATCAGGG ACCTTGCCGA GGAAATGGGA       60

CATAAAATTG AAGGACCAGA TCACAATTGG TCGTTCCTTA TCATAGCCAA GATATATATA      120

TATATCTGGG ATAATTACAG CGCTTGGTAT GTATACCTCC TACATACAAA TACTTACATA      180

CACATAAATA TAATACAGCT ACTTGTAAGG CGAGAAAGGT TACTTCTGGA GAGCCATTAG      240

AGACGCAACG AATGTCAAAA TCAACCTCGG GCGGACTTCA TTGATATCTT CAGGAACCAA      300

CCAGATTAAA GCACCAAGTT TTCTCGCGAT AGAAATTGCC AATTTAGCGT TTGCATACTT      360

CTCTTCCTCT GTTACGGCCG GGAGTAACCA AGTCATAATC CACATATCCT GGAGCTAATC      420

CGTTCAATAC ATCCAATAGG AAATGGGCAT TGCTCAACGA AGCATCCCTG GAAAGACATA      480

TCCTGCTCGA TTTGCCACCC TTGGCACTTG CCTTGCGCCC ACTTTAGATC TGACATCTGA      540

ATNCTCTACC AAACAAACTN TGAGGANATN TGTTTGACAA GTTTTCTGCN CCTCACTGCC      600

AAACTAAACT AAGGTCACAC CTNTTTGCNT CCCCAATTCG AACCCCCTNN GCCCCCCCAA      660

AAAAACTTNA ATTCCCAAAT TCANNCCCTN TTTGGTTTCC CCCCCAATNA NCNTNAATTT      720

CNNCCCNTNN CTGGNCCCGG NNGAAACCCN TGAAATAACC CCCCGAATAC CTNCNTTGCC      780

CGAAC                                                                 785

(2) INFORMATION FOR SEQ ID NO:447:

(i) SEQUENCE CHARACTERISTICS:
        (A) LENGTH: 866 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1324UP (xi) SEQUENCE DESCRIPTION: SEQ ID NO:447:

GATCTTAAAG AGGCTCAGTA TGCAGAGGCA GTTTCCAGAA GAAGACAGGC TGGGCTTCGA       60

AATCCCTCAG CTCCCGCCGT GGAAGAGTCC GCAGATGAAG CAACACACAC AACAGGGCCA      120

GCAAACGCCG CTGCGGCGGC CGCGCTGCAT CCTCGGTGCC CCTTATGAAC CGAGCAGGGC      180

GTCGTCCACT GGTGCAGGCC AAAAGCGCGA CTACGACTAC TCCGTGTTCA ATGAGAGCAG      240

GCTCCTCACT GAGAGCAAGA TAGACCAGTA CTTGAAGAGC GAGGCCGCAA CGCACAAACG      300

CGTATTCCAC CGCGACCGTC CCCACGACGA CAGCTACCGC CCCGACTTGC AGCCGCTCTG      360

CTGCGACAGC TCGGACGAAG GAAGGGAGAG CCCCGGCGCG CGCAGAGCGC GCCGTTGAGA      420

ACGCCCCGTT TGGTGGGTCN AGCATCCCCC GGANATNCNT CCCAGAAAAA ANTNTTTCGA      480

ACACGCCGCC CGCCCGCCCC CCNCAGAACC TCCCNTTAGC GAACNTTNNA AGAAGAATNT      540

TNCCANTTTG CGNCCCTNCT TGGANAATGG TGGGCCNGCT TNACNAAACG CTAGGTTGNC      600

GCGCCGAAAA NCACTTTGCT TNACCGCATN CTCCCCNGAA AGANAGANAG NTCCCCNCAC      660

TTTTNCGCAA TTTTNTCCCC CGCGANAAAG GTTCCCGTTN ANCCGANGGG NGGCGCANNA      720

ANAAACCTAC NCANTTTNAA CATTCCCCCC CNTTTTTTNC AAAAAAGANA ATGNNTTTTT      780

CACCNTGACA ANTGATNNCT TTTNTGAAGG GNGGNAGTAC CCCCCGCTTG CCTNTCCTCC      840

CCTTAGANCT NCNATTTTGT TTTTNT                                          866

(2) INFORMATION FOR SEQ ID NO:448:

(i) SEQUENCE CHARACTERISTICS:
```

(A) LENGTH: 749 base pairs
    (B) TYPE: nucleic acid
    (C) STRANDEDNESS: single
    (D) TOPOLOGY: linear (ii) MOLECULE TYPE: DNA (genomic)

(vi) ORIGINAL SOURCE:
    (A) ORGANISM: PAG1325RP (xi) SEQUENCE DESCRIPTION: SEQ ID NO:448:

```
GATCAATGCG GGAGTGGCAA AAAGCGACTC AAGGTGAACG TGTTTCAGCA CTGTTCATGA      60
TGGGGGGTGG TCATTTTGCC GCAGCCATCG TATCTCACCA ACGCATAGAT ATCAGTGGCA     120
ATGCCAAGAG GCATGGAGAA TCGTTACAGG AACAGGCCGT GCACTTTCTT GAGCACAAAA     180
CGTTTCACAG ATACACCACG AGGCGGAAAC AAGGAGGTTC ACAATCGGTT ATGGATAACG     240
CCAAGGGGAA AGCAAATTCC GCAGGCTCTA CGCTACGTAG ATACAATGAG GCGGCATTAC     300
GGAATGACGT TCAGGACCTG TTAAAGAAAT GGAGGCCATA CTTGGAACGC TGCGAACACA     360
TATTTATTAG GGCCAAAAAT GTTGCGGACA GGAGCGTATT CTTTACGGAA AATACCCCAT     420
TGACCAAGGT TAGACCCGAG GATTCGGACA TTCCCATTCA CAACCCGTAG ACCTACCACA     480
AATGAGCTAA GGCGAGCATG GTGCGAGATA ACATACTTGA AGAAGACATT GAAGCCCAGC     540
CATCACATCG GAGCGGCATA CTCCTAAAGC GACAATGATC CACTGCCAAT AAGCGACGTT     600
GTACGCAACT TAACCCCGNG GNAAACCTTA NCAGGAACGG CTTCTTTCTT TGGATTCNAG     660
GCCCCNNNNT ATTCCCTNTT CNAAAANCNT NTTTCCCCAA CCTCTTTTTA AACCCCCGGA     720
AAAANNTTTN AAACCCNCNC CCCCCCCCA                                       749
```

(2) INFORMATION FOR SEQ ID NO:449:

(i) SEQUENCE CHARACTERISTICS:
        (A) LENGTH: 801 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1325UP (xi) SEQUENCE DESCRIPTION: SEQ ID NO:449:

```
GATCGTGCCA TGTCTGATGT GGTATTTCGA TGCGGGGCCG GGTGGGAGTG CCAGCTGGAC      60
TACGAAATCA AGGACGAACG TGAATTTTCA GCCGCCCTAG ATACTGTCAA GGGTGCGCTA     120
GCCCCCGAAA AGAAGTCGCC CTGCCGCACG ACCGTGCAGC CTGGGCCTGG AGCAGGCGGG     180
AACAACACGC CGACACGCGT ACCTCTGTCC AAGCTCTTTG TAGGTGCGAA AAACACCAAG     240
TTCAAGCCAG TGATGCGCTC TGCGGATGCC GCTATCGCGG CAGGCAGTGC CGCTTCGGGC     300
CGCCACTGTG CGCTATTCGA TAAGACACAG ATAGATGACC CACTGGTCAT GAACAAAGCC     360
GGTGACGACG AAGTCGAAGT TGTAGTCGAT CCTATTTTGT CAAAAAAGCT ACGCCAGCAT     420
CAGAGAACAG GTGTTGAATT CATGTATGAC TGCGTCCGGG GGCTCGCAAG GTCCGAGAAG     480
GACGATGATA GAACAGTGAT GATCTTGGAA TATGATAGTG ATGTCAAGGG TTGTCTGTTG     540
GCGGACGAGA TGGGATTAGG GAAAACATGC ATGACGATTG CTCTGATCTG GACGCTACTG     600
AAGCAGCATC CCCAGGCCAT CGTCTGTTCC DATGCTCCGC AATTGGGGGG TTTGGTTTGC     660
AGGGTTTTTT GCCANAAATT CTCNTGGTAT GCCCGGGTGA CTCTGATTGG CGACTGGGAA     720
AANGATTTCN CCNATNGGNN GCCGANGAAT AAATTGGANC CTNGAANCCN ATTGCNAANT     780
```

```
ACCCCCCAAA ANAAAAAATG N                                               801
```

(2) INFORMATION FOR SEQ ID NO:450:

(i) SEQUENCE CHARACTERISTICS:
        (A) LENGTH: 774 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1326RP (xi) SEQUENCE DESCRIPTION: SEQ ID NO:450:

```
GATCGAATTA AGTCAGATTT GATTGCGATG GCTACTAACG AACGTGCATT GTCAGACGGA     60
CCGAATCAGG TACACATTGA AACTCGTGAG TGGCTAGTGC AGACAATCAT AAATGAAAGT    120
TGTGGCTGGA GCAAGGGAAC TGCGATGCCT TAACTTTCTC AAAACACTCA TGGGTGGTCA    180
AAAATCAATC TATTCAGTAT ATAGTATATC AAAACATTAA ACCAAACTAG GCGCCCAGAA    240
TATTGCCAAA ACATTGCACT GGAGTATTAG TATGCAGAGA AGTAGCAATG GGCGGCTAGC    300
TGGTTACGTG GCATTCACGG ATGACTTATA GAAGCCCATT AATCATCTTT TAGTGACAGT    360
AAGATCAGAC ATTAAATAAC GTATCGAATT TTAGGGGAGA AGTCATCACA CTTGCATTAG    420
TATACCGCAA TAATTCGCGG ACCACATCAG TTAATACTGG GCATGGTTTC TAAAAAGCGA    480
AACTGGGTTC ACATTCAGTG TGTTTTGCAA CATAGATGTC TCTCCTCATG CTGCTTCTCG    540
GTTGAATAAC CATGCTTCAG TAGGCACCGT TCCCAGTATT TGGTAATTAG TTGCCAGACT    600
CCTTTATAAA GGATGACCCG AATATGANCT TCCATTAACA TTGCCNGGAA AANANATTTG    660
GCANCCGTAN ATATTTTCCT GCCAATTGAN ACCGTTCTNT GAACCCCTNC TTGGGGNCCN    720
GCTTCCCAAA AACGAANTTC CCCGGTNGNT NTTTTATAGG TNCNAAGAAA AANA          774
```

(2) INFORMATION FOR SEQ ID NO:451:

(i) SEQUENCE CHARACTERISTICS:
        (A) LENGTH: 779 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1326UP (xi) SEQUENCE DESCRIPTION: SEQ ID NO:451:

```
GATCAACAAG CGGTTCGCGC AGCTGCCGGA GAACCTGCGC CTCAACGGGG TGACGCCGAG     60
CGGCAAGCCG CGGCTGTTTG TGTGCCACAC GTGCACGCGC GCGTTTGCGC GGCAGGAGCA    120
CCTGATCCGC CACAAGCGGT CGCACACGAA CGAGAAGCCG TATATCTGCG GGATCTGCGA    180
CCGGCGGTTC AGCCGGCGGG ACCTGCTGCT GCGGCACGCG CACAAGCTGC ACGGGGGGAG    240
CTGCGGGGAC GCGCTGCTGA AGAAGGGCTC GCCGCCGCGG CAGCGGCTGA GCCGGGCGGT    300
GCGGCGGCGC AAGAGCGCGG AGGGGCTGCG GGCGGCGGGC AAGCCACGGC GGCGGCTGTC    360
GTTCTCTGCG CAGTCCGGGG AGAGCTACGC GTCGGTGCGG CCGCGCAGCG CGGGGGGGGG    420
CGAAGAAGGT GCAGTTCTCG ACGCCGCAGC TGCTGCCGGT GGACCTGACG CAGGAGCCGT    480
CGACGTTCAC GGCGCTGGAG GCGAACGGTG GTTGCAGGAC GTGAACAGCC TGTCCGCGCT    540
```

-continued

```
GGACGGACGC CGGAGGAGGG GAGCTGCAGC CCGCGTCGGC GCTGTCGTGG CAGGCCACGC    600

ACACGCCGTC GCTGTTTGCC CACCCTTCCC NGTTGGCCGT CCTTACGGGA ACCTGCTTGN    660

CGCTTTTGCC CCGAATTGCA GGTTCGAAGG GCTTNCCCCG CGNGGGCNCN CCGCCCCCCC    720

CGCATCCCCC CCCGTNNCCC AAAATTTCAA GTTAACCCAA NAACATTCCC TTTCTGCCT     779
```

(2) INFORMATION FOR SEQ ID NO:452:

(i) SEQUENCE CHARACTERISTICS:
        (A) LENGTH: 763 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1327RP (xi) SEQUENCE DESCRIPTION: SEQ ID NO:452:

```
GATCCAAGCG TCTGGAGTAT GCTAAACGAG CGTCTCATGC CAGGAACAAC GTATTATCTC     60

GTTGAACGCT GTCCTCGAGC CTCGAGCCAA ATCTGACCGT TTTTTTGCTA GAGCATACCC    120

AAAAAGAAAC ATCTTGATGC GCTAAACAAC ATGACAATGA TTAGCGCGAG GATGCCTTTC    180

ATGTTCTAAA TTCATGCCTC GAGGTCCCAG TCGGTGCCGC ATGTAGTCCT GCCGGCCGAT    240

TATATTGCGG CGTAGCTGTG GTGAAACATC GGCGCTAATT GACGGATAAG CAGCTGTGTA    300

CCTTATTTTC ACTATTTCTT TTCACATACC AACGACTAAG GTTGATTCCA AGAGGTACTG    360

ACTGACCCAG TGGACAGCGT AGTTATCGGA GTAACTGGGC AATGTCGTAC GGGTTCTCGG    420

GGAGCGGAGG AATGGGCTGC TCAAGGCCGA CGACGCCGGA GCTGACGAAG GAGCTCAACA    480

TCCCCAAGGA CGTGGCGAGC GCCATGAGGA AGTCGCTGTC GTACGACTTC CTTAATGTGC    540

CTGGCGGGGA CGAGCAGGCG AGCCCATCGG GACGCCGACG ACAGCGACAG CTGAGGACGG    600

CGCCGACGGA ACTGGAAAAC CAAACCGGCG AANGGGCCCN AGGGCNGNGG ANCAANGNCG    660

GAAAGGGGGA ANTTTGCCGA NTACCNCTGT TGGCCCNCCC CCGCGGTTCC GANTTTGGGT    720

TGNCAAAATC CCCTCCTCAC TTNCAAACCT NCTGAGTNNA AGT                      763
```

(2) INFORMATION FOR SEQ ID NO:453:

(i) SEQUENCE CHARACTERISTICS:
        (A) LENGTH: 794 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1327UP (xi) SEQUENCE DESCRIPTION: SEQ ID NO:453:

```
GATCGGAGGC GTCGCTGGAG CGTGCTCTTG TTCTGTCTCT GCTTGGCTAC GCCCGACTTG     60

GCAGCCGCGG CGCTCCTGAG CGTCTCATAC TTGCTGCCTG CTACTTGCAT GGTTTCTATC    120

GTCACGGTGC AGCAACTGGG ACAACAGCAC CCAGCAACGG TTGCATTTAT ATAGTGTCTA    180

CCTGTACGAT AGGGGACTGA TCGCTCTGCG ATGCGTATCT ATCTCATTGC GGAAGGTTCT    240

CGAAACGAAA AGCGCCAGTC GCTGTCGAGC GACAATAGCG AACCACAATG ACACAATAGT    300

GCGCGTCGGC GACCCGATCC CTGCATGAAG ACCGAATGCT CGAGCAGATT CTTGTGCGGG    360

CGTCAGCGGG TAGCGCGGCT CGTCGTGTGG CGGAGCCCGG ATATGCGATG GCACCGGATG    420
```

```
GCGATGTGCT CGGCGCTCGG GATTAATCTA GCTCTTCGGA GATATGCTTC TGTAGGAGGA      480

AGAGGGCGTA GGGAGAAGGC CTGGACGCGG GCTTGGGGAG CTCTGCAACG TTGCGGGGGC      540

GTGCCGCCGT AGGCGGCGGC ACACCGGGNA AATNCNCNGN GANCCTNGTN CCCTCCNTTC      600

CNCCCCCCAA ACTTGCGGGC NTTNCCCNCC CGAATNNCAA GGNNGNCCCC NAAATCCTNA      660

ACCCCCCGNA GGAAAGNNTT GGCCTNTTGA NCAAANNACN CGCGTTNAAA NTCCCGGGGG      720

TTTGNGGCCC CCGAAAANGG GGATAAACCN GGCNACNACC TTTTGAAATC GCGTTTCNTT      780

TTNCCCCCAN ACNT                                                       794

(2) INFORMATION FOR SEQ ID NO:454:

(i) SEQUENCE CHARACTERISTICS:
        (A) LENGTH: 757 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1328RP (xi) SEQUENCE DESCRIPTION: SEQ ID NO:454:

GATCTCTTCT GCAAGTTTCT TTATCGGAAG CCCAGGCTCT GGATTTCCTT TCTCAACACC       60

AATGGTATTG TCTTCGATAT CAGAGAAGGA GCGCTTCGAA TTTTGCGCAC CACCATATGG      120

ACTCTCTTCA TTATTTTCGT TATTTTCTCC ATCACTTTCG CTTGCCAAAG AAGAATCCAT      180

CGCACCCATT ACATCGAATT CTTCATTATC AGCTTCTCCA CCTGTTGTAG TATTTCGTTC      240

ACCATTATTA TCCTGTTGCT TATTGATTGC ATCACGGCCC ACACGGCTCA TTTGTATCAT      300

GCTAGATGTA TATGGGACAT AATCCACCTT TTCCAACAGA GGACCGAATC GCTCAACCAA      360

GTATTGATTT AAAACCAGGA AGTTCTTTGT ACTGACCTCG GCATATTCCT GATCTTGCCC      420

GAAACGTGCC GAAATTACCT TAAATAAGTC GAGCACGCAT GAGTTGGCCA TGTTATCAAA      480

GTAAAGATTT TCTTGTAGCA GCTGACAAAT TGGATCAAAA AGATCTTAGA TATGAGATAG      540

TTGTGATAAA ATTCATCATT TACAGCCACG ATACCCTTGA TACCCGAACT GCAGCCAGCC      600

TTAACTGTAT AATATGGATG GTTCCATTAG TTTCCAATAG TCAATAGATG CCATTTTCCA      660

ATATNAACCC CCCTTGACAG CATAATATCA GTTCCNTGTT NTNATAATCC CCCCATTTTA      720

CCAAACCNGC NCNGTTGATT NCCCNNCCTC CACCCCT                              757

(2) INFORMATION FOR SEQ ID NO:455:

(i) SEQUENCE CHARACTERISTICS:
        (A) LENGTH: 794 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1328UP (xi) SEQUENCE DESCRIPTION: SEQ ID NO:455:

GATCGGAGGT ACATAAGTGC TCTACCGACC AACCCCGCTC TCCATGCATC AACCAATGGA       60

GTTGAAACAG TTGACTGGCG AGCAGGCCGC CGCACTAGAT GCGGAACTCA TGGGCCCAGA      120

CGTTGGCTAC TCGCTGCATC AATTGATGGA GCTAGCAGGT CTTGCCGTGG CGCAAGTCGT      180
```

```
CGTGCGCCAT TGGGGCGCCG CACAGGCGAA GAAAAAGGTG CTTGTGCTAT GTGGGCCTGG      240

CAATAACGGC GGCGATGGCT TGGTTGCTGC ACGGCACTTG CGGCTCTTCG GCTATGACCC      300

TGTGGTCTAC TTGCCGCGGC TGTCGGCCAA ACAGCCCTTC TACGCACAGC TTGCCAAGCA      360

GCTACACTTC GTCGGTGTCC CAGTGCTCTC CGAGGGCGAT GACTGGCGTG CGCATCTTGA      420

GCCACGTGAC ACGCTCTGCG TTGTGGATGC GCTCTTTGGC TTTTCTTTTC GTCCGCCGCT      480

GCGCGAGCCC TTCGCTAGCA TTGTCGCAGA GCTCAAACGC CATGAGGATG ACATCCCAAT      540

TGTCGCTGTC GACATTCCCA GTGGTTGGGA CGTTTGACGC AGGACGCTCA CCCCTTCAGA      600

CTTATGCACG TGTGCTGATN TCTCNTGAAC GCCCCCCAAA AGCTGCTCCC NCNCACATTG      660

AAACTGGTTT TTTACCNCCC ATTANTTTCG GNGNNGTTTC ATCCCNAANC CCCNGCCCGN      720

CCTCCNTGTT TTTANTCCNT CCCCGTATCC TGNNCCCATC CANANTGCGT TTTTGANTTG      780

CCATTGCNTN ATCT                                                       794

(2) INFORMATION FOR SEQ ID NO:456:

(i) SEQUENCE CHARACTERISTICS:
        (A) LENGTH: 176 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1329RP (xi) SEQUENCE DESCRIPTION: SEQ ID NO:456:

GATCCCGTAC GCGGTGCTGC ACTTCGGGTT CTTCGCGCTG GGCTTCTCGT TGCCGTTCGT       60

GGCGGTGTAC GTGCAGTTCA AGAAGGCCGG CTTGTGAGTT AAGTAGAATA TAGTCTAATG      120

CTATGCAGGG CCGCGGGCCG CGCGCCGCGC GGCGGCGCGG TCACGTGACG CGGATC         176

(2) INFORMATION FOR SEQ ID NO:457:

(i) SEQUENCE CHARACTERISTICS:
        (A) LENGTH: 176 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1329UP (xi) SEQUENCE DESCRIPTION: SEQ ID NO:457:

GATCCCCGTC ACGTGCCCGC CGCCGCGCGC GGCGCGCGGC CCGCGGCCCT GCATAGCATT       60

AGACTATATT CTACTTAACT CACAAGCCGG CCTTCTTGAA CTGCACGTAC ACCGCCACGA      120

ACGGCAACGA GAAGCCCAGC GCGAAGAACC CGAAGTGCAG CACCGCGTAC GGGATC         176

(2) INFORMATION FOR SEQ ID NO:458:

(i) SEQUENCE CHARACTERISTICS:
        (A) LENGTH: 767 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1330RP
```

(xi) SEQUENCE DESCRIPTION: SEQ ID NO:458:

```
GATCTTGGAT TTGACATTGT CAATGGTGTC AGAGGACTCG ACCTCAAGCG TAATAGTTTT      60

CCCTGTCAAA GTCTTCACAA AAATCTGCAT ACCTCCCCTC AAGCGCAACA CCAAGTGCAA     120

CGTAGACTCC TTCTGGATAT TATAGTCGGA CAACGTGCGG CCATCCTCTA GTTGCTTACC     180

CGCAAAGATC AAGCGCTGCT GGTCTGGGGG AATGCCCTCC TTGTCCTGGA TCTTCGATTT     240

GACGTTGTCA ATGGTGTCAG AGGACTCGAC CTCAAGCGTA ATAGTTTTCC CTGTCAAAGT     300

CTTCACAAAA ATCTGCATAC CTCCCCTCAA GCGCAACACC AAGTGCAACG TAGACTCCTT     360

CTGGATATTA TAGTCGGACA ACGTGCGGCC ATCCTCTAGT TGCTTACCTG CAAAAATCAA     420

GCGCTGCTGG TCTGGGGGAA TGCCCTCCTT GTCCTGGATC TTGGACTTGA CGTTGTCGAT     480

GGTGTCAGAG GACTCGACTT CGAGTGTGAT TGTCTTTCCC GTCAAGGTCT TGACGAAAAT     540

CTGCATACCA CCTCTCAAAC GCAACACCAA GTGTAAAGTA GACTCCTTCT GGATATTATA     600

GTCGGACACG TTGCGGCCAT CCTCNNNTTG CTTACCCTGC AAAAATCAAA CGCTGCTNGT     660

CCTGGGGGAA TGCCCTCCNT GTCCCTGATT CTTCNANTTT GACATTGTCN ATGGGTNCCN     720

AAGANTCCNC TCAATTNTTG ANTTTCTTCC CCGNCAGGTN TTGAANN                   767
```

(2) INFORMATION FOR SEQ ID NO:459:

(i) SEQUENCE CHARACTERISTICS:
        (A) LENGTH: 794 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1330UP (xi) SEQUENCE DESCRIPTION: SEQ ID NO:459:

```
GATCAGATGT TTTGTGCTAG TACGTCGCGA TAGTACTAAA ATTACCATAT GCCCATCAGC      60

ATTATACTAA CTAGTGTTGT TTTGCAGTAA GCGGTAAACC ACCCATTACG CCTGTTGTAT     120

CACCAGAATC CAAATGCGTT TTTGAAAAGA GGTTAATTGA GCAGTATATC GATGAGCATG     180

GGGTAGACCC AATCTCCAAG ACAAGCTTGA CTAAGGATGC GCTAATTGTC ATTGCCCAGA     240

CACCCCAGCA GTACGCGCTC GCAAACGCAG TTAACTCGGC TACGCTCAAC GCCAATTACA     300

GCATCCCCAA CCTTCTGTCA ACACTACAAA ACGAATGGGA TGCCGTGATG CTGGAGACAT     360

TTGAGCTGCG GAGTCAGCTG GATATGTGCA AAAAGGAGCT ATCGTCAGCG CTGTACAAGT     420

GCGACGCGGC TATCCGCGTC GCGGCACGCG CGAAACAGGA GAATGATGAA CTCAGACACA     480

CGTTGACGGA GCCTGACGGA GGCAGTCGGC GGGCAGGCTG CCGATGCCCC GCCCCTTCCA     540

GCGGAATTGA TTACCGCGAT GGCAGAAACG CACAAGAATA TGTGCAGCAA ACGAAAGAAA     600

GAAGGAAATG AAAGCCAGGT AGTGACGGCA TTTGCTCCTG GAACAGCCGG TCCAAACGGG     660

NTGCGAGGTC AACCGGTTTT TTGGTTACCC GTTTNNTTGG TTCCGGAAAA ANAATTANCT     720

NNCTTTTTAA CCCAAAGGCA GGGCCNTNTT GCTGAACAAA AAGGGTTTTT GCTNCTNNAA     780

AATTNGCCNC TNAC                                                       794
```

(2) INFORMATION FOR SEQ ID NO:460:

(i) SEQUENCE CHARACTERISTICS:
        (A) LENGTH: 776 base pairs
        (B) TYPE: nucleic acid (C) STRANDEDNESS: single
        (D) TOPOLOGY: linear (ii) MOLECULE TYPE: DNA (genomic)

(vi) ORIGINAL SOURCE:
        (A) ORGANISM: PAG1331RP (xi) SEQUENCE DESCRIPTION: SEQ ID NO:460:

| | | | | | |
|---|---|---|---|---|---|
| GGATCATTCT | CAGGTATTAG | AGATTGCTGA | TGGGCACGCG | CTTTTTCTTC | AAGGAATTCG | 60 |
| ATCGGAGGCG | CCTCTAGAGT | TGAAACGAGT | TTATTATACT | CAGCCATTGC | TACAAGCATA | 120 |
| TAATCAATAG | CCGCAGCGCA | ACTCTGAAGA | TGATCTAAAG | AAGGAGCATC | TGCCTTTTCT | 180 |
| CGTAGAACAT | TGAGAGCGGT | TGCCTCTATA | ACTTCATGCT | TATAAGTGGA | AGCACTCGAA | 240 |
| ATAACATGTG | ATAAAGGTGG | AGAGTTGGCC | AATGTGTTCA | AAGCTTCTAA | TTCTGAAACG | 300 |
| GAAATTAGTG | CATACCCAGC | AGCTGCAGCT | TTATTCTTCA | AATGATCGAG | AGAAGGTGAT | 360 |
| TCGGCTACTG | TTCTCAAATC | CAGAAGAACG | TTCGAATCAA | GGATTTCCAA | GTTTCTTTCA | 420 |
| GATGCATGTT | TCTTGAGGAA | GCCTTCATCT | GGGCTCTCCG | TATATCTGCT | TCAACTCATC | 480 |
| CATAGTAATC | AGCAGAAATG | ACAATCCATA | TATGGTTCTT | GGCTTTCGTT | TGTAGTTAGT | 540 |
| CGATGGCTGG | ATTTTCCCAT | GGTAGAAAGA | AGAAATATCG | TGCTCTTTCTT | TTCAAACAAC | 600 |
| AAATATCATA | TGCCCTTGGC | TTTCTCCTGC | CAAAATTCCA | AAATTAGANA | TTTCTNATCC | 660 |
| CCTTTAATAN | TTCCACATGT | TCCCAATTCC | TCCCATNANA | TNACTGTCTA | ACTGTTTGTT | 720 |
| GCNNACCCAA | AAANATTCCT | TCCTNTCCCT | TTTCCCCANA | TGCTCCTTTN | CCAGTC | 776 |

(2) INFORMATION FOR SEQ ID NO:461:

(i) SEQUENCE CHARACTERISTICS:
        (A) LENGTH: 808 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1331UP (xi) SEQUENCE DESCRIPTION: SEQ ID NO:461:

| | | | | | |
|---|---|---|---|---|---|
| GATCGTGCGC | CTGCTCCACG | AGCGGCTGCC | CAAGGCCACG | CGCTCGGACG | TCGCCTGCAT | 60 |
| CAAGAGCTAC | GTCTACGGCG | ACGGGCTGGA | CGAAACCCCC | TGGTGCGCCT | CCCATGCACG | 120 |
| CCCCCCGGAC | TGCCCCGCGC | AGTCGCAGGA | ACGCCAGGGC | ACGTGCGGGC | CGGGCGACGA | 180 |
| CGAGCTGCGC | ATCTTCACGC | TCTCGCAGCT | GCTGGAGGAC | CAGTCCGCGT | CCGAAGATGT | 240 |
| CATCCCCGAT | AGCATGGATG | CGGGCGACGC | GGTCAGCCTG | GGCTCCCCGC | AGCCCCAGGC | 300 |
| AGGCCTCTCG | CAGCACAGCT | TCTGCCCAGA | TTCCACGCAC | GCGTCGCCCC | TTGGCGCCCG | 360 |
| CCGGTTAACC | CCCTTGACGC | GCGCGCCCGC | CTCCCCACTC | CCCGTCCGCG | TGTACACCGC | 420 |
| GCCCGCCTCC | CCGCTTGACT | ACATTCCCGA | CAGCAAGGGA | TGAACCCCTA | CGTCCTCCAG | 480 |
| GGCCCCAGCC | AGGCCCGCAG | CCCGCCCTCC | CTGNTTGAAG | GTNNGAANGC | CACCCTNCCA | 540 |
| AAANTTTAGG | GGTNGNGGCC | CNGGGCCGCT | CAACCGNTTG | GCGTCCGNAA | AANCCNNTGG | 600 |
| CGGCGTNNCC | CCNNCTTTAA | GGCGGCNTCG | AACNCNGCNT | NTTTCGGGNA | GGGTTTCCAN | 660 |
| ACNCAAACNG | TNNNNCCCCC | CCTTTTTTCT | TCNAANAAAG | GCCTNTTTGT | GTCNNTTCCG | 720 |
| CCNGGNNGGN | AATTTTNTTT | TGTGGGGCTG | NNCCCTNAGA | AAACNCCCNC | NGGGNCNNNG | 780 |
| GGGAAAAAAA | AANTTTTTTT | CCNTNGGT | | | | 808 |

(2) INFORMATION FOR SEQ ID NO:462:

(i) SEQUENCE CHARACTERISTICS:
        (A) LENGTH: 762 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1332RP (xi) SEQUENCE DESCRIPTION: SEQ ID NO:462:

```
GATCTTTTAT GTTCCTTTAG AGCAAGGTCA ATTTTCACAC CACTTCTATC ATCTTATATC      60

CAGAATAATT TGAACAAGAA GGTACCGTCT AGTGAACGAC GTGATTTCAT GCCGGCGTCC     120

AAGGTTCATG AGTCATTACT GAAAATGAAG CAGCACTATA TCGAAAATAG GTTGCTCGAA     180

CTACAAAAAC TTCATCAGTT ATTCTGTAAA GATAACGTGA ATTTTTCCAA AAAAATGATA     240

AATGTCGAAG AAAGAAGAAT CGTAAATCTT CTAAATGACC TAGATGATGA TGCTAACTTT     300

ACTTTTGAGA CTGTCCATAC TAATTTTGTG AATAATGAAC TATTCATGGA ACTACATGAT     360

CACAAGTCAG TGATATCGCG CGTTTGGACA TTAGATACTG CGGAGGATTG CAATCGCATG     420

AAGAAAAGGT TACGACCATA TACACTCAGC TCCTCGACTA TTTCAGGCTC AAGTTGTCCA     480

ATATTGATGT AGATCCAACC GCCACTATGA ATTTNAGTTC CGAAACTCCN TTGANCAGTG     540

TTACCTCCTT ATTGTGTTTG TTACNCCAAT TGATCCCTCC ANTTTCCGAT TCTGGAAAAT     600

GGNGGAAAAC CNNCGAAANT GCNGAAAAAC CTAAAANAAG GAANACCGTT AACNGGGTTN     660

GGAATGTCTA TTGGGGGGGG GCCNNANCTT TTAAAGNNNC TTTCNNGGGG AANANNCCNN     720

NCTCCCNTNA AANTTTTTTC CCCNGGGNAA AAANTTNTCT GG                       762
```

(2) INFORMATION FOR SEQ ID NO:463:

(i) SEQUENCE CHARACTERISTICS:
        (A) LENGTH: 798 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1332UP (xi) SEQUENCE DESCRIPTION: SEQ ID NO:463:

```
GATCTTTTTC AGACGCAGTG TACTATCGAT GAAGCATATG ATTATTATAC AAAACTTCTG      60

TCCGATACTA TTGCATTAAA CCCGCTTAAT AGAAACGAAT TTTTGGAAAG TTGCGACACA     120

TTAGAGATGT ATGGAGTCGC TTCTATTGAA AATGGCAAGA ATGGCAAAAA GGCCAAACAA     180

TTGGTAAAAC TGATCAAGAG TACAGTTGAT GAAAAGGAGT TCCATGATGA AATATGTNAG     240

ATGGACTTGC TTAAGAAATT GATAATATAA AAGGCTACGA GCTTCAATAT TATAATACGC     300

ATTGCATAAT TTATTACATT AAATTGATAT AGGTATATTT TCTTCGAAG AATTAATTCT     360

AATCATTTCC ATGTGAAGAT ATCGCCCTCT GTGTTACCTG CGGATATTTC GACTCTTAGT     420

ATATCTACAT ATTTTGGCGA GCCATTATTT AAACTCGCCA GCTTGACTCT GGACCCAAGA     480

GCCGTAATGG CAGCAGCTCT TCCTGAGCGC AATTTCTTCC AGCAATTGAG GCACCATGTG     540

CCGTCCTTTA ATTCCAGCAC ATATAACAGA CCGTCCCGTC CAATAACCCT AACACAATTA     600
```

```
TTCCCTTTCT TTCCCATCAT GTTTCCGATA CTGGACATTC CCTGAAATGC AANTTTAACA    660

AGCCTTATAC CAGTGAAATC NTGCGTTTTG AAANATGCCN TGCCAATTTC AACCCGTGAG    720

GTGCGTAACC TGAACTTTTT TTGAAATTTC AACCCCCCCA ATNANTNTTC NTTTTTGNAA    780

CCCCATGCCT TGTTCNCT                                                   798
```

(2) INFORMATION FOR SEQ ID NO:464:

(i) SEQUENCE CHARACTERISTICS:
        (A) LENGTH: 138 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1333RP (xi) SEQUENCE DESCRIPTION: SEQ ID NO:464:

```
GATCACCGGG TGAATATGCT GCTTGGCATA GTTGATATAC ATTGTGAGAA AGTGCACCGG     60

AAGGATGTCC GACTCGGACA CATGGGCGGG CTTGTCCTCT AGGTAGAGGC TGGTCAGGTG    120

CTTGGCTAAT TCTCGATC                                                   138
```

(2) INFORMATION FOR SEQ ID NO:465:

(i) SEQUENCE CHARACTERISTICS:
        (A) LENGTH: 137 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1333UP (xi) SEQUENCE DESCRIPTION: SEQ ID NO:465:

```
GATCGAGAAT AGCCAAGCAC CTGACCAGCC TCTACCTAGA GGACAAGCCC GCCCATGTGT     60

CCGAGTCGGA CATCCTTCCG GTGCACTTTC TCACAATGTA TATCAACTAT GCCAAGCAGC    120

ATATTCACCC GGTGATC                                                   137
```

(2) INFORMATION FOR SEQ ID NO:466:

(i) SEQUENCE CHARACTERISTICS:
        (A) LENGTH: 766 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1334RP (xi) SEQUENCE DESCRIPTION: SEQ ID NO:466:

```
GATCATAATC CAGTCGCTGT CGAGATACTC GACAGGAATG GACGTCAGCG ATTTCGTCGA     60

AGAGCGCCGG AAAACCTTGT CCGTTGGCTC CGGCGTTGCG GTGAGCGTCC CGGGCGGCGT    120

GCCACCGCTC GACTGCAGCC GCGCACGCTT CCGCATTATC TGGTTCATGG AGAATAGCGA    180

CGATACTGGA CGCTTCATGA TGCACTTTAA GGCCACAACC TCGGCCGTAT CATGCTGGCC    240

CCGCCGGCAC CCGGCCACCC GTCGCCCCCG CAGGACAGTC CCGAAACGGC CTCGTCCTAA    300

CCGACCCTCC AGCATATACT GGTTCACCTG CACGCTTTCC CGGCCCCCTA TCAGCCGTGT    360
```

| CGTCTTTTGC AGCAGAACCA TCTCCACCAG CTTGTTATAC TCCTCAAATA ACGCTGCGTA | 420 |
| TGTTACTGCG TCCCCGCCGC AACCGCTCCT CCCCAACACC GTGTCCGTCA AACGAGAGCT | 480 |
| GCTACGGCTG GAGATGCTGC GCAGCAAGAG AGAGTGTCTC CCTTCATTGA ATTGCACGAT | 540 |
| AGTAGGGTAC GAACTCATGC NCCCTATGCC CTACACCATG NANCTGGTTT CTATTGTTNN | 600 |
| TCNGGCCCCC NATNNCTGTT CCAACTNTTN TTANCTGGGC CACNTTTTTT TNTGGTTGCC | 660 |
| CCCCGAACCT CCTTCCCTTA ACCAATCCTG GCCCNCTTTC NCAACAGGAA ACCTTNTGAA | 720 |
| CACTTTCCCC NAAANGTNGC GAANAAAAAN TTTTTTTNAT TNCCCT | 766 |

(2) INFORMATION FOR SEQ ID NO:467:

(i) SEQUENCE CHARACTERISTICS:
        (A) LENGTH: 796 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1334UP (xi) SEQUENCE DESCRIPTION: SEQ ID NO:467:

| GATCCTGCGC GGCTCCGGCG AGCCGGACAG CGCCGCCGTG GCCATTCTGG AAAGCGCGTC | 60 |
| CGCCGGCGGG CCGCCGGTGC GCGGCCTAGT CCGGGCTGTA CAAGTCGCCC CGAACAAAAC | 120 |
| GCTTTTCGAC ATCACTCTCA ACGGGCTGCC CGGGCCTGCG CAGTACTACG CCTCGATCCG | 180 |
| CGCGTCTGGT GATGTGTCCC GCGGCGCGGC GTCCACCGGG CCCGCGTGGC ACGTGTTCGA | 240 |
| AGACGCCGTC GCGTGCGAGC GCGCCAGCCC GCTCGGCGCT GACCTCTGCG CGGGCTCCGC | 300 |
| CCTGTTCGTC GCGCCGCTCG CCGTGCAGGC GCTGATCGGC CGCGGCTTCC TCGTGGGCGC | 360 |
| CGACCGCGGC CACGCGCTCG CCGGCGCCGC CGCCGTCGGC GTGCTGGCGC GTAGCGCCGG | 420 |
| CGCGTGGCAG AACGACAAGG TCGTCTGCGC GTGCTCCGGC GACACGCTGT GGCAGGAGCG | 480 |
| CGGCTCCGCG CGCTCCGCGA ACATCGCATG AACTGTATAC TACATACCTG CTACGTTGTG | 540 |
| CTCGCGCCCC CCGCCAAGCG CTNCCTCCAN CCGGGGGGGC CCGCGGGGCC TTCCAACTCA | 600 |
| CCGCCGGGGG GCCCGCGCTG GCCCGAAAAC CCCCTTCCGC AACGNCCAAN AANNCCANNC | 660 |
| CCNTACNACN CCCANTTANC CAACACNTTC NTCAACGGGT TNNTNGCCCC CCCCCGNCNC | 720 |
| TTCTCCGGNG TTTTTTTTTT CCGGANNATT NCTGNTCCCN CCGTNTCCCN CCTTATTTTG | 780 |
| NNNGCCCCCC CCCCCC | 796 |

(2) INFORMATION FOR SEQ ID NO:468:

(i) SEQUENCE CHARACTERISTICS:
        (A) LENGTH: 791 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1335RP (xi) SEQUENCE DESCRIPTION: SEQ ID NO:468:

| GAGGCAACGG AGGTGGCGGT GGTATCAAAG GTCTGGTAGT CGCTATGTCC TTTCCGAGCT | 60 |
| TTTGGGGTTT TGTGGTCTTG CTTTTGTTGG ACGCTAAGGT TGGGCGCGGC GAAATCACAT | 120 |

-continued

```
GCAGTGGGCG CGATTCCAGG TCCGCCAAGT TAATGGGANA CACCGCGCCG CTCAGCATAG      180

TGCTGTGGGT CCTCCTATGT GATTGCGACC CAAACGTATG GTCCGCCCTT GGGTTGTCAT      240

TTTCTGACGT TGTTATTCCC TCCGGGCCAC TAAAACTGCG CCTACTCTGA TTCTCTGTCA      300

GTAACGCAGA GTAAGACACA CGCTTGCTTC GTGTGAGCGA TAGTGTGCGA CATAAATTAC      360

TATGCGGGGA NCCNTNCCAA NTTTAACCTN TGNNAANAAA ANACCCAAAC TNTTTCAAAA      420

CCCAAANTTC NATTTNGGGN NCNGAAAATN CCGNTTGGGN AACCCCCCGT NNNGGGGTTT      480

AAATGGGGTT TCCAAAAAAA ACCCNCCANT TTTCCCCCCC CCCCCNAAAT TNTTAAAAAN      540

NCCTTTTAAA AANNTNNTTT NTGTGGNGNC CCCCCCCCCC CCCNAAAAAA AATCCCCCCN      600

AAAAAANCNG GTNTTTTCCC CNTNGGGGGG AAACCCCCCC NAAAANNCNN ACNTNCNANN      660

NNGGGGNCCC CNNCCCCCCN ANCNCNNTGG TNCCCCCCTT TNANAAAANG GNCCCCCAAN      720

CNTTTTTTTN NNNNNNNNAA AACNCCCTTT TTCNNCCCCC CCCCNNAAAA AATTTTTNNN      780

NTNNNTTTTN G                                                          791
```

(2) INFORMATION FOR SEQ ID NO:469:

(i) SEQUENCE CHARACTERISTICS:
        (A) LENGTH: 807 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1335UP (xi) SEQUENCE DESCRIPTION: SEQ ID NO:469:

```
GATCAGATAA GAATTGAAGC TCAGCGGCTG ATGAGCGCAC TGCTTCCGAT ACGGTGGTCC       60

TGTACCAGGC TGATAAAATG TGACACTATC ACCATAATGG GGTTGTAGCT GGATACGATG      120

TCCGGATGCG GATGGACTGT TCTGAACAAG ACGTGCAACG TGCGAGGCCC ATAGTGGGAA      180

ATCTAATTAA CGTATTTACA TATCAGTGGC GATGTGTCTA GGTGCCGGCC ACCTCGATTT      240

CCTGTCACTG GACAGCGCCG TCATATAAAC ATTATTGTTT AGGGTTTAAA GTTGCTTTGT      300

GCGGTGGAAA ACAACGTCAC ACACTAACTA AATCTAACTC GAGCCAGCAA GCAACTATGT      360

TAAATAAGCC GAACAGTTTA CGATTCCAAG GGCACGGTGG AACCCCCCAA GGCCCCGCTC      420

CNANTCNTTC CCTTACAAAA AGGGAGGGGG GCCCTACCAC TACCGAAACC ATACNGGTTN      480

NAAACAACCC NAANCCCGTT TTTCCCCCCC CCAAAATTAA ANANTGGGCG CCCCCTGNNC      540

NCNATTTGTT NNTNTNANGG GGANAGGACC CCCCCCCGGG GNNNGGNTCC CCCCNNTCNA      600

AAACCANNAC CCCCACCCCN ANAAAAANGG GGGGGGGGN GGAACNCCCC GATTTCTAAA      660

AAATTTAAAA ATTNNNNGAA ACCGNAAAAC GGNGTGNNCN TNCCCNNNNG AAAAANGTTT      720

TTGTNGNNNA CANCCCCCAA CNTTNTNAG NNNCCCGNNC CCCCAAACNN AAAANTTTNC      780

TNGNANGGGG AACCANTCCC CCCCCNT                                         807
```

(2) INFORMATION FOR SEQ ID NO:470:

(i) SEQUENCE CHARACTERISTICS:
        (A) LENGTH: 782 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
            (A) ORGANISM: PAG1336RP (xi) SEQUENCE DESCRIPTION: SEQ ID NO:470:

GATCATGTTT AACCCAGATA CGAAAACTGA GAAGCTAGAG TGGATAGAAA AGCTGCGAAA    60

AGTAATAGAG CTGAACAGGT TTCACCAACC ATGGGTTAAA AAGTTCTTGA ATAGCAGTGA   120

GAATATTCTC TGAAGAAAAG CATGACCACA GGATTACATA GAGTAACTTT TGTGCAAAGT   180

TTATCTGTAT GTACAATTTC ACGTTATAAA TTTTAAAAGT ACTCGGGCAA AATCGGCACT   240

TGGTAGCGAT AACGCACACT CGAGTGAAGT CCATCCAGTA CATAAACATT ATGTCAACTA   300

CTTACCATTA TTGCCATTGC CAGATGAAGT ACCCATGTTC TGGTGATTGC CTGACCCATT   360

GTTACCACTT GCAGCGCCCA GGTTTGGGGG AATCATGCCA GGAAAGGGAA AGGGCGGGAA   420

ACCCCGAACA TGGGTGGCAT ACCCATGGGA AACGCCAGGC GGCTGCGGCA GAGAACCGTT   480

GTTTTTGTTC CGCCAAATTG AAGTTCTTTG GTTTNCCNNN CCCCCCGGCA AAANCTTAA    540

CCCCGTCCCC CNGCCCCCNN TCCCCCAANC TTTCCCNNTG NNGTTGGAGC CCCCAAACCC   600

CCCCATATNT TNNCTGCGCC GGGGTTTNTN CCCCCGGGA GACCCCCCC CGCNTTGTGN    660

NTNTTACCCC CACCCNCCCC CCCCCCGGAA ANCCNGTNTT AAAAAATNCN AANAANNTNT   720

GGCCCCCGNG CTCCCCGGGG CTCCCNTATA CCCCCCGGNN GTAAAATNNC NAAGNGGNCC   780

CN                                                                 782

(2) INFORMATION FOR SEQ ID NO:471:

(i) SEQUENCE CHARACTERISTICS:
        (A) LENGTH: 793 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1336UP (xi) SEQUENCE DESCRIPTION: SEQ ID NO:471:

ATCGCCATTT TAGGGATGAT CCCGATCACC ACAGCTCCGA GGCCCTTGTA GAAAGCCAGC    60

AAGCCCTCCC CGCTGTAGAT GTTGGCCCCC GTGCGCAAAA ACCCAGGGGG CTTCGTGCCC   120

TCGTTCGCGC GCCTGTAGAT CTGCATGCGC ACCTTGATCG TGTCCAATGG GTGGCAGCAG   180

AGCGCCTCAA ACAGGCCCGC GGTCCCGCCC GCAACTAGGT TCACGGCCGG GTTGGTAGAT   240

TTCTTAGACG ACATGTGGTT ATCAGGGTAT GGCTGCTGGC ACACTGCGCT GCACGGATCC   300

GCTACGCTTC TGCGTCGCGC ACCTATATAT ACAACGGGCA CCGACGGCGG GCCGCCCGCA   360

CCTTGTCTCC GACGCAGCGC CAATAGGAGC TCGCGCATAC CCCCGGGCGA ACGCGGTGAG   420

TCAACCCGGC CCGAAGCGCG GGCCAATGGA ACCGTCACGT GAAAAGCAAA GACTTAAAGT   480

ACTATGTAGC TACACACTTA GGCCTCGGCC ATCTCGCGCA GTCTGCGGAT CGTGGAGCGC   540

ACGTCGCGGC GGCAGCCGTG GAGACGTGTT ACGCACCACC GGCCACAGTC NTCCTTTGCA   600

CNAACTTGCA NTTCCCAAAN NCCCGNAGCG CCGCGCTTCN CCGCCTTCTT TGCCGCAAAA   660

AGAACATCCT TACCAACTTC TTGTTGCCCT NCCACTTCTT NAACCTGTTT CCNNCACGAA   720

NAANCCTACC CCCCCCCNTT TTNCCGNNAA TCCNACCTTN TNCNTNCTTT TACCATTTNT   780

NTTNAAAGGG TGN                                                     793

(2) INFORMATION FOR SEQ ID NO:472:

(i) SEQUENCE CHARACTERISTICS:
    (A) LENGTH: 767 base pairs
    (B) TYPE: nucleic acid
    (C) STRANDEDNESS: single
    (D) TOPOLOGY: linear (ii) MOLECULE TYPE: DNA (genomic)

(vi) ORIGINAL SOURCE:
    (A) ORGANISM: PAG1337RP (xi) SEQUENCE DESCRIPTION: SEQ ID NO:472:

```
GATCTTAATT TAAAATTTTA ATTAACTATT TATAATTTAG AAATATATAA TCTAGAGATA      60
TATAATCTTA AAATCATAGG TAAAAATACA TAAGATAGTA AGAATAAAAT TAGTAAAATA     120
AATAGAAAAC CATAAGTTAA TTGATTCATA AGAAAAATG GAATTATTTG TGGCATCTTA      180
ATTTTTATTA TTTAATTGAT TATTATCTAT TTAACATAAA ACATTTTAAA ATGTTATAAA     240
ATAAATAAGA AATTACTTAT AGAATATTTA TTAAATAGTA TTTAATTTAA TTTTAATATT     300
AAATATACCA TTTTTATTAA TAAATAGATT ATTAAGTTTA TTAATATTAA GTGATATATA    360
ATTTAATTTA TATAAATTAT TTAATTTACT TCATTGATAT ATATAATTAT TAAATGTACC     420
TTTCATAATA TTTATTTTTA TTAGTCTAGT AATATTTCTA TTTAATAGTC TCCCTTTAAT     480
TGGATATTAC TACCTACTAA ATATTTACCT AATAATATAT TATTAAGAAT ACTTAAATCT    540
AATAATTTAT TATCTAAAGG TATATAAATT AATTAAATCC TTTTTTATTA TTATTTAAAT    600
TATTATTAAT AGTAAATTAT ATTATTTATT TTATTCACCA TAATTTTTTT GATNATAATA    660
TATCCTTTNN TAAATGGGGA ATTTATNAAT AATTANCTTC NANGAATTTT AATGAANAAC    720
CCCCNTTANN ATAAAATTAG TTAANNNTGN NCTCAAAANN CCNATCA                  767
```

(2) INFORMATION FOR SEQ ID NO:473:

(i) SEQUENCE CHARACTERISTICS:
        (A) LENGTH: 799 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1337UP (xi) SEQUENCE DESCRIPTION: SEQ ID NO:473:

```
GATCAATTAA TAAATGGTTT AACTAATAAA GTTAATAATA AATCTATTAA TTATATAAAA     60
CTACCTGATT TTATTGAATC AAATAATATT TTCTTAATGA ATACTACTAA ATCATCATCT    120
ATTGAGTTTA TATTAAATTC ACCACCTCTT ATTCATTCAT TTAATACTCC TCTAATTCAA    180
TCTTAAAATA TTCTTAATTA TTAAATTATA TAATAAAAGT TAGTGGATAT AGTTTAATTG    240
GTAAAACATA TGTTTTAGGG ACATATATCT TCAGTTCAAA ACTGAATATC TACATATTAT    300
ATCATTAATA TAATAACTCT TTAATTAGAG TGGTACCACA AGAATGCTGA AAGCATTAGG    360
GGTGTGTACC TTAGCTCTCT AATTAAAGTT ATAAAATTAT CTTAACTAAT AAAAATAATT    420
AATTAAATAA ATAAATAATT AATTAAATTT AAAATGTTTA AAAAAAGAAA TAAATAATAT    480
GTTATATTTA AATAGATCAA AATTTCAACA ATTTCCATTT CATTTAGTAC TACATCACCA    540
TGACCAATGT TACATCATTT AGTTAATAG GGTTTACTAA TAACCTTTAN CCTTTTACCA     600
AANNANGGT ANTANTNGGA AAAATTATNC CCTTAATAAT AACCTTNATN AANNNATTNT    660
ATATACCAAA ANNTTNTGAN ATTTNAAAAA ATATNGGCCG AANCNNCNTA TTTTGNGTAN   720
```

```
CCCCCNCNTA CNCCNGAAAA AANGNTTACC CGTGTTCCCC CNTATNNTGN NTNCCCNAAA    780

ATAAAAAATG NGCCCCCAC                                                799
```

(2) INFORMATION FOR SEQ ID NO:474:

(i) SEQUENCE CHARACTERISTICS:
        (A) LENGTH: 771 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1338RP (xi) SEQUENCE DESCRIPTION: SEQ ID NO:474:

```
GATCAACCGC AACCCGTCAC TCANGTCCAG ACCGTTATAG AGACGGTCGT CGATGGCACT     60

ACAAGGCCGG CAAATGCTTT GCTTATGAAT AGCACGGTTG AGGTGATAAC CGTTAAGGAA    120

ATAGTGAAGG AGACAGTTTT CGTGACTGAG AAGGTGACTA ACTAACTCCA ATGCAAGCAG    180

AACGCTTTCT GTCTTTTTGT CCAAACCTAC CTGAACACCT AAACTTAGTT ATTACAACAT    240

GAGTTTTATT TACACAGTAG GGTGCCACAG CCACAGGAAA TATCCAAAGA AATTAGCTTT    300

GCCTTGATAA AAGATATTCA TCCCTATTCA GCGACCCCTC TAATACGCAT TCTCTAGAAA    360

GTTCCTTGGC TTTCATTTTA AATCCTCGTG CACCTCGTCC GTAACAGTGT CTATAGTATC    420

ATTCCGTATC ATTTCTGAAT GAAGTAGATT CCATATCAAC ACTTGCTTTG GTGGAAAGCT    480

CATTATTCTG AGCAGTAATG GCTTCACCTC TATCCTGTTC CAACATACTT TTTTTAGCTG    540

CCCGGATTAA CCTCCCTGAA TTCCCTTACG ATGCAGTCGA GACCCATGCC GATTTATCAA    600

ATTTATCTGT CCTTTAAANA ATTTTAAACC TTTGACNCCC CTATTATTAT TTTTTAGCNT    660

ATCGTAATGC TGCCNGANCC CCCNAANGAN ATGGGGTTTT CCNTATTANC CTTTGGTTCC    720

CCAANTTAAA ACCCNCCCCG GNCCCCCCCC CCCCCCACCN GGTGGGANAA T             771
```

(2) INFORMATION FOR SEQ ID NO:475:

(i) SEQUENCE CHARACTERISTICS:
        (A) LENGTH: 796 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1338UP (xi) SEQUENCE DESCRIPTION: SEQ ID NO:475:

```
GATCAGGTTT TCCGGTACGT GAGAACGTAT CTAAGGCACA AAGGGCTTTG GGCGACTGTG     60

CGGACGCTTG AGTTGCNAGA TACAGGACAA AGCTGTTACG GCGGCAACTG GTGCANCACG    120

AGCAGCCGAG GAGCGATTCT GCGCGAAGCG ACGGTGAATT CGAGCCAGCT GGTAGCAGGA    180

GTGCCGGATC GTCTATTTAG TTGCGACGGG CGTCGGAACA GGATGCACGT AAACGTTGCG    240

GTAACACGCG ACGCTGACGC GACGGCTGCT ACGCCGATAG CACGGGAGCG CAAACGACGG    300

CAGCCGCTGT CGCCAGAGAT GTCTTCACCA CTGCGCGGTA GCAAGCTGCA GCGGCGGAAG    360

CAGACACTTG AGGCCGGTCC GGGTCGCGCC AGTGGGACAC ACACGGTGGA CGAGCTGGCC    420

GCGCAGCTGG AGCGCGGCTG CGAGCAGGCG TCGGAGCGGA AGCCGCCGTA CTCGTATGCG    480
```

-continued

```
GTGCTGATCG GCGTTGCGAT CCTACAGTCG CAGGAGGGCA GCTGACGCTG TTCGCNAAAA      540

TACCGNTGNA TTTCCNCCNT CTCCCCTTAN TAACCGGTGT TTTTAACCCG GGGTTGGAAA      600

ANANCTTCCG GACNACNTNT TNCTTAAACA ANGGTNTTGT TTTAAGGGGN GGNNNCCCCC      660

TCAAAGGANG GGCCTTTTGG AAAATTAAGG GGGCCNTTNA NGGGGGCCTC NCTTNNCCAA      720

AAAGGGGGAA TNATTTTNNG GGCCCANATT TNNCAAAAAT TNTNCANTAG GGGGNCTNNG      780

NNAANTTTNT TCNCTT                                                     796
```

(2) INFORMATION FOR SEQ ID NO:476:

(i) SEQUENCE CHARACTERISTICS:
        (A) LENGTH: 764 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1339RP (xi) SEQUENCE DESCRIPTION: SEQ ID NO:476:

```
GATCATCGCC TTTAGGCCCA TGTCAACCTT GCCCGCACCG ATCAACTCCG TCACGTCGGA       60

CGGGTTCGTG GGCTCGAGCA GCGCAATGTC CACACCCTCC TGCTGAAAGT AGCCCTTGGA      120

CTGGGCTAGA AAAATCGCAA TGTGGTATGG CGCAGGCTGC CAATTCAATA GGAATGAAAC      180

TTTGCTAGAC ATCTTCGGTG CAGTCTCCGC AGCTACACCC CATTGCATCC AGGCTCATCA      240

GCCGCTTTAT ATACCGCTGG GCCAAAGATG ATTGAATACG GTTCGCAGAC GGCTACTGGA      300

ATACCCGTCG CGCCACAAGC CCGCCACTGG ATGCCATGCG CCAATGCGGA AGCCTCCTAT      360

GTGACATGTA CTAACAGAGC AGCTTCCTTA TGCACTTATC GAGCCAAAAC CAACATCTGC      420

GGAATCACAC TTGACGGAAT CCGGCCCCAT GCGCAGCTGC TGGAAACACA AATCCAGCAA      480

CTAATAGGGC TCAGTGGTAT AACGGCCCAT CGCTCTCTCA ACGCCAAGTC CCTCTCTGGG      540

GAAAACATGT GATCACGTGC TACATATTCA ACCCCCGTCT TACCTCATAG CTGCGCATGT      600

CCAGCCCTGA ACTGTTCCGA CCTTCCGTCT TCCNGAAANC CTGATTGCCT TGCTTTAATT      660

CCCCCTCTCC NCCAACCATG TNTCGCCCAT TTACTTCCGT TGCTTTTTTA TTTCGTGCAT      720

TGTTTTTNTA AAAGNNCCTG TTAANTAAAT NCCNTCATTN TGGA                      764
```

(2) INFORMATION FOR SEQ ID NO:477:

(i) SEQUENCE CHARACTERISTICS:
        (A) LENGTH: 778 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1339UP (xi) SEQUENCE DESCRIPTION: SEQ ID NO:477:

```
GATCAGCGCA TTTGTCGATA GTGGCTTTGA TTCGAAAAAT CCGATCATTA CCATGCTGAC       60

TATACGTCTA CTGACCAACG CCTTTGCAAA CAAAGACTGG GGCGTTAACC TAATGTCGTC      120

TGCGCCAATG TATAACTCGA TATTTGGGTT GATTGATGCA GACCACCCAA CTTGTCCTCC      180

TAAGCAACAG TCATCACTGG CCGTAGCAAT AGCTACCCTA ATATACAACT ACTCAGTGTT      240

GGTAGTAAAA GAGAACAACC ATGACATCCT AGCAATTGTT GCAGAGGTTC TAAACAACAA      300
```

```
ATACGGCTCC TCTTCCTTTA TCCTGCGGAA CGAGGAGGCC GCATACAGAC TCCTTGTTGC      360

TTACGGAAAC TTAAGTACTG TGGAAGGCAC CTTCGCACAG TTTGCTCCTT CTATCTCATG      420

GATAAGGAAG CTGAAGAGCC AGTATGGCCA CATATCGAAA TTCCAGGATA TTTTAAATGA      480

TATTTAAAGA AAGGTGTACG TATATATCCT ATTCTTTCGA TCGCTGTCCC GAGGCCTTCC      540

CGGAAAAATG GTGAAAACTT CGCTCTTTGA CACACAGCCT TTGCCCTTCA ACAGGATAGT      600

TTGAAGGGAC ATGTTCTGTT GACAANNCTT GAACCAGGGT ACTGGTGNAA AATTTNAANA      660

TCTTTTCTCC NCCGAAANCN ANTTCTNCGG AANTTAACGG GAAAAAAANC CCCCTCNNNC      720

CTTTNTTTAN TAACCCCCCC CAGGNTTNTG ACCTTGATTT TTACAAAACC TTTTTNTT       778

(2) INFORMATION FOR SEQ ID NO:478:

(i) SEQUENCE CHARACTERISTICS:
        (A) LENGTH: 766 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1340RP (xi) SEQUENCE DESCRIPTION: SEQ ID NO:478:

GATCGCCTGA TATCGACAGG CACTTTTGTA TATTAGCAGT ATTCTTGACG AGATAATGCA       60

GTCAACTCCT ATATAGAAAC CGGATACAGT GGTAAAAACG CAAATGTAGG CAATTATATA      120

TTACTCTTCT CGACACCACT AACTTCTCGA TAGCGGCATA TCTTGTAAAT TTGCATACAC      180

CTTTTCCCAA CTTTCAGTGG TCTCGTTGGC GTACTTTACA TGCATCTTGG CCCATTCCTG      240

GAAGACATGT GTGATACAAA ATTGAGTCTC CTGGAAAATT ACAAATTCCT CTAAAATGCA      300

CTTTCTAATT AGCCAGGACC TGTTTAGTTG CTCAGCAATT GTCCGTTTGT CCCGTTGAAT      360

TGTCTGTCTG AGTTTATCAT ATTCTGCACC TTTAACGTCC GGATTACTCT CCATAGATTG      420

AAGTTTGTCC ATATTTATTT CCACTCTCCT CTGCAAATGT GCTATGTTAT TCCCCGCCAT      480

AATTTTATAC CTATCAAAGA CCCCTTCAGT GCTATAATAA TATCTATGAA GGTCTTAAAC      540

TTCACCGATA GGTGTTCCTC CACTTCCTGA CGCTCCTTTC TTAGAGGTAT CGGCCACGCT      600

ATTGAGATGT TTTTGATATN NTGGAAATAT GANATTTAAA TATCNTGAAT AGTGCCTCTT      660

CCTATTGGGT ANAANTGTTN CNGAATTATC AANCAATTCC TCCATCACNC NGCCAAGCAC      720

CCNCCGTCCT TCNAANACCT GCNCNTNGCC CCGTNCGGTT NNNNNA                    766

(2) INFORMATION FOR SEQ ID NO:479:

(i) SEQUENCE CHARACTERISTICS:
        (A) LENGTH: 790 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1340UP (xi) SEQUENCE DESCRIPTION: SEQ ID NO:479:

GATCTGCTGT ACCTGAATGG ACTTTGTCTC CTGAAGTAGA AATGTAATGG CCCCTTCGGG       60

AATACATAAC AAACATAGCG GAGACAAAAA CAAAAGCGTT ATACACGCAT CTGCCGTTAC      120
```

-continued

```
ATCACCGTCA GCTCCTTGCA GACCAATAAG CCTTCAAGTT AAATATAGGC TAGCTATAAC      180

ATATTATGTC GCTAAGAAGG GCCAAATCGT TGCCATCGCT TAAGAATATC GCTGAGGTGG      240

CCAAGCCCAT CACCAAGGCC CCCCCGCTCC CCCTGCTTGC GTTTGAGGGC CCTGGGCTGT      300

CCACATGTCG CTGGTATCCC ACCACCGTGC GCACAGTGCA CAATACCCCC AGTAAGGCGC      360

AGACGACGCT GCTCTCGACA GCGAAGAAGG AGAGTGCGTT TTCCGCAATG AACCTGAAGG      420

CCTTGCGGAA CGAGTGCCGC TCCCGAGGCT CAGGGTCTCC GGGCGGAAGT CGGATTTGAT      480

CGAGCGCATT GTCGACTTCG AGCTGAAGGG ACCGCTGGGC AGGCGCGGGA CACGGCGGGC      540

GTTCCACAGC CCGGGCACGA GCAGCGCCAG CGTATGCCGC CCGTGGACAA GGTCACCATG      600

CCCGACATCG CGCTTGACAG AACGAACCCC GTGCCACACC CTGAGAAAAA CTACATACTC      660

CGGANTCCNT CNTTGTNCCN CCAAGGGGGT TTCCCTCCCC GTTACCNATT CCNAAAAGAT      720

TTTTGCCNCG GAACCCANGA AGAAACCACC CGAACTCCCA GAAGGGGGNT TTNNNANCCG      780

AACCGAANCT                                                            790
```

(2) INFORMATION FOR SEQ ID NO:480:

(i) SEQUENCE CHARACTERISTICS:
        (A) LENGTH: 765 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1341RP (xi) SEQUENCE DESCRIPTION: SEQ ID NO:480:

```
GATCACATCC GATGCGAAAC TCGTATATTG TTTTCCCACA ATGATGAAGG TGAGTGTGGG       60

GCAGCAATTG TCCGGTTGAC GACTCCTATA GGCCCGGGCA TGCCCACGTG ACCAGAAATT      120

TGCAATGTGA TTCATGATGC AAATGGAAAC CCCATCCAAG TTTCACAGTC GCAAAAGAAC      180

AGTTGGATCC TGACAAGGTT CTTCTGTTAG CAGCTCTAT AGACACTCCG GTTGCTGTTG       240

CTGCGGATGC AACGAAAGTG TCCGCCCATG CTTTACTCCA GGCCCTTTTT ACCTCTAACG      300

AAAGTGAAGT AACTCCTGGA TGTATTACCT TTCAGCAAGT CAGAAACCTG ACCAGGTTCG      360

ACTAGTTTTT TATTGAAGTC CGTGCTGTCT CAGTATTTGA AGCAGTTAGT CCCACGAATG      420

AGAAACTTAA AGAATAATAG AATGGGGAAG ACTCAAAATT TACGGCTACC ATAAGACTCA      480

CAGACTTACT CGACTCGAAC GTTTTCGTCC GCACTTTGTC CTGCGAGTCA TATACAGAGC      540

CCTGTATCGC GTAAAACACC GGATGCGCTA CAGCAAGGTA CTCGCCTACA AGACAACACC      600

CTACGTACGC CGTTTCACAG TATGCAAATA ATNGAAGGCA TTTCCTCCNG ACTTTTTAGC      660

NAAAGGNTTT ATNCGAACTG ANCCCTGTCC ATACTTTATT CCCCCNANCC CNGTTTTCNA      720

AAAANCAGNG AACCATACNA TGCGTTTAAT AATGAACNTT CACNT                     765
```

(2) INFORMATION FOR SEQ ID NO:481:

(i) SEQUENCE CHARACTERISTICS:
        (A) LENGTH: 810 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1341UP (xi) SEQUENCE DESCRIPTION: SEQ ID NO:481:

```
GATCAGAGTA GATTTAGTAA AGAGGTAACC ACCACTGTTC CAAGAAGTCC AGGGCCTTGG    60
CTTGACCAGC ATTGGTAAGT GCTGTGGCTG GAAATTTGCA CTTAAACGGT CTGAGCTCAT   120
CTGGTTCGCC AAAGACCTAT GAAGTTTCAA AACACCAACT TTGCTGCCCA TTCTATATTG   180
AAATGTATGA CAGATGGCAG GTGCCTTACC GTACACTGTT TTATTGGTAA CTGGGTCTAC   240
ACCTTTCACG TTCACCTTTG CCACATGGAT CAACATAGAA ATTAAAAGAG AGCCAACCTT   300
AGCCTTGATA TTGTGCGGCC AAAGAACTTT AGACTCCTCA ATTTGTGTAT TTCTAAACGT   360
GGTTTTTGCC CTTTGGACCA GCTTCTTGAA TTCGTTACTA TTGGCCCTAA CTTCCTTAAA   420
AATCGATTTC TCACTCTTCA ATAGTGCTTC CGATCTGTAT TCCATCTCGA CAGCCTTACC   480
TATAGCCAGA ACCGCTCCTG GTTGTTCTCA TACCTTCACT GACGCCTCCA GTTAGAATTC   540
CAAGCCTTTA CCNATTCCCC AAATTGTTTA TGAANACACA TTTCNCCTNG ANTNACCCCA   600
AATTGAAATT ANGGGGNCTT TTCCANNCCN TGAAANAAAA TGTNGAACGG NGTTTCAGTT   660
AAGCCCATNT ATCACTNGGN ANCATTCNNN AAAAANGCTT CCCCCCTCCC TTTTTAAAAC   720
GGGATCTTNC CAAAAAACCN CCCCCTNAAT GAACCATTTT NCGAAANCCG GAAGCCCNNG   780
CCCTCNCCGN CTANATTCCN GCAANNCATN                                    810
```

(2) INFORMATION FOR SEQ ID NO:482:

(i) SEQUENCE CHARACTERISTICS:
        (A) LENGTH: 759 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1342RP (xi) SEQUENCE DESCRIPTION: SEQ ID NO:482:

```
GATCCTGATT TTGATTTCGC CATTGCTGAT GTTAATGCAC TCAGTGCTGA TGTCCTATAT    60
ATCCAGCATG AATTATCCTG GTGGATATGC GCTATCTGCA TTCAACAAAT ATGTGCTGGA   120
CAATAATATC TCGAATGCGA CCGTCCACCT AGATGTCTTC ACTTGTATGA CGGGTGCAAC   180
GCTGTTTGGA CAGCTGCCGG ACTCCTACGG GATCATATAT GACAAGACTG AAGGTGATGA   240
ATTATTGGAC GCATGGTCAT CGTTCGATTA TGTCATTACA ACTGATCCCA ACAGCTCACT   300
GCCTCCTGTT ACAGGCTACA AATGGGAGCG CATCCAAACT ACTGAGGCCT TTGACCGCTT   360
CGACCTTAAA ACTATACCGG AAATAATCAA CTCAGAAGTT GCTAAGGGAT TCCCTATCTT   420
AAAAGATGCA ATACTCTCTG CAGACCTGCA ACCTGTGAAG GCTGCGTTCA CAGATGTGAT   480
CAGGTGCAGG GATTCAGTGT ATACATATAA AAGAGTTGAG AATTAATAGA ACCAGCGCTC   540
CGCTTACGGA CAGTTTCCAT ATAAATATTT ATTTATTAAA CTTAAAAGTT CTGCGAGTTG   600
AGGAGGAATT TGACTGCTGG AGATTCCGAC ATACTGAAAA CATAAAGTGC ACATTTACAG   660
GATTCGGCAG TTACTTGATT CCCCNTCCTN NNCCTTAAAT GCCTGATCNA ACTTNAAACA   720
TCCTATTGAA CCCCCTTTGG TGNTCCAANC AAANTNTAA                          759
```

(2) INFORMATION FOR SEQ ID NO:483:

(i) SEQUENCE CHARACTERISTICS:
        (A) LENGTH: 802 base pairs
        (B) TYPE: nucleic acid (C) STRANDEDNESS: single
        (D) TOPOLOGY: linear (ii) MOLECULE TYPE: DNA (genomic)

(vi) ORIGINAL SOURCE:
        (A) ORGANISM: PAG1342UP (xi) SEQUENCE DESCRIPTION: SEQ ID NO:483:

```
GATCGGGCAG GCCGCGGAGC AGCAGTCGCG CGCCTTCAAG GAGGCCGCAG ACTTCGGCGC      60

CATCATCCTG ACCAAGATGG ACGGGCACGC CAAGGGCGGC GGTGCCATCT CCGCGGTGGC     120

CGCCACGAAA ACACCCGTGA TCTTCATCGG CACAGGCGAG CACGTACACG ACTTCGAGAA     180

GTTCTCGCCG AAGTCGTTCG TGTCGAAGCT GCTCGGCATC GGCGACATCG AGTCGCTGCT     240

GGAGCAGTTC CAGACCGTCT CCAACAAGGA GGACACCAAG GCCACCATGG AGAACATCCA     300

GCAGGGCCGC TTCACGCTGC TGGACTTTCA GAAGCAGATG CAGACCATCA TGAAGATGGG     360

CCCGCTGTCC AACCTCGCCA GCATGATCCC CGGCATGAGC GGCATGATGA GCGGCATCTC     420

CGAGGACGAG ACCAGCCGCA AGATGAAGAA GATGGTCTAC GTGCTCGACT CCATGTCCCG     480

CGAGGAGCTC GAGTCGGACG GCGCTCTTCA TCGACGAGCC CGCCCGCATG CTGCGCGTCG     540

CCCCGCGGNC CGGGCACCTT CCGTCTTTCC GAAGTNTGAA AATATCCTCC NTTGCCTCAG     600

CCANATGATT GCCCCGCNTT GGCCCANGGC GCCNANAACA TTGGCGGCTC CCCTGGCNTG     660

CCCGCCNGCC CCNGGNATGT CCCCGCCTCT CNCCTCCAAA NGATNTNACC NGCCCNANCN     720

TCNNTTNNCT CAACCCNCCC NTGANNCCCN CATAATGGCT NNNCCGNNGG GGNCCNGGGC     780

CCCCATGCCC CCATTAGGCN AT                                             802
```

(2) INFORMATION FOR SEQ ID NO:484:

(i) SEQUENCE CHARACTERISTICS:
        (A) LENGTH: 844 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1343RP (xi) SEQUENCE DESCRIPTION: SEQ ID NO:484:

```
GATCAACCAA TGTGTTAAGG AAATTTTTAA CGTTTTCCGG GGATTTGGCC ATCTTTCCCT      60

CTAATTGGTA GGAAACATAG TCTGTAGCAC CCATGATATT AGCAAGTTTC CGCCGAAGCT     120

GAAGCAAACT CTTAAGCCTC TTCACTTGTT TTTCGGAACA ACTAAACATT GCGGTCCATA     180

CCTGCCTCCG AATAGCCTCT GAAGGACAAG CATTCAATAG TGTATACGGA GCATACCCAC     240

TAGTTGGTAT CTTATAGTTA TTACCCATGG TGTCCTTGGT GAGCTGACGA AGAACAAGAT     300

GGCTAGTGCC ACTCGATTCC AAATCTTTGC ACGGAATCTT TATGTAGCTG AAGATAATG     360

ATTCTGTGTT GTTGATGAAG TCTTGGCCAA TAATGCTGAT GTTTTGGGAT AACTGTATAA     420

ACTGCTTTCT GACTTCGGGC GACGCATATG CGCCTGCTTT TTCAAAATCC TCTAGCAATA     480

TATGGCCTAC CCGTATCTCC TCGCTGCTCA GTTACTGCT TATATTCTCG TCCGATAGCA      540

CTTGTTTTAA TCTTTTGCAA AGCACAACAT CTGTATTCAA GATATCATAA TCTCAAACAT     600

CTGTTCATGA CATTCCCTGA GCTGCGGCAA CAAATTGTTC ATCCGGATGT TGCAACCCGT     660

TAAACTCCNC ACAATNCAAT CCCCCGGCAT AAAATCCTGA TTTGATCTAT CNAATGATNT     720

NCNCCCAACC TCTTGTGACA ACCCTCNCAG TCCTTACAAC CCTACCCGTT ATGATTTTNG     780
```

```
NAATTCCTAC CCTCCNGCAT TTAGTTGTTC NNNATACCTT TNGNCCCCGG GGNGGACTTA        840

TCAN                                                                    844

(2) INFORMATION FOR SEQ ID NO:485:

(i) SEQUENCE CHARACTERISTICS:
        (A) LENGTH: 676 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1343UP (xi) SEQUENCE DESCRIPTION: SEQ ID NO:485:

GATCGATTAA AGGAAGCATC TGCTTCCCGT CATATCATAT AACATTGTAC CCGGGGCTGA         60

GCGGGACCAG TAGCGAATTT GATAGCAGTG TTCTCCACGT CCCCGCTCCA CTGTGAGCTC        120

CTTAAAGTAT ACCGGCTTCA TACACCAGTG CCCACAATGA TGCGTACTTG ACTTGTAATC        180

GAGAGCATTG GGCTTATACT GTGATTACGA TGAATGTAGC CAAGAGAGAA AAGGTTCATT        240

CACGATATAC AGTACTCACA TTCATGGCAT GCCATCCCCA AATTCCAATA CAGCCATTAG        300

CACCAATGTA GCGCTACTAA TCCGGCGAGC TTAATTGGCG TCAGTTCAGA GTGAATCTCG        360

AGCTTAAAAG TCAGATTGAT TAAGTAAGAA AATGACGATC AACAGGGTGC TCAAAATAGT        420

TGATTACCAG ATTCGGGCGT GTGGTCTAGT GGTATGATTC TCGCTTTGGG TAAGCGAAGT        480

TGCGGTTCAC TGCGGCTTAA CTACTAAACA TGTGAGAGGC CCTGGGTTCA ATTCCCAGCT        540

CGCCCCAAAT TTTTTGCTCT CGCCTCCCGC GGGAAAGGTG AATATCATTT TACAAGTAGT        600

TAACTCCTCC CACGTTACGT CCTTCTGCAG ACAAGTTGCA GCGGTTTACA ATGCTCAGGC        660

TATTTTGCGG CTTCAA                                                       676

(2) INFORMATION FOR SEQ ID NO:486:

(i) SEQUENCE CHARACTERISTICS:
        (A) LENGTH: 827 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1344RP (xi) SEQUENCE DESCRIPTION: SEQ ID NO:486:

GATCCTTGCG TACTAAGAGT TAGACTTTAA TTAATAATAT TATTTGTAGA AGATAGAAAC         60

CATACTGACT CACGTCGTAT TTAACCCAAC TCACGTAACC TTTTAATTGA CGAACAGTCA        120

AACCCTACTT AGCTGTTACA ACCAAGAGGA TAGGTTGAGT CGACATCGAG GTGGCAAACA        180

TAACTTACAA TAGCTACTCT ATCGTTATAT TACCCTGTTC AATTTTGTTA TCATAATAAC        240

ATTTAATTAT TATTTCAATA ATTCTCATTA TTGTTCAGAC TATTTCATTA TGTATTATTT        300

ATTAATTAAT ACATATTGGG CTTTCGTGGA TATAATTATT GTTAATCCTA CTCATATATC        360

TAGTCGTTGA ACGTTCTTAT AACTTTATAA AAAGGATTGT TATAAGCTTC GCTGCAGATT        420

GTCCTTTATT ATTATAAAAT AATATTAGGA GTTCTTTGCA ATTAACCCAA TTTACTCAAT        480

ATATTTAAAT ATTGATAATT AAATTTCACA ATTTAATGGG ACTATTAATT AATCCCTAGC        540
```

| | | |
|---|---|---|
| GTAACTTTTA TTCGTTTATC AAATACCATT ACAATATGTT ATATTTGTTC ATTATGCCAA | 600 | |
| ACTTACGTTA TTGTNCTACT TGTAGTATTA CNATTATAGC ACAGTTACCC CATCATATTT | 660 | |
| ATTTAATANA TACCCCAANT AGNTTTTTTT ANCATAAAAA GGANCTAATT TCCCTTTTTT | 720 | |
| CNCCAANTCC NNCTCTCTCA ATATTNTTAA AAATTTTAAA CNNAANTAAG AAACCCCNNN | 780 | |
| TNAACCNCAN CTTTTTTCAN GGCTTTCNAN CCTNTTNAAT ANCCCCN | 827 | |

(2) INFORMATION FOR SEQ ID NO:487:

(i) SEQUENCE CHARACTERISTICS:
        (A) LENGTH: 872 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1344UP (xi) SEQUENCE DESCRIPTION: SEQ ID NO:487:

| | |
|---|---|
| GATCCTTATA AAATGGGCAA TAGACGTGTT ATAATATAAT ATACAAAATT ATAAATAAAT | 60 |
| ATTTAATAAA ATATAAAATT AATAATTAAA GTATTATAAT AATTAATAAA ATTATTTATT | 120 |
| AATAAGTATG GATTTTTAAC TGAAATTTGT TAAAATGAAA TAAGAATTGC TAGTAATCTA | 180 |
| TTAATAAGAA AGTAATGGTG AATACTCTAA CTGTTTCGCA CTAATCACTC ATCACGCGTT | 240 |
| GAAACATATA ATTAAATAAA GAATATTAAT TAATTTATTA ATTATTAATT ATTATTAATA | 300 |
| TTATTTAATA AATATAATAA ATATTTTAAT TTAAATTATG AATTAATGCG AAGTTGAAAT | 360 |
| ACAGTTACTG TAGGGGAACC TGCAGTGGGC TTATAAATAT CTTTAATATT CCATTTTTAT | 420 |
| ACAAATAAAT ATATTTTTTA ATATATTTTA TAATAACTAT AATTAAATAG TTAAAATTTA | 480 |
| AATTATAATT TAATAATTTA ATAACTTATT AATTAGAGAG TTAGGGTACA TCCCCCCTAA | 540 |
| TGCTATGCAT TATGGTTGGT ACCACTCTAA TTAATAAACT ATAATAAATA AATACTAATA | 600 |
| TTTTATATCA ATTAAATTAT AATTATTTTT TATTAATATT TTAATATTAT TTAATGAAAT | 660 |
| ATATAAATAA AGTATTATAA TTTAATAATT AAATAAGAAA TGAAGANAAC GACTCTCANA | 720 |
| ATTAAATTGC ATTNATAGTT TACCATTAAA CAACATTCCC TTATTCATAT TATTTNATCN | 780 |
| ANTAATTAAT ATCTTATTAT TNATTAGAAG GANAGGNTNC CNCCCCTAAT GCTNNGCATC | 840 |
| TTGTGGTACC NCNNATTAAA AAGTTTACAT NA | 872 |

(2) INFORMATION FOR SEQ ID NO:488:

(i) SEQUENCE CHARACTERISTICS:
        (A) LENGTH: 835 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1345RP (xi) SEQUENCE DESCRIPTION: SEQ ID NO:488:

| | |
|---|---|
| GATCCCAACG TCTGATTATG TGTGTGAATG CTGTTCTCCT GCTCCTCCTG AGTCTCCTTA | 60 |
| GCCTTGGCCT TGTACACTTT GCCGTATGTT CCTGCTGCAA TATAGCCGAT GATTTCGTAC | 120 |
| TTCTCCAGCA CTGACACCCT ACCGGCGTCT TTCCGCTGCC GATATGGCCC TATCGAGAAC | 180 |
| ACATTGTTAT TCGCCATTAG CATCGGCGAT TTGGACGTGC TGGCGCTGCC TTTGGTATCG | 240 |

```
AGAAGCTGCT GTTGCTGTTG CTGCGACCAC AGGCTCCGGG TGGATGCCTG GTTGGATACG    300

TTGAAATACT TATTCTGTTG TGTTTGATGC TGATTATTCA TACTATCGGA GGACTGTAAA    360

CGTATCCCCA TAAAATAGAG AGCTCGAGCT ACCACCTGAC GACTTGTGTT ATTTGTAGTG    420

TTAAATGGAT ATCGGCTATG TTCTAAGCTC GTTTTTAAGT GTAAAACATT GCAAATCCAT    480

ATGCACACAG CTCATCCGGT TCTACCGACA ACCCTCTTGC GACCGGAGCG GTGGAGCTGG    540

GGTGGATAGT TCCCGAGCCC CTATGTAGTA TATACAGCGT GCCACGGCTG CGCCTGCGCG    600

GCTGCAGGGC CTCAGCACGA NTGCCCCTTC CNCCACTGCT TTATCCTCCT GAAAGCCGTA    660

CAACCNCCGG NNAAATACGG GGCACCCAAA GCNGCCCGAN GCCCCCGAT AANAACNTGA     720

CCAGCCNTAG NGAGGCCCCG AAANAACANT GCCCTTTTTC AGCGGGCCGT CGCACAAACC    780

CCAAGGNGGN TCCCCNTTGG GNNTTTTAAT NGCCNNGGGG ANGCCCCNTT NCTCT         835

(2) INFORMATION FOR SEQ ID NO:489:

(i) SEQUENCE CHARACTERISTICS:
        (A) LENGTH: 863 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1345UP (xi) SEQUENCE DESCRIPTION: SEQ ID NO:489:

GATCCGGCGT CAGCGCAAGC CAGTCTACTG GGGGACGGAG ACGCGCACAG CATTGGCGGA     60

GGGAGAGCTG GAATATCGCG ATGACCACAT TTCGAAGGCA GCTTACGTTT ACTTTCCGCT    120

AACGGAGGGC GCGAGCGCCA CGCTACGCGA GCGCCTGGGC ACGTCCCTCC CAGAACAGCC    180

CATCGTGTGT CTCATCTGGA CGAGTACACC GTGGACTCTG CTGTCAAACA GAGCCATCTG    240

TTTCCACGAT GACCACGCGT ACCTGCTTCT GCAATGGAAG GGTATGCTGG TGGTAGCCGA    300

GAGAACTGAA CTAGCTGACT TTAAATGGAG TGGTGACACG CCGGTGGTGG TCACCTCATT    360

CCGCGGTTCT GACCTCCGCG GGCTCTATTA TACCAATCCA CTTCTTGGGG ACGCCGTTAG    420

TAGGCCGCTG CTGCATGGAG ACCATGTCAC CGCCGACACA GGTACTGGTC TGGTACATAC    480

TGCGCCAGGG CACGGCCAGG AAGACTACCT AGTAGGTCAG GCGCACGGCA TTGAAGTCTA    540

CTCGCCAGTC GACCATGAGG GGAGGTATAT TCTGGATGAT ATTCCTCCAC ACCTCCGTGA    600

TATGCTAAGA GAAGAGAGCG GTAAGCCGCT GAAGGTTACA GACCACAAAG ANTGCNGGNT    660

CTTCATCAGT TTGCTANAAA AACCCAAGAT GCTCCTGCAT TCCCTGAATA CCACNCTCNT    720

NTCCCTNCAA TGGAGTCNAA NAACNTGTTT TCNAGANCTA CCCNNCCGTN GTTGCNAACT    780

GATGGACTGA ACTTCCCCCN GGAAACCTGA ACACTTTATT TTTCCCTNCC AGGGGAAAAA    840

NCGNTCAAGG TTCTCNAAAN CGA                                            863

(2) INFORMATION FOR SEQ ID NO:490:

(i) SEQUENCE CHARACTERISTICS:
        (A) LENGTH: 836 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
```

(A) ORGANISM: PAG1347RP (xi) SEQUENCE DESCRIPTION: SEQ ID NO:490:

```
GATCATCATG CCAGCGCCCA TGCCGCCGGC GGCACACCTT CACACCCACC CGTAACTGAC      60
AATACTCGAG CACCTTCGTG CGCTGGCCCG CTGGCGGCTG CCTGGCCCAT TATGCAACCA     120
CCCACACGTT TTATTCCACT TAAAAATTAC TTAAGCTGAC GTTACGCCTG TTGAAAAATT     180
TTCGCTTCAC GGAATTTTTC TGGGTGAGAT ATAAAAGGGG CTAAGTTGCA CAGTGAAAAG     240
GTGAAGTTTT TTGTGTTTAG ACTTCTTTTA TGACCTCATA GAAGGAATTT GGGAAATCTG     300
ACTTTCTAGC AGCCTCTCTC CAGTTGGAAG TGTTTACATA CTACTGCTAA ACGTGCGCTA     360
AGTTAAGATT TTCTTTTCTT TAGTTTTAAA CTCAGTACCT TATTCCATAA AGCGACACTA     420
CGATGTCTTC TAGATTCTCC CTCGTCTCGA ACCTAACGAG ATCCTTGAGC TCTGTGGGGC     480
GGATGCAACA GATGCGGTTC GCATCGTCGA AGTCGATGAC TGTGCGGGAT GCGTTGAACA     540
GTGCGATGGC CGAAGAGATG GACCCGTGAT GACGATGTGT TCATCATCGG AGAGAAGTTG     600
GCGCCAGTAC AACGGTGCCG TTACAAGTCA CCCAAGGCTT GTTTGACCGT TCCGGNAACG     660
CGGTTNGTNG ANACCCATCA CCGAAANGTT TTTGCCGTCT TGCGTGGGTN CNCCTGAAGG     720
CNTGACCCTA TGTCATTCAN TNGTTCACTC TCCAGCAGCA NGACANTTCT GAATCCGCGC     780
CAAATACANN TTCGTGTGTG CNACCNTCAN TGTTTCCAGC NAAGNGCGNC NCGNNC         836
```

(2) INFORMATION FOR SEQ ID NO:491:

(i) SEQUENCE CHARACTERISTICS:
        (A) LENGTH: 869 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1347UP (xi) SEQUENCE DESCRIPTION: SEQ ID NO:491:

```
GATCCTACAG AACTCAACTC TTATATCCAG GACTCAGTCA CGGCGTCTGC AATCCGCAGC      60
AGCCACGCGT GCTCCAGGCT GGGTGGCCAT TGGATGGGTG GGCACGACCC GAGTGGGCAT     120
GTATTCCTGA TAACGTTAAT GTGTATGTTT ATGCTGGGCG AGCTGCAGGT ATTTGGCCGC     180
CGCGCAATCG GGAAGCTTTC TGCTGATTGT CAACAGCTGC AGGGCGCTCC TGGTAAAATT     240
GTGGCACGCA TTTTGCAAGC AAGTCCGATT AGAGAGCTAA TTAACTCTGA AGCCCCCCAA     300
CATATTTTAA GACGCCTTTT CGTTCAACTG CCACTAGAGA GTCTTGCGAT TCTGGTGAGC     360
GCGGTTGTTT TTGGCTTTCG GTTCATTGTG CTGGAAAACC CGATTCTATT GCTTGTCGGT     420
CTTATTCTGA CATGGACCTG GTCACTCCTG GTAACTATAC TCTCTTTCCA TTCGTTTGCG     480
GAGCATTTGA CCGGTTTGCT CTTCGCATAC CTTCTAGTTT TGGCGTTATA CTGGTACATA     540
TAATGATCTA AGTAAAATCT GCAATATTAC ACACGAACGT TAAACTCGCC AGCTGGATAT     600
AGGCAAAGAT TGCAGATGCT GTGCTTTCCG CCTAATATGC GGAAAGATGA GCAGGCCAAA     660
CCCAATGCAG AGTAGGTTCG TCATATAGTA ACCATCGCGC AGAATGACAA CTTCCGCCCG     720
CTTTCGAAGC ACTCCCCTCC GGAAGGAACA TCCNATGGGC GAATTTTGGC CACCTTANAA     780
TTNAANAAAC TATCATCGCC ATAATACATC CGANACAATT ACCCCCANAA TATCAAGTAT     840
CNGAAATTTT CNTTANTTCN CCAATACGN                                      869
```

(2) INFORMATION FOR SEQ ID NO:492:

(i) SEQUENCE CHARACTERISTICS:
        (A) LENGTH: 772 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1348RP (xi) SEQUENCE DESCRIPTION: SEQ ID NO:492:

```
GATCCTTCCG CAGGTTCACC TACGGAAACC TTGTTACGAC TTTTAGTTCC TCTAAATGAC      60

CAAGTTTGAC CAGATTTTCC GCTCTGAGGT GGAGTTGCCC CCTCCTCTAA GCAGATCCTG     120

AGGCCTCACT AAGCCATTCA ATCGGTACTA GCGACGGGCG GTGTGTACAA AGGGCAGGGA     180

CGTAATCAAC GCAAGCTGAT GACTTGCGCT TACTAGGAAT TCCTCGTTGA AGAGCAATAA     240

TTGCAATGCT CTATCCCCAG CACGACGGAG TTTCACAAGA TTACCCAGAC CTCTCGGCCA     300

AGGTTATACT CGCTGGCTCC GTCAGTGTAG CGCGCGTGCG GCCCAGAACG TCTAAGGGCA     360

TCACAGACCT GTTATTGCCT CAAACTTCCA TCGGCTTGAA ACCGATAGTC CCTCTAAGAA     420

GTGCGCAACC AGCAAATGCT AGCAGCACTA TTTAGTAGGT TAAGGTCTCG TTCGTTATCG     480

CAATTAAGCA GACAAATCAC TCCACCAACT AAGAACGGCC ATGCACCACC ACCCACAAAA     540

TCAAGAAAGA GCTCTCAATC TGTCAATCCT TATTGTGTTC TGGACCTGTG AGTTTCCCCC     600

GTGTTGAGTC CAATTAAGCC GCAGCTCCAC TCCTGTGGTG CCCTTCCGTC ATTCCTTTAT     660

TTTCAGCCTT GCGAACATAC TCCCCCCGAA CCCCAAAAAT TGATTCTCCT AGGTGCCGAT     720

TGTTNCATAA AAACACACCC ATCCCTATTC GCATATTTAT GTTAAATACA AG             772
```

(2) INFORMATION FOR SEQ ID NO:493:

(i) SEQUENCE CHARACTERISTICS:
        (A) LENGTH: 823 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1349RP (xi) SEQUENCE DESCRIPTION: SEQ ID NO:493:

```
GATCGTTATA TATCAGTCTC TTGCTATAGA TTACTATAGA GCCCACCACT AATGTACAAG      60

TTATAACTAC TGGTAACACG TTATATAACA GGTAGGAAAC GGGGCCGCCG GGGATTTTTG     120

CCTATGGCTT GGCCAGGTAG CAACTGCTAT AAAGGCGGAC GTTTCTCCCG GAGCTTTTTC     180

ATCTTGCGCA GTTTCACTTG CTAGTTAGTT TAGGGCTAGG TCGACAAACA TATTCCACAT     240

CGTTTTAATG GCTGGTGTAC CTGATAACGT CAAGGGCGTG GTTGAGCTGG ACCCCTGGTT     300

AGCTCCTTAC GGGGACATCC TCTCTGCGAG ACGGTTCCTT GCCGACAAGT GGAGGCACGA     360

TATCGAACAT GCGGTGCCCG GCGGGCGGCG CAGTCTAGTT GAGTTTGCGC GCGACGCATA     420

CAAGAGCTAC GGGCTGCACG CGGACGCGCA GAGCAAAAGC ATAACGTACA GGGAGTGGGC     480

GCCCAATGCA ACCCGGGCGT TTCTAGTCGG CGACTTCAAC GGGTGGATGA GACCTCGCAC     540

GAGCTCCAGA ACAAGGACGA GTTCGGGTGT TCACGGTGTG TTCGGACCTG GCGGACGGC      600

GAATTCATAA TCCGCNTACT CACCCTTTAA GTTGTGTTCN AACTTGCCAC CGGANCCCGA     660
```

```
TACCCGGTTG CCACNTTGAT TCAAAGGNAC CCACCCCACC AGAANCCCAA GATTTGGGCC      720

NCCTTACAAG CCGTCCTGAC CCNCCCCCCT ACATTCCACA CAAAGCCCCC NGACCAACTG      780

ATNCCTNAAA NNACAGNCNC TTGCTCTCAC CCGACCCGTT TGT                        823

(2) INFORMATION FOR SEQ ID NO:494:

(i) SEQUENCE CHARACTERISTICS:
          (A) LENGTH: 879 base pairs
          (B) TYPE: nucleic acid
          (C) STRANDEDNESS: single
          (D) TOPOLOGY: linear (ii) MOLECULE TYPE: DNA (genomic)

(vi) ORIGINAL SOURCE:
          (A) ORGANISM: PAG1349UP (xi) SEQUENCE DESCRIPTION: SEQ ID NO:494:

GATCGCGAAA ACTAACGCAC CAAACCCGAC GGAAGCCAGA GCTCTCTTGT AAAGTGGCAA       60

GATAGTGTAT GTCTGGCCGG ATGGCTCAGA GGATTTCTTG CGAGCATAGT GGCAGCGATT      120

GACATATGGA GTTATCATTG CAAAAGCAGT GGCAATAGCA AGACCGGTTT TGTTCCAACC      180

GCCGTTCTCT TCTTTCATTA TTGGCCACAA GGGATTGTTC GAGTAGAAGG CCATCTTCAA      240

CACAACGCTC GCAACAAGGC CTAGAGACCA AGTAATGGCA AACTGCGCGA CACGCGCGTT      300

GTCCTTCACA ATGCTCTTCA AGGTCACTGC AAAGTTCATC GTGCTGAGAC CCGTGGCAAC      360

CGCAACCGTC ATCAACCTCC ACTCCGGTTT CTCAACTATG TACGCTCCGA TACCGATTAC      420

ATTAGCAAGT AAAGGGCCGT ACTGTTGAAT CAACGTTGGG AAAAATGGAA CATAAAGCAG      480

AACTGGGCTC AATACCGCCG CTATCACCCG CCTCATAGCC GGAGATACCC ATGTACCAGA      540

GCGGGAAAAA CCATATCATA CACAATAGGG CAGTCAAGTT CGTCCAGAAC ATAAACGAGT      600

CAAAGGTACT GACAACAATG TAAAACAGAC TTGCCTGATT GGTGATGGGC TCGTCCGGCA      660

GGTAAACGAG TTCTCGTGCT CCTGCGTGAT AATCACCTCC TCCCAGCATT TCCTCCATTG      720

CGCCGCCGCC GAGTCCCTTG CCGGGCTAGA NAGCNNGGTG CTTGTCTTTG ANTGCACAAC      780

CCCCNCGAAG GCCTGTGCCC TGGGTTGCCN AACTTTNCCT NAGTCCTCCC AGTTTGCNTT      840

ACTTACCCTC CNAAAAATTC CAAATATCCN GGACNCCCN                             879

(2) INFORMATION FOR SEQ ID NO:495:

(i) SEQUENCE CHARACTERISTICS:
          (A) LENGTH: 829 base pairs
          (B) TYPE: nucleic acid
          (C) STRANDEDNESS: single
          (D) TOPOLOGY: linear (ii) MOLECULE TYPE: DNA (genomic)

(vi) ORIGINAL SOURCE:
          (A) ORGANISM: PAG1350RP (xi) SEQUENCE DESCRIPTION: SEQ ID NO:495:

GATCTCTTGC AATTCCTGCT CGGTCTCTCT GTGATCTCTA TTGATCACCT TTTCGAGTTT       60

GGTCGCCTGA GAAAGCGTCG CAAAGTTGTT CATAAGTTTC TTATACCGTG CCAGTTTCGC      120

AGCCAGCACA TCGTCGCTGA TCGTGTGGAG CGCAATTGGA TCCCCATCGG CGGCCATGTT      180

ATCCTTGACC GCGATATTGC GTGTTGATGA AGTCTGAACG GCCTCGTGGC CTGGACGTAA      240

GGCGAAAAAG TAAAATTATA TAGAACAGGC ATGAGATTGG CTGGAAGTTC AGGGAGCCAG      300

GCCTCGTGCG AAGCAGCTTA GAGAGCCATA GGAAGCCACA TGCGCAGGAA CTAGAGATGA      360
```

```
GACCCACCCA AGGTGAACTC GCCCACGGCA CAGGGGCAGT CTTAGCAACG TGGTAAACAT    420

TAAAAATAAT ACATACGTTA CAAGCAGCCG GCATAGCAAC TGCCTGGAGT CATGTTTTAG    480

AGAAAAATAG AAAAATTATT ATAATATTCC TTGTGTATGA AATAAAGCTG CTTTGCAACA    540

CGCGGCAGAG ATTCAGACCT GCCTGAAGCC GTAAAAGGAC GAAAAACCGA ACGAATAGAA    600

TTAAGATAGA AAAGCAGCAC TCGGCCAAGG CGAAGCGGGG CGCGCAAGCC GCCCGCGCTT    660

TCCCTCNCNC TCAGCTGCAA ATGCTCCTCA GTGGATCCTG CTCCCCCTGT CCCCGTCTCA    720

CCTCCTCCAC TCCTCGTCNT ATCCTTTTGA TGAAACNAGG CTGACGCGCG TGTTCACTCC    780

ATCTTCNCNC GCNCCGCTCG ATAAATTGCT CAGCNCTACC TCTTGGNNG               829

(2) INFORMATION FOR SEQ ID NO:496:

(i) SEQUENCE CHARACTERISTICS:
        (A) LENGTH: 875 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1350UP (xi) SEQUENCE DESCRIPTION: SEQ ID NO:496:

GATCCGCATT AAGCGCGACG ACGAAATCAA TACCAAGAAG CTCGACGAGG AGAAGGAGCG     60

GCGCCTCAAC GCCATCATCA ACGGGGGAGC TAGTCATATA AGCGTGCATA TAGCGCAATT    120

AAAGGTTTAG CGTCATCGAT AGTTACATAA AGTTAGAATG CATGCTCCGC CACGCGCGCG    180

TTCGACTCGG CGAGCCAGCG CGAAAGCGCG TCCTGCGCCG CGGGTACGAA GAACCGCCGC    240

AAGAAGTGGA GTTCCTCCGC CCACCGGTCG TAGAGGTCCT GGCTGAGTAC GTTGTACTTG    300

ATCGGGTCGC CCTTGGAGAT GGCATTCATG AGCCACTGTG TCTCGTGCAA CGAATGCGTC    360

GGCGCGCTGC TGTGCGACTT CATCATCGAC AATTCGCGGA ACGGCTCGAA CCGCGTGATA    420

AGCGCAAGCA AGCAGAGCCC CGCAGCGTAC ACGTCCGTGC TGTGCGTCGG CTGGCCGCCG    480

CCGATCAAGC CCGGCGCGCA GTACTCAAGC GTCGTCGTGA GCGGCTCCGG CGCCGCGTCG    540

CACACTGCCG CCGACGTGAA GTCCGCCAAG AATGCTCCTG CCCGCGCACG AGCACGTTCG    600

CGGTCTTGAT GTCCCGGTGC ACCACGCAGC TCTCGCGAAG GAACTGGAGC GCCCCAACAA    660

GGTCACGTGC GTACCGCCAC CACTGGCCCT TGTCNCGGGC GCGCGCCGGT GCNCCGCTTC    720

CANGTGGGGT TCAACCGCTC TACACAACGC CGGGACCNCC TCGCCACCGC GAANCGGCGG    780

GTATCCCNAC GTTTNCCGCC GCNCCCCCGN GGAANGGACC ACTTNCGGTC NCGANCCNCC    840

CCCGCCNGGT GGCAAGNGGG AATTNTTTAC CNTCT                              875

(2) INFORMATION FOR SEQ ID NO:497:

(i) SEQUENCE CHARACTERISTICS:
        (A) LENGTH: 832 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1351RP (xi) SEQUENCE DESCRIPTION: SEQ ID NO:497:
```

```
GATCATAATG ATTTGTCTTA ATTCTTTTCT TAATTATTCA TTAAATAATT AATTAATATT      60

TTATTAATAA AAAATATTTA GAGTTATGTT CGTTTATGAT AAATTCTAAA ACTTTGCAGC     120

ACGAACTGAA GACAACTATG TAACGCCTGT AATTAATTAT AAATTATTAT AATTAAATAT     180

TCAAAAAATG GTAAGATTTA TCGAGGATTA TCGAATTAAA TAACATGTTC CACTGCTTAA     240

GTCTGTAACC GTCTATTGTT TTGATTTTTA TTATTGCTAA CGTAGTCATC AGGCGGAATA     300

CTTTAATTTT CATTTAATTT ATTCTTTAAT TAATAAAAAA TAAATAGGTA TTCATTGTTT     360

ACTGCTAAAA CTACTCGGGT ATCGAATCCG ATTTGCTACT TTAGCCTTCG TTCCTCAATG     420

TCAATTAATA TATAATTTAA ATTTTCACTT TATAAGTCTT ATTCATATAA TTATTATTTC     480

ATCTTTACTT GAATAATTCT TAAATTATTT TTATTAATTC TAATTATTAT TTTAAATAAT     540

CATCTACGAA CCCTTTAAGC CATTACGAAT AACGCTAACC CCTTTGTCTT ACCGCAGCTG     600

CTGGCACAAT TTTGGTTGGA NNGANTTAAT TATATATCTC TTTTAAAAAT ANAATCTCCC     660

TCATATTAAT AATTTTATAT TGANANTAAT TATCNNTATT TAATAATTAT TGAATTTATT     720

GTTACCCANA NTAANAANAN ATTATTATTT ACATCCCCNA GTACNGANCA CTTCACATTG     780

CCAAATCCCN CGCGTTCCNA NAAATGATAT ATTCNANCAC GGATNTCTTC TT            832
```

(2) INFORMATION FOR SEQ ID NO:498:

(i) SEQUENCE CHARACTERISTICS:
        (A) LENGTH: 863 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1351UP (xi) SEQUENCE DESCRIPTION: SEQ ID NO:498:

```
GATCATTATA TTATAAAATA TAATAAAGAA TATATTTAAA TAATAATAAT AATATGAAAT      60

ATTATATTAA TTCTCCATTG GAGCAATTTG AGATTAGAGA TTTATTAGGT TTAACATCAC     120

CAATAATAGA TTTTAGTTTT ATTAATATTA CTAATTTTGG TTTATATCTT ATAATTCTTT     180

TATTAGTAAT TTTACTAATG AATTTAATAA CTAATAATTA TAATAAATTA GTAGGTTCTA     240

ATTGATATTT AAGTCAAGAA ATAATTTATG ATACTATTAT AAATATAGTT AAGACACAGA     300

TTGGTGGTAA AGTATGAGGT TATTATTTTC CATTAGTTTA TACATTTTTT ATTCTTATTT     360

TTACTATAAA TTTAATTAGT ATAATTCCTT ATTCATTTGC TATAACTTCA CATGTAGTAT     420

TTGTAGTATC AATAAGTATA ATTATTTGAT TAGGTCTAAC TATTATTGGT TTTTATACTC     480

ATGGTTTAAA ATTCTTTGGT TTATTTTTAC CACTAGGTAC ACCATTAATT TTAGTACCAT     540

TATTAGTATC AATTGAATTA TTATCATATT TTGCTAGACT TATTTCATTA GGTTTAAGAT     600

TATCAGCTAA TATTATAGCT GGTCATTTAT TAATGTTATT TAGGTGGTTT AATATTTAAT     660

TTAATAGCTA TAAATATTTT AACATTTTAT TAGTTTCTTA CCCATGAATG CNAATTTAGT     720

ATGGTTGTTT ANAATTGGCC ACCCTANTAT CCACCTAANT TGAGGTTTTT TAAATCCCNC     780

ATTTTAAAAA TCCATTTATT TACATNNATT AANAATAANA TATTTAATAA TATCCANNAT     840

TNAANATTTT ATAANTTTAA AAN                                             863
```

(2) INFORMATION FOR SEQ ID NO:499:

(i) SEQUENCE CHARACTERISTICS:
        (A) LENGTH: 831 base pairs

```
    (B) TYPE: nucleic acid
    (C) STRANDEDNESS: single
    (D) TOPOLOGY: linear (ii) MOLECULE TYPE: DNA (genomic)

(vi) ORIGINAL SOURCE:
    (A) ORGANISM: PAG1352RP (xi) SEQUENCE DESCRIPTION: SEQ ID NO:499:

GATCCTGCAT CGTTTCGTCG GCCTGCAGGT TGATTTTGTT GCTCTCAATT TTATCCTTTA      60

TCAAATTCAC AACCTGGCAA TCCACCTCAT GCTTTATCTT CAACGAATGC CTCATCGTAT     120

TGTCTAACCT GAGGACCATC TCCACCTTCC GTTTAACAAG CTCGACGGTA TCCTGTGTCA     180

ACAGGTTTAT GGCTGGGTCG TCGACCCCCA ATTGGGCATC CCAGGCAGTT ACGTGATCTA     240

TGTTGTTCTT GGTGTTCGGA GAGAAGCGAT ATGTAACCGA CTGCATGTTA AGAAGGCCGT     300

AGGGCGAGTC CTGCTCCCGC ACGTCCGCGT CGAGCAACTC GCTGGTGTTG ATGTTGATGG     360

CGTCCTCACA CAAATCGCTC AACAGCGAAA GCTGCTTGAA GGGGAAGCGC ACGTGGTGGA     420

ACAGCGACCG TGCGTCCTTG CCCGAGCGGC TCGCGCGGCG GAACGGGTTG TGCTCGTCGT     480

CGGACAAGTT CGGGCAGCTC AGGGACGGAT GGAGCATCAC GGGCGCCTGC TTCGCAGGGC     540

CCAGGTCGCT AGGGTCCGGC TGCGGCAACG CGAGACCTTG TACTCCGCCG CCGCGCCGGG     600

CTGGCCGAGC GCCCCNGTCA GTCTTCTACA CCNCTTGACT CCCCCCACTC CTCCGTNGAT     660

GACTGNCCGC GCTCTNCATC CGGTGCTCGC ACACNCACAT CTCCGAATGN TTTCCACCAC     720

CACCCNGNAC AACTTTCCAC ACCCGGAAAC TCNNTNGNNT TTNGGACCCT GTCTTTACNC     780

TCCAATCCCN TCTGCTGCAT TTTTGNAAAA CTCCCCCCAA CCCACCCCTC N              831

(2) INFORMATION FOR SEQ ID NO:500:

(i) SEQUENCE CHARACTERISTICS:
        (A) LENGTH: 832 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1353RP (xi) SEQUENCE DESCRIPTION: SEQ ID NO:500:

GATCTAACTA TTAATGTGTT CCTTGAAATT GTGCTGAAAT ATAACGAGCT CTTAAATGAT      60

GTCTATCTTG ATGACGATGT CGTCAAGTTG AGCCAATGGG TACTTCAAAC GTGTAATGAA     120

TAAAAATATA CAAGCGCAAA GCCCAATAAC CTTTACCCTA TATATCTTGT AATATATTAA     180

GTTAATTGAA CCATTTACGT GCCATATTCT GCGCTGGCAT GGTATCCGTG ATTTTATAAT     240

ATATATTTCT CGCAGGGGAA GCAGAAACAC TCAAGATCGG CGATTGCCGA TAAAAGAATT     300

GCTCCCTGAT TGATTGTTGT TCGAAGGAGA TGCAGATGGA TTGTCCAGAA AAACCGGTTT     360

TAAGACTCGT TCATCAAACT TGTTAAACCA TTGCCCATCG GCTTGCAGTA TATTGCCCAA     420

GGTTTCGCGG ATATTTCTTC TGTCTAATGA TAATCGTCCC ACAGGCTGGT CAGCGCCTGA     480

TGCAGAGCGC GAAGAGGGTC GGTCTATCAT AGGAGGAAAG CTTTCTTGAT CCGGGGAGCC     540

GGTCGGGCTG TCGGCTAAAA ATGGAGGTGC GTCTAATGAA GACATTAGCT GGACAGGTCT     600

AGGGGCTTCC ATATCAAATT CATCATCCGT ATCCTCCTGT TCTTCTACGC ACCCTGTCCT     660

TATGTTTAGA TCTCCAGCAT ACCGCAGTAT ACCTCCCAAT ATGATACGGT GAGAACCCCA     720
```

| | |
|---|---|
| CTACCACCCA GTGGCCNAAA AGAACTTGAC CCCCTGTNAC CCTNCATGCA TCCACNACCC | 780 |
| CACCCCCCCA ATCNCNCTGT ATGGTATGAC CCTCAGANAN CCNCCTCNGA TC | 832 |

(2) INFORMATION FOR SEQ ID NO:501:

(i) SEQUENCE CHARACTERISTICS:
        (A) LENGTH: 877 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1353UP (xi) SEQUENCE DESCRIPTION: SEQ ID NO:501:

| | |
|---|---|
| GATCGGCGCA CTCTGTGGTT CATGTCCTGC ACAAGTTGAC CACTGTATAC CAGTTTGACA | 60 |
| TCAGAGGGCG AAATCATCAG TGTGTGGCCG TACACAGAGC AAATAAACTC CTTTACTTCC | 120 |
| TGCACGGTGG TGTCGACTGT CACTTTCATA GTCTTCATCG CCAACACGGA GTCCGAAACG | 180 |
| AACTCGATAG TTACACCATC CCCGTCCTGG CCGTGGTTGG TACGGAACAT AATTAAGCAA | 240 |
| TGCGAGAATG GGGTGGGCGC AAAGTCAAAG CCCAATACCT CCTGTAGGCT CAACCCCGCG | 300 |
| TGTTCTGCCG CGTCTTCGGC GCCCAGGTAC ACAGGGGTAC GATCGCCCTG CAACTTGGAA | 360 |
| TGCAAGCATG TCGTTGGGCA CATGGTTCTT GTTCGAACAC AGGTTCTTGC AGCTGCTGCG | 420 |
| CTCGTACTCG TTCACTATAT CACATGCCAT CGTCCGCAGC GCCAGCACAG ACGTCTTCAG | 480 |
| AGGCACACGT TGCCTTATCA CCGCCACCAC TTTATCCATG GAAAGCGTGT TGACCTGGAA | 540 |
| CTTGACGTTC ACATACGCAA ACTCACTGTC GCCATCGTAA GCCAGGTCTA CAGTGCCGCC | 600 |
| TCCGACCTGC TCCGCACATC CAGCTCCAGA TGGACCAACC CCGCGCCGCA GCCTGCAATC | 660 |
| TCCTCGCACA ACATGGTCAG ATTCGAGCGG ACGCTGTTGG TATTCAGACA GTATTGCTCA | 720 |
| GGCGGCCAAG CGCCATGTTC TCCCCTGATG CATGATAACC AATGCCNTAC TGCNATACCT | 780 |
| NGCNACTGAT AANTTGGGGG ANGCCCGCCC NTTCACGAAG AAGATCCANG CTCCCNTTCA | 840 |
| AATAGNAANN CNGANTGAAC TGGCGNATNC CNAATCT | 877 |

(2) INFORMATION FOR SEQ ID NO:502:

(i) SEQUENCE CHARACTERISTICS:
        (A) LENGTH: 871 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1354UP (xi) SEQUENCE DESCRIPTION: SEQ ID NO:502:

| | |
|---|---|
| GATCGAACAC GCCTGTGCCA GGGAGCTTAG GGTCGTGTGC ATCCAATTGA GATCGAAGCA | 60 |
| AAAACCGACC ATGCTTGTTG AACCGAAAGG CGGATGTAGC ATGGCCCTTT CCCAACGGTT | 120 |
| GAGATCCTGG TTGCGCCCTC TTACCCTTGT CGTAAATTCT CGCAAAGTCA GCCTGGTCCG | 180 |
| TCGTCAGCAG CGCCTCAAGG GCATGGCCCA GCTGCGACAG AATGATCTCG CGGTCTGCAG | 240 |
| AAGAGTCTGA GCTCAAGCTG AAAATTGGGG GGGCCTGCGA CCGGCGCTGC AGCAGCATTG | 300 |
| ACGACGTCAT CTTGCAGCAC TTCGTCACCT GGGCGTCTTT CCGCAGCAGC GTCGCAGACA | 360 |
| GGTGCCGACC ATTCAGAGGC CGGAAGTTGG ATAGCAGATA ATGCAGGTGC GACAGCACAC | 420 |

```
CAGACATCGC ACTGGTTGAC GATACATACC GTGCTTGCCC TTCCTTGGCG CGCTCCAGCA      480

GTCGCAGGTC CCGCGAGGGC GGCACGAAGT CTGCGATGGC CTCAAATCGA AGTCCTGCAC      540

CTTGATCACC CGCTCGATGA AGGGCTCGAA GTTGTACACC CCCGACCGCC GGTCCCGGAG      600

CGGCACCACC GACAGCGGGC TGGAACAGGC AGCGTTCCAG CCCGTGCGCC AGCCGCGGCG      660

GCAGCTCTGT TGCACTGCTC NTNCCACCCC ATTGCTGAAC GCCCCNTGAT TACAAATTGT      720

TCNCCTCCCG GCCCCGCTTG CCCCGGTTGC CCCTCCCNGC CGCGGCACCC CCGCNCNNNT      780

GGATGANNGT TCNCTGATTN NCCAAACCCG TTCANNTTGT CCGGTTTTNT CANGGNCANT      840

NCCCNNTCNT TGTNCCNNTT NAATGCCCNC N                                    871

(2) INFORMATION FOR SEQ ID NO:503:

(i) SEQUENCE CHARACTERISTICS:
        (A) LENGTH: 1166 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
         (A) ORGANISM: PAG1355RP (xi) SEQUENCE DESCRIPTION: SEQ ID NO:503:

GATCATGGCC AAAAAATTGG GAATAGGAAA CTGTTTCCAG TACTCATCAA GGTCAGTAAA       60

AATGTTTGCC AGCAGTGAAG ATTGCATCCT TATCTTGCCA TTTGCGGATA GGACATTTGT      120

TTCGATATAC CTGTGGTGAG AGGAAAAGAG TGTTGCCAGT TGGGTAAGTT CTCGTAAAAA      180

CAAATAAACT TCTCTTCTGG AAGTCTTACC GTACGCGATT CTATTCAAAA TCCTCTCCAA      240

GTCCTGGCCA TCACGCAACA TATTATTTAA CGACTCAATG AAGATATTAC CAACTTCGGT      300

TGAAATGCAC TGAACTGCGT CCAATCTCTG TTGTATCTGA TCAATATTTA TTAAAGGCTT      360

TGCAATCCAG TTCTTCAAGT TCCTTAACCC GTAGTTTGTT CTAGTATGAT CTAATACCCA      420

TAACAGGGAG CCTTTACTGC TCCTATCTGT ACTGTTCTCA AAAATATCTA AGCTTTCAAT      480

AGCGCTAAGA AGGAAGAATC ATGTGCGTCT TCGAGCAGAA TGGTTTAAAG TTTTCCTTGA      540

AGAAGAGTAA ACNNNCATTT TTGAAGTTTG TTAGGTAGCC ATGCACCAGC ATGAGCGCTG      600

TTTGCAGAGG AACGTTGCCC TTAAAGGCTG GGTGCGGCTC ACTGAAGATT TCTTCATACA      660

ACCCGACGAG CTCGATCCTA TTTAGAGTGA TATCGGAATC TGAAGTATGA AACACCTTTT      720

CGATTTCTGA GCCAAGGCCA TCTCCGACCA CAACTTCACT CGGGTTTGTG TATTTTATTC      780

GCGTCTCCAA AGCCTCCGTC AGAAAACGCT CCTCTTTGAA GTCATCGAAG ATAACTTCAC      840

CGCTGTTGAG ATTAACACTA ACCAGGAAGT ATCGCGTGTA TGAAGGTTGT CGCTTGCACA      900

CAAGACCCCA CACAGAAGCG CTATCACCCA GGACCCGACG ATCTTTGGTT CGAACGTCTC      960

ATTGATGCCA TAGGTAGCCC TCGTGAATAT ATTGGGTACT TCCCTCGAGA AAACAGAGCT     1020

TGAGGTCCCA CTGTTCTTTT TCACTGCGGA TGTCTCTGTC TGCTCCACGA CCCCCACTTT     1080

CAGATTGTGG TGCATCAAGC GCTGCAAGTG GACTTCGAGA CGGGTGTCTG GGAATGGTGC     1140

AGTACGCAAA CTTCTTGTGC TTGTGA                                         1166

(2) INFORMATION FOR SEQ ID NO:504:

(i) SEQUENCE CHARACTERISTICS:
        (A) LENGTH: 887 base pairs
        (B) TYPE: nucleic acid
```

(C) STRANDEDNESS: single
        (D) TOPOLOGY: linear (ii) MOLECULE TYPE: DNA (genomic)

(vi) ORIGINAL SOURCE:
        (A) ORGANISM: PAG1355UP (xi) SEQUENCE DESCRIPTION: SEQ ID NO:504:

| | | | | | |
|---|---|---|---|---|---|
| GATCATGCTA | TCAAGTGCAG | AGAACACGGA | TAGAGCCTAC | TCTGCAGGTT | CGGCCTCGCT | 60 |
| GAGCGCGGCG | CAGAAGTCGA | AGAAGCCGCC | AAATACCGCC | TTCCGGCAGC | AGAGGCTGAA | 120 |
| GGCCTGGCAG | CCCATCCTGT | CGCCGCAGAG | CATCCTCCCA | CTGCTAATAT | TGCTGAGCGG | 180 |
| GGCGTTTGCG | CCAATCGGGA | TTGCGCTGAT | CATCAGTGCA | AACAACGTGC | AGAACCTGGT | 240 |
| GATCGACTAC | AGCCAGTGCG | GCAAGCACGC | CACGTCCGAA | TACACGCCCA | TCCCCGAGAA | 300 |
| CCTGGTGAGC | TACCACTTCC | GGACGTCCAT | GTCCGAACAG | CCTAAGTGGC | GGCTGCATTC | 360 |
| CAAGAATGAG | TGCGAGCTAG | AATTTGAGAT | CCCCAACGAC | ATATCGAGCT | CGGTGTACAT | 420 |
| ATACTACAAG | CTGACGAACT | TCTACCAGAA | CCACCGCAAG | TACGTGCAGT | CCTTCGACCT | 480 |
| CGACCAGCTT | AAGGGCAAGG | CTGTTGCACC | AGACAAGCTG | TCCGACACGT | GCCACCCGCT | 540 |
| CTCGACTAAG | GACGGCAAGG | CTGTCTATCC | CTGCGGCCTG | ATCGCCAACT | CAATGTTCAA | 600 |
| CGACACCTTC | ACGCCGGTCC | TCCGGGGTGT | CCAACGGCGT | CCCCCGACTA | CAACTCAGCC | 660 |
| AACAAGGAAC | ATCGCCTGGC | ACACNGACCG | CAACAGGTNN | CAAGAAGAAC | AAGCTACAAC | 720 |
| CCGCCAGANA | TNGTGCCGCC | CCCCGCCTTG | GCACGAACGT | TTCCCCCNAA | TGGNTANNAC | 780 |
| AANCCAACCT | GCCTGACTNN | CTACTTGGGA | GAATTTCCCG | TNTTGGANTG | NNCCCTGCAG | 840 |
| NCTGCCNCCT | NNTAAANCTN | CNTNCAAAAA | AAAAGCAACN | CCCTCCC | | 887 |

(2) INFORMATION FOR SEQ ID NO:505:

(i) SEQUENCE CHARACTERISTICS:
        (A) LENGTH: 823 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1356RP (xi) SEQUENCE DESCRIPTION: SEQ ID NO:505:

| | | | | | |
|---|---|---|---|---|---|
| GATCTACATA | TGCATCAAAA | CATGTGCCTT | CATGCGCATC | AGTAGTTATG | TTTGCGCTGA | 60 |
| GAGGCGAGCC | ATTTCCAGCT | TGTCTGCACA | ACTCCATATC | ATTTGCATCA | TCAACCTCAT | 120 |
| TATCGCTATC | ACCATCCTTA | GTCGAGTATG | GAAAGGAGGG | TGACACAGCA | AGGCCAGAGG | 180 |
| TATCAGTTGA | AGACATATCT | GTGCTCATGC | GGTGGGCCGC | ATCATAGTCC | GATGACTTCG | 240 |
| TGGAGGATTT | AAAGTCATTC | TGCGGAGGAT | TCTGTGGCTC | TACTGACCTT | GCAGATTCGT | 300 |
| TTTCACTTTC | GTACAGAATG | GACTCATCTT | CGAACTTGAG | ATCTATCCGT | TTGTGATCAT | 360 |
| ACGCGACTCT | TTTTTCAACC | TTCTTTGTCG | TCATTGGCAC | GGAGTTTATC | AAGCTAGAGC | 420 |
| CCAAGGAATG | CTGCTTATCA | AGTTCTTCT | TAGCCATGGG | CATTTCGTAT | CTATCATCTA | 480 |
| TCCCTTCGTT | CGAACCATAC | TTCACCTGGT | AGCCATACTT | TGTATTATAA | TAAGAGTTGC | 540 |
| GATAATGCTT | CGTACCAGAA | CTACCGGCAC | TGCTAGACTC | CAATATGGCT | TGGATGAGGA | 600 |
| CTGCGCACGC | GAAGTTTACT | GCCATCCATA | TCAATTTGGG | CNTGGCTGCC | ACATTCGAAA | 660 |
| ANANTAAGAA | GAAGTACGAC | TAATCCTCCA | CTNGCTACCC | CGTCCNTAGC | AGCGAACCGG | 720 |

```
CTGCTGTCTN NCNCATCCAC CCCCGTGCTT GCTTAGCTCC TACNCCCNTG TGGTTCCATA      780

ACCCACCCCG TGTCACCCCA TCCCCTGANC ATTNTGAGAG ANN                        823
```

(2) INFORMATION FOR SEQ ID NO:506:

(i) SEQUENCE CHARACTERISTICS:
        (A) LENGTH: 873 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1356UP (xi) SEQUENCE DESCRIPTION: SEQ ID NO:506:

```
GATCTGAACC ATATTACCAA AACCAAACAA AGAATTCGGG CCCAAGCGAC CCGTCCGCGC       60

GTAAAGCCCT ATAACCAGCT TACGCGTCTG TGGGCGCCAT AGAAATTTGC ATTTTCAACG      120

GAACCAACAC GTCAATCCCA AACTACACTT ATCATGCCTT AAAAGGGATT ATCTTTTCTA      180

ACGAGGAGGC CCGCCTGCGC AGTAGGAAGC GGATCTTAGC GGCGTCCGGC CGGCACATTC      240

GGCCGTTGGA CTGCAATATC CTACTTCTGC AGCGGAAGAT AGCGCACGAA AATCTGCGGC      300

GGAGCAAGCT CAGAATTATA TGTAGGACCA ACATTGTCA GCAACGCCTG CGCCGAGTTC       360

TGTTATCGAG TAGGGGATT TCCTGCGAAT GCCGTTCCTT TTTATCGTTT CTTTTTTGAG       420

GGGCATCTGC AGAAGCGATG AGGTCCAAAG CATCTTGTTG CATCGATCAC CGAGCCCACA      480

GGGCAGGTAG AGTAAAGCCT AGTCACCATG GTGGTAGTTG ATAATAGCCG CGGAGGCGCA      540

TTCGCATACT ACGCGGGTAA GCTGCGAAAC AAGGTAGCGA CGCGGCGCGG GCTTTTAGGC      600

GACTACGACT ACAAGTACCT GTTCACGCCG CAGATATTCA AGCGCAGAG AAGCTTCAGC       660

CATTTTCTCG ATCNATGCAA AATCCCCGGT GGTGCTTGGG TGGCNTTTGG GGNTNCACNC      720

CCCNNGCAAN NCTGGCGGNT TNNTTNCNCC NCCAATNNTG AATACCGGNG GNGGGAANTT      780

TGAAAGNNAA NCCNACATNC TTATTGGGCT TNCCNGNTGT NGAACGGGGC TTCNTNNAAG      840

GNGNAATANN CCCTTGNGAA TCCTTAANAA AAT                                   873
```

(2) INFORMATION FOR SEQ ID NO:507:

(i) SEQUENCE CHARACTERISTICS:
        (A) LENGTH: 840 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1357RP (xi) SEQUENCE DESCRIPTION: SEQ ID NO:507:

```
GATCCCAGCG AGGACATCGA AGAGGGACTA CTGTACCGCA TGGACAAGCT TCGCTGCCGA       60

TTGATGAGCG AAGACCGAGA TGAAATGACA GATGGCGGGA CCGTCGGGAG CGTGATCTGG      120

AAGGAAATGT TTTCTGCCGT CGGTATGGTG TCCAGGCTCA TGGTAGTACC TGCATGATTC      180

TGTCTTTCCG TGATCGGCTT CATGGTGGGC GTTAGCGACT TATAATAGTC GGTGCCGGTT      240

GCTGGCGCAA GCAGCTGGCA TGCAGTGTTG TCCGACAAAT AGGAGTACCG GTTGGTGTTC      300

TTATTCGTGG TGTTGTCAGA AATGTTTGCA AAGGAATAGA AACCATTTTC CATGGTGGTC      360
```

-continued

```
GAGGGGACTT GCGAGTTCTG TGCGGGTGTC TCGGCGACAT GACATTTCAT TTCTTGTTCT      420

GCGCCCGCTT CCGCAGGAAA ATGCGGCCGC TGTGCCGCCA TGTCCTCTTC CTGCTTGTGT      480

CCGTTCTGTC CCATCTCCCC TAGGGGCTTG CCCTGAAGAG TTTCAAAGCT TTTGAACTTC      540

AAGGAGGGCG ACGCCGGGCC CACGAAACGA TATCGCTTTA CTCCTCCTCA GCTTCCCGAT      600

AGGCATCTCN ATGCCATTTT ATTAATATAT TTCCCCCGTC CGAACCCCAA ATGTATGTCT      660

CCCGGTTGGC AAGGGATTCC GACTTATATA TTATTTGATG TCCACCACAG GTTTCCNAAA      720

TATTATACAT CNATTGCCNA ACCTCCCCNT TATNCATCAT CCGACCNCNC CNCATTTGTA      780

CNCACTAACN TGCACATNNC CCNATNTNNT AACCCATCAA CNCACCTTNC CTGCCCATCT      840
```

(2) INFORMATION FOR SEQ ID NO:508:

(i) SEQUENCE CHARACTERISTICS:
        (A) LENGTH: 888 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1357UP (xi) SEQUENCE DESCRIPTION: SEQ ID NO:508:

```
GATCCTCGCG TTCCCATGCA ATTGTGTTGC TTCGGTTGAC CCGATATGAC CTCAAAACCG       60

GGTCCGAAGC CACCAGCACC TTGTCGCTAT GTGACTTAGC CGGCTCAGAG AGAGCAGTGA      120

CACAGATAGT ACGCCGGAAG GAGGGTGCGT TCATCAACAA GTCATTGCTA GCGCTTGGAA      180

CGGTCATAGC CAAACTTAGC ATGTTGGGAA GCCAGGCCAA TGGCCTGCAG CCGTCTCCCG      240

CAGCCGGCCA CATACCGTAC CGTGACTCAA AGTTGACCCG CATCCTTCAG CCAGCATTGA      300

CAGGAGACAG TATCATTACG ACCATCTGCA CCATCGATTC GAAAGCCGAG TCCTCAACCG      360

AAACGACCAA TACCGTCCGC TTCGCGTCTC GCGCCAAGAA TATCGCCCTC AACGTGCGCA      420

AGAATGAAAT GGACTCGCAC GCCGAGAAAG ACACCATCAT CCAGAACTTG CGCAAGCAGC      480

TTGACGAGCA GCACGAGACC ATTGTGATGC TCCGGCGCAG TGCTGCAGCG CCTAGCGGCA      540

ACGGCTCGAC CAGCCCGCTG GACAGCCCTG GCGTCGGCGG CACCCAGCTT TGAGCGAGCG      600

CACGCCACAA CATTGGAAAA AAGGNTTGCT AAAGGTNGAA AACAGCATCC TCCAAGAAGA      660

ANCTCCGAGC CATTGCGAAA AAGCNTCTCG AANNAGGAAA TGATGTCCTC CGAAGAACCG      720

CANTTTCNCA NATTCTTNAA ATCTCCCCCT TGGAAATCCC CCCGTCCCCC CAAAACCAGG      780

NTNCAGGGGT TGATTTCCNC NGCCCCATTA CCGNNTTACT TTCAAAANTA AATNCACNCC      840

CCCAGGNCCN NGAAAATNCN TTCCCCCCCN TNTGGNGTTC ACCGCCNA                  888
```

(2) INFORMATION FOR SEQ ID NO:509:

(i) SEQUENCE CHARACTERISTICS:
        (A) LENGTH: 833 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1359RP (xi) SEQUENCE DESCRIPTION: SEQ ID NO:509:

```
GATCCATGTT TATTCACCCC GCTCACTCGC GTAAACGATG CTTTACGTTG CTCACATCGC       60
```

```
CGCCACCATT AACAGCGTAT CACATTTTAC GTTTCCGTGC AGCAAAAAGT CGGTCGGAAC      120

ATAATGCTCC AATACCACGA TAGGTCCGCG CAAGCGCCTA ACACGTGCCA TCCTGCTCGC      180

CTCCCCACGG GCCGCTCGCG CTGTGCTGGA TGAAACTCCC CTCCAGCGTA TGAGCGGACG      240

GGCATTCGCC CTGCCATTAC TGCACGCCCC ACCGACAGGT TTCCCATGTC AGCATCGACG      300

GCAAACCCGC AGAAATCGAT AAGTAGCAGG ACACGCGTCA GAAAGACCAG TGTGGTATCA      360

TGGCGCACGA GGAGCTAGGC AACCTCGCTT TTCCGCAACC ATGCCCGGCC GCAGGTTCGA      420

ACGCGGGAGC GCCTCACCAA GCCGGGATTG CTAATGTCCC TTCCGGCCAA AGGCCGTCAC      480

AGCTAAAAGA GAGGCGCCCA CGAAGGCATA TAGCTGGCAG GAAACGATAC GATTCAGCGC      540

ACTCGCAGCG TAAGGAACAG GAGCATCACA TCGAACAGTC GCCTGTGGTN TCCATCCCTG      600

AAGGTNGACA CTAACCTGAA AAGCGGCGGT TGGCACTAAN TACAAACNTT ACCACAGTAG      660

ATGCCNAATA CTGCTGACAA ACGAACTGGG ATTNCTNACC GGTGCTGNGG ANANAAATCT      720

NCCAAGAACN TTNAACNCAA TTGGCCACTA CCCCTCTTGA TCCCTCTTNN ATCNCACGGT      780

TTGGGANCCG GNGNGCAAAG CCCTGATGGN ATCCCTGACN AANTTGGACT NNT            833
```

(2) INFORMATION FOR SEQ ID NO:510:

(i) SEQUENCE CHARACTERISTICS:
        (A) LENGTH: 871 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1359UP (xi) SEQUENCE DESCRIPTION: SEQ ID NO:510:

```
GATCGGTGTA GTACACGGTT TCCGGCGCCG CTTCTGGCAG AGCAGCTCCG ATCACCGCGG       60

TACCCCAGAA CTGCCCGGGC GCGTCGCAAC ACTAGTGCCT GCTGCTGATG CCCGCCTTCT      120

AGTCGTTGCC TATTTTATTC CTGCCGCGCA TGTTGCCGCT GTCACGGCGT ATCTCGATGT      180

GCGCGAGCAG GACGGCTATC TTCCGCAGAC CGTTCCTGTG CATCTGGTGG CACCACCGCA      240

ACCGCCGCAC GAGCTGCGTG ATGCGCTGGA CGCCCTGCCC TGTGATTCGG TTTCTGGACT      300

ACCCGTCGTA CAATCCGTCA TATACATCGG CATCCCCGAT GCCGCCACCT TTGTTGGTCC      360

AGAAGAACTG CAGCGCACTG CTGCCGTCAT CGCGCACAAT CACGGGCCCA GTGGGCCCAA      420

CTACGAGTAT CTGAAGCTGC TCCACAGCGC GCTGCACTCA ATAGCCGAAA CGTTTGGCGC      480

CCGCTTGTGC GAGCTGGAGG ACCATTATCT GGACGAGCTG CTCGAAGCGG TCGACCGTCT      540

ACGGGCCCAG GCCTGTGCCG CGGTAGGTGC CTGATCTTCT GCTAAACCCA CGCCGAAACA      600

AAGATAGCAC CCGCCGCTCC GGGTAGCGGC CGGCCGTCGT GACCAGTTGC TAGCGTTTAC      660

TTGCATACCC GTATCTGCTT TAACCGTTTG GAAGGTTTAN CATCATTAGT TNNTTTGTGC      720

GCTTTGCTGC CCCTGCNTTG GCAAGGGGCN CCTATTTTAA NTTACCNCCC GNTTAACGNC      780

NCCTGAACAA AAATGAATTC NTTTNGANAN TCCCNATTT TNAGGATATC CCNGTTTGA       840

ATTCGANAAA CTGATTTGCC NTTTTNTNT A                                      871
```

(2) INFORMATION FOR SEQ ID NO:511:

(i) SEQUENCE CHARACTERISTICS:
        (A) LENGTH: 850 base pairs
        (B) TYPE: nucleic acid (C) STRANDEDNESS: single
        (D) TOPOLOGY: linear (ii) MOLECULE TYPE: DNA (genomic)

(vi) ORIGINAL SOURCE:
         (A) ORGANISM: PAG1360RP (xi) SEQUENCE DESCRIPTION: SEQ ID NO:511:

```
GATCCTTCTC CTCCGCATTC ACAGAATATA TCCTCGCGGT CATATCCTTC GCGGTCGAAA      60

TAATGAACCG TGAGTCCCGC GACCATGTGA GCGATGTGAT GTCGGCGAAA TGCCCCGCGT     120

GGACCCGGTA GCGCACAAAA GGCGCAAACT GCCGCTCAGC ACTGACCCCT GGAGTCCGCC     180

AAATCTGAAG AAACCTCCCA CATGCCAGAG CAAAGAGCTT ACCGTCTGTC GAAAACTTCA     240

CGTCGTTTAC TTTGTCCTTA AAGTTGAAAT GATGTATCAC ATTCCTCGTC TTTATATTCA     300

CAAGGATTGC CCGACCGTCC ACGTCAACCG AAAGAAGCAG TGTACCCTGG GCATTGACGT     360

CGATCCTCCG CTATATTCCT TCTATGCTCA TATTCAAAGG TAAACGACTT GTTACCAATC     420

AGGTCAAACA CCGATACCCT GTTGCCAACG GGCGAGAATA GCAGCGTTCC ATCCTCCGAA     480

AACACCACAT TTCCCTGTCT GTATACAGTG CCTAGCAGAT TGGAAAACTT GAAATCAGAC     540

TTCATCGTAG TCCAATGCCT TGCCTTGCTT GATCTTTCAG TGGTGTAGCT CATCTCATCT     600

CGAATTAAAT TTTCCGTACC ACCCAAAAAA ACANATCCTC CANCTGCATC TCAAGATTAT     660

ATATATATGT TCGAAAATTG AANATCCACT CNTCTAAATG GTACACNGTC ATATGAATGT     720

GTTTNTTTGC TCCANTATCC CNACCATTAC CCACTCCAGA ATGGGAATAT ATGCCAGGAT     780

NTCCGCCACT TCACCCTGTT TTGACANATT TCTTGAGNTG CTGACAGCCG AGAAAAAAGG     840

TCAAGGTTAT                                                            850
```

(2) INFORMATION FOR SEQ ID NO:512:

(i) SEQUENCE CHARACTERISTICS:
        (A) LENGTH: 851 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
         (A) ORGANISM: PAG1360UP (xi) SEQUENCE DESCRIPTION: SEQ ID NO:512:

```
GATCGATGCA AACCAGGACA ACTACTTAGA AGAGTGCTTG AAAATTAAAA GTGTATTGAG      60

TGAATTTGAA AATGACGTAC CGGATAAGAC AGATATCAGA GGAGTTCTCA ATCCGGTTGC     120

AATTGTTGGT TCCCGTGAAC ATGTGTTCTC TGAAAAAACC GGTGTATTGG GAGATCTCGC     180

GGCTGGAAAG GAGCAAGTAT TCGGAACATT CTTTGCACGT ACCCTTTCGT ATATTGGTGC     240

AAAGTTACAC TATGGCCATC CTGATTTTGT TAATGCTATA TTTGTCACTA CCAGAGGTGG     300

TGTATCGAAA GCTCAAAAGG GCTTACACTT AAGCGAAGAC CTTTTTGTTG GGATGAGTTC     360

CATATTACGT GGGGGTAGGA TTAAGCATTG CGAGTACACT CAATGCGGGA AAGGCCGTGA     420

TTTAGGATTT GGGTCCATTT TGAACTTCGC TACTAAGATT AGTGCGGGTA TGGGGGAGCA     480

AATACTCTCA AGGGAATACT TTTACTTGTG TTCAAATCTC CCACTCGACC GTTTCTAGTT     540

TCTACTATGC ACATCCGGGA TACTACTTGA ATATGTTTCC AATATCCCTT CTAACCCCTT     600

AATTANGNAA TTTANTCCCG NATTAATGGC GGTCCTGGTC AANCCNACCA AAAATNTNNA     660

NATTCTNTTA ACCCCCAAAN CTGCAAAATT TATTGTTGCC ATTNAACCCN TAACCAAGGT     720
```

```
NCCCCNTCNC GNTTNANCNA TCCNTNTCCC NCCGGTNCCC TTCCCAGTTT TGNAAGAAAA      780

ATTTAAAAAC CNACNCCGGG TTNCCCCGAA AATGAAACTN NTANAAGNGC CCCCTTTCAA      840

ATTTTTTTTT C                                                          851
```

(2) INFORMATION FOR SEQ ID NO:513:

(i) SEQUENCE CHARACTERISTICS:
        (A) LENGTH: 831 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1362RP (xi) SEQUENCE DESCRIPTION: SEQ ID NO:513:

```
GATCATAAGC TATTGGGTAC CCGTTGTAGC CTAGCCTTAA AATAATCGAC ATTTTGGAAT       60

TTAGTTATTG CGTGGAAATA AGGTATATAT ATTGCTTCCA AGTTTAATGT CGCTTTTAAC      120

TCACTAAAAT ATGGATGTAA ATTGTCTCAA TTGGACTTTC ATGTTCTATC TATACACTAA      180

CTGCGATGCG ACTCATTGTG CTTCAGTATT CAAAACATGT TTTATATATG TAATATGCGG      240

ACGTAGAAGG CAACTAAATA TGAGAGGCAA CTTAGTCGCT GTCGCTGTCG CTGTTTGAAT      300

CGCTGGAATC TTTTTCATAC ATGATCTCGT CGCCATTATC TTCTTTTAGA ACGCTAAGTT      360

CCAAGTCCTT ATGAGATTCC TTGTTCTCTT GAGAGACCTC GTCATCAAAG ATGATCTTGG      420

TGTTGGAAAC GACAGGCAGG TTTTCTGCTT GCGACCTGTG ATAGCCTTCA CTTAGCAGTG      480

ACCCCTCGAG GGACACCATT CTGCCCGCAG TGTAGACATT TTTAACAGTA AATTTGAGTT      540

TTCCGTCCAG CTGCTTACCG TTGCCGTCAC CCAGTGGCCT AGAGACCGGG CCTTGCGCAT      600

CCCTGTGGAG AATCGTTTCG CTGCTCCCGT TGGTACTCTC TTCGTTATGA ATAAAGTCCA      660

ACCATCCGGA ATGTTATTTC CTAATGAAGC GTTTGAACTT CGTGATCCAN CAACCATNTT      720

GTTGAGGTGA CNNTTGAAAT CCNCCCNCGA CNATCCCNAT TTTNGNGACA NCCNCAATTT      780

CCCNGCCCCN NTTAANCCAG GNTATCTGNT CCANTGANTA CATCTCNCTT T              831
```

(2) INFORMATION FOR SEQ ID NO:514:

(i) SEQUENCE CHARACTERISTICS:
        (A) LENGTH: 854 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1362UP (xi) SEQUENCE DESCRIPTION: SEQ ID NO:514:

```
GATCATAGCT GCAGGCTGCC AAGCAGACAT GCTGACATCA TACAGCCAAG AGAGCAGCTA       60

CGCTGTCACC GAGCTGGAAC AGAGGCTAAA CGAGTTTCGC ACTAAATGTA GAAAAAATGC      120

AAGCCACTTT CAGGCACTAC TTTCACTGGT AACTGAGATA GACCATCCCG ACAGCAGCCG      180

GCTAAGTCAC CGTACAGTAG TCTTGACATA CATGGAATAT CGCTAAGGAA GGAGGTGTAA      240

TAGGACACAA AATCATGAGA AGAGTATTGG CTTGTGCACG ATGCCGTGGG CACAAGATCA      300

AATGCGTGCA CAACAACGAG CCACCCTGCT CTTACTGCCA GCACAAAGGC ATAGCGGAGA      360
```

```
AATGCGTGTT ATCATTTCCG CCCAAGAAGA GGCGCAAGAA GCCGGAACTA TACTTAGAAG       420

GGGTTGGCAT GGCGCTGGGC GGGTATCCGG TGCAGCAGTT GGAAACTGCA GATCTGCACG       480

AGCATAAAGC CAGAGCGGAC GGCTCTGATG AAAGCCAAGC TCCTGTGCAT GCGCAGGACT       540

ATACGATCGG GAGCAAGCTG CGCAGATGTA CGAGCTGGCC AGCAGATGTA CTACGGCTGC       600

CCAGGCGTAC TCGACGGTTA TGTCGAGTAG TGCGAAGGTT CCCAGGCGGG TTGATTCTCC       660

CGCCAATTGC CACCCGGATT CTAAACCGAA ANAATGCAAC NCATGGAACC NGCCNTACTT       720

TNTTGGACTG TCCCCAGTGC CCNATGCATN GTGCACTTGC ATNGAGANNT TGTCATCCTT       780

CCCCACTGCG NTGTTTANAT GANACCNCCC AAGAATACCC CCTGACCGTC TTTGGTTCTT       840

TTTGCCCCCC NCCT                                                        854

(2) INFORMATION FOR SEQ ID NO:515:

(i) SEQUENCE CHARACTERISTICS:
        (A) LENGTH: 853 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1363RP (xi) SEQUENCE DESCRIPTION: SEQ ID NO:515:

GATCATTATC AGCATTAATC TTCAACTCCG CATTGCCTCT TAAACCAATA ACAAAACCGG        60

CAGATTTGCC TCCAATTGCG TAAGGATCCT TTAACCCCTT GAGGGATACT TCAAAAAGCC       120

CTTCACTAGG CCAGCGAATA TTAATCTTGG CATGGAACAT ATTCCTAATT TTATCCCAGA       180

AGCCTATTTT CTTGGATGGA TCAACTGGAG GTTTCGAAAA ATTGTCTAAA CAATTCATGG       240

CCTGTTGTAT AGCAGCTTCA TAAGAGCCAC CCCATGTCAC CATCGTGATG TCTTTCGAGT       300

GTATATCCAT TGTTACCTGA CTGTAAATTT TAATAGGCGT TAAAGACCGG CGGAAGCGCA       360

ACGAATAATA TAGGTCTATC TCAGAAGAAG TAACGGAAGG AACAAGCGGC ACAAATATCG       420

TTCGTAGCTC CTTGGTTGAT TGAATCATAT CCTCCAGTAA TAAAGAGGTC ACCATACAAA       480

TGTATAGCCG GAAAAGAACC TTGTTGGGAA GGCATAGCTT CGGCATATGG ACTAACGGTA       540

GTNGGGTTAA CCTTNAAANA GCCCCCTTAA TTCACCCANC TTGGCTTCCA ATNTAAAAGG       600

GAAGCCNCCA NTTATTCTGG GTTANTTTTG GAACCCCNTT TNCCCNCAAN TTTAATNAAT       660

TCNCNNTTTT ACCCTTCCCA CATNANGGCT TAAANTNNCA TGTTTTACCC CCCCNGCCAA       720

GANNTCCNCC ATTTTGGAAA TGTTANANTC CANACCCCCT TTNCATNTTN NAGGANCTTC       780

AACTGTCCNT TTNCCCCAAA AANTTAATCC CCCNAAAAAT TCTTTCCTCC TGGGGNTTTT       840

CCCCCCTTAC CNT                                                         853

(2) INFORMATION FOR SEQ ID NO:516:

(i) SEQUENCE CHARACTERISTICS:
        (A) LENGTH: 858 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1363UP (xi) SEQUENCE DESCRIPTION: SEQ ID NO:516:
```

```
GATCGAGGAT ATTTCCGTAC GCTGGATGTC GCTCGATGTC AAGTACATGG GTGATCGGTT      60

GGCCTTTTCA GTGTCGCTTC AAAATATCAA GCACAATAAG GTCTGTCTGC TGAAGTCTGG     120

TGCGCTCGAG GTTCTCGGCT GTTTCACAAA AGACAGTCCC TTTGGACTAA CATGTGTTGA     180

ACTGAGTGTC AAGTTTCTTC AACTCACAGT GCCTGTGAGT AACCTACTAG CACTATTTAC     240

CTTGGGCAAA GAAGAAGATG AGGACGTCGA AGGCTTTGCT CGTAATATTT TCGATGGCAT     300

GACCGAAGAT CCACAACTGA ATGCACAGAA TTGTGTGGAG ATGATGAGAT CAAGAGTTAC     360

CACGTTGCAT AGCTACTTTT CCCATCTAAC TAAGGTTGAT TTTTTTGTTG ATAAGGTTAA     420

CCTGGCAGAT ATACCACCCA GCTTATTGCC TGAGTTGTCA TCTGCCTGTG AGCCTTTGAA     480

ATACGAAGTT GCGCTTTCTA GTTTTACTTT TCAAGTCACC CGTTTTAGCA CCCGAACAGC     540

CAGGTATAGT ATCCTTTTCA AAAGTCTGAT AGACCGTAGG GTCCGTATCA CATTGTCATC     600

GTTGCAGTGC GCTCTCAGTT AATGCCCCTA AAATCCCCCT GAAAAGGCTC CTGAATACAT     660

CCGGTTTTTG AAGTTCCCAN TTATATCCAT ATGGTGANAC TATACTTTTC CTGAAAATTT     720

GACTGGTCCA CGCTGTTTCT GANACAAAGT CAATGGTGGG CAGTTTCTCC CCTACCNTAA     780

NATTGAAATG AAACCCCCAN CTTGAACCCC GTTNGCAATA CTGTANGACT ATTTNTTCCN     840

CANAACCCCN CCACGNAN                                                   858

(2) INFORMATION FOR SEQ ID NO:517:

(i) SEQUENCE CHARACTERISTICS:
        (A) LENGTH: 842 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1364RP (xi) SEQUENCE DESCRIPTION: SEQ ID NO:517:

GATCAGATCG ACGTCACGTT CCGTGCGCTG GGCACACCTA CGGACAAGGA CTGGCCTGAG      60

GTCTCGTCCT TCAGCGCGTA CAACAAGATC CAGGTATACC CGCCTCCGTC GCGCAGCGAG     120

CTGCGCAGCC GCTTCATCGC TGCAACTGAG AATGCCCTCG ACCTGATGTG CGGTATGCTG     180

ACGATGGACC CGCACAAACG GTGGGACACG ACTCGTTGCC TGCTCAGTCA GTATTTTGTA     240

GAGCTTCCGG AGGCGACACC TCCTACGGAA CTTCCAAAAC TAAATAAGTA ATGACTATGA     300

TAACCTAGAT GGTATACTCG GACGTTTTGT GTTTGTGCTT TGAGGCGATG ACATTGGCTT     360

TTATGGTATC GCAGACGTTG CCTGAAAAAG ATTCAACGTC TCGGTAACAG ATTTGCGCAG     420

ACTACTTGTT GAAAGAACAA AGACCAGAGC GCTGGGATGC TCACCCCAAT GACGAACCCA     480

CTCCGCCTTA TTGGCGCTGG CTGCAGGTTC CTTAGCACCA ACAATAGGCC GCCACTGCAC     540

AAGATCTTTC CCTCCAAGAA GCTGGTGAAC AGGATGCTGT TCCGACCTTG ATAGCCGACT     600

GACCTTCCGG AAATTACTTG CCTTGTATAC GAGCAGTTGT ACACCCAATT AGACAGTTAT     660

TACGGGCAAT TGTTATACC CCNCGNCTTG ANGGCNCCGA CNTTNTATCC TGAAAAGNTG      720

CTNGAAAAAA TCCCCGCNAA NGAAAANNCC ATCGCCATCT ANTTGNCTNG AAACAACTGC     780

TTTACTGCTG CCCAATNGAN ACCAAAATCN CGGCCGTACC TTGACCCTNT CACCCGCTNC     840

CT                                                                    842

(2) INFORMATION FOR SEQ ID NO:518:
```

(i) SEQUENCE CHARACTERISTICS:
        (A) LENGTH: 869 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1364UP (xi) SEQUENCE DESCRIPTION: SEQ ID NO:518:

| | | | | | |
|---|---|---|---|---|---|
| GATCTAGTGC | TTCACAAGCT | AGAAGCTCCA | ACCATGAAAG | AGCGATCGAT | CCTGAGAACA | 60 |
| CTTTTTCTGT | GGAGGCTTAT | CAATGCTCTT | TCTATCCGCA | GCTTCTTCCA | GGCAGATGAA | 120 |
| TACTGGCAGT | CGCTGGAGCC | TGCGCATGTT | AAGGCGTTTG | GATATGGTGG | GCTGACTTGG | 180 |
| GAGTGGCAGC | ATGGGCTGCG | CAGCTATGCA | TTCCCGATGC | TCTTTGAAAT | GTCGTACTAT | 240 |
| GTGGCGTGGA | TACTGGGTGT | GGCCACCCGG | ATGGCGCTGC | AGGGGTTGGC | ACATGCGACG | 300 |
| GCGCTGTGTG | GGGCGGTGGT | GCCGAGCGGC | GCGGCGGGCG | TGGCCGCGAT | GAAGGCCGTC | 360 |
| TGGGAGCTGC | CGGAGGCAGC | GCAGGAACTG | GTGGAGTACT | ACGGGGTATT | GTACGGGCCG | 420 |
| CGAGTGGTGA | TGGCGGCGGT | AGCAGCGTGC | GGGGAGTTCT | ACAGCGTGCT | GCTGGTGCGC | 480 |
| AAGCTGTATC | TGCGAGTCGC | GGATAAGGGG | GACGACCCAG | AAGGGCGACG | CGGCGCCGGT | 540 |
| CAGCCGGTTG | GCGCTGAATG | CTGACCATGA | CAAACTTCTT | CAACTGTTTC | TTCGCGAACG | 600 |
| CAACGTTCAT | CACTCCTNCA | AAATAACCCC | CACNGCGNTC | CCCTCTAACC | NATTTGGATT | 660 |
| GGANCCGGGG | CCCANCTTTG | GTTCTCNTGG | GCTTCCACCN | CAACTTTNGC | GGTGGCTGCN | 720 |
| TTTGCCTGCC | CTGCACGGCC | NATACTTTTT | ATCTTGGCCT | CCCTGCCTGT | TCTTGTGCCA | 780 |
| ACCTGTTGCC | CACCAAAGGT | GCACTCNNTT | ANCCTGTCCC | TAGGTTGCCC | CGNGCCCCGC | 840 |
| GGGTTTTTCN | ATACCANTNA | NACNCTCCT | | | | 869 |

(2) INFORMATION FOR SEQ ID NO:519:

(i) SEQUENCE CHARACTERISTICS:
        (A) LENGTH: 839 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1365RP (xi) SEQUENCE DESCRIPTION: SEQ ID NO:519:

| | | | | | |
|---|---|---|---|---|---|
| GATCTGCGGC | CGGCGGAAGA | CGCAGAGGAA | AGCGAATCGA | GCGCGGGAGA | GCGCTACTCG | 60 |
| ACGGACAAAA | GCAGTTACGC | GTCCTCCGTG | CAGGCGGTGC | TCAGAGCGAG | GACAGCGTCG | 120 |
| GCAGCCAGCG | CAGATACAGC | AATGAGCAGT | TCAACGGCAG | CCAGCGATAG | CGCGGGCGGC | 180 |
| GCTAAGATGG | ATGCAGCCGA | CGCAGATGAC | GCGACGCGCA | GCTTGGAGCT | GCGGCTTGCA | 240 |
| GCCCTCGCCA | CGCAGGACCC | GGCTGTGGAC | AGCGCAGACA | CGGCGAGCGG | CGCGTCGCCG | 300 |
| GCGTCGCCCG | CCGCGCCGCC | CAGCCCGCCG | CCCANCGCGG | CGACGGAGGG | GTCGGACGAG | 360 |
| GCGGCCGCGC | CGCTGGAGGT | GCCCAAGCAG | CGCGGCGACG | CGGGCACGGC | GGCCGGCGGC | 420 |
| GAGCGGTGC | GGCGGCGGCC | CACCAACCCC | TTCCGCGTGA | TTTCGGTCGG | CGGCTCCAGC | 480 |
| ACGTTCAAGC | GCGCGGCGGG | CGCGGACGGG | CAGGCGTCGC | GCACGTCGTC | CGCGGGCGAC | 540 |
| AAGGCCGCAC | CCGTGTCCGC | GAACGAGCAG | AGCATGCTCA | AGTTGCCGCG | CNAGCNCANC | 600 |

```
TACCCTGACC ATGAATTCNT CNACTGTTCA AAGANATTAA TTTCCTGANA ACNTGAANAA        660

ANCGGTCCCT GTNCTTGAAG AANCCCCCNN ANTAACNACC CCCTNGACAG CTCNGATTTC        720

CTCCNCCTTA TTNTAAAAAA TTTCAAATNC GGGTGGTNCT TCCCCCNCTN CCCAACNTTT        780

TAAAANGTTC CCACGGCNTN NTGNNCCCNN NATTTGGCCC CCCGTTCCNT TNCCCNGGT         839

(2) INFORMATION FOR SEQ ID NO:520:

(i) SEQUENCE CHARACTERISTICS:
        (A) LENGTH: 851 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1365UP (xi) SEQUENCE DESCRIPTION: SEQ ID NO:520:

GATCACGTGA CGTTCATGGA GCGTGCAGCA CTGCACGACA GCGAAGCGGT GGTGCGCGCG         60

ACGCGGCGGG CGGCCGTGCA GCTGTATGTG GGGCCCGGGG GCGGGCTGCG GGGGCGCCTG        120

GCGGAGGCGC TGGACGAGTT GCTGGGCGGA CCCTTAGCGG CGAGCCCACT GCGGCCGGCG        180

TGGGATGTGT ACTTTATGCA GCTGGCGCGG CTCGCGGCCT CCCGTTCCAA CTGCATGAAG        240

CGGCGTGTCG GGTGCGTGAT TGTGCGCGCC TGCCGCGTCA TTGCCACCGG GTATAATGGG        300

ACGCCGCGCC ACTTGCGCAA TTGCCACGAC GGCGGGTGCG CGCGCTGCAA CGGCGGCGGC        360

AGTGCGCTGC ACACCTGTCT CTGCTTACAC GCGGAGGAGA ATGCGTTACT GGAGGCCGGG        420

CGGGAGCGCG TGGGCGAGGG CGCGGTGCTG TACTGCGACA CCTGTCCGTG TTTGACATGT        480

TCGGTGAAGA TCGTTCAGAC GGGGATCACG GAGGTGGTTT ACTCGCAGAC CTACCGGATG        540

GACAGCGACA GCTTCAAGGT ACTGCGGGCG GCGGCGTCA GGTCCCGGCA GCTACAGGAC         600

GCGTTCCCCC GCACTTTTTA TTATATNNGC NGGCNGCTTT CCCNGCAACN GCTAAACTTG        660

CTGTTTTTNC ATATAAGGNC CCGGCGGTNC CGACTNCAAA GNAATNCCNC AACCNTTCTT        720

TNTTTCCGAG GCNGGGGAAT TTTCCCCGGA TNTNNGGCCC CCCCCCGTNN TGCCGTTACC        780

CANTTCCCCT GCCCAATCCT CCCCGCGAAN CCNCCNCCAA CCGTCTCGNN TTNCTCCACC        840

CGNCCTGNCC T                                                            851

(2) INFORMATION FOR SEQ ID NO:521:

(i) SEQUENCE CHARACTERISTICS:
        (A) LENGTH: 823 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1366RP (xi) SEQUENCE DESCRIPTION: SEQ ID NO:521:

GATCCAACGG TCAACCAATG CCTCCGAGAT TGCCGGCATA GCGGATGAGA TTGCCAAAGC         60

GGAGAAGCAG GACAGCTCCG CGGCGGTGTC TGCCATGGGT GCCGTCCTAG GCATGCAGC        120

GAGTCCTTTC GGTGCTTTGA ACGTGCTTAA CAGTTCTGCC GAGCTCTTGA ACCAGCCGGG        180

AGCAAAGCCT GCTGCCGGTG CTCTCAAGGG CATGATGGAG GCTGCGTCTA ACACGACTAA        240
```

-continued

```
GGCAATTGAC TTCATCATGG AGCGTGCAAG TCATCCAAAG GCTGGCGCGG CAGAGCAGGT      300

GATGGGTCTA GATATGGTAC TCCAGAATGC CGTGAACTCA AGCGAAACCT TGCAAATAT      360

CATAAAAATG CAGATGGCAT CGACCGAGGA GTCGCAGAAG GCCCTCCCAA GTTTGTTGGG      420

CTTGTTGTCG TACTCGACTG ACAAGATCGA GAGCATGAAA TCCGTGATTA AGCTGATAGA      480

GTTCGGTGAA AAGAGCCCTG ATGTATTGAA TCCTGTCCTA GAAGTGCTGC AAGCTTCCGT      540

GAAGGTCAAC AGATTGATAC CCTCCGAAAG AATTTTNGAC TTACACCCAC ATCCTGGAAA      600

CTTCATNTTT GCTGCGAGTT ACAAACTGGC ATTTCCCAAT CTGCCATTTG TTCCCTTAAC      660

GGNCCCCAAA GGTTTGCACA CCNCNNTCCT NCAGGNTTCA ATNCCTACTC CTNTNNCCNA      720

CCNANGAATC CNNTTGGCCC TTNTTTAANN CAAATCNGNC CANATNTACC CCCAGGTTTT      780

TTTTGGAAAN CCCTTTTANA CCTTTCCCCC CCTCCCTTTN NAT                       823
```

(2) INFORMATION FOR SEQ ID NO:522:

(i) SEQUENCE CHARACTERISTICS:
        (A) LENGTH: 854 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1366UP (xi) SEQUENCE DESCRIPTION: SEQ ID NO:522:

```
GATCTTATCA GGATAAATGA TTTGCTCCCG GAAAGTCGAT AAATTGCTCA TATATGCCCT       60

CTGGGGAGA TAATATATCG GACTTTCGCC ATTTTCAGCA TTTCTACGCG GCATGATTAG      120

CTTCGTAGGC TTCTTAGGGT TAGTAAACGA TTGCAAAACA GGCCACAACC CCCCAAGGAC      180

CCTGAAAAGA GAAGACTTGC CGCAGCCATT AGGACCTATA ATCAATAGAT GGTTACCATG      240

CTTCAACTCG AAGTTAAGTT CGGGGATAAG GACCTGATTA GCAGGTGTCA CTAGTGGAAC      300

ATGAACGAAT TGAATCTTAG AATCGTCGTA TTCTATAATG ACCTTTTTCC CATCAGTCTT      360

CGAACTACTT CCAGCGTCTA GCCTGTCATT GAAATTTGTT AACCGTAGGG CCTCTCCCTT      420

TAGCTGCTGG ATACTACGGC GCAGTTCGAC ATAGCGGCCA ATAGATGCGG ACGCAGTTAG      480

CAGTAAACGT CTGTTGGTGA TAAAATCAGC GGTGACATCC TCAGCCATAT TAGAACGAAA      540

GAAGACGGGG ATAGAGCATA ATATCAAGCC CAGCAGCGCC CCAGACGTAC TTCACCACAA      600

AGCTAGTACA ATTCGTACAG TGCTCTTAAA TTTATCTCCC CCGGCTNAGA ATAAGTTACT      660

GGTTANAAAN AAAAACCCAA TCCCATATTC GGTNTTTGAC CNTGAATAAA CNNTNCCNCN      720

TTGCTTGACC NCACTTGAAT TTATGACCGA ATTACCNCCA TTTTCCCCTG ACATACCGTT      780

CAATTGGNNG TTTGACCTCC CACTNATTAT GATTNAAATC AACCCATCCN GTCCTTCNGC      840

TTTCCCTGGN GATC                                                       854
```

(2) INFORMATION FOR SEQ ID NO:523:

(i) SEQUENCE CHARACTERISTICS:
        (A) LENGTH: 824 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1367RP (xi) SEQUENCE DESCRIPTION: SEQ ID NO:523:

| | | | | | |
|---|---|---|---|---|---|
| GGATCCGCCC | CCGTTCGCCC | CGTGTGGCCC | CGTGCCCGCC | GCCAGGGCCT | GCGCCGCGCG | 60 |
| CAGGCCCACC | GCGCCTCCGC | CGTGTTGCCC | TAGCGGATTG | TTCATTCCCT | GTGTTGCCTC | 120 |
| CTGACTGTCC | ACTCGACCTC | TTGTATCCGC | ACCTTTCTGC | CAAGTGCGCC | CCAAACTCTG | 180 |
| TTTTCCTGTC | TGTCCAGAGT | TTCCGTCTCT | GGCTGCGCTA | CTGCCTACCT | GCCGTTTGGT | 240 |
| ATGGAGGAGA | AGTGTGTGTG | TATCTGATTT | GTTTATCTGC | TTTCCTTCTC | CTATAAGCTT | 300 |
| TTTGTAATGA | AAAAAATTAT | GAAAACGGGA | AATCTGTGGA | ATTTGGAAAT | GCTGCTGGCG | 360 |
| CTGCGTTGTT | CAACTTCCAG | CGCCGCCGTC | TCGTTCTACT | GCTCTGTTCT | TGGTCTAGCT | 420 |
| TTCGGTATTT | TTTCTGCTCG | GTTTCGCTTC | TTTTTTCTGC | AACGCAAGGG | CGCGCTGCGT | 480 |
| GCCTGAGGTG | CCAGGTGGCT | GCACAAGTGC | GGGCGCCCGG | GAACCGAGCC | GGGTAGTTAC | 540 |
| CGGGCAACTC | TGCCGCCGAT | CCCCTGCGGA | GGCTTACGGA | AGCGCTTATT | TAATTGTTAC | 600 |
| GTAAGTCACG | TGGAGCTAGC | ACGTGCTTGG | CAGCTCAGCC | GCACGTCACG | TAGCGTGTGA | 660 |
| CTAATCGCGG | CGACCTGGTG | GGTTAAANGA | CGGGTTACNC | CGTTAAGTTG | GAAACGCNCC | 720 |
| AATAAATTAC | NTACCCNTTA | AACACACGGG | ANAAAAANAN | NCCCGGCNCA | NAAGNANCTT | 780 |
| TTGCCCTTGA | AGCCCGGTGC | CCCAAGCCCG | GNCCNCCCCA | GAAN | | 824 |

(2) INFORMATION FOR SEQ ID NO:524:

(i) SEQUENCE CHARACTERISTICS:
       (A) LENGTH: 850 base pairs
       (B) TYPE: nucleic acid
       (C) STRANDEDNESS: single
       (D) TOPOLOGY: linear (ii) MOLECULE TYPE: DNA (genomic)

(vi) ORIGINAL SOURCE:
       (A) ORGANISM: PAG1367UP (xi) SEQUENCE DESCRIPTION: SEQ ID NO:524:

| | | | | | |
|---|---|---|---|---|---|
| GATCTTATGG | GTGGTTCTCT | AGGGCTGAAA | GGCGGATATG | GACAGTCGAA | ATGGGCAGCA | 60 |
| GAATTTATTA | TAAAACGTGC | AGGTGAGCGT | GGGTTACGCG | GTTGTATATT | GAGGCCAGGC | 120 |
| TATGTGACTG | GTTCCCCTTC | TACAGGAGCT | TCTAACGCGG | ATGACTTTCT | GCTCCGGTTC | 180 |
| CTACGGGGAT | GTGTTCAGTT | AGGCAAAATT | CCTGATATTG | AAGGAACTGT | TAATATGGTA | 240 |
| CCAGTTGATT | ATGTGGCACG | GTTAGCAACA | GCGGCTTCCT | TCTCGTCATC | AGGCAATACA | 300 |
| CATATGATGG | TTGTAAATGT | CAATGCGAAA | CCAAGAATAT | CATTCAGGGA | CTATCTACTA | 360 |
| GCACTGAAGG | AATACGGGTA | CCAGGTAACA | TCAGTTCCTT | ATGACGAGTG | GAGTAAGGCG | 420 |
| CTTGAATCGT | CGAGTGATGA | AGAAAATCCT | TTGTATCCGC | TATTGTACCT | TGTCCTAGAT | 480 |
| GACTTGCCTA | AAAACTGCGC | AGTCCTGAAC | TCGATACTAC | TAATGCGAAA | TTTGTTTTAG | 540 |
| AAGAAGATTT | TGCGCGGACG | AATATTGAGC | CAATTATCAT | TACTTCGGTG | TCATTAGAGT | 600 |
| TGTGGGTCCC | CATATCTCAT | TTTTGCATAA | TTTAGCTCCC | NANAANAACC | ACCTAAAGTT | 660 |
| CCCAGCCCCT | GCCNATATTC | NCTCTCCCGA | CGAACAAATT | CCTTAATANC | NCATACCNCT | 720 |
| GCNCCGAACA | TACANCAACC | CNTAAATACC | NCAAATTGTN | GACAACATGA | NTGTTTATTT | 780 |
| TTTTTATATT | ACAACCTATT | ATTAACCAAA | TTNTNATCAC | GATCNTCTNT | GACGCCCTCT | 840 |
| CTGACAAATT | | | | | | 850 |

(2) INFORMATION FOR SEQ ID NO:525:

(i) SEQUENCE CHARACTERISTICS:
        (A) LENGTH: 825 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1368RP (xi) SEQUENCE DESCRIPTION: SEQ ID NO:525:

| | | | | | |
|---|---|---|---|---|---|
| GATCATCTGA | AGTAATATAG | AATCTGCATG | GGCGCAAACC | GTTGCGGTCC | AATGTAGCGC | 60 |
| CGGTGTAGCG | GCCATCGGTA | AAGGTGAGCA | ACGCAGGGCC | ATCCCATGGT | TCCATCAAAC | 120 |
| AGGCGGCCCA | GTCAAACCAA | GCCTTCAGGT | TAGAATCCAT | GTCCTTGTGG | TAGGCTTCTG | 180 |
| GAACCATCAA | GCACATCGCT | TCGGGTAATG | ACAGAACACC | ATTTATCACT | AGTAATTCTA | 240 |
| GCACATTGTC | CAGCGCGGCA | GAGTCGGATC | CGCCTTCTTC | GATAATCGGA | TAAAGCTTCT | 300 |
| CCAGTTGGTC | TTGGAAAACG | GCGGATGCCA | TGACACCTTC | CTTCGCACGC | ATCCAGTTTT | 360 |
| TGTTGCCTCT | TAGGGTATTA | ATTTCACCGT | TGTGTGCAAG | CCAGCGCAGA | GGCTGGGCAC | 420 |
| GGTCCCAAGA | TGGAATGTA  | TTGGTTGGAG | AAACGAGAGT | GTACCAGCGC | CAGGTGAGAC | 480 |
| TTGAAATGAG | CATTGGTCAA | GTCGTGGTAA | TAATTATACA | CCTGGCAGGG | TCAATTGACC | 540 |
| TTTGTACACA | ATTGTCCGGT | TATTTAGGAG | CACACAGTTA | ACAGTTCTGA | TACCGATGGC | 600 |
| CGTTAAACCC | NNCTTTCTTT | AAATNTTAAA | CTGGCATCCN | GAAGTCTCTC | GTNATTANCC | 660 |
| TGAATCTNCN | CCCGATACTC | CTGCCCATAT | TTCTTTCNCN | CAACAACGTT | TTTGAAATGG | 720 |
| TTTCCCAAAA | CCAAGGAACC | NAAAGAAATN | CTNTGGACNC | CTCCAACCCN | AACCCNNATT | 780 |
| TAACAATCGG | TACTNGCCAA | TTTNTTCAAG | CNNAACCTGT | NNNCT | | 825 |

(2) INFORMATION FOR SEQ ID NO:526:

(i) SEQUENCE CHARACTERISTICS:
        (A) LENGTH: 839 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1368UP (xi) SEQUENCE DESCRIPTION: SEQ ID NO:526:

| | | | | | |
|---|---|---|---|---|---|
| GATCGTGACG | ACTTTGTGTT | TTACTTCAAC | CGTATTGCAA | CGATCTTGGT | TTCGCGGGCT | 60 |
| TTGGATGACA | TTGCTATCGT | GCGGGATGAA | CTGCCATTGG | TGACTGCATC | CGGATATCAA | 120 |
| CTGGAGAAGC | CTGTTCATGT | GAATTTTGAC | AAGATTACGG | CTGTGAATAT | TGTGCGCTCT | 180 |
| GGCGACTGTT | TCATGGCTTC | CCTACGCAAA | ACAGTGCCAA | ATATATCCAT | CGGTAAATTG | 240 |
| CTCATTCAGT | CTGACTCTCA | AACAGGTGAG | CCGCAGTTAC | ATTGCGAGTT | CTTACCAGTG | 300 |
| AACATTGGCG | GCTCTTTCGA | CCAGGTCCTA | TTGATGGATG | CACAAATAAT | CTCAGGCGCA | 360 |
| GCAATTATCA | TGGCTATTCA | AGTGCTAGTT | GACCATGGTG | TTGAACTATC | AAAAATAAAG | 420 |
| GTTATTGTCT | ACTTAGCCAC | TGAAATTGGA | ATAAGAAGGA | TAATAAATGC | CTTTAACAAC | 480 |
| AAAGTATCAT | ATATGCGGGC | GAAATTATAT | CAGACGAAAG | TATGACAGAT | GGCCAATGTA | 540 |
| CTGGGCGAGG | GTGAGATTCA | TCGACTCAAG | ATACTTTGGC | TGTGACTGAT | TCAGAGCTTT | 600 |
| TGCTGCCCAN | GCAGGAATTA | ANAACTTTTG | GTGCTATTGC | ATGTTACAAT | ATTAGCATTT | 660 |

```
ATCATCCATA CCATAGCTGC TTTACNATAG CATNTAATTT TACTATCTTT NAACCCACCC      720

AGACTATTTT TCCCCCCNTA CTTTACNAAN ANTTTAANCA ACTGACCCCC CGNTATAATT      780

GCCCATCCAA CACCCCCCNC CTCNTAANAA ANACCNACTT GGAACGAGTG GGAACCNCC       839
```

(2) INFORMATION FOR SEQ ID NO:527:

(i) SEQUENCE CHARACTERISTICS:
        (A) LENGTH: 851 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1369RP (xi) SEQUENCE DESCRIPTION: SEQ ID NO:527:

```
GATCGCCTAC TTGTCTCAGG AACTTGTTAT CATGAGAGAT GATATGTGCA ACAGGTTTAA       60

GCGCAATAGC ATTATTTTCC CAACAGTGGA AGAGGAACAA AAACAGGAAT ACATGCTGTT      120

ACAGCAGGAG CTCCAGGATG ATGAACGTAG TTCGGATCTC TCCATTAGTC AACTGATTAA      180

GTCCAGGGAC CAATTGCCTG CCAGTGTCCA GGAGTCCAGG AAGATAGTCA AAACCATCCT      240

CGATCAGCAA CACCTTTCGC CCTTTACCTC GCAGGTGCGC CCTATAACGT GGGACTATGA      300

CTACACGTTG CACCTGTCCC CAATACCCTC CACTATGATC ATTTGCGACC CAACTGCACC      360

GAAATATGAT GTTACTTACA ACGGCTGCAA GAGTATCAAT CCAGGCTCAT TTCTCCACAA      420

GCGGAGCGTC AACTATACTG AGTACACTCC TTCGTTACGG AAAGCAACAG AGGAAGAAAT      480

TGTCGTGTAG GACTTTAAAC TTACATATAA TGTCAAATAT AAAGGTTTCA GACGTCGTCA      540

TGTTTCGTAT GGATATTTCT TGAACTTTTC CCGTAATATC GTATGGCATA CAGTAGAGGG      600

GGTCAATNGG AACAACCCGN CGTGCTTCTT CAAACTGGNC CCCANNCAAT CCCAAAAAAT      660

TNTGGAAAAC TTCCACCTAG ATTTTCTGGC CATCGCNGAT GCCCNCCNCT CTTTGATTCC      720

TNCANCCCCA GANNAATCNC CCNCTTTCCT GNTCATCCAT NCCCNTTNGC CCAATTCCNA      780

NCGTTAAANG CCCCCCCCNC TTTTCAACTT TNGGATTTTN NTNGTTTCCG TCGGCNNCCC      840

CCGTNCAGAC C                                                          851
```

(2) INFORMATION FOR SEQ ID NO:528:

(i) SEQUENCE CHARACTERISTICS:
        (A) LENGTH: 858 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1369UP (xi) SEQUENCE DESCRIPTION: SEQ ID NO:528:

```
GATCAAGACG AAGCAGAAGA AGACGCGGTA CGCATGTACG TGCCACCTGG TGCCGTCGGA       60

GGCGGCCAAG GCGATCGCTC TGGAGCGCGA CACGCGCCTG GGGCTGGTAA TATGCGTGGA      120

CCCGACGGTG GACACACGGG CGCCGCACAT ACAGAGCATT CTGGCGCAGC AGCAGAGGAA      180

GTACGGGCGC ACGGTGCCAA CCATCCGTGT GGCGGTGATT AATTCGATCG AACATTGCGA      240

GTTGTTTTTC GGCAAAACGC TCGACCGGAA CACACGGGAC TACCTGGTAA ACGTGAGCGC      300
```

```
TGCAATGGTG GTGTTGCGCG ATGTGGTGGG GACCCTGCCG CCCGACCTGA GGCCAATATA    360

TTCGCAAAAC CTGAGGTACC TGATAGACTG GTTGGATACC CCTGAGAGGC CATGGCCGTT    420

GCCGGACTTC TATCCGGTGA AGGTATACAC TGCAATGGAC GTGGAGCGCT CGCTGCTGAC    480

CGAGGTGAAA TACTCCCCAG AATAATGACT CCCTTGGAGG ATGCGTTTTA CCAACGGCAA    540

GAAACTTACC ATAGTTCCNT GGACAAAGGA ACCGTGGAAA TGCGCCGATC TCCCTACTAC    600

CCAAATAAGC GTTTTGAAAA ATGACTACAT TNGAATCCCN CCNACCAAAA TTGAACACTC    660

CCCGGAANNA NCATACNAAN CCAAAAGTTT GCTAAATATC TCTTTCCNTN GTACACTGAC    720

CCCNACTNTT GCAGGGAAAG GNCTGTTTTT AAACTTCCAC TCNGACTTNA TTTTACCCCT    780

CCCNGCATCC ACCNAANCAA CACCTNTTCN AACCATAGAA CNNTTTTCCT TTTAAAACAC    840

TNAGAAGCAT TTNAAAAT                                                  858
```

(2) INFORMATION FOR SEQ ID NO:529:

(i) SEQUENCE CHARACTERISTICS:
        (A) LENGTH: 834 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1370RP (xi) SEQUENCE DESCRIPTION: SEQ ID NO:529:

```
GATCTTGTAC AACTGAGCCT AGGTCTTGTT GTTGAACGGT AACCTCCACA TTCATTATTG     60

GCTCCAATAT GGAGAACGCC GAAGTTGGTA AACTCGTCAG TGCTGATATG ATTAAAGGAC    120

GCACAGTCAG CAGAATGGAT GCAGCTGCTG CGCAGTCTAG CGGTAGCCGC CAGCGTTTAA    180

CATGAATCAC ACACGAGTGT AGAGGAAAGC CTGCGGTTTT ACCACCTCTT TGCAAAGCCA    240

CTATGCAACA CGAGATGATA GAGTTCACGA ATGCCTCATA TTTCAATGGA AATGGCCAAT    300

TGTCTTCGTT AAAGCGTGGG TTTGGATCTA TGACAAGATA GTTATTATCG CTTCCCAAGG    360

GGTACCATCC GTTACTGAAT AGTACTTTAT CTTCTTCATT GTATTGCCGA ACTTCGAGTT    420

CGAACGAATA TCCATCATCT GTTTCAGAGT GCTTCCTCTC TGTAGCAGTA TTAATGGTTT    480

CCTTGTATGA AACTGCTACC TTGCCTACTC TTACAGGCGC CTTAAATTCA TTGAGCAGCC    540

GTCCGCTGCT ATTTCCAGTG CATTCCCCCC ATCCCATTCA TCACTGTCTG ACCAGTCTCC    600

TCATCCCTCA CNAATACCAC NACGGTTCCC CNCTCGTTAG CTGCNNCANG ATCACCCNAT    660

ANCCTTTTNT TCCCCAANTT CCCCGGTCCN NCANCGNCCT AAAANGGTGG NGGTANTCAT    720

GGGTNTTTCC CANTTGNANT TCNGCTTTTG AAAAACAATC CCCTTTAAGN TNNAAGNCNA    780

AANGGGTTCC CTTCTAANTG TGTCCCCTTG GGCCCNCNNC CCCAATNCCG AGAT          834
```

(2) INFORMATION FOR SEQ ID NO:530:

(i) SEQUENCE CHARACTERISTICS:
        (A) LENGTH: 840 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1370UP (xi) SEQUENCE DESCRIPTION: SEQ ID NO:530:

```
GATCGCAGAG GAGGAGCCCA TTCGGACGCT TGCATGGAAG GAGGACACCT TTGAGAATTT      60

TCTGGCGGAG GTGACATCCG ATGAGGCGCG CGAGACGCTG GTTTCCGAGG AGGATGCCGC     120

CACCTACCTG GCCAAGCTTT TATGACGGCT GTCCGTGCTT TTAAATTGTT ACATACTGTA     180

CATATTCGCT TTAGTCGTAC CACATTTTGA TCAGCTCTTC GGAAACCGCG CTGGGCGTCA     240

GCACGCCCAG GTCTGTGATC AGCGCGGTAA TGTGCTCGTG CGAGGTGTAG TCGATGGACG     300

GGCTTAGCAG CTGCTCTGAC TCGTCGCTGC GCGAGAAGTC CAGCGGGTCA CGCTCCATGG     360

GCAAGTCGTC GGGGGAAAGC GGGAACATCC TTACAAACTT GTGCGATTCG CTTACCACGT     420

AGAATGGCTT GCGTGCGTTC TTGGCGAGGA CCCCTACCGT GTACGTCCCC ACGAGATTTA     480

TGATGCCGCC GGACTCGGCC ACGCCCTCCG CGCCAACCAG CACTTGTCGA TTTTGTGTAT     540

GATGGACCCA CCGCGCTGTC CACGATCATC GTCACCGGAT GCCCTTTGCT TGCAGCAGGT     600

CATACAGCTG CTTGCCCTGC CCCGAAGGCC CGTGCTCCGT CACGANACAC CGGAAGCAAT     660

CACTCTCACC TGTTACTCAC ACGAAANNCG CCCGCAAACC AGTTCCCAAA AAGTCTCCTC     720

TGTTAGATCC NCCCATCTTT GTNCTTTTTN TNGACGCTTG CCCGAANCAA AACGTCCNTT     780

CCNCNGTTGC TGCTGNACCC CCCTCCCANA TNTTTTTTCC CCCCCCNCCC NATTTCNTCT     840

(2) INFORMATION FOR SEQ ID NO:531:

(i) SEQUENCE CHARACTERISTICS:
        (A) LENGTH: 835 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1371RP (xi) SEQUENCE DESCRIPTION: SEQ ID NO:531:

GATCGAGAAC AACTACGACA ACAGCCACGC AGACGGCGCG GAAGCGCTCA AGCCGAGCTA      60

TATTTTTGAG TACCTTGCCT CGCTCATGTA CCAGCGCCGC TCAAAGCTGA ACCCGCTCTG     120

GAACGCCATC ATCGTCGCCG GCGTCGAGGA CGGCCAGGCC TTCCTGCGTT ATGTGGACCT     180

CAAGGGCGTC AAGTACTCCG CCCCAAGCTT GGCTACTGGC TTTGGCGCCC ATATGGCCAT     240

TCCTCTCATG CGTAAAGTCG CAGATGCCGA AAAAGACGTC GCCGGCGTCG ACCTCTCAAT     300

TGCGCGAGCG ACTATCCTGG AGTCCATGAA GGTGTTATTC TACCGCGATG CGCGTAGTTC     360

CCGTCGCTTC TCGCTTGCCA TCATCGACAA TGATGCCGGT GTCAGCATGG AGCAACTGGA     420

AGTGGAAAAC ATGACCTGGG GGTTCGCCAA GGATATTCGG GGCTATGGCA CCCAGAATGT     480

CTGAGTACCG GCGCGCAAGC GCCGCACCTG TATACTATCT TGTCGCGGCT GCTCGCCAAC     540

CGCTGGCTAC TCACATACAT ATCAAGATGC ATAATCAATC TGCTCATGAA CGCACCTCTG     600

TTTTGTGGAT ACTCTTCTCG CGCGTATCCT GAGTACGCTG GAGTGCAAAA AGAGCCACTT     660

TGAAACAACA CGAGTCGCAG CTAAGGNGAN ATCCGANTAA NCAACNCACA CTTCAATTGA     720

CTTATGAAAT GCCCAAGGTT GATTGAACTG ACGTCCTTGG AACNNTGGGN CGTGGAAACG     780

CCCTCTTCAN TTGAACCAAA GTCCACAANN AGGTATTTNT TTNAACCGTT CCGCC         835

(2) INFORMATION FOR SEQ ID NO:532:

(i) SEQUENCE CHARACTERISTICS:
        (A) LENGTH: 850 base pairs
        (B) TYPE: nucleic acid
```

```
        (C) STRANDEDNESS: single
        (D) TOPOLOGY: linear (ii) MOLECULE TYPE: DNA (genomic)

(vi) ORIGINAL SOURCE:
        (A) ORGANISM: PAG1371UP (xi) SEQUENCE DESCRIPTION: SEQ ID NO:532:

GATCCATTGT GCGTTTGGAG GTCACGCCAC GGACGTGGAC ATGTACGTGA TGAGCTTCGA      60

CGGGCAGCTC TTCATTCGTG CGGCACGCAA GAAGCTTGAG TTCCCGACGT CTCCGCGGGA     120

GAGTTGGGCG TACCTTGCGT ATTACAGCGG ATACAAATTC GAGCGCATGG CGCTCCTGGA     180

CCGTCCGGTG GCCGAAACTC CGCGCGAGGT TCTGGAGAGC CGCGGCAAAC AGGTCGTCCG     240

CAACGGTCCG CAATACAGGA CTGTGATGAG AACCGGCGTC GGGGAGCACA AGCTGGTGCT     300

CGGAGCTGAG ATCGACGGCA TCATTGACTT CCGCGAGCCT ACGGGCGACA ACCTGAAGCA     360

CTACGTGGAG CTGAAGGTGT GTCAGAAGAA CCGGAACTTC TCAGAGAAAC TTTTCTCTTC     420

TTGGCTGCAA TGCTTTCTGG TGGGCATAAA CAGGGTTATT ATTGGATTCC GGGATGAGAA     480

ATTCGTCCTG AAGAGCGTCG AGGAGTTCGN TACGTCAGAG ATCCCACACC TGTTAAAGGG     540

CACGGAATAT TCCAATGTAT GTGTGGACGC AATAGAGTGG TATGGTGCTC TTACGAAGTG     600

GCTATGTGAG CTCCGCGGGG CCTGAANACA CTTCAACTGT ACAGCTCTCC NGCTCCCNTG     660

GTGCTTACGT NTGCNCCCCT GCCCNACAAT ACTCCCCNAN NGGGACNATT NTCCTGTTTG     720

TTCCCCAATT GGCGCGGCCC CNATATAANN CANATTCCNN CNTTNTTTCC CTTNTGNTTT     780

TAAAAACCCN TTNTTCCCAC CNATTTNCCC AGANNACANA GGNNNTCCCC ACCANNCTTN     840

CCCANCCNCA                                                           850

(2) INFORMATION FOR SEQ ID NO:533:

(i) SEQUENCE CHARACTERISTICS:
        (A) LENGTH: 835 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1372RP (xi) SEQUENCE DESCRIPTION: SEQ ID NO:533:

GATCTTAAAA TAAGATAGAA TGGTAATAAA TATCATTCAG GTACAATAGA TGCTGGTGTT      60

ACTAAAGGAT TACCTGGAAT ATAATTATCA GGATGTCCTA AAGTATTAGG TGAAAAGAAT     120

ACAAATAATG AAAAGAAAAT TATAAATACA AATACTGTTA CTAAATCTTT AAAAATAAAA     180

TAACCATGCA TTGGTAATCT ATCTAAATTA CCTGTAATAC CTAATGGATT TGATGAACCA     240

TGTACATGTA ATAGCATTAA ATGCATAATT ACTATTGCTG CAATAATAAA TGGTACTAAA     300

TAATGAAATA GAAAGAATCT TATAATAGTA GGATTACTAA CACTAAATGA TCCTCATAAT     360

CATAGTACAA TATCATTTCC AATAAATGGA ATAGCACTAA ATAAATTAGT AATAACAGTA     420

GCACCTCAAT GTGACATTTG TCCATATACT AAACAATAAC CTAAGAAAGC TGCTGCTATA     480

GTTAAAATAA AGATAATAAC ACCAACTGTT CATACAATAA CTCTAGGTGA TTTATAAGAA     540

CCATAATATA AACCTTTACC AATATGAATA TACATACAAA TAAGAAGAA TGAAGCACCA     600

TTAAGATGCA TATATCTAAT TAATCAACCT AGTTGTACTC TCTCATAATA TGTTCTACTG     660

ATGANAAAGC TAATCCATAT TANATGAATA AGCATNNCTA AAAAATACCN GTNAGAATTG     720
```

```
AATACTAACN TAACCTATAA AACCNAATTC NTCCATATAA TGAGAAGGTG AGGGAATCAT        780

ACNACTATAA CNATTTAATA TATTGATTCT ATTNCCATTT TNTTNTNAAT TTTTC            835

(2) INFORMATION FOR SEQ ID NO:534:

(i) SEQUENCE CHARACTERISTICS:
        (A) LENGTH: 854 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1372UP (xi) SEQUENCE DESCRIPTION: SEQ ID NO:534:

GATCTAGAAT TATTAAGTCA ACTATTAACT AATATCTATA ATAATAATGG TTTATCATTA        60

AAATCATTAA AGATAATTAT TAATAAATTA CCATTTAATA ATGATATATT ATTATCAAAA       120

AATTATGTTA ATAAAATAAA TAAATATAAT TTACTAATTA ATAATAATTT AATAATAAT        180

AAAAAAGATT TAATTAATTT ATATACTTTA GATAATAAAT TATTAGATTT AAGTATTCTT       240

AATAAATATAT TATTAGGTAA ATATTTAGTA GGTAGTAATA TCCAATTAAA GGGTAGACTA      300

TTAAATAGAA ATATTACTAG ACTAATAAAA ATAAATATTA TGAAAGGTAC ATTTAATAAT       360

TATATATATC AATGAAGTAA ATTAAATAAT TTATATAAAT TAAATTATAT ATCACTTAAT       420

ATTAATAAAC TTAATAATCT ATTTATTAAT AAAAATGGTA TATTTAATAT TAAAATTAAA      480

TTAAATACTA TTTAATAAAT ATTCTAAAGT AATTTCTTAT TTATTTTATA ACATTTTAAA      540

ATGTTTTATG TTAAATAGAT AATAATCAAT TAAATAATAA AAATTAAGAT GCCACAAATA      600

ATTCCATTTT CTTTATGAAT CAATTAACTT ATGGTTTCTA TTTATTTTAC NATTTATCNC      660

ACTACTNATG TTTTTTTACC NNTGAATTTN ANAATATATA CTCNCNANTA NATATTCNCA      720

AATTATAATA TTAATTAAAT TTAATTAATC TATTATGATC CTNNTTNTAA ANATATCAGA      780

ANAATTTAAT ATATATATNG AAATATNTTT ATCCCCCNGG NCACTTGAAN AAAANTATAG      840

TTTCNTCCCC ACAT                                                       854

(2) INFORMATION FOR SEQ ID NO:535:

(i) SEQUENCE CHARACTERISTICS:
        (A) LENGTH: 827 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1373RP (xi) SEQUENCE DESCRIPTION: SEQ ID NO:535:

GATCTTAATT TAAAATTTTA ATTAACTATT TATAATTTAG AAATATATAA TCTAGAGATA        60

TATAATCTTA AAATCATAGG TAAAAATACA TAAGATAGTA AGAATAAAAT TAGTAAAATA      120

AATAGAAAAC CATAAGTTAA TTGATTCATA AAGAAAAATG GAATTATTTG TGGCATCTTA      180

ATTTTTATTA TTTAATTGAT TATTATCTAT TTAACATAAA ACATTTTAAA ATGTTATAAA      240

ATAAATAAGA AATTACTTAT AGAATATTTA TTAAATAGTA TTTAATTTAA TTTTAATATT      300

AAATATACCA TTTTTATTAA TAAATAGATT ATTAAGTTTA TTAATATTAA GTGATATATA      360
```

| ATTTAATTTA | TATAAATTAT | TTAATTTACT | TCATTGATAT | ATATAATTAT | TAAATGTACC | 420 |
| TTTCATAATA | TTTATTTTTA | TTAGTCTAGT | AATATTCTAT | TTAATAGTCT | ACCCTTTAAT | 480 |
| TGGATATTAC | TACCTACTAA | ATATTTACCT | AATAATATAT | TATTAAGAAT | ACTTAAATCT | 540 |
| AATAATTTAT | TATCTAAAGT | ATATAAATTA | ATTAATCTTT | TTAATTATAA | TTTAAATCAT | 600 |
| TATAATAAGT | AAATATATTA | TTATTTTATT | AACATAATTT | TTGATAATAA | TATACCATTA | 660 |
| TTAATGGNNN | TTATAANAAT | TATCTTNAAG | GATTTNNTGG | AAANCCTTNN | TTTTAGAAAT | 720 |
| TNGGTAAANG | TGNNCTAAAN | NCCAATCCCN | AATTATTAAA | TTAATTTAAN | AANAANNANC | 780 |
| CTTTTNTTNA | ATTTAGTTTN | AATTTAACCC | NCTCCCCTNT | TTAANAT | | 827 |

(2) INFORMATION FOR SEQ ID NO:536:

(i) SEQUENCE CHARACTERISTICS:
        (A) LENGTH: 831 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1374RP (xi) SEQUENCE DESCRIPTION: SEQ ID NO:536:

| GATCAATGAT | AAATCGAAAT | AAACTGATAC | TATTGTAGCC | ATTTTTCTGA | ATTAGCACCT | 60 |
| GGAAACACTT | TTTAACCTGT | TCCGGAGTGG | TCTCTGACTG | ATTGGAGTTG | AGCGTCTCGC | 120 |
| GCGTAACTGC | CTCTGCTGTC | GTCTTAGCTC | CGACGTTTTC | CACTGCCCGC | CGCTGGGTCG | 180 |
| CCACACGCGT | CTTCTTCTGA | ACTGCGAGTG | GCCCCAACAT | GTGGTCCACT | AGCGTTGGTG | 240 |
| CGCCGCCAAG | TTGCTGGAAT | AACGCACCCA | TCTTAAACCA | GTTGAACTGT | GCAAAATCTC | 300 |
| CATACGCTTC | GAATTGCCTG | AGATAGGAGT | TGCGCTGCAT | GCTCTGGCGA | AGAGCAGCAT | 360 |
| CCGCATGCTG | ATTGGTGCTC | TCATCTAGAG | CGTCGCTGGT | AGCATCTCCA | TCATTTTCGA | 420 |
| TGCTGTCGTT | CTGGGTATTG | CTAGCATCGT | CTGTTTCCGG | ATACATAGAG | CCAGGTACAC | 480 |
| TCACGTGATT | CAACTCAAGG | TAGTCTTCCA | GCAGAAACCG | CTTCGCCCCG | TTGACAAACT | 540 |
| CCTCAGGGCT | CAAAAGCTTC | CCCGCATTTG | TCAGTTTTAG | ATTGCGTATA | CTCAAGCTTG | 600 |
| CAAGTCGCTG | ACGCTCATCA | CGGCATGCGA | ATCCTGGGCA | AAAGAGAATT | GACCTCAGTT | 660 |
| CAATCGCCCG | CCCTGCTTTA | AAAACATATT | AACTCTCCCN | CCGCNCNCAG | GANAGAATNC | 720 |
| TCCCGTACTT | CNANGNAGNC | ANCTNTGCCC | NTCATCTCAA | ATTGCGNACC | TNGTNANTTG | 780 |
| GANCCNTTCC | CGAGCCCCTC | TGCCCCCCTA | TTGANGNTCG | NCCCCGTTCG | A | 831 |

(2) INFORMATION FOR SEQ ID NO:537:

(i) SEQUENCE CHARACTERISTICS:
        (A) LENGTH: 856 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1374UP (xi) SEQUENCE DESCRIPTION: SEQ ID NO:537:

| GATCTTAAAG | GCGGATATAA | AAGCTGTACA | AAAGAAGATG | AACAAGCTTC | CAACGCTTCT | 60 |
| AAACTTTGAT | ACTTCCGCCA | TTGCCTTGGA | AGATGAAGGC | GAAACAAAAG | AAAGTACCGA | 120 |

```
ATTTAGGGCT ATTATTAAAG AGTTTGAAAC ACAAAATAGT TTCCAGAAGA TTTTATATGG        180

GAATTAATAG ATAAGACTAG CATCTTTCGA AAACTTTATA TAAACCAGGC AGATTAGCTA        240

CCTCTACAAT GTCCTTCAGA AGTCTCGTCG ACGCTAGGAG TCGCCTCTTT ATCGTTGGGA        300

AAACCACTTG TTCCAGAACT GTCCCAATAT GCTCTGCCTT GGAAATATAA TAAGCGCGAA        360

CATCGCCATC GATTGTGTCG TCGTTTATAT CTACGTGCTC AATAATCTCA GGAATATAGA        420

ACAAGGCAAG TTGTCGAAGG ATTCCTTCTA GGCACTCCTT TTCCGACGAC CAATCTACCT        480

TAGTTCCCAT TCTGTAGAGG AAAAATGGAA GTTTAGAAAG AGGCGGGACA TAATCCTTTA        540

AAAGTAAGGG TACACTCTTA ATGCGAACGT TCGTCAAATC GGTCTCGTCT CCACATATTT        600

CAATCGAGTA ATAGTTCTCT AGCATTCTCT CATGTCCACA CTGTTGAGTT ATTCCAAATA        660

TCGAATGCGA CGCATTATCC ATCTTAGATA NCGTTGGTAT ATCGCTAACT TCCGCAATCT        720

CAACCNCANC CTNGATATNA TTTCCCGAAN TTTGNNAATN NNNATCCCAT TGANAAAATT        780

CCTTCCTTAG GACCTATCAC CCAAATANTT AACCGCGNTT NANGATCCCT GNTTGGTCAC        840

AACCNCNGGT CTTNNN                                                       856

(2) INFORMATION FOR SEQ ID NO:538:

(i) SEQUENCE CHARACTERISTICS:
        (A) LENGTH: 828 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1375RP (xi) SEQUENCE DESCRIPTION: SEQ ID NO:538:

GATCTTAATT TAAAATTTTA ATTAACTATT TATAATTTAG AAATATATAA TCTAGAGATA         60

TATAATCTTA AAATCATAGG TAAAAATACA TAAGATAGTA AGAATAAAAT TAGTAAAATA        120

AATAGAAAAC CATAAGTTAA TTGATTCATA AAGAAAAATG GAATTATTTG TGGCATCTTA        180

ATTTTTATTA TTTAATTGAT TATTATCTAT TTAACATAAA ACATTTTAAA ATGTTATAAA        240

ATAAATAAGA AATTACTTAT AGAATATTTA TTAAATAGTA TTTAATTTAA TTTTAATATT        300

AAATATACCA TTTTTATTAA TAAATAGATT ATTAAGTTTA TTAATATTAA GTGATATATA        360

ATTTAATTTA TATAAATTAT TTAATTTACT TCATTGATAT ATATAATTAT TAAATGTACC        420

TTTCATAATA TTTATTTTTA TTAGTCTAGT AATATTTCTA TTTAATAGTC TACCCTTTAA        480

TTGGATATTA CTACCTACTA AATATTTACC TAATAATATA TTATTAAGAA TACTTAAATC        540

TAATAATTTA TTATCTAAAG TATATAAATT AATTAAATCT TTTTTATTAT TATTTAAATT        600

ATTATTAATT AGTAAATTAT ATTTATTTAT TTTATAACAT AATTTTTTGA TAATAATATA        660

TCATTATTAA ATGGTAATTT ATTAATAATT ATCTTTATGA TTTATGACAA CCATATATTA        720

TAGANATTGT TAATAGTTGA CTAATATCCN ATCCAACCTN TATTNATTTA NAGATCATAN        780

ACCTTTTATA CAATTATTTT NATATAACAT NTACCTNATT ANAATATN                    828

(2) INFORMATION FOR SEQ ID NO:539:

(i) SEQUENCE CHARACTERISTICS:
        (A) LENGTH: 688 base pairs
        (B) TYPE: nucleic acid
        (C) STRANDEDNESS: single
        (D) TOPOLOGY: linear
```

(ii) MOLECULE TYPE: DNA (genomic)

(vi) ORIGINAL SOURCE:
(A) ORGANISM: PAG1376RP (xi) SEQUENCE DESCRIPTION: SEQ ID NO:539:

| | | | | | |
|---|---|---|---|---|---|
| GATCTATTTT | GCCGACTTCC | CTTATCTACA | TTATTCTATC | AACTAGAGGC | TGTTCACCTT | 60 |
| GGAGACCTGC | TGCGGTTATC | AGTACGACCT | GGCATGAAAA | CTATTCCTTC | CTGTGGATTT | 120 |
| TCAAGGGCCG | TCGTAAGCGC | ACCGGACCCA | GCATAGATGC | TGGGCTCTTC | CAGCCATAAG | 180 |
| ACCCCATCTC | CGGATAAACC | AATTCCGGGG | TGATAAGCTG | TTAAGAAGAA | AAGATAACTC | 240 |
| CTCCCAGGGC | TCACGCCGAC | GTCTCCACAC | TCAGTTACGT | TGCCGTGAAG | AATCCATATC | 300 |
| CAGGTTCCGG | AATATTAACC | GGATTCCCTT | TCGATGGTGG | CCTGAAAAAT | CAGGCCTTTG | 360 |
| AAACGGAGCT | TCCCCATCTC | TTAGGATCGA | CTAACCCACG | TCCAACTGCT | GTTGACGTGG | 420 |
| AACCTTTCCC | CACTTCAGTC | TTCAAAGTTC | TCATTTGAAT | ATTTGCTACT | ACCACCAAGA | 480 |
| TCTGCACTAG | AGGCCGTTCG | ACCCAGCTTT | ACAGCCTAGG | CTTCGTCACT | GACTCCACGC | 540 |
| CTGCCTACTC | GTCAGGGCGT | CATATTCTGC | CCTGACGGTG | GAGTATAGGT | AACACGCTTG | 600 |
| AGCGCCATCC | ATTTTCAGGG | CTAGTTCATT | CGGCCGGTGA | GTTGTTACAC | ACTCCTTAAC | 660 |
| GGATTCCGAC | TTCCATGGCA | CCGTCCCG | | | | 688 |

(2) INFORMATION FOR SEQ ID NO:540:

(i) SEQUENCE CHARACTERISTICS:
(A) LENGTH: 757 base pairs
(B) TYPE: nucleic acid
(C) STRANDEDNESS: single
(D) TOPOLOGY: linear (ii) MOLECULE TYPE: DNA (genomic)

(vi) ORIGINAL SOURCE:
(A) ORGANISM: PAG1376UP (xi) SEQUENCE DESCRIPTION: SEQ ID NO:540:

| | | | | | |
|---|---|---|---|---|---|
| GATCCAAGGA | ACCTTTCCTT | CTGGCTAACC | TAGGGTACTT | GTACTCTAGG | CGAACCANGA | 60 |
| CTTTTACTTT | GAAAAAATTA | GAGTGTTCAA | AGCAGGCGCA | AGCTCGAATA | TATTAGCATG | 120 |
| GAATAATGGA | ATAGGACGTT | TGGTTCTATT | TTGTTGGTTT | CTAGGACCAT | CGTAATGATT | 180 |
| AATAGGGACG | GTCGGGGGCA | TCAGTATTCA | ATTGTCAGAG | GTGAAATTCT | TGGATTTATT | 240 |
| GAAGACTAAC | TACTGCGAAA | GCATTTGCCA | AGGACGTTTT | CATTAATCAA | GAACGAAAGT | 300 |
| TAGGGGATCG | AAGATGATCA | GATACCGTCG | TAGTCTTAAC | CATAAACTAT | GCCGACTAGG | 360 |
| GATCGGGTGG | TGTTTTCTTA | TGACCCACTC | GGCACCTTAC | GAGAAATCAA | AGTCTTTGGG | 420 |
| TTCTGGGGGG | AGTATGGTCG | CAAGGCTGAA | ACTTAAAGGA | ATTGACGGAA | GGGCACCACC | 480 |
| AGGAGTGGAG | CCTGCGGCTT | AATTTGACTC | AACACGGGGA | AACTCACCAG | GTCCAGACAC | 540 |
| AATAAGGATT | GACAGATTGA | GAGCTCTTTC | TTGATTTTGT | GGGTGGTGGT | GCATGGCCGT | 600 |
| TCTTAGTTGG | TGGAGTGATT | GTCTGCTTAA | TTGCGATAAC | GAACGAGACC | TTAACTACTA | 660 |
| AATATGCTGC | TGCATTTGCT | GTTGCCCTTC | TTAAAGGACT | ATCCGTTTCA | ACCCANTGAN | 720 |
| TTTGAGCATA | CAGTCTGTGA | TGCCCTAACT | TCTGGCG | | | 757 |

(2) INFORMATION FOR SEQ ID NO:541:

(i) SEQUENCE CHARACTERISTICS:
(A) LENGTH: 821 base pairs

```
            (B) TYPE: nucleic acid
            (C) STRANDEDNESS: single
            (D) TOPOLOGY: linear (ii) MOLECULE TYPE: DNA (genomic)

(vi) ORIGINAL SOURCE:
            (A) ORGANISM: PAG1378RP (xi) SEQUENCE DESCRIPTION: SEQ ID NO:541:

GATCCTTATA AAATGGGCAA TAGACGTGTT ATAATATAAT ATACAAAATT ATAAATAAAT       60

ATTTAATAAA ATATAAAATT AATAATTAAA GTATTATAAT AATTAATAAA ATTATTTATT      120

AATAAGTATG GATTTTTAAC TGAAATTTGT TAAAATGAAA TAAGAATTGC TAGTAATCTA      180

TTAATAAGAA AGTAATGGTG AATACTCTAA CTGTTTCGCA CTAATCACTC ATCACGCGTT      240

GAAACATATA ATTAAATAAA GAATATTAAT TAATTTATTA ATTATTAATT ATTATTAATA      300

TTATTTAATA AATATAATAA ATATTTTAAT TTAAATTATG AATTAATGCG AAGTTGAAAT      360

ACAGTTACTG TAGGGGAACC TGCAGTGGGC TTATAAATAT CTTTAATATT CCATTTTTAT      420

AAAATAAATA TATTTTTTAA TATATTTTAT AATAACTATA ATTAAATAGT TAAAATTTAA      480

ATTATAATTT AATAATTTAA TAACTTATTA ATTAGAGAGT TAGGGTACAT CCCCCCTAAT      540

GCTATGCATT ATGGTTGGTA CACTCTAATT AATAAACTAT AATAAATAAA TACTAATATT      600

TTATACCATN AATTATAATT ATTTTTAANA NATTTAATAT TATTAATGAA ATATATAATA      660

AGTATTNTNA TTTNATAATA ATAAAAATGA NAAAACGACC CCTAATAATA ATTTGCATTT      720

ANANTTACCC TTACACCTCC CNTTAAATTT TTACCCTNAT ANCCNTNTTA ATTAAGGANG      780

GNGNNCCCCN TGCTCCCCNN TGTCCCCCCC ATTNNANTTT A                          821

(2) INFORMATION FOR SEQ ID NO:542:

(i) SEQUENCE CHARACTERISTICS:
            (A) LENGTH: 852 base pairs
            (B) TYPE: nucleic acid
            (C) STRANDEDNESS: single
            (D) TOPOLOGY: linear (ii) MOLECULE TYPE: DNA (genomic)

(vi) ORIGINAL SOURCE:
            (A) ORGANISM: PAG1378UP (xi) SEQUENCE DESCRIPTION: SEQ ID NO:542:

GATCCTTGCG TACTAAGAGT TAGACTTTAA TTAATAATAT TATTTGTAGA AGATAGAAAC       60

CATACTGACT CACGTCGTAT TTAACCCAAC TCACGTAACC TTTTAATTGA CGAACAGTCA      120

AACCCTACTT AGCTGTTACA ACCAAGAGGA TAGGTTGAGT CGACATCGAG GTGGCAAACA      180

TAACTTACAA TAGCTACTCT ATCGTTATAT TACCCTGTTC AATTTTGTTA TCATAATAAC      240

ATTTAATTAT TATTTCAATA ATTCTCATTA TTGTTCAGAC TATTTCATTA TGTATTATTT      300

ATTAATTAAT ACATATTGGG CTTTCGTGGA TATAATTATT GTTAATCCTA CTCATATATC      360

TAGTCGTTGA ACGTTCTTAT AACTTTATAA AAAGGATTGT TATAAGCTTC GCTGCAGATT      420

GTCCTTTATT ATTATAAAAT AATATTAGGA GTTCTTTGCA ATTAACCCAA TTTACTCAAT      480

ATATTTAAAT ATTGATAATT AAATTTCACA ATTTAATGGG ACTATTAATT AACCCTAGCG      540

TAACTTTTAT TCGTTATCAA ATACCATTAC AATATGTATA TTTTGTTCAT TATGCCAAAC      600

TTACGTTATT GTTCTACTTG TAGGTATTAC AATTATAGCA CAGTTATACC ATTATATTTA      660

TTTATATATA TCCCATATAA GTTTTTATTA ACATATAAAC TGTNCATTAT TTATCTNTTT      720
```

| | |
|---|---|
| TATATAAAAT ATNATTATAT TAATNATTTA TTAANATTTA NACCCNTATA TTAAATATAA | 780 |
| TCNTTTTTAA TAATAAATTA TTAAGGACTN TCCAACCTTT TTGAAAGACC CCCCACTNCC | 840 |
| ATTAAATGTC NT | 852 |

(2) INFORMATION FOR SEQ ID NO:543:

(i) SEQUENCE CHARACTERISTICS:
        (A) LENGTH: 845 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1379RP (xi) SEQUENCE DESCRIPTION: SEQ ID NO:543:

| | |
|---|---|
| GATCCAATTC TCTCGGTAGT TTCCTTCCAT ATAGAGACTG ATCAACTAGC CACATTCCCA | 60 |
| CAACAAAAGA GTTTCTATCT AACGTGCCAT CGCGTCTTGT ATCTACCATG TCGTAGATTT | 120 |
| GAGCCAAAGT ATCTTGAGGT AGATTGCTTC GAGACCAGAT ATCTGTAACA ACTAAGTTCA | 180 |
| ACATTAGACC ATCCTCTGGC ACCTCTCTTG TCTCATCGTA GTTACCGTTA TTCCACCATG | 240 |
| GGAGCAAGTC AAGATAAGTG TCTCTATTGC TGACCCACAT TCCCTCGTAA CGCTTTCTTT | 300 |
| CCCTTTCAGT TACGTACCCA ACATCAAGGT GCGACTTCCA AGGTTTGTCT TCGTTGAAGG | 360 |
| AATTACGGTA TCGAAGATTT TGACGTATCT TCTCGCGCTT TTTGCCGGAT CTTCTTCCTG | 420 |
| GACTTCGACT ACGGGAGTTG CGGTCGCTTC CGTAATCCTC TTCAGAGTCT TCGCTGTCAT | 480 |
| CGCTTAGTTG ATGGGCTCT GAGCTGGAAC TGTCATTAAG TATACCCCGC ATAGTGGTTT | 540 |
| TTAGCCGCAC ATGCAATTTA CTCTGCACGA GAGCGTTATC GTTCTGCGTA TATATATGTG | 600 |
| ACGTTGGCGG GTGATTCTTG CTGGGGCCTA GCCCAGTTTG CCCATGGCGC TTGAAAGCTT | 660 |
| CATCCACTTG GANTGCTGCG TTGANANTTT GGTATTAATN CAGGAANATT CCTCCGTAGT | 720 |
| CCAGTTCATA GGAATTTGTT CATGTCAATT ACAANCTTTC NACGGAATC TTTTGCGACT | 780 |
| CNTGTCACGT CGANGNATNT GTCNTCCGTA CANCTCCCGA TNCNCCAAAN TNNCCNCATT | 840 |
| CNCNN | 845 |

(2) INFORMATION FOR SEQ ID NO:544:

(i) SEQUENCE CHARACTERISTICS:
        (A) LENGTH: 855 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1379UP (xi) SEQUENCE DESCRIPTION: SEQ ID NO:544:

| | |
|---|---|
| GATCCGGAAG TTAACACTGC CTGGGATTCA TAACTTGGCA ACAGCGTATG TGCGTGTGAA | 60 |
| CATAGTCGAT GGAGCACATG AATTGGGGTA TCAATACTGA TTTCATAATG CTTTCTGGAG | 120 |
| CCATTGACCT TGCGTGACAA CCTCAAACAT ATTTGGAGCC AATGGTTGGA CTTTATGTGG | 180 |
| GGAGATGCAG TATTCGGATG TATGCACTGT TGGTAGTTCA ATCTTTCGGG ACAAAAACC | 240 |
| TGGTAAGTGA ATTGTCTCTT TGAAGCGCCA CCCGCTCCAT CATCCAGCAG GTTTCCTAAG | 300 |
| TTTTTAGCAC GCGAAAGGCT CGCGCCTTCG TGTATACCCT TAAGTGGTGG TGCTTTGTGC | 360 |

```
TCGACCAGCA AGAACTTCTT TGTAGGCTCC ACTCGGTGTA CTTTCCGACC TTTACAATAA      420

TACTCTAAAG TTTCCGTCAG GAATATTCTA ACCCTGTGGA GCACGAGATT AGCCCGTGGG      480

TTTAGCGAGA GCGATATTGG TAGAAATGCG TCCAAAACTA TATCTTTCGA TGCAATTACG      540

ATTTCATAAC TCAATTCTTT TTCCCAGTCA CGTGATATGA CTATCGGTTC GGTATCTTCT      600

ACAGAGTTCG GAGATAGTGT GCGGATAAGT TAATCGGAAC ACGACGTGGA CATTGGACTT      660

AAGGTCCTAT GCCCTCAATG TCACTCAAGC AGGTATTTAC GTTCCCNATG TTACTAGAAT      720

CTTCTTGCTC GACNCCGGAN TNGANCCCCA AGAAAAAATA TCCCCGCCNG AAAANAATTT      780

CCCTGGNGTG ACGTGTGNAT NACCCNACGA AAACNTCCTC CTTCGAANGT NCCTTATATT      840

CNNTNAAANA ATANA                                                       855
```

(2) INFORMATION FOR SEQ ID NO:545:

(i) SEQUENCE CHARACTERISTICS:
        (A) LENGTH: 847 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1380RP (xi) SEQUENCE DESCRIPTION: SEQ ID NO:545:

```
GATCGCATCG ACCTCGCCAA AGTAAGGCAG GCTCTCGACG GAGATCCAGT CGACAAGGTG       60

AGGAAGCGTG GTGTTCTTAC CCTCGAACAC AATTGGCTCC TTCTCGCCCG GCAAGTGGAC      120

CGCCAAGGTC GGCTTCTTAG TTGGGTACTG CACAAATACA AAGTCGTTCC GGAGCAGGTT      180

GGCCAGTTCG TAAAAGGACT CGTTCAGGCC CTTCACGCCA CCGTCAACCA CCACTGCGGT      240

CTTGGACTCC GCAAGCAGGT CCTCCAGGTC CTGGGCGGCC TCCTTGCCCT CCAGCACCGT      300

CACGGCCGGC TCGGCCTGGC GCAGCATGTA CGCCACAATT TCCTCGGCCT TGCGTGCGCC      360

CGTGTATGGC ATGCCCTCCT CTGACGCCCC ACTGTGGAAC ACCTTCAGCG TCGGGTACCC      420

GCGCACGTTC TGGCCCGCGC ATAGATCCAG CTCCTGCTCG CAGTCCACCT GCGCCAGCTT      480

GATGCCCTTC TCGGCCAGCT CCCCAGCCGC CTTCACGTAC TCCGGTGCCA GGTGCTTACA      540

GTGGCCACAC CATGGCGCAT AAAACTCCGC CATCACAAGC GGGTTCTCCT CTAAGAACTT      600

CCCGAACGTC TCTCCGGTCA ACTTGACACT GCAGAGTCCT CTGGTGCAGT GGCATCTTGG      660

GCCTGTGCAA CTGTGCCAGC AACCGGCGAT GGACAACACA AACCGCTTGT CCAAAANCNT      720

TCTCGCTGCG TCTATCCTAC CCGTGGTTTN GTGNACTCTG TGGCGATCAA ANCCGGNTNG      780

CNATTTTTGT TTTATACTGA TCCAGAATTC ACCCTNTCNC AAAACNNTTN CCNGAAAAGA      840

NCGNGTN                                                                847
```

(2) INFORMATION FOR SEQ ID NO:546:

(i) SEQUENCE CHARACTERISTICS:
        (A) LENGTH: 860 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1380UP (xi) SEQUENCE DESCRIPTION: SEQ ID NO:546:

```
GATCTCGCCT GTTGTGAGTG ACGCCGAGTT GCGCGAATTG TAGCAGTGCG AGAGGAACGT    60

GCCGACGGTA TCGTTTGCCA GCGCGACAAC GCGCACGCTG CCCAACCCGA CCGCGTCCAA   120

CTGCTCCTGG TACATCTTGA CCACGTCCTT GCCGATCGCA TCCTTGATGT TGAAGCCCTT   180

CGTCCAGCGG ATCAAAGTGC CGCTCGATAG CGATGTCTGC GCCACGGGAT ACGAGAACGT   240

AAACCCGAGC TTCAGTTGGC CGCCCTCGCT CTGGAGCACT TCAGAGTGGT AGCGCTTGAC   300

AAACGCCATT GTGCGCTTCG CGATGAAGCC GAACAACTCG TCTGATGTTA CGTCGTCGTC   360

AAGGAGCTCC TCGGGGATCT TCGACTTCAA CTGCTCCAGC TTGAACGTGT GATCACCGTT   420

GAGACGCACC GAGCACACCC GGAAATTCGT GCCGCCAAGG TCCGCCGCCA AGAACGTGCC   480

CTCCTCAGTG CCATTGGGCC TGCCCATCAC GTACGACGGG ATCATCGGAA GCCCACGGTA   540

CTCCCGTCCG TCTCTCCGTT CTTGAGACCT GTTCCATACA TTCGATGAAG TACGCGGTCA   600

ACTCGCGGAG TTTGTCCTCC GTCACCTCGA ATCCTTACA TATTTCGTCC ACTGCTCCTC    660

GACTTTCCCG CGTTGCGCTT GTGCAAATCT TCNAAAANAT CCTGGTACTG TAAANATTAG   720

ACTTCGANAC GTTGGTCGAG TCTTTCNNGC TTNCCTACTC NCCNGCCNTG TCNTANTATT   780

TTGANGGCGN TCCAATAAAA AACCCTTTNG GGGGTCNCAA GNGACCTCCC ACCCTCTTTT   840

GTTTCCCCNT CCCNNAATGA                                               860
```

(2) INFORMATION FOR SEQ ID NO:547:

(i) SEQUENCE CHARACTERISTICS:
        (A) LENGTH: 835 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1381RP (xi) SEQUENCE DESCRIPTION: SEQ ID NO:547:

```
GATCATTATA TTATAAAATA TAATAAAGAA TATATTTAAA TAATAATAAT AATATGAAAT    60

ATTATATTAA TTCTCCATTG GAGCAATTTG AGATTAGAGA TTTATTAGGT TTAACATCAC   120

CAATAATAGA TTTTAGTTTT ATTAATATTA CTAATTTTGG TTTATATCTT ATAATTCTTT   180

TATTAGTAAT TTTACTAATG AATTTAATAA CTAATAATTA TAATAAATTA GTAGGTTCTA   240

ATTGATATTT AAGTCAAGAA ATAATTTATG ATACTATTAT AAATATAGTT AAGACACAGA   300

TTGGTGGTAA AGTATGAGGT TATTATTTTC CATTAGTTTA TACATTTTTT ATTCTTATTT   360

TTACTATAAA TTTAATTAGT ATAATTCCTT ATTCATTTGC TATAACTTCA CATGTAGTAT   420

TTGTAGTATC AATAAGTATA ATTATTTGAT TAGGTCTAAC TATTATTGGT TTTTATACTC   480

ATGGTTTAAA ATTCTTTGGT TTATTTTTAC CACTAGGTAC ACCATTAATT TTAGTCACCA   540

TTATTAGTAT CAATTGAATT ATTATCATAT TTTGCTAGAC TTATTTCATT AGGTTTAAGA   600

TTATCAGCTA ATATTATAGC TGGTCATTTA TTAATTGTTA TTTTAGGTGG TTTATTACTT   660

AATCTAAANC CACAAATATT TAACNTTTTN TTAAGTTCNN CCNATGAATG CTATTTNAGT   720

ATGTNTGTTA GAATTTNTAT CTTATACCNG CTTANTNTGA AGTNTNAATA CNCCNTATNA   780

AACTATTTAT TCCTTATTAA ATTAACANTT NAACNCCCNA TTANTTTNTA TNCTT         835
```

(2) INFORMATION FOR SEQ ID NO:548:

```
    (i) SEQUENCE CHARACTERISTICS:
        (A) LENGTH: 863 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1381UP (xi) SEQUENCE DESCRIPTION: SEQ ID NO:548:

GATCATTGTC CAATATTCCC CACTGCTGTA TCATATAGAT ATTGATTATA ATTTCTAAAT      60

CAACGTGATT GTTCTAACTT TAATTAACAA TTATGAATTT TTGGCTAGTT ATTATTTTTT     120

AATTAACTAA TACCTAAATC ATTATAAGCT TGACTTAAAA CAAATAATTA TTACATTATT     180

CTTTATTTAT TATTTAATAT TTAGTTAAAT TTTAAGTTCA TTATTCTTAA TTTTTACTCA     240

CGAGTACACC ACTTATTAAT ACTATTAATT AATAATATTA ACGTTTGATT CGCATGTGTA     300

ATGTCCTTAG TTAGCGCTTA ATCTGAACCA ACATCATGTT CTCATTATTA TTAACTATTT     360

TTAATTATTT TAAATAATTA TTTAATACGA AAGTTATAGG ATTCGAACCT ATGAAATCAT     420

AAAGATTTAT AATAGCTCAA ATATTACACT TTAAACCACT CAGTCAAACT TTCTTAATAT     480

ATATACCTTA TATATGGTTT GATAATTTAC TTATAATATA TAGTATATAA TTTAATGATA     540

AACTCTTATC ATTTAGGTGC GTAGGGTTCA CCCCCCTATT GCTAGTCAGC AATATGATGT     600

ACCTCCTAAA TGATAAAGAA GTATAATATA TAAATATTAA TATTAAAGTA TTTAATGAAT     660

ATTATTATTA TTTATTTAAT TATTATTTTT ATTTAGTAAA TAAATAAATA TTTCCACTTA     720

TTGAAATATA GGTTCTTNGA TTAGAAATAA GCNATNATAA TGTNCCATTG ACTATTAAAT     780

ANTGTGCTCN CNNGACTTCC CTATTTNCCN NNGANAANTC NGAANATCAG AANANAGATT     840

CCNANATNTT TAATNNNCCC CCA                                              863

(2) INFORMATION FOR SEQ ID NO:549:

(i) SEQUENCE CHARACTERISTICS:
        (A) LENGTH: 845 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1382RP (xi) SEQUENCE DESCRIPTION: SEQ ID NO:549:

GATCTCACAC GTGACTAAAA TCACTAACAC CACGTGACTT CGTGCACGTG GCATCGTCCC      60

ATTCTGTGCG TCGCTAGCAT TCTGCCCGCG CATCTGTGTC AGGCCACTGC GCAGCTGACC     120

ACGCCGTACC ACGGCAGGCT TCACGACAGA CGGCAAGCTC AATCGCTATC TACGGTTTCA     180

GGTGGAATTT CTTACCGGCA TCCGATTAAT TGCTTTTTTG GCTTCCTTTT GCCCCTCTTT     240

TTCCAGTGGG TTGCTTCCTG AAAACAGGGA GCTAGCTTCC CGTAGTACGT AACAGTCGTA     300

GAGGGTTAGG CATCGCTGAG CTCGAGACCC GGTGATGCAA TGTGCACAAC CCTCGTCTGC     360

GCAAAACGGG CACGAAGATT GAAAGTATCC AGGAGTGCAG CCCAGGGTCA TGCGAGACAG     420

AATGGGCCAG AAAAAGCGAA AAAATGGACG ACGCTTTTAT ATATATATGT AGCGAGGCCG     480

GGCGTTCCCA GAACGGGACC CGACACAACT TGTTGTAGAA TTTCTATCTG CAAGGAATCA     540

AATACAAAAT GGAATCTAGA TTGGGATGGC TAACTCGTTT GAACTACGAC ACTGGTTCTG     600
```

```
CATTGAGAAG AACTCCATCA TCCGGACAAT GGTCCTAAGA CCAACCACCC AGANACTTNG      660

TGGANCTTAA AAAGGNGGGT TGAACATCCT GAGAATGAAC TTCTCGCNCG GTCCTACAAT      720

TNCCACCATC GGTGNTCNAA NACCCNNAAT TCGAGATTNT NCCNGTTAAC NTTGGCCTTG      780

CTTTGAANCC AAGTNCCTGA ATNAAATGTN CCTNTCGAAA NTTANTACCN TCCCCTACCC      840

AAANC                                                                 845

(2) INFORMATION FOR SEQ ID NO:550:

(i) SEQUENCE CHARACTERISTICS:
        (A) LENGTH: 862 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1382UP (xi) SEQUENCE DESCRIPTION: SEQ ID NO:550:

GATCTATAAC AGGTGCCAAG TTGGCAGATT TGTTTCAGGG GCTCGACGAT GTAGAGTCCA       60

GTAGAATGCT CTGTAACCCC AGAGCATACT TTGCGCGAAA GTCTTTATCT GTTGAAATCA      120

ACTGGGGTAT CCGCTTTGAT GCTGTCCCGG AGGTTGATGC CTTTCTTGAT CGCCTTGTCC      180

AGTATCTGGT TGGTAAGCTC AATGAGCTCC GCATGACCAC GTCCCATATT GTTTTGAAAA      240

TAGCACGCAG AAGCAGGGAT GCCCCCATCG AACCCCCCAA ATACTTGGGC ATGGGTGACT      300

GTGACAGTTA TAGTAAATCG TGCAGATTAG GTCTTGCTAC CAATATTCCT GGGGTTATAT      360

CTGCAGAGAT AAAGGCAGCT TTTCGCATGC TATGCTGCCC CGCAAAGGAA CTGCGTGGTA      420

TAGCCGTTCA GTTTCTTAAA CTGAAGGAGG CATCCATTTC TCAAATGCCC CGTCAGCTCA      480

GGTTTCCATT TGGTACAATC AGACCTTTAA CAACTCCAAA GAATCGTATC ACAGCGTCGG      540

TTACAGAATT GCCACCTGTA GTTTATAAAA GGGCCACTCC TATTAAGGAT TTTTTTGACC      600

GGCACAAGAG GACTCAGATT CACCATCACC TGATTCACTC ACATGATGTC TGCGTCAGCC      660

TTGTGCGAGT CATTCCTGGT GGATTACCTA CGATCTTGCG GAAAAATCCN AAAAAACATT      720

GACNATCTNA AACCAGACTT CTTTNTTGCN ATTCCCAAAA AAATTGGGNN GNGCCCNGGT      780

TNNATCCCAN CATGCCCTTA AAATTTAGAT CCTTGACCCT ACTCCNANTT GNTNCCCNAA      840

AAAAAAACTA TCAATGTNTN CT                                              862

(2) INFORMATION FOR SEQ ID NO:551:

(i) SEQUENCE CHARACTERISTICS:
        (A) LENGTH: 823 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1384RP (xi) SEQUENCE DESCRIPTION: SEQ ID NO:551:

GATCTGCATC GCGTCCACCG TGGACTGGGC GGTCGTGGGC GGTCACGGAA AACTCGGCGG       60

ACTCGGTGAT GGTGCCGGCA AGCGTCTCGT AGCGGATGGG CACGACCTTC GCAAAGTAGG      120

AAAAGAAGTG GCTATGGCCG TTCGGAACCT CCATGGCGCG GCCATTGAGC GGCCCGGGGT      180

TGCCGGCAAT TTCGGGCCCA AAGGAGAGAC TATGGATCAC GTGGTTGAAG GAGAGATGGG      240
```

-continued

```
GGTGTTCCTT GTAGAAGGAA TCGTCGTGGG CGTGGCCCTT GCCAACGTGC GCAGAGCCCG      300

GGGCGAAGTG AATGTTCCCG TGAACGCGGT TGAGCTGCGC GGTGCCAGCG ACGCGGCATC      360

CCTCGTTGAT CTGCTCCTGC AGGCGCTCCG TGTAGCCCTC GCGCTTGCAC TGCTCAAAGC      420

CTTTGCCATC GAAAGTGGCC CAGTTCATCT CTGCGTACGC CGCGCGCACC TCCCCGCACG      480

TCTGACAGCA CACGCGCTCG CTGCGCGGCA GGTTCTCGTT CTGGTCCTGG TCGCGTGCGC      540

CATACACGGC CACAGTAGTC TTGGTCGTCT GTAGACGGCA ACGTCTCGCC ACTCGGAATT      600

CCTCCTTCCC CACGTCCGTC CNTGTTTGTC CACCNTTTTT CCTTGATCCT CCTCCAACNA      660

ATTCACTGTG CTCCCTGTTC TCTNTANNTC CATTTCATAC TCCCCCGGAT CTTGCAAACT      720

TATATCNAAC CCCACTCCNC TCTGCTGCCG TCCTTCAANC ACTGNGCGTC TCCCTCCCCA      780

NTTCCCTCCT ANCAAANACN CGTTCACAAC ACCNCNTATN CCT                       823
```

(2) INFORMATION FOR SEQ ID NO:552:

(i) SEQUENCE CHARACTERISTICS:
        (A) LENGTH: 849 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1384UP (xi) SEQUENCE DESCRIPTION: SEQ ID NO:552:

```
GATCACTTTG TTTGTGTCTG CACGATAAAT GGCCTCGGTA CAGAGTTTTA CGAGTGTTTC       60

TTGGCTGAGA CCGGACAGGT CAATCTCAGA GTTTTTACTA TTCATTAGTG AGTAGATTGA      120

CGCGTAGTTA TTATCAAAGG CCACCGGGGA ATTGTTAAAG AAGTTGGAAA CAGATGATTT      180

CGACATGGTA TAGTTCTGTA GCTTAATTAG AACGGGCAGG TCTGAGCTCT CCGCGACGGG      240

AGTACTGTTT TGAATGGGTG GCACAGCCAG TGGCGGTTGG GGCGTGACCA TGCCAAGCTG      300

TGCGCCCGCT GTCAGGCCCG CTGGTACTGG AGCCGGCACG CTTATCGGCG GGTCTGCTGG      360

TGTCGGCGAT TTGGAAATAC GGTTGTTGCA CGCTGCTAGG TATTTTTCGC GCTCCGCTGG      420

GCTCATCTTC TTCTCGGTCA AGCAGGGTC GAAGTTCAGA ATACCCTTAC TCTTCGTCTC      480

CTCTGCAATC ATGTGCAACG TTTGCGCGAT CTTCCCCAGC TTGTGGTGAT AGGGCGCCAG      540

GTCGCCCGAG TTCCGGATCA GCTGCGCTTT CATGCCAAAG TTAACGAAAT TCTTGTAACA      600

GCGTTCGACG CAGCGCTTCC CAAGCGGTAC CGCAGCGCAA ATCGTTTTCC TGCTGGTACT      660

TGTTGTCNAT ATTGAATCNA ACAGGCCCCC CAATAANCCT GTCCCACGGG CCCCGTTCCT      720

GANNAAACCA GCATCACACC GCNAAAAAAC GGGCCCCACN CGTCGTCATC NAACTTACCC      780

CTCCAGACTG NNTATCCANN GCATNCNCCT TTTTTNTCCC GTGTNTCTGA AANTNCNAAG      840

CCCCCACCT                                                             849
```

(2) INFORMATION FOR SEQ ID NO:553:

(i) SEQUENCE CHARACTERISTICS:
        (A) LENGTH: 862 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:

(A) ORGANISM: PAG1385RP (xi) SEQUENCE DESCRIPTION: SEQ ID NO:553:

| | | | | | |
|---|---|---|---|---|---|
| GATCGACCTC | GTCATCATGG | GCAAGCAGGC | CACCGACAGC | GACAACAACA | ACACCGGGCA | 60 |
| GATGCTGGCG | GGCCTTCTCA | ACTGGCCGCA | GGCCACCAAC | GCCGCGCGTG | TTGAGCTGGA | 120 |
| CGCGACTGGC | ACGCGTGCGA | CCGTCACGCG | CGAGGTCGAG | GGCGGCGAGG | AGGTCGTCAG | 180 |
| TGCCGCGCTG | CCACTCGTGG | TCACCACGGA | CCTGCGGCTC | AACACGCCGC | GCTACGTCAC | 240 |
| GCTGCCCAAC | AAGATGAAGG | CGAAGAAGAA | GCCGATGGCG | AAGCTCAACC | TCGCCGCGTT | 300 |
| CCCCGGCGTC | GACTCCGCCG | CCCGCCTCAA | TCTGCTGCGC | TTCGAGGAGC | CGCCCGCGCG | 360 |
| CGCGCCGGGC | ACCGTCGTCG | CGTCCGTGGA | CGAGCTGCTC | GCCAAACTCA | GGGAGGCCAA | 420 |
| GGCCGTTTAA | CACCTATATA | AACTAACAGC | CCCTATTTCC | TCCGCGGACG | CAGCGTCCCG | 480 |
| CTCTCCAGCA | GCCCCGGCGG | CTGCTTGCGC | AGGTACGTCT | GCTCGTACCA | CGCCTCCCAC | 540 |
| TCCCCGCCCT | GCGCCCGCGC | CTGCTGTACG | CTCTTCCAGC | ACGCGCCGGC | ACTCCTCGTC | 600 |
| CCACGCCGCG | AGGTTGCTCC | CCCGGTCGCT | GCCGCCCGCG | CTATCTTGCA | ACNCCGCCAG | 660 |
| CTTGCAGTTT | CGCCCGCCCC | CCCCGCATGT | NNCCCNCCAA | CNCNTTTTTA | CACNGGATNT | 720 |
| TNCCCNTTTG | TTNTCCNTNN | NTTCCNCCCC | GTGGAANTGN | TTTGCCNTTG | CTTGANAATG | 780 |
| CTANCCAACC | CCCCAATTTG | ATNGNGCCCC | CCCAAAATNA | ACTTTCCACT | TTGCCGAGAC | 840 |
| CCCGCCCTGT | NCCCTTNTTT | AA | | | | 862 |

(2) INFORMATION FOR SEQ ID NO:554:

(i) SEQUENCE CHARACTERISTICS:
        (A) LENGTH: 851 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1385UP (xi) SEQUENCE DESCRIPTION: SEQ ID NO:554:

| | | | | | |
|---|---|---|---|---|---|
| GATCCTTGAG | GGCTGGTTCC | TGGGCTTCGA | GCCCGCGGCC | GAGGCCGAGC | TCGCGCGCGC | 60 |
| GGCCGGGACC | TACGGCGCGG | CCGCGCTGCG | CGAGGTCAAC | GCGGCGCTCG | AGGACTACTC | 120 |
| TGCGTGTCTG | TGGCGCGCGG | CTGGCGTGCC | CTCGGTCGGC | ATCGTGTTCG | ACGCGCAGGT | 180 |
| TCGCGAGTGC | GTGGCCCGCT | GGCGCATCCA | GCAGGAGCAC | GAGCTGCGCG | AGCGCTGCGG | 240 |
| CGCCGGCATG | ACCGACGCGC | AGGTGCACGC | ATTTCTGGAG | CGCTACCTGG | TGTGCTACGA | 300 |
| CGTCTACTAT | GCGCGTCTGG | TGCGCGAGGG | GCTCGGGAAC | CTGCACCGGC | TGACTGTGGG | 360 |
| GCTGGACGGA | GACCGAAAAG | TTACGTATGT | TAGCCAGAAG | AATATGTAAT | GCCGAGTCTA | 420 |
| TAGTTCCTGG | TCCGAGATGT | CCTCCCAGGG | GATGAGATAG | CGCGTCTGGT | GCGCCTTGTC | 480 |
| GCGCGTGCGC | GCGGCGGGGC | CCGGCGGCGA | CGCGCGCTGG | CGCGGCGCCA | TGCTGGGCGG | 540 |
| CGGCGTCGAC | GGCAGCACGC | TGCCGCCGAG | CTCGTCACGT | GGCGCGCCAG | GAAGGCCTCC | 600 |
| GTCTGCGCCT | GGCGCGCGCT | CAACGCCTGC | AGTCGCGCGA | ACGCTGCCCA | NCACGTTCGT | 660 |
| CGCGCNGTCC | ACTGCNCGGG | ACTTNTTAAA | CACTCCTGCT | TTCCTGGAAT | CCTTGAACNA | 720 |
| NCGCNGTTGC | GCTTTNCNAC | TNTNATGANC | CCCCCAAACC | CCTNTTTGNG | GGCTGCGGGC | 780 |
| NCCCCGCCCC | NNNNCTCTCG | CCNGGTTNNG | TGTCCTTNAC | CCTNCCCCTT | TNCNTTAACC | 840 |
| GTNTANNTTN | N | | | | | 851 |

(2) INFORMATION FOR SEQ ID NO:555:

(i) SEQUENCE CHARACTERISTICS:
        (A) LENGTH: 857 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1386RP (xi) SEQUENCE DESCRIPTION: SEQ ID NO:555:

```
GATCGCACGT CATTTTACCT ACAGGCTGGG CTTTTGAAGA AGACGCCTGC ATGGTACAAT      60
GTCGTAGCCA GGATCCCACC TGTGACCAAG TTCGCCAGAG AACCGAAGCT GCATGACCCA     120
GTTAGCGGCA AGTACAAGGG CGAGCTGGAT ATAATGACGG ATAGATTAAA CAGAAACACA     180
GAGACGTACA AGACACGCGC TGGGAGTTCC GACCGGCAGA CGGCCGCGGT GCACAAGCCT     240
TCTAAGCTGC GGTTTATCGA GGACAAGCTG CGGTCGCTGT TTTTCCAGCA GCATCCCTGG     300
GAGCTGTCGC GGCCGAAGGT GCTGGTGGAG AACATGGGAA ATGAGCAGTA CGACTGGTCG     360
CGGATGTTGC AGCTAGGCAA GCCGCTTGAC GGTGAGTCTG TGGTGCAGCG GACGCTGTAT     420
CTGCTGAAGT CGGGCGCGCA CCGGGAGATG CTGGCGGCAT ACGACCAGGC GCGGTTTGAG     480
TTCTATCGTC TGAGGATGCA GCAGGAGCTG GAGGAGCAAA TAGCGTACGA GGAGGCCACG     540
ATGGTTGGCG CTGTGTTCAA GACAACCGCT GTGGAGCACG GTCTGCAGCA AGAGCAGAAG     600
GTCCTCGACA GTGGAAAGAA GACTTTGTTG CCGGGTTTGC CCTGATTTTT GCNAAAAAAA     660
ACTCTACAAA GCAGTCCNTG GGCCNAACCC ACCGAAGAAA AGAAGAACC AGGACNNTGC      720
CGAACCCNAA GACNCCACCT GTGNACTCCN TTGCCAACTT TGTTATAAAT TCTTACNNTT     780
TTATTCCCTT NGTACAATNC NANNTACTGT TNTGTGCCAT CATGTGCCCC AACAGGTTCC     840
CCCCNTTGGA NAAANGC                                                    857
```

(2) INFORMATION FOR SEQ ID NO:556:

(i) SEQUENCE CHARACTERISTICS:
        (A) LENGTH: 856 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1386UP (xi) SEQUENCE DESCRIPTION: SEQ ID NO:556:

```
GATCCATGCC TCGTTATAAC TGAGCAGAAG TGTGCATGCG AACAGAGGCG TTTCCTTGTT      60
CCTTGCCAGT TCCCCCATTC CCCAAGTTGC ACTGCAAAAT GTGAATCATT GATGTCTTGT     120
CGTCGCCATC GGTGCGCTGA AAGATGCTGT TCCGGTAGAC CGCATTCTGT CAAGCGGAAC     180
TCTAGGCGGC GCCGTGAGAG TCCAGATGAT GAATCTGAAG TTGAGGCCCA GCACGTGTGC     240
TTAAAAGATT GTAATCGGGT GCTGCTTTGT GGTATCCACA TGTGCAATTA CAAATGCCAT     300
GCAGGCAAAT GTCCTCCCTG CTTAGAATCA GATTCCAATG ACCTTATCTG TCCCTGTGGT     360
AAGACAATCG TACCAGCCCC TGTCCGTTGT GGAACAAAGC TCCCTCGCTG CACTCATCCA     420
TGTCGAAACT CGCTGCTGGA TACTTGGCCC TGCGGACACA GTCCACCTTC GCATAATTGT     480
```

-continued

```
CATCCCTTAG ATGAACCTTG CCCCCATGTA CCATCACAGT CAAGAAAACT TGTCGCTGCG    540

GTAAAAACGA GATCAGGACA TTCTGCTACA ATGATGATTG TCGTGTTCGA GACCGTGTAA    600

GAAGCCATGT CCTATTGCAA TCACTTCTGC CAATTNCCTG TCATTCCGAT GGCAATGCCA    660

GCAAACTTGT TAGCAAGCCT GTGGTCNACC ACCGAAAGCC GCACNTGTTT GTTAGGGAAA    720

TGCNTGGCNT NCGNATGCCT GAATCCCTGT NCNAAAAAAA AANCNCCGTC CGTTGTCCAT    780

CNCCACCAAT NTGCNTGATT TGCTGGAAGA GAANGTTCCG ACACCNCCCC GTCCTGNAAG    840

AATGTGCAAT CNNCGN                                                    856

(2) INFORMATION FOR SEQ ID NO:557:

(i) SEQUENCE CHARACTERISTICS:
        (A) LENGTH: 830 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1387RP (xi) SEQUENCE DESCRIPTION: SEQ ID NO:557:

GATCAACCAC TCGTGTGCCT ATACATAGGA ACCAAAAAGC CTTCTGGCCT GGTCCTCAAG     60

TAGTATTGTA TAAGTTTGGA ATCCTTGTAC GCGGTTGCCT TCCGCGCACC TTTCATATTT    120

TCGGTAAAAG CCTCCACAAG GTTCCTATCT TTATCCTTGA AGTTGTCTCC ACAGGACTCC    180

CACAAGAACG CCCCAGCAAG CTTCTTATCT TTCACGTATT CCTTCTTTAT TTTCATTGAA    240

TCCACATTGT CGTAGACGAC AAGAGTTTTA GTATTAGGAT CGTAGCTATA TGCAGAGACC    300

CAAACATTGT CAAACTTCTC TGGGCCGTGA GCTAGCGGCA ATTGGTTGTA TAGCCACATA    360

CCCGGTTCCC CTTCTGATCC TCCGCCTACA CCAGAATATT TCTGGCCAAT TAGTTGTTCA    420

CCATCGCCCC GAACGTTGGT GAAGCCACGG CCATACGCTG CCATGCCGAG TGCAATTTTT    480

CTTGGGCTGA CCTTAAATTG TTCGGTCATC ATGAGTATCG CATCATGTGC ATTCAACTCA    540

TCAAAGTTGT CAATACCCAT ATCTTCATAC CGACGCTTAT CTAGGTGCGA TTGTACGGCG    600

AATTCGTAGC ATTGTACAAG TTGCTATGGT AGCCTGTTCG CTCTGACCAT GCACCGTGGT    660

ATCGTATGTC ATCATATCCN CATGCTGAAA ACTGTTCACT CNCAACCGGA AATGCAATNT    720

CTGAAGAAGC NGGCTGCCAG CTTNATTGAA CCGTCCTGTN TCCCCGGGCC CNANATNTTT    780

CCATCTCNNT GTTNGCAGCG GTNCTTTNNA AAACTGGNTC GNNCNCACCA              830

(2) INFORMATION FOR SEQ ID NO:558:

(i) SEQUENCE CHARACTERISTICS:
        (A) LENGTH: 857 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1387UP (xi) SEQUENCE DESCRIPTION: SEQ ID NO:558:

GATCACCACA ACACAGAAGC ACGCAACGCT ACAGGACTTC CCTGTTCTTT TGCTTGCACA     60

CGTCCAGCCC AGAGGACGAT TACACCGCCG TCAGGGTTCG CTAGTCTCCG GCAGCACAGG    120

CTCCTTATCA CATTTTGCAT TTTCACGCTC GCACATGTCA CAAATAACCA AATACATCCC    180
```

```
CAAAAGCACG CTTTTTCTCT GCCCGTTCTT TCTCATCGCG TCAGACTTCG TACTCGCTAT        240

GAGCGGCAAG GCACGCGCG CAGGGAGCTC ATCTACAGGC ATCGGGTCGC GGCCCACGCG         300

TCTGCAGCGG CTGCGGCAGC TCGTAGCGCA TCGAGATCCG GCAAGAGGCC CGTCAGGTGC        360

ACTTACGAGC ATCGAAGAGT TTACTAGGAG ATGACAGCGC CTGCACGTCC CTGAGGCTAG       420

CCTCCCGAGG CGGGCGGGCC GCTTGGTATA GGGTTTACAT AGCAGAATGG CACGAATATT       480

TGCTCTAGGC AACTGCAGGG ACGGAAGGGG CTTCATGCGA AATCCTTGCA CCGCCGGGTG       540

CCGTATATAA GGTGACGCAG CTGCGCAGCT GGGGCGGGCA TGCTAACCAC GACAGGATGT       600

GGAGTGGTGC GCGATTATAT ACGACAAGCC GGCGTGGACG GTCGGTGCAC AGGCAGGACA       660

CCTGGCGGAA ATCCCAANTC GTTGAACAAG GGAACTGGTG CAGCNGGCGC AATCTACAAG       720

AGTTGTTGAN GGCGGCCGTC ACATTTGCCG TTNCACTGAC CCTGTCNCGA TCCANGAAGA       780

GGNCTGGCAT NTCCCANAAC CTCCCCACAG CTGTNGACTT GAACTCCNGC CTACCTTGAT      840

TTGCANNCCA GAAAAAN                                                      857

(2) INFORMATION FOR SEQ ID NO:559:

(i) SEQUENCE CHARACTERISTICS:
        (A) LENGTH: 821 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1388RP (xi) SEQUENCE DESCRIPTION: SEQ ID NO:559:

GATCCACCCA AATTCGTCTG TGCTGGACCA GCTTTCCCAA CAGTCTCCGA GGTAATCAGG        60

CTACTGCGTT CCTATTTTAT GGCCTTCAAT AACTCTTTAT ACTTAATTTA GACGTTAACT       120

TCCACATCCG GTATTTTTCA CATCTGAGAT ACTGGCAAGC ACGGCTAGCT TTAGGAGAAC       180

TGTATCCCAT GACTTGTGGA CAGGGGCTTT ATGAAAAAAC GCCTGTCCGT GTAAGGATAT       240

AGAAAACATA CTGAGATGGC TTTTGTTGCT GAATCAGACA TTCTTAGGTT ACATTTTGGG       300

CCTGGCTGTA CAAGGCACTA ATATGAAGAT AGAGTTATAG CGCGTGAGAA GGAAAGGCTC      360

CACTGGGTGT TGCATGGGAT TTCAGGGTCG TGATAATAAT GCCAGGCAAT CATATAGATT      420

ACCACGAGGG AAACATCAAC GCTATTTAAG GTCATCCTTT TTGACATCTG TCGAGGAAGT     480

GCGAATAGCT GTAAGCGCAA CTCTACAAGA TGCCGCCGTC TCCAAGACCA ATGCTAAGCA     540

CCACAACTCC AATGACCTGA TTACTGGGGA GCAATTCCGT CCTCGAAAGT TGGCACGTCG     600

ACTGACTGGT TTTCTGCCCA GAGATCAATC NATTGATCCN TNATCCCTTA CATCNCCGGA     660

CTTTNGAAAA CCCAAATTAA AATTCCGNAN NCCAAAATCC NGGGATTCNC CACCCTTGAA     720

CTACCCACNC GGCCCTATTA TTTTATAATT GCNNACAANN CCCGATCCCC CGNNAACCGN     780

GTAAANCGAA AACCCCCCGG NNTTCGGACC NNCNTTTTNC T                          821

(2) INFORMATION FOR SEQ ID NO:560:

(i) SEQUENCE CHARACTERISTICS:
        (A) LENGTH: 838 base pairs
        (B) TYPE: nucleic acid
        (C) STRANDEDNESS: single
        (D) TOPOLOGY: linear (ii) MOLECULE TYPE: DNA (genomic)
```

(vi) ORIGINAL SOURCE:
    (A) ORGANISM: PAG1388UP (xi) SEQUENCE DESCRIPTION: SEQ ID NO:560:

```
GATCCAGCGG CTTGGTAGCA TGCTGGCCGA GGAGTTCGGC TGTTCTGGTT TTGCGCGCTG      60
AGGCTCACTT ATAGGTGCCG ACTTCGATTG CCACTTGTGG CCAAGACTTG CTTCTTTACA     120
TAGCTAAATG CCACTGATCA TATAGACTGC TTATTCCTGC TTAACTGCCT CAACGTTCCA     180
TACCATCTCC GCGTACTCCT CTATGCAGCG GTCACTGCTG AAGAAGCCAA CGTTGGCGAC     240
GGACAGGATC GACTTCTGGA GCCAGGCCCG GCGGTCGCCG TGGTAGACGC GGTCAACGAG     300
AGCCTGGCAG GCTATGTAGG AGTCGAAATC GTCGCTCACC AGGTAGTAGT CCCCGTGCTG     360
GGCGACGGAG TCCACCAGAG GTTGGAATTC ACGCAGGTCC TGAGGGGAAA ATGCGCCCGA     420
GGAGAGCGTC TCCAGTACGC GAGCAATGGG GGCTGGCAAC TCTTGGCGGT GATACCGGTG     480
CCGGTAGCGG AGGTCTTCGA CATCTTCTGC GAGATTACCA AGAGGAAGA TGTTGTCTTC      540
GCCGATCTCG CGTGTGATCT CGACGTTGGC GCCATCGACG GTGCCGATAA TGAGACACCA     600
TTCATAACGA ACTTCATGTT NGAATTCCCN GAACCTCATT ACCCGCTGTC AAANGTGCTC     660
ACTAATCGGA ACNGGGANAA TATTCGCCCG GAANATGTAT CCCGAATGAA ACCCCTCAGA     720
AATACNATCC CTCTCTTANA CACNGCCCNC TTATTACCTA TATNGCTGCC NTTTTACCCG     780
GCCCTTNCCC CNAAAANACC TTGAGAAGNC CCCCTNTNTN GGNNCCCGTN CCNTTTTA      838
```

(2) INFORMATION FOR SEQ ID NO:561:

(i) SEQUENCE CHARACTERISTICS:
        (A) LENGTH: 826 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1389RP (xi) SEQUENCE DESCRIPTION: SEQ ID NO:561:

```
GATCTTCTTT TTGAAGCCCA CAGACACAAA CTGTGATGGA GTGCTGGAGA CGCCAGCTTT      60
GGACGACTTC CTTTTCTTAG ACCGGCGAGT CTTTTTCCTA GGTGTATGTC TTTCCTTGGT     120
GCCGTGTTTG CTCACAATTG CCTTTAGCTC TTCGACGACA ATCTTTGTGG ATAACCTTTG     180
GCCATCTAAT GAGCCCTTTT CAATTGCACC TTTGATCCAA CATCTTCCAT TCCAAACGAT     240
ATTGGTCACC ACCAACATAT TAGTGGAGTT ATCTTTCCCC CATGATAAGT AGAATCTGGT     300
ATGTATTTCA AACGCACCTC CCGAGGGTAC ATCTGGCGTC TTCGTTATCT GCTCCACTAC     360
TATGTGAGAG TTCACATCGC AATGTAGGAT TTTTTCCTGG ATCAAGCATC GCGTCTGCTT     420
AGGACCAACA GGATTGTTTA ATGGCTTGAT ATATTCATAT TCCCTCACAT TATCTGAGAA     480
TTCAGACGGT ATAGCTGAAA TATTATGATT AGCCTGTTTT TCTAATATCT TTTGCAAGTA     540
GGACGTGTCC TCACCAAATA ACAGCTTGTA CACGACACCC AATGGTGCTG CGATGGAATC     600
GAATCATCAA CAATAACATC TCCTGGTTGC TCGTATAGGT GTTCTTCGTC GGAGGANGCT     660
ACTAGGGCGA TATTNGTAAA TATTAAGANA CANTTGTTGA CTGTTNGAAC TGCCNCGTAC     720
TTGATTNTAT AAAACCTCNN AATGTTACCG TTCNACNCTT TNGAGANTTN ANCCCTCNAA     780
TCCNTTCCNC GTGANTTTNC ATCTCCCCTC NTCTATACTG ATACNT                   826
```

(2) INFORMATION FOR SEQ ID NO:562:

(i) SEQUENCE CHARACTERISTICS:
        (A) LENGTH: 839 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1389UP (xi) SEQUENCE DESCRIPTION: SEQ ID NO:562:

```
GATCCGTCGC ACTTTCAACA TTGTGAACGA CTTCACACCG GAAGAAGAGG CTGCCATCCG    60
CCGTGAGAAC GAGTGGGCCG AGGACCGCTA GCCACGGCCC GCCTCTATGT ACCATAAGTA   120
GCCGATATCT ACCGCTGCCG GCGCGGGCCC CGCCCGCGCC ACCGTTGCGT GCCAGGAGCT   180
GGTCTGCCGA CTATCCGTGC CAACGTACGA AACGATGCTG GTTTATGTGG TCCGCCCGCC   240
GCTGGTTACA ATTAACCGCC CCAGGTCATC GGTAGACGGA GCTAGCTACT CGTTGTCCTG   300
TAAGTGAGTT AACGCACAAG GGGAACTATT CGTGTGGTCA GGCAGCAGAG ACGCTGCAGG   360
ACATACTACG AGTTATTTCT CATAACTAAA CATTTTTGAA ACCTTTGTTG CGGGGGCCAG   420
GTCGTTTCGC AAAAGGCGGC GGAATAAACA GGGAGGAGAG GTAGATGCTC TTCTCAGGCA   480
GAGGCTAGCA AGGATGGCAG AACAGCGGAA GCGGTCGCGG TCGCTCAGAG AGAGCGCGCG   540
GGCACTTTTC AAGAAGCATA CGGGGGAAGG GGCGGCGGAA GGGGCGCGCG ACAGTGCCAA   600
AGACGGTTAC GACCCGAATG GGGAACCGCG GANCGGGCCC GAGCGGTNAT TTCAAGTTGG   660
CGCNGGGAAG GCCCGANTTT NAAACCGGTG TNTAGACAAA AACTTGTCCA GTTCNCACCC   720
GTNGTTTACC AANNNNNNAA TCTCCNCCCC NGGGTNGGTG GCCNGAACCC CCNCTGGCTT   780
ACGGGGNCCA CATCTCTCCC CCCCCTCCCA TTAAANACCC CGNCNCCTTT TNTCTGNCC    839
```

(2) INFORMATION FOR SEQ ID NO:563:

(i) SEQUENCE CHARACTERISTICS:
        (A) LENGTH: 740 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1390RP (xi) SEQUENCE DESCRIPTION: SEQ ID NO:563:

```
GATCAAGTAA TCAATCAGTT AATAATATTA AGAATATAAT ATGTAGACAT TTAGTCTAGT    60
CTATTAATTA TTAATTATTT TGTAATTTGT TGTTAATTTG TTGATATTTT ATTGATTTTG   120
TTGACATTTT GTTGACATGT TGATATGTTA TAAAATATAA TTTAATATTA TTTTATATAA   180
TTATTATTAT TATCTAGTCA TAGACTCATA TAAATATGAA TATATTCCAT TATTAATTGT   240
TTAGGATAAA CATAAATTAA TATAATAACT TATTTTTAAG TTCAATAAAT ATGTTCATAT   300
TTATATGATT AATTCATAAC GTATTCGATA TAAATATCTC ATACCCTTTT ATGAATTAAT   360
TAAGCGGTAT TAAATTATTC TGATTGGATT AAGTTATTAT TTAATTTATG TTCCTAACAA   420
TTAATTGATT CCATAAATAT CGATATTTAT TATTATTTAT TAAAATATTA ATGATAATAT   480
TGTAATACTT CAATTATTTT ATCAAATGGC AAGTAATCTA TTAATCNTTT AATACGATTG   540
ATAAGAAAGA AAAGAATATC ATCTATCGTA TAATATATTT CAAGTATGAC CTCTTCAATA   600
```

| | |
|---|---|
| TAATTAGAAG TTTAAACTTG TAGAGAATTA AGAATTTAAT ATGAGTCTTA CATTAAACCT | 660 |
| GATATGAACC TTTAATCTAC TTATTTGTTT AACCGTTGAA GAGAGAATAG TTAATCTNAG | 720 |
| TATNACTTAT ATATTGATAC | 740 |

(2) INFORMATION FOR SEQ ID NO:564:

(i) SEQUENCE CHARACTERISTICS:
        (A) LENGTH: 773 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1390UP (xi) SEQUENCE DESCRIPTION: SEQ ID NO:564:

| | |
|---|---|
| GATCAAACTA AGAAACCTAA TAAACTAATA GAACCTATTA GATAAATTAT AGAAATTTCA | 60 |
| CCAAATACAG GTTTTTTAGA ATAAGTTGAT ACAATATGTG ATATTATACC AAATAGTGGT | 120 |
| ACAATTATAA TATATACTTC AGGATGACCA AAGAATCAAA ATAAATGTTG ATATAAAATA | 180 |
| GGATCACCAC CACCTTGTAC TTCAAAGAAT GATGTATTAA AATTTCTATC TATTAATAAT | 240 |
| ATAGTAACAC CAGCTGATAA TACTGGTAAT GATATTAATA ATATAACAGC AGTAATTAAA | 300 |
| ATTGATCATA GAAATAAAGG TATTTTATGT AAAGTTATAC CATTAGTTCT TATATTTAAA | 360 |
| GCTGTAACAA TAAAATTAAT AAGTCCTAAT AATGAAGAAA TAGTAGTTAA ATGTAAAGAG | 420 |
| AAAATAGCTA AATCAACAGA AGCACCAGAA TGTGATTGAA TAGAAGATAA AGGAGGATAA | 480 |
| ACAGTTCAAC CAGTACCTAG ACCAGATTCA ACTATAGTAG ATGTTAATAA ACAAATTAAT | 540 |
| AGTGGTGGTA ATAGTCAAAA TGAAATATTA TTTAATCTAG CAAATGATAT ATCAGAAGCA | 600 |
| CCAATTATTA ATGGTAAATA ATAATTACCA AAACCACCAA TTAATATAGG TATTACTAAA | 660 |
| AAGAATACTA TTAAAATAAG ATGTCCAGTA ACTAATACAT TAAATAATTG ATTTTGACCT | 720 |
| TGTAAATATT GTTGACAGGT GCTGATAATT CTATTCTAAT AATAAATGAT ATA | 773 |

(2) INFORMATION FOR SEQ ID NO:565:

(i) SEQUENCE CHARACTERISTICS:
        (A) LENGTH: 749 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1391RP (xi) SEQUENCE DESCRIPTION: SEQ ID NO:565:

| | |
|---|---|
| GATCTTTTTG CTCCAGGTTA TTCCCTTCTT GGACACATTT ACGAAGTGTA TTTTCAAGAC | 60 |
| CTGACTCGCG CATTTAGGTG TTACGTTAAA GCCTTTGAGC TAGATGCCGG CGACCTCGTC | 120 |
| GCTGCTAAAT ACATGGTGGA ATACTATAGT GACCTGTGCA ATTGGCAGGC GGCGGCCAAC | 180 |
| ATCTGTGACC GTGTAATCAA GAATGATATG CATCTCAATT CCGTCAACTG GCCGTACAGA | 240 |
| GTTCTGGGTG TTTATTATTT GGAGCTTCAA CAGGAGGCTG AATCGATCGA ATGGTTCCAA | 300 |
| TCTGCTTTAC GGATTGATTC GTCTGATGTT GAGGCATGGA TAGGCCTGGG ACAGGCGTAC | 360 |
| GCCGCATGTG GCAGAATCGA AGCCTCGATC AAGGTTTTTG AAAGGGCATT AGAGCTGTCT | 420 |
| CCAGAACATA AGTATGCAGG GTTATTCCTG GCTATATCAT TATGCCAGCT TTCAGAATTC | 480 |

```
GAAAAAAGTC TCGAGGCCCT GAGAAAACTT GTGAATAAGT ATCCACAAGA AGCTATCTTC      540

AAAGAAAGAC TAAGTGCAAC GTTGGTGGAG CATGCTTTGC AGTTCTTCGA CCAAGGTTAC      600

CTGATAAAAG CGGCAACTTG CGCTGCTGAG GTGATATCGA TCATAGAAGG CATTGTATCT      660

GAACAGGTAG AATATACAAC CAATATGTGG ATTACTTTAT CAAAGGCTTT GAATATTTTT      720

ATTTCCACGC GTTCTCAGTT CGACAACTT                                        749

(2) INFORMATION FOR SEQ ID NO:566:

(i) SEQUENCE CHARACTERISTICS:
        (A) LENGTH: 767 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1391UP (xi) SEQUENCE DESCRIPTION: SEQ ID NO:566:

GATCGCCGCG CAGATTGTGC AGAACGTGCT TGCACTAGGG TCTCTTACGA CAAAGGACTA       60

CATGCAGTCG TTGGCTTCCG ATGTTTCTGT GAATGATGTG GCGTCCATGT TTGTGAAGCT      120

GGTTGAACTA GGCTTTCTGG TCCCGCTTTC CAACGTGCAC TACATGCCAC TGGCCGATCT      180

ATGGGATGTG CTCTACAAGA AGGAATACAA TGCTATTCCA AAGAATTCGA CGTTGTCAGA      240

TGCCAAGAAA CGTGCAGAAA CAAAGGCGAA GACGAAGGTT CAGTTCAATA CGTTGCTGAA      300

GAATGTCGAA ATGAGCAACG TACTAATGAC TGATATGCAG ACTTCAATGA GACGTGTCCA      360

AGACAATCTT CCTCTAACAT TTAACTTCGG CCGGTACATG AAGCACCGGC GTTCTCGGCA      420

GCTTGTACAG TTTGCACGTT CCCGTGTGGG GAGCGTACCA GCCATGATCT ATAAGGTGGC      480

ACTGAAGATA ACCGAACAAT GTGCCCGTGC GCTTTCAGAT CCGCTATGTG AGACAGGCCT      540

AATGCAGGAA CTTGAGGAGC AACTGGCTAT TCAGGAAGAT ATGGCGCTAG ACGATGAGAA      600

GCTACCGGGC GTTACATTCA ATGCGGTGGA CATATCCAGA AACTTACCAA ATAACATGGA      660

CCTACGTGGC ACACTGACTT CTATGCCAAG AAGATCACCA GAACGTTGCA CGCACCAAGG      720

TCAATCCCAT AAGCGGNTGA AGGCTGAAGA TGGGATGGCT GTAGCAG                    767

(2) INFORMATION FOR SEQ ID NO:567:

(i) SEQUENCE CHARACTERISTICS:
        (A) LENGTH: 753 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1392RP (xi) SEQUENCE DESCRIPTION: SEQ ID NO:567:

GATCCCCACC ACCGTCACCC GCGTGCCCGG CACCACCCGG TTCGTGAGGT ACCGGTCGCA       60

CGTCAGCAGC AGGTTGCGCG GCATCTCGCC GATCGGTACG GACTCCGGCA CCTCCTGGAG      120

CTTCAGGAAC TGCTGGTCTA CGAAGCGCGA GCTCTCGTGA ACGATCATGT ACGGGTCCTG      180

GCCGCAAGGG TTCCCCGCCG CGCTGCCATC GTCATTCGAG TGGTCTGCCA GGCACGCCCG      240

CGGTAGCGCC ACGTTGCTCC CCGCAAGCGA CTGGAAGTTG TTGAGGTCCA GCGCCGTCGT      300
```

```
GTGCCGGCAG TTGCGGCACA TCAGCGCAAC GTGAGTCGCA CGTGACGTCA GCACCGACGT      360

TGACACCACG ATCCCGCTCA GCCGCACCAG CCGCGAAACG CTCTGTGAGT CCAGCTGCCG      420

CAGCGCCGTC TCAGCCGCCG CGCTCTGCAG CTCCACCTGC ACCGCGGCA GCGCGCCCGC       480

GTCCTCCGCC CGGAGCCGCG CCATCCGCCG CGCTATTTCC GTCACCGCCT GCTCAAAGAG      540

GGGCACCGTC TCCACAGGCT CGTCGCGCAC AGTTTGTACA GCGCCTCGTT GTACCAATCA      600

GATGCTCCGT GTTGACGCGC AGCGCGTACG CCGCACCAGC AGGTTGTTGC GCAACTGCTC      660

GCGATATAAN NAACCGCGCG TCNAACGAAA CTCCNGCACA AANCNCCNGA AGAGCGCACC      720

NCCTCCGANC GGTCGTTGCG CGCCCGCCTC CTC                                  753

(2) INFORMATION FOR SEQ ID NO:568:

(i) SEQUENCE CHARACTERISTICS:
        (A) LENGTH: 752 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1393RP (xi) SEQUENCE DESCRIPTION: SEQ ID NO:568:

GATCACGGAT TGCCCCAAGT ANTGCGCAAC AGTCGTCAAN TCTGACATAT CTCTTGCAAA       60

TGCTAGCCTC TGGGGGCTTG AACTAACCAT TACTTCTAAT ACCTGGCTAG CTGCCTCCAA      120

ATCCGGATCC AAAAAAGCAA TATTTATACA TAACTATACA CGAAATCTCA GTTCATCGCT      180

AGCTAGCTCA TCGTATCCGG GACTGGGAGA GGAACTCAAT GCTGTGGAAC CCTTCGAATA      240

TGGCAGCGTC GGCGATGTTG ACCAAGGACT CGCCTGGGCC AAACATGCGG ATGCCACNTA      300

GGTGGGTGTC TTTGCCGTTC TCGTGGTTAG TCACGACCTC GATGCGCAAA AACTGGCACT      360

TGAGCAGGCC GTCGGAGGGT CGGTTGTCCT CGAAGGTGAA CTTGACCCAC CCATTGACTT      420

GCGGACTTCT AGGGTCTTGT AGTAGGTTGC GTCGGAAGGG CTGTGGCCAG CGTATATGCG      480

GAGCGTCTCC NANGTGTAGG ACTCATCGAC GAAGAGCGAG AAGTACATGG CAAGCTGGAT      540

GATGTCAACG CGCTTGCTGA AGAAGACGTC TATGGTGTGT GGCTGGGAGC CGTCGCTTTG      600

CCANAANGTG GCGGGGTTAT CATCCNAAGG CGTTTTCCAT GGGGTANCCG GCCTTGAANG      660

AAGAAGGCTT CCANTAGGCC AACNAAGTGA TATCNACTTA CCCTGGTTCT CCAATGTTTG      720

CAAGCCCNCC TGTTATTTNG NCCAGAAAAG AC                                   752

(2) INFORMATION FOR SEQ ID NO:569:

(i) SEQUENCE CHARACTERISTICS:
        (A) LENGTH: 773 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1393UP (xi) SEQUENCE DESCRIPTION: SEQ ID NO:569:

GATCCAGGAT ATCATGCCCA AAATCCTTGA AGCCGCTGCA AAGCGCCTCG TGCAAATCAA       60

GAATCTGCAC ACGGCAGAGA ACTTACTCTT CGTATTTTGC TACCTGACTT CTATTGATGC      120

GCGGCAGACA GTGGACTTTC TTTCATCAAC GATCATCGAT GAAGGCGGCC GTACCGCCCT      180
```

```
CCAGGCTATC GTTCCGCGTT GGCTAGAAGC ATTCGAGGTT CTCCGCGGAG AACATAAAAT     240

CAAAGAGAAC ATTTTATCCC TTTCCAAGCT TTTCTTCCTT GAGGATCCCC GTATAGCGGG     300

CATCACGGTC AATGGGGATC TGATTCCCCA CGATGGCGAC ATCATAATCA CCCGCTCCAT     360

GGCCAAGAAA ATGCCTGATA AGTACACGCA GATCTCCGCG GCCGAGAAGA TAGTCAAGCT     420

CTTTGTTGCA GAACTAGCCT TCCAGCAAAA CCAGCCTGAC CCTGGCCGTT ACCCTAAAGA     480

CGGGTCTGGC CCTGCTGACC CACATGACTC CGAGGGAGAC TCAGCTGATG AAGACTGGGA     540

GGATGTCGAT GACATCCTTG ACTACGAAAA ATTGCGGGAG TACGCGGATG ATAGTGACAT     600

TGACGACACG GTGACAGCCT TTTATTCACA AGTAACATCG AAGAGGATGT AACCACTCTG     660

CTTACTCAAT TCTTCAAGGA AGCGGTTGCC AGAAATGCCT CTGGCTTCCA GGAGATCTAT     720

AGCAGGCTCA CTGAACAAGA GAAGAAGAGC TATCTGCATG CATGGTATAG GAT           773
```

(2) INFORMATION FOR SEQ ID NO:570:

(i) SEQUENCE CHARACTERISTICS:
        (A) LENGTH: 755 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1394RP (xi) SEQUENCE DESCRIPTION: SEQ ID NO:570:

```
GATCTCGACG ATTACCGCGT ATGATTATAT CCCAGCAACA TGGGCACACG CCGCACACAC      60

AGACATGATA CTGGTCGGTG ATTCGCTGGC AATGTCCACG CTGGGTCATG TGTCCACGGT     120

GGACCTGGAT CTGCAGGAGT TCCAATACCA CGTCCGGTCG GTGTGTACAG CACCAGGCTC     180

GTCCTTTATA ATTGCAGATA TGCCATATGG TAGCTTTGAG CGAANCATTG AGCAGGGAGT     240

AGAGACGGCG ATCTCGCTTA TGAAGACATC CAGCAGGGTG GGTGCTGTTA AGCTCGAGGT     300

TGGCGCGGAA GAAAACGACT ACTGTCTTGA GCTTGCCGCA GAGCTCTGCA GGCGCGGGAT     360

CCCAGTAATG GGCCATGTCN GGCTGACCCC GCAGCGCATG CATGCATTGG GCGGGTACAA     420

GGTTCACGGC GCAAAGGACT TGGGCCAGGC GCTGGCGGCG TACCACCGGG CTAAAGATCT     480

GCAGGCTGCA GGCTGTTTTT CCATCGTCAT CGAATGCATT CCAACTAAAC TAGCCGGTAT     540

CATAACCGAG AAACTCAGTA TACCTACTAT TGGCATTGGC GCGGGCCCCC AGACAAGCGG     600

GCAGGTGCTC GTACAGTCGG ATCTGCTGGG CATGTTGCCA NGGAAGGCCC CAAAATTTTG     660

TGCNGAATTC CCCGGACTTC CNCNGGGACG CCATANGTTC CTTGTGCCCC CTATGTTGAA     720

AANGTGCCCA NGGCNTCTTC CCNAAAGTNG GGGCA                               755
```

(2) INFORMATION FOR SEQ ID NO:571:

(i) SEQUENCE CHARACTERISTICS:
        (A) LENGTH: 773 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1394UP (xi) SEQUENCE DESCRIPTION: SEQ ID NO:571:

```
GATCGAACTC CATGAAGGAG CGTAATGGCC TCGTGGAGCT GCACCGCACT GGGTGCGTAC      60

ATAGCGGGAT GTAGGAATGC GGGGATAACG ATTCGGAAAA GCTGACTGGG CTGCGCCTCT     120

AGCTTCAGCT CAAGCTGGCG CAGCAGCGTT GCTATAGGCG GTTGTGGCGA CAAGGTCGAC     180

ACTTCAGTTG CAGTAGGAGC AGGTAGCATA CGACTAGTTA TATCGAACTG GTGCCGGTAA     240

TGAGGATGAG GGTCAATTTC TGGCTCCGAG CGCTGGCTAG CACCACAATT ATCACCAAGT     300

CCATACCTCC ATGCAATTCT GAGATCTTGG CTACGTGCGA CCGGTTTTGC ACCCCCTCCG     360

GCTAAGTTTT GCACCGTGAC CTTCGATTCC TCCTGGGAAA TGCGAGATTT CTTTACCTCT     420

TTACGTGTGC CCTGGAATAT CCCCGGCAGC TCCTTCGCAT ACTGAGTGTT GAGCGTGATG     480

ACCACCACAT GCGTATTCCC TCCCCGCTGT GCGCCGCGAC TTTCCGCGCG GTTATGTGCT     540

GCTCCCTGCG CTGCAAAGAG CTTTCCAAGT ACCGATGCAA AGTCTGTACC CCCTTGTTCT     600

TCCACCAGAA GCATCTGGCC CATTGGCAAG CCCATATGCC CTAGGAGCCG ATCCATATCT     660

GCACAACCCG TGGATGTTGT GGGATGCGAA GTAACCGGCG ACGGACGCAA GCCCGGATGC     720

GACTGCCTGC CNCCTCACTG TTGGATGCCA ACCTCTCCAC GCCTCTNGAA ANC            773

(2) INFORMATION FOR SEQ ID NO:572:

(i) SEQUENCE CHARACTERISTICS:
        (A) LENGTH: 746 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1396RP (xi) SEQUENCE DESCRIPTION: SEQ ID NO:572:

GATCAATCAT TCTAGAGCTG GAGCAAAGGA TACCTATAGG CTTGCCTCGT CATTGGCCCC      60

TTTCATTATT ACATACCCAT CGTTCCACAG CGTGTCACAT TCTGCCATTC GAGAGCAGGA     120

CACCCAAGTT TTCAAACAGA ACAGCCTCGT TCTCTTGGTA AAAGTTGGAC CTTCTAACGG     180

TGTCCTCATC GAAGCCGTCG TCGCCACTGA GGACCTTGAG GGCGTTGGAG GTGGCTTTGA     240

TGTAGTCGTT GAGCATAGGA ACCGGGTCGT CGGCAAGCTT ATTGAAAAAT TGGTACTTGT     300

TGGCTGTGGA GCTGANCTGC AGGGGAGAGC AGTTGGGTCT TCTTTTCGAG GGTTGCCAGC     360

TGCGGCTCGA GCTGGCTGGT GACTGTGTTG AATTCTGTGA GCAGCAGCAT CCCCTGTTGG     420

GCAAGGGAGT TTTGGGCGGA CGCCGGTTCG GGATCCTTAA CCGGGACACG TGGCACGCGG     480

ATGTCGAAGA CCAGTTCGCC GTAGGTGGAG GTCTTGTCGA CCTGGATGGT GTAGTTGATG     540

CGCACGGGGG GGATGGGCTT GATGTGGGCG TTGACACCTG GGGCAGCTCG GTGAGCTTGA     600

GGTACTTGCG AGGCTCTGCG GCGGGCCGCA GGAACTTAAC GATCATGGCG TCCACCTTGA     660

TGACAACTTG TCGTCGTTCT GCGTGCTCTT GGCGTTGCCG CTNGGGTCTG CGACNAAGAA     720

CTCTTGAACA GGATTTCTTG TNAACC                                         746

(2) INFORMATION FOR SEQ ID NO:573:

(i) SEQUENCE CHARACTERISTICS:
        (A) LENGTH: 772 base pairs
        (B) TYPE: nucleic acid
        (C) STRANDEDNESS: single
        (D) TOPOLOGY: linear (ii) MOLECULE TYPE: DNA (genomic)
```

(vi) ORIGINAL SOURCE:
    (A) ORGANISM: PAG1396UP (xi) SEQUENCE DESCRIPTION: SEQ ID NO:573:

```
GATCGGTTAC TTAGAGGGAG TGCAAGACCT GGCCTGACTT ATCTTAGGGT TATTAGCTAT    60

GACGGGTGTG TTCGGATTTC TGTCCAAGGG TTTAGATGCC ATCAACTCCC TGAATTCGCA   120

CTACTTTGCG TTGTCGGTGG ATGAACAGAA GGCCATGACT TTCGTTGAGC GTATTAGATA   180

CTACAATTGG ACGTTTGAGG GGATCTGTGT GGTCCTGCTC GGGCTGATGT ATGCCGTGTA   240

CGTGGCGGGG ACCAAACTAA CGAGCGGCG CTCGGACCGT CTGTTCGAAC AGCTGAACAA    300

GTTCTTCTGG GAGGAGCTGC AGTTTGCGCG CGTGGGTTTT TCGTCCCGGG ACAAGGGACG   360

GCTGCCATAC ATCAGCGATC GGAATGGCAC ATGGTGCACC GCATTCGCTA CGGGGCGCAC   420

GTGTGTGGAC CATATTGTGG TGAAGGCTCA CTACCCGGCG CGCTTCAACC CTGTGGGGCT   480

GCTGGTGGAG AAGCTGCTGG GGATGTTCTT CCCGCAGGTG GTGGACCGCA CGGCGATGAG   540

TTTGTGCAGG TGACGGTGAC CCCCAACGGG AAGTGGACGA AGGACGAGAA CAGCGCGGTT   600

CAGGCGACGG AGGACGGGCT GAACCGGTTC CGGTTCATCG CGTCGATCGT CCACAAGAAC   660

GGGATGAACG ACTCGCGCGG CAAGAACTAC TTCCTCTCCT TGACTCACNC GTCCGANGGC   720

GAAACTCTCC CATGGAANTA CTCTTCATGT CCGANAACAA CCACTGAACA AC           772
```

(2) INFORMATION FOR SEQ ID NO:574:

(i) SEQUENCE CHARACTERISTICS:
       (A) LENGTH: 753 base pairs
       (B) TYPE: nucleic acid
       (C) STRANDEDNESS: single
       (D) TOPOLOGY: linear (ii) MOLECULE TYPE: DNA (genomic)

(vi) ORIGINAL SOURCE:
       (A) ORGANISM: PAG1397RP (xi) SEQUENCE DESCRIPTION: SEQ ID NO:574:

```
GATCCCATTA TTCTACAGCA AATATTACAC GGCCGGCGGA CCCTCGACAA TGCAGAATTC    60

GATGCATACA CAAAACATAT TACTACAAAG CTTTCAAAAG GTGTCTCTCC CACAGACGCA   120

TTTCTAGGCG CACTCAAGGT TTACATTCTC AATTGCAGTT TGAAACGTTT ACGCTTGCAG   180

AAAGCACACG TTATACTTCT TGATAAAATT GCGATATTCA TCAATACAAA TGTGGTCCAT   240

GTGTCTGTCG AATCGATACA TACGATACTG AAAAGTTTAG CTGAATATTT TATTGATGCC   300

AAGGAATATA AGCGACTCAA CAACGTCGTC AATATTTCAT TCAACGCATA TGTGATGTAT   360

AAGCATGAAA GCCTTATACG ACTTGCAGCA GATCTCGAAT TATTTCTCTT TATGTCCGTC   420

AAACAGGACT GGTCAATGTT TACCAAGTTC GAGAAGTTTA TTTCTGTCGC TTCAGGAGAC   480

ATCTCAGTAT CGCTCTTTGA ACAGTGTTTC AATGTTTATG TTATGTTCGC GGATCCCTCA   540

TTGGCCGGCC TATGGGATGT CTGCTTGAAC AAGTCGTTGA AGTGTTTCAA GAAATTGGGA   600

CTAACTAGTT ACACAGACTT TAAGGCATCG TCCGAGCCAA TGCTAGTGTT GGTATACAGT   660

GGATTTGTTT CTGATATTTT TACAATACCT TATAATGGCT GGGCTCCGCT ATCGAAAATG   720

TTATTCATGG CATTAAATGG GGTCTATAAA TTG                                753
```

(2) INFORMATION FOR SEQ ID NO:575:

(i) SEQUENCE CHARACTERISTICS:
       (A) LENGTH: 767 base pairs
       (B) TYPE: nucleic acid

```
        (C) STRANDEDNESS: single
        (D) TOPOLOGY: linear (ii) MOLECULE TYPE: DNA (genomic)

(vi) ORIGINAL SOURCE:
         (A) ORGANISM: PAG1397UP (xi) SEQUENCE DESCRIPTION: SEQ ID NO:575:

GATCTGAAAT ATTGCTCACC CCCACCGTGA CCTATGTAGA TGAACGTGCT GGAGTTCGTG      60

ATCATTCTGA CGAATTCATC CTCTTCTGGC TTTGAGCCAG TTACTATCCG TGTTGAACCC     120

AAGTCGCAAC AAAGTCTGGT AAAATGTTCT TTAAAGCGCA GTTCAGTCCT GGTCAAGTCC     180

CCATGCGGGT TTAAAACAAT GGAAAGTCTG CTGTCTAGGT TAATCTTTGG AGAGATCTCT     240

CCTCTGAATT TAGTTAGTAG CTCGTGAAGG AAATTTATGG ATGGTACGCG GCTCACAGAA     300

GCATCGGAAA ATATACTGAG AGATTCCCAT GGAACCAAAC TGCATTCGGA GCTTATTACC     360

AGAAACGTGT GTCCTAACCT TGGCGCCTCT GGTGCCTTGG CATGATAGTC GTGAATTAGT     420

TCCTCAAGTT GAATATGTAT GAGATGAACG TCAATCTCAT CATAGGCATT TTCTTCGCCA     480

TGGAAAAGCA ATATGTCAAA GATGAAGTAT ATCAAGTCCT CCATGAATTC CACCTTCTTT     540

TCGTGAGGAA GGGCATCCCA ATCCACCTTT AAAAATAACT CTAATATGAA ATCGTCCACC     600

TGTTAGAACA TAGACGGGTT TCCATACTGT CTTCTTGTTG GAAGATTTGT TGTAAAACCT     660

TTGAAATCCT AATTTGAATA NTGCAAAATG GTTTTATCCA ACTGTTTTTG GNTGAAGAAA     720

CCGCNGAATC CCATATCCAG ATCTCATGCG GGGCNTCNAT CTACATC                   767

(2) INFORMATION FOR SEQ ID NO:576:

(i) SEQUENCE CHARACTERISTICS:
        (A) LENGTH: 774 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
         (A) ORGANISM: PAG1398UP (xi) SEQUENCE DESCRIPTION: SEQ ID NO:576:

GATCGCTCTT CTTTGAAAGA ATATGTAGGC ACCCTCTCCT ATCTTGCGCC GGAATTGGTT      60

CGCTGCAAAG ATATGAAGAC GATGACACCT GCAGAAGCAG AAAGAATCCC AGAGTACGGT     120

GCAGCAGTCG ACATATGGGC TCTTGGTGTC CTCTGCTACT TCATGATGAG TGGCTATATG     180

CCGTTCGATT GCGAAGACGA TGCCGAAACT AGTGACTGCA TCTTGAAGGG TGACTATTAC     240

GTTGACGAGG AAGCTCGTGC CAACGCCAAT GAGAGCTATA ACAGCTGCTG GAACTTCATG     300

CAGCGCTGCT TTACGATGGA TGATAATATC CGGCCGCGCG CACACGAACT CATGGGCCAC     360

GCATTCATGC GGGAATACTT CCAATCGGCT GCGGCCAATG ACTTCGCATC TATCCCGCTA     420

CTCGAGAGAT CAAGATCCTC GAACTCCCTG CACCACTTAG CGCCGCCATC ACGCGCACCG     480

TTTATCTCGT CTGGCGTGCC GGTTATTAAC GAGCGCCCTG TGCCACGTGT TGGCTCGCGT     540

GAGCGCAATT TGGATAAGTT GCGGGATACT TTGCGGAAGA CCTTTCCCTC ACTTCGCTTG     600

AACCTATGCG CTTTGTTGCT CAAGCGAATA CTCCTAATCC TAATAAGAAG AACTCTACTT     660

TTGTTCTTGA GCCAGCTCCT CCCACGGGGA GTCTAATGAA TGGGTGTTTC ACGTCACACC     720

GGAAAGTAAT CCAACCTCAA TACGCCAGTC CTTTCGCGCA GAAGCTCCGG CCAA           774
```

(2) INFORMATION FOR SEQ ID NO:577:

(i) SEQUENCE CHARACTERISTICS:
        (A) LENGTH: 756 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1399RP (xi) SEQUENCE DESCRIPTION: SEQ ID NO:577:

```
GATCATTACT CGCAGAAACT GAGATGTTAG GGGGACCAAA CTCTTTTCTT TGATGAGATA      60
CGGGAGGATG CCCTCGGAGA ACCAGAACAA TGCAGCAAAA GGCACGAAGA ATGCCAACGA     120
GAAAAGCACG CATCGCTGCA TATGCAGTCC CACCCCATAG TAGTTCCTTG CGCCATATGC     180
CTGGGGCAG AGTGTATCTA AGCTTGTTGA AATACCCTCN AATATTGCGA AAGTGATATT     240
GGTGGTCATG GAAGCCAGGG AAACCGCTGC CAACTCATTC TTTCCCAGGT GACCCACAAC     300
TAATGCACAT ACAACCGGAA ACATCTGCTC AAGCAGAAAT GTAAATATGA GCGGCACGGA     360
GTAACACAGA AGCACCAGAC TCTCGGACTT CACGGTGGCT GGTTCGTCGT CGAGATCCTC     420
GGACCCTCGG AACGCGCTGG AGGGGCCGCC CTTGCTGCCA ATGGAGTAGT AAGACAGCTT     480
TCGGGGCCGT AGAACACGCA CTTCTGCCTT GTCCGACGGC AGTTGCTGCT TAACCCGATG     540
CATGAAGTGA GTGTAGTGCA CCATGTCTGG CGCGGCGCCC TCCACATCGA CGGCCACGAT     600
GTCCTCGGCG CTGCCGTTAA CAGTCGAGTA CCGCCGTTCG TGCTCCTCCA ATATCCAGTC     660
TACATTCAGT GCAGAGGACG GCCCGCCTCA CTCGCAAGCG TCGACGGCAG CGAGACTGTC     720
CGCGACAGCT CTCCTCCGTC AAGCACGCCC TCCTCC                              756
```

(2) INFORMATION FOR SEQ ID NO:578:

(i) SEQUENCE CHARACTERISTICS:
        (A) LENGTH: 775 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1399UP (xi) SEQUENCE DESCRIPTION: SEQ ID NO:578:

```
GATCTTGTAC GACGGCCGCG GAAGAATCGG TGCCATCGTT TCCAACAGAC AGTTCCAGTT      60
TGACGGCCCA CCACCACAGG CTGGCTCCAT CTACGCCAAG GGTTGGGCCC TAACCGAGGA     120
GGGCAACTTG GCCCTAGGTG ACAGCGACGT CTTCTACCAN TGTCTGTCCG GCAACTTCTA     180
CAACCTATAT GACCAGAACA TCGCACCACA ATGCTCTCCA ATTAAGCTCC AGGCAATCAA     240
ATTGGTCGAC AACTGCTGAA CAGCCACAAA GGTATATAGT GCATATATTG TATTAGTTAA     300
ACTAGGAATT TTTGTTGGCA GCTAGACTGC CCTACGTGGA TTTCTCGTTG CGGATCCTGG     360
GCTGCCGCTG GCGCTGACGC ACAAGAGCAA CTGCACAACT ACTGGCGTAC CGCATGCCTC     420
CTTGTGCATT TTTGCCGCGG TGGACGTCGC TGACGTCAGC GTGGCACGTG ATCATAATAT     480
GTCCCGGGCC AGGCCCCTAT TGTGGCGGAC AGGAATGCAT GCGGAGGTGC AAAATGGTGC     540
AAAATGGTGC CCGATGCAAC TCTAGGCCCG AGCTGAAACA AGATTACCTG GGCAGCCTAA     600
ATTTGCAGCG GCTGCCTGGC AGCCCACATG TGTATTGTGC TTTTACAGTT CTTGCTGCGG     660
```

```
CTGTCCAATA CAGCCGATCG CGACTTTGCT GCGCACGGGC CACTAGGCCT GCGCGACAAA    720

AACTGCAGGC GCGCCGGCGT GAATGGCGCC GGACGATGTG CTGCCGCGGA ATTCC         775
```

(2) INFORMATION FOR SEQ ID NO:579:

(i) SEQUENCE CHARACTERISTICS:
        (A) LENGTH: 757 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1400RP (xi) SEQUENCE DESCRIPTION: SEQ ID NO:579:

```
GATCCTGTCA AATATGGCCA ATACCAAGCA GCCGCGTGTT GTAGAGCATG TGGTTGAACT     60

CAAACCCTCA AGCAGCCGGG TTTTGGACTG TGCACAGGAG ATATTGTCTC CATTTCCACA    120

GTCCAAGAAC AAGCCCAGGC CGGGGGACTG GAATTGTCCC TCTTGTGGTT TTTCTAACTT    180

CCAACGGCGC ATTGCATGCT TCCGGTGCTC CTTCCCAGCC ACTAGTGCAG TGACGGTCAG    240

CAAGCTGTAC AAGCCACAGC AGCAACGCCA TTATCAGAAC CCACACCACG TCCCATCGAA    300

ACAACAGGTG CAGCACCCGC AGATTCACGA CCAAGACACA CAGCAGCATT CTCAACATTT    360

CAACATCCAG CAGATGCCGC AGCAACTCCA AATGCAACAG CAAGCGCACG GTACCGTTCA    420

AGGGGGCAGT AGCATGCAGC AGTACAAGCA CAGGCCTCAG CACGGCTTAC AGGCGTATCT    480

TGGCTGCTAC CAACAGCAGC AGGCGAAGTC ACAGCAGCAG TACCAGATGA ATCAGCAACA    540

GGTGCAGATG ATCGCTGGCG ACGCCAGAGA CGGTATAACC GGTACAACAA AATGGTGCAG    600

GGCAACGGGC AGAACGGTAA TTCTTGTACG GAAATGGCTC CCTGGGCAGT AGCAACGTGC    660

CCTTCAGAGC TGGCGACTGG AAGTGCTTGA ACTGTTCTTA CCATAATTTT GCCAAGAATA    720

TTGTTTGTCT GCGTTGTGGT AATCCAAAGA CGGCCAT                             757
```

(2) INFORMATION FOR SEQ ID NO:580:

(i) SEQUENCE CHARACTERISTICS:
        (A) LENGTH: 775 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1400UP (xi) SEQUENCE DESCRIPTION: SEQ ID NO:580:

```
GATCGGCGGG TACTTCAGGT CATTCTCCTC CACCACCACC ACCAGCTGCC CGGGCCCGCG     60

CTCATACAGC TGGTACGCCA CGCGAACATG TCGCTCCGCC TGCGGCACAT CCGCCTCGTA    120

GAACTGATCC GCAGCCACCA GCCGCGTCGC GCACTCCCCG CCGCCGGCTT GCGTCAGCGT    180

CCCCACTAGC TGCGCGACCG GTGTGAGCTG CACCATCTCA GGGGGCATCA GCCAGCTCAG    240

CGTCGATGGC ACCACCAGTG CGGCCGAGTA CCGCTCGCCG AGCTTCCCGC TGAACTCGAC    300

CTGCGGCTCG GCCCCCGCGA GAAGCGAATG CGGGTCCATA GGGCCGAGGC AGTCCAGTTG    360

GTGTCTGGGA AGACGCTCAG ATTGCCATTG TTTGAACTGT CCACAGTTAG AACTTGCACT    420

ATGCTACCTC CGCGGCGCCT GCGCGACCCC ATAGTCACAT ACTATCATCC TCACACAACT    480

CAGTACTTGC TGCGAGTCCC AACTCAAGCT AACGAGTACC AGACTTGGTT TTGGCTGTTG    540
```

```
CTGTATGCAT TCCAATGGTT TGTATAATCG AAAAATTGTT CAGTTGCTCA GCACATCTCA      600

TACAAGCAGG AACAAGAGCG AGTCGCGAGC CAAAGACCTC TTAGGCATTA GTATCGGTAG      660

CTAGGATGTC GGCAGAACAG TTGCGACAAG TACACGCAGT TGCAGGGCGA ATTGGAGGAG      720

CTGGTGGTGA CAGACAGAAG CTGGAGACGC AGCTGCAGGA GAACAAGATC GTGAA           775
```

(2) INFORMATION FOR SEQ ID NO:581:

(i) SEQUENCE CHARACTERISTICS:
        (A) LENGTH: 723 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1401RP (xi) SEQUENCE DESCRIPTION: SEQ ID NO:581:

```
GATCTTGTTG TTGGCAATAC CCTGTCTTAC GTTGAAAAGA AGTGTCTCTG AGGTGTCCAT       60

CAACAAAAAT ATTACCAGTT ACAACACCCA CCCGAACTCT ATTGGCCAAA ACATCCAACA      120

ATGTCGTCTT ACCTGCACCT GAATAACCCA TCAGAGCAGT CAAAGTCCCA GGCTTTACCC      180

AACCATCCAC GTTGGTTAGG ATCCTCCTGG TTTCATTCTT AATCTGTATA TCATAGCAGA      240

CATCTCGCCA GTGAAAATG CTATCAGAAC CAATTCTCTG AATAAGTTCG CGGGATTGGT       300

CACTTCCTAT AGTACTAGAT TCCTTTCCTG GTGCATTACC AAATTCTATG TCGCAGTTGA      360

TGGCCTTTTT ATTTTGCTTT TTTATTTTCT TCAAAGTTGA CCTTAGGAAT ACAGCCATTT      420

CACCTTTTTG CATCCCACTT TTATTATACT CAATTAAGAT CAGATAAACA CCTAAGAAGA     480

AAAATGCATA AGCAAGAACG ATCCCCCAAT TCATCCACTT GTTTTTGGTG TTGTAACCAT     540

AAGCAAACTC TATGTAACGG GTCCCATTTA CAAAGCTCTG ACCAGGAACT GCTCCCACCG     600

ACAAGCAGAC TTTATTCGAA ATAGGGAATC CCTCATAGAA ACTACCATCG GGTACCATTC     660

GAGAACATTC GAATATGCGT CCGTCAAATT CATTCGCAAC CATGGCTTCC ATGATGCGTG     720

CGA                                                                   723
```

(2) INFORMATION FOR SEQ ID NO:582:

(i) SEQUENCE CHARACTERISTICS:
        (A) LENGTH: 720 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1401UP (xi) SEQUENCE DESCRIPTION: SEQ ID NO:582:

```
GATCTGCTGA GATTAAGCCT TCGTTGTCTG ATTTGTTTTC TATTTGGAAG TCTGCAGGAG       60

CAGGCTTTGA AATAGAGTTC TTATGTTATT TAACGTCCGG GTAACGAGTA TACAAGCATA      120

TGTTTATGCG TATGCTAGTT ATATGCTTTG AAGAGGTGGT CTGCAGCTGG CGGTCTATTT      180

TATTTTATTT TTTCATTTCA CTAAGACTTT ACATTTTTTT TTTAAATTAT TTTTTTTGCG      240

CTAAGACTGT GAACAGCGAT TTTAGAAAAA AGCGAAAACG TTCAGGAGGC CTCAGCTACA      300

TGATATCCCA GGCCTTGTAT TTGTGAGACT GCACTCCCGG GCTAGGTTGT GACCAAGAGT      360
```

-continued

```
TGACGTGCGG CGGCGTGCGG ATTGCAGGGC TTCACAGTGT GGTTAATTTA ACAATTTATA      420

GAGAATAGAG ATGCCCGAGC TTAATCAACT GTCGGGCGCG CCAAATTCGA TTTTTTGGAG      480

TTTGTCGATT TTCACAGCAG ACGAGAAAGC AGGACAGGCG GCGCGCGCCA GGCAGTCCCC      540

CCTGCAGGCG TGAGCGGACA CAGAGAGAAA ATACAGGAAG ATGAATACTG ATAATCTACA      600

GATTTCATTG ATATCTCATT GATCCGCTGA TTATCAATGA AAGTACCCAA TGATCCATGA      660

AGCCAGTAGA TGTTAGTATA TTTTATTAAA TATATGCACC TTTGTTATCC AATCTCTGTT      720
```

(2) INFORMATION FOR SEQ ID NO:583:

(i) SEQUENCE CHARACTERISTICS:
        (A) LENGTH: 719 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1402RP (xi) SEQUENCE DESCRIPTION: SEQ ID NO:583:

```
GATCAGGAGC CCATCAAGGC GCCTAAAAAT CGCATCCCCG CTGTCGGTTT TCCCGACTAC       60

GCCGCTGTTG CTTGAAATAC AATTACTGCT GTAGTTCCTC CTGTGATGCT GGTTGAAATG      120

TTGCGGCGCG AAAGGGTCTG CCTGCTGAAA GGAGCTGAAA GGTGGTGACG TGGTTCCGGG      180

ACTACTAGCG TCTGCAACCG TCTTTGAGCC CAAAACACGG AGGCCGATTA CATTCCCGTC      240

AGCCGGCCGG AGGGTAGAAG ACCTCCCCTG ATGGGAGTTC ATGCTCTTAC TGCGGGTGTG      300

GTAATAGTAC TCACCACCAC TGCTCGACGA AAGCGGAGCA GGGGGTAGCG CTGCCATCTG      360

TTGTTCCCTC CTGCGACGTG CTTCTAACTG TGCCAAACGC AGCTGTGCCT GTTGCTCCTG      420

GTGCGCGTCC ACCTTGGCCA AGAGCTCCGG ATCATCATGC AACATCTCCA GCACCTCCAA      480

TTTCGCCCCT AAGCCACGTG ACTCGGCTTC CAGGTCGTCC ATTTCTCGAT GCTTGATCAT      540

GACCTGCAGA TGGAGCTGCT CCAGAATCTC GCGCTTCGCT ATCTCGTATT TTATCCGCTC      600

CGTCTCCTCG CTCTCACGCC CCAGCGGCCC CTCCTCCGCA CGCAGCCCGC TGTATTCGTC      660

GTCGCCCAGG GAAAGCTCGT GCGGCGACTT CGGTGTCGCC ACCTGGTAAT ATGCCGGCC       719
```

(2) INFORMATION FOR SEQ ID NO:584:

(i) SEQUENCE CHARACTERISTICS:
        (A) LENGTH: 726 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1402UP (xi) SEQUENCE DESCRIPTION: SEQ ID NO:584:

```
GATCAAGTTA TCGTTGATCA AAGCGTCAAT ACCCTTTTCT CTAAGCATGT GCCAGGTTTC       60

CTTCGCGGCG CGTAGGTATG GTTTCCCGTA CAACGCAATG AAGCAGTAGG CATAGTGGTT      120

GAAGTACTCT GCCATCCATT CAAAGACACC AACAACGGCA TCCAAGATTA ACCACAAGCA      180

CTGCATCCAC CCACTGTCGG ATATCCCGGA ATAATCCCA TTGCGAAGCA GCTGAATAAT       240

CTGCCGCAGT AGTTGAATCA GAGACACAAT CAGCGAGCCA AAGCAAATGG ACCCAAAGGA      300

AGTGGTCAAC GCTCTCTTTA ATGAGCCAAA AGCTGGCCAA CGTGGCATGC CTTGGTCCGA      360
```

```
CTTCGAAAAA TAGTACCAGC AGCCGTAGAT GCCCGCGATG GTGCAATGAA TCACATTCCT        420

GATGACCTCA GAAATGTAGA ATCCACAGAA GAAAACGAGT ACCAAAATAC CAATTAACTT        480

TCCACGTGAG CAAGAGCCAC CAGATACATC GCAGCCACCA TTCTCGCTCT TCGGGTCATA        540

CTTTATGTAG GTCGCAACCA ACACTACAGA GAATATGACA GAGAACGCAG CCGACACAAT        600

GGTACCTAAT AATGACACAA GCCACGTCTG TGGATGTTTC TTCATAACTG ACATGACCGT        660

ACGCAAGACA GCGACACTAA ATGGAATCCT TGAGCGCATT AACCAGTAGC ACACCGCCGT        720

CAGAAT                                                                  726

(2) INFORMATION FOR SEQ ID NO:585:

(i) SEQUENCE CHARACTERISTICS:
        (A) LENGTH: 731 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1403RP (xi) SEQUENCE DESCRIPTION: SEQ ID NO:585:

GATCCGTTCC TTGAGAAGCA CCTAAAGCCT GAACTCCTGG CAGAAGCGAT CAAGGGAACC         60

TCTTGGGAGG GTAAAGTTAG TATTAACTTG GTAGACGGAT TCGACCACTC GTATTACTTC        120

GTCAGCACGT TCGTGCCGGA ACACGCAAAG TACCATGCAG AAAAGTTGGG TCTAGTTTGA        180

GATTTGACGT TGCGCCTGTT AATTGGTATA TACTTACATA TTTAGTCATA TGACGGCTTC        240

AAGTACTCTG ATTCTGCATT ATAAGTGCAG CCGAATGCCA GCCTCCGGCA GTAATGGCAA        300

CGCAAACTGA ATTTGCCGGT AGTTCAACCT TGGCCGGTTG CAGCACGCGT ATGCTCCGAG        360

CAGACTCAAA CGTCGCTATT TGGCGGGTAT CTACAGCCTC GTCGGGATCT CCCTGCCCAA        420

GACAGCCACA GATATCACTC TCCAGCCCCC AGGAGTAGAG TTCACCTTTG TCGGTTAGAG        480

CTAGGTTGTG GTAGTCTCCC GCAGATACAG CAATAAACTT CTGGCCTTGT TCCAAATTCA        540

TCTTCATGAA TGAGTCCTCG ACGATATCAC CATTATTCAC CTTCAGGGTG TATGTGCTAT        600

TCTCGGTACA TAAAACCAGT GTCATGCAAG ATGCCTCAAT CTTCGTTTAA CCGTCCATCA        660

AATGGCAAAT CAACGGTTTT TGAAACGCCA TGAGTGTATA TCCACAGTTT GCGCCCATTG        720

TTAGTAATGT A                                                            731

(2) INFORMATION FOR SEQ ID NO:586:

(i) SEQUENCE CHARACTERISTICS:
        (A) LENGTH: 717 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1403UP (xi) SEQUENCE DESCRIPTION: SEQ ID NO:586:

GATCTCAATA TCAACCAACT TGTGACGTCG CTTAAAACAC CATATGCGGA GGACATTATG         60

TCCATCACCG TGTACAAGGA CAATGTTTTT GCCACGCACA AGCAGGGCAT TACGCGGTTC        120

CACCAAGGGA ACGTGAACTT CTGGAATGCT CACCAGGGAC TCGTCTTGAG TAGCGAAATA        180
```

```
TTGCGCAAGA GCTGTACCAG TAATCGTATA GATCGGATGG TTACTGGCGG AAATGATGGG      240

TCATTAGCGT TGTGGAATAT TAACGAATGG CTGAACGGTA CAGCGTCCCC GGGTGGATCA      300

GCCCCGACCG AAGAACACTC GCTTCCCTCT GGCGAGCGCC GAAATTCTTG GACCGAGTAT      360

CAACAAATCC AGTTAGATAA CGATCACATG ATTGCAACAC TGCGGGAATT CATTAGTTAC      420

CAGACTGTTT CCCAACTCCC AGAGCCCCAA AATATCATCG ATTCGCGTAG GTGTGCGAAC      480

TTCCTGCAAA ATCTCTTCAC TAAGCTCGGT GCTAACCATT GTGGGCTTAT ACCTGTCAGT      540

ACAGGCAGCA ACCCGGTGGT TCTCGCGCAG TTCAAGGGCA ATGCAGCCGC GCCCAAACGC      600

ATACTATGGT ATGGCCACTA CGATGTGATA TCCGCGGACC ACCGTCGCAG TGGGACAACG      660

ACCCTTCACG CTCACTTGCG AAAATGGGTA TCTTAAGGGA AGAGGCGTGT TGATAAC        717

(2) INFORMATION FOR SEQ ID NO:587:

(i) SEQUENCE CHARACTERISTICS:
        (A) LENGTH: 710 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1404RP (xi) SEQUENCE DESCRIPTION: SEQ ID NO:587:

GATCTGCAAC GTTACTGATT ATCCTGTAAG CCCTCTTTTG GGTTAAAACA TCCTGTGAGT      60

TAACAGTCGT GTTGAAGATA GAAAATAAAG CAGTGTATGA TGATGCTGGA ACAACCCTGG     120

ACATAACCAC CACAAGATCT AGAAGTGTGG CACTCATTTT TGGCTGGCCC TTCACAGGTT     180

GGCTAGACGC CTCCTTATCC ATGGCATCTT TTAGTAATGC GCATACGTTA TCAAACGTGT     240

TAGACAGGTT TTCCGCAGAA GTAATTTTCA AGTATGCCTC GATGGTTTCC AAAATATAGC     300

TCCGAGCGTT GGGTGCAGTC TGCGTGTAGA CATTGAAAAG AACGGCCAAC ATATTGGGCG     360

ATTTCTGGGA GAGGTATTCT ATGTTTTTCT CCGCTTCTGT CGGCGGGAAT TGCTGTCCCA     420

TAATAATGTC GTCCTTATAC GCACCATCTC TGTATAGAAG ATTACTTGTG ACCAAGACCT     480

TCAATCCATT GCATATGACA GTACGCAGTT CAATTCTGGA ATAAAGTAGG GACGCTAACT     540

CTGCAGCAAA CTCATCCGTG AATACATCGT TTAGATCTTT TGGAAGAACG CAGAACTGAG     600

GGAAGGTAGA CCACAATTGG TCAACAACAG TCTGAAGTAA TGTGCACTGG ATAGACTCCT     660

TATCCAGTTT CTCAATGGTG GACTCGAAAT GACGAATGGT AGGAATAAAT                710

(2) INFORMATION FOR SEQ ID NO:588:

(i) SEQUENCE CHARACTERISTICS:
        (A) LENGTH: 715 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1404UP (xi) SEQUENCE DESCRIPTION: SEQ ID NO:588:

GATCTTCAGC AAGATCAGCA CCACTTGACG CACTACAAGA AGTACCGGCA CTGGCGGTGG      60

CAGGCCAAGC GCAGGCTGGC CGGCTGCGAG TCAGGAAAAG TCGGAGCAGG TCGTACAGGA     120

GCCCGAAAAC GCCGAGCCGC TGGCGAAGCT GGGCGACGCG CTGACGGTGA CGGCGCTGAC     180
```

```
GGGCAAGATG AGCTACTACC GGCAGCTCCA GGGAAGCGTG AGCTCGTTGC TCAGTTCTGT       240

GTCGCAACTA ACGACGTCCA CCCGGGCGCC AGAATGCGAC TTCACTGAGC AGTTCATCAC       300

CTTACTCGTG AACACCTACC ACGAGATGTG TCTGGATGCA ACCGTCACAC CGTTCGACAA       360

GACTAACCCG CCATCTGCTT TTCTCAACAA GGTAGCGCGT GCTGCGGTGG AGCGTTCTGA       420

GCAGCAGAGC ATCGCCATCG GACGTCCGCG CGATAAATGG TTGTTGACCT GCACGCGGAA       480

GCGGCTTCTA CAGGAAATAA AGCGGGAGAC CGAGGACGTT CCACAGGGGT CCGTGCGCTC       540

GGTGGCCTGT TCCATGAACC ACGGCACCCT ACAGCGCGAT CTAAGCTCCG CTTTTGCAGA       600

GGAGGGCGAT TTCTTCTACT GGGATCCGGA CTTCCAACTG TTCCAAGGCA TCACGGCAAA       660

ACTTCTAACC GACACTGGAG ACATCTCGGG CAAAAATACC CCATGTCTTT GGATC           715
```

(2) INFORMATION FOR SEQ ID NO:589:

(i) SEQUENCE CHARACTERISTICS:
        (A) LENGTH: 729 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1405RP (xi) SEQUENCE DESCRIPTION: SEQ ID NO:589:

```
GATCTTTCAT ACTTTCGGGT TCGTGCTATA TAACTAAGAT TGGACAGAAC TGCAAGGGCC       60

ACAGAGGAAG AGCTGCTGCA TTGCACATTA GGCAGGAACA GCGAATGTCT ACAAATGCAC       120

ACTACACACT ACCGCTCTCA GCCGATCCCA ATCTCAGATG CGCACAGCAA GGGACCCAGT      180

TCTTTGCCCA TGCCGCTGTA CTCGCAGCGG GGCGCAGATG GGCTGCTAAC CATTAATGCG      240

AGCGCTGTGG GCTCGCCTGT GGGCCCCCAG CCGGTGATAC CTCCACTCAT GCACCAGGTG     300

GCGGTCGACA AGCACGCTCA TATCATGCCA GGCTCGTACG CGCTGCGACA GAGCTCGCCC     360

CAGGTCACGG CGATTATGGG CGAGTTAGCG ATGCTGAAGA AGTCGATATT CCAGTCGCTG     420

AACGGCGAGT TGACGACGGA GGAATACAAC AGCATCTACC AACATTTGAG TCAACTGCTG    480

GCGTCCCTCC CACCGCCCGT CGAGCCATCT GCAGCGCAGC CCCAGCTGCG ACTGCCGTCG    540

ATATCTCAAA TTATGCCGGG AACAGAGCCC CAGGAAGTCC AACGTACCTT CATCATAGCA   600

TCCTCCGAGT CACAGCAGGG CCAGCCGTAC ATCTCGCCGC CGTTAAGCTC GACAATGTCT   660

ACGCACCCGC TTTCACCGGG CATGTCGGTA GCCAAACCGA ACTACTCCGT GAGCACCAAG   720

AAGAATGTT                                                            729
```

(2) INFORMATION FOR SEQ ID NO:590:

(i) SEQUENCE CHARACTERISTICS:
        (A) LENGTH: 715 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1405UP (xi) SEQUENCE DESCRIPTION: SEQ ID NO:590:

```
GATCCAAATA ACACCACGGT TTTCATCGGC GGGTTGTCTT CGCTCGTGAC TGAGGATGAG       60
```

-continued

```
CTACGGGCTT ACTTCCAGCC ATTCGGACAG ATAGTCTACG TGAAAATCCC GGTCGGCAAA      120

GGATGCGGCT TTGTCCAGTA CGTGGATCGC AGTTCGGCAG AGAACGCGAT CGCCAAGATG      180

CAAGGATTTC CAATTGGTAA TTCGAGGGTG CGGCTCTCAT GGGGCAGGAG CGCAAAGCAA      240

ACAGCCGCTA TGCAGCAGGC GTTTGCCATA GCACTACAGC AGCAGCAGCA GCAGCAGCAG      300

CAGCAGCAGC AAGCCCGCCC GCAGCATTCC CAGCAACATC AGTATCAGCA TCAACAGCAT      360

CAACAGCAGC CTCAACATGT CATTTCTGCA CAGCCGTTGC TGCAGCAGCA ATTGCAACTA      420

CAATTTCCCT ATCAGCATCA ACCTGCCATG CCGCAGGCCT ACGGTTACAC ATTGGACTCG      480

TTGAGCGGCA CCGGTTCGAA ACATGTTCCA ATGCAGGGTT TTCTTTCCGG TAATATCGGC      540

TTCCAACCTT CTACGGCAAT TGATAGCTCT CCAGCAACGA CCTTGCTTCC CAACCTTTCT      600

TCGTTGGACT ACTCTGGGTT TCCACCTTCC ACGTCAGCGT TCACTTTTCA CCCACGAACT      660

CTTTAGGCAC AGCTTTCACA ACATCGCCTA GATTCTCAAC AATGGCAGCG TGTCC          715
```

(2) INFORMATION FOR SEQ ID NO:591:

(i) SEQUENCE CHARACTERISTICS:
        (A) LENGTH: 699 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1406RP (xi) SEQUENCE DESCRIPTION: SEQ ID NO:591:

```
GATCTCCTTC CAGTGACGCT GATGCACAAC TGCGGACCTC AGCCCGCGTG CCTCACGTGA       60

CCACAGTGGA CATTTTCTCA GTTAGCGCTC GTTTAGCTTA GCTATACGAG GGATGGCACC      120

ACTTAGGCGC TGCTGCGGAA CCAGATACGA TGAAGCCGCC CAAATTCGAT AGAATGCTGC      180

CTCGCTGAGC CGCCGTCATA GGGAAACGAC CAAAGGTTCC GTCTGCCGCA TCGTATGTAT      240

GTGTCTGTGT ACGAGGACCG AAAAGTTGAC TTTTAACGAA GTAGATTTTT TTATTAGATA      300

TTTAAGCACG TATGCGTTAA CGAGCAGCTT GCAAGGCGTA TACCAAGGCT CTGTGCGCTT      360

ATCATTAGCA GGGCGACATG TCAGAATCCT TGCTACAGAC AGTGGTGGCG TACGTGGAGT      420

TGGTGCTGCA CCACTTCATG GCGTTGTCGT GGACGCAGCA GCTGTCCATA GTAATAGTGG      480

CACCATTCAT ATACTCGCTG GTGTGGCAGA CGTTATATTC ATTCAGGAAG GATAGAGTAC      540

CGCTAGTGCC GTTCATGGTA CCCTGGGTGG GTTCCGCGCT CGCGTATGGG AGGGCTCCGT      600

ACGAGTTTTT TGGCAAGTGC AGCAGAAGTA TGGCGATGTG TTTGCGTTCA TGCTGCTGGG      660

GCGTGTGATG ACGGTGTATC TGGGGACGAA GGGCCACGA                             699
```

(2) INFORMATION FOR SEQ ID NO:592:

(i) SEQUENCE CHARACTERISTICS:
        (A) LENGTH: 709 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1406UP (xi) SEQUENCE DESCRIPTION: SEQ ID NO:592:

```
GATCTTCATT AGAACGCGCG GATTAGTCAA AAAGTGCCGG AATGTTCCAT CCACTAGGCC       60
```

```
ATCTGCCTTC ACCCACGGAT TGCAAATGCA GACAAGGTTT ATTAGAATTA TACCGATTGC      120

CCAAACGTCG CCTGCAGCAG TAGGAGCTCG GAGCTCACGA CCGAGCGATC CGCGCTCGGG      180

TGCCATGTAG TAAGACGAGC CTACGCAGAC ATTGGGGGCG AGCTCCGGCA CGGGTGTGGC      240

CAGCCCGAAA TCGCATACAT GTACGTTGTA CCATTTGTCC AGAAGAATGT TCTCCGGCTT      300

TAGGTCGCAA TGATAGACGC CGAGTCGGTG GCAGTAGAAA ATAACCTCGC ACAGCTGCAG      360

GAAGACCTTC TTAATCAGTA GGCCATCCTT AGCAAAGACT TGCTCGTTGA CAATGGCTGA      420

GAAAAGGTCG CACGTGATGT AATCCATAAC AATAAATGTT GCCAGGCTTG ACTCCATCAC      480

CTGATGTATG GTAACCACAT GTTCGTGGGT GTGCACAGTC AGGTGCATCA GCAGCTCCTT      540

ATAATGTGGC GCGTGGGCCA GCTGCTCTTG GGATAATGTC CGGATCGATT CCAGGTCCAC      600

AGATGGTAGA TACAGCCGGT TCTGGAAAGA TTGAAGAAGT GGTACAGCTG CGTGCGCAAA      660

ATTGTCGACC GGCCTGACGC CTCGTCTGCG CTGCCGCTGT GCTGCTTCA                  709
```

(2) INFORMATION FOR SEQ ID NO:593:

(i) SEQUENCE CHARACTERISTICS:
        (A) LENGTH: 707 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1407RP (xi) SEQUENCE DESCRIPTION: SEQ ID NO:593:

```
GATCAACCAG ATAACTATCT TAAAGAACAA CCCGAAAATG CGCAAAGCAC ACCACGGGTC       60

CTTCGGTGAT AGACTGATAG AGATACAGAA AGTAACTTCT GTGTCAAGCG AACCGGAGCT      120

CGGGTTTTTA CACCTTCGCA ACAGCTGCCC CCATGCCATA GCACTCTTTG AGTTCCTCTA      180

GTTGCTTTCC ACTAAACACC GCTCCGATGT TTCACAGAAC AGGTTTAATA TCGGCAACCA      240

AAGAGGAGGT TACACTCAGA GAATCACAGT GTCGAAACAC CGGCTATTCA ATGAGGCATT      300

CCCCCAAGTC GGTTTCTTTG GTTTGGATTG CCATTGGCTA GTAATCCACC AAATCCTCCG      360

CTGCTCACCC ATGGGATCGC TAGATGCCCA GGATGAGACT GTTCAGGTTA GGCAGGTGTT      420

GTATGCGCCG CCAGAGGGAA ACCCAATGAC TTTGCATAGA ACAAACCCGC CATCACCCAT      480

GTCTTGCGCT GTATAGAGAC TAAGGTATCT GACGATCCCT TAGCGACTCT CTCCACCGCT      540

CGACGAGGCC ATTGAAGCTC TTACGAACTG CACAAACCTA CTCGAACTCT GTTTCCAGAC      600

TTCTTTCTGT TTGTCTTCAA CTGCTTTCGC ATGAAGTACC CCCCAGGCTA TTTTTCTTAC      660

CCGCCTGGTG TTTGTCTATA TACCCGGTTG TATTTTTTGA TAAAAAA                    707
```

(2) INFORMATION FOR SEQ ID NO:594:

(i) SEQUENCE CHARACTERISTICS:
        (A) LENGTH: 571 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1407UP (xi) SEQUENCE DESCRIPTION: SEQ ID NO:594:

-continued

```
GATCGTCGAA TTTGGGTATA GGGGCGAAAG ACTAATCGAA CCATCTAGTA GCTGGTTCCT      60

GCCGAAGTTT CCCTCAGGAT AGCAGAAGCT CGTATCAGTT TTATGAGGTA AAGCGAATGA     120

TTAGAGGTAC CGGGGTTGAA ATGACCTTGA CCTATTCTCA AACTTTAAAT ATGTAAGAAG     180

TCCTTGTTGC TTAATTGAAC GTGGACATAT GAATGAAGAG CTTTTAGTGG GCCATTTTTG     240

GTAAGCAGAA CTGGCGATGC GGGATGAACC GAACGTGGAC TTAAGGTGCC AGAATACACG     300

CTCATCAGAC ACCACAAAAG GTGTTAGTTC ATCTAGACAG CCGGACGGTG GYCATGGAAG     360

TCGGAATCCG CTAAGGAGTG TGTAACAACT CACCGGCCGA ATGAACTACC CCTGAAAATG     420

GATGGCGCTC AAGCGTGTTA CCTATACTCC ACCGTCAGGG CAAATATGAC GCCCTGACGA     480

GTAGGCAGGC GTGGAGGTCA GTGACAAGCC TTAGGCTGTA AAGCTGGGTC GAACGGCCTC     540

TAGTGCAGAT CTTGGTGGTA GTAGCAAATA T                                    571
```

(2) INFORMATION FOR SEQ ID NO:595:

(i) SEQUENCE CHARACTERISTICS:
        (A) LENGTH: 658 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1408RP (xi) SEQUENCE DESCRIPTION: SEQ ID NO:595:

```
GATCCCGCTT ACCAAGCAAT TACAGGAGAC AGAAAAGAAG GATAATAATT TACCACAGAA      60

CTCCAAGCCT GACAGAGCAG CGATTTACAT TCTGAGTCAC ATGACAGCAG ACTCTCTTTG     120

CTTTGGAGCT TCAATAAGCA CCAATATGAA TATGAATAGT TTTAGATGCT TTGTATAATT     180

ACCACTATTA ACTTTATCTT GATTAATATT TATTATTTTG TTATTTTATT ATTTTATTAT     240

TTTATTATTT TATTATTTTA TTATTTTATT ATTTTATTAT TTTATTATTT ATTTTATTAT     300

TTATTTTATT ATTTATTTTA TTATTTATTT TATTATTTAT TTATTTATTA TTTATTTATT     360

TGTTTGTTTG TTTATTATTT TTTTATTTAT TACCTTTTTA TTTTATGTTA TTTTATTTTA     420

TTTTATTTTT ACTTAGTATA TAATATTATA TTATATCATA GTATAGTTAT ATTATGGTGA     480

CTTTATTCAT TATATAGATT GTATTTTGTG AACATAATAT ATATGCTATT TCTATTTCTA     540

TTTTATTTTA TTTTATTTTA TTTTATTTTA TTTTATTTTA TTTTATTTTA TTTTATTTTA     600

TTTTATTTTA TTTTATTTTA TTTTATTTTA TTTTATTTTA TTTTATTTTA TTTTCACT      658
```

(2) INFORMATION FOR SEQ ID NO:596:

(i) SEQUENCE CHARACTERISTICS:
        (A) LENGTH: 722 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1408UP (xi) SEQUENCE DESCRIPTION: SEQ ID NO:596:

```
GATCCGCCTT CCATCGAAGA GGGTACTGTT TGATTATGGT GATTTCTTGG TGTGGGTTCG      60

ACATTCAAGT GCATAGTTGG AGGTTACCGA TAACTTAGAT TTTCTTATAA ACGGTTACCC     120

TACGTCTTCG CGGTTGGCGG ATATACTGAT TAACAGTTGG AGAGCCTTGG CGGGATACTG     180
```

```
TGAATGCCTT CTCTTCAACA TTATTTGAAT ATGCAAACGT TATTTAAATT AAGTAACACA      240

CTTGTGCTTA TATATTCAAT TGTTCCAAGC GCGCCATCCA ACATGGCGAT TCTCATCTAG      300

TTTGAGAACT TGCGTCTATT CTTATTCTGT GTACGGCAAC GGTATTAGGA GAGACTTCGA      360

GTTTTTGGAA CTTCAAAGTC AATACTTCAT CATCGTAAGT AGCAGTTACT TGGCCTAAAC      420

CAGTGCCCAC CTTTGTAGGG AGCCTGATTG TTCGCCGAAA CTCCGGGTTT GTGGGTTCTC      480

CAGTAGTCCA CGCGTCTGTA TTCTCATCCG TATTAATGGC TGGCACGACA ATAGAAAGAA      540

CTGCATCATT CATGTCTCGA TGCAGGGCAA TATCTATGTG GTCTTGAGAC ATTACGCCAG      600

GAACTCTGAT GTGGATCTCA TAGGCGTCCG AACGCTCCAA AATTAATAAT GAAGGAAGAA      660

CGTCAGAATT TGCGCGCGAG AGCTTGTATT CTGAACTAGC TGCCACACTC TCAGCTTTGT      720

GT                                                                    722
```

(2) INFORMATION FOR SEQ ID NO:597:

(i) SEQUENCE CHARACTERISTICS:
        (A) LENGTH: 710 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1409RP (xi) SEQUENCE DESCRIPTION: SEQ ID NO:597:

```
GATCCTGGCT ATCTACCTGC TGCTGGGCGC GCTGCACGCC ATACTAGGGG GCACATTCAG       60

CGGATTAATG TATGTGGAAT ATGCGCGAGT AGAAAACGCA CGTKCATGTG ACAACAAGGC      120

CACCGGACTA ACCAATTTAC AGAACCGCCG CTATTTACAG GGCTGCCCTG ATCGCGATGA      180

GTACTTGGAT TCCGCTTGCA TCCGCAGTCG TACAGGCCCT GTACCTGCTA TGCGCAGCAT      240

TTGTGGCACA ATCCAAGCTG ATATAGGATA CAGACATCCA GCAAGACGCT GGATGGATCG      300

GTTGTATCCC TCTGCTGCAT CAATACGCTA TCGCGGGCCG GCAGCTTATT GTCACGTGAT      360

TCGCTATCTT GTGGAGCACC CAGACATATG TTGCTGAGCC TCCCTCAGCT ATATAAGCGT      420

CGAAGAAGGG CGCGAGTCGA ATACATGTCT CTGGCGCTGT GTGCCTCGTG CAGTCCTCCG      480

CGATGTCGTC AACTCTCATA AACCGTTCCT TGGCAACTAT CCGTACAGAG CTTGCCTTTT      540

TGGTTGATTC CGGGGTCATT ACGCGGCAGC AGTCAGAGCA GATTGAATCT AATCTTCCAA      600

ACCCTAACGA AGCCCTCCGT GGCGCTCCCG CAAATAACGC AGGGCCTGTG GAGTATGTGG      660

AGGCACTTTA TGCGTTTCAG GCGCAACAGC CTGGTTGACC TAGACTTCAA                710
```

(2) INFORMATION FOR SEQ ID NO:598:

(i) SEQUENCE CHARACTERISTICS:
        (A) LENGTH: 715 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1409UP (xi) SEQUENCE DESCRIPTION: SEQ ID NO:598:

```
GATCGGGGAC CAGAAAACCA CACAACTGGT CCTTGAGGCG GCGGTGGGCG TATACGCTGC       60
```

| | |
|---|---|
| TACTGTCTCT TCTTGTCGTA GCTGTGGCCT ACGGCTCTGC GTGCGTAACC GCTGGCATGT | 120 |
| GGCTCATCAC CAGAAAATAT GATGTCTCAA CCGAAGTTGC AATATTGTCC TGTTCCCTGG | 180 |
| TGGTTCTGGG CTACGGTGTT GGACAGCTGG TTTGGGCGCC TCTGTCAGAC CTGTACGGCC | 240 |
| GGCGGATAAC GTACTTCACA TCTCTATTCC TTTACGTGGT ATTTAATATT CCATGTGCGG | 300 |
| TGGCTCCCAA CATCCAGACG CTTTTGGTTT GCAGGTTTAT TTGCGGCGTC CTGTCGTCGT | 360 |
| CTGGACTATG CCTAGTCGGC GGCTCTCTCG CCGATATGTT TCCAGCCGAC CTGCGTGGGT | 420 |
| TGACCATCGC GTTCTTTGCA TTTGCACCAT ATGGAGGTCC GGTATTTGCG CCACTTATAA | 480 |
| ACGGATTCAT CGCTGTCCGC ACAGAGAGGC TTGACCTTAT CTTTTGGGTC AACATGGCGT | 540 |
| TAGCCGGAGC TGTTTGGCTG TTAGTCGCAC TGGTGCCCGA AACATATGCG CCAATTATTT | 600 |
| TGAAACGGCG CGCAGAGAAG CTGAGGAAAC TAACAGGCAA CCAGAATATA ATGACAGAAC | 660 |
| AGGAAGCACA GGGACTCTCC CTGTCGGCAT GGTGCAGACT TGTCTACTGA GACCG | 715 |

(2) INFORMATION FOR SEQ ID NO:599:

(i) SEQUENCE CHARACTERISTICS:
        (A) LENGTH: 709 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1410RP (xi) SEQUENCE DESCRIPTION: SEQ ID NO:599:

| | |
|---|---|
| GATCAATTCG TCACATTTCG CGTATGCAAT TTCTACCATC TCCTCTTTGG TAGCCTTTAA | 60 |
| TTCCACTCCT GGTGTAACAT CACTAATGCC AATAGAAAAG CCTCTATTTC CCAGATAGCG | 120 |
| CGCACAAAGC TTTGCCATCC TATTCATAGC CTGCGTTGCT TCTTGTGGCC CGAAATCTCT | 180 |
| CAGAATAGTA TAGAATACGG AATGTTTCTT ACCATCACCA AGCACAGACT TATCCATGAC | 240 |
| ACCAGACAGA ATATTAGAGC CTCTGATAAC TACATAACCA TCATTAGCAG ACATCTCATT | 300 |
| TGGATAGGCC TTATTCTTAG GCGCAATATA AACCTTATTC TTTGCATCCA AATTAATAAT | 360 |
| AACGGGAGAT TTCTTGTTCG GTTTTATCAA TAGAGAGAAG AGCTGTTTTC CAGTCCATAA | 420 |
| GTAGTGTGGT CGCATAATTG CAGGCGGCGG TATGTCAAAC TGCAGGTTGC CGTCAGACAT | 480 |
| CATAGAAAGC ATTTGGACAA AAGTTGCGCG GTCGAAGAAG GAGTCTTTGT GAGAAATCAA | 540 |
| ATATGATCCA GTGATGAAAT CCTGGGTAGC TGCAATGATC GGTTCACCGG ATTTCGGAGT | 600 |
| CAATAAATTG TTTTTGACAC CCATAAGGTT GATTGCTTCC GGGCGAGCCT CTTCCGTTTG | 660 |
| AGGAACATGC AAGTTCATTT CGTCACCATC AAAATCGGCG TTGTAGGGG | 709 |

(2) INFORMATION FOR SEQ ID NO:600:

(i) SEQUENCE CHARACTERISTICS:
        (A) LENGTH: 727 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1410UP (xi) SEQUENCE DESCRIPTION: SEQ ID NO:600:

| | |
|---|---|
| GATCTGAGCC CTAGCATCTT CGGTTGGAAG CGGGAACTCT ATTTTCCTAT CCAAACGACC | 60 |

```
GGAACGCAGA AGCGCTGGAT CAAGGACATC GACTCTATTC GTAGCAGCCA AGACTTTTAC        120

CCTATCGTCA GAACCAAAGC CATCTAGTTG GTTTAGCAAC TCAAGCATGG TTCTCTGCAC        180

CTCTCTATCA CCGGACTTCT CCGAGTCAAA ACGCTTAGTT CCAATAGCAT CCAACTCATC        240

GATGAAGATA ATGGTAGGTG CCTTTTCCTT CGCCAAGGCA AAGGCGTCGC GGACCAGCTT        300

CGCACCTTCA CCTATGAACA TCTGGACCAA CTGCGGAGCG GCCAGCTTCA AAAAAGTCGC        360

ATTGGTCTGA GCGGCACAGG CTCTTGCCAG AAGCGTCTTG CCGGTACCCG GTGGACCATA        420

CATCAGAGCA CCTTTCGGTG CCCTAATACC CATATCCTTG AACTTGTCTG CCTGCTTCAT        480

GGGTAACACG ATTGCTTCGA CTAGTTCCTC GATCTGCTTG TCTAGCCCAC CAACGTCGGA        540

GTATGTTTCC GTAGGCTTGT CATCCACTTC CATAGCTTTC ACTCTAGAGT CAAACTCCGA        600

AGGAAGCGTA TCCAAGATCA GGTACGAGTC CTTGTTCACA CCCACCAGGT CGTTCGGCTT        660

CAACTGCTTA AGGGTCCACT AGCCCAACCA TGGGGAGAAA AACGGTTTGT CGCGACGAAG        720

TTTCACA                                                                  727

(2) INFORMATION FOR SEQ ID NO:601:

(i) SEQUENCE CHARACTERISTICS:
        (A) LENGTH: 720 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1411RP (xi) SEQUENCE DESCRIPTION: SEQ ID NO:601:

GATCAAATGC CCTTCCCTTT CAACAATTTC ACGTACTTTT TCACTCTCTT TTCAAAGTTC         60

TTTTCATCTT TCCATCACTG TACTTGTTCG CTATCGGTCT CTCGCCAATA TTTAGCTTTA        120

GATGGAATTT ACCACCCACT TAGAGCTGCA TTCCCAAACA ACTCGACTCG TCGAAAGAAC        180

CTTAGATGGC ACTAGCACCC CCGCCAGACG GGATTCTCAC CCTCTATGAC GTCCTGTTCC        240

AAGGAACATA GACAGGGACT AGCAACCAAG GTACTTTCTT CAAATTACAA CTCGGACGCC        300

GAAGGCGCCA GATTTCAAAT TTGAGCTTTT GCCGCTTCAC TCGCCGTTAC TAAGGCAATC        360

CCGGTTGGTT TCTTTTCCTC CGCTTATTGA TATGCTTAAG TTCAGCGGGT AATCCTACCT        420

GATTTGAGGT CAAACTTTGG GAATACTATT CGCCTGGAAG GCCTTGTTTG TCGTACGTTC        480

TTCAAGCGCC AGCTCCACTC CACGATCTGG TCGAAACCTA ATACGCAGTG TAGAAACTAG        540

CTCAGACCGC AGTCCGCGCA AGTTCCGCCC ATGGCCAGCA TTTTCAAGTT AACCTTGTCT        600

TACGACCGAG TATCACTCAT TACCAAACCC GAGGGTTTGA GAAGGAAATG ACGCTCAAAC        660

AGGCATGCCC CTGGAATACC AGAGGACGCA ATGTGCGTTC AAAGATTCGA TGATTCACGA        720

(2) INFORMATION FOR SEQ ID NO:602:

(i) SEQUENCE CHARACTERISTICS:
        (A) LENGTH: 717 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1411UP
```

(xi) SEQUENCE DESCRIPTION: SEQ ID NO:602:

```
GATCGTCAGA TACCTTAGTC TCTATACAGC GCAAGACATG GGTGATGGCG GGTTTGTTCT      60

ATGCAAAGTC ATTGGGTTTC CCTCTGGCGG CGCATACAAC ACCTGCCTAA CCTGAACAGT     120

CTCATCCTGG GCATCTAGCG ATCCCATGGG TGAGCAGCGG AGGATTTGGT GGATTACTAG     180

CCAATGGCAA TCCAAACCAA AGAAACCGAC TTGGGGGAAT GCCTCATTGA ATAGCCGGTG     240

TTTCGACACT GTGATTCTCT GAGTGTAACC TCCTCTTTGG TTGCCGATAT TAAACCTGTT     300

CTGTGAAACA TCGGAGCGGT GTTTAGTGGA AAGCAACTAG AGGAACTCAA AGAGTGCTAT     360

GGCATGGGGG CAGCTGTTGC GAAGGTGTAA AAACCCGAGC TCCGGTTCGC TTGACACAGA     420

AGTTACTTTC TGTATCTCTA TCAGTCTATC ACCGAAGGAC CGTGGTGTGC TTTGCGCATT     480

TTCGGGTTGT TCTTTAAGAT AGTTATCTGG TTGATCCTGC CAGTAGTCAT ATGCTTGTCT     540

CAAAGATTAA GCCATGCATG TCTAAGTATA AGCAATTTAT ACAGTGAAAC TGCGAATGGC     600

TCATTAAATC AGTTATCGTT TATTTGATAG TTCCTTTACT ACATGGATAT CTGTGGTAAT     660

TCTAGAGCTA ATACATGCTT AAAATCTCAC CTTTTGGAAG AGATGTATTA TAGAATA       717
```

(2) INFORMATION FOR SEQ ID NO:603:

(i) SEQUENCE CHARACTERISTICS:
        (A) LENGTH: 710 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1412RP (xi) SEQUENCE DESCRIPTION: SEQ ID NO:603:

```
GATCTGGAAC CAGGATGACT GTCTGGCAGT TAACTCGGGC GACCAGATTC GCTTCCTACA      60

CAACTTCTGC TCCGGTGGCC ACGGTATTTC CATCGGGTCT GTTGGCCACA AGAAGGGCGA     120

CTCAGTCACC AACTTCCTCG CACAGGACAA CCAGGTCGTC GAGTCGGACA ACGGTCTAAG     180

AATCAAGACT TTCGTGGGCG CCATTGGCAA GGTCGACAAC ATCAAGTTCA TCAACAACAA     240

GGTCAAGAAC ATCCGCAAGT TCGCTATCGT CATCCAGGGC GACTACAAGG ACGGCACCAC     300

CACCGGCACC CCAACCGGCG GCTGCCCAAT CACCAACCTA GAGGTCAGAG CAACACCGG     360

TAACACCGTC GGCAAGGGCA GCAAGCTCAA GATTCTCGTC AAGAATGCGT CTAAGTGGAC     420

CTTCGCCGAC AACAACATTT TGGGCAAGAC CTTCCCAGGC TGCTCTGGCG CACCTAACGG     480

CATCAAGTGC TAAGCGCCTT TTTTTTTTTT GGCTGCGCCT CGAAACTATT ACTATGAACA     540

TTGGCGTCCA CCGCCACTAC AAAAGCATCG GGTCTATCCC ATTATAACAT TAAAATCTCA     600

GTTGATATTA TATTTACAT TCGAATGTCC TTAGGGCTTT TTTATATTAT ATAAACTTTA     660

GATTAAAAAA ACGAGGTACA AGCAGATCAA CGAAGCTTTT CGGCCAGCCA              710
```

(2) INFORMATION FOR SEQ ID NO:604:

(i) SEQUENCE CHARACTERISTICS:
        (A) LENGTH: 728 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1412UP (xi) SEQUENCE DESCRIPTION: SEQ ID NO:604:

| | |
|---|---|
| GATCGAACGA GATAAACAGA GGTATTGGTT GTTATCACAA ACATATAATC CTGGGGATAC | 60 |
| AACGCTGTCA AACTCTGGGC CTTCTGCTTT GTGTCTAGAT TCCTTTTGCA GGCTTGAGAA | 120 |
| TAACCTGTAC AATTTTTTGA TGTGGTTAGT AAGAGACGCA TCAACGATAT CATCGCACAA | 180 |
| AGTTCGGTTT CTTTCCCCTG CAAGCGGGAA TGCGCCTTCA TTACTTCCCG AATCTTCTCC | 240 |
| ATGAGTCGAT GGTCTCGGCG TTGAAGCTTG TAGTGTCAAA GGTTCTATTC TTGGAGAAGG | 300 |
| TTCTATCTCT ATTTTTTGTC CCCAGAAAGA ATCATTTGAC ATCCAATATC TTGTAACTTC | 360 |
| CCTGGGATGT AATCTTTGAA TAGCGGGGTT TCGGTACAAG CTGCTACCTG CCAGATTATT | 420 |
| ATTTAACGAT TCTTCTGGTC CGTGAAGGTG ACGTATAAGG TGGACGCTAT TGGGTTTCTT | 480 |
| TTCCAACATA GGTTGTTCAT CAAATGAGAG GTAAAATGGT TCCTGCTGGG AACGCGACGA | 540 |
| AGGCTCCTTT ACTTTAAGTC TTAACAAGGC GTCAACATAT TCTTTTTGAA TCGTTCTAGA | 600 |
| AGTGGTTACA AAATCCATAT TGCGTCTTAG ATCTGACTCC TGAACGCCTT TGTCTAGTTT | 660 |
| CTCATCCCCC AGTGGTAAAT CTGAACGAGG GACAAAGTAC ATGCAACTGT CCTCATCATT | 720 |
| GTAAGTCA | 728 |

(2) INFORMATION FOR SEQ ID NO:605:

(i) SEQUENCE CHARACTERISTICS:
        (A) LENGTH: 732 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1413RP (xi) SEQUENCE DESCRIPTION: SEQ ID NO:605:

| | |
|---|---|
| GATCTGCTGG GAGTGACTCA GGAAGCTTTG TCAGTACCTG GAATGAAAAA ACAGTCTCTG | 60 |
| ACAGAGCGGG GAAGCTGGGC CTGATGGTCG TTACAGCGGA CCAGTTCAAA GAATATGAAC | 120 |
| AATTGAAGAC TGTCAGCCCC AAGGATCAAC TTGCTCAGCA GGCGAAGGAG CTAGATATGG | 180 |
| TGCTAATTGA TGCTGCTGAA CTATACGAAT TAAGAAGCAA AGTTTCCGAT GGACTGTCTG | 240 |
| GCGATTTGAA CTCTGACTTT GTCTTGAGCA AGGAGATCAT TCTTGAGAAT GCTCATAGTT | 300 |
| ATGGTTTAAC GGTTCTTCAA ACGGAAGAGT ATCTTCAATT ACAGAGTAGT TTGGAGAGAG | 360 |
| AACAGGTAAC GTCCTACAAC ATTGCCGAGA AAGCAACTAC AATTGGCTAC GTTGCACTTC | 420 |
| CAAGAACCGA GTACGATGAA CTTGTAGCTT CGCAAGCTTC TACGAAAGAA CAGAATTTTG | 480 |
| AGGTATACGC GGCGGAAAAT GGCAAGGTCA TAGTGGATAA ATCTGAGTAT CACGATTTGA | 540 |
| AGATCAAAGC TATCCCAGTG ATTTCACCAT TGCCTCAAAT GAGCAAAGAG CAGATGGTTG | 600 |
| AAAAGGCCAA GGAACTTGGA ATGGTAGCTT TGCTCATTGA CGAGTATGAG AAGTTAAAGA | 660 |
| GCCCTATTTC CGATAACGCT TTGAATGCAA CAGCGAAGGG ACCGTGGAAA GGTTGTTCTC | 720 |
| CTAAAGGAGA GT | 732 |

(2) INFORMATION FOR SEQ ID NO:606:

(i) SEQUENCE CHARACTERISTICS:
        (A) LENGTH: 721 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
    (A) ORGANISM: PAG1413UP (xi) SEQUENCE DESCRIPTION: SEQ ID NO:606:

| | | | | | |
|---|---|---|---|---|---|
| GATCCAGTTT | TAGGTCCACT | TCAAACTGGA | TTTTCGGGTA | CTCCCCGCAC | ACCACCGTCA | 60 |
| AGTCATCGGC | ATAGATGGAC | TCAAGCACTT | CCAGCTCCTG | CTTTTGCTCC | TCCTGATAGT | 120 |
| CCATACCTAT | CCGCTCGACC | AACTATGAGC | CCACGCGCAG | CTTAGGGCTA | GACCGTTACA | 180 |
| GCTGCAGGTG | ACCGTCCGGG | GGACGATGCG | CTATCGCTGG | CGAAATTTTT | CGCCTATACC | 240 |
| ACCACTTATG | TTACCCGGTC | TATAGTGCTG | CTCTCCGACC | TCACTGATGG | TGCTGTCCCG | 300 |
| CGGGGACTGC | TGCCTCGTGC | GGCCAAATCC | CCACCGCTCT | GAACGCTCGT | TCCATCTGCG | 360 |
| TCACGGGTTG | ACCGAACGGG | AATTGCGCGC | GCCGAGAAAT | CTTGGCGAAC | CATGCTGCAC | 420 |
| GTAGCCTTAC | TGCCAAAATT | AAGCCGTCAA | ATGGCTGGCT | ATCCTTCCAC | GCACGCCCAT | 480 |
| AGTCACCTGA | AGCTGGCTGG | AACAGTGGTC | ACGCAGCTTT | CTGACGCATA | CCAGGAACAG | 540 |
| GTGGCCGAGC | CCGAGGCCAA | CGGTGGGTGA | TTATGTCAGC | GACTTTTGGT | GGATTACGTA | 600 |
| AATCTGGGTG | CATGCCTGGC | ACGACAGCGC | GCATCGCACC | CCAAGACAAA | CGTGCCACAC | 660 |
| CCATTCAATA | TTAGAGGACT | TTGCTGCACA | CCCTAATCAT | CCGTTGGGTT | GTGAGATACG | 720 |
| C | | | | | | 721 |

(2) INFORMATION FOR SEQ ID NO:607:

(i) SEQUENCE CHARACTERISTICS:
        (A) LENGTH: 729 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1414RP (xi) SEQUENCE DESCRIPTION: SEQ ID NO:607:

| | | | | | |
|---|---|---|---|---|---|
| GATCCGTAAT | CGAGTTTAGC | TTCCGTGTCG | CATCATCGAC | AGGTGGAAAT | GCTCGCTTGT | 60 |
| CGGCCGTCTG | AAAACGAGTC | AGATGTGCAG | AGAGGCTGAA | GTCCAACATT | TTAACCACCG | 120 |
| CTGAAGACCG | GGAATAGTAG | GGCAACGTAG | TTCCGCGAAC | TTCAGTTTTG | TTTTCTTTTA | 180 |
| ATTTAATGGA | CTACACCAAA | AAAAGCTCAA | CAACAGTCCC | AATTAGTTCT | GCTAGAAGAT | 240 |
| GCAAACACGT | TAGTGATCAG | TAAGTATGTG | TACTCGTGTA | CTCGTCCTGC | ACTGCAAAGT | 300 |
| TCGCGTCACA | ACTAGCTGTG | AACCATGGTT | TGAAAAAAAA | TAATGATAAT | GATTCCGCCC | 360 |
| AGGATCGAAC | TGGGGACGTT | CTGCGTGTTA | AGCAGATGCC | ATAACCGACT | AGACCACGGA | 420 |
| ACCACCTATA | AGCCCTTAAT | TATACTCAGA | TACTAGTGAC | CATTTTCTAG | TCACATGATG | 480 |
| CTAGTTTCCT | GAATAAAAGA | TGCACGTGAT | TACCAAATCT | GTATTTACTA | GGTAAAATGC | 540 |
| CTTGGTGAAT | AAGTACGTAG | ATATTATATA | TGTATACATA | TGCATTTTAG | ATGCAATAAA | 600 |
| AGCTCTATTA | TGTATGCGCG | CGGAGCTTTA | AGCCAGTGTG | TTTTCCGATT | GTTTTGTGGA | 660 |
| TGCAATGGTC | TTTGCATAAA | AGCCTGACTT | TCATCTTTTT | CGTGCTTGGA | TGTTAACTTC | 720 |
| CAACTCTGA | | | | | | 729 |

(2) INFORMATION FOR SEQ ID NO:608:

```
       (i) SEQUENCE CHARACTERISTICS:
           (A) LENGTH: 639 base pairs
           (B) TYPE: nucleic acid
           (C) STRANDEDNESS: single
           (D) TOPOLOGY: linear (ii) MOLECULE TYPE: DNA (genomic)

(vi) ORIGINAL SOURCE:
           (A) ORGANISM: PAG1414UP (xi) SEQUENCE DESCRIPTION: SEQ ID NO:608:

GATCTGGCCC CGCGGGCGCA CCGCGGCCAG GGGCCAAAAA GGAGAGCGCC CGCGGTGGCG      60

GCCGCCACTG CGGCGGTTGC ACAAGACATA TATGTCGGTA TATAAGACCG CGGGTGCCGC     120

GTGGCTGCCG TGCAGAACCC GCCGTGCGCG CGCGGGCAGA GATTTCTAAT ACTCTGCGTT     180

TTCTTTTTGC AGCGCCTGGT ATATAAGTTC GGGCTGTGTC GCGGGCCGTC GGCGCCGTTC     240

GCCAGGGAGA TAGGGGAGCA TTCCGCAGCA GCCGTCTGTA GCCGGACCAG TACGACAGGG     300

ACGCAGGACA CAAAGCAGGC GACGGCGAGT GCGCGGGATC AGCAGCGCAC AGCGAGCCAG     360

GGGTATAAGA GCCGCGGTAC GAGGCGGCTG GTAGGTATAG GCCAGATGG AGGTGGGTGC     420

TAACGGGATT TTTCTGCACC AGAACGACTC TGCGGAGACG ATCAAGCTGG AGATGTCGCC     480

TGTCGGCGGT TCGGGGAGCG CAGGCAGCGG CATCGCGATG GGCAGCGCGG ACGACGAGCT     540

GACGAAGTGC ATCAGCGACC TGAACATCTT CGATCTGCTG CACAACAACC CGCCGTCGAG     600

TTCGGACGAC AACAAGGAGG GTGGGCGGCG GGCGGCTGC                            639

(2) INFORMATION FOR SEQ ID NO:609:

(i) SEQUENCE CHARACTERISTICS:
           (A) LENGTH: 688 base pairs
           (B) TYPE: nucleic acid
           (C) STRANDEDNESS: single
           (D) TOPOLOGY: linear (ii) MOLECULE TYPE: DNA (genomic)

(vi) ORIGINAL SOURCE:
           (A) ORGANISM: PAG1415RP (xi) SEQUENCE DESCRIPTION: SEQ ID NO:609:

GATCGTGGTT CTGTTATCGA AACGTTGGTT GCTAGAACAT TGCGCCAGGT TGAAAGTAGC      60

CAGAGCATGA TACGAATTCT GGGATTATCG GCTACATTAC CTAACTTCTT CGACGTCGCA     120

GACTTTTTGG GGGTTAACAG ACATGTGGGA ATGTTTTATT TTGATCAATC GTTCCGTCCA     180

AAACCCTTAG AACAGCAGCT GCTTGGTTGC AGAGGCAAGG CGGGCAGCAA ACAAGGAAGG     240

GAAAATATTG ATAAGGTTTC ATATGAAAAG CTTTATGAAC ATGTCTTAAA TGGCTCCCAG     300

GTCATGGTTT TTGTGCACTC AAGGAAGGAT ACTGTGCGCA CTGCGCGGAA TTACATTTCT     360

TTTGCCCAAG CCAACCAACA GTCCGATGTT TTCCTAAGTA GCGATCAAAG CGTTACCAAG     420

TTTTCCCGAG ACATCTCCAA ACATAAGGAT AGAGATATGA AGGAGCTCTT CCAACATGGG     480

TTTGGTATAC ATCATGCTGG TATGTCTCGA TCTGATAGAA ATCTAACAGA AAAGATGTTC     540

AAAGAGGGAG CTATTAATGT GCTTATCTGT ACAGCGACGC TGGCCTGGGG TGTGAACTTA     600

CCGGCTGATG TTGTCTTGAT AAAGGGAACT CAGATATMTG ACTCTAAAAA AGGTGGTTTT     660

ATAGATTTGG GGATTCTGAT GTGATACA                                        688

(2) INFORMATION FOR SEQ ID NO:610:

(i) SEQUENCE CHARACTERISTICS:
```

(A) LENGTH: 703 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1415UP (xi) SEQUENCE DESCRIPTION: SEQ ID NO:610:

GATCATCAGG AGTTCGTCAC CTTGGAAACC AATTGCGAAC CACAATTCCT TCTGAGCCTT      60

TGGAAATTTG TCACACCAAA CTCTGAAACC GTCTTTGTAA CTTTCATTAT GGCGGAATGC     120

TACAAGTGTC AACTTATCAG GGTTGGATTG GTCCTTAAAA TGTACCTTAT CCAGAACAGG     180

AAGCATCGAG GCTTCACGTA TAAACTTATC TTTCGCCGCT CCTTGAATGT TATGCACGCG     240

GCACACTGAG CACAACGCAG CATAGCCCAT CCGACCTAGC TTCTCCAACG TCAGCATCTC     300

GCCACTATAC TCATAGGGAA AGCCATCATC CCCGAATAAT TCGGGTCTA AGCGTTGTAG      360

CGTAATTCCA GGCAAAGCAG TCACCGGGTT GTCCTCATAC CATGTTCCCT GCTTAATGCA     420

CTGCATGGCT TTAATCATAG TCATAACTGT CCTGAGGTAC CCAGATTCGC TTGCAATATC     480

GATATAGGCC TGTAGAATAC GTAGCGCCTG GTCGAGAACT GAGATCGTAT CTTGGTAATA     540

ATCTGCAATT GCTAAGTCAG CTCTACTTAG GTAAGCTTGT AAAAGCAAAA AGGCTTTGAC     600

ATGGGGTCC CATATTGGTA ACTCTTGTTC TCCTGTAAAA GTACTTTCAA CGGAATATCT      660

AAGAGTTTCT GACATTTCAA CATTCATGAT AGTCTCGCCC CCC                       703

(2) INFORMATION FOR SEQ ID NO:611:

(i) SEQUENCE CHARACTERISTICS:
        (A) LENGTH: 718 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1416RP (xi) SEQUENCE DESCRIPTION: SEQ ID NO:611:

GATCATCATT ATTTCCTGCG TTCGTGCCGA CGATTCGAAG GGCGGGGTCG GTTTCTTGAA      60

GGATTTCAGG CGTATGAATG TTGCTCTCAC CAGAGCAAAG GCCAGTCTCT GGATCCTGGG     120

TCACCATAAA TCTTTATACA AGAACAAGCT ATGGATGCAT TTGATTTCAG ATGCGAAAGG     180

GCGTGACTGC CTCCAAATGG CATGTCCGGG CTTCCTTGAT CCACGGAACA GAGCCGCCCA     240

GGATGCTCTT CATAGGTTCA AAAATCACCA TAATTATATC GAGAACGCAG ATGATTATGG     300

GCCTGAACCG GTGATGACTA AATCAAGAGG ACGCAATAGA TCATCCAGAA AACGCAAACA     360

TATGGAAGAT AATCCAGATG ATAACTACGA TCCCGTTGCT GAATTCAAGA AGGAAAATCA     420

AAGAGAAAGC AACACAGGCA CCGGTGGTTA CCGTGCGGAT ACATCTAACC ACAGATTGGC     480

ACCTGCTAGG AACGATAGCA AGAAGGCCAA GACGTGCTCC AATGCCGCCG GTATTTCCGA     540

GGCTACTTCA GAGGATGGTG ATCGAGGTCA GAAAGGACAT GGAACTAAGA AGAAGTCTTC     600

CATATTCGGG AATTTTATGC CCCCAGTTGA TGACGCGACC CCTGCTGCCC ATGTGTACGA     660

CCCTAAGGAA CGCAAGCCCA AGAATGCTGC ATCCGCTTAA GCGGCTGGCC TTGGGAAC      718

(2) INFORMATION FOR SEQ ID NO:612:

(i) SEQUENCE CHARACTERISTICS:
            (A) LENGTH: 712 base pairs
            (B) TYPE: nucleic acid
            (C) STRANDEDNESS: single
            (D) TOPOLOGY: linear (ii) MOLECULE TYPE: DNA (genomic)

(vi) ORIGINAL SOURCE:
            (A) ORGANISM: PAG1416UP (xi) SEQUENCE DESCRIPTION: SEQ ID NO:612:

GATCTTGCCC GGCAAGACCA GGAAGTCGTT GTACGTCAAC CCGCCCCGCG TCTTGGAGTC       60

CATCAACTGC TCCACGGGAC AGCCCGTCCT TCTCGGCGTA CGTCGCCAGG TGCTCCAGTG      120

CCGTGGCTGC GTCTCTGTAA GTCATTGCGC TTTGTTCGGG GTGCTATGAA GAGAAGGAGT      180

CAACACTAAA CCCAAGCTCT CAAGTTGACC CATCCATCAA GTAACTATCC CGAACAGACG      240

CCGGTAAACC CAGCTGGGAT TTGGCGCATC TAGAAAACCT ATTTATACTG CAGCTCATCG      300

CTGCAAACTT TTCACGTAAA AGAAACGATG ATCCAGCGGG GGCCAAAAAG CAATGGGCCT      360

GCGCCGCACG ATGCGAGCCC TACCGGCGGC CAGCACCAGG TAGGAGCTGT CAGGGGCCTA      420

GAACGCGCGC ACGCTAGACG GGCTCCTCGG GGGCCGCCGC AGGCGTCCGA CGGGCGCCTC      480

GCAGCAGCAG GCGTGCCAGG CGGACCAAAA GACCGACCAG CCAGCGCAGC AGTCTGTAGA      540

CGGCGCGGAG CAGGCGAACG GCCAGGAATA CAGTCCAGAG CACGGCGGAG AGCAGCAGGA      600

AGTTGAACAC GCCGTCCATG CCCACGCGCG CACAAACGGG AACAGCGCCA GCGCGCGCTC      660

GCAGAGCGGC TGCAGGAATG CGACGACGGA CAGGAACGGC AGGATAGGAC TA             712

(2) INFORMATION FOR SEQ ID NO:613:

(i) SEQUENCE CHARACTERISTICS:
            (A) LENGTH: 715 base pairs
            (B) TYPE: nucleic acid
            (C) STRANDEDNESS: single
            (D) TOPOLOGY: linear (ii) MOLECULE TYPE: DNA (genomic)

(vi) ORIGINAL SOURCE:
            (A) ORGANISM: PAG1417RP (xi) SEQUENCE DESCRIPTION: SEQ ID NO:613:

GATCCCCTTG GCGTCGTCGT TGACCAGGTA GCGGCGCTGT AGCCCGAAGA AGCCGGACAT       60

CGGGTCTGAC GCGGTCGTGA GCGGACGCGC CATCATGCGC GCGCTACTGG AGATCACGCG      120

CCGGTACAGG GGCCAGTCCT TGTCGATTCC GACGCCGGGC GCGTAGCGCG TGCCCAGCAC      180

GAACGGATGT GTGCGTAGTG AGTCCAGAAG CAGCGGTACG CTCTCTGGCG GATGCTGCAG      240

GTCCGCGTCC ATGCACACCA GGTACTCGCC CTTGGCCTCG TAGAAGCCCT TGAGCACCGC      300

ACTCGACAGC CCGCGCTCGT CCGTGCGCAC GATGATCCGC ACGTTGTAGC CCTGCTTGGC      360

CAGGGCCTCC ACCTCTTCCA CAGACCCGTC CTGGGAGTTG TCGTCGACAA AGATCAGCTC      420

AGTCTTCTTG GAGTCCGCGT TACCGAGCGC GGCAAACAGC CGCGTGGCAA GGGGCTTGAT      480

GTTGGGCCTT TCGTGGTAGG CCGGCACGAC CACAGAGTCT CGATGCTCAT GGCGCTCGTA      540

TGGTCCTTAA TGTAGTGAGT AGCGAACGTC GGTAGCTGTT TCGCAAATAA GTGAGGCCTG      600

CGCGCCTAAT GTCGTGTCCT TATCGTTGCT TTTTGGTTCG TGTCACGGGG TTACCCGGCC      660

ACCAGGCTAG ACAGCGAGAC CCGCGGTGAG CAGCCCACGA CCAAGAAGCG CTGTA          715

(2) INFORMATION FOR SEQ ID NO:614:

(i) SEQUENCE CHARACTERISTICS:
    (A) LENGTH: 715 base pairs
    (B) TYPE: nucleic acid
    (C) STRANDEDNESS: single
    (D) TOPOLOGY: linear (ii) MOLECULE TYPE: DNA (genomic)

(vi) ORIGINAL SOURCE:
    (A) ORGANISM: PAG1417UP (xi) SEQUENCE DESCRIPTION: SEQ ID NO:614:

```
GATCTGCGTA GGTAGTAGAT GAATTGAGGG TATAGGGAAA AGTTTGGTGC CAAGCGGAAG    60

GAGCGGGGGT CGCCCTTGTT GTAGTCGGCG TACTTCTGGC AAAGCTTGAT CAAAGTTCTA   120

TCGATCCACC GGATGACGTC AGCGCCATCA TCGGAATCTG CCTTATCGAC TGCAACACGC   180

GCCATTAGTA CAGCAGCGGC CTCCTGGTCA AGGAAGCAG CGATTGCCGG GTTACCGAAT    240

GGCAACATCT GGTTAGCAAC TGTAGTCACT CTGACACGGT TGGTACCAGA TGCATGCTGG   300

TATGCAGTAA TGAATTGGGT GTATGCCAAT TTTGGTCTGT CCCCCATGAG GCTGGCAGTT   360

GCAGCGGTAT TTGCAATCTC GAAAAGATA GCGTAAGAGT GGTGAGGGCT CAAGGACGCC    420

ATTTTCCATG TAGAAGTGCC CCCAATACCG ATTTCTGAAT CGCTCACGTT CTGTGCATCA   480

ACGTTAACCG GCGAAGCATG GCCAATCAGT CCCTGCAGCT TTAGATCTGC ACTGGTTTTA   540

ATGCACATGG AAGCATTGAA CGCCATGGTT AGGTACCCTC CTCATCTTTA GAAAACAGTC   600

TGATGAAAGA TTGCTTGAAG ATGGCCGTCG AGAATGCGTC AGTCAACAAC AAAACACCAC   660

CAGTGGAGTC GGTCAACTTC TTCATCTCAG ACATACAACC TGGTCGTAGC ATCCA        715
```

(2) INFORMATION FOR SEQ ID NO:615:

(i) SEQUENCE CHARACTERISTICS:
        (A) LENGTH: 728 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1418RP (xi) SEQUENCE DESCRIPTION: SEQ ID NO:615:

```
GATCCGCGAG ATTCATCGTG GACCCGCCAC AGGCAATTAC TATAACAACA TCCTGCGGTG    60

TTAAAGGACC TAACTCACGC TCAAGTATTT CAGGATGATA TCCTAGATGA AGAGCTGCGC   120

CACACGCTGG TTCGGTTACA ATATTGCTCT CTTCCGCAAA ATTTAAACAT GTCTGTACTA   180

CAGCGAGCTG GTCAAGCACA ACAGATTTTG TCCTGTATTT TTGGGCGTAA CTCAGAGTAA   240

GATCCGTCAC GAAAGATGTG CATAAAGAAG TAGCAACGCT TTTAGGATTC ATCGAAACGT   300

TCCTGCCCAG CAGCAAAGAT CTGTGCAAAA CCTCGCACCC CTCTGTTTCC ACTGCTACAA   360

CAGGGATAGA GTCTGCCAAA CCATGTTTCT CCAGCCCATA TACAATCCCA TTATATAACC   420

CCCCGCCACC TACGCTGCAG ACGATACCTT TCACGCTCTC CAATTGCACG CCTTGGAGAT   480

GCAGTGCTTC TACTACTTCA TCTACCATTG TTGCATGCCC TTCCCAGATG AGTGGGTTGT   540

CGAATGGATG TGCATATATC GGAGCGACTT TTTCTAAATT CACATTCCCC ATCAACTCGG   600

AACGTAAGTA GTCATCGCTC TCTTTCAATA CACTTCCCAT TGATATCACA TCTGCCCCCG   660

TTGACCGTAT CCGCTCTACC ATCCGCCGTC GAGTAGTTTC AGGCACTACC ACTGTGCAAG   720

GTATCCTA                                                            728
```

(2) INFORMATION FOR SEQ ID NO:616:

(i) SEQUENCE CHARACTERISTICS:
        (A) LENGTH: 713 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1418UP (xi) SEQUENCE DESCRIPTION: SEQ ID NO:616:

```
GATCATCTGC GTGCGATACT GGCAAAAAAT GAGAGACAGC ATGATGAAAA TATAGTTAAT      60
AAGATATTGC ATGATATAAG CACAGGCGGG TTTCGTCGAA GAGGAAAGGG TGCACTTGAT     120
CTGGAAATGA GTGAAAATGA AGACCAAGAG TTACAACAGT TTAGACAGAA AAGACGAGAA     180
CTTTTGAAAC AAAAGATATT GGAAAATGGT GATACTAGCA AGCTCGTATC TAACCCCAAG     240
TCATACGCCT TTTTTCAGAC GATGGTGGAC GATGTTACTG AAGCATCATT TGGAAATACA     300
TTTGATGCCA ATATAGATGA AAAAACAGAT CCATCTGCTG CAGGTCGGAA AATTGTCATA     360
TCAGAACAAT TTGTAAAGGA AACCCTGTCA TTCTTGTCGA GCAAGAGTGG CGACTCAGAA     420
ATCCCTGCAG AAACTAAATC TATTTCATCC AGCACAGTTG AACGTGAAGA AATTCAAGAC     480
CTTCCATACA TTGAAGCAAA ATAGTAACAT TAAACATTTG AAAGGAATCT AGAACTTCCT     540
GCTCAGATGG CTGAACTCAG CAGTGGAGAT GAAGGTGATT ACGGCTTTTC TTTAGATAGA     600
TTCGCTCTGC GGCAAAAAGT TTAATAATGG AACTAACGTC GACGATAAGT TTAAAAGTGG     660
CACCAAGGCA GTGCGAATCT TAAAGGCAAT AAGACAATTG GCGGTCAAAA GCC            713
```

(2) INFORMATION FOR SEQ ID NO:617:

(i) SEQUENCE CHARACTERISTICS:
        (A) LENGTH: 723 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1419RP (xi) SEQUENCE DESCRIPTION: SEQ ID NO:617:

```
GATCTGGGGA GTCTCATCGA AACGTATTCG ATGAGGCTTG GTGGTGGCAG GCGGCTCCTC      60
GCTCGATTGG CGAGCTGGTG ATGACTTCGC ACTTCTCCGG GCCGGAAAAT TCGTGTCAGA     120
CAGTCGGCGT TGGCGTTGAA GCTGCCGCTG TTGCTGCACA CGTGGTGGCG CCCTTAGCTG     180
AATACGTAAC GCTGGCGCGG TGTCCCGCGC ATCCAGGTAT TCTTCGAGGC TTTCTTCTTC     240
GGCGATGTCT GAGATATCTG GAGCACCGCG AGCATTCTGA TACACGTGGC CCGAAGATGT     300
TTGCTTCGCG GTGAAGTCTC CCTCAAACCC GTAGAAGTCA TCGGGGTATT CTCCATCCGG     360
CATTGTCATT GTAGTAGTGG TCTCCACATA GCGTACGCCA TTGATGTGCT TCACCGTCTG     420
GCGAGTCACG GTCCGTGTAC GGCCCTGGAG GTCCTTCGTT TCCGTCGTCT TCACCGTTAT     480
CGTATTGCCA GCTGCGACAG CAGGAGGGCC AAAGCCGTTG TTGCTGCGTA GCGAATTCGC     540
GCGTCGTTGC GAGCTCATAC TGTAAGTCCG CGGAGGCGCA CCGAGGTAGC TGGGCCGAGC     600
AGCTCCTAGC GACCGCGTCC GCCCGTACCC AGTCAGTGAC TGAGTCCGCC CCATCCCAAC     660
```

```
CCCTGGTCTT CGGAGTGACG CAACCGACGC CGCCGCAGAC GACAAGCCGC TGCCTGTTGA    720

ATA                                                                 723
```

(2) INFORMATION FOR SEQ ID NO:618:

(i) SEQUENCE CHARACTERISTICS:
        (A) LENGTH: 721 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1419UP (xi) SEQUENCE DESCRIPTION: SEQ ID NO:618:

```
GATCCGTCCG CGCCTGCGTA CCCATAGGGG CGAGGTCGCC GCCGGCCCGC CAGGTCACTG    60

CGCCCAAACC GCACCTGCAC CTGAACCGAG CCTGCAGCCC ACGAAGGAAC GCCACGCTAC   120

ATGTGCCCGT GCAGAGCACC GCCCTTGTCT TGCGGGGCTG AAGTGACTGT GGCACGCTCC   180

GCAGGACATA TCTTTTTAAT GAGCTGTGTC ATGCGCACAT TCTCACCGTC GCGCTACCGT   240

AGCGTCGCCC TCTGTCACCG TGTGAGCTGC TGCCAAAACA AACAAATCGG GACGGGCCCG   300

CATGCAGTAA TTACCTCCTC CCGAAGGCAA CGCCTTGGTT TTGTTTACGT TGGCCAGAGA   360

TTTTCTCTTT GGGGTGGATT AGCTCACGCG TCATCCGCGT GGCAGAGGTG CCTGCCCTGA   420

CAGTTCTTCG AATATTAGAT GCTGGTATGC GGGCACGCCT AGCGCAACCG ATTGTAGTTT   480

ATTGTTTCGT CACACCCGGC TAGAGGGCCG AGCTACAGGA TCGCCGATGT GGCGTGACGG   540

ACAGCGTCAA CGTTACGATC TCAACGGTCG CTCGTGCGGG CCCGTCTGTG GTAGGCGTTG   600

AGATACGCTT AGGATGAAAG CACGAAAATT AAGGTTGTCG TAAAAACACA AAGTCAACTG   660

GGGTTTCCGA ATGGGTTAGA GTGCCATCGT AATGGCGGAC GGAGAGTGTC CATGGTGCGA   720

G                                                                  721
```

(2) INFORMATION FOR SEQ ID NO:619:

(i) SEQUENCE CHARACTERISTICS:
        (A) LENGTH: 721 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1420RP (xi) SEQUENCE DESCRIPTION: SEQ ID NO:619:

```
GATCAATTCA AGGTTGCTTT CCCAGACATC TACGCTGTTT TCCAAAAGAT CGCTCAGCAG    60

CACCCCGACT ACGAAGTGAC TGTCACGGGT CACTCACTGG GTGGCGGTTA TGCCTACTTG   120

ATGGGCTTGG AGCTCCAGCT ACTTGGCCAC AAGCCACATG TGATCACCTA CGCCGGCCTG   180

CGTATGGGTA ACGCTGACCT CAACAAATGG TACGACAAGG TGTTCGACAA CGTCAAGAAG   240

GTCGAGGACT TGAAAAACGG CGGAAACCCA AGAAACGCCT ACATCCGTGT GGTTCAGAGC   300

CGTGACATTG TTCCTATGGT TCCAACTGGC CCTATCTACA CGCACGCGGG TATCCTATTT   360

ACCATCACTG ACGTGGACAG CGAAGTACCT CTACAATCGG GCGTCAGACT TGATGGCTGT   420

AACACCAAGC TAAAGGAGTT GGTCGGCGAC ATCCTCTTCA GCGGGAAGTT GCTAAGCTTG   480

GTGCGTCTCC TGAACCACAA CAAATTTTTC AGAAGAATGG CTTTGCCATG CACTGATAAT   540
```

```
TCCTTGAAGC TATAATTCCG AGGAAGTAAT GAATTTTAAG TACGGAACGT GCAGTCGCTG      600

CAGTCTTCTG CCTCTTCCTT ATGCCCTATA TAGTTAATTT GATGTTCTGT TCTATTTTTT      660

TACATTTTCC AAACACTGGG AATGCCACCT TGTAGATGTT GTTCCCAAGA TGGATATTTA      720

G                                                                     721

(2) INFORMATION FOR SEQ ID NO:620:

(i) SEQUENCE CHARACTERISTICS:
        (A) LENGTH: 626 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1420UP (xi) SEQUENCE DESCRIPTION: SEQ ID NO:620:

GATCCGTCGC GAGGCGCGCA CCAAGCGCAA GTGCATGGTG GTTGTGGCCG GCCTGGAGGT       60

CTTCGAGATT GACATGAAGA AGCTGGCGAA GACCTTCGCG TCCAAGTTCG CGACGGGTTG      120

CTCTGTGTCC AAGAACGTCG AGAAGAAAGA GGAGGTCGTG GTTCAAGGCG ACATCGCGGA      180

CGAGGTCGAG GCCTACATCC ACGCGCTGCT AGAGGAGAAG GGGATGAAGG GTGTCAAGGT      240

CGAGCAGATA GACGCTGCCA AGAAGAAGAA GAAGACGCCG ACGACGACGA CGCCGCCGCC      300

GTCGTGAAGA GCGGGTCCGG ACATGTGTAT CAGATTCGTA TGTAGTGATT AATGATTGCC      360

GCGATTTCCA GTGTCTTACC AGTCCAAGAG GACAGGTGTC TGGCATGCTT GCACATTGCT      420

GGCGTCTGCG TGGGGACCAT GAGCCTGGAG ATGGATCTAA TTGAATGGGC GCTTAACCTG      480

CGTGCTGCGG GAGGCGGGGT ATTTGGCAGT GGCAGCGAGG AATTGGACAG AGTGCTAAAA      540

CTGCACTACC GAGTGACATA CCATGCGTTT GACCGGGGCA CCAAGCGGTC GGTGTGGGAA      600

GTCTGCTGGC GGAGGCCGAG AAGATC                                          626

(2) INFORMATION FOR SEQ ID NO:621:

(i) SEQUENCE CHARACTERISTICS:
        (A) LENGTH: 582 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1421RP (xi) SEQUENCE DESCRIPTION: SEQ ID NO:621:

GATCCCTCAG TTCCCCATCT TGCCTTCACA GCCAGGATGG ACCATCCGTA ACTGGGAGTT       60

ATGCGGTTTC ATTTGTCTTT TTAGTACAGT ATTATCTCTC TGGTTTTACA TCCTACTTGT      120

TTTATCGTTA CTTGGGTATG TATGGCATCT TAAATTTTAT CGACTCTAGT ATTTTTATGA      180

CTGTGTAAAC TAATGAAAAA TAATGAATCG AAGTCTCGTT TACCTAGAGC TGATTATGCC      240

ACATGCGTAC TATCGGCGTG CCACCGCAAT TATGTATCTA TCCTACAGAT AATCCTTTCT      300

ATTAGCAGTT CTCACGAAAC GTCTCAGTTG CCACTCGACG TCAGCATCCT TGTTCTCCAA      360

GGTGCCCAGT GTCAGCTCGT AGAGCTTCAT TTCGAACCGT GGTCCCACCT CCGCCAATTC      420

AACTCCATCT CTCGTCTTGA CGTATACGTG CTGCCGCACA CTAATGAAAT CGCCGCGGTT      480
```

```
CGCAAATGTG ATGACCCTAG GGCTGTCTTT CTTGACTCCG GGCGGGAACA TGTGCTTCAG      540

TATTTTAACG ACCCGTTGCC CCAATGGAGT ATTGAAATTA TC                         582
```

(2) INFORMATION FOR SEQ ID NO:622:

(i) SEQUENCE CHARACTERISTICS:
        (A) LENGTH: 1152 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1421UP (xi) SEQUENCE DESCRIPTION: SEQ ID NO:622:

```
GATCATCATA CCGTGTCCAA CATCGCCCAC GGAACCACCA GTCACTTGAA GTGGAACGCA       60

GGTAACATAC GCGATGGCCT CCACGACGAC TTGGCCAGCT TCAAGGACGC AGTCGTGCAC      120

TGTCTCACGT TCCGCAGCGG CCAGTCCCGC GACTACCGCC ACCAGTCGTC CATGTTCGGC      180

AACGGTTCTG CTGGCAGTGC CAAGTCCGGG TCGTGGTTCG GTGGCGCGAC TGACTCGCGC      240

GATGGACTAC TCGAGCGCGG GCGCGAGGCC GGGCGCGAGG CCGGTCGCGA GGCCAGCTCG      300

TGGTTCCGCG GCGACAGCCG CACCGAGGAT TCGGGCCGGT CGTGGTTTGG GCGCGACGCC      360

CGCGACACCC GCGACACTCG CTCGGACCGC TCGTGGTTTG GCCGCGACGC ACCGGAGGCC      420

CGCACCGACG GCACCTGGCT CAACGGAGAG CGCGACCGCT CGTGGTTCGG TCGCGAGAAA      480

CACGCCACCC TCGACGAGTC CGACCGTGTC TTCCGGAATG GCGGCCGTCT CGGCGTCGAC      540

ACCACGCGCT AGGCGCCGAC GCCCGCGGCA AGGTCGACGA CATCAAGCAG GCAGGTGCAG      600

ACCTCGGCCG CTCCGCGCAG GCCAAGGTCG ACGACTTCAA GCAGGCCGGC GCTGACCTCG      660

GTCGCTCTGC CCAGGACCGC CTCCAGCGCG GCGTTGCCGA CGCCAAGCAG ACGCTCTCAG      720

GCGCCGCCTC CACCGTCTCC GGCGCCGCGG CCTCCGCTGC TGGCGCCTCT CGCGACGCCG      780

CCTCGTCCGC CGCCGACAAG ACCCAGTCCC TCTTCAACTG GGGCTACAAC AAGGCCGAAA      840

AGTCGAAGGC CATCGCCATC GGCGAGTACG ACAAGGCCAA CAAGGACTAC CAGCAGGCCC      900

TCGACGCCTA CAACCGCTCC AAGCGCCTGC TCGCCGACGG CGACCAGCAC CTTCGCACCG      960

GCCTCGAGAG CGCCCAGGCC CAGCTGCGTG ACTGTCGCGA CAAGCTCGAC GCCATCTCCG     1020

CGGAGTTCGA CCACTACGCC CGCGAGAACA TCTCCGACAT CTNCCGGCGN CTGGACCACG     1080

AGGACCGCGA TTCCGCGGCT TCCGGCCTCT TTAGCTGGTT CCGCTTCAAG GCCCGGCTGT     1140

CGAAATCGAC CT                                                         1152
```

(2) INFORMATION FOR SEQ ID NO:623:

(i) SEQUENCE CHARACTERISTICS:
        (A) LENGTH: 713 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1422RP (xi) SEQUENCE DESCRIPTION: SEQ ID NO:623:

```
GATCCGTGTC CTGGGGCTGG TCGAGAACAT GAGCGGCTTT GTGTGCCCAT CGTGCGAAAA       60

CGAGTCGACC ATCTTCAAGC CAACAACAGG TGGTGGTCGC GCCTTGTGCG AGGAGCTGGG      120
```

```
GATAAAGTTC CTTGGAGCCG TGCCGATTGA TCCGCGAATT GGAAGATGCT GCGACTCTGG      180

CGAAAGCTTT TTGGACGCCT ATCCGGACAG TCCAGCGTCG ACCGCCATCA TGCATGTGGT      240

AGAGGCTCTC CGTGACGCCG TCGGCGACGT ATAACGCGCC TAGCAGTTCC TGCCAGTGAC      300

AGACTGATAC CAGTTTATAC ATACATACAT ATTTGTAAAA AAGACGCTTA GTGTTACGTG      360

GATGCGAGCG CCCGTTTCAG GTAGATAGTT TCGGGCTGTC CCAGCGGCAA TGCAAGTAAT      420

CTGTCTTTAA AAGACGGGGT CTCCAACGCT TGTCGATAAT TCTCAAGGAT GATATGACAG      480

ACAAGTTTGG ACATGACACA GCAAACGACG GAGAGTTCTC GGTGGGAGCC GAAATCCGTG      540

GCCAGGACGG GCAGAACCCG GACCAGATCG GAAAGCAGCT CTTGGTTGTG GTTGTTGTCA      600

AGTGCTATCT GGAGGTACTT CTCAAATACC CCCAGGCCGT GAGTCCAAGT TTCCATCTGT      660

TGTGCGGGGA AAGTCTCCAA TAATTGACGC AGTGTCTGCA AGTTAGCAGC TGA            713
```

(2) INFORMATION FOR SEQ ID NO:624:

(i) SEQUENCE CHARACTERISTICS:
        (A) LENGTH: 642 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1422UP (xi) SEQUENCE DESCRIPTION: SEQ ID NO:624:

```
GATCTCCTAG GCGCCAAGTC GACGACTACA GGCGGGCTTT TTGGGCCAAA GACGGAACAG       60

AAGCCCGCAG GCGGCCTTTT CGGACAGAGT AGTGCCGCTC CCAATGGCAC TGGCGGCGGT      120

GGTCTCTTCG CTAGCACGGG CAACAGCGGC AGCACCCAAT TGGGTGGGCT GTTCGGCAAC      180

AGTGCTGCGG GCGGTGGTGG GAGTCTTTTT GGCGCCGGCT CGGCCGCGAA CAACAACGCA      240

TCCACCTCGT TGGGAAATCT CTTTGGGAAA CCTAATGACA CGGCACCGGC AGCTGGTGGA      300

GGTCTTTTCA GCAATCGGCC GAACACAGCC ACCACAAATA CCGTTTCTTC CACTAACAGT      360

CTTTTTAGCA ATAATCAGGG AAATGGTGCG CAGAATAATG GGGGGCTCTT TGGTGCGAAA      420

CCTACCGGGG GGCTCTTTGG AAACAGCACC GCTCAGCCAC AGTGCTCGCT TTTTGGAGCT      480

TCCTCCTCAC AGAATAATCA GCAGCAGCAG CAGCAAACAC AGCAACTGTC CCTTCTGGGT      540

TCCAATCCAT ATGGCCTGAA TCTGACTGGT GTTCCTGTTA CTACCATGCC GGAATCTATA      600

ACGGCAGCAA TTACGTCTAA GAAGAAGACG AAGCCTACCG CT                        642
```

(2) INFORMATION FOR SEQ ID NO:625:

(i) SEQUENCE CHARACTERISTICS:
        (A) LENGTH: 719 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1423RP (xi) SEQUENCE DESCRIPTION: SEQ ID NO:625:

```
GATCGAACAC AAATTCATCT ACGAACACAA ACTTGGAGCG GTTCGTGTTG GTTATATTGG       60

ACAGGAACAT TGACCTACCT TCAATGTTTG CGCATTCGTG GATCTACCAA TGTTTAGTAT      120
```

```
TTGACGTATT CAATCTCTCC AGAAATACGA TTTCAGTACC GAATACTGAT GAAAAGGGAC      180

AACCCACATA TAAGAAGATG GATATTGAGC CTAAAGACTT CTTTTGGACG ACAAATGCGC      240

ACTTGCCGTT CCCAGACGCA GTGGAGAATG TCGAAAATGC ATTGGCAGAC TATAAGGCCG      300

AGGCGGAAGC GATAACCAGG AAGACAGGCG TTGACAATAT AGGCGATTTA GATCCTAACT      360

CTCAAAATGA TACTTTGCAA ATTCAGGAGG CAGTGAACAA GTTGCCGGAA CTGACTGCTA      420

GGAAGAATAT CATTGATACA CATATGAATG TTCTGGCTGC GTTGTTGAAA GAGCTAGAAA      480

ATAAAGGGTT GGATTCGTTC TTTGAAATGG AGCAACAAAG TGACTCTGCT AAGGTGAGGC      540

AAGCATTCAT GGACGTTTTG AAAGATGGCA AGACCAATAA CCTCAAGGAC AAGTTAAGGA      600

CATACATAAT CATCTATTTG ACTAGTTCGG AGAAGCTTCC CGATCAATTC GTCCAACATG      660

TTGAGAGTTA CTTCCAAGAT AATAATTTCG AAACGCCAGC GTTGAAGTAC TCTATAAGT      719
```

(2) INFORMATION FOR SEQ ID NO:626:

(i) SEQUENCE CHARACTERISTICS:
        (A) LENGTH: 719 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1423UP (xi) SEQUENCE DESCRIPTION: SEQ ID NO:626:

```
GATCATCCTG TTGAACTGCA TGCTCATGTC GTCCGATGAG TACACATGAT TGAAGTCAAA      60

CAAATGTTTG CCCGACTTGA CCTTGCCGCC ACGCAACGTC GCAAACAATC CGTCGCTGGA      120

CCGAAAGTCT GGGATGCCTG CAGCCACAGA GATCCCCGCA CCCGTGACCA CCACGATGTC      180

CCGACTGTGC TGGAGCGCAT ACCGAATGAA GTCGGCGTCC CGCGCGCTCA CCAGCTCCGG      240

GTCACTGACG TAATGCGCTA GCTGAAATAC CGAGTTCGTC GCAGGCCTGT ACGTCAGCCG      300

CGGCTTCCTC CGCACCGGAG CCCGCGCCTT GCGCAGCGCC GGTAACAGCT CCTTCGGTGT      360

GACCTCCTCG GACACGCTCG GCCCGCTGTC GCAGGCCTCT GTCTGCTTCT TTTTGACGCT      420

CGACGGCGGC GTGATCGGCA GCTTCACCTT CATCGGCGAC CGGTACCGCT TCACACCGAT      480

ACCACCAGTA GCCTCCGTCA TCCCGCACGT TCCACAAACC TCTGCCGCTT GCTGCACTCG      540

TGGTTGCCCC GCTGCGTGGC GTGTAGCGGA CATGAAATGA GTGACGGCGG GCCCAATTTT      600

GCCGGCGTTC GCTTTCGACC AATCCGGAAA ACTTATCCCC CGTAAAACAA AGGCAGGACT      660

TCCGGTGTGG CGATAGCGGC TTTTGTCGCA TGGGCTCCTG GTCCCGTTAC GCCTACATT      719
```

(2) INFORMATION FOR SEQ ID NO:627:

(i) SEQUENCE CHARACTERISTICS:
        (A) LENGTH: 724 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1424RP (xi) SEQUENCE DESCRIPTION: SEQ ID NO:627:

```
GATCTCATCT GTATTTGGAA GGGAACGCAC CAGACGGGGG TGACTCGCAG AAGCTGCCAG      60

AGGAGAGAGA AAACATAGAA AATATATTTA TATTATCTAT ATTCAGTTTA CATAAGAATG      120
```

-continued

```
TGTCATAATT TTATTGTTTT TAGATTTCGA CTTGCGAGTG CCCTGCATAT GACTATCCTT      180

TTATTCTAGA TTCAGTGCTA GCTAGTCGCA AGGAAATCGA TATCGTAATT CCCATTTAGA      240

ACAAGATACA AATTAGCGAA TTTCCCGGAA AAACCGGTCT TATAATACAG CATCATTGCC      300

GAATCCATAC CAGTCCTTCA ATTAAACTTC CGAATCAAAA AAGGCCCGGC GCGGTCTCAA      360

GAATCTTTTC GCCAGTACTC GAATGGTGAC TATCAGCAAG CGACTCTTCA CTACCCGAAA      420

CGACCAGTAT ATTTGTGTGC AGCAAATGAT TTAAGGCTCT CGAGACACCT CTTATTGGCG      480

TCCTATGTGT TCTGTGCACG CCCTGGCCCC GATAAAGAAT GCAGGTCGCC TAATAGTAAT      540

TACTAACCGT TTTTTAAATC GCCGTCTTGG TTGAGACCTG TGAAACGATA ATCCCATTTA      600

TACCAGATGA ACTCGCCGCA CTATAGTGTC CGTAATTCAG CACTGTGGAT TCCGAGTTAG      660

GGTGCGCGAA GTAGCAAATT TGTGTATCCT CCATAATAAG GATATCCAAT GCCAGTATAA      720

TAGT                                                                   724
```

(2) INFORMATION FOR SEQ ID NO:628:

(i) SEQUENCE CHARACTERISTICS:
        (A) LENGTH: 720 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1424UP (xi) SEQUENCE DESCRIPTION: SEQ ID NO:628:

```
GATCATCGTA TGCACTCAGT TGTATTCTAG CATAGCCCGT GCGATTGCCG TGATTTCGAA       60

CGATGATGAC AGGCAAATCA CCATGAGGAG CCGAGGATTC TCCGCTAAAT TCAGCTGCAT      120

TTGCAACAAA GATGGCGTGT TTCTATGCGA GCCCCTTCAC ACGGGCGTAA AACATGTTCG      180

AAATGCTGCT CGCTCTGCCT TGCGCTGCGT GTGCCCTCAG CCAGACGGTC TGTTTGCTTC      240

TAATGTGGGG GAGAGTCGTT CTACTCACGT GTTCAGCGTG CTGAATAACT TGCCTATCCT      300

TACAGCTGCT GACCTGAGGC AATGCACGTT TCCAAGTCCA ATAGTCTACG GGCCCGAAGG      360

TTGTCGCGAA TGCACAGTGA TCGGTAATCT ATTACTACAG CCCACTGCAA GCGTACAGAC      420

AACCTACAAT GACGGCGCGT TGTACAATAA AATCAATTCC GCTTGCTCGA CCGTTAACCC      480

AAAGCTATAC CGTACCTTGT GTCCTTCCCT GTTTCCATTA GCCGTTGCAT GTGCTTTTTT      540

ACTGTGATTA CAGAGCCTTT CTGTAGAATG TGTACGTGAA TTTAATACTA GAGAGCTATA      600

AAGCTCTCTT GTTCTTGTAA TGTCTGTTTC AGAAGATAAA AGGTAACACC AGAAAACGAG      660

GTACGACCCA ACGGCTATTG GACTACGAAC TGGACAAAAA CTAAGAGTCG TAAGTAAGAA      720
```

(2) INFORMATION FOR SEQ ID NO:629:

(i) SEQUENCE CHARACTERISTICS:
        (A) LENGTH: 710 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1425RP (xi) SEQUENCE DESCRIPTION: SEQ ID NO:629:

```
GATCAGCTCC CACTTGGTTG CAACAGTATT GCTGAGACTA TCATTCTTGT AGAGCGATTC         60

TTGTGAAGCA GTTGGCCCGG TGTATGAAAC CGCGTGTTTA CCAAGTGGAG GCCTTTGTTC        120

AGAAATTTTA GTTCCTTCTC GAACGTATTC GTGGTCCTGG AGAATAAAGT TTTGTTGCTC        180

GACATAGTCA GGGTCAAAAA CATTCACAGG TGTGTCATCA TATGGCGGCC GGCTGCCGGA        240

GGTTGTGGGA TCAGCCTTTC TGTTGGCTTC CGAGTCTCCA ACCTTCGAGA TAGCTTTTGA        300

TAAGTTGTAG AAGTCGTCCA AAATATCGTC TTCGCCGAGA GGAGCAACGC TCGAGCCCCT        360

GAACAGTGAT CCACTAGAAC TTCTTGCAGT AGCCTCGCCG TCAGCATTAT TGCTATTGTG        420

TGTACTGCTC GAGTTGCGCA GATTAGATAT ATCAAACTGT TTCGATTGTG TGGAACCTTT        480

ATATTCATCA TATGCTCCAA AAGAATCTCT GCTTTGCGGA GAGCCTCGCG CTGCATGAGG        540

AGGAGGAGCC ATAAAAGATG AATCCCTGCC AGGAGAGTTG TGTAACCGCC CAAATGGTGA       600

TGCAGCGTAG TTGTCATAAA TTTGAACCAG ATCTGCACGC GACTTGTACA GGTCCCTGGG       660

GTTGTATCCT GCCTTGGGGT CGCCAACTTC TTTAATGGAC CCGAAGAAGC                  710
```

(2) INFORMATION FOR SEQ ID NO:630:

(i) SEQUENCE CHARACTERISTICS:
    (A) LENGTH: 711 base pairs
    (B) TYPE: nucleic acid
    (C) STRANDEDNESS: single
    (D) TOPOLOGY: linear (ii) MOLECULE TYPE: DNA (genomic)

(vi) ORIGINAL SOURCE:
    (A) ORGANISM: PAG1425UP (xi) SEQUENCE DESCRIPTION: SEQ ID NO:630:

```
GATCATACAC GCGCTGCGCA TACAGTTGGC CAGCACCAGC ACCCGCGACA GCCTCCAACG         60

GCTAGAGACG GACACCGCAG GCCTTGTCGC CCACGACCTT TCCCGCTGGG CCGACAGCAC        120

CAATGCATAC ATAAACGGCA CAGAGGCCTC CGTAAATGCC GGCCTCCTCG GCTGGGTTAC        180

CACAGCCACT ACAGCCCTCA ATACCACCGT CGCCGCCCTG CTCGCCGACA TCGATTCCAC        240

CGTCGACCGC GCGTTCGCAG ACACGCCACT TCACCGCCCC ATGGTGACCG TTGTCTCCTG       300

TGTAATCGGG AACAAGTTGC GCGCCATCGA GGCAGGCCTC ACCTGGACCC ACGACCACGT       360

ACGCATCGCC CTGCCGCGCA TCCATACCGC CCGCCTTCGC GACGCTGTCG CAGAACCAGA       420

CCTTCCAACC CATCCCGCCT ACACAGCCGT GCTCCAGTCC CTCAGTGACC GCTTACGTCA       480

TTCGGTTGAC CGTGTGCTAC ATCAGTGCTG TGCCGCGGTC CGCATTGAAC TCTACGTATC       540

GCTTGCCCTG CTCGGCCTCT GGATTCTGCA GACACCTCTC GGCTTGGCAA TGCTGCTATT       600

CAAGTCGCAC TGCCGTCGCA GGAACCTGCG CCGCAGAATG CCTTGAGCCT AATTCTTACA       660

TAATCTTAAT TCGCCATTCT GCTGCTCGAA CACGAACTCC GCGTTAGCCG G                 711
```

(2) INFORMATION FOR SEQ ID NO:631:

(i) SEQUENCE CHARACTERISTICS:
    (A) LENGTH: 722 base pairs
    (B) TYPE: nucleic acid
    (C) STRANDEDNESS: single
    (D) TOPOLOGY: linear (ii) MOLECULE TYPE: DNA (genomic)

(vi) ORIGINAL SOURCE:
    (A) ORGANISM: PAG1426RP (xi) SEQUENCE DESCRIPTION: SEQ ID NO:631:

```
GATCTTCTCT CCGCTCGACG TCACTGGCGG CATGCACGAC GCCATGAACT GCTGCTGCCG      60

CTCCTGATCG CCCTCGTGCA CTGCTAGCCG CGACTGGCCC TCCAGAAACC GGCCCATCTT     120

GTTCGCATCC TGCAGCAGCA CCACCACATG CGGAACCACC GGCTGCCTGG CTGCTTTCGC     180

TAGCTGAAAC GAAAGAAGAC GCCCTATAGG CGCGCTGCCT AGCATATACA CCCACGGGAC     240

ACCCATAACA GCCCTTCTAA CCCTCAACCG AGTCACTGAG AACTGGCGTA GTGCGCATCA     300

TCGACCTCGC GATTTTTCAT TCTAGTGAAT AATCCTTACA CCGCCAACAC AAAGGCAGCT     360

TCACCACCAT TCTGGCTCAA CTAGGAGGCG TGTCGGGCGA ACCAGGAACG CGTTACTCGG     420

TAAGCGGGCA TCTAGTCAAG TGGGCAGTTG CAGGCGACTT CTTTTTGTGT GTTATTCAGG     480

GTGTAGGATG CTTGTTATAG GGTTGACAGG AGGTATTGCA TGCGGCAAGT CGACGGTGTC     540

GCGGAGACTG CACGAGCGAT ACCGGATCCC GGTGATCGAT GCGGATGCGA TTGCGCCGGA     600

GATTATGCGG CCGGGGAGC GGGCGTACCA CGGGTGGTGG AACGGTTTGA GCAACGGGTG      660

CCGCAACTGG TGCAGGCGAA CGGGGAGCTG AACCGCGCGG CGCTGGGGGC GTGGATCTTC     720

CA                                                                   722
```

(2) INFORMATION FOR SEQ ID NO:632:

(i) SEQUENCE CHARACTERISTICS:
        (A) LENGTH: 703 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1426UP (xi) SEQUENCE DESCRIPTION: SEQ ID NO:632:

```
GATCTGCTCC AGCGCCTGCT TGAACCAATC TCCAGAAGAG TGTCCGCCTC GTCAAGAACC      60

TTGAAGTCAA CCTCGGTAAA GTACTTTGGA CCGCAAGCCT CGAGCATGTC GATCAACCGG     120

CCGGGCGTGG CAACCACGAT ATTGGGCCTC CTGCGCTCTA GGGATCTGAA AGTTTCAGTC     180

CGCGAGGAGC CGCCCATCAT GACAACCGCA TTGAAACGGC GAAGCTTCCT GTTGGCGTTG     240

CGCATCTCGT TGATCTCGTT GAAGATCTGC GCGGCCAAGT CCCTGGTTGG TGCAATCACA     300

ACAGCCTTGA CATTTTCCGA AGGAGGCCCC TCCAAGAGCC GCTGGAACAG CGGCATCAGA     360

AACGCAAGTG TCTTACCTGT TCCAGTTTTC GCCCGTGCCA CCACATCGTG CTCCGTCTGC     420

AGGATCGGCT TCAGCGTCTT CTGCTGCACC GGTGTTAGTT TATCGAAGCC GCGTGACTGC     480

AGCATCTCGT ACAGCTCGTT GCTGAGCACG CCCTCCTCCA CCAAGGTCCG CGGTGTGCTT     540

TCGACCCCCG CAGCTTCGTC GGCCACACGC ACCACCTCGG TGTTGGGGCC GAGGCTGAAT     600

CCCTCGCGCG CCGCGCCGTC TGTACGGCCG CGTCTGCCCT GTGGCTTCCG CCACATGCCG     660

CCGCGGGGAC CACGCTCACC ATCCTCCCTG TCGCTGCCCG GCT                      703
```

(2) INFORMATION FOR SEQ ID NO:633:

(i) SEQUENCE CHARACTERISTICS:
        (A) LENGTH: 711 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:

(A) ORGANISM: PAG1427RP (xi) SEQUENCE DESCRIPTION: SEQ ID NO:633:

| | | | | | |
|---|---|---|---|---|---|
| GATCTTTCTA | TCCGGGAAAG | AGTCCATCGA | ATACAAGGTG | CTTCTAGAAG | GGCCCTATGG | 60
| AAACACCATT | CCGCGGCTTG | CTGCTCCTGA | CCGGCGCTAC | GTGGGCGCCA | GCGCAGGTCT | 120
| TGGCGTAGCA | GCGGTCTACC | CACACTTCGT | CTCTCTGTTG | GACAAGGAAA | GCCAGTTCAC | 180
| CCATTCATTC | TACTGGATTA | TAAATGACCT | TTCATATCTG | CATTGGTTTT | CGCATGAGCT | 240
| GAGGTACCTG | GCGGACCGGA | ACTGCGACAT | CAAAATTATT | TACACGAGGA | GCAATGAGTC | 300
| GGCTAAAGAA | CTGACCCCAG | ATGTTGCCGA | TTCCGCCTCT | GCGAAGTTCG | TGGATTCGCT | 360
| GGATATCTGC | AGGCTCCTCC | TGCGCCCAGA | TCTCAAAGAG | ATCGTGGAAG | AGCAGATCCT | 420
| GCTCTCGTCT | AACCAGGCAC | AGGACGTCAC | GTTTATTAGC | AGCGGCCCTT | CGACCTTTAA | 480
| TGACCATTTC | CGCTATGCTG | TGAAATCTAG | CATCACGGGC | AAACTCCAGT | GTGATGTCGA | 540
| CCTAGAGGAG | GAAAGCTACA | CCTGGTAGAT | AGATACCATC | TTATTAGTTA | ATTGTACTTA | 600
| TTTATTCCTC | TTCCTGTATC | TTAAGCAAAT | CCCGCCATGT | CTCAACCAGC | TTCTGCATGC | 660
| TTTGCGGATT | GAGCCCTGCC | TCGACCACGT | CCAGAGGTAC | CTGGTTTTCC | G | 711

(2) INFORMATION FOR SEQ ID NO:634:

(i) SEQUENCE CHARACTERISTICS:
        (A) LENGTH: 718 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1427UP (xi) SEQUENCE DESCRIPTION: SEQ ID NO:634:

| | | | | | |
|---|---|---|---|---|---|
| GATCATCTTG | TCCATGCCCT | TGGGGCCCAG | CGACGTTCTG | ATCGCATCCG | CGACTGCTCT | 60
| GGCAGCAATA | ATGTTCGCCT | TTCTCACTTC | CTGCGGCTTC | TCGCGGTTTT | TGAACGTCGC | 120
| ATTGCTGGCA | CTGACCTTCG | GTGGCATCTT | AATATACTTC | CTGATTCCGC | GCCCCAGAAG | 180
| CCTTACTTGC | TGCTAGAGAA | GTTAAGGTTG | TTTGTTTATG | CTGACAACGC | CTAAGTTACC | 240
| GTCAAACGAT | CAGATTTTTG | CCACTGGAAT | TTCCCTTCGT | ACAAACGGAT | ACTTGATCCT | 300
| TTGATCTCCA | AGAGCTGTTC | CATCGGGATG | GCCTGCTGAG | TAGTGCCGGG | TTGAAGGGAA | 360
| AATCGGGGCT | CGACAACTTG | GGAAATGTCT | ACGGAGGACG | CGGCGTTAAC | AGGGATCGCG | 420
| GTGACGGCAG | AGCTCAAAAA | AAAATGCGCG | TTTTCCAGCT | GGTATGAGGC | GTTCAAGGGC | 480
| CACACTCCGC | GGGCCGAGGT | GATTCGGCCG | CTGCCCGAGG | AGTTCGTGAG | CTACGTGGAT | 540
| CAGCGCGGGA | TCAGGCTGGC | GCGCGAAGAA | GGCTCGAAGT | ATTTCTACGG | CCAGGAATGG | 600
| AGCCTACGAC | GGACGGAGAG | TACAGCGACT | GGGAAGGCGG | CGACAGCGCG | AGTGAGCGGT | 660
| CGTTCGTGCC | GCTGGACCGG | TGGCGGACTT | CCCGGAAGTG | CACGCGCGGG | TGAAGCAG | 718

(2) INFORMATION FOR SEQ ID NO:635:

(i) SEQUENCE CHARACTERISTICS:
        (A) LENGTH: 723 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
    (A) ORGANISM: PAG1428RP (xi) SEQUENCE DESCRIPTION: SEQ ID NO:635:

```
GATCATACAC GCATTGCAGG TATACATTAT AGTGCTCATA ATTATCGGAT TGCAAATAGA    60
ATGGGGCCCT TACCGTAGTA CTGTCTTGGT AATGCAGCGA CGCTCAGGCT TAAGAAGCTT   120
TTTGTTCTCC GTGTATTACT AACAAAATAA TTTCCTCGAG CACAGGGAGT AGAGATGAAT   180
TACATAATCC ATATGGACAC CTCGTCACCT TCCAGCGACA TTAACATTTC CTTATGAATG   240
CCCAATAATG GTGCCTAAAT GATGTGCTTG GTGTAATGCG CATTATAAAA TGTATGTGGA   300
TTATATATTG TTTGTAGCAT CTAGTAGAAC CATGGTAGCG AGGTCTTTGG CCATACCCTT   360
CTGAAGAGAG ACATAGCAAC AGTGTCTTGT GCAGACAGTC TGCCGTCGAA TGTTGCCTTG   420
AAGTAACCAT GAGTACCAAG ACTCTCCTTA ATGAAGCCAG AGCGTCCAGA TTTCGTGAAT   480
AGTGGGATCG ACTTGAACCA CTCGACATCT TCTGGCCTAA AGAACATATA GCGCACTGTG   540
ACGACGCGCT TGTGGAACTT GAATGGATGG CCAGTTAATA TGATTCTCTT GGCCAATATC   600
CGTGTGTGGT CTGCGTTCAG GAACGTGCCG TGGCCCACGA ACGTCAGGCC CTTTGGATCA   660
GAGGGGTTTT CTTTGAAGTA GATGGCCGGT GACTGGGTCA GGTCCAAGGG AAGCATGCAT   720
GTC                                                                 723
```

(2) INFORMATION FOR SEQ ID NO:636:

(i) SEQUENCE CHARACTERISTICS:
        (A) LENGTH: 726 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1428UP (xi) SEQUENCE DESCRIPTION: SEQ ID NO:636:

```
GATCAAACCA GAGTGCGAAG CGCACACGCG GCACTGGCGG GAGCCCTTAC CGTAGTTTCT    60
TGGGTGGGAG AACCAAACGT TTTCGTGAGC CATCTTGTCT GCAATGCGTT AGTACTCTGT   120
CTGACCGCTT GGAAGCGCTC CGGCCCTCGT GAGCTGCCCA CACGCTCGGC GTCTGCGGCG   180
TCCTCATTGC CCGCACCGTA TTCTGCTCGC ACCGACAGCT CTAGACCACA CTTCGCCCCA   240
TCCTGTGCAC ATACGATTAT GCTTTGTCTC TTGGTATTAT CCTTAGATTC GCTAGACTTC   300
GACACTATGG TTATCACCAC TGTTGAAGTC TGCTTCGGTT GGCACCCAAA GTCTCGGGAC   360
TGTAGTTGGA AAGCGCAGTT CGCGGCAAAT CAAGCATCTC ATAATGTGTG GGTGCAACCG   420
TTGAATGTGT GGGTGCAACA GTCAATTGTA ATTTCTTTTT TTGATCGAGA GATGGGATGC   480
GATGAGCTAG TTGAAAAATT TTAGTATGGC AAAACTGGCA TGCATATCTG AGATGGGCCA   540
TCAATTGCGG CAGCTTAGTG TTAGACGACC AATCCAGAGG TGGTAATTGG CTATGGCAG   600
GTCACTCGCA CAGGTCGTCG GTAAAAAAGG GCCACAAAAC GTTCAAGTCG AAGCATGCGA   660
GCAAGGGCGC GTTGAAACGG CTGCACAAGG GCAAAGTGGA ACAGGAGACC GCTGCTGGGG   720
TGAAGG                                                              726
```

(2) INFORMATION FOR SEQ ID NO:637:

(i) SEQUENCE CHARACTERISTICS:
        (A) LENGTH: 712 base pairs
        (B) TYPE: nucleic acid

```
        (C) STRANDEDNESS: single
        (D) TOPOLOGY: linear (ii) MOLECULE TYPE: DNA (genomic)

(vi) ORIGINAL SOURCE:
        (A) ORGANISM: PAG1429RP (xi) SEQUENCE DESCRIPTION: SEQ ID NO:637:

GATCAAAGTT TAGCATGTAA ATGTGCAACA AACTATTTAT TACCTCTGCA CTGCCCATGT      60

CGCTTGAAAC CGCCGAGGAT CCAAACCAGT GCTTTCATAA TGGAATTGCA AAATTGAGTG     120

CAGTAATTGA TAAGTATCTT GAGAAAAGCC CTCCCGACTT TACCCTAGAT GATTGCTTAA     180

TATGTTCAAA AGCCTCCGAG TTAATAAAAA GGCTTGCTAC ATCCAAGGTG CATATAGATG     240

TGATAGATGA GACTAACAGC ACCATTCATA AAAAGCGGAA GCGCAATTTT CGAATCACAT     300

CACCCAGAGC AGTATACACA TCCATTTGGA ATGTCGTATT AAGAAAGTTG GATAGCGTTG     360

TCGACCAAGG AAAGGTAGAA ACCGTCCAAT CCTTTGATCA GATACTTGAG AATTTCCTTA     420

TTAACTTGAA AGAAGTCGAC TTTACTCTAT CTGGGGTTGC TCTGATGTAT AGCACTATTG     480

ACTACTGGAA CCCCCACATG ATCCCAGGCT ACGGCAAAGT TACGACTGTA GAGCATTTCC     540

TGGTGCAGTA TATCTTACAT CGATATGAGG TATTATATGT GGCCGGCGAT GAAAGCCTAC     600

TAGATAGTCT GGTTGGTGCC ACTATTCGGA AGCTATTTGA ATGCATGCAG TCACAGCATG     660

ACCACCAGAG CCTGGTAGCG AATAGCCAGG CTGATACCGC ACGAAGAGAT AT            712

(2) INFORMATION FOR SEQ ID NO:638:

(i) SEQUENCE CHARACTERISTICS:
        (A) LENGTH: 718 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1429UP (xi) SEQUENCE DESCRIPTION: SEQ ID NO:638:

GATCAACCGA TAGCGGAAGG CGGACGAGCC TCGGAAATAG TACTAGGCAG TGGTTGGCTT      60

TTGTTTTTAG CTGTGTTTCA AGATGTCAGC GAGAACAAGC AGGGAGGCAG GCGCCTCCAG     120

GGTGATGGGA GGTCGGAGTA GTATGGATGG AAAGTCCGGG ACAGGAACAG GGTATTTGGA     180

ACAGCTGAAC TCGCCAAGCA TTCAGAAGCT CATGCACTCG GACGCTTCCA CGACAGCACT     240

ATTGGAGAGG TTGAAGATGT CCCTAGTGAC TTGCGTGGAG TTCACGAAGT TCATAAGAAA     300

GAAATACTTG CTAGAAGAGG GCCATGCGCA GGAGATGGGC AAGGCTTATA AGAACTTCTT     360

TCCGGAGGGC GGTGAGTGCA GCTTGCAGAA TAGCATACAT AAGGTTTTGG AGTATGACGG     420

AAAACTTGCG CAGGTGAAAC TTTCATATGT TGCTGCGTTG CAGAAGATGT ACGATGAGTT     480

AACGTCGCTT CTTGCATCCA TGACTAAAAT GCGCAAATCC CTCAAGGAGA GCAGTCGGCG     540

GTTGGAAAAA GAAGTCGCAG ATGCTATACA TAGCGCCGAA AAGGCAAAGG CAAGATATAT     600

GTCCTTGTGC ATGGATTGGG AGAAGCTCAA GCTTGTAGAT CCTGCAAAGA CGAAGTTGAC     660

ATTGCGGGGC TCAAAGACCA CTCGAGAGCA GGAAGAGGAC TTATTAGAAA GATTGATA      718

(2) INFORMATION FOR SEQ ID NO:639:

(i) SEQUENCE CHARACTERISTICS:
        (A) LENGTH: 730 base pairs
```

(B) TYPE: nucleic acid
            (C) STRANDEDNESS: single
            (D) TOPOLOGY: linear (ii) MOLECULE TYPE: DNA (genomic)

(vi) ORIGINAL SOURCE:
            (A) ORGANISM: PAG1430RP (xi) SEQUENCE DESCRIPTION: SEQ ID NO:639:

```
GATCGCAGAG AGACACAATG TCCCTGTGCC CACTTTGTCT ATGCTTTATC ATTTATTGAT      60

TCTTGTGCAG GGGAAAACTG AAGGCCCAAC AGGGAATTGT CAACCATGTT TAAACTTTTC     120

CATGTGCATG GAGCTCCGTA TGTAGCAATA TATTCTCATA GCTAGAGATC TCACTATATA     180

TTAGCTTGGC ACATTTATGT CATATCGACG TTCGTTTTTG TACACCTTTG TGTCAGGTAG     240

CAGGGGCCGC ACATAACTAG TTATAAAAAC GATGCCGCCG GAGAACGAGA TCTACTATCT     300

CTCTGAGTAG GCACAGTTTC CAACGTATTA GTCCTTAATG AGCAAGCGAA TCATTCAACT     360

CATACTTCTC TCTGCCTTTG CGCGAGCTAA TTACGTGGAG CCCTTCAAAT CAAATCCATA     420

CATTGCTTGC TCAGAGGCAA GCCATTGCCC AAAGGAATGG CCATGCTGCT CGCAATATGG     480

ACAATGCGGG AGTGGGCCGC TATGCATTAG TGGCTGCAAC CCAAAATTCT CGCATAGCCC     540

TGAGAGCTGC GTGCCAGTGC CGGCGCTACT ACCGCAATTG GAGATAGTGG CCAGCGATGA     600

TAAAGGAGTA TACCTAGAGA TGTCGGGTCA GCCTGCCTTG GTCACAAAGT TCCAGCGCAA     660

GAGCTCGGCG CAGTTGTTGG AGGTACATCA CGAGGAACAG CAGTATGGTG TGTCGGCATT     720

AGAGCAGGAC                                                            730
```

(2) INFORMATION FOR SEQ ID NO:640:

(i) SEQUENCE CHARACTERISTICS:
            (A) LENGTH: 719 base pairs
            (B) TYPE: nucleic acid
            (C) STRANDEDNESS: single
            (D) TOPOLOGY: linear (ii) MOLECULE TYPE: DNA (genomic)

(vi) ORIGINAL SOURCE:
            (A) ORGANISM: PAG1430UP (xi) SEQUENCE DESCRIPTION: SEQ ID NO:640:

```
GATCGATTTG GTTACCTTGT TGTCCAACCC ACGTACTTCA AGAGATTCCG ACGCAGAGTT      60

GTAGACAGCG TACCTATTCC GAGCGACAAA AGTCGCAAAG CTTCCCTTAT CCTCAACTAT     120

ATTTGTGGCA TCAACAGCAC CGCTAGCCTG TTTTGGAAGC AGGCAAAGAG CATACCTATC     180

GCCATCCCTG CTACTTGAGT TCACGAGGAG AGAGTGTTGC GAGGGATTAT AAGAGATGGA     240

CTTGAACACG TTATATGGCT TTCCAAAGTT TTTTAGAGAA ACAAATGGCA GAGAGGACAC     300

CTTCTTTTCA TAGTCAAACA TTTGGACCTG CTTCTCTTTG TTGACAAAGT AAAGCTGGTT     360

CTGGTTCACA GCCACAGGTG GTCTCTCACG GTCCAGTTTA AAGACCATGA TACCCGAGTC     420

ATGCGCCGCG CCAAAGAGGT TCACATTAGG GTGCGCCCTA ATCGACCAGA ATCTGTCCTG     480

TTCTCTTTTG AACTGTTTTA CAGGAGTGCG CTTGTCTAGA TCCCAGACCC TAATGGTAGA     540

ATCCTCGCCG ACAGAGATAA TTAGGTTTTG AAATGGGTGA ATATTACAC TGTCGACGTT     600

GTTCGTATGA CCCTGCACTT GTCGACCTCC CACGCTTTGG TGGAGCTCAT ACGCCACAAC     660

TTGACCTGTC TGTCTTCAGA ACCGGAGACA ATCAAGGGCA GAATCGGATG GAACGAAGG     719
```

(2) INFORMATION FOR SEQ ID NO:641:

(i) SEQUENCE CHARACTERISTICS:
        (A) LENGTH: 730 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1431RP (xi) SEQUENCE DESCRIPTION: SEQ ID NO:641:

| | | | | | |
|---|---|---|---|---|---|
| GATCATGTTA | TACAGACCTT | CAAAGTTGAT | ACCAAAACCC | TCAATGGACT | CGCTGACCAT | 60 |
| ACTTGGTACT | TCCTGTTTAG | AGGCCCTGCG | GCACACTTAC | TGCCTCTACA | AGAAAAAACT | 120 |
| GTTGCCTCTG | AATTGGATCA | CCCTTTTTCG | GACACTAACC | ATTTGCAATA | CAATGCTATA | 180 |
| TTGCCTCTAT | CAATGGTCTA | TTGACCTTGT | TGAATCAAG | CTCGAAATCC | AGCAATGTGT | 240 |
| AGAGATACTG | CAGCATTTCG | GTGAGAAATG | GGTTTTTGCC | AAGGAGTGTG | CGGTCGTCTT | 300 |
| TCAAAATATT | GGAAATGCGA | TACTAGATAT | AAGTCTCTCC | CGAGGACAGG | TAGAAAACGT | 360 |
| TGATAAATTG | ACTAGGGAGC | TATTTGGAGC | TAGCAATGAA | TACCAAGATA | TATTGGACGA | 420 |
| AAATAACGTA | GATATATCCT | GGATTGACCT | GGCTATCTAA | TTTCTGAAAC | CATTGAGAAC | 480 |
| CTGTTTAAAC | TATTTGGCAG | TAATTCATAA | TGTATTGGTT | GTTCCATAGC | TGAATTGCTA | 540 |
| TTGCCGCTAT | GGAGTTGCTT | ATGCAATACA | CGGGTTAGTG | GGTGATTGTC | GTGTTCTTAT | 600 |
| ACCCAAACTA | ACCGAATCCG | GTCTTAATCG | ACTCCGGTAG | ACTTTGTCAT | CCAGTAAGAC | 660 |
| ATGTCTTACA | CGCCCGATTA | ATGGTTGTAA | TCTTTAATCG | ATGAATGAGA | AATGGTATAT | 720 |
| GTATGTGACT | | | | | | 730 |

(2) INFORMATION FOR SEQ ID NO:642:

(i) SEQUENCE CHARACTERISTICS:
        (A) LENGTH: 722 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1431UP (xi) SEQUENCE DESCRIPTION: SEQ ID NO:642:

| | | | | | |
|---|---|---|---|---|---|
| GATCTCCTGT | ACCATCATGA | AAGTCTTTTT | ATCACGGGAA | AACCCGTTTC | TCAGGCACAT | 60 |
| CTGACGCAGT | GCTTGTCGCA | CATCAAAGGT | CAAGTTCCGA | TCCCTTGTGA | GCGCTTCCAA | 120 |
| CTCCCAGAAC | TCCTTCTGCA | GATTTTTTAC | TGGGCGCGGC | ACAACTTCTG | CCTGCCTCTG | 180 |
| GGGCACATAT | TTCTTTAACA | CCTCCTTCGG | AATCTTAAAG | TCCTTCACAT | TATAGCGACT | 240 |
| TACGAGACCT | TCGAATAAGA | AGAGGCACTT | TATATATACG | TTTGACATAT | CCAGTTTCAT | 300 |
| CTCGCACCCC | CGCACGATCA | GGTCCCGGTA | GTCCAAGTGC | GCCTTTCTTC | TTGAATTCGT | 360 |
| AGAGCTCGCC | CCCGAGGATG | AGCCTCGCTG | ATCAGAGGTG | CCTGTCTTCA | GCGAGAGCTG | 420 |
| TGGCATACTC | GGCTGTGTGG | CAAGCTCCAC | CTTCACCTGC | TTGGCAAAGT | TCACATTTAG | 480 |
| GCCCTGCGCA | AACGCGTCCA | GTCGAGCGAA | GATATGGTTC | ACCAGCTCGA | GTGGCATCGC | 540 |
| CATCTTGTTC | ACGTCCAGTG | ACACGTTCCC | TTGGCCTAGC | TGGTGCACTA | GGGCCGCGCT | 600 |
| CTGTGTGAGT | TGTCGCTGCC | ACACAGAGTC | CAATTCCACT | CGCATCATGC | GCATCGCGTG | 660 |
| CTTCAACGCA | CGCTCACTGA | TCTCCCCTCG | CTCAGGCATC | TGTGGAGCCT | CTTCTCGGCT | 720 |

```
TC                                                                        722

(2) INFORMATION FOR SEQ ID NO:643:

(i) SEQUENCE CHARACTERISTICS:
        (A) LENGTH: 724 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
         (A) ORGANISM: PAG1432RP (xi) SEQUENCE DESCRIPTION: SEQ ID NO:643:

GATCCAGGAC TGCCGTGCTT GGTTGCGCTC AAGGGAGACT TAGAAATGAG GTGTTGGGCC      60

GCATTCTGCG CTGCAGATAG AAACGAAGAC AAGATGCCAC CGTTACCCAA TTCCTCAGCC     120

CCAGAGAAAA AATTCCCGTA CCGGTGCTTC CCAGTACCAT CCTGGTCAAA GGGTGTGATA     180

TCCGAAAATT TATCCTCAGT GTCCTCCTTG TATCCTGCAT CCGAGCGCGT GCTTTGGCCC     240

GCCCCCGCGG GCTCGCCGCC CGCGCCAGAC CGCACATGCG AGTGCCGCGC GCTCATCTCA     300

ATTGGCATGC TGAGCGACGA CGAATTGCTG TGCCCCCCGC TATGCCAGCT GGCGGCGTCC     360

CGGCCACCCC ACCCCAGGCG GAGCGACGAG TTTGTGCTGT TCGCGTAAAC CACCGGTCGC     420

GACATGAGCC ACGATTCTGC TCCTGACACC CGGCTCTCCA CATCCGAGCC CTCCCCCGCC     480

GCCACCTCGA CATCACCCGC CTCCGGCCCC GTCCGCCGCT CCCCATTCCG CGTCGCTACC     540

CGTCTTTTGG CACTGCTCGC GCGCCCCTTC CGCCGCCCCT CCCCCGTATG CTTCTTGAAA     600

AGTGCCGCGC GCTCTCTCTG AGCGACCGCG ACCGCTTCCG CTGCTCTGCC ATCCTTGCTA     660

GCCTCTGCCT GAGAAGAGCA TCTACCTCTC CTCCCTGTTT ATTCCGCCGC CTTTTTGCGA     720

AACA                                                                  724

(2) INFORMATION FOR SEQ ID NO:644:

(i) SEQUENCE CHARACTERISTICS:
        (A) LENGTH: 615 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
         (A) ORGANISM: PAG1432UP (xi) SEQUENCE DESCRIPTION: SEQ ID NO:644:

GATCCCGGTC GGCCGCTCCT CCTCGAACAT GTCCTGTACC CCGCGCAGCG GCTGGAACAT      60

CCCGCCCACC CCACCGTACT GCCCCGGGAA GAACTGTGTG TCCACCAGCT GTTCGTGGCG     120

CGCCTGGTCC GGCGGCCGCA TATTCTCCTC CTCCTGGTAA GCCTCCTGCT GCAGAGACTC     180

CGCCAACTTC TCGTCGTCGT ACTCCGCGGC CGGCCGCGCG CTTGCAGGCC CACTGCGTGC     240

GCCAGCCTGC GTGTCGCCGC CGTGCTCGAA GTACAGCGAG ATTGCCGTTT CCACGTCGCC     300

ACCTGCCATA TCCAGGAACT GCCGCGCCAG CTCCGCGTCG GCCACACCGC AGATGCTTTG     360

GAATACGCCG AGCTGCTTGT CTGAACTCAT GCTCCTACTT TCTGGCGCTG CCGTGCTGTG     420

TGGCACACTC AGGAGTTTGT CTGACGTTGT CGCTGGCTCC AGCCTTTTAT ACCGGCGCGT     480

GCCACACATG CGCCGCGCCC AAACGCTTAT ACATATACAT GCTACTTAGT CCGCCGCTTG     540
```

```
GTCACCCGCC CGTCCTCGAA GCGCGTGTGC GTGCCCTGGA AGTGCACCGG CTGATCGCCG      600

CGCGCTCGGG CGCCG                                                       615

(2) INFORMATION FOR SEQ ID NO:645:

(i) SEQUENCE CHARACTERISTICS:
        (A) LENGTH: 688 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1433RP (xi) SEQUENCE DESCRIPTION: SEQ ID NO:645:

GATCGATGCG GACCACCGTG CGGAGGAGGC CGCAGGTGGA TATGCAGTTT GCGGCGCTGA       60

GCGCGCCGAT TTCGAGAGCT CGCGCGTCCG CTGGCGTGCC CGCTTCGCGC AGCCACGGAA      120

CCAGCTGACG CGAGGTGTCT CCCCCGCGGC TGGCCGTTTG CCCGACAGTG CTCGCCGCCT      180

GGTAGTTCTG TAGCCCACGC GGCCCGTTAA TCTCGGCCAT TACGTAGCCG AGCATCTGCA      240

CGAGCAGCGG CGACTCGCGC ATCTTCTGTA TTTTGAGCAG CTCGCGCTCG ACCTTCTCGT      300

CTGGGTGCGC CATGTCCGCG CCCAGCCGGT ACTGTTCCTG CAGTCCAGCG TCTGTCACGT      360

ACCGTGCTAT TTGCCGCTCG TTCAGCACTT CGTCATTCTC AGCCACCGGT ATTCCCAGGA      420

GCTTGCATAT TGCCCGCCGT TTCTGTAGGA GAACGTGGTA GCGCCGGATG ACCTTACGTG      480

CTTTGGATGG TTTGATTGCC GGCGTATGTT TGACGGCGCT CTTGCCCGTA ATGCTTCTTC      540

GCTTCCTGGC CAGCATGTAT GAAAGTTAAA CCGCAGTTAC TACTGGTACT AGATATGCCC      600

TCGGAATGCC ACCCGATGAC CTGCTGGTGT ACCTTGCTTT TGTCATCACG ATGCTTCGAG      660

CTGAATCGTT GAAGAATTTC GAGTGAAA                                         688

(2) INFORMATION FOR SEQ ID NO:646:

(i) SEQUENCE CHARACTERISTICS:
        (A) LENGTH: 712 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1433UP (xi) SEQUENCE DESCRIPTION: SEQ ID NO:646:

GATCACGGAA GAAGGCAAGG TCAAGAAGGT TACATTTGAT ATCGAGCCGT ACAAGCCCAT       60

CAACACTAAG CTATACAAGT GTGACAATAA GTTCCGGACG GAGGTGCTCT CGGAGCTGCT      120

GGAGGCTGAC GAGAAGTTCG GGTTCATTGT GATGGATGGT CAGGGGTGTC TTTTCGGTAT      180

GTTGTCCGGT AACACCCGGA CTGTTCTACA AAAGTTCACT GTGGACTTGC CGAAGAAGCA      240

CGGTAGAGGT GGTCAATCCG CGGTGCGTTT CGCCCGTTTG AGAGAGGAGA AGAGACACAA      300

CTATGTGCGC AAGGTCGCTG AGGTGGCAGT GCAGAACTTC ATCACAAACG ACAAAGTTAA      360

TGTTAAGGGG CTAATTTTGG CTGGTTCTGC GGACTTCAAG ACGGACTTGG CCAAGTCTGA      420

ACTGTTTGAC CTGAGGTTGG CAGCCAAGAT TGTGAAGATT GTAGATGTAT CGTACGGTAG      480

TGAAAATGGT TTCAACCAGG CTATTGAGCT GTCCGCCGAG GCGCTGGCCA ACGTTAAGTT      540

CATTCAGGAG AAGAAGTTGC TCACCGAGTA CTTTGATGAA ATTTCCCAGG ATTCGGGCAA      600
```

```
ATTCTGCTAC GGTGTTGACG ATACTCTGAA AGCGCTAGAT TGGGTGCGGT GGAGAAATTG      660

ATTGTGTTTG AAAATCTAGA GATTGTTCCG GTACGTGTTT AAGACTTCTG AA             712

(2) INFORMATION FOR SEQ ID NO:647:

(i) SEQUENCE CHARACTERISTICS:
        (A) LENGTH: 716 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1434RP (xi) SEQUENCE DESCRIPTION: SEQ ID NO:647:

GATCAGATGC TTCTGTGGTC CTAGAGAAGA CTGCTATTCT TAACCCTTCG TCAACGAATA       60

TAGCCGAGGA CGAGTTTGTC GATGCCATAG CGGAACCTCC ATCGGCGTCC GTGGATAGTA      120

CGCCTTATGT GACCGCGGCG CGCGATTATT CCTCGGAAGA CACCGGGGAA CGTTCTGAAC      180

CTACAATAAC GGAATACAAA ACTGCAATTG AATCACCATC CACCTTTGGC GACGATAACG      240

AGAGTGTATT TCTTGTAACT TCTGCGGACC TGCATCCATC GGTGTCCTCT GCGAGTCAAA      300

CATTAACAAC GGAAGAGCTT CAAGCCGTTG CGAACAGCCA CCAATATAAG ACCGAGGTGC      360

AGATTGTAAA ACAAGACGAA GATGAAGTAG AGGATGTTCT AGAATTGGAC TCGCCACCAG      420

CATCTCTGTA TGATGGTGAT GTTTTGAAGG AGGCAGAGAA AAATGATAGT AGCAATGTTA      480

TTCCTGATGA TTCCATAGAT ATCGATGAAT ACCTCGATGA AAACTTGGTT AAAAACTTCA      540

CATTGGAAAA CGCTCTTTCT TTAGATGAAA TCTTCGACGA TGATAATGTA GTTTTTGGAG      600

AAGAGAAGCT GCTTGTGGAT CCAGACCTAG AATTCCCGGA ATTAACTGGA ATGGAACAAG      660

ATATGGAATC TGACTATCTG CCGCTGATTG AAAATGGTAC GGAGGCTGTT CTACAA         716

(2) INFORMATION FOR SEQ ID NO:648:

(i) SEQUENCE CHARACTERISTICS:
        (A) LENGTH: 715 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1434UP (xi) SEQUENCE DESCRIPTION: SEQ ID NO:648:

GATCAGGTTT TCCGGTACGT GAGAACGTAT CTAAGGCACA AAGGGCTTTG GGCGACTGTG       60

CGGACGCTTG AGTTGCGAGA TACAGGACAA AGCTGTTACG GCGGCAACTG GTGCAGCACG      120

AGCAGCCGAG GAGCGATTCT GCGCGAAGCG ACGGTGAATT CGAGCCAGCT GGTAGCAGGA      180

GTGCCGGATC GTCTATTTAG TTGCGACGGG CGTCGGAACA GGATGCACGT AAACGTTGCG      240

GTAACACGCG ACGCTGACGC GACGGCTGCT ACGCCGATAG CACGGGAGCG CAAACGACGG      300

CAGCCGCTGT CGCCAGAGAT GTCTTCACCA CTGCGCGGTA GCAAGCTGCA GCGGCGGAAG      360

CAGACACTTG AGGCCGGTCC GGGTCGCGCC AGTGGGACAC ACACGGTGGA CGAGCTGGCC      420

GCGCAGCTGG AGCGCGGCTG CGAGCAGGCG TCGGAGCGGA AGCCGCCGTA CTCGTATGCG      480

GTGCTGATCG GCGTTGCGAT CCTACAGTCG CAGGAGGGCA AGCTGACCTG TCGCAGATAT      540
```

```
ACCGGTGGAT CTCGTCCTTC TTCCCTTACT ACCGGCTGTG TGACGCGGGG TGGCAGAACA    600

GCATCCGGCA CAACTTGTCG CTGAACGAAG CGTTTGTCAA GGGCGGCAAA TCGCTCGATG    660

GCAAGGGCCA CTTCTGGGAG ATCAAGGCAC TGTGAAGGCG CTTCTCCGCG ATGGG         715
```

(2) INFORMATION FOR SEQ ID NO:649:

(i) SEQUENCE CHARACTERISTICS:
        (A) LENGTH: 538 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1435UP (xi) SEQUENCE DESCRIPTION: SEQ ID NO:649:

```
GATCCGATGC TACCCGTCGC CCTGCCAACC CGTTCGCCTA GCGTTGACGC CTAGGTCTGA     60

AACTGAACAA CAGGTGGCAT TGTGGGCGGG CCAGCAGGCC CTGGCGCGAC CATGCCGCCA    120

TGGGCGGCGA ATAATACCAC CAGTTGTGAA GCCCAGGTGT CTGTAATCTG CACCGAACAT    180

CTTTATCTAC CAAGGAGGAG CCTTGAAAAT TATATATCTA CCCCTCCCCC TAATATATTT    240

GACCAATTCG CTCTCCGGAA ACCGAATGAT CGAAGACGCC ATCAGGGCAG CGGACAGCAC    300

AGGAAGTGAG GAGTGATCTC GCAGGTACGA TGGAAGCACA GTCTATACAG TCTATTCGGT    360

CGAACCAAAG CGTACGGAGC ATCSCGAGCA CGAGCGGAAC CGCAGACGAG TCGCTAATCT    420

TTGAACGGAG CGTTGAGGAT CGTTTGGCCC CGTGAAGGAC GCGAAGGGTT GCAGCCTGTG    480

TGGTGTCTCC CAGGCAGGGT CTCTGCACGC CGGGGTATCG GCGACTGGGG GCGCGTCT     538
```

(2) INFORMATION FOR SEQ ID NO:650:

(i) SEQUENCE CHARACTERISTICS:
        (A) LENGTH: 728 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1436RP (xi) SEQUENCE DESCRIPTION: SEQ ID NO:650:

```
GATCAACCTC GGAAACGTAT TTAAAAGCTT GTACTCGACA TCATTAAGTC TTCTCCTCGT     60

TTCCTTTGGT AAAGTATWAG CATCCAGTAA AGTAACAACG AAATGCAATG CTGAAAGATC    120

GTATACCCTA GACGACCTAA ATGGGTATT TTGATCATCC ATACTAGCTT GAAGATCAAT    180

GAAGTCAATA ATAGTGTTGA CAGACTCAGG GGAGAGTTTG GACTTGATGT ATTCCTCAAA    240

GCCAGTCCAT CCCACCTTCC TAGCACTAGG AGTAATCTTC AGCGATTCTT TAAACGGAAT    300

ACTTCTGATA AAATCCTCCA GCTTTTTTTC CTCGTAAAGG ATCTGTACAA AATTAGCAAG    360

CGGGGTGGTA TCCTTGTTAA TTATGATTCT TCCAACTTCA ATGACCTTGT GGTTGGGGAT    420

TTTCTTGATA AGCTCACCAA ATACCATCGG AGATTTTTCA ATACTTGGA CCATTAGAGT    480

GACCAATAGT TCGTTAATAA TCGCCTTATT TTCAACCATA AGACTGAAAT GCTTCGTTTC    540

TGAGATCAAA GTCAAGGCCA ATATTCGGG AACAATATTG TAATCATCGA AGAAACAATC    600

ATGGAATAAT TGGAACATAG GACTGGAGCC AAACTCCTCT CTTGATAAGA ACAGTTCAAT    660

ATCGAGCTTC GATACCGATG TGAGATATAA CAAGGAGTTC TTTGAGTTTG GGAGTACTTT    720
```

```
AGAGACTT                                                                  728

(2) INFORMATION FOR SEQ ID NO:651:

(i) SEQUENCE CHARACTERISTICS:
        (A) LENGTH: 713 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1436UP (xi) SEQUENCE DESCRIPTION: SEQ ID NO:651:

GATCCAGAAG ATTATCCGAC AATATTAGTG ATATCAAGGC ACAGATCGCT GCCAACACTA         60

GAGGTATTCA ATTGCTTAAC CAACTGGTTG ACGTTTTCGG TCTAGGGACT GTTACAAGGT        120

ACATGGACGC AATTCAGGAA AATGCAGCTC TTACTGTAAA GAATGTCTTG CGAAAGATTA        180

CCAAGCATTT TGGCAAAACC GTCTATTCGG CCGAGGATTA TATGGATGAT GGCTCTGTTA        240

TAAAACTTAG GGTGGAGCTA AATGCTAAGG AAGATAAGTA TATTTTTGAT TTTACGGGGA        300

CTTCTCCACA GGTCCACGGT AACCTCAATG CACCTGTTGC TATTACCAAC TCTGCCATCT        360

TATACTGCTT ACGTTGTTTT GTAGACGAAG AGATTCCGCT CAACCAGGGC TGCCTAAAGC        420

CCATTACTGT TATTATTCCA GAGAGCTCTA TCCTATGGCC GACCAAGGGT GTCGCGGTAG        480

TGGGAGGTAA TGTCATGACG TCTCAGCGTG TAACTGACGT AATTCTCAAA ACTTTTAAAG        540

TCATGGCGGA CTCCCAAGGA GACTGCAATA ACTTTACTTT TGGGACAGGT GGGAACGACG        600

CTTCTACCGG TGAATATACT CAGGGTTTTG GATATTATGA AACCATATGT GGCGGGCATG        660

GTGCAGGTGG AGATCATGGC GTGGTCCGGG GTGGCATGGA ACACATCCTG TTC              713

(2) INFORMATION FOR SEQ ID NO:652:

(i) SEQUENCE CHARACTERISTICS:
        (A) LENGTH: 587 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1437RP (xi) SEQUENCE DESCRIPTION: SEQ ID NO:652:

GATCGCGCGC GAGCTATCGC TTCCGCCGGT CAAGCTGCAC TGTAGTATGC TCGCGGAGGA         60

CGCCATCAAG GCCGCCATCA AGGACTACCG CAGCAAGCGC AAGGCGACCG AGCTGCGCTG        120

AGCGCAGGCC GCCGCAGCCT GTCGGCGGCC GGCCGGCGCC AGCCGCAGAG GGACGTCCGC        180

GGGCCGGCGA GAGCCGCCCG TTTTCTATGT AGCGACTCKA GCATCTAATA GACATGGTAA        240

TAGCTTCTCG TTTTCTACGT TTGCACACAG TATACAAAAT TTTCACGCAG CTCATCGCCA        300

CTTCCACTTG CTGAAGCGCA GGTACGGCAC CAAGACCTCG GCTATGTCCT CGACTCTCTT        360

TGACGACATC TTCACGATCC AGGAAGTGGA CCAGGGACGG TACAATAAGG TATCGCGGAT        420

TGAGGCCATC TCCACGTCGC AGGACACGTG CAAGCTGACG CTGGATGTGA ACACAGAGCT        480

CTTCCCGCTG CAACCACAAC AGCAGCTAAC GGTGATGCTG GCGACGACAC TCAACCTCGA        540

CGGAACGGAG GACAGCCACG GGTCCTGGCG GCCTCCGGCC CCTGGGG                     587
```

(2) INFORMATION FOR SEQ ID NO:653:

(i) SEQUENCE CHARACTERISTICS:
       (A) LENGTH: 260 base pairs
       (B) TYPE: nucleic acid
       (C) STRANDEDNESS: single
       (D) TOPOLOGY: linear (ii) MOLECULE TYPE: DNA (genomic)

(vi) ORIGINAL SOURCE:
       (A) ORGANISM: PAG1437UP (xi) SEQUENCE DESCRIPTION: SEQ ID NO:653:

| | | | | | |
|---|---|---|---|---|---|
| GATCCGGCGG | GACCGCTACA | ATATTCCCAT | ATGTATTAYA | GGCAACTTTA | TACCCATCTC | 60 |
| CTAAGTGCAG | TACGTACTGT | TTGTCAGTCT | AGCGTCTCGC | TCGCGGTGAG | CCCCGTGTTG | 120 |
| CGGTCCACCA | GCGCGCCGAC | CGCGCGCCCG | GGCCCGACGT | GCAGCGCGGC | CGTCGCGCCC | 180 |
| GCCTGCACCG | CCGTGCGGCA | GGCTGCGACG | AACTCGACCA | CGTTCGTGCT | CGAGCGCACG | 240 |
| AACTTCTCCA | CGGCCACGTC | | | | | 260 |

(2) INFORMATION FOR SEQ ID NO:654:

(i) SEQUENCE CHARACTERISTICS:
       (A) LENGTH: 728 base pairs
       (B) TYPE: nucleic acid
       (C) STRANDEDNESS: single
       (D) TOPOLOGY: linear (ii) MOLECULE TYPE: DNA (genomic)

(vi) ORIGINAL SOURCE:
       (A) ORGANISM: PAG1438RP (xi) SEQUENCE DESCRIPTION: SEQ ID NO:654:

| | | | | | |
|---|---|---|---|---|---|
| GATCTCTTTT | TAACGGCTGT | TACCAATAAC | GATACCGCAG | CTACATCTGG | AGAATAGTCT | 60 |
| GCATCCCATG | CCTCCAAGTT | CCTGTGAACA | TACTCCTGGG | GATCGACCTC | GAAGCTCTCC | 120 |
| AAGGTCTCTT | CGCTAGGACA | AAGAAGCGGG | AAGATAACAT | GTTCCAAAAT | GGTTGCATAA | 180 |
| TGTGGGTCAA | CTATCGGCCA | AGTAGACTTT | TGGACCACTG | TTTGTTCAAT | GAACTCCAAT | 240 |
| ATGTAATATA | GCGACTCCTT | GCTTAACCAC | AATTCGCCTG | CACCCACCT | TTCAATCTGC | 300 |
| TGGAAATGCA | ACTGCAATAG | TTGCGGCAGA | AACTGCTCCA | CATACAGCAT | TTTAAATTCA | 360 |
| GTGTACTCAA | ACTTTTTGCT | GAGAGATTCT | GAGGCATAAC | GTTGGAATAA | TCGATACATG | 420 |
| TTAGCATATG | CCCACTTTTT | GGCTCTGACC | CATGGATGCG | CCCGCCTATC | ATCGACCGCC | 480 |
| AGCGCCATCA | CATGCTCCGG | CAGCTGGCTT | TGTATACAG | AAACATGAA | GTTGGCCCAC | 540 |
| GGAATGAAGT | TTTCCGACCG | TTGGAGAGTG | AACGGCAGGT | CATTATATGT | CACAAACTTG | 600 |
| TAGATCTTCA | GCACAAGCTT | CAACATATTC | CCCACGATCT | CGTTGTGCTT | TCCTCGCTGT | 660 |
| ACAAAAGCGC | GTTTGCGTAG | TGCAGCAAGT | CTGGGAAATA | TCTCATGATC | AGCATCTCCA | 720 |
| GCTCCTGA | | | | | | 728 |

(2) INFORMATION FOR SEQ ID NO:655:

(i) SEQUENCE CHARACTERISTICS:
       (A) LENGTH: 774 base pairs
       (B) TYPE: nucleic acid
       (C) STRANDEDNESS: single
       (D) TOPOLOGY: linear (ii) MOLECULE TYPE: DNA (genomic)

(vi) ORIGINAL SOURCE:
        (A) ORGANISM: PAG1438UP (xi) SEQUENCE DESCRIPTION: SEQ ID NO:655:

GATCGGCAAA CCTAATGCGT CTGGACGTAA TGTAATCCAA CAGCGACTGT AGAGCTGCCT    60

GCGGTTCTCC GACAGAAATC AGCTCATCTG CCCGCTTCAA GGCGTTTTCA GGGCGCAAAA   120

CAGGTGGAGC CATGCTGAAT TAGAGCTATT TGGTGACCTG TTTGAGTAGT GTGGACTTCC   180

TTTGAATGTG GTGAACTTTG AAGTAGGTTA TTCAACTAGA AAATTTTTCA CCCAGAAGGA   240

TGCCCTCTAT CAGCGGCCGT GTCTGACGAT GATCTCAACC GCGTAAAGGA CGAGAAGTCG   300

TAGGTCGAGT CTAATCTACT ATTGGTACTG ATGAACGGGA CTGGCCAGCT AACGTGAAGG   360

CACTGTCTGC GGGATGAGGC CCCAGCGCCA GCGCACGGGC CCTGCGATGA GCACAGGTTG   420

CCTCGAGACG ATTCGCATCG GCTGACGGGA AGCCAGGTTT CCACAGCGTT GGCGGACTCG   480

CGTCGTCAGG CTGGAACTGT AGAAGGGTTG TCTTGAGCTC CGCGCACGCC GCACGCTGCC   540

CAGGTAGCTG GCGGGCCGTG TTCATCGCGC ACAGCGGTGG GCTCGCTGTC ACGTGGCATC   600

GAATATGTCA CGTGATTACA CGCAGCAGGG CATCGCAGAC AATGCGCAAG CAGCAACAGG   660

AGGAGGGTGT GATCGGTGGT GTGCGTTTAA GAGTATGTGA GCTGTGCAGC TGGCTCCCCA   720

TCTCTGGGTT TACTCGTACC TGTGCGCTTA TATAGGCATT GCCAAAAGGT TTCC   774

(2) INFORMATION FOR SEQ ID NO:656:

(i) SEQUENCE CHARACTERISTICS:
        (A) LENGTH: 728 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1439RP (xi) SEQUENCE DESCRIPTION: SEQ ID NO:656:

GATCCTGTTG GACGTCTTGC AAAGTCGTGG TCACCCCGAC CAACTTCTCC TCTGTAATAC    60

CGCTGTACTT CGTTAAGTAG TCCACAATGG GCTCATCTGG CTTGACAAAC TTGTCATAAA   120

CTAAGTTACA ATCAAAATCG ACGACGCTCA CACGCGTCAA CACGTATCCG TTTTTTGAAA   180

GGCACATCTC ACAGTCGATG GCAAACGTGT GAGAACCGTC GTGTTGGAAA CTGACAGTGT   240

CCACCCACCC ACTGTACTTC TCCTTATTCT GATACTTTAG CAACAAAGCC TTTTGGTACT   300

CCTCCGATAA GCCAGGTGTG TTTAGATGGA TGGGGTACTC ATTATGCAAT AAGTCATCAA   360

CGGTCATTAG CAAATCAAGC AAAGTGATTT CCTTTTTGTT CAATTGTTCC ACCTTTGCGA   420

TCTTCTCCTT TTTTGACAAG CCTACATTGA CAAAAGAATT GTATGCAGAA AATAGGGAAT   480

TCTTTGATCC CGGCGCTGAT AACGGCAAGA TACACATTTG CTTGCACATC TGTTCATTTT   540

CACTAATCGA GTTAGATGT GCGTCTTGCA ATTTCGGAAT ATTTTTATGA AACAATGAAT   600

CCTTCGGTAG ACTGAAGTCC TCGGGTAAAA GGCCTGGAGT GAATAAGACG ACCACCTTCT   660

TCAAAGAGGC CTATTTTCTA TCGTAATCCA GTTGGGAGAG TTGTTCGTAT CGTGGAATAT   720

GTACTGGA   728

(2) INFORMATION FOR SEQ ID NO:657:

(i) SEQUENCE CHARACTERISTICS:
        (A) LENGTH: 694 base pairs
        (B) TYPE: nucleic acid

```
        (C) STRANDEDNESS: single
        (D) TOPOLOGY: linear (ii) MOLECULE TYPE: DNA (genomic)

(vi) ORIGINAL SOURCE:
         (A) ORGANISM: PAG1440RP (xi) SEQUENCE DESCRIPTION: SEQ ID NO:657:

GATCTATTCT TCATTCAGCA ATCAACAAGA GCTGGTGAAA CTTGGGCAAG AAGCTGAGCA      60

AAGCGGTAAA TACAACTTGG CATTCAATGC ATACTGGATT GCAGGAGATA TCAACAAGGC     120

CAGGGACGTG CTTTCGAAGA GCGGACGCCA TTCCGAGGCT GTGCTTCTGG CATCCACATA     180

CACCTCAGAC AATGACGCCA TCAACGCTGC TGTAGAAAAA TGGAAGGAAC AACTGAACTC     240

AGCTGGAAGA GTATCTATCG CAGAAAGAAT TATACTTTCC GGAGAAGACG ACTTCCCTGC     300

AGCTCCCCAG ACTTTGGTCG AAATGGATGA CGGATCAGAG TCCGCGTCTA AATAAACTAT     360

AATTTTAAAG ATAACAGCAG GAATAAATTA ATTACCACGA AGGAAATTTG TATGTACATT     420

CTAACTAGAC CCAATGGTAG AATTTCATTG CGTAAACACG GCAACCTTAT CAATATCTTT     480

CCGTTTGTCC AGTCCGACAA AGTAAAGTTC TTTGGATTCA GATCGGCATG CTTCCGGCTT     540

AAAACGCCGC ACTTTGGTGA ATACCTTTCG CAGACGCCGT TCTAATAGCT GGTCTTCCTT     600

GCCAGTGTAT AACTTGCAAA CGAATGAGCC ACCGGGCCTC AACAATGCAA TTGCACATAG     660

CAGTGCTGCG TTCACACAAG TCCATCGACA TGTA                                694

(2) INFORMATION FOR SEQ ID NO:658:

(i) SEQUENCE CHARACTERISTICS:
         (A) LENGTH: 712 base pairs
         (B) TYPE: nucleic acid
         (C) STRANDEDNESS: single
         (D) TOPOLOGY: linear (ii) MOLECULE TYPE: DNA (genomic)

(vi) ORIGINAL SOURCE:
         (A) ORGANISM: PAG1440UP (xi) SEQUENCE DESCRIPTION: SEQ ID NO:658:

GATCCTACAG AAATAATCCA GTACAAGGTA CCTCTAATCT ACTGTGTTAA CATGGAAAAC      60

ATTTCGCCTT TAGGCTTTTT CTTTTCACCG AAAAGGTAAC GTGTTCGAAA CATATATCAC     120

GGGTTCGAAA CTGACTAAGG TTGCTCATGC CTAAACCAGA TAGGCAGCAA TGGCAAGGGG     180

CTTGAGGTGG TACCAGAAAA GCTGCCACCT CCTGCTGCGT GCTTACTCTC GCAAACGGTG     240

TATACTATTA GTGTTGGAGT ATTTATTGCT TATTAAATAA CCGAATTGTG GGCCTAGAAG     300

TGGCGATTAT CACTGAGCAG CAGCGGCTGG CAGCGCAGAC TGCTCGCGAA GCCGAGCACG     360

TGCGTTTGAG GCAGCGTTTA GAGCTGCAGC CGTGACCATC AAACCCTCGC CGCGGAGGAC     420

GAGTATGAGG GCTAGCTCGA GGCGCATCAA GAGCTTCTTC GATATGCCGC AGACCTTGCT     480

GAAATACTCG TGGGAGTGCA CGGTGTCTTC CACAATCTTG GTTGAGACAC GTATCAAGGC     540

CACTATGAAG CGATGCACAT ACCTCTCGGC GATGGGCCAG CGGATCTGCA CCGGACCGGT     600

TTCCGAAGGA GGCCATTTTA GCGTGAGGCG GAGTAACAAG CAGCCCGCGG TCTGGTAGAC     660

TATGGGCGCA AACATGCATT TGGCGTTGAT GCCGTCTAGG TACTGCGTAT AC            712

(2) INFORMATION FOR SEQ ID NO:659:

(i) SEQUENCE CHARACTERISTICS:
         (A) LENGTH: 712 base pairs
```

```
            (B) TYPE: nucleic acid
            (C) STRANDEDNESS: single
            (D) TOPOLOGY: linear (ii) MOLECULE TYPE: DNA (genomic)

(vi) ORIGINAL SOURCE:
            (A) ORGANISM: PAG1441RP (xi) SEQUENCE DESCRIPTION: SEQ ID NO:659:

GATCGTTAAT TGTAGCAAGC GACGACCAGA GATGGTCTAC CAAGGCCGTC TACGACAGAG    60

CACGCAAGCA GTCCGTCCCC AGGAGCAAGC CCCCGAGGAC AGACCACAAG CACACTTGCC   120

GCGTCTGACC AAGGCCCTCA CTACCCGATC CTTAGAGCCA ATCCTTATCC CGAAGTTACG   180

GATCTATTTT GCCGACTTCC CTTATCTACA TTATTCTATC AACTAGAGGC TGTTCACCTT   240

GGAGACCTGC TGCGGTTATC AGTACGACCT GGCATGAAAA CTATTCCTTC CTGTGGATTT   300

TCAAGGGCCG TCGTAAGCGC ACCGGACCCA GCATAGATGC TGGGCTCTTC CAGCCATAAG   360

ACCCCATCTC CGGATAAACC AATTCCGGGG TGATAAGCTG TTAAGAAGAA AAGATAACTC   420

CTCCCAGGGC TCACGCCGAC GTCTCCACAC TCAGTTACGT TGCCGTGAAG AATCCATATC   480

CAGGTTCCGG AATATTAACC GGATTCCCTT TCGATGGTGG CCTGGAAAAT CAGGCCTTTG   540

AAACGGACTT CCCCATCTCT TAGGATCGAC TAACCCACGT CCAACTGCTG TTGACGTGGA   600

ACCTTTCCCC ACTTCAGTCT TCAAAGTTCT CATTTGAATA TTTGCTACTA CCACCAAGAT   660

CTGCACTAGA GGCCGTTCGA CCCAGCTTTA CAGCCTAGGG CTTCGTCACT GA           712

(2) INFORMATION FOR SEQ ID NO:660:

(i) SEQUENCE CHARACTERISTICS:
            (A) LENGTH: 718 base pairs
            (B) TYPE: nucleic acid
            (C) STRANDEDNESS: single
            (D) TOPOLOGY: linear (ii) MOLECULE TYPE: DNA (genomic)

(vi) ORIGINAL SOURCE:
            (A) ORGANISM: PAG1441UP (xi) SEQUENCE DESCRIPTION: SEQ ID NO:660:

GATCCAACCG AACCTTTCCT TCTGGCTAAC CTAGGGTACT TGTACTCTAG GCGAACCAGG    60

ACTTTTACTT TGAAAAAATT AGAGTGTTCA AAGCAGGCGC AAGCTCGAAT ATATTAGCAT   120

GGAATAATGG AATAGGACGT TTGGTTCTAT TTTGTTGGTT TCTAGGACCA TCGTAATGAT   180

TAATAGGGAC GGTCGGGGGC ATCAGTATTC AATTGTCAGA GGTGAAATTC TTGGATTTAT   240

TGAAGACTAA CTACTGCGAA AGCATTTGCC AAGGACGTTT TCATTAATCA AGAACGAAAG   300

TTAGGGGATC GAAGATGATC AGATACCGTC GTAGTCTTAA CCATAAACTA TGCCGACTAG   360

GGATCGGGTG GTGTTTTCTT ATGACCCACT CGGCACCTTA CGAAAAATCA AAGTCTTTGG   420

GTTCTGGGGG GAGTATGGTC GCAAGGCTGA AACTTAAAGG AATTGACGGA AGGGCACCAC   480

CAGGAGTGGA GCCTGCGGCT TAATTTGACT CAACACGGGG AAACTCACCA GGTCCAGACA   540

CAATAAGGAT TGACAGATTG AGAGCTCTTT CTTGATTTTG TGGGTGGTGG TGCATGGCCG   600

TTCTTAGTTG GTGGAGTGAT TTGTCTGCTT AATTGCGATA ACGAACGAGA CCTTAACCTA   660

CTAAATAGTG CTGCTAGCAT TTGCTGGTTG CGCACTTCTT AGAAGGACTA TCGGTTTC    718

(2) INFORMATION FOR SEQ ID NO:661:

(i) SEQUENCE CHARACTERISTICS:
```

(A) LENGTH: 722 base pairs
            (B) TYPE: nucleic acid
            (C) STRANDEDNESS: single
            (D) TOPOLOGY: linear (ii) MOLECULE TYPE: DNA (genomic)

(vi) ORIGINAL SOURCE:
            (A) ORGANISM: PAG1442RP (xi) SEQUENCE DESCRIPTION: SEQ ID NO:661:

```
GATCAATTGC GTCTTCATCC GATGAGACAT TTTGAAAATT GTTGGAATAT TGGGCAACAT    60

CAGGGTATGG TAACACCTCC GGTTCTAAAC TTCTAATCGG TAGCCTCGTC GCGCGTGTAA   120

CGCATGGATC ATCAATGGAC GGTGCTGGGG GCGATCTAGA CACGCCCGAA TTGGGGCTTG   180

GTGTGAGGTT TTCGTCCGGA CTTCTCACTT TATCAGGTAT GACTATCACT TGATGATTCA   240

TTAGATTCCG TGTATCCACA ACATGGACGT GGCTTTGGTG TTCCGAGATA AATAGTAGGT   300

CATCAAACGA GCGGCTAAAC TTGCACACCC TAAAGGACCC GTTCTGTGCA TGTCTTCGAG   360

TTGAAGGTAT CTCCGCAAGA GGCGTGTCCA TTTTTCTCAT ATCGTACACC AGACAGAGGC   420

CGTTTTGGAA TATCGTAGCC ATGTGCACGT CGTTTTCGCT ATAGCTTGTG TAAAAGCCGT   480

TATCACCACC AGGCGAATCG TAAATACGAT CTAGGACTTC GGATCTATCG ACCGCGGCAT   540

ACCTTGGAAC GCACTTTGTG CGCGACCATT TTGAACCCCA CTCAGGAGCG GCGTCATATT   600

GTAATGAAAA ACAACCGCTT AGTTCATCTG TCTATAGACC GCAAACTTGC TGGAATCTCC   660

CGAAACCACC ATCGTCTTCC CATCGTGTGA TATTGCCGAG CAGTTTAAAG CAAATTTTAA   720

GT                                                                 722
```

(2) INFORMATION FOR SEQ ID NO:662:

(i) SEQUENCE CHARACTERISTICS:
            (A) LENGTH: 720 base pairs
            (B) TYPE: nucleic acid
            (C) STRANDEDNESS: single
            (D) TOPOLOGY: linear (ii) MOLECULE TYPE: DNA (genomic)

(vi) ORIGINAL SOURCE:
            (A) ORGANISM: PAG1442UP (xi) SEQUENCE DESCRIPTION: SEQ ID NO:662:

```
GATCAAGGCT GGGAAGTTGG CGTTGACTGG CTTGGCCTGC GCAGGCTCTC TGTTGCCGCT    60

CTTGCCGCCT CTGTTGCCGC CCTTGCCGCC TCTTTTGTTG TCTCTCTGGT CGCGAGACTT   120

AGGAGCAAAG GACTCGGTGC CATCAAACTC TAGGAACTGC TTGGCCTTCA AGTGCTTCGT   180

CTTGACGTTC TTGACCTTGG TAGCCTCCAT GAAGACCTCC TGCTTCTTAA CGAACAACTC   240

AGCGTCGTCG AACTTCTCGA CCTTTCTGGC GACAGGGGCC TTGTTCAGGT CGGAGTTCTG   300

CTGCTCCAAG TACGCCTCCA AGGTGACGGC AGCTGCAGTG GCCTGCTCCT CCTCGGCAGC   360

GTCGGCGGCC AACTCCGCCT CGGCAACAGC GGCACCAGCC TCCTCATCGG CCTGCTCCTT   420

CTCGTTGTCG CCCCACGCCT GCTTGATCTT CTTGGCAGAG TCAGTCTTGC CGGTTCTCGA   480

GTGGCGGTCA AAGGTCTTTC TGCTGTCCTT GGCTGGCTTG CCTGGCGCAA GAGCGTCCTT   540

GGACTTGTTC TGCGAACGGC CGGCCTGCTT GTCTCTGAAC GCAGCCTCGT TGCCGGTTGG   600

CTTTGGTCTG TTGTTCTTGG CACGCGATGG GTCGGCAGAT GGAGGAGGCA CGTCCGCCTT   660

CTTGGAAGAG GTGGTCTTCT TCACAAGCTC CTTTGGAGGA GACACAACAA CGGTGGCGTC   720
```

(2) INFORMATION FOR SEQ ID NO:663:

(i) SEQUENCE CHARACTERISTICS:
        (A) LENGTH: 716 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1443RP (xi) SEQUENCE DESCRIPTION: SEQ ID NO:663:

```
GATCTATGCG GTGCTGTGCG CGTGCATCGA CCAGCACAAG AGCTTCGAAT TCGATAGCGG      60
GAGCTTCTTC TTTCAGTACG TCGAAGGCAT CTACTCGTAC AGGACTGCGA GCCTTCTTGC     120
GGGCTATCTG CGGACGCACT CCGTGCCGAC GGCCAGCCAG TACGCCAAGG TCTTCCTAGA     180
CCGCGCGCCC TCGCCACGTC AGGCCGAGGT GCTGCTGCTG GCATAGTTG CGGATGCCGA      240
CGCCATGCAG CGGCTAGTGC AGGAGTGCAA AACGAGTGGA GCCGTGACAT CTGCGAGCTT     300
CTCGCTTCTC ACAGAGTGCC TCGACATATA CCTGTCGTAT GTGAACGATA CCGTTTTGCT     360
GGGGCCCAAG AGCAACTTCC CGCTTGAAGA TCTCGTGGTG TTTTGCAACT TGGTGCGTGA     420
CGCGATATCT CAGGCTTTGC GTGCTGAGCA TGATTATGAG GTGAACAAGA TGCGCCGCGC     480
GCTCTCCTTA CTCCAAAAGC TGTATATTAG GGATAGAAGG ACCAATTTCC TCTCCGCGGC     540
CAAGGGGGAC GACTTCTGGG TCATTGCGGA TACCACGGTG AAAAACTGCG ACATTACATC     600
TCTCCTTCTT TACTTTGATG AGTTCTACAG AGAACAGTTG GATTTGTTCC TGGCGCAGGG     660
CCGTGCTCGG CACGAGGTCC CAGCGGCGAT CTCGTAGCGT GGGAAAACGA TATAAA         716
```

(2) INFORMATION FOR SEQ ID NO:664:

(i) SEQUENCE CHARACTERISTICS:
        (A) LENGTH: 711 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1443UP (xi) SEQUENCE DESCRIPTION: SEQ ID NO:664:

```
GATCCGGCAT TTACATCTGA CATGTAACCG GGTGGTTCTG TAGGTAGGGT GTTCAATGTA      60
AACTGGTCGC AGTTCGAAGT TGGGGTAGTA CTAAATTCGA ACCCCGGTGG CGGTGGTAGA     120
AGATGGCCAT CGTGAAGGTG TTCCACAAAA CTATTCGTTT CACCCTCGGA TACTTCATCT     180
TCATAACTGC TTTCTAACAA TACATCTCGG TCATAGTCTT CGTAGGCTGG TGGAGGCAGC     240
TTCATGCCGT TCAGCTTTGC ATATCCCCAT TTCTTTACGT TTGCTTCAAT GTAGACGAAT     300
CCGTAGGTCC CGAAATTAAC GTGTATCTTG CATGGGACAT TCGCACCAAC AATCGGGTAA     360
AGATACTTAA TTTTCCAGCC CTTTATGTGG CCACCAATGC GTTTCTCATT TAACTTCTTG     420
CCATTGCGCG TGAAGAAAAC TGTGCCGCTC CGAGTTCTGT AGCCAATCCC GATGACGTCG     480
CCCTTTTCGC AGCGGGGAA TAGTGAAGAG AGTTCCTGCG GGAGCTTAAA CGAGTTGTTT      540
AACCTACGTG CTCCATTAGA GTCATATGCA ACTGAGTGAT GGTGTCTGCC GGGAAGCCTA     600
AAATAGGGAT ACGGCGATGT AGCAAGACCA AAGGAAACTA TTTGGTTTTC TGAGAGATGG     660
CTGACCGGGC GGCCAAGCCT GTCACAGAGT CGAAGATCTT GCACTCGAAG T              711
```

(2) INFORMATION FOR SEQ ID NO:665:

(i) SEQUENCE CHARACTERISTICS:
        (A) LENGTH: 736 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1444RP (xi) SEQUENCE DESCRIPTION: SEQ ID NO:665:

```
GATCTGGTTT TATAGGTTCA CGAAGGGACT CTGGACGCGG ACCCTGCTGA AGTGTGCCAA    60
CATGCTGTAC TTCGTGGCCG TGATGCATTT CTACGACGAC TACGAGCACG CGCCGGTACT   120
GAAGAACATT GGGTACTCGA TCTTTATTCT GAGCATTGGG ATGAATCAGG CACTGCATCA   180
CGGCGGGCGG CTATTCAGGG GGCGACGCCG GCGGCGGTCC TGGTGGTGGC GGTCCGACAC   240
ATTTGTGCTG CAGCCCGCAC TATATATCAG CCAGTTCTAC CTGCTGCTAC TGAATGTACA   300
GAACCCGAGC TTTCATTCGA CGCCGAAGCT TGACATAATT AATCGCACGG TGCTGGTGGC   360
CTACGTGCCC CTGGCGCTTC AGTGCTTTCG TCGGCAGCTG ACGAGCTAAG TCACTCGGGC   420
AGGAGCTGCT CCGTGAGCTC GTGTGCTATG CGTGCGGCGT ATTCGTCAGC GGCATGAACA   480
TCTGTTATCT CTAAATAGCG TTCTCTAGCT TGCTTAATCC TGGTTACCAC ACTGTCGAGC   540
GGTATATCTG CCTGCAAGGG ATCCAGCTCT GCGAAGGCTG CAGCGGTCGA CGCGTGCATA   600
CGCAGCATAC GCTCGCTCCA GGGGATGGAT ATCCAGCAGC TCGCGCACAC TTCCCGCCCC   660
TGCTGTTCCC CCAGCTCGTT TGTGCCGCGC TCGCGCCATC TGAGAAGCGC ACGTCGTGCA   720
CTTCGAGGGC ACGCTC                                                  736
```

(2) INFORMATION FOR SEQ ID NO:666:

(i) SEQUENCE CHARACTERISTICS:
        (A) LENGTH: 709 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1444UP (xi) SEQUENCE DESCRIPTION: SEQ ID NO:666:

```
GATCCAAATA CATCCGGTAT ATATGCTACT TGTGCCAGAA GACATGAAAA GCAAGCATCA    60
AGGGAGCTAA TGAGCATTCT ACAGGAAAAG GCGGAAGAAT ACTACGTTGA TGAACTCAAA   120
GCTATCGCAG AGACTGAACT CTTGAGCGAC AAAGAAGATG AAGAAGAACT ATCTGTGGAA   180
GAGCAGGTGC AGAAAGAGCT AGAGCAATTG AAGAAAGGCA GTGGTCCTGT GGATACCAAA   240
AAGAAACCGG TCCTGCAAGA GATTCAGTTG GGATGTGAAT GTATGGTCTT CATCAAGACT   300
AGAAGACCAA TCAAGCCGGA ATGCTTTGTC AAACGCCTAG TACAGGAACT TGCATCGTCA   360
GAAAATACTA CCAAGGTTTC GCGGTACGTC CAGAGATTGA CACCCATCAC TGATTCCTGC   420
AATGCTAGTC TAACAGAATT GGAAAAACTC TGCAGAAGGG TGCTTGCTCC TCATTTCCAT   480
ACTGACAAAG AGATAAAGTA CAAGTTCGCG GTCGAGGTGG TAAAACGTAA CTTCAACACG   540
ATAGACAAAA TGGATATCAT TAAACTTGTG GCGAAGGAGG TCGGTAAGAG TGGGGATTGG   600
GGGCACTCTG TGGACCTAAA GGACTACGAC AAGCTGGTCA TCGTGCAGTG CTATAAGAAC   660
```

```
AATATCGGCA TGTCTGTGGT GGACAAGGAT TACTCTGTGG CTCTTAAAA              709
```

(2) INFORMATION FOR SEQ ID NO:667:

(i) SEQUENCE CHARACTERISTICS:
        (A) LENGTH: 717 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1445RP (xi) SEQUENCE DESCRIPTION: SEQ ID NO:667:

```
GATCATCTTC CGAACATACT CGAGGGAGTT CGCGTTCGGG AAGTTCTTGT ATCGTTGCAT   60
GTAGTGGAAT TGCTCGTAAT CGTCTGTAAA TAGAAAATTG GCGTCAATCA TGTTGTCCCC  120
GTTGGACGCG CCGGAAATGA ACATGAACGG TGGCAGCCCG TAGCGCACCT TCTGGCCCCG  180
GCACGCGCGC AGAATCGCAT CGTTGGTGCG CAAAATATCG CTGTACGCGA CCGGCATCTT  240
CTCTTCTTCG ATGGGCTCCA ACACCGCCAT CTTCAACAAC TCGCGCCCAT AGCTCATCTC  300
CATCTCCCGC GAGAGGAGAT TGTAGTGCGC CTGCGGGGGC CGACTCGTGC CCGACTGCTC  360
CGAACGCAGC AACGTCGACG TGCTATTCAA GCTAGTGTTT GAAAAGTGCA CATGCTCGTC  420
ATACGAGGAA CAGCTGAGCG CCATCTCGGT CACGCTGAGA AGGTACTGTT CTTCCCGCGT  480
GTACAAAGAC CCCGCCTTGT ATGTCGAGCC TCTGGTGCAT TCCATTGGTG TCGCCATTGC  540
TCTGGCGCAG CCTGATACAC TCGCCGTCGA AATACTACCG CACCACCGCA CGAACGACCT  600
TTCCGCCATT CTTTTGGTTT ATAAAACCCG ACTACGCATA TATTTCATCC TGCTCTGGCA  660
TGTCCCGATG CCGTCCTCCG TGTGACATAG CTGCTTATTC ATCCTGGGCG TTCATTT     717
```

(2) INFORMATION FOR SEQ ID NO:668:

(i) SEQUENCE CHARACTERISTICS:
        (A) LENGTH: 717 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1445UP (xi) SEQUENCE DESCRIPTION: SEQ ID NO:668:

```
GATCCTTACT GACGAGGAAG AATCGAGCAA TAAAGTTGAC GCCGCTTCGA GCTCTAATAG   60
CGGTAAGAGC ACCGCTAGTA AACGTCCAGC CAAAACTAGG AAGCCTAAGG CTGACACTGC  120
GGCTACGAAA AKCGGAACCA CCTCCCGGAT GCCCAAGACT GCTGCTTTGC AGGCGCTGCT  180
GAACAAGAAA AGGGGGGCTT CGGCAGAATA GACTACTGGT AAACGTAAGT AATAGTATAA  240
ACTTGGTTTT TTAATCCCTG GCTATCTCAG ACTGCTAAAG CATGGCCGTT TAGGTGTGGC  300
CTCCTCGGTA GATGGTTTGC ACCACGCAAG GTGAAAAAAA GATCACCAAC CCTGAAAAAC  360
GTTTAACACT TGTCAATCTC TAAAGGCGCT GCAATCAAGG CATATTACCA TTGTGGAGCC  420
ATGAATCTTG CCAATGAACC GAAGTTCCAA ATACAAGTTG ATGAAACAGA GGATACAGAG  480
TGGAACGATA TTTTGAGGCA GCATGGTGTC ATCCCAGAAC GGCCACCTTC ACCGACCGCA  540
CAGCTCGAGG AAGCGCTCGA GGAAGTGCTA CNGAGACCAC ACGAGAATAG ATTAGAGAAC  600
```

| AAAGACTCTC TGAACTGGAG GACTGGAAGA TGAAGAAGAT GATGAATTTT TGGAGTTTTA | 660 |
| CCAACGTAAG AGAATGGCAG AAATGCAGAA GCAACAAAGA AGCGCAAGTA TGGGGAC | 717 |

(2) INFORMATION FOR SEQ ID NO:669:

(i) SEQUENCE CHARACTERISTICS:
        (A) LENGTH: 775 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1446RP (xi) SEQUENCE DESCRIPTION: SEQ ID NO:669:

| GATCTGCAGG CTGCTACGGA GGAACTCGTT TCCGAGGTTG CTCGCCTGAG TAAAGACCCA | 60 |
| AACTTTCCTA GCATTTTCGC GCAGGAGCTA CAGAAGCTTA CTGGTGAGCC CCATATAGGC | 120 |
| GGCAAGGTGG ATGATATAAC GGTAGTGATG GTGAAGGTAG ACTAGTAGAT TGCACATATG | 180 |
| TAGAATTACT AATATCATTC GAATTTCTGG CTTAAGACAA TGTTCTTAAT CCGCTCTCTC | 240 |
| TCGCTCTTCA ATCTCTGCTC GCCTTCTAGT ACGTCATGAA CAAACTTGAC GTCGGTCGGC | 300 |
| AGGCATATCG GGCGGAGTTG AGTCCGCTTT CCTGATTTGC TGAGAAACGT AAAGGGCACC | 360 |
| TTACCCGCTT CGACTTTTGA TGACAGATTG CTGTTGACCT GTGTGCTGGT CCCAGATCCA | 420 |
| ACGATAGGAA TGTTGTTCAT GGGGATTTTC TCATTCTTGC GGGATTCTAA AGATTGTTGC | 480 |
| ATCACAGCTT GGTACATCTT TTCCATTTCA TCTTCTGCTC TCCGCTCCTC CTCCGACTTT | 540 |
| AGCTTTCTTT CGTATTCTTC GTTTATCTTT TTGCGCTCTA GATCTCTGTC AATAGTAAAC | 600 |
| ACGTCTGTGT CGTCGTCAGT ATCTTCTTCA CTTTCACTGC TTGACGGGGA ATCACTATCG | 660 |
| TCGTCATCCT CATCGTTATC TTCCTCTGAT AAGTGCTATT AACGTCTTCT TCTTCTACCT | 720 |
| CGCTGGAGTC GGCACTGTCT CCACTACTAG ACTCGTAGCC ACTATCTTCG TCCTC | 775 |

(2) INFORMATION FOR SEQ ID NO:670:

(i) SEQUENCE CHARACTERISTICS:
        (A) LENGTH: 631 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1446UP (xi) SEQUENCE DESCRIPTION: SEQ ID NO:670:

| GATCAATTAC ACTACTAGCA ATCTACTTTT CAACAATCTG ACTGTCCGCG AGGTTAAACT | 60 |
| CTACCGTGAA CAGCTGATGG TACTCAAAGA GCAGAGGTTT ATAGTGGAGG GCATGCTCGA | 120 |
| GAACGCCAAG AAACAGCGGC GTTTTGAAGA GGTTAATACG TTAAAGGAAA ATACCAAAGA | 180 |
| GCTAGACAAT CAGATAGCCC AGCTCGAAGA AACCCTAGGC GACCAGGGTT TTGTTTAGTA | 240 |
| TCTAGCATGG AGTTTTTTGC TTAACTATAA TTACTGTGTA GATGCCGCAG ATAGCATGTC | 300 |
| GTAGCATAAT TGCGAATTTT CACCAACATG AAAAAGTGTA TGTGTATAAG GCATCCAGTG | 360 |
| AACTCCTAAC ATGCTGATGA GGTTTTAAGT AAAGATATCA CTAGCAATGA ACGTAAGTGC | 420 |
| AGTTTTTGAG CTTTATGTCC TCTGTAGAAC ATAATATTAA CGACAGGGGG ATAGGATGAA | 480 |
| AGAAGACAGC AGTTATTTGA GCTGAACAGT GAAGCCTGGT CTGGAATTGA TGCGTTCCCG | 540 |

```
AATAAAACCA GCAAGCTTGA CTCAAGCATC AAGAGAAACA CAGGGTTTAT CAAAAAGCTG      600

AAACAGGGTA TCACGAAAGA CTCGAAAGAT C                                    631
```

(2) INFORMATION FOR SEQ ID NO:671:

(i) SEQUENCE CHARACTERISTICS:
        (A) LENGTH: 703 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1447RP (xi) SEQUENCE DESCRIPTION: SEQ ID NO:671:

```
GATCCAGGAT GATGAATTTG ACGAGGAGGG GGGTGCAGAA GAGAATGACG ACTACTCACG       60

GTTTAAAAGA TCCTGCATGT CCTCCCACGT CCCCGCGTTG TAGTAGGCAT AGCGCTCGTG      120

GTACGCGCCG TGCGCCATGG CCGGCGCCAT GGGCGCGGGC CCATGCGCCC ACCCCGTGGC      180

GTACATGTCG TACATCCGGC GCCGCGACGC GTCCGAAAGC AGCGCGTAGG CCTCGTTAAC      240

CAGCTTGAAG CGCCGCAGGC GTTCGTGCTC ACCCAGCCCC TGTTGGGCAG CCCCCGCCGT      300

GTCCGGGTGG TACAGCTTCG CGAGCTCGTG GTACCGCTTC TTTAGCTGCC GTGCATCGAC      360

GCCGGTCTTC ACCAGTCCCA GTACCTCGTA GGGCGTCGGC TGCTTGCCCT GGGGCCACGA      420

TAGCCCCCCC TGCCACCCGG CGACGGTGCT AGCGCACCGC ACCGTACTCC GACCTGACGC      480

TGTAAGCGAG ACCGCCAACG TGCGCCAGTC CTGAGCAGTG CAGTCGGACG CGACAACATA      540

ACACTTAAGC TCCTAGTTAA CGCTTTGGCG ATGGAGATCT TGTCGGTGCA TGCACATATC      600

CAGGACGCCG CTCCGCCTCC GCTCGACTGC TGGCCGTCCA GGCTCCAGTT GGCGCGCTTA      660

GCCATATCGG CGAAAAAATA AAGTCCTGCT CGAGGCGCGA TGA                       703
```

(2) INFORMATION FOR SEQ ID NO:672:

(i) SEQUENCE CHARACTERISTICS:
        (A) LENGTH: 684 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1447UP (xi) SEQUENCE DESCRIPTION: SEQ ID NO:672:

```
GATCCAGCAG ACGCTCCGGC TGGCTGTTGG AGATGCACTG GCTCTTCGCG GCCGAGTGGC       60

GGCAACGCGC CCGCCGGCGC AGACGCGCCC GCCGCCGCGC CGTGCGGGTA CATCCGCACC      120

AGGTTCTGCA GCTCAAACTC CAAGGCCAGC TTGTTTCTGT TCTTCTTGCG CTTCGGCTTG      180

TACTTGTAGC CCGGGTACTT CTTCGCGTGC TCCTGCTKCT CCAGTTCCGC CTTGTCGTGC      240

CACTCCTTCT TCTCCTCCGC CGTCAGTTTT TTCCACTGGT AGCTGATGAT CTTGCTCACC      300

TCGCAGTTGT GCGGGATGTC CTGGCCGGAC TGCTTCCAGT AGTCTGTCAG CAGCTTCTGC      360

TGGTGCGACC GGAACAGGAT GAACGCGTTG CGCGGCCGCG GGATGTGCTG CTTCTGCTTG      420

TAACCAGCGC GCCCGCGCCG GCCTCGCCGG CCTCGCCGTC CTCGTCCGCC ATCCTGGTGC      480

GCTGCCACTC CTCGCCGCCG GGGGCTGGT GCGAGAAAAA CTTCTGTGCC AGAGGCGCTG      540
```

| | |
|---|---|
| CCGCGCTGCC GCTGGCTCGC CGGCTCGTCC GCCGCGGCTG CGCGTTGCCT GCGTTGGTCA | 600 |
| AAGGCAACAA TTGCCCGGAT CTCCCGCCGC TGCTGGCGCT GGTGTACGAT CCGTGTGATG | 660 |
| GTCAGCTTCT GCTCCAATCA CAGA | 684 |

(2) INFORMATION FOR SEQ ID NO:673:

(i) SEQUENCE CHARACTERISTICS:
        (A) LENGTH: 718 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1448RP (xi) SEQUENCE DESCRIPTION: SEQ ID NO:673:

| | |
|---|---|
| GATCCGCTAC GTATACAACG ACATATTGCT ACGTATCGAA TGTGATGTGA CAACATGCAA | 60 |
| GATTCTCAAC AACAAGCGCA AGTGGTTTAG TGGTAAAATC CATCGTTGCC ATCGATGGGC | 120 |
| CCCCGGTTCG ATTCCGGGCT TGCGCATATT TTTCACAACA TGCACACACT GTGTGGCTAT | 180 |
| CGAGACGGAG TCCACTACGA GCATCGTCAT TTTTGTCTAT AATTTACAAG CATATTGTAA | 240 |
| CTATTGTGTC ATTGATCTAA ATGTCGAGTC GATAGAATCC TTCAGCTCCT TGTAGCTAAT | 300 |
| GATAATGCAG TTCATCTCGT CCGGTGTCAC CAAGATTATC TTTTCAGATA CGCCGGTGTC | 360 |
| GAGTTTGTTC AGGCACCGGA GTACGTGGGT GAGGTCCATC ACGGATTTGC CGTTCTCGTC | 420 |
| CACCTGGTGG AACACGTAAT CGTAGAACAG AATGATGGGG AACTTGTCCC CCGCCTCAGA | 480 |
| CCAGTGGATG TCCATGCTGG ATTCCATCCT ACCAAAGATG AAATTTAGCT TGCACATGAG | 540 |
| CCTGAAGAGC CTGCCATTCT CTAACTCCCG CGACAAGTGC TGCTCGATGT TCTCCGAGTA | 600 |
| GGTCTGCGAC GAACTGATTA TGTCTAACAT CTTGTGGCTG AACAGGGCGG TGAACTCCGC | 660 |
| AATCGTCTTC TTCTCGTCCG ACAAAAGGTA CGCCAGCACC CGCTTGAACA GCGGGTCG | 718 |

(2) INFORMATION FOR SEQ ID NO:674:

(i) SEQUENCE CHARACTERISTICS:
        (A) LENGTH: 724 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1448UP (xi) SEQUENCE DESCRIPTION: SEQ ID NO:674:

| | |
|---|---|
| GATCTCGCCA GCGCTGGCAT CCGCAGCGCC GCAGGCGCCG CGCGCGCGCG CGCGGCCGCG | 60 |
| GCCACTGCGC CACAATGCTG TCCCATAGCC CTCAACATCC CAACTAGCTA GTCACCTTGT | 120 |
| GCAATCGGTC TACCGATGGT GTGTGCGGCG GGGACAAAGC CGTGGTGAAA CGGACACTTT | 180 |
| TCAAAATGGG CTGATCTGCA GCAGTACACG ACCGATGAGC TGCGCGCACG GCGACAGCAG | 240 |
| TCGCGGTTCG GCGCCTGGCT GCGCATAGGG AACTTACGTA TAGTATAGAA GGGCCGTCTA | 300 |
| CTTGGCGTAG GCAGCGAGGA TGTCGTCGTT GTAGCGGAGG TATTTGCCGT TCGCGCAGTC | 360 |
| CGGGATGCCT CTCAGCGCCA GGTTGGCGAA GATGGTGGCC GGGATCTGCG GGTCCAGCAG | 420 |
| CTCGCTGTTC TTCTTGAGCT CCGTGAAGCG GCGCAGTGCC TCCGGCGCCA TGCGATGGCC | 480 |
| GAACTTGTCG CGGATGTCGT TCTGCATCTG CGTGTCGACC ACGCCCGGCG CCACGGCGAC | 540 |

```
CGCGCGCACC GCAGGCTCTT CCGCGGCCAG CGTCATCGCA AAGTGGTTCA GCGCGGGCTT      600

CGACGAGCCG TACGCGCCCC ACGCGGACTG TCTCCGAGTT AGTAGCTGCC CCTGCCCTGC      660

TCTGCGTCGT ACATACATAT GCCTTCGTGC TCGCGCCCGA GCTCACGAAC ACCACACTGC      720

CGCC                                                                  724

(2) INFORMATION FOR SEQ ID NO:675:

(i) SEQUENCE CHARACTERISTICS:
        (A) LENGTH: 697 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1449RP (xi) SEQUENCE DESCRIPTION: SEQ ID NO:675:

GATCCAAAGA CCGCGTGCTC GCACTTCCAC ATGTCTCCAA GCTGGACGCG AACAACGATA       60

TCTTACTGGC GGTGAAAGAA AGCCCGAATC ACAAATGCCC ACGATGCTGG AAGCACGCAT      120

CTCCCGAGGC CGACGCTCTA TGTAATCGCT GCGCCAGAGT CCTCCAGTAA GCCAAACCTG      180

AATTTTTCAA AAATTGAAAA CTTCACCATG GCTCACATGC TGACTGCTTT AATATCCTGT      240

AAATACAACC GGACTCTGCA GGTCGATGCT CCCTCACCTG GCCCCCAAC TCTCCCTTGT       300

ACCGGGTCGC GGCGTCGCTG CCTCATTCCG CCTGCATCTC GCTTCCAGAG GCGGCGCTTC      360

TGGGGTGCGC GCGCGCCTGC CGGCATTCAT CGCGCGCGCC TACGGCAGCC CACCGGGCGA      420

CGCGAGGCAG ACCCGCGCGT GGACGTACCT CGCGCGCTCG CGGCTCTTCC AGCGCCTTTA      480

CGCGCGCCCT TCGTTCGCCG CGTACATCGA CCGTCTGCTG GCCAACGGGC CGGTGCCAAC      540

ACTCGCCGCC TTCCTGCTGC TCCATGAGGC CACCGCCATC GCTCCTCTGG CGCTGCTGTG      600

GTGGGGGTC TACAGCTGCG ACGTGGTGGC GCTGTTGCCG CAGGGCCTGC TTGACTACCT       660

GGCCGAAGCA CGCATCCTGC CGTCRAGAGG TTCGTGG                              697

(2) INFORMATION FOR SEQ ID NO:676:

(i) SEQUENCE CHARACTERISTICS:
        (A) LENGTH: 715 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1449UP (xi) SEQUENCE DESCRIPTION: SEQ ID NO:676:

GATCGGCTCA ATGGGTTGCT GAAGCCGTGT CTTTCGTAAG ATGACCTCAA CTTAAAGGCA       60

GGCTCTCGAT ATCTCGTTTC TTTTTTTAAC AGGTGAGCTT TGGAAAATTT TTGGTTCTCA      120

GCTCATCTCA TCTACAATAG TATGTCTAGC ACGCCAGCAA AGCTTGCGTA ACCGCTCTAT      180

TCAATATGAG TAAGCAGGTA AATGATACTA GCAAGAATGG TCTTGACCTA AAGACGCTGT      240

TTGTCCGGAA TATTCCGTTT GATGCTACGG ATGCAGAGCT GACAGACTTC TTCTCGCAGT      300

TTGCACCTAT TAAGCATGCT GTGATCGTAA AAGATAATGC GGGCTCGAGC AGAGGGTTTG      360

GGTTTGTGTC GTTTGCTGTG GAAAGTGATA CACAGGCTGC ATTGGACAAG GGACGGAAAA      420
```

```
CACAGTTCAA GGGCCGTCTT CTGAGGGTGG ATGTTGCCAA AGAAGAGAA CGTTCGAAAA      480

AAGGCGATGA GGCCGAGGCA CAGACCTCCG CGGAGGACGC GGAGAAGCCG ACTACTGCTC      540

CCGAGGGTGA CGAGGCGCTC ATGCGGGGCA AGCCCAAGCT GATCATTAGG AACATGCCGT      600

GGTCCTGCCG CGACCCGACC AAGCTGAAAA AGATCTTCGG TAAGTTCGGA GTGGTTGCGG      660

AGGCTCCATC CCGCGCAAAG CGGATGGAAA GCTGTGTGGG TTGCATTTGT CACGA           715

(2) INFORMATION FOR SEQ ID NO:677:

(i) SEQUENCE CHARACTERISTICS:
        (A) LENGTH: 705 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1450RP (xi) SEQUENCE DESCRIPTION: SEQ ID NO:677:

GATCAATTCT GTCTTGAAGT AGGTATTAAT CAATGGGTCA GGCTGGGTGG AATTGCTTAC       60

AAAAATACCA ACCCAATCAT CTTGTAAGTT GGTGAGCGAT ACGTAGACAA TTTGCCTCAC      120

ATCAATCTTA TAATCGACAG CATAGGTGAG TTGATTATTA ACCAGTGTCT TTCCGATAAT      180

GTAGAAATGG GATGGCGTAA GTATAAAGGT TTTGGGTAGC CTTTGGGCCG ACCTACCAAA      240

TTTTGAATGT AGCGCTTGCC CATTGATAGA GAATACGACA TGATCATTAA TTCCAGCTTT      300

CCTTTTGACA AACGCACCCT TCGATTTCAG CTCATTACAA GAAAGGTAGT CTCCCAGGAA      360

TGCCCTGTAA CCTAACAAAG ACATTGCACG CCTCTCCTTT CTGCCACCCA ACAACTTGTT      420

ACCGTAATCC CGGAGTTGTT CGAATTGGTT CCCATGTTTC ATCTCACGGA TAGCACGCTG      480

GATACGAATC GCAGAATCGA TACGCCGTTG TAAAAACCGC CGCCAGGCTC TCTGAATGCG      540

AGATGCCATA TTATGCCAAT ACTTATCCCT CATGTTTTCC AAAGCAAACA AGGTCTCAGG      600

TGTTTTAATA AATACCTTCG TTACACCCAA CTGATATTCA GTCACAGGAA TTGAAGTATC      660

TCTCAAAATT AAATTGACAG CATCTAAGGT ATTACCTTGC CATGT                     705

(2) INFORMATION FOR SEQ ID NO:678:

(i) SEQUENCE CHARACTERISTICS:
        (A) LENGTH: 699 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1450UP (xi) SEQUENCE DESCRIPTION: SEQ ID NO:678:

GATCGCAAGT TGGAAGAGCG AGTATCCATA TGATTACTCG CGCGAGACGC CCGGCTCGCG       60

CATCAAGCCT CAGACAGTTA TCACTCGGCT CTCCGAAATC GCAAACGCCA CCGGAAAGGA      120

GGTCATCGTG ACGACCGGTG TAGGTCAGCA CCAAATGTGG GCCGCCCAGC ATTGGACGTG      180

GAAGAAACCA CGCACATTTA TCACATCAGG CGGCCTCGGT ACCATGGGCT TGGTCTACC       240

GGCGGCCATT GGTGCCCAGG TAGCCAAACC CGATGCGATT GTCATCGACA TCGATGGCGA      300

CGCCTCGCTC AACATGACCT TGATGGAGAT GTCCAGCGCG GTGCAGGCGG CGCCCCAGT       360

AAAGATATTG TTGTTGAACA ACGAAGAGCA GGGAATGGTC ACTCAATGGC AGTCTCTATT      420
```

```
CTACGAGCAT CGTTATTCTC ACACCCATCA GCTAAATCCG GACTTCGTCA AGTTGGCTGA      480

TGCAATGGGG TTCAAAGCAA TGCGCCTAGA GGCGCAGTCG GACATGGAGC CCATGCTGCA      540

GGAGTTTATT AATTGCAAGG AGCCCGTGTT ACTCGAAGTG GCCGTCGAGA AGAAGGTTCC      600

CGTCCTCCCG ATGGTCCCTG CCGGTAAGGC CTGCATGAGT TTATCTACTT CGACCCAGAG      660

GTCAGCGACA GCAAGCGGAG CTTCGCAGCA GGCGTACGG                             699

(2) INFORMATION FOR SEQ ID NO:679:

(i) SEQUENCE CHARACTERISTICS:
        (A) LENGTH: 708 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1451RP (xi) SEQUENCE DESCRIPTION: SEQ ID NO:679:

GATCTTGGTG GTAGTAGCAA ATATTCAAAT GAGAACTTTG AAGACTGAAG TGGGGAAAGG       60

TTCCACGTCA ACAGCAGTTG GACGTGGGTT AGTCGATCCT AAGAGATGGG GAAGCTCCGT      120

TTCAAAGGCC TGATTTTCCA GGCCACCATC GAAAGGGAAT CCGGTTAATA TTCCGGAACC      180

TGGATATGGA TTCTTCACGG CAACGTAACT GAGTGTGGAG ACGTCGGCGT GAGCCCTGGG      240

AGGAGTTATC TTTTCTTCTT AACAGCTTAT CACCCCGGAA TTGGTTTATC CGGAGATGGG      300

GTCTTATGGC TGGAAGAGCC CAGCATCTAT GCTGGGTCCG GTGCGCTTAC GACGGCCCTT      360

GAAAATCCAC AGGAAGGAAT AGTTTTCATG CCAGGTCGTA CTGATAACCG CAGCAGGTCT      420

CCAAGGTGAA CAGCCTCTAG TTGATAGAAT AATGTAGATA AGGGAAGTCG GCAAAATAGA      480

TCCGTAACTT CGGGATAAGG ATTGGCTCTA AGGATCGGGT AGTGAGGGCC TTGGTCAGAC      540

GCGGCAAGTG TGCTTGTGGT CTGTCCTCGG GGGCTTGCTC CTGGGACGG ACTGCTTGCG       600

TGCTCTGTCG TAGACGGCCT TGGTAGACCA TCTCTGGTCG TCGCTTGCTA CAATTAACGA      660

TCAACTTAGA ACTGGTACGG ACAAGGGGAA TCTGACTGTC TAATTAAA                   708

(2) INFORMATION FOR SEQ ID NO:680:

(i) SEQUENCE CHARACTERISTICS:
        (A) LENGTH: 722 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1451UP (xi) SEQUENCE DESCRIPTION: SEQ ID NO:680:

GATCCCTTAG CGACTCTCTC CACCGCTCGA CGAGGCCATT GAGCTCTTAC GAACTGCACA       60

AACCTACTCG AACTCTGTTT CCAGACTTCT TTCTGTTTGT CTTCAACTGC TTTCGCATGA      120

AGTACCCCCC AGGCTATTTT TCTTACCCGC CTGGTGTTTG TCTATATACC CGGTTGTATT      180

TTTGATAAAA AACTCAGCTC TTCCTCTACG GCAGAAATAT ATATCCAGTC CTTAGCGCCA      240

TGCGAAAATC TGCCTTTTTA CCGCTGTTTC TCCCAGTCTT AGCACTGGCA GAAAAAGAT       300

GTATGGCGTA TAGGCGCTGG CCCCGCGGAA AAAAAAAAA AATAGAAAAA TAGAAAAATA       360
```

| | | |
|---|---|---|
| AAAAGACGTG GGCCGCCCCG CGGGCAGACG AAGAAAAAAT AGGCGCCCAC CCCTCCAAGC | 420 |
| AGACGACAGG CGAGACATAA TAAAATCCCA CACCAAGGGA AGAAAGTCTT GTGCACGCTC | 480 |
| CCGGCCTCAT ACGCTGCCAT TCTGTTCCAT CCGGCTTGCA AACCCAGTAG TGGCATGTCA | 540 |
| AAGCATTGCT CCGACGCTCC GCTGCCTTGC AGTCGACATC CTCTTCCTAA CCCCAGCCAG | 600 |
| ACTTCCCATA CTTTGCACTT CACATAGCAT ATCACTTTTC AGATCACTAC GTGACATTCG | 660 |
| GTACGGAATG GCACTCCAAT GCCGACAAAC CTCTTCCTAC CCCGTGACTT ACCCCGATGT | 720 |
| GC | 722 |

(2) INFORMATION FOR SEQ ID NO:681:

(i) SEQUENCE CHARACTERISTICS:
        (A) LENGTH: 719 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1452RP (xi) SEQUENCE DESCRIPTION: SEQ ID NO:681:

| | | |
|---|---|---|
| GATCAAATGT GGCTCTACAA GGGCGGAAGT GGCAGAGAAT ATTAATGAAT CAGTTCCGCT | 60 |
| GACATATTTG TATTGTCACG GTATTCCACA TTCCTTTGAG TACGTATGTC CGTCTAGGAA | 120 |
| TGGCTGGCTT AGTAAGGCTT AATATTAACT GAAAAGCGCA GCAGTGTAAT CCATCTAGTA | 180 |
| ACTAACACAT ATCCATTAGC ACATGTTTCG TTCAGTACTA CGTCATTCTT ACGCCGTCCC | 240 |
| TACTGTGAAT TACACATGGT CCTCGAGAAG CCTCATAAGA TTCTTCACTA GCGATGAGAA | 300 |
| GGCAGCTCCT CCATCGCTTC CGAGAGAAGA GCAGAAAGAG TTCGAACGGC TTCAGAAGAT | 360 |
| TGCACAGTCA CAAGCTGCCA TCGACGAGTA CAACAGACAG TTCGAGAATG ACCATACGAA | 420 |
| GGAGTCAGCG AACTCTCCCA TCCTCAAGAC AGAAATAGGC TCGTTCTCAC CGGAATTCAG | 480 |
| CAAGACGTTG CCAGAGTTCG AGGGCGACAA GAATCCCGAG ACAGGGGAGA TTGGCGGGCC | 540 |
| GCGCCAAGAC CCACTGCGGT ACGGGGACTA CTCATACAAC GGCCGCGTGA CGGACTTCTG | 600 |
| AGGTATAACT TGTGTTTATA TGTTTGCAGG TTGGTTAAAT ACATAGCTTG CGCTCCAACT | 660 |
| CTCTCGCAGC TGCAGACAGG TTGTCGGTGC ACTCCGTGAT GAATTTCGAG TCCAGCTTT | 719 |

(2) INFORMATION FOR SEQ ID NO:682:

(i) SEQUENCE CHARACTERISTICS:
        (A) LENGTH: 718 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1452UP (xi) SEQUENCE DESCRIPTION: SEQ ID NO:682:

| | | |
|---|---|---|
| GATCACCAAC TCTACAGCAA GAAATCCTAC GCCCAGCAAA AGCTGTCCTC GATGTTCTTC | 60 |
| TATTCTGTAA ACAGTTTGTT ACTTCTGGTC GCTTGTATCT GCATGCGCTA TCATCTTTTC | 120 |
| ATCTGGAGCG TTTTCAGCCC GAAGTTGTGC TACCTTCTGG GCTGGAACAT CCTCATCCAC | 180 |
| TTTCTCACTG AGACGGTGCT TGAACCTTTC TTGCTCATGG TGGCGGGCTG ACTGTCTCTA | 240 |
| GTTCCACTTG TATAATATTC CTTCATCAGT GAGAATCTCA TAGTATTGTC ATATATTAGA | 300 |

```
TATTATCTAG GTCATGTTTT AGAGAATAGG TCTCTTCCGA AAAAATTGGC TACCACTGCC      360

AATCATTACA TGTCAGAACC GACCATCTCC AAGTGTCGAA CCGTCCCCAC TGCAAATGCT      420

CTCACTTAGA TCCAGCTTCA GACGCTTATT TTCTGTTTCC TGCAGGGTTT ATGACCAGCA      480

GGCGCAGAAG GCCGTGTCTT CCTGCCCGGC TGGCACACCG CTGAATCTGC TTATAAAGAA      540

GGGCGGGAAG GAGCCGTTGG CTCTCGAAGA TCCGACTACC CGAGTGGTTA TGGAAGGTGC      600

TTGACCTGAG GCGCAAGCCG CAAAGCTGGC AGAGGACCCA TTAAAGCGCG GAAGAAGGCT      660

CTGCGGCGGA TGAACAGAGA ACACATCCAG CAGCAGAACT TCCTGGCGAA GATGTGAA       718
```

(2) INFORMATION FOR SEQ ID NO:683:

(i) SEQUENCE CHARACTERISTICS:
        (A) LENGTH: 724 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1453RP (xi) SEQUENCE DESCRIPTION: SEQ ID NO:683:

```
GATCTTAATT TAAAATTTTA ATTAACTATT TATAATTTAG AAATATATAA TCTAGAGATA       60

TATAATCTTA AAATCATAGG TAAAAATACA TAAGATAGTA AGAATAAAAT TAGTAAAATA      120

AATAGAAAAC CATAAGTTAA TTGATTCATA AGAAAAATG GAATTATTTG TGGCATCTTA       180

ATTTTTATTA TTTAATTGAT TATTATCTAT TTAACATAAA ACATTTTAAA ATGTTATAAA      240

ATAAATAAGA AATTACTTAT AGAATATTTA TTAAATAGTA TTTAATTTAA TTTTAATATT      300

AAATATACCA TTTTTATTAA TAAATAGATT ATTAAGTTTA TTAATATTAA GTGATATATA      360

ATTTAATTTA TATAAATTAT TTAATTTACT TCATTGATAT ATATAATTAT TAAATGTACC      420

TTTCATAATA TTTATTTTTA TTAGTCTAGT AATATTTCTA TTTAATAGTC TACCCTTTAA      480

TTGGATATTA CTACCTACTA AATATTTACC TAATAATATA TTATTAAGAA TACTTAAATC      540

TAATAATTTA TTATCTAAAG TATATAAATT AATTAAATCT TTTTTATTAT TATTTAAATT      600

ATTATTAATT AGTAAATTAT ATTTATTTAT TTTATTAACA TAATTTTTTG ATAATAATAT      660

ATCATAATTA AATGGTAATT TATTAATAAT TATCTTTAAT GAATTTAATG ATAAACCATT      720

ATTA                                                                   724
```

(2) INFORMATION FOR SEQ ID NO:684:

(i) SEQUENCE CHARACTERISTICS:
        (A) LENGTH: 732 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1453UP (xi) SEQUENCE DESCRIPTION: SEQ ID NO:684:

```
GATCAAAATT TCAACAATTT CCATTTCATT TAGTACTACC ATCACCATGG ACCAATTGTT       60

ACATCATTTA GTTATTAGG TTTACTATTA ACTTTAGCTT TTACTATACA TGGTATTATT      120

GGTAATATTT ATCCTTTATT ATTATCTTTA TTAGTAGTTT TATTACTAAT AACTTTATGA     180
```

-continued

```
TTTAGAGATA TTGTAGCTGA ACTTACTTAT TTAGGTGATC ATACTTTAGC TGTAAGAAAA    240

GGTATTAACT TAGGTTTCCT ATTATTTGTT GTATCTGAAG TATTAATTTT TGCTTCTTTA    300

TTTTGAGCTT ACTTCCATTC AGCTATAAGT CCTGATATTC TATTAGGTAA TGTTTGACCA    360

CCAGTAGGTA TTGAAGCAGT TCAACCAACA GAATTACCAT TATTAAATAC TATTATTTTA    420

TTAGCATCAG GTCTAACTAT TACATATAGT CATCATGGTT TAATTGAAGG TAATAGAAAA    480

CATGCTTTAT CAGGTTTACT TATTACTTTC TGATTAATTG TTACATTTGT ATTATGTCAA    540

TATATTGAAT ATAGTAATAC ATCATTTACA ATTACAGATG GTATTTATGG TTCAGTATTT    600

TTTGCTGGTA CTGGTTTACA TTTCTTACAT ATGGTTATGT TACTAATTAT GTTAGGTATT    660

AATTATTGAA GAATAAGAAA TTATCATTTA ACATCAACAC TCATGTAGGA TATGAGACTA    720

CTACTATTTA TT                                                       732
```

(2) INFORMATION FOR SEQ ID NO:685:

(i) SEQUENCE CHARACTERISTICS:
        (A) LENGTH: 714 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1454RP (xi) SEQUENCE DESCRIPTION: SEQ ID NO:685:

```
GATCATGCCT CACCGGCGTG GAACATGCAG GTGAGGCGTA TGTACCCCAT GTTGCCTTAT     60

TTTTTCACCT GAAGCGGATT GGCTCTTGTT TATACAGACT TTTCTGCATC CCTTGGGGCC    120

CAGAGCTAGG GCCTAGAATC CGTGTCGTAA GCGTTGGGCA CTGATTCAAC ACGAGCACAA    180

TTCCAGTGCT GCTCGTAGAA ACGAGGCCCC TGAAGTATAT GGTGATATCC ACATTGCCGG    240

AGTATAGTTC TCTGTGGGGG CGACTTCATG CCATGTGCAT CTCCGGCTTA CTCCACAGCC    300

GCACACGCTG CATTGTTTTG GGAACATCAT GTGAAATACT GGTATAGAGC GCATTTCATA    360

GGGGTGCCAG CAGCTGTAAT AGGGCGGCAT ACCCCGCTCT ATTTCATGTG TTCATGTGCT    420

AGTTTAGAGG TATTTTTGAG GTGCATGGGT TATGGCTTAC TTTGCATATG GAGATCTCAT    480

TCGCTCGTAA CGTATATAAC TGAGGTAGCC GTAAACTTGC ACTGGTTCCC ATTGCCAGAG    540

CGAAGCTACA ATAGCACCAT CTGGCTGCAA GTTGTGAACA ATGCATTGGA ATCGCATACT    600

CTTTTGGGGC TGTGCGCTTT TGCTGCAACA ATTAACAAAT GCCTTTGATG AAGGAGTGCT    660

AAGGAAATGT TATGAATCTG GTGTATGCCA CCGGAACAGG CATTACGGAG AGAA          714
```

(2) INFORMATION FOR SEQ ID NO:686:

(i) SEQUENCE CHARACTERISTICS:
        (A) LENGTH: 720 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1454UP (xi) SEQUENCE DESCRIPTION: SEQ ID NO:686:

```
GATCAAGCGC TGTATGGTTC CCGGAGCGCC AGTAACAGCG GTCCTGTACG ATTTCAACGA     60

TTCCAACATG GACGATGATG GCTCCAAAGT TATGTTCCCG ACCACGCTTG AACTCAAAAA    120
```

```
GGTTTTTCAG GCTATTCGTT TTGAGGCCAT CAAACGGGGG CTGCAAGTGT TTCCCATTAG      180

GAATATTGCT CCTATCTTCC GACAGGTCGG ATTCAAGAAC GTAAAATATA CCGTTCTGAC      240

ATTCAAGCGC GGCGATTTCG TGAATGAAAT GGGGTTCGTG AACGAGCTAC TTGCAACGTT      300

TCACTACGAT TTTCTAGTGC GAACCTTTTT AACTGATCGT AGTAAGTATC CAGTTGGAAC      360

TGACCCACAG ACACTGCCGA GGAGGTACAT TGATGAGCAC ATGGGCCAAA TAGATGACAA      420

TGCAGGATGC TTGCGTCTTA TTGCAATCAC GGCGGAAAAA CCAGAGTAGG TTTCCACCGT      480

TGCTATTGCT ACCCGGGGCA ATTCTCCCGG TCATTATATA TGTTAGCAGG TGTCAATACC      540

TCCTTACAAC CTAATATTTC AAAACCTAAT ATCTTCTGCT CCTTAGAAAG AGCCACTTCC      600

TTATATGTTA ATATCTACCG CTAGTTCTAT CTAATAATTT TATAATTTTG ATAAATCTTG      660

ACGTACATCT TATCACTAAG GAAGATCTCA TCACAAACTC CGCAAAGTGT TTCATATATA      720

(2) INFORMATION FOR SEQ ID NO:687:

(i) SEQUENCE CHARACTERISTICS:
        (A) LENGTH: 712 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1455RP (xi) SEQUENCE DESCRIPTION: SEQ ID NO:687:

GATCTCTTCG ACATAGTGTC TTAATAGGCC TGCTGAGGAC TTCACTGAGA AAGCTTCAAT       60

AGCGGGCAAT GGCCCATCTC ATCAACACTT AAAATTTTTC GTGGCAAAAG AAACAACACT      120

GGAATCACGT GACCACACAA AACTCACGAT TTACTGTTGA AGGGGAGCAG GCTACGACGA      180

CTCTTCTTCG CATGGTAACT CGCTGCTGTC CACTTGCCGC TTGCGAGCCT TCTTTGCTGA      240

CGCTCGCTCT TTCTCCTCTT CTAACAGCCT CTCCCGGTTA GCTGTGATGT AGTGGATGAA      300

GAAGTCGCCA TCCTTGCTGC GTTTCGCATC ACGCAGGAGC GTCTCGACAT CGTCGTATAT      360

ATCAATGCGT CGCTTTCGCA GTTGGTTTAG CAGCTTGTTA TCACGCCCTG CACATTGCAA      420

CTTCGCGATG GCTTTGGTCG ACTTGAACGA CACCTCGCCC GGTTTCATAT ATCCAGATTT      480

GCGCAGGTTG TGCCAGGGCG TGCTCACAAT GCTACATTGT GCCTGCTTGT TCCCTTGTAC      540

AGACTCTGAC TTGCACAACT GCAGGCAGGC ATGCAGCACA TCCCGCGGCA CGTCGCTGGA      600

GCTCTGCTGC TTTGCATGTA ACTTGAGATA GACATGTGCG CTGGCATACT TGTCTACGTT      660

GGAACCAGAA GTAGTTTAAT CCCGGTACCC GTGCTTGAAC AAAAGGTCGT TC             712

(2) INFORMATION FOR SEQ ID NO:688:

(i) SEQUENCE CHARACTERISTICS:
        (A) LENGTH: 720 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1455UP (xi) SEQUENCE DESCRIPTION: SEQ ID NO:688:

GATCCCATCA CATGAAATGT CTAGAACTCC CTGCATGACG CGAATGAGGC CAAGAATGTC       60
```

```
TGGTGGGCTT GGCTAACCGA TGTTCGCAAC TGCAACAAGG GGTACCTGGT GTTTATAGCC      120

GTATGTCGTC ATCCGGGATT CGTGCAACAG GAGAGAAGAA CGGGACCACA AGGAAACGCG      180

GTAAAGCATC TAGAATCAGC AACCCTAGAG AACGTTTGTT CGTCGTTGGC GCAAGAGCAC      240

GGAGCGTAGG GGCTGGGAGT TGCGGTGGCT ATTCATGCGT GGGCACGCCG GGTATATAAG      300

TAGGGTATGC GTCCGTTGAA CAGAATGGAT CCGTCTCAGA ACAATACCAA AATCGCATTT      360

GGAAAAACAA CCACTAATAT GAAGTACACC TCCGCTATTC TACTCGCTCA AGTCGCTTTT      420

GTTGCAGCAC AGTCATCCTC GGGGTCTGTT ACCGGCAGCG CTGCCCCCGC TCCGGGTGCG      480

GGGTCGGGCG CAAGCATTTC TAGCACCACG ACAGTCACCG CCTCAGGTTC TGGACCAGGC      540

GCGACGTCCG GTGCTAGCTC CGGTGCAGCA GGCGGGGCCG CTGGCGGGGC CGCAGGTGGC      600

GCCGCATGTG GCGCCGCAGG TGGCGCCGCC GGTTCTAACT CCGGCAACTC TGGCTCCAAT      660

GGATCTGGCT CCCGGCCAGA ACACTCTGGA ACAGAACACT CCGGCCCAGA ACACTCTGGA      720
```

(2) INFORMATION FOR SEQ ID NO:689:

(i) SEQUENCE CHARACTERISTICS:
        (A) LENGTH: 696 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1456RP (xi) SEQUENCE DESCRIPTION: SEQ ID NO:689:

```
GATCCACGCC GCGCTGCTGA CCAACGTCGT CATCATCGGC GGGACCTCCC TGCTCCAGGG       60

CCTGGAGCAG CGCCTCGTCA ACGACCTCAG CCTGCAGTTC CCGCAGTACA AGCTCTCTAC      120

CTACGCCACG CCCGCCCACG TCGACCGCCA GCTGCAGAGC TGGCAGGGCG GCGTCAACAT      180

GTGCCACCTC CCGGACTGGA AGCTCGGCTC CTGGGTCACC AAGCAGGAGT ACCTGGAGTC      240

CCTCGACAAG TAGCTGTGTA GTATGTAACC GTATGCCGCG ACCCTGCGGT TTCTTTCCCG      300

CTCCCCCACC CCCATGACGC CCCCCGCCCG CTTCGCCGCC TCCCACGCGC TGGCGCCCGC      360

CGCGCCCGCC CGCGACACCG TCGAGCTCTA CCTGGACTAC TGCTGCCCCT TCTCGCGCCG      420

CCTCTTCCTC GCCTGGCACG ACGCCCTTTT CCCCCGCGCG CGCGCCGACT CGCGCTTCCA      480

GATCGTCTTC AACCACGTCA TCCAGCCCTG GCACCCCGCC TCCCAGTACA TGCACGAGGC      540

CGCCCTCGCC GTCGCCCGCC TCGACCCCGC CGCCTTCCTG CCCTTCTCGC GCGAGCTCTT      600

CCTCCACCAG GACCGCTGGT TCGACACGCG CACCGCCGAC AAGTCGCGCC ACGCCGTGTA      660

CCGCAAGCTC CGGACTTCGC GCGCGACGCC GCCGGC                                696
```

(2) INFORMATION FOR SEQ ID NO:690:

(i) SEQUENCE CHARACTERISTICS:
        (A) LENGTH: 739 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1456UP (xi) SEQUENCE DESCRIPTION: SEQ ID NO:690:

```
GATCTGGAAT ATTACCGGCA CAAACTTGGC GCTGTGCTTC CACACCAGCC TCCGGTACCG       60
```

```
CTTCACGGCC ACCAGCTCCT GCAGCAAGCG AATGCACACG TATGCCAGCT CCATGCGCTC      120

CAGATTAGTC AGAACCCGCA GGTAGTTGGG GTTCGACACC AGCGCCTCCA CCAGCTCCTC      180

GCTCTGCAGC CCCTCCTGGA TCAGCAGCGA GACAACGTTG AAGCACGACA GCAGCACGAA      240

CTGGTCGTCC GCCGCGCTGT CCGTCAGTGT CGACTCGTAC AGCTTGCGCA CAAGCTCCGG      300

GCCCTTCTTG AAGTACCGCA GCACCTCGTG CACGTACTTG TCGCTCGTGA ACAGCTCCGA      360

CAGCAGGTTC AGCACCGCCC GCTTCGCATC CAGGTTGTTC GACGTCGCCA GCAGGTGCAC      420

CAGCGCCTGC ACGCCCTGTT CCAGCGGCAG ATCCAGCGCG CCGCCGCGCG CGTGTTTCAA      480

CAACGTCGAC TCGAGCTTCT TGGCAATCCC CGCGTCAAAC TCGCTCAGCT CGGGCGAACG      540

CACCAGCGCG TCCCACGCCA CATGCCTCGA GCTGATCGTA TTGCGGATAT CGTTGAAGTG      600

CGTGCTATCA AGCAGAATCT TTTGAACCCC CTGAGCCACG GGCATCGTCA CAGCTAAGAT      660

CTACGCTTCC ACGCCACCGT ACTGCCCACT TTGAAACCCG TGGGACTAGT CAATATCTGG      720

CGTGGTCTGG CGGACTCCC                                                  739
```

(2) INFORMATION FOR SEQ ID NO:691:

(i) SEQUENCE CHARACTERISTICS:
        (A) LENGTH: 688 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1457RP (xi) SEQUENCE DESCRIPTION: SEQ ID NO:691:

```
GATCAATATC GGGACGAAAT CTGTTGTATC TACTACCGGC ACGGCGACTG CGCCCAGCGC       60

ACCAGGATCT CAGGCTTCGT CAGCGAGTCC GGATTCGTCA GCTAAACAAA AGAAAGATTC      120

ATCTCCACTA CCTCTTGACT TACCTCCACC GAAGGATTTT AGCAAAGAAA TCGAGGAGAT      180

TATAGAACAC GATTTGACTA AATTGGCCTT TCAGAATCCT CTTTTTAAAG ATGAACTTCC      240

ATATTGGTTA CAGGCCAAGA GGCCATTGAT CCAACCGTAC AGCACTATGT CTGAAAGAAT      300

GTTGAAACAG CTGGAATCCT CATTACTTAA CTGCCCAGAT TCGCTTGACG CTGACACACC      360

ACATCTCTAT CAACACCCGC TCTCTTTACC GCATCCCACC TCCATTTTCT TCCCTAGTGA      420

ACCGATCAGG TTCGTGGCTG CTGGCTGGAA TAACGATAAT ACGTCCACTA AGATATCTA      480

TGGAAAAACT TCTATGGTTC AGATAATGAC CAAGTTCGAT TTGGATACCC TGTTTTTTAT      540

CTTTTATCAT TATCAGGGAA CGTACGACCA ATTCCTAGCT GCCAGGGGAA CTAATCATCC      600

GTGGGTGGAT ATTTAATAGA GTCAATCGGT GCTGGTTTTA CAAAGAAGTT GAAAAGCTGC      660

CCCCTGGAAT GGATCAAAAA GAAGAGGT                                         688
```

(2) INFORMATION FOR SEQ ID NO:692:

(i) SEQUENCE CHARACTERISTICS:
        (A) LENGTH: 711 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1457UP (xi) SEQUENCE DESCRIPTION: SEQ ID NO:692:

```
GATCGAGGAC TTGAAGCAGT TCCGGCAGGT CGGGTCCAAG ACCCCTGGGC ACCCTGAGTA      60

CGAGCTTCCC GGCGTGGAGG TGACCACCGG CCCTCTAGGC CAGGGTATCT CCAACGCCGT     120

TGGCTTGGCG ATCGCGCAGG CGAACTTGGC TGCCACTTAC AACAAGCCGG GTTACGAGTT     180

GTCGGACAAC TATACGTACG TGTTCTTGGG CGACGGCTGT TTACAGGAGG GTGTGTCCTC     240

CGAGGCTTCC TCGCTTGCAG GCCATCTAAA GTTGGGCAAT TTGATTGCGT TCTATGACGA     300

CAACAAGATC ACCATCGATG CCACACTGA GGTGTCCTTC GACGAGGATG TCTTGAAGAG      360

ATACGAAGCA TACGGGTGGG AGGTGTTGAA CGTTGCCAAC GGTGACGAGA ACTAGAAGAC     420

ATTGCCAGTG CCTTGGAGCA GGCCAAGAAG AACAAGGACA AGCCAACTTT GATCAAGTTG     480

ACGACCACTA TTGGGTTTGG CTCCTTGAAT GCGGGCTCCC ACACTGTGCA CGGCGCGCCA     540

TTGAAGCGGA TGATGTCAAA CAGTTGAAGA CGAAGTTGGG CTTTAACCCA GATGAGTCCT     600

TCATTGTGCC TCAGGAGGTT TATGACCTCT ACCACAACAG CACTATCCAG CCAGGTGCCG     660

AGTCCGAAAA GGAGTGGAAC GCTCTACTCG AGAAGTATGC GGGTGAGTAC C             711
```

(2) INFORMATION FOR SEQ ID NO:693:

(i) SEQUENCE CHARACTERISTICS:
        (A) LENGTH: 688 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1458RP (xi) SEQUENCE DESCRIPTION: SEQ ID NO:693:

```
GATCCGCAGT AGCTGATTGT TCGGGTGGCC AGGCGAATAT TGCTGGAAGC GGTTCAGGCG      60

CGTATATTTG CTCTGCGGAC CGCCAAAGTA CCCGCCGAGG TTACTCTTGC TGGTCGTACT     120

AGAGAAGTTG CGCACTGCCC TAGCAAGTGC GGTGCTAGGT ACGGGATTTA GCTTCGCCAG     180

TAATGGTGTG AAGACGTTGC GAAATGGCAC AGACGCCTGT ACTGGTCGCA CTTGCAAGTG     240

GATAGCGTTG CTAAGAAAGA AACACCGCCC ATACGAGCGC GTGAACGTAG ATAAGCTCAT     300

GGTCAGCAAT CAACAAGCCT AATGATGATC TTCCTTACAA AATGAGGTTC TAAAGCGACG     360

TTAAAAAGGG ATGCCCAACG CTATGTTCGA CACCTATGGA ATATCCGTAT GAATGACTGT     420

GTATCATTAA CGACGGTACT TCCTTACAGG GCAATGGCAG GATGGTAACG CCGAGTAATG     480

TCCAATAATC ATCATATATA CTCTAGTTAT ACGCTATGAG GGGTCATTTG ATGTATTGTT     540

CGTTCGCCTA TCGGCTATGC TTCAAATTCG ATGAGGTTGG GCAGCTCGCC ATTCGTACCT     600

GCGGGTGGCA TGTTCACTTT CTCTAGTCTC TTTTGTGGGC GGTTGTCTTC GTCTTGGTCC     660

ATGTCAAGGT CCAAGAGATC ACAGAAAA                                       688
```

(2) INFORMATION FOR SEQ ID NO:694:

(i) SEQUENCE CHARACTERISTICS:
        (A) LENGTH: 724 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1458UP (xi) SEQUENCE DESCRIPTION: SEQ ID NO:694:

```
GATCTGTTGC ACCTGCTATT TCAGGCAGAT TTGTCGCTGC AGCAGCGCAT GGCCATACTA      60
TCTGCTTTGG CGCTCGCTGC GCGCGAGTTG CGGGGGCTGG AAGACAAATA CGTGCTCAAA     120
CCCGTCTTTG ATTTCCCCAC ACGCCGCCTG CCCAGAAATG ACGCACCATC AAGAGCCCTT     180
GAAAGCCGCG AATCCGGTAC AAGCTCCGAG GGGACCATCT CTGCACACCA CACCGTCTGG     240
CGGTCGCGCA AACTTGACTC AGCGCCAGCA CCAGAACGTC CGAACGCCTT TCGGAAGCAT     300
GCACCTGCGT TTTTCTTCCC GCTGGCGCAC GCGTGGCTGA ATGGCATCGA CCTGGGCACT     360
TTTGACGCCC TGTTCAAAAA GCACTACCTA AGCACCCTGC GCCTTATTCT TGCAGCCGCC     420
AACCCGCATG CAGAATTTGA CCGGATGTCC GAACTCATGA GCTACGTTTT GCAGGACGCT     480
GAGGCGCACG ATATCAGCAT TGAGTAGCCC GTCGCGCATG TGTCAGCGCA TCTGTGGACA     540
ACTCCTGCTT GCAAACTGTA TCCCGACCAC TACCATGCAT TAGTATGAGA TCTATAGAGC     600
GCCAATTGCA CGCCTAGAGA GATGTGAACC TCGCAATGCA TCTCTTGGGA GTCTCTGTGG     660
CCGGCAGTAT CTGCTAGTAC ATACTCTTTG TAACTCTACA GAGATGTGAA GTCTTGTTAC     720
CCGG                                                                 724
```

(2) INFORMATION FOR SEQ ID NO:695:

(i) SEQUENCE CHARACTERISTICS:
        (A) LENGTH: 569 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1459RP (xi) SEQUENCE DESCRIPTION: SEQ ID NO:695:

```
GATCATGCTG GGGCATATCT GAATGCTCTT GAACAACGGA CTAGATTAAT GGAGCCTTGC      60
ACTCAGAGGC TTGGGCAGGA TGCAGCTTAT GCGGGAGCGG CTGTTGGAGC TTTACAATAC     120
CAAGCAATAT GTGGTGCTGC CCCCAGATGA GACAGTAAAA CTGCAGCGAG AGGTGACGGC     180
GAGCCTGAAC TCAGCAGATC CAGGACTCAA CGACGTTGAC CGCATGGCCC TAATGGAGAT     240
GAACTTCTAT TTGTTGGTGT ACATTGGCGA AGAAATAGAA GCAGACGTGC TCTACCGCAC     300
ACTTGTTGGA CGTATAGGTG AGAACTCGCC CCGGATGCAC CTCATGAAGG CTACGTTACT     360
GCAGGTTACA GAAGGTGATC CCGCTGCCGC GAAGTACCTG AAGAACCTGC TTGAAAAGCA     420
GCTTGAATAC GATACAGATT CCGTGGATTA CCTGCAGGTG GGCAAGAAGC TAATTGCGCT     480
GGAACGGCCC GCGTTGTCCA CCGAGCTGTG GATGAAAAAG CTGCTGTCGC CTGCTAGAGA     540
AGTTTCCACT GGACGCCGAA CTATGGTGG                                      569
```

(2) INFORMATION FOR SEQ ID NO:696:

(i) SEQUENCE CHARACTERISTICS:
        (A) LENGTH: 572 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1459UP (xi) SEQUENCE DESCRIPTION: SEQ ID NO:696:

```
GATCACGTGC CTGCGACATG GCGACTTCAT CCACTGGCGC CCAGCTACGT GGTATATGAC      60
ATTATGGCCG AGAGGTTAAG GCGTGAGACT CGAACTAAAT TGAGGGATCT CTTGGGCTCT     120
GCCCGCGCAG GTTCGAATCC TGCTGATGTC GTTATTTTTT GCTTGCGCGG CCTACGGGGG    180
GCTGTATTTT GCTTGTTGCT ATTTAGATAA ACGAGATAGC TAAACTATGG GTAGAACTCG     240
CGGTACTTCC CGTAGTAGTA GGCTGTGCCG AAGCCGCCGA GGGCGGTGAG CACCAGCGGG     300
ACGGGTTTGG CGAAACGCGA TGGCACGCCT CTGATGAGGC CGGTCAACAG CATCACGGAG     360
CTCGCGCCAA GGGCGAGCTC GAGGCCGCCC TCTGCGTTCT TCCGGAGCAA GTACCCTGCT     420
ACAGCGTAGG TGCTACCAAA AACGAGACCT GCAGCCAGCG AGGGCACAGA CCCTTTACGC     480
CAGTAGCCCA TCGAGCCACC GATGACGGTG AGCGCGGCGA GAGTGAAAGA GGGATGTTCC     540
CTTGCGGTGG TGGTGGGTGG TGCTGTGGGG AA                                   572
```

(2) INFORMATION FOR SEQ ID NO:697:

(i) SEQUENCE CHARACTERISTICS:
        (A) LENGTH: 688 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1460RP (xi) SEQUENCE DESCRIPTION: SEQ ID NO:697:

```
GATCCGGGTG GAGACACGAA AGTAGACAGA CACGGACGGC TGTTGGGTGG AAGGAACTAC      60
CTCGTGGATA CATTCCAGCT GCCCCAAAAG ACACATAATT TCTATGTGCT TGTCGACGAG     120
CTGATAGAGA TTTTGCATTT CGAGGGGAGC GGCTCTGACT TTTTGCACCT GCATAATCAG     180
CTGTACCCGC TGGAGCTCAA AGACAACGAG CGGGCCTTGC TTGCAGACGC TGGGTTGATC     240
AAAGGCGAGC TGCGCTCCCC ATACTACGTT ACTGCACTCT CTTCATACAT CATTTTTGGT     300
GCTGCTATTG TGGCGAGCGG CTGTAGGATA ATAGATGACT ACTGGGAGCA GCCCTTAAAG     360
GAGCAGGGAT TCACCATGCA CCACCGTGTA TTCTCTCTGA ACGGCACGCA ACTTTCATTG     420
CTACGCCTGC TGAAACCCCC GCGTCCAGAA TCGCATCAGC AGGGTGAGAA GCTGGATACC     480
AACTGGCTAC AGAAGTGGGA GGATCCATAC CCAACGATCC AGGAACAACC AAATGCTGAA     540
GCACGGCGGG AATACGCTAG AGAACACGCC AGAGGTGAGC ACATAACGAT GATTGTTCCA     600
GGTCAAAGTA TTAGCGGCAG TATAGAACTG AGCCTAAATT ATAAACTTCC TAAGTACCAC     660
TACAAAAACT CATTTGCTAA TGGGTTGA                                        688
```

(2) INFORMATION FOR SEQ ID NO:698:

(i) SEQUENCE CHARACTERISTICS:
        (A) LENGTH: 649 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1460UP (xi) SEQUENCE DESCRIPTION: SEQ ID NO:698:

```
GATCCAACAA TTCCCGCAGC GCCGCTCCAG CCGTCGTCTC CGTCGCATCA AATGAGTCCA      60
```

```
CGCCTGTCTC AATCCCGCAC AGCTGCCGTC CATGCGCCAC CTCGAACTGC ATCCGCGACG      120

CAAACAGCTG GATAAACAGC CCGTTCTGCT CGCACCCCCG CCGCAGCTGT CCAAAGAGCG      180

CCTCCGCACC AGCTGCTATA TCATCGCCCC AGAAACTCTC TACGAATGCC CCCATCGCCG      240

TGTACCTCGT CGTAGTTGTG CATGTCGCTG CCTCTTCCGG CTGAATTTTG ACAGTCTGGC      300

CCCCCACCCC AGCTCCGGAA CGCTACGTAA TACAACACAC AACCAAATGC CCTACCCGAA      360

GGTCGCAATC GTCTTCTGCA CCGGCTGCCG CTGGGGCTTG CGCGCAAGCT GGTATGCTCA      420

AGAGTTGCTA CAGACTTTCG GCGACTCCCT AGCCGAGATT GCCCTCGTAC CGGGTCCGTC      480

CGGTCAATTC CAAGTCCTCT GTTACGCAAG CCAAGAACAA GAGGCCACGG GACAGCGGCA      540

ACACCATCTG GGATCGGCGC CGCGACAATG GTTTTCCTGA TAGTAAATAT CTGAAGCAGG      600

CTGTCAAGCC ACTCTTTTTG CAGACAGCGG AACCGCCTGG GCGCCACAT               649

(2) INFORMATION FOR SEQ ID NO:699:

(i) SEQUENCE CHARACTERISTICS:
        (A) LENGTH: 688 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1461RP (xi) SEQUENCE DESCRIPTION: SEQ ID NO:699:

GATCAAACCA CCACGGCACA TCATCATAGT TGATTAAATC AATTAGGTAA GGCAACCATA       60

GTTGCAGACT TTGTTTCTGT ACCATTTTCT TGGGATTAAA GAAGTAGGGA GTCACGAGGA      120

AATGCACCGC ACATGCTTTG AGATTGGTGT TTTGGGATTT TAGAAGGCCA GTAACGAAGA      180

CGGTGAACGA GCTGTCCAGC CATAGATTAT TTTTAACTGG ATGAACCTTG TAGCACTCGA      240

TGTATAGGAC AATCGCCAAC CAGAGCAATG TCTCGTGCAA CGGGTTCTGG ATGACAAGCG      300

CACGCGGGGT GCTCGTGAAT GGTAGGAGTT GGTTGCTTCC TATCCCACGG TTGCTAAATG      360

CCATGTACTC TTGGTCCTTG GGGTTCGGCG CGACGCTGAC CTTTAAAATG TATTTGAGGT      420

CCAACTGGTG ACCATAGCGG TCCACTAGTG ATAGCATGAG TGCCTCTAAC GGCAGAAGAA      480

GCCCTTGCGG AAGCGAAACC ACCTCCCGGC ATTTGAGCAC CGCAGACATT AACTCCAAAA      540

GCGTGTTGGC CCAGGAGATC TCTGCTCGGG AGTCATCTGC TTCTCATTCA TCCCCGAGGA      600

AGTGTATCAA AAGCCCGGGC AAACCCACGG GCACAGCCCG CCGCACATCC GCGTCCCCAT      660

TACAGTAGTC TATCCCACAG TTGTTCAA                                       688

(2) INFORMATION FOR SEQ ID NO:700:

(i) SEQUENCE CHARACTERISTICS:
        (A) LENGTH: 728 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1461UP (xi) SEQUENCE DESCRIPTION: SEQ ID NO:700:

GATCGCGCAG TTTAAACTTA AAGTTGATAG AGTTCCCGTC GTGCTCTCTG GATACAATAG       60
```

```
AGGCCACCGA GTCGACGTGG CCCTGCACGT AGTGCCCGCC GTAGCGCCTG TCGTCCGAGA      120

TGGCCCTTTC TAGGTTGATC TTGGAGCCAG CTTTCCAGCT GCTGACTTCC GTCCGATAAA      180

CTGTTTCTGG TGCGATCCCG ACCTTGAAGC TATCGGCCGT GAACTCCGTC ACCGTCAGGC      240

AGATACCATT GCATGCAATC GAGTCACCGA TGTGGCAATC CGCCAGTATC GGAGCCGCAT      300

CCTTGATAAG GACTGACACA CCGTTGCCGC CTGCCTCGCT GGCATCGTTC TCCAAGTACT      360

CAGCAACAGT GCCAATGTGT TCCACTATAC CGGTAAACAT CCTATCAACT TCTATGGGCG      420

ATATAGGCTT CGGTATGCCA TCTATGCATC TTCTTTTCTG CTACCGCGAG CTTTTTAAAC      480

TCGTAAGACA TGCATAAGGA AATGGCGGTT CGCCATGTAG CTGACTAATA AAACTAGAAG      540

ATACGACTAA CTATCTGATT ATACTTTAGG ACTATCTCTC CTTGCGCTGG TCACAGAAAC      600

ATCGTTGAGC AAGTCGCGTC TATCGGGAAA ATCACTTGGT TCCTTTGTCG TAGAGCTAAC      660

TGCCTGAGAA GCTGGAAAGC GCTCTTTTAA AGTCTACTTC GAATGGTGGT GTACGTCTGG      720

GTGCTGGC                                                              728

(2) INFORMATION FOR SEQ ID NO:701:

(i) SEQUENCE CHARACTERISTICS:
        (A) LENGTH: 701 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1462RP (xi) SEQUENCE DESCRIPTION: SEQ ID NO:701:

GATCTTAATT TAAAATTTTA ATTAACTATT TATAATTTAG AAATATATAA TCTAGAGATA       60

TATAATCTTA AAATCATAGG TAAAAATACA TAAGATAGTA AGAATAAAAT TAGTAAAATA      120

AATAGAAAAC CATAAGTTAA TTGATTCATA AAGAAAAATG GAATTATTTG TGGCATCTTA      180

ATTTTTATTA TTTAATTGAT TATTATCTAT TTAACATAAA ACATTTTAAA ATGTTATAAA      240

ATAAATAAGA AATTACTTAT AGAATATTTA TTAAATAGTA TTTAATTTAA TTTTAATATT      300

AAATATACCA TTTTTATTAA TAAATAGATT ATTAAGTTTA TTAATATTAA GTGATATATA      360

ATTTAATTTA TATAAATTAT TTAATTTACT TCATTGATAT ATATAATTAT TAAATGTACC      420

TTTCATAATA TTTATTTTTA TTAGTCTAGT AATATTTCTA TTTAATAGTC TACCCTTTAA      480

TTGGATATTA CTACCTACTA AATATTTACC TAATAATATA TTATTAAGAA TACTTAAATC      540

TAATAATTTA TTATCTAAAG TATATAAATT AATTAAACTT TTTTATTATT ATTTAAATTA      600

TTATTAATTA GTAAATTATA TTTATTTATT TTATTAACAT AATTTTTTGG ATAATAATAT      660

ATCATTATTA AATGGTAATT TATTAATAAT TATCTTAATG A                         701

(2) INFORMATION FOR SEQ ID NO:702:

(i) SEQUENCE CHARACTERISTICS:
        (A) LENGTH: 728 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1462UP (xi) SEQUENCE DESCRIPTION: SEQ ID NO:702:
```

-continued

```
GATCAATTAA TAAATGGTTT AACTAATAAA GTTAATAATA AATCTATTAA TTATATAAAA      60

CTACCTGATT TTATTGAATC AAATAATATT TTCTTAATGA ATACTACTAA ATCATCATCT     120

ATTGAGTTTA TATTAAATTC ACCACCTCTT ATTCATTCAT TTAATACTCC TCTAATTCAA     180

TCTTAAAATA TTCTTAATTA TTAAATTATA TAATAAAAGT TAGTGGATAT AGTTTAATTG     240

GTAAAACATA TGTTTTAGGG ACATATATCT TCAGTTCAAA ACTGAATATC TACATATTAT     300

ATCATTAATA TAATAACTCT TTAATTAGAG TGGTACCACA AGAATGCTGA AAGCATTAGG     360

GGTGTGTACC TTAGCTCTCT AATTAAAGTT ATAAAATTAT CTTAACTAAT AAAAATAATT     420

AATTAAATAA ATAAATAATT AATTAAATTT AAAATGTTTA AAAAAAGAAA TAAATAATAT     480

GTTATATTTA AATAGATCAA AATTTCAACA ATTTCCATTT CATTTAGTAC TACCATCACC     540

ATGACCAATT GTTACATCAT TTAGTTTATT AGGTTTACTA TTAACTTTAG CTTTTACTAT     600

ACATGGTATT ATTGGTAATA TTTATCCTTT ATTATTATCT TTATTAGTAG TTTTATTACT     660

AATAACTTTA TGATTTAGAG ATATGGTAGC TGAACTTACT TATTTAGGTG ATCATACTTT     720

AGCTGTAA                                                              728
```

(2) INFORMATION FOR SEQ ID NO:703:

(i) SEQUENCE CHARACTERISTICS:
        (A) LENGTH: 688 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1463RP (xi) SEQUENCE DESCRIPTION: SEQ ID NO:703:

```
GATCCCTGAG TCTGCTACCA AGGAGGTCGA GGAGGAGGAC ATCGATATCG AGCAATTGAA      60

GCAGGAGATG AAAGGCAACA AGGAGGCCTC TGCTTTGTAA GCTTGCTGTT TGCCGCTTGT     120

GCTAGCCAAT CGTTGCTGAG ACTATCTAAC TTGTATACAT GCCGCTATCG CGGCACGCGA     180

AGCGAACACT ATAATGTATA TGTCAAGTTA AATACATCAT ATATTATCTT GTGCCTCAAG     240

GGTCTTAAAG ATGTCATAGG ACAGTCGCGT GCTCAGACAC ACGAATATAA TCATAATAAT     300

AAATATATGG CGGTCAGCTT CATGACCACG TCAAGCCTTG ATACCAGAAG ACACTTCTAG     360

GAATTTCTCA ACGGGAGAGA AAACACTAGG GTGTAGGTCG TCATTCGTCA AGGACATCTG     420

CTCCTCGGTC CACAAGTTGG CCTCTGGTAC ATAGTCTGGT TCACCGACAC CCAATAAGCC     480

ACCGTGCGCA GCCCAATCGC TGACACGTGG AAGCTGTAGT GTCTTCCAGA CGTCATCCAT     540

GGCGTCCAAT AGGACATCCG ACAGGTCGTT CGTGTGGCCT GGAGTAGGAA TGATACGGAG     600

TCTCTCGGTC CCGCGTGGAA CGGTAGGAGT TGAAGGGCCT GTACGTAGAT GCGATGCTCT     660

CCATCAAAAT GTCGGAAGCA CGCTTGGC                                        688
```

(2) INFORMATION FOR SEQ ID NO:704:

(i) SEQUENCE CHARACTERISTICS:
        (A) LENGTH: 704 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:

(A) ORGANISM: PAG1463UP (xi) SEQUENCE DESCRIPTION: SEQ ID NO:704:

GATCAAACAG TAGAAGTATT AGAGCTGCTT GCAAAGGGCG TCATAAACAA GAGAGCTGTA      60

ATGTCGACAA ATTAAACAGA AAAATATCAT TATTAGTGGA TAAATAACCA ACTTGCACTG     120

AGAGTATAGT TCTACATGTT TATTCCGTAA CAGAATTTCT ATCCAAATAG TTTAATTCCG     180

TTTTACTTAT CTACGGAGTA GCAGTGCAAG AACCTTGTAT CCCAAAATGC TAGAGGGACA     240

TGCAGATGTA TAGTAAAGCA ACGTCTGTTT CTTTGGATTT AGCAGCGTCA GGCGAACAAA     300

AAAAATAGAA AGTCAACAGG GATTGGGAAG TTATGAGAGT TGATATGTTT GTCCATTAGT     360

AAGTCATTCA GTTGATATGA GGTGCTTAAA TGTTTGTAAG AAGCAAGAAC GAAGAGAGAT     420

ACAAAATGTG CAGTTGTGAA TCGTGAAATT GACACCAGAG GACGTCACTT CCCGTTGCCA     480

CTGTTTGCCA ATTGCTTCTC GAGCTGCTCA ACCTTGCGCT GTAAATCTCT ATTGACTTTC     540

TTTAGTAGTT CCAATTCAAT ATGCGTTTCC TTCGATCTTC CATAGCTGAG CAGTTTCGCC     600

ATCTCCTGGT TCTCTTTTGT CAACATTTCG AGTCGGACAA TCATCTTGTG AGCGAGGGCT     660

TCTTCGTCAT AACGGCCGAA TCGGGTAACG GAATTAGAGG GATT                     704

(2) INFORMATION FOR SEQ ID NO:705:

(i) SEQUENCE CHARACTERISTICS:
        (A) LENGTH: 699 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1464RP (xi) SEQUENCE DESCRIPTION: SEQ ID NO:705:

GATCGAAATA ACTTCCGCTG AAAACGCAGC AGAGGCAGCC AATGGTCAAA TGGAGCGAGA      60

ATATCCACGA TATTTCTAGG GTACTGTTGC TTGCCAGTTG GTGCTCGGAA ACATAACCCT     120

CAATGGCGCC CAGTGTGTTG TACATACCCC ACACCGGAAA CAGACCCATG AATGACCCGA     180

AAACCACCAG CCACGCGCGT AAGCCGCCAT CCGGGTATTC GTTGGAGTTA TCGAGATATG     240

CGCGTTCTTC TTCCTCTACC TTTTCGTCGC TGAGAGGGAC AGTCTGCTGA GCGCACGTGG     300

TCGTTGGGCC ATCGCCAAAA AGCTCTTTGT CGCCCACAGC TGTGGCTCTG CCGCTGTCAG     360

ACGATGGGCT GACGTCTAGG GCTACGGGCT CATCGCCATG CCGTACTTGA ACGCTGTCCT     420

TGTCGATGAC CACCATCGTT CCTAGCACGT ATGGGAGATG CTCCGAACCG CGTCAGCGCC     480

ACCACAGACC ATCTATCTAC TTAAATACCT AATTATCTGG TGTCCAGCTA AAAATCCGAG     540

TATCAGTCAT CCTGTGGCGG CCTTATCACC CATTAGGGTC CGCTTTGCGG TAGTGCATTA     600

CCGTCGGCGG GATTCATCCT CCAAAATGTC TCAAGCGATG CCTTGATTCC GAGTGTACAA     660

GGGCCAGATT CCAACGGGCC AGGAGGCAAC TAATAGAGG                            699

(2) INFORMATION FOR SEQ ID NO:706:

(i) SEQUENCE CHARACTERISTICS:
        (A) LENGTH: 710 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
    (A) ORGANISM: PAG1464UP (xi) SEQUENCE DESCRIPTION: SEQ ID NO:706:

```
GATCTTGCGC TTTTTCTTCA GACCGCGGTG GGTGTAGTAT TGTTCCTCCT TAATGTTGGA      60
GTTGAGGCGG GACGAAGAGG GCGCAGAGGG GTCTGGCGAG GCACCGGTGG AAAGGGGCCT     120
GTCGGCGCGT TGCAGGGGCA GCGCGCGGTC GTCGTGGTCG TAGTCGTGAT GTTGGGGCGC     180
GGGCGGCGCC GACTGTGCGT CCAGCGGGTG GCCGTCGGAC GCGAGCGCCG AGAACTCGGC     240
GTCGCGGAAC TCGTACTCCT TCTGCGGGTC CTCGCGGCGG CGCTTGGCCG GCGGGTCCAC     300
GGCACGGCGC GGGACCTTGA GCCCGTTGGA GATAATGAAC TTGTGTTCGA CCGAGCCCTT     360
CGGATGCTTC TTTCCGCCAT TGCGTTTGGG CGCCGGCGTC TGCGCGTCCG GCACGGGCGC     420
GGCCGGCGCG GCATGCAATT CGTTCTCGTC TGGCGAGACT GGGGGGGGAT AAACTCGCCC     480
AGGATCGCGT CCACGTTAGT GAGGTCGCGG TTGCCGTCCT CTGCGGCTGC GTGGTGGTGG     540
TTGGCGCGGT GAGCCGCGTG CACCGCGTCC TCCTCGTGGG GCTTGGGCTC CTGCTCCGGC     600
ATGCCCCGTT CGGCTGCATG CCTCCAATCG ACTTCGACGT CGTACGATCC CATCCAACGA     660
ACCCCGTAAC TTATCTCGAA GTATGCCTGC ATACCTATAC TGGTCGTTCA                710
```

(2) INFORMATION FOR SEQ ID NO:707:

(i) SEQUENCE CHARACTERISTICS:
        (A) LENGTH: 703 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1465RP (xi) SEQUENCE DESCRIPTION: SEQ ID NO:707:

```
GATCCACTTC TTTGGCGACA AGACATTCGA GGGCGGCAAC GACTGGGAAA TCTACAACGA      60
CCCGCGCACC ATCGGCCACA GCGTCCGCTC CCCCGAGGAC ACCGTGAGGA TCCTCAGAGA     120
GCTGTTCGAC CTGTAGGCGC CGCCGCTAGC TAGTTCTTTG TAATTGCTCG ACATTTACAA     180
TGCATATTCC TATATACACC GCGCGCAGCG CTCAGCTGAG CAGCCGTACG TACGCCAGCA     240
CGAGCGCAAA CGTACCCGTG CACACGCCGA TCAGCCACTG CATGACCTGC GTCTTGACCG     300
AGTCGATTTG CATCTTCATA TTACTGACCT CCTGGTCAAT TCGCGTGTCA ATCTCCTTGA     360
TCTGCAGATT GTGGTTGCTG GACTCCTCCC GGATGCGTCC CTTTTCCAAC GAGAGATCCA     420
GCTTGAACCC TGCGTTCGCC TTCGTGATCT CCTCTCGGAG CCGGTTCCGC AGCTGCTCTA     480
GGTCGTTTCG AATCCGCTCC TGTTCGTTCT GGATGGAGTG GATCTCGCTG CGGTCCGCCG     540
TCAGCAGTTG GTCCCGCAGT TTTGCAAAAT CCACCCGCTG CTGGTACGTC AGCTTCGTAA     600
GCTTCTCGCG GGACGCTAGG TCCTGCGAGA CATGCGTCAC GCCCCGCGC AGTGCGTCCG     660
ACATGATATC CACGATCGCA TTCGCCTGCT GGCTTGCTGA AGT                       703
```

(2) INFORMATION FOR SEQ ID NO:708:

(i) SEQUENCE CHARACTERISTICS:
        (A) LENGTH: 619 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
    (A) ORGANISM: PAG1465UP (xi) SEQUENCE DESCRIPTION: SEQ ID NO:708:

```
GATCCCGCAA TAGCTTGATT CGATCGTCTG GTCGCGTACC TGCTCGACTT CTCTTGCTCT      60
TCTCTATGTT CGTTGCTCAC GGCCGGAAAA CCACTACAGC ACAAAAAATT CACAAGGTCC     120
GCCGCACCAG CCTTTTTAAT TAGCGCAATG GCAGCGAGTC CTGGTATATA AGGCAAAAGA     180
CGGGAGGCGG ACAGCTACTA CAGGCTCATC GAGGCATGGT ATGTTGCGCG ACAGTGGCGG     240
CAGGGGGCAG GACTAACCTT GATGTTCGAT AGAATGCGTT GTACAACCAC GCGGTGAAAC     300
AGAAAAAGTT GCTGGAGCAG GAGCTGAATC GATTTGAGCT CGGGGTGGCG GCGCCGGTGG     360
GGCTGCAGGG TTCCATATCG ACGGCACTGG TGGGACTGGA GCGCACAATT GAGCAGTATC     420
AGGCGCAGGT GGCGCAAACG GGCAGCGGCG CGGAAGCCGG CAAGCATGCG CAGCGCGTGG     480
GCGAACTGAC GGAGTGCGCA ACGAACGCGC GGCGGCGGTT CGAGGGGCTG CGGGCCGCGA     540
GCATGCAGCC GGTGGCGTTC CAGAGCGGGG CGGCAGCGCC GGAGGGCGCC GTGAACCAGC     600
CGGCGGCGGG GGCGCGCAC                                                  619
```

(2) INFORMATION FOR SEQ ID NO:709:

(i) SEQUENCE CHARACTERISTICS:
      (A) LENGTH: 715 base pairs
      (B) TYPE: nucleic acid
      (C) STRANDEDNESS: single
      (D) TOPOLOGY: linear (ii) MOLECULE TYPE: DNA (genomic)

(vi) ORIGINAL SOURCE:
      (A) ORGANISM: PAG1466RP (xi) SEQUENCE DESCRIPTION: SEQ ID NO:709:

```
GATCTCTTAC TTTTCCTACT CACCAATGTC TTTAACAGAC ACCCAGAGTC ACGGCCGGCA      60
GCCTATCTGC CGTGCTGGCG CCATGCCCCG CCCCTGGTAC TGGCCCGCTC GTGCTCGCGG     120
TAGTCTCACA GCAACGGAGC TTGCTCCAAT TGGGCTGCAT TCTCCCGACC ACAGTCTGTT     180
TGTCACGTGA CTCTCAGCCG TCCCGAATGT ACATTTCTAT TTATCTACTT CTTGCCGCCT     240
TGCCGCCACC ACATCCGGTG CCGGGCAGCA CACCGACCGC GCATCGCGGC CCTCGCGTTC     300
GTAGAACTGC GCACAGCACG TGTACAGTGC CTCCACTGCC GCCGCGCAAC GGCCCTCCTC     360
GTACCCTGTG CGTTTCAGAC ATGCCTGGAT CGCACATGCC TGGGCCTTGC ATGGGGCTG      420
TCCCTCTGCG CTGCGCCGCC TATTGTCCAT GTTTTGTGTT CTATCTGTTG GCCGGTACCA     480
CGTTGTTGTA CCAGAGTACA TTGTCGCGGT GACCCCGTGT AATGTCACCC CGTGGGCCAC     540
AGATGACCCT GCCACATGCC TCATTTCTTT GACCGCACCG TGCCGCGAGA CCGCCCACAT     600
GGGCCGTGCG CACTCCGACG ACACCCACGG GGCGGCACTG CAAGGGTCGC AGGTGCGGAT     660
GAGTCAAAAC AAACCAGGTG TGGCGCTGGG CGGGTGAAAA TCGACTCATA GAGAC           715
```

(2) INFORMATION FOR SEQ ID NO:710:

(i) SEQUENCE CHARACTERISTICS:
      (A) LENGTH: 694 base pairs
      (B) TYPE: nucleic acid
      (C) STRANDEDNESS: single
      (D) TOPOLOGY: linear (ii) MOLECULE TYPE: DNA (genomic)

(vi) ORIGINAL SOURCE:
    (A) ORGANISM: PAG1466UP (xi) SEQUENCE DESCRIPTION: SEQ ID NO:710:

```
GATCTTATTA ATTTTGATGG TGCTATATTC TAAATTCAAG TAATGATAGC GCGTGATGCG        60
GTACGTACCT ATACATATAA CGCACAGTTC ACCATCGTCT ATGCGTGTAT GAAAATCACT       120
CCAGCCGTGC GACACGCCAC GTGTAATCTA GTGAGTTTCA AGTTCTTCCT CCTCATCGGC       180
AGAAAGTTCG CCCGCGGCGG TGAGGTTCTT GAGCCGCTCC TTGAGCTGCG CGATAAGGCT       240
ATTCTCCCTT TGAGCATGCA TGCGGATACC CTCTAGAGAC ATATGAGCCG AATCTGCACC       300
ATCTAAACCA TGTTCGCTGT TGCTGCCAGT GGCAGCTGCC AGTTTGGGAC TGGACAGACC       360
TGTCTGTCCA TCTTTGTAAG AATCCTCGGT CGTTGCCGAG TTGGAATTCA TGGTTCCCAT       420
AGTGTGCAAG ATTTTCTCCT CTTCTGTTAG TTCCAGATGG GTACCTGTCA GATTGATCAA       480
GGACCTGCCG CTTTTACGGC GCGAGAGCTT GGGCAGAAGA GAGTGCCCGG TTGGCGTCGC       540
TTCACCAAGG TTTGTAATGG AGGTGTGAGA TCTCGGAGTC CTTGGTAGTC TCAGACACGA       600
AGCACCGGCA TCATGTATCC ACTTCGCAAC AAGCGAAGTC CAGCCACACT GGTGTGATGC       660
GCCCAAGCCC CTACCAGTGT CACCATCGAA GTAT                                  694
```

(2) INFORMATION FOR SEQ ID NO:711:

(i) SEQUENCE CHARACTERISTICS:
        (A) LENGTH: 690 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1467RP (xi) SEQUENCE DESCRIPTION: SEQ ID NO:711:

```
GATCGCAGAC TCCGCCGGAG AGACTTTCGC ACCTCGGGCA CAGGTCTTGA AAGAGAGCTC        60
CGGCCGTTCC GTGCCAGACT CTTGTTTATC ATGTCCGTAA GAGCAGCGTT CGTGCCAGGT       120
ACGCCCTTCT TGTTCGTGTT TCCACCAATT GATGGAATTT GAGACGTGAA CCTCTGCGGA       180
TTCRRKCTAT TGAGCACACC ATTGGCACCA CTTGAGCCCC TTCGCTCTGC CATCCCTAAT       240
CGTCCTATCC TACGGCCGGC TAATAAGTTA CTACCAGACT CTGGCCCTCA TCTGGGACTG       300
ATGTTATCGT CTGCAGCCAG ATCCTGTTTG TGACCCGATC GAAATCATCG AGTACGAATA       360
ACCACGTGAC CATTATTCAC GTGATGAATT TGGCGGTCCC TGTTGCCGAC TCTTACTCCA       420
GGTTAACCAT GACTAGATGG GCATACCTCA GATACGTTAT TCATGGGATC CGGAGTTGCC       480
GCGTCGGCCG AACCGCCCGG TGAATCTGTG CTGACGACCT AAAAAATAGT GTGCGCAAGC       540
TTCCTTAATC TGTGAGATGC ACACTGACAA ACTTGAAGGC TGAACCATCA AAGCGATACG       600
CCTCATGCAC GTGCTCAATA AGGTCCAGGA AGTCTCGCAA TGGGGCAAGC AGACGGTAGA       660
TTGCAAGACA CAGACGATTG GGTTGTGCCA                                       690
```

(2) INFORMATION FOR SEQ ID NO:712:

(i) SEQUENCE CHARACTERISTICS:
        (A) LENGTH: 700 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
            (A) ORGANISM: PAG1467UP (xi) SEQUENCE DESCRIPTION: SEQ ID NO:712:

```
GATCGTCCGA GTGCAAATCC ATACCAAAAA TGTGGACCCA GGTACGGGAT TCGAACTTCT      60

CGAAGAAAAA TAGCCTCAGT GAAGTGCCCA ATTGCCTTAT AGTCGTTTTG CAGAGCATAT     120

AGAAATGTGG GACAAGGCGG TGGGGGGGCT TGTCGGACGC GACGGAAGAA GGGATCTGGG     180

CGGGAATTAC GGCGGTGAGA GGCAGGGGTG CGGAAGAGAA AAAGGTGAAG CGAGTTGTTG     240

CCATGAGCGA GATGCAGCAG CCAATACCTA TCCCAATGGT AAACGAGGCG GTCCAGATGG     300

CCCAATGGCG GAGGGCAACA GGGCCCGCGT CCTTTTTGCG CGGTCTGCGG TGCTGTTTCT     360

TGGACTTGAC GGTCAGCTCG GTTTCATAGC CGGACTCGGA CTCGTTGCAA AGGTTGTGCA     420

GGTGCTTGAG CAGGCGGTGC TTCTCGTGGT GGTTGGACAT GATTATAGGG CTGCAGTATA     480

CTCGGATGCA TTTGCGTGCG GTGTAGCGCT TCAGGAGAGC CGCCAGCGTG CTCTTCTGGC     540

CCTTCTGGCA CACGGGAATC ACGGTGGGGC AGGGCGCCTT CTCGCACAGG CCGTCCAAGA     600

GCTCTGGCGC CTGCGCTATG TCGTGGAAGA CCACCATAAC CGCGAGGTAC CGCTGGCCCA     660

CGTCCCAGCG CGTGACCATG CCGAGGTTCT TCACGTCAAA                          700
```

(2) INFORMATION FOR SEQ ID NO:713:

(i) SEQUENCE CHARACTERISTICS:
            (A) LENGTH: 689 base pairs
            (B) TYPE: nucleic acid
            (C) STRANDEDNESS: single
            (D) TOPOLOGY: linear (ii) MOLECULE TYPE: DNA (genomic)

(vi) ORIGINAL SOURCE:
            (A) ORGANISM: PAG1468RP (xi) SEQUENCE DESCRIPTION: SEQ ID NO:713:

```
GATCTCGTCG CTCATTGTCG ACCTGCAAAA AGTGTTCAGA AGGAAGGCAA CATGTGTTTT      60

TAATCCTACG GCCGTGGCCT CAGAGATTGT TCACTCAATG TCGTTCATCA TTATGAATGG     120

GTCGCCGGCG CCTGCCGGCC TCGAACCCGC GCCACACGGC CTCCGCCGCG CGCTGCCCCG     180

CTGGGCCACG CAGGGTCCAA AACCCACCCA AACTCACCGC GCCCACCCGG CTACACCGCC     240

GCCAGCACGT CACGTGCGGT TACCCGCCCT GCCGGCACTG AAAATTTTTC GCCGCCAACA     300

CTATCGCGCC CGAAAAAGCA ATTTGCCGGC CAACCACACA ACGATCTGTT ACCGAACAGG     360

ACAGGACTCA TGCCCCGTTC CCTTCTTTAT TTATTTACTA GCTCCACATA GATATTTTTG     420

ATATTTATAT GGTGTGTTTT CCTCCGCACG CCGCAACCCA GCACTTAGCA GACCACGGGG     480

GCAGGGACTG ACACCCAGCC AGAACAGAAC AACAACAGGC GACCTTACAA TGAGCATGGA     540

AACGCCCCCT GTAGATATCG ACAACATCAT CGACCGCTTG CTGGAGGTGC GGGGCTCGAA     600

GCCGGGGCAG CAGGTGGACC TCGAAGAGCA CGAGATCCGC TACCTGTGCT CCAAGGGCCG     660

CAGCATCTTT ATCAAGCAGC CCATTCTTC                                      689
```

(2) INFORMATION FOR SEQ ID NO:714:

(i) SEQUENCE CHARACTERISTICS:
            (A) LENGTH: 620 base pairs
            (B) TYPE: nucleic acid
            (C) STRANDEDNESS: single
            (D) TOPOLOGY: linear (ii) MOLECULE TYPE: DNA (genomic)

(vi) ORIGINAL SOURCE:
        (A) ORGANISM: PAG1468UP (xi) SEQUENCE DESCRIPTION: SEQ ID NO:714:

GATCTCAGAA TTATCGGCTA GCAATTGATA TTAGCATACT TAATTCGTGC TAAATACTTT        60

GGCATCGCAT CTAGACATAG GAAGTAACCT CAAAAAAGCT ACGCAGATAG TAAACCTGGA       120

AGAGAGATTG CGCAACAACA ACGGCCAGTT GGAAAATAGA CCACCACTTG ACCCTGTCAT       180

TTGTAGACTC AGCAGTGTTC CTGTGTGTGC GTTCGCGAAT CTCGATGTAC TGTTGCTCGT       240

TCATTACTTC CATTGTGAGC ATGGAGAGCT TGCGCACCGC ACCCTCTAGC GTCTCCGAGC       300

TGGAATCAGC GGCATCGGGG GAGAGAACAC CGTAGGTATT AAACGTGACA TCCTTAGTCA       360

GGTAGCCCGA ATTGTCGTTC GCAAAGCAGT ACTGGTATTT GCCATCTGTA GGCGCCTTCA       420

AGGTCAACTC ACCGTGCGAC GACGCACGCT GCGCATCCAG CACTGACCGT CCGTCAATCC       480

CGTACACCAG CAGGTCTCCA GACAGCTGTT GATGTGATTG TGGGTCTCTG TCGCCGAATT       540

GATAAGTGAT TGTCAGCACG TCCCCGCCTT TCAACTGCTC AAAGAAACAG CGCCGCCCGT       600

AGGGGGGAAG AAGTACATTG                                                  620

(2) INFORMATION FOR SEQ ID NO:715:

(i) SEQUENCE CHARACTERISTICS:
        (A) LENGTH: 686 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1469RP (xi) SEQUENCE DESCRIPTION: SEQ ID NO:715:

GATCAACTAC ATCTGCGAGC AGCAGCCGAA TTGTAAGGTG GCCATCATAG CATATGACAA        60

GTGGCTGCGT TTCTTCAACC TGCGCCCGGA GTCGAGCCAG GCACAGGAGC TGATTGTGTC       120

CGAGCTCAGA GAAGTCTTCC TGCCGCTGTA CAGCGGCCTC TTCGTGAGGC CTGCGGAGGC       180

AATGCATGTC ATACAGGACA CGTTGGTCAA GCTCGAGTCG TTTATCCAGG ACGACAAGCT       240

CTCGCACGGC GCCGAGGCGT GCTTCGGGTC GGCGCTCGAG GCCGCGCTGC TGGCGCTGGA       300

CACTGCCACC AATGGTAATG GCGGCAAGAT CATTGCGACT CTGAACACGC TGCCCACCGT       360

GGGCAACGGC AATCTGACGC TGCGGCGCGA CGACGGCCTC AAGAAGAGCC TGAAGTGCGA       420

CAACAGCTTC TACACCGCGC TGGCGGACAG GATGCTGAAG GCGTACGTCG GCCTGGACCT       480

CTTCTGCACA GGCAGCGCCT TCATGGACTT TGCCACGCTC GGCCACCCCG TGCTGGCCAC       540

CTCCGGGACG TTCCGCCACT ACTCGAACTT CCAGCTCGAC GCGACGAGTT CCCGCTGGGT       600

CAACGACATG CTGCACGCCG TCAGCAGCAC CGTCGGCTAC CAGGCGCAGC TCAAGGTGCG       660

CTGCTCCTCG GGGCTGTCGT CAGTCG                                           686

(2) INFORMATION FOR SEQ ID NO:716:

(i) SEQUENCE CHARACTERISTICS:
        (A) LENGTH: 572 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
    (A) ORGANISM: PAG1469UP (xi) SEQUENCE DESCRIPTION: SEQ ID NO:716:

```
GATCGGGCGA GCAGGACTAG AGATGAGCAG CAATGACAGT GATTATCTCC TGGTTACCTT      60

CAAACTCTTC ACTCTCCTCA AGAACTTGTT ACCTGATGAC TCCTTCTTAT TGTCTGTGTC     120

ACGCGCGCCC GTGTAGGCGT CTTCGTCGTC CTCCTTCTCG TCCTCAAGAT AGCCAGAGTG     180

GGTCTTAGTC AGCTTCAGGT TGCCGTTCCT GGGGTCGGGG CCAATCGCCG ACGCGGACGG     240

AGGGCTTTTC GCCAGCCTGT GGCTCAGAGA CTTCTTCCTG CCCACCGTGC TCTGCTTCAT     300

CGCCTCTATA GCGACAGGGG CCGCCGGCGC GCCGTCGAGG AACGTCGTGG AGCCAAGCCC     360

CTGTGTCACG GGCCCATGCA CAAGGTCCGC GGTTACCTTG GCGTCGAACT GCGTCACCTC     420

CGAATGGTTC TTGATAGCGT TCACCGTCGA CGACGAGCGC TCGCCGACGT CGCGGCGCGA     480

ATACAGGTAC GAGTCGTCGT CCTCGTCGAT GCCGAAGACC TCGTTCATCG CAGACTTGTG     540

TGCGGTGGCC CCGACAACGT CGAGTTCGGC CG                                   572
```

(2) INFORMATION FOR SEQ ID NO:717:

(i) SEQUENCE CHARACTERISTICS:
        (A) LENGTH: 699 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1470RP (xi) SEQUENCE DESCRIPTION: SEQ ID NO:717:

```
GATCTTGCTG CTATCCAGAA ATGGGAAGTT CTTAGACRAC GGGGAATTAA GCCCCTTTTC      60

CAATATTTTG AGCGTCGTTT CATAGCTCGG AAGACGCAGC AGAAGCCCCC CCAGTAGTGT     120

CTGTTCATGT TCGCTCATGA AAGGTGTCTC TATCAAATCT AGCTCCATCA TCGCAGAGTA     180

GTTATTATCT TTCTTCCAAG ACAGACGCAC ATGCCGCAAC TTCGTCAGGA TTACAGTAAA     240

ATAATGGTAG AACCGCGGAC TCACAGAATC GACGACCGCT CGAAATGAAG TCGGCCCGTA     300

GAAGATCGTG CGGCCCTGCT TCTCTATCAC AAGATGGAAC TGCGAAAGTC TGTTCACGGG     360

GGACACCGTG CCCATAACGT GCTTCTGCAT GAACAGCTGC GGTACCATCT CGCTCTTCAT     420

CCGCGCGAGC TCAGTCTCAA GCTCGTCGAT CCGTCGCAGC AGCTCCACAT TGGGCGTTCG     480

AGCTGAACAG CTCCCGTGAG TTCACGTCGT GCGTAAACTC AGACAGGTAC ACACACTCGG     540

GCAGGCCCTT CCCAATACAT TTAGAGCACT TCGGCCGCGC CTTGTTGCAC TTGACGCGCC     600

GCTTGCGGCA GAACACGCAC GACTTGCTGA CCTTCCGCCT GGTTTTCACA ATCTTGCCAT     660

CGGACTCTGC CATCCCGCCA GCTTCAGCAA AATGAGTAG                            699
```

(2) INFORMATION FOR SEQ ID NO:718:

(i) SEQUENCE CHARACTERISTICS:
        (A) LENGTH: 655 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1470UP (xi) SEQUENCE DESCRIPTION: SEQ ID NO:718:

```
GATCGCGGAC GTGGAACACT GGCCGGAGAT GCGCGCGGCC ATCCTGGTGG TTTCTGCGGA      60

CCGCAAGGAC ACGCCATCGA CGAGCGGTAT GCAGCAGACG GTGCACACGT CGGACCTCTT     120

CAAGGAGCGC GTCGCGACGG TGGTGCCGCG GCGGTACGGA GAGATGGCGG CGGCGATCCG     180

CGCGCGCGAC TTCGCGACGT TGCGCGCCT GACGATGCAG GACTCGAACT CGTTTCACGC      240

CACCTGCCTG GACTCATTTC CGCCGATCTT CTACATGAAC GACACTTCGC GCCGGATTGT     300

CAAGCTGTGT CATCTGATCA ACGAGTTCTA CAACGAGACC ATCGTGGCGT ACACGTTTGA     360

CGCGGGTCCG AACGCGGTGC TCTATTACTT GGCGGAGAAC GAGGCGCGGC TCTGCGGCTT     420

CCTCTCTGCC GTCTTTGGCG CCAACGACGG CTGGGAGACC ACGTTCTCGA CGGAGCAGCG     480

CGCCACTTCG CCGCGCAGTT CGACGAGTGC GTGCGCGGCA AGCTTGCGAC GGACCTGGAC     540

GACGAGTTGC ACAGAGGAGT TGCCCGCCTC ATCTTCACGA AGGTCGGGCA GGGCCCCAAG     600

ACACTAAATC CTCGCTCATC GACCCCGAGA CGGGCCTGCC CCGCTGACGC TATTC          655
```

(2) INFORMATION FOR SEQ ID NO:719:

(i) SEQUENCE CHARACTERISTICS:
        (A) LENGTH: 708 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1471RP (xi) SEQUENCE DESCRIPTION: SEQ ID NO:719:

```
GATCAATTAA CTATCTAGAT GAGTCTAATT AATTAATATA CTTAAAAGTC CCGTTAATAT      60

CATTAGCTAC CCTATCGGAA CAGACCGTCT GCTACTAGGC CGAAAGGGTA AAGCAGTTGT     120

CAGTCAGTAC TTGCTGTTGC TTATGGAATG CCTGTCATAT GCCGGCAGCT TGTTTGTCAC     180

TGGAGTACGG CGCGTGCCGC CTTGCAGAGG GTACCCATGA TTCTGAACGC CAAGGTACCA     240

CACCTTCCTG CCACATCTCC TCGACCTCTT CCAAAGTCAA ACCCTTTGTC TCGGGGACAA     300

AGAAGAAGAT GTAGAAGAAC GCAAAGATCA AACAACCCAT GAACACGTAG CCGTAGTAAA     360

ACCTGATCGC ATTGGTAATG TATGGTGTAA AGAAGGCGAT CAAAAAGCCC CATATCCAAT     420

TCGCGGCTGT GGCGATAGCC ATGCCCTTGG CTTTGACTCT TAATGGGAAA GTCTCCGAAA     480

CAATGACATA CGCAATTGGG GCCCAGGTAG TTGCAAAGAA GAAAAATGTA GAGGCAGGTA     540

AAAACAATCA TAGCATTGCC TGCCGGTCTG GAAGAAGGCT GATCGGGTCC ATTGGGCCAT     600

AGTCTTGTCA CACCAACGGA GGCAAAAATA ACCATACAAA CGGCCATTGC CGCGGCACCG     660

TAGAAGCAAA CATTTCCTCC TGCCAAATCT ATCGACAGTG TTACATTG                  708
```

(2) INFORMATION FOR SEQ ID NO:720:

(i) SEQUENCE CHARACTERISTICS:
        (A) LENGTH: 718 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1471UP (xi) SEQUENCE DESCRIPTION: SEQ ID NO:720:

```
GATCTTCGCC TTCTTCTACA TGTTCTTCTT TGTCCCAGAG ACAAAGGGTT TGACTTTGGA      60

AGAGGTCGAG GAGATGTGGC AGGAGGGTGT CGTCCCATGG AAGTCCGAGT CCTGGACTCC     120

TTCCTACAAG AGAAATGCTT ACGAGACTGA GGAGGTGAAG CCAGAGAAGA CCTGGGCTTA     180

AAAACTTTAA ACTACAAACT TTTTTGTTCT GCTAATCATC GGGTTAAAAC CTAAACCTAA     240

TCTATGTTCA TTAATATTGT TATGACGTTC ACGAGATAGC ATATGTAAAT TACTATTAAA     300

AATATGCGAT TAATCTGTAT TTATTAGTTG TAATTGCAAT GCCATATGAT ACTGCAAAGC     360

AATACATGCC GAGATAACCA ACGCCACTGA GGCGGGACTG GGCCCCTTCT CCGGCCCGGC     420

GAACATGCCT GTCGTTGGTG GGCCGCGTGC CCGTCGCCGG CCAGCCGCAT GCCCGTCGTC     480

GGTCATCGCC CCACTTTCAA ACTTTGTAAT CGAGCAGGAA ATTAAGATTC GTTATAAATG     540

ATATCAAATT TTTCGTCGTT TCTTTTCAGT GAGTAATATT GTTCCGGCAC CGCACGCCGA     600

TGATGCCGCT ACATCGCACA GGGCCAAAGC ACAGGTGCTA AACTATTGCT TAGTTGGCGT     660

CGTTGAGCTC GTTTATGCTT AGTGGAATAT CTGCAGCATA TTCAATATCA AGTCTGAA      718
```

(2) INFORMATION FOR SEQ ID NO:721:

(i) SEQUENCE CHARACTERISTICS:
        (A) LENGTH: 695 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1472RP (xi) SEQUENCE DESCRIPTION: SEQ ID NO:721:

```
GATCTATCTC CCAGCTTAGA GAGACCGTCC GGATGTAAGT GATACCCAGA CAGCCAATGA      60

TACTGGTCAA GTTTTGTAGT TTTATAAGAA AACATATATT AAACGGCTAA AGACAGAAGG     120

CGAAAAGCCC GACTTTTATG GGCGTAGAAG TCGTGAAAAA GGCGAAAAAC TATATTTCCA     180

CTTAGGGCTC CTCCTTCCTC ACGTAAACGC GCATCATCAT ACGCCTTCTG TGAGTCAAGA     240

GCACTACGAC ACGCCGTGCA TTCCCTCATA CAACCTTGCC AACACATGAT CATGTCCAAG     300

GATATTGCTA CGACCCCAGA ACTGTCCGAA CCAGACAAGT ACTTCGTTGA GCAGCGCGAT     360

TTGCTGCTAC AAGAAATCAC CTCCACGTTA GACTCCATCC TGAACAACTT AAATGGCCTG     420

AATATTTCCC TGGAGAACTC CATCGCAGTA GGCAAAGAGT TTGAGAGCGT GTCCGAGCTT     480

TGGAAGGTCT TTTACGACGG ACTCGCGAAC GGAGCGGCTC CTGGAGTTGC CGCAGCCAAC     540

CCGTCGTCTC AGGACCTGCC CACTGAGCCC GTCGCCGCGC ACCAGAATGC TGCAGCGGGC     600

AATAGTGACG CACCAGCGCC ATCGCAGTAG CGTTTGCACT CTGCCCTGGC TTTACACCCG     660

TGCACCCACA TTGCGCTCTA CTTTTATGTG TCATC                               695
```

(2) INFORMATION FOR SEQ ID NO:722:

(i) SEQUENCE CHARACTERISTICS:
        (A) LENGTH: 719 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1472UP (xi) SEQUENCE DESCRIPTION: SEQ ID NO:722:

```
GATCTCGATT GAATGCCAAT GAAGGTTTAT GGCCGTCACG GGAGGTATAA CAGACTTGTA      60
ACGACTTTTG GTAAGACCCA CGGTGAGGAA GATAGCTGGT TTAGCAGCGA CGATGAGAAC     120
CACGGCAGAC CAGTTAGCGA CGACACAACC AAACTCAGCC TGAGCCAAGA TCGATGCAGC     180
GAATTACCGG AGGAGACGAT AGGTGCGAAT AGAAAACGTC CGGCGGAGCG AACGCAGACG     240
GATCCGGTGT GGGAGTTTCT GGAACGGCCG GCATCGGGGC AGAAGCGGAG AAGACGAGCA     300
ACATGCGATT CTACAGAATA TAGAGAGAGT GCCAGTCAAG AGTTTCTAAA CGCTGTGAAC     360
GTTGTGCAGG GCATAGTGTC TTCTCTCAAG CCTGCAAAAG AGGTAGTTGA GCACTGGGCG     420
GAGCTTGAGG ATGTGCCAGA GGATCGGGGC AATAACGGGC AGGCGGTCTA TGGCAAAACA     480
AGAACATGCT TGCAAAAGCG GAAGAGGATT CTGACACCGA AGCTGCTGCA CATGAGTCTG     540
ACGAACCGCT GCACAGGGCG ACGAAGCACT ATCGCGGCAC TTTAATGAGC TGCGTACGAT     600
GGGCGAGACT CTTAAGTACA GCGAAGATCT GGACTTTATA TTGTCCGACA ACTCCATGAC     660
GACACCGGAA CATAGACGCA CCACATGCTG CGCTTGTGTC TGGATATGAT GAACAACGA     719
```

(2) INFORMATION FOR SEQ ID NO:723:

(i) SEQUENCE CHARACTERISTICS:
        (A) LENGTH: 675 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1473RP (xi) SEQUENCE DESCRIPTION: SEQ ID NO:723:

```
GATCGCATCA TCCTGTACAC CAAGCGCGAC GTCTGCGCCG CGCCCACCCC CGCCGCGCTC      60
CACCGCTGGC ACGCCGAGAC CGGCGACGAC TACATGCTCC TCGACGCCCG CAGCGCCGCG     120
GACGCCGCGG CGCTGCTCGC CGCCGTGCGC GCACGCTACG ACGCCGCCGC TGCCGCGCCC     180
GGCGCGCTCC CCCTCGGCTA CCGCCTGCTC GTTGCGGGCA TGCCCAACGT CGGCAAGTCC     240
ACGCTGGTCA ACCGCCTCCG CGCCTCCGGC ACCGCGCGCC GCGCCAAGGT CGCCGCCACC     300
GGCGCCCACC CCGGCGTCAC GCGCGCTACC AGTGAGTGCG TGCGCATCGC CGATCACCGC     360
GCCGGCGTCT TCATGCACGA CACCCCCGGC GTCGCCCTGC CCGCCCGCGC CTCCTCCGTG     420
CGCCGGATGC TCGCCCTTGC TCTCGCCGGC TGCGTCGGCC CCGCCGTCGT CGACCCCGTC     480
ATCCAGGCCG ACTACTGCTC TACCTCCTCA ACCTTCAGGG CCTGGCCCCC TCCTACGCCG     540
CCTACAGCCC CCCCACCAAC GACATCGCCG CCCTGCTCGC CGCCGTGTGC ACCCGCCACC     600
GCCTACGCTC CGAGACCGCA GCCGCCCTGC ACTGGCTTGC CATCCGGGCC CCGGGCCTCT     660
GCCTGGAACC GGAAG                                                     675
```

(2) INFORMATION FOR SEQ ID NO:724:

(i) SEQUENCE CHARACTERISTICS:
        (A) LENGTH: 703 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:

(A) ORGANISM: PAG1473UP (xi) SEQUENCE DESCRIPTION: SEQ ID NO:724:

```
GATCTAGACG GAGTTATTAT GCCGCGGCAC CTCCAGCGAC TGATACTCAA GAATGTGCGC      60

TCCGTGCGGT GGTGGAGGTT CCGAGAGATC CACGAAATTA CGCTAGATCC TAATACGTTT     120

ACCAAGAAAC AGGGCTTTGT GGGAACTATA CACGGGCCAG ATCAGGATCG GGTGGAAGTG     180

CGGCAGATAA ACAGGGCTGT CATGAGTCAG GACACATACT TCCACTTTGA TAGTCTTTTG     240

AGGGCCAGGT TCCAGAACCT CAACTACATC AGTCTGCACA ACGTTTCCGA GGAAATTACT     300

GGCATCATAG TGCCTCACCG ACTGTATTGC AATGGCCGCA TCAGCATTGC AGGCTGCGTC     360

GTGAAGGGGG TTGTAATGAT CTAAACTTGC CCGGATATCC CTATTGAGAA ATAAACACAT     420

GGGTGAAGTT ATACATAGGC GCGGAAGAAG CCGCTTGAAT ATTGATAGAC CGAATAGTGC     480

GATCAATGTA ATTAAATAGA TAGGTTACAG CCCTACCGGG CTGGCATTTG GTCCGAGATT     540

GGTCTGCCTC TACCAAGTCA GCCAGTTACC GGAGGGTGAA GTAGTAGGAC ATCATAACTC     600

ATAAAAAACG TTACATTCGT TGTGCTTGTC GGGAAATCAG TAATCATGCA GGTGCGTCGT     660

GAAACCGAAG GAAACGTAAT GGCGTGGAAT AAGTAAAAGA TGC                       703
```

(2) INFORMATION FOR SEQ ID NO:725:

(i) SEQUENCE CHARACTERISTICS:
        (A) LENGTH: 716 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1474RP (xi) SEQUENCE DESCRIPTION: SEQ ID NO:725:

```
GATCGTTCAG TTTAATCACC TGGGACGCAC TGCCTTGCGG TTCCAGCACT GCCTGAAACT      60

TGGCCAGGCG TTGCATCACG GCATTAAGCT CCTGTACATC GCGCTCGTGC TGGGCCTCCA     120

GCTGCAAGCG CAGTTCAGCG CTGATATGCT TCCCGCCCGG TGTAGACATC TGCGGCAAGC     180

TAGGGTAGCT GCCCGACCGC CGCAGCGGCG AGCTGCGCGC GCCCTTGTCA GCCGTCTTCT     240

GTGCCCCCAT TAGTGGCCGT ATCATCGTCT CGATCCCGCC GTTTGCCATC ATCGGTATGG     300

GTGTGTTGTA ATCGTCAATT ACCGCACTCC AGTCCTCGTC CAGGTCCGTA AAATACTTGT     360

CTTTTTTGCC GCCAGCGTGG TTAGACCCGC CCGTGGTGTT GCTCCGAAGC GGGCTCAAGT     420

GCACGCCGCG GTGGCTGCTG CTGTGGCTCG ACAGGGACG TGCATAGTCT GCGACCTCCT     480

GATGGCGCTA ATATTCCCAT CGCTATCTGC AGGCTCCAGC GATGGCGACG CCAGCTGATT     540

CGACTTCGCC GATGACGGCG TCTTCCACGA CTTGATCAGC GAGCCCACAA GCGACGAAGA     600

TGATGAATTT GACTTTTGGT ACATTTCTTT GGACCCATTC CCATTATGGG GAACCGTCCT     660

GATAGCCATC ACAATGTATA GCTCGCTACT CTGAACCGCG TGGCAACCAC TGCAAC         716
```

(2) INFORMATION FOR SEQ ID NO:726:

(i) SEQUENCE CHARACTERISTICS:
        (A) LENGTH: 699 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
            (A) ORGANISM: PAG1474UP (xi) SEQUENCE DESCRIPTION: SEQ ID NO:726:

```
GATCGAATTC TCACAGGCCA GTACCTGCGT ATTACAGGTT TGCCATAGTA TGATTAGAAC      60

CGTAAAGCCC AAGAATGCCA GGGCCAAGAG AGCTCTGGAG AAAAAAGAGC CGAAATTGAC     120

GGAGAACGTG AAGCAAGCGC TTTTAATTCC TGGCCAAACT TCGAATAAGC TCTTGCACGA     180

TGTTATGGTG GACCTTGGTG GACTCAAGAA GCCTGATGTG AAGCGCTTCA CGCGGAAGAA     240

CGAGCTTCGT CCGTTTGAGG ATGCGTCGGG TGTCGAATTT CTCAGCGAGA AGAATGACAG     300

CTCGTTGGTG GTGGTCTGCT CCAACTCGAA GAAGCGGCGC AACAACTTGA CATTCATAAG     360

GACGTTTGGG TACAAGGTTT ACGACATGAT GGAGCTGCAG ATTGCAGAGA ACTACAAATT     420

GCTAGCGGAC TTCCGGAAGC AGACGTTTGC AGTGGGGTTG AAACCGATGT TTTCCTTCCA     480

AGGTGCGGCA TTCGACTCTC ACCCAGTATA CAAGCACGTC AAGTCTTTGT TCCTCGACTT     540

CTTCCGCGGT GAGGTGACCA AGCTGCAAGA CGTTGCAGGG CTTCAGCATG TGATAGCAAT     600

GACGATCCAG GGCGACTTTG AGGATGGCGA GCCATTGCCC AACGTCCTTT TCCGCGTCTA     660

CAGGCTTAAG ACGTACAGAA GCAGCCAAGG TGGTAAGAA                             699
```

(2) INFORMATION FOR SEQ ID NO:727:

(i) SEQUENCE CHARACTERISTICS:
        (A) LENGTH: 749 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1475RP (xi) SEQUENCE DESCRIPTION: SEQ ID NO:727:

```
GATCCGACCA ACGAGCGCAT CTGCAGCCAC ATCGTTGATA ACGTCACCAT GATCGACGAA      60

ACCGAGGAGG ACCAGGGCGC AAAGAAGGGC GCCTTTGCTG TTTGAAGCCG GATCCTGCGG     120

CGTTCAACCG TAAATAGTCT TATAGCCAGC ACGCCAGGCG CCGGCCGGTT CCTATGTAGT     180

CCTGCAATCG CTCGCTTGCT AGCCGCACGA TCACAGAATA CAGCTACTTT ATCCTAAATC     240

CACTCCTATC AAAATATCCA GCCGCGACAT TTGTTCTCTG TCTCGTGGGA TGTGGCGGTC     300

GCCATTGTGG AGTAGGGCCG CAACTCGGAC AGCGACCACA GGTCGCCATC ACAGCTGCCG     360

GTCCCGTGTC CGTCCCTGGA ATCCTGCTCC AAGCCCTTCT GGTCAAAGCC AGCCAAGCTC     420

CCCTGTCTGA TGGCGTCCTC GACCGCTGCG TCCAGCAAGT CCTGGTATGG ATCTGCGCCG     480

ACGCTTCTGG GGGCCGCAGG CGTTGTGTGA AGCCAGTCGC ACAGAGAGGG TGTCGCTGTT     540

AGCGCAACAG ACGAGGCGCC TGTGCCGGCC GCATGGGCCC CCGTGCCGAA TGCGTGCGGG     600

TTCATGTAAT TGCTGCCCTG GTCCGATGTG TATTGTGTCT GCGAACGGGA AATCGGGGAC     660

GCAGGAACGT TCGCCTCGCC GCCATCGTTC TCGCAGCTCT TCGGTTGCGG CACCAAAGCC     720

TCCTTCTGCA GCATCCGCCC TGAGCCGTT                                       749
```

(2) INFORMATION FOR SEQ ID NO:728:

(i) SEQUENCE CHARACTERISTICS:
        (A) LENGTH: 740 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1475UP (xi) SEQUENCE DESCRIPTION: SEQ ID NO:728:

| | | | | | |
|---|---|---|---|---|---|
| GATCTTCCGT | CCCGAGTACG | GTCGTCTCTT | CGAGATATNA | GCACGCAGCG | CAACTGTATC | 60 |
| AAGCTAACCA | ACACAGTKCG | CACGCTTTTC | GAGCCGAGCT | CAGGCGCGAG | GTGAACCAGC | 120 |
| TCTGAGACAG | ACAGACGCCC | CTTGTTCAGA | AGTAGCTCAA | TAACACGTCC | GGCTCGCTCG | 180 |
| CCGAGGTGCG | ACCGCGCTAC | CTCTGTGTAC | AGGAAGGTTT | CAGGACTCAA | TGTCCTCATC | 240 |
| TCCAGTGTCG | ATACCGGCAC | CTCCGCAGCA | CGCTCGTTTT | CGACTTGTCC | ACCTGCAGCA | 300 |
| CCCATAGATC | CGTTCATTAT | GCACTACGAC | CTCGCCCTCA | CTCAAGCCCA | GGGCCGTCTG | 360 |
| GAACGCAATA | CTCGCTAGTG | CTAGTTCCCA | CCTAATATCT | ATCTCATCGC | CCATCGAGCA | 420 |
| GCGGGCCAGC | TAAAAAATCA | CCACTGCGCG | CTCACCACGC | ACGGTTCACT | AAATACGAAA | 480 |
| CAGTTGTTCG | TCACGTGTTG | CTCACGTGAT | TTTACCCGGC | CCGTATAATA | TCGGGTTCTC | 540 |
| AGCGCGCCGA | GCCAAGGACA | CTTCCTGTAT | CATAACAAAC | CAGCACAGGC | GGTAGGAGCT | 600 |
| ATCGGCAGAG | TCCCAATACC | CTTGCTACTG | TTGACATTAG | GTGGTTCAAA | TGAGTGTCTG | 660 |
| TTTAGTGGTT | ACCAAGAGTG | TGGCGACAGC | CACATTGGGG | ATCTACACCG | GGATGGTGGT | 720 |
| AACGCGGCAG | TTGGTCCTTC | | | | | 740 |

(2) INFORMATION FOR SEQ ID NO:729:

(i) SEQUENCE CHARACTERISTICS:
        (A) LENGTH: 707 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1476RP (xi) SEQUENCE DESCRIPTION: SEQ ID NO:729:

| | | | | | |
|---|---|---|---|---|---|
| GATCGTATCG | CTAACTGTAA | TATCGAAAGA | AGCACAGACA | TCCCGGAAAA | ATGACATCTC | 60 |
| AGTGACACTC | TTCAACAAAT | CATAAGAAGA | AAAGTATGTG | ACTAATGCTT | GCAGAAAAAT | 120 |
| AAATTGCTCG | CTACCAGTAA | GCGATGTTAG | TAGCGTGCCA | TGGCATTCAA | TAAATCGTAA | 180 |
| GAGATACGTG | GGTGGTATCT | CGATGCTTTT | GAGGTACGCA | AAAATTGGGC | CATATAAATC | 240 |
| GATCTTGAAT | GGTAGCCTTT | TGCATATCGA | TTCTTCAAGA | AGTCTGTTTA | TAAGTTCTTT | 300 |
| ATCAGAATGC | TGCATAGACT | GATGCAGGAG | AGCACTTAGC | ACATGCCCTT | TATTCCTAGG | 360 |
| ATAGAGCAAA | TATTCTTTGA | ACGAAGCTGG | GTCTTTCCGG | AAGTCAGGCT | TCATACCATA | 420 |
| AAGGTACATG | TATACATTCC | TTGCGACATC | CATATCCTCA | ATACTGCTTT | CAAGCATCGC | 480 |
| AAGGTAAAAT | TCGTAGGAAA | ATTCGGGTAC | CCAGGAATGC | TGTTGAAATT | GCGTCCAGAG | 540 |
| TTTGTATGCT | GTCTTGGGGT | GGTTCCTTGC | GACGGCCAAC | AGGAAGTTGG | GACAGAACCA | 600 |
| GCGTCTGACA | GGGAATCAAG | ACCATCTGTT | GAGCGAATTT | GCGTGAGAAG | GCGATCAAGC | 660 |
| AGCTTCACAG | CAACTTCCAG | GGAATCTAAG | CTGACAAGCC | CAGCTAC | | 707 |

(2) INFORMATION FOR SEQ ID NO:730:

(i) SEQUENCE CHARACTERISTICS:
        (A) LENGTH: 635 base pairs (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1476UP (xi) SEQUENCE DESCRIPTION: SEQ ID NO:730:

```
GATCTGAAAC TAACAACAGC AGTGCGTGAA CCAAGAGGCA TTGGAGGCGT ATGACGGCGT    60

GTCGCAAGGC AAGTACACTA TCGGCTTGGG CCAGACCAAC ATGAGCTTTG TGAACGACCG   120

CGAGGACATC TACTCGATGT GTTTGACCGC GTGCTCGAAC TTGATGAAGA ACTACGATAT   180

CAAGCCGGAA AGCATCGGCC GCCTCGAGGT GGGTACGGAG ACGTTGCTTG ACAAGTCGAA   240

GTCCGTGAAG TCTATTTTGA TGCAGTTGTT CGGCGAGAAC ACCGACTTGG AGGGTGTCGA   300

TACCGTGAAC GCCTGCTATG GCGGTACTAA CGCGTTGTTT AACTCCTTGA ACTGGATTGA   360

GTCCAGTTCG TGGGACGGTC GTGACGCAAT CGTTGTTTGT GGTGACATCG CAATCTACGA   420

CAAGGGTGCC GCCCGGCCCA CTGGCGGTGC GGGAACTGTC GCTCTCCTGA TCGGTCCAGA   480

CGCCCCCATT GTCTTTGACT CTGTGCGTGG CTCGTACATG GAGCACGTCT ACGACTTCTA   540

CAAGCCTGAC TTCCGCAGTG AGTATCCATA CGTGGACGGC CACTTCTCAC TAACATGCTA   600

CGTCAAGGGC CGTCGACCAG GCTTACCGCG CCTTA                             635
```

(2) INFORMATION FOR SEQ ID NO:731:

(i) SEQUENCE CHARACTERISTICS:
        (A) LENGTH: 719 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1477RP (xi) SEQUENCE DESCRIPTION: SEQ ID NO:731:

```
GATCTTTGCG AGGGACCACT CTGCAATCCA AGAAGACTAG AGGAGTTGTC TAGGACAACA    60

AAGTTTATAA GGAGACTTCT GGTGTTTTAC CGTCCTTTTC GATACCGATT CTCGACAGTA   120

TATTCAAAGG CCAATAACGC CAAACAATAC GTTAAAGTTG GCTGCCAGTT TTTCAACACA   180

CTACTACAAC ATTATGAGGG CATAAAGGTG CTTCTAGATG ATAGCAAAAT CATTCCTCAG   240

CTCGCCAGTA CTCTCTATAA GGCTATGGAA GGGCATATTT TACCCAGTAA GCTCTTCTCC   300

TCTTGGGCTC TCCAGAATAC GTTATGTGGC TCCTACTTCA AATTCCTCGG ATTGCTAATG   360

AAATCTAAGG AAGGAATCAA TATATTAGAA AAATGGAACA TGTTCACTGT CATCTATAAA   420

ATGTTTCAGC CATCACCCCT AGCGGAAGAA TATTTGTTAC TCATGCTTCC AGAGTTGGAC   480

CTCTCTCACA GCATACATTG TAGGATTATT TTTAGCAAAG CGCTAGTCGA CAGTAGAGAA   540

GTCATAAGGA TCAATGCTAC CAGGGTTTTA GGCGAAATGA TCAGCAGCGT CAAATTATCT   600

GATCCCACTC TGGAAGAGTT CATGTTAAAC CTGTTGGTCG CTCAGTTGTA CGATTTATCG   660

AGTGAAGTGG TAGCAGTGGC CGACCAGATA CTGTACCATT ACTGTTTAAG TCAAAGTAT    719
```

(2) INFORMATION FOR SEQ ID NO:732:

(i) SEQUENCE CHARACTERISTICS:
        (A) LENGTH: 726 base pairs
        (B) TYPE: nucleic acid

```
        (C) STRANDEDNESS: single
        (D) TOPOLOGY: linear (ii) MOLECULE TYPE: DNA (genomic)

(vi) ORIGINAL SOURCE:
        (A) ORGANISM: PAG1477UP (xi) SEQUENCE DESCRIPTION: SEQ ID NO:732:

GATCCGAATG TCCTTAGTCT GTGGGAAGGA ACCGATGGTG GTGGTTGGGA ATAGCGGGAG    60

CTTGAAAATT GGCTGCTGCT CCTTGAGACG CTCCCCGAAT GGTGCGGCTC TCGTGGATAG   120

CTTCTCGTTC AAACCAGCAA CACGTCCTGG ACAGCAGGAT CGTTGGTGAT CGCAGAGGCG   180

GCACGCGCAG CAATCGAGTC TGCATTTGCC TTCAACTCAG AGGAAAAGTC TTCGCCAGAA   240

GCGTTCTTAG CGAGGACAAC AACCTCATGC AGCTTCTGGG TTGCAAAAGA GAACCAGTCC   300

TTGATCTCTG GCTCCAAGGC AGACTCGTTT TCCAAGTCAA CTGGAGTGTG CAACAAGGAA   360

GAGGACGTGG CAACAATAAC GCGGTCCCCT CCTAGTTTCT CAATTGCCTT AGAAATAGTG   420

GCAGCCGACT TCGCGAAGTC ATTCTTCCAG ATGTTTCTAC CGTCAACAAC ACCTACAGAC   480

AACGACTGGT TTTCGCCAAC GATCGCTAGA ACGTCGTCCA ACTGCTCTGG GTTTCTCACC   540

AAGTCGAAAT GTAGGCCAGC CACTGGAAGA TCCACAAGCG CCTTCAAGTT CGGAACGACT   600

GTCCCGAAGT AGGTGGTCAA CACAATGTCG AGAGACTTTT CCGCACCTAT ATGTTCATAA   660

GCGGTCTTAA ACGCAGACTG TACGTCCTCT GCAAGATCTA AGACCAACAC AGGCTCATCC   720

AGCTGA                                                             726

(2) INFORMATION FOR SEQ ID NO:733:

(i) SEQUENCE CHARACTERISTICS:
        (A) LENGTH: 675 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1478RP (xi) SEQUENCE DESCRIPTION: SEQ ID NO:733:

GATCATTATG CATTTTATGA TATACACTGC TATCAAAGAC GACCAGTCGG TAGTGAATAC    60

ACACCGGCTG GCAGACACAA CCAATGCCGA GGATGAGGCT AGTGAGGACG AGTTAGAGGA   120

GCTCGTTAGT AGCACTGCAC ACAGCGGCGA TGCTACTAGC GAGTGAAGAG GTATTTTACC   180

TGAGCTTTGG AATATATAGG TAGGTGATGA GCTTTACAAT ACGTATTCGC TAACAATGAA   240

ATGCAGGAAC TCCTCAAGCT CTTTAAGTTC TGTAAAAACG GTATCAAAAA CCGTTTTTCC   300

AGCGCTGTCT GCGTAAATGA CCTGGATTAT CGCATTGCAA TAGTTGCTGC TCTTCAAGGT   360

CAGATCTATG ACGCCTTTTG CGCCGAGGCT GGTACGCAGT TCGCTGCGTG GCATGCGGAG   420

GATCTTGTCA AATAGGCCTA TCTGTTTGTT TAGGCTAGCG ATGTTCGCCT CACGAGCATG   480

GAGCGTATCG GGCTCGCTTC GTTGTGGAAG CAGCTCGATG GACGAACCAG GAACAATGTT   540

CAAGACGCAC TCCGTAACAA CTCTTTTAAC CACCTGTAAG TAGTTTCTAT GCCTTATTCT   600

ACCCAAAACA GGTCTTAATA GGAGAAGGTC ACCATCAGCT CTATATTTAT GCTTGGAAGT   660

TGCTGGCTTG AGGCC                                                   675

(2) INFORMATION FOR SEQ ID NO:734:
```

(i) SEQUENCE CHARACTERISTICS:
    (A) LENGTH: 706 base pairs
    (B) TYPE: nucleic acid
    (C) STRANDEDNESS: single
    (D) TOPOLOGY: linear (ii) MOLECULE TYPE: DNA (genomic)

(vi) ORIGINAL SOURCE:
    (A) ORGANISM: PAG1478UP (xi) SEQUENCE DESCRIPTION: SEQ ID NO:734:

| | | | | | |
|---|---|---|---|---|---|
| GATCTGAGTA | TCAAGATACC | ATGAGCGATT | CTTGCTCACT | CTTGTACGGG ACTGCCCCGC | 60 |
| TTATCCAAGT | GCAGACAAGA | TGCAACATGC | ATACTGGCAG | ACCAGGCCCT CTCGATCATC | 120 |
| GAGTTGCTTT | AAGCAACATA | GTAGGAGGCT | TCGAAGGAGG | AGTTCTTCGG CTACCTATGT | 180 |
| AAGAGATGCA | GCGGATGGTT | ACTGCTGGTC | ACGTGCTAGA | ATCATATACC ACGGAAAAGT | 240 |
| GGATATGTTG | CTTGCCCTTT | AGATATGGCA | GTTTTGCCAC | CCTACTTGAC ACAGCTGTAA | 300 |
| CAACGTTGAC | TAAGGATAAA | CAAGAGCTAC | TGTCAACGGG | CTATCCATAC AATGACATCT | 360 |
| GATCTAATGG | AGGTGGACTC | GGCCCATACA | CCGGATGTTT | ATAGCGCAAG CAAGGACAAC | 420 |
| GTTGACAAGT | TTGTCGATCT | GCTTCGCCAG | GTCTCCAAGA | CTACTATAAC ATTGGACTCC | 480 |
| CGCTATGTGT | GGAAGTCTCT | TCGCGAGCTA | ATGTCTTTGC | GCAAGGAGCT GCAGCAGCAG | 540 |
| ACCCTCACCA | TCCTTATCAC | GCTCCTATAT | CCGGACGACT | CGGCATTCAA GGTGCCATTG | 600 |
| CTTCGTGTGG | TGAACCAGAA | CTCAAAAGCA | GCGTCGAGGA | TGCGGAGGCA TTCCAGGGCA | 660 |
| AGTACCCCGC | AGACTTTATC | AGCTGACTGC | TGACGGCAAG | ATTGAC | 706 |

(2) INFORMATION FOR SEQ ID NO:735:

(i) SEQUENCE CHARACTERISTICS:
    (A) LENGTH: 695 base pairs
    (B) TYPE: nucleic acid
    (C) STRANDEDNESS: single
    (D) TOPOLOGY: linear (ii) MOLECULE TYPE: DNA (genomic)

(vi) ORIGINAL SOURCE:
    (A) ORGANISM: PAG1479RP (xi) SEQUENCE DESCRIPTION: SEQ ID NO:735:

| | | | | | |
|---|---|---|---|---|---|
| GATCCGCTTA | CAGTAGCATT | GTCTCCGCAG | GTTGCCTGCC | TCAATTTTAT CCCGGCCCTC | 60 |
| GAAGAACTCC | AACTCGAAGA | GGAAGTTCGT | GCGGCACTGG | CATAAATTGT CTATGCCCAG | 120 |
| CCCCTGTTGG | CAGAACGCAT | GCTTGCACTC | TGCAAACTGC | TGCACCTCGA ATTCGCGGAT | 180 |
| CAAGAGCTGT | AGCTCCACGA | GCGCATCCTT | GGTAAGCCTG | CTGCCTCCGG AGCGGTCGGC | 240 |
| GCACCGTTTG | TCGATGCATT | CGTTGATCTC | CTCTGTTAGG | TTGCCGTCTG TCGTCGGCGA | 300 |
| ATTCTCGAAA | AGCGTCGGGC | GCACTATCTC | CCTGCCTGAA | GGCACCTTGT TCTCCTTGTT | 360 |
| CCGCTCGTCG | TTTTCGTAGG | GCGAGGTGAC | TGATGATGAA | TCATTCATAA AGCTGTTTTT | 420 |
| ATTCCGGAGG | CTGCGCTTGC | GCTGCACGTT | CACGTCAAAT | TGTTTCAACG CCCTCTTATA | 480 |
| AGGTCTTTTC | TCCATTATTA | TAGCACTATG | CCAAGATCCA | GATGTGGCAA TCTGGGATTA | 540 |
| CTAGACCTGT | TGCGCCAGCA | TCGAGTTCTC | TTATATACAC | TGGCAGTTTG TGTCTGACAC | 600 |
| AAAGACGTAA | AATTGGGACT | ACGAAAAGGG | AGTCGCCAAA | CAAGTGGCAA ACGTTGTAAA | 660 |
| AGGATAGTGT | ATATTTATAC | TATTAGTAAT | TATGT | | 695 |

(2) INFORMATION FOR SEQ ID NO:736:

(i) SEQUENCE CHARACTERISTICS:
    (A) LENGTH: 716 base pairs
    (B) TYPE: nucleic acid
    (C) STRANDEDNESS: single
    (D) TOPOLOGY: linear (ii) MOLECULE TYPE: DNA (genomic)

(vi) ORIGINAL SOURCE:
    (A) ORGANISM: PAG1479UP (xi) SEQUENCE DESCRIPTION: SEQ ID NO:736:

| | | | | | |
|---|---|---|---|---|---|
| GATCCGGGCA | TTACGGTGCC | CATCTACGAG | GAGGACATTG | TCGGGGACCA | GGGCGGGACG | 60 |
| GACGTAGACG | GGCAGCCGCA | GAAGCTGGGT | TCGTACCGGG | CGCGGGCCGG | GCGCTTCTCG | 120 |
| AACACGCTGT | CCAACCTGCT | TCCCAGTATC | AGCGCGAAGC | TGCACCACAA | CCGGAAGGGC | 180 |
| GGGACGGGGA | AAGTCGCGCC | GTCTGCTGCG | GACGCGGACG | CGGGAGCCGG | GTCTACCGTG | 240 |
| GTTGCGGGAG | AGATGGCGGG | CAGCATCACG | CCTCCGCAGG | ACCTACATAA | CGTGGTCAGC | 300 |
| TTCCCGGAGC | CATACGGGCT | TGCACAGCCA | CGCACTTCGA | GCGAATCGTA | TACGTATGGT | 360 |
| TCTGGATACA | GTGGCCACCT | GCAGCCCACA | GTCTCCAACC | CTGCTACGCG | GACTCGGAAT | 420 |
| AATACTGTAT | CTTCGCAGAT | TACTTCGCTT | TCAAGCATGG | GCCAGCTGGG | AACCCCCAGC | 480 |
| ACGAGCAACA | TCTGGACCAA | CAATGGCTCA | AGCCCGGCAG | ATCCAATCAG | CAACATGCTC | 540 |
| ACGACGCAGT | TCAACCCGAT | CCCCCTCCCC | GACTTTGGCC | AGTCGAACTA | CTACGACGTA | 600 |
| ATCACGCAGC | AGCAGCCTCC | GCAGTCGACG | AACTCACTGA | ATGTGCCCTC | CGGGGGTAAT | 660 |
| ATTTCTGGGA | AAAACGTACT | CGTTCTCAAT | CTAATGCTTC | TAGCATATAC | GCAGAT | 716 |

(2) INFORMATION FOR SEQ ID NO:737:

(i) SEQUENCE CHARACTERISTICS:
        (A) LENGTH: 748 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1480RP (xi) SEQUENCE DESCRIPTION: SEQ ID NO:737:

| | | | | | |
|---|---|---|---|---|---|
| GATCCTCTGA | GGCGAGCCCT | ATCCCAAGTT | TATTCCAACT | TCTTGCCGAA | AGGTAACAAA | 60 |
| CCGTTTATTT | ACATGAGTTT | ACACATAACA | CCGGAGAATG | TTGATGTTAA | TGTGCATCCT | 120 |
| ACAAAGCGTG | AAGTACGATT | TTTGTATGAA | GAAGAGCTAA | TAGAGCGCAT | TGGTAATTTG | 180 |
| CTCCATGAGC | GGTTATCTCA | GCTGGATACT | TCGCGAACTT | TTAAACCGGG | CTCTTTGACA | 240 |
| CCTGGGAAAC | ATAGTTCAAC | TGTGTCCTCC | GCATTCCGGC | AATCAGCGAC | CCCCGCAAGT | 300 |
| ACACAACCAA | AGGCAAAACG | TGCAGAAAAC | ATGCTTGTCA | GGACTGATGG | TAGCCAAGCT | 360 |
| AAAATTACTA | ATTATGTCAG | AGCAAGTCAA | AGCTCTACCA | GCTCATCCTT | TTCCACTTCT | 420 |
| TTAAGAAAGA | AATCACATGC | GGCAGCAAGT | GATGAACTTG | GCAGCATTGG | CGAGGACTCC | 480 |
| CAAGATACAG | CAACATCGAT | GACAACCTCT | ACACAAGAGC | CTAATCATAC | CAAGTCTAGA | 540 |
| GCCATTTTAA | CCTTATTGAA | TAATGAGTAT | GAAGTCGTAC | AGCGGGAAAG | AACGGAAGTA | 600 |
| AATCTCACCA | GCATCAAAAC | TCTAAAGCAG | GAAGTAGACG | AAGATATGCA | TAAGGGAATT | 660 |
| AACAAGTGTC | TTTGCAGATA | TGACCTATGT | TGGTGTCGTT | GATGCAACAA | GGCGACTTGC | 720 |
| ATCTATACAG | CATGGTTTAA | AGTTATTT | | | | 748 |

(2) INFORMATION FOR SEQ ID NO:738:

(i) SEQUENCE CHARACTERISTICS:
        (A) LENGTH: 727 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1480UP (xi) SEQUENCE DESCRIPTION: SEQ ID NO:738:

```
GATCGCGTCA TGGGATACAT AAACCACGGA ATCAATGAAA AGCTCGCTTA CGAACAGTTT     60

GGATCTGTAC CGGAGAAGGG CTACTATATT CCTCCCACAA TATTTCTGGA CGTTCCTCAG    120

AGCTCGAGAC TCTGCCGTGA AGAGATATTC GGCCCTGTGG CCGTAGTTGC GAAATTCAAG    180

GACTACGATG AAGCTATTCG TTACGCTAAT GACACTAACT ATGGGCTGGC ATCCTGCGTT    240

TTCACTGAAA ACATACGCGT TGCGCACCGC TTTGTCCGTG ATGTCCAATC TGGCACTGTG    300

TGGGTTAATT CCTCTAATGA TGAGGAGGTG GGAGTGCCTT TTGGCGGGTT CAAGATGAGC    360

GGTATCGGAA GGGAGCTGGG GAAGGCAGGC CTGCAAACTT ACCTCCAGAC TAAAGCAGTA    420

CACCTGAACT TTGCTTAGAT AGAGCAACTC ATATATTAGA ATCACTTCAT ACATCAACTA    480

TATATCATTA TGTATATGAC TATGCCAGAG GTGTAGTGGA ACCACTATTT ATCACGTGAT    540

AGGCGTTGCG CGGTCATCCC GCCAGTACCT GCGTTGCAGA ACGCGGGCGA CACATTCAGC    600

AGGTGCTATA TACAGTTGTC GAGGACAGTA TGGCACGCAG TACCATTATA GCAAGTAAGC    660

CGTGTGCTGT TTGCATAAAG CGTAAGGTCA AGTGCGACCG GCTGGTTCCC TGCACGAACT    720

GTGTCAA                                                              727
```

(2) INFORMATION FOR SEQ ID NO:739:

(i) SEQUENCE CHARACTERISTICS:
        (A) LENGTH: 683 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1481RP (xi) SEQUENCE DESCRIPTION: SEQ ID NO:739:

```
GATCGATAGG CCACACTTTC ATGGTTTGTA TTCACACTGA AAATCAAAAT CAAGGGGACT     60

TTTACCCTTT TGTTCTACTG GAGATTTCTG TTCTCCATGA GTCCCCCTTA GGACATCTGC    120

GTTATCGTTT AACAGATGTG CCGCCCCAGC CAAACTCCCC ACCTGACAAT GTCTTCAACC    180

CGGATCAGCC CGTATAGGAC TTTAAATGCT AGAAGGTGGA AAATGAATTC CAGCTCCGCT    240

TAATTGAATA AGTAAAGAAA CTATAAAGGT AGTGGTATTT CACTGGCGCC GAAGCTCCCA    300

CTTATTCTAC ACCCTCTATG TCTCTTCACA ATGTCAAACT AGAGTCAAGC TCAACAGGGT    360

CTTCTTTCCC CGCTGATTCT GCCAAGCCCG TTCCCTTGGC TGTGGTTTCG CTAGATAGTA    420

GATAGGGACA GTGGGAATCT CGTTAATCCA TTCATGCGCG TCACTAATTA GATGACGAGG    480

CATTTGGCTA CCTTAAGAGA GTCATAGTTA CTCCCGCCGT TTACCCGCGC TTGGTTGAAT    540

TTCTTCACTT TGACATTCAG AGCACTGGGC AGAAATCACA TTGCGTCAAC ATCACTTTCT    600
```

```
GACCATCGCA ATGCTATGTT TTAATTAGAC AGTCAGATTC CCCTTGTCCG TACCAGTTCT      660

AAGTTGATCG TTAATTGTAG CAA                                             683
```

(2) INFORMATION FOR SEQ ID NO:740:

(i) SEQUENCE CHARACTERISTICS:
        (A) LENGTH: 657 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1481UP (xi) SEQUENCE DESCRIPTION: SEQ ID NO:740:

```
GATCGGGTGG TGTTTTCTTA TGACCCACTC GGCACCTTAC GAGAAATCAA AGTCTTTGGG       60

TTCTGGGGGG AGTATGGTCG CAAGGCTGAA ACTTAAAGGA ATTGACGGAA GGGCACCACC      120

AGGAGTGGAG CCTGCGGCTT AATTTGACTC AACACGGGGA AACTCACCAG GTCCAGACAC      180

AATAAGGATT GACAGATTGA GAGCTCTTTC TTGATTTTGT GGGTGGTGGT GCATGGCCGT      240

TCTTAGTTGG TGGAGTGATT TGTCTGCTTA ATTGCGATAA CGAACGAGAC CTTAACCTAC      300

TAAATAGTGC TGCTAGCATT TGCTGGTTGC GCACTTCTTA GAGGACTAT CGGTTTCAAG       360

CCGATGGAAG TTTGAGGCAA TAACAGGTCT GTGATGCCCT TAGACGTTCT GGGCCGCACG      420

CGCGCTACAC TGACGGAGCC AGCGAGTATA ACCTTGGCCG AGAGGTCTGG GTAATCTTGT      480

GAAACTCCGT CGTGCTGGGG ATAGAGCATT GCAATTATTG CTCTTCAACG AGGAATTCCT      540

AGTAAGCGCA AGTCATCAGC TTGCGTTGAT TACGTCCCTG CCCTTTGTAC ACACCGCCCG      600

TCGCTAGTAC CGATTGAATG GCTTAGTGAG GCCTCAGGAT CTGCTTAGAG GAGGGGG        657
```

(2) INFORMATION FOR SEQ ID NO:741:

(i) SEQUENCE CHARACTERISTICS:
        (A) LENGTH: 694 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1482RP (xi) SEQUENCE DESCRIPTION: SEQ ID NO:741:

```
GATCCATTCG TTAATATGGA TTGTCTACAG TGAGAGCAAA GAGGGCGGGG GATTTAAAGC       60

ATGGTGGGC GACGCCTATT TTAAATGGGG GTTGTTTGCA ACGGTTTTGG CCGGGCTTCT      120

TGTCCTGCAT AGTGAAAAGT TCATTCGCCA AAGAACGTAC GAATTCTTTC TGATACTGCA      180

CAAGCTCTTC AACATTGTCT TTATTGTATG CATGTATATG CACATCAAAA CGCTGGGATG      240

GCACGGCTGG GTCTGGTCGA TGGTTGCCAT CTACTGCTTC GAGCGTGTGG CCCGGATAGC      300

TCGCATTGTA CTTGCTGGAG GCATCAAGAA GGCCACATTA ACAGATGTTG GGATCGCGT       360

GCTCAAGATG ACAGTGGAGA AGCCAAAGCA TTTCAAATAT TACCCGGGGG CTTATGTTTT      420

CGTTTATTTT ATTAGTGGGA AGGATGCTTG GTTCTATCCA TTCCAGTCGC ACCCGTTCAC      480

CGTCCTTAAT ACACCCAAGA TCGATGGCGA CAACCTGGTG ATTTATTTCA AAGTGCACAA      540

GGGCGTGACG CAGCAGCTGC TAAACAGGAT CTTTCTATCC GGGAAAGAGT CCATCGAATA      600

CAAGGTGCTT CTAGAAGGGC CCTATGGAAA CACCATTCCG CGGCTTGCTG CTCCTGACCG      660
```

```
GCGCTACGTG GGCGCCAGCG CAGGTCTTGG CGTA                              694
```

(2) INFORMATION FOR SEQ ID NO:742:

(i) SEQUENCE CHARACTERISTICS:
        (A) LENGTH: 691 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1482UP (xi) SEQUENCE DESCRIPTION: SEQ ID NO:742:

```
GATCGCGCGG TTCGGCGCGG TGGCGCCAAA GCTGAACCGG TCCGCGCCGA AGGATGCGAT   60
GTGGCGGCTG CGGAATTACT CGATGAAGTG CAATGAGGCC AACGATGTGT ATCTGCTGCT  120
GAACGGGTCC AGCCACGTAG CCTGCGACGT GAGCGACACA CTTCTCGATT GGTTGGCCAG  180
CACCGAGGAT GAGCCGGTGA TGGAGCTGGT GCTGCGAGAG TGGCTCGACG TGAACCCGGC  240
GCTGGAGTTC CGCGTGTTTG TACGAGGTGG GGAGGTCCTG GGCGCGTGCC AGCGGGACCT  300
GAACTACTAT GACTACCTGA AGCCGCTGGA GGAGAAGCTG AGGACGGCCA TTGAAGACTT  360
CGTGCACGAC GTGATGCTGC AGCGGCTCCC GGACGACACC TTTGTTGCGG ACGTGTACAT  420
CCCGCGGCCG TTCACAAAGG TCTGGCTGAT CGACGTGAAC CCGTTTGCGC GGGAGACGGA  480
CCCGCTGCTG TTTTCATGGA ACGAGCTGTG CACCTGAAGC CCAACGCCGA AGGGCACCGG  540
AGCTGCGCCT GGTTGCGGAA AACTACATCG GTCGCTTCGC GGAAAACAAC ATCGGTCGCT  600
TCGCAGCGAA AGGAGCACTC GGAACACCAG GTACCTCTGG ACGTGGTCGA GGCAGGGCTC  660
AATCCGCAAA GCATGCAGAA GCTGGTTGAG A                                691
```

(2) INFORMATION FOR SEQ ID NO:743:

(i) SEQUENCE CHARACTERISTICS:
        (A) LENGTH: 581 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1483RP (xi) SEQUENCE DESCRIPTION: SEQ ID NO:743:

```
GATCCAAAAA ACCTCTWAAG GTACAGTCTC TAATTGCTTC CATSTCTTTT TGAACATACA   60
TGGACCATGC ATCCTCGTTC TTGTTACGGA CAGAATCCTG YAATGCAGCA ATGGCACTTG  120
GCTCGTTGAC GTGCTTATAA CCACCATCCC TCCAATGGTA TTCGCCGGCT TCAGGCAAGT  180
TGACAGATCT CTTAATCKTA AACCTCGATG GATAMCCGCG CTCGTGCAAT GAAAAGGCGT  240
CTTGSGCAAT GTATTCAAAG GTAACACCCT TAATTCTAGA AGCGGTTCCG GCAAAACACA  300
AATCAATCAC TGAGTTATCA ATACCTAAAG CTTCAAATAT CTGCGCTCCC TTGTAAGATG  360
CCAGAGTAGA GATACCCATC TTCGACATGA CTTTTAGTAT ACCGCCGTCA ATTGCTTCCT  420
TGTAATTATG CAACAGTTGC TCATCTGTAA TATCAGAGTA GTCATCGTTA ACATTCCGAA  480
CTAAACCTTC GTTATTCATT CTGACCAGGG TTTCCATCGC TAAGTAAGGG AAAATACCGT  540
CACACCCATA GCCAAGAAGA ACACAGAACT GGTGAACTTC G                     581
```

(2) INFORMATION FOR SEQ ID NO:744:

(i) SEQUENCE CHARACTERISTICS:
        (A) LENGTH: 668 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1483UP (xi) SEQUENCE DESCRIPTION: SEQ ID NO:744:

```
GATCATCAGC CCCGCTGCTC CGCCGCAGTA ACGGCTCCAC GTCGTAGTCT GGCGTCCCTG      60

CTAGTCCGTG GCTCATCGAG AGGTCCTCTT CCTCAGGCTC GGAGTTGGCC ACGGAGGCAC     120

TTGAAAGACT CTGTCTTCGA TTCAATCCCC CCGCCCCGTA TTCCTCGCCC TCGTGGCGTG     180

GCTTGGTGAG GCCCTCCCGC TGCAGATCTT CAACGTCATC CTTCAGCTCC TGGAAGTTGG     240

CAAGAATTCC GGTTTCCTGA GAGACATAGA ATTTGTCAAT TCGCCTCAGC TCCTTATCCA     300

GCGCCGCAAT GAATCTTTCG ATGTAGCTCT GTGCAAGCGG CACCCGCTCG GGGTCCTGTG     360

CAAACGTCTC ATGCTGGTAC AGCTTGTCTT TCTGCAGTGT GTACACGAGC TTCTTCAACT     420

GCGAGTACGC GATATACTTC GACGAACACT CAGGGACCGC GTTGAATTGC AGCGAATGTG     480

AGAACTTCAT CTTGGCTTCT ATCGCCTAAC GGCCCTGGTC CGTCGCGATA CAGGTCTGTC     540

TCATTGAAAG TACGCAGCGC AGGCATAGGT TTAATTCCAG GCTCCCAGGA GATTTTCGTG     600

CAAGAGGACG TTTTAATTCT CATTATATCA CGTGCCCTGG CTATATTTAT AAAGTTGCCT     660

CTAACGGG                                                              668
```

(2) INFORMATION FOR SEQ ID NO:745:

(i) SEQUENCE CHARACTERISTICS:
        (A) LENGTH: 707 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1484RP (xi) SEQUENCE DESCRIPTION: SEQ ID NO:745:

```
GATCCTCTTC TATAACTCAA TTAACAATGT TTCCTCCTGT GGAGTCGTTC CTGCATCTTC      60

CGTAACCCTT TCATTCTGAG GTGTAGCCAT TTTTATCTTC TGCGCTGGAA CACTCGGGAA     120

TTCAAATTGA GTTATTGGCA CCTGTGCCTC CTTCTCCTTG TCCGGTATAC TTTCTTCAGG     180

AGGATAAAGA GGCTCCGATG GTGATGATAG CAGTGTTTTC TTAATATCCG GTTCTGAGAC     240

CTGCGGCTCA AAGCCAGTTA CTGATTGCGA CTGGCGATTC TCCATCGGCG AACTTTGTGT     300

GGTATGTAGG ATTGCTGGAG TGAGTTCTGC AGCGTTGGAA GAGCTCCTGG CATAGCTACG     360

ATATGTTGGC TCAGGTTGCG TCTTCTCGTA CGGAACAGTG TTGGCTGGAG AGGACTCTGG     420

TTGTCGGTGC ATTTGATAAG TGTATGGATC AGAAGGTAAG TGTGGCATGG AATATTGTTG     480

CGAAAGATTA ATATTCCTCA ATTGTCTCTC TAACATGGTG TCATAAATGC TCATTATATC     540

CGAAATTTTG GCATTCATGT CTACCAAGGT ATTATATTTG TGAAACGTAT CGTTAAGGGA     600

ATGGTTTAAC CGAGGCCGAG TTCCAAGGAC CTTCTGGTAT AGCATCTGCA GCTGTGTATC     660

CTCTAACACG GCATTCATTG GCTGACCCTT CCTCTTCCTC CACTAGG                   707
```

(2) INFORMATION FOR SEQ ID NO:746:

(i) SEQUENCE CHARACTERISTICS:
        (A) LENGTH: 716 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1484UP (xi) SEQUENCE DESCRIPTION: SEQ ID NO:746:

```
GATCTCGGAG AACGTGCTAC AACACTCGTG CCGGGTCAAG CCGGACCCGA AGCTGATCGA    60

CCAGCAGCCG GAGATGAACC CCCAGCACAC GCGGACTGCG ATCGTGAACT TTGCGTTCGA   120

GCTGGCGCAG AAGACGCGGG TGACGAACGG GATCTTTTTC CACGCGGTGC GGTTGTACGA   180

CCGTTACTGC TCGAAGCGCG TGGTGCTACG GGACCAGGCG AAGCTGGTGA TTGCGACCTG   240

CCTGTGGCTG GCGGCGAAAA CGTGGGGGGG GTGCAACCAC ATCATCAACA ACGTGACGGT   300

GCCTACGGGT GGGCGCTTCT ACGGGCCCAA CCCGCGGGCG CGCATCCCGC GTCTGTCCGA   360

GCTGGTGCAC TACTGCGGGG GGTCGAACGT GTTTGACGAG TCGATGTTCA CGCAGATGGA   420

GCGCCACATC CTGGACACGC TGAGCTGGGA CGTGTACGAG CCGATGGTGA ACGACTACGT   480

GCTCAACGTG GACGAGAACT GTTTGATACA GTACGAGCTA TACAAAAGGC AGCTGGAGCA   540

CAATCGGCAG TACGCCAACA AGCGCAACTC GCAGGACAGC AACGCGACCG AGGAGGACGT   600

GTCCGAGGAG GACGAGGACC TGGATAACAA GATCCAGTTA ATCAACATCA AGAAGTTTCT   660

GATAGACCTG GCCGTCTGGC AGTACGACCT CTTGAAGTAT GAGGTATTCC GAGCTA       716
```

(2) INFORMATION FOR SEQ ID NO:747:

(i) SEQUENCE CHARACTERISTICS:
        (A) LENGTH: 748 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1485RP (xi) SEQUENCE DESCRIPTION: SEQ ID NO:747:

```
GATCCCCGCG TTATTAGCAC GGTGCCTTAA CCAACTGGGC CAAGGAACCA ATTACACTTA    60

AGATGCTATT TGCAGATATT TGTAGTCCAC TCAAGTCAAC ACGGGCATAT TTTACTTTCT   120

AATTCTTAAA TTCTTAACTC TAAGCCAATC TAAGTAGTTT ATCCTATCAT CACTTGATCC   180

TTGCGTTTGT TTGGTCTATA ACCTTTAATT GGGTAGTGCT TATGGAAATA TATATAATGA   240

GATATTACAT GGGTCCCATA TAACTTCCGT ATGAGAGTTT GGCCGAGTGG TTTAAGGCGT   300

CAGATTTAGG TTATTCTCCT AAAATCTCTG ATATCTACGG ATTCGCGGGT TCGAATCCCG   360

TAGCTCTCAT TATTTTTTGT ATATTGTCTT TCTCAGGCAT GTGACATTTT GCATCATAAT   420

CATACCGAAG ATATGGCTCC CACCGTGACC TGATACATTC TCGCATCTGA AGGCATGCAA   480

TTTAATGCAA CTGTGGCTGC AGATGCTCTA GGTAGGAACT AGCACAACAT CTAACAACTA   540

GCCTGCCATA TACAGCGCAA TGACAGCGTC TGAGTCGTTG TGGCACCGAT CATAAGCCAA   600

TTCTGATTGT CTGAAGACAG GCTATGAGTC TCCCACAGTC CTCCTTGCTG TCCCATACGC   660
```

```
ATATAAATAC CCTTAAAACT CAATTAGCCG GTATTTTATT TGAGCTGCAG AAGGTATCTT    720

AACTCAGGTA TAATATACTG TAATGGGG                                      748
```

(2) INFORMATION FOR SEQ ID NO:748:

(i) SEQUENCE CHARACTERISTICS:
        (A) LENGTH: 755 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1485UP (xi) SEQUENCE DESCRIPTION: SEQ ID NO:748:

```
GATCGGAGGT AGTGTTTTCG GTGGGCACGG AGCTGTAGCA CGCGGGGTCC AAGAGCGGCA     60

TTGTGCTGTG TATGTTGGTG ATGACCTCGA TGAGCTGCTT GCGGAGGTGC TCCACGTAAT    120

CTTCGGTGCG GAGCCCACAT TCCTTCGGGT CGCGGAAAAT GGTTGCCAAG TACTCGAGCT    180

GCTGCGAGAC CTTCTTGTAT TCTAGCTCGC GGTTCAAGCA GACGATGGCG TTGCGCTGAA    240

GGATCGTGAG CTCGTCGAGC ACGTCAACGA GGTCGTCGAA TTGTGGCACC GCGCTCAGCG    300

CGCCGTCGAT CGCCTTAACA AAGGCGCGCC GGGCCTTCAG GGCCTGTCCA CTAAAGAGAT    360

CACTGCGCTC GAAAATGCTG ATTGCCTCGC GCATGTACGG CACAAGCTGG CGCGACACGA    420

ACAGATAGCT CATGTGCCGG GAGTTCGACG TCACGCTAAC TGCCGAGTGC TTGGTTGAGT    480

GGCTGAAGGG CCTACTGCCC CGGTAGGGCG ACCCGAGAAA TGCGTCATCA CCTCGTCTTC    540

ATCTGGCTTG AGATACAAAT CCGAAAGCGG CACGTTGCCT GTCATCGCAG AGTTGTTTGA    600

CAAGAGCAGC TCGTCTAGTC GCTGCTGGAG CTGGCCCACT TTGCTTTTGA GTAGTTCCAC    660

TTCACTGCCC TTTTCGGATA GCATGAGCTG CAAGTGGCAG TTCTCGTTTT GCAACGCCAG    720

CACCTCATCG GGCGCGGTAC CGCTGCTCTT GCAGA                              755
```

(2) INFORMATION FOR SEQ ID NO:749:

(i) SEQUENCE CHARACTERISTICS:
        (A) LENGTH: 729 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1486RP (xi) SEQUENCE DESCRIPTION: SEQ ID NO:749:

```
GATCCTTCTT GTACATTTCT GATTTTAACA ATGTCTTCAT AGCGTATATT TTACCGGTAT     60

CTTTCTTCTG CACCAGACGG ACCTCACCGA ATGCACCCTT TCCTATGACT TTAACAGTGT    120

GGAAATCTTC CAGGGATAGC CGTGTCCTAC GCAAGCGCAG AAACTGCGAC TCCTTTTTAC    180

CCAGTGAAGA AAGCTGTCTG TTCTTTCTCT CTTCAGACCA GCCATGAGAT AATAGCTGGG    240

ATTCAAGTTC CACGCGTCTT TGGTTGCGCT CAATGGCATG ATTGACAGAT GATTGGTAGA    300

AATTCTCGAC TTTCAGCTTC ACTGCAGCCG CTTTTTCTTG TGTGGATTTG CTCAGTAGCT    360

CTGGACGTCT CTCGAAGTAC ATATAGTTCC CCACTCCCGA GGTTTGCCGT TGGCCCCCAT    420

TGGGCGATTG TGGAACTGAA GAGCACTGCA GGGACTGACG GGATAGCATA GCGCCCTGCG    480

AGCTCTGGTT TCCCACTAGC GTCTGATCGC CAAGGCTTCC GTCTAGTAGT CCAGGTAGAG    540
```

```
CTGCAGGCTG TAAAGGGGAC TCCGACCCCC CAAACTGTTT ATACGCAGAG GAAGCAGGCT        600

GCTGCCCACT GTAGTCCGAG CTGTTGGAGT AGTGTCCTGG TGAAGAATGG CCGGGGGCAA        660

GAGTAGTGTC GTTCACGTTC CGTAAAAGAG TTGTTGTTCT GGCTGTAAAT GCTGGTCGCC        720

GTAGGCGGG                                                               729
```

(2) INFORMATION FOR SEQ ID NO:750:

(i) SEQUENCE CHARACTERISTICS:
        (A) LENGTH: 719 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1486UP (xi) SEQUENCE DESCRIPTION: SEQ ID NO:750:

```
GATCAAAACA GCATGTCTAA GTCTGTTGCG CGCTGCCCGC AGTGCCACAC GGAACTGCGT         60

AAGTGCCTCA TACAGCAGAA CTACAGCATC GTGATTTGCC CGAACGAGCA GTGCATGTAT        120

CCGTTCAATG AGGCCGAGGT GATCCAGCAC CTGGTGCAGA CAAGTGACAA GGAAATCCTG        180

GAGGCTGCAA AGGTGCGGCT GAAAAACGAT AATATCACAG GCAGCGGAGG CGCGCTCATG        240

GAATAAGGAA CCAACCGTGT GCTATATACG TGTACTGTCT ATGTTAAGTA GGTCTCGTGC        300

GCCGCGAGCC CTGCGTGGCT AAAGCTTTAG ATTGGAGTTG TACATGATGT CGCCATCGAC        360

GCTGATGCTG ACACTGAACT CAAGGTCTTC GTCGGTGGAT ATGTCCCACG TTTTATATAT        420

CATCATCAAC GCGAACACAT TGCAAATGCT GCCGATGAAC AACCCGTCGA GGTAGTGCTT        480

GACGCCCTCG CAGATCTCGT ACGAGATGGT ATACATCAAC ACCTGCCCAG TAGTTATAAA        540

AATGACACCC AAAATGGTCG ACCCTGTCAT CCAGAAGTTG GAGAGCACGA AGATGGAGAC        600

CACGAGCTGG CACACCGAGT ACATTAGGAA CGCGAGGCCA TTGAGGCCGT ACATTACAAC        660

GAAAAGGCGG TCGTGTTTGT TTTCATGTCG GGTGGTGCT GAATCCAATT TGGTGAAGG         719
```

(2) INFORMATION FOR SEQ ID NO:751:

(i) SEQUENCE CHARACTERISTICS:
        (A) LENGTH: 703 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1487RP (xi) SEQUENCE DESCRIPTION: SEQ ID NO:751:

```
GATCGAGCGC GAGCCCATCA ACAACGAGGA GTTTGCCTAC CAGCAGGAGC TGATACGAAA         60

GCGGGACGAG GAGATAGCCA ACATCGAGCG TGGTATCGTT GAACTCAACG AGGTCTTCCA        120

AGACTTGGGG TCCATCGTGC AGCAGCAGAG CGAGCTGGTA GACCACATAG AAAACAACAT        180

ATACACTGCG GTAACCAGCA CGAACCATGC ATCTAACGAA CTGTCGCGCG CACTGAGATA        240

CCAGCGGCGT TCCAACAGGT GGTGCCTATA TCTGCTTCTC GCTCTGCTGG CATTGCTCTT        300

CCTGATCGGG GTGACAGTGC TTTAGAACAT CTCAACTAGT CTACTATGTA ACGCTTTAAT        360

ATACTACTGG CTGACCTACT CCTCCCGCAG TTCCCACACG TTCACGCAGC CGTCATCGCC        420
```

```
GCCGGTCACC AAAAGAACGC GCCCGTCTAA CGCCAGCCAT TTCACCACAT TGATCTCGTA      480

GACCGTGTGC GCGCAATCTA CGCGGGCTAC CACTTCCCAC CGGCCAGCCT GTACCTCTTT      540

GTATACCGCC AACACACCAT CCGAGCCAAC GCTCGCGATA AGCCCGTCCG CGCTCCAACT      600

TACGCTGTAC ACAGCCCGCG TATGCACGGC CGGCAGGACC GTCTCTTGGA TCCACTCTTT      660

GTCGAAGACG TCGGCGTCGT CAGTGAGGCA CCGCCAGATG CGC                       703
```

(2) INFORMATION FOR SEQ ID NO:752:

(i) SEQUENCE CHARACTERISTICS:
        (A) LENGTH: 612 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1487UP (xi) SEQUENCE DESCRIPTION: SEQ ID NO:752:

```
GATCCCAATA CTGGGACTTT ACTAATACCA GCCATGCGGG CAGCTCTGCA GCAGCTGGTA       60

ATGACAAGGA GGACAAGAAG AACAAATACT GGAACGCAGA CGCCGAGTAT CTGATCGAAG      120

AGGTGAAGAA AAACAAAAAG AGTGTAGTAA ACTACCTTGA ATCGAAGACG AACGACGAAA      180

TGACCCGCAA GGGTCTGATC CGGAACCTGC AACGATTTGC AAAGACAATT CTAATGAAGG      240

AAGGGTTCGA AAACCTGGAG GATATCGTCA CGCTTTCTCA TTTGGAAAAT AGACTGCTGG      300

TAGCCCTAAA ACTTAACGAG ACAAATGAAT TTACCAAATT ATTGAAAGTC TATTGCATCA      360

GCCTAGCAGA AATGGGCTTC AAAAATAGAT TGGATGATGT GCTGAGCTGG CTGTATAACG      420

ATGGAGAATA CAAGGTTGGC ACAATAGCTA ACGAGAAGCG GGAGGAACTG CTGAAGCAGA      480

TATTGGTTGC ATGTGCTGAT ATCCGGCAGG TCCAAAGAGT GACAACCAGT TACGCATCTG      540

CTCTTGGTCT TCTTGATGTA TCTTTATAAT TATTGCTAGT CTATAGACAA AGTTGGGAAT      600

CTGAATATAA CT                                                         612
```

(2) INFORMATION FOR SEQ ID NO:753:

(i) SEQUENCE CHARACTERISTICS:
        (A) LENGTH: 715 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1488RP (xi) SEQUENCE DESCRIPTION: SEQ ID NO:753:

```
GATCAACAAA TGATTTTCCT ATTTTCCGCG CACCGATCAA CGAGATATCA TAGGAATCAA       60

TGTTGCAGGC AAATCCCTCA CCGAGTATGA AGCTCTGGTA TGCTGTTGGC GTTGTTCCTT      120

TCATTAACTG CCGGTCCCTG GGCAGTTCCC TTAAGTTTGG ATGATCGAGA TATCCACAAT      180

TTGGCTCATT CATCGTCTCC AATCCAATGA TGCAGTTTTC TTCGAACAAC TCAGGCGCGT      240

TGTCCTGAAT GTACTTGTAG AACGTCATTA CGGCTTTCAA GAAGTGCCCC TGGAGGTAGT      300

CTTGAATATT TCTACCATTA ATTACACATT TAGGGGCAAA TAACTTGCCG CTAAAAAAGA      360

GAGTGAACAT AGTCTGGCAG GCTAGGCGGT AATAGTTTGT GGACCAAATC ATTTCTGGAT      420

ACTGTGCTTT TTCCGCCTGC GTCTCTGAAT CGATATAGTA GTTGTGCAAT ATGGCAGCCT      480
```

```
CAGTAGCTAG GAACCTCTTC GGCTGAAAGC CTGCGCAATG CAACGTCCAT AATGGCGCTC      540

CTGATCCCCC AGAAAAGCGA GACCACACGT CCTGGTGGGG GTCTAGGTAT ACGTACATGC      600

CGCCCGCCTC CTTGATCTTT TTAAGCACCA TCACCGTGTA CTTCATGTAT TCCTCATCGT      660

ATATCCCTGG GCCGCCATGC TCCAAGGCCT CCCAGGTGAA CAAATAACGG ATACA           715

(2) INFORMATION FOR SEQ ID NO:754:

(i) SEQUENCE CHARACTERISTICS:
        (A) LENGTH: 684 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1488UP (xi) SEQUENCE DESCRIPTION: SEQ ID NO:754:

GATCTCGTTT AAGCTGCTGG TGAAGTTTGC GAAGGGGTAT GAGCTTTCAC GACGCGAAAC       60

AAACCAGCTG AAGCGGTCTA TGGGCGATGT CTTCCGGTTG GTGCCCTTTT CTGCCTTCCT      120

GATTATTCCG TTTGCAGAGT TGTTGCTGCC CTTCGCGCTT AAGCTTTTCC CCAACATGCT      180

GCCATCCACA TATGTTTCTG GGACGGAGAG ACAACAGAAG AGAGTTAAGC TAGAGGAGGT      240

GCGGCGCAAG ACGTCCAACT TTTTGCAGGA GACACTAGAG GAGTCCTCAT TGATCAATTA      300

TAACTCGGTA GAAGGTTCAG AGAAGCGCAA AAAGTTTCTG AGCTTCTTCC AGAAGGTGAA      360

CTCCCCTAAG GATGGCAAGA CCAGTGTTTT TACCCATGAA GAGATTTTGT CCATCTCCAA      420

AATGTTCAAG AACGACACTG TGCTAGACAA TCTCTCCAGG CCGCAATTGG TTGCCATGGC      480

GAAGTATATG TCCTTGCGGC CTTTTGGCAC TGACAACATG CTTAGGTACC AAATCCGTTA      540

TAAATTGAAG AGCATCGTGG AAGACGATAA GAAGATAGAC TACGAAGGTG TTGAGTCACT      600

GAGTACAGAG GAGCTCTATA GTGCCGCCGC TTCGCGCGGG ATCAAAGCCT TCGGTGTTTC      660

TAGGGAAGAT TTGGTGGAAA AAAT                                             684

(2) INFORMATION FOR SEQ ID NO:755:

(i) SEQUENCE CHARACTERISTICS:
        (A) LENGTH: 728 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1489RP (xi) SEQUENCE DESCRIPTION: SEQ ID NO:755:

GATCACGCCG GAGCACGTGC AATCATTGAA CGAAAGCCCG GGGTTGCTTG CTTTGGCGAT       60

GGAGAGTCAC AGGGACCCAA TTACCGGTGA GAGTACATTG GTTGGTTTTC CCTACGTTGT      120

TCCGGGCGGT CGTTTTAATG AACTTTACGG CTGGGACTCA TACCTAATGG CTTTGGGTCT      180

TCTAGACTGT AACAAAGTGG ACATAGCACG TGGGATGGTT GAGCATTTCA TCTTTGAGAT      240

AGAGCATTAC GGTAAAATAT TGAACGCCAA TAGGAGCTAC TACCTCTGTC GGTCACAACC      300

CCCGTTCCTA ACCGACATGG CTTTGAAGGT CTTCGAAAAG TTCGGTGGTG ACCAAAATCC      360

TACCGCTGTG GATTTCTTGA AAAGAGCATT CATCGCAGCC ATTAAGGAAT ACAAGAGTGT      420
```

-continued

| | |
|---|---|
| ATGGATGGCA GAACCGCGGT ACGACAAAAC CACGGGTCTT TCATGTTATC ATCCAGATGG | 480 |
| TATCGGTTTC CCACCAGAAA CCGAGCCTGA CCACTTTGAC GCAATTTGCC GGAAATTTGC | 540 |
| GGAAAAGCAC AATGTAACGA TTCCGGAGTT CAGGTGCATG TACGATGCCG GCGAAGTACA | 600 |
| CGAGCCCGAA CTAGATGAGT TCTTTTTGCA TGATCGTGCT GTACGTGAGA GTGGACATGA | 660 |
| CACCTCTTAC CGTCTAGAGA ACGTCTGTGC TTACTTAGCG ACGATTGATT TGAATCGTTA | 720 |
| CTATACAA | 728 |

(2) INFORMATION FOR SEQ ID NO:756:

(i) SEQUENCE CHARACTERISTICS:
        (A) LENGTH: 698 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1489UP (xi) SEQUENCE DESCRIPTION: SEQ ID NO:756:

| | |
|---|---|
| GATCGTAACA TTGCCCAATA GCTTGTTTAG CTCGTCATCG TTTCTGATGG CTAGCTGTAG | 60 |
| ATGTCTTGGG ATGATTCTGG TCTTCTTGTT GTCTCTGGCG GCGTTACCGG CCAACTCTAG | 120 |
| GATTTCGGCG GCCAAGTATT CTAGCACAGC GGTTAGGTAC ACAGGCGCGC CCGACCCGAT | 180 |
| TCTCTGTGCG TAGTTGCCCT TTCTGAGCAA TCTGTGGACT CTACCGACAG GGAAAGTCAA | 240 |
| ACCGGCCTTA GCCGATCTCG ACTGCGAAGC CTTGGCGGCA GAACCAGCTT TACCTCCTTT | 300 |
| ACCAGACATT ATTTGTGTTG TGTGTGTGTG TGTGTGTTTA GTGTGAACTG CGTGTGCTAT | 360 |
| GAGAAAACAC TACGCTGAAA CTGCTAAATA ATCCAGACAG GTCCCCCCAC CGCAAAGGAT | 420 |
| CCACGCTATA CTTCTCTCTA CATATTTATA CTTGTCCTTT TGCCTTCTAA TCCTCGATCG | 480 |
| TACGCGTCTG ACGCTTCAAC AGACCTTCAC TAGACGCTCG ACCTGTGCGG GCTGGTTTTT | 540 |
| TCGCATGACA TGTCCGTGCT GGTTTTTTCG CGCTGAAAAG GAAAGCGCGT GGCTCCCAGC | 600 |
| ACCAGAGCCG TACTAGCTCT TTCGCGTTGC TGTCCTATGT GCACGCGAAA TTTCATACTG | 660 |
| TAGAGTGTGC CATCAGCTTC ACAGAGTACA ACGGTAGG | 698 |

(2) INFORMATION FOR SEQ ID NO:757:

(i) SEQUENCE CHARACTERISTICS:
        (A) LENGTH: 727 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1490RP (xi) SEQUENCE DESCRIPTION: SEQ ID NO:757:

| | |
|---|---|
| GATGACCTTC CGATACTATG CGAGCGCTTC ACGACATCCA AACTGAAGTC GTTCGAGGAC | 60 |
| CTGAGCCGCA TCCAAACGTA CGGGTTCCGC GGAGAGGCAC TTGCCAGCAT TTCTCACATT | 120 |
| GCGCGACTAC ATGTGGTGAC GAAAACGAAA GAGAATCAGT GTGCATGGAA GGCTGTCTAC | 180 |
| GAGAATGGGG TAATGGTGGG GGAGCCGAAG CCGACGGCAG GCAAGGATGG GACGACAATC | 240 |
| CTCGTACAGG ACCTCTTCTA CAATGTGCCG TCCAGGCTGC GGGCGCTGCG ATCTCCAAGC | 300 |
| GAAGAGTTTG CGAAAATAGT GGATGTGGTC GGCAAGTACG CAATCCATTC GGATGGTGTG | 360 |

```
GGATTTTCGT GTAAGAAGTT TGGCGAAACA CAGTACGCGT TAAATGTACG TGGGACTTCT      420

TCAAAATCAG ACAAGATACG GGCTGTATTT GGTGCTCCAG TCGTTGCCAA TTTAGTTGAG      480

GTAGATATTT CTGCAGACCC TGAGCACGGT CTTACATCCA GTTCGGGCCA GATTACAACT      540

CCAGACTTTA ACAACAAGAA GTCTATACCT GCTGTGTTTT TCATTAATAA CCGCCTTGTT      600

TCCTGTGATC CTCTGAGGCG AGCCCTATCC CAAGTTTATC CAACTTCTTG CCGAAAGGTA      660

ACAAACCGTT TATTTACATG AGTTTACACA TAACACCGGA GAATGTTGAT GTTAATGTGC      720

ATCCTAC                                                                727

(2) INFORMATION FOR SEQ ID NO:758:

(i) SEQUENCE CHARACTERISTICS:
        (A) LENGTH: 728 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
         (A) ORGANISM: PAG1490UP (xi) SEQUENCE DESCRIPTION: SEQ ID NO:758:

GATCTCAAAG ACCCAGTACG ATCGCGTCAT GGGATACATA AACCACGGAA TCAATGAAAA       60

GCTCGCTTAC GAACAGTTTG GATCTGTACC GGAGAAGGGC TACTATATTC CTCCCACAAT      120

ATTTCTGGAC GTTCCTCAGA GCTCGAGACT CTGCCGTGAA GAGATATTCG GCCCTGTGGC      180

CGTAGTTGCG AAATTCAAGG ACTACGATGA AGCTATTCGT TACGCTAATG ACACTAACTA      240

TGGGCTGGCA TCCTGCGTTT TCACTGAAAA CATACGCGTT GCGCACCGCT TTGTCCGTGA      300

TGTCCAATCT GGCACTGTGT GGGTTAATTC CTCTAATGAT GAGGAGGTGG GAGTGCCTTT      360

TGGCGGGTTC AAGATGAGCG GTATCGGAAG GGAGCTGGGG AAGGCAGGCC TGCAAACTTA      420

CCTCCAGACT AAAGCAGTAC ACCTGAACTT TGCTTAGATA GAGCAACTCA TATATTAGAA      480

TCACTTCATA CATCAACTAT ATATCATTAT GTATATGACT ATGCCAGAGG TGTAGTGGAA      540

CCACTATTTA TCACGTGATA GGCGTTGCGC GGTCATCCCG CCAGTACCTG CGTTGCAGAA      600

CGCGGGCGAC ACATTCAGCA GGTGCTATAT ACAGTTGTCG AGGACAGTAT GGCACGCAGT      660

ACCATTATAG CAAGTAAGCC GTGTGCTGTT TGCATAAAGC GTAAGGTCAA GTGCGACCGG      720

CTGGTTCC                                                               728

(2) INFORMATION FOR SEQ ID NO:759:

(i) SEQUENCE CHARACTERISTICS:
        (A) LENGTH: 716 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
         (A) ORGANISM: PAG1491RP (xi) SEQUENCE DESCRIPTION: SEQ ID NO:759:

GATCATCTCC GAATAGGTCT CGGGCACGAC GGACACAAAG CGCGCGTCCG AGTCACTGCC       60

GTCCTGCTGG GCGGGTGCGA AGAAGGAGAA GATGAACGAC CCCGACTTCG ACTTGTGCTC      120

CGACGCCAGC TCCTGGACGA CCGTGTCCAC CTTGACCTGC ACCAGCGTGC CAGGACACGA      180
```

-continued

```
CAGAAAGTCG TCCTTATTCT CAGACAGCTT GTTCACAGCT GTAGGCTGGT AGTCCACCAG     240

CGCGTCCGCC GCCGGCGTGG CCCCGTCTGG TCCACCACGG ATGTGCTCTG TGTACACGAC     300

CGTCGCGTCC ATGTGCAGGA TCGAGCCGAC CGGCACTGGC GCGCGGAAGG TGGTGGAGTC     360

CAGCGATACG AACCGCGGCA GAGAGTGCGA GATCGATGAC GCCGCGCAGT ACGCCAGCTC     420

AAATGTCTGC CGCATCAGGT AACCGCCGAA GATCATGTAC GAGTGTCGGT TCCGGTATTG     480

CGGCTGCATG AACATCGTCG ACTTCAGGTT CGTGTCCTGC ATCGACACCA CGCCGCGCGG     540

ACGCAGCTCG CGCGGCGTCG CGCGCGACGC GCGCCACAAC CCGTGGATCA TCCGCGACTC     600

CTCCGCGGTA GGCGGGTTCG TCTCTAGACT CTCGCTCTGC GCCTGTAGCT TCTTCGCGCT     660

GTTGTGGCTC TCCGCGCGCC GGAACTCCAC CCACTCCTGC TGGTTCTGCG GTAGCA        716
```

(2) INFORMATION FOR SEQ ID NO:760:

(i) SEQUENCE CHARACTERISTICS:
        (A) LENGTH: 729 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1491UP (xi) SEQUENCE DESCRIPTION: SEQ ID NO:760:

```
GATCTTGAAC AAAAAGTAGT TTGTTATTCT CCAGCTGCGC AGTCTCTTCC AGGGTTTTAC     60

TTCCGATGCT TATTAATACT GGTTCTTTAG ATGGTTCCTG ACTTTGGCTA TAGGCCATTG    120

GTTCCGGCGA CTTGTGAAGG TATGCATTGA GAGTCCTCTG GGTAGAACGT GTGGTCCTCC    180

CTGTAGTTTT AGCAGCGGGC TTGGCCGGGA CTGGTACATC AGGCTGAGGT AAAATCTCGG    240

CTGGCGTTGC AGGTTCTATT TCTGTGGGTG GCTCTACACT AGGATCCAAT ACTTGGGCGC    300

TACTAGTATC GCATTCGTCA ATATCATCTA TGGCCACGAT GACAGAACTT TCTTCTTCCA    360

TAGGCTGGGA GCATGCAGTA ATCTCGGAAC ATGTGGTAGT ATTATGTAGG TGATCGTCTT    420

CGAATGTCCC AATCAGCTCC TGGCTGGGAA CGAGTTTGCG CCTTTTGACC TTCAACTCGG    480

AGTCTTGATG TGGGACTGGC AGTGACGGTA AAGATTTAGG CAGCATGAGC TCCTGTTCGT    540

TAAAATGCCC GTCCAGTTTC TCTGCTAAAC TTTGGAGGAC ATACTCTTCA TTGTGAAGCA    600

ATACAGTCCT CTTATCCGGA GTCACATTCA CGTCTACAAA CTGCGGGGAG AGCTCAAAAT    660

TTAGAATAAT GACGGGATAC TGGACGTTGT TGAAGCTTCG ATATATGTCA TTGCAACACT    720

TCAGGACTT                                                           729
```

(2) INFORMATION FOR SEQ ID NO:761:

(i) SEQUENCE CHARACTERISTICS:
        (A) LENGTH: 610 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1492RP (xi) SEQUENCE DESCRIPTION: SEQ ID NO:761:

```
GATCTACTTC TCCAACAACG ACCTCCTGTG GTCCAATGGC TACCCCGTGA ACCGCTTTGG     60

CCAGGGCGCG TTCCGCATGC TTATCGAGCG CCTGTACGGC GAGCTCAACG CCGGCTACAG    120
```

```
CCTGGCCCAT ACCACCTACG GCAAGCCCAA CCGCATTGCC TACGACTATG CTGCCCGCGT      180

CCTGGGCGCC TGGTCCGGCC TCCAGACCGC ACAGCCGCCC GCCACGGTAT ACATGGTTGG      240

CGACAACCCC CACAGCGACA TAATAGGCGC ATACAACTAC GGCTGGCGCA GCTGCTTGGT      300

GCGTAGCGGC GTCTATCGCG ATGGAGACAC GTTACCATGC CAACCGACCC TCGTCGTGGA      360

CTCCGTCTTG GACGCCGTAA CCGCCGCTCT CCAGCACTCT TCACATTAAC TTCTATACTT      420

TTACGTCTTC TATATACCCG GCTCGTCCGT CCGCAGATGC CTAGATCTGA ATCTTCGCCA      480

CCACAGTTTG CTCCTGAGCC AACTTGTCTG CGTTGCGCCG GCGCATATGC TCCTTGCACG      540

TGCGGAGCCC GCGGCACGTA TGGTTTTCCA TCAGCCGGTG GCGCGAACAG AACTGGCCGT      600

CACAGAACTG                                                            610

(2) INFORMATION FOR SEQ ID NO:762:

(i) SEQUENCE CHARACTERISTICS:
        (A) LENGTH: 553 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1492UP (xi) SEQUENCE DESCRIPTION: SEQ ID NO:762:

GATCATGTTG GTGGCCTCCT GCGTCGGCTG CGGCGTGAAG TTGGGGTTTG ATTCCGCGAC       60

GAGCGCCTGC GTGAGCCGGT TGATCTGCCG CACGTTCGCC TCGAGCGCCG AGGCCTTGTA      120

CTCGTCGGCC GACACGTCGT CGTCTAGGGA GAGCTGCTTC GAATTGGAGT TATACTGGAG      180

CATTGGTGAT CTGCCTGTCC GCAAGAGTGG TGGAAGACGT GTTCTTTGGC CTGTTCGCTG      240

AACAAAGCAC TCCGTGTTTT TCATGGACGG CGTGGTCCCA GGAGCGCAGA CCGGAGAAGC      300

GAGCGTCAGG GCCGCGCGGC AGGGACGTAG GCGGCTGCTC CCCACTATGT AATGCTGGAT      360

ATGAAGAACA GAAATACTAG ATAATATATT TGTATTAGAC AGTCGTGCGG ACCGGCAGAG      420

GGCGGCGTTC ACAAGTCCGC ATCGTCCTCA TCCGGCAACG GCAATGCCGT AGCGCGCTCC      480

AGCTCCTGCT GGTACTGCTG CATCAACTGC TCGTCCCCCT GCACCTCTGG AGGCGCCTAG      540

GCAGGCGAGC CAC                                                        553

(2) INFORMATION FOR SEQ ID NO:763:

(i) SEQUENCE CHARACTERISTICS:
        (A) LENGTH: 719 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1493RP (xi) SEQUENCE DESCRIPTION: SEQ ID NO:763:

GATCGAATAA AGTAGGTTTG GCGCTGACCG GCATCACCCG CGGACGTAGC GGGAACAAGT       60

TCCCCGTGTA AATGTTTGCG TAGTCGATGA AGGTATTAGT ATTCATCTTC TCCAGCAAAG      120

ACAATTCATA CTGTTGGGCG GGCCGCGAAG AGTTACCAGT GTATTCTGCC AACGCTGCGA      180

CGCTTCGGCA ACTAGATTCG AGTGCCTTCT GGAGCTCTGA AACATTATCT AGGATGTTGA      240
```

```
ACGGATCGAA AGCGGTGTCG CGGGGCATAG CGGACATGGC AGTTCTCAGA TTCTGCATAG      300

AACCGGCATA TAGAGCCAGT GCCTCCTGAT GCTTGCCTTC CTCTTGGTAA AGGGGAGCGA      360

GCCCGCGGCC TACAAGCTGC GCACGGTAAA ACACCTTGAC AAGCTTCAGA TATGCAGTGA      420

GCTCATCGTC TGAGTAGACA CCGGGTAGAC CCATAGCCTC CTCTGCATGG GTGATTATGT      480

TGTTGATGAC GTGGTTCAGC TGCTTGTACT TCGTGAAGCG AGCGGTCCTG CGGCCTTCTT      540

GCCATTCGAC CCACAGAGGT TGCAACAGCG CAACATCGCG GCCCATCGTC GCGCACAAGT      600

AGTTGAATTG GAGGTATGTG AGCAATATCT GGTCGTCCTC TCCCTCATAG TGCACACCTT      660

CCTCCTGTCT GCGCTCCATT GACTGCCTCT GGGCATCAAT TGCCGCGTTC CACTTCAGT      719

(2) INFORMATION FOR SEQ ID NO:764:

(i) SEQUENCE CHARACTERISTICS:
        (A) LENGTH: 726 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1493UP (xi) SEQUENCE DESCRIPTION: SEQ ID NO:764:

GATCATACTT ATCCACCGGT CAAGCCAGGT CTCAATCTTG ACGATGAGCC AGCCGGGCGG       60

CGTCGCCATC TGGAGCCAGC GCTCCCGGAA GCCAATTAGG TACCCTAGAC CAAGCCCGAT      120

TAGGTGGCCG ACAAAGCTGG AGCCGGGCAT TAGCAGCGTG ACAAGTACCA GGAACACCAG      180

CGGGATATAT AGGGTCGGCA TCTTCAGACT TGCGAGCTCG TAGTGGGGGC GGAAGCCCGC      240

CTCCTGCACT GCGAAGTAGC CACACAGCGT AAAGCACCAC CCGCTCGCCC CGCCTACGTA      300

AACGTTTGGG TACAACAACA TGCCAACTAA GCAGTACACG ACGCCCGTCA CAATGGCCAG      360

GAGGTTGAGC GTGATTCCCG TAAACACCGT CCCGTGTGAC GCTTCGAACA TCGACAGCGG      420

CACAAACAGC GACATCAGAT TCAACAGCAA ATGGAAGATT GACAGGTGCG CCAGTGGATA      480

GAGGGAGAGC CGCGTCAGCT GCAGCTTCCT AAGCGCCCCC GGATCCAACA GGATCTTCTC      540

GTTGATTGGG AACACCCAAT TCAGCACATA CACAAGCGTA AGGGAACACC GACAAGCCTG      600

CAGTAAGAGC GCCCGGCTTA TGGACCCCGG TCCGTAACAT CGACTTCCAA TCCATCTTGC      660

TCAATCAAAG TGGCAGTTTG CTTGGGCGTG GCAGTGGACT ATGCCTCGCC AGTTGCCCAT      720

CAAAAC                                                                726

(2) INFORMATION FOR SEQ ID NO:765:

(i) SEQUENCE CHARACTERISTICS:
        (A) LENGTH: 717 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1494RP (xi) SEQUENCE DESCRIPTION: SEQ ID NO:765:

GATCTTCGTT CGTGAAAACC TTGCACGTCT TCATGAGCTC AAGAATTGCC TCTGCATCTA       60

TTCTGTCCGG TTGGATTCTG CCTTCCTTAT AGTCCTGAAT CATGCGCGCA AAGCGCGCG      120

GCGTCCAGTC ATGACGGGAT CGGCCCTTAT AGGACTTCCC TGCAAGCCGC ATGAGGCTCC      180
```

```
GCCAGCCATT TTCTTCAATA ATATTGACAA GTCCTTCGTT TTCCAACACG ACCTTGTTCG      240

CGAGACTGTG GAACGTGTTC ACGTCTATCT GCTCAAGTAT TTCTACCCTT TCCTCAGCAG      300

ACCATCGCAA GTTGCAATCT GCCTCTTGGA ATGTCTCCAT AAGCTTTTCA TTGATGTTAT      360

CCACTGCTTT ATTTGTCAAG GAGAGGATTA GTATTTCATT AGGAGCTACA ATCCCTTCGT      420

AAACCAGGTT GTAGACTTTA TGCAGTAGTG TCACGGTCTT GCCAGACCCA GGTCCCGCTA      480

CCACATTGAC AGTTGTACAA GGCTCATATG GATGTGTTAC TACTCGTGAT GGGACGTCG       540

TCAGTGCTTT CATTCATGTA TGATACATGC TCGAGCGTCG GCGAAGGAAA TAAATTCGTG      600

AATTTCCGTT TTAAGATACT CAAAAGAGAT GAGATAACCG CCCGCAAGGC GGAGTAGAAT      660

TACAGCAGCT ATTGAATATA TTTAGTTTAT TTATCTGGCT AGCTTAACCA CTAGTGT        717
```

(2) INFORMATION FOR SEQ ID NO:766:

(i) SEQUENCE CHARACTERISTICS:
        (A) LENGTH: 606 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1494UP (xi) SEQUENCE DESCRIPTION: SEQ ID NO:766:

```
GATCCTTTAG GCCATCCTCT CCAAATTACC CGTGCTTGGC TTCAGTAGCT CAGTCGGAAG       60

AGCGTCAGTC TCATAATCTG AAGGTCGAGA GTTCGAACCT CCCCTGGAGC AAGTTTTTTG      120

CTCCGGGAAA TAAGTATTTG GAGCTGGACT GAAGCGCCAA CCTATGCAGC TTTGCTGGTG      180

CGAAGTGTTC ATTCATGTCT GCGGACTATG TCTATATATC TTGCGCGTCT TGTTCTTCTG      240

CTGGCGAAGA GGAATTGGAT TCTTGGGCGT GGTCTGCAAG CTCTGCTAGC TTCCTGGCGG      300

GCAGAACACT TTCAAACGCC TCTTTCCAGT CATGGTTGTC AAAGTATCTG AGCATGATCT      360

GGATAACGTG GGTGGTGGTC AGCACCTTCC TGCCGCATAG CTTGATGTAC TCTCCTATTG      420

GTAGGCGACG AGTAGGAATG CCCAGTTCTT TGGCCTTATT GTAACAGAGA GCTTTGTGGC      480

GGTTCTTGTC CACAATGCCG CCCACTATAT ACGTCGTACC GGGTTCCAGC GTCTCCAGCG      540

TCTCATCAGT ATCTGCAGTA AGGTAAACTG CGTTCGTAGT TGGAAGGGGG GATTCGTCTG      600

TGAAAT                                                                606
```

(2) INFORMATION FOR SEQ ID NO:767:

(i) SEQUENCE CHARACTERISTICS:
        (A) LENGTH: 715 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1495RP (xi) SEQUENCE DESCRIPTION: SEQ ID NO:767:

```
GATCGAATTA GCGGGTTTTA ATGAAACATA AGGAACGAGG TCTAAATGCG CAACATCCTT       60

GAATGCAGTG CCAAGATGTA TGCCGTTCTT GGTAAAGAAA ATTGTACCAT CGACATAGTT      120

AATGCCACAT CCGATCACGT CGTCTCGACC ATAGGGCTTC GAGTACGACT TGAACAAAGA      180
```

-continued

```
GCCGTCATTT ATGTAACCGT CCGACCCGTT GTAAATGTAG ACATCCTTAC CAGTGCTACT      240

CTGTTGCGAA GTTGGCCTGG AACCCTCAAA AGGCCCTCTT AATATGTTGG AAGTTTGCCG      300

GTTCAAGGCA GAAAATTCAC CCGGGTCCCT CGAAGGTGGA TCGCTAGTGT TTGCTTCGCC      360

AGCATTTGAC GCGACTTTTG ACCAGTCCTT AAATCCAATA TTGATATTGC AGGTTTGGCC      420

TGACTGCGCG CTGGTCACCG ATAGTACCTT AATTTCATAG TAAAAGATAG CCACTTTCTT      480

ATGATTAATA CAAGCATTCG CCCAGGTGGA AGCCCACTGC TGCTTCTGGT TATTAACTGA      540

AGTCCGTAGC CTATTATTTA CAATAGGGCT GTTGTCATAG CCAGAGTAGA GCTGCCAGTT      600

GGGGTTAGGC CGCAAGTTTG TGAAACCGTC TGTTGAGACC AAAACTGAGT TGTTCGACTG      660

TGTGGTCCAG AGGTGGGGCA AAAGGATACC TATCGAGGAG TATACGTCTG AGAAA          715
```

(2) INFORMATION FOR SEQ ID NO:768:

(i) SEQUENCE CHARACTERISTICS:
        (A) LENGTH: 706 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1495UP (xi) SEQUENCE DESCRIPTION: SEQ ID NO:768:

```
GATCAGCCAA CAGCTGAGTT CTGATTCGAT GAGAGCTATT AGTAAACTTT TTGTGTTTAC       60

GGTGCTGGTC CTGGGATCGT TACAGTACTA CTGTGGACGC TACGGCGCGT GCCCCGCGCA      120

GATTGCAGTG ATAAGCCATT ATACGTGGCC TTGCACGTAC GCGCCGGCAG TACGGGATAA      180

ATTAGGGAAG GCCAGCGAGT GGTACGGGGC CAATGCGGCT CCGCATGTGT CGGTGGCGAG      240

CGGGTGGATG CAAGGGAAGG TGATGCCGCA CCTGACGAAA GTATCCCAGT GGACGGAGAA      300

GCATGTACAA CCGCGGATGC GGCAGGCTGG CGCGGACGCG ATAGTAACAG CGCGCGTGGC      360

ATGGAATGTC GTACAGCAGT ACCAGCGGCG GCATGTGGTG CCTCTGACAG GGCGACTGCT      420

GGCGAAGTGT CCGTGTCTCG AGAGGTGGGC CGAACAAGCT GCGCGCGGCT GGCAGTGGCT      480

CTGCAAGCAT GCTCGGGCGC TACCACAGCA GTACAGCAGC AGTATCCTGC GTTTGTGGCG      540

CATATGGGGG GCATATGGGA GCCTTTGCAC GGCGCCTACA ACCGGATCTA TCTGGACTTG      600

GGCCGCCCAG TGCAGGAGAA GACGTCCGAG GACSCAGTGC GGCGCCCGGG GGGACTCAKT      660

ACATCACATC CACTATCACA ATGACCATGA CTCGCTCGAT GAACTC                    706
```

(2) INFORMATION FOR SEQ ID NO:769:

(i) SEQUENCE CHARACTERISTICS:
        (A) LENGTH: 749 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1496RP (xi) SEQUENCE DESCRIPTION: SEQ ID NO:769:

```
GATCGTTTTC TGTCAAACCG CAGTCGGGTT CAAGGAGTAC GTTGAATTTA GCTCTTGCAT       60

TCAACAAGTC TTTCCCAGTT TCCACAATGT TGTCGATAAT GAAGGGTTTA AAGTCTAGAA      120

GCTCTTCTTG CGTGAAGCCG TTCTGGTGAA GAATCTTCAG TTGTTGCAGT ACGGTCGATT      180
```

```
TCCCGCTCTC GCCAGAACCC AACAACAAAA CCTTGAGCGC GCGATTGCTG GCACTCGGTT        240

GCCCCATTGA CCCTGGTCCA GCCACTGCCG TTGTCTGCTG ACTCGTCCCG GATACCACGG        300

AGCGTTTCCT GCCGCCCGCT GTAGCGCCGG ACGTGCTATG ACTGGGTGAC GTCTCAGGTT        360

TGACTTCTGC ACCGTAATCT ACCCTCTTTG CTCCTGTTTC TACCTTCTGA GAAGCACCAT        420

GTCTGTCCTG ACGCCGCTTT TCCGCGTGTG TTGCTGATCC CTTGTCCTTC GACGCGCACA        480

ACCCCATTAT GTCGGGCTCT ATATCCACCA GTACTTGGAG CACTCTAGCG CCTGGCTTTC        540

TTTGAAATAT TACCGTCCGG GCAAAAGCCA CTTATAGCGC CTGATCAATG GATTCCACTG        600

CTAGAGGCTA ATTAGGCTGC CGCTTGTCAC TTCGCGGGCC ATCACATTAT ATTCATAGCA        660

AAGTAGGTGC AACAGAAAA AATCAGCCCG CCTCCTTTAT TGATCACGTG AAGAAATCCA         720

CATGAACAAT CACGTGAACA CACATTTGG                                         749

(2) INFORMATION FOR SEQ ID NO:770:

(i) SEQUENCE CHARACTERISTICS:
        (A) LENGTH: 754 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1496UP (xi) SEQUENCE DESCRIPTION: SEQ ID NO:770:

GATCGAAGTC AATGCCAGAC TATCTCGTTC TTCTGCATTG GCGTCCAAGG CAACAGGATA         60

CCCCCTTGCC TATACTGCCG CTAAGATTGC TCTTGGGTAT ACATTACCAG AGTTGCCTAA        120

TCCTGTTACC AAGTCGACGG TCGCCAACTT TGAACCCTCA CTGGACTACA TTGTGGCCAA        180

GGTTCCAAGA TGGGATCTCT CCAAATTTCA ACACGTGGAT AAGACTATTG GGTCTGCCAT        240

GAAGTCCGTA GGTGAAGTGA TGGCGATCGG CCGGAATTTT GAGGAAGCTT TCCAAAAGGC        300

TTTCCGTCAG GTTGATCCAT CTCTACTAGG TTTCCAGGGC TCTGACGAAT CGCAGACCT        360

AGATGAAGCC TTGCAATTTC CTACAGATAG AAGGTGGTTG GCTGTGGGAG AAGCGCTAAT        420

GAACAGAGGT TACTCTGTGG AACGTGTACA CGAGCTTACG AAAATTGATA GATTTTTCCT        480

GCACAAGTGT ATGAATATTG TCCGAATGCA GAAGCAATTA GAGACCCTAG GATCAATAAA        540

TCGGCTAGAC GAGGTTCTGT TGCGGAAGGC TAAAAAGCTC GGCTTCTGTG ACAAGCAGAT        600

TGCACGGGCT ATTTCAGATG ACCTCTCTGA ATTGGATATT AGAGCGCTCA GAAAAAGCTT        660

TGGCATTTTG CCATTTGTTA AACGTATCGA CACCATGGCG GCAGAAGTTC CTGCGGTAAC        720

CAACTACTTG TATGTTACCT ATAATGCGGT CAAA                                   754

(2) INFORMATION FOR SEQ ID NO:771:

(i) SEQUENCE CHARACTERISTICS:
        (A) LENGTH: 740 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1497RP (xi) SEQUENCE DESCRIPTION: SEQ ID NO:771:
```

```
GATCATTTGG TCTTCTTCGC CTCTACAAAC TGTGAATATC ATACTAGACC TGAAGTCAGG      60

TAGGGAGCAA CCCAACCCTT CGGTCGCAGT AGAGGCTGGC AAATCCATTA AAAAGACCGA     120

TTCGAATGGG AACTCTAAAA TTGAAACTAA GCAATTTCAT GAACTCTCGA CAGTTCCTGG     180

TCTTTCCAGT ATTGACTATT ATAACCTTAA GAGAAGGTAT CGAACTTACA AATCTCTGAA     240

AAGGGCGACT ATTGAAGATA TATTACATGT TGTTGTCGAC AGAGATCTGG CGGAGCGCAT     300

TGTTACTCAT ATCCAAAGAG AATCTGAGCT GCAACAATAT GAGGAGGATG GGAGGAATGA     360

GGTATGAAAT GTTCCCCATT TGGATTAAGG TATCAGGTGG TCACGATATC CACTATATGG     420

TGCTATTAAC GGCATGCAAA GTGTAGAATT AACCTAAAGA ATATGTTATA TATATATATT     480

ATAAACTACA AACTAACGGA CGCAATGAAA TCTAAGTGTC GCAAGGTTAG CCTTAATACC     540

GGTACTTGGA TAAAATCTCC TTTTTCAAAT GATACAAGCG TCCCATTTCA AACGCCATGC     600

CAGAATCACT GGCTGGATTC ATCATGATTG TGATTGCGGT TGCCTCAGTC GGAAATAAAT     660

TAGCAATACT CATTATACCC TTCGCGACCT CCAGCCGCTT CTCTTGGGTA GGTTCAAATG     720

AGGCAATTTG CATACTCTTT                                                 740

(2) INFORMATION FOR SEQ ID NO:772:

(i) SEQUENCE CHARACTERISTICS:
        (A) LENGTH: 720 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1497UP (xi) SEQUENCE DESCRIPTION: SEQ ID NO:772:

GATCCTGTCA CAGCGGGCGA CGCCGCAGGC CGCGTACGGC GACCTGCAGG ACGAGGTGAA      60

GGTAGGAGGG TCCGAGGCGG CCTTTGGCGA TCGGGCGTTG TTCGGGGCGA TGGGCGGGCG     120

CGCGCCGGAG GATGGCGACG AGGGCCCACA ACTTGGTGCC GGGGTGGCGC CCATGGTGAC     180

GCCGCACCTT CCGATGGAAC CCTCGCAGCC GCACGCGCTG CCACAGCAGG CCCCCACTCC     240

GCACCAGCCA CAGCAGCCGG CCCAGAAGCG AATGCACATG CTCCAACAGC TGCACGAAGA     300

GCAGAAGAAC TATTCTTACG TGGACCGCCA ACCGTCAATT ATGCAACAGC AGCCACACAT     360

GATGCAGCAA CTGCCGCAAC AACGGCCTCG GATGCAGCAA CTGCCGTTGC AGGGCCAGTC     420

CGAGACGCCG AAGCCCGCAG GCAGTTCTCC AATGGTGGTG CCCGTCAACC ATAGGCAGCT     480

GTTGCAGAAC CTCGACCCCA GCATCCAGAA AAGAGTATCA CAGGATCTGA ACAGCAAGCA     540

GTATGAACTA TTTGTGAAGT CTTTCATGGA ACATTGTAAG CGGTGTAATA TTCCGTTTAA     600

CCCAACCCTG AGATAGGCGG GACGCGGGTG AACTTATTCA TTTTATACAT GTTGGTACAA     660

AGAATGGGCG GGGCAGATAA TATCACGAGG CTGCAGCAAT GGCGCGGCTT GGCAGAAAAA     720

(2) INFORMATION FOR SEQ ID NO:773:

(i) SEQUENCE CHARACTERISTICS:
        (A) LENGTH: 713 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1498RP
```

(xi) SEQUENCE DESCRIPTION: SEQ ID NO:773:

```
GATCACTACG TGACATTCGG TACGGAATGG CACTCCAATG CCGACAAACC TCTTCCTACC      60
CCGTGACTTA CCCCGATGTG CCAACTACCA CACATCTGCG CCATAGCCCC AGCCATCTGG     120
CACCAAATGT ACTCGATATC GTTATTACAT GTCTACGCCC TCACGTGCAT CCACCATCTG     180
ATATCATGTC TGCTCTAGGC TATATATTTC GGTTGCGGCC ATATCTACCA GAAAGCACCG     240
TTTCCCGTCC GATCAACTGT AGTTAAGCTG GTAAGAGCCT GACCGAGTAG TGTAGTGGGT     300
GACCATACGC GAAACTCAGG TGCTGCAATC TTTTTTTTTT CCTCCTCCTG CAAGCTGGCC     360
GCCAACACAG GTCACCCTAG TATGGCTCAC ATGCAATTCA GATATCTACT TCTGACTGGT     420
CTGGTGGGCG ATGGCCATCA TTGCAAACAG TGTGCTCGCA TGGGACTTTA ACGACCTCGC     480
GATAATAATC AGAGATCGTC TACTTATAAA ACATCAGGCA CAAAAGAAA GGTGCAGCGA     540
AATGGTATAT ATAGGTCCTC CAGATCCACC CACCGGTACC TCCTACTTGG CCGTATCTGC     600
GTCTCCGTGG CGCTTGCCGC TGAGATGCTG TGGGCCCGAA ATGTACTCTC AAATGGGCTT     660
GTTCAGTGGC CCATACAGCT CATTAAGCTC AGTGGCCCCG ATGCTTAGTA GTA           713
```

(2) INFORMATION FOR SEQ ID NO:774:

(i) SEQUENCE CHARACTERISTICS:
        (A) LENGTH: 699 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1498UP (xi) SEQUENCE DESCRIPTION: SEQ ID NO:774:

```
GATCTCTTGG TTCTCGCATC GATGAAGAAC GCAGCGAATT GCGATAAGTA TTGTGAATTG      60
CAGATTTTCG TGAATCATCG AATCTTTGAA CGCACATTGC GTCCTCTGGT ATTCCAGGGG     120
GCATGCCTGT TTGAGCGTCA TTTCCTTCTC AAACCCTCGG GTTTGGTAAT GAGTGATACT     180
CGGTCGTAAG ACAAGGTTAA CTTGAAAATG CTGGCCATGG GCGGAACTTG CGCGGACTGC     240
GGTCTGAGCT AGTTTCTACA CTGCGTATTA GGTTTCGACC AGATCGTGGA GTGGAGCTGG     300
CGCTTGAAGA ACGTACGACA AACAAGGCCT TCCAGGCGAA TAGTATTCCC AAAGTTTGAC     360
CTCAAATCAG GTAGGATTAC CCGCTGAACT TAAGCATATC AATAAGCGGA GGAAAAGAAA     420
CCAACCGGGA TTGCCTTAGT AACGGCGAGT GAAGCGGCAA AAGCTCAAAT TTGAAATCTG     480
GCGCCTTCGG CGTCCGAGTT GTAATTTGAA GAAAGTACCT TGGTTGCTAG TCCCTGTCTA     540
TGTTCCTTGG AACAGGACGT CATAGAGGGT GAGAATCCCG TCTGGCGGGG GTGCTAGTGC     600
CATCTAAGGT TCTTTCGACG AGTCGAGTTG TTTGGGAATG CAGCTCTAAG TGGGTGGTAA     660
ATTCCATCTA AAGCTAAATA TTGGCGAGAG ACCGATAGC                           699
```

(2) INFORMATION FOR SEQ ID NO:775:

(i) SEQUENCE CHARACTERISTICS:
        (A) LENGTH: 742 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:

(A) ORGANISM: PAG1499RP (xi) SEQUENCE DESCRIPTION: SEQ ID NO:775:

```
GATCAGCTTC ATCGATTACC CAGAATTCCG CTTCAACAGC AACGAGGCCA CCGAGATGCC      60
CTTCCGCTAC GTACTGGACG CTGCTGGCAG GCCCATTCTG CCATCAGGCA TGCTAGAGCT     120
CATCAAAAAG GACTCCGAAC AGAGTCTGGA TGACCTACTT TAGGCTCGTT GAACAACAGC     180
TTATAGATGA TGTATATATG CGCGTCGTCC GCCAGAGACT GGCATCGGAA GCCACGCAAC     240
CTAAAGTCGA TAGAACTCTG TCAACAGAAT CAGTTCTTTT CCTCCTTCAG CATCTCGCCA     300
AGCAGCTGCT CGAAATCGAT ATCATCAGAA GTGGTTTTTG CAGGAGCAGC TACGGCGGGC     360
TGCTGCGACG CACGTCCTCT AGCCTTGTAC AATGACACAC CCCCGAACAG CGTGAATAGC     420
GTGCCAAGCA CCAAAACATG AGGCTGAACC GGCTTTCCAA AGATGTTGTA AGCTTGACCC     480
ATCGCTAATC ACCGAATCCG CTGCAGATAT GGGGTCTGAT GGTCTGGTGT GTAGCGGTGT     540
GCATTTGTGA GCTCCTATTG GCGGAGGAGG CAAGTCGATC TAGAGGGCTA CAATGAGGTG     600
TTCGGGTGTT TGTCAGGGTA CGGAGGAGGT AGCACGTGAT CGTTCAAATA TCTGTACCGC     660
CCCATGAACA TCTATTCGGT GCATTGGGTT TGGAGCACGG GCGATCATTG GAGACTAACA     720
CTCACGAATT TTGCCTGGCG GA                                              742
```

(2) INFORMATION FOR SEQ ID NO:776:

(i) SEQUENCE CHARACTERISTICS:
        (A) LENGTH: 716 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1499UP (xi) SEQUENCE DESCRIPTION: SEQ ID NO:776:

```
GATCGCAATG GAGAAGGTAA CGCTGCTACC GAAGGTTATC AGTGTTTTGA ATAAGGCGAA      60
CCTTGCAGAC ACAATTTTGG ACAATAATTT GCTACAGAGT GTGCGGATCT GGCTTGAGCC     120
ACTGCCGGAT GGATCCCTAC CATCCTTCGA GATACAGAAG TCTCTCTTTG CCGCGATTGA     180
GAACCTCCCC ATAAAAACAG AGCACCTCAA GGAGAGCGGA CTGGGGAAGG TGGTCATATT     240
TTACACCAAG TCTAAGCGTG TAGAACACAA GCTGGCCCGG CTAGCTGACC GGCTGGTTGC     300
AGAATGGACG CGCCCTATTA TCGGCGCTTC CGATAACTAC CGGGACAAGC GTGTCCTGAA     360
GATGGACTTC GACGTGGAGA AGCACCGTAA GAAAGCGGCA CTTGATTCTG CCAAATCTAA     420
GAAACGGAGA AAGGCTGCAG TGGACGAGGA GAAACACAAG TCACTCTACG AGCTTGCCGC     480
TGCGAAGCGG AACAGAGCCG CAGCGCCTGC GCAGACAACC ACCGATTACA AATACGCACC     540
AGTCAGCAAT ATCTCGAACG TACAGACCGG GATCCGCACG GCAGGCGTGG GCTCCACGCT     600
CAACAACAAC GATCTGTACA AGAGACTCAA CTCGAGACTT GCCAAGTCTA AACGGTCCAA     660
GTAACCGCTG TGTACTTCAG CTAATAGTAT TATAATAACG TTTAATGATA CTGAAA         716
```

(2) INFORMATION FOR SEQ ID NO:777:

(i) SEQUENCE CHARACTERISTICS:
        (A) LENGTH: 719 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1500RP (xi) SEQUENCE DESCRIPTION: SEQ ID NO:777:

| | | | | | |
|---|---|---|---|---|---|
| GATCAGCTAA | TGGCTGCTTG | TCAAAGACCA | AATCCTTCAC | CCCTAGAACT | TTTCCTAGAG | 60
| CATCCATTCC | GATAACCTAG | GTCGCTTTGT | GTCCTTAAAG | AATATTGGTT | TAATTTGCTT | 120
| TCGCGGACGG | AGTAAAGCGT | TATGTAGCAT | TTTTCAAAAG | AGGCTTAATG | GACACATCCC | 180
| AGGATAGTAT | GAATGAGAAA | GTCCAATTCG | TGGCACCATT | GTGCTAGTTC | TTATATTTAC | 240
| TGTTATACAT | CTACTGCAGA | GTCAAGCATA | TATACCAAAT | AATTCACCAA | ATACTAGCTC | 300
| TTCTAAGTCT | TCAGCTGATG | GATTCGCGCC | AAGGCGCCGC | AGAGCTGCAG | GTAGGTACCC | 360
| ACACCTTCCA | AAATCCTCAT | GTGCGTGAAT | CCTATTTCTT | TAATCATCTC | CAGCCGCAGG | 420
| GGTTCTTTAA | TCTCTGTCAA | GTTCTTCATG | ACACGGAAAC | ATGTAGTGAT | TATGTCCACC | 480
| GCCGAGTACC | TTTGCCCCAC | AATTCGCGTA | AGTAATTGAG | CGACTCATCA | AGAGTAGCAG | 540
| ATAGCAGCAT | TTTCTTGATG | ACCAGGGGAT | GCGGCGAGTC | CACTATCTTA | AAAACGTTGT | 600
| CGCCGTTCAC | TAACGTGAAG | CCCGCCACGG | TGCTCTGCAG | ATTGTTGATG | GCCTGCCGCA | 660
| TGTCACCTTC | CGCAGTGAAT | ATCAGCGCCT | CCAGACCATC | ATTGGTGTTC | TGTACGTTT | 719

(2) INFORMATION FOR SEQ ID NO:778:

(i) SEQUENCE CHARACTERISTICS:
        (A) LENGTH: 664 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1500UP (xi) SEQUENCE DESCRIPTION: SEQ ID NO:778:

| | | | | | |
|---|---|---|---|---|---|
| GATCGCGACC | CCCCGCGTCA | CGGCAAGGCC | CGCCAACCGC | GAGGAGGAGA | TCAATGGCTT | 60
| TGACCTCGAG | GCGCCGCCCC | AAAAGAAGAC | CAAAATACTA | TAGTAGTACG | TACATTGTAA | 120
| TACATGCGCA | AGACTTGCCG | CCAGTTAGCC | GCCCGCCTCC | CAGGTCTTCA | CCAGCGCCGT | 180
| GCCGTCCGCA | GACGTGCTCA | GCAGCTGGCG | GCTACCCTCC | TTGTAGACGG | TGTCAATGAC | 240
| TGCGCCCGCA | TGCAGAGACG | CCAGCTCGTC | GGACACCACT | ACCTCGCTGG | TCACGTCCAC | 300
| TACGTAGCCG | TACGCCGCAA | CATAGCGTTT | GTCCTCTACG | AAAGCGCACC | GTGCCAGGAG | 360
| GCGTCCGGTG | TTCCGCGCAG | GGAGGGCAAA | TCCCCGCCTT | AGACGCTGTC | CGGCCTGCTG | 420
| GCCGTAAAAG | CTCACACTGT | CATCGAAGCC | CAGCGCACAC | ACCTCCTCTC | CATGCGCGGA | 480
| AGTGCACAGC | GAGGTCACAC | CACTCCGGTG | GCCGGTCTGC | GTCTTCCACA | CTGCGTCCTC | 540
| GCTGCGCCGC | TGCTCGTAGG | CTCGTACCAC | TGGCTCAATC | CCCGACGTGT | ATACCCGCCC | 600
| GGCCGAGACC | GGGCAGACGG | CGGCTGATAG | CAGCGGAAAG | TCGGTGGCCA | CAAAAGCCGC | 660
| CGGG | | | | | | 664

(2) INFORMATION FOR SEQ ID NO:779:

(i) SEQUENCE CHARACTERISTICS:
        (A) LENGTH: 696 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
            (A) ORGANISM: PAG1501RP (xi) SEQUENCE DESCRIPTION: SEQ ID NO:779:

GATCTATTTA AATATAACAT ATTATTTATT TCTTTTTTTA AACATTTTAA ATTTAATTAA     60

TTATTTATTT ATTTAATTAA TTATTTTTAT TAGTTAAGAT AATTTTATAA CTTTAATTAG    120

AGAGCTAAGG TACACACCCC TAATGCTTTC AGCATTCTTG TGGTACCACT CTAATTAAAG    180

AGTTATTATA TTAATGATAT AATATGTAGA TATTCAGTTT TGAACTGAAG ATATATGTCC    240

CTAAAACATA TGTTTTACCA ATTAAACTAT ATCCACTAAC TTTTATTATA TAATTTAATA    300

ATTAAGAATA TTTTAAGATT GAATTAGAGG AGTATTAAAT GAATGAATAA GAGGTGGTGA    360

ATTTAATATA AACTCAATAG ATGATGATTT AGTAGTATTC ATTAAGAAAA TATTATTTGA    420

TTCAATAAAA TCAGGTAGTT TTATATAATT AATAGATTTA TTATTAACTT TATTAGTTAA    480

ACCATTTATT AATTGATCAT AAATAATATA AAGGAATAAC ATTAATGATA TAATAGTTAT    540

TATAGAACCA AATGAAGATA CTAAATTTCA ACCTAGGAAT AGATCAGGAT AATCAGGAAT    600

TCTTCTTGGT ATACCATTAA TACCTAAGAA ATGCATAGGG AAGAAAATAA TATTAAGACC    660

TAAGAAAATT AATCAGAATT GAATTGTGAT AATTTT                              696

(2) INFORMATION FOR SEQ ID NO:780:

(i) SEQUENCE CHARACTERISTICS:
            (A) LENGTH: 722 base pairs
            (B) TYPE: nucleic acid
            (C) STRANDEDNESS: single
            (D) TOPOLOGY: linear (ii) MOLECULE TYPE: DNA (genomic)

(vi) ORIGINAL SOURCE:
            (A) ORGANISM: PAG1501UP (xi) SEQUENCE DESCRIPTION: SEQ ID NO:780:

GATCAAATAA AAATAGAAAT TAGCTTAATG GTAGAGCATT CGTTTTACAC ACGAATAATT     60

TGAGTTCGAT TCTCAAATTT CTAAATAATA ATTAACAATA ATTTAAATTT GGGTAAAAAT    120

TAATAAAATAT TAACGTATAT AATAATTATA TACTTTATAA AATTACTCAA TGTTATTAAT    180

AAATTTATTT CTTATCATTA ATAATGATGT ACCTACTCCA TATAATATAT ATTTTCAAGA    240

TTCACTACTA CCTCATCAAG AAGGTATTTT AGAATTACAT GATAATATTA TATTCTATAT    300

GTTACTTGTT TTAGGTTTAG TTTCTTGAAT AATAATTATT ATTATTAAAG ATTATAAAAA    360

TAATCCTATT CTTTATAAAT ATATTAAACA TGGTCAAATA ATTGAAATTA TTTGAACTAT    420

TTTACCAGCT ATTATTTTAT TAATAATTGC ATTTCCATCA TTTATTTTAT TATATTTATG    480

TGATGAAGTT ATTTCACCAG CTATAACTAT TAAAGTTATT GGTTTACAAT GATATTGAAA    540

ATATGAATAC TCAGATTTTA TTAATGTAAA TGGTGAAACT ATTGAATATG AATCTTATAT    600

AATTCCTGAA GAATTATTAG AAGAAGGTCA ATTAAGAATG TTAGATACTG ATACTAGTAT    660

TGTTATTCCG GTTGATACTC ATGTAAGATT TATTGTTACA GCTCTAGATG TTATTCATGA    720

TT                                                                   722

(2) INFORMATION FOR SEQ ID NO:781:

(i) SEQUENCE CHARACTERISTICS:
            (A) LENGTH: 710 base pairs

```
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1502RP (xi) SEQUENCE DESCRIPTION: SEQ ID NO:781:

GATCGCTCCC AACCCCTGCT TGATCTCCAT ACTCATCTGG TTTTTCAGGT AGCGCGGGTG    60

GTTGAATACG GACTTGTCGA AAACGAACAC ATAAGAGAAT GACGCCACGA TCAGGTACAG   120

CAGCCAGCCA AACACTGTCG TCACCAAAAA CAGAGACAAG CTCTGCCGCA ACAGGCTGTA   180

TCGCGGCAGC ACCGACCCGA AAGCATGCGG GCTAACCTCG AACATAAACG GTGCATACCC   240

ATATACCTCC AGCGGCCTCT CAAGCGACCT CCCGAACACG CGCGTCGCAT TTACCATCTG   300

CTCCTTAATC ATCGCCTGCT GCCAAGTCCC GCCCATCTTC GGCGACAGCG ATGCTGGCAG   360

CAGTGTGGCA TACACATAGT CGAAGAAGTA CGAGTCGCAA AACTCGAGCA CTAAATCCAT   420

GGTCGGAGAA CGCTATAGAC TAGGAGAAAC AATTTTAGCT CTAGGTTGCC TGCCTTCTAG   480

CGTGATAACA GATCCTGCTA CAGCTACTAA AGCCCATCTG CCGCTCTCCT CTGGCTTTTT   540

GCACTTTTAT ATGGTCCATC CCGGCACTGA CCTAACGTAC GCGGCTCTAT ACGACGCTAA   600

AAAATCAAGT TACGAATGCA CTATACGAAT GCGTTGAGCA AGGAACGAAT CCCTTTTGGA   660

ACGACGATAT CACGTGAACG AAGCCGCAAC GTTCGGGTGC CGGGCGCCTA              710

(2) INFORMATION FOR SEQ ID NO:782:

(i) SEQUENCE CHARACTERISTICS:
        (A) LENGTH: 692 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1502UP (xi) SEQUENCE DESCRIPTION: SEQ ID NO:782:

GATCAAAAAT ATTCGACGCA TTTGCCGCTC TTTAGTGTAC TTCGGGTCAT TATGGAGATG    60

GCCAATTTAC ATCGGTATTT TCGCCTTACT CATAAGAGTA TACAGTGCCA ATTTCCGTGA   120

ATTGAGGCCT ATAAACATCT GGTATGTCTT ATCTTCAGTT CTCTCTGGGG ATTCGCCCAT   180

CACTGGGATT CCATTCAGTT TCAGGCTGCC AGGAGTTGGA ACTAAAACGT GGTTTTTGGA   240

TCCTCTGAGA TCTCTGTTGC CATCAAGCGC AAGATAGGCA GCGGTGCTTT TGTATGAATA   300

TGCGGTTGAG GATGTCTCAC TCCAGGTTGG AAACCTATAT TATGGTGCAA TATATATTAA   360

TGATAAGAGC TTTCTCTGAC TAACAGCAGT AACTCTTAAT TGAAGTATTT GTTATTTCCA   420

ATCTTCATAC AGTATGTCAC CCTGTTGTAT TATAGATTTC GTTTACGAAT TGGATCGTGC   480

TTTCGTGGCT GCGAGGTCAG AAGATCGATA TAATAATATA TATATTATTA AATTATGGTA   540

GGTAGGGAAT TGCTATTTGT GTCTAGTACT CGATGCCTTA TCTACAACTT CTAGTTGCAA   600

CACATGATAT GCTGTGGACC AAAACGCTAC GGCGTTATTG ATTTTATTCA AGGTCAAGAT   660

CATATATTAG CGTAATATCT GTGGAGGTTC CT                                 692

(2) INFORMATION FOR SEQ ID NO:783:

(i) SEQUENCE CHARACTERISTICS:
```

(A) LENGTH: 716 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1503RP (xi) SEQUENCE DESCRIPTION: SEQ ID NO:783:

GATCTTCGTA TACATGTCGC AAAGCTCCTC CAAAATCTTT TCGTCTCCAT CATGAGAGGC      60

TGCTACAGCT TTTGAGCCGA TAGAATTGGA AATACCATTG GAGATTGCTA TTAGTAGGAA     120

GACAATATAA GTACCATCTG TCGATGGGGC AGAGGCTTTA TCAAGAAGGT CCATCAGCTT     180

GTTCTTGGAT ACAGCAGTCT CATTTAATAA TAATGCCTGC TCACCACTGG GCAAAAATTC     240

AGAAACATTG AGCAGTTCAG AGAGTGAGTT CGACTCAAAG TTTTCGGTCA TTGTCTCTAA     300

CAAGACAAAA ACAACGTCCT TCCTGCTCTC ATGAACATCA TAAGCCTTGA AAACCTCGAG     360

CAAAATAGTA TTGTCCTGGA TCACGTTCAA AAATACCTCT AGAATTAATG CCTTCCTCCA     420

CAATAAAGTG TCAGATTTAG GAGACAGAGT GTGGATTAAT AATGATAAAA TAACTTCCAA     480

TTCCAATTCC AGCAATGTCA AATACTGAAC CTTTATGAGA AGTGTAATAC ATCTGGCGCT     540

ACGAACCACA ATTGCAAAAT TTTTGGATGA GGAAATGTAC CTCAATAGCA GCGGCACCGC     600

CTTTGTTCGC AACAGAAATA ACAGATCTCG GTGTGTCAAA AATAATAATT CATAGTTCAA     660

TAAAACCAGT TCTAGGAGCT CTAATCCATA CTCCTCATTT ATGCAATTGC TATCCA        716

(2) INFORMATION FOR SEQ ID NO:784:

(i) SEQUENCE CHARACTERISTICS:
        (A) LENGTH: 637 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1503UP (xi) SEQUENCE DESCRIPTION: SEQ ID NO:784:

GATCTGCGCG CTTCGAAGGG AAAGGCGGGC CCCAATCCCC AGTCTATGTT CAAGAGGGCG      60

AACAGCAGGC CGTCATGGCA TTCAATAAGC GAATGGGCAC TCGAGCGTTG GCACATCATG     120

TGCTGGATAG CATCATATAC TACACAGACA AGGTGGTGGT GAAGGGGCTT GGAAATTTGT     180

CCGCGAGCTT ACCTTCCAAG ACCTCCTCGG CGACAAGCGT CAGGGGTCGT GTAAGGAAAC     240

GCATTGGTCT CGAAGGCGCA AATGATGTCT TTGTATACCG CACAAAAGAC CTGGTATTCG     300

ATAGTGATGA AGATATACCC AGAACCTAAC TACTTGTGTC GATATTTCTC ACACCGCCTG     360

GTGCGGAACC GGGGGCATAC ATTCGTTTTA CACAAGAGGG GTTGATGCAT AAAACGCGCT     420

TTCAAAAGTG GCAAGCGAGA GCTGCCGACT GTCGTTGCTT TTGGTGCGGC GACTGTAGGC     480

AATGTGCCAT CCCGTGCGCC TTCTTTTACG CGAGATCCAG TCTCGCAAGC CTGGCTGTAA     540

CCAGAACACT CGGCTGAAGC CCGCGACAGG TCCCTCGTGG ACCAGGCAGG CAGCCTTGCA     600

TCTGATAGGC CGGATACTGG GTATCTGCCA AGAGAGG                             637

(2) INFORMATION FOR SEQ ID NO:785:

(i) SEQUENCE CHARACTERISTICS:
        (A) LENGTH: 708 base pairs (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1504RP (xi) SEQUENCE DESCRIPTION: SEQ ID NO:785:

```
GATCAATTAA TAAATGGTTT AACTAATAAA GTTAATAATA AATCTATTAA TTATATAAAA      60

CTACCTGATT TTATTGAATC AAATAATATT TTCTTAATGA ATACTACTAA ATCATCATCT     120

ATTGAGTTTA TATTAAATTC ACCACCTCTT ATTCATTCAT TTAATACTCC TCTAATTCAA     180

TCTTAAAATA TTCTTAATTA TTAAATTATA TAATAAAAGT TAGTGGATAT AGTTTAATTG     240

GTAAAACATA TGTTTTAGGG ACATATATCT TCAGTTCAAA ACTGAATATC TACATATWAT     300

ATCATTAATA TAATAACTCT TTAATTAGAG TGGTACCACA AGAATGCTGA AAGCATTAGG     360

GGTGTGTACC TTAGCTCTCT AATTAAAGTT ATAAAATTAT CTTAACTAAT AAAAATAATT     420

AATTAAATAA ATAAATAATT AATTAAATTT AAAATGTTTA AAAAAAGAAA TAAATAATAT     480

GTGATATTTA AATAGATCAA AATTTCAACA ATTTCCATTT CATTTAGTAC TACCATCACC     540

ATGACCAATT GTTACATCAT TTAGTTTATT AGGTTTACTA TTAACTTTAG CTTTTACTAT     600

ACATGGTATT ATTGGTAATA TTTATCCCTT ATTATTATCT TTATTAGTAG TTTTATTACK     660

AATAACTTTA TGATTTAGAG ATATTGTAGC TGAACTTACT TATTTAGG               708
```

(2) INFORMATION FOR SEQ ID NO:786:

(i) SEQUENCE CHARACTERISTICS:
        (A) LENGTH: 711 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1504UP (xi) SEQUENCE DESCRIPTION: SEQ ID NO:786:

```
GATCTTAATT TAAAATTTTA ATTAACTATT TATAATTTAG AAATATATAA TCTAGAGATA      60

TATAATCTTA AAATCATAGG TAAAAATACA TAAGATAGTA AGAATGAAAA TTAGTAAAAT     120

AAATAGAAAA CCATAAGTTA ATTGATTCAT AAAGAAAAAT GGAATTATTT GTGGCATCTT     180

AATTTTTATT ATTTAATTGA TTATTATCTA TTTAACATAA AACATTTTAA AATGTTATAA     240

AATAAATAAG AAATTACTTA TAGAATATTT ATTAAATAGT ATTTAATTTA ATTTTAATAT     300

TAAATATACC ATTTTTATTA ATAAATAGAT TATTAAGTTT ATTAATATTA AGTGATATAT     360

AATTTAATTT ATATAAATTA TTTAATTTAC TTCATTGATA TATATAATTA TTAAATGTAC     420

CTTTCATAAT ATTTATTTTT ATTAGTCTAG TAATATTTCT ATTTAATAGT CTACCCTTTA     480

ATTGGATATT ACTACCTACT AAATATTTAC CTAATAATAT ATTATTAAGA ATACTTAAAT     540

CTAATAATTT ATTATCTAAA GTATATAAAT TAATTAAATC TTTTTTATTA TTATTTAAAT     600

TATTATTAAT TAGTAAATTA TATTTATTTA TTTTAATTAA CATAATTTTT GATAATAATA     660

TACATTATTA AATGGTAATT TATTAATAAT TATCTTTAAT GATTTAATGA T              711
```

(2) INFORMATION FOR SEQ ID NO:787:

(i) SEQUENCE CHARACTERISTICS:

(A) LENGTH: 710 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1505RP (xi) SEQUENCE DESCRIPTION: SEQ ID NO:787:

```
GATCATCTTT ATACCATTGG CTCCTGTTCC GTGTGCACCA ACGTAATCAA AAGCGTGTGC      60

CCCCTCGCTA CGCAGGAAGC ACTAGAACTA GCTGAGTAAA GCAACGGTGA AAGTCGATCC     120

CTGATATATA TACGAAACCA GAGATACCTT CATCACAAGG ATCTTGTTCC TCGTGGCCCA     180

ATGGTCACGG CGTCTGGCTA CGATAGTAGT TACTTCTGAA ACCAGAAGAT TCCAGGTTCG     240

AGTCCTGGCG GGGAAGTCCT TATTTTTTTT GTTCCCTCTT GTTTCAGCTT TTTGTCTTAA     300

AAGGAGCAGA AAGATTATTT TGCAGCTCTC TTTTGGCGCC AGCTGGCAAA AGCGAACTGT     360

TGATTGACAA GCTTTTAACC TGTTATTAAC CACCAGCAAC CTCTCGAATT TATCATGTCT     420

CCATCAAATA AGGATATTGC TGCCCTAATT GTTGACTTCC TAACTACGTC CGCCAAAACT     480

GTAGGAGAGG ATTACGAAGA TTCCCTCAAA GTGGCAATTG ATTGTATCAC TGAAGCTTTC     540

GAACTTGGAC CAGGCGAAGC TGACACATTA GTTTCCGAAA AGTGTGGCGG AAGAAGCCTC     600

TCTCAGTTGC TCACCACTGG CATGGCTCAC ACCTCAGATG CAGGCGAACC GAAGGTAGCC     660

GCCGAAGAGT TGAAGAAGGA AGCTGAGGCC TTGAAACTGG AAGGTAACAG                710
```

(2) INFORMATION FOR SEQ ID NO:788:

(i) SEQUENCE CHARACTERISTICS:
        (A) LENGTH: 715 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1505UP (xi) SEQUENCE DESCRIPTION: SEQ ID NO:788:

```
GATCAAGCTG GACAAAAACT TCCGTAACTA TCTGAACCTA CTGGAAATGG TTCAGGGGTA      60

CGTGGAGCTT AACATGTATG AAGATGTCTG GCGAAAGCTC GTTCAATTAA ATGGGAAAAA     120

TGAGCCTGAT AGAGTTCCAG GATATTATAT TACGAGGTCT ATCTCACTGA ACCAGCTTTC     180

CACCAGTATA TATCCTGAGG AGTTGGATAA GTTTAATCTA TCTCCTGTCA CCGAGATAGA     240

AAAGAGGGTC GTGCAAGCCA CTGAGTGTTT CTCGAAACTA ACATTAACAA ATAGCCATCA     300

TGAAAAGGCG CGCATACTGA TATCAACCTT TCAAAAATTG ACAACGAAAA CTTCTCAAGC     360

TACTTTGGAT CCAATGATTG ACGCAGATAC CTTACTGGGT TTGATGGTTG TTGTAGTTTG     420

TCGCGCACAA GTTAAAAACT TGAAGAGTCA TCTAGATTAT CTTAGAGAAT TTGCGCAGAA     480

TTCGGATGAC GTAAAGTTTG GGCTCCTTGG GTATTCGCTA TCGACGCTCG AAGCGGTGGT     540

CGGATATTTC GATATTGGCG GCAGCTCAAT TAAACTTGAA AGATTGATCA CACCATGTCC     600

AAGGAATAAG ATCTTCTGGA ACTTGATAGA GCAAGGAATT CCAATAAATT TAAAGGAACA     660

TGAAGAAGTC CTCATATCGC GCACTCCGTC CTGTGAATCA TTTTGTCTTT ATGTT         715
```

(2) INFORMATION FOR SEQ ID NO:789:

```
    (i) SEQUENCE CHARACTERISTICS:
        (A) LENGTH: 720 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1506RP (xi) SEQUENCE DESCRIPTION: SEQ ID NO:789:

GATCTACCGG TTCGGTATCC CCCTTTGAAA ATAAATTCTT TGTCTTTTGC ATGCAACTAA      60

AATGGGATGA AGATGCAAGG GATGTTATTT TTAAGTATCT CCATCTTTTG GAGCTTTCTT    120

CACAGGCTGT AACATTAACA AGGTCAAAAA CTCTACAGGT TATAGAAAGG CTTTGTCACA    180

GAAAATTAGC GTATACGAAG TCGGATGAGT CTATTTTCAG CAGCATTAGT GATATTCCGA    240

TTGATGGACA TGACTTGTCA ACCGCTGAAA CATCTTCCGA AGAGCAGCCG AAATCTCAAT    300

CTTTGTTCGA GCTATTTGAG GAGAAAATAT ACAGCCTAAA CACCGACGCT CCTTATATGA    360

CTCACGATGA CCACTTCATC CAATTTGTGG CTCCTCAAAT TCAATTGAGC ACTAAGGAAT    420

CGCCCGGAAC GTGTGTGCTT GTTACTGCCC CTTCGATGAA ACTGAAAATT ATAGACTTCG    480

ATTCAAATAC TTCGGACAAT GAGTATWATG AAAATGTCTT TATGACGAGG TACACTGCAG    540

CATTGATTCA AGCAAATGTA TTTATCTTCC AAGAAAGTGA CTATAAAGTC TTTGAGAACT    600

CATTGTTTAA TCCCAAAGGC TACGGTGCTA AAAGTACAGA AAATTGGCAA CCTTGGCTAG    660

GACTGGAACT ATGTTTTGAA CCGGAGCCCT TGCAAACTAA TACGGTTATT AAAGAATTTC    720

(2) INFORMATION FOR SEQ ID NO:790:

(i) SEQUENCE CHARACTERISTICS:
        (A) LENGTH: 713 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1506UP (xi) SEQUENCE DESCRIPTION: SEQ ID NO:790:

GATCTCCCCA TAAGCTCAAC ATTTTCGATA TAAGATATTT GCGTCCCCGC CCAAAACACG      60

ACGGTCGGTC CCAAACTCAA TGCCCCATTT GCAACAAACG GCAAATCATG ATTCCATCTG    120

TCCCTCTCGT CAATCACCGA ACTTAACAGT AGTTGACGCT TTGTCACTTG GACTAGATAG    180

TTGTTGGTAA CGAAGTAGTA TATCGTGGCG CCAGCCAAGT CGCTAAGGAT GCCATCAACT    240

TCGTCGCATT CCATGTCTTC TTCGGAAGAA AAATAAAGTA CAAACGCCCT GGTTATGGTC    300

GCCCCATCAG AACCAATAAC CAAATAACCT TTATAGCGTC TATCATCGCC ACAAAGTCTT    360

GTATACACTT CTTCGGCAAC GGCATCCAGT CCTATGGTCC ATATGCTGTT AAAACGCAGG    420

AATTCTCGCA GGTACAATAT GTTTTTAAAA TGGGCTACAT GACCATTAGT TGATATGTTA    480

GACAGCACGG ATGATGAGCA AGAACATAAC TCTTCCTGTA TTGTACCTGA AATGGCAGGA    540

GTTTATCGC GGAAAGAGAT CAGCTCTTCC GCGTATGCAA AGCTGGTATC CTTGGTGTGT    600

CTTCTAAGAA TATTTGACAT AGACTCCACA TAGGCTCTGT CATCGAGGAT TGCAATGCCA    660

AGAGAGATCT AGCGTTATCT CAAATACCTT CCAAAACTTA TAATCTGTAA TTT          713

(2) INFORMATION FOR SEQ ID NO:791:
```

(i) SEQUENCE CHARACTERISTICS:
    (A) LENGTH: 707 base pairs
    (B) TYPE: nucleic acid
    (C) STRANDEDNESS: single
    (D) TOPOLOGY: linear (ii) MOLECULE TYPE: DNA (genomic)

(vi) ORIGINAL SOURCE:
    (A) ORGANISM: PAG1507RP (xi) SEQUENCE DESCRIPTION: SEQ ID NO:791:

```
GATCGGCTGC GCTCCAACGA TGGCAGCATT GCTCCTAACG GGGCTGAAAT ATATGTCGGA        60

CTCATGGCTG ACTTTAGCGT CGGCGGGCCA GACACGTCCA ATGCGCCCGA GGGCTGTGTG       120

CTGCGGATCC ACCTCGAAGG ATGGCGGTGC CAGATGGTTC TAGACGGGAT CCATATCCCG       180

AACGCTATCA ATTGGAGTGC AGATGGCTCG CAATTCTATC TGACTGACTC GCTAGCATTT       240

ACCATATGGG CGTGCCCGGT AGTGGACGGT AGCCCACAAC TCCTCAAGAG AACCCCATTC       300

TACTGTACCA AAATACTGG CAATGACTCA CACACTTCGC CGGAACCGGA TGGTGGATTT        360

GTGGACTGCT TTACTGGGCA CACTTTCGTG GCCGTGTGGT CCACTGGCAA AGTCCGAGAA       420

CTCGACAACG CAGGCAGACT ATTCGCTGCA TATACACTAC CGACGCCACG AGTCAGCAGC       480

TGTTGTGCGG GCCCCGCAGG CGAACTGCTC CTGTCCACGG CGCACGCAGG CGATTTCAAG       540

ACTGGCGCAC ACTCTGACGG CGTCGGAGGC AGCATTTTCA GAGTGGTAAT CCCGGGCCGC       600

CGCGTTATCC CAAGCCGCAT CCCCGCGTCT TGCGGAAGCA TCCTTTAAAT AATATTTACT       660

TCTACACCCT CTCGTCCCCT CTACCGCCCA GCTCATTGAT GGGCCGT                    707
```

(2) INFORMATION FOR SEQ ID NO:792:

(i) SEQUENCE CHARACTERISTICS:
        (A) LENGTH: 570 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1507UP (xi) SEQUENCE DESCRIPTION: SEQ ID NO:792:

```
GATCGTACCA GTATAATACT GGGAATTGAC GCGCGCAGCC AAGGCGTCGT AATCATCGTG        60

CTGATAATTA TGTCCATAGC CATCCATWAT GGAATTAGCA TCAGCTATTT GCTTACGGTG       120

TTGACGAGCG ACTGTTAATC TCCATAGAGA ATTCTCCTCA ATAATTTCTG AGACWGTCCT       180

CTTTTTTAAA ATCGGCTTTG GCCCCGGACG TTGAGGGGGG CCAGTGCTAC CACCAGACTT       240

CTTCTTCGAA ACCCGCTTGG AATTTTCGTC ATCGGAACCA TAGACAAGCT CTTCCATATC       300

CGCTACGGCA TTGCGTGTCA ATGTCTGAGC GTGACCGCTA TCACGTAATA TAGGCCCATA       360

CAGCCATGTG ACGTCCGAGT CCTTGGACCA GTTGACAACC TCTGGGCTCA CGGTGCGTAG       420

ATTATTCCGG GCTTTGGCCC ACCTCCTCCA GGATGCGTTC TCGAGCCGCG CCGCGTTCAC       480

GAGGTCCTGC TCTCCCTTCT GTCTCTTCTT CAGGATGATG TACTTCCAGG ACTGAGAGAT       540

GTCTCACTCA GCCCAGTCGT GCGAAAGGTA                                       570
```

(2) INFORMATION FOR SEQ ID NO:793:

(i) SEQUENCE CHARACTERISTICS:
        (A) LENGTH: 692 base pairs

```
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1508RP (xi) SEQUENCE DESCRIPTION: SEQ ID NO:793:

GATCCACAGG CAAAATTTAT GCATATAGCT TGCTTATATT TATGCGGTGG ATTCTATATG      60

TCGCACGCTA AATACTAATA GCCGCCGGTA AAAAGTAGTC CTCGGCAAAC TCGGTAACGG     120

CAAGGTCGGA ATTATAGAAA CGGGACTCAG AAAAACTAAT CCAGAGTAAT TAAGGGACTC     180

GGAAAGCGGA GCCGGTTCTT ACCGAAAACC TCAACGGAAG TATATGAAAA AATTTATCCT     240

GCAGATTATA CCCATGCCTG TTTTATCCAA GGTAGCCCAA ATATATACTA CAGGAAATGA     300

GTGACTTTTC ACTTCGAGAG CCCAAATAAC AATAATTTTA GTAAAATTTT AGCATTGCTG     360

CTACTCCAAC TTTCCAATGA ACACTTCTGA AAGCGTAAAT ATATAGCTAT GCGGTTTGCC     420

TCCCAGGCTC TAACTACAAA TTCCACCTTA TGTGTGTTAT TCAGGAAATG CAGGGGAATA     480

GTTGAATCAA CGAAATAGCG TTAATTTGCA ACCGCCTTGT ACGTGTATAA AACCCACCCC     540

CCTCCGAAAA AGATGACTAT CGTTATAAAC TAAAAAACAT CATCAAAAAA GAACTAAGTT     600

ACTGAAAAGA AAATGGTTTA CCGTCTAGCA GTGAATTTCA GCAACCAGCC CACATGGGTA     660

ACCAATTTCC GAATCTATCG TTGCAGAATA CT                                  692

(2) INFORMATION FOR SEQ ID NO:794:

(i) SEQUENCE CHARACTERISTICS:
        (A) LENGTH: 716 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1508UP (xi) SEQUENCE DESCRIPTION: SEQ ID NO:794:

GATCTGGTAA CGACTAAATA AGAATCCTTA CGCAGCAACG CCGGCCGCGT CTCGGCAGTG      60

TAGTGTCTCT CAAGTGCGCG TCTGGCACTA GTTAGGTCTT GCAGGTTGCC TTTGAACCAG     120

TGCGGCTCGG TAAGCACCGA GATGGCGGAA ACTCCCGCCT CCGCATATGC AAGCGCCTGT     180

TCTGCTGCAA GCGCCTCGCT AATATTGCCA CGCGACGGAG ACGCACGTTT TATCTCGGCT     240

ACCACAGCCA GCCGCGGGGC GTCCCGCGCC AGCCGCTCAT GGAAGTCCAC CACGCCCGGC     300

AGAACCCCCA ATCGAAAGCT CGCCTCCAGG TCCGCCATAC CAGTTCCCGG CATAGCCATC     360

TGCGCTGCCA CGTCCTCCTG TCGTTGAGCG TATATCTCGC TCAGCACAGA GCCCGCGCCT     420

GCCCGCAGCT GGAGCTTGTC GTTCTCAGCC CACGTACCGC CTTCCAGCGC TAGCATGTTG     480

CGCACCATTA GCTGCCCGTG GTCCGTCAGA ATCGACTCCG GGTGGAACTG CACACCCTCC     540

ACGGTGTACT TGCGGTGCCG CACGCCCATA ACCACGCCTG TCTCCGTGCG CGCCGTCACC     600

TCCAGCTCCG CCGGGAACGT TGACGCCAGT CCAGCCAGCG AGTGGTACCG TGTCACTGCC     660

ACGGCTGGGG TACCCCTGGA AGAACCGCGC CCGTCGTGAC GCAGCTCCGA CGTTCT         716

(2) INFORMATION FOR SEQ ID NO:795:

(i) SEQUENCE CHARACTERISTICS:
```

(A) LENGTH: 716 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1509RP (xi) SEQUENCE DESCRIPTION: SEQ ID NO:795:

GATCCAGTTT CTCTCGCATT TTCTGAACGA TGAGATATGA GTCTAAGTTG GCTAGATTAC      60

TATATAGCCA GTTGTTCGCT CGACGGGCCA AAACCGAGAC CGGTTCCTTC CTTTGACAAG     120

AAGAATAATC GCCATCTACT TTGTTTGAAT TCTTTAAACC GTCTAACTCT TGCAGTACCG     180

TTTTTGGTAC TACTATGCGA TAGCTGTATT TTGGGGCAAG CACTCGTAGT TCTTCAAGGA     240

TATCCAGATG TGATAACACA TAATTAGTAT CAACGACCAG TGCAATATTA TGCAAGTCTT     300

GCCGCACTTC AACCTGCGGC TGAATTACTT TTGCGAAAGT CTCTTCGCCC GGAATATCGA     360

CTCTCTTGTC AGGAATAGTC TTAATGTTGT TAATTTCATG GCTGTGATAT TCGTCTATAT     420

CCATCATCGC TTCAGCTTCG TGTTCCCTTA TAATTTCTGC TTCAACCAAT GCATCCAATT     480

CTGCAATGCT ATATTTCTTA TTAGAGTGCT TAGGGTTCCA AGTATGCGGC GAGCTTATGG     540

TATGCGTCTT ATTCTGATGC CTACGCTTGC TCTTCCTCCC ATGGTCCCTA GACATCTCCT     600

GTGTAGCTTG GTGCATAGAC TGTATATGAT TGGACTCCAT CGGAACTAGT GGCACGTTTA     660

AAAGACATTA ATTAGGTATC ACCTCCATTA ACGTACCTTT GATATTTATT ATATGA        716

(2) INFORMATION FOR SEQ ID NO:796:

(i) SEQUENCE CHARACTERISTICS:
        (A) LENGTH: 590 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1509UP (xi) SEQUENCE DESCRIPTION: SEQ ID NO:796:

GATCTCGAGT TTCATGACGA GTGCATGGAA GATGTGTTTC TAAATGCAAC TAAGGTCCGT      60

AAGGTCAGTG AGGTGCAGTC CTTTATCACT CTAAAATTCC CCTCTTCCTT TGATGATGAG     120

ATACTCGAGT CATCGATGCC AACTACAAGT CACCATCAAG ACTTAACAAC TCAAGACGTA     180

CTTGGTGGAT TGGTCGATGC TATGGATGAT AGGCGCGACC AAGAAGACGA TATCGATTCG     240

CAACAACCCC TGGATGTACT TCCTTTGATC GGCTGCGACA GTCCAGTTTC CAACTTGCCG     300

CGGATTACGG GGGTTGCTCG TTCGGAGGAT GCAGACGAAT GGGATCTTGG ACAGAGCAGT     360

ATTACTCCTA ACAAACTAGA AATCCATTCG GTCCAGACGC CTACCACACA CCGTGTGCGT     420

GTGCTAGAAG AAGAACAATC GCCTTTGATC ATGCTGCAGA AGCGCAGACT AGCCAGGAAT     480

GGGTCAAGAA CATTAGCCAC AGCTACAATC AACCATGACC AGGAACTGCA ACTAGAAGTG     540

CCAGATAGAG AAGCCGCTTC GCCTGCCATT GAACACGAGC AAGCCACCTC                590

(2) INFORMATION FOR SEQ ID NO:797:

(i) SEQUENCE CHARACTERISTICS:
        (A) LENGTH: 723 base pairs
        (B) TYPE: nucleic acid
        (C) STRANDEDNESS: single (D) TOPOLOGY: linear (ii) MOLECULE TYPE: DNA (genomic)

(vi) ORIGINAL SOURCE:
        (A) ORGANISM: PAG1510UP (xi) SEQUENCE DESCRIPTION: SEQ ID NO:797:

```
GATCAGAATT GGAAGGGATG TTTGCCGGAA GAAGTTCGTG ATATCGAGGA GCCCACTATA      60

CCCGTCATTG GCCGGAAGTT TTTCAAGTAC GAATCTCCTA TAAAGCACTT GCTACCCCCC     120

AACGCCACTA TAAACGACCC CATTCCTCAG CCAACTGAGG GAGCGGTCAA TGCTCCACCA     180

TTGGTTGGCG CCGTTTATCT ACGCCCAAAA ATTAAAAAGG ACGACTTAGG TGAATATTCC     240

ACCTCCGATG ATTGTCCCAG GTACATTATC AGGCCTGGTG ACCCGCCTGA GGTTGGTAGA     300

ATCGACCCAG AAACGGGAAC CATCATTACC AATTCCCAGA CCGCCAGTGT ACTACCGAAA     360

ATGAATATGT CTACACCACG TCTGTCGTCT TTGAACCGCA ACGGTAGCTA CTCGAATTTG     420

ATAGGCCGTT CCGGTAGCCC AATTAACATG ACCAGGTCCA CCCAATACTT CGCACCAGTT     480

CCTAACGGCG ATCTGAGAAA TCTGCCAATC GTGCAACAAA TACCGAATAG CACTATCCCA     540

TCTGCGCAGT CGTCTGCAAA AGGCGGCATA CAGGGGGACC ATGGGCGGTT CAATTAACGG     600

TACTACCCCT GCATACCAAC CCCCTTCCAT TATTAATAAC CTAGCCGCCC AGGCTAAGAC     660

AAACAATACC GTTCTTGGAA ATATCTTGGT CGATACGCCC GGTGCCTACG TTCTCCTATA     720

TCT                                                                   723
```

(2) INFORMATION FOR SEQ ID NO:798:

(i) SEQUENCE CHARACTERISTICS:
        (A) LENGTH: 693 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1510UP (xi) SEQUENCE DESCRIPTION: SEQ ID NO:798:

```
GATCGCCGCT ACTGTTCTAC GACCACGCGC GGGGGCTGAA CCTGGCGATG GGGTTCAAGC      60

TGGAGGACCC GCACGCGCGG GGGAACGAGC GGCGCTACTG CCTGGTGCTT ACGGTGGACC     120

TGCGAGAACG GGCGCCGGCA ATGGAGATCG TGTCGCAGCA CTGGAAGTTC ATCTCGGGCG     180

CGTTCGAAAA CATGATCGAG TACATCAAGC AGCAGCGGCG CGCGGAGCTG CTGCGGGTGA     240

TGCAGCAGGG GCAGGTGCAG GGCACATCGA ACTTTTCGTC CATGGTCAGC GGCACCTATC     300

TGCGCGGGAA CAACCTGAAG ATACCGAAGA ACATCACGGA GCTGACCAAC GATAGACTGC     360

TGTTCGTCAG GATACACAAG TGGAATGCAT TTATACTGGA TAGACTGGGA GGGCAGCTGG     420

ACTGAACCCT TGGGGCGGTG GCTGCGCGGC AACAGTTGGA AGATAGAAGA CAGAAACGCC     480

CGGGAAGCCG AGGCCGGAGG TCGGAGGCGT TACATAACTT ACATTCTTAA CTAGATAGTG     540

TTCGCCTGTA CATCAAGTTC AGACGTTAAG GTTGAACGCG GCATCGGTGA TGTGTTCGCT     600

GAAGGGGGCC AATGCAGATT TGACGTCCTT GTTGATGAAC TTCTCCACCT GCTGTGGGGC     660

CCTGCCCACA AACGTGGAGG GGTCCAGCAG GGA                                  693
```

(2) INFORMATION FOR SEQ ID NO:799:

(i) SEQUENCE CHARACTERISTICS:

(A) LENGTH: 676 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1511RP (xi) SEQUENCE DESCRIPTION: SEQ ID NO:799:

```
GATCGACCAG CTGGTGATGG ATAGGCGGCT GGTGCCGCTG GGGCGCTTCG TGCGGGGCC       60

CGATTTTGGG CTGTTGTCGT GGGTGAGGTG GACGCTGCAC AAGGTGGTGG ACCTGTCGTG     120

GAGGAGCCGG GTGCGGGAGA ACGGACGGTA CCTGCGGAAC TGCGCATACG TGAACATGGA     180

CGTGCTGGCG GCGCGGCACG GCGCGGTGGA GGGGGCGCTG GAAGAAAAGG TGGTGGCGCG     240

GGCGACGCGA TATACGGACC TTGTGTTCTC GCGGGAGGAG TTCTACGGCG TGGTGCGGGA     300

GAGCCTACGG GGACGCGGGG AGTACGATGT GGTGCTGGCG GACCTGGACA AGCACCGCAA     360

GGCGATTCTA GTGGACGGAG ACGTTGTGAA GGTGGTGATG CCGGCGGTGC GCGCGCTGGT     420

GCAGCCGTTC GGGCCTGACC GCGTGACCGC AAACGACCGC CACATCGCAG AGTTCAAGGG     480

CTCGCTGCGA TTGGTGGAGC GGCAGGTCCA AGCGATCCAC GGGCACGTCG AAGAGACAAC     540

CCGGGCGCTG CGTTGGCGCC GTCCCGGCGG GCGCCGCACC CGATGTGCAG CGGCGGTACC     600

TGCGGATGAA CAACTCGCGC AGGCCAGCCT GTCTCGCGCG CTCAACCAGT TTACGAACCT     660

AATGGAGATC AAGGAC                                                     676
```

(2) INFORMATION FOR SEQ ID NO:800:

(i) SEQUENCE CHARACTERISTICS:
        (A) LENGTH: 722 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1511UP (xi) SEQUENCE DESCRIPTION: SEQ ID NO:800:

```
GATCTTGCCC CACGGCCCGT CGCTCAAGTT CCCCCCGTCC GCCACAAACG CCCGGAACAT      60

GCCGTCATCC ACGCTGGGCT CGCTCCACGG CGTCTCCCCA GTCAGCAGCA CAAACACAAG     120

CACTCCCGCA GACCAGATGT CCGCCGTGTC CGCGTGGTAC GCCCGCTCGC CCACCACCTC     180

CGGCGCCAGG TACGGCAGCG TCCCCCGCCG GTCGCGCGCC AGCCGCCGCG TCCCGTCGCG     240

CCGCCGGAAC CGCGTCGCCA GCCCGAAGTC CGCCACCTTC AGGTTCCCCG CCCGGTCCAG     300

CAGCATGTTT TCCGGCTTGA TGTCCCGGTG CGCCACGCCG CACGCCTCGT GCAGGTGTGT     360

CAGCGCCCGC ACCAGCTGCT GGTAGTAGAA CGCGCCACCT CCGAGTCCAC CCCCACGTCC     420

GGCTCGATCT TGTCGAAGAG GTCGCCCCCG TCCGCCAGCT CCATCGCGAT CCATAGGTAC     480

TCACGTGACA CATTGCAGTC CAGCACCCTC ACCACATGTC GGTGCCCGCG CACCGCGTCT     540

GCAGCACACC TCGCGCGTCA GATCCTCGTC CGTCATCCCT CGCGCTTTGC AGCGCTCGAA     600

GTGCACGAAC TTCACAGCCA CTATCGTCTG CGGGTCTGCG CGCAACGAAG CGGTTTTGAA     660

GAACGCAACG TGCCCTGCCC AATCGTCTCC CGAAGCTCTA ATTCCTTAAT CTCCGGGAAG     720

CA                                                                    722
```

(2) INFORMATION FOR SEQ ID NO:801:

(i) SEQUENCE CHARACTERISTICS:
  (A) LENGTH: 722 base pairs
  (B) TYPE: nucleic acid
  (C) STRANDEDNESS: single
  (D) TOPOLOGY: linear (ii) MOLECULE TYPE: DNA (genomic)

(vi) ORIGINAL SOURCE:
  (A) ORGANISM: PAG1512RP (xi) SEQUENCE DESCRIPTION: SEQ ID NO:801:

```
GATCTTGACT GGAAGGATGA GGAGCAAACC CCCGACAGCG GAGAAACTGC TATTTGCGTG      60
TCTACACGCG GCTCTACTCG CATCCAAGTT TAGCTATACC TGCACTATTA CTAGATATCT     120
AATGCCTACC ATATGTTGTG ATGACACTGA CATTCAGCCT TTAACCACTT CAGCTTATTA     180
AAAGATTCCA GACATACAGA AAAAATCCGG TGTTAAAAGT TATACATATA CACCATTTTA     240
CCTATATACG TGTAGACGAG TAGAGCTACT AAGCAGCCCA AGAAACACTA CCATATTCAT     300
AATGGCGAGC CTAAGGACTT TCGATGCGTT CCGTATGTGC CGAGGGTTAT AGTGCACACA     360
CGATGCAGTA CTAACAGTCG TAGCAAAAAC CGACCAGCAG CACGTCCGTC GGTCATCTCG     420
CGGGGGCATT ATGTCCATAA TGATGTACCT GTTCCTGCTG TTTATCGCGT GGGGGGAATT     480
TGGCAGCTAC TTTGGGGGCT ATTTGGACGA ACAGTACATC ATCGACCCCG AACTGCGGCA     540
GACAACGCAG ATTAACATGG ACGTGATGGT GCAAATGCCG TGCAAATACC TCGACGTCAA     600
GGCAACTGAT ATTACCAGGG ACATTAACGA CGTGTCGAAA AGACTGGTGT TCAAGAATAT     660
CCCTTTCTTC GTACCGTACG GCACCACATT TGACTCTGTT AATGAGGGTC CGCACCCCGG     720
AC                                                                   722
```

(2) INFORMATION FOR SEQ ID NO:802:

(i) SEQUENCE CHARACTERISTICS:
  (A) LENGTH: 679 base pairs
  (B) TYPE: nucleic acid
  (C) STRANDEDNESS: single
  (D) TOPOLOGY: linear (ii) MOLECULE TYPE: DNA (genomic)

(vi) ORIGINAL SOURCE:
  (A) ORGANISM: PAG1512UP (xi) SEQUENCE DESCRIPTION: SEQ ID NO:802:

```
GATCGAATGG CATCCCATTC ATCCGATGAG GACGCTATGT TAAATAAATA TTATCTATAT      60
ACTCTAAATA CTATATGGTT TCATCCGTGT TACCCGGATT TAGAGATGCG CGTTCTCGTC     120
TCCAAGCTTT AACTCGTGTG GCTGACGATT CTACATAACG TGTATTGACC AGGCTGAGCA     180
GTAACGTTAG CAACTTGGAC ACCAGTTATG AGTACCGATT TCGACAGAAT TTATTATAAC     240
CAGTCAAAGG TGAGCGGTCG CTTCCGTTTG GGCGAAGGTG GCCTGGGATG GAAGGCTTCC     300
GCCACTGGCG GGTCGGCTGC CATGCAAAAC AACGAACCAA TTCTCTTGAC TGCGGACGAA     360
CTGGCTTCCG TGCAATGGAG TAGAGGGTGC CGTGGCTACG AACTAAAGAT TAACACGAAG     420
AACAAGGGCG TGGTGCAGTT GGACGGTTTC TCGCAGGAAG ATTTCACATT GTTAAAGAAC     480
GATCTCCAGC GCAGATTCAA CGTGCAGTTG GAACACAAGG ACCACTCGCT TCGGGGATGG     540
AATTGGGGTA CTACCGATCT GACAAGAAAC GAGCTGATCT TCTCCCTAAA CGGGAAACCA     600
ACTTTCGAAA TACCATATTC GCATATCAGT AACACGAATT TAACATCAAA GAACGAAGTT     660
```

```
GCGCTGGAAT TCGACTTGC                                             679

(2) INFORMATION FOR SEQ ID NO:803:

(i) SEQUENCE CHARACTERISTICS:
        (A) LENGTH: 721 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1513RP (xi) SEQUENCE DESCRIPTION: SEQ ID NO:803:

GATCAACTGT TGCTCCAGTT GCTCCTTGGA CTTGGTTCTC AATTCAAAAG CTTTAACACC    60

GGCCTGAGAT GAGATGTTAG TACTCCGCGC ACCTATCAAG CTTGGAATGA CATTGCTGGC   120

AACCTGCGGG GCCGCATCTA CCCCTCGGCT ACCGCTCGCT GGCTAACCCG GTATGCGCTG   180

CTGTCGCGCA CTTCTGTCCC ACGGATTTAA GCCTCTAACG GTCACCTCGA TACCCAACGA   240

AAAGCTGCAT GCCATCATCC CACGCTATAC ACCGCCTGAC ACATACCATT ATGATTGATT   300

TTGCTGTATT TTGCACTAAG AGCCACTCCA AATGAACTGC CTCTTCTGTT GAAGATGTTG   360

GCCTGCTGTG GAAACCGACT GTGCTCCGCT CGGTGTGCGC GAGCGAGTCT GTCGGACGAC   420

GCAGAATCTT CAGCTATACA ACCCACACAC CTCCGAATGT ACGGATGCAA CAGTCAAACA   480

CAATTCACAA TCACGTGACC TACAGGTGAA ATTAACGATT TCGGCAGATC GCAAAGTGAG   540

CGCCAAAGGC GCGACGGAAC ACCGGAGCGG GTACACGATG GGTGCGACTT CTTACACTAT   600

ATATCGATGG TAACAGTGCA CGCACAAAAA AAGTAGTAT ACTAGGGTCT ACGAGACTTC    660

GCTAGTTCAT TTACAGCCTA ACCTAAAGAT TAATTATGCC AAGACAGTGA TTGGAAGGAG   720

A                                                                 721

(2) INFORMATION FOR SEQ ID NO:804:

(i) SEQUENCE CHARACTERISTICS:
        (A) LENGTH: 726 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1513UP (xi) SEQUENCE DESCRIPTION: SEQ ID NO:804:

GATCTTTAAA ATTTGGCAAG AACAGCCAAC ACTCCCGTCA AAATAAAGAG CAAAGCGCCT    60

CCACACCTCT ACGAATCAGG TCCGAAAGGC GATCTTGCAA TGACGAGCAA GGTTACAAAG   120

AAAGTTAGAG AGTCGCACAG TGCATGTGAC GACCAGCAGC ATAGTTCTCG GGCTCGCGGC   180

ACTGCAGCAG AGGGAGCGCC TAGTAACGTG GTTCAACCGT CCCTCGGTGA TTTGAAGAAA   240

CTCGCAGAAT ACACACTCTC CACCCCTACG TCGAACGAGT GCATTAATAA ACGGCTGCGG   300

TCCACGAACG TGCAGGAGGT GAAGCTGGGG GGACTGCAGT TTCTGTTTTA CAAGACGCTA   360

CTACTGTGTC TTTACATGGC ATATGCGTTC TACCGATACT TCCAATACCA GTACAACAGG   420

CTGCGTATCA AACTACTGAA TCTGGCCTAC TCGCCGTCCA ATACCCCGCA GCTGATCAGA   480

CAGGACGTGC TAAAGTTGCA GAAGGTCCCT AAGCGGCTGG CAGCGATTTT GGCATACAAG   540

TCTGAAGGGG AGGTCGGCGG TGGCGTCCAC GGCTTGATAA ACGACGGAAG CAACGTANTA   600
```

| | |
|---|---|
| TGCTGGACTG TGTCTGCGGG CATCAAGCAC CTGTCGCTTT ATGATCATGA CGGGGTGCTC | 660 |
| AAGGCCAACG TGCACCAGTT CCGCCAGGGC GTGTACGATA CCTGGCGCGC TACTACGGCC | 720 |
| CAACAA | 726 |

(2) INFORMATION FOR SEQ ID NO:805:

(i) SEQUENCE CHARACTERISTICS:
        (A) LENGTH: 736 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1514RP (xi) SEQUENCE DESCRIPTION: SEQ ID NO:805:

| | |
|---|---|
| GATCTGCGTG TATATTTGGA TGTATATGGA CTTCACACTT TCGGAAGCAA TGGAACTCGA | 60 |
| AAGCTGGTTG ACCACTCTGC TGTATTCTCG TAGTCTTTCT GAAACGACGG TAAGAAAATT | 120 |
| AACCTTGAGC GGCGATAGGG AAGATGCAAC TTTAAATTTC TCTACTTGGT TACTCAAATA | 180 |
| CTGATATAAT AATGCAGCCT CAAATATGCT GTGGAAAACA CCACTTTCGC CGTTCGGAAC | 240 |
| ATTGGGTGGG ATTTCGATAA CCTGATTGGA GATCGGGAAC AAACTCGACG TAGTAGCCAG | 300 |
| TAACGTGTAG GAAATATACT TTAAAACGTC GGCCTCGGGC ACCATGTTGC TGTAGTATGG | 360 |
| GTTAGACAGA TATGCCAATG GAGTATCGTG CTGCTGCGGC CGCTTGGGGA CCGGGCCGCC | 420 |
| GTATGCAGAG GTTACCGCCG ACCGGCGCTC TGAAAGCCGC TCCACATTCT CGAACGACTC | 480 |
| TGCATAGACA CTAACCGCCC TCGACGGCGT CATCAGCGAG TTGTGCCGTT GCAGCGTGGC | 540 |
| GTTCGTAAGA TATCCAGACG CGGTGCGCCT GTGTCGGAAG GGCGTGCTCT CCTGCGGCAC | 600 |
| GCTGTTCAGC ACCGTCAGGT ACTTCAGCAC CTGCTCCTTG CTACCGAAAC TCTCCAGCAC | 660 |
| TTTCACGAAC ATCTCGAACT TCCCCCACTG CTGCGTCTGC TCCGGCGTCC GCACCATCTC | 720 |
| CGCCCGGTAC ATGCTC | 736 |

(2) INFORMATION FOR SEQ ID NO:806:

(i) SEQUENCE CHARACTERISTICS:
        (A) LENGTH: 717 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1514UP (xi) SEQUENCE DESCRIPTION: SEQ ID NO:806:

| | |
|---|---|
| GATCTCCACC GCGTCCAGCA CCACGATCCG GTCACCGTCC CACCGCGTCA TCGCCACTGT | 60 |
| CCGCGCGACG CTTTCGAAAA CCGCCCGTCC CTCCGCCGTC GCAGCCCCTC CCCCGCTGTC | 120 |
| GTGCGTCCGG TGCTCGGCCT CCCGCGACCG CAGCGTCGCC ACCACCCGCT CTATATTCAC | 180 |
| GCCCGCGGGC TTCAGCGTGT CGCGCTTGAT GCCAGGGCTG GTGGGTTTCT CTCCCACCAC | 240 |
| CTCCAGGCTC TTGATAAACG TCGTCTTAAT CACCTTAAAG CTCGCAGTAT GGCCCTTGCG | 300 |
| CCCACATAGT AGCGTCAGCG TATGGTTTCC CGAATCGTAC GCGTATATCT TGCCCTGTGT | 360 |
| TACACCGTCG AGGACGTTGG TCACCCGCAC CTTGAATCCA AGGATATGTT CCAAGTTGAT | 420 |

-continued

| | | |
|---|---|---|
| GCTCATTCTG CTCACTTCCA AGCCCACACA GCTATCCTGG CCACCTTAGA ATGCCACGCC | 480 |
| TGCTCCCCGT CCACTGGCTG ACTCCCAATC GTTCAGTTTG CGGTGTGGGT ATTTTTTTGA | 540 |
| AGTGGCGCTC TAGCGATGAA GTAAGATTTT CTATGTATTA CTATGTCGCA CAAAGGTTAG | 600 |
| TTCCAATAGT GCTTGCAACT ATCAGGTGCT GTGGAGTTCC CAAGCAGACG AGTTGCTGAT | 660 |
| AGTGGAGCCG ATAGAGAATC CGATAAAGAT TATTCCCGAA AATCTAAGGA CAGGTGG | 717 |

(2) INFORMATION FOR SEQ ID NO:807:

(i) SEQUENCE CHARACTERISTICS:
        (A) LENGTH: 714 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1515RP (xi) SEQUENCE DESCRIPTION: SEQ ID NO:807:

| | | |
|---|---|---|
| GATCCTTCGC CGCGTGGTCA AAGCCCGGAT AGGATATCAC AGGGCACTGT GCAAAGGTAT | 60 |
| CGCATATTGT TTCCATGAGC GTTTCGCCCT TCGGTCTCTT CGCCGGCTTC CACTTGCACG | 120 |
| TGGCCGCCAG GAGCTTACAG AGCTGCAGAT AGTTATTACT GTCAAACGTC CAGGGTGCCC | 180 |
| CGCGCCGTTT GTGCGCCGCA GCAGCATCCG CGAAGTGGTC CAGGTGCGCC CGCGACAGAT | 240 |
| GGAACCCGTC CATGGGCACC ACCTCAGCTA TATTGACCGA TGACGCTGGA TCCAGGGCTT | 300 |
| CGCTCGCGAT GCGCACCGAA TTGGGGAGCC CGCCGCGCCC GAAGATAACT GCGGTCCCAT | 360 |
| CCCCATCGTA GAACTTGTGT GGCTTGAACC CCGGGTCCTC CACGTGCGCG AAGAACCCCC | 420 |
| GTCGCGCCTC CTCGACCAGG GCGCCTGACG CAACCGGCAC AGTCTCGTCC AGGCTTTCCG | 480 |
| CAGCAATGCC CGCGGAAATC CTCAATCCAC CCCTTCGTGC CTTCAGGTGA CTCTGGAATT | 540 |
| CCTGGTTCAG GTCCCGCTTA AGCCTCTGCG CCATCGTAGA CTTGCCGGAC CCAGGATGCC | 600 |
| CCACCACCAC TACAGCCACC CGATAGTTGC TCTCGATATT CTGAGCAAGG AGATCCCACA | 660 |
| CTCGCTTCTT TAAGTCTTCG TAGTCCATGC CGCTTGCTGT GTATGCCTGC TGGT | 714 |

(2) INFORMATION FOR SEQ ID NO:808:

(i) SEQUENCE CHARACTERISTICS:
        (A) LENGTH: 725 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1515UP (xi) SEQUENCE DESCRIPTION: SEQ ID NO:808:

| | | |
|---|---|---|
| GATCTAACGC CGGCTGTCTC CTCCAAGCGT GTTCCTGCCT CTCTTATATC TGTATCTGGT | 60 |
| AGCTTCAGCA TTAAAAAACC GTCCAGAGAA TTGGCTTTCG GCCATGCTCG AAAGCTCACT | 120 |
| AGTCGGAGCG CAGCATCTAG GACACCAGTA GGATGCAGAC AGTGTTTAGG CCATTGAGAA | 180 |
| GTGTGATTCT GACGCCCGCT CGAGGCCTGG CGCGGTCCAG CAGGCTGCAG TCGGGACACA | 240 |
| ACAAGTGGTC GACGATCAAG CACGATAAAG CGAAGAACGA TGCTGAGCGG AACAGGCTTT | 300 |
| TCACGCGGAT GGCCAACCAG ATATCGGTGG CAGTCAAGCA GGGCGGGTCT GCCGACCCGA | 360 |
| CGCTGAACCT GCGACTGGCG GCGGCGATAG AAGCGGCGTC CAAGGCCAAT GTGACCAAGA | 420 |

```
AAGTGATCGA AAACGCAATC CGCAAGGGCG TCGGCGAGGG TGGGGCGCGC GACAACGCCG      480

AGGCATGCAT GTACGAGGCG ATACGGCCCG GTGGCGTGGC GTTTGTGCTG GAGGCCTCAC      540

CGACAACAAG AATCGGACCG TGACCTGGTA CGCGCCGCGT TCAACAAGCA TGGCGGCAAC      600

ATGTCGCCCG CTCAGTACTT CTTCGAGCGC CGCGGGTACG TGGCAATCCA GCCACCGGCC      660

TCGTGCGAGA GTTACAACGC GGTGTTTGAG GTTGTGTCCG AGGTCGAGGG CGTAGAAGAA      720

CTGGA                                                                 725
```

(2) INFORMATION FOR SEQ ID NO:809:

(i) SEQUENCE CHARACTERISTICS:
        (A) LENGTH: 687 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1516RP (xi) SEQUENCE DESCRIPTION: SEQ ID NO:809:

```
GATCCGACCT TTGGTGGCTT GGCTCGAGTC TTTCTTCAAT TTAAACCCCT GTTCAACAGC       60

AGATGAAATT GTTAGTCTAT CGAGTCCACG TAAAAGACAA TTTTCGACGC TTGAGATGAA      120

GGGTACGGCC TCTCCCGACA AGCGGCATCG CCTGCACCGA AAAGTATCCG GTCACTCCTT      180

CATCATACGG TACCTTCACT ATCTCTTTCC GCCGGAAACT AAATACAGAA ACATACCTTT      240

AACATCCTTA TTCTGTTTAT CCTTTCCTGA TTTCGACTGG AATGTAGCGG CGAAAGGGAT      300

CTGTTTCAAA AATTGGAAAC GCTTACCACC TCACCAACAC ACCAGGACTT TATTTCGTAG      360

AAACAGGCGA TCGGCCTGAA CAACAGTCAC TAGAAACGGT GCACCAAGGC AGCTTGGCAA      420

CGAGGAGGCA CCCTAGGGCT CAATGCGTTG ATAGTAAAGC ATGTACACGA GCTTTGTCTC      480

CGAGAGAAGG AACGACGTCT TGCACTCCGA CACGTACGAA TCTGAGATAC ACCACCACGG      540

GTGCGTAGTG GTGCGACGTA AAGCCTTCAG TTTGCGGGGA CGGCCTGGGG ACGGGGAGT      600

ACTTCGTGGC AGCCGAAGAT ACGCCGATGA GCTCGCAGAG CTGGCTCCGG AGCTGTCCTG      660

CTCGGCTGAC GCGTCCGGCT TGGAGAC                                         687
```

(2) INFORMATION FOR SEQ ID NO:810:

(i) SEQUENCE CHARACTERISTICS:
        (A) LENGTH: 724 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1516UP (xi) SEQUENCE DESCRIPTION: SEQ ID NO:810:

```
GATCATTAAC GAAATTCTTG TGGTTGATTA CGATGTTCGA TGGGAAGATA TAGCTGGTCT       60

TACAATAGCA AAGAAGTGTT TGAAGGAAAC AGTTGTTTAC CCATTTTTGC GGCCAGACCT      120

TTTTCGGGGT CTCCGGGAAC CTATCTCCGG GATGTTGTTA TTTGGACCTC CAGGAACAGG      180

TAAAACGATG ATTGCCAGGG CCGTTGCGAC TGAATCGAAT TCAACTTTCT TTTGCATCAG      240

TGCTTCCTCT TTGTTATCGA AATACTTGGG TGAGTCGGAA AAACTTGTCA AGGCCTTATT      300
```

| | |
|---|---|
| TTACCTAGCC AAACGGCTTT CCCCCTCAAT TATATTCATT GACGAAATCG ACTCTCTACT | 360 |
| AACTAGCCGT TCAGATAATG AGAACGAATC ATCCAGAAGG ATTAAGACGG AGCTCTTGGT | 420 |
| CCAATGGTCC TCCCTAACGA GCGCCACGGC TAAGGAAACA AGAGAAGGCG AAGAGGCCAG | 480 |
| ACGCGTTCTT GTCTTGGCCG CAACCAACTT ACCGTGGGCG ATAGATGATG CTGCTATTAG | 540 |
| ACGTTTTTCA CGGCGTCTAT ACATTCCATT GCCGGAATAC GAAACAAGAC TGTATCATTT | 600 |
| GAAGAAGCTT ATGGCCCTTC AAAAGAATGA ACTTTCTGAA TCTGACTTTC AACTCATTGC | 660 |
| TCGCATGACT GAGGGCTACT CGGGATCTGA CATAACTGCT CTTGCCAAAA GAAGCAGCTA | 720 |
| TGGA | 724 |

(2) INFORMATION FOR SEQ ID NO:811:

(i) SEQUENCE CHARACTERISTICS:
        (A) LENGTH: 710 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1517RP (xi) SEQUENCE DESCRIPTION: SEQ ID NO:811:

| | |
|---|---|
| GATCAATGAA AAACATGCAT ACGATTTCAT GAAGCAAAAT TTGGCTTGGA ATATTGCCAA | 60 |
| CTCTATTCAC AAAACAGAAA TACTAAAGGA AGAGAACTTC ACGTTATTAT CCAAAGCCCA | 120 |
| AAGAGATGAC GTGAAAGGAA GAGAAGCGGA GTTATTACTT CCAAGCGAAT TAAATCAATT | 180 |
| AAAGATGGTC AATGAGCGTG AGCTGAACGG CCATGCAAGA AAAATAAGAC TACTATCCAT | 240 |
| GTGGGAAGTC TTCAAAATGC TTTAGGTTCT GCATTATTAT ATACACATTG TAGATACAAC | 300 |
| TCGAAACTAA TGCATTTCAC GTCAGCAGTC TAAAAGTGGT CATGCAGTAA CTTCACACCT | 360 |
| TCTTTATTCC AAGGACAAAG GTATATTCCC AGCTGTGTCT TAGACAGTGT CCCCAGCTTG | 420 |
| AAACATGTGT TACTCAAATG GTTGGCAGTA ACCTTACATT GCCCAGAATG GGTGATGCGG | 480 |
| TTAGAAGTGG TATAATCCAA CTGCTTCCAA ACATCAGCGT TATTAGGTGT AAAGAAAGCG | 540 |
| GATCTCTGCC ACAGAATTTT AGATGGAGCG CGCAAATTCA GTGCTCTGGA AATCTCATCC | 600 |
| ATGACAAGTG GAACATCTTT GTATTTGTCC GACAGGATGC CTTTTAATGG TAGGTTAGCT | 660 |
| AAATCTTTCA TCAAAATTGA AAGTGGTCCA CCTTGTTCTC CATGAGACAA | 710 |

(2) INFORMATION FOR SEQ ID NO:812:

(i) SEQUENCE CHARACTERISTICS:
        (A) LENGTH: 662 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1517UP (xi) SEQUENCE DESCRIPTION: SEQ ID NO:812:

| | |
|---|---|
| GATCCTCAAA ACTACAGAGC GAAGTTGAAA AAGATCATAT TTTGATAGAG CGTAAGCAGT | 60 |
| GGGATGAAGC ATACGCTCTT CTCAAAGGTG TTGTGGATAG ACATCCACAT CTATATGATG | 120 |
| CACATTCAGC ATTCGGTTGG TGTCAGCTGC AGTTGGGCGA CACTGAAAGC GCTTTAGAAA | 180 |
| CATTCCAGCT TATTATTAAT AATGTGAAGA GCAGCGACGG CACGTCGTCT CAGTTCATTA | 240 |

```
GCTCAGTACA CTGGCGAACC GCACAAGCAC TTATTACTAA GCAGCAGCAT GAAGATCCTT      300

CAGGTAATGA GTTTATAAAG ATTGCTTTCC AGCATCTGGT ACAATCCCTG AAGATAACCG      360

ATCTTTTTGC TCCAGGTTAT TCCCTTCTTG GACACATTTA CGAAGTGTAT TTTCAAGACC      420

TGACTCGCGC ATTTAGGTGT TACGTTAAAG CCTTTGAGCT AGATGCCGGC GACCTCGTCG      480

CTGCTAAATA CATGGTGGAA TACTATAGTG ACCTGTGCAA TTGGCAGGCG GCGGGCAACA      540

TCTGTGACCG TGTAATCAAG AATGATATGC ATCTCAATTC CGTCAACTGG CCGTACAGAG      600

TTCTGGGTGT TTATTATTTG GAGCTTCAAC AGGAGGCTGA ATCGATCGAA TGGTTCCAAT      660

CC                                                                    662

(2) INFORMATION FOR SEQ ID NO:813:

(i) SEQUENCE CHARACTERISTICS:
        (A) LENGTH: 700 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1518RP (xi) SEQUENCE DESCRIPTION: SEQ ID NO:813:

GATCAAATGC CCTTCCCTTT CAACAATTTC ACGTACTTTT TCACTCTCTT TTCAAAGTTC       60

TTTTCATCTT TCCATCACTG TACTTGTTCG CTATCGGTCT CTCGCCAATA TTTAGCTTTA      120

GATGGAATTT ACCACCCACT TAGAGCTGCA TTCCCAAACA ACTCGACTCG TCGAAAGAAC      180

CTTAGATGGC ACTAGCACCC CCGCCAGACG GGATTCTCAC CCTCTATGAC GTCCTGTTCC      240

AAGGAACATA GACAGGGACT AGCAACCAAG GTACTTTCTT CAAATTACAA CTCGGACGCC      300

GAAGGCGCCA GATTTCAAAT TTGAGCTTTT GCCGCTTCAC TCGCCGTTAC TAAGGCAATC      360

CCGGTTGGTT TCTTTTCCTC CGCTTATTGA TATGCTTAAG TTCAGCGGGT AATCCTACCT      420

GATTTGAGGT CAAACTTTGG GAATACTATT CGCCTGGAAG GCCTTGTTTG TCGTACGTTC      480

TTCAAGCGCC AGCTCCACTC CACGATCTGG TCGAAACCTA ATACGCAGTG TAGAAACTAG      540

CTCAGAACGC AGTCCGCGCA AGTTCCGCCC ATGGGCAGCA TTTTCAAGTT AACCTTGTCT      600

TACGACCGAG TATCACTCAT TACCAAACCC GAGGGTTTGA GAAGGAAATG ACGCTCAAAC      660

AGGCATGCCC CTGGAATACC AGAGGACGCA ATGTGCGTTC                           700

(2) INFORMATION FOR SEQ ID NO:814:

(i) SEQUENCE CHARACTERISTICS:
        (A) LENGTH: 706 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1518UP (xi) SEQUENCE DESCRIPTION: SEQ ID NO:814:

GATCGTCAGA TACCTTAGTC TCTATACAGC GCAAGACATG GGTGATGGCG GGTTTGTTCT       60

ATGCAAAGTC ATTGGGTTTC CCTCTGGCGG CGCATACAAC ACCTGCCTAA CCTGAACAGT      120

CTCATCCTGG GCATCTAGCG ATCCCATGGG TGAGCAGCGG AGGATTTGGT GGATTACTAG      180
```

```
CCAATGGCAA TCCAAACCAA AGAAACCGAC TTGGGGGAAT GCCTCATTGA ATAGCCGGTG      240

TTTCGACACT GTGATTCTCT GAGTGTAACC TCCTCTTTGG TTGCCGATAT TAAACCTGTT      300

CTGTGAAACA TCGGAGCGGT GTTTAGTGGA AAGCAACTAG AGGAACTCAA AGAGTGCTAT      360

GGCATGGGGG CAGCTGTTGC GAAGGTGTAA AAACCCGAGC TCCGGTTCGC TTGACACAGA      420

AGTTACTTTC TGTATCTCTA TCAGTCTATC ACCGAAGGAC CCGTGGTGTG CTTTGCGCAT      480

TTTCGGGTTG TTCTTTAAGA TAGTTATCTG GTTGATCCTG CCAGTAGTCA TATGCTTGTC      540

TCAAAGATTA AGCCATGCAT GTCTAAGTAT AAGCAATTTA TACAGTGAAA CTGCGAATGG      600

CTCATTAAAT CAGTTATCGT TTATTTGATA GTTCCTTTAC TACATGGATA TCTGTGGTAA      660

TTCTAGAGCT AATACATGCT TAAAATCTCG ACCTTTTGGA AGAGAT                    706

(2) INFORMATION FOR SEQ ID NO:815:

(i) SEQUENCE CHARACTERISTICS:
        (A) LENGTH: 699 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1519RP (xi) SEQUENCE DESCRIPTION: SEQ ID NO:815:

GATCAGACTG AACCCATATA TCAGCGAGGT ATGGTACGAT TTGGGCACTT TGTATGAGAC       60

ATGCAACAAT CAGCTCAGCG ATGCCCTGGA TGCATATAAA CAAGCTGTTC GCTTAGATCC      120

GAATAACGTC CACATAAGGG AGAGACTAGA GGCTTTGACT GCCCAGCTAG CCAACCCAGG      180

GGCCCAGCAG CCTCAGCAGC AGCCTCAACA GCAACAGATG CAACAGCCTA GAGGGCCAGC      240

ACCCATTATG TTGCAGCCAA CATTGCAGCA GCAAGACCAA ACAAATCCGT TGAATAACAA      300

ACCTGCGTTC TACCGGTCCT CTCCCCACGG AGTTGCGGTT GCCGGAACAG AGTCCGCAGG      360

CCACACACCA ATGTCAGGAC GGCCTCAGCC GTTGCAGCAG TTGAACAATA ACGGAAGTAT      420

CCTGGAACCG TCATTGTTGC CGCAAAAGAG GCCTATGGAG GGTGGAATGG ATACATTGGT      480

AAATGCCATT TCGCAGCAGG AGTTGCAGCA ACATCAGAAG AAACATATGC CTTCTCAGAA      540

CCATCCTAGT TTGGCCCTGG CTACAGGACA GCCGCAGCAG TTACCACCCG ATGCCGCTCC      600

CATAATACCG CCCGAAAAGA AAGGTGCGCC TCTCCCCCAG TTTCAGAAAA CTGAACCAGA      660

GCATGCGGCA AAAAGACTGA AGCCCGAGCA GAATAACGT                            699

(2) INFORMATION FOR SEQ ID NO:816:

(i) SEQUENCE CHARACTERISTICS:
        (A) LENGTH: 696 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1519UP (xi) SEQUENCE DESCRIPTION: SEQ ID NO:816:

GATCAGGTAT CGGCCAACAT ATCGCGTCTG TCGATAGCGT CGAAGATTAT CGTGATAGAT       60

ATAGACTATG AAGTGACGGA CGGCAAGGTG ATCGATGTTA AGCTGGTGCT GGCAAGCAAC      120

TTCGACAAGT TGACTACTT CAATGGCGAG GCCAACATCC TGCACCGGTC ACTTACCACG      180
```

```
TATAGCGACC TGCACGAGTT CCACCACAAC CTGAAGTTCT TAACCCTACT CGACGCGTGC      240

TCAAGCATCG ATATCGAGTC CAATGTGTCG CAATTCGATT TGTTCGAGTA TTACTCGATG      300

CTGCCGCAGT ACATGCAGAG CTACCTGGAC GACAATGGCG CGCAGCTCAC GGTGCAGACG      360

AACCTGAACG ACCGTTTTGG GATCTACTTG CTCGACCATT CCGAAAAGAA GGTCGCCAAG      420

CTGACATTTG CCGCTACGCA GGACCCGAAC CAGCGGTATT ACGAATACAA ATACTCGAGC      480

GAAACGAAGG AGTGGATCAA CCAGTCGGCC GAGTCCTATA CGACCGGCAT CACGCTGGTG      540

TTCGAACTTC TCGGTGACCC TCCGACGTAC CTGCCTAAGG ATAGTTTGCC GCCAGAACAC      600

CCTGATGAGG GCTTCACGAG TGCTTCTGCG TCCGAGCTGC AGCGCCGCTT TGCATTCAAG      660

TGTCAAAATC CACGAGTCAC CCTCGTAAAT GACTTC                                696

(2) INFORMATION FOR SEQ ID NO:817:

(i) SEQUENCE CHARACTERISTICS:
        (A) LENGTH: 710 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1520RP (xi) SEQUENCE DESCRIPTION: SEQ ID NO:817:

GATCTTCTGG ACGCTTTCCT TGAGTTCGTT CATCTTGCCA AGCACGTCGA CGTTGGGGTT       60

GCCCGCAAAA GAGTTGAGCA TCGGCCCAAG GCGGCCTGCA ATGGCGCCAA ACTTGTCTAG      120

CACCTTCGTG AGCGTAGTTG GGAGCTGCAA AAAGCGCAAC GTATGGCCCG TGGGCGCGGT      180

GTCAAAGATC ACCGTGTCGA AGTGCTCGCC GTCGCCCTGC TCCTGCTTCT TGATGTGTTT      240

CATCACCTCC ATGAACGAAA GCGCCTCGTC GATGCCCGGA ATCGACCCCG TGAGATCTGC      300

GAGTGCGCCG CCCTGTAGCA AGCCCGAGAG CCCGTCATCA TCGCCGCCGT TCGCGATCGC      360

CATGTCGTTC ACGTCCTTCA ACGCCGCCGA AGGGTCGATT TCCATACACG ACAAGTTGTC      420

CATGCCCGTG ACCTTGCGCG CGTCCTTCCC AAACTTCTCG TTGAACGCAT CGCTAAGGTT      480

ATGCGCAGGA TCCGTCGAGA TCAAAAGAAA CTGCTTAGTG GGCTGCGCAA GCGCCATCTG      540

GATGGCAATG GAGCACGAAG ACGTGGTCTT GCCCACACCG CCCTTCCCGC CGACGAAAAT      600

CCACTTGTGT GTTGTAGAGT TGATCAACGA GCGCAAAGAG GCCTCTGGTG TAATATCAGT      660

CATGGTTGGT GTACCGCGTG AATCTGAGAG TGCAGGCGAT CTGAGATCTT                  710

(2) INFORMATION FOR SEQ ID NO:818:

(i) SEQUENCE CHARACTERISTICS:
        (A) LENGTH: 685 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1520UP (xi) SEQUENCE DESCRIPTION: SEQ ID NO:818:

GATCAAACAG TAATGACTTT GTTAACGGTT TTGAAGTACT GCACGAGCTG CGACTCCTCA       60

CTGCCCTGTG GCGCCACAAG CGCCGAAATC ACAGCAACTT CGCTTTCAAA CTGAATGGCC      120
```

-continued

```
TCCTGCATGT TCCGTGGGAA CCCAAGTAGC ACGACGCTGT CCCCAGCCTG GCACACCTCC      180

TTCAGATAGC GGCCCATCAA CGCAACCAGC GCACCCTTGG GCAGGTGCGC CGAGTAGTCA      240

TCGCCATGCA CAGCATGCAA CTCCTCTAAT AGCGCGTGGT ATTTGTCGTG CTCGTCGGTG      300

CGGAACCGCT CCAGCGCCTG CTGCACGCGT ACGGCGCGGG CCCCGCTGG CGCCCGGATC       360

TTCTCTACGG GCACATCGGC AAGCACCGCC AGCACCTCCA GCTCATCTGG CTTGAACACC      420

GTCACCCGCC GCCTCAGGCC GGAGCGGACC TTCTCGAACT CCGCTTCGCT GAACTCTGTC      480

TGCGGCTTGC TCCGGTCAAT CGACTTCGCC GCCTGCACGA AGATGAGCGT GCTGACCACC      540

GCAACGCCAA CCATCTTCCA CGCGCTAGGT AGATCTTCCG AACCAGGGGC CTTGCTGGCG      600

TATGGCCGCA AAAGTCCCTG CTGACGCCGC AGAAGGAACA ATCTAGGCTT ACAAGTCTGC      660

GAAACATTTG TCCTGCGAGT TAGCC                                            685
```

(2) INFORMATION FOR SEQ ID NO:819:

(i) SEQUENCE CHARACTERISTICS:
        (A) LENGTH: 722 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1521RP (xi) SEQUENCE DESCRIPTION: SEQ ID NO:819:

```
GATCGAATCT KGTCTGAGGG TCTTCCACGA WTTGCAATGC AATCTCCGGA TATCCGGCCT      60

TCTGTAGATA CGAGATGATG TTCTGGCCCA CAAGGTTGGA CGTACGAATG AGACGCAAGA     120

CTTCAGGGAA GTTCTTGTTC ACCAAAGCTT TCTTAAAGCG GTACTCGGTT GGGTCAATGG     180

TCAATATCTC AATATCGCCG TCTCTGTTCA AAGCATATAT ATGCTTGCCA TGAGCTTTGG     240

TAATGTATAG GGTCTTGCTC AAAGTTTTTA TGATCCCGCT GTCACCATTC AATAGGCAGT     300

ACTWAATATG GTTCAAAGTA GACAAGAGCA GAACACCAGT TTCATCCCAC GCCGCTGACT     360

TGATCCTGAT CGTCTCATGG TTAGACGTAG TAATCTCCAA CTTCCTAGTA GCAATGGTCA     420

GCGTGTGTTT ACTCATTAAA GCAACGTATT GCCCATCTGG GGACCAGACT GCATATTTAA     480

CCATCTTCAG AGCTACCTCC GCCAATTTTT TCCCCTGCTG CACGTCGAAC AAGACTACCG     540

CCTTTGGTTT CAAGATGAGT ACCGCACCAG GGCCTCCATA GACAATGTCT TTAACAGTTC     600

CTTCTATCTT GATCGATTTG GTTACCTTGT TGTCCAACCC ACGTACTTCA AGAGATTCCG     660

ACGCAGAGTT GTAGACAGCG TTACCTATGC CGAGCGACAA AAGTCGCAAA GCTTCCCTTA     720

TC                                                                    722
```

(2) INFORMATION FOR SEQ ID NO:820:

(i) SEQUENCE CHARACTERISTICS:
        (A) LENGTH: 577 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1521UP (xi) SEQUENCE DESCRIPTION: SEQ ID NO:820:

```
GATCCACTTC CCAGATTACA TGATAACATC GAAGCCGAAG GTCGCAAGGG AAATGTTGGA      60
```

```
GCAGTATGAC TTTATWCATA GCGGCTTCAT CAGCGTAGAC GGCAAATCAG AAAGCCTCAT      120

CTTGGGCATG CCGAAGAAGA CCACCGGCAG TTTGATCAGC TCATCGAAAG TTTTCCTATA      180

TGGCAGAGCA GCCGTCACCA TGAAGACAAG CAGAGGCCCA GGCGTCATCA CCGCAATTGT      240

ATTCATGTCA TCTACCCAGG ACGAGATAGA CTACGAGTTC GTGGGGAGCG AGCTCCATAC      300

TGTCCAGACG AACTACTACT ACCAGGGCGA GCTCAACCAC TCGAGAATGC GCCGCCATTC      360

GCTACCCTCC AACAGCCACG AGGAGTACCA CATATACGAG GTTGACTGGG ATGCCGAACG      420

CATCCACTGG ATGGTCGACG GCGAGATAGT GCGCACCTTG TTCAAGCGCG ACACCTGGGA      480

CCCGGTCCAC AAAATATACA AGTATCCACA AACGCCCATG ATGCTCCAGA TTTCCCTCTG      540

GCCCGCGGGC ACCCCCGATG CGCCGCAGGG CACCATC                              577

(2) INFORMATION FOR SEQ ID NO:821:

(i) SEQUENCE CHARACTERISTICS:
        (A) LENGTH: 705 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1522RP (xi) SEQUENCE DESCRIPTION: SEQ ID NO:821:

GATCAAAAGC GAACAGCGCA CTTATGTCCT GCCCAACCGA CGCGTGCTCC TGAATACCCA       60

ACGAGCACTC CCTGGCCTGC TATCTGCGCG TATTCTGTCA GAACGATCGC CGCTAGAAAG      120

TTACCAAGCG CGTCACACCT GTATTCCCTG GCTTCTCTCT CGGCCTTCGA TGTGCTGGCA      180

AGTAGTTCTC CACGTTCTGC AGCTGCCACT GGAAACGTGC AAACCAAAAC AAACCTGACA      240

CCACTTCTGT CTCTCGATCG CGTCCAGCCT CCAGAACTCC CAGCGCACAG ATTTTGACTA      300

TAGCAACCCC CGCGACTAGC ACTCAAGAAC TTTCAATTTT CGCTTGAGCC CGACCTTGTT      360

TTTCGAAGAT TCTGACCTAT CCTCCTATCG ACGTCAGGGA CACAAATCAC ACTATAGTAC      420

CTCGAACAAC AGTACAGAAA AGAAAACCAG CTGCTCCAGC CAAAATTCAC AAGTCCCGTT      480

AGCTGCTAAG GCCAATTGGT GATACTCAGT CTTTAATCTT TACCCAATTG GGAAACTTCA      540

CCAAGGAGAG TCTTGCGTCT TAAGGTTTGG CAGTTTGGTT TAAAAATTTT CTTGCACGAA      600

ATGTCAGAAT GTCTGGGTTC CCCTTGTCGG TCACGTGGGT GTCGGTCACG TGGGTGCTAA      660

TCACGTGACA CGTGGATGAC GACTGAGGCG GAAAATTTGC AGGTT                     705

(2) INFORMATION FOR SEQ ID NO:822:

(i) SEQUENCE CHARACTERISTICS:
        (A) LENGTH: 718 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1522UP (xi) SEQUENCE DESCRIPTION: SEQ ID NO:822:

GATCGACAAT ATTCCCCCAC CAGGCGCAAG AATCGAGTGC ACACAGGCCA CGCGCGCATC       60

CGGGCTCGGA TCGGCGGGCC TGGGCTGCAG TGGGCGGCTG GGGGGCGAAG CACACTACCA      120
```

-continued

| | | |
|---|---|---|
| CAGTGTGCTG TGGTGCGGCG GGGACGCCAC GCCGCGCAGC TGCGGGCTGC ATTCCAGCCA | 180 |
| CGCATGCACG AAGAGCCGGG TGACACTGCC ACCGCTGGCG TCGCTGCTGC AGTCCAGCGG | 240 |
| CTACATGGGG TTCAACAACG AGCCGCGGGC CGTCACGCGC TCGTGTCTAG GGGCGACACA | 300 |
| TCCCGAAGGC CATTACGGCA GGGACATGCT GAGCAGCGCG GTGGGCACG CCGCGTGTTA | 360 |
| CGTGGGGCGC CAGAGCCCGT TGCTACCGCT GGGCGACGCG ATTGCGCCGG CGCTCCCACC | 420 |
| CAAGCCATCG CATCGCTGCG TCGCGGGGAA CGCGCAGCTG CGCCGGCCAG TGCTGCCCAT | 480 |
| CGTGGGGCCC GCGGCGTCCC ACGCTACGAA ACGAACAAGA CATGCCTCGT TTGTGGCAGA | 540 |
| CGATGTACCC GTCCCAGCAC GCTCAAGAAC ACATGCTCAT CCACACGGGC GAACTGCTTT | 600 |
| TCAGTGCAGT TGGCCCGGGT GCTCCAAGCG GTTCAACGTC AGGAGCAATA TGAACCGACA | 660 |
| TGTGAACTCC CACAAGCGCC CGCTGATGAA GGAAAGCAAG AAGAAATCCA GTTCTCCC | 718 |

(2) INFORMATION FOR SEQ ID NO:823:

(i) SEQUENCE CHARACTERISTICS:
        (A) LENGTH: 712 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1523RP (xi) SEQUENCE DESCRIPTION: SEQ ID NO:823:

| | | |
|---|---|---|
| GATCTTATCT AAACCGCTCC GCGATGATGC TTTGGTAGCA ACGGAAGCCC GCATTTCAAA | 60 |
| GTCAACATCA GCGGAAGCTT GGATAGATGA GAAAATCACA GGTGTCACAT GGCGCGAGAG | 120 |
| CTGAATTGGA TTCACCGCTT TGCTATCAGT GGGTWAGAGG CGTTCACTGG GCTGTTCTGA | 180 |
| ATTTGAACTT CTGGAGCTAT WCGAGGGGTT ATGAGCAAGT CCAAGTTCCC GCGTGAAAAG | 240 |
| CTGATCCTGG TAATACTCGG TGTAATCCAC GCTTTTCTGC CAGCAAAAAG CTGGCGAGTT | 300 |
| TGGAATCTTT CCTTTATCGG CGACGTCCGT GCGTACATGG CGTTCAATGG TATTTGCTGA | 360 |
| TGTAACTGTG GGGAGAAGTC GTAGGGAATG TCTAGATAAG GTTGACGCTG AAAAGCTATT | 420 |
| ACGTTGCAAT AGCTGCGGTT GAGAATGGTG TACTGGGCA CAGCAACCTG CTGCGCTGCA | 480 |
| TCTGGGTGAG CTATTAAAAA TCTCGGCCAC CGAATAGAAG AGCATCTTTG GGTGAGCGCG | 540 |
| ATTCAGTTCC ATGAGATCAA CAAAGGATAA AATCCGGAGG TTATCAAGGG AGAATTTGTT | 600 |
| ATCATACAAG AGCCAATCAT CACTGCAGTT GGCTATATTT GGATTATTGT GATATTGCCT | 660 |
| CACAGCAGTG TTTATCCGGT CTTTTTCGCA GTCATATACC ACAATGGATT GT | 712 |

(2) INFORMATION FOR SEQ ID NO:824:

(i) SEQUENCE CHARACTERISTICS:
        (A) LENGTH: 649 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1523UP (xi) SEQUENCE DESCRIPTION: SEQ ID NO:824:

| | | |
|---|---|---|
| GATCGACAGA ATGAGCAGAG CCATTCTGAG AAAGCAAACA CGGCCCATTG CGGTTCTGGG | 60 |
| ATCCCTGCCA CAGAGCGAAA TGGGCCCAGA AGGTTTGTAC TCGCCGATCA AGGATCATCT | 120 |

```
GGCCTTAGCG CCATGCGACG TAGTAAAAGG ATGGCATGGA TGCTGGTCGG AAATGCGGTG        180

CGACTGGCGC AAGACATGGA TTTTATCAAC ACCAGCTCCA AGATATTCGT CGCAACACAC        240

ACTTCGGAGA CGAATTGCGC AATGAACATG GGTCAGAACA GTACATTATC CCATTCTCTG        300

ATGAACGCAA ATATTATAGG CTCAGAGTCA AGCACGGCCA TTAGCAATCC ACCTATGCCA        360

TCTGAAACTG AGGAACGTTA CAAAAGTGTT TTACAGAGAC TCGGTAAGCA TGTCCCTCGG        420

GGTAGAGGCC TATCTCAGCT TTATAATGAG TTTTTGGAGG ACGAGCGCAT CCTCTACGGC        480

TTAGGTGGTG GAAGTGAATA TGTTGAAGCA TACTGCGATA GTTTGGATCA AACAAAAAAC        540

AATGTGAGCA TCGAGACTGC GTATGAATCT TCTTTGCTAG AGCGCGGGGG CCAGCAGGTT        600

TTTCTGTCTT TCGCCCAACG CCCGAAGATA GAGCTACTGA GGATCATGT                    649
```

(2) INFORMATION FOR SEQ ID NO:825:

(i) SEQUENCE CHARACTERISTICS:
        (A) LENGTH: 660 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1524RP (xi) SEQUENCE DESCRIPTION: SEQ ID NO:825:

```
GATCTTTTGA AACAAGTGAA TTTCTGGAAA TCGAAGTGCG GTGACTTGGA CAAAATTAAG         60

CAGGACTTAC TGGCCAACAT GGCGACGAAA GAGACGGACT TCAACAATCG ATGCACCGAC        120

TATGAACGTA ATATAGTTGA ACTTCAGCGT CAACTATCAG AAAAGTGCGA CGCTACAAAC        180

GAACGCTCTG TCACTTCAAC CTCTGCCGAT GTACCTGGAG AAACCAAAGA ATATATTGAG        240

TCTCTCAAGG AAGTCAACCG TAGACTGGAA GAAGATATGT TTGCTGTTTT TGCGGGGAAC        300

ATAGTGTTAC TGGAGAACAT CGGCCTGCTT CTTTCTAGAG GCCCTGACAA CAAGTTACAG        360

ATTATACGCG TTAAAGGTTT AAGGAAAAAC ATAGATGATA GTATAATAAA GGACAGCAGC        420

CCTGTAATAA ATTCACATAT GGTGAAGAGC ACAGTTTTCC AGGATGTGAA GAACTTATTT        480

GACGAGCTTC AACTGAGCCA AGGTGTTAAC GACCAACTCC ATTTTGTTAG TGAGCTGGAA        540

CGCTTTTATG AAGAGGATCT ATTTCCAACT TCCGTGATCA AGAGGTTCAC CGATGTAGAG        600

AACCTGGCTA AGAGCTCAGA AAGGAAAATA AGGCTAAAAA AAGCGTATTG AAAGACACCA        660
```

(2) INFORMATION FOR SEQ ID NO:826:

(i) SEQUENCE CHARACTERISTICS:
        (A) LENGTH: 671 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1524UP (xi) SEQUENCE DESCRIPTION: SEQ ID NO:826:

```
GATCTATCGA AAGTGTGAAG CTCCTAGACA AGTTCGTCCA TCCCAAAACC GGGAGAACCT         60

CTTTGTGCTA CCGTATCAAC TACCAGTCCA TGGACAGGAC TGTTACCAAT GCCGAGGTCA        120

ATGTCTTACA AGAGCAGGTC AGTCGGGAAC TAGTCAGGCT TTACAACGTT CAATTGAGAT        180
```

```
AGCCCAATCA GGCCGAGACT AATAAACTTG TATATACAGC TTTGCGGACA TCGCACCCAT    240

GTAACGTATA GTATGATATC TGCTTACTCA TATCGCACCT GAATGCTAGC AGACTTCGAG    300

AAATGCCTTA ATACGCAGCA TATCCGATAA CTAGTGCCTA AAGCCAAGTT CTTGGATCTT    360

CACAGCTAAC CGTTTTTCTT TGCTCCTGAT GGCAGCTACA AGAATAGCAA TCCTTTATGG    420

ATCTGAAACC GGTACTGCAC AGGATTTCGC TAATATACTG TCCCACCAAC TACGTCGTTT    480

TCATTACAAG CATACGGTGT GCTCTATTGG AGAATATAGT GCCCAGAATA TCCTCGCATG    540

TCAGTACCTA TTTGTCATTT GCTCCACCAC CGGGCAGGGT GCGCTGCCGC AAAATGCGCG    600

GCAGTCTCCG CAGGGCAAAG TGGAAGGTAC ACCATGGAGT GTGCTCAAAA GAAGCTCTCT    660

CCCACCAACT C                                                        671

(2) INFORMATION FOR SEQ ID NO:827:

(i) SEQUENCE CHARACTERISTICS:
        (A) LENGTH: 712 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1525RP (xi) SEQUENCE DESCRIPTION: SEQ ID NO:827:

GATCTTCTCT CGCTGGAACT GGTGATGCGT CCAAAATTTT AACTTAACAA TTTTTCACCT     60

TGACCTCGCC AAGCATCTAT ATCACGTGAT TCCATCTGAC CAACCTCATC CCAAATGCAG    120

GCCATTGGCT GCTGCATTAA CGGTCTCAGT GCCCGGCTAG AGAACTAGCG TTACGCTTTG    180

GGGTTTACTA GCAAGTGGCC GTGCCGTGGG ATTCGCAATG TGGGCGCGCA CCTTATCCAC    240

GCGACACAGA AGTGGGTATT TTCGCTTGTT TACATAGATG TCCAAAAACA GTACGCGCAA    300

AGCACCAAGC AAGCTTCAGC AAGACTCAGG GAGGTGTTAG AGGCGATAAT CCAATCTGTG    360

CTGAATGGAG CAGGCGACGG GACCAAAGTG GATATTTGCA GGCGAAAGTG AGACGATGGC    420

AGCGCAAGAG GGCAATGGAG TAAACGGGGA CCTGGACGGC GGCATGCAGA AGACGTTCAA    480

CCCCGTCAAG CCGCTGGACT TCAACGTGAA TTTGGCGGTT TACCGGGGCA AGGCGGGGCT    540

CGGGGAGACC CTGAACTGGC GCGCGGCGGG GCAAAAGCTC AGGGTCGGAG GAGGAGACAG    600

ATAGCGAAGC GAGCGGGAGC TCCAGCCGGG GGCGGGGGAG TGCAGACACG TCTAGTCTGG    660

AGCCCCCGAA GGTGGACCGG TCGTTGACGC CTTGGCGGCT GAAGTCGTCG CC            712

(2) INFORMATION FOR SEQ ID NO:828:

(i) SEQUENCE CHARACTERISTICS:
        (A) LENGTH: 703 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1525UP (xi) SEQUENCE DESCRIPTION: SEQ ID NO:828:

GATCATCGCG ATTTTCGGTG GCGTTGATGA GAAAGGCCCT CACTTATACA TGCTTGAACC     60

AAGTGGCGCT TACTGGGGTT ATAGAGGAGC CGCTGCCGGA AAGGGCAGAC MAGCCGCTAA    120

AGCGGAGCTG GAGAAACTGA TTGGGAACGA TAAGTCAGAG CTGTCAGCTA GGGATGCAGT    180
```

```
GAAAGAAGCG GCTCGGATCA TCTACGTGGC CCATGAGGAT AATAAGGAGA AAGAATTCGA    240

AATTGAGCTG AGCTGGTGCT CCGCTTCGGA GACGGATGGC TTGCACAAGG AGGTACCAAA    300

AGAGCTATTT GATGCAGCGA TTGAGTTTGC GAAGAAGGAG ACCGGTCAGG AGAGTGATGA    360

TGATTCAAGC GATGACAACG CATCTGGAGG TGAAGAGTCC TCAACAAAGA AGGATGCTGA    420

CGGTGATGTC CAGCTTTCAT GATAACAGCC CGGCATTATG TGGAGGTTCA TTTCATGACA    480

ATTGACGGAT GTTACTAAGT GTATATTAAG TTAATCCACC TATATAAATT AATAACATGC    540

AAAGCAATTT AGAATTTGTC GGAAAGCAGG TTAAAGCATG TCTACTCTCC TTAATCTTTC    600

GCGAAGCTGT ACATTTTCTT CTCAAGTGAA CGAATTCTAT CCACCGGCTG CGTCTGATTC    660

TAATTTCCTA CGTTCGCGTT CTGTGTACCA TTTCCGCGTC AGC                      703

(2) INFORMATION FOR SEQ ID NO:829:

(i) SEQUENCE CHARACTERISTICS:
        (A) LENGTH: 725 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
         (A) ORGANISM: PAG1526RP (xi) SEQUENCE DESCRIPTION: SEQ ID NO:829:

GATCTGGCCG CGACCTTGAG AGGCGTCTGT ACCTTCTTTC AGCACAACTA TTGTGGGAGC     60

TTGGTTTCCA AAGTTCATCC TGAGCTCGGT GGTCGTTCAG ATATGGTGGG TGATGGCCTC    120

GTCACGGTCT GTCAGCTTCC TGTACCGACG ATGACGGCAG TTTTTGCCAC TAGGCCATTT    180

TTTTTTTCAG CTCTAAGATG GCAGACGGCA AGGAGAATGC TCCAGGACAC CGGATAGAGC    240

TCCAATCTCA GCAAAACATC GCCTACTGGC CCATTGCTGC TGCTGCATAA CACTTCTATG    300

GCTTAGTTTG TGCACGTGGT CGGCGCTTCA CATTGTATCT CGTGAATTGC GTACCGGTAC    360

TATATTACGG TTGTGTGGCC GAGCGGTCTA AGGCGCCTGA TTCAAGTGTA TGCTTACAGC    420

TGTTCACAGC TGAACACTCA GGTATCGTAA GATGCAGGAG TTCGAATCTC CTCGCAACCA    480

ATATTTTTGC GGGCGTTTTT GGGGCGCCAG CGAAACTGAA CCGCACACTA TTTCGTGGTA    540

CCGTTGGAGG TAAACTGTTG GAATCCGACA GTGGGGTACC GAAACCATCC CAGCCTCTTA    600

TTACTAAGCT GGATCGTGCA CTGCAAGCGG TGATATTGGA ATCGTCCCCA CGTATTATTA    660

CTAAGCCGCC ATCTTGCCGG CCATGAGGAG GGTACCGAAA ACCAATCCCC AATTTGCATT    720

ACTAA                                                                725

(2) INFORMATION FOR SEQ ID NO:830:

(i) SEQUENCE CHARACTERISTICS:
        (A) LENGTH: 701 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
         (A) ORGANISM: PAG1526UP (xi) SEQUENCE DESCRIPTION: SEQ ID NO:830:

GATCGTCACC AGGTCCCCGG TCTTCGGGAA CGTCTTGCCA TCGCCTGGCG ACAGTCTGTC     60
```

```
GATCTTCACG TTACCTTCGA TTACCTCCGA CATGCTCGTT GCTGCTCCCG TGGCTGCCGG        120

AGAGTGATCA AGTGCGTGTT ATTAAGGCCC CCAACGCCAC CCGCCTGGCC GGGTAACACG        180

TGCCCCGCGG CTCGCCGCGG TGGGGCTGTG CGGCCCGGCC GCCCCATGCA CCGGCACGCG        240

GGCCGGTGCA CCGCGTGCGC GCACTTTGCG CCCGCCGCGG CGCCCACTGC CCGAAGCGGT        300

AAACTTAGTA CGCAACCGCC CAGCGCCCGT CATAGCATAC GGACGCCAGA CGGGGTAAGG        360

CCGTAGCCCA GTCGGGAATG CGGGCACGAT ACCTCTTTAG GCAGGATACT ATTTTAAGGC        420

GTACAGGCGC GCAGCCCATC GTGCAGGCTG CAGTAGCAAG CTGAGACAGG CTGGGCAAGT        480

CTAGACCTGG GACACAGCCC GCAACCTAGA GGCCGCGGTG GCCGCGAGGC GTCAGACATT        540

TTCGGTGCGA GGGCGCGTGG CAGCAGGACA AAGAGCCGCG AGAGAAGCAA ATGCMCAACT        600

AAACGGGGAG GAAGGGCAGC GGATTTCTTT TTGGGCTTCT GTGCGAGGTG GAAATTGTAT        660

AAATAATGGG AGCGGCGGCT GGTCTTGGCG GCTGAGACTG T                            701
```

(2) INFORMATION FOR SEQ ID NO:831:

(i) SEQUENCE CHARACTERISTICS:
        (A) LENGTH: 705 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1527RP (xi) SEQUENCE DESCRIPTION: SEQ ID NO:831:

```
GATCTTGCTG CTATCCAGAA ATGGGAAGTT CTTAGACAAC GGGGAATTAA GCCCCTTTTC         60

CAATATTTTG AGCGTCGTGT CATAGCTCGG AAGACGCAGC AGAAGCCCCC CCAGTAGTGT        120

CTGTTCATGT TCGCTCATGA AAGGTGTCTC TATCAAATCT AGCTCCATCA TCGCAGAGTA        180

GTTATTATCT TTCTTCCAAG ACAGACGCAC ATGCCGCAAC TTCGTCAGGA TTACAGTAAA        240

ATAATGGTAG AACCGCGGAC TCACAGAAGC GACGACCGCT CGAAATGAAG TCGGCCCGTA        300

GAAGATCGTG CGGCCCTGCT TCTCTATCAC AAGATGGAAC TGCGAAAGTC TGTTCACGGG        360

GGACACCGTG CCCATAACGT GCTTCTGCAT GAACAGCTGC GGTACCATCT CGCTCTTCAT        420

CCGCGCGAGC TCAGTCTCAA GCTCGTCGAT CCGTCGCAGC AGCTCCACAT TGGGCGTCGA        480

GCTGAACAGC TCCCGTGAGT TCACGTCGTG CGTAAACTCA GACAGGTACA CACACTCGGG        540

CAGGCCCTTC CCAATACATG TATAGCACTT CGGCCGCGCC TTGTTGCACT TGACGCGCCG        600

CTTGCGGCAG AACACGCACG ACTTGCTGAC CTTCCGCCTG GTTTTCACAA TCTTGCCATC        660

GGACTCTGCC ATCCCGCCAG CTTCAAGCAA AATGATTAGG CTATA                       705
```

(2) INFORMATION FOR SEQ ID NO:832:

(i) SEQUENCE CHARACTERISTICS:
        (A) LENGTH: 718 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1527UP (xi) SEQUENCE DESCRIPTION: SEQ ID NO:832:

```
GATCGCGGAC GTGGAGCACT GGCCGGAGAT GCGCGCGGCC ATCCTGGTGG TTTCTGCGGA         60
```

```
CCGCAAGGAC ACGCCATCGA CGAGCGGTAT GCAGCAGACG GTGCACACGT CGGACCTCTT      120

CAAGGAGCGC GTCGCGACGG TGGTGCCGCG GCGGTACGGA AAGATGGCGG CGGCGATCCG      180

CGCGCGCGAC TTCGCGACGT TTGCGCGCCT GACGATGCAG GACTCGAACT CGTTTCACGC      240

CACCTGCCTG GACTCATTTC CGCCGATCTT CTACATGAAC GACACTTCGC GCCGGATTGT      300

CAAGCTGTGT CATCTGATCA ACGAGTTCTA CAACGAGACC ATCGTGGCGT ACACGTTTGA      360

CGCGGGTCCG AACGCGGTGC TCTATTACTT GGCGGAGAAC GAGGCGCGGC TCTGCGGCTT      420

CCTCTCTGCC GTCTTTGGCG CCAACGACGG CTGGGAGACC ACGTTCTCGA CGGAGCAGCG      480

CGCCACCTTC GCCGCGCAGT TCGACGAGTG CGTGCGCGGC AAGCTTGCGA CGGACCTGGA      540

CGACGAGTTG CACAGAGGAG TTGCCCGCCT CATCTTCACG AAAGGTCGGG CCAAGGGCCC      600

AGGACACTAA ATCCTCGCTC ATCGACCCCG AGACGGGCCT GCCCGCTGAC GCTATTCTCC      660

TGCTATTTTC TGCTCTGTAT ACCCTGCCAG AACGCGCTAT ATATATAGAA TATGCATT       718

(2) INFORMATION FOR SEQ ID NO:833:

(i) SEQUENCE CHARACTERISTICS:
        (A) LENGTH: 701 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1528RP (xi) SEQUENCE DESCRIPTION: SEQ ID NO:833:

GATCACTGTA TCGAATTTGA CACCCAAGGA AGCCAAAACA TCGTGGGCGG ATCCCGACAA       60

TGTGGAACAT ATGATATCGC TTTCTGCAAG GATGCGTGCC TGAGCTTTCC TCTTATTCAA      120

TTCTCTATTT CTATAATTCA CCGCATTCCT TTCCCTCAGC TCATCGCGCT GCTTACCTAG      180

CTCATTAATC TTCTTGCTCA AGTCCCTCAA CTTTAGCTGT ATCTTAGATA TCTCATCAGT      240

TGAGAGTTTA CTAGTCGGCG AACCATCCTC TTTATTCATC ATATCCCTGA GCTTTCTCCT      300

CTCCGCTACG GCGTCATGAA AACTCTGATC TAAGTTCGGA TCGTGATTTA TTTCGTACGA      360

CTGATTCAAA GCTCGCTTGT CAACCAGCTC TTCCAACGTT AGGTCTCTGA TAGCAGCGTT      420

AACTGCATCT GATTTACCAA TCCGCACTAA TTTTGGTTTG AACAACTTGC CGTCAGTATC      480

GACCAAACCT TCTCTCAGAC GCAACACAAG CTCGTCAACG GCTGCATTAC TGGGTGCACA      540

TATCAGAACT TTTTGTTTCT GTAGTAACAT CTCAGTAGAG GTAGCGTTCG ATTCTGTGGG      600

ATTTCTGATA ACATTTGATG GTAGTGCTTT TGCGGTAGTT AGGAAAAAGC CGACGACACC      660

AAGAATAGTC TTAGTCTTAC CAGTACCAGG GGGTCCCTGG A                         701

(2) INFORMATION FOR SEQ ID NO:834:

(i) SEQUENCE CHARACTERISTICS:
        (A) LENGTH: 711 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1528UP (xi) SEQUENCE DESCRIPTION: SEQ ID NO:834:
```

```
GATCCAGCAT TTCGCGGTAA ATCGGCGTAT TCCGCACGCG AAGGTGGGAA GCTTCAACGA    60

GTTGATCTGC ATGTGGCGGG CGCAGATGGT TCTTCCACTG CTGCGAGACT TTGATGCCTG   120

CAAAGTATCA GATGCTGTTA TTCTGGCGAT GTATGAGATA CTGCTGAATC CGCAGATGCT   180

CCGGTGCTCG CCGGAACTCA AGTACTACTA TGATCTAGCA TTCAAGGGCA TGTATGAGAC   240

GGGACATGAG CTTTTAGACC ACACAAAAGA ACAAGGTATC AATCTGCTCG TACCTGGAGT   300

CGTATATTCA CAGATGTACG GCTGCCCTGA ACAGAGTTCT TGGGCAACAC GTCTCTTGCG   360

GCACTTCTTC GAGAACGAAT ACTCAATCAC AAATGAAAAC GTGACAACCG AACTGCTTGA   420

CGAAATCACC TATCATTTTA TTCAGTTACA GTTGAGCAGG AGCAACAGCT CGTATTTGAG   480

CATGATTGGA CTATTCTGGA GCAAGATGTG CCCGTTCTTT GCGCTGATGC ATGTTGATGT   540

CTTAAAGGAG TACTTTATTG AGCTCAAGAA TATTAAGTCA TTGCGGTCCA CGACTAATGT   600

TCATATTGAA TCTGTTTTCA AGGTATTTTA TCACCATCTC ATAATGCAGG TAAGATCAAA   660

ACCGTTGGAT ATTCTGCTCC GTATTTTGAA ATTATCCTGG AAAAACTAGG G            711
```

(2) INFORMATION FOR SEQ ID NO:835:

(i) SEQUENCE CHARACTERISTICS:
        (A) LENGTH: 722 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1529RP (xi) SEQUENCE DESCRIPTION: SEQ ID NO:835:

```
GATCAAAAAG AAGGCGATTG CTATGGCGAC GGTGACTGCT GCTACCGCCG TCTACGCTCT    60

ATATCCTTCC TCTCCGATGT TGGTTGACAG CTCCGCGTTG ATCAAGCTAG AAGGCACCAT   120

TTCTCTCAGT AGCAAAGGTG CTACTAATGA TACTGATGTT TTCATATTAC CAGAAAAACA   180

TTCTGCTGTT CCGGGCTACA ACACAATCAT TCGTTTCCTC GTACCCGCCA TGAATGCCTT   240

CAGGCTTTAT GGCAGGCCGA AAACACTATC GGCGAGCAAG GATGACACAA ACTCACTCCT   300

GTTTAGTCTA CCAGCGCTTC CACATGTGCA CTACTTGCTG GTCTAGGATT TGCTTCCATT   360

AGTGAATTCA GCCTCTGGCT CATGGACGAC GCAGGAGTGG CGGAGACAAA TCAAGGCTCT   420

ATTACAACGG AGGGTAGCGG CTGGCTATCA GGGATGTGGT TCAAGCTCCG GTCTATCCGG   480

CGCTCTGTCC TCCCCTGCTC TGGGTCCATT GAGTCCTACT TCTTTGTCAT CGCCGCATTT   540

TGCTCCGTCA ATTGCGTTTT CGCCTACTGA GTCCAACTAC ACTTTTATGT CAAGTCACTC   600

AAGAATAACT TCACTACATG ATAATATCCA GAGACCATAT TGAATACCGT GGCCAGCACA   660

TCCGATAATA CWCTGCACCC AAACAATATG CTATCTCCCG CAGGTCTTGC CCCTGATGCA   720

TT                                                                 722
```

(2) INFORMATION FOR SEQ ID NO:836:

(i) SEQUENCE CHARACTERISTICS:
        (A) LENGTH: 691 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1529UP (xi) SEQUENCE DESCRIPTION: SEQ ID NO:836:

```
GATCCCGCTC AATGCCAAGT AGAATGTTTC TCGGGGAGC CCATACAGTA CCGCCTCCTC      60
CTCATCCCCG CTCTCCTGCT CCACGTCCTC TCGTGCAACA TCTAGCAGTT TCCCGATAAC    120
ACTGGGGATG GTCATGCTCA CGGCTCCGGA TATCACGATC AGCACCAAGG CGCATACTAG    180
AGACTTGAGC TCAGGCCGCG CCAATTGGAA CAGTCTACGC ACATCCTTGG CACCTGATGC    240
GTTGCCCGTC GCCGTCGACA GCTCGAGTCT TTCTTGGTGG GGTTTCTCTT CCGTACTTGC    300
CCGAGGGTTT GCTGTTGAGT TTAGCCTCGT TTGAATTCTT GTCGATGCGC TGAACGAAAA    360
GCGGGTGCGT TGATGTAGAT GATTGAACGG CGGCCATCGC TGCATCCCAA TAACAGGCCT    420
CGGCACCTGC TTAACAGCTA GCGATAGCCA CATATATGTT CTCCTCGAGG TCATATTCCC    480
AGTTTTCTTC TAACCTCACC AGCCTTGTAG GCCTCTCGAG TTCGCTGTAA GTGGTGAATT    540
TGCGCATCGG ACTCATTTTT CATGGAGAAT AAATAATTGT ATTACAAAAT AGAGATGCAT    600
GCCCAGCTAG TCGAGGCCAG CTACTATACA GCTCCTGGAG CTTTGCAGTT GTAGCGCACC    660
GGTTTTCGGC TCCATGTGAC TACAACATTT T                                    691
```

(2) INFORMATION FOR SEQ ID NO:837:

(i) SEQUENCE CHARACTERISTICS:
        (A) LENGTH: 714 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1530RP (xi) SEQUENCE DESCRIPTION: SEQ ID NO:837:

```
GATCCCTCTG CTACAAACAC ATACCTAGAT TTCTCATATT TTATACTGAA TACATATAAT     60
ATATCATTTA ACTGTCTTCA TTCATGAGAC GTCGTCTAAG TTCTGTGCTG CTCAACTTGT    120
TTTTCCACTT GTCAGCCTCT TCGCCCCCCA GTACGTTCAC CACATGCACG GCTAGCTTCC    180
TCATTCCTTT GCTCTCACGC GTATCGTTGA TTGTCTGGGC ACCGGCCACA GTTTCCTCAC    240
TCACTACCAG GGCTTCGATA CCAGGTTCGC TACCCGTGGG CCCGCACACG TCATGTAACG    300
CAAATATTTT GATTTCCAGC CCCGGTTTCA GCCTGTGAAG GAAGCTGCAC ACGTTATCGC    360
ATCGTTCGTC GAAGGACTGA AGCTGCTCCC TGTATTTCTT GTTCCGCAGC AGTTCTTCAT    420
CTGTAATCCC CACGATCAGC CGGGACGCAG TCACGAGCGC GGCAACACTG AGCAATATTT    480
TATGTCCGTC GTGTAAGTGG TCGAAAGTGC CTCCCAGCGC GCTAACAGCG TACTTGTCTC    540
TACCGCCACT CTCGACCGGG CCCGCAGCCG CCATCGCCGG ACTATCAAAC AGCTCTATCT    600
GCCTGTGCGG GAACGCATCC TGCAGCAGGC GATCGCTCAG GAATACAACG TCCCACTTCA    660
TTCGGCTGTA CGCTTCCATA CTGACGTTGA ACAAAACATT TATCGGGGTC GTGT           714
```

(2) INFORMATION FOR SEQ ID NO:838:

(i) SEQUENCE CHARACTERISTICS:
        (A) LENGTH: 716 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:

(A) ORGANISM: PAG1530UP (xi) SEQUENCE DESCRIPTION: SEQ ID NO:838:

```
GATCCTGGGA CGACATCGAC ACCATTTCTA TCGGTAACGA ACTTGTGAAC AACGGCCAGG      60

CGACCGTGGA CCAGATGGCT GGTTACATGA AAACTGGCCG CAAGTGCCTC GCTGAGGCCG     120

GCTACAAGGG CCCAGTTGTT TCCGTGGACA CTTTCATCGC TGTAATCAAC AACCCTGGTC     180

TATGTGACCT ATCAGACTAC ATGGCTGTCA ACGCCCACCC ATACTTCGAC TTCCACACTT     240

CTGCTGCTAT GGCCGGCCCT TGGGTTTTGC ACCAGATCCA GAGAGTCTGG AGCGCCTGCA     300

ACGGTAACAA GAAAGTTGTC ATCACCGAGA CCGGCTGGCC TACTCAGGGT CAGACTTACG     360

GCAAGGCCAT TCCATCCAAA GCCAACCAGA AGATGGCCTT GGAATCTATC AAGGCCACTT     420

GTGGTGATAG CGCTATCCTA TTTACTGCTT TCGACGACTA CTGGAAGCCA GATGGGCCTT     480

ACGGTGTCGA GAAGTTCTGG GGTATGCTAT AAGTTGCCGT GTGCTTCTTT ATGACCTGTC     540

TCTTTATTTT GCTCGGAACC CTTACATGCA GATGGGGGGT GGCGGTGCAT GGGCCTGCAG     600

CCTCCGGGCC TGCAAGTTTC TACATCGCCC TACTTTAGCT GCCACGGGAC TTTTGAATTT     660

CTTTGGCACG TGGTACTGCT GGCATCCTTC TCATAGAACA CAGTGTGCCC ACAGGG        716
```

(2) INFORMATION FOR SEQ ID NO:839:

(i) SEQUENCE CHARACTERISTICS:
        (A) LENGTH: 723 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1531RP (xi) SEQUENCE DESCRIPTION: SEQ ID NO:839:

```
GATCTGCATC CTCGTGATGG AAAATACGGC CATGCAGCTA ATTTTGGAAT GGTTTCTGCA      60

TACCGTAAGA GAGATGGCTC CAAATCATAC CCAGTTACTA TCCTTGTGAC TAACTTTTCA     120

AAGCCGACAC CTACCAGACC TGCTCTTCTG AAGTTGGGAG AACTCACAAC GTTCTTTCAT     180

GAGTTAGGCC ACGGCATACA CGATTTGGTG GGTTCCAATG ACTTGGAGTC GCTCAACGGG     240

CCTGGGTCTG TCCCATGGGA TTTCGTCGAG GCGCCCTCTC AGATGCTGGA ATACTGGACG     300

GCACGGCGTG ACGTTTTAAC TATGTTATCC AAGCACTACG AGACAGGTGA GAAAATCCCG     360

AAGTCGCTGC TGGATGCCTG GTTTAGTGTT GGCGGCCTCA ATTCAGGATT GGCCAACTTG     420

GGCCAACTGA AACTTGGCTT GTTCGACATG TATGTGCACA CCCGCGATTA CAAAGGAGCG     480

GAGGTACGGA AATTATGGAA TGATCTCACC AGAGAGATCG GGCTCATGAA CTTAAAAAAC     540

TACACTAGCA CCGGCTATGA CTCCTTTGGA CATATTATGG CTGGATATGC TGCTGGCTAC     600

TATGGCTACC TTTGGTCCCA GGTTTTTGCT GCAGATATGT ACGACACAAA GTTCAAGCCC     660

AACCCATTCA ATGCTACGGT GGGTGTGGAA TACAGGGACA CTATTTTAGC TACCGGTGGA     720

CTT                                                                    723
```

(2) INFORMATION FOR SEQ ID NO:840:

(i) SEQUENCE CHARACTERISTICS:
        (A) LENGTH: 692 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
             (A) ORGANISM: PAG1531UP (xi) SEQUENCE DESCRIPTION: SEQ ID NO:840:

GATCCAATCC TGGAGGCGGG TTAAAGTGCT CCTCAATGCA GCGCAGCCGG CACTGGAGTA      60

TGGCACGGAA ATCGCACTCT GGAGGAGGCG CGTGGTTGGG AACTGGATCG TCCACCTCGC     120

GCAGAAAGGC CGTTTCGAAG GCGCAGGCGA GGACCGGAAT GAGCATTAAT AAAGAGGTAA     180

CGTGCATGCT GTGAAGAGTT TCACTTTATG CGTTGCATTC CTCCCCCCCT GAAGACGAAA     240

ACACGGCGCA CATGCGCTAT ATATACCCTT CGTGTCTACT ATTGTGCGCT GCCCGCTCTC     300

ATGTCAGTTT TTACTTTTTG ACGCCGGGAA CGCGACATCT GCCACAACGC ACCAACGCCC     360

AGTGACCAGC TCTATGCCGC TTGCTCTGCC AATAACCAGC CCCTACTAG CCGAGCATTT      420

TGCCTTAGTC CACCAGATAT TCCATTGTTA TCGTTGCTCG CCAGCCTCGG GCTGGGACAT     480

AAAGATCGGA AGCTCCTGTG CAAACCTGCA CAGCGCGCCT TCGAGAATAC TCCGCAGGGA     540

CCCCCCCTCC CATTAGTCCT TGGCAGTTTT TTGCTTTGTC CCGCGATAAT GTATCTAAAT     600

ACAGAATATC GATTACGGCG AATAGGCAAG TTTTGTGGTC TGACATGCCG AGTGTCAGTT     660

CATGATTACA TAATGTGTCG TGCCATATCT GT                                   692

(2) INFORMATION FOR SEQ ID NO:841:

(i) SEQUENCE CHARACTERISTICS:
             (A) LENGTH: 722 base pairs
             (B) TYPE: nucleic acid
             (C) STRANDEDNESS: single
             (D) TOPOLOGY: linear (ii) MOLECULE TYPE: DNA (genomic)

(vi) ORIGINAL SOURCE:
             (A) ORGANISM: PAG1532RP (xi) SEQUENCE DESCRIPTION: SEQ ID NO:841:

GATCTKTTGA AAGAGTAACC AGGATCAAGC CTGCGGTATA GCCAGCGAAA TATGCATATG      60

AAGTCTTTCT GCGTGGGCTG TTTCAATGAC TTCAGTGATA TCGCATGCCC AGTTTCTATG     120

TCAAACTTGC GCGACTGCAG ATAATCAAAT ATCTCCTGCT GCAACACTGC CTGGTAGTTT     180

TTGTCACGGA GAGGTCGCGG GTCGCGGGTA CTCTGCAGCG CACCGTAAGC TGACGGACCC     240

CCGCCGGGAA CAATCGAAGG CCGCTGCGAA GATCGCAGAC TCCGCCGGAG AGACTTTCGC     300

ACCTCGGGCA CAGGTCTTGA AAGAGAGCTC CGGCCGTTCC GTGCCAGACT CTTGTTTATC     360

ATGTCCGTAA GAGCAGCGTT CGTGCCAGGT ACGCCCTTCT TGTTCGTGTT TCCACCAATT     420

GATGGAATTT GAGACGTGAA CCTCTGCGGA TTCAAGCTAT TGAGCACACC ATTGGCACCA     480

CTTGAGCCCC TTCGCTCTGC CATCCCTAAT CGTCCTATCC TACGGGCGGC TAATAAGTTA     540

CTACCAGACT CTGGCCCTCA TCTGGGACTG ATGTTATCGT CTGCAGCCAG ATCCTGTTTG     600

TGACCCGATC GAAATCATCG AGTACGAATA ACCACGTGAC CATTATTCAC GTGATGAATT     660

TGGCGGTCCC TGTTGCCGAC TCTTACTCCA GGTTAACCAT GACTAGATGG GCATACCTCA     720

GA                                                                   722

(2) INFORMATION FOR SEQ ID NO:842:

(i) SEQUENCE CHARACTERISTICS:
             (A) LENGTH: 619 base pairs
             (B) TYPE: nucleic acid (C) STRANDEDNESS: single
          (D) TOPOLOGY: linear (ii) MOLECULE TYPE: DNA (genomic)

(vi) ORIGINAL SOURCE:
          (A) ORGANISM: PAG1532UP (xi) SEQUENCE DESCRIPTION: SEQ ID NO:842:

```
GATCATCTGA ACGCTCATGA ACAGTTCGCG AACATCGTG  TCCACGACTA TGCACTGCTG      60
GATGTCCTTC TGGCCGAAGT ACGCGCGGTC CGGAGCAACA ATGTTGACCA GCTTAGCAAC     120
GACCGTCGCC ACACCGCGGA AGAAGCGTGG ACGGGTGCGA CCCTCCAGCA TCTCGCTGAC     180
GCCAAGCACC GACACAAACG GCCCGCGCTG CGCCTCGACC TCCAGTGGGA TGCCGCGCGG     240
GTACATTTCC GCGGGAGAGG GAGCAAAGAG CACGTCCACA CCGGCCTCTT CCAGCAACGC     300
GCGATCCGCT GCCAACGTCC TGGGATAGCG GTCAAGATCT TCGTTCGGCG CAAACTGCGA     360
AGGGTTTACG AAGACTGAGA CAACAGTAAA GTCGTTTTCC GCGCACGATC TCCGCACGAG     420
CGTCATGTGT CCCTCATGTA GGCAGCCCAT CGTTGGCACA AACCCAATCG TCTGTGTCTT     480
GCAATCTACC GTCTGCTTGC GCCATTGCGA GACTTCCTGG ACCTTATTGA GCACGTGCAT     540
GAGGCGTATC GCTTTGATGG TTCAGCCTTC AAGTTTGTCR GTGTGCATCT CACAGATTAA     600
GGAAGCTTGC GCACACTAT                                                  619
```

(2) INFORMATION FOR SEQ ID NO:843:

(i) SEQUENCE CHARACTERISTICS:
          (A) LENGTH: 564 base pairs
          (B) TYPE: nucleic acid
          (C) STRANDEDNESS: single
          (D) TOPOLOGY: linear (ii) MOLECULE TYPE: DNA (genomic)

(vi) ORIGINAL SOURCE:
          (A) ORGANISM: PAG1533RP (xi) SEQUENCE DESCRIPTION: SEQ ID NO:843:

```
GATCACGAAC TCCATCATTA CAAAGTCCAT CGCGTCGATA CGAAAACAAA ATGCACAGCC      60
GCTACCGACC TTCCGAAACC TCGAGAAGAT CAACCAGCCG CCAAAGAACG CTGACCATGC     120
GTGGGAGTAC ATAAAATCGT GAATTATTGG GGTTGTATGT ACTATATACT ATCGCTCTGC     180
CGCCCAATGA TGGTTACGCC TCTTGCACTG GCATTCTGGG TGACGAGGTT GTCTCCGTAC     240
ACCTCTACTA TTTCCAGGTT GGGCGCACAT TCGCTGATAT GGGCGAGCAA TTTGTCGTCA     300
ACGCAGCGGA CGAACCCTAC ATTCAGTTGC TGCAAGTTTG GACAGGACAT TAGCTGGAAC     360
CCAGCTGCCG TCAGGTTCCT GGCTGAGTTC AAGTTTAGCT CTTTGAGGAA TTTGGAACAT     420
GGATTCAACC ATATCTCCGC AATTGATGCA TCATCCAGCT GATGGCAGCG CCTCAAGTTG     480
AGGTAGTGAA GTCGGGGAAG CTGGACCGAA GAGAAAAATG TAATGAATCC ATCGGACGTA     540
ACCTGGTCCA ATTCCTCTAG GGAT                                            564
```

(2) INFORMATION FOR SEQ ID NO:844:

(i) SEQUENCE CHARACTERISTICS:
          (A) LENGTH: 720 base pairs
          (B) TYPE: nucleic acid
          (C) STRANDEDNESS: single
          (D) TOPOLOGY: linear (ii) MOLECULE TYPE: DNA (genomic)

(vi) ORIGINAL SOURCE:
            (A) ORGANISM: PAG1533UP (xi) SEQUENCE DESCRIPTION: SEQ ID NO:844:

| | | | | | |
|---|---|---|---|---|---|
| GATCCGGAGA | CAGACGTGTA | TCTGAGTTCT | ACCGCTGGGC | GCTGAAACGC | ACGTCGTTAG | 60 |
| CGCACATCCT | GTGTGCTTGC | ACCGGCCCAG | AGCAACCAAG | TATTCCTATA | TTCGTGAAAA | 120 |
| CTGCGGTAAT | AACCATGTAG | AAGATTCCGC | GCCCGAATAC | CCGTTTTACC | CCAATATGTC | 180 |
| CGTCATGTGA | GCTATTGGAT | CGAAGAGTTT | TTAATGACGT | ATCCCCTATC | ATAAAGCGGT | 240 |
| GCTGGATTAT | TGGAGCATGC | ATCTGGTTCA | GCTCGGGCGT | GCCAAATATA | TGGTGCAAGA | 300 |
| AGAAACTATC | GTACCAACCC | CGTCTGTTCT | GACCTGTGTC | CTCTTAATCG | GCATGACTAA | 360 |
| TATGGGGTAT | CCTTAAAACC | TTTAAGATGT | TACCTCCGGT | CTCCAGGCGG | GTTGTCTAGT | 420 |
| TTACAAGAGT | AAATACCACC | TTGCCCCTGG | GAGGGTTCTT | ACTTTACAGT | AGGAAAGAAT | 480 |
| CGATACCACT | GGTGGGGGA | TTTGGTATAT | TTTGAAAGAT | GGATGGAATG | GAGGGCTCCT | 540 |
| TATTGACAGC | AAAGCCACTC | CGACAGAATA | CCCACACCTT | GGATTTGGAA | GCTGCGGATC | 600 |
| GACAGAACAT | GGTTACGTAA | TCGAATTGTC | CTGTCGGGCC | GCCCTTCCGG | TTAATCAAGA | 660 |
| AGAACAACCG | CGGGGCACGC | AGGGAACTAT | TGAATTCAGT | GCTGCCAAGC | CTAATTTATG | 720 |

(2) INFORMATION FOR SEQ ID NO:845:

(i) SEQUENCE CHARACTERISTICS:
        (A) LENGTH: 727 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1534RP (xi) SEQUENCE DESCRIPTION: SEQ ID NO:845:

| | | | | | |
|---|---|---|---|---|---|
| GATCCACATT | GGAATATGGG | TATGGGACTT | GATGGTTGAA | CGCTTCGCTT | CAACCACTGC | 60 |
| AACATTGGCA | AACCGTTTGA | AGTGCTGGAT | GATTTTCTCC | TTCTGGATCG | CAGTCAAGAT | 120 |
| GTGGCCGAAT | CGTTTTTCGT | TGTATAGGCC | TTGCTCATCC | TGTGCTTCAT | CCTCATCAGA | 180 |
| CGCTAATGGA | ACGTCTGGCA | CAATCTCGAC | GCCATCGCAG | GATGCGATAC | TCAAGGTATT | 240 |
| GAGCATGTTC | AAGGCATGTT | CCCTTGCTAC | TTTAAACCCT | GCATCAACTT | CCTCCTCGTT | 300 |
| TTTCCATAGG | CGAGGGACAT | CGTTTTGATC | GTAACGAAAC | TTACTTTCAA | AGCGTTCTCT | 360 |
| CAGTATAGAA | ACCACATTGT | CTTCCTTCAA | ATACTGGTGG | ATAATATCAT | ACAGAATAGT | 420 |
| CCATGCATTT | GACCGGATCT | TCAGGTATAA | AGCATAATTG | TCCTCCTCGA | TGAGGTCGAG | 480 |
| CTGGAAGTCG | TAAGCGGTAC | TTTCATCGGT | GACATCCCCT | AAATTGGGTA | GTTTATACTT | 540 |
| TAGAACTGAA | CGGCGGAAAA | CATCATCAAA | GTGGTCCATA | ACAAGTTGCC | AGACGTTATC | 600 |
| CTGTGGATGG | GAGAGTAAGT | GGACAATATC | GTCTCTAGTA | TGTGTGAATT | GGTACTTTTT | 660 |
| CGCCCTCAAT | ATAATAGCTT | TCATCTCCTT | ACCACGCTCT | CTTTCCGCTA | GTTCACTATC | 720 |
| TTCTCCA | | | | | | 727 |

(2) INFORMATION FOR SEQ ID NO:846:

(i) SEQUENCE CHARACTERISTICS:
        (A) LENGTH: 682 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
            (A) ORGANISM: PAG1534UP (xi) SEQUENCE DESCRIPTION: SEQ ID NO:846:

```
GATCAGCGTG GACTTGATCA TGGTGTGTCT CGTGCGGCCG TGTGGTAGGC GGGGGACGCT      60

GCTGCTGTCC TTTGTGCGGC CGCGGCGGC  GGCGATCAAA GATCGCGCAC CACGGTCGCC     120

GCCGGGGGGG CTCCAAGACA CACGCGCACA GCAGCGCGCG CGTGCCGGGC AATGCAGCGC     180

GCACAGCTAT CCTCGCGCCT CGTACCGGTG GCTGCCTTCG GGCGGATTGC GCTCGTCAGC     240

GGTCACGTGA CCCGAGATAT GTTGCAAACC AAGCCATCGA TCGGCATAGG AACGCATTAC     300

CAGCCGATTC GAAAACCCTC ACAACCCGCC ATCTGCTGGT ACGACCACCG CAAGTCGCTG     360

GCACTGGTTG CACAGTGGTA AGGTCTTCGT TCAAAATTAC TCTGCCAGGG CCGCTCTCAA     420

AACCTGTCAA GTGCAGACGC ACTGACAGTC CGTCAAGATG CGACATTACA ATGCTCTGGA     480

AGCTCTCCAG TAGGTTCTCG CGCGCGTGCT AGACAGTCAG GGGCAGGCTT CATCGACAAA     540

GACGCGCAAG GATGTCGCAA TTCGTTCGCA CAGTCCACTC TAGGGTCGGA CGGGAAAAAC     600

AGCGCTACTC TGCGTTGACT GGGGCGAGAC TGGTAGCCGG CTGCGTGGCC TCAATGAGGA     660

CAGACCAAGG TGATCATGAT AC                                              682
```

(2) INFORMATION FOR SEQ ID NO:847:

(i) SEQUENCE CHARACTERISTICS:
            (A) LENGTH: 663 base pairs
            (B) TYPE: nucleic acid
            (C) STRANDEDNESS: single
            (D) TOPOLOGY: linear (ii) MOLECULE TYPE: DNA (genomic)

(vi) ORIGINAL SOURCE:
            (A) ORGANISM: PAG1535RP (xi) SEQUENCE DESCRIPTION: SEQ ID NO:847:

```
GATCTTGCTG CTATCCAGAA ATGGGAAGTT CTTAGACAAC GGGGAATTAA GCCCCTTTTC      60

CAATATTTTG AGCGTCGTTT CATAGCTCGG AAGACGCAGC AGAAGCCCCC CCAGTAGTGT     120

CTGTTCATGT TCGCTCATGA AAGGTGTCTC TATCAAATCT AGCTCCATCA TCGCAGAGTA     180

GTTATTATCT TTCTTCCAAG ACAGACGCAC ATGCCGCAAC TTCGTCAGGA TTACAGTAAA     240

ATAATGGTAG AACCGCGGAC TCACAGAAGC GACGACCGCT CGAAATGAAG TCGGCCCGTA     300

GAAGATCGTG CGGCCCTGCT TCTCTATCAC AAGATGGAAC TGCGAAAGTC TGTTCACGGG     360

GGACACCGTG CCCATAACGT GCTTCTGCAT GAACAGCTGC GGTACCATCT CGCTCTTCAT     420

CCGCGCGAGC TCAGTCTCAA GCTCGTCGAT CCGTCGCAGC AGCTCCACAT TGGGCGTCGA     480

GCTGAACAGC TCCCGTGAGT TCACGTCGTG CGTAAACTCA GACAGGTACA CACACTCGGG     540

CAGGCCCTTC CCAATACATG TAGAGCACTT CGGCCGCGCC TTGTTGCACT TGACGCGCCG     600

CTTGCGGCAG AACACGCACG ACTTGCTGAC CTTCCGCCTG GTTTTCACAA TCTTGCCATC     660

GGA                                                                   663
```

(2) INFORMATION FOR SEQ ID NO:848:

(i) SEQUENCE CHARACTERISTICS:
            (A) LENGTH: 649 base pairs
            (B) TYPE: nucleic acid
            (C) STRANDEDNESS: single (D) TOPOLOGY: linear (ii) MOLECULE TYPE: DNA (genomic)

(vi) ORIGINAL SOURCE:
        (A) ORGANISM: PAG1535UP (xi) SEQUENCE DESCRIPTION: SEQ ID NO:848:

| | | | | | |
|---|---|---|---|---|---|
| GATCGCGGAC | GTGGAGCACT | GGCCGGAGAT | GCGCGCGGCC | ATCCTGGTGG | TTTCTGCGGA | 60 |
| CCGCAAGGAC | ACGCCATCGA | CGAGCGGTAT | GCAGCAGACG | GTGCACACGT | CGGACCTCTT | 120 |
| CAAGGAGCGC | GTCGCGACGG | TGGTGCCGCG | GCGGTACGGA | GAGATGGCGG | CGGCGATCCG | 180 |
| CGCGCGCGAC | TTCGCGACGT | TTGCGCGCCT | GACGATGCAG | GACTCGAACT | CGTTTCACGC | 240 |
| CACCTGCCTG | GACTCATTTC | CGCCGATCTT | CTACATGAAC | GACACTTCGC | GCCGGATTGT | 300 |
| CAAGCTGTGT | CATCTGATCA | ACGAGTTCTA | CAACGAGACC | ATCGTGGCGT | ACACGTTTGA | 360 |
| CGCGGGTCCG | AACGCGGTGC | TCTATTACTT | GGCGGAGAAC | GAAGCGCGGC | TCTGCGGCTT | 420 |
| CCTCTCTGCC | GTCTTTGGCG | CCAACGACGG | CTGGGAGACC | ACGTTCTCGA | CGGAGCAGCG | 480 |
| CGCCACCTTC | GCCGCGCAGT | TCGACGAGTG | CGTGCGCGGC | AAGCTTGCGA | CGGACTGGAC | 540 |
| GACGAGTTGC | ACAGAGGAGT | TGCCCGCCTC | ATCTTCACGA | AGGTCGGGCC | AGGGCCCAAG | 600 |
| ACACTAAATC | CTCGCTCATC | GACCCGAGAC | GGGCCTTGCC | CCGCCTGAC | | 649 |

(2) INFORMATION FOR SEQ ID NO:849:

(i) SEQUENCE CHARACTERISTICS:
        (A) LENGTH: 717 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1536RP (xi) SEQUENCE DESCRIPTION: SEQ ID NO:849:

| | | | | | |
|---|---|---|---|---|---|
| GATCATTTGT | CCTTGCAGCA | CAAACATCCA | CAGCTGTCGC | ATTTGCAGTT | GCAATCCGGA | 60 |
| GCAGCAGCTC | CTTCGCAGCA | TTTGCAAACG | CCAGGCTCTC | CCACCTCTTT | CGCATGTTCT | 120 |
| TCTGACATTT | TTGTTTGTTC | TAAATCGTGA | TTTTGAGTCG | ATGGTTCCGA | GACCGCCGCA | 180 |
| GCTGACTATA | GGGGGACCA | AGACCCTTTA | TATATTTTCG | CAACCAGATA | CATTAATGCG | 240 |
| ACGCCAAAAC | ACTATCAAAA | ATAAGGTATA | GCCTCATTTT | TATTGTGACC | CATGGGACAT | 300 |
| GCTGTAATCG | GATTATTCTA | ACTAAGCTAG | TATTATGTCG | GTATCCTTTT | ATTAATTACA | 360 |
| ATCACTGCTG | AGTTCGGGTA | TCGTGCAACT | GCACACGCAG | CTCATCAGTG | GTTTCGTTCC | 420 |
| CGCGCAGATC | ACGTGCCTGC | GACATGGCGA | CTTCATCCAC | TGGCGCCCAG | CTACGTGGTA | 480 |
| TATGACATTA | TGGCCGAGAG | GTTAAGGCGT | GAGACTCGAA | CTAAATTGAG | GGATCTCTTG | 540 |
| GGCTCTGCCC | GCGCAGGTTC | GAATCCTGCT | GATGTCGTTA | TTTTTTGCTT | GCGCGGCCTA | 600 |
| CGGGGGGCTG | TATTTGCTTG | TTGCTATTTA | GATAAACGAG | ATACTAAACT | ATGGGTAGAA | 660 |
| CTCGCGGTAC | TTCCCGTAGT | AGTAGGCTGT | GCCGAAACCG | CCGAGGGCGG | TGAGCAC | 717 |

(2) INFORMATION FOR SEQ ID NO:850:

(i) SEQUENCE CHARACTERISTICS:
        (A) LENGTH: 710 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
             (A) ORGANISM: PAG1536UP (xi) SEQUENCE DESCRIPTION: SEQ ID NO:850:

GATCAGCTCG GTACTGGAGA AACAAGGCTA CTGTCCCTTG CCTTGACGAA GTTACGCGAA         60

ATCGAAAGCA GCAGCAACAA GCAACATAGC AAGACCGCTA AATACATTCT CAAGTCATTG        120

GAATAAGCTC TAAAACTACC GATACGTATA TTTACTGCGT TAACGTTTAT ATACATATAT        180

CTAGGCGTGC GTATGGGTGT TGTACGTGTA CATCTAACCA AATAACTCCA CTATAGCTGT        240

AGTACATGGC ATTCCCTTGT AAGCAACTTC AGGTTCTGGA CTACCCAATT GCTGTCCCGC        300

ATCCCAGCCT TGGGGTCGTG GCCCTGTGTT GACCTCAATT TAGCGAAGAC CGACTTGTAG        360

TCGCTCTCAT ACTGCTTGAA TTCGCGAATG ACGCGGTTAG AGTCGAACTC AACATACACG        420

CGCGTATCGA CTATCCTGAA GAGGACATCG TCCACACGCA GGAAGAAACG ACTCAAAATC        480

AGCATACACT CGTTCATCAC TCTCACCTTA ACATTCAGAA TGCTAATGCC ATTGTCCGCT        540

AGTTCGTCCT CAAATAAAAT CATGTCGTCG TAGAAAAGAA TGGGGTCCGG GCTCGAAAAG        600

CTTCGCCAGA GGCAGCTCCA CGCTGTCGTC TCTGACCATC GCCCTGCCAT CTATGGTGCC        660

CTGGTAGAGC GTCGTGTACG TCCAGTCGTA CTGGTGGGAT ATGTTTAGGG                   710

(2) INFORMATION FOR SEQ ID NO:851:

(i) SEQUENCE CHARACTERISTICS:
             (A) LENGTH: 737 base pairs
             (B) TYPE: nucleic acid
             (C) STRANDEDNESS: single
             (D) TOPOLOGY: linear (ii) MOLECULE TYPE: DNA (genomic)

(vi) ORIGINAL SOURCE:
             (A) ORGANISM: PAG1537RP (xi) SEQUENCE DESCRIPTION: SEQ ID NO:851:

GATCTCCGTA CTTTAGGATG GCTTTATAGA GGGCACGAAT TTCCCTTTCG CCTATAGAGT         60

TCAGGTTGTT GGATTTCGCA CGTTTTTTGG AGCGTGAATC CTCTTTGTCG CTTAAGCTCT        120

GAGCTCCATC TCCATTGACG CTATTTTTTA TCTTATTCAG AGCAACATTC CTACGATTCA        180

TCATTTGCAG TTGTTCCTGG ACATACTCTT CATCCTTCCG CTTCTGTTCT TCGTCTTTGA        240

GTTTGCGTAG CTCGTCTTCC GGAATGATAT CATCCCATTC CACGTCAGCT TTATAATCGG        300

TGACTTCAAA CTGTTTTAGG AATTCCTCAC CTCCGAGATG AGACTCTCCC AAATCTGGTG        360

TGGTGACGTG ATCTTCCGCA TGATTCAAGA CATCATCCAA GTTCAAATCT TCAAGCTTCT        420

TTTGATTATC ATGCGCTTTG AACATATTGC CTGCACCAAA CTTGAGAATC TCAGACAGCT        480

CTCCTGCACT AGGTTCGGCT TGCTCTTGC TCGTATATTT ATTCCCATCT GTAACACCTA         540

ACGAGATGAT AGCATACTCC AAGATCATCT TTTTGCGTGC TCTTTCTAAG ACTTCTTCTT        600

CAACGGTATT CTTAGACACA AAACGGTAAA CCATAACATG ATTCTTTTGA CCAATTCTAT        660

GCGCGCGAGC CATTGCTTGG AGATCGGCCT GTGGATTCCA GTCGGAATCA AATATGATCA        720

CAGTGTCTGC CGTCATC                                                       737

(2) INFORMATION FOR SEQ ID NO:852:

(i) SEQUENCE CHARACTERISTICS:
             (A) LENGTH: 716 base pairs (B) TYPE: nucleic acid
(C) STRANDEDNESS: single
(D) TOPOLOGY: linear (ii) MOLECULE TYPE: DNA (genomic)

(vi) ORIGINAL SOURCE:
(A) ORGANISM: PAG1537UP (xi) SEQUENCE DESCRIPTION: SEQ ID NO:852:

```
GATCTAGACC ACCCGGGCTC GTTACCCGGA TACGAAGTAA AAGCAGTCGG GAGCGGTCTT      60
CTGGCAACGA CGTTTTCTTC TACACACCTC CTCGCACAGG ATCCAGCATC CTGCCGCATA     120
ACGTCAACGC CGGCGTTGTG ATGGTTCCCA GGTGCCACTG GCGCCAAGCG CTGCGTGAGA     180
AACAGCAGCG CTGCACTTCG CTGCTTCCGG GAGGCTCCTG GGAGTGGTCC GGGGGTTTTG     240
CCACCGCTCA ACCTAGCGGG GCGTCGCTGT GCCGGGCTCT CCATGCAACT GGGGCGCTCC     300
CATGATGGCG GGGGCCTTAC CAGGGTGGTG TTTGGGCTGC CTGGCTGTGC GTGGCCACAC     360
GATGGCCTGC TGGAGGAGCT GAACCTGCTT CCGTGGTGCA AAGGTGTGTG CGACAGCGCA     420
CCTGCGTGCA AGCTGTGCCT GCGGGGGCGT GTCGATTGCT GCGTCCGCGG GTGCAACTGT     480
GGTGACAGCG CTTTGCAGGC ACGTGATGGT TGGTGCGGGG CCCAGACGTG CTCGGTGTGT     540
CTCAGACAGC TTTTCCGCGG GCTGCGGCGC CGCCGTTGCC GCCATATGAT TGATTCCGTC     600
TCGATTAGTG CATGGTGGTC AGCTTCCAGA TGGCCAGGCT GTACTTGTGC TTGCCCCGGG     660
CCGGCAGGCT CTTTGGCTGT GCCGGTGGGT CTTGCTTGTC GGGCTGGCGC CGTTCT        716
```

(2) INFORMATION FOR SEQ ID NO:853:

(i) SEQUENCE CHARACTERISTICS:
(A) LENGTH: 733 base pairs
(B) TYPE: nucleic acid
(C) STRANDEDNESS: single
(D) TOPOLOGY: linear (ii) MOLECULE TYPE: DNA (genomic)

(vi) ORIGINAL SOURCE:
(A) ORGANISM: PAG1538RP (xi) SEQUENCE DESCRIPTION: SEQ ID NO:853:

```
GATCCCTCTG CTACAAACAC ATACCTAGAT TTCTCATATT TTATACTGAA TACATATAAT      60
ATATCATTTA ACTGTCTTCA TTCATGAGAC GTCGTCTAAG TTCTGTGCTG CTCAACTTGT     120
TTTTCCACTT GTCAGCCTCT TCGCCCCCCA GTACGTTCAC CACATGCACG GCTAGCTTCC     180
TCATTCCTTT GCTCTCACGC GTATCGTTGA TTGTCTGGGC ACCGGCCACA GTTTCCTCAC     240
TCACTACCAG GGCTTCGATA CCAGGTTCGC TACCCGTGGG CCCGCACACG TCATGTAACG     300
CAAATATTTT GATTTCCAGC CCCGGTTTCA GCCTGTGAAG GAAGCTGCAC ACGTTATCGC     360
ATCGTTCGTC GAAGGACTGA AGCTGCTCCC TGTATTTCTT GTTCCGCAGC AGTTCTTCAT     420
CTGTAATCCC CACGATCAGC CGGGACGCAG TCACGAGCGC GGCAACACTG AGCAATATTT     480
TATGTCCGTC GTGTAAGTGG TCGAAAGTGC CTCCCAGCGC GCTAACAGCG TACTTGTCTC     540
TACCGCCACT CTCGACCGGC CCCGCAGCCG CCATCGCCGG ACTATCAAAC AGCTCTATCT     600
GCCTGTGCGG GAACGCATCC TGCAGCAGGC GATCGCTCAG GAATACAACG TCCCACTTCA     660
TTCGGCTGTA CGCTTCCATA CTGACGTTGA ACAAAACATT TATCGGGGTC GTGTACAGCT     720
TCTGCTTCAG AAG                                                         733
```

(2) INFORMATION FOR SEQ ID NO:854:

(i) SEQUENCE CHARACTERISTICS:
    (A) LENGTH: 725 base pairs
    (B) TYPE: nucleic acid
    (C) STRANDEDNESS: single
    (D) TOPOLOGY: linear (ii) MOLECULE TYPE: DNA (genomic)

(vi) ORIGINAL SOURCE:
    (A) ORGANISM: PAG1538UP (xi) SEQUENCE DESCRIPTION: SEQ ID NO:854:

```
GATCCTTGGG ACGACATCGA CACCATTTCT ATCGGTAACG AACTTGTGAA CAACGGCCAG    60
GCGACCGTGG ACCAGATGGC TGGTTACATG AAAACTGGCC GCAAGTGCCT CGCTGAGGCC   120
GGCTACAAGG GCCCAGTTGT TTCCGTGGAC ACTTTCATCG CTGTAATCAA CAACCCTGGT   180
CTATGTGACC TATCAGACTA CATGGCTGTC AACGCCCACC CATACTTCGA CTTCCACACT   240
TCTGCTGCTA TGGCCGGCCC TTGGGTTTTG CACCAGATCC AGAGAGTCTG GAGCGCCTGC   300
AACGGTAACA AGAAAGTTGT CATCACCGAG ACCGGCTGGC CTACTCAGGG TCAGACTTAC   360
GGCAAGGCCA TTCCATCCAA AGCCAACCAG AAGATGGCCT TGGAATCTAT CAAGGCCACT   420
TGTGGTGATA GCGCTATCCT ATTTACTGCT TTCGACGACT ACTGGAAGCC AGATGGGCCT   480
TACGGTGTCC AGAAGTTCTG GGGTATGCTA TAAGTTGCCG TGTGCTTCTT TATGACCTGT   540
CTCTTTATTT TGCTCGGAAC CCTTACATGC AGATGGGGGG TGGCGGTGCA TGGGCCTGCA   600
GCCTCCGGGC CTGCAAGTTT CTACATCGCC CTACTTTAGC TGCCACGGGA CTTTTGAATT   660
TCTTTGGCAC GTGGTACTGC TGGCATCCTT CTCATAGAGC ACAGTGTGCC ACAGGGTATC   720
ACTGG                                                                725
```

(2) INFORMATION FOR SEQ ID NO:855:

(i) SEQUENCE CHARACTERISTICS:
    (A) LENGTH: 706 base pairs
    (B) TYPE: nucleic acid
    (C) STRANDEDNESS: single
    (D) TOPOLOGY: linear (ii) MOLECULE TYPE: DNA (genomic)

(vi) ORIGINAL SOURCE:
    (A) ORGANISM: PAG1539RP (xi) SEQUENCE DESCRIPTION: SEQ ID NO:855:

```
GATCAGACAT GGTGTTTTGC GGCCCTCGCT CCTTGTGGGT GGGGTCACCG CAGTTCACTG    60
GGCCAGCATC AGTTTTGGTG GCAGCAGAAA CCCTTAGGAA TGTGACTTTC TCTTCGGAGG   120
AAGTGTTATA GCCTAAGGTT ATACTGCCAA CCGGGACTGA GGACTGCGGC TTCGGCCAAG   180
GATGCTGGCA TAATGGTTAA ATGCCGCCCG TCTTGAAACA CGGACCAAGG AGTCTAACGT   240
CTATGCGAGT GTTTGGGTGT AAAACCCGTA CGCGTAATGA AAGTGAACGT AGGTGAGGGC   300
CTCTTTAGAG GTGCATCATC GACCGATCCT GATGTCTTCG GATGGATTTG AGTAAGAGCA   360
TAGCTGTTGG GACCCGAAAG ATGGTGAACT ATGCCTGAAT AGGGTGAAGC CAGAGGAAAC   420
TCTGGTGGAG GCTCGTAGCG GTTCTGACGT GCAAATCGAT CGTCGAATTT GGGTATAGGG   480
GCGAAAGACT AATCGAACCA TCTAGTAGCT GGTTCCTGCC GAAGTTTCCC TCAGGATAGC   540
AGAAGCTCGT ATCAGTTTTA TGAAGTAAAG CGAATGATTA GAGGTACCGG GGTTGAAATG   600
ACCTTGACCT ATTCTCAAAC TTTAAATATG TAAGAAGTCC TTGTTGCTTA ATTGAACGTG   660
GACATATGAA TGAAGAGCTT TAGTGGGCCA TTTTTGGTAA GCAGAA                   706
```

(2) INFORMATION FOR SEQ ID NO:856:

(i) SEQUENCE CHARACTERISTICS:
        (A) LENGTH: 743 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1539UP (xi) SEQUENCE DESCRIPTION: SEQ ID NO:856:

```
GATCACTACG TGACATTCGG TACGGAATGG CACTCCAATG CCGACAAACC TCTTCCTACC      60

CCGTGACTTA CCCCGATGTG CCAACTACCA CACATCTGCG CCATAGCCCC AGCCATCTGG     120

CACCAAATGT ACTCGATATC GTTATTACAT GTCTACGCCC TCACGTGCAT CCACCATCTG     180

ATATCATGTC TGCTCTAGGC TATATATTTC GGTTGCGGCC ATATCTACCA GAAAGCACCG     240

TTTCCCGTCC GATCAACTGT AGTTAAGCTG GTAAGAGCCT GACCGAGTAG TGTAGTGGGT     300

GACCATACGC GAAACTCAGG TGCTGCAATC TTTTTTTTTT CCTCCTCCTG CAAGCTGGCC     360

GCCAACACAG GTCACCCTAG TATGGCTCAC ATGCAATTCA GATATCTACT TCTGACTGGT     420

CTGGTGGGCG ATGGCCATCA TTGCAAACAG TGTGCTCGCA TGGGACTTTA ACGACCTCGC     480

GATAATAATC AGAGATCGTC TACTTATAAA ACATCAGGCA CAAAAGAAA GGTGCAGCGA      540

AATGGTATAT ATAGGTCCTC CAGATCCACC ACCGGTACCT CCTACTTGGC CGTATCTGCG     600

TCTCCGTGGC GCTTGCCGCT GAGATGCTGT GGGCCCGAAA TGTACTCTCA AATGGGCTTG     660

TTCAGTGGCC CATACAGCTC ATAAGCTCAG TGGCCCCGAT GCTTAGTAGT AGCTGCGCCG     720

CTCTTCATAC TGCTGTCTGT ATA                                             743
```

(2) INFORMATION FOR SEQ ID NO:857:

(i) SEQUENCE CHARACTERISTICS:
        (A) LENGTH: 716 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1540RP (xi) SEQUENCE DESCRIPTION: SEQ ID NO:857:

```
GATCTTTTCT TTGTCAAAGT TCAACACCTG TAAGCCGCCT CTAGATACCG CTCTAGAAAG      60

GGCCACATAC GCTTGGCCCT TTTCAAAAAC ACGTCTGAGA TCCACTTTCA CTTTGTTTAG     120

TGTTTGGCCT TGAGATTTAT GAATGGACAA GGCCCATGCA AGCATGAGTG GCAATTGAAC     180

TCTCGTTACT AGAGGCTTCT CATTTTCGTC CTCGATAGCC CATGCCTCTT CTCGAACTAA     240

AACTGTTCTG GTGGTATTGT CGGGCTGGAA GAATTGCACT AATGGCAACT TCTTACCCTT     300

TGAGCTCATG TGAACTTCCT GTAAGAGCTG CTTCTTCCGT TCTAGATTGG CCTTCACTTC     360

AGGATCTGTG ACTTCTCGAT CATCCTTTAA GAAATCGAAT ATCGTGTCGC CAAGTGGTC      420

TACAGTGTCA TCTGTGTCTA TCGTCCTAAA CTTCTCTCGC AGAGCTTTCT TGACCATGCT     480

TGTGCGGGTC TCCTTCTTGG GCTCCTCATC CTCATCAAGC TCGGGGCGT TCCAGTCGTT      540

TTTCGCTAAT GCATCCCGAT ATTTCTCCCA TTCTGCAACG TCAAGATCAT CATCGCGAAC     600
```

```
ACTTTGATAG AACATAAATG TTGCCTCATC GATGAAGTCA ATGACCTTCC CCAGTGATCC    660

GTTTACGAGT GTATCATCGA AGTTCTTAAT GTTCATAACC TGTGCGCCGA CTTTAA        716
```

(2) INFORMATION FOR SEQ ID NO:858:

(i) SEQUENCE CHARACTERISTICS:
        (A) LENGTH: 643 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1540UP (xi) SEQUENCE DESCRIPTION: SEQ ID NO:858:

```
GATCTCCTGC GCGAAGAGCA CGCCCTGCGC CCATCCGGCA TAGGGCCCCC ACTTTTGTAT     60

GAACATTTCC CGCACAAGCT CCAGCTCCAT GTTCAGTTTC TTGCGCACAC TGGGAAGGTC    120

CTTGTATCGC GCTTTCAGCG CAGCGATCTT CGCTGCCGAT GCATTGAACT TGTAGTCTCT    180

TTGTGCGATC CTGTTGATGT GCACGTCTAC AGGCACATGG TCGTCCATCT GCATGCCCAT    240

GAGGCAGACG CAATCTGCGA CCTTCGGACC CACCCCCGGA ACCTCCATAA ACCGCTGACG    300

GATCTCCTCC CGCGATATCA TGTCTAGCCA GGATTCCAGG TGTTCAGTAT CGCTCATGTG    360

TGCCGGTTTA CTTGAATCCA TCCATTCTGC CGCAGCCATG ATATACTTGG CGCGATACCC    420

AAACCCCAAA TCCCGCAGTG CGTCCTCGCT AGCGCCTTCC ATCAGCTGCT TGCTGGTGGG    480

GAATGAGTAG TATGGAGTAC CGTCGAGCTC GCCGAGGAAG CTCCCGTACT GCGAACACAG    540

TGCATGGCAC ATCTTCGTGA TGCGCCCGAT ATTGTTGTTG CTAGAGCAAA TAAACGAGCA    600

CAGTGTCTCC CAGGGTTCCT GTCGCAGTAT TCGCACGCCA CGA                     643
```

(2) INFORMATION FOR SEQ ID NO:859:

(i) SEQUENCE CHARACTERISTICS:
        (A) LENGTH: 720 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1541RP (xi) SEQUENCE DESCRIPTION: SEQ ID NO:859:

```
GATCGAACAA CCATACTTTA GGCCCACACG ACCGTTCCCC TCGGGATAT CCTGCCGCCC      60

CTCTACAAGA TTGGATTCAA TCATCACCCC ACAAATGGCA TTCTCACCTT TACTCAGCTG    120

CTCATAGATA TCTTGGGCGA CTTTCGGCTG GTTGCGGTAA TCCTTGTTGG AATTTCCATG    180

CGAGCAGTCA ATCATAATCC TCCGCTGGAC CCCAGCGCTG TCAACTAGCT TCGCATTGAC    240

CAAGTCCTGC TTAGCCTGTT GTACACTGGC AGCGTCATAG TTTGTGCCAT CTTTACCACC    300

GCGTAGAATG ATGAAGGTGT CCTCGTTACC TTCAGTCCCA ACAATCGCAG TCACTCCAGG    360

CTTGGTAACC GAAAGAAAGT AATGAGAGTG AGCAGCGGCA CGCATAGCGT CAATAGCAAC    420

CTGTAAGCAG CCATCTGTCC CGTTCTTGAA TCCGATCGGG AACGATAGTC CAGAAGCCAG    480

CTCACGGTGC AGCTGCGATT CTGTCGTCCG GGCGCCAATG GCGCCCAAGG AGAAGCAGTC    540

GCTTAAGAAC TGCGGCGATA TGGTGTCTAG CATTTCGCCC GCAATTGGAA TGTGCTCCAC    600

CAGCTGCGTG TACATCTCCC GCGAGATACG CAATCCCTTG TTTATTTGGA ACGAATTATC    660
```

```
GATGTCGGGG TCGTTGATGA GCCCCTTCCA CCCCACCGTG GTCCGCGGTT TTCCAGATAC        720
```

(2) INFORMATION FOR SEQ ID NO:860:

(i) SEQUENCE CHARACTERISTICS:
        (A) LENGTH: 732 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1541UP (xi) SEQUENCE DESCRIPTION: SEQ ID NO:860:

```
GATCAGCTGA TGAAGATTGT ACGTCATCAC TGCTATTTAA CACAAACATA ACATAATTCA         60

TCCGCGATAG TTTAATGGTT AGAATTCGCG CTTGTCGCGC GCGGGATCGG GGTTCAATTC        120

CCCGTCGCGG AGCTTTTTGT GACATTTATT GAAACGGTTG TCGTTATAAC CGTTCCGATG        180

GAATGTGGCA GGACCCTGTA ACGGCGACGT ATCCTGCAAC TTCGACGTGT TGTCGCGTCT        240

ACGCCAGGGC TTGGGCTTCC AGAAATTGGC TTTCCCCGAG CCCGAGTTTT TGTGACCCAA        300

TATTTGAGCT GCTGATCATC AAGCTCTAGT CGCACACAGG GGGCCCGAGT ATCCATTGAC        360

AAAGGTCGGC GCAACATCCG ATCGCCGGGT CCCTTTATAT ATAAATATAC ACTAATGACA        420

CATGCGAATA CCCGACTGCC GTGGATAGGG ACGTTTGAG GCCTCATACC CCTCAATACA         480

GATAACAAAA TTGGAATATA GGAGAAGAAA TGTTCGAGAG GCTAAAACTT AGGTTCCGGC        540

GATGCAGAAG ACTCAGAGCC AACCGTTTAG CAGACGTTCC ATACCCGAAT CCCACGTTGA        600

ATTCCGCAAT CATTTCCAGA ATCGACACAA TCACGGTGTC AATCTCGGGT CGCTATCGTC        660

CTTGAGAAGT GGATATCGAG TCGATGTTCC AATGTGGCGG CGAGACCGAG CATGCGGGGA        720

TCAGGAAGAT GA                                                           732
```

(2) INFORMATION FOR SEQ ID NO:861:

(i) SEQUENCE CHARACTERISTICS:
        (A) LENGTH: 614 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1542RP (xi) SEQUENCE DESCRIPTION: SEQ ID NO:861:

```
GATCATGTGG AGGAACTCGG GCAGCGTCTC GGAGCCGGCG TAGTGGGCTA CTGTGGCGGC         60

GCGGGCAGCC GACTGCTCGG GGTATTCGGG CGCCGGCGCA GCGGCGTGTG AGCCGATGCT        120

GCCTCCGGGG TGGCGGGCGG CGAAGGCGTC TGCGCGGCGG CGACGGGCGC AGGGCGAGCC        180

CCCGTCGGAG AGCGCGAGCA CAAGGCAGTC GAGGGCGAGG AGCATGAGGG TGGTGGCGAT        240

GGTGGGGGCG TTGAGGCCGT CCTGGACGAC GCGCTCGCGC AGGTGGGGGG GCTGGAAGAC        300

GGTGATCACG TGATGCGCGC GGCGGGCCAG CGTCCAGGCG GATCGCCGG TGACGGCGAT         360

GAGCGGGCTG GCGGGTGCGA AGCGCGCGCT GCGCAGGTAG GCGGCGAAGT GCAAGAGCTC        420

GTCAGTCTCG CCGGAGTGGG AGCAGAGCAG CAGGGCGTCG CCGTCGGCGA CGATGCCGAT        480

GTCGCCGTGC ATGGCCTCCG TGGGGTGGAA GACGGCGGCG GGGATGCCGA ACGAGTGGCA        540
```

```
GGTGGCGACA GTCTTGGCGA TGATGCCGAA GGACTTGCCG CAGGCGACGA ACACGAGCTT      600

GCGGCCGTCC GCGA                                                       614
```

(2) INFORMATION FOR SEQ ID NO:862:

(i) SEQUENCE CHARACTERISTICS:
        (A) LENGTH: 654 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1542UP (xi) SEQUENCE DESCRIPTION: SEQ ID NO:862:

```
GATCATTTAC CTACGCATCG GCCTGCCGCG CATTGCCGCA GACGGATCGC TGCGAGACGG       60

CTACCTGGAA CACTACTACG AGAACGCGTA CGCCGCCGCC CTTCTGGACG GCTGCCGTGT      120

GCAGCGCCTG ATAGGACTCC ACGCGCTGCC GCTGTAGCGA GTCATGCCGC TGTGCCGGAC      180

CCGAGCGGTT TGCCGTCTCG GGAGCCTCCG GGTTCGCACC GCTGGAAAAA GGAGGGCCAC      240

GCTGGTATAT AAACGGCACA CGAGCCATCC GGCGTCAGGA ATAGCGTGAG TCGACAAGAT      300

GGGTGCGGAA CACGGTCCTA AGGACCTTCA GAAGAAGCCT GTGAGCTTTT CCAACATTGC      360

CCTGGGAGCG GCGTTGAATA TGTGCGAGGT CACGACGCTT GGGCAACCGC TTGAGGTCAC      420

CAAAACGACC ATGGCCGCAA ACCGGCAGTT CGGCTTTTCG CAAGCGGTGC GGCACGTGTG      480

GTCCCGTGGG GGCGTGTTCG GCTTTTACCA GGGGCTGATT CCGTGGGCTT GGATTGAGGC      540

GTCCACCAAG GGCGCGGTGC TGCTGTTTGT TTCTGCCGAA GCCGAGTACC AGTTTCGGCG      600

GCTTGGTCTC AGCAACTTCG GTGCAGGCAT CCTGGGCGGG TGTCTGGCGG CGTA           654
```

(2) INFORMATION FOR SEQ ID NO:863:

(i) SEQUENCE CHARACTERISTICS:
        (A) LENGTH: 714 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1543RP (xi) SEQUENCE DESCRIPTION: SEQ ID NO:863:

```
GATCCCTTAG CGACTCTCTC CACCGCTCGA CGAGGCCATT GAGCTCTTAC GAACTGCACA       60

AACCTACTCG AACTCTGTTT CCAGACTTCT TTCTGTTTGT CTTCAACTGC TTTCGCATGA      120

AGTACCCCCC AGGCTATTTT TCTTACCCGC CTGGTGTTTG TCTATATACC CGGTTGTATT      180

TTTGATAAAA AACTCAGCTC TTCCTCTACG GCAGAAATAT ATATCCAGTC CTTAGCGCCA      240

TGCGAAAATC TGCCTTTTTA CCGCTGTTTC TCCCAGTCTT AGCACTGGCA GAAAAAAGAT      300

GTATGGCGTA TAGGCGCTGG CCCCGCGGAA AAAAAAAAA AATAGAAAAA TAGAAAAATA      360

AAAAGACGTG GGCCGCCCCG CGGGCAGACG AAGAAAAAAT AGGCGCCCAC CCCTCCAAGC      420

AGACGACAGG CGAGACATAA TAAAATCCCA CACCAAGGGA AGAAAGTCTT GTGCACGCTC      480

CCGGCCTCAT ACGCTGCCAT TCTGTTCCAT CCGGCTTGCA AACCCAGTAG TGGCATGTCA      540

AAGCATTGCT CCGACGCTCC GCTGCCTTGC AGTCGACATC CTCTTCCTAA CCCCAGCCAG      600

ACTTCCCATA CTTTGCACTT CACATAGCAT ATCACTTTTC AGATCACTAC GTGACATTCG      660
```

```
GTACGGAATG GCACTCCAAT GCCGACAAAC CTCTTCCTAC CCCGTGACTT ACCC            714
```

(2) INFORMATION FOR SEQ ID NO:864:

(i) SEQUENCE CHARACTERISTICS:
        (A) LENGTH: 680 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1543UP (xi) SEQUENCE DESCRIPTION: SEQ ID NO:864:

```
GATCCGTAAC TTCGGGATAA GGATTGGCTC TAAGGATCGG GTAGTGAGGG CCTTGGTCAG       60
ACGCGGCAAG TGTGCTTGTG GTCTGTCCTC GGGGGCTTGC TCCTGGGGAC GGACTGCTTG      120
CGTGCTCTGT CGTAGACGGC CTTGGTAAAC CATCTCTGGT CGTCGCTTGC TACAATTAAC      180
GATCAACTTA GAACTGGTAC GGACAAGGGG AATCTGACTG TCTAATTAAA ACATAGCATT      240
GCGATGGTCA GAAAGTGATG TTGACGCAAT GTGATTTCTG CCCAGTGCTC TGAATGTCAA      300
AGTGAAGAAA TTCAACCAAG CGCGGGTAAA CGGCGGGAGT AACTATGACT CTCTTAAGGT      360
AGCCAAATGC CTCGTCATCT AATTAGTGAC GCGCATGAAT GGATTAACGA GATTCCCACT      420
GTCCCTATCT ACTATCTAGC GAAACCACAG CCAAGGGAAC GGGCTTGGCA GAATCAGCGG      480
GGAAAGAAGA CCCTGTTGAG CTTGACTCTA GTTTGACATT GTGAAGAGAC ATAGAAGGTG      540
TAGAATAAGT GGGAACTTCG GCGCCAGTGA AATACCACTA CCTTTATAGT TTCTTTACTT      600
ATTCAATTAA GCGGAGCTGG AATTCATTTT CCACCTTCTA GCATTTAAAG TCCTATACCG      660
GGCTGATCCG GGTTGAAGAC                                                 680
```

(2) INFORMATION FOR SEQ ID NO:865:

(i) SEQUENCE CHARACTERISTICS:
        (A) LENGTH: 686 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1544RP (xi) SEQUENCE DESCRIPTION: SEQ ID NO:865:

```
GATCTCAACA AGATCAATAG GCATATCCTG CCGGCTAGGG ACACCACTGA ATTTTATGAC       60
GAGAAGGCCG AAGAGTTCGA CCGCAGTGTG AGAATGGAAG AAATGGCCAT TCGGATGGGC      120
AAACGGCGCA AGTGGCTGAT GAAGCACTGC GAGGGCGATG TGCTAGAAGT TGCATCTGGT      180
ACTGGTAGGA ATATAGATTA CCTAGACTTG AGCAAAATCG ACACAATCAC CTTTCTGGAT      240
GCGTCTAAGA ATATGATGAA GATCGCCAAT AAGAAGTTCA GAGAAAAATA CCCACACTTC      300
AAACAAGCTG CATTCGTAGT TGGAAAAGCA GAAGATTTAG TGGACCTGGC GACTGGGCAT      360
TCGCCTCAGC AACAGAATCT GGAATTGGTC AACTCTCCTG AGCAGGTGAT CCCGGAGTCC      420
AAGCCCAAGG TTAAATACGA TACCATCATC GAAGCCTTCG GTCTGTGCTC TCACCATGAT      480
CCTGTACGGG CATTGAAAAA CTTTGCGAAA TTGCTAAAGC CTGGCGGAAG AATAGTTCTG      540
CTTGAGCATG GCAGAGGGAC CTATGACGTT GTGAACAAGA TTCTAGACAA GAGAGCCGAG      600
```

| | |
|---|---|
| CACCGTCTCG AGACCTGGGG CTGCAGATGG AACTTGGATA TTGGCGAAAT TCTAGATGAC | 660 |
| TCTGATCTAG AATCGTCACC GAAAAA | 686 |

(2) INFORMATION FOR SEQ ID NO:866:

(i) SEQUENCE CHARACTERISTICS:
        (A) LENGTH: 683 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1544UP (xi) SEQUENCE DESCRIPTION: SEQ ID NO:866:

| | |
|---|---|
| GATCAAATTC CAATCTCCGT CAGCGTCAGG CAGCCGCGTT ATGTGTTGAA CTCTTCGCTG | 60 |
| CTTCTCTTCT CTTCGCTGAA CCCGCAAGAA AATTCCACCT CACGCCGAAC CAGAGGCGAA | 120 |
| AAACTGAAAA TGAAATAAGG CGCCGGCTTC CGAGGACGTT GCGGGCTCGT GCAGCTCTAC | 180 |
| TTGCAATACC CGCAATAGGA CTACCAGACC TTATTAGACA CTGTAATATG TGGGCAGCAG | 240 |
| TAGGTGCAGT CTACAAACTT TTATAGCGCA GCCGGGCGTA TTACTCTTTT CTGCTCCCGC | 300 |
| GTCCGCGATA AGTTGTGACT CACAGTCCCG CGGACGGAAC GTGCGACCGA GTGCGGCGAA | 360 |
| TAATGAGTAA TGTTCTATGT ASTGGTTGCT AGGGGGCTGA AGGCTATGCT CTGGGGTAGC | 420 |
| TGGAATGTCA CGCAGAACAT GGGCTTCGTA GGTGCCACTT TGCGCACGAG GTGGAACGAC | 480 |
| AGCGCAGTCA TCGGCAGGAT GTCTGCGCTG GTGTGCATTA TCTCGAGCAC ACGGCGGTGT | 540 |
| ATGCGGGCGT GCAGGTCTGC TGGCGCGGGC TCGGGCTCGT CGGGGCTGTA TTTCTCGAAA | 600 |
| CAGTGACAGT GGATGTAGGG CAGCACCAAW TGCTGGGTCG GCAGCGGCGT CCTCCGAGAT | 660 |
| CCGTGGCGCG AGTACAGCCC GGC | 683 |

(2) INFORMATION FOR SEQ ID NO:867:

(i) SEQUENCE CHARACTERISTICS:
        (A) LENGTH: 714 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1545RP (xi) SEQUENCE DESCRIPTION: SEQ ID NO:867:

| | |
|---|---|
| GATCATTAAT CAGCCATCGC ATACCCGGGC AAGATGACCA TTAGCTCCTG CTTTCGACAG | 60 |
| AAACAACGGA CTATGGGTAT AGAACTTGAT GATAGAAGGT TGAGGCATTT AAAAAAGTGG | 120 |
| CTAGACCGGG CTTTAGATCC GCCTACGACA GACGAGAGCG TCACAGCCCT TGTGAAGGAC | 180 |
| TATGTACTAC AGGTACTACT AGAGTGCGAC ATCGCAGCTG TGAAGGGCCG AAAGAACGAG | 240 |
| TTCTGCGAGC AGATGAGCCA GTACCTGGCA GGTATGGTGA AGGACCACAG CTGTCTAGAT | 300 |
| GGGTTGTTTT ATCAGCTAGT GGACTTAGGC GAGCCTCCCG CGGGGAATAG TTGCGGGCGA | 360 |
| CAGCTGCGTG TCCTGAAAAT CCCAGCGGAC CGGCTTCGCT GGGAAACCTT GCGTGCGGAG | 420 |
| TTTGCGCCTT TTGGAGCGGT CACCAGGGCG AGGATTGATT ACGTGCATCG TGAGGCATTC | 480 |
| TTGGAGTATG CGGATGCGGC CAGCGTCGTC CGATGTTGTT CGGTCCGGAA GGCTTTCTTG | 540 |
| GGGAACCGGT TCGTTGAGGT GCAGCCCTGC TCGCGAGGCG TGGGAATCAC TAAGCGGTGT | 600 |

```
CGACGTCTGG CCGCCGGATC ACGAAACAAC TGTGCCCGAG CATGGATCAT CTGGGGTGCC      660

TCCGCGAACT GGTGTTGTCT TGGATCGTGG ACGTGCGCCT CCGCCTGTCA TCTT            714

(2) INFORMATION FOR SEQ ID NO:868:

(i) SEQUENCE CHARACTERISTICS:
        (A) LENGTH: 576 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1545UP (xi) SEQUENCE DESCRIPTION: SEQ ID NO:868:

GATCATCTTG CAGGGACCGC WCCACGTGGC GTAGAAGTCC ACGACCACGA GCTTGTCGGA       60

GCCCACGGCG GACTCAAATT CAGAAAGGGA CTTGATTTCG GACACCATTG CGTTCTGTGT      120

GGCTGACTGT ACCTTGTGTA TACGCAGTAC CCAGGAAGCC GGGCGGAGCC CCGCCTTTTA      180

TACCCGGCCG CCTGCGGTCA CGTGTCACCA CGTGCGGGGT CTCCCCTCTA TTTCCGCTCA      240

GGAGATAAGG ATGACAAACG CGTCCTCGCG CGGTCCGCAT TGACGTCTTC GACAGCAATG      300

GAACCTCTGC TATAAGCGGT GTCTGCGCGC CGAGCCTTCT CAATCGTCCG TCTCTCTGTT      360

CGCTTTGTGT ACGCCAGGCG CGGGTTTGTT TACGTTTCGG ACGGGGTTGG ATCTCCAACG      420

CACGGTCGAA TAACGAACAT GAAAGCCAGT TGTACAGTAG CTACACCCCA GCAGACGAAG      480

CATCAGCAGG CAGTTGAGAG CGCGTACGAG AAGTTCCGTT ATAGAGCACA CTCGAGACCA      540

TAGAGGTCAT CCGCTAGGCG GTACTTCAGG TCAGGC                               576

(2) INFORMATION FOR SEQ ID NO:869:

(i) SEQUENCE CHARACTERISTICS:
        (A) LENGTH: 741 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1546RP (xi) SEQUENCE DESCRIPTION: SEQ ID NO:869:

GATCTTGCTG CTATCCAGAA ATGGGAAGTT CTTAGACAAC GGGGAATTAA GCCCCTTTTC       60

CAATATTTTG AGCGTCGTTT CATAGCTCGG AAGACGCAGC AGAAGCCCCC CCAGTAGTGT      120

CTGTTCATGT TCGCTCATGA AAGGTGTCTC TATCAAATCT AGCTCCATCA TCGCAGAGTA      180

GTTATTATCT TTCTTCCAAG ACAGACGCAC ATGCCGCAAC TTCGTCAGGA TTACAGTAAA      240

ATAATGGTAG AACCGCGGAC TCACAGAAGC GACGACCGCT CGAAATGAAG TCGGCCCGTA      300

AAAGATCGTG CGGCCCTGCT TCTCTATCAC AAGATGGAAC TGCGAAAGTC TGTTCACGGG      360

GGACACCGTG CCCATAACGT GCTTCTGCAT GAACAGCTGC GGTACCATCT CGCTCTTCAT      420

CCGCGCGAGC TCAGTCTCAA GCTCGTCGAT CCGTCGCAGC AGCTCCACAT TGGGCGTCGA      480

GCTGAACAGC TCCCGTGAGT TCACGTCGTG CGTAAACTCA GACAGGTACA CACACTCGGG      540

CAGGCCCTTC CCAATACATG TAGAGCACTT CGGCCGCGCC TTGTTGCACT TGACGCGCCG      600

CTTGCGGCAG AACACGCACG ACTTGCTGAC CTTCCGCCTG GTTTTCACAA TCTTGCCATC      660
```

```
GGACTCTGCC ATCCCGCCAG CTTCAAGCAA AATGAGTAGG TCATATTATT TACCTGCTGG      720

TAATCTTGAA TAATGCTCAC T                                               741
```

(2) INFORMATION FOR SEQ ID NO:870:

(i) SEQUENCE CHARACTERISTICS:
        (A) LENGTH: 707 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1546UP (xi) SEQUENCE DESCRIPTION: SEQ ID NO:870:

```
GATCGCGGAC TGGAACACTG GCCGGAGATG CGCGCGGCCA TCCTGGTGGT TTCTGCGGAC       60

CGCAAGGACA CGCCATCGAC GAGCGGTATG CAGCAGACGG TGCACACGTC GGACCTCTTC      120

AAGGAGCGCG TCGCGACGGT GGTGCCGCGG CGGTACGGAG AGATGGCGGC GGCGATCCGC      180

GCGCGCGACT TCGCGACGTT TGCGCGCCTG ACGATGCAGG ACTCGAACTC GTTTCACGCC      240

ACCTGCCTGG ACTCATTTCC GCCGATCTTC TACATGAACG ACACTTCGCG CCGGATTGTC      300

AAGCTGTGTC ATCTGATCAA CGAGTTCTAC AACGAGACCA TCGTGGCGTA CACGTTTGAC      360

GCGGGTCCGA ACGCGGTGCT CTATTACTTG GCGGAGAACG AGGCGCGGCT CTGCGGCTTC      420

CTCTCTGCCG TCTTTGGCGC CAACGACGGC TGGGAGACCA CGTTCTCGAC GGAGCAGCGC      480

GCCACCTTCG CCGCGCAGTT CGACGAGTGC GTGCGCGGCA AGCTTGCGAC GGACCTGGAC      540

GACGAGTTGC ACAGAAGAGT TGCCCGCCTC ATCTTCACGA AGGTCGGGCC AGGGCCCCAA      600

GACACTAAAT CCTCGCTCAT CGACCCGAGA CGGGCCTGCC CGCTGACGCT ATTCTCCTGC      660

TATTTTCTGC TCTGTATACC CTGCCAGACC GCGCTATATA TATAGAA                   707
```

(2) INFORMATION FOR SEQ ID NO:871:

(i) SEQUENCE CHARACTERISTICS:
        (A) LENGTH: 710 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1547RP (xi) SEQUENCE DESCRIPTION: SEQ ID NO:871:

```
GATCCTCCGC CTACACCAGA ATATTTCTGG CCAATTAGTT GTTCACCATC GCCCCGAACG       60

TTGGTGAAGC CACGGCCATA CGCTGCCATG CCGAGTGCAA TTTTTCTTGG GCTGACCTTA      120

AATTGTTCGG TCATCATGAG TATCGCATCA TGTGCATTCA ACTCATCAAA GTTGTCAATA      180

CCCATATCTT CATACCGACG CTTATCTAGG TGCGATTTGT ACGGCGAATT CGTAGCATTG      240

TACAAGTTGC TATGGTAGCC TGTTCGCTCT GACCATGCAC CGTGGTAGTC GTATGTCATC      300

ATATTCCACA TGCTGAGATA CTTGTTCATC TCCTCAACCG GGAAAATGCC AAGTGTCTGA      360

GGAAAGGCCG GTGCTGCCAT GCTTAAGTGG AAGCGCGGTT CTGTAGTCCC GCCGGGGCCC      420

CAGATATTGT CTTCCAATTC GTCCATCTTG TGTCGCAAGC GGCTACACAT TTCTAGATAC      480

ATCTGGGGTT CGTAGCCATC ATCCTTAGGG AACTCCCAGT CAAGATCTAT CCCATCGAAG      540

CCGTACTCAA ACATTGCGTC GATCGCCGAG TCGATGAAGT TGTTAAACTT CTCCTCGTCA      600
```

```
CGCACAATTT TATGGAACGG CTCCCGATTG AACAGCCGC CAACGGGCAT CATGAGCTTG        660

AAATCGGTCC CTGGCCGCGT CTTGAGGTAA TTAAGCTTCG CCTATTGCCC                  710
```

(2) INFORMATION FOR SEQ ID NO:872:

(i) SEQUENCE CHARACTERISTICS:
        (A) LENGTH: 608 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1547UP (xi) SEQUENCE DESCRIPTION: SEQ ID NO:872:

```
GATCTCTGAG GGTTCCAAGG CAAGCCCGCC GGAGCTTGCC CAAATTGTGT CACCCGCTCT         60

CGAGTAGATG GTGGCCTTGT CGACCTTCCC GGTTGCTAAC AAGTTGTCAG TGTAGGCTAA        120

AGCTCTAGTT AGTACCCACG AACGGGCCAC GAGCAGAACA CGTAAAAACA CATACCTTGC        180

CAAGACATGA TGCGTTCCGG ATGAAATCTG AGTTAGTGCT AACACTCGCA GATGCTCTGG        240

TGAGTGGAAT CTACGTATCA ATAGTATTGA TTTGTCAATA AATATACCTT GGCTTTTTGT        300

AATCTTTTTA TATAAGGGGT TCCGATCTGC TGACATCATA GCACACGAAT TAAGTATCCG        360

GGTAACGAAC TGCCCGGGTA ATGCGGGGCA CAGGGCAAGT GCCGGGTAAC GGCATCCACA        420

TACCGCAGAG ATGCACTGGC GGCTACATAC TGTACACAGG CTCGCAGCTA CTCGTCGTCT        480

GAGTCGAGAA CAGCCACCTT GCGACGCTTG AGAGCGACCT CTTCATCTGC GCGCGGGCC         540

GGCGGGGCAG CAGCGTACTT GGCTGCGCCC TCGCGTTTCA GCTGCTGCAG ACGCGCGGCG        600

TTTAGGTC                                                                 608
```

(2) INFORMATION FOR SEQ ID NO:873:

(i) SEQUENCE CHARACTERISTICS:
        (A) LENGTH: 706 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1548RP (xi) SEQUENCE DESCRIPTION: SEQ ID NO:873:

```
GATCATCATT GCTCGGTTAG CGATTGCCGG CAATTTTACA GCTGGTTCAT CGCTAGGCGG         60

TAAGGCGACC GCGGGTAGTT TCCTGTCCTA CGGGTCCGTG GTGTTTGGTT TTGCATCGGG        120

ATGGACAACA TATGCTGCAG ACTACACTGT CTACATGCCC AAAAATTCTA ACAAATACCG        180

CATCTTTTTC TTCATGATTG CGGGTCTTGC GACCCCGTTG CTGTTCACGT TGATTCTTGG        240

AGCTGCTGCC GGGCGCTGTG TGCACACAAA TCCTACGTGG GGCGAATATT ACAAAAAACA        300

TTCCGTGGGA GGTCTGTGCT TTGCTATACT GGCTGAAAAC GCTCTGGGCG GGTTTGGGCA        360

GTTCTGCTGC GTTGTACTGG CCATGTCCAC AGTTGCAAAC AATATTCCAA ACATGTATTC        420

CATCGCTCTC AGCACCCAGG CGCTGTGGAG TCGTTTCGCG CGTGTGCCAC GAGTGTTCTG        480

GACCCTGGTC GGCAACGCAT GCAGCTTGGT CATTGCAATC GTTGCGTACT ACAAGTTTGA        540

GACCTTCATG ACCAGCTTTA TGGATTCAAT TGGCTACTAC CTCTCCATAT ACATCGTAAT        600
```

```
ATGTGTCACT GAGCACTTCG TCTTCCGCAA GGGCTTCCGT GGTTACACGT CAGCCACTGG      660

GAACGTCCCG ATCTTCCTCC AGCTGGTTAC GCTGGCTGCG CTGCGC                    706
```

(2) INFORMATION FOR SEQ ID NO:874:

(i) SEQUENCE CHARACTERISTICS:
        (A) LENGTH: 590 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1548UP (xi) SEQUENCE DESCRIPTION: SEQ ID NO:874:

```
GATCGACAGA TTACAGTTAC AAGCGAGAGT TCGGCCTATT TAAGGAACAG AACCTATACC       60

ACATTTGAAG CTCGAGTTTT GGCACGCCAA GACCGATTTG CGGATTAAGT ATCTTGAAGT      120

TTGCACTCAG ACTCAAGAAC TACTATTACG ATACTATAAC AAAGACGATG ACTAGCACAG      180

CCGACCACAA GCAGCCCATT TCGTTGAAGG TTAACGGGGC TCTATTCGAC GTCGACGGGA      240

CCATCATCAT CTCGCAGCCC GCGCTAGCGG CCTTCTGGAG GGAGTTTGGC AAGGACAAGC      300

CGTACTTCGA TGCGGAGCAT GTCATCAGTG CCACCCACGG CTGGAGAACC TACGACGCCA      360

TCGCTACCTT CGCGCCAGAC TATCTGAGTG AGGAGTACGT GACGAGACTG GAGGGCGAAA      420

TCCCAGACAA GTACGGCAAG TTCTCCGTGG AGGTTCCCGG CGCTGTTACG CTCTGCAATT      480

GCCTTGAACR AACTTCCGAA GGAAAATTGG GCCGTTGGTA CTTCCGGCCC CTTCCAGATG      540

GCACCAAGTG GTTCGATGTC CTCGGCATCA AGCGTCCTAG CACCTTCATT                590
```

(2) INFORMATION FOR SEQ ID NO:875:

(i) SEQUENCE CHARACTERISTICS:
        (A) LENGTH: 736 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1549RP (xi) SEQUENCE DESCRIPTION: SEQ ID NO:875:

```
GATCTGCTTG GTCTGACCAC CGAAACCCGA CTGCTTACGG TCATATCTTC TCTTACCCTG       60

AGCAAACAAG GAAGCCTTAC CGGCCTTGTA CTGGGTCACC TTGTGCTGGG TGTGCTTGCG      120

GCAGGCCTTG CCCTTGCAGT AAGTCTTTCT GGTCTTTGGA ACGTTAACTG CACACGTTAG      180

TATACGTCCT CTTGGCGAGT CCCTTTTCGA TCTGCAGCCG CGCCGTCAGA AGGCCCTGCT      240

GTAGCGAGCC GTGGCCCCCT GGCGGCGCTC CGCGCTTCCC CTCCGTCATA TTGAACATAC      300

CCATTGCGAG AAGTAGCTTC TGTGATGCTC TGTGCTTACT ATCAAGCAGG ATGACACCCG      360

GCCTTGAATC CTGAAATTTA CCATGTTTTT CGCTTCGCGA GCTCGGCCCG CGGGCCGGCC      420

GGCTGCCGCG CCGGAAGGTC CAGTGCTGCC CGGCCTGCGT CGCCCCAGTT CACCCGGGCC      480

ACCACGCAGC GTGGTGATGC ACGCATGTGC AGTATGTGTG GGTGTTGAAT AAATAGATGT      540

ATGGGTGTAG TCATGTGTTT GTCACAGGCA CTCCTCCGCG GCTAACGCCT CGAGATTGGC      600

CAATGCGTGT GGCGGCATAG GCGATGGCAG CCATGCCTTG AGCTCTGCGC GGGGTTAGAG      660

CCCAAGTCAT TAGACTGCGG CACTGCAAGC GTCTGACCGG CAGGTTTTAA GCTGGTGTGT      720
```

```
GGCCCTGCGC TACGTT                                                  736

(2) INFORMATION FOR SEQ ID NO:876:

(i) SEQUENCE CHARACTERISTICS:
        (A) LENGTH: 707 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1549UP (xi) SEQUENCE DESCRIPTION: SEQ ID NO:876:

GATCCATGTA TAATCACCCC ACAGCACCTT TTGCAGGTTC TCGCGCTTGG CCCCCAGCTT     60

CTGCTCGTAG AACTTCGCAA ACAGACTGAC GTTGAACCCC CACCCATCTG CAGCAGAGGC    120

AAAAATCACA TTGTTCCGGG ACGGGTCGAA GTATATGTCC GCATCATCCC GCTCCACATA    180

CTCGGCCTGG GCGTCCTGCT CCAGTTTCTC TCTCCACGAG AGGTCATCCA GCAGCCGCTC    240

CCCGGCAAAG AAGGACCCCA GTACAGAGTT GACCTGTTCA ATCGTCTTCG ATAGATGCAC    300

GTAGGCCTCC TGTGGCGTCA GCTGGAGCTC CGTGATCAGC CGATCGATCT TGTTCAGCAC    360

CAGGATTGGT CTCAGCTTCT CCGTCCAGCA CTGCCGCAGC ACCGTAATCG TCTGCGAACA    420

CACACCCTCG ACCACGTCCA CCAGCACGAT CGCGCCATCA CATAGCCGCG ACGCCGCGCT    480

AACCTCGCTG GAGAAGTCTA TGTGGCCCGG AGAGTCGATC AGGTTGATTA AATGTTCGTT    540

GACCAGCGGC TCGCTGCTCC CCTCCTGTTT GTGAAGCACT CCGAAGTTAC AGAGAAATCG    600

CACTGGACTC CATCGTGATG CCTCGCAGCT GCTCATCTGG CCGCGAGTCT AGGAATCGCA    660

CTTTCCCCGC TAACCGCTGT GAGATAATAC CGTTGGATGC GAGGAGG                 707

(2) INFORMATION FOR SEQ ID NO:877:

(i) SEQUENCE CHARACTERISTICS:
        (A) LENGTH: 706 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1550RP (xi) SEQUENCE DESCRIPTION: SEQ ID NO:877:

GATCGAGTAC ACAAAGTACA TGGATGCTGC CAATAACTAT AGTCTGAAAT CAATGCGTTC     60

CTTAGCGAAT GCAGATGAGT TGGCGCAGCT GGCATCATTT AACTCCATCA GCCATTATTT    120

ATTGGCTGAA TCGCCATCTG TCCAGACACT ACAATTTTTA TTAAGCTCAT CTAAATTGTA    180

CCCAAAATTA ACGAAGGAGA ATCAAGAATC TGCAATTATC GAAACACTGC TGTCTCTCAG    240

TGAATTTACG TTGCTGCACG ACTTCTCTCT CCAGGCAGGT TTCCAGGTCG AAAAATCGGT    300

CATTTTGAAG TACTTTTGGC GCTTTTTCAA CAGCGCACCA AATGGGTCCA GGGGACCGGC    360

CAGAAATGAC AAAGGCGAGG AACAATCTTC GCTTACTGCC CAAAAAGGAC TATTATTATC    420

TTGAGACTCT TCTTGATGTC GCAGACGCCT TGGCAAAGTA TTCGCTAAGC TACTCACGTG    480

GACAACCCTT CAGACCATCG CATATATTGG ATCTCAAAGA TGATCCATTC AGAATCATAA    540

GCAAACTGCT AGAAACGAAT CCCAGTCTGT ACCGTGACGT TGAAACGACT TTCGAAATCC    600
```

| | |
|---|---|
| TCAAGCAATT ATATGAAGGA TTGCAACTGC AGCCTCATGA TCCAAAGTAC ACAAGTGAAT | 660 |
| ATACCCGTTT GCTAGTCTGT CACATTGATT GTGCATTGGC AAATAT | 706 |

(2) INFORMATION FOR SEQ ID NO:878:

(i) SEQUENCE CHARACTERISTICS:
        (A) LENGTH: 736 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1550UP (xi) SEQUENCE DESCRIPTION: SEQ ID NO:878:

| | |
|---|---|
| GATCTCCTCC CGCGATATCA TGTCTAGCCA GGATTCCAGG TGTTCAGTAT CGCTCATGTG | 60 |
| TGCCGGTTTA CTTGAATCCA TCCATTCTGC CGCAGCCATG ATATACTTGG CGCGATACCC | 120 |
| AAACCCCAAA TCCCGCAGTG CGTCCTCGCT AGCGCCTTCC ATCAGCTGCT TGCTGGTGGG | 180 |
| GAATGAGTAG TATGGAGTAC CGTCGAGCTC GCCGAGGAAG CTCCCGTACT GCGAACACAG | 240 |
| TGCATGGCAC ATCTTCGTGA TGCGCCCGAT ATTGTTGTTG CTAGAGCAAA TAAACGAGCA | 300 |
| CAGTGTCTCC CAGGGTTCCT GTCGCAGTAT TCGCACGCCA CGATGTGTTT TCCCGATGAA | 360 |
| ACGTGTGTCT GCTTTCTGCC ATTCTGCTAA CAAAGCCTCT AGGTTCACCT CCATCCGTAG | 420 |
| GTAGCGCATC AGCCATTGTC GTGCCGCCCC GCTGCAGTCG TCATCTTTAT TCCCAGCTAC | 480 |
| GCTGAATTCA ATACTGCACT GATCGGGCTG CTTCAATACA ATAATACGAT AGCCCAGCTT | 540 |
| GTCATTTAGT AGCATGCTCG CGGAATAGTA CCTTTTCTCA TGATTCCAGA TCCACCTGAA | 600 |
| CGCTTGACCA CATTGCAATA CATGGTCCAG GACTATTTCT CCCTTTGGGA ATATCAATCT | 660 |
| GTTAAACTTC ATAACTGTCG ATACAGCACT GACCTCGCTC TAATAATCAG CGTCACGGCG | 720 |
| CTGGCTCGAG CATGTT | 736 |

(2) INFORMATION FOR SEQ ID NO:879:

(i) SEQUENCE CHARACTERISTICS:
        (A) LENGTH: 702 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1551RP (xi) SEQUENCE DESCRIPTION: SEQ ID NO:879:

| | |
|---|---|
| GATCTCACGT GAATCGGATA TCTGCTCAAC GGCCAATTCT CGTATATTCT GACGAGATCT | 60 |
| TGGCGTCAAT TACGTGCACT TTGGCCGAAG CCTTCGCACG AGCTTCTACG ATACAGAATG | 120 |
| CTGCCAGGTG CATCTTAAAA AGCGGGTTTA CAGTGAGCCC TCCGTCCTTC AGGGCACCAG | 180 |
| CCCCTAACTG TACATAGTTT CTGTTATGTA GTTTGCCTTT CCTCGCGATG CCTGCCTCTT | 240 |
| GTGGAACAAA AACAGGCGGT AGAAGGAAAT TCCCGTGCGT CATCGGTATC GGACGGCGTC | 300 |
| TGCCTGGATC TGCGGAGTAG CTTTATGAGC CATTAGTGAG GAACGCCAGT TTCGACGACA | 360 |
| GATTTAGTCT TTTCTGTGTT CCTGCAAACA GGCTTGGAAT GTATCAGCGC GCTGGCGCAG | 420 |
| CGACAGGCGA CACCGCTTCA CATAGGGAGA GGCCACCCAC TGAACACGCG GTGCACTGTC | 480 |
| AGGGGGCGCA GCGTACTGCC TACAATGGTA TCGTCCGCAA ACGGCAGGCC AACCGGCAGA | 540 |

```
GCGGGCATTT AGATCTAAAT TTATCAGCCC ATGGACGGAT GGATTTACGG CAGCGTGTCG      600

CCGCAGCACG GGGCACGCCA GACTGCGAGG TGGCAAATAA TTCACATAGC AACCTGCATT      660

ATAAACATCC CAAGTCATTA AACTTACTAA ATATTGTTGC GT                         702

(2) INFORMATION FOR SEQ ID NO:880:

(i) SEQUENCE CHARACTERISTICS:
        (A) LENGTH: 735 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1551UP (xi) SEQUENCE DESCRIPTION: SEQ ID NO:880:

GATCCCGGTG AAGCTGCGCA ACTGCACGGT GCGCTACGAG GACCCGGGCG GCGCAGTGGA       60

GCTGGCGCAC TACGACTACT CGAGCGAGCT GGACGCGTAT CTGAAGGATA TCGAGGTGGA      120

GTACGAGGTG CTGGCGTACA ACTGGCCGAC GTTTCTGGCG TACGTGCAAG AGCTGGAGGA      180

GGGGGAGTTC CGCGAGTTCT TCTGCGAGCT GCTGCCGTAC GCCGCGGAGA ACGAGGTGTA      240

CGGCGCGAAG CTGTGGGCGG GGCTCGTGAA GGAGCGCTCG ATGCAGGAGC TGATCACGCG      300

CAGAAAGCGC TCGTCACTCA CGCCTTGTCG CGCGCGAGGA GGAGACGCAG CGACGGCAGG      360

TGGAGGACGA CTGGCACAGC AAGCTCGACG AGCGCGACCG CTTCCTGCGG CTGCGGAGCA      420

AGCTCGTGGC CAAGCGTGCC AAGAAGACCA AGGACGCGCT GTGGACGGTG CTGTGGGAGC      480

GCTTCCAGAG CGACGCTAAG ATCGAGAAGA TGCGGCGCCG CAACGAGGCC GCCACGCCCG      540

AGGCGGGCGG CGACGAGCTC CTGACGCCGG CGGAGCGCTA CGCGCTGGAG CAGGGGCAGG      600

GCTTCCTTGG CGCCTGTCGT CCCTGTCGCG GAGCCGGCGC CGGCCCTGGC CGTGCCCTGC      660

AACGAGCTTC CCGATGAATA CTGCATCACC AAGACTGACT TCGACCGGCT CGCTAGCCAC      720

GGCATCCCGG TCGAG                                                      735

(2) INFORMATION FOR SEQ ID NO:881:

(i) SEQUENCE CHARACTERISTICS:
        (A) LENGTH: 804 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1552RP (xi) SEQUENCE DESCRIPTION: SEQ ID NO:881:

GATCGTCGGC TCATGCCACC ACAACTTCCA CGTCCACTGC ATCTACCAGT GGCTCAACAC       60

CTCCACGTCC AAGGGCCTCT GTCCGATGTG CAGGCAAGCG TTTTCACTCC GGGAGGGCAT      120

CCGCATTAAC GAGCCCCACC GCGACAAGTT CGAGAAGGTG TTGATGAAGG CGCGCCAGCA      180

GAGCGTGGTG AGCGTCGCGG GCGCCAACCC GGTCGGCCGG GACCAGGACG ACGTCATCAT      240

CKACCAGGAG TTCATCCGCT GACACTAACT AGCCTGTGTA CCCATGTAAA AATAATGCTT      300

CCAACCAGAT TCGAACTGAT GATCTCCACA TTACTAGTGT GGCGCCTTAC CAACTTGGCC      360

ATAGAAGCAA TACGAGCGTC TAGCGGACTG CGCCGGGCTA TATGCGCCGG GCGTGACCGC      420
```

```
GACGAAACGC TGGCGCCCAA ATACCTGATC CCAGGTTTCC AACGCTGGTC ACGCAACTTC      480

TGCCACGTGC ACTGCACACC ACGCCAGCAC TATATAGCCC CGCACCCGCC AGGCGTTCTT      540

GCCAGGTCAC CGCGTCCAGC TGTGCTGGCA GCATTCCACC TGAAAAAGTT TCACCAGCAG      600

AAAGACTTTT CCACTTCTCA ATAGCACTTC TATCCCCTAT TTCCTCAGCA GTTTTGCAAT      660

GAGCTACACT ACCAGACAGA TTGGAGCTAA GAACACCTTG GACTACCGGG TGTTCATCGA      720

GAAGGCGGCA AGGTCGTCTC GCCGTTCCAC GACATCCCAT TGTACGCGGA NGAGAGAACC     780

AATCTTCNAC ATGGTGGTGG ANAT                                             804

(2) INFORMATION FOR SEQ ID NO:882:

(i) SEQUENCE CHARACTERISTICS:
         (A) LENGTH: 490 base pairs
         (B) TYPE: nucleic acid
         (C) STRANDEDNESS: single
         (D) TOPOLOGY: linear (ii) MOLECULE TYPE: DNA (genomic)

(vi) ORIGINAL SOURCE:
         (A) ORGANISM: PAG1552UP (xi) SEQUENCE DESCRIPTION: SEQ ID NO:882:

GATCTTGCAG ACACGCCTGC GCCCGTAGTC CGTGCGAGTG CAGACTGCGT CGCCGAATAA       60

ATAGCTTTGT GCCAGGCGGT CGCCGAGGCG TTGCGGGACT CACCGCATAA AAGAAACACG      120

CTGCGGCCGC GCGGCCGCAA AGCAGCCAGG CGCAACGGGC GCGCCGCAAA AGCAACCGTG      180

ACACACGATA TGGCAGATTC ACRTACATAT TATACATAGC CGGCCGCGGC ACGCGGCTCA      240

GCCGCCGAAG CCGTACAATG TGCGGCCCTG GCGCTTGAGC GCGTACACGA CGTCGAGCGA      300

GGTGACGGTC TTGCGCTTGG CGTGCTCGGT GTAGGTGACG GCGTCGCGGA TGACGGACTC      360

CAGGAACGAC TTGAGCACCG CGCGCACGTC CTCGTAGATG AGGCCGGAGA TGCGCTTGAC      420

GCCGCCACGG CGGGCCAGGC GGCGGATGGC GGGCTTGGTG ATGCCCTGGA TGTTGTCGCG      480

GAGGATCTTG                                                             490

(2) INFORMATION FOR SEQ ID NO:883:

(i) SEQUENCE CHARACTERISTICS:
         (A) LENGTH: 691 base pairs
         (B) TYPE: nucleic acid
         (C) STRANDEDNESS: single
         (D) TOPOLOGY: linear (ii) MOLECULE TYPE: DNA (genomic)

(vi) ORIGINAL SOURCE:
         (A) ORGANISM: PAG1553RP (xi) SEQUENCE DESCRIPTION: SEQ ID NO:883:

GATCCGCAGG TCGTACACGT TCACAAACTG GTCCGGGTAC ATCATGTTGA ATCGCTTCGA       60

CTTCCCCGCC GTCACCAGCG TGTGGTCGCG GAAATCCATC GAGCTGACCA TGCACGAGTG      120

CCCCGAGAAC GTCTTCACCA CCGTGTTGCT GTTTGGGTCC AGCAGGTCGA GCATCCCGTT      180

CTGCCGCGCA ACCGCCATCA GTCGGTTGCT CGACTGCATC AGCTTCACCT TCGACGAGTA      240

CTGCACCGTG TTGCTCAACC GCCCCTTCAC CAGGTCCACC GCCACCAGCC CACTCGCCAG      300

GTTCGTCCCC CCGCAGTACA CCGTGTTCTG CGAGTTGCTG CCGTAGCACA TCGCCCGCAT      360

GTCGCATAGT TGTGCGATGT CCGCCGACGT TACGTGCAGT TTCGTCACGC TGCGCCGGTT      420

CGCGAAGTTC AATGACTCGC CGCCCAGCGA CAAGACGCCC TGCTTGTGGC TCAGCAACTC      480
```

| | |
|---|---|
| CACCACCGGC TCTGCCCCGA TGTGTGCCGT GTGCCGCGTG TATAGCGAGT ATGACGGGTC | 540 |
| GTACGACGAC ACCCGTCCGT ATGTGTCCCC ACCCAGATCA GATTGACGTC CTGGTCAAAC | 600 |
| GCCATCTTCG TCGCGCTCTT CTCCTTGGCG TCGTAAGCCC AATACAACTT GCGCAGGTGC | 660 |
| TCGGTGAGCT CCACCGGCGA CTGGTATGAA A | 691 |

(2) INFORMATION FOR SEQ ID NO:884:

(i) SEQUENCE CHARACTERISTICS:
        (A) LENGTH: 708 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1553UP (xi) SEQUENCE DESCRIPTION: SEQ ID NO:884:

| | |
|---|---|
| GATCCGCGCT GTGTGCCCCC ACGCAATGCC TACCTGTTCA CCTGTCTCCA GGCTCCACAC | 60 |
| CCGAATCGAG CGGTCATCCG AGCATGATGC AACCAGTCGC CCGTCGTCGC TCACCACCGC | 120 |
| GCAGAAGATC GAGCCCTCGT GGCCCTCCAG CCGCTGCACC ACCGCCCCG TGTGCAGCTC | 180 |
| CCACACCACC ACCCCGCCCA TCACCGTCCC CGCGCACACA TACACCGCAT CGCCCACCAC | 240 |
| CTTCACCGAC CCCGAGTACA GCAGCGACCG CTCACCCGCG TTGATGCTGC GCACCACACG | 300 |
| CATCTCCAGG TCCATCTCCA GCACGCTGTT GTAGCACGTC AGCAGGTAAC ACGAGCGCCC | 360 |
| GTCCGCGCTG AACGCCGCCC CGAGCACCCA CTCCGGCGTC ATGTACTCGT GATACTTCAG | 420 |
| GTTCCGCCGC GTCATCACGT CCTCCAACTC CAAGATGCTC ACCGACCGGT CCCCATATGC | 480 |
| AATTACCCAC CCGTCCTGCA CGCATATCCC GTGCACCTTG TTTCGCTGGA AAACCCGGCA | 540 |
| GCGGTTCAGC AGCACTCCGC CGCGATACTC GTATACGTAG ATTTCCGCGC CGCACCCTGC | 600 |
| TAGGCACCTC CCGTCCCCGA GAATCCGCAC TGCAGTGCAT GGCGCAATGT CATTGACCTT | 660 |
| ATCCAGCGAC ATATTCATCG TTTAATCGAC TATGATCCCG ATCTAATG | 708 |

(2) INFORMATION FOR SEQ ID NO:885:

(i) SEQUENCE CHARACTERISTICS:
        (A) LENGTH: 705 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1554RP (xi) SEQUENCE DESCRIPTION: SEQ ID NO:885:

| | |
|---|---|
| GATCAAACTA GGAATTTTGT ATAATACTGA AGAAGGTCCC ATATTCAAGT CTCTATCCAG | 60 |
| CGATGATGAG GAAGTGGGTG AGATTGTGCT GCACGACCTG ATGAACAATC TCGATTTCAT | 120 |
| AACTATGGAT CATCCTGACA GATCGAGAAA CCAAACTCAT CAAGATAGAC CGATGATGAT | 180 |
| CAAGAACTAG TTTGAGATCC CTCTGCTACA AACACATACC TAGATTTCTC ATATTTTATA | 240 |
| CTGAATACAT ATAATATATC ATTTAACTGT CTTCATTCAT GAGACGTCGT CTAAGTTCTG | 300 |
| TGCTGCTCAA CTTGTTTTTC CACTTGTCAG CCTCTTCGCC CCCAGTACG TTCACCACAT | 360 |
| GCACGGCTAG CTTCCTCATT CCTTTGCTCT CACGCGTATC GTTGATTGTC TGGGCACCGG | 420 |

```
CCACAGTTTC CTCACTCACT ACCAGGGCTT CGATACCAGG TTCGCTACCC GTGGGCCCGC      480

ACACGTCTTG TAACGCAAAT ATTTTGATTT CCAGCCCCGG TTTCAGCCTG TGAAGGAAGC      540

TGCACACGTT ATCGCATCGT TCGTCGAAGG ACTGAAGCTG CTCCCTGTAT TTCTTGTTCC      600

GCAGCAGTTC TTCATCTGTA ATCCCCACGA TCAGCCGGGA AGCAGTCACG AGCGCGGCAA      660

CACTGAGCAA TATTTTATGT CCGTCGTGTA AGTGGTCGAA AGTGC                      705

(2) INFORMATION FOR SEQ ID NO:886:

(i) SEQUENCE CHARACTERISTICS:
         (A) LENGTH: 727 base pairs
         (B) TYPE: nucleic acid
         (C) STRANDEDNESS: single
         (D) TOPOLOGY: linear (ii) MOLECULE TYPE: DNA (genomic)

(vi) ORIGINAL SOURCE:
         (A) ORGANISM: PAG1554UP (xi) SEQUENCE DESCRIPTION: SEQ ID NO:886:

GATCACTGAG GAAATCAAAA CCTTGAGCAG CTTCCCTGTG TTGCGGTTGT ACGGTGTGGA       60

CTGTGCCCAA GTTGAGACTG TCCTCCAGGC CAAGGCTCCA GGCCAAAAGC TCTTCCTAGG      120

TATCTTCTTC GTCGACCAAA TTGAGGCCGG CGTGAAGGCC ATCAAGGAGG CTGTTCAGAA      180

GCATGGATCC TGGGACGACA TCGACACCAT TTCTATCGGT AACGAACTTG TGAACAACGG      240

CCAGGCGACC GTGGACCAGA TGGCTGGTTA CATGAAAACT GGCCGCAAGT GCCTCGCTGA      300

GGCCGGCTAC AAGGGCCCAG TTGTTTCCGT GGACACTTTC ATCGCTGTAA TCAACAACCC      360

TGGTCTATGT GACCTATCAG ACTACATGGC TGTCAACGCC CACCCATACT TCGACTTCCA      420

CACTTCTGCT GCTATGGCCG GCCCTTGGGT TTTGCACCAG ATCCAGAGAG TCTGGAGCGC      480

CTGCAACGGT AACAAGAAAG TTGTCATCAC CGAGACCGGC TGGCCTACTC AGGGTCAGAC      540

TTACGGCAAG GCCATTCCAT CCAAAGCCAA CCAGAAGATG GCCTTGGAAT CTATCAGGGC      600

CACTTGTGGT GATAGCGCTA TCCTATTTAC TGCTTTCGAC GACTACTGGA AGCCAGATGG      660

GCCCTACGGT GTCGAGAAGT TCTGGGGTAT GCTATAAGTT GCCGTGTGCT TCTTTATGAC      720

CTGTCTC                                                               727

(2) INFORMATION FOR SEQ ID NO:887:

(i) SEQUENCE CHARACTERISTICS:
         (A) LENGTH: 712 base pairs
         (B) TYPE: nucleic acid
         (C) STRANDEDNESS: single
         (D) TOPOLOGY: linear (ii) MOLECULE TYPE: DNA (genomic)

(vi) ORIGINAL SOURCE:
         (A) ORGANISM: PAG1555RP (xi) SEQUENCE DESCRIPTION: SEQ ID NO:887:

GATCATACAC GCATTGCAGG TATACATTAT AGTGCTCATA ATTATCGGAT TGCAAATAGA       60

ATGGGGCCCT TACCGTAGTA CTGTCTTGGT AATGCAGCGA CGCTCAGGCT TAAGAAGCTT      120

TTTGTTCTCC GTGTATTACT AACAAAATAA TTTCCTCGAG CACAGGGAGT AGAGATGAAT      180

TACATAATCC ATATGGACAC CTCGTCACCT TCCAGCGACA TTAACATTTC CTTATGAATG      240

CCCAATAATG GTGCCTAAAT GATGTGCTTG GTGTAATGCG CATTATAAAA TGTATGTGGA      300

TTATATATTG TTTGTAGCAT CTAGTAAAAC CATGGTAGCG AGGTCTTTGG CCATACCCTT      360
```

```
CTGAAGAGAG ACATAGCAAC AGTGTCTTGT GCAGACAGTC TGCCGTCGAA TGTTGCCTTG        420

AAGTAACCAT GAGTACCAAG ACTCTCCTTA ATGAAGCCAG AGCGTCCAGA TTTCGTGAAT        480

AGTGGGATCG ACTTGAACCA CTCGACATCT TCTGGCCTAA AGAACATATA GCGCACTGTG        540

ACGACGCGCT TGTGGAACTT GAATGGATGG GCAGTTAATA TGATTCTCTT GGCCAATATC        600

CGTGTGTGGT CTGCGTTCAG GAACGTGCCG TGGCCCACGA ACGTCAGGCC CTTTGGATCA        660

GAAGGGTTTT CTTTGAAGTA GATGGCCGGT GACTGGGTCA GGTCCAAGGG AA               712

(2) INFORMATION FOR SEQ ID NO:888:

(i) SEQUENCE CHARACTERISTICS:
        (A) LENGTH: 689 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1555UP (xi) SEQUENCE DESCRIPTION: SEQ ID NO:888:

GATCTGGGAA ACAAGCATTC CAACCTAGTT GGAATGGCTG GCAATTAGCA GCTGCGGCAA         60

GGCAGATAAA GCTAACTGTG GCATAGTTTC CGTGAGTTTT GATTCGGTTT CTCAAGCAGG        120

AATACTTTGC TGGCCGCCAC GGNCGCCGTT TTTATACTGT CAGGCCAGCC CGCGGCCTGC        180

CGGGTAATGC CTGGCAGACC CGCTCTAGGG CACGCCGAAT CGCCCGTGAC AACGCCTGCC        240

GCCGCAAGAT GAGCACCTAA AGGGCCGGCA GCCTCCGCTA GACAACCTGA TGGTAACGTC        300

GTATTGTAAT ACTTAACTTA TACAGGGTTT ATTGATTATA TTACTCAGAA ACTGCCGTGA        360

GACCCACAGC CCGCCCGCCG AATTGTGTAC AGTAGGCGGC AGCGGGCCGC CCGCCGCTCT        420

TAACGGTACT TGTGGAAACC AATGTCGTTG GCCTTCTCTC TGAAGCACTG ACGGCAGATG        480

TTCAAGCCGT ACTTTCTGAT CAAACCAGAG TGCGAAGCGC ACACGCGGCA CTGGCGGGAG        540

CCCTTACCGT AGTTTCTTGG GTGGGAGAAC CAAACGTTTT CGTGAGCCAT CTTGTCTGCA        600

ATGCGTTAGT ACTCTGTCTG ACCGCTTGGA AACGCTCCGG CCCTCGTTGA GCTGCCCACA        660

CGCTCGGCGT CTGCGGCGTC CTCATTGCC                                         689

(2) INFORMATION FOR SEQ ID NO:889:

(i) SEQUENCE CHARACTERISTICS:
        (A) LENGTH: 700 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1556RP (xi) SEQUENCE DESCRIPTION: SEQ ID NO:889:

GATCAACCAG TCGGCCGAGT CCTATACGAC CGGCATCACG CTGGTGTTCG AACTTCTCGG         60

TGACCCTCCG ACGTACCTGC CTAAGGATAG TTTGCCGCCA GAACACCCTG ATGAGGGCTT        120

CACGAGTGCT TCTGCGTCCG AGCTGCAGCG CCGCTTTGCA TTCAAGTGTC AAAATCCACG        180

AGTCACCCTC GTAAATGACT TCACGGTAGA CGTATACCCG GCCTCAACCT TCCAGCTGCT        240

CAATGATAAT ATCTGCTTGT GTTTTGATAT TCTGAGAAGG CAGAAGTGGT GGCACACCGT        300
```

| | | |
|---|---|---|
| CTTATATCCT ATTTCCCAAC TTTTGCTGCA TCAAGGCCAG GATTCTGCGG TAGGAGACGC | 360 | |
| CCCAGCACCC GCAGCCCAAC CCCCGCTCCA CCGCCGCCGA TCAAGCAACA AGGGCTGTCG | 420 | |
| CCGAGCAAGT GCGGCCGAGT CAGCCACGCT AGGGGACGAA AATATGCACC AACTTACCTT | 480 | |
| AACGGAAATT ATGAACAAGT CTGTGATTCC CGAAGATGAC CGATGATGGA TGACCGCATT | 540 | |
| GAGCTCTATG TTAACGAGAA CTACGTCTAT CTGGGGACCA GGAGGGTTGC AGCTTCTATA | 600 | |
| ACGATCCGAT TGAGAGGTGG GAGGCGTTTG TAGAGTCACT AAGACAGATG CTTACGTAGG | 660 | |
| TATATAATTC TCATCTCACG CCTGGTATGT ATGCGCTTGT | 700 | |

(2) INFORMATION FOR SEQ ID NO:890:

(i) SEQUENCE CHARACTERISTICS:
        (A) LENGTH: 718 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1556UP (xi) SEQUENCE DESCRIPTION: SEQ ID NO:890:

| | |
|---|---|
| GATCCGAATA ACGTCCACAT AAGGGAGAGA CTAGAGGCTT TGACTGCCCA GCTAGCCAAC | 60 |
| CCAGGGGCCC AGCAGCCTCA GCAGCAGCCT CAACAGCAAC AGATGCAACA GCCTAGAGGG | 120 |
| CCAGCACCCA TTATGTTGCA GCCAACATTG CAGCAGCAAG ACCAAACAAA TCCGTTGAAT | 180 |
| AACAAACCTG CGTTCTACCG GTCCTCTCCC CACGGAGTTG CGGTTGCCGG AACAGAGTCC | 240 |
| GCAGGCCACA CACCAATGTC AGGACGGCCT CAGCCGTTGC AGCAGTTGAA CAATAACGGA | 300 |
| AGTATCCTGG AACCGTCATT GTTGCCGCAA AAGAGGCCTA TGGAGGGTGG AATGGATACA | 360 |
| TTGGTAAATG CCATTTCGCA GCAGGAGTTG CAGCAACATC AGAAGAAACA TATGCCTTCT | 420 |
| CAGAACCATC CTAGTTTGGC CCTGGCTACA GGACAGCCGC AGCAGTTACC ACCCGATGCC | 480 |
| GCTCCCATAA TACCGCCCGA AAAGAAAGGT GCGCCTCTCC CCCAGTTTCA GAAAACTGAA | 540 |
| CCAGAGCATG CGGCAAAAAG ACTGAAGCAC GAGCAGAATA ACGTTTAAGA GCAACCGGTC | 600 |
| CGGTCTCGAA TATACCTTCG ATTACGCACC CAGCTTCCAT GGAACATTCT GGTCCGGGAG | 660 |
| ATCAGAATCA CATTCTATCT GGGCCTTCAG TCCACGCAAC CCACGTGTTA CTCCGGTA | 718 |

(2) INFORMATION FOR SEQ ID NO:891:

(i) SEQUENCE CHARACTERISTICS:
        (A) LENGTH: 720 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1557RP (xi) SEQUENCE DESCRIPTION: SEQ ID NO:891:

| | |
|---|---|
| GATCAGGCGA GACATTGCGT AGAAATATCA ATTGGTTCCA GAGGAGATCT GTCTCCTGGT | 60 |
| CATTGTAGAG AAGCGGCCAG ATATAATTGT CCAAAGTGAA CTCGTCTTTT TGAGAAAACA | 120 |
| CGCTTTCATA CACAGCGTCC GACTTTTGGG CTAGACCATA AGCAAGGTCT ATAACTTCCG | 180 |
| TGGCAGTATA ATTCCAGACC GGCGGTGGTT GCGGCGGGAC AAGGGACTCC CAGTACCCAA | 240 |
| GTAAATCCTT CGTCATTGAG CTTTTTTAAC ACAGAGCCAA CTAAGATCGA CATGGTAAAC | 300 |

```
GACGCGATTA MTTTTGTACC ATTTTTATAG GAGACCAGAT ACATTTACAG AAGCACCAAC      360

CGCAATCGTT TTAATCGGTG CAATCAGTGC CATTCTTGCA GCTGGGTCCA AACTCTAGAT      420

TTACAAACCC CGCACGAATT AGCTAGTGTT GAACCAGCGA ACATGTAAGG AGTTTCATTT      480

CCCCACACTA TTGAAAACTA CTGCGGTGAA CGCAGGTGGG GCCGCATTAA CGCCATATAA      540

CTGTGCGGTT TGATAACAAT TATCTCATAT TGTCTTTTTT ACGCACAAAT ACATCCACTC      600

ATAGAGAGCA TTACGCCAAT GCAGTCAAAT ATAACGGAGA ATTTGCATAT CAGTACGTGG      660

AATCGCAGCA GTTGCTGTGA TTTTACTATT GATAACGGGC GCAGCATAAG GGCTGTGTTT      720
```

(2) INFORMATION FOR SEQ ID NO:892:

(i) SEQUENCE CHARACTERISTICS:
        (A) LENGTH: 726 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1557UP (xi) SEQUENCE DESCRIPTION: SEQ ID NO:892:

```
GATCCGCGGA TTTGGGCACC ACAGGGTAGT GTGGCCGCAT CAAATGATGG CACACACGCG       60

ACGTGCGTAC TCAGCCCCCT TATTTGATTT GAAGAACAGA TTGATTAGGT CTGATCCTAT      120

AGCTCTGGGC AAAGCGGGGC GCCTTGGCGC CTGTGTGGCC GCGAAGTATC GCTTAGGAAA      180

ATGCTGGTGA ATGTATATTA TACGCTGACG GGAGCATTGC AGTCAGGTGT CATGTATGGA      240

CTTGCCTGCG ATTAACTATC GCAGCAGCCA TCTGATGCTT ATGCACATCA ACTAGCACAG      300

CAGCCATATG ATGCTTATTC ATACCGGCGG CCTATCGCCA TCTTCTTCAT ATAAAGGCAG      360

TGTTGTACAG ATAGGTGCAT TGTCCTCTGA ATTCCAAAAG CTCATCGCGA GTGCAGATGA      420

AAGATCTCGC TTCTTTGGTC CCGCCGCAGG CGGCACCATC GTGGAATTTC AGTGCACAAG      480

ATGTTATTAG TCTTAGCCAT CAATTGATCA ACCAAACCGA GGCGGTTTAC CACAACGTGT      540

TACAAGAAAA GCCACCAACA ATTGACAATT ATATCATGCC TCTAATATAC CATGAGGAGG      600

AAACAGACCT GCTATGGAAC CAGTTGGTGT TTCTCCGCAA TGTTTCGCCC GATCCGGAGA      660

TTCGTGAAGC GTCGAAGAAC GCAACATCCA TGCTGGACGA CTGGATTATT GGCCTTACGT      720

CAAAGT                                                                726
```

(2) INFORMATION FOR SEQ ID NO:893:

(i) SEQUENCE CHARACTERISTICS:
        (A) LENGTH: 708 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1558RP (xi) SEQUENCE DESCRIPTION: SEQ ID NO:893:

```
GATCTATTTT GCCGACTTCC CTTATCTACA TTATTCTATC AACTAGAGGC TGTTCACCTT       60

GGAGACCTGC TGCGGTTATC AGTACGACCT GGCATGAAAA CTATTCCTTC CTGTGGATTT      120

TCAAGGGCCG TCGTAAGCGC ACCGGACCCA GCATAGATGC TGGGCTCTTC CAGCCATAAG      180
```

-continued

| | |
|---|---|
| ACCCCATCTC CGGATAAACC AATTCCGGGG TGATAAGCTG TTAAGAAGAA AAGATAACTC | 240 |
| CTCCCAGGGC TCACGCCGAC GTCTCCACAC TCAGTTACGT TGCCGTGAAG AATCCATATC | 300 |
| CAGGTTCCGG AATATTAACC GGATTCCCTT TCGATGGTGG CCTGGAAAAT CAGGCCTTTG | 360 |
| AAACGGAGCT TCCCCATCTC TTAGGATCGA CTAACCCACG TCCAACTGCT GTTGACGTGG | 420 |
| AACCTTTCCC CACTTCAGTC TTCAAAGTTC TCATTTGAAT ATTTGCTACT ACCACCAAGA | 480 |
| TCTGCACTAG AGGCCGTTCG ACCCAGCTTT ACAGCTAGG CTTCGTCACT GACCTCCACG | 540 |
| CCTGCCTACT CGTCAGGGCG TCATATTTGC CCTGACGGTG GAGTATAGGT AACACGCTTG | 600 |
| AGCGCCATCC ATTTTCAGGG CTAGTTCATC GGCCGGTGAG TTGTTACACA CTCCTTAGCG | 660 |
| GATTCCGACT TCCATGGCCA CCGTCCGGCT GTCTAGATGA ACTAACAC | 708 |

(2) INFORMATION FOR SEQ ID NO:894:

(i) SEQUENCE CHARACTERISTICS:
        (A) LENGTH: 671 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1558UP (xi) SEQUENCE DESCRIPTION: SEQ ID NO:894:

| | |
|---|---|
| GATCGGGTGG TGTTTTCTTA TGACCCACTC GGCACCTTAC GAGAAATCAA AGTCTTTGGG | 60 |
| TTCTGGGGGG AGTATGGTCG CAAGGCTGAA ACTTAAAGGA ATTGACGGAA GGGCACCACC | 120 |
| AGGAGTGGAG CCTGCGGCTT AATTTGACTC AACACGGGGG AAACTCACCA GGTCCAGACA | 180 |
| CAATAAGGAT TGACAGATTG AGAGCTCTTT CTTGATTTTG TGGGTGGTGG TGCATGGCCG | 240 |
| TTCTTAGTTG GTGGAGTGAT TTGTCTGCTT AATTGCGATA ACGAACGAGA CCTTAACCTA | 300 |
| CTAAATAGTG CTGCTAGCAT TTGCTGGTTG CGCACTTCTT AGAGGGACTA TCGGTTTCAA | 360 |
| GCCGATGGAA GTTTGAGGCA ATAACAGGTC TGTGATGCCC TTAGACGTTC TGGGCCGCAC | 420 |
| GCGCGCTACA CTGACGGAGC CAGCGAGTAT AACCTTGGCC GAGAGGTCTG GGTAATCTTG | 480 |
| TGAAACTCCG TCGTGCTGGG GATAGAGCAT TGCAATTATT GCTCTTCAAC GAGGAATTCC | 540 |
| TAGTAAGCGC AAGTCATCAG CTTGCGTTGA TTACGTCCCT GCCCTTTGTA CACACCGCCC | 600 |
| GTCGCTAGTA CCGATTGAAT GGCTTAATGA GGGCCTCAGG ATCTGCTTAG AGGAGGGGGC | 660 |
| AACTCCACCT C | 671 |

(2) INFORMATION FOR SEQ ID NO:895:

(i) SEQUENCE CHARACTERISTICS:
        (A) LENGTH: 622 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1559RP (xi) SEQUENCE DESCRIPTION: SEQ ID NO:895:

| | |
|---|---|
| GATCCAGAAT CCAAGTTGCG TGTTCGTAGC AACCGCCGCC TGCGCAGGTT ACGAAGCAGG | 60 |
| CTAAGGAAAA GGGGCCTGGA TGCCGAGCAC ATCTCAGAAG TAGTACAACG CATAAAGGAG | 120 |
| AAAAGCAAGC CAAGCGCTGA AAACAAGACC GTGCGTGAGC GGACTCCCTC ATCCGCTGCG | 180 |

```
GTTGCTGATC CTAAGAAGCG GGTAGTCGAT GTCCCAAACA ACCCGCCAAA CAAAGTATTG      240

CTCGTACAGG ACCTGCCAAC AGACATTACC GAGCAAGAGC TGGTGGATAT ATTTGCAAAC      300

GATAAGTTGC TCCAGGTAAG ACTAGTCCAA GTCCGGCAAC TGGCGTTTGT AGACTACGCC      360

GATGTACAGA GCGCTACGGC GGTCAAGAAC AAACTGGGTA CAAATTATGT GATCAAAAAT      420

CAAACAACCA TCATAGGGTA TGCGAAGTAC ATAGGGCCGT GGGGATATGG GTTCTTACCA      480

GTGGGTGGGA ACCCGACAGA TCATTTAGGT AACTACATAA TGATAGTATT TACMAGACTC      540

CTTAAGTCGC ACGTGCCTCG ATGTCATTTC CCAAAGAGGA CTGTTCTCAT AGCTGTGAGC      600

AACGACTCTT TGCTGCGTCC TT                                              622

(2) INFORMATION FOR SEQ ID NO:896:

(i) SEQUENCE CHARACTERISTICS:
         (A) LENGTH: 643 base pairs
         (B) TYPE: nucleic acid
         (C) STRANDEDNESS: single
         (D) TOPOLOGY: linear (ii) MOLECULE TYPE: DNA (genomic)

(vi) ORIGINAL SOURCE:
         (A) ORGANISM: PAG1559UP (xi) SEQUENCE DESCRIPTION: SEQ ID NO:896:

GATCCGATGA CCGTCATGTT CTTCTACAAG AACAAGCACA TGCGATGCGA CTTCGGCWCG       60

GGGGAACAAC AACAAGATGA ACTTCGTCGT TGACAACAAG CAGGAGATGA TAGACATCAT      120

AGAGACGGTC TTCCGCGGCG CCAGGAGAAA CAAGGGGCTG GTGGTGTCGC CGTATGACTA      180

CAACTACAAG CGGATACAAT AGAACATTTT TTGCAGCTAG TGTTGTCCCA CGATAGAAAG      240

TTTATACGCA ACCCGGCACA GGCGCCGGGT TGCTTGGCTC CACAGCTGGC GATGGAGCCT      300

TGGGTAGGGC CCTGCTGGCC ATTATTCCTC TGACTCGACC TTACGCCTAT AGATGGTGTC      360

TGGGCTGTTC TGGCGGTGAT AGTGAAAATT TTTTGGCTTT ACGCTCCACC GGGTTCAGGG      420

CTAGGCAGCA GGATAAGTAC WTAGGTCTTT CTGCTTCAGG CATTATATAA CCTCAAGCGA      480

GCTTTTCAGA CCTTTTAGGC CAATATATCT CCAAAGTGTG GGCATCTGGA CTATTAAGCA      540

GGAGGTTCTA TTCCAGCGTC ATCAAGAAAT CTGTCAGAAT AAGAACCATG GCCTCAGAGG      600

ATGTGCAACT GGCCAGGAAG GCTGTTGAGT TTAACAGGGA GAA                       643

(2) INFORMATION FOR SEQ ID NO:897:

(i) SEQUENCE CHARACTERISTICS:
         (A) LENGTH: 139 base pairs
         (B) TYPE: nucleic acid
         (C) STRANDEDNESS: single
         (D) TOPOLOGY: linear (ii) MOLECULE TYPE: DNA (genomic)

(vi) ORIGINAL SOURCE:
         (A) ORGANISM: PAG1560RP (xi) SEQUENCE DESCRIPTION: SEQ ID NO:897:

GATCGCGCGG AGGTTCTGTA AAACCTTCC ATGCACAAAC CCCACACCAT GCTCCCGCTC        60

GTCCTCTTCA AACTCCTTCG CACTAATGGT GCCGTCGTCC ACGACTTTAT CATTCCCGTC      120

AAACACTAAG TCAGGGATC                                                  139

(2) INFORMATION FOR SEQ ID NO:898:
```

(i) SEQUENCE CHARACTERISTICS:
        (A) LENGTH: 139 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1560UP (xi) SEQUENCE DESCRIPTION: SEQ ID NO:898:

GATCCCTGAC TTAGTGTTTG ACGGGAATGA TAAAGTCGTG GACGACGGCA CCATTAGTGC      60

GAAGGAGTTT GAAGAGGACG AGCGGGAGCA TGGTGTGGGG TTTGTGCATG GAAGGTTTTT     120

ACAGAACCTC CGCGCGATC                                                 139

(2) INFORMATION FOR SEQ ID NO:899:

(i) SEQUENCE CHARACTERISTICS:
        (A) LENGTH: 688 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1561RP (xi) SEQUENCE DESCRIPTION: SEQ ID NO:899:

GATCCAAATA AGCGTGCGGT CCATACAAAT GAACGGTTGA GTGAAGCTAC TTCGCTCGGT      60

CGCGTATGAT TACTCGCACC AGGCTCTGGA TGACGCCGGG GGAGATGGCG CTGCTGCTAC     120

GGCAGCCAAT ATATACATCT TCTATAGGTC TAATTCATGT CCGCTTTTTA AAAAATGGCT     180

TGCGTCAATT TGTATGTAGT AGGCTATGTA ACGGCTCAGT CGGTGGACTC GGCGAAGCGT     240

TCCTGGATGG AAGCAAAGAG CTTTTCGAAC TCTGCGTGGA CCTCGCGCTC GCCGCGGCTG     300

GGCTCGAAGA ACTTGGAGGA CGAAACGGCG TGTTTCACGT CGCCGGTTGC CTCCGACAGC     360

ACGGCCCAGT TGGCGCCGTT GGACACGCTC TTTTGTGCCT CGTCGAAGTA GGACACAAAC     420

GCTTTCATCA TATCGTAGGT CTTCCAGATG GGGCAGAATG CGTCGTAGGT CGAGTAACCG     480

TTCTGCTGCA AGAAGTCTTC TTTGATTAGC GTCGCGACAT CCAGTACGAT CTTGTCTTTG     540

TCAGAGAGCG CGGACTTACC GACCAGCTGA ACAACTTGCT CCAATTCCTC GGCGTTGGAG     600

AGGATCTCCT TGATACGGTC TCTCAGGACT GGGAACCGGG GTAATTGCTA TCATAGTATT     660

TGTTTAGGAC GTTGGTGTTC CTTCGAGT                                       688

(2) INFORMATION FOR SEQ ID NO:900:

(i) SEQUENCE CHARACTERISTICS:
        (A) LENGTH: 711 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1561UP (xi) SEQUENCE DESCRIPTION: SEQ ID NO:900:

GATCGCAGTC TGTAGTTGCT GGTACTGGAG TCTTGACTGC TCTATGCCTC TTGCTTGTGC      60

TAAAAGCGAA GGAGACTCGG TTACTTGTAT GTTTTGCTGA CCTTCTGGTG GCAAAAGGGG     120

```
TGGGGCGCGG GGTCGGACAC TATTTTGGAG CGGAATCAGC CTGAGTGTTC TTTTTGTTTT        180

CACCAAGGGC GGGTAACCTG GCGCCAGCCG CTGGCCGGCG AGGTGATGGG CCATGAGCAC        240

AGCAGGTATC GCGGGAATAT GGAGTGTCCG GGGGCGCGCT TATGTAGACC CAGCACGGTC        300

CCCAGCCATC GCGCGGAATT GCGGCTTTTG TAGAGTCCCG CTAGGCGCGC TGCCGCGGGC        360

GTCAGCGCCT GTGACACAGA CAAATAAAAT TGGGCAAGCG CGAGACACAA GTCCCACAAG        420

CCGCCACTGC ACGAAGCTAT GCACGCATTC AAGGAAGACT TACCCCATAC CGTGGGTTTT        480

GCCCTCGACA ATGAGGAGAT CACATTCCCC AACTACGTGC CCACGCATGT GCAATCGTTG        540

CCCCACACGT CCAACGGGAT CCGACAGCTA GTCATAGATA AGCAGAACCA GCGCGTCCTC        600

CCCACATATA ACCGCCTACT CGACCGCATG GAGGACGCGC TCGTGCGCTG GCGGCCGCCC        660

GCCAGCTCCC ACGTCGGCTC CTCGCTAGCA ATCCACGGCA CGCACCCGTA C                711

(2) INFORMATION FOR SEQ ID NO:901:

(i) SEQUENCE CHARACTERISTICS:
        (A) LENGTH: 720 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1562RP (xi) SEQUENCE DESCRIPTION: SEQ ID NO:901:

GATCATTTGA GTGCAAAGGG AGAAGTAGCG CTTTTGACAG TACGTCGCGT GTGTGGACAT         60

CCTAGGTACT GTTGACATTC ATGTGGGTCA GTCAGATTAC AAGTACACAA AGTCGATATG        120

ACAAGCCACG TGACCATATA TCCAAGACGC CCCCCAGCGC ACGCCTGCTC TGTGCATAGG        180

ACTGGCTACC TACCAGTTAC AATGGGGTTT GCAACTTAAC TGCTCTAATC CTCACACGCG        240

GAGTTATATA TGTGCTATAG GGCATGCTCC CGGGGCGCAA TTCAGGGCCA ACGGCCTGCC        300

ACCATGCCAG AGCAGCCATA CCAAGCGCTG CAACAGGATG CGATATCTCG TTCTATATAT        360

ATACAGATAT ATATATATAC TGTAACAAAA TCCCTAGCGA TCTCGCTGTG AAAGGCCGGT        420

ACTTAAATCA TATCGTCGTC TTCTTCAGCC CCGATCGACA AAGCCCGCCC ATCGTTCCGG        480

AAGCTTGGAA GCTCGGGCGC AGAAGAGCTC AACTCGAGTG CCGCGCATAT AAAGCCGGTC        540

ATGAAGAGCA TTGTAAATGC GCAAACTTGG AAAAAGCCTG CTGGCAAAAG CATCACTGCC        600

AGGAGGAGTT GTAGGAGGGC GCGACCCATG TAACTATAGT AGAAGGACGC GTATTGTTGA        660

AGCAATGGTA CTGGTCGGAA TTCGAGGTAT ACCAGCAGGA CGGAGAGTGG AAGGCCGAAA        720

(2) INFORMATION FOR SEQ ID NO:902:

(i) SEQUENCE CHARACTERISTICS:
        (A) LENGTH: 592 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1562UP (xi) SEQUENCE DESCRIPTION: SEQ ID NO:902:

GATCTGGCGT GCATATATAA CGTATCTGCG CTCACGCGAC CTGGTGCGGA CTTCTTTAGC         60
```

-continued

| | |
|---|---|
| CGGCTACTAA CTCTGTAGCT GTTGGGGCTG CCTGCGGCGC CGCCGGGCGA GCTTGGCAGA | 120 |
| ATCCGCCGTT GCGTCACGGC CAGTGCCAGC CGAACAGGAC GCCCTTTTCT AGCAGCAGCG | 180 |
| CTTCCGCAGC GGTTTCTTTT TTTTCCCAGC TAAGGTCGTG TATTTTCTCG CAGAGGGTTA | 240 |
| GAAAAGTACA CTTTACATCT GAACACACCA CAAAGTCGTT CTGATTGGAG AGGCACGAAA | 300 |
| CCAAACAATT GAAAGGTATG TTGAGTGGTA AGCAGACGGT ACACTGAGCT GGCCGTCTTT | 360 |
| TAGCAGCTGG CGGCCACCCG CACTTTCTCT TTTCCCGCTC TGTTGCTTCT TGCGCGCCCC | 420 |
| CTTGGCCTGG ATCTCGAGAG CCGCGGAGCT ACCGCCCGTC CCGCGCCAGC CTGGGCTTCC | 480 |
| CAGGCGGCCA GTGGTCAGAG CCGGTCGCCC ACGGCAGCCG GCTTCATGGG CGGCTGGCGG | 540 |
| CTCTGTTTAC AGGGATCGGT CACGTGCCGT GTGAGGCTAA GCCGGTGGCG AG | 592 |

(2) INFORMATION FOR SEQ ID NO:903:

(i) SEQUENCE CHARACTERISTICS:
        (A) LENGTH: 732 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1563RP (xi) SEQUENCE DESCRIPTION: SEQ ID NO:903:

| | |
|---|---|
| GATCCTCGCT ACTTTGACAA CATCAGGAAG GCGCTTGCTG CAGGCTTTTT CATGCAGGTA | 60 |
| GCGAAGAAAC GCTCGGGAGG GAAAGGCTAC ATTACTATCA AAGACAACCA AGACGTGCTC | 120 |
| ATCCACCCTA GCACGGTCAT TGGCCACGAT GCAGAGTGGG TAATCTACAA TGAATTCGTG | 180 |
| CTGACTACTC AAAACTACAT ACGGACGATC ACCTCCGTCC GTCCTGAGTG GTTGATTGAA | 240 |
| CTCGCACCTG CGTACTATGA CCTTGATAAC TTTCAAAAAG GTGATATCAA GCTCAGTCTG | 300 |
| GAACGGATTA AACAAAAGAT GGATCGCATC GAAGAGCTAA GTAAAGAGCA ATCCAAGAAG | 360 |
| CATAGACAGA GCCGCGCGTA NTTCGTGAGC TTGTTGTAGC TAAATATCTC TCTGATATAG | 420 |
| CATGTACACA ATAATAGGAC TTTTGAGCTG TCCTTCGTTA CTTCGGATTA GCAAATTATC | 480 |
| GCAGAAGTTA GCAGGCACCG CCGCCCTTGT TGGTGCGCTT GCACGAAAGC AGCTGGTGAT | 540 |
| GTTCGGCGTC GCTAAAAACC CTCATTTGTG CCTATCATAT GCCCAGCGCT ACAGAGTCTT | 600 |
| CGCATCATCA TGTTTGAGAA GGACGAGATA CTCCCACTTG ATGAGGCCAG GTCCCAAAAG | 660 |
| ATAAAGGAGT TCCTGAGCCT CTCCCTCGGG CTGATCACCG AATCCATCGA AAAGAAAGAA | 720 |
| TATGACTCCA TA | 732 |

(2) INFORMATION FOR SEQ ID NO:904:

(i) SEQUENCE CHARACTERISTICS:
        (A) LENGTH: 717 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1563UP (xi) SEQUENCE DESCRIPTION: SEQ ID NO:904:

| | |
|---|---|
| GATCGGTTGT CTTCCGACGC TGGTACAGGG CTGCGATGCG CGTCTGCGGC TGGCGGTGCA | 60 |
| TATCGGAGAT ATGGCGCCGT GCCCGTACGG CAAAGAATCA GCAAGACACT AGCGTCTGGC | 120 |

```
ATTCTTTTTC AATGCATTAT TTAGCTTTTT TTTTTTTTTT TTTTTTAGTA TAGACACAAT      180

ATAAAGTAGA GTTCGTCATC AGTAGCGCTC GTAAGGTTAG GGGCCGGCTT CACGCCATAG      240

TAGCATCTCC GTCAGACTCC TGGATTGGCG CTTGCTCTAT GCCGGCGGAT TCCGCAACTG      300

CGTAGGGTCT TTCGTTAGCG GACTGGTTCC CACCGGCGGC ATGGGCAGGC CACGAGGGAG      360

CTCCGGTAGC AGCCTGTGAC TTGTCTGGCA GCGAGCGGCC TGGTGGGTGC TGGAAGAAGC      420

AGTGGGCGTT GCGACATTCG GCGCCGAATT TGCAGGGCTC GTTGATGGGG TGGCCGAAAA      480

AGCAATCTAT GCGCGTGCAC GCAGCGCCCT CGCGGCACAT AATGTGTGAA CGCGCATGGC      540

GGTACTTACA CCGTTTGTTC GTGCACTTGA CGCCGAACTT ACACTGCTCG AGCGAACGCT      600

CCGCTGGTGC AAACGCACCG GCTTGGAAGG ACGTGGCGCA GCAGCAATAG GCTGAACATC      660

TCGTATCTTG GACAAGGAAG ATGCGCCTTG TCGCAGTCCT CTTGTCACAG GTTAGGT       717
```

(2) INFORMATION FOR SEQ ID NO:905:

(i) SEQUENCE CHARACTERISTICS:
        (A) LENGTH: 688 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1565RP (xi) SEQUENCE DESCRIPTION: SEQ ID NO:905:

```
GATCACATGT TTTCCCCAGA GAGGGACCTG GCGTTGAGAG AGCGATGGGC CGTTATACCA       60

CTGAGCCCTA TTAGTTGCTG GATTTGTGTT TCCAGCAGCT GCGCATGGGG CCGGATTCCG      120

TCAAGTGTGA TTCCGCAGAT GTTGGTTTTG GCTCGATAAG TGCATAAGGA AGCTGCTCTG      180

TTAGTACATG TCACATAGGA GGCTTCCGCA TTGGCGCATG GCATCCAGTG GCGGGCTTGT      240

GGCGCGACGG GTATTCCAGT AGCCGTCTGC GAACCGTATT CAATCATCTT GGCCCAGCG      300

GTATATAAAG CGGCTGATGA GCCTGGATGC AATGGGGTGT AGCTGCGGAG ACTGCACCGA      360

AGATGTCTAG CAAAGTTTCA TTCCTATTGA ATTGGCAGCC TGCGCCATAC CACATTGCGA      420

TTTTTCTAGC CCAGTCCAAG GGCTACTTTC AGCAGGAGGG TGTGGACATT GCGCTGCTCG      480

AGCCCACGAA CCCGTCCGAC GTGACGGAGT TGATCGGTGC GGGCAAGGTT GACATGGGCC      540

TAAAGGCGAT GATCCATACG CTGGCCGCTA AGGCACGTGG TTTCCCGGTC ACTTCTGTTG      600

CATCGCTGCT GGATGAGCCG TTCACCGGGG TTCTGTACCT GCGTGGCAAC GGAGTCACAG      660

ATACTTTCAG CTCTCTTCAG GGGAAGCG                                        688
```

(2) INFORMATION FOR SEQ ID NO:906:

(i) SEQUENCE CHARACTERISTICS:
        (A) LENGTH: 558 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1565UP (xi) SEQUENCE DESCRIPTION: SEQ ID NO:906:

```
GATCCCTTTC ATACAGGTCA ATATTTTATG CAGAGACAGG GGCTGGACGT TGTAAAGGTC       60
```

-continued

```
TTTCATCCAG ATATGCTAAG AGGCGAAATT TCATGCACGA GTATGATCAC AAAAAATGAC      120

ACAGCCAAAC AAATTGCCAT TATTTTTAGA GGATCTACAG TGATACAGGA TTGGATTATC      180

GATGTTCTAT CCACCCCTAT TCCATTCATT CTCGCTCCTA CCCCCTATCA GCCCGTCAGT      240

GGAGCTGCAA AGTGCCCAGG GAACTGTCTC ACGCACACTG GCGTCTACGA TCAATTTAAA      300

AAAGCATTTA AGGATATTTA TGCTGTTTTT AAGCCGCTAA AAGACACACA TCCGGATTAT      360

GAGGTGATAG TTACTGGTCT TTCCTTAAGT GGCGGCTATG CTCACTTTAT GGGTATTGAA      420

TTGCAACTTC TGGGCTACAA GCCTCATGTT TGCGCCTTTG GATCATTGCG TATAGGCMAT      480

AAGGACTTTA ACGATTGGGT GGATGATATA TTTCCGTCGG AAGACGTTTC GAGAAGAATC      540

CCAAATAATG AGATGCCC                                                    558
```

(2) INFORMATION FOR SEQ ID NO:907:

(i) SEQUENCE CHARACTERISTICS:
        (A) LENGTH: 645 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1566RP (xi) SEQUENCE DESCRIPTION: SEQ ID NO:907:

```
GATCGCGAAA CACAACGCGC GCGGCGCGGT AGCGCCGCGG GCGCTGCTGC AGGACGTGCG       60

CGACGCGCTC GCGGCGCACT ACGGGGTAGG AGTACATCAA CCGGTACGTG GAGGACGAGT      120

GGGTGTTCAA CAACGCGGGC GGCGCTATGG GGCAGATGCT GATTCTGCAC GCGTCTGTGA      180

GCGAGTACCT GATTCTGTTC GGCACGGCCG TGGGCACGGA GGGCCACACG GGCGTGCACT      240

TTGCGGATGA CTACTTCACG ATCCTGCACG GGGAGCAGAG CGCGGCACTG CCACACGCGC      300

TGGAGCCGGA GGTGTACACG CCGGGTATGA CGCATCACCT GCGCATGGGC CACGCGAAGC      360

AGTACGCGAT GCCGTCGGGC TCTTTTGCGC TGGAGCTGGA ACAGGGGTGG ATCCCGTGCA      420

TGCTGCCGTT CGGTTTTCTG GACACGTTCA ACAGCACACT CGACGTGTAC ACTCTGGCGC      480

GCACCGTGCA GCTGACAGCG CGCGACATGT TCAAGAACTT GGTGTACAAT TTCAAGTTTT      540

AGCCTAGATA CATAACCACC ACCAATGTCT GCGCAGGCCT CGCCCGCGAC AGAGCTGCCA      600

GAACCCGACG CTCGGGCAGG TGTACGCCAC GCTGACGCGC CACTC                     645
```

(2) INFORMATION FOR SEQ ID NO:908:

(i) SEQUENCE CHARACTERISTICS:
        (A) LENGTH: 701 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1566UP (xi) SEQUENCE DESCRIPTION: SEQ ID NO:908:

```
GATCCTCAAG TCTACGAACG CCTCGAAGGT GTTTACGACG GCCGTTTTGG CTGATGTCAT       60

CACAGCTGAG GCTAAGGGTG ATTTTGACGC GAAGTCTGCT GTCCCAGGTC ACGTGCAACA      120

GGGCGGCCTA CCATCGCCAA TCGACAGAAC CAGAGGAACT CGTCTCGCGG TCCGTGCGAT      180

CGGCTTCATC GAGGCTAAGC AGGACGTCAT TCGCGAAGCC AGGGGAAAAT GAGGAGGCCT      240
```

```
TTGACTGCGC CGACAAGGCC GTCTCTCACA CCGCCGCCGT CCTCGGCATC ACCGGCTCCC      300

AACTGAAGTT CACCTCCATC AGGCAACTCT ACGACCTGGA AACAGAGTTC TCCAAGCGTA      360

TGCCAAAGGT TATCCACTGG GAGCCTACCC GCGCGATTGC GGACCATTTA GAAGGCCGCA      420

AGAGGGTAAC AGTTTAGTGT CTCTGTTTCG CCCGCTGCCC CACTATATGT ACCACTAGAT      480

ACCACGATTA TGGATAAACT TAACATGGCA GAGTACACTC TCATCCACCT GCCATGTATA      540

TAATGTGATT TTACTGACGA AAACTGTTTT AAACGCCGTT GCAGGGTCCG TCGCAGCTCG      600

TATAAATATC TTGACGCCAC CTCGATCTCC ATTGGTGAGG AAGTACCCGT CGAGATACAA      660

TAGTGCCAGC TTGCTAAGGG GTAAGCTGAC CACTCTACAC A                         701

(2) INFORMATION FOR SEQ ID NO:909:

(i) SEQUENCE CHARACTERISTICS:
        (A) LENGTH: 697 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1567RP (xi) SEQUENCE DESCRIPTION: SEQ ID NO:909:

GATCAAATGC CCTTCCCTTT CAACAATTTC ACGTACTTTT TCACTCTCTT TTCAAAGTTC       60

TTTTCATCTT TCCATCACTG TACTTGTTCG CTATCGGTCT CTCGCCAATA TTTAGCTTTA      120

GATGGAATTT ACCACCCACT TAGAGCTGCA TTCCCAAACA ACTCGACTCG TCGAAAGAAC      180

CTTAGATGGC ACTAGCACCC CCGCCAGACG GGATTCTCAC CCTCTATGAC GTCCTGTTCC      240

AAGGAACATA GACAGGGACT AGCAACCAAG GTACTTTCTT CAAATTACAA CTCGGACGCC      300

GAAGGCGCCA GATTTCAAAT TTGAGCTTTT GCCGCTTCAC TCGCCGTTAC TAAGGCAATC      360

CCGGTTGGTT TCTTTTCCTC CGCTTATTGA TATGCTTAAG TTCAGCGGGT AATCCTACCT      420

GATTTGAGGT CAAACTTTGG GAATACTATT CGCCTGGAAG GCCTTGTTTG TCGTACGTTC      480

TTCAAGCGCC AGCTCCACTC CACGATCTGG TCGAAACCTA ATACGCAGTG TAGAAACTAG      540

CTCAGACCGC AGTCCGCGCA AGTTCCGCCC ATGGCCAGCA TTTTCAAGTT AACCTTGTCT      600

TACGACCGAG TATCACTCAT TACCAAACCC GAGGGTTTGA GAAAGGAAAT GACGCTCAAA      660

CAGGCATGCC CCCTGGAAAT ACCAGAGGAC GCAATGT                              697

(2) INFORMATION FOR SEQ ID NO:910:

(i) SEQUENCE CHARACTERISTICS:
        (A) LENGTH: 712 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1567UP (xi) SEQUENCE DESCRIPTION: SEQ ID NO:910:

GATCGTCAGA TACCTTAGTC TCTATACAGC GCAAGACATG GGTGATGGCG GGTTTGTTCT       60

ATGCAAAGTC ATTGGGTTTC CCTCTGGCGG CGCATACAAC ACCTGCCTAA CCTGAACAGT      120

CTCATCCTGG GCATCTAGCG ATCCCATGGG TGAGCAGCGG AGGATTTGGT GGATTACTAG      180
```

| CCAATGGCAA TCCAAACCAA AGAAACCGAC TTGGGGGAAT GCCTCATTGA ATAGCCGGTG | 240 |
| TTTCGACACT GTGATTCTCT GAGTGTAACC TCCTCTTTGG TTGCCGATAT TAAACCTGTT | 300 |
| CTGTGAAACA TCGGAGCGGT GTTTAGTGGA AAGCAACTAG AGGAACTCAA AGAGTGCTAT | 360 |
| GGCATGGGGG CAGCTGTTGC GAAAGTGTAA AAACCCGAGC TCCGGTTCGC TTGACACAGA | 420 |
| AGTTACTTTC TGTATCTCTA TCAGTCTATC ACCGAAGGAC CGTGGTGTGC TTTGCGCATT | 480 |
| TTCGGGTTGT TCTTTAAGAT AGTTATCTGG TTGATCCTGC CAGTAATCAT ATGCTTGTCT | 540 |
| CAAAGATTAA GCCATGCATG TCTAAGTATA AGCAATTTAT ACAGTGAAAC TGCGAATGGC | 600 |
| TCATTAAATC AGTTATCGTT TATTTGATAG TTCCTTTACT ACATGGATAT CTGTGGTAAT | 660 |
| TCTAGAGCTA ATACATGCTT AAAATCTCGA CCTTTTGGAA GAGATGTATT AT | 712 |

(2) INFORMATION FOR SEQ ID NO:911:

(i) SEQUENCE CHARACTERISTICS:
        (A) LENGTH: 696 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1568RP (xi) SEQUENCE DESCRIPTION: SEQ ID NO:911:

| GATCACGAAA CGGTCGCTAT TAGGTTCCCA TGCAAAGCGC ATGCAGCGGT CCTTAATCTC | 60 |
| CACCTTCTCA AATGGAAACT CTCTGGCAGT CAAAGAGCAA ATCTCCATGT TGGTGAAGAT | 120 |
| GGTCTTCCTA GACTTCGTGT GACGGTCCAC CTGTACACAG AGGAACTCTG CCTGGTTCTG | 180 |
| CCAATGGAAG GAGACATCAG TAACCTGCAC CAAGTTGATG GTACGCAGAA CACGGCGGTT | 240 |
| CGGTAGCTCA ATCAGGACAG CTTTACACGA CTGGTTGTTC GACTCTGGAG TCCAGTATAC | 300 |
| CATGACAGTA GATGGTGGGT CGTTGGGTCT GTTTGACGCC AACTTGATGC CCTTAGGAGC | 360 |
| AAAGGAGAAG TCCTGAACAT CCTCGATCTT CATCACCTTA CCGCCCAACA GCTGGAAGTT | 420 |
| CTTCTCGGTC TCGTACACAG CAATTGCGCC AGGGCCAAGA CGAGCGCAGA ACTTGTCGTC | 480 |
| AAAGGACCAC TTGACCATAG GCCATTGCAG CTGCTGCTGA GGCGGCAGCG CAAAGGTCTT | 540 |
| CACGCAGACA CCTGTTGCCA CATCCCATAT ACATAGCTGG TGGCCCCGCG ACTCGGGCCC | 600 |
| GAATGGACAA GCCTCGTTAG GTTCATCCGA GACTTCTAGA GGTTCCGACG AAAAGGTAAC | 660 |
| CAGGTACTTC TCGGTCGAGG ACATGGAGAT CGCCTT | 696 |

(2) INFORMATION FOR SEQ ID NO:912:

(i) SEQUENCE CHARACTERISTICS:
        (A) LENGTH: 697 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1568UP (xi) SEQUENCE DESCRIPTION: SEQ ID NO:912:

| GATCATCTAC GTGGCCCATG AGGATAATAA GGAGAAAGAA TTCGAAATTG AGCTGAGCTG | 60 |
| GTGCTCCGCT TCGGAGACGG ATGGCTTGCA CAAGGGAGGT ACCAAAGAG CTATTTGATG | 120 |
| CAGCGATTGA GTTTGCGAAG AAGGAGACCG GTCAGGAGAG TGATGATGAT TCAAGCGATG | 180 |

```
ACAACGCATC TGGAGGTGAA GAGTCCTCAA CAAAGAAGGA TGCTGACGGT GATGTCCAGC      240

TTTCATGATA ACAGCCCGGC ATTATGTGGA GGTTCATTTC ATGACAATTG ACGGATGTTA      300

CTAAGTGTAT ATTAAGTTAA TCCACCTATA TAAATTAATA ACATGCAAAG CAATTTAGAA      360

TTTGTCGGAA AGCAGGTTAA AGCATGTCTA CTCTCCTTAA TCTTTCGCGA AGCTGTACAT      420

TTTCTTCTTC AAGTGAACGA ATTCTATCCA CGGCTGCGTC TGATTCTAAT TTCCTACGTT      480

CGCGTTCTGT GTACCATTTC CGCGTCAGCT CTTCTATCAT TAATTTTGAA TGCTGATCAA      540

ATGTATCTGA TTCATCCGAG CCCTGCGACA CCTGGGATAG ACGTTTGATT CTTCTGTCCT      600

TTTCCTTTAA CAGCAGCTTT ACATGTTCCT CCACTATTGA TGATGTGGCA TTTTGGGATG      660

AACATATAAA TAGAATCCCA TTTCAGCTGG TTTCTTC                               697

(2) INFORMATION FOR SEQ ID NO:913:

(i) SEQUENCE CHARACTERISTICS:
        (A) LENGTH: 672 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1569RP (xi) SEQUENCE DESCRIPTION: SEQ ID NO:913:

GATCCGATAT ACGCTGAGTG CTATATTACA AACCATCAAT TTGATGTTAT CTTGGACGTA       60

TTGTTGGTTA ACCAGACGAA AGAAACTTTG AAAAACTTGC ATGCGCAGTT TGCAACCCTG      120

GGCGACCTGA AGATTATATG CAACCCTCCA AGCACCAATC TAGTTCCTCA TGGTTTCCAC      180

AGATTTAGCG TTACAGTGAA GGTTTCAAGT GCCGATACTG GTATAATCTT TGGGAATATA      240

GTTTATGACG GTGGACACGG CGAAGATGCA CGCTATGTGA TCTTAAATGA TGTCCATGTT      300

GCTACAATGG ACTACATTAA GCCTGCAGTT TGTGATGAAG CTTCTTTCCG CAAGATGTGG      360

AATGCATTTG AATGGGAGAA CAAAATGGTT GTCAAATCTA AGCTACCGAC TCTGCATGAC      420

TACTTGAATA AGCTGATTGA GGTCACCCAT ATGAATGTCC TGACTCCTGA AGAATCATTT      480

GCCGACCCCG AATGTCGTTT CTTAAGCTGC AACTTATACT CGAAGTCCAC CTTCGGCGAG      540

GATGCTCTGG CTAATTTGTG TATCGAGAGA GACCCTACTA GTGGTTCCAT CATCGGAGAA      600

GTTCGCATCC GCTCGAAGAC GCAGGGCCTT GCTTTGACCC ACGGAGACAG TATTGCGCMC      660

ATGGAAAGGT CC                                                         672

(2) INFORMATION FOR SEQ ID NO:914:

(i) SEQUENCE CHARACTERISTICS:
        (A) LENGTH: 698 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1569UP (xi) SEQUENCE DESCRIPTION: SEQ ID NO:914:

GATCTGCAAT GCTCTTCAAC AATTTGCTGC AAGCTATTCT CCTGATGACC TTGCCATCTT       60

GAGTGAGCTT TTTGATTCCA ACAGCAAATC TGAATAGGCC TCTATCTCCT TTAAAAGCAG      120
```

-continued

| | |
|---|---|
| CGTCGTGCAT GGGGCTTTGG GTTTACATTG GAAAAAGCCC CAAAGAACAA GGTAATGCAT | 180 |
| GCCAAAAGTA GCCTTTAATC CACTTCACAT TTAGATATTG TTACGCAGTG TATCTATACA | 240 |
| AAAAATAACG ACAAATAATA TCTTTTAGAG CTGGTTCTTT AGACTAAAAT AGGGCTCGGT | 300 |
| ATGCAATACC TCAGATGCTA TCTTGATATC CGTGTGGATA TCCTCGATTA AAGCCTCTTT | 360 |
| CGTGGTGTAG TTTAATTCGG GCCGGATGTA GCCAAGGAAG CTGAACTTAA TTTTGGCGCC | 420 |
| ATAGAAGTCT TCTTCAAAGT CGTTTAAAAT GTGCAACTCA ACCGTCTTCT TACTGTTGTT | 480 |
| ATAGAACGGG TTCCATCCTA CCGATAACAC GATTGGAAAG ACTCCACGCT CTGTTTCCGA | 540 |
| CAGCTTGGAG CCAAAGTTGT ATATGACCTC GCTCCCATCA TTTCTGTGAT GGGACCTGCG | 600 |
| CTTCTTGGTC CATATTAGCC TTAACCGGGC CCAGCCAAAA TATACTCCTG TGGCCATTTC | 660 |
| GTTAACTTCC CTAGGCAATT GTTCTATTGG GAACATTC | 698 |

(2) INFORMATION FOR SEQ ID NO:915:

(i) SEQUENCE CHARACTERISTICS:
        (A) LENGTH: 688 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1570RP (xi) SEQUENCE DESCRIPTION: SEQ ID NO:915:

| | |
|---|---|
| GATCCACAAC ACACACAGCT TGCGGACTCT TTTTCTCAAA GACAGTTCAC CAGTCCAACA | 60 |
| CTTGCAAAAC CATCTGCTAA CGTTTCAACG ATTGCGCAGC AGCAAACCCA GCCAACCGCT | 120 |
| CTCTCTCAAT CTCATCCTCA GCAACAACAA GGTTCACAAG CTCAGCAGCA GCTACTTCAA | 180 |
| CAACAACAAG GTTCACAAGC TCAGCAGCAG CTACTTCAAC AACAACAACA GCAACCACCA | 240 |
| CCACCACCAC CACAACCACA GCAACAAACA CAACAACCAC AACAACCACA ACAGCAGCAG | 300 |
| CAGCCCCAAC CTCAACCGCA ACTACAACAA CAACAACAGC TTGGTTTACA GCCTCATCAG | 360 |
| CCACAACTGG CGCAGGCGCA GGCGCAACAA CCACAACCGC AGCAGCAGAC GCAGCAGCAG | 420 |
| ACGCAGCAGC AGCAGCAGCA GCAGCAGCAG CAGCAGCAGC AGCAGACACA GCAGCAGACA | 480 |
| CAACACCAAC CACAACCACA ATTGAAACCA CAATCACAGC AACCACAACC GGTTCCACAG | 540 |
| CAAGTCCAGT CTCAACAACC ACAGCAAGTC CAGTCTCAAC AACAACCACA GCCTCAGCAA | 600 |
| CTTTCACAGC CTGCCCAACA ACAATCGCAA CAACAACAGC AGCAGCAGCA GCAGTCTCAG | 660 |
| CAGCAGAAGC TTCGCCAAGT GCAGCTGC | 688 |

(2) INFORMATION FOR SEQ ID NO:916:

(i) SEQUENCE CHARACTERISTICS:
        (A) LENGTH: 714 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1570UP (xi) SEQUENCE DESCRIPTION: SEQ ID NO:916:

| | |
|---|---|
| GATCTTCGGG CCCGCGGGGC CGCTGGGCTA CGTGCTGACG CTGTATGCGA ACGCGCAGTT | 60 |
| CTTCACAACC ATGATCGTGA ACTCGCACCT GGCGACGCCG CTGTTGGACT ACACCATTGC | 120 |

```
GTCGCTGATG GGTATCCATA TTGAGTACAA GCGCCATAAC CCTGAATTGG TGGAGCCGGA      180

GGCGTTCAGC GCATACGATG TGCTGACGGT GCTGCGCCTG GTCATGAGCG TTGCCGTGAT      240

GGTGGTTCTG GTGACCATCC CGATTCTGGG ACCTGTTCTA CTGATGTTTG TGATGAATGT      300

AAAGTTTTCA TACGACTTCT ACGAGCGGTT CTTAATTCTA CGGGGACTAA ACCAGGTGCA      360

GCGCCGTGAC GTGTTCTACC AGCATATCTT ACAGTTTGCA TACTTCGGGG GGTCGTACAC      420

GGTTTTAAAT TTCGTGCCTC TATTCTCAGT CTGGGGCTTT GTGTGCTATC CGTTGGCAAT      480

CAAAATGTGG GCGACTTCCA ACATCATCCA CTTTACAGCG GAAGAAGTGG AGTCCATCAC      540

TGAATGAAAT CATTCATTTA ACATGTCCAT CTATACATAA AGATAGATAT AGCCAGAATC      600

AATACCCTGC CCATTAGTAA AGTACCATGC TGTCGACACA GCCGAATCCC GCGCAACACC      660

GCCCTCGTTG GACGAAGGCA ACTTGGAACG CAGCAGCCAT CCCAGCGTAG TCGT           714

(2) INFORMATION FOR SEQ ID NO:917:

(i) SEQUENCE CHARACTERISTICS:
        (A) LENGTH: 658 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1571RP (xi) SEQUENCE DESCRIPTION: SEQ ID NO:917:

CGCAGGCCGT AGGCAACACC GTTGGATATC TGCACCTGGC AAAGGTCCTG ACCCGGCAGC       60

AGAAGCTCGC GCGAACGCGT AGTCCACGCA TACAAGTCGC CGCGGCGGTC GATTGCCAAG      120

TTGCAACCCT CCTCTGCCAG CGCCACATCC CGCAGCCGCT CGCCCTCAAA CCCCGGCACC      180

CGCAACGGGA ACCGCGTGGA GCCAGCGTCC TCGCCCAGCC GCGCGCCCCA GTAGTAGAGC      240

CCGGGCTCTC CTGGCTGCGG CGCCGTCACC GGGATCTCGG GGATCCCGCG CAGCTCCTTC      300

TTGCGCTTGA TCTCCTTCAG CCGCTCAAGC GTGTTGTCGT CCACCCGCCG GTCGCGCGCT      360

AGAATCCAGC CCTTGATCTG CGGCCATTGA AGATACACCG TGCCTGCTAC TCCGATCCCG      420

ACGACCACCG CCAGGCCCTG GAACACCGCC ATCAGCTTCT GCATCTTCTC CACCTTGTCC      480

GCATACTCCT GCTCCAGTTG GCGCGGCGAT TTGTCACTCC ACTGGTAGTC CAGCTTGCTG      540

CGCTTGGCCT TGTATGTGCC ATGGTTCAGC TGCTCTTGCC ATCATCTCGG GCTCATCAAA      600

ACGCTGCCCC TTGCGCAACG CCCTTGCTTC CATAGCGAGC GCCTCGCCAC TCGCAGCC       658

(2) INFORMATION FOR SEQ ID NO:918:

(i) SEQUENCE CHARACTERISTICS:
        (A) LENGTH: 657 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1571UP (xi) SEQUENCE DESCRIPTION: SEQ ID NO:918:

GATCACGTGA TGGGATGAAA ACTCTGACAA ATGCACCGGG AATATATAAG GCATGGAGCT       60

GCGGACTCGG CCAGACAGTG CGAGCAGCGA AACAACAACA TCATCCAAAA TGGCCAGAAG      120
```

| | | |
|---|---|---|
| ACCAGCTAGA TGCTACCGTT ACCAGAAGAA CAAGCCTTAC CCAAAGTCTA GGTACAACAG | 180 | |
| AGCTGTGCCA GACTCCAAGA TCAGAATCTA CGACTTGGGT AAGAAGAAGG CCACCGTTGA | 240 | |
| TGAGTTCCCT CTATGTGTGC ACCTAGTGTC CAACGAGTTG GAGCAGTTGT CCTCCGAGGC | 300 | |
| TTTGGAAGCC GCCCGTATCT GTGCCAACAA GTACATCACC AAGATGACCG GTAGAGACTC | 360 | |
| GTTCCACTTG AGAGTCAGAG TGCACCCATT CCACGTCTTG AGAATCAACA AGATGTTGTC | 420 | |
| GTGTGCAGGT GCAGACAGAC TGCAGCAGGG TATGAGAGGT GCCTGGGGTA AGCCTCACGG | 480 | |
| TTTGGCTGCC CGTGTCGACA TCGGCCAGAT CATCTTCTCC GTCAGAACCA AGGACAACAA | 540 | |
| CAAGGACATC GTTGTTGAGG CTTTGAGAAG ACCAGATACA AGTTCCCAGG TCAGCAGAAG | 600 | |
| ATCATCATGT CCAAGAAGTG GGGTTTCACC AACTTGGACC GTGCCGAGTA CGTCAGA | 657 | |

(2) INFORMATION FOR SEQ ID NO:919:

(i) SEQUENCE CHARACTERISTICS:
        (A) LENGTH: 625 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1572RP (xi) SEQUENCE DESCRIPTION: SEQ ID NO:919:

| | |
|---|---|
| GATCTATTAT TAGAGGTAAT ACATTTAAAC TATTATCTAA ATTCTTCTTC TTCTTATTTA | 60 |
| TTCTTAACTT TATCTTATTA GGTAAATTAG GTGAATGTCA TGTTGAAGTA CCATTTATTT | 120 |
| TAATAGGTCA AATTTGTACA TTTATTTATT TTGCTTATTT CTTAATCTTA GTACCTATTA | 180 |
| TTTCTATAAT TGAAAATATT TTATTTTATT TACTAAATAA AAAATAATAA TTAAATAAAT | 240 |
| AATAATAATA TTCATTAAAT ACTTTAATAT TAATATTTAT ATATTATACT TCTTTATCAT | 300 |
| TTAGGAGGGT ACCTCATATT GCTGACTAAC AATAGGGGGG TGAACCCTAC GCACCTAAAT | 360 |
| GATAAGAGTT TATCATTAAA TTATATACTA TATATTATAA GTAAATTATC AAACCATATA | 420 |
| TAAGGTATAT ATATTAAGAA AGTTTGACTG AGTGGTTTAA AGTGTAATAT TTGAGCTATT | 480 |
| ATAAATCTTT ATGATTTCCT AGGTTCGAAT CCTATAACTT TCGTATTAAA TAATTATTTA | 540 |
| AAATAATTAA AAATAGTTAA TAATAATGAG AACATGATGT TGGTTCAGAT TAAGCGCTAA | 600 |
| CTAAGGGACA TTACACATGC CAATC | 625 |

(2) INFORMATION FOR SEQ ID NO:920:

(i) SEQUENCE CHARACTERISTICS:
        (A) LENGTH: 677 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1572UP (xi) SEQUENCE DESCRIPTION: SEQ ID NO:920:

| | |
|---|---|
| GATCCGTGTA TTTTTTATTT ACATTATTTA ATTAAAAATA ATGATTTAAA TAAATATTTT | 60 |
| TTATAAAAAA TAATTAGTGC ATTGTTACAT GTTCATTAAA GAATGATTAT TATCAAAACC | 120 |
| ATCAACTAAT TGTTATATAT TTATTAAATA TTAATTTCRC TTAATTAAGA ATTAGGAACT | 180 |
| TTATCTATTA GTCTGGGCTG TTTCCCTTTT GATTATTAAC CTTATCGCTA ATAATCTGAA | 240 |

```
ATATTTAATT TTAGATTAAT AATATATTCT GAGATTTAAT ATTTTTAATA AAATAAATAA      300

TTATTCCCTA AATAATATTA ATAACTATAC CATATATATC TAATATTTAA ATAATCATAC      360

TAACATATGT TTCGTAGAAA ACCAGCTATT TGCAAATCAG ATTTGACTTT CTCTACTTAC      420

CATTATTCAT CAGATAATAT TGCTACATTA ACCTGTTCAA TCGTTTTTAT ATTTTATTAT      480

ATTTTAAATA TAATAAATAT ATATTTTAAT CATTTGATAA TAGTAAGATC ATCTGCTTTC      540

GGGTTAATTA ATATTAACTA AATTTAATTT ATTTTAATTA ATTTTAACAT TGTTAAATAT      600

TTATATTATT TTTAATATCA TTTTTTATTT TAATATTATG CTAATATTAA TTACTTGCTG      660

ACCCATTATA CAAAAGG                                                    677

(2) INFORMATION FOR SEQ ID NO:921:

(i) SEQUENCE CHARACTERISTICS:
        (A) LENGTH: 623 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1573RP (xi) SEQUENCE DESCRIPTION: SEQ ID NO:921:

GATCCGTATG GAAATTATTT TTTTATTTGA ATTATCTTTC TCCAGAACAT CCAAGAAGAG       60

TGTCAGAGTG GTGGGCAGAT ATGGCTTAAA CTCTCCTTCC AAAGATTTAG AAATAGATTC      120

GATAACAGAA ATGATTGTAA TTTGCAGTTT AATAAATGGG AAGAACTCTT TAATGACTTC      180

AAATATTTCG TCAACATATG GCCTGATATG TTGCTTCACA ATTGATACCA TAACACCTAA      240

TTGTTGAAAA TAAAACTCAA GTATTGATGG AGGACAGCTA CGCATCACAT TAATCATTCC      300

TGGAATAATT TGCTTTAGGA AGGAGACGCA GCGGAGTCCC AATGTTTGGA AGATGTGCAT      360

CACTGCCTGT ATGACAGCAG TGTGATGAGA AGATAAAGAA GGATCCTTCA AAATTTTCAT      420

TAGAGTATTG ATCACGACGG TTGGATAATA TTCTTCATTG GAGGGTGACA TACCTTGCAT      480

TAACAAAGCA ACATCTATGG ATGGGGCATT TTGTTCGACG GATATAGGCG TGCTGGATGT      540

TCTTTCAACT TCTCTATGTT TATAAGGGTC CAGAGCTCCC AGAATCCCTA TTAGTCTAAC      600

TGTTTCCCTC CTTATGCTTT GGG                                            623

(2) INFORMATION FOR SEQ ID NO:922:

(i) SEQUENCE CHARACTERISTICS:
        (A) LENGTH: 715 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1573UP (xi) SEQUENCE DESCRIPTION: SEQ ID NO:922:

GATCSGATAG GACAGCGAGT ACGACGGCCC CTGTGCCGCT GCCAGCGCCT CGTTGCCAAT       60

GTAAAAGTCG AGGTCCTCCG TCCCGCGCTT CCCAGCCAGG TTGTTCGACA TCAAAGAAGA      120

TGACGTAAAG CCCGTGAACG ACGTCGCCGA CGTCGTGTTG CCAAAGAATG CAGACCCGCC      180

AGCGCCCATA CCGCTCCCGC TCTGGCCCAT ACCGCTCATA CTGCTACTCT TGGCCGTCTT      240
```

```
GGAAGGCTGC GCAGTCGCAA TTGCCGTTGG GAACACCCAT GAGGGCGAGT CGTTACCTGC      300

AAATCCCAAT TTGGTCAATC CTGTACCATT GTCCATGACA ACAGCAGGAT TATTGAGGTA      360

TGACATGCTG TATTCCTGGT CTCAAATGCT TCTGGTAGAC TTGTGTGAGC CTTTGGCTTC      420

GGATGGCTTG TCACTTACTG GCTTAAGAGT GCTGGCAGTG GAAAAGGGGT CTAATGCGCC      480

TTTCGTTTTA GGTGATCACC ATCACCAACC ACGGTACACC TGACGAAAGG CAACGCCGTG      540

GCTTGTGAAG CCAGGAGAGC CCTCGTAGGT ATTCCGCGGA GCCAATTGGT GGCCCTCTGC      600

GTTCCTCGAG CGCTCCTGCT CCATCTGCCC TCTTGACTCG TTTATGAACC TTGAAACACG      660

GCATATAGCG ACACGGACTT TCTGCAGGTC TGTAGAGTAG CCCACATCCG GCGAA           715

(2) INFORMATION FOR SEQ ID NO:923:

(i) SEQUENCE CHARACTERISTICS:
        (A) LENGTH: 602 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1574RP (xi) SEQUENCE DESCRIPTION: SEQ ID NO:923:

GATCCCGAAG CTGGTCTGTT TCGAATTCGG GATATTTTTA GGAAGTACGT TTGTTCCAAC       60

GACGTTGCTT CCATGCATCT TGCGGGGTTG TTGACGCAAC ATTTTCAGTC TCACATTCCC      120

TGAACAGCTT TGCTATCTAC TAGGAGTTAC TGAAGCTTTT AATGTCTGTT AATAAATCTT      180

TTGAGTTAGA TAATTCGCTG CGCTACAGTC TCCATGGGTT TTCATTGGCC AACCCATCTG      240

TAACTCTAAT TGAAAGGGAG AAGATCCTAT ACAGGAAATT AACAAAGGAG TCTGTGGCAC      300

TAGTTTCGGG TGGGGGGTGC GGACATGAGC CTGCGCACAG CGGGTATGTT GGGGAGGGCA      360

TGTTAACCGC GGCTGTCGCA GGAGACATTT TTGCGTCGCC GTCGACGGCT CAGATTTTGA      420

CTGCAATAAG GATTGCTACA AAGCAAGCAG CTGGAGCATT GCTGATCGTG AAGAACTATA      480

CTGGCGACGT TCTTCACTTT GGCCTGGCAA CTGAGCGTGC TCGGTCTATG GCATTGATT       540

GCCGCGTGGT TATTGTTGGT GATGACGTAC TGTTGGTCCT ACCAAGGGTG CAGGAATTGG      600

AC                                                                    602

(2) INFORMATION FOR SEQ ID NO:924:

(i) SEQUENCE CHARACTERISTICS:
        (A) LENGTH: 722 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1574UP (xi) SEQUENCE DESCRIPTION: SEQ ID NO:924:

GATCAAAAGC GTGAAGCTGG AGCGTAATGA GGAGCAGCCA GTTGTTTCGA TGGACTGGGA       60

CCAGCTGTAC GACGTGTCTT CGAACATAAT GGAAGAATTT ACAAAGGAAA TGGACGAAAT      120

AGTGGCAGAG CTCAACCAGT CGTTCAAGGT ATGTAGCACG ATGAACACGC AGGGCGGGCG      180

GGTTACTAAC GCGATGGGTG CAGAAGCAAT TGCTTTGGCA GGAGGCGGCG TTTACCGTCG      240

ACTCGCACAG AGGCGCCACC CGGTTCGGCG CTGCGGAAAG CTGGATGAAG AGCAAAGAGA      300
```

```
CGCACCTGGA ACAGAAGCGG CGGGAGCTCA ATGCATCGGC GCGCATCATC AAGAGCACGC      360

TCGAAAATTT GACGCAGGGA TAGTCCCGGC CGGCATCCGT CATGCAATGC CTTGCTCAAC      420

ATTACATGGA TGGGTATTTC TGCCTATGTA CAAACATAAT TTACGCGAAT TTAGCTTTCT      480

TCCAAGGCCT GTCCTCGGTG TCTGCGCCAT CGGCGGCTTC AGTTTCACTC TCCGAGACAC      540

CGGCGTCTGA GTCAAACTCC TCCGCGACGT CATCGTCTTC CGACTCCGCC TGGAAATCCT      600

CGTCCACAGA CTCATCGTCC TCTGCAGCAG AACCATGTTA ACGTCCTCAT CTCGCTGTCA      660

GAACCAAGGG CTGTTTGTAG GCGCTGCTGA ATCTCTTTCT CTTCGTTTTT GACGCGGACG      720

TT                                                                    722

(2) INFORMATION FOR SEQ ID NO:925:

(i) SEQUENCE CHARACTERISTICS:
        (A) LENGTH: 589 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1575RP (xi) SEQUENCE DESCRIPTION: SEQ ID NO:925:

GATCCAGTAA ACTTCAGCTC ATCGTGAGCA ACCGACGTCA CCCCACCACG CGCAGGCGAT       60

ACTCCGGTGG AAATCACCTG AGTATATGCA GTACTCTTCG AACCATCGTG AGCAACCGAC      120

TCCACCTCAC CACGCGCAGG TGAAAGTCCG GTGGATATCA CCTGAGTACG TGCAGGCGAA      180

CTGCCTGCGG AAATCACATC ACTATCAGCA GGTGAAACTC CAGTGGAAAT CGCCTGAGTA      240

CGTGCAGTAG GCCTCGACTC ATTGTGGGCG ACCGATGTCA CCTCACCCCG CGCAGGCGAA      300

CTGCCTGCTG AAATCGCATC ACCACGCGCA GGCGAGACTC CAGTGGAAAT CACCTGAGTA      360

CGTGCAGGCG AACTGCCTGC GGAAATCGCA TCACCACGCG CAGGCGAGAC TCCGGTGGAT      420

ATCAGCTGAG TGCGTGCAGT AGGCCTCGAC TCATTGTGGG CGACCGATGT CACCTCACCC      480

CGCGCAGGCG AGCTTCCAGT GGAAATCACA TCACCACGCG CAGGCGAACT GCCTGTGGAA      540

ATCACCTGAG TACTTGCAGT AGGCCACGAC CCANCGTGGG CAACTGACT                 589

(2) INFORMATION FOR SEQ ID NO:926:

(i) SEQUENCE CHARACTERISTICS:
        (A) LENGTH: 684 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1575UP (xi) SEQUENCE DESCRIPTION: SEQ ID NO:926:

GATCAAATAT CAACTAAGGC ACTAGTTTTT GGTGTAGCTG CTCAAGCATC ACCGGATGCT       60

CAGAAGCGTG TAATTAACCT ACAATCTCGG ACTTCACCAC CCAAATCTGA ACACATTCG      120

CATATACGGC ACAACGCTTC TAGCGTGTAT CAGTCGGAAA CAACAKATAA TATAACTAAA      180

GATACCGGGA TGTTTTCTGC AGTGAAGTCA GGCTTTCCCC ATATCAACA GAAAACCATA      240

TCAGCAGGCT CTGAACTTGA TGACACTGAC TTTCAGAGAA CACAAACTAC CAGCACAGGC      300
```

-continued

| CCACTTCCAA CTTCAAGCGA ATATGACTCT GCCCCTGTGA CAGTTCATGG AGGACTTGAT | 360 |
| ATTTCTCCAA GACCACCTTC CTCTAGCTCC ACAGATTTCG ACGAGTATCC AACTGGTACA | 420 |
| ATAACAGAGT CACACAGACG GCCTTATAAC GTTAGCCAAC TTCCCGAAAA TAATGGGAAC | 480 |
| TCAGCTGCCA CTCGTGTGAT TAAGAGAAAC AGTTCTGTTC TCAGCTCGCC TGGAAGCGTG | 540 |
| ACCACCACCC CAATGGTTAA TCRAGCTACA GTACTCAGCG CCTCGCCGGG AGCGGTTAAA | 600 |
| TTAACCGAGA AACAGCATAG TCCGGCATCA TCTTCAGATA TTTCCACAGC CAATAAAACA | 660 |
| CATTCGAATT CTATTGATCT AAAC | 684 |

(2) INFORMATION FOR SEQ ID NO:927:

(i) SEQUENCE CHARACTERISTICS:
        (A) LENGTH: 732 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1576RP (xi) SEQUENCE DESCRIPTION: SEQ ID NO:927:

| GATCTTGTTG AGAACACTCA ACATCGGCGT AATTGCAGAG CCCCCGGTGA CCATACCGAT | 60 |
| TTTCTTGTAC GCATTCGTCA CATAGCTGAA CCGTCCTACA GGACCTTTGA ATTCCACAGT | 120 |
| TTGGCCTGGC TGTAGCCCAG CAAACCATTT GGATACCTTA CCGTCGACAT AAGATTTGAC | 180 |
| AATGATATCG AAATGGCCCT CGGCAAATTT GTTGGAGATA GGCGTGTAGT AACGCACTTC | 240 |
| TTCTACACCA TCCAGCATCA CCTTCGCAGC TAAATGAAAG CCAGTAGGTA TATCAAGAGT | 300 |
| TTCCACGCTT GAACGGAGCT TGAATCTGTA TATCGCAGCA TTTTTGCTTA GAACGATCCG | 360 |
| TTCTTCCAAT TCTAATGGCG TCCACTCATT TGGAAGAATT GAAGTCCTGC TTCTGTATGC | 420 |
| TAGTAGCAGG CGTGCACCTA CAAACATTGC CAAAGCTAGA ATGCCTAGAA GGTACCATGC | 480 |
| GTTCCCCGCT GACCAGGCGA TAACAAGAAC GCCCAATGTA AAGATGCCGC TGGGGATGAA | 540 |
| GATCCCATGA ATGGGATCAT CCAATATCTC CATACCTCTG CGTTCGGTCA TACTAATATT | 600 |
| TTGAAAGCTC GTCGTAGCTA TCGTCTAGTA AGGATGAGAC CGGTTAATAT ATGCTTCCTC | 660 |
| CTAGTTCTAT AAGCACGGAC TCTTTGCAAC TGGTGAAGTA TCGTCTAACG GTCATCATGC | 720 |
| ATCTGCCGAA AA | 732 |

(2) INFORMATION FOR SEQ ID NO:928:

(i) SEQUENCE CHARACTERISTICS:
        (A) LENGTH: 724 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1576UP (xi) SEQUENCE DESCRIPTION: SEQ ID NO:928:

| GATCAGGCCG GACGGGTACT TGCAGGAAGG CCTCACGAAA CCCAAGGGGG GCGAGGAGGG | 60 |
| CTTCTCGACG TTTTTCAACG AGACGGGCTC GGGCAAGTTC GTGCCGCGCG CGGTGTACGT | 120 |
| GGACTTGGAG CCGAACGTGA TCGACGAGGT GCGCACGGGC GCGTACCGCG AGTTGTTCCA | 180 |
| CCCGGAGCAG TTGATCAGCG GAAAGGAGGA CGCGGCGAAC AACTACGCGC GTGGGCACTA | 240 |

-continued

```
CACGGTGGGG CGCGAGCTCT TGGACGATAT CCTAGACCGC ATCCGCAAGA TCTCGGACCA    300

GTGCGACGGG CTCCAGGGCT TCCTCTTCAC GCACTCGCTT GGCGGTGGTA CGGGCTCCGG    360

CTTGGGGTCG CTGCTTTTGG AGCAGCTTTC TATCGACTAC GGCAAGAAAT CGAAATTGGA    420

GTTTGCCGTG TATCCCGCGC CACAGGTGTC CACCTCGGTC GTGGAGCCAT ACAACACCGT    480

GTTGACCACC CACACCACAT GGAGCATGCC CGACTGTACG TTCATGGTCG ACAACGAGGC    540

CATCTACGAG ATGTGCAAGA AGAACTTGGA CATCTCGAGA CCTAGCTTTG CGAACTTGAA    600

CAACTTGATC GCCCAGGTCG TCTCCTCGGT GACCGCGTCA TTGCGTTTCG ACGGCTCCTT    660

GAACGTGGAC TTGAACGAGT CCAGACCAAC TTGGTGCCAT ATCCAAGAAT CCACTTCCCA    720

TTGG                                                                 724
```

(2) INFORMATION FOR SEQ ID NO:929:

(i) SEQUENCE CHARACTERISTICS:
        (A) LENGTH: 686 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1577RP (xi) SEQUENCE DESCRIPTION: SEQ ID NO:929:

```
GATCCGTTTA GAGAAAAACG GTAGCCCGGT GAAATACGCA TTTGAGTGCG CAGAGCGGCG     60

CGAGCCGTCC GAAAGGTAGA TTTTGTCCAG TGGGAAGTTG ACTCGTTTGC TTATTTCGAC    120

AATCGACGTC TTCAGCTCCC CGTCTTCCAA CGGGGTGAGC TTGTTGAATA AAGCTGTAAA    180

AACTGGCTGA AGAGCAGTCA GCACCAGATA GAAGAACAGC ATCAGGATAG AGACGTAGCT    240

GACGAAGCCA GTCGAGAACT TTTCAATTAC CTTCAACAGC GCATAGGCTG CAGGAGTGGT    300

AATCATGGAG GAGATCATAA ACACTTTTAG CTGGTCCGTT AGCCATAGCT TGACCGTGGA    360

CTTGTTGAAC CCGAATTTTT CCTCGAGCAC AAAGTTGTAG TAATAGCTCC CAAACAACCC    420

CTGCCACCAG TTCAGCTGTA GGTAGACGAT CAAAAAGTAC AGCGACTGCG AGATGGTCGA    480

TACTGGCACC AGCATGGCGG GCATGCGCTG ACCTACCGCC ACTCCTAGGT TCCACATCCG    540

TGGCAGCCAG TCGTACTTAA TCATTACCAG ATTTAGTCCC AGGAACACCA GATCTCTAAC    600

CATACGGTAG CGTTACTTGG CCCGCTCGTA CGCCTGCGTC TTTTGCATTG TTTCTTTATC    660

AATAACGCCC TCCAGTTCGC TGGGTA                                         686
```

(2) INFORMATION FOR SEQ ID NO:930:

(i) SEQUENCE CHARACTERISTICS:
        (A) LENGTH: 699 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1577UP (xi) SEQUENCE DESCRIPTION: SEQ ID NO:930:

```
GATCTTCGAC ACTATGTAGG CCGCGTAGAT GAGCAACATT ACCACGCAGT CCAGGACGGA     60

CACAGCGTTC ATCAGGCATA CGTAGCCGAT AATGCAGACG GCCAGCATCG CAAACAGTAG    120
```

-continued

```
GTCCACGATG ATCGAATGGC GCTCCGCCGC GCTAAGATTT ACCCACGCAG ACCTCATCAC      180

CATAAATATC GCGCCCTGTA CCACACAGAT GATAACGCCG CAGGCGCCCA GCACCTCACC      240

CACAGACAAG GCGGCGGCAT TGTTGGCCGC GTTCCACGAC ATCAGACTGG AGAACAAGTC      300

GGGCGACGAA TTGCACCATG CCAGTAGGAT GGCTGCCAGA ATGCCCTTGT GCGGCCGGTT      360

CCGTTGGCTC GTCAAGGTCA CCACTATGGG ACATAAATAA TCAGAAGCGG AAACGCCCAG      420

CAACACAAAA CACACGCTCA GATGTAGAAC CGTCAGCACC ACGAACCCAG GGATAGCTTG      480

TTCGTCTCGT ATAGATACAC TGGATGTGTG ATCCGTGCCC ATGTACTTGG TGCATGGTCC      540

ATCCTTGCAC TCTGCCTTTC CAGGTACTTG GTAATAGTAG TGGTAGCCAC CGCAACACTG      600

GTCAAAAAGC ACACCTRAAA CCTCAATATG TAAGGCGTGC GAATGGTAGA TGCGTTATTT      660

AAAATGCAGT GCTTGAGATG AACAGATAGA CTGGTGCCC                            699
```

(2) INFORMATION FOR SEQ ID NO:931:

(i) SEQUENCE CHARACTERISTICS:
        (A) LENGTH: 672 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1578RP (xi) SEQUENCE DESCRIPTION: SEQ ID NO:931:

```
GATCATCCTG CTGCGAGTTG AAGTCATCTT GCGATTCCTT CATGCATAGG AGTTGGTTAG       60

CACCAAACAT AGGATTCATT CTCAAGTCCA CCTGCGTTAA CCGTTCTGTC CTATACTTTA      120

AGTAGTCGAT GAACTGTCTT GTAGAGTGAG CCAGGTTATT AAAATTAAAC CTGTGGGAAC      180

TATCCCGGTC TAGTCGGATG AGATTATCGG TAATCTTATT CACGACACCC CAGTCCTCGT      240

TCGATAGACG CTGGCTACCC GCAGCCTCAT TCCGCAACTC CTTATCGATA TCTATTCCAA      300

GGATCTCGTC CAGGAGAATG CTACCATTTT TATCGTTCGT AATGAACTTG CCTCTACATC      360

GAGCAAAGCA TAGGTGTTTA ATGTGGATAT CCGCTAGATC GAACCCAGAC TCATCGCCGA      420

CTTTCTCTGT ATCTAGCCCA AAACCATGCA TTAGCAGCTT CAAGACAATC GCCACAAGCT      480

GCGATTGTTC CCATGTCCTG CAAGGAAGCT TTACGACATA TGGGATTCGG TCATCGCGGC      540

CATGTTCAAA GTTTTGCAGC ATTAGCACGC AGCTAGTGGA TGGGGTGAAC ACGATCCTAG      600

TAAGGACCGC GACGAACTCA ACCTTCTGTG CTACAATATC ATCACTGGAG AAAAACCTCA      660

GAAGTTCCGC GG                                                         672
```

(2) INFORMATION FOR SEQ ID NO:932:

(i) SEQUENCE CHARACTERISTICS:
        (A) LENGTH: 737 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1578UP (xi) SEQUENCE DESCRIPTION: SEQ ID NO:932:

```
GATCTTTTTC TGGTTCTTTT CCTTTAAACA GAATAATAAT TGAACAGGTA CCGTATTATC       60

GCCGCATGCT AAGTGCACCT TTGACCGAGA CACTTTAGTG ATATTTATTT TGGTAGTGTG      120
```

```
CTCGTATACG TGGGCCACGA CTTTCTTGCC ATTAATCTCG TCCTTGGCGA AGCCGTCCTG     180

GTAGCATCCT AACGCACTCA TTAATGCCAA TGATCGCGGG TTGATCGCCT CACGCCCATC     240

CGAAACAACA CAGACACATA TCCGTTTCCA GGCATCGGGG CCCCAAATAT CAGAACGCTT     300

CCGTCGAGTG AAATATTTTA TGTTGTCCAT GACGCCTTTT AATGTCCGTG CCAATAATAT     360

GTCGTTTTCG TTGTACATCG TTATCACGAT CATGATTTCT GTCCTACGCG GTACAGCGTA     420

TTTTAATTGT CTCACGGTAA AGTTCTTTAG CTGAAACTCA GCTGGCTCAC AGGTGACAGC     480

CTGATATCGC ATGAATTTGT ATTCGTTCGT GAAGTAATCT TCTCTCATGC CACGTGCGTA     540

CTGCGACACT AGCTGTTCAC TGACTGGACA ATCAAAGATA AAGTTTCCTC GATATAGCTT     600

GAACTTTCGT AATACAATGC GATTTTTAGG CTGTTTCGAC TGCGGTAAAC CACTCAGAAG     660

CCGTTCTGAG CTGAGATCGC TGCAGTCGCC AGAACCTTCG GAACCGGAGT ATGCCGATTA     720

GGCGCTACGC GAGAGAT                                                   737
```

(2) INFORMATION FOR SEQ ID NO:933:

(i) SEQUENCE CHARACTERISTICS:
        (A) LENGTH: 663 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1579RP (xi) SEQUENCE DESCRIPTION: SEQ ID NO:933:

```
GATCGAAATA CCACTGATCG ACCGCGGTGC CTCGCTTTGC AGCTGCTCCG AGAGCCGCTC      60

TCCGAGATAC CGCGCAGAGC ATGCCTTTTC CAACACCATC TTCTCGTACC GTTCGGGAAG     120

TGACCCTACT ATACTTATGA TAATGACCTT CTTGTCCTTC AGAGTGCCCT CTGTTTCCTT     180

CTTCAGGTAA AGGTGCGATT CTCGGCCAGG CTCGTAGTAG CCACGGACCG CAGACGCAAT     240

CCGCGTCGTC CACGGCATGG GATGGAAGTA CTCCACCGGA GAGTGGCCCG GCAGAAGCAC     300

CGAGTTGTTC ACGCCGACCA CGTACTCCGA CTGGTGCTCC AGCGGACACA CCTCGAGCGG     360

ATACTCCTTC AGCGGCAACT GGCAGTTCTG TGACCCGGTG TTCGCAACGC TCAGCTCGCC     420

CTCGACCAGC CCCCAGACCC CCGCCATGTC TCCCATGTCC GGCAGGTACT CCGTGTGCCA     480

GCACCAGGAG TCATTTCCCC GCGCTACCGC CTGCAGCGCC TCCTGCTCCA GCGTATGCAC     540

CTGCTTCGCA GTCAGCTGAT GGTACTCCGT GCTCTGGTCG ATCAGCAGCC CGTCCTCGGG     600

GGTCTGCCAG AACGGCATCC ATCCCACCAC GCTTTGTAGA AACGAGGTCG TGGGGCGCCT     660

GCA                                                                  663
```

(2) INFORMATION FOR SEQ ID NO:934:

(i) SEQUENCE CHARACTERISTICS:
        (A) LENGTH: 720 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1579UP (xi) SEQUENCE DESCRIPTION: SEQ ID NO:934:

```
GATCGCACGG ACCGCGAGAC GAGTTCCTCT GGTTCTGTCG ATTGGCGATG GTAGGCCGCC      60

CTGTTGCACG TGACCTGGGG ACAGCAGACT TCGCGTCAAA ATCACCCTTA GCCTCAGCTG     120

TGATGACATC AGCCAAAACG GCCGTCGGTA AACACCTTCC GAGGCGTTCG TMGACTTGAG     180

GATCAGTTTA CCGTGCTTAC CCTTCCCGTG CGCCTTTTCG AAGGACTCGC GGAGCGTCTC     240

AATATCTTGT GAGAGCTGTT CCAGCGAGAT ACCCTCTTCT GGAACGTAGG AAACCTGTGC     300

GCCCACCGCC AAGGCAGCAT GCGTTGCCAG ATAGCCTGAG TTACCACCCT GGACATCGAC     360

GACAAAGACC CGCGCTCTTG TGGAGGCTGC CGACTGCTTC ACAACATCAC AGTACTCCAT     420

TAGGGCATTC AGAGCTGTGT CTGAACCGAG CGAATACTCA CTGCCCGGGA CGTTATTCGA     480

AAGTGTTGCT GGAATGAGTA CCATTGGTAT TCTGAAAGCT GGGTAGTTCT CACGGGCCCG     540

CTCCAATTGA TGCAAGGAGA CGAAGGCTCG AACCCACCAA CAATAACCAA GCCGTCAAAC     600

TTGTACTTTT GGAAGTAGTA GGCAATCATG CCAATGTCTG CATCTTCTGG GACAGTTCTG     660

TTGGTTCCCA ACTCGGAACA CCGCGAGATT GCCAGCCAAG CATATCTTTC CAGTTCAACG     720
```

(2) INFORMATION FOR SEQ ID NO:935:

(i) SEQUENCE CHARACTERISTICS:
        (A) LENGTH: 718 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1580RP (xi) SEQUENCE DESCRIPTION: SEQ ID NO:935:

```
GATCCGTGTC GACAAGTTGG TCACGTATAT ATGGCGCGTG TTCGAGCGCG TCTGCGTGTA      60

CCCGCCGAAC CAGCAGCGCT GCCATCTCGA AGACATCATG CTCTTGCGTG TGTACTGCGG     120

CGAGGCGCGG GGGCACCCGC TCTTGCTCAT GGCGATCGTT CAGGCGGTGG CGGCACGCTA     180

CGGGGTGCAG ACGCTCCTCT GCGAGCAGGT ATTGATCATC ATTGACCGCA AGTTGCGCGG     240

CGGACAGTCA TACTTGATGA TCCCGCTGCG AGGGAACGCA AAGCCGCGCA TCTTCACGCG     300

GCGGCGCTTG CTCGACACTA TGCGGCACAC AATACCCAAC ATTGCCGACC CGCGGAGCCT     360

GGCGCTCGCC CGGTTCCTCA CTCCGCTCAC GAAGCGCGCG GGTGCTGAGA AAATCTTCAA     420

AGACTGGTCC ATCTACTGCG ACAAATCCAT ATGGCGGACG ATCCCTGATC ACTCGCCCAA     480

TGGCATTCTG CGCTACCTCC CGCACTCCTG CACGCCGATG GACGAATCCA TCTTTGAGTA     540

TTTCATCGTC TATTGGAAAA CCGCAACAGC AAACCACTCC ACGAACAACA TTTTCCACAC     600

CGTTCTTCTC AAGCAATTCG AAACGATCTT GGTCAAGAGT ATCCCGGCGA CGCATCCACT     660

TTGTCGATTG CCGGGAGCAG CTCATGGACT CCATTATCGA GATGTCTTTC GCGAGTCC      718
```

(2) INFORMATION FOR SEQ ID NO:936:

(i) SEQUENCE CHARACTERISTICS:
        (A) LENGTH: 705 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1580UP (xi) SEQUENCE DESCRIPTION: SEQ ID NO:936:

```
GATCCTTTTC ACCAACAGCT GTCTGGGCCA GCTGCGGCCT GGGATGAACT ACAACGAGGC      60

AGTGAAAGCG CTGACGAACC TGGCGCTGGA CAGCTTTACA CTGCCGGGGG ACGGTGGGGT     120

TTCCGCTGAA CAACGTGTAC TCTGTGCCGG TAGAAGACGG TGCTCAGATG GAGCTGCTGA     180

AGGGGTACCT GCAGCAGTTG CGGCAGGAGC TGGCCACGCG GCTGCTGGAC CGTGTGTATG     240

GGGCGGAAAA GGCACAGCCC TCGAAGTTCT GGCTGGCCTT CACAAGGCGC AAGTTTATGA     300

ACAAGGCGCT GTAAGGCGAA ATAGGTACGT AGCTGGCGGC GCCAGGAAGT ATTTACAAAG     360

TTGGCTGTAT CGCTACGAGG TTTTGGTGGC GTGTGCCTTG TTGGAGCGCA CGAGGAGTTC     420

AACGGCGGAA GCTCGGAGCT GTTCCGCGTC TTTCACGATC GCGTTCACGT CAATGCTGAG     480

GTCGGTGTTT TTGGCGCGGA AGCCTTGGAT CCGCGCCTGC AGGTCTGTCA GCGCCTGGAG     540

GACACGCTCA TAGTCTGCAT CTTCTTTCAC GCGCTCTTTG TATGTTTGGA AGGACTGAAC     600

GATGTCTTCG ATACCGGGCT CGACTCTGCT GATCATCTCG ATGCGCTGGC GCAACAACTG     660

ATCGCGGTCG CTGTTGGCGT CGCGTCCCTA ATCATCTGCT GGATT                    705

(2) INFORMATION FOR SEQ ID NO:937:

(i) SEQUENCE CHARACTERISTICS:
        (A) LENGTH: 665 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1581RP (xi) SEQUENCE DESCRIPTION: SEQ ID NO:937:

GATCTTAATT TAAAATTTTA ATTAACTATT TATAATTTAG AAATATATAA TCTAGAGATA      60

TATAATCTTA AAATCATAGG TAAAAATACT TAAGATAGTA AGAATAAAAT TAGTAAAATA     120

AATAGAAAAC CATAAGTTAA TTGATTCATA AGAAAAATG GAATTATTTG TGGCATCTTA      180

ATTTTTATTA TTTAATTGAT TATTATCTAT TTAACATAAA ACATTTTAAA ATGTTATAAA     240

ATAAATAAGA AATTACTTAT AGAATATTTA TTAAATAGTA TTTAATTTAA TTTTAATATT     300

AAATATACCA TTTTTATTAA TAAATAGATT ATTAAGTTTA TTAATATTAA GTGATATATA     360

ATTTAATTTA TATAAATTAT TTAATTTACT TCATTGATAT ATATAATTAT TAAATGTACC     420

TTTCATAATA TTTATTTTTA TTAGTCTAGT AATATTTCTA TTTAATAGTC TACCCTTTAA     480

TTGGATATTA CTACCTACTA AATATTTACC TAATAATATA TTATTAAGAA TACTTAAATC     540

TAATAATTTA TTATCTAAAG TATATAAATT AATTAAATCT TTTTTATTAT TATTCTAAAT     600

TATTATTAAT TAGTAAATTA TATTTATTTA TTTTATTAAC ATAATTTTTG ATAATAATAT     660

ATCAT                                                                665

(2) INFORMATION FOR SEQ ID NO:938:

(i) SEQUENCE CHARACTERISTICS:
        (A) LENGTH: 732 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1581UP
```

(xi) SEQUENCE DESCRIPTION: SEQ ID NO:938:

```
GATCAATTAA TAAATGGTTT AACTAATAAA GTTAATAATA AATCTATTAA TTATATAAAA      60
CTACCTGATT TTATTGAATC AAATAATATT TTCTTAATGA ATACTACTAA ATCATCATCT     120
ATTGAGTTTA TATTAAATTC ACCACCTCTT ATTCATTCAT TTAATACTCC TCTAATTCAA     180
TCTTAAAATA TTCTTAATTA TTAAATTATA TAATAAAAGT TAGTGGATAT AGTTTAATTG     240
GTAAAACATA TGTTTTAGGG ACATATATCT TCAGTTCAAA ACTGAATATC TACATATTAT     300
ATCATTAATA TAATAACTCT TTAATTAGAG TGGTACCACA AGAATGCTGA AAGCATTAGG     360
GGTGTGTACC TTAGCTCTCT AATTAAAGTT ATAAAATTAT CTTAACTAAT AAAAATAATT     420
AATTAAATAA ATAAATAATT AATTAAATTT AAAATGTTTA AAAAAAGAAA TAAATAATAT     480
GTTATATTTA AATAGATCAA AATTTCAACA ATTTCCATTT CATTTAGTAC TACCATCACC     540
ATGACCAATT GTTACATCAT TTAGTTTATT AGGTTTACTA TTAACTTTAG CTTTTACTAT     600
ACATGGTATT ATTGGTAATA TTTATCCTTT ATTATTATCT TTATTAGTAG TTTTATTACT     660
AATAACTTTA TGATTTAGAG ATATTGTAGC TGAACTTACT TATTTAGGTG ATCATACTTT     720
AACTGTAAGA AA                                                         732
```

(2) INFORMATION FOR SEQ ID NO:939:

(i) SEQUENCE CHARACTERISTICS:
        (A) LENGTH: 694 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1582RP (xi) SEQUENCE DESCRIPTION: SEQ ID NO:939:

```
GATCTCAACA CGGTCGTTGG AGAAGTGTGC AACACACGAG TACGTAGTAC CCAAATCAAT      60
ACCGACTGAT TTAGACATGA TCACTGATTA GAAAACGAAA TCTCTGGTTT TCGGATAACC     120
GGGAGAAATA CCAATGGTGA TAACCGTACG TAAGGCCAGA GGTACAAAGC TACTCCAATC     180
TGAAGCTACA CACGCCCAAC CCTTTTATAC AATTTCAATT TTTTCTCTCC CAAACGAACA     240
TGGCAGATAG TAAGAGTCTT CGAGCCCAAT GCCTGTTCGG TTTTTTTTTG TTCTGGAAAA     300
TTCTACCATA ACGTATGTGG CCGTTGAAAA CTGATCAAAC GGGTCTCGAA GATCTTAGAA     360
TAGAGGCTCC GACAGAAAGG GGGAGGCCGA TTCAAAAAAG ACCGCATGAG CCTCACTCGT     420
GCTTCGAGGC GGGAGAGCCC ATAGGCTTCT TTCCAGCGGC CACCGACGGT TTCTGGAAAG     480
GAGCGAAAAC AGAGAATGAA CCGAGGCGGT TGATCTGCAT CTTGGACTTG GCGTAGGCCC     540
GTTTCAACTG AGCGGGAATG CGTGGATGCG AAACTACGCC GTCCGCACGC ACCTCCCACT     600
TCCGTACCAC CGCACGCATG TTGGCCGATT TTCGTAGCGC GCCTTGATGA AAAGCGAGTA     660
TAGAGCCAGC ACAATCCACG AGCGGCGGCG ACAA                                 694
```

(2) INFORMATION FOR SEQ ID NO:940:

(i) SEQUENCE CHARACTERISTICS:
        (A) LENGTH: 707 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
    (A) ORGANISM: PAG1582UP (xi) SEQUENCE DESCRIPTION: SEQ ID NO:940:

```
GATCTTGTTC TCCGCATCCA GATACTGGTC GAAGCGCGAG TTCATCTCGT CTACAATCGG      60

CTTCCACGAG TCGGTGTTAT CTATCGCGTC CCCGAAGCCC GGCGTGTCCA CCACCGTCAA     120

CTTCAACACC ACGCCGTTCT CCTCGATCTC CGTCGTGACG GTCTCAATCT TCACCTTGTT     180

CTCGCCGTCC TTGGCCCGCG ACTCGTCGCC GTCCTCACCG TCCTCAAGCT TCAACGCGTT     240

GAACTGCTCC GGCGTGTCGT CCTTCGCCGT GTATAGCTCC TTGTTGAACA ACGTGTTGAT     300

CAAGGTCGAC TTCCCCAACC CCTTGGCGCC CACGCAGAGC AAATTGAGGT TGAACCCGCG     360

CCGGATCGAC TTGCGATGCC ACTGCTTGGG AAGGTTTGCG AACCCCACGT ACCCCGAGAT     420

CTTGCGGTGG ATGATCCGCA GGTCTGGCTG GTCTGGCAGC ACCTGGCCCG CCGCGAGCTC     480

GCCACCCAGT GCCGTCGCCA CATTCTCCTT GTCGTCCGGA AGGTCCAACC CCATCTCCTC     540

CTCCTTCACG TTCATGTCCG AGCTTGTGTC CTTCGCGCTC GCCGTCCCGT TGCTCATTAG     600

TGCGCCCCCG TGCTGGTTGT CACGCCTCCC GCCGTCGTGG CACTGTTGGT GTTTGCCGAA     660

TCCTCCTGCG AGCCTGTAGG TAACATGCTT GTTCTGATTT GGTAGTC                  707
```

(2) INFORMATION FOR SEQ ID NO:941:

(i) SEQUENCE CHARACTERISTICS:
        (A) LENGTH: 717 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1583RP (xi) SEQUENCE DESCRIPTION: SEQ ID NO:941:

```
GATCAATTAC CCTGGCGCCA ACCATATTTG GATGAATATT TGCATTGTTG CCGATAGGGG      60

TTCCCTCATC GTGTATGTTA TAGACCTTCA CGTCTTCATT AAAAGGGCAT GTGATGACTT     120

TCTTGCTGTC GGCAGAGAAG GTCAAACAAA TTACAGATTG TTCTGTACCG GCCAAAACTT     180

TATAAACCCT GAAGTTGTTT AACACGTCAT ATATGAATAC CTTACGATCG CTGGAAGGGT     240

CAGTGGATGC ACTGGCCAAA TACCGACCAT CTGGTGAGAA TTGGAGGTAC CAGATTTCAT     300

CTTTATTTTC CGAAAGAGTC TTCACATGAC TGAAATTGAA CATGCACATA GAGCCAACGT     360

TATCTTGAAG CAAGTTATAA GTGGTTTTCT CTCCAGAACG GTTTCCTTCG TGGTTGTGAG     420

GATCGTCGCT GAAGCTTAAC AGGTCGCTGG ACCGCTGGAA CTGTATAGCC TGTTTTAACA     480

ACGTAATGAG CCTGCCCCGT GGAACCAAAT CATTCGGGTT GATATATTGT GAAATCTGAT     540

CAAGCGCCAA TTGCCGCGAG GCTGCCAGAG ACCCTCCCCA TATTTTGTT GCCTCTGCGG     600

ATTCCGCAGG ACACGTCAAA ATAGTCGTCA CTGCAGAAGA GCTGTGTCGG GAGTCATAGC     660

CCACTCTCCC TCGGGCTCCT CCACCATAGA TATGGTCTGT ACAGCCACAG CGAGTCC       717
```

(2) INFORMATION FOR SEQ ID NO:942:

(i) SEQUENCE CHARACTERISTICS:
        (A) LENGTH: 716 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
    (A) ORGANISM: PAG1583UP (xi) SEQUENCE DESCRIPTION: SEQ ID NO:942:

```
GATCGACTGG AAGTACACGT CCAGCGACCG GTCAAGGCCC ATGTCCTGGA CGGACTGCTC      60
GAAGGTCTTC ACGAGGTTCT TGGCGATGCG GAGCATTGGT GTGCGGTCTG GGGCGGGCGA     120
CGCTGCGGAG GGCTCACCGA ATTTGCTTGT GCGTGTGGTC ACGTGACACT TGGGCCGCTG     180
GCCCCGCCGG GCCCGCCTGG CCCGGAATGG CTGCCCCGCC CTGGCACGCC GTTCCTGCAA     240
TCACATGATT CATGATTCCG CTTTTGGGGG GGATCACTGC GCAGCCGTTT TTGCTGCTTT     300
TAGCCTCCCT GACACCCTCG GCTGCGTCTG GACGCAGGTC CCCGCCGGCT GTCCGCTGCG     360
TGGCTGTACG TGTGGGGTGA CGCCATTTTG TGGGACAGCG GCGACGCATG ACGACGAGCT     420
CGGAGGGTCC GCCGTTGACG ACAGCCCCCT AAAGGAGTTT CTTTTATTCG ACGCGGCCCC     480
TCAAACACTA TATATGAGCA AAGGCAGGAT GGAAGGTAGG CTAAAGCAAG AAAAGACCTC     540
GACCAACGGT ATCGAAGTCT AAAATCTTAG CAGGTACCAG GATGTCTTTC GAAGATTTGC     600
ACAAGGCGCA ACGCGGGAAA GTCGAGGAGG CAGTGGACGA AATATGTAAG GATTTCGAGG     660
TGACGGAGGA CAAACTCCGC GAGTTGACCG CGTACTTCAT CGAATGTTTG GAACAG        716
```

(2) INFORMATION FOR SEQ ID NO:943:

(i) SEQUENCE CHARACTERISTICS:
       (A) LENGTH: 677 base pairs
       (B) TYPE: nucleic acid
       (C) STRANDEDNESS: single
       (D) TOPOLOGY: linear (ii) MOLECULE TYPE: DNA (genomic)

(vi) ORIGINAL SOURCE:
        (A) ORGANISM: PAG1584RP (xi) SEQUENCE DESCRIPTION: SEQ ID NO:943:

```
GATCCAAAAA GCCTTCCGGG CGCGGGCACA TTTATCACAC CCGCTGTGCT TGACGGCCTC      60
GACAATACAT CCTATGACAT GCGTAATCCC TCCTATGTTG TTCCGACGCG GCGCAAACGT     120
GCCAGCGTCT CGAAGGCTTC GCGCGCGAGC AAGAGTTCCT CGCCCCTTGA AGAGGAGGAG     180
AAGCCATTTA AATGCCAAGA ATGCACCAAG GCCTTCCGCC GCAGCGAGCA CTTGAAGCGC     240
CATATACGCT CTGTGCACTC ATCGGATAGG CCGTTTCCGT GCACCTATTG TGATAAGAAG     300
TTCAGCCGCA GCGACAATCT GTCGCAGCAT CTCAAGACAC ATCGCAAGCA TGGCGATATA     360
AAAGACACGC CACCAACCAC CAAGAAAGGC TGACTTTCAC ACATCTATGC GAATACCCGA     420
TGTTGCATTA AGAGATACAT ACAGCGCATA CAAGCTGACA CAACGTCCCG TACGCCAACA     480
GAGGAGATGA TAAATACTAC ATACTCAATA TATCAATACC TCCTACTTTT GGTAATCATA     540
TATAACTGTT TTCTTTCGCA CTGTTCTGGT AACGTTGTCA TAGGTTTCCC TGTTGCTGCT     600
AGCTGGCCAG GATTCCCTTA ATGGATGAGG TCCGGCGCGC AACCAGACAA AAGTTGCGCA     660
GCTTAAGATA GTTGGAC                                                   677
```

(2) INFORMATION FOR SEQ ID NO:944:

(i) SEQUENCE CHARACTERISTICS:
       (A) LENGTH: 706 base pairs
       (B) TYPE: nucleic acid
       (C) STRANDEDNESS: single
       (D) TOPOLOGY: linear (ii) MOLECULE TYPE: DNA (genomic)

(vi) ORIGINAL SOURCE:
    (A) ORGANISM: PAG1584UP (xi) SEQUENCE DESCRIPTION: SEQ ID NO:944:

| | | | | | |
|---|---|---|---|---|---|
| GATCCCATTT | TGTCTTCTTC | GGCTACCGGG | ACGGCCAGTA | GAGCATCCAG | AATAGATGTT | 60 |
| CACCAGTAGG | CTTGCCAAGT | GCTCATTAGT | TGCCGTCACA | TGGCTGCCCG | TGTACATGAC | 120 |
| AGTGACACAC | CATGTTGTAT | TCATATCGAA | GGTGGAAGGC | CCCTCGATGC | GCCCAACGCT | 180 |
| CAATCCAATG | GACGGAGTTG | CATCGGACTG | GGTTTTGGTG | TGGAAGCTTG | GAAAGACTAA | 240 |
| TATTCGGAAC | CTGAATCATG | GGACGTGGT | GATCTTCCGC | TCACCCATGA | ACCCCAAGAA | 300 |
| AGTATACTGC | AAGCGCATCC | AGGGTAAGCA | GTATGATACG | GTGCGCACGC | GGTATCCTTA | 360 |
| TCCGAAGAGT | ACCTGCGAAG | TGCCAAAGTC | GCACATATGG | GTCGAGGGGG | ACAATGTCAC | 420 |
| GCAGTCGGTG | GACTCGAATC | ACTTCGGGCC | GATTTCGACG | GGGCTTGTGG | TAAGCGAGGT | 480 |
| GACACGGGTC | ATATGGCCGC | CATCGAGATG | GGGCGCAGAC | CTGCACGAGG | GCATGGGTCG | 540 |
| ACGCGCAGTT | GTTGCTTCAT | GATTGCGGGA | GCCGGGGTAG | GCGAACCTAC | CGCTACGTGT | 600 |
| ACATAGCTGA | AAGACTAGAT | ATTATATAAT | GTCGAACAAC | GTGCTGCACT | GCGGCAGAAG | 660 |
| GATGGCTTAA | GAATCGTTGT | CCTCCTCCTT | GACGATCTCT | GGGAAA | | 706 |

(2) INFORMATION FOR SEQ ID NO:945:

(i) SEQUENCE CHARACTERISTICS:
        (A) LENGTH: 716 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1585RP (xi) SEQUENCE DESCRIPTION: SEQ ID NO:945:

| | | | | | |
|---|---|---|---|---|---|
| GATCCCCGTT | GTTGTGCACG | TGTGATTCAA | TATATACATA | CTGCAAGTCT | GTACATGTGC | 60 |
| TCTATTATAT | ATGGTGCTCA | TGTTGCGCTT | ACATTCTTTC | TTTATACAGT | TCATGTCCTT | 120 |
| CCGTCGTGGC | ATACCCAGTG | ATGCCCGTCA | TACCTGGTAA | CCACAGTTTC | TATAATCATT | 180 |
| CAGGCTGAAC | TGATCAATGG | AGCTGCGTTT | GCCGAATTTG | ACGCAGAGGT | TTGTATACAC | 240 |
| ATTGATGTCC | GCCCTCGTAA | AGCCCTTGCT | AAACGTGCAG | AAGCAATTCT | TCCGTTTGGA | 300 |
| ACACGAAGTG | CAAGGCTTGA | ATGCTATCAA | CTTATCCACA | TGCTTCAGCA | GCGTCAGTTC | 360 |
| CTTTGTGAGC | AGCGCCTGCC | TCACCTCGTC | TGGAATCTGG | CTAAGCCACT | CGTTTGCCAG | 420 |
| CTCAGACACA | TTTACCGGTG | CGTGAAGCAT | CTCGTTGAAC | GAGCCTGTGA | CCGAGGCGTC | 480 |
| CTGGAACAGT | ATCGTGATCG | TGGCGTCACA | CTTAATCTTC | TTGGAGCGGC | AGATGTCGCA | 540 |
| GCTGGGGCCC | GTCCGCTGAC | GCTTGTACTT | CGACGCCGTG | ATAACGGTTG | GCTCCTGTAG | 600 |
| CAGCGAGTTC | GGTGGCGAAC | AGTGCGCTGC | ACGTCCCCCG | TTGGAAGCCC | GAAGCAGATT | 660 |
| CCGACATCAG | CGGCGACATC | GACACGCCGC | GCGCGGACTC | TGGCGAGCGC | GCGTGT | 716 |

(2) INFORMATION FOR SEQ ID NO:946:

(i) SEQUENCE CHARACTERISTICS:
        (A) LENGTH: 740 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
    (A) ORGANISM: PAG1585UP (xi) SEQUENCE DESCRIPTION: SEQ ID NO:946:

| | | | | | |
|---|---|---|---|---|---|
| GATCACTCTA | CGGGGACAG | TTGATTGAGT | CCAGTGACGT | GAATGTCAGA | GAGTCACCAT | 60 |
| TTTTCAACCT | ATGACCCTCA | TCGGCCAGCA | TGAGTCCAAC | CTTGCAGCCT | TTTAAATTTT | 120 |
| CTACATTTCG | CCGCAGAGTC | TCATAGGAAA | TAATCAATAC | AGGCTTGACT | ACATTACGGC | 180 |
| CCTGGGCAAT | CGCCCACTGC | CTGACGGACT | GTGCAACCGA | GCCGTTCGAA | AGGGAACTTT | 240 |
| TACGTCCATC | GATAGCCAGT | GGCGAAAGGG | CATCGGGTCC | CAACCACTTC | ACAATCTCAT | 300 |
| TAGCCCAGTT | ATTAACCAGG | GACGAAGGGC | AGACAATGAT | GCACTTTTCA | ATTGTAGGAC | 360 |
| GACCTTGGGA | GCCCTGCCGT | AGTAGCGTCC | ACATTAACGC | TATACATTGC | AGCGTTTTAC | 420 |
| CTAGACCCAT | TTCATCAGCC | ATAATACACC | CATAAGCCCC | CCTATTTGAT | TCTCGAGTCA | 480 |
| TAGCTGCATT | GGCATCCAAG | ATCTCAGGCG | AAGGCGTCGG | CGTCGGCGTA | AGAATCGGCG | 540 |
| TCGGCGTCTC | CTCAAGCACC | TCCACAACTA | TTGGCTCACT | ATCTTTACTA | CCCGGATCCT | 600 |
| TACCAGTGCC | ATCGTCTTGC | ACCTCGCCGG | CTGCCAAGAG | AGCCTGTGTA | TCCAAAAAAT | 660 |
| CCTTCATCGC | CAGACCAGTC | ACACAGCGGT | ACAGGAATCT | TACCCCTTCC | ACTTGATGAG | 720 |
| GGCGTTAAAT | CCGCGCCAGA | | | | | 740 |

(2) INFORMATION FOR SEQ ID NO:947:

(i) SEQUENCE CHARACTERISTICS:
        (A) LENGTH: 702 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1586RP (xi) SEQUENCE DESCRIPTION: SEQ ID NO:947:

| | | | | | |
|---|---|---|---|---|---|
| GATCAGGCGT | AAGGGCAGGA | TATGAACTAT | GGAGACGTCT | ATTTTAAACT | CAATGGCATA | 60 |
| TAAACACCGC | ATATTTCTTG | TGGTTATGAT | AACTTCAATT | ATCGAATCAG | TCGCAGCGTA | 120 |
| GAGGGTTGGT | GAGAGTTTAC | CACGATATCC | AGTTGTTGCT | GCGCCCGCAG | CACCAAATAT | 180 |
| AACTGAGAAT | TTAAGTTTCT | CGAAGAGAGT | ATGCAACGGG | GGCTTGTCCA | CTACGATTAA | 240 |
| AAGAGCACCA | GCTTTCTCAT | GCCTTCAACT | ATGTCAATAT | AAATATATTG | CAAAAGGCTT | 300 |
| AAGCTCTGTA | TTGAGCCCCG | GAAATGTTTC | TAGCAATGTA | GCTCTCTCAT | CTTCACATTA | 360 |
| GGCTGCGAAT | GTGCTGACCA | ACTGCAAAAA | CCCAGTCATA | TCGTAAATAG | TGATGATAGT | 420 |
| CAGCGCGATA | TTTAACCGCG | GGTGCAAAAA | ATTGATTTCG | CCCAGGATCG | AACTGGGGAC | 480 |
| GTTCTGCGTG | TTAAGCAGAT | GCCATAACCG | ACTAGACCAC | GAAACCAACC | TTGAAGAACG | 540 |
| CACGCCGCGA | AACCGACCAA | CACAACCGGT | GCAAACCACG | TGCCTGACGA | CTCTTTAGGC | 600 |
| GTGTGCTAGG | GGGGCGCCCA | CTCGTACTTA | TTTTATAAAC | CTTGGATCCA | GGTGCGTCCA | 660 |
| TATACAGGGC | GATCCGCGCC | ATCTGCAGCA | GCCAGGAACG | CA | | 702 |

(2) INFORMATION FOR SEQ ID NO:948:

(i) SEQUENCE CHARACTERISTICS:
        (A) LENGTH: 720 base pairs (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1586UP (xi) SEQUENCE DESCRIPTION: SEQ ID NO:948:

```
GATCAACAAA GTCAAATCCA AAATTGTGCT GGGAGAGAAA AAGATTCCGC CATCATTGGG      60

CCTTTTCTAT AGCCATCAAT TCAACAATCG GTTAAGCGAT TTGAAGCCTT CAGCCCTTTA     120

TGAGGGTGAT CCTGAGAAAC AAGATGGGAC TGCTACCGAT GGAAGCAGCG GTAGTGTCCA     180

TGGGTATGCC ACTGATGATG ATATCATTGT CACAGGCGAG AACACCGTTT ACAGCCTAAG     240

CCAAGGGATT GCATATCATA TAGATGAGGA AGGAAACTAT TATTATGCTG GTATCGATCC     300

GTTTACTGAT GCATTCGAAC AAGAGGCAGA TTGCTTATAT CATGAAAGTG AGGTAGAAAG     360

CGTAAATGTC AACAACTTGG ACCATCTTTC TTCCGATATC AAGGAAGAAA ACATAGACCT     420

CGATGGTAAC ATAGAATTGT ACGATTCTGA CTTTGACCAC ACTTCCCTCG ACCAGGTCCC     480

GAAGGCTACA GAAACAATCG AAAAATACAA TAATAACCAA TACTACAAGA TGAACACGCT     540

AATCACTGAC TCATCAAATT GCCAGGGCAA CACTGTAGCG CTCTCATCTG ATTATGGAAC     600

AACTTCCGTG CATGTTGAAA ATGTCTCTAA TGAGAATTCC TTGGGGTCAT CAGGCTACAA     660

GGAGATATTC CTGAAAACTA TGATGACTAC CTTTACGAAG GGGACGAAGA TGATTTCGAT     720
```

(2) INFORMATION FOR SEQ ID NO:949:

(i) SEQUENCE CHARACTERISTICS:
        (A) LENGTH: 678 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1587RP (xi) SEQUENCE DESCRIPTION: SEQ ID NO:949:

```
GATCATCGAG AAGGAGCTGG AGGGCGTGGG CATCCGGCTG AACAAGTCGC CTCCGGACAT      60

CATTGTGAAG AAGAAGGAGA AGGGCGGTTT ATCGATCACG AACACAGTGC CGCTGACACA     120

TTTGGACCAC GACGGGATCC GCGCGGTGAT GAGTGAGTAC CGCATCAACA GCGCGGAGAT     180

TGCGTTCCGG TGCGACGCGA CAGTTGACGA CCTGATTGAC GTCCTCGAGG CTCCCAGCAG     240

GCGTTACATG CCGGCTATCT ACGTGCTGAA CAAGATCGAC TCGCTGTCAG TGGAAGAGTT     300

GGAGCTGCTG TACCGGATTC CGAATGCTGT GCCTATATCT AGTGGACGGG AGTGGAACCT     360

AGATGAGCTG CTCGAGGTCA TGTGGGATCG CCTGAACTTG GTGAGAGTTT ACACCAAGCC     420

CAAGGGGACC ATGCCCGACT TCAATGACCC GGTTGTGTTG CGGTCAGACC GTTGCACAGT     480

GCGGGATTTC TGTAACCAAA TCCACAAGTC TCTGGTTGAG GAGTTCCGGA ATGCTTTGGT     540

TTACGGTAGC AGTGTGAAAC ACCAGCCTCA GTACGTGGGT CTTGCACACA CTCTAGAGGA     600

TGAAGACGTT GTGACAATTC TGAAGAAGTA ATGTCTTGGC ATTTATGCAT GGTTTCAATG     660

CACACGTTCT CGCGCTGC                                                    678
```

(2) INFORMATION FOR SEQ ID NO:950:

(i) SEQUENCE CHARACTERISTICS:

(A) LENGTH: 702 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1587UP (xi) SEQUENCE DESCRIPTION: SEQ ID NO:950:

GATCCTAATA AAAGCTTTTC TGCAATTGCT CTACCTACGC CTGGAAGGTC GCGTAGGGCA        60

CACGTTTCAA ATAGATGTGC AGGAGATACG ACCTGCGTAT CACCCCCCTT AATTGATTCT       120

TTAGTGCAAA CCAGATAGCC ATCAGGTTTC GCACGTTTGA AAGCCAACCG GGCTAGAACT       180

AAGGACGGTG CGCACCCCAC GCTTACCGAA CAGCCGCCTG TGCGCTCTGC TACTTCTGAT       240

CGGATGCGTA TACACAAGTT TTGACAACTA AGTGTATCGA GCGGCATGTC AATAACACAG       300

ACAGCCTCAT CCACCGAAAT TGGATACACT GCGTCGAAAG CCTTTAAACC CTCCAATACC       360

TCGTAGAAGG CATTCGAAAT CGTTTCGTAT TCATCGTAGG TATAGGGGAG GCAAACCAGT       420

TGGGGGCACA AGTTCTTGGC TTTGGAGACC CACATGCCAT TTTGTATTCC ACATTCCCGA       480

GCAGCATAAT TACAGGAGGC AACGTCCGAA GATGAACCCC CATGACACAC TGCCAACGGT       540

ACTTCGGCCT TGCTTGGATA GCCCGCCTTG ATGCCTGAAA TAGTCGCAAA AAAGCAATCA       600

AAATCCACGT GGAAGACGTG TGCTGGTGGA GCCCGCAAAT CATTTAGCGC ACCTTCATTC       660

ATCCGGAGAT GCCTGTCGAG AAACTCTCGC GTAGAGCCGC CT                         702

(2) INFORMATION FOR SEQ ID NO:951:

(i) SEQUENCE CHARACTERISTICS:
        (A) LENGTH: 685 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1588RP (xi) SEQUENCE DESCRIPTION: SEQ ID NO:951:

GATCCTTTAG TTCCTCGGAG TTTGAGGCTA GAGGTGCCAG AAAAGTTACC ACAGGGATAA        60

CTGGCTTGTG GCAGTCAAGC GTTCATAGCG ACATTGCTTT TTGATTCTTC GATGTCGGCT       120

CTTCCTATCA TACCGAAGCA GAATTCGGTA AGCGTTGGAT TGTTCACCCA CTAATAGGGA       180

ACGTGAGCTG GGTTTAGACC GTCGTGAGAC AGGTTAGTTT TACCCTACTG ATGAATGTTA       240

TCGCAATAGT AATTGAACTT AGTACGAGAG GAACAGTTCA TTCGGATAAT TGGTTTTTGC       300

GGCTGTCCGA CCGGGCATTG CCGCGAAGCT ACCATCCGCT GGATTATGGC TGAACGCCTC       360

TAAGTCAGAA TCCATGCTAG AACGCGATGA TTCTTTTTCT CGCACATTAT AGATGGATAC       420

GAATAAGGTG CTTTTAGCAT CGCTGAACCA TAGCAGGCCG GCAACTGGTG TTCAGACGGA       480

AAGGTCTGGG CGCGTGCCGG CGGATTGCAA TGTCATACTG CGCGAGAGTA AATCATTTGT       540

ACACGACTTA GATGTACAAC AGGGTATTGT AAGCAGTAGA GTAGCCTTGT TGTTACGATC       600

TGCTGAGATT AAGCCTTCGT TGTCTGATTT GTTTTCTATT TGGAAGTCTG CAGGAGCAGG       660

CTTTGAAATA GAGTCTTATG TTATT                                            685

(2) INFORMATION FOR SEQ ID NO:952:

(i) SEQUENCE CHARACTERISTICS:
    (A) LENGTH: 723 base pairs
    (B) TYPE: nucleic acid
    (C) STRANDEDNESS: single
    (D) TOPOLOGY: linear (ii) MOLECULE TYPE: DNA (genomic)

(vi) ORIGINAL SOURCE:
    (A) ORGANISM: PAG1588UP (xi) SEQUENCE DESCRIPTION: SEQ ID NO:952:

```
GATCCCGTAC ACGAAGAAAA TCGGACGGGC CAACCAAACC CAAAGTTCAA CTACGAACTT        60

TTTAACTGCA ACAACTTTAA TATACGCTAT TGGAGCTGGA ATTACCGCGG CTGCTGGCAC       120

CAGACTTGCC CTCCAATTGT TCCTCGTTAA GGTATTTACA TTGTACTCAT TCCAATTACA       180

AGACCCGTAT GGGCCCTGTA TCGTTATTTA TTGTCACTAC CTCCCTGAAT TAGGATTGGG       240

TAATTTGCGC GCCTGCTGCC TTCCTTGGAT GTGGTAGCCG TTTCTCAGGC TCCCTCTCCG       300

GAATCGAACC CTTATTCCCC GTTACCCGTT GAAACCATGG TAGGCCACTA TCCTACCATC       360

GAAAGTTGAT AGGGCAGAAA TTTGAATGAA CCATCGCCAG CACAAGGCCA TGCGATTCGA       420

AAAGTTATTA TGAATCATCA AAGAGTCCGA AGACATTGAT TTTTTATCTA ATAAATACAT       480

CTCTTCCAAA AGGTCGAGAT TTAAGCATG TATTAGCTCT AGAATTACCA CAGATATCCA        540

TGTAGTAAAG GAACTATCAA ATAAACGATA ACTGATTTAA TGAGCCATTC GCAGTTTCAC       600

TGTATAAATT GCTTATACTT AGACATGCAT GGCTTAATCT TTGAGACAAC ATATGACTAC       660

TGGCAGGATC AACCAGATAC TATCTTAAAG AACAACCGAA AATGCGCAAG CACACCACGG       720

GTC                                                                    723
```

(2) INFORMATION FOR SEQ ID NO:953:

(i) SEQUENCE CHARACTERISTICS:
    (A) LENGTH: 741 base pairs
    (B) TYPE: nucleic acid
    (C) STRANDEDNESS: single
    (D) TOPOLOGY: linear (ii) MOLECULE TYPE: DNA (genomic)

(vi) ORIGINAL SOURCE:
    (A) ORGANISM: PAG1589RP (xi) SEQUENCE DESCRIPTION: SEQ ID NO:953:

```
GATCATTCAA GCATATTTAT TAATTAGATG ACATTAAACT ATTAGACCTT GGTTTGGGTT        60

GCTGGACTTA GGGTTGTGGT AGTCCGTGGG TTATATATTT TTTGTAGACA GTCACCAACA       120

CACTTGATGT ATTTCTTTGA GCTGTGTGCG ATAGGCTCGC ATTGGATGCG GCACTGCTCA       180

TTGGCATCCT GCCCCTCAGC AATAACCATA GCGGCGCCCG CTAGAAGACC GAAAAAGTAG       240

GTTAGCTTCA TCTTGTGATA TTATTCTGTG TTTAATTAAA TGGAACTTTA GTGCTCTGGT       300

TCTCTGCCAT AGAGATCAGG ACCTTGGTTA GATATCCGTG CCCTTATATA CACTGCTGCC       360

AAGGATCGAT GGACTGTAGC CGAGCACCTT CCAACTCAAA AGATCCGACA TCAATGTATT       420

ACTGAGAGCC AGTATACTTA CCGCTTATCA CACTAAACCC CATAGCCATG GTTACGAAGA       480

TGCTGATCTA TCATCCCACA CAGCTCGCCA CTGTAAACGG ACTTGAGGTG GGCGACAGAA       540

GGCCACTACA GGATGAGCGT AAATCTCCAA CAGCTAGCAA CACATGCCAT TATTCTATAC       600

GAACAGTAAC GTGCTTGATA TTACAGAATA CCGATTAGGT TTTTTCCTGC CAGACCAAAT       660

GCTATTGGTC AAACTCAAAT TTAGTCAGGC TTACATTACC TGCGTACCTC GAAGGTAGCA       720
```

```
ATGTTAGGCA CTCTGGCAGT A                                                  741

(2) INFORMATION FOR SEQ ID NO:954:

(i) SEQUENCE CHARACTERISTICS:
        (A) LENGTH: 696 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1589UP (xi) SEQUENCE DESCRIPTION: SEQ ID NO:954:

GATCTTCTTG GCCATTATTG CAGTAGCGGT AGGCGGGCAT ATGAAATGAG ATCGCGGACG         60

TCCTGCGCTT GAGCACCTGA AAAATGGCAG TAAAAAGAAA CGATCCCCGC AACATTTGTT        120

CGAGTGACTT TTGAGGCAGA AGTACAGGCT TCAGCCCCGC GCTGCTTTGC TGTGGATTCA        180

GACCACCGGT GGTGAAGGTG GTGGTACACT GGGGTCAGCT ATGCTCTCAC GCTGCAGTCC        240

AGGACAGACA TACCGCCCAC TATAGCAGGC CGATCACATA CATAAGTAAG AAAATTAGCC        300

CCAGTAGATT ATTGTCGGGG TCATGCAGTG CTGCACCATT GCGTGATGTG GTGTTGCCGG        360

GTAGTCTGCC ACCATCGTGA TACCCGGAGC CGCCAGATCC AACCGGAGGT ATAAAAACTG        420

GTAATGGGAC AAATCCGGGG CCGCCCCGGC CGCCGCCTCC GCCCCCGTAA GAAGGCAACC        480

CCGGCCTTTG CGCTCCTCCA TTCGAGTCTT TTGGGCTGTT CGGTGGCGGC TGTGCTCCGC        540

CGTTTGGGCC TTTAGGGCTG TACGGCGGCG GCTGTGCCCG CCGTTCGGGT CTTTCGGGCT        600

GTACGGAGGC GGTGCGCCTT TCGGATCCTT CGGGCTGTAC GGAGGCGGTG CTCCTTTCGG        660

ATCCTTCGGG CTGTATGCCG GAAGAACACC CTTGGG                                  696

(2) INFORMATION FOR SEQ ID NO:955:

(i) SEQUENCE CHARACTERISTICS:
        (A) LENGTH: 640 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1590RP (xi) SEQUENCE DESCRIPTION: SEQ ID NO:955:

GATCATAATG ATTTGTCTTA ATTCTTTTCT TAATTATTCA TTAAATAATT AATTAATATT         60

TTATTAATAA AAAATATTKA KAKKKATGTT CGTTTATGAT AAATTCTAAA ACTTTGSARC        120

ACGAACTGAA GACAACTATG TAACGCCTGT AATTAATTAT AAATTATTAT AATTAAATAT        180

TCAAAAAATG GTAAGATTTA TCGAGGATTA TCGAATTAAA TAACATGTTC CACTGCTTAA        240

GTCTGTAACC GTCTATTGTT TTGATTTTTA TTATTGCTAA CGTAGTCATC AGGCGGAATA        300

CTTTAATTTT CATTTAATTT ATTCTTTAAT TAATAAAAAA TAAATAGGTA TTCATTGTTT        360

ACTGCTAAAA CTACTCGGGT ATCGAATCCG ATTTGCTACT TTAGCCTTCG TTCCTCAATG        420

TCAATTAATA TATAATTTAA ATTTTCACTT TATAAGTCTT ATTCATATAA TTATTATTTC        480

ATCTTTACTT GAATAATTCT TAAATTATTT TTATTAATTC TAATTATTAT TTTAAATAAT        540

CATTCTACGA ACCCTTTAAG CCATTACGAT TAACGCTAAC CCCCTTTGTC TTACCGCAGC        600

TGCTGGCACA AATTTTGGTT GGGATTATTT AATTATATAT                              640
```

(2) INFORMATION FOR SEQ ID NO:956:

(i) SEQUENCE CHARACTERISTICS:
        (A) LENGTH: 713 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1590UP (xi) SEQUENCE DESCRIPTION: SEQ ID NO:956:

```
GATCTATTAT TAGAGGTAAT ACATTTAAAC TATTATCTAA ATTCTTCTTC TTCTTATTTA      60
TTCTTAACTT TATCTTATTA GGTAAATTAG GTGAATGTCA TGTTGAAGTA CCATTTATTT     120
TAATAGGTCA AATTTGTACA TTTATTTATT TTGCTTATTT CTTAATCTTA GTACCTATTA     180
TTTCTATAAT TGAAAATATT TTATTTTATT TACTAAATAA AAAATAATAA TTAAATAAAT     240
AATAATAATA TTCATTAAAT ACTTTAATAT TAATATTTAT ATATTATACT TCTTTATCAT     300
TTATGAGGGT ACCTCATATT GCTGACTAGC AATAGGGGGG TGAACCCTAC GCACCTAAAT     360
GATAAGAGTT TATCATTAAA TTATATACTA TATATTATAA GTAAATTATC AAACCATATA     420
TAAGGTATAT ATATTAAGAA AGTTTGACTG AGTGGTTTAA AGTGTAATAT TTGAGCTATT     480
ATAAATCTTT ATGATTTCAT AGGTTCGAAT CCTATAACTT TCGTATTAAA TAATTATTTA     540
AAATAATTAA AAATAGTTAA TAATAATGAG AACATGATGT TGGTTCAGAT TAAGCGCTAA     600
CTAAGGACAT TACACATGCG AATCAAACGT TAATATTATT AATTAATAGT ATTAATAAGT     660
GGTGTACTCG TGAGTAAAAA TTAAGAATAA TGAACTTAAA TTTAACTAAA TAT           713
```

(2) INFORMATION FOR SEQ ID NO:957:

(i) SEQUENCE CHARACTERISTICS:
        (A) LENGTH: 720 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1591RP (xi) SEQUENCE DESCRIPTION: SEQ ID NO:957:

```
GATCATAAGC ATCTTTAGCT CCACTATCCA TGTCTGAAAT TTGCAGCTGA TAATAAAGTG      60
GTTGTGTGGC CGAGCGGTCT AAGGCGCCTG ATTCAAGTGT ATGCTTACAG CTGTTACAGT     120
TGGACACTCA GGTATCGTAA GATGCAGGAG TTCGAATCTC CTCGCAACCA ATTATTTTTT     180
TTTTTTGGAG TTCCAATGCA ATATCAATTC TACTGCTGCG AAAAGGTCTC GTCAGCAGAT     240
AAAAGAATAT AGAATATGTA TATTTATATA CAAGAAGCGT TAACTGACTT TTTATTGTTA     300
TAATGCCATT CGAAGAGATA TCGCTTATTA ACAGCAATAC CCCCCTGCAG GTCCCCGCCA     360
ACCGTTGTCC AGTGATGCAA AATATATACC TCGCATGATA AGAAGGCCC TTCATATCAA      420
ATGGCCCAGG CATTAATATC ACCGTTCGCG CGGCCTTCAA CCAAGTAGCC ATCTTTATAT     480
CTGACATATT CCACGGCATT CTCACTATGC TCATCACCGC CGCAAAACCA ATGCTTCTTC     540
TCTTGCCGGT TGTAAACCTT CACTGTACCT TCCTGGTTAG CGACAACTAT CTTATTCAAG     600
TCAAACTGCA AACATGTCAC CGGGTGTTCA TACGAAAATG TATCAGCCAA TGTACCGGTA     660
```

-continued

```
CGTAGATCCC AGATCTAATG CTGTTATCCA AGGAACCAGT CACAAGGTTT AGAGAATCAA        720
```

(2) INFORMATION FOR SEQ ID NO:958:

(i) SEQUENCE CHARACTERISTICS:
        (A) LENGTH: 697 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1591UP (xi) SEQUENCE DESCRIPTION: SEQ ID NO:958:

```
GATCCCCAAT GATCCCTCTC CGGGCTACAA CATCGAGCAG CTCGCTAAAC AGTGCAAGAA         60
CAAGGACAGG CTGGTGGAAC TGCCTTATAC TGTGAAGGGG ATGGACCTCT CCATGAGCGG        120
TATTCTCGCC CACATCGACT CGCTCGCGAA GGACCTATTT CGTCGAAACA CGAAGAACTA        180
CAAGCTCTTC GACCGCGAGA CCGGCAAGCA GCTCGTCACC GTAGAGGACC TGTGCTACTC        240
CCTACAGGAG CACCTGTTTG CCATGCTCGT GGAGATTACC GAGCGTGCCA TGGCACATGT        300
GAACTCTAAC CAGGTGTTGA TTGTCGGCGG TGTGGGCTGC AATGTCCGAC TGCAGCAGAT        360
GATGGCGAGT ATGTGCCAGA GCAGGGCCGA CGGCCAAGTT CATGCGACGG ACGAGCGCTT        420
CTGTATTGAC AACGGTGTCA TGATTGCACA GGCTGGTCTA CTTCAATATC GCATGGGCGA        480
TATAGTAAAA GACTTCTCAG AGACCGTTGT CACGCAGAGG TTCCGGACTG ATGAGGTTTA        540
CGTATCGTGG CGCGACTAAG TGTGTACCAA GTTTAATAGA AGTTTTACCG CCCTAATATA        600
GCTGTTAACC ATCAGTGGCC TGCGATCAGC TGGTCCAGAA CAGTAGTCGC CGGTGGCTGT        660
CACCAGCCTA CGGGCCCAGC GCCAGGTATC CTGTTCG                                 697
```

(2) INFORMATION FOR SEQ ID NO:959:

(i) SEQUENCE CHARACTERISTICS:
        (A) LENGTH: 669 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1592RP (xi) SEQUENCE DESCRIPTION: SEQ ID NO:959:

```
GATCAGGAAC TCGCAGACCT TGGCTCTCTG GTCGCCCTGC AACTGGATGA TCTCGCCCAT         60
CTCGTCGTCC TTGACCATGT TGCCGTTGCA GCCAAAGTCC TTCCGCAAGA CCTTCCAAGA        120
TGCGCTTGAG GTCGTACTCC TCGGGGATGC CCTGCACGGT GGTCAACGTT TTTCTGCCGT        180
TTCTCTGCTG GATACGGATG TGGATGTAGT TGGAGGAGGA GGCTTCGTCG TCGCCGGTGT        240
CAGCAAAGGG GTCGAACGAC TTGAGGTTTT CGATAGACAT GGTGGCGGTG GGGTGTGAGG        300
TACAAGGTAA GCAGAGAAAA TTTTCAGCTG TCCTTTTAAA AGCGCGCACC TCGCGTCTTG        360
GAACGCATTC GCTTATTTGT GAACCATATT CTTATCTGTA TAGGTGTTAA CCCGCATTTC        420
TCTGCAATTG CCCGTCTTTC TTTGGCGTTG GGACAACGCT TCCTTTCAAA CACACTTTCC        480
AGGAACTCCT TGTTTCCTT GGGTAACACT GTTCTTCTTC GCTGTTTATC TCCTGTTAGT        540
AAGGCAGAGG CTGGGATTAC AATGAGACTC GTCACACATA CTTCACCTAG CAGAAACACTG        600
CAAATCGCCT GGATTGCTTG AGCTGTTTCT TCAATACYTG ACATTTGAGT TGTGGGGAGC        660
```

GAGGAAAGA                                                                      669

(2) INFORMATION FOR SEQ ID NO:960:

(i) SEQUENCE CHARACTERISTICS:
        (A) LENGTH: 588 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1592UP (xi) SEQUENCE DESCRIPTION: SEQ ID NO:960:

GATCCACTTG TTAACGTCGG CGCCGCCAAT CCTCATCCCT CCATATGTAA CCACAAGTGG      60

TTTGTATCCC AACAATTGCA GCTCAATTGC CATCAAGTAC GCGTATCCCC CGCCTAGAGA     120

ATGGCCAGTT ATAATTACCT CATAGTCTGG ATGAGCATCA TGTACTGGCT TAAACGCGGA     180

ATAGATATCG TTGTACGCCA ACTTAAATTG CTCATATACG CCCGAGTGTA CAAAGCAATC     240

TCCCGTACAC TTTCCAGCGC CACTAAGTGG CTGGTATGGA ACCCCAGGAA AAATGAAATC     300

CACAATCCAA TCTTGAATTG TTACCGACCC TCTAAATATG ATCGAAATCT GCTTAGCCGT     360

GTCATTTATT GCTATCATGC TATAACAGGA AAACTGCCCG CGGGTCATGT CCGGATCAAA     420

AACTTTAACT ACTTGAGTCC CTGTTGTTCC ATGTACCACT TACCGTCATG AAAAGGGTCA     480

GTGAGTATTA AAGTATTCAC GCAGTAAACG CTGTTAGTGA GATATGACAC ATATTTCAAT     540

GTATCAAACA TCTCATCAGA GAAAGAATGG ACATGAAGGA AAAAAGGC                  588

(2) INFORMATION FOR SEQ ID NO:961:

(i) SEQUENCE CHARACTERISTICS:
        (A) LENGTH: 718 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1593RP (xi) SEQUENCE DESCRIPTION: SEQ ID NO:961:

GATCGAAATA GACAACTCTG CAACGGTGTC CAAATGGCCC AGCAACTTCC AGGAATAAAC      60

ACAAGTAGAC CATAGCATCC AAGTACCTAT GCTCCTCGCC TTACTATGTC TTTGGAATGC     120

AAAGGACCAA ACGTGCTGCA AGACGGAGGG AGAATTCTTC AGAAGAATTA CATTATACAG     180

GCTCGAAGGT GTGACAGCGA ACCTATCATG GTCCTCCTTT GTCGGTTCTG CCAAAAGAGA     240

AGACCAGACC TCTTCAAGGG TGACTGCAAT TCGTTGTCTA AGGTCGCCAG TGACACGAAC     300

AACCGCTTTT CTGGGCAAGT CAGCGAGTTT TATCGTACTA GTAACCCGGT TATTTCCCAC     360

TAGGAGCAAT GCATTCAAAT AAGCAGCCCA CAGTTCCCAA TCAAATTCAC TGGCATTCCC     420

ATCTGGAGGA ACATTATATT GGATTAACAG ACTTTTGTAC ATTTCCAATA TAGTAACGCA     480

TGTCCTCAAA AATAGGGCAT GTAGTGAAAT CCACTTACGG GAGGGCATGT ATCCATCTTT     540

GGTCAATATT GTTACAGTAT TAACGGCACT TATAATATCT TCCTTGGTAA ACCGCGTAAT     600

GTTAAATACA GATGTTAAAA TAGGATCATT GGCGCAATCT TCCACAACTT GTATAAATGA     660

GCTGCCATGT CCATATATTT CTTCCTACAA TTTGGGCTAA AGTTGCCAAT ATAGTACC      718

(2) INFORMATION FOR SEQ ID NO:962:

(i) SEQUENCE CHARACTERISTICS:
        (A) LENGTH: 652 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1593UP (xi) SEQUENCE DESCRIPTION: SEQ ID NO:962:

```
GATCGATCTG TTGTAATTTG GACACGGGGA GCTGCAAGCA GGGTAACGTA TGAGGCGTGC    60

TGTGGGGCCT GGCGATGGCT ATAGATAGGG TCATACCACA TCATCGGTTT GGCGGGGTGG   120

TATAGCATTT GGAGGACAGG TTAGCCCGGA GCCACAGCAT AGACAGGTTC ACGAGGCTTG   180

CAGCAGAGGA AAAGATGGGC AAGCGATTTG ACTGGCAGCC GACGGGGAGG CTCGTGCGCG   240

GCCGGATTAT CCGGGCGTTT TTGCCCTTGA AGCGGCACCC GCAGCAGCTG CTGGACAACC   300

CGAACTACAC GAACCTGTAC CCGGGGGATG AGGTGTACAG CTTTGAGGAG ACGGCGGACG   360

GGCGATGGTG TCGCGTGTAC CAGGTGGTCC AACCGCTGCC GGAGGACTTT ATCTCGACCA   420

TGAAGCGGTT CTCGGACAAG CTGCCGGAGG AGCAGCACCG CGTGGTGGTG TGCCCGAAGG   480

CGTTTGTGCA CTGGTATGAC GACGAAGTGG TGACCTTTCC GTTCCTGGAC CTGCCCGACG   540

AGCGGGAGGT GAAGCGGGAG GTGGCGGAGA CGGACGTGCC GAGCCTGCAC GACCTGCTGC   600

ATAGGGACGA CTTGGGGGAC CTGGAGCTAT TCCGGCAGCT GCGGCGGACG CG           652
```

(2) INFORMATION FOR SEQ ID NO:963:

(i) SEQUENCE CHARACTERISTICS:
        (A) LENGTH: 716 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1594RP (xi) SEQUENCE DESCRIPTION: SEQ ID NO:963:

```
GATCAAGACT GCCGAACTGC TAGTTTCCTG CTTCATGAGG TTTGGAATCT TGTCCACGAT    60

GCGGGCGTTC ACCAGGCGGT TACGCAACTC AAAGTCGTCA TTAAAGTCGC GAGCAAACCA   120

GTAGGAGGAT TCTAGAAGAC TGGTAAGCCG GATGGCGTTT TTGAAGGGTA TTGCGTTTGC   180

GAAGTTCTCA TCCGCAAAGA GCTCGCTAAG CGACTCTATC ATAAGCAGCT GCAGGACACA   240

TTTTACCACG ATGGTATTCT TAATACTTAC ACGGTGCCCA ATCTCCTCGC TGCTTTTCGT   300

GCGCACGAGT CGGCTCATAG GCTTATCCTC TTCAGTACTG GCGTTGCCAA CATCCTCGCC   360

CTTCTCCTCG CGTTGGGCAC GCTCGACTTC CCGATCAACA TCACTGGCAC ATGATTGGGT   420

TTCAGCAGTA CCGTTGGTGT TGATTGTGGC TACTGATGGC TTTCTTCCAC GCTTCAATGG   480

ATCTGACTCA AAAAGTTCTG TGGCAGTGGT AAGCTCAAAT AACCGGGCAA ACGAGTTGGT   540

AACCTGCTCC CAATGCGTTG TCCCGAACTT GTTGGTGTTC TGGATAATCA ATTGCTGCAG   600

ACAAGACCTA CCAATCCTGG CAATGGTGTC ATTTTCCTGA CAGATGCAAG AGACTAACAA   660

AACCAGGAAG CCATCCAACA TTTCGTTCAG TGAATCAAAG TAATGCGTAA CAGGGC       716
```

(2) INFORMATION FOR SEQ ID NO:964:

(i) SEQUENCE CHARACTERISTICS:
        (A) LENGTH: 695 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1594UP (xi) SEQUENCE DESCRIPTION: SEQ ID NO:964:

```
GATCTGAATT TAAACGTGAG ATACCCGTTT TCTGACAGA GATATATTTC CCTATATCTC      60

ACATGAAATC TTCTACTCCA CATCAGAAGA GGTATTTTTT GAGTGTTATC CAACGACTAT     120

GCAATGACCC GAGAACCTTA ATTGAATTCT ACCTAAATTA TGACTGCGAC AGTAGTATGC     180

CTAATATTGT CGAGACTGTT GTGGATTATT TGACGCGACT GGCGCTAACA CGTGTCGATA     240

TCACCGCATC ACAGCGTGCG TACTATGATG AACAAGTGAA CAAACCCCTT GCAACGTWTA     300

ACCTATCGCA GTTGCCTTTA TTATCCATAT CTAATGTTAG CAGTATGTCT GTTGCTCCAC     360

AGCAACTCCA ATTCCCGGTG GAATTTGCGC TTAAAATGAC CTCGTTGAAA TGTATGTTGG     420

CCGTGCTAAG ATCACTAAAT TCTTGGGCCG ACAAGGCGAC GGCTCCAAAT GGCACATTAA     480

ACCACAATAG GGCATCTGTT GGCTCCAGTA CGATTGAAAG GAAGCACTCT TCGGCTTTTA     540

GCTCTTTCAG TCACACTATG AACACAACAC CTGTAGGAGA CCAGAATAGT GTCCAACAAT     600

CGGAAGCGAG TGAGGATATT GATGATCCCA CACAGTTTGA AAATTTGAAG TTAAGGAAAA     660

CAGAACTGCA AAAATGTATT CGGTTATTCA ACTTC                                695
```

(2) INFORMATION FOR SEQ ID NO:965:

(i) SEQUENCE CHARACTERISTICS:
        (A) LENGTH: 709 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1595RP (xi) SEQUENCE DESCRIPTION: SEQ ID NO:965:

```
GATCTTGCTG CTATCCAGAA ATGGGAAGTT CTTAGACAAC GGGGAATTAA GCCCCTTTTC      60

CAATATTTTG AGCGTCGTTT CATAGCTCGG AAGACGCAGC AGAAGCCCCC CCAGTAGTGT     120

CTGTTCATGT TCGCTCATGA AAGGTGTCTC TATCAAATCT AGCTCCATCA TCGCAGAGTA     180

GTTATTATCT TTCTTCCAAG ACAGACGCAC ATGCCGCAAC TTCGTCAGGA TTACAGTAAA     240

ATAATGGTAG AACCGCGGAC TCACAGAAGC GACGACCGCT CGAAATGAAG TCGGCCCGTA     300

GAAGATCGTG CGGCCCTGCT TCTCTATCAC AAGATGGAAC TGCGAAAGTC TGTTCACGGG     360

GGACACCGTG CCCATAACGT GCTTCTGCAT GAACAGCTGC GGTACCATCT CGCTCTTCAT     420

CCGCGCGAGC TCAGTCTCAA GCTCGTCGAT CCGTCGCAGC AGCTCCACAT TGGGCGTCGA     480

GCTGAACAGC TCCCGTGAGT TCACGTCGTG CGTAAACTCA GACAGGTACA CACACTCGGG     540

CAGGCCTTCC CAATACATGT AGAGCACTTC GGCCGCGCCT TGTTGCACTT GACGCGCCGC     600

TTGCGGCAGA ACACGCACGA CTTGCTGACC TTCCGCCTGG TTTTCACAAT CTTGCCATCG     660

GACTCTGCCA TCCCGCCAGC TTCAAGCAAA ATGAGTAGGC TATATTATT                 709
```

(2) INFORMATION FOR SEQ ID NO:966:

(i) SEQUENCE CHARACTERISTICS:
        (A) LENGTH: 731 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1595UP (xi) SEQUENCE DESCRIPTION: SEQ ID NO:966:

```
GATCGCGGAC GTGGAGCACT GGCCGGAGAT GCGCGCGGCC ATCCTGGTGG TTTCTGCGGA      60
CCGCAAGGGA CACGCCATCG ACGAGCGGTA TGCAGCAGAC GGTGCACACG TCGGACCTCT     120
TCAAGGAGCG CGTCGCGACG GTGGTGCCGC GGCGGTACGG AGAGATGGCG GCGGCGATCC     180
GCGCGCGCGA CTTCGCGACG TTTGCGCGCC TGACGATGCA GGACTCGAAC TCGTTTCACG     240
CCACCTGCCT GGACTCATTT CCGCCGATCT TCTACATGAA CGACACTTCG CGCCGGATTG     300
TCAAGCTGTG TCATCTGATC AACGAGTTCT ACAACGAGAC CATCGTGGCG TACACGTTTG     360
ACGCGGGTCC GAACGCGGTG CTCTATTACT TGGCGGAGAA CGAGGCGCGG CTCTGCGGCT     420
TCCTCTCTGC CGTCTTTGGC GCCAACGACG GCTGGGAGAC CACGTTCTCG ACGGAGCAGC     480
GCGCCACCTT CGCCGCGCAG TTCGACGAGT GCGTGCGCGG CAAGCTTGCG ACGGACCTGG     540
ACGACGAATT GCACAGAAGA ATTGCCCGCC TCATCTTCAC GAAGGTCGGG CCAGGGCCCA     600
GGACACTAAA TCCTCGCTCA TCGACCCGAG ACGGGCCTGC CCCGCTGACG CTATTCTCCT     660
GCTATTTTCT GCTCTGTATA CCCTGCCAGA CGCGCTATAT ATATAGAATA TGCATTGCGA     720
CGCTTACGCT T                                                         731
```

(2) INFORMATION FOR SEQ ID NO:967:

(i) SEQUENCE CHARACTERISTICS:
        (A) LENGTH: 672 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1596RP (xi) SEQUENCE DESCRIPTION: SEQ ID NO:967:

```
GATCGACAAT CTGAGCGAAA TATTTAGCAC GACATGCTAC ATGGGCTCTA CGGTGATAGT      60
ATGGGAGTGG AGCAACCGGC TGTCCATACT GGAGGCCAGG CGCCAGGCGC AGAGCATTCT     120
GGGGCGGCCG GTGTATGAGG ACGAGGAGCA GGGGTACAAC TTTGCGCGAT ATGCGCTGAA     180
GATTCAGACC GCATTGACCA GCAAGTCAGA TGAAGGCGAC ACCACATCAG CGACTACCTT     240
TGCTGCACCG AGATCTGCGC GCTTCGAAGG GAAAGGCGGG CCCCAATCCC CAGTCTATGT     300
TCAAGAGGGC GAACAGCAGG CCGTCATGGC ATTCAATAAG CGAATGGGCA CTCGAGCGTT     360
GGCACATCAT GTGCTGGATA GCATCATATA CTACACAGAC AAGGTGGTGG TGAAGGGGCT     420
TGGAAATTTG TCCGCGAGCT TACCTTCCAA GACCTCCTCG GCGACAAGCG TCAGGGGTCG     480
TGTAAGGAAA CGCATTGGTC TCGAAGGCGC AAATGATGTC TTTGTATACC GCACAAAAGA     540
CCTGGTATTC GATAGTGATG AAGATATACC CAGAACCTAA CTACTTGTGT CGATATTTCT     600
CACACCGCCT GGTGCGGAAC CGGGGGCATA CATTCGTTTT ACACAAGAGG GGTTGATGCA     660
```

```
TAAAACGCGC TT                                                               672
```

(2) INFORMATION FOR SEQ ID NO:968:

(i) SEQUENCE CHARACTERISTICS:
        (A) LENGTH: 722 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1596UP (xi) SEQUENCE DESCRIPTION: SEQ ID NO:968:

```
GATCTTCGTA TCCATGTCGC AAAGCTCCTC CAAAATCTTT TCGTCTCCAT CATGAGAGGC     60

TGCTACAGCT TTTGAGCCGA TAGAATTGGA AATACCATTG GAGATTGCTA TTAGTAGGAA    120

GACAATATAA GTACCATCTG TCGATGGGGC AGAGGCTTTA TCAAGAAGGT CCATCAGCTT    180

GTTCTTGGAT ACAGCAGTCT CATTTAATAA TAATGCCTGC TCACCACTGG GCAAAAATTC    240

AGAAACATTG AGCAGTTCAG AGAGTGAGTT CGACTCAAAG TTTTCGGTCA TTGTCTCTAA    300

CAAGACAAAA ACAACGTCCT TCCTGCTCTC ATGAACATCA TAAGCCTTGA AAACCTCGAG    360

CAAAATAGTA TTGTCCTGGA TCACGTTCAA AAATACCTCT AGAATTAATG CCTTCCTCCA    420

CAATAAAGTG TCAGATTTAG GAGACAGAGT GTGGATTAAT AATGATAAAA TAACTTCCAA    480

TTCCAATTCC AGCAATGTCA AATACTGAAC CTTTATGAGA ATGTAATACA TCTGGCGCTA    540

CGAACCACAA TTGCAAAATT TTTGGATGAG GAAATGTACC TCAATAGCAG CGGCACCGCC    600

TTTGTTCGCA ACAGAAATAA CAGATCTCGG TGTGTCAAAA ATAATAATTC ATAGTTCAAT    660

AAAACCAGTT CTAGGAGCTC TAATCCATAC TCCTCATTTA TGCAATTGCT ATCCAGCAAT    720

GT                                                                  722
```

(2) INFORMATION FOR SEQ ID NO:969:

(i) SEQUENCE CHARACTERISTICS:
        (A) LENGTH: 688 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1597RP (xi) SEQUENCE DESCRIPTION: SEQ ID NO:969:

```
GATCCATCAG CGCGGCTACG GAAATCCTGC CCATAGAATG ACTCTCCAAA CCCCTCTGAA     60

CTATCAGCAA AAGCTCAACA GCATRCACGG GTCGCATGCC CAGCAAAAAC AGATCCAGCG    120

TCAGATAAGC GCTGCCARCG CACTCGATGA CGGGAATACC ATCACCGCAA TGGTCCAGCA    180

TTTGATGCCC AAGAAGAAAG ACCAGCCACC GCAGCAACAG GGACCCTATG GCTCTCCGCC    240

AAACTCTGGC AACAGCTCCA CGTACGGCGG CAGCCCTGCT GCCACCGCGC CGTCTGCATC    300

CGTAAATGCT CCCGCCGCCG ATGACGGCCA AAACGCTGTG CCACAGCCGC ACAGCGCCCC    360

TGCGCTATCC GCTAACGGTA ACACAGCCCC TATGTCGGGA AACTCGGTTA GCCTTAGTAA    420

TGGCTCATCA GCAGGGCCCG GTTTGTCACA ACAGTCAAAC TCTCTGGACT GGAAGCAGAC    480

ACCGCCAAGC AGTGGCGGAA GCGTAACCGA AAGAAAGCCA AAGCTCGCTC TATTCGCTAA    540
```

```
GAAAAAATAA TATCATGCGA CCTATCATTT ACACATATTC TAACGTTCCA CCTGTGTTAG      600

TGTACTCATT TAATTAATTC ATTAGTGCTG CCACTGCTGC AGACATGTGG CAAGAGGCAA      660

AAATGGTTCC TAGCGGGATC GAACCGCT                                         688

(2) INFORMATION FOR SEQ ID NO:970:

(i) SEQUENCE CHARACTERISTICS:
        (A) LENGTH: 712 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1597UP (xi) SEQUENCE DESCRIPTION: SEQ ID NO:970:

GATCGAGGCA GCCGTACCGT CTTTTGGTAC GCATGCGCAG AGTACTGCCG GATACAGCGC       60

AACATCTTAC GCTGACTACA GTTCCTGGAC ACACCACCTT ACAGCTTTGG GCCTGCGTTA      120

TTGGTGCTCG AAGATATGAT GTTCGGAATT TTTCACTCGC CGTCCGGCCT GATGAAACTG      180

GAAGACAAGA CCTACAGTCA TCTAGCCAAC ATAACGCCCT GTAGTCGGGC TCTCGAACCG      240

AGCGTAGAGC GTAGGAGATG CTCCACGCGC CCCGGTGCGT ACAGAGAAGA ACAAGACCGC      300

CGGCATTCTT TTTATTTACT TGATTAAACT CTTGGCCAGT CTGGTTTCCA CTGACAAAGT      360

GCCCACCAGA TGGATCGCGG GCGCGGTGAT CCTGCCCCGG CGATAGCGGG CGACCGGAGC      420

TTGCGTGGGT TTCACCTGCA TCTGCACAAG ATGTTGCTAC GGCGTAGAAG CAGCGCGTGG      480

GAGGCGCAGC GCGCGCAAAC AGGACGTCAG TCTGACGCGC TACTTCGCCC GCGCTGCTGC      540

ACCGGCTGAA TTGGGCTCCC GGCAAGTCCT GATTGCTACG TTGAGTCATA GTCTCAGTAA      600

TTATCGCATG GTGTTACTGG CGTTGCACGT GACCACACTG TGGCGTCCTT TTGGCCCACA      660

GATGAACCTG CCATCAGCTC TCCGCCAGGA CGGTCACAAC AGGCAGCAGT AC             712

(2) INFORMATION FOR SEQ ID NO:971:

(i) SEQUENCE CHARACTERISTICS:
        (A) LENGTH: 740 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1598RP (xi) SEQUENCE DESCRIPTION: SEQ ID NO:971:

GATCCTCATA ATCATAGTAC AATATCATTT CCAATAAATG GAATAGCACT AAATAAATTA       60

GTAATAACAG TAGCACCTCA ATGTGACATT TGTCCATATA CTAAACAATA ACCTAAGAAA      120

GCTGCTGCTA TAGTTAAAAT AAAGATAATA ACACCAACTG TTCATACAAT AACTCTAGGT      180

GATTTATAAG AACCATAATA TAAACCTTTA CCAATATGAA TATACATACA AATAAAGAAG      240

AATGAAGCAC CATTAAGATG CATATATCTA ATTAATCAAC CTAGTTGTAC ATCTCTCATA      300

ATATGTTCTA CTGATGAGAA AGCTAATTCA ATATTAGATG AATAATGCAT AGCTAAAAAA      360

ATACCAGTAA GAATTTGAAT AACTAAACAT AAACCTAATA AAGAACCTAA ATTTCATCAA      420

TAATTAATTG ATGATGGTTG AGGTGAATCA ATAACATAAC TATTAACTAA ATTTAAATAT      480

AAATTTGATT TTCTATATGC CATATATTTT ATTATTAAAA TATTATTAAA TTATTATTTA      540
```

```
ATAAATATTA GATTATAATA TAATTCTTTA TAATAAATTA TATTATTTAA TTAATATATT      600

AATTTATTAT TTATTATTTA TTAATATTTA TATAATCTTT ATAGGGAATT GAACCTAATA      660

AACCATTAAG ATTTAATTAT TTAATTATTT AATTTATTTA ATTATTTAAT TTATAAATTA      720

TTAATTAGAG AGATAAGGGT                                                  740

(2) INFORMATION FOR SEQ ID NO:972:

(i) SEQUENCE CHARACTERISTICS:
        (A) LENGTH: 688 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1598UP (xi) SEQUENCE DESCRIPTION: SEQ ID NO:972:

GATCTTATCG TCTAATGGTT ACGACATCAT CTCTTCATGT TGAAAATATC GGTTCAATTC       60

CGATTAAGAT TATTAATATA TTTTAATAAT TATTATAATT AACAATATTA ATTAGAGGGG      120

TACCAACATA TTGCTAACTA GCAATAGGGG TGTGTACCTT ATCTCTCTAA TTAATAATTT      180

ATAAATTAAA TAATTAAATA AATTAAATAA TTAAATAATT AAATCTTAAT GGTTTATTAG      240

GTTCAATTCC TATAAAGATT ATATAAATAT TAATAAATAA TAAATAATAA ATTAATATAT      300

TAATTAAATA ATATAATTTA TTATAAAGAA TTATATTATA ATCTAATATT TATTAAATAA      360

TAATTTAATA ATATTTTAAT AATAAAATAT ATGGCATATA GAAAATCAAA TTTATATTTA      420

AATTTAGTTA ATAGTTATGT TATTGATTCA CCTCAACCAT CATCAATTAA TTATTGATGA      480

AATTTAGGTT CTTTATTAGG TTTATGTTTA GTTATTCAAA TTCTTACTGG TATTTTTTTA      540

GCTATGCATT ATTCATCTAA TATTGAATTA GCTTTCTCAT CAGTAGAACA TATTATGAGA      600

GATGTTCAAC TAGGTTGATT AATTAGATAT ATGCATCTTA ATGGTGCTTC ATTCTTCTTT      660

ATTTGTATGT ATATTCATAT TGGGTAAA                                        688

(2) INFORMATION FOR SEQ ID NO:973:

(i) SEQUENCE CHARACTERISTICS:
        (A) LENGTH: 625 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1600RP (xi) SEQUENCE DESCRIPTION: SEQ ID NO:973:

GATCTAAAAG AATCCATGTA TGTACACATA TTACGGAGGG TTAAGGTGAC GAACGGTAGC       60

TACAGGCCTA TAAATCTGGG TTCCTTTGCA AAAGTTCATG CAACTCATCT GGGACGTTGC      120

GCCAGTCTTC GGCAATCCAT TTCCTTATCC TATCCTCATC GGCCTGTGCT AGTATATCTA      180

CTTCAAGAGA GCTCCTGGCA CATGTAAAAT TGCCAGCGGG AGAGAGGAGA GGCGAAGATT      240

CTTGAGTGGG GTAAGAAACT TGTTTTGATG GTATGCTGCT AGCCATCTTC TTCCGTCTGT      300

GTTCCTTACC GTTGTTTAAT GATACTCCGA TATAATGTTC TATTAACTTC TCTGCGTATG      360

GGGGCAAGTT TTTGGGCCTG TAGTCGCCCA CATATTTGCA CCTCCAGTAT ACAGACCAAT      420
```

| | |
|---|---|
| GTAGTTCACC ATATGCCGGG ATGTTCCTAT GTCTACCAAG GTTAGGCACA TAAACGTTTT | 480 |
| TCCATTGGCA ATTTTTATCT TCAATCCTTA TGCCGATGAA CATCATTTCC ACTATCCACC | 540 |
| AGGCAATGAA CTGAAATATA CTCTTTGTTC CATGTCCATC GTTCTTTGCT GGCCGGATTA | 600 |
| TACATCTCCG GAAGGAAGGC CTGGG | 625 |

(2) INFORMATION FOR SEQ ID NO:974:

(i) SEQUENCE CHARACTERISTICS:
        (A) LENGTH: 656 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1600UP (xi) SEQUENCE DESCRIPTION: SEQ ID NO:974:

| | |
|---|---|
| GATCAAGCAG CTACTGCTCA CCTGGAAGAA GCAGGGCCAC AAGGCCCTGC TCTTCACCCA | 60 |
| GTCCAGGCAG ATGCTCGACA TCCTGGAGGC CTACATCTCG CACAAAGATC CCGAGCTGGC | 120 |
| AGGCCTACAG TACCTCCGGA TGGACGGAAC CACAAACATC GCACACCGGC AGGCCCTCGT | 180 |
| GGACCGTTTC AACAACGGCC CGTACCACCT CTTTCTTCTG ACCACCCGCG TGGGGGGCCT | 240 |
| CGGCGTCAAC CTCACGGGCG CGAACAGAAT CATCATCTTC GACCCCGACT GGACCCCTC | 300 |
| CACGGACCTG CAGGCCCGCG AGCGCGCCTG GCGCATAGGC CAGAAGCGCG ACGTGACTAT | 360 |
| CTACCTGCTC ATGGTCGCCG GCTCCATCGA GGAGAAGATA TACCACCGCC AGATCTTCAA | 420 |
| GCAGTTTCTC ACCAACAAGG TCCTCAGCGA CCCCAAGCAG AAGCGCTTCT TCAAGATGAA | 480 |
| CGAGCTGCAC GACCTCTTCT CCTTCGGCCC GGGCGCCGCC AGCGACTCCT TTGCCTCTGA | 540 |
| GATCGAGCAG CAGACCGCCT CCCTCCGCCG CCAGCCGGCC GCCCACGGCA CCGACGACTA | 600 |
| CGACTCCGTC CAGCGTTTCG AGGGCGTCTC CAAGCTGGAG GGCTTCTTCA ACGCCA | 656 |

(2) INFORMATION FOR SEQ ID NO:975:

(i) SEQUENCE CHARACTERISTICS:
        (A) LENGTH: 715 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1601RP (xi) SEQUENCE DESCRIPTION: SEQ ID NO:975:

| | |
|---|---|
| GATCTTTTTC CCCCGCAAAC CGCACACCTC GTTCCAGGGG TACTTGGGCA ACAAAAAGGC | 60 |
| GACGGAGAGC AAGGTTCTAC GCGATGTTTT CAGGAAGGGA GATGCATGGT ACCGGTCAGG | 120 |
| CGATCTCTTG AAATCCGACA AGTACGGGCA ATGGTACTTC GTGGACCGGA TGGGTGATAC | 180 |
| GTACCGGTGG AAATCCGAAA ATGTCTCGAC TACCGAGGTG GAGAATCAGT TGCTCTCGTT | 240 |
| CAACAAGGAC CTCTTTGACT GTTTGGTTGT AGTGGGCCTG AAGATTCCAA GCTACGAGGG | 300 |
| TAGAGCCGGG TTTGCTGTTA TCCAACTGAA TCCAGCGCGC CGCGGACTGG ACCATGCCAG | 360 |
| TTTGTTAGAC GACCTTGTCG AGTATTTGAA ACATGCTCTT CCTCGGTACG CCTTGCCGCT | 420 |
| GTTCATCAAG TTCACAAACC AGCTGGAAAC AACCGATAAC TATAAGTTCG CCAAGAAACA | 480 |
| GTACAAAAAC CAGCAGTTGC CTCATGGTGC GGATGGGGAC GAGACAATTT ACTGGTTAAA | 540 |

```
AGACTACTCC CAGTACAAAG TCTTGACCGA CGAGGACTGG GAGCAGATAT CAACCGGAAA      600

GGCAAAGCTT TAGACCAGAC AATGCCGGGA TTGACACCGG TAGGGAGTTC AAAATAAAAA      660

AAATACCTGG GAAGCCATCC ATAAAAGCCA TTATCAACTA TAGAAATAGA AAAGT           715
```

(2) INFORMATION FOR SEQ ID NO:976:

(i) SEQUENCE CHARACTERISTICS:
        (A) LENGTH: 699 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1601UP (xi) SEQUENCE DESCRIPTION: SEQ ID NO:976:

```
GATCGCCCTG TCCCGGGACG GAGAGCGGGC GCTGCGCTAG CATAAAAGCA CGCAGGTCAC       60

TGTGCATGAA ACTCGAATCG AACGCCGTAC TCGATGGTAG AACTAAACGG GCTCCGCTTC      120

GAAGTACGCA CAGTTGAGTG AAATGTCAGT GTCGGCGCAA CGCGCCCAAG AGCAGAATAG      180

CATGGACATC GAACAGAGGT CATCGCAGCC GAGTCGAAGC AACAGCCATG CAGGATCGCC      240

GGGGTACGAA AAAGTGCAGC CGCTGTATGC CGCAGAGAAC GGTTCCACGG AGACTGCCCC      300

GACAGCCACC GGGCTGTTTG ATAGCTCGCA CGTTGTACCG GTGTCGCAAC GGCGCGGACT      360

GCTGAGTAGG CTGGCGCTTG TGCCCGAATT CCGGGACGCA CGTCTCTATC CCCCGCGGGT      420

CAAAAAGCTG ATCCTGGTCA TCGTCGCCTT TGCATGTATT CTGGGTCCCA TGGGGACCAA      480

CATCATCTAT CCTGCGATCG GGACTATCAT GCAGGATTTT GGCACTTCGC GGTTTCTGGT      540

CAGTGTGTCT GTAGGCACCT ACCTCGCTGC GCTGGGCATC TTCCCCATCT GGTGGTCGTC      600

GCTGGCGGAC AAAAACGGCC GCCGAACAGT GTACGTGCTG TCGTTCGCGC TGCTGGTGGT      660

GTTCAGCGTT GGGCACGGCT TCTCGCGCAA CATCGAGAC                             699
```

(2) INFORMATION FOR SEQ ID NO:977:

(i) SEQUENCE CHARACTERISTICS:
        (A) LENGTH: 704 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1602RP (xi) SEQUENCE DESCRIPTION: SEQ ID NO:977:

```
GATCCAAGCG CCCGCACAAC CAGCGATGTT TGCAACATAT TCGGCTAGTA TTCTCCGTTC       60

GACTTTACCC CTGCGTAGCG TTGGCGTCAG ACTGCTGAGC CAGGAAACTC GGCGGGCCAT      120

TGAGGGCGCC ATTTCCTCTG CCCCAGTGGT TCTGTTCATG AAGGGCACCC CAGAGTTCCC      180

TCAATGTGGC TTTTCGAAGG CCGCCATTGA GATCCTGGGC AGACAGGGCG TGGATCCTGC      240

GAAGTTTGCG GCGTTCAACG TGCTGGAGGA TTCTGAGCTG CGGAGCGGGA TAAAGGAATA      300

TTCCGAGTGG CCTACAATTC CACAGCTCTA CGTCAACAAG GAATTTGTTG GGGGTGCGA      360

CATCCTCACC AACATGGCGC AATCCGGCGA GCTAACTACT ATGCTCGAGG AGGCATCCGT      420

TCTTGTGCCG GATACTGAGT GATGCCGCGT ACGGCTCCCG ACTATATTTA TAGGAATACA      480
```

-continued

```
GCTTGTAATT TACGACTTGT ATTCTCATGC CTTTAGACTT GTAAATCATG GTTGTTTAAT      540

TCACAAACTC CGTTCTTTCA GTTGAAAGAA GTGAGAACAG CTTGCTTTCC GTCATGTGTG      600

AAAGAGGCTT CTGATGGAGG AGGCGTGCAC ACGCCAGCAG AGAAAGTCTC TCAAAAAATG      660

ACGTTCTAGT GGAAGGGCGG ACGCAATCAC CCTTGAATGC GCGA                      704
```

(2) INFORMATION FOR SEQ ID NO:978:

(i) SEQUENCE CHARACTERISTICS:
        (A) LENGTH: 476 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1602UP (xi) SEQUENCE DESCRIPTION: SEQ ID NO:978:

```
GATCGTGCCC GGGCTTGTGC TTGTGCCCAG AGTTGTGCTT GTGCCCAGGC TTTTGCTCGC       60

TGCCTCCGTC GCTGCCCGCG GGGTAGTACA CGCCGAACTG CTTCAGCCGC AGCGGGCCGC      120

GGAAGTGCAC CGTCAGCTCC TGGTCCAGCG GAGAGAGACT GCCCGAGAAC TCCAATTTTC      180

TCTGCTTACA CTTGCAGCTC TTCTCGTCCA TGCTGGTGAC GTCCAGGTAC GTGCCGCTGT      240

AGCCCACATT GGCATACCGG ATATTTTCTG CCTTCGAGCA GTAGTAATTC CCTCCGATGA      300

AATCACAATC GCCCAGCACC TGCTGCGCAG CGAGCAGGCC ACCTGCAACG ACTGTCGACA      360

GCTTCATAAT TTGTAAACGC TTGTAAAAGA ATGACTAGTA GTTAGAACAG ATAAAAGAGT      420

GCTTTGCTGT GTGCGCTGTC GCCCGTCCAC GCCTTCCGAG CTCACCCGCC TTCTTA         476
```

(2) INFORMATION FOR SEQ ID NO:979:

(i) SEQUENCE CHARACTERISTICS:
        (A) LENGTH: 724 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1603RP (xi) SEQUENCE DESCRIPTION: SEQ ID NO:979:

```
GATCCGGCAA GATCGTCGTT CAGTTGACCG GCAGATTGAA CAAGTGCGGT GTCATCTCTC       60

CAAGATTCAA CGTCAAGATC AACGACGTCG AGAAGTGGAC TGCCAACCTA TTGCCAGCCA      120

GACAGTTCGG CTACGTCATC TTGACCACCT CCGCCGGCAT TATGGACCAC GAGGAGGCCC      180

ACAGAAAGCA CGTTGCTGGT AAGATTTTGG GTTTTGTCTA CTAAGCGGCT GCTATATAGC      240

GTATCTAGCT CTAATGTACG ATACTCAGTG TCTATTACGA CGGCCGCGAG CTCCACGCGC      300

CACATACGAG GCCAGCCGGC GACGGCAAGC GGGAATTCAG ATGCGTTAAT TAGCAGTAGA      360

TTAGTAGTAT ATATGTACAA ACAGCATACA CATGAACGGC GTCGCCGATC ATAATCTTCT      420

ACCTCTTCTA CCACCCTTCT TTCTGGTAGA GTCGGATGGG ATAGGAGTGA CGTCCTCGAT      480

ACGGCCGATT CTCAAGCCGG ATCTGGCCAA AGCTCTCAAA GCAGCCTGAC CACCTGGACC      540

TGGGGTCTTG GTCTTGGTAC CACCGGTAGC TCTGATCTTG ACGTGCACAG CAGTGATGCC      600

GACCTCCTTA CACTTGGCAG CGACGTCCTG AGCAGCCAAC ATGGCAGCGT ATGGAGAGGA      660

CTCGTCTCTG TCGGCCTTGA ACTTCATACC ACCGGTAACT CTGGCAATAG TTCTCTGCCA      720
```

GACA 724

(2) INFORMATION FOR SEQ ID NO:980:

(i) SEQUENCE CHARACTERISTICS:
        (A) LENGTH: 721 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1603UP (xi) SEQUENCE DESCRIPTION: SEQ ID NO:980:

```
GATCTATTTG TGCCGTCCGC CATTAAGCAA GCGGCAAGCA TCGATCCAAA TCATGAGAGT      60
ACCCTCGGGC TTTCACTTTC CAAGCCTTTA TCAACAAATC TGGTACACGA TACATCCATC     120
GCGACAGCAC ATATACCAGA ACGGGAAAGC CGACAAGATG GCACTAGACT CTGGTAGGTA     180
ATCTGAGTTC GACCATATCC ACTTCGTTAA TGGTGATAGT TGATAAAAAG AAACGATACT     240
GAAAATTTTA ATGGTTACCA ATCTCATCTC ATCGCCATAC TGAAAGAATA TTGTAGGTCT     300
CGCAGTGGAA CAAGGATCAA GCCCAGGCTA AGACAATAAT GGTTGCAGCG GAGGCAGTAC     360
AGGAACTACC CCCAGATGAA GAAGAACTGG CCTTGGCTAA GCTAGTGTTT GGCGACACAG     420
CAGACTTCCA TGAAGCGCTG CGAAATGCAG ACCTTAATTA TGTTTCTTCA GATGAAGACG     480
TATATGGCCA GGAGTCGTCC AGTGATGACG AAGAGGGGAC TGAAATTGGT CACCTGAATG     540
ATGACCAATT GTTTTTTGTG GACGAGGGTG CAGATACCGA GGGAGGAGCA GATGGAGAAC     600
GGAGGCCATG GAGGTGGACC AGGTTAGCGA GGAAAGCGAC TCCGGAGAGG AAAGCGGTAG     660
CAGCGCTGCA TGGTCAGATT CGGATGACGA ACACTTAAAC GTTACAATAG GGCAAACCAA     720
T                                                                    721
```

(2) INFORMATION FOR SEQ ID NO:981:

(i) SEQUENCE CHARACTERISTICS:
        (A) LENGTH: 638 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1604RP (xi) SEQUENCE DESCRIPTION: SEQ ID NO:981:

```
GATCCCTATT AGAAGAGGTT ACTGGGGCTC CAACCTTGGT CAGCCACACT CTCTAGCCAC      60
GAAGACCTCT GGTAAGTCTG GTTCCGTCAC TGTGCGTTTG ATCCCTGCCC CACGTGGTTC     120
CGGTATCGTC GCCTCTCCAG CTGTCAAGAA GCTTCTACAG CTTGCTGGTG TCGAGGATGT     180
GTACACTTCC TCCACCGGTT CTACCCGTAC CCTAGAGAAC ACCTTGAAGG CTGCCTTCGT     240
TGCCATTGGT AACACCTACG GTTTCTTGAC CCCAGACTTG TGGCCAGAGA ACCAGTTGCC     300
AGCTTCTCCT CTAGACGTCT ACGCCGACGA GGCCGTTGCC CAGAAGAAGA GATTCTAAGT     360
AGTGTGTGTA CATACCAACA GTTTGTTTCT TTGCACGTGA ACCGCCCGCC TAAGCCTTTA     420
GGCGCATGGC ACACAGACTG CCGTTGGGCA GGAGATCGGT TGTCTTCCGA CGCTGGTACA     480
GGGCTGCGAT GCGCGTCTGC GGCTGGCGGT GCATATCGGA GATATGGCGC CGTGCCCGTA     540
```

```
CGGCAAAGAA TCAGCAAGAC ACTAGCGTCT GGCATTCTTT TTCAATGCAT TATTTAGCTT    600

TTTTTTTTTT TTTTTTTTTA GTATAGACAC ATATAAGT                            638
```

(2) INFORMATION FOR SEQ ID NO:982:

(i) SEQUENCE CHARACTERISTICS:
        (A) LENGTH: 710 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1604UP (xi) SEQUENCE DESCRIPTION: SEQ ID NO:982:

```
GATCAGAGCA TCCGATGAGG TGGCACCGGC CGCGTCCGCT GTGTCTTTCT TCGCGGTATC     60

GGCTTCCGAA ATACTTAGCT TCTCAATACT TGGGACTGCC TTATCTTCAG AGGAAGCGGT    120

AGCATCCTCA CTCTTAGGAG CGCCCTCTGC GCTGCTCTTA GGCTCCTCCT TTGTTGGCTC    180

CTCCGCCTTA GCCTCTTCTT TCTTCGCGAC AGGTTTCTTA GCACCAACTA GCTTGATACC    240

GGAGCTGGAA GCCAACTTGA GGGTCTTCTT TGGTTTTGGA GCAGTCGCAT TCGGCACAGT    300

TCCCTTCTCA AGTTGTTCA GCGTCACCGG AGCGGTGGCT GACTGGCCCT GTCCGTAACC     360

ATAGCTCTGG TTCCCCTTAC GGTTCCCCTG TGGCTGTGAG TTGTACTGCT TGTAGCTCTG    420

ATACCCACCT TGCGCATTGT ATTGCTGGTA ACCTTGGTAG CCAGCTTGTG CTGGGTTGTA    480

CTGCTGGTAT CCCTGATAAC CCTGGTACCC GCCGGCTTGC TGGTTGTATT GCGCATAGCC    540

TTGGTACCCA CCTGCCTGTT GGCCATACGC CTGGTAACCT CCCTGAGGCA CATACCCCTG    600

GTAATTCTGG AAGTTACTTG GGTTGTAGTA TTGGCCGAAA TTTGCTGCCC CTGACCTTGA    660

TTTTGACCTT GATCCTTGGC TTGCGACTGG CCTTGGTCGT TGCCTTGCGA               710
```

(2) INFORMATION FOR SEQ ID NO:983:

(i) SEQUENCE CHARACTERISTICS
        (A) LENGTH: 688 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1605RP (xi) SEQUENCE DESCRIPTION: SEQ ID NO:983:

```
GATCTTCTCA AAAGTAGCAT TTACAATCTG CGTTAGCGTT GCTTGTGCAA TTCCCTGGTT     60

GGACGAGCTT AGTGACAGGA TGAAAATATT ATAGATTTGT CTGACGGCCT TTAATAGTGA    120

TGCACCGTGA CAATTGCAAT AAGGCTCATC TGTCAATATA CAGCTTGCGA GGGCGCGGAC    180

TACCTGCAAC TCGACCTTCC CATCAGTCGC TTCTCCATCA AAACAGTCGG TTATGGTATC    240

AACGGCAGCA TCTATCAGCC GCATTCTTGG AGGTGGTGTA ACACCAGAGT CTGGCAACGT    300

CGTGCCCTGG TCGTTTGATG CTGCGGAATT TGGAGGGTTG ACTAAAACAT TCTCGTCTAA    360

CGCCTTAAAG GCAAACAACT TGATAGACA ATCAAGAGCG CTAACCTGTA TTTCTGGAAC     420

ATTAGTTCTA CAGCAAGCAC GTAGTGCCTC AAAGACCAAC AGAGAATCCA AAACTTTGG    480

ATCGTTTTCA GATTGCAGGA GTTGCTCGGT CAAGTTTTTC ACAGTTTTCT CAACCAGTTT    540

TTCATTATTA GGATGTTTGT GCATGGATTT TGCTTGTAGT ATACCCTCTA ACCTTAGTTT    600
```

```
CACAAGATGC ACTGCGGATT TCATCGTCCA TGGACTACCA GAGACATTGG AATATGCCCT    660

TGTGTGACGC TTGAGATTAT CCTGCGAC                                      688
```

(2) INFORMATION FOR SEQ ID NO:984:

(i) SEQUENCE CHARACTERISTICS:
        (A) LENGTH: 725 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1605UP (xi) SEQUENCE DESCRIPTION: SEQ ID NO:984:

```
GATCAGAGCA TCCGATGAGG TGGCACCGGC CGCGTCCGCT GTGTCTTTCT TCGCGGTATC     60

GGCTTCCGAA ATACTTAGCT TCTCAATACT TGGGACTGCC TTATCTTCAG AGGAAGCGGT    120

AGCATCCTCA CTCTTAGGAG CGCCCTCTGC GCTGCTCTTA GGCTCCTCCT TTGTTGGCTC    180

CTCCGCCTTA GCCTCTTCTT TCTTCGCGAC AGGTTTCTTA GCACCAACTA GCTTGATACC    240

GGAGCTGGAA GCCAACTTGA GGGTCTTCTT TGGTTTTGGA GCAGTCGCAT TCGGCACAGT    300

TCCCTTCTCA AAGTTGTTCA GCGTCACCGG AGCGGTGGCT GACTGGCCCT GTCCGTAACC    360

ATAGCTCTGG TTCCCCTTAC GGTTCCCCTG TGGCTGTGAG TTGTACTGCT TGTAGCTCTG    420

ATACCCACCT TGCGCATTGT ATTGCTGGTA ACCTTGGTAG CCAGCTTGTG CTGGGTTGTA    480

CTGCTGGTAT CCCTGATAAC CCTGGTACCC GCCGGCTTGC TGGTTGTATT GCGCATAGCC    540

TTGGTACCCA CCTGCCTGTT GGCCATACGC CTGGTAACCT CCCTGAGGCA CATACCCCTG    600

GTAATTCTGG AAGTTACTTG GGTTGTAGTA TTGGCCGAAA TTTTGCTGCC CCTGACCTTG    660

ATTTTGACCT TGATCCTTGG CTTGCGACTG GCCTTGGTCG TTGCCTTGCG ATTGAATTTG    720

ATCTT                                                               725
```

(2) INFORMATION FOR SEQ ID NO:985:

(i) SEQUENCE CHARACTERISTICS:
        (A) LENGTH: 678 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1606RP (xi) SEQUENCE DESCRIPTION: SEQ ID NO:985:

```
GATCAAGCAT ATCAAATTTC CGGCAATCTG CGGCGTCATT TTTTTGGACA ACAGGCGTCT     60

CCACAGGGTC CATCTCCATC AGCGGAGCTA TACGTTGCGA CAGTGGCCTC AGCTTGGTAC    120

TCTGCGAGAG AATTGAGACG CCCTTGGAGC TGGCTGTATG GTAACTGTCG TCCGTCGCGT    180

AGGTGGTCAA AGACAGCGAC TCTGAATACT CGCATTTCGC ATCCCGGTTG CGCCGTACGT    240

ATCCGTCGCC CGTGGACTTG ATGGCAGTGG TGTCCGAGCA CGAAGACAGC GAAGGTAGTC    300

TCAGTGGCCG CGTCGGCGAT ACGTCGTACT CGAGCACAGA CTCGTTGTGT CCCCTCCCGG    360

TCATGTTCTT CGGCTCAGTT CGCGACAACG CTCCCGACCA TGCCTGCCCC CTCCCCTTCT    420

TTCTGTGGAA GCGCCCAAAC ATTAAATCTA GCTGCTTCTT CCTGGTACTC TGTTCGCTCT    480
```

```
GTTTCTGCCC GGCGAGCCCC TCGGATTCAA TCTCTGTACA GCCTTTATGC CGCACTTGCT      540

CGTCCTAATT GGCTGCCACA CTCCTGCTGC TCGAACCTAA GGCGTCTGTA CCGAACGCTT      600

TCGTTGACTT GACCGTTGGG GCGTAATCTA TTATTGGAAC CTTGTAAAAG CGGGCTTCTG      660

TACGCTATTA GTTAGCCC                                                    678

(2) INFORMATION FOR SEQ ID NO:986:

(i) SEQUENCE CHARACTERISTICS:
        (A) LENGTH: 703 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1606UP (xi) SEQUENCE DESCRIPTION: SEQ ID NO:986:

GATCCGCTTG AGTACTGAGA TATTAAGTCA ATACCAGGAT AAGCTTTCAA AGCACCGTAA       60

TCCTACTGTG CAATGGTGGG GACCTACTGA TTTCTCGCAC TACGTCCTAG CGCCTGAAAT      120

TTTATCATAC GTGTGCCGAG ACGAACTGGG CCTTGCAGAT ATCGATGAGG CTTGGACTTA      180

CATGGAAAGT ACCACGGAAT ACGGGTTAAA TGTGGCGGAC GAAGAGCCTC TAGATATTTG      240

GGAATTAGAA TACGAAGAGA AAAGCTGCA ACGGTTAGGA TTAGGACCCA AGTACAGCAG       300

CATGACTTAC AGAAAGCATC CTGCCAGGGC GTCGGCTGTA TTAGATACAT CCAAAAATGG      360

TTCTAAAGAG CATAAGCGTA AAGGAAAGCA ACACAAATTA AAAAAGGAC AGCAGTCTAC       420

AAAGATAAGG GTATCAAAAA AAAGGCGACG CGTACAACCA CACAGCATAT GCGATTAATA      480

ATCTTACAAT CGTACTAAGT AATACATACC GCGCTTATAG AATCTGCTGC TGCACGGAAA      540

GTTGCATATG CGAAAACATG CTATGCAGTG GATGATCGCG TACCACTTTT TAATCCGATA      600

AAAGTGGACT AGCGATAAAT AGTAATTTCA ATAGGGAATG TGAATTTGAA TTGAGAATTG      660

GGATAATGCT GTGGATTTCT GTGATTATAA TACCATAAAT ATA                       703

(2) INFORMATION FOR SEQ ID NO:987:

(i) SEQUENCE CHARACTERISTICS:
        (A) LENGTH: 622 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1607RP (xi) SEQUENCE DESCRIPTION: SEQ ID NO:987:

GATCACACGA CAGTGCCAGT CGGGGCAGCC GGTACCCGTT GGCCGCATCG TGAAGCTGAC       60

TCCGAAGAAC CCCTTCTACA AGTCCCCGA GACGGAAGAC CTGTCGACGG TCATGGGCAT       120

CCTTGGCTCC GGCGTGCACC GTGTCGCCAT TGTGGACTCC ACCTCTTCAT CTATCCGTGG      180

CATTCTGTCG CAGCGACGTC TGATGAAGTA CCTGTGGGAC AACGCCCGCC AGTTCAGCAA      240

CCTGGAGGTG CTGCTCAACT CGTCGCTGCA AAAGTTGGGC ATCGGTGTGC TGGATCCACA      300

TACCCCTCCT ACTTCGCGGC AGTCGCGTGT TATTTCCATT CTCGACACAG AGCCGCTGCT      360

CGTTGCCCTG CACAAGATGC ATACAGAACG GATATCCTCC ATCGCAGTGA TCGACCACCA      420

GGGCATGCTG CTCGGGAACA TCTCTGTGAC AGACGTCAAG CAGGTTACGC GCACCTCGCA      480
```

```
GTATCCGTTG CTGCACAACA CCTGCCGCCA TTTCATCAGC GTGATCCTCA ACAACCGCGG      540

CCTGGAGATG GGCAAGGACT CCTTCCCCAT CTTCCACGTT TACCCCACCT CGTCCCTGGC      600

CCGCACGGTC GCGAAGCTGG TC                                                622
```

(2) INFORMATION FOR SEQ ID NO:988:

(i) SEQUENCE CHARACTERISTICS:
        (A) LENGTH: 674 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1607UP (xi) SEQUENCE DESCRIPTION: SEQ ID NO:988:

```
GATCGGTGCC CGCACCTCCG CCCGATTCTT CGCCAGCTCG TTCGCAATGT TCGGTATCGA       60

CTTCTGCTTC TTCATCCCAT CCACCTCCGT CCCGCCGCTG TCCAAAGCTC GCTTGGCTGC      120

GCCGCCACTC GTACCTGCCT GCCGTTCTTC ATCTTCAATA ACTATCACTT GCATCCCGTT      180

AGTAGCTGCA CGGTGCAGAG GGCTGTAAAC CTCCCCTCAG CCCTTCAAAA CGCCCCACCA      240

CATACCTTCT CGTCCTGGAA TCATGATTGC CCCTGGTAAT CTTCACGCTA GCACTAATTT      300

GGTCACTAAC TGCGCTCTTG CGGACTGGAA TTGGTGGTGC AGATGGTGAA GTCTCATGTC      360

GTCCATTTCT GCCGATGTTA AAATATGGGT TTCCGAAAAA GCCCTGCTTG CCCTTGACTG      420

ATGCTCGACT CACAGAGGAC TCACCAGAGC TTGAACCGCA GCCAGGAAGC ATTCCTGTCA      480

TACCAGAAAG GGCCCACGGC GAGAATCAGA ATCGATGTTG CATAGTCGGG CAGCAAGAGT      540

GCTCCAGCGC TCGGGGTCCG CAAGCGCAGA TGCAACAACT CCGTGCACAG CATCACAAGC      600

GGTATAGCAT GGCTTCCCCA ACGATTTCGC AGGTGCCGGA CTTCAGCAAG TATTCCCGAC      660

CTGGCCGGTT ACAG                                                        674
```

(2) INFORMATION FOR SEQ ID NO:989:

(i) SEQUENCE CHARACTERISTICS:
        (A) LENGTH: 733 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1608RP (xi) SEQUENCE DESCRIPTION: SEQ ID NO:989:

```
GATCAAAACC ATCACCAAGT TTATTCATGA AGTGTCCGAC GATTTCAAGG TCATCATAAT       60

CGACGCAATT CGTACTTTGT CGCTAAAGTT CCCAGATGAG TGGAAGAATA TTCTATCCTT      120

TTTAATTGAC ACTTTGAAAA GTGCAGAGGG TGGGTATACA TTCAAAAATA ATATCGTAGA      180

TGCGCTGTTT GACCTGATCC AACATGTACC TCAGTCAAGG GAACAGGCTC TGGAACACTT      240

GTGTGACTTT ATTGAGGACT GCGAGTTCAA TGAAATCTCA GTCAGGATCA TTTACTTATT      300

GGGTAAGGAG GGCCCCTCGA CAGAAAAGCC TTCGCTTTAC GTTAGACACC ATTACAACAG      360

AGTTGTCTTG GAAAATTCAA TCATCAGATC TGCTGCTGTT AGCGCATTGT CCAAGTTTTC      420

CTCTCCGAAG AAAGATCCGT CGTTAGCTTA TTCCATCGAA AAATTGCTAA AGGGTATCCA      480
```

```
AACCGATGAG GATGACGAAG TGAGAGACAG GGCAACCATT CTAGTAAAGC TCCTTGAGGA     540

GAACAAGGAA AAGCCTGGTG TTGCCGATGA ATTTATCCAG CCAAAGCATA GTTACGATCT     600

ACTTGCCCTG GAAAAGTAAA TTAACGAACT ATCTCCACCA TAATGAAGAT GGCTTTGCCA     660

CACCATTTGA CGCGTCGAGC ATTCCAAAGT TACACAGAAG AGGAGCTCAA GGCTATTAAT     720

TTGAAGCAGA AAC                                                       733
```

(2) INFORMATION FOR SEQ ID NO:990:

(i) SEQUENCE CHARACTERISTICS:
        (A) LENGTH: 723 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1608UP (xi) SEQUENCE DESCRIPTION: SEQ ID NO:990:

```
GATCTGCGCA AGGATAAAGG TGTTCATCAA GTCATTGTGA ATGACGCCGG CAGCCTGTGG      60

CGCCTTAGTG CCATTTCTGA TGGTCCATTC TCTGACTTCG TCGGGCCCGC AGGTGAAGAA     120

CGAGATCAGA TCCAGCTTCT GTCTCATGGT GGTGATGATC TTTGGGAAGG CGGACTGGAC     180

GCCGATCTTC TCGCACTCCT CGACAGCCTC CTCGGCGCTC ATGTGCGACA GTCTCTCCTC     240

CAGGCACACC GAGAAGGGTA TAATTAGATC GCCAGGGGAG TACTTGTCGA TCCACTCCTT     300

GATCTTCAAG AGGTGCTTGT TCTTCTTTCT AATGTAGTCC CGCTCCGATA GGTTGATCAG     360

GTAGATGGAT GGCTTGGCGG TTAGCAGGAA CATCGAGTTG ATGACCTCCA CCTCCTTGGT     420

GCTCCAGGAC TGGTTTGCGA CTCTCTGACC CGACTTCAAA AGCTCGATAA TGCGCTTCAC     480

CAGCTCGGCC TCCTCCTTCT TCTGTTTCAC CTCCAGGGAC TGGCCGCCTC TCTTGGTGAT     540

CTTCTCCACG GCCTCCAGGT GCTTCTCCGC GAACTCAATG TCCTTCAAAC GCAATTCCGT     600

GTTAATGATG TCCAGGTCTC TGACCGGGTC GACGTCACCC TCAATGTGGA TGATCTCGGC     660

GTCGTCGAAG CAACGCACGA CCTGGTAGAT CGAGTCCACA GATCTGATGT GCGATAAGAA     720

GGC                                                                  723
```

(2) INFORMATION FOR SEQ ID NO:991:

(i) SEQUENCE CHARACTERISTICS:
        (A) LENGTH: 692 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1609RP (xi) SEQUENCE DESCRIPTION: SEQ ID NO:991:

```
GATCAGACGG TAATGGCGCG CATGCTGGCG CAGGTGGAGC ACGTATCTAG CGTCCATCGT      60

CTCTTGCTGT GGTGGCGGCG GCGCGGCAAG GGCCTCGCTG CGCGAGAAAT ACAGTAGGGA     120

TCTGTCGCGC CCGCGCACCA GGGCACGCGG GGCCGCGAAC AGCGCCGTTT GCCCCTTAAT     180

CGGGACAAAC GCATATAAGT AGAGGCTTAG GCGCTGCTCG AGGGACGGCA GAACACACAC     240

AAGGACCAAT GAACACGATT ATCAACTTCC AGGAAGGCAG CGCGCAGGCT CTCAGCGAGC     300

ACAGCATCTT CCCAGATGTG CTGGTGTCCA CTGCTGAAAA CGGTCCATCA GGACACCTTG     360
```

```
TAGTGGAGTA CCCGGGCGAG TCTACAGCGG TGACGCTGGG GAACGTTATG CCTGTGGAGG        420

CTACGCAGAC GGTGCCCAAC CTGATGTTAA TCACGACCGA GCCGGGAATC GTCAGGGAGG        480

GGGACCTATT CACGCTGGCG ATGACAGACC CAGATGCTCC CTCGCGGTCG GACCACAAGT        540

GGTCGGAATA CTGCCACTTT CTGGAAACGA ACATAACGCT GGGCTCGGAT GACGGGGTGT        600

CGCACGTGGT GCTAAAGGGC ACCCCGCAGG TGGAGCACAT GGGCCCTGCG CCGCCGGGCC        660

GGCACAGGGG CTCACCGGTA CGTGTGGTTG TT                                     692
```

(2) INFORMATION FOR SEQ ID NO:992:

(i) SEQUENCE CHARACTERISTICS:
        (A) LENGTH: 720 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1609UP (xi) SEQUENCE DESCRIPTION: SEQ ID NO:992:

```
GATCGAGAAG ATTTGGAGAA GGAAAGCGTC TTGGTGCTAG CCTCGTGACC CCCTCCCGGG         60

CTGGAACTGC GCGATATACT ACATAAAATA CGTTATCCCT GGAATTTGTA GCATTAAAGG        120

ACTTATGGAC TATTCTGTAT ACCTGCGCTT CCCGCTGCCA CCCGTAGCAA TGCCAAACTC        180

ACTCCGAGGC CTCGCTGCTG GCCCAACAAT CGGACTCACG CGGACCCGAG CCCCGCAGTC        240

ACGTGCCCCC CGCATTCGCG CCCACATCAC TCCGCTTGCC TCGCTTCCGC ACCCCGCCAC        300

GCGACTCCGG GCCCCGCAGC CCCACGTGAT TCTAGTTGCA TAGGAAACTA GGCTAAAATC        360

ACGTGACTGA ATCGCGCGGC CACATCATAC CATGGGACAC GACCCCGACT ACCCCCCCCC        420

CCCCGCGCCG CGCGCTGCAC AGCAGCCGTA TACGGCGCAG GCGCAGTCCG GTCGCGCGCC        480

TCTGAGAGGG CGCATGGCCG CCGATGCTGC ATGGCTGCCT CGGTGTTGCC GAAGATGTGG        540

AGGCACGTAC GCGGGCAGCT CAGTTACCCG AAGTTACCCC TTCTTCTGAT TAAATTTGGA        600

CTGAAACTTA AAAGCCGTCA GCAGTGGCAA ATCCACGGTG AGAATAATTA CAGGAAACAG        660

CGGTGGACCA GCTGCGGAAC TAGACGACGG GTTGGTGTGG CACGCATAGA AGGTATGTTC        720
```

(2) INFORMATION FOR SEQ ID NO:993:

(i) SEQUENCE CHARACTERISTICS:
        (A) LENGTH: 731 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1610RP (xi) SEQUENCE DESCRIPTION: SEQ ID NO:993:

```
GATCAATTTC CTTTCGTATA GTTGGCGTCC CAGGCTCCGA GATAGCCCCA CATGATAAAT         60

TGCTATCGCA CATGATGTCC TGGTTGTCAT TGTTGTCCAA ATTGCTCAAA TCAAAAATGA        120

AACTACCATC ATCTGGTTTC ACTTTCAGTA AACTATCGTT TTTCTCTGTT GCAGGGTCGA        180

AATCCATATC ATCCCGTAGA TATTCTATGT ACAGCAGAAA CGGAACCTTC TCTGCTGAGT        240

TCAACACCTG AGCTTCGTTA GCAGCAATAT TTACAATTCG ATGCAGCTTG CCCTTCTTAT        300
```

```
TAGGCGGCAA CAGTGTAGGG ATATCTACCT CAGCTGGCAA GTCCCTATTC ATGATAGAAA      360

GCTCAGCTCT CAATGAAGTT AGGCGAGCTT CAGTGGGAAC TTGCGCCAAC TTCCTGGATA      420

TCGTTTCTAG AGCAATCACA AACTGCATCT CGCAGCGGAA GTAATTTGCC TTCAAGATTT      480

TGATTTTATG TGTGGCTGAT AAACTGGAGG GCTCCAGGTT ATAGATGTTT GCTCCATGCC      540

GAGATGTCTT CCGTTTGTGG CTCTTCTTTA AATCATTGGA CGGAGACTGC GTGATGCTAC      600

CACTTCCATG CTGCTCCAAT GATTGCTGAT CCTTATACGA GTGGAGTGAC GTGCTGGATC      660

GAGAATTCAG ATGCAAATTA GGCATAGAGT TTGTGTATTC CTCTAGCTTA GCACCATCGT      720

TATCTTTGGG C                                                           731

(2) INFORMATION FOR SEQ ID NO:994:

(i) SEQUENCE CHARACTERISTICS:
        (A) LENGTH: 729 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
         (A) ORGANISM: PAG1610UP (xi) SEQUENCE DESCRIPTION: SEQ ID NO:994:

GATCGATCTG TACAGAGCCG TTACAACAGG CACTTGTAAA AAGCAATATC GTTACTTTTT       60

TGCATGTCAG TTTTTTCCTC GAGCCTCGTC AGCGCGAGGA ATGAGTAATG GATACTTTGA      120

CGACAGAAAA AGTGAAAACT TTGAGCGGAC ATCGCAACCT GCTCGTTAGT AGCACCTAAG      180

CGCAGGTTAG CACAATGGCG CCAAAGGATA CGGCGGTGTC GGAGACCTCT ACGCGGTCTC      240

GCTATATCAA AAAGGGCAAG ACTTTAGAGA ATGACATTGA GCTACAGTCG GTGACGCCAG      300

CCACCGGGGA GTTCCCCGAG GACCACACGG AAGAGGGCGA CTACCAGGAG ACGGAGGTCA      360

AGAGGGCGCT GAAGGCGCGG CACATCTCGA TGATCGCGCT GGGCGGGACG ATAGGCACAG      420

GCCTGTTCAT TGTGATTGCA TCCCCGCTGC GGACAGCGGG GCCAGTGGGG TCGCTGTTGG      480

CGTACATCTT CATCGGTACG GTGGTGTACT CGATCACGCA GTCGCTGGGG GAGATGGCGA      540

CGTTCATTCC TGTGACTCCT CGGTGACGGT ATTTTCAAAG CGGTTTCTGT CGCCTGCGTT      600

TGGCGTGGCA AACGGGTATA TGTACTGGTT CAACTGGGCG ATCACGTTTG CTGTCGAGCT      660

TTCTGTGGTT GGCCAGATCA TACAGTACTG GACGGACCGC GTGCCAATCG CGGCGTGGAT      720

TGTGATTTC                                                              729

(2) INFORMATION FOR SEQ ID NO:995:

(i) SEQUENCE CHARACTERISTICS:
        (A) LENGTH: 666 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
         (A) ORGANISM: PAG1611RP (xi) SEQUENCE DESCRIPTION: SEQ ID NO:995:

GATCCATCGT GGTGTCGTTC ATTACCTGTA ATTCCATTGA TATCCTGGCT ATGCAGTGCT       60

GGAAACGCTC CTCCAGCGCC TCTATTTTGT TATTCAGCTC CAAGTACTCC GCGAGCTTAA      120

AGGTCAACGA GAGCGACCCT GGATTGCACC TGACGGCGAT CTCAAGGACC TTCTCGTGCT      180
```

```
CGTTCTCGTC CACAAACATG GCGTAGTTGT ACCATATCTC CGGCGCAAAG CACATGTGCT      240

GCACAGCCTG GCGGTGCACG TATTCCACGC GCTGGCGCAG CACGACTTCG GGCAGGTCGA      300

GCTTGTTGTC CAGCTCCCAC TGGATCCACT TCGTCCAGAT CTGCAGCTGG TACTCATCGT      360

ACTGACCGGG CGCAGGCAGG TTCTGCTGTG TCGCCTGGTT TAGCTTCGTG GGCAGCGAGC      420

GCCGCAGGCC CTTCGTCAGG TTCGACCACT CCTGGTACAG CGAGCGCGCA TTCATGTAGC      480

TCGCCGAGAG CTCTCCGATG AACTTCCGCG CCGTCAACTG GTTGACCTCC TGCTCCCACT      540

GCGTGTATTT CTCCCAGTAC CGCTCCAGCG ACTCCACTGG CAGGCACAGC AGGCGCTTGT      600

ACAGCTTGCG CAGAATCTCG ACCCGGCTCT GCTCCTCCCA CTTGCTCACC GGCTTCCACT      660

GCTCCA                                                                666
```

(2) INFORMATION FOR SEQ ID NO:996:

(i) SEQUENCE CHARACTERISTICS:
        (A) LENGTH: 623 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1611UP (xi) SEQUENCE DESCRIPTION: SEQ ID NO:996:

```
GATCTAAGGG ATGGGTGACT GCTGCCGGTG CTCACAGCAG TGGCACGTAG CTAGTAATGG       60

TGCGAAATCG ATCAAAGAGG GTGCGTCTGG CGGTACAGGC AGAAAGCACG CCCGCCGATA      120

CAAGTTCCAG TTCTACAAGC ACCTGCAGTT CCAGGGTACG AGGTACCAGG TGGTGACTTC      180

GCGGCCGTAT CTGATAGAGC GGTACGGGGA GCGCAAGGCG GCGACGATCA GGTCGTTTGT      240

CAAGTGCATC CATCGGAAAA TCAACGACGA TGTGACACGG ATCAGCGACG AGCGGGTGAC      300

GCACGGGGTG TCGAAGTGGG AGAAGTCGAA GCTGTTCCTG CTGCTGGTGA CGCTGTCGCA      360

GCGGGGCGGG CCGGAGTACT GGCTGGACAA GACGAACGGG TGCCAGAGCC GCGCGGGCGG      420

AGACGGCGCG CGGAAGAGCG ACCAGGTGGA GGAGGGCGGG AGCCGGCGGG GCCAGAGGCT      480

CGTCTGCACA CTGGTGGAGC AGATCATGCG CGAGAACATC ACGGAGGACT ACGACGAGAG      540

CGTGCACGAC GAGAACTACG TGTTCTCGTC GATATGGGCG AACTTCATGG AGGGGTTGAT      600

AAACCACTAC CTAGAGAAGG TCT                                             623
```

(2) INFORMATION FOR SEQ ID NO:997:

(i) SEQUENCE CHARACTERISTICS:
        (A) LENGTH: 708 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1612RP (xi) SEQUENCE DESCRIPTION: SEQ ID NO:997:

```
GATCCATGCG ATAAATCTCC TAGTGGTGTG GTTTCACACG AAGCAGCTTC CGTCGTTCTC       60

GTGGTTTTTC CTGCAGCTCT GTTCGAGCTT GATTTTGGTG TTTTTGGGGA CGTGGACCAC      120

GAGGTGGCGC GAGCTTCGCG ACACGTTTTT TGAGGGTCTC ATAGATCAGG AACCTATTAC      180
```

-continued

```
GGGTGGGGCT GAGTCTCCCT ATCATGGCAG TTCTCAGAAC AGACAGCAGT TTGAGATGAA      240

GGACTTGGAG GCACAGAAAT AGCCTACATT ATAAATACGC TTGAGATCAT TCTAGCGCCA      300

CGGTGAGACT GATCATTCGT AAATAGCATT TTAATAACGT AATATATCAT ACGCTGGTTA      360

TTTCGGATGC AGGACTCCGA AATAGTCTGA CAATTATGTA CTGTTAAGTT ATTTATTTTC      420

AGACGGCGTA TCTCGCTTGA AACCTGTTCC AGTGCACAGC AGATCCAGCA GCTCGAATAC      480

TGATTTTTTC GTATTGTTAC CTGGTCGACA GATCTCCAAG CCACCCTCCA ATCGCTGCCG      540

CAGCTGCAGC ATTGCTACCG TAGACTCCAG CCTAGTGACA AGATGATCCA ACAAGGATAT      600

CCAATCGTAT TCCGTGTTCT GGCTCAGCGC TTTATCAACC TTTTTATCAC GAGTCATATG      660

TGTGGGTAGT TGTAGGACAC TATTGTCGAT TTCGATCAGA CCGCCGTT                   708
```

(2) INFORMATION FOR SEQ ID NO:998:

(i) SEQUENCE CHARACTERISTICS:
        (A) LENGTH: 732 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1613UP (xi) SEQUENCE DESCRIPTION: SEQ ID NO:998:

```
GATCAAATAG ATGTGCGCTG CCACATAGGA CGGAGTCGCG GCTAAGCTGT GTGTTTTACC       60

TGGAGGCAAC TGTTGGACTC CTGTGTCAGC AATCGCGCCC CGACCTGCCG AACAAGCGAC      120

TATATAACAA GCGAGGAAAC CACCTTGTGA TACGCACGGG GACCAACGAC ACAGCAACGA      180

CACAGCAACG ATGGCGGACC TCGGGGCTCT TATTGACTTG ACGCGGATAT CGGAGACGCG      240

GTATGAATCG ACGAACCATC ATAGGATGAT ACACGGCGGC AAGGCGCTCT ACGGGGTCT       300

GCTAGTGGCA CAGGCGATAC TGGCGTCGTT CTACTTTGTC CCCAGGGACT TTATTCCGCT      360

CTCGGTGCAC TGCCTGTTCA TGGTCGGCGG AGACAATGCT ATCAAGACGC AGTACGAGGT      420

TGAACGGCTG CGGAAGGGGA GCAACTTCGC GCACCTGTTG GTGCGCGCGT ACCAGAAGGA      480

CAAGGAGCTG TTCACAATGC AGATCATCTA CCGGCGCGAC CTCGGCAAGC AGCCGGACAC      540

GCTGCACCGC AAGGACAACC TGGGCCCTGT GGACCGGTCC CACCTGGAGG ACGCTGGCAC      600

GCTATGCAGG CGGGATCTAC TGTCCAACCG TGAGAACCTG CAGGCGGTGA GCGCGTCTTC      660

GAGACGGATA AGGGCCTTAA TAACATTCTG GAGGGGTTCG ACAACACGTC GTCCGAGTAC      720

AGGCTGCCTG GC                                                         732
```

(2) INFORMATION FOR SEQ ID NO:999:

(i) SEQUENCE CHARACTERISTICS:
        (A) LENGTH: 727 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1614RP (xi) SEQUENCE DESCRIPTION: SEQ ID NO:999:

```
GATCGCGGCG ATGGACCCGT GCTTCGACCG CCTTCTGGCG CACCGCGCGG CGTTCTTCGC       60

CGCGGTGCAG GAGCAGGTGC AGCGGGACTA CGGGGCGATG GAACAGTTCC ACAAGTTCCC      120
```

```
CGACACGATC CGTGTCGACA AGTTGGTCAC GTATATATGG CGCGTGTTCG AGCGCGTCTG        180

CGTGTACCCG CCGAACCAGC AGCGCTGCCA TCTCGAAGAC ATCATGCTCT TGCGTGTGTA        240

CTGCGGCGAG GCGCGGGGGC ACCCGCTCTT GCTCATGGCG ATCGTTCAGG CGGTGGCGGC        300

ACGCTACGGG GTGCAGACGC TCCTCTGCGA GCAGGTATTG ATCATCATTG ACCGCAAGTT        360

GCGCGGCGGA CAGTCATACT TGATGATCCC GCTGCGAGGG AACGCAAAGC CGCGCATCTT        420

CACGCGGCGG CGCTTGCTCG ACACTATGCG GCACACAATA CCCAACATTG CCGACCCGCG        480

GAGCCTGGCG CTCGCCCGGT TCCTCACTCC GCTCACGAAG CGCGCGGGTG CTGAGAAAAT        540

CTTCAAAGAC TGGTCCATCT ACTGCGACAA ATCCATATGG CGGACGATCC CTGATCACTC        600

GCCCAATGGC ATTCTGCGCT ACCTCCCGCA CTCCTGCACG CCGATGGACG AATCCATCTT        660

TGAGTATTTC ATCGTCTATT GGAAAACCGC AACAGCAAAC CACTCCACGA ACAACATTTT        720

CCACACC                                                                  727
```

(2) INFORMATION FOR SEQ ID NO:1000:

(i) SEQUENCE CHARACTERISTICS:
        (A) LENGTH: 726 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1614UP (xi) SEQUENCE DESCRIPTION: SEQ ID NO:1000:

```
GATCCTTTTC ACCAACAGCT GTCTGGGCCA GCTGCGGCCT GGGATGAGCT ACAACGAGGC         60

AGTGAAAGCG CTGACGAACC TGGCGCTGGA CAGCTTTACA CTGCCGGGGA CGGTGGGGTT        120

TCCGCTGAAC AACGTGTACT CTGTGCCGGT AGAGGACGGT GCTCAGATGG AGCTGCTGAA        180

GGGGTACCTG CAGCAGTTGC GGCAGGAGCT GGCCACGCGG CTGCTGGACC GTGTGTATGG        240

GGCGGAGAAG GCACAGCCCT CGAAGTTCTG GCTGGCCTTC ACAAGGCGCA AGTTTATGAA        300

CAAGGCGCTG TAAGGCGAAA TAGGTACGTA GCTGGCGGCG CCAGGAAGTA TTTACAAAGT        360

TGGCTGTATC GCTACGAGGT TTTGGTGGCG TGTGCCTTGT TGGAGCGCAC GAGGAGTTCA        420

ACGGCGGAAG CTCGGAGCTG TTCCGCGTCT TTCACGATCG CGTTCACGTC AATGCTGAGG        480

TCGGTGTTTT TGGCGCGGAA GCCTTGGATC CGCGCCTGCA GGTCTGTCAG CGCCTGGAGG        540

ACACGCTCAT AGTCTGCATC TTCTTTCACG CGCTCTTTGT ATGTTTGGAA GGACTGAGCG        600

ATGTCTTCGA TACCGGGCTC GACTCTGCTG ATCATCTCGA TGCGCTGGCG CAACAGCTGA        660

TCGCGGTCGC TGTTGGCGTT CGCGTCGCTA ATCATCTGCT GGATTTCGTC ATCGGTCAAG        720

CCCGAT                                                                  726
```

(2) INFORMATION FOR SEQ ID NO:1001:

(i) SEQUENCE CHARACTERISTICS:
        (A) LENGTH: 704 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1615RP (xi) SEQUENCE DESCRIPTION: SEQ ID NO:1001:

```
GATCATTCAG CTGGACGTCA GCCGACTACT GTTGGACCCC ATATTCACGG TCCCCGAGGT      60

GCAGAACGAC ATGGTGGAGA TTCTGCGCCA GTATATGCTG GAGTCGGGGC GGCCGTACAA     120

GCAGGGTTTC CATGAGCTAT GCGGCATGTT CTACATGCAG CTTTACCGCA ACGGCTACCG     180

GGACGGCATC CAGCACACCA CGCTACATAT GTTCAAGGAG TTCATCGCAG AGGTAGCTGT     240

GACCTTCTAC GACGAGGGAA ACCTCATCGA GTGGACGAAG AACACGTTTG AACCGATACT     300

TCGACACGCG TTGCCAGGCT TGTACGAGCA GCTTCTAATG CACCATGAGC TGGACAACTC     360

GATATGGCTC ATCCGCTGGA GCAGGCTGCT CTTTCTCCGA GAGTTCGAGC TGGAGTACAC     420

GCTTTGCTTG TGGGATCACC TGCTGACATT TAGATACCCA GTATCCCAGC TCGTAGCAGC     480

CATTATCGTT GTCTGTCTGA CACTCATTGT ACAAGAACTG CATTCCTGTG AAGACCACGG     540

CGACCTGATG TCTATTCTAC TGCACTACCC TCCTCGAAGC TGCTGAGCGC CCCCAGATGA     600

TCCGCTCCGC CCGGACGCTT CCTGATCTGT GGCTCGCCGA ACAATATGAA GACATGCAAC     660

TCATCTGCGA TTCACTAATT AAGTCGCACA ACGGCGCCTG GTTC                      704
```

(2) INFORMATION FOR SEQ ID NO:1002:

(i) SEQUENCE CHARACTERISTICS:
        (A) LENGTH: 706 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1615UP (xi) SEQUENCE DESCRIPTION: SEQ ID NO:1002:

```
GATCTCGTTA TTCTGGACAA CATTGCGTAT AGGGACTGCT CCTGCTTTGT GTGAGGAGAC      60

GTGTGCTGAC TTTAAATAAG TACGATGAAA CGGTCAGCCT ACGGTGGGGC CCCGTTTTTC     120

AGTTTCGCAC GGAGAGGGTA TCAAAGGAGG TCGAACACAG CTACGTTATT GGTTCGTATA     180

GCATGCTTTT GAAGCCCCTA GCTTCACGAG CGCTCCGACC ATCCCAGCCA CCGCGCCCCT     240

ACGCCCAAGG CCAGCTCCCG CAATACGGCA GCGCCGTGGG CCCCTTTTCG TAAGTATATA     300

TGGCGTGGCC GCGCCGCGCG GCCGAGGTCG CGCGGTCGAC AATGGCTTCT CGACTTGACA     360

AGCTCCCGGA GGCGGTCAGT CGCCTGCAGA GCCTCAGCCA TAGACAGCTG CTCCGTCTGG     420

CGCAGGGCGT GTGCATCCCT GCCCTGTCCC CGTCCCTGCA CAAGGGCCAG AGTGGACGCG     480

TGTGCGTCGT GGGGGGGTCG CTGGAGTACA CCGGCGCGCC GTACTTCAGC GCGCATGCCG     540

CGGCGCTCAT GGGCTCGGAC CTGGTGCACG TGCTGTGCGA GTGGAACGCT GCAACGCCGA     600

TCAAGGCCTA CTCGCCGGAC CTGATGGTGC ACCCGCACCT GCGCGACAGT AGCTCCCTGG     660

CGCGCGGGCT GGAGCCCGCC ACAGAAGCCG TGCGCGCGCT CGTGGA                    706
```

(2) INFORMATION FOR SEQ ID NO:1003:

(i) SEQUENCE CHARACTERISTICS:
        (A) LENGTH: 687 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1616RP (xi) SEQUENCE DESCRIPTION: SEQ ID NO:1003:

| | | | | | |
|---|---|---|---|---|---|
| GATCTGCTTC | AAGAGCTCCT | TCTGGTAGGA | CGAGCCCAGG | ATGAAAATCT | TGGAGACGGT | 60
| GACAGGGTCC | AGGAACGGCT | TGAACAGGCG | GAATGCGGCG | GAGAAGCCGA | ATGGCGCGTT | 120
| GATCATGTAG | AACTTGCCCA | TGCGCTCGGG | GTAGTAGTTC | TGGCCGATGT | TCGAGGCCTC | 180
| GCGCACGTAG | CTGAGCACCT | GCGCGGCTGC | GGAGATGGAG | ATGCCCTTGA | GGTCTAGGAT | 240
| GGTGCAGGAC | GTCTCGACGA | GGCAGTCGGC | CTGTCTGGAG | CTGGCCGGCA | AGCGGTACCG | 300
| CGAGAAGGAC | TCGTACTCCC | ATATCAAGTT | CTTCAGCATG | CGCTCCTGCG | TCGTGATCTT | 360
| GTACATCTCC | GTCAGGTTCA | CCGCGCCCAG | CTCCTCGATG | TACACCGGCC | TCCCGTCCTT | 420
| GTCCGTCTTG | TGGTAGTACT | GCGGGTAGAA | CTTGGCCACC | AACGGCTTTT | CCTCGTAGTG | 480
| GAAGTCCTCG | AAGATCGTGT | CCACGCCGTT | TTCCTTACGC | CACTTCTCGC | AGTTCTCAAA | 540
| CATTGCCCGC | GCAGCCGCCC | ACGTTCGAAC | TTGCGCGCCC | GCAGAAACCG | CAAAAGCGTC | 600
| GAGTCGTCCA | GACGCTTGGT | GAATCCGGCC | TGCTTCAGCA | CCTTGCGCAG | CTCCTCCAGC | 660
| GCCGCCTCCG | TGCTCCGCTC | CGTCAGG | | | | 687

(2) INFORMATION FOR SEQ ID NO:1004:

(i) SEQUENCE CHARACTERISTICS:
        (A) LENGTH: 685 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1616UP (xi) SEQUENCE DESCRIPTION: SEQ ID NO:1004:

| | | | | | |
|---|---|---|---|---|---|
| GATCACCTTT | TGGCACGAAC | GCCACAGAAA | ATCCATTACG | CGATTCTGCC | CGTTCATTTC | 60
| TGTACGAATG | GGGAAATGAC | TCGTCGCCAT | GGCACAGGTG | ACTATCGCAT | TTCGTTTCGG | 120
| GGGCGTGATG | CCCAGATTTT | CTTGCAGAAA | GCCGCCACCC | TGCGGGATAG | GGCTTTACCT | 180
| CACATGAGGC | GCAAAGCGAC | AATAATCGCA | GAGCTGCTTC | TTACTTCATT | CTCTACCCCA | 240
| CTAACGTAAT | CGATCGGACA | GGCACAGTCC | TACGGTAATC | CTCTGAGATA | CCAGATTCGG | 300
| TTGCATAATG | ATCTCGCCTA | CAGGGCCGTG | TTTGTTCGAG | CCCATATCTC | ATGCAAGATC | 360
| GCGATGCCCG | TGACGATCCA | CCTTCACCAT | TTACTCGTTT | CTTTTTCATG | TTTTCAAAAA | 420
| GAAACGAAAA | GGTGAGATAA | AAAGCAAACA | TTACTACCGA | CATTTAAAAT | AGGTGATGTC | 480
| CAGGACTGTA | CCTCATTGTG | GGCGCTAACA | GCACCAGCAA | TGTCTGTGTC | ACCCCTTGTG | 540
| CTGTTTGACT | TTTCAACAGA | CAATCCGAAC | ACACTGCCCC | GGGAATACGA | CCTTGCAGTG | 600
| GCCCGAATCT | GTGTGCTGGG | CCACGGGGGC | AGTGGCAAGT | CATCACTCGT | TGCTCCGATG | 660
| GCTACACGGA | CTGGAGAGTG | GCCTG | | | | 685

(2) INFORMATION FOR SEQ ID NO:1005:

(i) SEQUENCE CHARACTERISTICS:
        (A) LENGTH: 703 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:

(A) ORGANISM: PAG1617RP (xi) SEQUENCE DESCRIPTION: SEQ ID NO:1005:

| | | | | | |
|---|---|---|---|---|---|
| GATCTTGACA | CCAATCGACT | TCCGGAACGC | CTGAGTCAAG | GCCTCGGTCT | TGGATAGCTC | 60 |
| CAACGAGAAT | ATCTCTGACC | CTGCCATCGC | TGTGAAGGGC | ACATCTGCGC | CCAGTGACTG | 120 |
| CGACAAGCCC | ATCGCCAGCG | CCGTTTTGCC | GGTCGACGGC | GGACCAGCAA | CCAACACGGC | 180 |
| CCGCCCGGCA | ATCGTACCGT | TCTGCACCAT | TTTGAGAATC | ACGCCTGCGG | CCCTCCGCGC | 240 |
| CTGTAACTGG | CCCACCATTC | CCTGCGAGCT | CGGCTTAGGC | TGTAGGTTCT | CGTCCAGTCC | 300 |
| CAGGCCAACA | ATGTGCGAAT | GTGTCGCAAT | TAGCGACAAG | GACTTCAGAG | ACATGTCATG | 360 |
| CGCCTCCTGT | GTTTGAATCG | ACATATTATA | GATCTTTGAA | ACTTTGAAAC | CGTCAAGAGA | 420 |
| GTCCAATGGC | CTTTGTCGAT | GACCGTCTAA | CTGTTCAAAC | GGTTGTGCAA | CATACCAAAT | 480 |
| TTTGCCGGAG | CCTGAGGACT | AAAACGCATG | TTATACGAAG | TCAAGAAGAA | GCATCGTTTG | 540 |
| AGCTGCTAGC | AGTTCCTTGA | CTCTCAACTT | GGTGCGAGCG | TGCGGTGTGA | TGCTTCGCAT | 600 |
| GGGAGAGTAC | ATATGTGGTT | GCAAGCCACT | TTGGAACCTG | TGGGCTAACG | ATGTACGCAT | 660 |
| CACCGTGAAT | GGGAAGCGGT | ACTTGGTGAC | TGGGCTCCTC | AGT | | 703 |

(2) INFORMATION FOR SEQ ID NO:1006:

(i) SEQUENCE CHARACTERISTICS:
       (A) LENGTH: 696 base pairs
       (B) TYPE: nucleic acid
       (C) STRANDEDNESS: single
       (D) TOPOLOGY: linear (ii) MOLECULE TYPE: DNA (genomic)

(vi) ORIGINAL SOURCE:
       (A) ORGANISM: PAG1617UP (xi) SEQUENCE DESCRIPTION: SEQ ID NO:1006:

| | | | | | |
|---|---|---|---|---|---|
| GATCAGTTCG | TCGAAGAATT | CATGTCATGC | AGAGAAATGG | GAAGCAATTT | ATGCTCAGCT | 60 |
| CCCTCCCCCT | GTTCTCTTTC | TACCGCCAGG | CCATGCAGGA | ATGTCAGGCG | CTCAACACAC | 120 |
| CTAGTGACAA | ACTCGCCGTT | GTCCTGACAG | CCTATGCGTT | CGTAAATGTT | AAGGCCATCC | 180 |
| GATGTTCGAA | GAGGTGACAG | AAATTCCCGC | TGTAAATTCT | CAAAGAAACT | GTCCAAGGGC | 240 |
| GTATCCTTCA | CAAAGTCGGG | GCGCCGCTGC | AGCACATCTT | CCAGCTTCCT | CTGTTCCCCC | 300 |
| GAGGCGTTGC | TCATGCTCGT | GGCGATTGCA | CTTGCTCAGC | TCGGCCTCTG | CAAGTACGTA | 360 |
| ATTTTAGCTA | TCGAAAATTT | TCCCTCCTGG | CGATGAGCTC | ACGAAGTCTA | CATACCGATT | 420 |
| GACTAAGACA | CTTGCCACCC | GTTTGCGCCT | CATGCCACTA | CACCAAGGAC | CTCTGGACAT | 480 |
| CGAGGATCAA | CTTGCCATCA | TTGCGGACGC | CCGCATAGGC | GATCTTGACA | GCCTCAAGCA | 540 |
| AATCTTTTCC | GAGCTCATCG | ATCCAAAGCT | CCTGCCATCG | TGCAGCGACC | CAGACACGCT | 600 |
| CTGCACGCCG | CTGCACATGG | CTGCCGCCAA | CGGACACGCC | GACGTCGCCC | GCTAACTGCT | 660 |
| CTCGCTGCTC | GAGCCCGCCG | CGGGACGCGA | CTGGGG | | | 696 |

(2) INFORMATION FOR SEQ ID NO:1007:

(i) SEQUENCE CHARACTERISTICS:
       (A) LENGTH: 360 base pairs
       (B) TYPE: nucleic acid
       (C) STRANDEDNESS: single
       (D) TOPOLOGY: linear (ii) MOLECULE TYPE: DNA (genomic)

(vi) ORIGINAL SOURCE:
    (A) ORGANISM: PAG1618RP (xi) SEQUENCE DESCRIPTION: SEQ ID NO:1007:

```
GATCCGGCGT CCGGAAGAGC AGCTTATGCT GAAGGGCTAC CTAAGGGACA CAATCCCCCC      60

CCCCCCCAAA AAAAAAAGCA TGAGACTCTG TATCAGTAGG AAGTCTATCG CATCTTCTTA     120

TTTAGCCTGT ATATGTCCTT TCCGCGTGTA GACAKTGCGT TGGACGAGTA TGCTCGATGC     180

GGAATATAAC GTACTTTTTT GAAGAGTAAT ATGGACTTTC GACCTGCAAA GTACCGTCTG     240

CCGTTGCGGT GTCAGACACT CATCGGAACG CAATTGTTGC GGGATCACGG TATGCTTCTG     300

TTGTATGCTA TGGTAGCTAT AGGGTCTGGA CGGCTATCCA GAGAGATATT ATCCCATTAA     360
```

(2) INFORMATION FOR SEQ ID NO:1008:

(i) SEQUENCE CHARACTERISTICS:
        (A) LENGTH: 637 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1619RP (xi) SEQUENCE DESCRIPTION: SEQ ID NO:1008:

```
GATCAACAAT GTGCCGCGGC TGCTCCTGTT CCGCCCGGGC GGTGATCTGG ATAGCTACGA      60

GCCTCTCGGG ATTCCGTCGC ATACAGGCGG CGCACGGGTG CGGGCGATCA TCGACACCCT     120

CAAGAGTTAC ACCGGCATCG AAGACTTCGA GTACCACGAA CCAGTGAACT GGGGCCAGTA     180

TGCCGCTATC CTCATGATGG CCGTCCCCGT AGTAATCATG CTGCGCAACT ACTGGTCGGT     240

TGTGGTGTCC ATCGCCCTTT TCCGGCCTCT GTGGGGGTTC TCCTGCGTGT CGATCGTCAT     300

CGCACTTGTG AGCGGCGCGA TGTTCAMCAA GATTAAGGAC ACTCCCTACG TGGGCTCGTC     360

CGGTGATGGC AATTACGTCC AGTACTTCGC AATCAGGCAG CAACAGGTTC AGTTCGGGGT     420

GGAAACTCAA ATCATCTCCG TCATATATGG CACCCTCAGC GCAGGAGTCG TACTACTTGC     480

CATTGGCACC AAAAGCATCA GAGCTTACTA CATCAAGTAC AACTATAGCA TGCACGCGGT     540

GGTGCACTTG TTGTTGTCCC TCGCCGCAAT ACTGCTTATC TATATCTCCT TCGCCGCCCT     600

GCTCGCAGTC TTCAAACTGA GAACTTTGA GTATTCA                               637
```

(2) INFORMATION FOR SEQ ID NO:1009:

(i) SEQUENCE CHARACTERISTICS:
        (A) LENGTH: 720 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1619UP (xi) SEQUENCE DESCRIPTION: SEQ ID NO:1009:

```
GATCGCTTGC TGGAGACCAC AGATTTTCTA GCGTTGTCGG TAAGGGCGAG ATGGCGTCGA      60

CAACCACGGA GGAAAAGCTC ATGAAGCTGA ATCCAACAGC TACAGATGCG AACAATTACA     120

TTAATACTGA TACCACTGCG AGCAAGCCGG CTCCACCTTC GTCAACAGAG GCTGGACAGG     180

CAATTGAACG AGAAAAAAAA CTAGACCGGA GGCAGACTGA GAAGGACAGT GTAGAGAGCA     240
```

| | |
|---|---|
| GCAAGGTTGA GCGCCCGGTA GTAGATGCAT CGTACGTAGG GTGGAAGCAA ATCGGCGGGT | 300 |
| GGGAAGAGCG CGACCGACTC ACCGAAGATG ACCTGCACTG GGAGCTTGAC AGAGAAACCT | 360 |
| TTTTAAGCCA TGTGCTGCCT GCTGCTGCGT ATGGCGACTG GTATCACTCC GTGGGGATAT | 420 |
| TCTTCCTCGG CGGATTTTTA TCGTTTGCGT TGGGCTACTT CAAGTTCAGT TTATCACCTG | 480 |
| TATTCTTCGT AATGGTTTTG ACGGCTTTGC TATACCGTAC ATCGATTTGG AAGTACAGAG | 540 |
| GGTCGATAAG GGAACTGGTG CAGAAGGAGC TCACAGTGCA GAAAGTAGAG GATGACTACG | 600 |
| AGAGCATGGA CTGGCTCAAT AACTTCTTGG ATAAATTCTG GACCAGAATA GAGCCCAACA | 660 |
| TTTCCGTGAT GGTTGTGGAT CAGGTGAACC ATGAATTGGC TAAGAACCGT CTGTGCCGGG | 720 |

(2) INFORMATION FOR SEQ ID NO:1010:

(i) SEQUENCE CHARACTERISTICS:
        (A) LENGTH: 664 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1620RP (xi) SEQUENCE DESCRIPTION: SEQ ID NO:1010:

| | |
|---|---|
| GATCAAACTA TTTCTTGTTT TGTTGGTGGA AGCATACTTT CGTCAGTACT AACTTCTTCG | 60 |
| CTCCACTCCA TAAATTCGTA TTCCCTATTG GGATTAAATT CCGGACCCAA GGTAACGACC | 120 |
| AAAAACATTA GAGCAATAGA TCCCCACACA AAATAGGCCA TAACTCTACC ATAATCATAC | 180 |
| AATTCTTTAT TGCCATTATC GAGTGGAAAA TTTCTTGCAA GGCTGCTTTC AAGCAACGAT | 240 |
| GAGGGGCTAG ATGCCAAGTT TCCCAATTGA TATGCCACGC CCACGAAAAA GGTTTTCGTG | 300 |
| TCTGAGTTTG GAGCTAAGCA GTGTAAATGA TGTGGGACAA GGCCCCATGC TCCTTGAACA | 360 |
| AAAAACTGTA GGAAGAACAC GGACACTATA ATACTTCTAT CATGTACAAA TCCCCACGGA | 420 |
| TAAACAAGAC AGGCAGCCAA CAAAATACAC ACGAGGATAA CAACTCTTCT AGAGCTTATG | 480 |
| CTGGAAAAAC GTGAAATGAA AAGTCCACCT ATTATAGCAC CAACGTTGGC TGCACAATTT | 540 |
| GTGACGGCTG ACTGATTGGG AGAATAACCA AGTTGTTTAA TGAGCATGGT TGGAAAGAGA | 600 |
| TCTTGAGACG CATGAGAAAA GTAATTATAA CCCGTCATAA GCAATATCAT GTAGATGACA | 660 |
| ATGT | 664 |

(2) INFORMATION FOR SEQ ID NO:1011:

(i) SEQUENCE CHARACTERISTICS:
        (A) LENGTH: 727 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1620UP (xi) SEQUENCE DESCRIPTION: SEQ ID NO:1011:

| | |
|---|---|
| GATCAAATAA AAATAGAAAT TAGCTTAATG GTAGAGCATT CGTTTTACAC ACGAATAATT | 60 |
| TGAGTTCGAT TCTCAAATTT CTAAATAATA ATTAACAATA ATTTAAATTT GGGTAAAAAT | 120 |
| TAATAAATAT TAACGTATAT AATAATTATA TACTTTATAA AATTACTCAA TGTTATTAAT | 180 |
| AAATTTATTT CTTATCATTA ATAATGATGT ACCTACTCCA TATAATATAT ATTTTCAAGA | 240 |

-continued

```
TTCACTACTA CCTCATCAAG AAGGTATTTT AGAATTACAT GATAATATTA TATTCTATAT      300

GTTACTTGTT TTAGGTTTAG TTTCTTGAAT AATAATTATT ATTATTAAAG ATTATAAAAA      360

TAATCCTATT CTTTATAAAT ATATTAAACA TGGTCAAATA ATTGAAATTA TTTGAACTAT      420

TTTACCAGCT ATTATTTTAT TAATAATTGC ATTTCCATCA TTTATTTTAT TATATTTATG      480

TGATGAAGTT ATTTCACCAG CTATAACTAT TAAAGTTATT GGTTTACAAT GATATTGAAA      540

ATATGAATAC TCAGATTTTA TTAATGATAA TGGTGAAACT ATTGAATATG AATCTTATAT      600

AATTCCTGAA GAATTATTAG AAGAAGGGTC AATTAAGAAT GTTAGATACT GATACTAGTA      660

TTGTTATTCC TGTTGATACT CATGTAAGAT TTATTGTTAC AGCTCCTAGA TGTTATTCAT      720

GAATTTT                                                                727

(2) INFORMATION FOR SEQ ID NO:1012:

(i) SEQUENCE CHARACTERISTICS:
        (A) LENGTH: 665 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1621RP (xi) SEQUENCE DESCRIPTION: SEQ ID NO:1012:

GATCCACCCA CCGGTACCTC CTACTTGGCC GTATCTGCGT CTCCGTGGCG CTTGCCGCTG       60

AGATGCTGTG GGCCCGAAAT GTACTCTCAA ATGGGCTTGT TCAGTGGCCC ATACAGCTCA      120

TTAAGCTCAG TGGCCCCGAT GCTTAGTAGT AGCTGCGCCG CTCTTCATAC TGCTGTCTTG      180

TATTATTCAT CTTCCTGTAT TTTCTCTCTG TGTCCGCTCA CGCCTGCAGG GGGGACTGCC      240

TGGCGCGCGC CGCCTGTCCT GCTTTCTCGT CTGCTGTGAA AATCGACAAA CTCCAAAAAA      300

TCGAATTTGG CGCGCCCGAC AGTTGATTAA GCTCGGGCAT CTCTATTCTC TATAAATTGT      360

TAAATTAACC ACACTGTGAA GCCCTGCAAT CCGCACGCCG CCGCACGTCA ACTCTTGGTC      420

ACAACCTAGC CCGGGGAGTG CAGTCTCACA AATACAAGGC CTGGGATATC ATGTACTGAG      480

GCCTCCTGAA CGTTTTCGCT TTTTTCTAAA ATCGCTGTTC ACAGTCTTAG CGCAAAAAAA      540

ATAATTTAAA AAAAAAATGT AAAGTCTTAG TGAAATGAAA AAATAAAATA AAATAGACCG      600

CCAGCTGCAG AACACCTCTT CAAAGCATAT AACTAGCATA CGCATAAACA TATGCTTGTA      660

TACTC                                                                 665

(2) INFORMATION FOR SEQ ID NO:1013:

(i) SEQUENCE CHARACTERISTICS:
        (A) LENGTH: 666 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1621UP (xi) SEQUENCE DESCRIPTION: SEQ ID NO:1013:

GATCTCTTGG TTCTCGCATC GATGAAGAAC GCAGCGAATT GCGATAAGTA TTGTGAATTG       60

CAGATTTTCG TGAATCATCG AATCTTTGAA CGCACATTGC GTCCTCTGGT ATTCCAGGGG      120
```

```
GCATGCCTGT TGAGCGTCA TTTCCTTCTC AAACCCTCGG GTTTGGTAAT GAGTGATACT      180

CGGTCGTAAG ACAAGGTTAA CTTGAAAATG CTGGCCATGG GCGGAACTTG CGCGGACTGC      240

GGTCTGAGCT AGTTTCTACA CTGCGTATTA GGTTTCGACC AGATCGTGGA GTGGAGCTGG      300

CGCTTGAAGA ACGTACGACA AACAAGGCCT TCCAGGCGAA TAGTATTCCC AAAGTTTGAC      360

CTCAAATCAG GTAGGATTAC CCGCTGAACT TAAGCATATC AATAAGCGGA GGAAAAGAAA      420

CCAACCGGGA TTGCCTTAGT AACGGCGAGT GAAGCGGCAA AGCTCAAAT  TTGAAATCTG      480

GCGCCTTCGG CGTCCGAGTT GTAATTTGAA GAAAGTACCT TGGTTGCTAG TCCCTGTCTA      540

TGTTCCTTGG AACAGGACGT CATAGAGGGT GAGAATCCCG TCTGGCGGGG GTGCTAGTGC      600

CATCTAAGGT TCTTTCGACG AGTCGAGTTG TTTGGGAATG CAGCTCTAAG TGGGTGGTAA      660

ATTCCA                                                                 666

(2) INFORMATION FOR SEQ ID NO:1014:

(i) SEQUENCE CHARACTERISTICS:
        (A) LENGTH: 676 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1622RP (xi) SEQUENCE DESCRIPTION: SEQ ID NO:1014:

GATCCGTGTA TTTTTTATTT ACATTATTTA ATTAAAAATA ATGATTTAAA TAAATATTTT       60

TTATAAAAAA TAATTAGTGC ATTGTTACAT GTTCATTAAA GAATGATTAT TATCAAAACC      120

ATCAACTAAT TGTTATATAT TTATTAAATA TTAATTTCAC TTAATTAAGA ATTAGGAACT      180

TTATCTATTA GTCTGGGCTG TTTCCCTTTT GATTATTAAC CTTATCGCTA ATAATCTGAA      240

ATATTTAATT TTAGATTAAT AATATATTCT GAGATTTAAT ATTTTTAATA AAATAAATAA      300

TTATTCCCTA ATAATATTA  ATAACTATAC CATATATATC TAATATTTAA ATAATCATAC      360

TAACATATGT TTCGTAGAAA ACCAGCTATT TGCAAATCAG ATTTGACTTT CTCTACTTAC      420

CATTATTCAT CAGATAATAT TGCTACATTA ACCTGTTCAA TCGTTTTTAT ATTTTATTAT      480

ATTTTAAATA TAATAAATAT ATATTTTAAT CATTTGATAA TAGTAAGATC ATCTGCTTTC      540

GGGTAATTA  ATATTAACTA AATTTAATTT ATTTTAATTA ATTTTAACAT TGTTAAATAT      600

TTATATTATT TTTAATATCA TTTTTTATTT TAATATTATG CTAATATTAA TTACTTGCTG      660

ACCCATTATA CAAAAG                                                      676

(2) INFORMATION FOR SEQ ID NO:1015:

(i) SEQUENCE CHARACTERISTICS:
        (A) LENGTH: 718 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1622UP (xi) SEQUENCE DESCRIPTION: SEQ ID NO:1015:

GATCCAGTTA CTTAGTAGAA TGATAAAATT AATAAATATT ATTTATTAAT ATTTGGTTAA       60

CAATAAAATT CAATAATTTA TTTAAATAAT GATTAAATAA TCTCAATATA AAATTATTAA      120
```

```
TATAATGAGA TATATATTTT TAAAAAGAAT ATATAATTAA ATAATCCCAA CCAAAATTTG      180

TGCCAGCAGC TGCGGTAAGA CAAAGGGGGT TAGCGTTAAT CGTAATGGCT TAAAGGGTTC      240

GTAGAATGAT TATTTAAAAT AATAATTAGA ATTAATAAAA ATAATTTAAG AATTATTCAA      300

GTAAAGATGA AATAATAATT ATATGAATAA GACTTATAAA GTGAAAATTT AAATTATATA      360

TTAATTGACA TTGAGGAACG AAGGCTAAAG TAGCAAATCG GATTCGATAC CCGAGTAGTT      420

TTAGCAGTAA ACAATGAATA CCTATTTATT TTTTATTAAT TAAAGAATAA ATTAAATGAA      480

AATTAAAGTA TTCCGCCTGA TGACTACGTT AGCAATAATA AAAATCAAAA CAATAGACGG      540

TTACAGACTT AAGCAGTGGA ACATGTTATT TAATTCGATA ATCCTCGATA AATCTTACCA      600

TTTTTTGAAT ATTTAATTAT AATAATTTAT AATTAATTAC AGGCGTTACA TAGTTGTCTT      660

CAGTTCGTGC TGCAAAGTTT TAGAATTTAT CATAAACGAA CATAACTCTA AATATTTT      718

(2) INFORMATION FOR SEQ ID NO:1016:

(i) SEQUENCE CHARACTERISTICS:
        (A) LENGTH: 747 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1623RP (xi) SEQUENCE DESCRIPTION: SEQ ID NO:1016:

GATCACAATC GCATGGTATG ATCGTTTTAG AATCAACGAA ATATGACAAA ATGAAGGAAC       60

ATATTGCCAT AAGGACTTCA GGTATTACAG TCGCAGATAT TCTATCGAAG TCCACTGAGT      120

ATGGTTTAGT ACCTATACCA AAAGAACAAT TTGAACAGAT TAAAATGGAA TTAGAGCATC      180

CAAAGTTTAC TAGAGAGATG ATTGTTGACC ACGCTGGTGA CTTCGACTTA ATTGCAGTGG      240

AATTAAAGGA ATACAATCGC CTCAAAAAGC AATCGCAGTT CTCCTTTGGT GACATTTTCG      300

ATAGCATTAA CACTGACGAG GAAAGTGAAG CATCTGATTT TGAATATCAT GATGACGAGA      360

TAAAGCAGCT TAACAAGACA GCCAAACGCT TTGGGTTATT ATGTATTCCA GAAGCTGCGT      420

TTATCGCTAC TTCCGTCGCT AGCACGCCTG ATGTCGATAA TGTCGTCGTG CTACCAATAA      480

GCTACTATAA TAAGTTGATT GCGAATGAAG CAAAGAGCCT CGAAAAGCTG ACTGACTGGG      540

ATCTTCAGTC AGAAGCTAAA AAACGTGGCT ATCATATAAA TTTCAGCTTC CAGAAGGAGG      600

ACGCCCCACC GCCGCCTTCA ACCCTATGTC CTCCACGGAT GCCGAAGTTT TCCCCAAAAC      660

CGTTCGACTT TGTCACTAGA CTCAAAAACT ACTAGAAGGG CGTTTAATGA GGCTGCTACT      720

GTCGCCGCAC AGAGCGAATT TGAACAG                                         747

(2) INFORMATION FOR SEQ ID NO:1017:

(i) SEQUENCE CHARACTERISTICS:
        (A) LENGTH: 758 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1623UP (xi) SEQUENCE DESCRIPTION: SEQ ID NO:1017:
```

```
GATCAGCGCA AAACACATCT GTATTCCCAG CAGCATGTCC TCCTCCACCT GCCGCATGGC    60

CTGGCTTGCA AAGCCGTCCA CCTCGCCGTC AAATGAAATG CTGTCCGGAA TATTCTCCAG   120

TTTCGCAACC ACAGGGTTCC CGTGCTCGTC GTACTCCTGT TCCTCATCCT CCTCACCTGC   180

CTCGTCTCCG CCGCGCACGT CCCACGGCCT AATGCTCAGC TGCGGAGCCT CCTCGGGATA   240

CCGCTCCGGC AGCGTAATGT CCACCACCAA GTGCTGCTCC TTGCTGATCG CAGCCGCCGT   300

GAATGAAGAG CTTGCCAGCG GGATCAGATC CAGTTTTAGG TCCACTTCAA ACTGGATTTT   360

CGGGTACTCC CCGCACACCA CCGTCAAGTC ATCGGCATAG ATGGACTCAA GCACTTCCAG   420

CTCCTGCTTT TGCTCCTCCT GATAGTCCAT ACCTATCCGC TCGACCAACT ATGAGCCCAC   480

GCGCAGCTTA GGGCTAGACC GTTACAGCTG CAGGTGACCG TCCGGGGGAC GATGCGCTAT   540

CGCTGGCGAA ATTTTTCGCC TATACCACCA CTTATGTTAC CCGGTCTATA GTGCTGCTCT   600

CCGACCTCAC TGATGGTGCT GTCCCGCGGG GACTGCTGCC TCGTGCGGGC AAATCCCCAC   660

CGCTCTGAAC GCTCGTTCCA TCTGCGTCAC GGGTTGACCG AACGGGAATT GCGCGCGCCG   720

AGAAATCTTG GCGAACCATG CTGCACTTAG CCTTACTG                           758

(2) INFORMATION FOR SEQ ID NO:1018:

(i) SEQUENCE CHARACTERISTICS:
        (A) LENGTH: 690 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1624RP (xi) SEQUENCE DESCRIPTION: SEQ ID NO:1018:

GATCGCACGT CATTTTACCT ACAGGCTGGG CTTTTGAAGA AGACGCCTGC ATGGTACAAT    60

GTCGTAGCCA GGATCCCACC TGTGACCAAG TTCGCCAGAG AACCGAAGCT GCATGACCCA   120

GTTAGCGGCA AGTACAAGGG CGAGCTGGAT ATAATGACGG ATAGATTAAA CAGAAACACA   180

GAGACGTACA AGACACGCGC TGGGAGTTCC GACCGGCAGA CGGCCGCGGT GCACAAGCCT   240

TCTAAGCTGC GGTTTATCGA GGACAAGCTG CGGTCGCTGT TTTTCCAGCA GCATCCCTGG   300

GAGCTGTCGC GGCCGAAGGT GCTGGTGGAG AACATGGGAA ATGAGCAGTA CGACTGGTCG   360

CGGATGTTGC AGCTAGGCAA GCCGCTTGAC GGTGAGTCTG TGGTGCAGCG GACGCTGTAT   420

CTGCTGAAGT CGGGCGCGCA CCGGGAGATG CTGGCGGCAT ACGACCAGGC GCGGTTTGAG   480

TTCTATCGTC TGAGGATGCA GCAGGAGCTG GAGGAGCAAA TAGCGTACGA GGAGGCCACG   540

ATGGTTGGCG CTGTGTTCAA GACAACCGCT GTGGAGCACG GTCTGCAGCA AGAGCAGAAG   600

GTCCTCGACA AGTGGAAGGA GGACGTGGTT GCGGGGTTGC AGCTGATGTC TGCGAAGAAG   660

AACTCTACAA AGCAGTCGTG GGCCGAAGCC                                    690

(2) INFORMATION FOR SEQ ID NO:1019:

(i) SEQUENCE CHARACTERISTICS:
        (A) LENGTH: 742 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1624UP
```

(xi) SEQUENCE DESCRIPTION: SEQ ID NO:1019:

```
GATCATATAT CTTCCTGTGG TAAGGTCTGT GGGAAGCAGC TCTCCTGCGG GAATCACACT    60
TGTCCCATGA CCTGCCACGA TGGTAACTGC ATGGATCCAT GCCTCGTTAT AACTGAGCAG   120
AAGTGTGCAT GCGAACAGAG GCGTTTCCTT GTTCCTTGCC AGTTCCCCCA TTCCCCAAGT   180
TGCACTGCAA AATGTGAATC ATTGATGTCT TGTCGTCGCC ATCGGTGCGC TGAAAGATGC   240
TGTTCCGGTA GACCGCATTC TGTCAAGCGG AACTCTAGGC GGCGCCGTGA GAGTCCAGAT   300
GATGAATCTG AAGTTGAGGC CCAGCACGTG TGCTTAAAAG ATTGTAATCG GGTGCTGCTT   360
TGTGGTATCC ACATGTGCAA TTACAAATGC CATGCAGGCA AATGTCCTCC CTGCTTAGAA   420
TCAGATTCCA ATGACCTTAT CTGTCCCTGT GGTAAGACAA TCGTACCAGC CCCTGTCCGT   480
TGTGGAACAA AGCTCCCTCG CTGCACTCAT CCATGTCGAA ACTCGCTGCT GGATACTTGG   540
CCCTGCGGAC ACAGTCCACC TTCGCATAAT TGTCATCCCT TAGATGAACC TTGCCCCCCA   600
TGTACCATCA CAGTCAAGAA AACTTGTCGC TGCGGTAAAA ACGAGATCAG GACATTCTGC   660
TACAATGATG ATGTGTCGTG TTCGAGACCG TGTTAGAAGC CATTGTCCTA TTGCAATCAC   720
TTCTGCCAAG TTCCCTGTCA TT                                           742
```

(2) INFORMATION FOR SEQ ID NO:1020:

(i) SEQUENCE CHARACTERISTICS:
        (A) LENGTH: 725 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1625RP (xi) SEQUENCE DESCRIPTION: SEQ ID NO:1020:

```
GATCAACTAC GAGGACTTGA CGACCGCACG ACGGGAGCTC GCGGCCGCGC TGGCCACTTT    60
GGAGAATATG TAGCGCACAA CATCAGCAAT GTTACAGTAC AGACGTCTAT CCGTGGGGTA   120
CGGCTATGAT GAATAGAAAT ATATACACAG CTGCCTGCAG GCAGCTTAGA AGCGCAGAGG   180
CTTGGGCTTC TCCCACGAGT ACTCCTGGTT AGTGAAGTGC CCGTACGAGG CGGTAGGTAG   240
GTAGATGGGC TTGGCGAGGT CGAGCTCTTT GACAAGAACA CCTGGTCTGA GGTCGAAGTT   300
GTTGCGGATG ATCTCGATCA GCTCGTCGTC GGACTTGGTG CTGGTACCGT AAGTCTCGAC   360
GTGGATGGAC AGCGGCTCGG CAATACCAAT GGCGTAGGCA AACTCAACCT GCACACGCTT   420
GCACAGGCCG GCGGCCAACA GCGACTTGGC GACCCAGCGC GCAGCGTACG CAGCCGAACG   480
GTCGACCTTC GAATAGTCCT TTCCGGAGAA CGCACCGCCA CCGACCGCGG CGGCACCGCC   540
GTACGCGTCA ACAATGATCT TTCTACCGGT CAGACCTGCG TCACCTTGTG GCCACCGATC   600
ACGAAGCGGC CGAAGGCTGC AAGTAATACT TGGTGTTTTC GTCTAGCATG TCGGCAGGGA   660
TGACCTTGCC TACGATGCGA TCGCGCAACG CGGAACGCAG GTCCTCGGTC GAGATGTCGT   720
CCGCG                                                              725
```

(2) INFORMATION FOR SEQ ID NO:1021:

(i) SEQUENCE CHARACTERISTICS:
        (A) LENGTH: 726 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
    (A) ORGANISM: PAG1025UP (xi) SEQUENCE DESCRIPTION: SEQ ID NO:1021:

| | | | | | |
|---|---|---|---|---|---|
| GATCTGGCTC | TGCGCCATCC | CAAACAACCT | GGGTGTTGAC | AAGAAGTACT | ATGATGAGCA | 60 |
| CAAGAAGGAA | TGGGCCATGT | ACCAGGAGAT | GATGAAGCAC | TATGCCAACG | AGGACCTTGT | 120 |
| CGACACCAAC | ATGCAGGGCG | GGTTTATCGT | CGCGCCGCCA | CTCCACGAAA | TAGAGCTGGA | 180 |
| CAACTTCCAG | CTCGGCGTCT | ACAAGGAGCT | CGTAACTAGC | ATGTTCCCCT | GACTTCATGG | 240 |
| AGTCCAGCAT | CGCCCATGTT | TTATGCCCAA | TACTTTTGAG | ACTATACTTA | TATTATATAC | 300 |
| TGATAAACAA | TTTCCCGCGC | TCTCTCACGC | CCACTACTTG | TTCTCCGCGT | AGAAGAAGTT | 360 |
| CACGGCCATC | AACTCGAGGT | TCTTCTCGCC | CGCAAACTCG | CCCACACCCA | CAGGGGGCCG | 420 |
| CTTCTCGGTG | TAGCCCCAGT | TCACGCGACT | CTGCAGGCGG | GTGACCTCCT | CCTCGCTCAG | 480 |
| TTCTAGCCGC | CCGGGCTGCC | GAAACAACAA | CCACACGTAC | CGGTGAGCCC | CTGTGCCGGC | 540 |
| CGGCGGCGCA | GGGCCCATGT | GCTCCACCTG | CGGGGTGCCC | TTTAGCACCA | CGTGCGACAC | 600 |
| CCCGTCATCC | GAGCCCAGCG | TTATGTTCGT | TTCCAGAAAG | TGGCAGTATT | CCGACCACTT | 660 |
| GTGGTCCGAC | CGCGAGGGAG | CATCTGGGTC | TGTCATCCCC | AGCGTGAATA | GGTCCCCTCC | 720 |
| CTGACG | | | | | | 726 |

(2) INFORMATION FOR SEQ ID NO:1022:

(i) SEQUENCE CHARACTERISTICS:
        (A) LENGTH: 643 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1626RP (xi) SEQUENCE DESCRIPTION: SEQ ID NO:1022:

| | | | | | |
|---|---|---|---|---|---|
| GATCCGTGGG | GACCATGCGC | AGATGGCGCC | CTTAATATAA | GCCCCTCCTC | GCAGGCATGA | 60 |
| CGTCTGCCAA | CTCCGACCAT | TCTAAATGGC | CAGCTGCTGC | TTTGATGGTA | GCGTCCGCGG | 120 |
| CTGGCGCAGA | AGTAAATATA | GCCATTAATT | CCCCTTCTAA | ATATACATTA | CATACCAGCG | 180 |
| CTCCAGAGGC | GCTCCCGAGG | CGCTCCCGAG | GCGCCCCACG | TCTCGCCGCA | GCGACGCCGC | 240 |
| TGCGAGCTGG | CCCTCTGGCC | ACGCAGACAT | GCGCGCCGAC | GCGCCCACGT | TATATACAGC | 300 |
| CTGGCCTGTC | TCATATGCAG | ATGGGTCTGA | GCGAAAGAAG | TTCCTCGCTC | TCGGAGAAGC | 360 |
| AGTCGTCGTG | ACCCTCGCGC | TCCGCGCCCA | ACCGCGCAGC | AGAGAATCTT | CCAGCGCTTC | 420 |
| CCGCCGACCC | GCACTCGGCG | TACCCGTGCA | GGTAAGGATA | CTTCGCGGCC | GCCGCGGCAC | 480 |
| CACCGCCCTC | AGCCTGACTT | GCGCAACGGC | CATACGCAGA | GGACCCGCCT | GCCTCCGCGC | 540 |
| TTTCGTGCCT | GTGCACGTGA | TCTCACCGCC | TGCCTCAGCC | GCCCTCGTCA | ACGATGCGCA | 600 |
| CCAGACCCTC | CAGAGCGTGC | CTTCGTGCCC | AAGTCGGAGC | CCA | | 643 |

(2) INFORMATION FOR SEQ ID NO:1023:

(i) SEQUENCE CHARACTERISTICS:
        (A) LENGTH: 704 base pairs
        (B) TYPE: nucleic acid
        (C) STRANDEDNESS: single (D) TOPOLOGY: linear (ii) MOLECULE TYPE: DNA (genomic)

(vi) ORIGINAL SOURCE:
         (A) ORGANISM: PAG1626UP (xi) SEQUENCE DESCRIPTION: SEQ ID NO:1023:

```
GATCCATGCA TATTTGCGAA CTTACGAAAA AAGGCGTGAA GAGGCGGAAC GTAATCTAGG      60

TTTGGAAGAA TTAATGAATG ACAACATAGA CCTTGTTACA GGAGAAAATA ATGAAGAACG     120

CCAGCTGAAA CAAAAGAAGT TGTTAGAGGA GCAGTTGGCA AAGTTGGAGA AATCAAAGGA     180

AAGACGACAA GCACGCAAGG CCGCGAAGGA GAAGAGCAAA GATGGCAAAG TCGTGAAAGT     240

AAAAAACACC ACGCGACGCT GCGCAACATG CGGTGCGATC GGGCATATCA GAACTAATAA     300

ATCCTGCCCC ATGTACAATG GTGGCGTTGC AGCAAACGCA AACGCAAACG CGAATGCGTC     360

GAGTGCAGCA GCTGCAGGTT CTTCAGGGAT GGCCTCAAAT AATAGCGCTA CCAGCAAGTC     420

TATAACTCCT AATGCCAGTA TTCCGCCGAC TTCATTCGAC TAGCTCGCAG TATAATATAT     480

ATCTAATATG TACCAATTGT ACTTCTTTCG ACTGCTATAG AACTTTCTCC TCTTCTTGCA     540

TCACATGTGC AGCACTGCAG CACCGTGCGC CTCGCAATAC TTATGGACCG CGGCACGGTC     600

GGCCTCGTAT CCAGCGTACG CTATGTATCC TGCGGGACCG TTATTCGTGC GCGACACGGG     660

ATAGTGCACA GACTCCACAG AAGTGTTCTC TACAATGCAG AAGA                     704
```

(2) INFORMATION FOR SEQ ID NO:1024:

(i) SEQUENCE CHARACTERISTICS:
        (A) LENGTH: 713 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
         (A) ORGANISM: PAG1627RP (xi) SEQUENCE DESCRIPTION: SEQ ID NO:1024:

```
GATCTTCCTT GAATTTACTT AGCAGCTCGT TAATTTCCTG CTTCTTCTGC TCTCTAAGCT      60

GGAATCTGTA AAAGTCCTGC TTGGCCTTCT TGTCCACCAT GCTGGGAGGC TTCTCCTTCC     120

GTGTATGCTT AAGAAGTGGA TTGCGGTTCA GAATCCTACG CCTTATGGAG TTTAACGATT     180

TTGTGTTCTT CCCTACTACA AGTGTGAACC CGTCCTCGTC CACAATACTC GATTGAACCT     240

CATCCTGCGC AAGTTGTTCC CGTTGCTCAA ATAACAACAT ATGCTCGTGA ATGTCGCTGC     300

GCAAGTACTC AAGGTCGAGT GGCTTATAGA AGCTCTGGAA GGTCGCTATC GAAGGAGACT     360

GGAACGCCCA CTCCACCAAT TCCTTTTGTT TGTGCGCGTA TTTGCGCAGA GCAGCCCAGC     420

AGTTCTCCAG AGATGCCTGG TCCACAAACT TCAACAGAGC ACTGTTTCTC GGTGTATACC     480

TTCTGTCCTC CGCATCCCCG GTGTCTCTGA AATCGGACGT CAGCGCACCC AAATCCACCT     540

CGTGCAATCC GAACTCGTCG TGATGTAGCA GCTCTGCCAC ATGCGCCACA GTCTCGTACT     600

GCGCGCAAAT CCTGCCAAAG CTCTCCTTGA TAGAGTCGAC CTGTGTCAAC AGAGGTAAAT     660

TGACAATAAA CAGGCAATTA GCCTCCGATT CCACCTTCGT CTGATGCTTC CTC           713
```

(2) INFORMATION FOR SEQ ID NO:1025:

(i) SEQUENCE CHARACTERISTICS:
        (A) LENGTH: 736 base pairs
        (B) TYPE: nucleic acid

```
        (C) STRANDEDNESS: single
        (D) TOPOLOGY: linear (ii) MOLECULE TYPE: DNA (genomic)

(vi) ORIGINAL SOURCE:
        (A) ORGANISM: PAG1627UP (xi) SEQUENCE DESCRIPTION: SEQ ID NO:1025:

GATCTTTGAG ACGCGGCCTG GAGAGTTTAG AGCAGATTGT TGACCAACGC ATAGCAGATG    60

CTAGACCTGA GTCATACACC CTCCGTCTTG TTGGAGACAC GGAATTGCTA AATTCAAAAA   120

TAAAGGAGGA GGCAGATGAA GTGATTGAGG CTATAACGCC AGCTGAACTA CAATGGGAAG   180

TTGCGGACTT GCTGTATTTC CTCATGGTTA AAATGAGGAG CAATAATGTG ACTTTAAAGG   240

AGGTGGAAGC CAACCTAAAC ATGAAGCACA TGAAGATTAC GAGACGGCCT GGAAACGCGA   300

AACCAAAGTA CCTACCCGCG CAGGAGTGGC AGAAGAACAA GGAAACTCCT GTAGATATTG   360

CACCATCTGC CATTTACTTG AACGTCGTAT CCTCAGATGA TGAGGCCGCA TTGAAAACAG   420

CAATTACAAG GCCAATTCAG AAAACTACTG ATATATTAGG TCTTGTTGAG CCTATAATAA   480

AAAAAGTGAT AGAGGAGGGC GACAATGCGT TGACTGAACT AACAGCGAGG TTTGATGGAG   540

TAAAGATAGA AACACCAGTA CTAGAGGCTC CTTTTGGCGA CGAGTATTTA AAAGGATTAA   600

CGGAAGACGT CCGTACGGCC ATAGATATTT CGATGGAGAA TGTCCGTAAA TTTCATGCCG   660

CACAGCTGAG AGACGATATT CTCAAGGTCG AAACGCAACC GGGGGTGGTA TGTACGAGAT   720

CCCGAGGCCA TAGAGA                                                  736

(2) INFORMATION FOR SEQ ID NO:1026:

(i) SEQUENCE CHARACTERISTICS:
        (A) LENGTH: 707 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1628RP (xi) SEQUENCE DESCRIPTION: SEQ ID NO:1026:

GATCTGCCCC TTTAAGCAAC CACATATTAA GCCGCTGACA CACAGACTGT CAGCGCTTAG    60

AAATACTTCG GTGAGTGTTC AGAAGCCCGA GCGCTCGGAG TTATTCATGA TCACGTGATG   120

GGTATTGACC TTGCGATCCA CAGACAGGCG GAAATATGCA TATATGTAAG CCAAGATGCC   180

GGCAACCAAT TGGTCTAACT GTAATGCATA ACACTGTATT CCGCGAAGCG GCTCTGAGCA   240

TGTATGGTAT TCGGCGCTAG ATTGTCAGCC CACGTATATT TCCACGTGAC GCCCTGATGC   300

TATTTACAAC ATAATCACTA TTGACGAGCA AGGATAGTGG TCGCACGTTA CGAAAAAGAA   360

ACGTTGAAAA ATTTGGATGG TGGTGATGAG GTAGAGATAT TAACGTTAAT GGGCGAGCAC   420

GAATTTGGTC GAAGTTCTAT ACTGCCAACG ACGTTCGCAG ATTGCTGAGT TGATGGGTTC   480

CAAAAGTATT AAAAAGGCGG TAGTCCCTAA ATTATCGGAA AAAGCCAAGG AGGAAGAGTT   540

GAGCACTTCG GGCTCCTCTG ATTCTACTTT AGAATCAAGT TCATCTTCCT CGTCGGAGGG   600

CAGCTCCAGC AGCAGCTCTA GTTCCTCCGG ACAGTGAATC GAGCTCGTCG GACAGCGGCT   660

CCAGCTCTTC TAGCAGCAGC TCGAGCTCCT CCGGCGAATC GGGCTCC              707

(2) INFORMATION FOR SEQ ID NO:1027:
```

(i) SEQUENCE CHARACTERISTICS:
    (A) LENGTH: 733 base pairs
    (B) TYPE: nucleic acid
    (C) STRANDEDNESS: single
    (D) TOPOLOGY: linear (ii) MOLECULE TYPE: DNA (genomic)

(vi) ORIGINAL SOURCE:
    (A) ORGANISM: PAG1629RP (xi) SEQUENCE DESCRIPTION: SEQ ID NO:1027:

```
GATCTCCCAC ACTAGGCTGG GTCTTACTGT CCATGAATAG CATTCGAAGA ATGGAGGAAT      60
CGGTCTTCAA GTCAGCGGGG AAATTTTCAG GGCAATATAA TGGTTCCCAA GTATTTAGAA     120
CTTCTCGACT GTCGTCAGTA CTTGGCCCCT TTAAATCGGC TGTTCCCCTT GAAGATATAC     180
ACCATTCATT CCAGTGTATC GTACCCGAAA AATTAGCAGT AATGGCACTT GGAACATCAT     240
CCGGAATCGT GTAAGCACTT GCAATAACTG AAAGCTTTGT AAGAGAGGTA AAAATCGGTG     300
CGCGCGTTCC AAAATTGTCC AATTGTGAGA TTTGTTGATC TTCATTAGGC CTACTGGCCA     360
GTTCCACTAG TGATCTAACG GGGCTTATTT CAGTGGTTAG AAATTTATCC TTCTCAGTTT     420
TCGACTTACA AGCAAACTCA GTGAACAAAG GGGGTATCG ACGAGCAGCT CTTGTGTAAG      480
CTGCTGAGGT TTTCCCTTGT GAAATAACAT GTTCTTTAGT TTCATGTAGG GCTCCAATCC     540
ATGCCGTTAA CTCTTTATAA CTGGTTGCTT GGAAAATTAA AGTACCAGAG TTATTAGAAT     600
ATTCTTCCTG AGGTGAAGAA GTTAATGGAG AAGAGATAGT CATTCGAAAG CAGTATTTAC     660
GTGCCTCTTC TGGATGGTGC ATGGCACTGA GTAATAATAC TCCAAATCTG TCCGTTTCTT     720
CGACTGCAGT TTT                                                         733
```

(2) INFORMATION FOR SEQ ID NO:1028:

(i) SEQUENCE CHARACTERISTICS:
    (A) LENGTH: 742 base pairs
    (B) TYPE: nucleic acid
    (C) STRANDEDNESS: single
    (D) TOPOLOGY: linear (ii) MOLECULE TYPE: DNA (genomic)

(vi) ORIGINAL SOURCE:
    (A) ORGANISM: PAG1629UP (xi) SEQUENCE DESCRIPTION: SEQ ID NO:1028:

```
GATCTCGGCT CGCTGCTCGC GCTCGAGCCC TACTGGGCAG AGCGCTACCC AATAAACAAC      60
GCCCTAATCG GCGGTGCAGA TAAATTGCAC AAGCTCTACT CAACCGATTT TGCGCCCATC     120
GTCGCCGCCA GGACTTTCGG CTTGAACCTC GTCGACAAGC TTGGACCGCT GAAAGACCTC     180
ATAATGGCAA AGGTCAGCGG CCCAAATTAA TAGTCACGTG TACATAAAGG TTTTCCTAAT     240
AGCTATACAG CTTGCCCGCG TCCTCAGCTT GCAGCGCGCA ACCGGCGTGC AGCCATGAGC     300
GTCCTACTGG AAACTACCAT TGGCGACCTT GTAGTAGACC TGGACTACAA GACATGCAGC     360
GCCGAGAGCT ACAACTTCCT CAAACTCTGC AAAACTCGCT TCTACGACTG TCAGTGCATC     420
TACGACCTCC ATCCTGAAGG CTCAGCACGC CTCGGCGATC CACAGGTGGG CTTTGCATTC     480
CGCACGGATT TGCCTGTACA CAATACCTCG ATCAAGGCC TGCGCGACAC ACGGGCGGTC      540
ACCCCGAAGC TCATTGAAGC CTCCGTTGCC GCTCAACCCG CAGAGCGCTT CGGACAGGTC     600
GCCTTTGTGC TCAAGCCCGG CACTCGCCTG CTGGGATCCA ACATACTGCT CGCGCTTAAT     660
CCCGAACTCG GCCCCACATC AACACAGTGC GCTTCGCGCA GGTCATCGAC GAGTCGCTGG     720
```

```
CAGTTCTGCA GCAGCTCAGC GA                                              742
```

(2) INFORMATION FOR SEQ ID NO:1029:

(i) SEQUENCE CHARACTERISTICS:
        (A) LENGTH: 692 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1630RP (xi) SEQUENCE DESCRIPTION: SEQ ID NO:1029:

```
GATCGACTTT CAAACATTAT TATACAGATG GAGGGCATCT CACATCTTGC ACAGCAAGAC        60
GGCAATCCAA CAGGTTCTGT AATGCAGCCT AAGAGGCGAA GGGTTGAAGA TGGAGCGTCT       120
AGTGATGGAG AAGTACGAGG AGAGATAAAG CGCAAGTATG GTATTGGCGC GCAGTTGATG       180
GCCAAGATGG GATATAAGGA GGGCAGCGGT CTAGGGAAAA AAGGTACGGG ACGCACGACG       240
CCGATATTGG TATAGCAGCG GCCGCAGGGC ATGGGGCTTG GAGCCAACGT CTCCATTTCC       300
TCTGACTCAG AGCAGAGTGA GGTGGAGCTT GTGACTCGCG AGGCAGTGAA GTTTGAATCG       360
AAAGGTGTGG AGACTGACAC AAGCAGAATA GCAGACAAGA TAGCAAAGCT GGAGATCGCA       420
GGAGTGCAAG TCCCCGCAGA AGTGATGAGT TTGCGTTCTG GACAAAGAC GCTGGGTTAC        480
CAACGGGCTG CAGCGATGGA AAGGGTGCTC TCGGAACTGC TGCAGGTGGG TGAGCAACTT       540
GCGACCCTAC AACTACGCGA AGATCAGCTG CAGCAAGGGC TAGATGCGGC CATTCAGAGT       600
AGTGACCTGT TGAACAAGTT CTCAACGCGC TGCAACAGCC GACTGCGCTG CCGGAGCGGG       660
TAGCGGCATA TTGGCCTTGG AGGACCCAGA AA                                    692
```

(2) INFORMATION FOR SEQ ID NO:1030:

(i) SEQUENCE CHARACTERISTICS:
        (A) LENGTH: 712 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1630UP (xi) SEQUENCE DESCRIPTION: SEQ ID NO:1030:

```
GATCGTCGCC TCATCGGTGA GCTGCGCCCC ACGGGCGAAC CTGGCAGCCT GCCCGGCGAC        60
CCGCGCGCGG TGGGCGACCC GCGTCCAGTC GGCGAGCCCC GTGGTCCCCG GACCATGGTT       120
ACCGTATCGT CCCCGACAAA TGGCGAGGGG TAGATGATGC CCTCCTCCGC CTCCGGCGTA       180
CCGCCGCGCT CCGGCGTGTG CGCCTCCTCT GTCCGGCCTG GCCGCGTCCC GTCCCCAGAC       240
AAACGGTGCC CGGCCGGCAC CCCAACGCCG AGGCCTTCCG CGGGCGGTGG CGGCGGCCGC       300
CGGCTCCGCG CTCCGCCAAG GCCCTTGCCC TGACCCAGTC CTGTAGGTCG CTCGTGGTCA       360
TCGAAGGGCG TCCAAGCAAT TCGTGTACGA TGATCTATGC CAGCCGCAGC CTTCGTCACC       420
AGCGGCGGCA GCTGCGGCAG CTTGGGTTTG GTCTCGTCCA TATCGTGGTC TCGGTCTCTG       480
TAGGCATCAT ACATCTCCCG CTATCTTTCT CTTGCGCCTG CACCGGTACC GTGCATTGGA       540
AACGCTGCTC CTGCCCGAGG GCAGTTCTAT AACGTTGCCA GTGAAAATCG TGCAGTACGG       600
AACAGTAGCT CATCGCGCAC CAGGCGAACA CATAGGCAAC AGCTTCGGTG TAGCGGGCTG       660
```

```
CGGGCCCGAC CACGATACTC ATGTTACATA GACTCACATG ATCAGGCAGC AC            712
```

(2) INFORMATION FOR SEQ ID NO:1031:

(i) SEQUENCE CHARACTERISTICS:
        (A) LENGTH: 729 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1631RP (xi) SEQUENCE DESCRIPTION: SEQ ID NO:1031:

```
GATCTAATTT ATTTACATTA ATTAATAATT AATAATATTT AATAATATTC AATAATTTAT    60
ATATTTTATT ATATTTAATA ATTATATAAA TACTTTAATT ACATAAATAC TTTAATTAGA   120
GAGTTAGGGT TCACCCCCCT AATGCTTATC AGCATTATGA GGTACCACTC TAATTAAAGG   180
TAAATATATA TATTTAATAA TAAAAGGATA TAGTTTAATT GGTAAAACTA TTGACTTCAA   240
ATCAATCATT AAGAGTTCAA ATCTTTTTAT CCTTGTTATA TTTTAATAAT ATAAATTAAT   300
AAATAATAAA TATGATAAAT CATAATATTA AAGATATTGA TTAATATTTT TAATTAATTA   360
AATAATATGC AATTAGTATT AGCAGCTAAA TATATTGGTG CAGGTATTTC AACAATTGGT   420
TTATTAGGAG CAGGTATTGG TATTGCTATT GTATTTGCAG CTTTAATTCA AGGTGTATCA   480
AGAAATCCAT CAATGAAAGA TACTTTATTC CAATTTGCTA TTTTAGGTTC GCTATTAGTG   540
AAGCTACAGG TTTATTCTGT TTAATGATTT CTTTCTTATT ATTATATGGT GTTTAATTTT   600
ATTAAATTAT ATAATAATTA ATATTCAAAA TAAGTTATAT TAGCTTAATT GGTAGAGCAT   660
CCGTTTTGTA ATCGAAAAGG TTAGGAGTTC AAATCTCTTA TGTAACAATT TAATTAAATT   720
AAATAAAGA                                                           729
```

(2) INFORMATION FOR SEQ ID NO:1032:

(i) SEQUENCE CHARACTERISTICS:
        (A) LENGTH: 716 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1631UP (xi) SEQUENCE DESCRIPTION: SEQ ID NO:1032:

```
GATCTTAAAA TAAGATAGAA TGGTAATAAA TATCATTCAG GTACAATAGA TGCTGGTGTT    60
ACTAAAGGAT TACCTGGAAT ATAATTATCA GGATGTCCTA AAGTATTAGG TGAAAAGAAT   120
ACAAATAATG AAAAGAAAAT TATAAATACA AATACTGTTA CTAAATCTTT AAAAATAAAA   180
TAACCATGCA TTGGTAATCT ATCTAAATTA CCTGTAATAC CTAATGGATT TGATGAACCA   240
TGTACATGTA ATAGCATTAA ATGCATAATT ACTATTGCTG CAATAATAAA TGGTACTAAA   300
TAATGAAATA GAAAGAATCT TATAAATAGTA GGATTACTAA CACTAAATGA TCCTCATAAT   360
CATAGTACAA TATCATTTCC AATAAATGGA ATAGCACTAA ATAAATTAGT AATAACAGTA   420
GCACCTCAAT GTGACATTTG TCCATATACT AAACAATAAC CTAAGAAAGC TGCTGCTATA   480
GTTAAAATAA AGATAATAAC ACCAACTGTT CATACAATAA CTCTAGGTGA TTTATAAGAA   540
```

| CCATAATATA AACCTTTACC AATATGAATA TACATACAAA TAAAGAAGAA TGAAGCACCA | 600 |
| TTAAGATGCA TATATCTAAT TAATCAACCT AGTTGTACAT CTCTCATAAT ATGTTCTACT | 660 |
| GATGAGAAAG CTAATTCAAT ATTAGATGAA TAATGCATAG CTAAAAAAAT ACCAGT | 716 |

(2) INFORMATION FOR SEQ ID NO:1033:

(i) SEQUENCE CHARACTERISTICS:
        (A) LENGTH: 658 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1632RP (xi) SEQUENCE DESCRIPTION: SEQ ID NO:1033:

| GATCTTCGCG CCGTTGCGGC CCAAAACCCG CAGCTCCCAT ATACCCGTGT TCAGGTTGAA | 60 |
| GCTGATGCTA GCGTGCTGCC GCGACACCAC TTTCGCAGGC CCCAGGTCGA TGTGTACTGA | 120 |
| CCGGTCCTGC GGAGACGTGT TCCGCCCGAT ACTCGTCATC ATGTCCTTCA CGTAGTACGT | 180 |
| CCAGTCTCGT CCCGATATCT TGGCGTACGC CTGTACTTCC GTTGCCGTGT TCTTGTCGTT | 240 |
| CGAATATACT TGCGACACTG TCGTCGCCTC CTTCGGCGCA TCCAGCACCG AAATCACCGC | 300 |
| ATTGATCACG TCCTGTCTCC GTTAGTACTC GGTCTCGTGC CGCCCGTCTC GCTCCTACAT | 360 |
| ACCTGCTGGT GCTGCTGAGA CGCAAATGGG TAATTCATCT CGTCGCCTCA ATTTCGCTCC | 420 |
| TCCACTGGCT GCCCCAGGGT AACGTCGGAC TTCCGTTGCT GTGGAAGGGG TGGTCGCTCA | 480 |
| GCGTAGCTCG GTACAGCTGA TCTCGGTCTT AGTATCAACA AAGCAAAAAT AAAAATAATA | 540 |
| ACAATAAGCT TTTCACTGTG TGTGAACGTC CCAGAAACTG ATTCCAACGC TCCAACACCG | 600 |
| CACTTCTTGA AGCAACCTCA CGCACCCTTC TGAATGACAG ATCACCCTCA CTAAACGG | 658 |

(2) INFORMATION FOR SEQ ID NO:1034:

(i) SEQUENCE CHARACTERISTICS:
        (A) LENGTH: 690 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1632UP (xi) SEQUENCE DESCRIPTION: SEQ ID NO:1034:

| GATCGAGACT GTGATATAGC TGTATAAGAA GGTTTGGAAA CCTTAGTAAA TACCCAACTT | 60 |
| TTTTAATTCG AACCTTGTAC AGGTTTTATA CTCAATTGTA GCTTTGAGTT GCAAATACCC | 120 |
| GAGGCATAAA ATCAAAGCGT ACTTAAAAAC AATCACTACA TACAGTCCTC CACACCCTGC | 180 |
| CAGAGTGGAA TAACATGAAG AATAAATATT AAGGACAGTA ATGCTATAAA TACATGTGCT | 240 |
| TCAAATAAAT ATATGCTTGC TAAGGGTTTT CAAATTCGGT TTGCGGCAAA GAGTACGCAA | 300 |
| TAAGTGGATC TTGGGAAAGT GATGGGGGCA GATAACGACC AAACAAGTGA GTTTCCACGT | 360 |
| TACCTATATC TTCCTCTGGG ACAAAACTGC CACTGTTGAC CATTGTTGTG CTAGGTGTTT | 420 |
| GATGTATGGA TGGAGTATCA GCACGTCCGG TAGAGGAAGT GGGAATTAGT GAAACTAACG | 480 |
| TCCCGGAGAA ACTGGATGCC ACACGATTGT TTGGTAGTGT GGGGGCGTG TTAGGATTTT | 540 |
| TAATGTTGGT TACTGGGGTG CCTGATGGCA ACGATGGGCC AGAAAAGTAT ACTTGCTCCT | 600 |

| | |
|---|---|
| GTGCTTTCAA AGATGGGTCA ACAGCCCAAT TGTGAAAGAA ACTGGCATTA CTAGTCTCAG | 660 |
| GGATGCTAAT AAGCTCTTGG ACAGAGTTGT | 690 |

(2) INFORMATION FOR SEQ ID NO:1035:

(i) SEQUENCE CHARACTERISTICS:
        (A) LENGTH: 749 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1633RP (xi) SEQUENCE DESCRIPTION: SEQ ID NO:1035:

| | |
|---|---|
| GATCAATTAA TAAATGGTTT AACTAATAAA GTTAATAATA AATCTATTAA TTATATAAAA | 60 |
| CTACCTGATT TTATTGAATC AAATAATATT TTCTTAATGA ATACTACTAA ATCATCATCT | 120 |
| ATTGAGTTTA TATTAAATTC ACCACCTCTT ATTCATTCAT TTAATACTCC TCTAATTCAA | 180 |
| TCTTAAAATA TTCTTAATTA TTAAATTATA TAATAAAAGT TAGTGGATAT AGTTTAATTG | 240 |
| GTAAAACATA TGTTTTAGGG ACATATATCT TCAGTTCAAA ACTGAATATC TACATATTAT | 300 |
| ATCATTAATA TAATAACTCT TTAATTAGAG TGGTACCACA AGAATGCTGA AAGCATTAGG | 360 |
| GGTGTGTACC TTAGCTCTCT AATTAAAGTT ATAAAATTAT CTTAACTAAT AAAAATAATT | 420 |
| AATTAAATAA ATAAATAATT AATTAAATTT AAAATGTTTA AAAAAAGAAA TAAATAATAT | 480 |
| GTTATATTTA AATAGATCAA AATTTCAACA ATTTCCATTT CATTTAGTAC TACCATCACC | 540 |
| ATGACCAATT GTTACATCAT TTAGTTTATT AGGTTTACTA TTAACTTTAG CTTTTACTAT | 600 |
| ACATGGTATT ATTGGTAATA TTTATCCTTT ATTATTATCT TTATTAGTAG TTTTATTACT | 660 |
| AATAACTTTA TGATTAGAG ATATGGTAGC TGAACTTACT TATTTAGGTG ATCATACTTT | 720 |
| AGCTGTAAGA AAAGGTATAA CTTAAGGTT | 749 |

(2) INFORMATION FOR SEQ ID NO:1036:

(i) SEQUENCE CHARACTERISTICS:
        (A) LENGTH: 732 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1633UP (xi) SEQUENCE DESCRIPTION: SEQ ID NO:1036:

| | |
|---|---|
| GATCTTAATT TAAAATTTTA ATTAACTATT TATAATTTAG AAATATATAA TCTAGAGATA | 60 |
| TATAATCTTA AAATCATAGG TAAAAATACA TAAGATAGTA AGAATAAAAT TAGTAAAATA | 120 |
| AATAGAAAAC CATAAGTTAA TTGATTCATA AAGAAAAATG GAATTATTTG TGGCATCTTA | 180 |
| ATTTTTATTA TTTAATTGAT TATTATCTAT TTAACATAAA ACATTTTAAA ATGTTATAAA | 240 |
| ATAAATAAGA AATTACTTAT AGAATATTTA TTAAATAGTA TTTAATTTAA TTTTAATATT | 300 |
| AAATATACCA TTTTTATTAA TAAATAGATT ATTAAGTTTA TTAATATTAA GTGATATATA | 360 |
| ATTTAATTTA TATAAATTAT TTAATTTACT TCATTGATAT ATATAATTAT TAAATGTACC | 420 |
| TTTCATAATA TTTATTTTTA TTAGTCTAGT AATATTTCTA TTTAATAGTC TACCCTTTAA | 480 |

```
TTGGATATTA CTACCTACTA AATATTTACC TAATAATATA TTATTAAGAA TACTTAAATC      540

TAATAATTTA TTATCTAAAG TATATAAATT AATTAAATCT TTTTTATTAT TATTTAAATT      600

ATTATTAATT AGTAAATTAT ATTTATTTAT TTTATTAACA TAATTTTTTG ATAATAATAT      660

ATCATTATTA AATGGTTAAT TTATTAATAA TTATCTTTAA TGATTTTAAT GATAAACCAT      720

TATTATTATA GA                                                         732
```

(2) INFORMATION FOR SEQ ID NO:1037:

(i) SEQUENCE CHARACTERISTICS:
        (A) LENGTH: 702 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1634RP (xi) SEQUENCE DESCRIPTION: SEQ ID NO:1037:

```
GATCCATCTG CGGTTTGTGC GACGTCCTGT GAAACTCTAC CAGGCGAATA GAACTCTGAT       60

AGACGACTGG CAGGTGTCTG TTGAGTGGCA ATAACGGGAT TTGCATCATC TATATGGGCA      120

TTCCTGGTAG TATCTATCCT TAGACTCGAT AGGGACCCAT GCTTTACAAG TTCAGGTTTC      180

GCTTGCGGAG CCACGACATC CTTTTCTCGA TTTAGGAATG ACAAAATTGA GGAGTTCCTC      240

CTATGCTTGT GTTCAAACTC ACCAGCAATG CTGGCTCGTT TATTGGTACT CGCAGATACA      300

TTCCTTGAAT GTCCATAGAT ACTCGAAGAC GGCCTTCCAG TGGGAGCTGG AACGGCCAGA      360

CTGTCTTGTG CACCTAGCCC TTCGTAATCG TTTGGAGAGG AAAGCATGGA AATTCGATTG      420

AACAACTCCA CAAACGAGCC ACCCGATTTT GTCTTCTTAT GTCTCGCTCT TATACTCTCT      480

TCCGGAATGG CCCTTTCAAA AGTACGCTGC ATCGAGATA TGCCAGGATT ACTGTAAGGA      540

TTTCCAAGGT CTGGGCCATC AGGCTGTTCG TCCACAGCAG GCTGCATAAA TACTGTGGGA      600

TAGATTGCTT TCTCGAGGAA GTGTAAGAAG CTGGTGAGTT TAGGGTTTGT GGGCCGTGTT      660

CGTAAATGGT AATGTGCTGA TTCCTGGCTT GATTCTGCAA AA                        702
```

(2) INFORMATION FOR SEQ ID NO:1038:

(i) SEQUENCE CHARACTERISTICS:
        (A) LENGTH: 736 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1634UP (xi) SEQUENCE DESCRIPTION: SEQ ID NO:1038:

```
GATCACAGCG TGGCCAAGCC CAGCATTGTG TCTAAGTTAC ATGTAGAGGT CGAACAGCAC       60

GAGGGAATGC TTTTCGCTAC GGCGGAATTC GAGACCTTCA GACTGACACC GCAGATTTTC      120

TGTGCGGCTC ACCGACCCTT AAATAGCTAC AGCAACACAG CTGCGCCGGT GTACACTGAT      180

AGCAAAGATG AACCGGTCTA TCCATTCGTC GGTGACTGCG ATGGCCTCGG ACGACGCCAG      240

CAGTCTTCGG CATGAGCGGT CGACGTACTC GGCGGAGTCA GAGGAAACGC TCGTCAACTC      300

GTATGGGCCC TACAGCACCA CGGGAATCGT GATGACATCT GTGATGATGA ACAAGGCCCA      360

GCGCAAGGGC GAAGTGTCCG AGCAGTGGAT GCGGCTCTTC CTGGACAGCA CGCCTGTCGA      420
```

```
GGACGTGGCG GTGCTGCAGC GCGGGATGTC GGTGACGGGG CGCTGCCTGG ACACGTTGCA      480

GCGCATCCTG CAAAGCATGC ACGGATACCG CCAGATCGTC CCGGGCCTGG CGATGTTCAA      540

AGAGGCATGG AACCTGCAGT GCTACCACGG CAACGAGGCG GACTTTCCGC TGCTCGACGT      600

GCCGATCAAG GTCAACAGCC TGACCACACT GGCCAGCCTG CTGGTCGAGC ACCGCGTGTC      660

CGGTTACAGC ACGCCGATCG AGCAACTCAC CACGGTGCTT CAGTACCTCA ACAAGCTGCT      720

GCAGGCGTCG CGCGTC                                                     736

(2) INFORMATION FOR SEQ ID NO:1039:

(i) SEQUENCE CHARACTERISTICS:
          (A) LENGTH: 737 base pairs
          (B) TYPE: nucleic acid
          (C) STRANDEDNESS: single
          (D) TOPOLOGY: linear (ii) MOLECULE TYPE: DNA (genomic)

(vi) ORIGINAL SOURCE:
          (A) ORGANISM: 1635RP (xi) SEQUENCE DESCRIPTION: SEQ ID NO:1039:

GATCCTAGGG TGGTTCATGG CACTGAGCGG GACCGTGTTC TTGGACCGGT CGAACCGCAG       60

CAAGAGTCTG AAGTCGCTGA ACGCGTCGCT GGAGCGGCTG AAGCGCAATC GGCAGGCGGC      120

GTGGATTTTC CCAGAGGGCA CGCGGTCGTA CACAACGGAG ATGCAGCTGC TGCCATTCAA      180

GAAGGGGGCG TTCCACCTGG CGCAACAGGC GCAGATTCCG GTGATTCCGG TTGTGATGTG      240

CAACACGAGC ACGGTGTTCA ACCCGCGGCT GGGCATCTTT AACCGCGGCA CGATCACGGC      300

GAAAGTGCTG GAGCCGATCG ACACGGCTAA CATGACCAAG GATGACGTGG ACAAGCTTGT      360

GAGCGACGTG CAGGCCAAAA TGCAGGCGGA GTTCGAGGCG CTTGGCTACG CGCCTGCGAT      420

CGTGGACACG AGCCTACCCG AGGAGGCGCT GCGGCCGGAG TTTGTGGACT GCAAGGAAGA      480

CATCACGGAG GTAACGCGCC TCTTGAAGTA ACCTTGGTTG GTATCATATA AACGTTGCGA      540

CGAGTTATGT ACATATAGCG CTGCTAAGTA GGCATTCAGT CCCACGAACT CATACCTGCG      600

TGAGCTCTAC GCCCGGCCGA TGTGGGCCAG ATACTTGTCG ACCTCGCCAG CGGACCCGAG      660

CCAGATCGAG GACTTGTCGT GGATGTGCTC GGGAGTAAGG TCCAGAAATG CGCTCGCCGC      720

GGTCGTTCAC GGCCTTG                                                    737

(2) INFORMATION FOR SEQ ID NO:1040:

(i) SEQUENCE CHARACTERISTICS:
          (A) LENGTH: 686 base pairs
          (B) TYPE: nucleic acid
          (C) STRANDEDNESS: single
          (D) TOPOLOGY: linear (ii) MOLECULE TYPE: DNA (genomic)

(vi) ORIGINAL SOURCE:
          (A) ORGANISM: PAG1635UP (xi) SEQUENCE DESCRIPTION: SEQ ID NO:1040:

GATCGGACTG ACGGTGAATA GGCCACCGTA GCATGCGCCG CTGAGCGCGC TGGCGAGCGA       60

TAGCAGCGGT CCGTCCGAGG CTCTGGTGGC CAGGACAACG ATCCACTGGC CCACCACGCC      120

CAGTAGGAGG ACTGCCCACT GGACTGACAT CGTCGACACA CCGTTGTGGA TGCAGAGGTC      180

AATTATCAAG CCCGACAGGA AGCGCGAGCA CGTCGAGGCA ATCGCAAATT CTGGCAGCAC      240
```

```
CGACGCCTGG CCCAACAGGC TCGACAGCGA GCCCATGTTG GTGAGGAACA TCTCCATCGG    300

GCCCAGCGAC AATAGCAACA CAAGGGCCAT GAAGTACGCC GCTGGGTCGT GGAAGAAGTT    360

GCGCAGCCGG CGGCGGATGT CCTGCGGCAG CAGCGGCTCG GTGGGGCTCT GCATGCCGGC    420

GAAGGTCAGT GTTGCGGCCT TGACCTTGAG CATAGTGACG ATGCTCGTCG CAAACCACAT    480

GCAGAAGCTG ATCAGCGTAT ATGCGACAGC AAGAGTCCTG AATACACGAG AAAGGTCAAG    540

GTACGGCAGG CCATTTCGAA ACCATGGTAT CTTCAGCAGC TGCGACCCTA GCACAGACGC    600

CATCCCGTAA AACGTGGCCG GCAGACTTAT CGAGCACAAC TTGCTCGCCG GGTACAGTTT    660

TGATGCGGTG AACAGCGCAC TGAAGT                                         686

(2) INFORMATION FOR SEQ ID NO:1041:

(i) SEQUENCE CHARACTERISTICS:
        (A) LENGTH: 720 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1636RP (xi) SEQUENCE DESCRIPTION: SEQ ID NO:1041:

GATCTTCTTC TGCTCGATGG ACGAGCCAGT TGTATCTTGG ACTCTACGGA TAACCCACAC     60

CTTTTCCTTC AGCGACAGGA ACTTGGCATC GGTTGGGTTA TTCGGGTATA GATATAGCGC    120

TACGANCGCT ACCACAAACG TTAGGCTGCC GATTATAATT GACAGAATTT TCCAATGTGA    180

GATAGCTGGG TTCTTTATCA GCAGGATCAA GTAGGAAAGG ACGCCCATTG GTATGGATAC    240

ACTGACCGTC GCGATAACAA AAATCGGGGC GGTCGCTGCC TTTTCATTCT CTGTTAAGAA    300

CATCAGCATT GTGTTGTTCA ATGCAGGAAT GATAATAGCC TCCGTGAAAC CTAAGCAGAG    360

ACGAAGAACA TATACACCTT TGTAATCCGT CATTGCACAT TGTACCATCA TAATGATGCA    420

CCATATCGTC AGGAGGACGA TAACAACGTT CTTCAAAGGA AACTTCTGGA TAAACAGCAA    480

GTTGATCTGT CCGGTAATAT AGCCAACGTA GAATAAGGTA TTCACATTGT TGTAACGATT    540

CAAGGACATG TTTACATCTT CAAAAAATCC TAACAGAGTG CTGTAGGACA ATTGCGCCTT    600

GTCTATGTAG GTGATGAAAT TAATGCTCGC CGTCAGTCCC ACGATGTACC ACATAACCTT    660

TCGTGCAAGC TTCTTTTCCT CGGCTTCTGT GATAGGAGGG ACATCCTTGT CTTGCTTCAA    720

(2) INFORMATION FOR SEQ ID NO:1042:

(i) SEQUENCE CHARACTERISTICS:
        (A) LENGTH: 677 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1636UP (xi) SEQUENCE DESCRIPTION: SEQ ID NO:1042:

GATCCGCAAG ATGACCGAGG GTAAGGGCCA CCTGCTTTCG CACCACCGCT TAGTTTCCTT     60

TGGAGGTGCA GGTGGTCAAC ATGCAGTTGC AGTGGCACAC TCATTGGGCA TAGAAACCGT    120

CCTCATGCAC AGGTACTCAG CAATTTTATC TGCGTATGGA ATGCTTTTGG CGGATGCGGT    180

AAAAGAGGAG CAAGTGCCAT GCTCCATTTT CTTGCAAGAT ACATCTTCTA AAGACCAGCT    240
```

```
AAATGAAATA TTCCACCAAT TGATTACCAG TACCTCAATT AGCCTTCTTA AGCAGGGATT      300

GGCCGACGAT CGGCTTGAAT TCGAGAGATA CCTGAACTTA CGTTATGAGG GTACTGAAAC      360

AAGTCTTATG GTTCTACAAG AAGGAGACTC GTGGGATTTT GTAGAAAGGT TCACAAAACT      420

CCACAAGCGT GAGTTTGGCT TTGTTTTCGC CGAGAAGAGG ATTTTAGTGG ATGATGTCCG      480

TGTGCGTGCT CTAAGTAAGT CTATGGTGCG GAACAGGAGC CTGTTGATCA GCAGTTATCC      540

CAGGTCACTC GTTCTACAGC TGACCCTTCT AAGGATGCAA AGTTCTTTAA GGACGTGTAT      600

TTCGTCGATG GGTTTATTAA GACCACCTAT TTACAGGTTA GATAGTTTAC CGGTAGGTAC      660

CTGTATTGAA GGACCTG                                                    677

(2) INFORMATION FOR SEQ ID NO:1043:

(i) SEQUENCE CHARACTERISTICS:
        (A) LENGTH: 726 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1637RP (xi) SEQUENCE DESCRIPTION: SEQ ID NO:1043:

GATCTGCTCA TACTGAGCGG CCAACTGGTC GTACTCCGTA TGCAAAACAT CTGTGGTTTC       60

CTGGAAGTGC GCCACCTTGA GCGATATCTC ATTAAACTTG GTAACCAGCT CTCCCAACTG      120

ATGATTGACT GCACTGGTTT CCGTCAGCAG GTCCTCCAGT TCGCCAGTTC TGGTGTCCAC      180

TTCCGCCACG TATCCGCTGT ACAATGTATA CTCGTCGTTC GCAGACCCCA GAGCAGAAGC      240

TCGCCGCCAC TCTGGCGCCA GCAGCTCAAT TACCTGAGGT TCAATCTCTG TTTCAACCGT      300

TGCCAACAGA GTGTCTACTT TTTGGCGTAA CGAACTATCC CCAAAAAGCG GAGGCAGCTC      360

ATCGTGAGAG GAGGCACCGG GATTTGCCGC TACATCCTGT ATGACTGAGT TCTTCCGGCT      420

CCTAGGCATG GTGCAGTTGC TGCCTCAACG GCTTTCTTCC TGGTGCAGGT CTGCAGTGGT      480

TCGTGCTTAT GCGCAAGCAG AATACCATGT TGAGCCGGCG AAATCTCATC ACGTGATCAT      540

CATCTTGCAA CGGCTCGGAG GACGCTGATG CACTGTTCCA TAGGCTTAGG GCGCAATTAT      600

ACGCTAGCTA GTTATATTGA ATAATATGTAC ATGATGCCTT CGGCACGACA GCGCACTCAG     660

TGCTCGGCCG CCGCGCCGCG CTCCGGCAAG CTCTTGTCTC AACTTGGGCC TTCTCGGCCT      720

CCACGT                                                                726

(2) INFORMATION FOR SEQ ID NO:1044:

(i) SEQUENCE CHARACTERISTICS:
        (A) LENGTH: 683 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1637UP (xi) SEQUENCE DESCRIPTION: SEQ ID NO:1044:

GATCTTGCCG TCCTTCTTGT CCAGCTGTAG GTCCGGATGA GGGTACGCCT CGCTCAGGTA       60

CTCCAGCCGC AGCTCGCCGC TCTCCATGGA CGCCTCCAGG ATCGAAGGCG CCGGCACAGC      120
```

| | |
|---|---|
| CTCGGAGGGG AGGGGCGGCT GCAGGAGGGG CATCTCCTGT CGCTCCTGGT GCATCTGCAG | 180 |
| CGCCGCAGCG CTCGGCTCCA GCGCCGGGTC GAAGTACTTC ACATTCGTCA GGCCCGACTT | 240 |
| GTACAGATTC AGGATGCAGC CCTTGAGCTG CGCACGGTGC AACCGGTACG CAGTCGCGAC | 300 |
| ATACTGGTAC CCGCTCGTCC CCCCTCCCGT GAAGTGCGGC CGCTCCGATC CGATCGAAGA | 360 |
| CAGTGACGCT GTTGGCTGGT GGCTGTATCG CCCCTCGCGC GCCGGCGCTG CGCCCTGCGC | 420 |
| CTTGTTCACC CACCCGAGCC GAAACACAGT CCCGTCGTAC GTCTCCCCGT TCAGCCCGCC | 480 |
| TCCACGTCGC ACCGGCGAGC CCGCCGGCTG CGAGCAGGGC GACACCTGCT CCTCGCAGCG | 540 |
| CGCACCCGCC TTCATGTCCT CACATGTCAG CGTCCGCTTG TGCGCTTGCC CCGTCGGCAC | 600 |
| CTGTAACTGC ATCGGCGTCT GTGGCTGCTG CTGCTGCTGC TGCGTGTGCT GTTGCGGTTT | 660 |
| GCCTGTTGGC CTTGTTGTGT GTA | 683 |

(2) INFORMATION FOR SEQ ID NO:1045:

(i) SEQUENCE CHARACTERISTICS:
        (A) LENGTH: 665 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1638RP (xi) SEQUENCE DESCRIPTION: SEQ ID NO:1045:

| | |
|---|---|
| GATCCTGTCG CTGGAAATGT CGCGGACGAG AACAGACAAC CGTCGGGGGC GGGCGGATCT | 60 |
| GCCGGAAGCT GTCCGAAGGA GACCAAGAAG GAAATTGTAA AGCTGCAGCC AGCGCCGATT | 120 |
| CCACAGAACT CTCCGTGGAA ACCGGTGCAG ATGGGGACGG GGGCCGGACG GGCCACCGAG | 180 |
| GACGGCCGCT GGCCTTCTGC GCACGAGGTT GCGACAAAGC TTGCTGACGA CGGCAGCGGG | 240 |
| CGGGGGCGCT CGCAACCGAT GGTGACGACC GGGAAGGAGA AGTGGGTGCC AATGAAGCCG | 300 |
| GCCATGCTTG TGCCCGGGCA GGGCTTGCGC AAGATGCAAC GCAAGAAGAA AAACGGGCAG | 360 |
| GCGGTCAACG GCGGTGCCGC GAAGCGCAAG ACCGGAAACA AGGCACCCCC CAGCCAGCAA | 420 |
| AAGAGAGCTC CAGACTCCCA CAGGAAGGCG CATGACGAGG CGAGCGCCGC GAGCGCCACG | 480 |
| CCATCTGCAC CGGAGGAGCA CGTGGAACAG CGCGAGCTCG GCGAGCAGCA GCAGGTCCCC | 540 |
| GAGGCCGCAG AACAGGGTGC GGAACACCCG ACACAGCATA TGGCGCAGAT GCAGCCCCAG | 600 |
| CCCAGAAGAC GCTTCTACGG CGGCAGGCAG CAGCACTCCG CTGACGGACA CAAGCCAGTT | 660 |
| TGTGT | 665 |

(2) INFORMATION FOR SEQ ID NO:1046:

(i) SEQUENCE CHARACTERISTICS:
        (A) LENGTH: 765 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1638UP (xi) SEQUENCE DESCRIPTION: SEQ ID NO:1046:

| | |
|---|---|
| GATCTGAGAA CTACTGTGTG TCGGCTAGCG CAAACTTATC AGAATTCCAT CAACTCACCG | 60 |
| AACCATAGCA CATCTACGTC ACCTCCCCCT ACCGCTACAG ATACCGGGAA TGATCAATTT | 120 |

```
TTGCGTGTTC ATGCTGTAAC CATATCGCAT GATGACAAGT ACCTAATATG CATGAGCAAT       180

GACACGTACA TTGATGTCTA CGACATGTCA GAATTATCGC CTGATTGTGA ACGCTCGCAC       240

GAAATTAGGA CTCCTAGACT ATCTAGACTT AATATTGGGA AGCAGATGAT GTCCATGAGC       300

GGGCCAGTTG GACCCGATGA TTCGCTTTTA CTAATCAGTG TACAGCCACA CGAGCTTCAG       360

CTATGGGATT TCAAAAGGCA GATTATGGTC CAAAGATATG TAGGACAGCG GCAGGTGGCA       420

TACATCATCC GTTCGTGCTT TGGGTATGGG GACAACCTAG TTGCTGGAGG TTCGGAAGAC       480

GGGAAGATAT ACATTTGGGA TAGATATTAT GGTAATATTA TTGGCGTTCT ATCTGGGCAT       540

AACATGGAGA GACCGGACGA CTCCAGAAAT AAAAACTTCC CAATGACCAA AGTTTGCAAT       600

ACTGTAGCAT GGAATCCCGT CAATTCAAGA CTATTTGCCT CTGGAGGAGA TGACGGTCTG       660

GTGAAGATAT GGAAGGTTGA CCCTAATTGA TGAATCCTAT AGCATGACGT TATTTGTCTA       720

TAGAACTTCG AGAAATCCTG CCGATCTGTT GTTTCCTAAA TTGTA                      765
```

(2) INFORMATION FOR SEQ ID NO:1047:

(i) SEQUENCE CHARACTERISTICS:
        (A) LENGTH: 658 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1639RP (xi) SEQUENCE DESCRIPTION: SEQ ID NO:1047:

```
GATCCATCTG ACTATTGTTT CACGCGATTC GGGGACCAAC TGTGCAGTCA GGCCCAGGAA        60

CCGGGAGAAA TAAGCCTTGA ACGAGCGCTG GTCGATATTA CAGTTGTCGC CACCTTGACA       120

TCCTGCCTCG TACAGGGTGT CGTTGCTGAG GAAGATTCTG GCGCTGTCCA AGAAACGCAG       180

TGTTCGCTGG TGCCACAGCT CGTCCTGGGT ATGGTTGTAG ATGAAGGCAC AGCCTGCCAT       240

GATCAGCCCA TGGTTGTAAG TCCACTGCAG CTTATTTAAG TTGGTACAGT TGTCGTTGAT       300

GTCTGTACCG TCGTAGACGA CGTGCCAGTT TGGCTGCACA ATCGAGATCA GCCCAACGCC       360

ATACATCCAG TCGTAAACCC GTTCCGCCCA CTCTAAGTAT GTGGCATTCC CGGTGTAACG       420

CGTTAATCGT GCCGCCATGT GGAACAGCGC ACCGTTGGAA ACGGAGTTTT TGTAGTGGTA       480

CCCGTCGTTC CAGCGGAAAA TCTGCCATCT GAGCCCGCCG TTGCACGTCT CCATATCCCA       540

GCGCAGGGCC ATGGTATTAA ACACCGCCTG CGCCAGCGCC AGCCATTGCG GCTGGTCCGC       600

GGGCGGGTTC GGGAAGTTGC GCTCCGCGGC AGCCATCACC GCCATCCCCC AGAAAAAA        658
```

(2) INFORMATION FOR SEQ ID NO:1048:

(i) SEQUENCE CHARACTERISTICS:
        (A) LENGTH: 730 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1639UP (xi) SEQUENCE DESCRIPTION: SEQ ID NO:1048:

```
GATCGAGCGG GTGAGGGACA CGGTGCACAT AACGACTGCG GACGGTGCCT GCTATGTTTC        60
```

-continued

```
CAAGTGCGCG ATTGTGACCG TGCCGCAAAG CGTGCTGGAG CTGTCTCTGA AACCAGAGCG      120

GGTGCCCGGG CGCATTGAGT TTCGCCCCCC CCTCAACGAC AACATCACGT CTGCGTTTGA      180

GCGAGCTCAC TACGCCTCGC TGGGCAAGAT CTTCTTTGAG TTTGACAAGT GCACCTGGGA      240

CACGCAGCGC CCGCGGGTTG CTATCGCAGC CAAAGTTCCC GACGACTTTA GTGCGCAGGT      300

CCGTAAGGCC CAAGATTTGC AGGAGCTGCT GCGATCCGCC AGTGCTCAGA CTGAGGTGAA      360

GCTGGGACAA GACTGCTTTG ACTTTCCACA AGAGTTTCAG AACATGGTTG CGCTGGCAGG      420

GATACCGACA CTTATTGCGT TCACGCAGAC ACCTCTTACT GAGCACGTCG AGCGCTTATC      480

AAAGCAAGAG ATTGTGGACT ACTTCAAACC CGCAATTGTT GTTGCACTAC GTGCACTGGG      540

GTCCAAGGAG GAGTGCCTCT TCGACCTCGG AAACACGCAA CCGCAAGACG ATAGTCATCC      600

AGGCCCAATC CTAAAGAACG TGATCTTCAA TCCGTGGTCA CAGGATACGT ATTCTCGTGG      660

CTCATACACC GGTAGTCACG TGGACGACGA CCAGCTGCCC TTGAACGTGG CCCTCAACAA      720

CGGCCAAGAT                                                            730
```

(2) INFORMATION FOR SEQ ID NO:1049:

(i) SEQUENCE CHARACTERISTICS:
        (A) LENGTH: 702 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1640RP (xi) SEQUENCE DESCRIPTION: SEQ ID NO:1049:

```
GATCAAGCCG AGCACGCTGA CCTTGGCTCC CCGACGCAAC ATCGGGTTGA CGGGCTCCCC       60

CGCCGTGCGC TCCTCGACGC CATCGCCCAG CTTGGCACTG GCGGCGTCGC GCGCCGCGGC      120

GAGGCGCGCC ATGTCCATGA AGACCGGGAT GTACGAGCCC TCCGTGATGG TGTATATAGT      180

GTTACAGCAG AGCATCAAGC AGTACAGCAC CGACATCAAA ATGAGCGCGC CGTAGGTCTT      240

GCTACCCTGG CTGACAAACG GCGTGGCAAG TGCGCCGTAC ATTACAATCG ACAGCGTCAT      300

GAGCCACTTG CGGTAGTTTG AAAAGTCCGC CAAACCCATG AGCACAATCG CAATGAGGCC      360

CTCGATGGAC GTGTACAACG CCCGCATATA AAGCACATAT GCCGTGAACT GCACGTCCCT      420

TCCGCCCACG TAGATGTAGC AGTCATCGCC GCGCGGGCGG CAGTGCGCGG CGGGGTGCCC      480

CTTGGGGTGC CCGAGCTCGT GTGCGATGGT CTGTAACGAC GCAGGCACAA AGAACGCAT      540

CATCACGTAG GTCGGCCCGG TCGAAAAGCA CACAAGGAGC CATGCAGGAA ATACCCACCG      600

GCCCCGCCAC CGCGCCAGCA CTCCTCGTCG GCGCGCTGCC CGCCCACTAG CGGCTGCTGC      660

TCGTCCAGCG TCACTGACAC CTGCATGTCA GCGCCCTTGC TT                        702
```

(2) INFORMATION FOR SEQ ID NO:1050:

(i) SEQUENCE CHARACTERISTICS:
        (A) LENGTH: 696 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1640UP (xi) SEQUENCE DESCRIPTION: SEQ ID NO:1050:

```
GATCAACGAG CTGGCGCAGC TGCAGCTGGA CGATGCGGAG GAAGGCCTGG AAGAGGCCGG        60

TGGTGCGCAG GAGGGCGCGG CGCTGTGGGC GCAATTGGAC GGTGACGACG ACCTGAAGGA       120

GTACGACTTG GAGCACTACG ACGAGGAGGA TGCGGGCGCG GGTGCAGAGG TGACGATGTT       180

CCCGGGGCTC TCGGGCGAGG CGCGCTTCCA CGAGGGTGAG GAGGGGCAGG ACGCGTACCT       240

GAGCTTGCCA ACCGTAGAGG AGGAGCAGGA GGAGCGGGCG GAGCTGCAGG TGTACCCGAC       300

AGACAACCTG GTGCTGGCAA CGCGGACGGA AGACGACATT TCGTACCTGG ACGTGTACGT       360

GTACGACGAC GGCGCGGGGT TCCACGACGA GGCGGTGCCG CAGGAGGCCG GGGACGCGCA       420

GGACCCCGAC GTGGCGCGCG GGCTGATACG GGACGCGTCG TTGTACGTGC ACCACGACCT       480

GATGTTGCCG GCATTCCCGC TGTGCGTGGA GTGGGTGAAC TACCGGCCCG GGTCGAACTC       540

TGACGCGCCG GCAAACTTTG CGGCGGTCGG CACCTTCGAC CCCACGATCG AGCTGTGGAA       600

CCTGGACTGT GTGGACCGCG CGTCCCCGAC ATGATCCTCG GCGAGCCCGC GGACTCTGCG       660

ACCGCGTCCA AGAAGTCGAA GAAGAAGAAG AAGGGC                                 696

(2) INFORMATION FOR SEQ ID NO:1051:

(i) SEQUENCE CHARACTERISTICS:
        (A) LENGTH: 725 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1641RP (xi) SEQUENCE DESCRIPTION: SEQ ID NO:1051:

GATCCCTTAG CGACTCTCTC CACCGCTCGA CGAGGCCATT GAGCTCTTAC GAACTGCACA        60

AACCTACTCG AACTCTGTTT CCAGACTTCT TTCTGTTTGT CTTCAACTGC TTTCGCATGA       120

AGTACCCCCC AGGCTATTTT TCTTACCCGC CTGGTGTTTG TCTATATACC CGGTTGTATT       180

TTTGATAAAA AACTCAGCTC TTCCTCTACG GCAGAAATAT ATATCCAGTC CTTAGCGCCA       240

TGCGAAAATC TGCCTTTTTA CCGCTGTTTC TCCCAGTCTT AGCACTGGCA GAAAAAAGAT       300

GTATGGCGTA TAGGCGCTGG CCCCGCGGAA AAAAAAAAA AATAGAAAAA TAGAAAAATA       360

AAAAGACGTG GGCCGCCCCG CGGGCAGACG AAGAAAAAAT AGGCGCCCAC CCCTCCAAGC       420

AGACGACAGG CGAGACATAA TAAAATCCCA CACCAAGGGA AGAAAGTCTT GTGCACGCTC       480

CCGGCCTCAT ACGCTGCCAT TCTGTTCCAT CCGGCTTGCA AACCCAGTAG TGGCATGTCA       540

AAGCATTGCT CCGACGCTCC GCTGCCTTGC AGTCGACATC CTCTTCCTAA CCCCAGCCAG       600

ACTTCCCATA CTTTGCACTT CACATAGCAT ATCACTTTTC AGATCACTAC GTGACATTCG       660

GTACGGAATG GCACTCCAAT GCCGACAACC TCTTCCTACC CGTGACTTAC CCGATGTGCC       720

AACTA                                                                  725

(2) INFORMATION FOR SEQ ID NO:1052:

(i) SEQUENCE CHARACTERISTICS:
        (A) LENGTH: 704 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
```

(A) ORGANISM: PAG1641UP (xi) SEQUENCE DESCRIPTION: SEQ ID NO:1052:

GATCGGGTAG TGAGGGCCTT GGTCAGACGC GGCAAGTGTG CTTGTGGTCT GTCCTCGGGG      60

GCTTGCTCCT GGGGACGGAC TGCTTGCGTG CTCTGTCGTA GACGGCCTTG GTAGACCATC     120

TCTGGTCGTC GCTTGCTACA ATTAACGATC AACTTAGAAC TGGTACGGAC AAGGGGAATC     180

TGACTGTCTA ATTAAAACAT AGCATTGCGA TGGTCAGAAA GTGATGTTGA CGCAATGTGA     240

TTTCTGCCCA GTGCTCTGAA TGTCAAAGTG AAGAAATTCA ACCAAGCGCG GGTAAACGGC     300

GGGAGTAACT ATGACTCTCT TAAGGTAGCC AAATGCCTCG TCATCTAATT AGTGACGCGC     360

ATGAATGGAT TAACGAGATT CCCACTGTCC CTATCTACTA TCTAGCGAAA CCACAGCCAA     420

GGGAACGGGC TTGGCAGAAT CAGCGGGGAA AGAAGACCCT GTTGAGCTTG ACTCTAGTTT     480

GACATTGTGA AGAGACATAG AGGGTGTAGA ATAAGTGGGA GCTTCGGCGC CAGTGAAATA     540

CCACTACCTT TATAGTTTCT TTACTTATTC AATTAAGCGG AGCTGGAATT CATTTTCCAC     600

CTTCTAACAT TTAAAGTCCT ATACGGGCTG ATCCGGGTTG AAGACATTGT CAGGTGGGGA     660

GTTTGGCTGG GGCGGCACAT CTGTTAAACG ATAACGCAGA TGTC                      704

(2) INFORMATION FOR SEQ ID NO:1053:

(i) SEQUENCE CHARACTERISTICS:
        (A) LENGTH: 678 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1642RP (xi) SEQUENCE DESCRIPTION: SEQ ID NO:1053:

GATCGCGGTT TCGGAACGGC TTGCTTCGCA CAAAACACAG GGTTCGAAGT TACATACTCT      60

TCAAGAAATT GACGAGGCCT TGAAAGCGCT GGAGCTACGC GGGTCAGGGA NTGATGGTAA     120

TGCCTCATAT AAGTGCAACT GCCAGGCCAC TATGCATCCT CTTTTTGAGC TAGCCCCAAA     180

TTGCCTGAAC TGTGGCAAAA TTATATGTTG CCGAGAAGGT CTTCATATGG ATTCCTGCAG     240

TTATTGTGGG ACGCTGCTGA TACCGAAGCA GCAGCAGCGG GATATAGAGA AGGTGTTGCA     300

GCGCGAACGC GAATTGGTAA AAGCCAAGAG ACAAGAGACC GGCTCGACTG GCAAGAAGAA     360

GGAAAAGGTC TTTAAGATTT CGAACGCAAA GGGGAGAAAT ATGTTCAGTG AGCAAGAGAG     420

GCTATTCGAC AAACTTGACA GGCAGCGGGA CGTGAAATGA AACGCAACCA GGTACTTGGG     480

GCAGAGGACT GTCTCAGGAG GAGGACTCGA TTCTGAAGGC TGAGGAAGTC GATCCGGAAC     540

TAAGGGCGGC CAGGCGCGCT TGGAGAATCT ATTGCACTTT CAAGCACACTA GCGAAGAGAG     600

GACTAAAATA ATAGATACTG CCAGTGACTA CAGTATGTCA AACGACGCAG GAATTTGGGG     660

GTCGGCATAT GAGAAGGC                                                  678

(2) INFORMATION FOR SEQ ID NO:1054:

(i) SEQUENCE CHARACTERISTICS:
        (A) LENGTH: 703 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
    (A) ORGANISM: PAG1642UP (xi) SEQUENCE DESCRIPTION: SEQ ID NO:1054:

```
GATCTCGTAC CCGGTACGGT GCGCGAGCTT GCCGCCGGCA GCCGCGCGCT GCCCTGCTTC      60
TCCGCCGACA GCCCGCCAAA TACCGTGTTC TACAAGCTGC ATGGATCGCT GCCACAGGCC     120
GTGCGTGTTG CGACGCTGCG GCACTTCTCC TCAGACGCTG CGGCAACCCG GGGGAAGCAC     180
CTGGTCCTGT TTTGTACCGA CGTCGCCTCG CGTGGCTTGG ACCTGCCGCG TGTCAGCACT     240
GTCATCGAGA TGGACCCGCC CTTCGCGGTC GAGGACCATC TGCATCGTAT CGGGCGGACC     300
GCGCGTGCCG GTGTGGCTGG CGAGTCGTTC CTCTTCCTGC TGCCCGGCGA GGAAGAGGGC     360
TACATGGAAC ACATCCGTGC CCACCACCCT CGTGGCTGGG AGCTGCTTCG CTACGATCGA     420
GACCTACTGG CGCCGGCCTT CGCGGCCCCT GTCGCCCGCT CCGACCGTCC GACCACCGCA     480
ACGGACGCCG CCTGGGACAG CAACGCGACA ACTTGGCACC TCAACGTCCA GCGCCGTGTT     540
GCTCGAAGAC CCTCCGCGAA GGATCTTGCC ATCAAGGGCT ACACCAGCCA TATCCGCGCA     600
TACGCAACCC ACATCTCTCA GGAAAAAGCG CTTCTTCAAC GTTCGCTGTC TGCATCTTGG     660
CCACCTGGCG AAAGCCTTTG GACTTCGCGA GCGCCCCAAA GCA                       703
```

(2) INFORMATION FOR SEQ ID NO:1055:

(i) SEQUENCE CHARACTERISTICS:
        (A) LENGTH: 616 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1643RP (xi) SEQUENCE DESCRIPTION: SEQ ID NO:1055:

```
GATCGGAACA AGGAGCAGCA GTCCATCCAG CTGTCGCAGC AGCAGCAGGG CACACTGCAG      60
GACAGGAAGC CGACATACCA AGTCATGTCT CTCCAGAGCG ACACGACGGT GACCAAGTTC     120
AAGGTCGACG ACTCCATCAG CAAGCGTTTC GAGTTCATGA ACAAGCCGAA GGCCAAGCGC     180
GCGACCGCGC CGCGGCAGGC GGCGACCAGC AGCCCTGCAA TGGCCTCGGG CGCCGGCAAG     240
CGCGTGCACA AGCCCAAGGT GCAGCAGGGC CGCGGCGGCG CCGCGCAGGC CGATTCGGCG     300
AAGCAGAGTA ATACGCCCAG GGGACTTCGG TGCGCTCGGA GAAGACCAAT CGCTGCAGGA     360
ATTCCTGTCG CAGTCCGAGA TTAAGAGCGA TCTGTTCGAA CTGGAGGAGC AGAACGACGA     420
GAGCGCAAGC TCCAACAAGG AGAACGTACC CCCGAGCTCC TCGTCGGTGT TCCAGCAGCA     480
GCTTCTGCCC ACAGATATGG ACGACTTTTT CAACCTCGAC CTCGACCATA TGAAGAACAC     540
CGATGATGAG TGGTTCCAGG GCCTGTTCGG CACTCCTCGG GACGCGACCA CCTGCAACAC     600
CATGCCCATC GAGGAC                                                    616
```

(2) INFORMATION FOR SEQ ID NO:1056:

(i) SEQUENCE CHARACTERISTICS:
        (A) LENGTH: 538 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:

(A) ORGANISM: PAG1643UP (xi) SEQUENCE DESCRIPTION: SEQ ID NO:1056:

```
GATCGTTGCA AAGAAGCTAT TACGGTGTCT ACACGTTCGA GAACAGCGCC CGATGCCATA      60

TCCCACACCG CCGCTGTCAA ACGCGTCTCT GGGCACGAGC GCTGACGGCG GGAGCGCCGC     120

AGGGCTGGCG CAGCAGGCGC CCGCAAAATC GTACTACCCG CTGGTGCCGG ACGGCGCACA     180

GCTCACGCCG CCACTGCTGC CCGTGTCCAC GGCCGGCGAT GACGCCGGCC TCTACCGCTA     240

CCACAAGCAG ATCAGCAAGT CGTTCCAGGA CGACCTGATC TACTGCCCGC GCGCGCTGCT     300

GAGCAAAGTC GAGCTGACGC AGTGCTACCA GCTGGACATG CTGCTGCTGA TGGAGCAGCA     360

GCAGCAGGCC CAGCCGAGTG TCAAGTTCAA CCCATATACG TCGCAGAGCT TCAACCCCGC     420

GGGCCCCGCA TCGCCCGGCT CCTAGGGCCG GCGGGCCGCC CGGGACCATT TAGTTCGACN     480

GAATCNCTAT GTCAAGACTG ACGCTTGCTC GCATCCGGGT TTATGTTTTA TTCCAGTT      538
```

(2) INFORMATION FOR SEQ ID NO:1057:

(i) SEQUENCE CHARACTERISTICS:
        (A) LENGTH: 560 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1644RP (xi) SEQUENCE DESCRIPTION: SEQ ID NO:1057:

```
GATCCTTTGC AAATTCGTCC ATAGGAATGT AAACGGACCT GCCCTCCCAC CTCTTGGTAT      60

TGCAAACAGG CATCTTGAGT TCGTTTGGCC ATTCCATCTT TATATGCTGT TCTTCATCGC     120

AAGGCACATT TTCGTCTTCT TCGGGCTTCT CAAAAACAAC CTTATGCACT CTCTCAGTAA     180

TATACACAGG GTACGGGGTC GCCGTCCCTG AACATTAGGA AGAACCAGCC AAATGGGCCT     240

GTGCCTGGCG ACTGGCCGGA CTTCTGCACK AAATCCCACC TCAAGTATAT GACCATCAAG     300

TCCCTGAACC GCGTGCTAAA CTGCTGGTAT GTTGTGTCGA TATCTAGCGG ACCGGGAGCT     360

AGCGAATCGG TATGCGGCAC TTCCAATAGG TAATCGCCCG GCGTTTGGAA CGGATGGTAT     420

ACCCTAGTAA CTTTGCCTGC AAACTCAATA TGGGGCTTGG GCTTTTTCCA GTGGGCCTGG     480

TTTGTAATTG GTATCAATGT CTGCGGAGAT GAGATGGAGC TGTCGCTCGA AGATATGTCC     540

TTTAGCAGGT TATCGTCTTC                                                560
```

(2) INFORMATION FOR SEQ ID NO:1058:

(i) SEQUENCE CHARACTERISTICS:
        (A) LENGTH: 706 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1645RP (xi) SEQUENCE DESCRIPTION: SEQ ID NO:1058:

```
GATCTTGGAA GAGGAGGACT ATTCAAGTAA AATGGCACGG CGGGAAGATA AGATGGAAGA      60

GGAGTGGATA CGAAAGTACG AGCGTGAGAA GAAGAAGAGA AAGAGAGGCG CATAATCCCC     120

AGTGTAATAA ATCAATTCCG CCGGTTCGCT GCGCTGTAGC ATAATAATAT GTACGATAGT     180
```

```
GGTCAGATAA GGTATTTCAA AAGTTAGGCA ACCCATGAAA CATCAAACTT TCAATGCAA      240

TGATATGTAA GTTGCATATA TTACGAGCTG TGAAATAGAG AAACTCAAAT GAATACTTTT      300

ACCACACCAT AACAAACGCA CAATGTTACG AGAATGAAGA CGATAATGCA GCTTGAATAG      360

TGCCACCATG GCGCCATATG GTACCTACTG AACAGCAGAA GCAAGCTAAA CGAGCTCAGC      420

ATGAGGGACA CCACTAGAGA TACCAGGATC AACGCTGTGA TATAATTACT ACCTTCAAAC      480

TCAGTCTGGT CATTTCCAAG AGCGCTGAAC AATGAAAACA TGATTCCCAC AGTGGTACCT      540

GTGGTTATGC AAGATACGAG CAGGGTCGTC AGGTAAAACA ATGAGACCAC CTCATCGTGC      600

TTGTATCCAT ATAGGACATC AAGTTCATCG TAACATACTA GCGCAGCCTC GTCATCCCAG      660

TTTGGAACTT GCAGTTGGCT ACCACTCCCG GCAACGTGCT TTGCAC                    706
```

(2) INFORMATION FOR SEQ ID NO:1059:

(i) SEQUENCE CHARACTERISTICS:
        (A) LENGTH: 705 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1645UP (xi) SEQUENCE DESCRIPTION: SEQ ID NO:1059:

```
GATCAGCGGC GGCTGCGCGC GCTGTTGCCG TAGCGCTGCA GCAAGCTCGC GCGCGCCGCC       60

GCGCTCTGCG CCTGGCCCTC CGGCTGCCGC GCACCGCGCT CGGGCGTCTG CCGCCCAAGC      120

TCCAGCCGCG TCGGGTTCGC ACTGATCACG TGATCCACCG TGCTGCCGTC CCGGCCGGCC      180

CTGTCCGGCG CCGCCGGCGC CTCGCCCGCC GCGCCATCGC CGCGGTACAC ACGGCTCTTC      240

GGATCGTACC GCGTCTCCTC GCCGCGCACG TCGTCGAGGT ACCGCGCGCG GTCATGCCGC      300

GGCCGGATCG CAGGCGCCCC CACGCCCGCC CGCGCCGCCC GCGCGTCCAG TCCCAACTTG      360

TACCGTTCCA CTGCTGCCGC CGCGTCCTCT GCCGCTGCCG GCGGCTCCGC CGCCGCGGCC      420

GCCACTGCCG GCGCCACCGG CCCCTCGAAC CCGTACCATC GGTCCCGCTT GGCCTCAAAG      480

CTCAGCGCAT TCTCGTCCCG GACCTGAAAC GCGCGCTCGC CACCATCGCC CCGCGCCTGT      540

TTGCGCGGCC GGAGCAGGCA GTCGCGCCGG TCATGATTGG CGCCGCAGTT TCGTGCACCG      600

CCCGCGTCCG CGCCCCCGCC CGCGGCGCGC TGCCCGCCAC AAAACGGTCA CTTATTACCG      660

AACCTGCTGA GCCACCGAGA AGTCCTGAGC GCCCTCGCCG GGCTC                     705
```

(2) INFORMATION FOR SEQ ID NO:1060:

(i) SEQUENCE CHARACTERISTICS:
        (A) LENGTH: 706 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1646RP (xi) SEQUENCE DESCRIPTION: SEQ ID NO:1060:

```
GATCGAGAAC CGCATGGACG ACAAGCCCAA CGTGGTGATC CTGGGGTCCG GCTGGGGTGC       60

GATTTCGTTC CTGAAGCACA TCGACGCGCG GAAGTACAAC GTGACGGTGG TGTCGCCACG      120
```

| | |
|---|---|
| GAACTACTTC CTGTTCACGC CGCTGCTGCC CTCGACGCCC GTGGGCACGG TGGACGAGAA | 180 |
| GTCGATCATC GAGCCGGTGG TGAACTTTGC GCTCAAGAAG AAGGGTAACG TGTCTTACTA | 240 |
| CGAGGCGGAG GCGACGTCGA TCAACCCGCA GCGCAACACG GTGACGATCA AGTCGGTGTC | 300 |
| GACGGTAGCA CAGCTGTCGC ACCCGGACAA CCACCTGGGG CTGACGCAGC AGGACTCCGC | 360 |
| GGAGCTGAAG TACGACTACC TGGTGTCTGC GGTGGGCGCG GAGCCCAACA CGTTCGGCAT | 420 |
| TCCGGGCGTG GAGGAGCACG GCAACTTTTT GAAGGAGATC CCACACTCGT TCGAGATCAG | 480 |
| AAAGCGCTTC CTGTCGAACG TCGAGAAGGC GAACCTGTTG CCCAAGGGCG ACCCCGAGAG | 540 |
| AAAGCGTCTG CTGACCATCG TGGTCGTGGG CGGTGGTCCT ACCGGTGTGG AGACCGCGGG | 600 |
| TGAGTCCAGG ACTACGTCGA CCAGGACCTG AAGAGATTCA TGCCCTCCAT CGCTGAGGAG | 660 |
| GTGCAGATCC ACCTGGTGGA GGCCTTGCCC AACGTGCTGA ACATGT | 706 |

(2) INFORMATION FOR SEQ ID NO:1061:

(i) SEQUENCE CHARACTERISTICS:
        (A) LENGTH: 657 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1646UP (xi) SEQUENCE DESCRIPTION: SEQ ID NO:1061:

| | |
|---|---|
| GATCAAATGG GTTAGCCCGT CTCCAACGAG CCCTGCAACA TAGTGGCAGT AGCGGTCGTA | 60 |
| GTCCTGGATC GTCTCCAACC CGCTCAAATT AAACTTCTCG TCCAGAATGT AGTCTGCCAT | 120 |
| GCCGTTGCCC ATCTTGTGTG TGATGTCTGC AATCACCTGC TGGTACTCGG GCTTCAGCTT | 180 |
| GTGGAACTCG GCTAGAATCG TGCTGAACTC CACCAGCACG TCACGGTCCT TCTCCGTCTT | 240 |
| CGCGTTGCCG TCGAAACTCC ACGTATCCAG CTTCAGTTTC TGGTCGAACT CCCGGAGTAG | 300 |
| CGGCACCTTT ACCTTGGGAC TGATCGTCAT ATCGTCTTCA ACAGTATCCA GCGCACGCAG | 360 |
| AATCAGGTAG AACAGCATCA CCGCGTTGCG CAGCTCGGGA TGTAGCTCCA TTATCACGGC | 420 |
| CGCAAAAGAC TCGAAGTCCG CTGTAGCAGC TGGTAGCACC GCTTGAGCTC TGCAGAGCCC | 480 |
| TGCGTGTCGT CCGCAGGATA AAGCGGTTCC CTCAGAAATT TGAGCTTCAG AGCTGCCTTC | 540 |
| AGCTCCAGTG GGTGTGTGAA TAATTGAACA ACCTTCCCCA TGGTCACGAT TCGATTAAGT | 600 |
| AATTGCCAAT TATGTCAAGC GCCTGTCAGT TGGTGATGTC GCGCTTGCTT GTACAGG | 657 |

(2) INFORMATION FOR SEQ ID NO:1062:

(i) SEQUENCE CHARACTERISTICS:
        (A) LENGTH: 727 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1647RP (xi) SEQUENCE DESCRIPTION: SEQ ID NO:1062:

| | |
|---|---|
| GATCCAGCTA GATAGCGTGC CAATTGCTGA TAAATCCTGC CAGAATGCGA TAACGCCTCT | 60 |
| CTGAAACGCG CAACGCCTCC GGAGCGCCAG GAGCTGTCGC GAGATGCGAG GCGTCTGGAC | 120 |
| TCGATGCACA ACTAATATTG AATTCAGTAT CCCGCAGTAG GCGGGTACAT AACTGCTTAC | 180 |

```
GTACTCCCAC TACGACACTG CGCCCCGCAC GCTGCACGTG CGATGCGGCT TACAAAGACC      240

AAGTCCTTGG CAACACCTGG ATATGGTATC CATCGGGGTC TCTGAGGACG GCGAGATTCT      300

TGATAGACCC CTTGTTGTAG CGCAACTCCC ACTCCAGGTC CGGGTACGTC TCCTCGATGT      360

CAGCGCAAAG AGGCGCAGGG TCACTGAGCG ACACACCCAT GTGGCTGTAC CCCGTGGGCT      420

CTGCGTTCCC GTTGTGATAC GAGAAGTCGG CGTCATCCTC GGTCCCCAA TTGTGCGTCA       480

GCTCCAGAAT GCTCTCGCGC TTCAACCGCT CGTCCGCTGC CGGATACCCC AGGAAGTAGA     540

GGGTGAATTT CGCATTTGCG TGCTCGCTCA CCTCCAGTAG CGACATACCT AGCACATTCT      600

GGTAGAACTC CAGCGACTTC GTTGCGTCCT TCACACGTAG CATCGTGTGG TTAAACTTGG      660

GCCCCAGGTC CACTGGCTCC GCGTCCGACA AGTTGTACTG TATCAACTCA ATCCAGTATC     720

CGTCGGG                                                                727
```

(2) INFORMATION FOR SEQ ID NO:1063:

(i) SEQUENCE CHARACTERISTICS:
        (A) LENGTH: 615 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1647UP (xi) SEQUENCE DESCRIPTION: SEQ ID NO:1063:

```
GATCCGAGCA CGGTGCGGGT GCAACAGAGG AAATATATGG CACTACAGAC AGTGCACAGA       60

TGCAGGAGCT GCGCCGCCTG GCGCGGCAGC GCTATCTGGA CCGGCGGGAG AGGGAAAAGC     120

TAGACTGGGC AATACGGGAC CTTGCATTGT TAGAAGAAGA CGTAAAGAAG TACGATGGG       180

ACAAGCTGAC GGAACGGGAG CGAAGAGAGA TTGGGACCAA GCGGCAGCTC GTGCAAATTG      240

TGCGCGAGCG CGATGCGGCG GCGGCGGCGG CGGAGCGTCC ATTCCATATG CCCGGCGAGA     300

CCGTTGTGGA GGCTACTGCG CGGCAGGAGA AGAGCTGGGA GGAGCAGCAG GTGCAAAAGG     360

CGGTGCGCGC GGAGGGGCGC TCGGACATAA TTGAGGTGGA GGGCTCTGAA CAGTACGAGT     420

TTGTTCTGGA CTCGCGGTCC GTTGTGCGCT TTACAGAGGA AGAGACGCTG GCTCCCGGCG    480

AGCGTGTCGA GAAGCAGCTC GAACAGAAGC TCGAGAAGGA AATTAAGCGC GTGGCGTCGA     540

TTCAAGAAAC TAGGAGGCAG CTTCCTGTGT ATGCGTACCG CGACGAGCTT CTGAAGGCGG     600

TGCGCGACCA CCAGT                                                        615
```

(2) INFORMATION FOR SEQ ID NO:1064:

(i) SEQUENCE CHARACTERISTICS:
        (A) LENGTH: 648 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1648RP (xi) SEQUENCE DESCRIPTION: SEQ ID NO:1064:

```
GATCCAGCTC ATGCAGTGCG CGATTCCAGC CCTGCCTGTC GTTTAAAGTC TTGAAGTAGT       60

TGGTGCTGAA ATGCTTGTCA AATTTGTACA GGTATCGTTT CGAAGATTTC GAGAATAGTC      120
```

-continued

| | |
|---|---|
| CTTCCACCAC TTTCAATGGG TTCTCCTCGA ACTTGTCGAG GAATGAATTC TCCAGCTTGG | 180 |
| AGAATGCATG CTGTGAAGAG TATATACGAG ACCCAGCTTT CGCCACGAAT TTGATGAGCT | 240 |
| GATTGAAGTC GTTGCGCATG TCGCTCTCGG GTATGAATCG TGGCACAGTC AGCGTCAAAG | 300 |
| CTCGCTGCGT CATAGGACGG TATGGTCCCG GTGGGTACTC GTGGACATCG AAGTTATCAA | 360 |
| GCAGATAGAA ATCCTTGATT TTGCCCTTGT CTGCGAGAGA CCGCAGGTAC GCCACGAAAA | 420 |
| GGTGGTACAG CGCGCTTCCC CGGTTACGGT AGATCTTGTT CAGAATAAGT TCGTCGTCGT | 480 |
| TGCCTTCATC GTTGGCATCC TTGTACTCTT CTACCGCCTT GCAAGAGGGG AAACACACCT | 540 |
| GGCCCGCGGT GAATATTAAG TCCATCTGCG TCGTCTTCTC CACCAACAGG TCCGTACGCC | 600 |
| CAACGATCGT CACCAGGATT TCCAGAAAAG CGTAAGTCGT GCACATGT | 648 |

(2) INFORMATION FOR SEQ ID NO:1065:

(i) SEQUENCE CHARACTERISTICS:
        (A) LENGTH: 715 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1648UP (xi) SEQUENCE DESCRIPTION: SEQ ID NO:1065:

| | |
|---|---|
| GATCTAGCAG GTGTTGAACA GATAATGGAA TGGCTCTCCT ATATTCCAGC TAAACGTAAT | 60 |
| ATGCCCGTAC CTATACTGCA GTCAGAGGAC AACTGGGATA GGGATGTTGA ATACACACCA | 120 |
| ACACTTCACA GCCTTATGAT GTACGCTGGA TGATTGAAGG CCGCCAAGGA CCTGATGGAT | 180 |
| TTGAATATGG TCTGTTTGAC AAGGGTTCCT TCCAGGAAAC ATTATCAGGC TGGGCGAGAG | 240 |
| GCGTCGTTGT AGGCAGAGCT CGCATGGGTG GTATCCCGCT CGGTGTTATT GCCGTTGACA | 300 |
| CTCGTACAAT TGAAACTGTG ATCCCTGCCG ATCCGGCAAA CCCTGCATCC ACAGAAACTT | 360 |
| TGATTCAGGA GGCAGGCTTA GTTTGGTATC CTAACTCAGC ATTTAAAACT GCGCAGGCCA | 420 |
| TAGCTGATTT CAACCACGGA GAACAACTTC CACTCATGAT ATTAGCAAAC TGGAGAGGGT | 480 |
| TTTCTGGTGG TCAAAGAGAT ATGTTCAATG AGGTCTTGAA ATATGGCTCC TTCATTGTTG | 540 |
| ATGCTCTAGT GGATTATAAA CAGCCTGTAT TCGTATACAT ACCTCCAACA GGTGAGTTGA | 600 |
| GAGGTGGTTC CTGGGTTGTG GTGGATCCTA CAATTAACTC TGACCAGATG GAGATGTATG | 660 |
| CTGATTCCGA CTCGCGGGCA GGTGTGCTAG AACCTGCTGG TATGGTTGGT ATAAA | 715 |

(2) INFORMATION FOR SEQ ID NO:1066:

(i) SEQUENCE CHARACTERISTICS:
        (A) LENGTH: 714 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1649RP (xi) SEQUENCE DESCRIPTION: SEQ ID NO:1066:

| | |
|---|---|
| GATCAAACGC AAAACTGTGA CGCAGAAAAA AGTTTCGCTG ACAGACGACA TGCTCGCAGG | 60 |
| GCACCAGCGG GTGGGCAACG GAGCGGTCGC GTTTCCAGCG ATGGACCTCG GGGCGACCAC | 120 |
| GAATCTTTTG CTAAACAACA CTATCAACAA GACCAAGTTC AGTCAGCTAA AAAAACGCGT | 180 |

```
AGATAGTATC GAACTGCATA ACCAGCAGCT GCGCGCAGAG AACAATAGTT TGAAAATCGA      240

ATTCCAAAAG ATGAGTTCCA GATATAACTC CATGGTGGAG AACCTCGTGT CTCTTAAAAA      300

CTACAATAAT TCCCTCGTTG AGAACTTCAA TCTGCTGGTA TCCACGCTGG CGCAACAGGG      360

CCTGAAGGTT CCCCATCCAT TAAACCTCGG CAACTATGCA TCTTCACAGG TTGCCAAAAA      420

TTCATCTGCT TCCGACGTTC AACCGCATGT ATCGCCGTTG GGTACTGTAG CACCTACGAA      480

CATACCCTTG GCGCAGGCTA CCCCGTCGAA AGAAGAGGCC AATCCTCCTA CAAGCCTGCG      540

CCCAGGCTTC CATGTTCTGC TGGTAGAAGA ATGATTCGGT TTGTATCCAA CTATGTTCCA      600

AATTCTTGAG AAAATATGGC TGTTCGGTGG AAGTCGTAAC GGACGGCCTA TCTGCTATTG      660

AAACAGTAGA GAAATTCCAG TACGACCTCG TTCTGATGGA TATCGTGATG CCCA            714
```

(2) INFORMATION FOR SEQ ID NO:1067:

(i) SEQUENCE CHARACTERISTICS:
        (A) LENGTH: 663 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1649UP (xi) SEQUENCE DESCRIPTION: SEQ ID NO:1067:

```
GATCGCTGGC GCGGGCAGCC ACATGCGGCG GCATTTGACG TTCTACCACA TGCAATCTAT       60

GGCGGCTGTG CGCGCGTTGC GCCCGCAGGG GAAGTACGGG CTGCGCGAGC CGCCAGCGGA      120

GGCACCACCG CCGGCGTTGC CCGACGTGGA TGTGGTGCTG ATGCCCGGTC TAGGGTTCTG      180

CGCCGATACC GGCGCGCGCC TCGGACGCGG GGCAGGTTAC TACGACAACT ATGTAAGCCG      240

TACGCAGCAG CTGCACGGCA GGAGACCGCT GCTGGTTGGG CTGGCGCTCA GCCAGCAGCT      300

GATGTTGCAC GTCCCGCTAG AGCCGCACGA CCAGTGCTTG GACGCGGTGG CCTGCGGCGA      360

CGGACAGTTG AGGTGGGCGC ANCGCGCGCC CGGGGAGATA GTTGATATAT AAGTGTATCT      420

AGCCTGTAGT GAAGCTCCCT TTCGCACGCA CGAATGTCCG CGTGCCGCTC TGGTTGATGA      480

TCTCGGCCTC CAGACGGACG TTGTTGCCGT GGTCCTCGAC GCGGGTGGTG CGGACCACAA      540

CGAACTGGTT CGCCAGGGTC GGGAAACAAT ACAAGATCTT GATGTGCTCG GTTACCTCCT      600

AATCGGTGCC GGTCACGAAT GTGACTGCCT CCCGCATCAG GTCGCTCAGC ACCGTGGCCA      660

GGA                                                                   663
```

(2) INFORMATION FOR SEQ ID NO:1068:

(i) SEQUENCE CHARACTERISTICS:
        (A) LENGTH: 706 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1650RP (xi) SEQUENCE DESCRIPTION: SEQ ID NO:1068:

```
GATCGCTCTG CCGGGACTCG ATTTTTGTGC ACCGGCCACG CAAGAAGGAC CTTGCGTGCA       60

TCATGTACAC CTCGGGCTCG ACAGGTGACC CGAAGGGTGT GTCGTTGACC CACGCTAACA      120
```

| | |
|---|---|
| TCGTGGCGGG CATTGGCGGT GTTTCCGTTG TGATCAACCG CGCGATTGTG AAGCCTGACG | 180 |
| ATCGTGTCAT CGCGTTCTTG CCGCTTGCGC ATATTTTTGA GCTTGTGTTC GAGTTGACCT | 240 |
| GTCTCTACTG GGGCGCCTTA ATTGGCTACG GCTCCGTCAA GACGTTGAGC GAGGCTTCGG | 300 |
| TCCGCAACTG TAAGGGCGAC ATGAAGGAGT TCCGGCCGTC CGTCATGGTC GGTGTCGCAG | 360 |
| CTGTCTGGGA GGGTGTCAGG AAGGCTATTG TTGCGCAGGT CACTAAGTTG CCTCCGTTCA | 420 |
| AGCAAAAGAT ATTCTGGGCG GCCTACCACA CCAAGCTACG CATGAAGAAG TGCCACATTC | 480 |
| CAGGCGGCGA TCTAATAGGA AGCATGATCT TTAAGAAGGT GCGTGAGACC ACTGGTGGCA | 540 |
| ACCTTCGCTA CATCTTGAAT GGTGGCTCTC CATTGTCGCG GGATACGCAA GTTTTTATTT | 600 |
| CCAACTTGAT TTGCCCCGTG TTGATTGGTT ACGGCTTAAC GGAGACTGTG GCGAATGGCT | 660 |
| GTATAGTGCC TCCACACCAC TTCAAGTACG GGGTTGTGGG AGACAT | 706 |

(2) INFORMATION FOR SEQ ID NO:1069:

(i) SEQUENCE CHARACTERISTICS:
        (A) LENGTH: 674 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1650UP (xi) SEQUENCE DESCRIPTION: SEQ ID NO:1069:

| | |
|---|---|
| GATCCATTTC TCATGGAGAT TAACGCTATA TGCGAGGAAA GCAATAACAA GAAGCAAGCC | 60 |
| AAGAAGTCTG TTAACTTCTC TATGCTAGGG TTGACTGATT TTACCAAACT CAAAAAAGCC | 120 |
| GATACTACAG ATGTCTGGAG AGCGTTTAGG ATGTACGACG AAGTACAAAT GAAAAAGAGA | 180 |
| TTTAGTTATA AATGGGATTA TGATAAAGTG TCCAGGGAAT TGGATGAAGA ACATGGAAT | 240 |
| AAGATTATTA ATAGGGAAAC TTTGAATTTA TTTGCATTAG TGGAAAGATA TACGGTAAAG | 300 |
| ATTGAAAACG ATGCCAATAT AACCTATTGG AGTTCTGTCG TTATGCGCAA CTCCTGTCGC | 360 |
| AAGCATGAGG CTACAGGAGT GAGGCAATGT GCCAACTTCT TCTGTGGTAA ATGGGAAGAC | 420 |
| CACCCGAAGC AGTTTCCCAA GTGCCGCCGT TGCAAGCGCA CAAAATATTG CAGTTGTGAG | 480 |
| TGTCAACTAC AATCTTGGGC ATATCATCGG TACTGGTGCC ATGATGTTGG CTCTGTCTTC | 540 |
| ACGGGCACCT CCTCAACGGC AAACACCACT GGGACACATA CGCCAAATGC TGTCGGTCAG | 600 |
| TCGGCTGGAA CCACGACCAC TACTACCACG GCGGCTACGG AGGTAGATCA ATCCATTTTG | 660 |
| ATGACAGCAA GGGG | 674 |

(2) INFORMATION FOR SEQ ID NO:1070:

(i) SEQUENCE CHARACTERISTICS:
        (A) LENGTH: 622 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1651RP (xi) SEQUENCE DESCRIPTION: SEQ ID NO:1070:

| | |
|---|---|
| GATGGCGACG TTTACCGAAG AGCAAAAAGA AAAGTACGCG ATGGCGTTGA AGGACAAGGG | 60 |
| GAACGAGTGC TTTAAGGACC AGCGGTACGA GGAGGCGATC AAGTTCTACG ACTGCGCGTT | 120 |

```
GAAGCTAAAA AAGACCCGG TGTTCTACTC GAATCGGTCG GCGTGCTACG TGCCCTTGAA        180

CAAGCTGGAG AAGGTTGTGG AGGACACCAC TGCTGCACTA AAGCTGAAAC CCGACTATTC        240

TAAGTGTTTG CTTCGTCGTG CAACAGCTAA TGAATCGTTG GGTAATTATG CTGATGCTAT        300

GTTGGATTTA TCTGCCGTAT CTCTATACGG CGGGTACAGC TCGCAGACAA TTGAGCCCGT        360

GCTGGAGCGG AATATGAACA AGCAGGCTAT GCAAGTATTG AAACAGAAAC TCTCTGGTGG        420

AGAGAAACAC GAACTTCCTT CCAATACTTC CTTAGCGTCT TTCTTCCGCA TCTTCCCTTC        480

GGAGACATCG TTGGAGAACT ACGATGAAAC TTCCGAAGCA GACCGCATTC TTCTCAAGGG        540

ATTGTGCGCC CTACACGCGC GCCAGGCAGG CTCCTATGAA ATTGCTGATG AAGCCTTTAC        600

CGATGCTGTA GAAAAGTTCA CC                                                 622

(2) INFORMATION FOR SEQ ID NO:1071:

(i) SEQUENCE CHARACTERISTICS:
        (A) LENGTH: 679 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
         (A) ORGANISM: PAG1651UP (xi) SEQUENCE DESCRIPTION: SEQ ID NO:1071:

GATCGTGATT TTCGCGGGCT GCATCCTGCA GGCTCCACAT CATGCCGTGC GCCAGGCTAT         60

GCTGAACATC CCCAGCGGGG TCTACTGCAC GTTCCGTGGG CAGTCATCGC CTGCGATCCA        120

GTACGGTATC TCGTCTACAA ACTTCATCAC ACACGTGAAT GAGATCGAAA CCCCAGACCT        180

GGACCGCTTT CTCGAGGTGG TACGCACGAT ACCAGACAAC ACCTACTGTA AAATCCGTCT        240

TGTGACCTTC GACAACGTGC CTTTTGCTAT CTCCCTGAAG ACAAACTACC ACTACTTCCC        300

CACCAGCGAG CTCTCCCGCA ACTCCGACAC CGGCCGCTGG ATTGAGCACC TCTGCAACGC        360

TACCCCCGCT AAAAACTAGC AATAGACTGA TATCTCTTAT AGAACGTATA AACTATTCAC        420

ATGTAACCCG ATCACGTGAC GAGCGCTGCA CGCAGCTCGT GCAGCATGCT CAGTGGTATG        480

GCAGTAGGCG CCGCAGACGC TTCAGATGGG CACTCGCCGC CATGGTCCGC CCAGAGAGCT        540

GCTTCAGCGC GCGCTGTCCC AGCCTGTGTT ACCGTGGCTG CGGCCAGCCT TCGAACGCTT        600

GTACCTCCTG CAGTCTTCCG CCATCTCTTA GCTGCGCCTT TGTGCGTCTT CATTAGTGTC        660

CGCACCATGA TCAGCGACG                                                     679

(2) INFORMATION FOR SEQ ID NO:1072:

(i) SEQUENCE CHARACTERISTICS:
        (A) LENGTH: 692 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
         (A) ORGANISM: PAG1652RP (xi) SEQUENCE DESCRIPTION: SEQ ID NO:1072:

GATCTTCGTT CGTGAAAACC TTGCACGTCT TCATGAGCTC AAGAATTGCC TCTGCATCTA         60

TTCTGTCCGG TTGGATTCTG CCTTCCTTAT TGTCCTGAAT CATGCGCGCA AAAGCGCGCG        120
```

```
GCGTCCAGTC ATGACGGGAT CGGCCCTTAT AGGACTTCCC TGCAAGCCGC ATGAGGCTCC      180

GCCAGCCATT TTCTTCAATA ATATTGACAA GTCCTTCGTT TTCCAACACG ACCTTGTTCG      240

CGAGACTGTG GAACGTGTTC ACGTCTATCT GCTCAAGTAT TTCTACCCTT TCCTCAGCAG      300

ACCATCGCAA GTTGCAATCT GCCTCTTGGA ATGTCTCCAT AAGCTTTTCA TTGATGTTAT      360

CCACTGCTTT ATTTGTCAAG GAGAGGATTA GTATTTCATT AGGAGCTACA ATCCCTTCGT      420

AAACCAGGTT GTAGACTTTA TGCAGTAGTG TCACGGTCTT GCCAGACCCA GGTCCCGCTA      480

CCACATTGAC AGTTGTACAA GGCTCATATG GATGTGTTAC TACTCGTGAT GGGACGTCG       540

TCAGTGCTTT CATTCATGTA TGATACATGC TCGAGCGTCG GCGAAGGAAA TAAATTCGTG      600

AATTTCCGTT TTAAGATACT CAAAAGAAAT GAGATAACCG CCCGCAAGGG CGGAGTAGAA      660

TTACAGCAGC TATTGAATAT ATTTAGTTTA TT                                    692

(2) INFORMATION FOR SEQ ID NO:1073:

(i) SEQUENCE CHARACTERISTICS:
        (A) LENGTH: 697 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1652UP (xi) SEQUENCE DESCRIPTION: SEQ ID NO:1073:

GATCTCCCCA CCATTCTCCT CCAGCGCCTT CTGTNAGCGT TCCCGGCGTT GCTCTCTCGC       60

CTTTTGCTTC TTCTCCTTAC GGATTTTCGC ATACAGCGGC TTATTCAGTT CGAACTGTTC      120

CTTCTTCCAC TGTTTCTTCC ATTGCGACTT CGACATGCCT TCGGGAACGG GCGGCAAGGC     180

AGCCCGTGGT TTTGGCCGAC TCAATGTTTC ATCATTATTA GTTCAGGAG TCATTGCCCA      240

GTTTGAGGAC TCTTAGCGCA AGGTCTTGTC ACTGAAGTAC AGTAAAATGG ATGCCCTTTC     300

GCGGTGATGA GGCAATGACC TGGTGAAATT TTTCGCCCAT GGTGAGGCTG TATAGTGGTC     360

ACGTGACAAC AGTTCAGCCC ATATATGGAG CCCCTAGGTC ATATAAAGGG TCAGGAGCCC     420

GCTAAAGTCT TTGTATTCTG ACCTTTTATT GGGGAGCTTT AGGGCGTGTG TCTCTATCCA     480

GAGCCGTGTG GTGAAAAGCG TCTCAGCTCA GCGCGTTCTA CTACACTGAG ATTTAAAAAC     540

CAACAGCGAA GCAGCAGAGT ATGACGTCCT TAGCAACTAA ACTCGAACTT CCATGGGTTG     600

AGAAGTACCG GCCGAAGCTG CTGAAAGATG TGTGGGAAAC GAWGAAACGG TGGAGCGCCT     660

GCAACAGATG CCAGGGATGG AAATATGCCA CACTTGA                              697

(2) INFORMATION FOR SEQ ID NO:1074:

(i) SEQUENCE CHARACTERISTICS:
        (A) LENGTH: 707 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1653RP (xi) SEQUENCE DESCRIPTION: SEQ ID NO:1074:

GATCTTTGAT GCTATTTCGT ACCTTAAGGG CTGTTCCGTG CTGGAGATGA TCTCCGGCTA       60

TATAGGGGAG ACCGTCTTCC TGAAGGGTGT TGCCTTATAT ATAAAGCGGA ATAAGTTTGG     120
```

-continued

```
CAATGCTACC ATGGAGGACC TGTTTGGGGC CATTAGTGAG GTAGCAGGCC TTGATCTCAT      180

GGCGAAGGCA AAAGATTGGA TTCTAAAGAT CGGGTACCCG GTTCTGGACA TCACTGTTGT      240

TGATGGGAAG ATTTCACTGT CACAGAGACG GTACCTTTCG AGCGGACAAG CTGACGCCAA      300

TGACGACCTA ACCACCTGGT GGATTCCCCT GGAACTGACA CAGGACTCAA CTTGCACTAC      360

AACAGAAATG GTTTCTAAAT CCCAAGAAAC AGAGATCTCA GCTACCGATT TTGTGTTCTT      420

TAACAACGAT GCCCACGGCT TCTTCCGGGT GCATTATGAG GATGAGACTA TTCTGGCTAA      480

CATCTGCAAG AACATAGCGC AGCTGTCCTC ACGCAGTAAA ATTGCGTTAA TTTCGGATGT      540

TGATGCCACT GGTACCTTCA CGCAACTCAT GGCTGTTCTG TCTGCATTCT CTGCAACGCA      600

TTCGCAAGAC TACTATGTTA TGGAACTCTG CATTGTCCAT TTTCCACTCG GCCTGCTCAA      660

TCATATATCG CGATGCGTCG CAGAGATCCG CAAGAAGCTT GCGGCGT                    707

(2) INFORMATION FOR SEQ ID NO:1075:

(i) SEQUENCE CHARACTERISTICS:
        (A) LENGTH: 689 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1653UP (xi) SEQUENCE DESCRIPTION: SEQ ID NO:1075:

GATCTAATAC TGGGAGCGAC TGGGCGTTGT GGCGGTGTCT ATCTGTATGC GAACCAGCGA       60

GGCTGTGATG GAGACANATT GTACTACGAT GGTTGCGCGC TCATTGCTGT GAACGGCCGA      120

GTTGTGGCCC AAGGCTCGCA GTTTTCGCTG AGGGATGTCG AAGTGGTTAC TGCAACTGTA      180

GACTTACAAG AAGTGAGAGA TTACCGGATG TCTGTGATGT CGCGAGGGTT GCAGGCAGTA      240

TCGAATAACG TGACTTTCGA ACGTATTCAA GTACCTGTAG AACTGGCCGC GATGCAAGAT      300

AGGTTCAATC CTACGATTAA CCTGACGAAG GCGAAAGCCC CATACTATCA CAGCCCAGAG      360

GAAGAGATTG CGCTGGGCCC AGCTTGTTGG TTATGGGACT ACCTACGTCG TTGCAGAGGA      420

ACAGGCTATT TTCTTCCACT ATCTGGGGGC ATTGACTCAT GTGCCACTGC TGTAATTGTG      480

CACTCTATGT GTCGGATGGT TGTCAACGAA ACATCTGAGG GTAATCTGCA AGTAATTGCA      540

GATGCGAGAA GATTGGCTCG TGCTAGCGAT GACTGGATTC CAACCGATGC ACGTGAATTT      600

GCAAATATGA TATTTCACAC TTGTTTTATG GGAACAGCAA ACTCCACAAA TGAGACTCGC      660

AGTCGGGCAA AGAAACTTGC GGAACACCT                                       689

(2) INFORMATION FOR SEQ ID NO:1076:

(i) SEQUENCE CHARACTERISTICS:
        (A) LENGTH: 598 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1654RP (xi) SEQUENCE DESCRIPTION: SEQ ID NO:1076:
    (xi) SEQUENCE DESCRIPTION: SEQ ID NO:1076:
GATCTTATTA ATTTTGATGG TGCTATATTC TAAATTCAAG TAATGATAGC GCGTGATGCG       60
```

-continued

```
GTACGTACCT ATACATATAA CGCACAGTTC TCCATCGTCT ATGCGTGTAT GAAAATCACT      120

CCAGCCGTGC GACACGCCAC GTGTAATCTA GTGAGTTTCA AGTTCTTCCT CCTCATCGGC      180

AGAAAGTTCG CCCGCGGCGG TGAGGTTCTT GAGCCGCTCC TTGAGCTGCG CGATAAGGCT      240

ATTCTCCCTT TGAGCATGCA TGCGGATACC CTCTAGAGAC ATATGAGCCG AATCTGCACC      300

ATCTAAACCA TGTTCGCTGT TGCTGCCAGT GGCAGCTGCC AGTTTGGGAC TGGACAGACC      360

TGTCTGTCCA TCTTTGTAAG AATCCTCGGT CGTTGCCGAG TTGGAATTCA TGGTTCCCAT      420

AGTGTGCAAG ATTTTCTCCT CTTCTGTTAG TTCCAGATGG GTACCTGTCA GATTGATCAA      480

GGACCTGCCG CTTTTACGGC GCGAGAGCTT GGGCAGAAGA GAGTGCCCGG GTTGGCGTCG      540

CTTCACCAAG GTTTGTAATG GAGGTGTGAG ATCTCGGAGT CCTTGGTAGT CTCAGACA       598
```

(2) INFORMATION FOR SEQ ID NO:1077:

(i) SEQUENCE CHARACTERISTICS:
        (A) LENGTH: 571 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1654UP (xi) SEQUENCE DESCRIPTION: SEQ ID NO:1077:

```
GATCCGGGCC GGGTCCGCSG CAACCAACGA TGTCACGTGT GGATACCAGC GACCTGGTAG       60

GCGTTACGGT GGGAGGAGCA GCGGTTGGCG GAAAACCGGC AGCAGAGCAA GTACTGGCTG      120

AAGTGGGGGC CGTATCTGTC GGAGCGGAGC TGGGCGACGG TGCGGAGGA CTACTCGTTT       180

GACGGCGACG CGTGGCGGCA CTTCCCGTTC GAGCAGGCGA ATGCGCGGGT CTTCCGGTGG      240

GGCGAGGACG GGATCTTCGG CGTGAGCGAC AACCGGCAGC TGGTGTGCCT GAACGTGGGG      300

ATGTGGAACG GCGTGACGA GCTGCTCAAG GAAGCGGATG TTCGGGCTGA CCGGGCCGCA      360

GGGCAACCAC GGGGAGGACT GCAAGGAGCT GTACTACTAC CTGGACAACC TTCCGAGCCA      420

TGCGTACATG AAGGCGCTGT AYAAGTACCC GNTCAAGCGG GCGTTCCCGT ACCAGGAGCT      480

TATTGCGGGC AACGACGCGC GCGGGTACGC GGAGCGCGAG CTCGAGGTGT ACGAACTTGA      540

CGGGCTGTAC CGCGAGGCGG CGACCGGCGA C                                     571
```

(2) INFORMATION FOR SEQ ID NO:1078:

(i) SEQUENCE CHARACTERISTICS:
        (A) LENGTH: 694 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1655RP (xi) SEQUENCE DESCRIPTION: SEQ ID NO:1078:

```
GATCCACTTT CCACTCTGAC ATCGGTCAAT CAACGCTGGG CACTCAGGTT CAGTTCTGAA       60

GCAATTGCAG TCCCCGCAGT TACCCTTCAT TTATTTAGAG ACTTAGTGGT GTTATAAGTC      120

AGTCCTATCG AACAGCTCTC GACAGTCATC GGAAACGAGA AGTTACCCGC CCTTGAGACA      180

CAATCTGTTA CCCGACTTTG ATTTACATGC GTTACCCGCT CTGGGTCACG TGCCGGGAAG      240

CACATGACAA AGGCCGAGAG CTAGTTACGT GAGGCTCATT GGGGTATGCC GGAAACTCTA      300
```

```
ATGACTAGAT CATCCGAGAA GCACCGGTAT ATAAGACGCA TCACGGTGGT GCTCGAGAGA        360

GTGTGTAAAA TGCCAATTGC TTAGCCACTG ATGCCAAATA CACTGGATAA GAGTTACGTA        420

CAAAACGGCC CTTGGAGGGA CGGGGTGTTC CAAGGGAAAG TGGTCTTCGT CACTGGCGGG        480

GCCGGGACGA TCTGCAGGGT GCAGGCGGAG GCAATGGTGC TACTTGGTGC CAAGGCTGCG        540

ATCATTGGGC GCAATGTGGA GAAGACTAAG AAGGCGGCAG CGGAGATCGC GGAGTTGGGC        600

GACTCGGCTG ACTGCGTGCT CGGAATTGGC GGCGTGGACT TCCGGGAGGT CCCGGACATG        660

AAAGCGCGCG GTGGAACAGA CGGTTGCCGC GTTT                                   694
```

(2) INFORMATION FOR SEQ ID NO:1079:

(i) SEQUENCE CHARACTERISTICS:
        (A) LENGTH: 675 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1655UP (xi) SEQUENCE DESCRIPTION: SEQ ID NO:1079:

```
GATCTCTCTG ACCGCCCCCA AACGCTGCTC CGCGCACATT GACACTGGTG TTACCACCCA         60

TTATGTCGGC GGCCGTTTCA TCCCAGATGC CCTGGCCCGT CGTCATGGTT TTGATCCGTT        120

CCCGTACTCT GGCACCGATC AAATACTGCG TATTTGAGTG CATATTGCTT TATTCTATAG        180

TCTGCGTACA TAAGCCGGGG TTTCAGAGGG CGGGTAACGA TGACGCGTAA CGTTTCTTTT        240

TCGTGATATG TAAAAAGAAA TGTGCAAACA TTTTTCATGA GATGAACGTT ATACTGGCTT        300

GTTTCTCTCT TGAAGTCAGC AATCTCTAAC CTTTGAAGGT GATTAATAGG CTGTTGCGTC        360

GTGTTGGAAC ATTGACGGAG CTTTGCTTGT TGTAAGCGAT TAATCTGTGT TGCGAGTTTC        420

ACTTTCTCGA ACTGGTAGCA GGTCTGACGG GTCTGCGAAG GGCGTCGGAG ACTTGCAAAT        480

ATAGGCGCAA GACAACCTGC GAGATACAGG GGAGCTGCTG CAGCGAACAG GTGGAGTGCA        540

GGCGGATCTT GAGGACTAGC TGCTCTGGGA CGAGATGGCG AAGGAAAGCC TGCGGATAGG        600

CGTAGCAAGC ACGGAGCCCA AGCGGGTGAA GGTGTTCATC CTGGAAGACA GCGAGTGGAG        660

AGACACTGGG ACGGG                                                        675
```

(2) INFORMATION FOR SEQ ID NO:1080:

(i) SEQUENCE CHARACTERISTICS:
        (A) LENGTH: 705 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1656RP (xi) SEQUENCE DESCRIPTION: SEQ ID NO:1080:

```
GATCTAGCGA TCAATCGCAG CTAACAGATG CTCTGACATT ATGCATGAGC GCAATCATGA         60

TGGACACATC GAAGCTCAAG CATAAAGTAG AGGACTCGGA CATGCAAGCG TACGCCATCT        120

GCAAAAGCGT GTTGACCAAT ATGAACGAGG ATGCGTACTA CAAGCGCATG AAGGCAGCAA        180

AGAATGACGT AGATGGCTTC TCACTCGATG AGATTCTTCG TAAGGACTAT AAAGAGTTGG        240
```

```
TGTTCCCGAG CCGCAGTGCA GATCTACGTG TTGGCGTACC TACTGTCGTG CGCTCTTTCG      300

AATGGATGCG CGAGAAGTTC GGCGACAATG GGACTACGAA GCTCTGGCAC AGTTTCCTTC      360

TGGAGCATAA GTTAGATTTC CTCGTGGTGC TCACAATTAA GAAGGCCAAC GAGGGTTTGA      420

AACGGGAGTT GGCTATCATG GCCAACTCCT GCGACCGTGC GCAGCAGGTC GAGTTCTTGA      480

TCCAAAGCCT CACCCCAGAG TTGCAGTTGA GCAAGACCTC TGTCTTCTCC CCCGGCTCAC      540

TCGTCATTGA GACGTGCGAC CAGAGAATGC TATCTGCCAG TCGCAAGCAA ATAGTACCTC      600

TCCTCAAGAG AACCGTCGCC GAGTTATAGC ATGCTTATGT AACTAACGTT CCAGTTACCA      660

TCTTCCCACA TCTCAGCGGC AATGTCGCGT TTGTGGTCTC CAACC                     705
```

(2) INFORMATION FOR SEQ ID NO:1081:

(i) SEQUENCE CHARACTERISTICS:
        (A) LENGTH: 670 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1656UP (xi) SEQUENCE DESCRIPTION: SEQ ID NO:1081:

```
GATCTCTTCC TACCCTGTAT TTCTACTTAG CAGGAACCTA AATATGTCGA AATCATCGCT       60

AGTAGGATGT TTTTTCTACA ACACAGACAT TTACGCCAAC CAGAACGCTA AGGCATGCAG      120

TATCTCGCGG AGTATCTGCC TAGGATCGGC GTAATGCTAA TAGTGGTTGC GGGAGAGGCT      180

GGTGAGGTTG AACTGGGAAA ATTGGGTGGG CATAGGTTGA CTGTCACAGT AAATGGAGCG      240

GCCGAGGTGA TCGAATTGCC CTGTGAGGTT GATCCGCTAG CGCGGCCGCG TATTAGACAC      300

TCCGAAGGTG CATTTGAGGT CCGGCTGAAG GCGGTGAATG GGACTGAGGG CCGGGGCGCG      360

GACTTCACTA TGCTGGCTGC AGAGGACGGG TGGGGGCGAA AAGACCTGGC GCGTGCTGAA      420

CTGCGCTGCG CGGCGTGCGA CGGGCTGCTG GTTACGGGCG AACATGCAGG CGCGTGAGCG      480

CGATGCCCTC CGAGTTTTGG ACGGAGCTGA TGGACTACTG GCACTGCCAC AAGCCTGCGG      540

ACGAGTCTGC GGGCGCACAG CAGTACCTGA CGAAATATAA CGCGCTGCTG CCTGCGGACG      600

GGGAGCTGCT GGTGGGGGAC ACATTCGTCA CGGTCGGCGA GGGTCTGCTG TCAGAGAAGC      660

TGGCGATGAG                                                           670
```

(2) INFORMATION FOR SEQ ID NO:1082:

(i) SEQUENCE CHARACTERISTICS:
        (A) LENGTH: 620 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1657RP (xi) SEQUENCE DESCRIPTION: SEQ ID NO:1082:

```
GATCGATTTA GATTTCACCT TCAGGCACAC TAAGAGATGG ACTCCTTACA CTAAGGGTGG       60

GCTGACGGGC GGCGTTGAAC GTGTTTTGCT CGACGGACAG ACTGTCGTGT TAAGCGGTGA      120

CCTAGTACCA TCTGCAGCTC TAGGTGAGGC CGTTGTACCT ACTTCAAACA ATTACACTTC      180

GACTCCTCTA TTGAACGCGG AGCCATTGCA CAGCTTTGTT CCACCTTCTA GCTCGGGTAA      240
```

```
GAAGCGGTTC TCCTTCTCCC GCGAGCGGGG AAACTCGTTT GCTTCAGCTG GTGACCACGA      300

GGAAGCTGTT ATCGACCAAC CGCTGGAACA AAGGTTGATG TCTTCAAGGC CACCAAAGGA      360

GCTGTCGCCC CCAAGTGCGC TGAGAGAGCT AGTCCGTGCG CACAATCCAT TCAGAGGAAG      420

GAATATCTTA TCTGTTAACC AATTCAAACG TTCGGACTTC CACGCCTTGT TCGCTGTGGC      480

CCAAGAGCTG CGTGCGGCTG TCGAGAGAGA GGGCGTTCTC GAATTGATGA AGGGCCGCCT      540

CTTGACGACC ATATTCTATG AGCCATCAAC GCGCACATCC TCCTCTTTTA TCGCGGCAAT      600

GGAGCGCCTC GGTGGTAGAA                                                  620

(2) INFORMATION FOR SEQ ID NO:1083:

(i) SEQUENCE CHARACTERISTICS:
        (A) LENGTH: 578 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1657UP (xi) SEQUENCE DESCRIPTION: SEQ ID NO:1083:

GATCAAGTCC TTCCAGCCGA GCCAGTCTCG CACCGCATAC CAGAAATGCA TTCGCGCACC       60

TAGCGGGATA TTCTGCGCGC TGTACTCGGT CCACGAAAAG GCCCAGCGGT GTGCCAACGC      120

AAAGGCTACC ATCTCCAAAC AGAGCGCCAC ATTGTGGTAC ACGTAGCCCA TGTTCGTGCC      180

CSCGCAGTCC TGAATCACGT TCAGGTAGTG GAGAAGCGTG ATKACCATAC CCTGCCAGTA      240

GGATGCAAAA ATGATCAACT TAACACATAA GAATTTAGGC CATGGGTTGT ACTTGCGCAA      300

CTCGTTGTAC AAGCACTTCC AGAAGAGCGC CAAGTTATAG AGCGACCATG ACGCGCTCGC      360

GTTGTATACA AGCGTCAACC ACTTACATCC CAGATCCCAC TCCAACACCT GGAACGCAGA      420

CATCCCCAAG CAGTACACCG GCTTGAACCA CACGTACTGT AGAATGCCCC GCTTCACAGC      480

CAATAACGCC TTGGGGTCCG CCATATCGAC CATGGGCAAC ACCCAACGTC CCACAACGGG      540

AATCGGGTGC TGGATCCTTT TCTGCTCCGG CGCAAGGT                              578

(2) INFORMATION FOR SEQ ID NO:1084:

(i) SEQUENCE CHARACTERISTICS:
        (A) LENGTH: 693 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1659RP (xi) SEQUENCE DESCRIPTION: SEQ ID NO:1084:

GATCAAAAGT TGATTAAACT AATAAAAGAA TTATTTTATG TATATTGATT GTATAGTCAT       60

TTTCAGACAA AAATCGTGGA AATTTTAGCG GCCAAACATA AAAGTCAGAC ATTAGAAACT      120

GACAGATACT TTATTTACTG CATAATTACA CTAAAAACAA CTGTTCTCAA AAACTACGGA      180

TTATTGACCG CCCCCTCACT AATAATGTAC TCCTTCTATC GGTTTCTTGC GGGTAGAAGC      240

ACGTAAAGAG ATCAGTTTCA CTTTGCAATT TGGGCACTTT TACGTTTCCA CTTAACGATC      300

ATTCTAGTGT ATTTTATGAC CAGGAAAGAA AAGGAGCCTA AAAACCTGAA GGCAGCCAGA      360
```

```
CCAGCGACTG ATCCCAAGAC AAAAACCAAA TATTTGTTAT TAGAGGTTTC TTCAGGTGAG      420

TATATTTGGG TTATCATCAT GATCAAAATC AAATTGGAAA GCATCCATAA CATGACAATT      480

CTAGTCCGCA CATCACGGTA GTGATCTGCT TGCTTTTGGA TAGGATCAAC TTTTATTTCT      540

ACCACTTCAT CCGATTTTAG ACGACCTTGA TTTCCTGGTA TTTATTATCG ATGTCCTGTG      600

GCCATTCAGT ACCCTCAACT ATTTGTTTGC CACGGGGCCC TGGGTAACCA TAGCTTCAGA      660

CTTTGGCTTG GACCCCTGCG AAGCGCCTTT TGT                                   693
```

(2) INFORMATION FOR SEQ ID NO:1085:

(i) SEQUENCE CHARACTERISTICS:
        (A) LENGTH: 726 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1659UP (xi) SEQUENCE DESCRIPTION: SEQ ID NO:1085:

```
GATCGAGTGG TCCACCAGGT AGTCCTGGCC CGGCTTCACG TTCGGCGGCG TCGAGAAGTA       60

GACCCGGTAC TGCTTGCACG CCTTCTTCAC CTCCTCGTAG CTGCCCGTCA GCCCCACGAT      120

GTCGGGGTGG AACTCGGCCA GGTACTCCTT CAGCACCGCC GGCGGGTCCC GCGCAGGGTC      180

GCACGTCACG AAGATCGGCT GCACGTCGAT GCCCCGTTGT TCAGTCCGC GTAGCCACGC       240

CGCCAGCTTG TCCAGCTCCG CAGGGCAGAT GTCCGGGCAG TGCGTGAAAC CGAAGTACAC      300

CAGCGAGAAC CGCCCGAGAA GGTTCTTCTC CGTGAACTCG TTGCCGTTGA AGTCCACCAG      360

CTGGAACGGC CCGCCCACCG CCGGCCGCCC GTACCCCCGG TTCGCCTCCG CCTCCCGCTG      420

CACCTCCAGC CGCCGCTTCT CGCGCGAAAA CACGTAGAAC AGCCCGCCGC CGAGCACAGC      480

AGCACCGCCG CCGCCTTCCA CGTCGTGAAC TCGATCGCCC CGCCCTCGAC CGCTGCGAGT      540

GCGTTTCCTG CGCCCCCAGC GGGATCCGGC TCAACGGCCG CCGCTTGCCC GGCGCCTCTG      600

GCCCGCCGGC GCCTCCTGCG TCGCCAGCCG TGTTCGCGAG AACTCCCGCA CCCCGCCAAA      660

CGCTGCTCTC TGCCTTGCAA TTCCCGCAGC TTGCCTGCAA ACACCGAGTC CTACTGATCA      720

TCTCTG                                                                 726
```

(2) INFORMATION FOR SEQ ID NO:1086:

(i) SEQUENCE CHARACTERISTICS:
        (A) LENGTH: 720 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1660RP (xi) SEQUENCE DESCRIPTION: SEQ ID NO:1086:

```
GATCAATTCG ATGCCAACCA AGATGAAGAC CATCTGGGTG AGTTAGCAGT GCACTCTGCG       60

GATACATGGT CTGAGACGGA TAGGAATCTA ATTTTGAAAT TATTGGGCAA GTTCAAGAAT      120

ATCAAAGCTA TTTACAAATC CGAAGATGTC CGCCAAAGGT TGATGGAATT ATTGGGTAGT      180

CGAACGCTGG AAGTGCAGAA ACTGGCCCTA GATGCGTTGT TAGCATACAA GGATCCAGTA      240

GCTGTGAAAT ATAGGGACAA TCTGAAGAAC TTATTAGATG ACACGTTATT CAACGACGAA      300
```

```
GTAACAAAGT TATTTGCTCA GAATGAGTCA AGGGTTATTG TCAACACTGA TGAAAGATTA      360

TTAATGCCCT TCATTTTGCG TATTTTATTT GGCCGTGTTC AGACACCTAA TACCAGTGGG      420

ATCAAAAAGA CAAGAAAAAC TGCGGTCATA ACTGTCCTGC CAAATTTAGG TGAGAAGAAT      480

ATTACTGACT TCTTGGCTCT GGGTAGTAAT GGTATCAACT ACCAGTACTT CTTTGAAGAG      540

AATGCGGTTA TTCCTGACAG TGAGCTTACA GCGATAAATT TTAGGAGAAT GCTTGGCTTC      600

ATAAATGTCC TAAGTGCCTC GTTGAATGTT TTAGGTTCCA ATTTCCCGGA GGCGGTCAAG      660

ACAACTATTA AACCTCTCGT TTACGCAATT CACATGTCAG GTCGTACTGG ACAGAATAAA      720

(2) INFORMATION FOR SEQ ID NO:1087:

(i) SEQUENCE CHARACTERISTICS:
        (A) LENGTH: 651 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1660UP (xi) SEQUENCE DESCRIPTION: SEQ ID NO:1087:

GATCTTATAG ATTTTCATCC CCAAGCTTAC AAAGAGAACG TTATCCACCT GTTTTAGCCA       60

GGCTTGGATG TATTTTTCAA TGGTACCCAT GTTCTCCTGG CCCAAGTTCT TGAACAAGTT      120

AGTTAGTAGC AGACTAGCCA TCTTCCTGCA TTTAGGAGAG TCGTCATTTA CTGATACGTT      180

TGCTAGGAAC ACGAAGAATG AGGATGAAAG TTTCATTAGT AAAGCGGGCC CAGATTTGTT      240

GATCAGAAGG TTAAGCAATT CCATAACAGA TTGACGACCT TCTTGAGATG GATACTGCAA      300

ATTGTTGACT AAAAATTTCA ATTGTTTTTC CAGCCTGCCT TTACTTTGAT CATATTCCAT      360

GAAGAACTGG TAATAGACAC TCCTGGCAAC ATCCCTGATT TCCTTAGCAT GATTCGTGAC      420

CATGACTTCT GCAACGTTAT CAATAATATC GTACAGCTTC GGAAGAACAA TATGTTTGGA      480

AACCAAGGAT TTCAAAAATC CAAAAGCCAG ACCTTGCTTA TTGGGCTCCA TCAAATCTGG      540

TTCAATCCGA CCCAAAACAT ATTCGAGCGC AGAATCCTTT AATTCAATGT CTTTATAGCG      600

GATAAGCGCA GATAAAAACT TCAGACCGAC TTGACAAAGT TCACCAGAAG T              651

(2) INFORMATION FOR SEQ ID NO:1088:

(i) SEQUENCE CHARACTERISTICS:
        (A) LENGTH: 96 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1663RP (xi) SEQUENCE DESCRIPTION: SEQ ID NO:1088:

GATCGCGGTT TCATCTCCCC ATACTTCATC ACCGATGCGA AGGCCAACAA GGTGGAATTC       60

GAGAAGCCAC TGTTGCTTTT GTCCGAGAAG AAGATC                                96

(2) INFORMATION FOR SEQ ID NO:1089:

(i) SEQUENCE CHARACTERISTICS:
        (A) LENGTH: 583 base pairs
        (B) TYPE: nucleic acid
```

(C) STRANDEDNESS: single
        (D) TOPOLOGY: linear (ii) MOLECULE TYPE: DNA (genomic)

(vi) ORIGINAL SOURCE:
        (A) ORGANISM: PAG1664RP (xi) SEQUENCE DESCRIPTION: SEQ ID NO:1089:

```
GATCCTAGGG TGGTTCATGG CACTGAGCGG GACGTGTTCT TGGACCGGTC GAACCGCAGC      60

AAGAGTCTGA AGTCCTTGAA CGCGTCTCTG GAGCGGCTGA AGCGCAATCG GCAGGCGGCG     120

TGGATTTTCC CAGAGGGCAC GCGGTCGTAC ACAACGGAGA TGCAGCTGCT GCCATTCAAG     180

AAGGGGCGT TCCACCTGGC GCAACAGGCG CAGATTCCGG TGATTCCGGT TGTGATGTGC      240

AACACGAGCA CGGTGTTCAA CCCGCGGCTG GGCATCTTTA ACCGCGGCAC GATCACGGCG     300

AAAGTGCTGG AGCCGATCGA CACGGCTAAC ATGACCAAGG ATGACGTGGA CAAGCTTGTG     360

AGCGACGTGC AGGCCAAAAT GCATGCGGAG TTCGAGGCGC TTGGCTACGC GCCTGCGATC     420

GTGGACACGA GCCTACCCGA AGAGGCGCTG CGGCCGGAGT TTGTGGACTG CAAGGAAGAC     480

ATCACGGAGG TAACGCGCCT CTCGAAGTAA CCTTGGTTGG TATCATATAA ACGTTGCGAC     540

GAGTTATGTA CATATAGCGC TGCTAAGTAG GCATTCAGTC CCC                      583
```

(2) INFORMATION FOR SEQ ID NO:1090:

(i) SEQUENCE CHARACTERISTICS:
        (A) LENGTH: 598 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1664UP (xi) SEQUENCE DESCRIPTION: SEQ ID NO:1090:

```
GATCCGACTG ACGGTGAATA GGCCACCGTA GCATGCGCCG CTGAGCGCGC TGGCGAACGA      60

TAGCAGCGGT CCTTCCGAGG CTCTGGTGGC CAAGACAACG ATCCACTGGC CCACCACGCC     120

CAGTAGGAGG ACTGCCCACT GGACTGACAT CGTCGACACA CCGTTGTGGA TGCAGAGGTC     180

AATTATCAAG CCCGACAGGA AGCGCGAGCA CGTCGAGGCA ATCGCAAATT CTGGCAGCAC     240

CGACGCCTGG CCCAACAGGC TCGACAGCGA GCCCATGTTG GTGAGGAACA TCTCCATCGG     300

GCCCAGCGAC AATAGCAACA CAAGGGCCAT GAAGTACGCC GCTGGGTCGT GGAAGAAGTT     360

GCGCAGCCGG CGGCGGATGT CCTGCGGCAG CAGCGGCTCG GTGGGGCTCT GCATGCCCGC     420

GAAGGTCAGT GTTGCGGCCT TGACCTTGAG CATAGTGACG ATGCTCGTCG CAAACCACAT     480

GCAGAAGCTG ATCAGCGTAT ATGCGACAGC TAGAGTCCTG AATACACGAG AAAGGTCAAG     540

GTACGGCAGG CCATTTCCAA AACCATGGTA TCTTCAGCAG CTGCGACCTA GCACAGAC       598
```

(2) INFORMATION FOR SEQ ID NO:1091:

(i) SEQUENCE CHARACTERISTICS:
        (A) LENGTH: 713 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1666RP (xi) SEQUENCE DESCRIPTION: SEQ ID NO:1091:

```
GATCCTTGCG TACTAAGAGT TAGACTTTAA TTAATAATAT TATTTGTAGA AGATAGAAAC      60

CATACTGACT CACGTCGTAT TTAACCCATC TCACGTAACC TTTTAATTGA CGAACAGTCA     120

AACCCTACTT AGCTGTTACA ACCAAGAGGA TAGGTTGAGT CGACATCGAG GTGGCAAACA     180

TAACTTACAA TAGCTACTCT ATCGTTATAT TACCCTGTTC AATTTTGTTA TCATAATAAC     240

ATTTAATTAT TATTTCAATA ATTCTCATTA TTGTTCAGAC TATTTCATTA TGTATTATTT     300

ATTAATTAAT ACATATTGGG CTTTCGTGGA TATAATTATT GTTAATCCTA CTCATATATC     360

TAGTCGTTGA ACGTTCTTAT AACTTTATAA AAAGGATTGT TATAAGCTTC GCTGCAGATT     420

GTCCTTTATT ATTATAAAAT AATATTAGGA GTTCTTTGCA ATTAACCCAA TTTACTCAAT     480

ATATTTAAAT ATTGATAATT AAATTTCACA ATTTAATGGG ACTATTAATT AATCCCTAGC     540

GTAACTTTTA TTCGTTATCA AATACCATTA CAATATGTAT ATTTTTGTTC ATTATGCCAA     600

ACTTACGTTA TTGTTCTACT TGTAGGTATT ACAATTATAG CACAGTTATA CCATTATATT     660

TATTTAATAT ATTATCCCTA TATTATGTTT TATTAACATA TAAAACTGTA CAT           713
```

(2) INFORMATION FOR SEQ ID NO:1092:

(i) SEQUENCE CHARACTERISTICS:
        (A) LENGTH: 677 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1666UP (xi) SEQUENCE DESCRIPTION: SEQ ID NO:1092:

```
GATCCTTATA AAATGGGCAA TAGACGTGTT ATAATATAAT ATACAAAATT ATAAATAAAT      60

ATTTAATAAA ATATAAAATT AATAATTAAA GTATTATAAT AATTAATAAA ATTATTTATT     120

AATAAGTATG GATTTTTAAC TGAAATTTGT TAAAATGAAA TAAGAATTGC TAGTAATCTA     180

TTAATAAGAA AGTAATGGTG AATACTCTAA CTGTTTCGCA CTAATCACTC ATCACGCGTT     240

GAAACATATA ATTAAATAAA GAATATTAAT TAATTTATTA ATTATTAATT ATTATTAATA     300

TTATTTAATA AATATAATAA ATATTTTAAT TTAAATTATG AATTAATGCG AAGTTGAAAT     360

ACAGTTACTG TAGGGGAACC TGCAGTGGGC TTATAAATAT CTTTAATATT CCATTTTTAT     420

AAAATAAATA TATTTTTTAA TATATTTTAT AATAACTATA ATTAAATAGT TAAAATTTAA     480

ATTATAATTT AATAATTTAA TAACTTATTA ATTAGAGAGT TAGGGTACAT CCCCCCTAAT     540

GCTATGCATT ATGGTTGGTA CCACTCTAAT TAATAAACTA TAATAAATAA ATACTAATAT     600

TTTATATCAA TTAAATTATA ATTATTTTTT ATTAATATTT TAATATTATT TAATGAAATA     660

TATAAATAAA GTATTAT                                                    677
```

(2) INFORMATION FOR SEQ ID NO:1093:

(i) SEQUENCE CHARACTERISTICS:
        (A) LENGTH: 707 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:

(A) ORGANISM: PAG1667RP (xi) SEQUENCE DESCRIPTION: SEQ ID NO:1093:

| | | | | | |
|---|---|---|---|---|---|
| GATCCATCGT | GGTGTCGTTC | ATTACCTGTA | ATTCCATTGA | TATCCTGGCT | ATGCAGTGCT | 60 |
| GGAAACGCTC | CTCCAGCGCC | TCTATTTTGT | TATTCAGCTC | CAAGTACTCC | GCGAGCTTAA | 120 |
| AGGTCAACGA | GAGCGACCCT | GGATTGCACC | TGACGGCGAT | CTCAAGGACC | TTCTCGTGCT | 180 |
| CGTTCTCGTC | CACAAACATG | GCGTAGTTGT | ACCATATCTC | CGGCGCAAAG | CACATGTGCT | 240 |
| GCACAGCCTG | GCGGTGCACG | TATTCCACGC | GCTGGCGCAG | CACGACTTCG | GGCAGGTCGA | 300 |
| GCTTGTTGTC | CAGCTCCCAC | TGGATCCACT | TCGTCCAGAT | CTGCAGCTGG | TACTCATCGT | 360 |
| ACTGACCGGG | CGCAGGCAGG | TTCTGCTGTG | TCGCCTGGTT | TAGCTTCGTG | GGCAGCGAGC | 420 |
| GCCGCAGGCC | CTTCGTCAGG | TTCGACCACT | CCTGGTACAG | CGAGCGCGCA | TTCATGTAGC | 480 |
| TCGCCGAGAG | CTCTCCGATG | AACTTCCGCG | CCGTCAACTG | GTTGACCTCC | TGCTCCCACT | 540 |
| GCGTGTATTT | CTCCCAGTAC | CGCTCCAGCG | ACTCCACTGG | CAGGCACAGC | AAGGCGCTTG | 600 |
| TACAGCTTGC | GCAGAATCTC | GACCCGGCTC | TGCTCCTCCC | ACTTGCTCAC | CGGCTTCCAC | 660 |
| TGCTCCAGAA | ACTGCAGGTA | GTCCTGCCAG | AACTGCATCG | ACCGCGG | | 707 |

(2) INFORMATION FOR SEQ ID NO:1094:

(i) SEQUENCE CHARACTERISTICS:
        (A) LENGTH: 723 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1667UP (xi) SEQUENCE DESCRIPTION: SEQ ID NO:1094:

| | | | | | |
|---|---|---|---|---|---|
| GATCTAAGGG | ATGGGTGACT | GCTGCCGGTG | CTCACAGCAG | TGGCACGTAG | CTAGTAATGG | 60 |
| TGCGAAATCG | ATCAAAGAGG | GTGCGTCTGG | CGGTACAGGC | AGAAAGCACG | CCCGCCGATA | 120 |
| CAAGTTCCAG | TTCTACAAGC | ACCTGCAGTT | CCAGGGTACG | AGGTACCAGG | TGGTGACTTC | 180 |
| GCGGCCGTAT | CTGATAGAGC | GGTACGGGGA | GCGCAAGGCG | GCGACGATCA | GGTCGTTTGT | 240 |
| CAAGTGCATC | CATCGGAAAA | TCAACGACGA | TGTGACACGG | ATCAGCGACG | AGCGGGTGAC | 300 |
| GCACGGGGTG | TCGAAGTGGG | AGAAGTCGAA | GCTGTTCCTG | CTGCTGGTGA | CGCTGTCGCA | 360 |
| GCGGGGCGGG | CCGGAGTACT | GGCTGGACAA | GACGAACGGG | TGCCAGAGCC | GCGCGGGCGG | 420 |
| AGACGGCGCG | CGGAAGAGCG | ACGAGGTGGA | GGAGGGCGGG | AGCCGGCGGG | GCCAGAGGCT | 480 |
| CGTCTGCACA | CTGGTGGAGC | AGATCATGCG | CGAGAACATC | ACGGAGGACT | ACGACGAGAG | 540 |
| CGTGCACGAC | GAGAACTACG | TGTTCTCGTC | GATATGGGCG | AACTTCATGG | AGGGGTTGAT | 600 |
| AAACCACTAC | CTAGAGAAGG | TCATCATACC | CAAGTCCGAG | CTGAAGGTGT | GCCAGCAGCT | 660 |
| GTACCAAGCC | GATGATGAAG | ATCATCTCAC | TCTATAACGA | ATACAACGAG | CTCATGGACA | 720 |
| AGA | | | | | | 723 |

(2) INFORMATION FOR SEQ ID NO:1095:

(i) SEQUENCE CHARACTERISTICS:
        (A) LENGTH: 722 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
    (A) ORGANISM: PAG1669RP (xi) SEQUENCE DESCRIPTION: SEQ ID NO:1095:

| | | | | | |
|---|---|---|---|---|---|
| GATCAACAGC | ACCTCCACCT | GCGACAGGTC | GAACTCATCG | TAAAAAGGCA | GCGACGCGAT | 60 |
| ACCCTGGTGG | GCGGGATGCA | CACCGGCATC | CAGCATGACC | GTCTTGCCCT | TATACTGCAA | 120 |
| TATATGGCAT | GAGCGTCCAA | CCTCATTGCT | GCCCCCAAGC | CCGAAGAATC | GGAACGAATT | 180 |
| CGTATCTAAC | TTCTCCTCCG | TCATCCGCAA | TTTGTTTATG | TCTGCCTGCT | GCGAGGTGCT | 240 |
| GTGCTCTCTA | CCCAATGCCT | GCGACACTGG | CTACTGAGAC | AATTCCACGT | AGCTGCTGCT | 300 |
| GCAACTTTTT | TGCAGCTATG | GAAATACCGT | GGTTCGGTAG | ATTTGATTCT | GTGGAGATGA | 360 |
| ACGATCAAAC | GGGAACACTG | GTTATCGGTG | ATGCGTGTTG | TTAGTACCCA | ATCACCCGCA | 420 |
| GAGACAAGTG | CCACTATTAA | TTGTAGTACT | TACAGGAACA | CCGATCGCAA | GAACTCTTAA | 480 |
| CGGCTCCGTT | TACCAACGAT | CAACACTTTT | CTCCTCGAAC | GTTATGCTGT | GCGGCGGTGG | 540 |
| CGATTGCGAA | TGATTGTTGA | ATTGAACCAG | AGAGCGGAAA | ATTTTCGTTC | TCACGTGACC | 600 |
| GTATCTTACA | TAAGCTACTG | AACTATATGA | ATACCGACG | TTGCTCGAGG | ACCGCTAGCG | 660 |
| CAGTGTCTCA | AGCAGTGATC | ATGAGATTGA | GTTGTTCTGA | TGTGTACATT | GAGAGTACTG | 720 |
| GG | | | | | | 722 |

(2) INFORMATION FOR SEQ ID NO:1096:

(i) SEQUENCE CHARACTERISTICS:
        (A) LENGTH: 675 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1669UP (xi) SEQUENCE DESCRIPTION: SEQ ID NO:1096:

| | | | | | |
|---|---|---|---|---|---|
| GATCAACAAG | TGCAACAGCA | AGGTGCAGTT | GCGCCATGTG | CCCTCGGGGA | TCGTGATTGA | 60 |
| GTGCCAGGCA | ACCCGCAGCC | GCGAACAGAA | CCGCAAGCTG | GCCCGCGAGA | AGCTAGCCGC | 120 |
| CGCGCTGGCG | CAGCCCCCCG | GTAGCGCCAG | CGAACGCGAG | CTGGCGTTGC | GCACGTGGGC | 180 |
| GCGGCAGGGT | AAGCACGCGC | AGGCGCGCAA | GAGCCGCGAG | AAACACGAGC | GCGCCCGCGC | 240 |
| CGAACGCGAG | GAGCTCGCGC | GCGCCCGCGA | CGCGGAGGAC | GCCGAACTTC | TGCGTCAGCT | 300 |
| GCTCGCGAAG | CCGCCCGCCA | CCTCCTAGTG | CCCCGCGGGG | CCGCGGGGGG | ACGCAGGGGC | 360 |
| GTCTTTTTCG | GCAATTCCAA | ATAGACACCC | TAGTCGCCTC | TGCTGCCCGC | GAGCGCAGAG | 420 |
| CAGGCAGCTA | GCACACCACC | GTCCACGCGC | AGCGCTTTTG | CTGGCGAGTC | GTGCCGCAGT | 480 |
| CCGCTGGCTC | TGGTGTGCAC | ATGCCGCTCC | GGCGTGGCAC | CGCAGTGCAG | AGCTACCTAC | 540 |
| GTACGTTTGC | AGGCTTCGCA | GTACGCCTGA | TACTGGCTCT | GGTGAAACTT | CCCGACAAGA | 600 |
| GTAAAATCTC | ACCAAAGAAC | AAAAAGATAT | GTTAGTGAGG | ATATCTCACA | TTCTGTTACT | 660 |
| GGAAGTACAC | AAAGT | | | | | 675 |

(2) INFORMATION FOR SEQ ID NO:1097:

(i) SEQUENCE CHARACTERISTICS:
        (A) LENGTH: 697 base pairs
        (B) TYPE: nucleic acid

```
        (C) STRANDEDNESS: single
        (D) TOPOLOGY: linear (ii) MOLECULE TYPE: DNA (genomic)

(vi) ORIGINAL SOURCE:
         (A) ORGANISM: PAG1670RP (xi) SEQUENCE DESCRIPTION: SEQ ID NO:1097:

GATCCGGCAA GATCGTCGTT CAGTTGACCG GCAGATTGAA CAAGTGCGGT GTCATCTCTC      60

CAAGATTCAA CGTCAAGATC AACGACGTCG AGAAGTGGAC TGCCAACCTA TTGCCAGCCA     120

GACAGTTCGG CTACGTCATC TTGACCACCT CCGCCGGCAT TATGGACCAC GAGGAGGCCC     180

ACAGAAAGCA CGTTGCTGGT AAGATTTTGG GTTTTGTCTA CTAAGCGGCT GCTATATAGC     240

GTATCTAGCT CTAATGTACG ATACTCAGTG TCTATTACGA CGGCCGCGAG CTCCACGCGC     300

CACATACGAG GCCAGCCGGC GACGGCAAGC GGGAATTCAG ATGCGTTAAT TAGCAGTAGA     360

TTAGTAGTAT ATATGTACAA ACAGCATACA CATGAACGGC GTCGCCGATC ATAATCTTCT     420

ACCTCTTCTA CCACCCTTCT TTCTGGTAGA GTCGGATGGG ATAGGAGTGA CGTCCTCGAT     480

ACGGCCGATT CTCAAGCCGG ATCTGGCCAA AGCTCTCAAA GCAGCCTGAC CACCTGGACC     540

TGGGGTCTTG GTCTTGGTAC CACCGGTAGC TCTGATCTTG ACGTCACAG CAGTGATGCC      600

GACCTCCTTA CACTTGGCAG CGACGTCCTG AGCAGCCAAC ATGGCAGCGT ATGGAGAGGA     660

CTCGTCTCTG TCGGCCTTGA ACTTCATACC ACCGGTA                             697

(2) INFORMATION FOR SEQ ID NO:1098:

(i) SEQUENCE CHARACTERISTICS:
        (A) LENGTH: 713 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
         (A) ORGANISM: PAG1670UP (xi) SEQUENCE DESCRIPTION: SEQ ID NO:1098:

GATCTATTTG TGCCGTCCGC CATTAAGCAA GCGGCAAGCA TCGATCCAAA TCATGAGAGT      60

ACCCTCGGGC TTTCACTTTC CAAGCCTTTA TCAACAAATC TGGTACACGA TACATCCATC     120

GCGACAGCAC ATATACCAGA ACGGGAAAGC CGACAAGATG GCACTAGACT CTGGTAGGTA     180

ATCTGAGTTC GACCATATCC ACTTCGTTAA TGGTGATAGT TGATAAAAAG AAACGATACT     240

GAAAATTTTA ATGGTTACCA ATCTCATCTC ATCGCCATAC TGAAAGAATA TTGTAGGTCT     300

CGCAGTGGAA CAAGGATCAA GCCCAGGCTA AGACAATAAT GGTTGCAGCG GAGGCAGTAC     360

AGGAACTACC CCCAGATGAA GAAGAACTGG CCTTGGCTAA GCTAGTGTTT GGCGACACAG     420

CAGACTTCCA TGAAGCGCTG CGAAATGCAG ACCTTAATTA TGTTTCTTCA GATGAAGACG     480

TATATGGCCA GGAGTCGTCC AGTGATGACG AAGAAGGGAC TGAAATTGGT CACCTGAATG     540

ATGACCAATT GTTTTTTGTG GACGAAGGTG CAGATACCGA GGGAAGAGCA GATGGAGAAC     600

CGGAGGCCAT GGAGGTGGAC CAGGTTAGCG AGGAAAGCGA CTCCGGAGAG GAAAGCGGTA     660

GCAGCGCTGC ATGGTCAGAT TCGGATGACG AACACTTAAA CGTTACAATA GGG           713

(2) INFORMATION FOR SEQ ID NO:1099:

(i) SEQUENCE CHARACTERISTICS:
        (A) LENGTH: 743 base pairs
```

(B) TYPE: nucleic acid
            (C) STRANDEDNESS: single
            (D) TOPOLOGY: linear (ii) MOLECULE TYPE: DNA (genomic)

(vi) ORIGINAL SOURCE:
            (A) ORGANISM: PAG1671RP (xi) SEQUENCE DESCRIPTION: SEQ ID NO:1099:

```
GATCGCTTTC AAACCATCCT GTAACTACGC TGAACCACAC TTTACAAGAC AACGGCATAT    60

CGACAATCAC AAGACTTCCT CGAGACATGC CCGCCACCAA TCTTCATCGT GTACTGACGG   120

ACTATAATCC AAGTGGCCAT TTGAATTCGC AGCATGATGC CACGCTTTCC AACCTGAGCT   180

CGAAAACTGG AGATGTACAT CGGCCTTCCA ATTCCTCTTC GAGTTTTAAT GGAGCACAAA   240

AAAGGGCTAG CATCCCAAAT ATCTTAGGCT CTGCTCCACT TAGTAATCAA TCAAGAACTC   300

CAGACAACCG TTTAACACAT GGTACATCGA TCCATGAGAA CCCGCGGTTA GAATTAAACG   360

GTGATCAGTC TTTACTCTTT GGCGGTAATA CAGGGCAGGC ATCGGGTAAC TTGGCGGGTG   420

TTTCACCGGC CGAAAACTCC CGAAGGAGCA ATTCGCATGA TCAGAGCCAA TATAGATTAC   480

ATTCCAACGC TTTCCATTCG ACTGCCCCTC CAAACGAACC TTCTAAGAAC ACTAGTCCAG   540

GTACAACTGT TGCACCTGCG AGCGTTGTTG GTACAAACAC AAGGAACACA CAACGTGGAC   600

CCACGGGAGA TGTCTCCCAA GAATCAGTCG AACAGCCGCA ATCAGCTTCG CGCGCATCCG   660

ATGAATCTAG CGCAAGAATT ATGTCGCCTA GTCATCATAC GGAGCCAGTA GTGTCTGTTT   720

CGACAATCTC TTCTAACACA CGC                                          743
```

(2) INFORMATION FOR SEQ ID NO:1100:

(i) SEQUENCE CHARACTERISTICS:
            (A) LENGTH: 661 base pairs
            (B) TYPE: nucleic acid
            (C) STRANDEDNESS: single
            (D) TOPOLOGY: linear (ii) MOLECULE TYPE: DNA (genomic)

(vi) ORIGINAL SOURCE:
            (A) ORGANISM: PAG1671UP (xi) SEQUENCE DESCRIPTION: SEQ ID NO:1100:

```
GATCAGGGAT GCGGAGGACA TTCCGCGACG TTATCGGCGA GCACGACCTA CGCGTCTGGA    60

ACTATGTCAA GTACGGCAAG AAAGCTATTA AGGCCTTCGG CTTCTCGCCA GACGCATATA   120

TTCAACAGAT CATCCAGCTA GCCATCTACA AGTATGTGGG CAGACAATTG CCAACCTACG   180

AGGCTGGGTC GACCAGAAAG TTCTTCAAGG GTAGGACCGA AGCGGGCCGC GGCGTTTCTC   240

CGGCCTCCGC CAAGTTTGTG AAGACTTGGC AGTCGCCGGA AGCATCTCCA AGTGAGAAGA   300

TTGCTGCTCT ACGTGAGTCT GCTAAGAACC ATTCGTCGCT GCTAAAGATG GCGGCGGACG   360

GCCAGGGTGT TGACCGCCAC TTCTTCGGTA TGAAGAACAT GTTGCGTGAT GGCGAGGAGC   420

ATCCTGCACT CTTCCGCGAC CCGCTGTTCC AGCACTCCTG CACGTGGTAT GTGTCTACCA   480

GTCAGCTATC TTCGGAGTAC TTCGAGGGAT ACGGCTGGTC GCAGGTGAAC GAAAATGGCT   540

TTGGTCTGGC GTACATGATC AACAATGACT GGTTACACAT CAACATTGTT ACMAAGCCTA   600

AGAAGTCGGG CTATAGTGTG CACGAGCTTT CACTACTACT TGACCGAAGC AGCAAACGAG   660

A                                                                  661
```

(2) INFORMATION FOR SEQ ID NO:1101:

(i) SEQUENCE CHARACTERISTICS:
        (A) LENGTH: 623 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1672RP (xi) SEQUENCE DESCRIPTION: SEQ ID NO:1101:

| | | | | | |
|---|---|---|---|---|---|
| GATCGTGTAT | TTGTCAGGCC | CATCCAAGCC | CTCCCCCGCA | CCCAAACCCA | CTATGATGGG | 60 |
| CAAGAAGTGC | TCCAACGTCG | GATGGGCAGC | CTGCAACAGT | TCTCGTCCCT | CCGCGCTCGA | 120 |
| GAAGAGACGA | AGTAGTCTGC | CGAATTTACA | GGCGTTGGGC | GGCGTGGTTA | GCAGGACGTT | 180 |
| GGACAGTGCC | CAGTGAAAGG | CAGATGAGCG | CGAGTGGCTT | TTTGCGATGG | CAGATCCGCA | 240 |
| GAAGAGATCT | CTCAGGTTGT | GCACAGCCAT | GCCAGACGTT | ATTATCAACC | CGCCGAGGTC | 300 |
| GCGGTACCTG | GACAGGAGGC | GCCCGAGCGC | ATACTGGTCC | CGCAGGTCGT | TTCCCGCCGC | 360 |
| CAGTGATATT | TGGACCAGCG | GTACCGGGAC | ATCCCAATCG | TCATCCACGC | ACTTCGAAGC | 420 |
| GGAGAACGCA | ACTTTTAGGG | GGACCCAAAC | GCCATGGTCT | ATGCCGCGTT | CTGTGAGCAC | 480 |
| AGCGCATAGC | GGGCTGCGTA | TGTGGTTGAT | GGTGTCCGCG | ATGTCGGTAA | CTAAAGCCAT | 540 |
| GCTTGATTTG | CTATGGAACT | CCTCCTCGTA | CATCCGGGTC | GAGAACCCAT | AAAAATCGTA | 600 |
| TATCAATTCG | TTCTCCAACG | GGT | | | | 623 |

(2) INFORMATION FOR SEQ ID NO:1102:

(i) SEQUENCE CHARACTERISTICS:
        (A) LENGTH: 694 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1672UP (xi) SEQUENCE DESCRIPTION: SEQ ID NO:1102:

| | | | | | |
|---|---|---|---|---|---|
| GATCCCAGAT | TAGATATTAC | TTAAACGTTC | CACAGCTTTT | TGATGGCCTA | GTTCTGCTGC | 60 |
| ACGTCTATAA | TGGTCCATCG | CCCTGTGCAT | GTCGGGATGA | CAGCCGACCG | CGTGCTCCGT | 120 |
| ATAGAAGCCC | AAGGCATACT | CCGCTTTCGG | TAGCCGGCCT | TCGGAAGCAA | TGGATGCTTT | 180 |
| ATACGCCCAT | TTGTAAGATT | CTGAAGCGTT | GGGTTCCAGC | ACGCCCTTGA | CACCAGTTAG | 240 |
| GTACCAACCA | CTCAAAGCGA | GCATAGCCAT | GGCATTTCCC | TTTGGTGCTG | CGTTTGCAGC | 300 |
| CTTCAAGTAC | CACACGATGG | ATTTCTCAGG | GCTATACGGC | AAGTGTAATT | CAGCGTACTC | 360 |
| GTAGCAGTGT | CCCAGCTTCC | ACTGAGCAAG | CGGATAATTA | AATTTAATGG | CACATCTGAT | 420 |
| GTAAAGGTCT | AGAGCCTTTA | GGGTATCTTG | TGGAACGTGC | TGCAACTTGA | CAGCCTGCTG | 480 |
| CAGCTGTGGA | TGCAAACAAT | CAAATTCATA | GATCTTTGCG | AGTTCGTATA | ACGCCTGGGG | 540 |
| AGAGACGGTC | TTGTCGTGTG | CAGCAGCCCG | CTCGAACCAT | CGTATAGCAG | AAATGACATC | 600 |
| CTGTTCAACA | ATAATTTCAC | CTGTGTCATC | ATCCACCAGG | CCATTCAGTT | GGGAACATAC | 660 |
| CCAACTTATA | CATGCTACTG | CTCTGTCCGG | AAGA | | | 694 |

(2) INFORMATION FOR SEQ ID NO:1103:

```
    (i) SEQUENCE CHARACTERISTICS:
        (A) LENGTH: 674 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1673RP (xi) SEQUENCE DESCRIPTION: SEQ ID NO:1103:

GATCCCAGCT CTTACGCTCG CTCAATTGAA AACCTTTTCT ACACTAGCTT TCTTATCAAG      60

GAAGGACGGC TAGTCCTAGA AGATGACGAT GAGGGCTTCC CGGCCATCCG ACCCAAGGAA     120

CCCCTCCCGC AGGATCCCGC CGAAAAGGAA CTGGAACGGC AGCGACGGAA TGACGCGCGC     180

CAGAAGCATA TCATCTTCCA AATGGACATG GCCACGTGGA GGAAGCTTAT AGACAAGTTC     240

CACATCACAG AGTCATTTTT ACCGTGATCA TGTATAAATA GCGCGCATCT ACGTATCACC     300

CGCTGGCCGG GCGCTGACCC AACCAGGCAC TGCTAGCAGC TCATCTATCG GCCACTTCGC     360

AATGGTCAGC GCGGCAACGT CTGTCGTCAG GCCGTGTCCC TCGTAGAGCT CGATGCCCGC     420

CCAGCCGATC ATCACCGCAT TGTCTGTACA TAGATCTGGA GCTGGATAGT GAAAGGAGTC     480

GAACGGTCTG AATAGTTCAG TCTCGAGTCT GGCACGCAGG CGCCGGTTGG CGCATACGCC     540

GCCGGAACAC ACAAACTGTG CCACATCAGC AACCTTATCA GCATTTGAGC CGCAGCACCA     600

GGTTAATCTT GGTAATCAAA TGGTCGAAAT ATGGCCTCCT GAATCTGAAW TGCTGCTACC     660

CGGCGTTCCG CCTC                                                       674

(2) INFORMATION FOR SEQ ID NO:1104:

(i) SEQUENCE CHARACTERISTICS:
        (A) LENGTH: 726 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1673UP (xi) SEQUENCE DESCRIPTION: SEQ ID NO:1104:

GATCGCTCTA CCGACGTACT GCATGCCTGT CTTGGTCTTA AGTTAAAAAC CACAGCACCC      60

AATCGTTTAC ACCGCAATCT TAGACCAGGA GCTAGTGCTT GCGAGCCCCT GTCGTTCAAA     120

TGGCAGGACT GTTGTTTGGT TGTGAACCTC GCGGACTGAG GAAAGGGGGC GGAAGATCTA     180

TTTTGCACCT ATTCGCAACC GTTTAGATAT TGAAAGCAGG GCAACACTAG TAAAACTCGA     240

AATTAGGACA TTCGTGAACA GATGTGAGCA GAGGATTCCG GATGCGCTTC GAAATGATGA     300

GGGCGCATGC TGCATACCCT GGCCGTGCGG CGTAGTGTAG ACCGTGCAGC GCATGCTGCA     360

AAACAACGGC GCCGTGGCGT CGGCATGCAG GTAGCACAGC ACCTGCAGCA GCGCAGGCGT     420

GCATCCAAGA GTAACGCCAC ATGTCGGGCG CGTTGCTCCG TATGTACAAG TTATGTCATT     480

ATTTCTACAG ATATCATGTT GAATATTAGC CCGCGATCAT CTACTCAATG GTATCGTTTG     540

GTCTATCTCG CTTACGTCAA GATGCAGGCT CCGCCCGGGG ACTACGCGCC AGGGTGCGCA     600

GAGCAGTTTG GTATAGGAGA AGCATGATAC TGCTTTGGAT GCTGGTCCAG ATGAACCTGG     660

GGCCCACACC GCTGAAGGCG CCACCCAGTC CCTCGTAGCG AAGTACGACT AACAAGCTGC     720

GGAAGA                                                                726
```

(2) INFORMATION FOR SEQ ID NO:1105:

(i) SEQUENCE CHARACTERISTICS:
        (A) LENGTH: 657 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1674RP (xi) SEQUENCE DESCRIPTION: SEQ ID NO:1105:

```
GATCTCATTG AGGTACACAG ACACAGCTGG CAGCGACGCC CACGCCTGGA TGGACGAGTT      60

GGCGAAGCAA TCATTCCGGT TGTTTGCCAG CCCTGTCGTG TGTTTGTCTT TCCTCGTGGA     120

GCTCTGGAAC ATAGCAGAAC TACCAGGGGA ATAGCCACGT GTAGATCGTC GGACCTAAGA     180

TATAGTATGA AAGTGCAAGT GTGCCACAAA GAAGAAGTCT TTGTGGTATG TTGTCCGTTC     240

CGTAGAGAAA GCTTCCGACC TTATTAATAG AGAGTGTACC GTCGTAAACA GAAGAGGGGT     300

ATGTCACCCT GTGCAGCATG TAGATGGACT TGGGTATCTA GTCAGCCGTT GTGCTTGAAG     360

GTGGACCAAA CTAATCCTTA GTGCATAGTA TTTATGTGGG GCGGCCTTTG AACCAGGCTT     420

TTGGGATGCT CGAAGGCGGA ATAATACTCC ACGTGACAAT AATATACGTC AACTATTAAC     480

GGCTAAATTA TCCCTTGCGA GGAGAACATC CCGTTAATTA CAATTATCAT TCTATATTAT     540

AAACATATTA TAAAACGTCC ATCTTGCTAA TATAAAAACA ATCTAGGTCG GCTTACCAAC     600

CATATTACAT CAGTAGGCAG CGCGATCTGC ATCCGTCATG GCGTGGAGTA TCCAGTT       657
```

(2) INFORMATION FOR SEQ ID NO:1106:

(i) SEQUENCE CHARACTERISTICS:
        (A) LENGTH: 695 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1674UP (xi) SEQUENCE DESCRIPTION: SEQ ID NO:1106:

```
GATCATCATC AACTATATCG AGAAGGAGTG TGACCGCGGC GTTGCTATGG GTAAATACCC      60

GTCTACCCTT GACCGGGAAG CGGTCCGAAA GCTGGTGGCA AAAGATTTGG AGAACTTCCG     120

CGTAACCAAC AGCCTCACGC TGAACAGTCT CTCCCTATAC TTTCGCAACC TAACACGGGA     180

GCAGCGGGAA ATATGCATAT ACAACAACTT CACCGACTGG AGCTTGCTAA TCCTTCCGGA     240

AGAGGAGAAA ACCAAGTACT GCAAAAGAAA GCAGGGTTCT TCGTCAGAAT AACAGTAATT     300

GTAACTATAT AATCTGGAGC TTCTCCCAGC GGTAGAAGGT CCCAATTTGT AATGTACTAC     360

TACCTGAGCA CTTGTGTCCG CCTCATCGCT CCTTAGAAAC TCGTGTTCAA GAGCTCGGAT     420

GGCATCTGAC ACAAAGGTTG CAGACGCAGG AGAGTATATC TCCAAAGCCT TGGGTTAACT     480

TTCTAACCTA ATATTTTGCA AATAAAGCCG AGTCGCAGTG TATCACTGCT CCAGTCAGTA     540

GATTCTGACT TCGTAAAATA TGTGTTCTAT GGGTGGAACA TTTTAAGTCA TAGTTTTGCT     600

TTTTCCCCTG ATATACTTCC AAATACATAT ATCACTGAAG TTCCATCGGA AGCACCTCCA     660

CAGTACGGCC TAAGAAGAGC AGAATAATTG CTCCA                                695
```

(2) INFORMATION FOR SEQ ID NO:1107:

(i) SEQUENCE CHARACTERISTICS:
        (A) LENGTH: 654 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1675RP (xi) SEQUENCE DESCRIPTION: SEQ ID NO:1107:

```
GATCCGTGCA ATAAACCGCT TGAATGCACT GTGGAAGTAG TTGCGGGTCT CGATATCAAA      60
GTCGACAAAG AATATCTGCA GGTTGTTACG CAAAATGTCA AGCACATATC CACGCACTGG     120
ACGCGAGCCC TTATGCGAGT AAGTTAGCAC TTCAAATGCA CCGAGCTTGT ACTTGTCGAT     180
TCGCAGAAGG CTTTCCAACG TCGACAGCAT GATCAGCTTG TCTTCGTGGA ACGGTCCTC      240
CTCTATCCCG AGCTCCTGGC CAATTTTGAG AAGCGGTAGA AGGAGAGCAG GGTGCCCCTG     300
CATGTTCCGC AAGATAAACA GATCGAAGAC CTTCGGCGGA ACGGTCCGAA AGAGCGGCTC     360
CAGCACGTAT AGTTGCACTC GTTTCGCGCA GGTGCCCTCA AGAAGATGCT GAACCACCTG     420
CTGCTCCCAC AACTGCAGCC ACATCTCCAG TTTATCCTCT GTATAGTGTC GCACATATAT     480
ATTGGCCAGC AAACTCGTCA CACTCTTGCC AACCGCCGTC GCAAGAGAGT CCGACCACAT     540
GTATCCCAGA GCCGTCGCAA TGAACTCCGG CCGGACCTCT AGAACAATTC CCAGGTCAAT     600
CCGCTCCGAT AGCACGTCCA CCATGAAGTA CACGAACCTC TTTGAAGGAC TCAG           654
```

(2) INFORMATION FOR SEQ ID NO:1108:

(i) SEQUENCE CHARACTERISTICS:
        (A) LENGTH: 715 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1675UP (xi) SEQUENCE DESCRIPTION: SEQ ID NO:1108:

```
GGATCCGCTT CCACACCGAA AACGCAGAGG ACCAGGACCG TGTCTCGAAT GTCGTTGGCG      60
ACGCCATCAC GCACGTCAAC ACGCTCTTTG GCGACAACGG CATTCACGCC TACGTTCATA     120
AGAACATCGT GTTCGTCCAG CAGTCCGGCC TGTCCGTGCA GGCCCTCAGG TTCCTGCTCA     180
ACCACTACAA CTCGGTCGAC GACACCCCTG GCTCCACCCC CGCGCACTCC CCGGCTGTCT     240
CGCCCGTCAT GACCCCGGTC AATTCCTCGC TGGCCATGTC TCCAAGCACC GCCGCATCTA     300
AAACCCCCTC GGCCGCGACC GCAACAGCCA GCTACTTTAG CAATGGCCGT TCCACCAGTC     360
GCGTCGAGTT TGTCTGTGTC ACTGGGACTT CATCGCCGGT CCTGGAGCCG CTGTTCCAGT     420
CTATCAATGA ACTGGCCAAA AAGGGCGACC TGCCCTACGG ATACACTGTC GCCTACGGCG     480
ACGCTATTAC CACATACGCT AAAGAGCACG TCGAAGGTTC CAACGAATTA TTTGGCATTC     540
TAGACAAACT GAACTTCATT GGCTGCTGAG CGCCCCTGTT ACATAGGTTA TTAATCAATT     600
AAATCCTTTC TCTGGAACCT TATAGAGCCC TGCACCTTGC GCTCCGGACG CATATCCTTG     660
TGACTAGTT GTCAGCGGTA GCCTTTAATA AATTACGTAA TATGTGGTAT TATCA           715
```

(2) INFORMATION FOR SEQ ID NO:1109:

(i) SEQUENCE CHARACTERISTICS:
    (A) LENGTH: 568 base pairs
    (B) TYPE: nucleic acid
    (C) STRANDEDNESS: single
    (D) TOPOLOGY: linear (ii) MOLECULE TYPE: DNA (genomic)

(vi) ORIGINAL SOURCE:
    (A) ORGANISM: PAG1676RP (xi) SEQUENCE DESCRIPTION: SEQ ID NO:1109:

```
GATCCCGACA CCAGCATGCG CTCGTCGAAC GGGTCGAAGT CTGTGTCCAG CACCTGTGCC      60

GTGTGCCCGC GGAACAGAGG AATTTGGTCT GGCGCCTTGC CCACCTCCTC CACCGGCACT     120

ACCGCGAACG CCCCTCCGCC CGACGAATTC CACGTAACCG AAATGAACTT GCCGTTAGTC     180

TTGATGAGAT TGGAATCCCA AGCATTGATT GTCACTTTGA GGTTCTCGTA GAAGAGTTCC     240

TTCTTTGTTG ATTGTCCGAA GACGTGTCTA TACTTGGAAG CCCGCACAAA CTTCCCACTG     300

CAGTGCCGTT AGTTTGCCGT CCGCACAAAG TCCAGTCCTG GAGAGTATGA CATACCTCAT     360

CCTTGCAATT CTTTGGGGTT TAGCAGCTCT ATATGCGTGT ACACCGTAAA CATCCGTAAC     420

TAAATATGTA ACGTGGAACT GAAGGGTACT GGAATCTAAA GGGGAAAGAA GTACCCGTTG     480

ATGGTGATGG TACTGTCAAG ATGGCTAAAG CGAACCTCTG GCCTGGTTGG AACTCAGAAA     540

GGTCACCAGA CTCTTCTTAT TCTTGTTT                                       568
```

(2) INFORMATION FOR SEQ ID NO:1110:

(i) SEQUENCE CHARACTERISTICS:
        (A) LENGTH: 568 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1676UP (xi) SEQUENCE DESCRIPTION: SEQ ID NO:1110:

```
GATCGCCGCG CTCGTGCCTC GCCTGTATTA CTACGCCACG AAGCAATTGT ATAACCCACA      60

TATTGTAACG TTTGTACTAT CCTCCATGGC CTCGCCCACC CGACACGCCG CCTTTCCTGC     120

ATTCGGGTGC CGGTGGCCGC CGCGTTTCAA CCTCGGCCCA TGGCTCGCGC ATTAGCTGCC     180

AGTAGCGATG CAACCCGAAT GGCGAAGATG GAGCCGGCAT TGGTGGGTAC GAAAAAGCTT     240

TTTACGCGTA CTGTTTGCTG GTCTAACGCA TCCACGCCAC GACGCTAACC AGTATGAATA     300

CCGACCTCTT TGCGCAGCTG GTACTTGTGC CGATCCTCCG GTCCCCATA GCGTTTTGTG      360

TGCTTCTATC ACGGTATGCA ATGTTATGAT GCGTGTGTCC GCGAACATGT WCTAACAGGC     420

GACAGCGTGC TCGATACGCC GTGCCCGCGG CTGGCAGCCG CACTGACGGT GTACACAGTA     480

GTTGTGAATG CGTGCCTAAG CGCCAACCGG CGCGCCAAGC TGGCAGGCCG TGGACGCCAC     540

TGGAGCAGAT GCCGGACGCG ACTTGCGT                                       568
```

(2) INFORMATION FOR SEQ ID NO:1111:

(i) SEQUENCE CHARACTERISTICS:
        (A) LENGTH: 653 base pairs
        (B) TYPE: nucleic acid
        (C) STRANDEDNESS: single
        (D) TOPOLOGY: linear -continued

```
    (ii) MOLECULE TYPE: DNA (genomic)

(vi) ORIGINAL SOURCE:
         (A) ORGANISM: PAG1677RP (xi) SEQUENCE DESCRIPTION: SEQ ID NO:1111:

GATCTGCAAT TAGGGCATAT AAACTGTGGG TACTGTGTCA TCACTAGTCG GCGTATGCAC     60

TGGTAGTGCC AACTATGCGA ACAAGGGGAT ATGAAGATGG CCTGGCAGGG CTTAATTTTA    120

CATAGGCAGA TTGAGCAATC TTCCTCCTCA AGGCCTGCCG TTAGCTTTTG TAGGTTCCGT    180

AGGCGGGCTA GTGCCTCTTT GTTGAACGCG TTGGCCCTTC GCTTCCACGA TTTGTTCAAC    240

TCGACTCTCA TTTTGACGCA TCTATATATC TCCTCTGTGC CGCCACGGAA ATCCATTCCC    300

AGCTGCAATA TGTCGCCGTC TTTCAAGGGG TAGTCTTTCG ACATAACCGA TGCCTGTGCA    360

AGCCGCATCT GATTAAGGAA CGTGCCGGAC GAGGACTTGA CGTCGCGCAC ATACCAATTG    420

CCCTGCTCAT CCACCTTAAA CACCCCGTGT GTGCGCGACA CAACCTTGCT CTTGAATACC    480

ACGGGGTGGA AATGATCCGG GAGCGAGCCG ATCGCCTCGC GAACCCGTTC TGTGTAACGC    540

CCGATAACCA ACTGCGAGCT GGGGCCTGCG GTCCGCACGA TGGGATCAAA AAAGAGCCCC    600

GGATTATTCG TGGTCGAGTG GTCAATGAAC GGCGTTAACC GGAGCGAGAA GAA           653

(2) INFORMATION FOR SEQ ID NO:1112:

(i) SEQUENCE CHARACTERISTICS:
        (A) LENGTH: 625 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
         (A) ORGANISM: PAG1677UP (xi) SEQUENCE DESCRIPTION: SEQ ID NO:1112:

GATCGTGGCC TTAAGCCCCT CGCCGCCTGC GCCTGCGCAG CCCTCAATGC ACTCCGTCCG     60

CGTCGGCTAC ATCCCAGAGC ACTTCAGCGC GCCGCTGCTG TTTGCGCAGA CGCTCGGCTT    120

CTTTGCGCAG CGCGGCGTCA CCGCCAAGCT CGTGCCCTTC CCTAGCGGCT CTGGCCACCT    180

GATCCAGGCG CTCGACGCCG GCGAGCTCGA CCTCGCGCTC GGCCTCACCG AGGCGTTCGT    240

GCGCGGCATC GCAGACACGC CAGCCGGCGC CGCGCCGCGC TACCAGATTG CCGGCACCTA    300

CGTGCGCTCG CCACTCAACT GGGCCGTCTC CGTCGGCGCC GCGTCGCCCC TGGAGCACGT    360

GGACCAGCTG GACGGCGGCC GCGTCGGCGT GTCACGCGTC GGCAGCGGCT CGTACGTCAT    420

GAGCTATGTG CTCGCCCTGC AGCGCGGCTT CCGCCGGCCC TTTGCCGCGC ATCCGGTGTG    480

CCACACCTTT GCCGGCCTGC GCGCCGCCGT CAACGAACGG CGCCGCGGAC GCTTTCCTGT    540

GGGAGCACTT TACCTCCAAG CGCTACCACG ACGCGGGCGA GATCCGCCTG CTGGGCAACA    600

TCCCCACCCC CTGGCCCTCG TGGGT                                         625

(2) INFORMATION FOR SEQ ID NO:1113:

(i) SEQUENCE CHARACTERISTICS:
        (A) LENGTH: 643 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
```

(A) ORGANISM: PAG1678RP (xi) SEQUENCE DESCRIPTION: SEQ ID NO:1113:

GATCCGCTGT CGGCATCATC GGAGACATCG CCTCCATGTT CCCCGATGGT AGGATAAAGC      60

AATTGTACGC CCAGACTTGG GTCACAGAGT TTATCAAGAA AACAAGAAGT AACCCCAACT     120

TTAGTCAGGC AACTAAGGAT ACTGCTAGAT GGGCTAGAGA ACAACAAAAG CATCAACTAA     180

CCCTATAGCC TTACACTCCA GAATAATTTA TCTTATTACT CATTTTCTTC TGCGTTATCT     240

CGCTCTCCTC CTGTTATTCT ATAATACTTC CCCTGCATTG TCTTCATTAT TGTGTCTGCC     300

TCGCGACAGA CCGCTTCGTT GTCTCTTCTT TTGTTCGACC CTGCACTGAC CTGGCCATGC     360

TGCTCTTTCT AGTGGTTTGG TACAGGTTGC GGGTCTTTTT ACACAACTTT TCTACTACGT     420

CTTCTATCTA ATCCCATCTA CTTTTCTACT TTCCTCTCCT ACTTTATCCG TCGGACCCGC     480

TGCTCGTCTT ACGTGGCAGC TTGTAGCATC TATATAATTG TATATATCGT GGTGGCAACT     540

ATCTACGGCT GCTATACATC TGCTGCCCGG TCTGATCGGC CGAGCCGTTC ACCAATGCAG     600

TAAAACCACA TAAACTTTTA AGAGTTACAA GCTCAAAAAC GTT                      643

(2) INFORMATION FOR SEQ ID NO:1114:

(i) SEQUENCE CHARACTERISTICS:
        (A) LENGTH: 721 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1678UP (xi) SEQUENCE DESCRIPTION: SEQ ID NO:1114:

GATCCGGGTT CGAGTCCCGG GAGGGGCTGC AGCGCACCAG CGCTTCTTTT TGGCGCTGGT      60

AGTCGAGGAT TGTTGACTGC TAAACCCATA CAACCACATA TTGCACTGGT GGCTTGCCCG     120

CCTAGGCCGC CCTGCGGCTC CCGCGTAGCC CGCCGGCGGG ACCCACGCAA CGAGACCGTG     180

CGGGCCCGGC ACGGCGATCA CCAGCGGCAG CCGGTGCAGC GTAGGCGGGA CAGCTGAAAA     240

GTTACTACAA TTTGAGGTCT CGCATACTGA CACAGAGGGT CTTACACAGC ACCAGACGAA     300

TCAGCAATGG CTAAGCAATC TCTAGGTATG TGACAGAACG ATGGTGGCTC CGAAACATTG     360

GGAATGAGCG TCTCTGGCGC TGCGATCCGT GGTAACCTGG GCATACGGCC CAGCGCGCAG     420

GCGGACCTAG CATAATCCAG TGCGTGGAAC AAGTTGGTGG CCCGGCACAG TACTAACATG     480

TCTGCAGACG TTTCCTCCGA CAGAAGAAAG GCCAGAAAGG CGTACTTCAA CGCGCCATCT     540

TCCGAGCGCC GCGTGATCAT GTCTGCTCCT CTATCCAAGG AGTTGAGAGA GCAGTACAAC     600

ATCAAGTCTC TACCAATCAG AAAGGACAAC GAGATTATGG TTGTGCGTGG CTCCAAGAAG     660

GGCCAAGAGG GCAAGGTTCT TCTGTCTACA GATTGAAGTA CGCTGTCCGC GTCGACAAGG     720

G                                                                    721

(2) INFORMATION FOR SEQ ID NO:1115:

(i) SEQUENCE CHARACTERISTICS:
        (A) LENGTH: 633 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
    (A) ORGANISM: PAG1180RP (xi) SEQUENCE DESCRIPTION: SEQ ID NO:1115:

| | | | | | |
|---|---|---|---|---|---|
| GATCCGTCTG | ACGGTGGTCG | AGTTCTGGAC | AAACGCCGTG | CTCTTTGACG | AGATCGTGCA | 60 |
| GCCACTGGGC | GAGATCATCG | ACCTCTACAC | CCAGTTCAGC | GGCGTCCACG | AGATAGACCG | 120 |
| CGCTGTGGCG | AAGACATTTG | AGGAGGCGAG | GGAGGTATTT | TTGTCGCCGG | CGATGATTAA | 180 |
| CGAGAACAGC | ATACTGATTG | CCACGGCCT | GGAAAACGAC | CTGAACGTAT | TACGGATTAT | 240 |
| ACATGATAAA | ATTATTGATA | CAGCTATATT | ATACCCGAAT | GGTAAGTTCA | AGTCCTCCCT | 300 |
| CCGGAATCTA | GCCTTTCAGG | AGCTCAGTAG | ACGGATCCAG | ACGGGCGAGC | ACGACAGCTC | 360 |
| AGAGGACGCC | ATTGCAGCAA | TGGACGTCGT | CAAGCATAAG | CTGGGCATCC | CGTCGACCG | 420 |
| CAAGACGTGG | TAGCCCTACG | GCTGCTCCTC | CAGCCGCGTG | AGCCTGTCTT | CAAGCTGGTC | 480 |
| CTGCCTCTCA | ATTAGCGTGT | GTATAAGCTG | CTTAAGGTTC | TGTAACTCAA | TCGCGATCAT | 540 |
| CCTATCTTCT | GGAAGCTCGA | ACTTGACGTT | CCTGCTGCGG | GTCACGATCT | GGCTCTTGCC | 600 |
| CACCTTGTAC | CTCGATGCCT | CCGGAATTTT | GCC | | | 633 |

(2) INFORMATION FOR SEQ ID NO:1116:

(i) SEQUENCE CHARACTERISTICS:
        (A) LENGTH: 706 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1680UP (xi) SEQUENCE DESCRIPTION: SEQ ID NO:1116:

| | | | | | |
|---|---|---|---|---|---|
| GATCGCGGCG | CGCGGTGGCC | GGCATTTCCG | GAAGCGGCCA | CGGAGCAGAG | GTGGCGCATT | 60 |
| CGAATCGCAT | ACGTCTTCGC | CACGCCGGAA | AAAAAATTTT | CGGCTATATA | AGGAGAGGCG | 120 |
| GCCGTCTTGC | TGCAGGCAGT | TTCACTTTCT | CTAAAACCAA | AGAACATCGA | TTTCTTTAGT | 180 |
| CACTCGCTTC | CTTACACCGA | AATGCAATTC | TCCACCGTCG | CTTCCATCGC | AGCCGCTGCC | 240 |
| GCCGTCGCCT | CCGCTCACGC | CAACGTGACC | ACGGCCACCG | CCACCAGAAA | CCAGACCACC | 300 |
| TTGGTCACCA | TCACCCACTG | TGAGGACAAG | ACCGCATGCA | CTGCGCACGT | CTCTCCAGCT | 360 |
| TTGGTCTCCA | CCGCCACCGT | CACCATCGAC | AACGTTGTGA | CCTTGAGCGA | GACCTGGTGC | 420 |
| CCACTATCCA | CCACTGAGGC | TCCTAAGCCA | CCAGTTTCCA | CCGCCAAGCC | ACCTGCTTCC | 480 |
| TCCAACGCGA | CTGTTCCTCC | AACTGAGACC | CAGTCGTCTC | CTCCTTCACT | GGTGCCGCTG | 540 |
| CCAAGGCCCT | ACCAGCTGCT | GGTGCCTTGT | TCGCGGGCGC | TGCTGCTTTG | TTGTTGTAAG | 600 |
| TTTAGTTCCG | CCGCGTGAGC | CCTCGTTTCG | TTTAGAGATA | TATAGGAACT | TATGTGACTG | 660 |
| ATTCTAAGCT | TTTACACCAG | CATGATTTGG | TTCTGCGGCG | CACCGA | | 706 |

(2) INFORMATION FOR SEQ ID NO:1117:

(i) SEQUENCE CHARACTERISTICS:
        (A) LENGTH: 696 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:

(A) ORGANISM: PAG1681RP (xi) SEQUENCE DESCRIPTION: SEQ ID NO:1117:

GATCATTCTA AACAGATTAA CCTTCCTCCA AATTACTTTA TTTCCTTAAT CTCCGATAAA      60

TGGTTACATT GCGACAATAA GGTGCCCGTG GTGCTTACAG ATATACATCT ACCGAGAAAA     120

TTTCCGCCAC ACACTCGTAT AGAAGAAAGA AATTTGATTG AAACTTCTGA GCTAGATCCG     180

ACGTTCAGTG GACTCTTCCC ATTTAAGGTT TTCAACAAAT TCCAAACTCA TGTGTTTAAT     240

GCCTTGTACC ATACCGATGA AAATGTATTT ATTGGAGCTT GTAAGGGCTC GGGTAAAACT     300

GCAATGGCAG AATTAGCTTT ATTGAGTCAC TGGAGAGATG GTAAGGGACG TGCCGTCTAT     360

ATATGTCCAT CTCAGGAGAA AATTGATTTT CTGGTGAAGG ATTGGCGAAA CAGATTTTTA     420

AATGTGGCAG GTGGAAAGGT TATTAATAAA CTCACATTGG AATTAACTAA CAATCTTCGA     480

ACGCTAGCCC AGTCGCATTT AATCTTAGCG ACCCAGAGCA GTTTGACCTG CTTTCTCGTC     540

GCTGGAAAAG AGAAAAAAAC ATCCAGACAT TAGAGCTGTT GATTCTAGAT GATCTTCATA     600

TGATCAGTAG TGACTTGCCT GGCGCAAGGT ATGAAAATAT AATATCCAGA ATGCTGTTCA     660

TTCGGGGTCA ACTTGAAAAC GGCCTTGCGT ATAGTC                              696

(2) INFORMATION FOR SEQ ID NO:1118:

(i) SEQUENCE CHARACTERISTICS:
        (A) LENGTH: 659 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1681UP (xi) SEQUENCE DESCRIPTION: SEQ ID NO:1118:

GATCAGGAAT GATCCCTCAA TTGTCAGGAA TTATGGTTCC ATATTGGTTG AATTTGCCAA      60

GATTACTCCT GATGGTATGG TANTGTTCTT CCCCTCATAT TTATATATGG AATCCATTAT     120

TTCAACTTGG CAGACAATGG GGATTCTAGA CGAGGTTTGG AAATACAAGC TCATCCTCGT     180

GGAAACACCA GACGCACAGG AAACTTCTCT AGCTTTAGAG ACTTACCGAA AGGCCTGCTC     240

GAATGGGCGC GGCGCAATAT TACTTTCTGT GGCCCGTGGG AAGATTTCTG AGGGAATTGA     300

TTTTGACCAC CATTACGGTA GGACTGTATT GATGATTGGA ATTCCTTTCC AGTACACTGA     360

ATCGCGTATT CTAAAGGCGA GGTTAGAGTT CCTAAGAGAA AACTATCAGA TACGGGAAAA     420

TGACTTTTTA TCCTTTGATG CAATGAGACA CGCCGCTCAA TGTTTGGGAA GAGTCTTGAG     480

GGGTAAGGAT GATTATGGCG TGATGGTGCT CGCCGATCGG CGATCTCAAG AAAGAAAAAC     540

CAACTTCCAA AATGGATCGC ACAAGGGCTC TCTGATGCTG ACCTGAACCT TTCTACTGAT     600

ATGGCGATAG CTAATACAAA ACAATTCCTA AGGACGATGG CACAAGCAAC TGATCCGAA      659

(2) INFORMATION FOR SEQ ID NO:1119:

(i) SEQUENCE CHARACTERISTICS:
        (A) LENGTH: 707 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1682RP (xi) SEQUENCE DESCRIPTION: SEQ ID NO:1119:

```
GATCGTAAAA TTTGCTATAC AATGGTTTGG GTAGGTCCTT TAAAAGGTCG TCAATCTCAT      60
AGTCGCTCAC ATCAAGGGGA ATGTTTAAAA AACGCACTCT CTGATGTGTA GGCGGAGGAG     120
GCCTTGCGTC TCGCCGGTCC CTGAAACGTG AGCGGCGCGA GGGGCCGTAC TCTCGCGCCC     180
GATACGTGCT TTCCCCCAGA CCCATGCGTG AAGCTAGTCC ATTACGTAAG TCTCGACGGC     240
GATATTGCTA TAATAACAAT GTAATCGTTA ATACTCACGC TCAAGTAACC TTGCGGTGGG     300
TCATGTATCA CTTACGGTAG TAGTGCGGTG TGTCTTTTTG CCGTTAGTAT CCGATGAAGT     360
TTGGTATCGA GGAGAAAAAG ATGTTCATAC TTTCTCACCA GTACCCTGGT TCAAGTGTTC     420
GTCAACAGAC ATTGTCCCTT CCAAACTATC CTGTTTGAAG GGCAAAGGCT GTGTGTCAAG     480
AACGAAGTTT TCACCATTTT TCCGGAAGGC TCGGACAGC GATCGAAAGA AATAGGATAT     540
ATACGTACAC CTTTCTTTAA ATATCATTTA AAATATCCTG GAATTTCGAT ATGTGGCCAT     600
ACTGGCTCTT CAGCTTCCTT ATCCATGAGA TAGAAGGAGC AAACTGTGCG AAGGTGCCTT     660
CCACAGTTAC TTAAGTTTCC GTAAGCAACA AGGAGTCTGT ATGCGGC                   707
```

(2) INFORMATION FOR SEQ ID NO:1120:

(i) SEQUENCE CHARACTERISTICS:
        (A) LENGTH: 700 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1682UP (xi) SEQUENCE DESCRIPTION: SEQ ID NO:1120:

```
GATCCAGTGT GTACGGCCAG AGTCGCGCTG GGGCACCAGC AGTACCTGCT CCGTCTCGTT      60
GAAGTTCGCA ACATTCCCGT CCGCATCAGC ACCGCGCCTG AAGTATCTTG TACCCGCCCT     120
GAATCTGCTC CGGCGCGTGA TCAGACCCAC ACTAACTGGC GTACTCTGCA ACACAGTGTC     180
TACCACTTTG ACGTAGCCGT AGATTAGCGG CAGAACGAAC TCGTTCGCCA GAGCGTTTTC     240
CTCCGCCAGG TTTCGCAGCG GCTCTGTGGC ATAGTAGTTC CAGAAGAACC GCGTGTCTGC     300
AGTGCGCCAC GAGGCTGGCC CCAACCCTTC GTTGCGCTGC ACAGAGTGCG TCAAGTCATA     360
CGTGTACGAA TAGTACAGCG TTGCCTTCGC GAGGTGGTCG CGCAGTAGCG CAAGATACTG     420
GTTGTCCTCT GCAGATGGCC GGATACTGGT GTTGACCAGC ACCAAAGAGT GCGCCGTCAC     480
TTTGAAAAGA GAATGGGCAC CCAGGTTTCC CACCACCTCC ACGCGGTCCG CCGTTAGCAC     540
CACGCGACTA TTGCGCAAAT GTAATATCCC GATCAGGCCT GCGATCTTGC GAGTTTCTCC     600
ATCTTTAGGG AAATTGCTGG GGTCTACGAG TGTCACGCCC GAATCGTGAT GCGAGATAGA     660
CAACACCGCT TCACTCTGGG AAGTATTAGA TGGCTTGAAA                           700
```

(2) INFORMATION FOR SEQ ID NO:1121:

(i) SEQUENCE CHARACTERISTICS:
        (A) LENGTH: 652 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:

(A) ORGANISM: PAG1683RP (xi) SEQUENCE DESCRIPTION: SEQ ID NO:1121:

GATCTATATC ACCAATCATC ATGGTTTTGA AACATTCGGT GCTTAAAAAG GGACACAGCA      60

AACTACAAGC AGGCAGCACG AAGCACTCTG CAGACTAAGG GCAGGCCTCA TCATAAGATG     120

CTTAGGGCTG AGCTAGTAAA TGCCATTCCG TGCCAAGGTG CTCAGTGTGT CGCTGTGGTT     180

GATGGCGTTC GACAACTTGT GGTGGTGCGA ATAATAGGG ACTTCTTGGT GTACTCCAGT      240

ATGGACGAGA GAGGCCTGCG TCTAGTTCAG ACATATACAG AATTGCTTGG CCCGAATTAT     300

GGTGTAGAAG AGCTGCTGTA CTCCGAACGG CTGCGGACAA TATTCGTCCG CACGACCAAG     360

TGCTTACTGC TACTTCATTC GAGCAACTTA CAACATTACG ACAAGATAGT TGACAAACGA     420

GGCATTGACC ATGCCTGGCT GTTTGAACAT CCATGTGGGA AGGCTGAGAC GTGGATGACG     480

GTGCTTGTTT ACTCGGTCAC AGGGTCGAGC AAGATAAAGA TGCTGACATG GGTGGGGCGG     540

CAGTTCCAAG CGGTGCATGA GGTCGCACTA GGCACGCGAT CGGAAGTCAT CCAGCTCAGT     600

AAGTGGCGGC CCGCATGCTG TGTGGTTGCT TACCTCCGAC GACTGTATAC CA            652

(2) INFORMATION FOR SEQ ID NO:1122:

(i) SEQUENCE CHARACTERISTICS:
        (A) LENGTH: 718 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1683UP (xi) SEQUENCE DESCRIPTION: SEQ ID NO:1122:

GATCTCGTCA AATTCTGCTC TAGCATTATC AACTTTGTGA CCACAACTTA GAATTCCCCC      60

ATCATGCATT ATGTTTATAG ATGTACAGTT CTAAAAAATT CGGTAATATA ATGAGACCTA     120

TCTCTTTTTC TCATCCTTAT AGTCACCCAA AGTTTTAACA TGTGACATGC TGCCAGATTT     180

ACAGTCATCT GCGGCTATGA TTTCTTGCAG AGACCTGCCA CAATTATAAT GTGTTAATAT     240

ATTGCTTCCT CTGAGGTTGA AGAGCGAGAA AAGTTCACTG CTCCCTAATG TTAAATTCTT     300

CTGGCAAACG TAGCAGCGGT TATCTTCATC TACCACCAAA AATTCAGATA TGATCTGGGA     360

TAAGCGATAG GTGCTTCCGA TGAGGTTGAC TTTCAAAAGA TTGTTCTGTA TACGCGATTG     420

GTTTTTCTTC ATGGACGCAC TTTTAATCCT TCTACTTAGG AATTCGTTAA GCGTGTTTAT     480

CGGAATATTG GGCGGCAGTT TCTCAAACAA TGTTATCGCA TCTAGCTTCG AACCATTCTC     540

TAGCAGAAAC AGATGAACGT TTCTCCATCC GCTAAATTCT ACCTTCGCAA GCAGCTTTTC     600

AAACAAGTTC ATGAGAGCTG CTGTGCCTGC ATTTTTGTTT GTGGCATAGA GCTCATTACA     660

ATATAGAGAA GCTTGGTTAT AATTCCCTAG ATCATCAACT AGGATCCCTA ACGCTGTT      718

(2) INFORMATION FOR SEQ ID NO:1123:

(i) SEQUENCE CHARACTERISTICS:
        (A) LENGTH: 577 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1684RP (xi) SEQUENCE DESCRIPTION: SEQ ID NO:1123:

```
GATCTGTACA CTTCAATATC GAACGAAGTG TCACCGGCAT ATTCTGCAGA GATTTGAAAA      60

AGCCACCAAA GCAATATGAC ATCAGGGTAG AGCTTCGAGC GAGTAATCTC CGGTGATTCG     120

TCGATCTCCT TTAACCAAGC AGCAAACCGT GTCTCATGTT GCTTTTCCCA GCTAATAATC     180

TCATGCACCA CAGCCATAGA TTCAGCATAA TGAAGGTATG TTGCGCGCGC CTCATTACAC     240

CATTTGATAT ATATTTTCCC CACGCCATCG ATGAACTTCC CTTTCGTCTG CAGCTTCCCA     300

AAAATAGGTG TCAAAAGCAG TTCCTTGTGC AAGTCAATCA GCGGATAAAA GATGTCAAAG     360

GCAAGAGAGG CGAAGTTTTC GTCGGTGGGC AGCAACGCCG GCGAGAATTG TGCGCCGTAG     420

ATTTCTACGG CAGCATGGGC CAGGTTCAGA CTTTTCTCTT CGAGCACAAT AAGGTCAAAT     480

ATGTAGCTCT GGCGCTTTAC TTCTCTAGGA TTAATCTCTG AAAGCTCCTC GTCCGTCAGT     540

TTCCAGTACT CGGTCCAAAG TCCCACCGGG CGGCTGA                             577
```

(2) INFORMATION FOR SEQ ID NO:1124:

(i) SEQUENCE CHARACTERISTICS:
        (A) LENGTH: 707 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1684UP (xi) SEQUENCE DESCRIPTION: SEQ ID NO:1124:

```
GATCCATGAC GAGCAGCTGG ACCTCGTCGC CGCTCTGGGC CTGGCGCCAG AGAACAAGGA      60

AACGCTGCAG AACCTCCCGC TCGCGCGCGT CAGCGTCACG TTCAAGGACG TGGTGACGGA     120

CTACTGCGAG GCGCACGGCC TGCTGCTCGA AAAGACGGGC GACGTCGCCA CCCTCCGCGT     180

CTACCAGCAT GCACGTACTG TCCCGGTCTT CACCGTCACA CACGTACACC GCCGCCGGCG     240

TGTAGCTCTG TGCGAGGACG TGCTTTGGGT TCAGGAAGGG ATAGGCTTCA AACCTACGTA     300

CTTATACGAA CTAGAAACTC TTCTAAAGAG CGCTTAGTCG TCTCATATAT ACAGGACCTA     360

GTACTCTTGG CGCACTCAGT GGCCCTCGTC GCTTTTCGCG CTCTCGGCCG CGGCCTCCGT     420

CTCGCGCACG GCCTGCTCCT CGCTCTCCAG CTGCTCCGCG TAGTGCTCGG GGTGCTGCCG     480

GAAGCATCCT GCATCACCTG GAATTCTCCA CGCAGTCAAT CCCCTTAGGC TCGGCCTCTG     540

AGTACACGAA GCACGCGAAC GCAGCCTTGA ACTCCTCGCC GCACGGCCCG TGCGCCATGC     600

CGCCCAGGCA TGGGCAGTCC CAGTTGATCT CGCCCGTGTC GGGATTGTAT GCTCCTGCTG     660

CCCTGCGCAG CCTCACCCGC GCTAGCTTTG TCCTCCGCGG CGCTCGG                  707
```

(2) INFORMATION FOR SEQ ID NO:1125:

(i) SEQUENCE CHARACTERISTICS:
        (A) LENGTH: 666 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1685RP (xi) SEQUENCE DESCRIPTION: SEQ ID NO:1125:

```
GATCAACTTC GCCTAATCCC TTAATCATTG TCACTGCTAA CTTGAACTTA GTCTGTGTGT       60

ATGCCTATAG TGAACGTTTA ATGTGATGGT TTTATAGTAA TCGATGGAAC TTTATCCGCG      120

AAGCCTCAAG CTGATCATCA CGTGAGTAAC CGTCGATATG CAGAACAGAG GATACCATAA      180

ATTGCTATTA GTAATCAATT AATAGACTTA CATATAGCTC AAAGCTGATC ATTGATGCGT      240

CTCAAACTCT TTTCATCGTC TGAACCTTTC GGATTTTCAC TTCCTGTATC ATTATACCAT      300

GTATAATCCT CTAGTACGCT AGTAGTCTAG TATCTCGGAT AACCCCCCTA TATTACATAT      360

AATATGAGTA AAATACAGAA TGACGTTAGC GGATAATCTA AGGCTAAGGT TGCCTACACT      420

AAGTTAACGG GGGGCTTCTT ATCTTGCAGC TTGTCCTTCT AATCAATAGA ATTCGTTTTC      480

TTTTTCCACT ATTTGGTCCC TGGCAAACTG CGAGCCACCC CGCGTATCCT TAGCCTCTGA      540

GGTGTCCTCT TCGACATCAC CTTCGTCCTC CGGGATCTCT CGGGACGTGG TTCAACTGTA      600

CGCTCGGTGC ATATTTAGTG TGCTCAAGGT TGCTGAAAAT AGATGCGAGC ACCTTGTCCA      660

GATATT                                                                666

(2) INFORMATION FOR SEQ ID NO:1126:

(i) SEQUENCE CHARACTERISTICS:
        (A) LENGTH: 642 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1686RP (xi) SEQUENCE DESCRIPTION: SEQ ID NO:1126:

GATCCTCTCC GAGGTCAAGA GTTGTGTCAT GAATTAACTT CATTTTAGGA ACAAACTTGT       60

CTAGGGTTCC CGCTACTAAT TCCTGCTCGA CTTTGAAATC CCAAAATTTG ACAGTCTTGT      120

CTGCGGACGC AGTCACTAGC CTCTTCCCAT CACTAGTTAG GTCTAAAGAC CAGATTGCAG      180

CGGTGTGTGC CTCTTCAATA TTTTCTAGCA TAGTAGAAGA TGCGAGATCA AATAGCTGAA      240

GTTGGCCCGC TCTTGTACCC AGAATAACCA AGGCGCCACC TGGTAAAAAC TTACAGCATA      300

AAGCATAGCC ACAGTCAAGA TTGCGGATAC AAGTTTTAGT CTTGATGTTC CAGACCTTTA      360

GGTTTCCATT TGAAGCAGTT GCTAGTAGCT TATCATCGCT ACTGATGTCT GCAGCACGTA      420

GATCAGTCCT ATGGCCCGGC GATTCGATAC TATGCAATTT GATCGCAGTA GGCTGGAGCG      480

GTTCCTTCTT TTTGTATGGG ATTGAGTAGT ACTCTATAGT GTTGTTTGCA GTCGTGATCA      540

CCAGTTCCAA TTTAGATGGG GTACAGACCG TCCATGAAGA TGCTTTTAGC TTAAATAGGG      600

ACCTTACGAG TTGGAAAAGG ATGCAAAAGT AAGTTCGCAT AC                        642

(2) INFORMATION FOR SEQ ID NO:1127:

(i) SEQUENCE CHARACTERISTICS:
        (A) LENGTH: 675 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1687RP (xi) SEQUENCE DESCRIPTION: SEQ ID NO:1127:

GATCAGGACA GTAGCAGCTT GACTGAGTAT CAGCAGGAAA AGCCTAGCTA ATTGGCGCGA       60
```

```
GTACAATTAC AAGTACCTGT CTGACTACTT CTTTTTGTGG GATGCCATAT TTTTTAGGAT      120

GGCCTGCAAC GGCCCGGTGG GGGCGCCATC CAAATTTATG GAGTTGAAGA GCTGTTCAAT      180

GCCCTTTATC CCATCTGCAC CGTCTTTATC GCCGAACATG GCATGCAACT CTTCAAGCAT      240

GATATCTTCT TCCTCGTGCT CTGATCCGGC GTTGTCGTCG TTTGCGCAGT CTTCGTAGGC      300

GCCATTTCTG TAATGTTGAA GCTGTTCTTT GTTCATCTTC AGACCCTCCG TCAGGAAATA      360

TTCAAAGAAA TCGTCTTCAC TAATATCTAC GCCTTCACTC TCGAAAAATG TCCGAGCCTC      420

TTCATCCCCA GCTGAAGACC CCTGACCAGA AACATGCTCA TTGCTACCTT CATCGTCATC      480

TTTAATATCT GTCAGGAAAG TCTCCAGCGA CAGGGCCAAG GCATCCATAG ACGCCTCTTT      540

GTCCGCAGTC GGTACCTCCG TAGTTAATTC AGTCGTAGAG AACTCCACCG GGCGCTCTAG      600

CTGTTTTGTA TGTACCAGAG CGCTTACTAG GTCACCCTCT AACTTTCCTT TGGGTTCAGC      660

TGTCGTTAAC TGGCC                                                      675

(2) INFORMATION FOR SEQ ID NO:1128:

(i) SEQUENCE CHARACTERISTICS:
        (A) LENGTH: 655 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1687UP (xi) SEQUENCE DESCRIPTION: SEQ ID NO:1128:

GATCCGTTCC AGTTTGGCCA GCGGAAGCTG GCGGACGAGG CGGACATCTG GGCTCATAAC       60

GCGTGGGATA ACGTAGACTG GGGTGACGAA CAGATCCGGC TCGCAAAGGA GAAGATAGAA      120

GAGCAGAAAG AATACCCGGT GCAGGAGTTT GACAAAAAGC TGTATCATAG CAACCCCGCA      180

AGGTACTGGG ATATATTCTA TAAAAATAAC AAAGAAAACT TCTTCAAAGA CAGGAAGTGG      240

TTGCAGATTG AGTTTCCCTC TCTATACGAA GCTACCAAGA AAGATGCTGG TTCAGTGACT      300

ATCTTCGAGA TTGGGTGTGG TGCGGGCAAT ACCATGTTCC CGATCTTATC TGCAAACGAA      360

AACGAACACT TACGCGTTGT GGGTGCGGAC TTCTCCCCGA AGGCCGTGGA ATTGGTAAAG      420

ACGTCGCAAA ACTTTAACCC CGCGAATGCC CACGCGACGG TATGGGACTT AGCCAACCCT      480

GATGGTCTTT TGCCCGATGG TGTCGAGCCG CATTCGGTCG ACATCGCAGT AATGATTTTT      540

GTTTTTAGTG CCTTGGCGCC CTCACAGTGG GCCCAGGCTA TGGATAATTT GCACAAAGTT      600

CTAAAACCAG GCGGTAAGAT CCTCTTTAGA GACTATGGCA GGTATGACTT GGCTC          655

(2) INFORMATION FOR SEQ ID NO:1129:

(i) SEQUENCE CHARACTERISTICS:
        (A) LENGTH: 716 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1688RP (xi) SEQUENCE DESCRIPTION: SEQ ID NO:1129:

GATCTTGTTG AGAACACTCA ACATCGGCGT AATTGCAGAG CCCCCGGTGA CCATACCGAT       60
```

-continued

| | |
|---|---|
| TTTCTTGTAC GCATTCGTCA CATAGCTGAA CCGTCCTACA GGACCTTTGA ATTCCACAGT | 120 |
| TTGGCCTGGC TGTAGCCCAG CAAACCATTT GGATACCTTA CCGTCGACAT AAGATTTGAC | 180 |
| AATGATATCG AAATGGCCCT CGGCAAATTT GTTGGAGATA GGCGTGTAGT AACGCACTTC | 240 |
| TTCTACACCA TCCAGCATCA CCTTCGCAGC TAAATGAAAG CCAGTAGGTA TATCAAGAGT | 300 |
| TTCCACGCTT GAACGGAGCT TGAATCTGTA TATCGCAGCA TTTTTGCTTA GAACGATCCG | 360 |
| TTCTTCCAAT TCTAATGGCG TCCACTCATT TGGAAGAATT GAAGTCCTGC TTCTGTATGC | 420 |
| TAGTAGCAGG CGTGCACCTA CAAACATTGC CAAAGCTAGA ATGCCTAGAA GGTACCATGC | 480 |
| GTTCCCCGCT GACCAGGCGA TAACAAGAAC GCCCAATGTA AGATGCCGC TGGGGATGAA | 540 |
| GATCCCATGA ATGGGATCAT CCAATATCTC CATACCTCTG CGTTCGGTCA TACTAATATT | 600 |
| TTGAAAGCTC GTCGTAGCTA TCGTCTAGTA AGGATGAGAA CGGTTAATAT ATGCTTCCTC | 660 |
| CTAGTTCTAT AAGCACGGAC TCCTTTGCAA CTGGTGAAGT ATCGTCTAAC GGTCAT | 716 |

(2) INFORMATION FOR SEQ ID NO:1130:

(i) SEQUENCE CHARACTERISTICS:
        (A) LENGTH: 676 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1688UP (xi) SEQUENCE DESCRIPTION: SEQ ID NO:1130:

| | |
|---|---|
| GATCAGGCCG GACGGGTACT TGCAGGAAGG CCTCACGAAA CCCAAGGGGG GCGAGGAGGG | 60 |
| CTTCTCGACG TTTTTCAACG AGACGGGCTC GGGCAAGTTC GTGCCGCGCG CGGTGTACGT | 120 |
| GGACTTGGAG CCGAACGTGA TCGACGAGGT GCGCACGGGC GCGTACCGCG AGTTGTTCCA | 180 |
| CCCGGAGCAG TTGATCAGCG GAAAGGAGGA CGCGGCGAAC AACTACGCGC GTGGGCACTA | 240 |
| CACGGTGGGG CGCGAGCTCT TGGACGATAT CCTAGACCGC ATCCGCAAGA TCTCGGACCA | 300 |
| GTGCGACGGG CTCCAGGGCT TCCTCTTCAC GCACTCGCTT GGCGGTGGTA CGGGCTCCGG | 360 |
| CTTGGGGTCT CTGCTTTTGG AGCAGCTTTC TATCGACTAC GGCAAGAAAT CGAAGTTGGA | 420 |
| GTTTGCCGTG TATCCCGCGC ACAGGTGTC CACCTCGGTC GTGGAGCCAT ACAACACCGT | 480 |
| GTTGACCACC CACACCACAT GGAGCATGC CGACTGTACG TTCATGGTCG ACAACGAGGC | 540 |
| CATCTACGAG ATGTGCAAGA AGAACTTGGA CATCTCGAGA CCTAGCTTTG CGAACTTGAA | 600 |
| CAACTTGATC GCCCACGTCG TCTCCTCGGT GACCGCGTCA TTGCGTTTCG ACGGCTCCTT | 660 |
| GAACGTGGAC TTGAAC | 676 |

(2) INFORMATION FOR SEQ ID NO:1131:

(i) SEQUENCE CHARACTERISTICS:
        (A) LENGTH: 700 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1689RP (xi) SEQUENCE DESCRIPTION: SEQ ID NO:1131:

| | |
|---|---|
| GATCGTGCAC AAGTTTGACG AGCTAAAGCT AAAGGAGGTG TTGTTGAGAG GTATCTACGG | 60 |

```
TTATGGTTTC GTTGACCCAT CTGCCATCCA GCAGCGTGCG ATCTTGCCTA TCATTGAGGG      120

CCACGACGTT TTGGCGCAGG CCCAGTCCGG TACCGGTAAG ACTGGTACCT TCTCGATTGC      180

TGCGTTGCAG AGAATCGACG AGAGCATCAA GGCCCCACAG GCGTTGATCC TAGCTCCTAC      240

CAGAGAGTTG GCGCTACAGA TCCAGAAGGT TGTGATGGCG CTTGCGCTGC ACATGGACGT      300

TAAGGTCCAC GCTTGTATCG GTGGTACGGA CCCTCGTGAG GACGCCGAGG CCTTGAGAGC      360

CGGTGCGCAG ATTGTCGTCG GTACCCCCGG CCGTGTGTTC GACATGATTG AGAGACGTWA      420

CTTCAAGACT GACCACATCA AGATGTTCAT CCTGGACGAA GCCGACGAGA TGTTGTCCTC      480

CGGCTTCCAG GAGCAAATTT ACAAGATTTT CACCATGTTG CCACCAACCA CCCAGGTCGT      540

GCTATTGTCT GCCACCATGC CAAAGGAGGT GTTGGACGTG ACCGACAAGT TCATGAACAA      600

GCCCGTCCAG AATCTTGGTC AAGAAAGGAT GCCTTGACCT TGGGAGGGTA TCCAGCAGTA      660

CTATATTAAC GTCGAGAGCG AAGAGTACAA GTACGACTGT                           700
```

(2) INFORMATION FOR SEQ ID NO:1132:

(i) SEQUENCE CHARACTERISTICS:
        (A) LENGTH: 657 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1689UP (xi) SEQUENCE DESCRIPTION: SEQ ID NO:1132:

```
GATCGCGCTG AACCTCAGCG AGGCACGGCT GGTGATCAAG GAGGCGCTGC AGCACCGGCG       60

GCGGGTGTTC GGGCAGTGGC GGGACGGGCT GGAGGAGGAC GAGGCGGACG GGGAACACA      120

ATATGACGCA GGAGAAGGAG CTGGCGATGC TGGACAAGCT GCTGGAGAAG ACGACGGGGG     180

GACAGAACCA GGCGCTGAAG CAGACGATGG TGTACCTGAC GAACTTCGCG CGGTTCCGGG     240

ACCAGGAGAC GGTGACGGCG GTGACGCAGC TGCTGGCGTC GACGGGACTG CACCCGTTCG     300

AGATTGCGCA GCTGGGGTCG CTGGCGTGCG AGGACGCGGA CGAAGCCAAG ACGCTGGTGC     360

CGAGCCTGGG GAACAAGATC TCGGACGAGG ACCTGGAGCG GATCCTGAAG GAGCTGTCGA     420

ACCTGGAGAC GCTGTACTAG ATAGCTACAT AGACAGGAAG AACTTGCCGC CGCCGCGGCG     480

CCACCAGTGG TCGAGACAGG AGTGCGATGT GTGCTCGATG TCGACGGCCT CGCGGCCGAA     540

GTTGCAGACG CAGCGCTGCG CGAGACGCGC GACGTGCGCG GACGGGCACG TGCCGTAGGG     600

CACGTGGAAG TTACCGATCT CCTCGAAGTG GTGCACCTCG TCCGCGCGCA GGAACAC       657
```

(2) INFORMATION FOR SEQ ID NO:1133:

(i) SEQUENCE CHARACTERISTICS:
        (A) LENGTH: 718 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1690RP (xi) SEQUENCE DESCRIPTION: SEQ ID NO:1133:

```
GATCTGAAAC TAATGTCATC CGCGGAAGAA CATACTAAGA GCTCATCGTT ACATCGAGAT       60
```

-continued

```
GAGACAAAGT ACCTGATGTA TAAGAGTTTT ATTGACATAT GCGCTCGGAG GCAAACGGCA        120

GGCTACCGCC TGCCCCGTGT TCCGTCTACA CATGACAACA TAATTGTGGC AATGTCAGGC        180

GGCGTGGACT CTTCAGTATG TGCTGCTTTA TACGCTCACT TCCCAAAAGT CCGTGGGCTC        240

TACATGCAGA ACTGGTCGCA GACGTCGGGC TCAGGGCCTG TAGAGGGTAA GGCCGAACCT        300

TGTTACGAGC AAGATTGGAA GGATATTGAG AAAGTGGGCG CGTACCTTAA TATTCCCGTC        360

GAGAGAGTCA ATTTCGAACG GGACTACTGG CTGGATGTTT TCGAGCCTAT GTTACAACGG        420

TATCAACAGG GTTATACTCC GAACCCAGAT ATTGGCTGCA ACAGGTTTGT AAAGTTTGGA        480

GCGTTGCGGG AGCACCTGGA CAAGGAGTAT GGACGCGGCA ACTACTGGCT GGTAACAGGC        540

CACTATGCGC GAATCCTATC CCCCCAGACT CGCAGAGAGA CCCACCTGCT GCGGAGCCAT        600

TATGCGCCAA AGGACCAAAG TTACTACTTA TCCCAAGTCC GGCGGGAGGC CCTCGCGGAC        660

CTCTTTAATG CCCATGGGAT TTCTAACAAA ACCGGAAGTC CGACAATGGG CCGCAGAA         718
```

(2) INFORMATION FOR SEQ ID NO:1134:

(i) SEQUENCE CHARACTERISTICS:
        (A) LENGTH: 696 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1690UP (xi) SEQUENCE DESCRIPTION: SEQ ID NO:1134:

```
GATCAGAAAC ATCACCATAT GGTGTCTGAA GACCTTACGG CGACGGTCGA TACACGCTAC         60

CATCTCCAAG CCGATGATGC CGGCTATTAT GGACACCGCC GACGCCGTGA TTGCCAGGAT        120

TCGCAGCTTC AGCAGCTGGC TCGAGGTGAA CGTCGAGAAC ATCCCCGGCA GTCCGAGCAC        180

GAGGTTCACC GTGGTTGTGT TGTAGGACCC GAATACACAT GTGTAGTTGC TGTCCATGCA        240

CTGTATCTGA GACGCGCCCT CCATCTTGCA CGTGCGTGCG CTACACGTCT AGCTCCCGCT        300

CGCACCTATA CTTTGTATCT GTTTCGCCCT TGCTGCGCGC TAGCCCCCTC GCGCTTGCCT        360

CTTATCCCTT CTCGAAGTCG TCTCCCCTAA GTTGGATCCC AGCGACCTCC TAGTCGAAAA        420

CTGCTGTCTA CGTTCGCCAG GCACTAGTTG CCTCCCACTG CAGGTTATCG ATAAGTCCTA        480

AAATACCACC AAGCAGGCGT TGTACTGCTT CTATACGCCA ACCCTCGCTT TTCGTTGGGC        540

TGACACACTC AAGTGACTGC AAGAAGACTA CCCTACTCAC AGATACCGTC GTCCGTTGTA        600

CGCACGCTAA AAGACAAGTT AAATCTACGA CACATATAGT GCCTCGCAAG CTCACCGCAT        660

CCGGAAGGAA CAAGCTATTA GAAACTGAGA CACCTC                                 696
```

(2) INFORMATION FOR SEQ ID NO:1135:

(i) SEQUENCE CHARACTERISTICS:
        (A) LENGTH: 693 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1691RP (xi) SEQUENCE DESCRIPTION: SEQ ID NO:1135:

```
GATCTTCTTT GTATTCTCGG TCTTACCTGC CCCAGACTCC CCTGTTACTA ACACCGACTG         60
```

```
GTCCTGCCTC TGTGTCAACA AGTTGCGGTA TGCCTGCTCC GCTACCGCAA AGATATGCGG        120

CTCGTTGTCT TCCTTGGGTG ACCCATGGTA CAAGTTCACA TAGTCCTGCG TGTACACCTT        180

GATGTTGCTG TACGGATTCA ACGCGACGAG GAATAGCCCA GAATAAGTAT ATATCATATC        240

GTCCTTGTAT CGGTTCTCCA AGTTGTACAA CACAGACGCC TCGTTCAAGT GGGTCAACTC        300

GGACATATCG TCTATCTTGT CAAACGTTGA CGGATTCACC GCCGCGGTCT CCACCTCCAG        360

CACTTCTCGT TCCTTGCCAT TCACTCTCAC AAGACAGACC TTCTCATCCT TGTTCTGTTT        420

GTTTTTAATT GTCTTTGTGG AAACCAACTG TCCTTTCACA AACACCTCCT CAGCATCTGG        480

AACCCAAATC ATTTGACATT GTTCACTCAT CGGGACAGAT GCTCTTGAAC TTATCTAATA        540

TGCAATAACC AAATTCAACT TTACTTTAAT CACCTGCCTG TTACACACGA AGCAATGTTG        600

GATCTCATAT TCACACGACC TACTTTTTCG AAACACTTAT TTGTTTATGT CGGGCTCGAG        660

CATACACGTC GGTCACGTGA CAAGCGCATG TAC                                    693

(2) INFORMATION FOR SEQ ID NO:1136:

(i) SEQUENCE CHARACTERISTICS:
        (A) LENGTH: 705 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1691UP (xi) SEQUENCE DESCRIPTION: SEQ ID NO:1136:

GATCATTATG CAACCGAATC TGGTATCTCA GAAGATTACC GTAGGACTGT GCCTGTCCGA         60

TCGATTACGT TAGTGGGGTA GAGAATGAAG TAAGAAGCAG CTCTGCGATT ATTGTCGCTT        120

TGCGCCTCAT GTGAGGTAAA GCCCTATCCC GCAGGGTGGC GGCTTTCTGC AAGAAAATCT        180

GGGCATCACG CCCCCGAAAC GAAATGCGAT AGTCACCTGT GCCATGGCGA CGAGTCATTT        240

CCCCATTCGT ACAGAAATGA ACGGGCAGAA TCGCGTAATG GATTTTCTGT GGCGTTCGTG        300

CCAAAAGGTG ATCTCCACCT GCGTGCTGCC CTGCGGGCGT GGTTGAGCAG AGCACCTGGA        360

AAAAGAACAG CACAGAAGGC CAATGCAGTT GGCCAATTGA GGCAATAGCC GAGCAGGAAC        420

AGTCGAAAGT GGGTGTTCTG GCGCTGTTGG ATCTGAAAAA TGCAGGAAGT TACAAAAAAC        480

AGTGGGGCAA TACATAGAAA CCGGCGACCC GGCGATCGCC TAATCATCTG CCATGGAGAC        540

GCGGGTCCGG CGCTCGAACC AGCGGTCGAA ACCTTGAGGG CATGGTGATA CGGGCCCGTC        600

GGCGGGGCAC TCAAACAGGC ACGTGTTAAT CCTGACAAAA CGCAGCGGGG TAATTCCTTT        660

CCGCAAGCCG GACGGGTATA TGAATCGTAC GATACCAGTT GTCGA                       705

(2) INFORMATION FOR SEQ ID NO:1137:

(i) SEQUENCE CHARACTERISTICS:
        (A) LENGTH: 636 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1692RP (xi) SEQUENCE DESCRIPTION: SEQ ID NO:1137:
```

```
GATCTAAATA TATATAATTT AATTTATAAA GATTAATATA AACTTTTTTA TTATAATATT      60

TAAGTATTAA ATTATTTAAA CTATTATTAT CATTATTTAA TAAATTAATT ATTTGATTAT     120

TAATACTTAT TATATAATTA TTATATAATT TACTTAATTC ATCATTATTA ATATTTATAT     180

AATTATAAAA ATAATATTTA ATATGAATAC TATTTAGTCT ATGTTCAAAT TTTAAATTAG     240

TTATTAAAAT ATTATTAGAT ATTATTATTT TCTTTAATAA ATTATTAAAT AGATTATCAA     300

TAATTAATAT ATTATTTATT AATTGTTTAT TAAAATAATA TATTTTATTA TTATAAAGAT     360

TTAATTTATT TAAATATTGT AAATTATTAT TTTTATTATA ATATCTATTT TTATAAATAT     420

TATGTTGATT TATATTATTT AATCTTTTTA TAAGAATTAT TATTAAAATT AATTTTAACT     480

TTAATTTCTT ATTATTAATT TTTATATTAT TTAATAAATT ATATTCATTT TATTTATTTA     540

TTTATTTAAT TAAATTAATT ATTTAATTAA TATTTTATCA TTATTTAATT AATTAATAAA     600

ATATTATAAA GAATGTAGTT AAAAATACTT ATAAAA                              636

(2) INFORMATION FOR SEQ ID NO:1138:

(i) SEQUENCE CHARACTERISTICS:
        (A) LENGTH: 719 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1692UP (xi) SEQUENCE DESCRIPTION: SEQ ID NO:1138:

GATCTTGATA CTAGAGCTTA TTTTACTTCA GCTACTATAA TTATTCTTAT TCCTACTAGT      60

ATTAAAGTAT TTAGTTGATT ACTAACTATT TATGGTGGTT CATTAAGATT ACTAACACCA     120

ATATTATATC TATTATCATT TTTATTTTTA TTTACTGTAG GTGGTTTAAC TGGTGTAGTA     180

TTAGCTAATC TATCATTAGA TGTAGCATTC CATGATACTT ATTATGTAGT ACTACATTTC     240

CATTATGTAT TAAGTTTAGG TGCTGTATTC TCTATGTTTG CTGGTTATTA TTATTGAAGT     300

CCTCTTGTTT TAGGTTTAAA TTATAATGAA AAATTATCAC AAATTCAATT CTGATTAATT     360

TTCTTAGGTC TTAATATTAT TTTCTTCCCT ATGCATTTCT TAGGTATTAA TGGTATACCA     420

AGAAGAATTC CTGATTATCC TGATCTATTC CTAGGTTGAA ATTTAGTATC TTCATTTGGT     480

TCTATAATAA CTATTATATC ATTAATGTTA TTCCTTTATA TTATTTATGA TCAATTAATA     540

AATGGTTTAA CTAATAAAGT TAATAATAAA TCTATTAATT ATATAAAACT ACCTGATTTT     600

ATTGAATCAA ATAATATTTC CTTAATGAAT ACTACTAAAT CATCATCTAT TGAGTTTATA     660

TTAAATTCAC CACCTCTTAT TCATTCATTT AATACTCCTC TAATTCAATC TTAAAATAT     719

(2) INFORMATION FOR SEQ ID NO:1139:

(i) SEQUENCE CHARACTERISTICS:
        (A) LENGTH: 714 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1693RP (xi) SEQUENCE DESCRIPTION: SEQ ID NO:1139:

GATCCCTTAG CGACTCTCTC CACCGCTCGA CGAGGCCATT GAGCTCTTAC GAACTGCACA      60
```

-continued

```
AACCTACTCG AACTCTGTTT CCAGACTTCT TTCTGTTTGT CTTCAACTGC TTTCGCATGA      120

AGTACCCCCC AGGCTATTTT TCTTACCCGC CTGGTGTTTG TCTATATACC CGGTTGTATT      180

TTTGATAAAA AACTCAGCTC TTCCTCTACG GCAGAAATAT ATATCCAGTC CTTAGCGCCA      240

TGCGAAAATC TGCCTTTTTA CCGCTGTTTC TCCCAGTCTT AGCACTGGCA GAAAAAAGAT      300

GTATGGCGTA TAGGCGCTGG CCCCGCGGAA AAAAAAAAAA AATAGAAAAA TAGAAAAATA      360

AAAAGACGTG GGCCGCCCCG CGGGCAGACG AAGAAAAAAT AGGCGCCCAC CCCTCCAAGC      420

AGACGACAGG CGAGACATAA TAAAATCCCA CACCAAGGGA AGAAAGTCTT GTGCACGCTC      480

CCGGCCTCAT ACGCTGCCAT TCTGTTCCAT CCGGCTTGCA AACCCAGTAG TGGCATGTCA      540

AAGCATTGCT CCGACGCTCC GCTGCCTTGC AGTCGACATC CTCTTCCTAA CCCCAGCCAG      600

ACTTCCCATA CTTTGGCACT TCACATAGCA TATCACTTTT CAGATCACTT ACGTGACATT      660

CCGGTACGGA ATGGCACTCC AATGCCGACA AACCTCTTCC TACCCCGTGA CTTA           714
```

(2) INFORMATION FOR SEQ ID NO:1140:

(i) SEQUENCE CHARACTERISTICS:
        (A) LENGTH: 692 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1693UP (xi) SEQUENCE DESCRIPTION: SEQ ID NO:1140:

```
GATCCGTAAC TTCGGGATAA GGATTGGCTC TAAGGATCGG GTAGTGAGGG CCTTGGTCAG       60

ACGCGGCAAG TGTGCTTGTG GTCTGTCCTC GGGGGCTTGC TCCTGGGGAC GGACTGCTTG      120

CGTGCTCTGT CGTAGACGGC CTTGGTAGAC CATCTCTGGT CGTCGCTTGC TACAATTAAC      180

GATCAACTTA GAACTGGTAC GGACAAGGGG AATCTGACTG TCTAATTAAA ACATAGCATT      240

GCGATGGTCA GAAAGTGATG TTGACGCAAT GTGATTTCTG CCCAGTGCTC TGAATGTCAA      300

AGTGAAGAAA TTCAACCAAG CGCGGGTAAA CGGCGGGAGT AACTATGACT CTCTTAAGGT      360

AGCCAAATGC CTCGTCATCT AATTAGTGAC GCGCATGAAT GGATTAACGA GATTCCCACT      420

GTCCCTATCT ACTATCTAGC GAAACCACAG CCAAGGGAAC GGGCTTGGCA GAATCAGCGG      480

GGAAAGAAGA CCCTGTTGAG CTTGACTCTA GTTTGACATT GTGAAGAGAC ATAGAGGGTG      540

TAGAATAAGT GGGAGCTTCG GCGCCAGTGA AATACCACTA CCTTTATAGT TTCTTTACTT      600

ATTCAATTAA GCGGAGCTGG AATTCATTTT CCACCTTCTA GCATTTAAAG TCCTATACGG      660

GCTGATCCGG GTTGAAGACA TTGTCAGGTG GG                                    692
```

(2) INFORMATION FOR SEQ ID NO:1141:

(i) SEQUENCE CHARACTERISTICS:
        (A) LENGTH: 673 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1694RP (xi) SEQUENCE DESCRIPTION: SEQ ID NO:1141:

```
GATCCGTTCC TTGAGAAGCA CCTAAAGCCT GAACTCCTGG CAGAAGCGAT CAAGGGAACC      60

TCTTGGGAGG GTAAAGTTAG TATTAACTTG GTAGACGGAT TCGACCACTC GTATTACTTC     120

GTCAGCACGT TCGTGCCGGA ACACGCAAAG TACCATGCAG AAAAGTTGGG TCTAGTTTGA     180

GATTTGACGT TGCGCCTGTT AATTGGTATA TACTTACATA TTTAGTCATA TGACGGCTTC     240

AAGTACTCTG ATTCTGCATT ATAAGTGCAG CCGAATGCCA GCCTCCGGCA GTAATGGCAA     300

CGCAAACTGA ATTTGCCGGT AGTTCAACCT TGGCCGGTTG CAGCACGCGT ATGCTCCGAG     360

CAGACTCAAA CGTCGCTATT TGGCGGGTAT CTACAGCCTC GTCGGGATCT CCCTGCCCAA     420

GACAGCCACA GATATCACTC TCCAGCCCCC AGGAGTAGAG TTCACCTTTG TCGGTTAGAG     480

CTAGGTTGTG GTAGTCTCCC GCAGATACAG CAATAAACTT CTGGCCTTGT TCCAAATTCA     540

TCTTCATGAA TGAGTCCTCG ACGATATCAC CATTATTCAC CTTCAGGGTG TATGTGCTAT     600

TCTCGGTACA TAAAACCAGT GTCATGCAAG ATGCCTCAAT CTTCGTTAAC CGTCCATCAA     660

ATGGCAAAAT CAA                                                       673

(2) INFORMATION FOR SEQ ID NO:1142:

(i) SEQUENCE CHARACTERISTICS:
        (A) LENGTH: 676 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1694UP (xi) SEQUENCE DESCRIPTION: SEQ ID NO:1142:

GATCAGCCCC CGACCGAAGA ACACTCGCTT CCCTCTGGCG AGCGCCGAAA TTCTTGGACC      60

GAGTATCAAC AAATCCAGTT AGATAACGAT CACATGATTG CAACACTGCG GGAATTCATT     120

AGTTACCAGA CTGTTTCCCA ACTCCCAGAG CCCCAAAATA TCATCGATTC GCGTAGGTGT     180

GCGAACTTCC TGCAAAATCT CTTCACTAAG CTCGGTGCTA ACCATTGTGG GCTTATACCT     240

GTCAGTACAG GCAGCAACCC GGTGGTTCTC GCGCAGTTCA AGGGCAATGC AGCCGCGCCC     300

AAACGCATAC TATGGTATGG CCACTACGAT GTGATATCCG CGGACCACCC GTCGCAGTGG     360

GACAACGACC CCTTCACGCT CACTTGCGAA AATGGGTATC TTAAGGGAAG AGGCGTGTCT     420

GATAACAAAG GCCCGCTGCT TGCCGCCATC TTCAGTGTAG CCGAGCTTTT CCAGAAAGGA     480

TACCTGAACA ACGACATCAT CTTTCTAGTC GAGGGCGAGG AAGAAAATGG CTCTCGCGGC     540

TTCAGGGAAA TTTTGCTTGC CTCCGAAGGG CTTCTCAATC AGCGGTGGGA CTGGATCCTG     600

TTCAGCAATT CCTACTGGCT GGATCAGAAG GTGCCCTGCC TCAACTATGG CCTCCGAGGC     660

GTCATAAACG CCGAAA                                                    676

(2) INFORMATION FOR SEQ ID NO:1143:

(i) SEQUENCE CHARACTERISTICS:
        (A) LENGTH: 711 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1695RP (xi) SEQUENCE DESCRIPTION: SEQ ID NO:1143:
```

```
GATCTGCCCC CAAAAGATTT CGGTGCCGGC TACCCCAAAA GATTTTCGGT GCCGGCTACC      60

CCATCACGAG ATGGCACTGG CTCATTGGCG AGCTCCTGGG CATTTGCCTA TGACAGAGGA     120

ATGAGTCAGC TTTACTCCGC CACACCATAC TCCCGGGCCT TCAACAAGCT TCTGTTTGCC     180

ATCGGCATCG TGGCCAGTTC TTACACTGCG GCCCCACCTG CATCGGCCGT CATCGCAGCC     240

GTTTTGTCAC AGTTCTCCCT CCGCAGGTAT CGTCTCCGCA CCGGTAACGG ACGCGACTAC     300

GCAGCGGCTG CCGCACTCAC GTGCGGGCGG GTCTTCTCTC CCACCGTGAT AGTCACTTTT     360

CAGTAGTGTG TGCTGCCTTG AATTGGCAGG GCAATCGTTC AAGCTGCTCT GGCGCGGACG     420

ACGACCCCAT CTCCGCAACG GCGTTGGCGG AGAAAGGGTG TTTCGGACCA GACATCGGCC     480

ATCTGCCGCA GTCAGCAGCT GCCTTGGTAC GGAGCTACCT GTCTATATTA TCCCCTTAAT     540

AAACATTGGA TATGCCTGTT ATTGTATGCC AACGGTTCTC CGGGTACAAC GGGGTAGTCC     600

CGCCCCTCCC TGAGCTATCC TGGCCGATGT GAAGTGCCTT TGGTTAAGTG GTCTGCTTTC     660

CCGGGCCACT TGTAAACACT ATGGCGGATC ATACAGCCAG GACTCAAATA C              711

(2) INFORMATION FOR SEQ ID NO:1144:

(i) SEQUENCE CHARACTERISTICS:
        (A) LENGTH: 654 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
         (A) ORGANISM: PAG1695UP (xi) SEQUENCE DESCRIPTION: SEQ ID NO:1144:

GATCTGAAAA GCAGGAAGTC GCAGTGGGAG GCGCCTGCGG GCACGTCGTG GCCAGCGAAG      60

GGTGCGCCGG ACGCGCCACC GGCGTACGAC ACGGCCGTCG CACGCGCCGC CGCGCACGGC     120

GCGCAGGCCG TTGCGCCCCA GCCCGACTAC GGCACACAGG CCGGATACGC GCCCCAGGGG     180

TACGGCGCGC GGGCCGGGTA CACGCCCCAG CCCGGCTACG GCGCACAGCC CGGCTACGGC     240

ACACAGCCCG GCTACGGTGC ACAGCCCGGC TACGGCGCAC AGCCCGGCTA CGGCGCACAG     300

CCCGGCTATG CGCCGCAACC CGGTTACGGA TACGCGCCGC AGCCGGGCTA TGGTGCCGCG     360

CCCGGGCCGT ACGCGCAGCA GCCCGCGCAC GGTTACCCGG CCGGCGCAGC CGCCGCGCCG     420

CAGAACGGCG GCCGCAACAA CATGATGATG GGCGGCCTGA TGGGTGCCGG CGTGGGGTTG     480

ATGGCCGGGT CACTAATGAC CACAGCCATG TATAACCACG ACAAGGACGT GGCCGATGCT     540

GCCTACGACC GCGGCTATGA AGACGCTTCA TCGACGGCGA CTTCTAGGCC GCACCCCGTC     600

ACGTGCCAGA CCCGTAGAGA GCTAGGACAA CTTACGTAAC GCGTCGACGT ACGC           654

(2) INFORMATION FOR SEQ ID NO:1145:

(i) SEQUENCE CHARACTERISTICS:
        (A) LENGTH: 711 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
         (A) ORGANISM: PAG1696RP (xi) SEQUENCE DESCRIPTION: SEQ ID NO:1145:
```

```
GATCTTGTTC TCCATTGACA TCGAGGCGTT TGAGAGCAAC ACATCTGTCG TCACAGAGGT      60

GGGAATCTCG GTCTACGATC CCCGCGAGAA CGAGGACACG CTCGTGCCCC ACTTCCGCAC     120

GTACCACCTC TGTCCTGAGG AGTCTCTCGG GTTGATAAAC AAGCGGTTTG TTCCGAATCA     180

CAAATGCGAG TTTCTCCATG GTGAAACCAT GGTAATGCCG CTCTCCGAGT GCGTTGAGTT     240

CATTAACGGG CTTATCGAGT ACTACCTGTA CCCACCCACG GGCGTGGACG ACAAGTACTC     300

GCGGGCAATT GTGGGTCATG GTGTCTCTGG TGATCTGCAA TGGCTTAGGA GTCTGCTCAT     360

CGACCTGCCC ACGATCGCTG GCCCAGGCAA CTCCCATCCG CGCGACCATG TTTCTGTCCT     420

AGATACCGCG CATTTATACC AGTACTTCTA TGGTCAGAAG GGTTCATCCC TAGGTAAGAG     480

CTTAAGATTG CACGGTGTCC CACATAGCTA TCTGCACAAT GCAGGCAACG ATGCATATTA     540

CACATTACAA CTGCTCATGA AGATGGGCGA TGTGCAGCAA CGCATCCGGC ACCAATGGGA     600

CGATCTATAT GCTGTCTTCC ACACGTTGAA GCAA0GGAA GAGTATGAGA ACTCCACGCC      660

CTCCACTCAG CACGCAGAAT CCGTCCATAA CAGCACCCGC GCTACCGGGA A              711

(2) INFORMATION FOR SEQ ID NO:1146:

(i) SEQUENCE CHARACTERISTICS:
        (A) LENGTH: 681 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1696UP (xi) SEQUENCE DESCRIPTION: SEQ ID NO:1146:

GATCCGTCAG AAACCCATCG CCTCGCTCGC TCGTCTGCTA ACGCCCAGAA CGCCACCTGT      60

TCGCCAGCGC GGTTGTCGTC ACCCGCAGCA ACAGGACGAG AACTCTCCGC TTTCGGCCTC     180

GTGAGATTTT GGATTCAGTC ACGTGATTCA CGTAGAGGTT ACCCGGAAAG AGCGGCTTGG     240

ATGCCAGTAA TCACCGCCGT TATCCCCGGC CTTCTTAAGC ATTCAGTCTG AGCCGCTTCT     300

CCCCGCTTCC TTGTTCTCCT GGAATTTCAA AGGGCGGGCG GTATATAGGC GGCGAGAAAA     360

ACACGGTGGC GAACGTTGTT GCCGCCAAGC GTTATCGTGA AGAACAAGCA TAATGGTTTC     420

CCCTTCGGTT ATTAAACAGG TGCAGGCGCT AATCCAGCAG AACCGCGTGT TCATTGCATC     480

CAAGACGTAC TGTCCGTATT GCCAGGCGGC AAAGCGTACG TTGCTGGAGG AGAAGCGCGT     540

CCCGGCAAGC GCAGTAAAAC TGTTGGAGCT TGACACCATG GGCGAGGAGG GCGCGGTGAT     600

CCAAGCGGCG TTGCAGGAGC TGAGCGGGCA GCGCACCGTG CCCAACATCT ACATCAACGG     660

GCGCCATGTG GGTGGCAACA A                                              681

(2) INFORMATION FOR SEQ ID NO:1147:

(i) SEQUENCE CHARACTERISTICS:
        (A) LENGTH: 667 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1698RP (xi) SEQUENCE DESCRIPTION: SEQ ID NO:1147:

GATCTGGTGC TTTTCAACGC GCCGCCCCAG ACAATTTCCG GAAGCATACA TATCGCCATT      60
```

-continued

```
TATATCTTAT TTCTGTATTC TCAGGTACTG ATCGCTGTTG ATGAACGGGC AACCCTGTGA      180

CTTGGGGATT AACACTGTAT GAAGCCGGAC GGGGGGGTAG CACATTGGTA CTAGGCTGGC      240

TGAATTCATA ATTGGAATAA GGTGCTGCTT GCCCCGATGG CTGGTATGTC CGGTGCTGGG      300

TTGAAGGCAT AAAATTGCTC GAGCTGTAGC ATGTTGCCTT CTCTAGCATC ATGTTGTATG      360

TAACCTCCGC ATTGGCCAGA ACCTCGCGCA ATGATGCAAG ATCTTCCTTC TTCTGCGCAT      420

ATTTACCGAT GAGTTTCGTG ACATGTGGTC TAAGCGGTGT GACGGTAGAG TAAAGTTCTG      480

ATATCTCGTC TTCGTGTGTC ACATCCACAT TCTGGGAGAC CCTTAGTTTC TGGAGCAAGT      540

TCTCGACATT GCCGGCTTGC GCAAAGACAG CATGCTCCTG AGCAGCCTCC TTAGCTACCT      600

CCTCTGCAGT TGGCTCAGGG CATACGCCGA CATAATTCAC TGGGAAAAAT ACCAACCTTG      660

CCGCGCA                                                                667
```

(2) INFORMATION FOR SEQ ID NO:1148:

(i) SEQUENCE CHARACTERISTICS:
        (A) LENGTH: 572 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1698UP (xi) SEQUENCE DESCRIPTION: SEQ ID NO:1148:

```
GATCAGCAAG CTGGCCGCCG CAGGTGTGCA TCTGGGGCAG TCTACGTCGT TGTGGCGCTC       60

CTCCACTCAA CCATACATCT ACGGCTCTTA CAAGGGCATC CACATCATTG ATCTAAACCA      120

GACGCTGTTT CACCTGAAGA GAGCTGCGAA GGTCGTTGAG GGTGTTGCGG AGAATGGTGG      180

CCTGATCTTG TTTTTGGGTA CCAGAGAAGG GCAGAAACCA CCTTTACGGC GGGCTGCAGA      240

GAGGGTGCGT GGCTGTTATG TCGCCTCGAA ATGGATACCG GGGACCTTGA CAAACCCAAT      300

TGAAATATCC ACTGTCTGGG GCAGGCATGA AGTTGACTTC GAGGGCAATC CAACTGGCAG      360

GGAATTGACA GAAGAAGAGA ACATCCGCAT CATAAAGCCG GACTTAATTA TTGTTTTGAA      420

CCCAACAGAA AACATGAACG CGTTGAGAGA GGCTATGCAG GCTAGAGTGC CACCTATTGG      480

GATCATTGAC ACCGACTCAG AGCCTTCAAT GGTCACATAC CCGGTCCCTG GTAACSAACG      540

ATTCGCTACG TTCTGTAAGT TTACTTGTAA AC                                    572
```

(2) INFORMATION FOR SEQ ID NO:1149:

(i) SEQUENCE CHARACTERISTICS:
        (A) LENGTH: 664 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1699RP (xi) SEQUENCE DESCRIPTION: SEQ ID NO:1149:

```
GATCTGCGTG TATATTTGGA TGTATATGGA CTTCACACTT TCGGAAGCAA TGGAACTCGA       60

AAGCTGGTTG ACCACTCTGC TGTATTCTCG TAGTCTTTCT GAAACGACGG TAAGAAAATT      120

AACCTTGAGC GGCGATAGGG AAGATGCAAC TTTAAATTTC TCTACTTGGT TACTCAAATA      180
```

-continued

| | |
|---|---|
| CTGATATAAT AATGCAGCCT CAAATATGCT GTGGAAAACA CCACTTTCGC CGTTCGGAAC | 240 |
| ATTGGGTGGG ATTTCGATAA CCTGATTGGA GATCGGGAAC AAACTCGACG TAGTAGCCAG | 300 |
| TAACGTGTAG GAAATATACT TTAAAACGTC GGCCTCGGGC ACCATGTTGC TGTAGTATGG | 360 |
| GTTAGACAGA TATGCCAATG GAGTATCGTG CTGCTGCGGC CGCTTGGGGA CCGGGCCGCC | 420 |
| GTAGGCAGAG GTTACCGCCG ACCGGCGCTC TGAAAGCCGC TCCACATTCT CGAACGACTC | 480 |
| TGCATAGACA CTAACCGCCC TCGACGGCGT CATCAGCGAG TTGTGCCGTT GCAGCGTGGC | 540 |
| GTTCGTAAGA TATCCAGACG CGGTGCGCCT GTGTCGGAAG GGCGTGCTCT CCTGCGGCAC | 600 |
| GCTGTTCAGC ACCGTCAGGT ACTTCAGCAC CTGCTCCTTG CTACCGAAAC TCTCCAGCAC | 660 |
| TTTC | 664 |

(2) INFORMATION FOR SEQ ID NO:1150:

(i) SEQUENCE CHARACTERISTICS:
        (A) LENGTH: 642 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1699UP (xi) SEQUENCE DESCRIPTION: SEQ ID NO:1150:

| | |
|---|---|
| GATCTCCACC GCGTCCAGCA CCACGATCCG GTCACCGTCC CACCGCGTCA TCGCCACTGT | 60 |
| CCGCGCGACG CTTTCGAAAA CCGCCCGTCC CTCCGCCGTC GCAGCCCCTC CCCCGCTGTC | 120 |
| GTGCGTCCGG TGCTCGGCCT CCCGCGACCG CAGCGTCGCC ACCACCCGCT CTATATTCAC | 180 |
| GCCCGCGGGC TTCAGCGTGT CGCGCTTGAT GCCAGGGCTG GTGGGTTTCT CTCCCACCAC | 240 |
| CTCCAGGCTC TTGATAAACG TCGTCTTAAT CACCTTAAAG CTCGCAGTAT GGCCCTTGCG | 300 |
| CCCACATAGT AGCGTCAGCG TATGGTTTCC CGAATCGTAC GCGTATATCT TGCCCTGTGT | 360 |
| TACACCGTCG AGGACGTTGG TCACCCGCAC CTTGAATCCA AGGATATGTT CCAAGTTGAT | 420 |
| GCTCATTCTG CTCACTTCCA AGCCCACACA GCTATCCTGG CCACCTTAGA ATGCCACGCC | 480 |
| TGCTCCCCGT CCACTGGCTG ACTCCCAATC GTTCAGTTTG CGGTGTGGGT ATTTTTTTGA | 540 |
| AGTGGCGCTC TAACGATGAA GTAGGATTTT CTATGTATTA CTATGTCGCA CAAAGGTTAG | 600 |
| TTCCAATAGT GCTTGCAACT ATCAGGTGCT GTGGAATTCC AA | 642 |

(2) INFORMATION FOR SEQ ID NO:1151:

(i) SEQUENCE CHARACTERISTICS:
        (A) LENGTH: 624 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1700RP (xi) SEQUENCE DESCRIPTION: SEQ ID NO:1151:

| | |
|---|---|
| GATCAGCAAC CGCAGCGGAT GAGGGAGTCC GCTCACGCAC GGTCTTGTTT TCAGCGCTTG | 60 |
| GCTTGCTTTT CTCCTTTATG CGTTGTACTA CTTCTGTGAT GTGCTCGGCA TCCAGGCCCC | 120 |
| TTTTCCTTAG CCTGCTTCGT AACCTGCGCA GGCGGCGGTT GCTACGAACA CGCAACTTGG | 180 |
| CTTCTGGATC AGCAAGCTGC GCTCGGTGTT TGCGCAGCCG TTGGCATGCT CGCGGATCCT | 240 |

```
CGCGTTCAAT ATACCAGAAT GCATCATGCT TCGCTGGCTC TATATTGACC TGGTGGCCAT    300

ATATGAAAAG GCGGTCCTTG AAGTTTTGTA AAAACTCGTC TGCCTGAGAT GGCGTAGCGA    360

ACCCAAGGAA GCATTTATTG CGGCATTTAC GAGGCCTGGA AACACTAACT ACCCCGTACT    420

TCTCATCTAC CAGTGGAAGG GGCACGTCTG CGGAAGGAAG CGGCTCTGGC AACGTTTTCT    480

CCGCCGATAG AGCATATGGG TTATCCTTGT TGATGGACTT CAACAGTTGT CGAGCATATT    540

CTATCCTGGA GGCATTTGAC GCTGGCAAAT TTGACAGGTA GACACTGGAT GGCGGGGTTA    600

GTATCGAATC GACAGCAGTA TAGC                                          624

(2) INFORMATION FOR SEQ ID NO:1152:

(i) SEQUENCE CHARACTERISTICS:
        (A) LENGTH: 603 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: PAG1700UP (xi) SEQUENCE DESCRIPTION: SEQ ID NO:1152:

GATCACTGGG CCTGGAGGGG CGCGCCTTTT TGCGGCTGTT GTAGAACAGC ATGCCGCGGC     60

GGACCTTGTC ATAGAAGTGT TTAGACTGTA GGGTTCCCAT CGAATGGGAG CGGCGGTAGC    120

TGTGACTTTT CATGATAATG GGGGTGCANA GCTTGAGGTG GTCGTCGTAC GGGGAGGAAA    180

TGAGGTTGCG GCCGAGACGG AGGTCGTCGG CGCGCGCGAG CGACGAGCCG CCGGATGGCC    240

ACTTCCAGGA CTTGCGCGAC GACGGCGCGT GGCGCGAGGA GTAGGAGCGG ATGGGGAAGT    300

CGCCGCCAAG CTGCGAGCCG CGGAGCCACG ACGTGAGCCG CTTCAANAAA CGGCGACGGC    360

GGTTGGCGGG CTGGAGCTGG CCGGCGACAA ACGCAGAGCC GCTGTCGGCG AGACCGGTGG    420

GCGCGCCTGC GCTGCTGGTA AGCCCAGTGG CGGACTCAGG CAAGCCGGAC ATGCCCGGGA    480

AGTAGCGCGC GCTGTTGGCG CTGAGCTTCG GAAACATCTT GGAGAAGAAG CCCGGCTCCG    540

TGGAGCGCAA CACGCGGTCC GCCTTGGAGA TGTGCTCCTG CGTGGAGTGC GCCAACTGCT    600

CCA                                                                 603
```

| TABLE 3 | |
|---|---|
| Sequence | Description |
| SEQ ID NO: 1 | Primer RP5 |
| SEQ ID NO: 2 | Primer RP3 |
| SEQ ID NO: 3 | AgLEU2 coding sequence |
| SEQ ID NO: 4 | AgLEU2 protein sequence |
| SEQ ID NO: 5 | Primer RP1 |
| SEQ ID NO: 6 | Primer RP2 |
| SEQ ID NO: 7 | PAG1489 |
| SEQ ID NO: 8 | Primer G2 |
| SEQ ID NO: 9 | Primer G3 |
| SEQ ID NO: 10 | S1 Primer |
| SEQ ID NO: 11 | S2 Primer |
| SEQ ID NO: 12 | Primer PTEF2-kan |
| SEQ ID NO: 13 | Primer TTEF2-kan |
| SEQ ID NO: 14 | Primer TEF2-15ORPG |
| SEQ ID NO: 15 | Primer TEF2-BglII |
| SEQ ID NO: 16 | PAG1001RP |
| SEQ ID NO: 17 | PAG1001UP |
| SEQ ID NO: 18 | PAG1002I1 |

| TABLE 3-continued | |
|---|---|
| Sequence | Description |
| SEQ ID NO: 19 | PAG1002I2 |
| SEQ ID NO: 20 | PAG1002RP |
| SEQ ID NO: 21 | PAG1002UP |
| SEQ ID NO: 22 | PAG1003RP |
| SEQ ID NO: 23 | PAG1003UP |
| SEQ ID NO: 24 | PAG1004RP |
| SEQ ID NO: 25 | PAG1004UP |
| SEQ ID NO: 26 | PAG1005RP |
| SEQ ID NO: 27 | PAG1005UP |
| SEQ ID NO: 28 | PAG1006RP |
| SEQ ID NO: 29 | PAG1006UP |
| SEQ ID NO: 30 | PAG1007RP |
| SEQ ID NO: 31 | PAG1007UP |
| SEQ ID NO: 32 | PAG1008I1 |
| SEQ ID NO: 33 | PAG1008I2 |
| SEQ ID NO: 34 | PAG1008RP |
| SEQ ID NO: 35 | PAG1008UP |
| SEQ ID NO: 36 | PAG1009RP |

TABLE 3-continued

| Sequence | Description |
|---|---|
| SEQ ID NO: 37 | PAG1009UP |
| SEQ ID NO: 38 | PAG1010I1 |
| SEQ ID NO: 39 | PAG1010I2 |
| SEQ ID NO: 40 | PAG1010RP |
| SEQ ID NO: 41 | PAG1010UP |
| SEQ ID NO: 42 | PAG1011I1 |
| SEQ ID NO: 43 | PAG1011I2 |
| SEQ ID NO: 44 | PAG1011RP |
| SEQ ID NO: 45 | PAG1011UP |
| SEQ ID NO: 46 | PAG1012RP |
| SEQ ID NO: 47 | PAG1012UP |
| SEQ ID NO: 48 | PAG1013I1 |
| SEQ ID NO: 49 | PAG1013I2 |
| SEQ ID NO: 50 | PAG1013RP |
| SEQ ID NO: 51 | PAG1013UP |
| SEQ ID NO: 52 | PAG1014RP |
| SEQ ID NO: 53 | PAG1014UP |
| SEQ ID NO: 54 | PAG1015RP |
| SEQ ID NO: 55 | PAG1015UP |
| SEQ ID NO: 56 | PAG1016RP |
| SEQ ID NO: 57 | PAG1016UP |
| SEQ ID NO: 58 | PAG1017I1 |
| SEQ ID NO: 59 | PAG1017I2 |
| SEQ ID NO: 60 | PAG1017RP |
| SEQ ID NO: 61 | PAG1017UP |
| SEQ ID NO: 62 | PAG1018RP |
| SEQ ID NO: 63 | PAG1018UP |
| SEQ ID NO: 64 | PAG1019RP |
| SEQ ID NO: 65 | PAG1019UP |
| SEQ ID NO: 66 | PAG1020RP |
| SEQ ID NO: 67 | PAG1020UP |
| SEQ ID NO: 68 | PAG1021I1 |
| SEQ ID NO: 69 | PAG1021I2 |
| SEQ ID NO: 70 | PAG1021RP |
| SEQ ID NO: 71 | PAG1021UP |
| SEQ ID NO: 72 | PAG1022RP |
| SEQ ID NO: 73 | PAG1022UP |
| SEQ ID NO: 74 | PAG1023I1 |
| SEQ ID NO: 75 | PAG1023I2 |
| SEQ ID NO: 76 | PAG1023RP |
| SEQ ID NO: 77 | PAG1023UP |
| SEQ ID NO: 78 | PAG1024RP |
| SEQ ID NO: 79 | PAG1024UP |
| SEQ ID NO: 80 | PAG1025RP |
| SEQ ID NO: 81 | PAG1025UP |
| SEQ ID NO: 82 | PAG1026RP |
| SEQ ID NO: 83 | PAG1026UP |
| SEQ ID NO: 84 | PAG1027RP |
| SEQ ID NO: 85 | PAG1027UP |
| SEQ ID NO: 86 | PAG1028RP |
| SEQ ID NO: 87 | PAG1028UP |
| SEQ ID NO: 88 | PAG1029RP |
| SEQ ID NO: 89 | PAG1029UP |
| SEQ ID NO: 90 | PAG1030RP |
| SEQ ID NO: 91 | PAG1030UP |
| SEQ ID NO: 92 | PAG1031RP |
| SEQ ID NO: 93 | PAG1031UP |
| SEQ ID NO: 94 | PAG1032RP |
| SEQ ID NO: 95 | PAG1032UP |
| SEQ ID NO: 96 | PAG1033RP |
| SEQ ID NO: 97 | PAG1033UP |
| SEQ ID NO: 98 | PAG1034RP |
| SEQ ID NO: 99 | PAG1034UP |
| SEQ ID NO: 100 | PAG1035I1 |
| SEQ ID NO: 101 | PAG1035I2 |
| SEQ ID NO: 102 | PAG1035RP |
| SEQ ID NO: 103 | PAG1035UP |
| SEQ ID NO: 104 | PAG1036RP |
| SEQ ID NO: 105 | PAG1036UP |
| SEQ ID NO: 106 | PAG1037RP |
| SEQ ID NO: 107 | PAG1038RP |
| SEQ ID NO: 108 | PAG1038UP |
| SEQ ID NO: 109 | PAG1039RP |
| SEQ ID NO: 110 | PAG1039UP |
| SEQ ID NO: 111 | PAG1040RP |
| SEQ ID NO: 112 | PAG1040UP |
| SEQ ID NO: 113 | PAG1041RP |
| SEQ ID NO: 114 | PAG1041UP |
| SEQ ID NO: 115 | PAG1042RP |
| SEQ ID NO: 116 | PAG1042UP |
| SEQ ID NO: 117 | PAG1043RP |
| SEQ ID NO: 118 | PAG1043UP |
| SEQ ID NO: 119 | PAG1044I1 |
| SEQ ID NO: 120 | PAG1044I2 |
| SEQ ID NO: 121 | PAG1044RP |
| SEQ ID NO: 122 | PAG1044UP |
| SEQ ID NO: 123 | PAG1045RP |
| SEQ ID NO: 124 | PAG1045UP |
| SEQ ID NO: 125 | PAG1046RP |
| SEQ ID NO: 126 | PAG1046UP |
| SEQ ID NO: 127 | PAG1047RP |
| SEQ ID NO: 128 | PAG1047UP |
| SEQ ID NO: 129 | PAG1048RP |
| SEQ ID NO: 130 | PAG1048UP |
| SEQ ID NO: 131 | PAG1049RP |
| SEQ ID NO: 132 | PAG1049UP |
| SEQ ID NO: 133 | PAG1050RP |
| SEQ ID NO: 134 | PAG1050UP |
| SEQ ID NO: 135 | PAG1051RP |
| SEQ ID NO: 136 | PAG1051UP |
| SEQ ID NO: 137 | PAG1052I1 |
| SEQ ID NO: 138 | PAG1052I2 |
| SEQ ID NO: 139 | PAG1052RP |
| SEQ ID NO: 140 | PAG1052UP |
| SEQ ID NO: 141 | PAG1053RP |
| SEQ ID NO: 142 | PAG1053UP |
| SEQ ID NO: 143 | PAG1054RP |
| SEQ ID NO: 144 | PAG1054UP |
| SEQ ID NO: 145 | PAG1055RP |
| SEQ ID NO: 146 | PAG1055UP |
| SEQ ID NO: 147 | PAG1056RP |
| SEQ ID NO: 148 | PAG1056UP |
| SEQ ID NO: 149 | PAG1057RP |
| SEQ ID NO: 150 | PAG1057UP |
| SEQ ID NO: 151 | PAG1058I1 |
| SEQ ID NO: 152 | PAG1058I2 |
| SEQ ID NO: 153 | PAG1058RP |
| SEQ ID NO: 154 | PAG1058UP |
| SEQ ID NO: 155 | PAG1059RP |
| SEQ ID NO: 156 | PAG1059UP |
| SEQ ID NO: 157 | PAG1060RP |
| SEQ ID NO: 158 | PAG1060UP |
| SEQ ID NO: 159 | PAG1061RP |
| SEQ ID NO: 160 | PAG1062RP |
| SEQ ID NO: 161 | PAG1062UP |
| SEQ ID NO: 162 | PAG1063RP |
| SEQ ID NO: 163 | PAG1063UP |
| SEQ ID NO: 164 | PAG1064I1 |
| SEQ ID NO: 165 | PAG1064I2 |
| SEQ ID NO: 166 | PAG1064RP |
| SEQ ID NO: 167 | PAG1064UP |
| SEQ ID NO: 168 | PAG1065RP |
| SEQ ID NO: 169 | PAG1065UP |
| SEQ ID NO: 170 | PAG1066RP |
| SEQ ID NO: 171 | PAG1066UP |
| SEQ ID NO: 172 | PAG1067RP |
| SEQ ID NO: 173 | PAG1067UP |
| SEQ ID NO: 174 | PAG1068RP |
| SEQ ID NO: 175 | PAG1068UP |
| SEQ ID NO: 176 | PAG1069RP |
| SEQ ID NO: 177 | PAG1069UP |
| SEQ ID NO: 178 | PAG1070RP |
| SEQ ID NO: 179 | PAG1070UP |
| SEQ ID NO: 180 | PAG1071RP |
| SEQ ID NO: 181 | PAG1071UP |
| SEQ ID NO: 182 | PAG1072RP |
| SEQ ID NO: 183 | PAG1072UP |
| SEQ ID NO: 184 | PAG1073RP |
| SEQ ID NO: 185 | PAG1073UP |
| SEQ ID NO: 186 | PAG1074RP |
| SEQ ID NO: 187 | PAG1074UP |
| SEQ ID NO: 188 | PAG1075RP |
| SEQ ID NO: 189 | PAG1075UP |
| SEQ ID NO: 190 | PAG1076RP |

TABLE 3-continued

| Sequence | Description |
| --- | --- |
| SEQ ID NO: 191 | PAG1076UP |
| SEQ ID NO: 192 | PAG1077RP |
| SEQ ID NO: 193 | PAG1077UP |
| SEQ ID NO: 194 | PAG1078I1 |
| SEQ ID NO: 195 | PAG1078I2 |
| SEQ ID NO: 196 | PAG1078RP |
| SEQ ID NO: 197 | PAG1078UP |
| SEQ ID NO: 198 | PAG1079RP |
| SEQ ID NO: 199 | PAG1079UP |
| SEQ ID NO: 200 | PAG1080UP |
| SEQ ID NO: 201 | PAG1081RP |
| SEQ ID NO: 202 | PAG1081UP |
| SEQ ID NO: 203 | PAG1082RP |
| SEQ ID NO: 204 | PAG1082UP |
| SEQ ID NO: 205 | PAG1083RP |
| SEQ ID NO: 206 | PAG1083UP |
| SEQ ID NO: 207 | PAG1200RP |
| SEQ ID NO: 208 | PAG1200UP |
| SEQ ID NO: 209 | PAG1201RP |
| SEQ ID NO: 210 | PAG1201UP |
| SEQ ID NO: 211 | PAG1202RP |
| SEQ ID NO: 212 | PAG1202UP |
| SEQ ID NO: 213 | PAG1203RP |
| SEQ ID NO: 214 | PAG1203UP |
| SEQ ID NO: 215 | PAG1204RP |
| SEQ ID NO: 216 | PAG1204UP |
| SEQ ID NO: 217 | PAG1205RP |
| SEQ ID NO: 218 | PAG1205UP |
| SEQ ID NO: 219 | PAG1206RP |
| SEQ ID NO: 220 | PAG1206UP |
| SEQ ID NO: 221 | PAG1207RP |
| SEQ ID NO: 222 | PAG1207UP |
| SEQ ID NO: 223 | PAG1208RP |
| SEQ ID NO: 224 | PAG1208UP |
| SEQ ID NO: 225 | PAG1209RP |
| SEQ ID NO: 226 | PAG1209UP |
| SEQ ID NO: 227 | PAG1210RP |
| SEQ ID NO: 228 | PAG1210UP |
| SEQ ID NO: 229 | PAG1211RP |
| SEQ ID NO: 230 | PAG1211UP |
| SEQ ID NO: 231 | PAG1212RP |
| SEQ ID NO: 232 | PAG1212UP |
| SEQ ID NO: 233 | PAG1213RP |
| SEQ ID NO: 234 | PAG1213UP |
| SEQ ID NO: 235 | PAG1214RP |
| SEQ ID NO: 236 | PAG1214UP |
| SEQ ID NO: 237 | PAG1215RP |
| SEQ ID NO: 238 | PAG1215UP |
| SEQ ID NO: 239 | PAG1216RP |
| SEQ ID NO: 240 | PAG1216UP |
| SEQ ID NO: 241 | PAG1217UP |
| SEQ ID NO: 242 | PAG1218RP |
| SEQ ID NO: 243 | PAG1218UP |
| SEQ ID NO: 244 | PAG1219RP |
| SEQ ID NO: 245 | PAG1219UP |
| SEQ ID NO: 246 | PAG1220RP |
| SEQ ID NO: 247 | PAG1220UP |
| SEQ ID NO: 248 | PAG1221RP |
| SEQ ID NO: 249 | PAG1221UP |
| SEQ ID NO: 250 | PAG1222RP |
| SEQ ID NO: 251 | PAG1222UP |
| SEQ ID NO: 252 | PAG1223RP |
| SEQ ID NO: 253 | PAG1223UP |
| SEQ ID NO: 254 | PAG1224RP |
| SEQ ID NO: 255 | PAG1224UP |
| SEQ ID NO: 256 | PAG1225RP |
| SEQ ID NO: 257 | PAG1225UP |
| SEQ ID NO: 258 | PAG1226RP |
| SEQ ID NO: 259 | PAG1226UP |
| SEQ ID NO: 260 | PAG1227RP |
| SEQ ID NO: 261 | PAG1227UP |
| SEQ ID NO: 262 | PAG1228RP |
| SEQ ID NO: 263 | PAG1228UP |
| SEQ ID NO: 264 | PAG1229RP |
| SEQ ID NO: 265 | PAG1229UP |
| SEQ ID NO: 266 | PAG1230RP |
| SEQ ID NO: 267 | PAG1230UP |
| SEQ ID NO: 268 | PAG1231RP |
| SEQ ID NO: 269 | PAG1231UP |
| SEQ ID NO: 270 | PAG1232RP |
| SEQ ID NO: 271 | PAG1232UP |
| SEQ ID NO: 272 | PAG1233RP |
| SEQ ID NO: 273 | PAG1233UP |
| SEQ ID NO: 274 | PAG1234RP |
| SEQ ID NO: 275 | PAG1234UP |
| SEQ ID NO: 276 | PAG1235RP |
| SEQ ID NO: 277 | PAG1235UP |
| SEQ ID NO: 278 | PAG1236RP |
| SEQ ID NO: 279 | PAG1236UP |
| SEQ ID NO: 280 | PAG1237RP |
| SEQ ID NO: 281 | PAG1237UP |
| SEQ ID NO: 282 | PAG1238RP |
| SEQ ID NO: 283 | PAG1238UP |
| SEQ ID NO: 284 | PAG1239RP |
| SEQ ID NO: 285 | PAG1239UP |
| SEQ ID NO: 286 | PAG1240RP |
| SEQ ID NO: 287 | PAG1240UP |
| SEQ ID NO: 288 | PAG1241RP |
| SEQ ID NO: 289 | PAG1241UP |
| SEQ ID NO: 290 | PAG1242RP |
| SEQ ID NO: 291 | PAG1242UP |
| SEQ ID NO: 292 | PAG1243RP |
| SEQ ID NO: 293 | PAG1243UP |
| SEQ ID NO: 294 | PAG1244RP |
| SEQ ID NO: 295 | PAG1244UP |
| SEQ ID NO: 296 | PAG1245RP |
| SEQ ID NO: 297 | PAG1245UP |
| SEQ ID NO: 298 | PAG1246RP |
| SEQ ID NO: 299 | PAG1246UP |
| SEQ ID NO: 300 | PAG1247RP |
| SEQ ID NO: 301 | PAG1248RP |
| SEQ ID NO: 302 | PAG1248UP |
| SEQ ID NO: 303 | PAG1249RP |
| SEQ ID NO: 304 | PAG1249UP |
| SEQ ID NO: 305 | PAG1250RP |
| SEQ ID NO: 306 | PAG1250UP |
| SEQ ID NO: 307 | PAG1251RP |
| SEQ ID NO: 308 | PAG1251UP |
| SEQ ID NO: 309 | PAG1252RP |
| SEQ ID NO: 310 | PAG1252UP |
| SEQ ID NO: 311 | PAG1253RP |
| SEQ ID NO: 312 | PAG1253UP |
| SEQ ID NO: 313 | PAG1254RP |
| SEQ ID NO: 314 | PAG1254UP |
| SEQ ID NO: 315 | PAG1255RP |
| SEQ ID NO: 316 | PAG1256RP |
| SEQ ID NO: 317 | PAG1256UP |
| SEQ ID NO: 318 | PAG1257RP |
| SEQ ID NO: 319 | PAG1257UP |
| SEQ ID NO: 321 | PAG1258UP |
| SEQ ID NO: 322 | PAG1259RP |
| SEQ ID NO: 323 | PAG1259UP |
| SEQ ID NO: 324 | PAG1260RP |
| SEQ ID NO: 325 | PAG1260UP |
| SEQ ID NO: 326 | PAG1261RP |
| SEQ ID NO: 327 | PAG1261UP |
| SEQ ID NO: 328 | PAG1262RP |
| SEQ ID NO: 329 | PAG1262UP |
| SEQ ID NO: 330 | PAG1263RP |
| SEQ ID NO: 331 | PAG1263UP |
| SEQ ID NO: 332 | PAG1264RP |
| SEQ ID NO: 333 | PAG1264UP |
| SEQ ID NO: 334 | PAG1265RP |
| SEQ ID NO: 335 | PAG1265UP |
| SEQ ID NO: 336 | PAG1266RP |
| SEQ ID NO: 337 | PAG1266UP |
| SEQ ID NO: 338 | PAG1267RP |
| SEQ ID NO: 339 | PAG1267UP |
| SEQ ID NO: 340 | PAG1268RP |
| SEQ ID NO: 341 | PAG1268UP |
| SEQ ID NO: 342 | PAG1269RP |
| SEQ ID NO: 343 | PAG1269UP |
| SEQ ID NO: 344 | PAG1270RP |
| SEQ ID NO: 345 | PAG1270UP |

TABLE 3-continued

| Sequence | Description |
|---|---|
| SEQ ID NO: 346 | PAG1271RP |
| SEQ ID NO: 347 | PAG1271UP |
| SEQ ID NO: 348 | PAG1272RP |
| SEQ ID NO: 349 | PAG1272UP |
| SEQ ID NO: 350 | PAG1273RP |
| SEQ ID NO: 351 | PAG1273UP |
| SEQ ID NO: 352 | PAG1274RP |
| SEQ ID NO: 353 | PAG1274UP |
| SEQ ID NO: 354 | PAG1275RP |
| SEQ ID NO: 355 | PAG1275UP |
| SEQ ID NO: 356 | PAG1276RP |
| SEQ ID NO: 357 | PAG1276UP |
| SEQ ID NO: 358 | PAG1277RP |
| SEQ ID NO: 359 | PAG1277UP |
| SEQ ID NO: 360 | PAG1278RP |
| SEQ ID NO: 361 | PAG1278UP |
| SEQ ID NO: 362 | PAG1279RP |
| SEQ ID NO: 363 | PAG1279UP |
| SEQ ID NO: 364 | PAG1280RP |
| SEQ ID NO: 365 | PAG1280UP |
| SEQ ID NO: 366 | PAG1281RP |
| SEQ ID NO: 367 | PAG1281UP |
| SEQ ID NO: 368 | PAG1282RP |
| SEQ ID NO: 369 | PAG1282UP |
| SEQ ID NO: 370 | PAG1283RP |
| SEQ ID NO: 371 | PAG1283UP |
| SEQ ID NO: 372 | PAG1284RP |
| SEQ ID NO: 373 | PAG1284UP |
| SEQ ID NO: 374 | PAG1285RP |
| SEQ ID NO: 375 | PAG1285UP |
| SEQ ID NO: 376 | PAG1286RP |
| SEQ ID NO: 377 | PAG1286UP |
| SEQ ID NO: 378 | PAG1287RP |
| SEQ ID NO: 379 | PAG1287UP |
| SEQ ID NO: 380 | PAG1289RP |
| SEQ ID NO: 381 | PAG1289UP |
| SEQ ID NO: 382 | PAG1290RP |
| SEQ ID NO: 383 | PAG1290UP |
| SEQ ID NO: 384 | PAG1291UP |
| SEQ ID NO: 385 | PAG1292RP |
| SEQ ID NO: 386 | PAG1292UP |
| SEQ ID NO: 387 | PAG1293RP |
| SEQ ID NO: 388 | PAG1293UP |
| SEQ ID NO: 389 | PAG1294RP |
| SEQ ID NO: 390 | PAG1294UP |
| SEQ ID NO: 391 | PAG1295RP |
| SEQ ID NO: 392 | PAG1295UP |
| SEQ ID NO: 393 | PAG1296RP |
| SEQ ID NO: 394 | PAG1296UP |
| SEQ ID NO: 395 | PAG1297RP |
| SEQ ID NO: 396 | PAG1297UP |
| SEQ ID NO: 397 | PAG1298UP |
| SEQ ID NO: 398 | PAG1299RP |
| SEQ ID NO: 399 | PAG1299UP |
| SEQ ID NO: 400 | PAG1300RP |
| SEQ ID NO: 401 | PAG1300UP |
| SEQ ID NO: 402 | PAG1301RP |
| SEQ ID NO: 403 | PAG1301UP |
| SEQ ID NO: 404 | PAG1302RP |
| SEQ ID NO: 405 | PAG1302UP |
| SEQ ID NO: 406 | PAG1303RP |
| SEQ ID NO: 407 | PAG1303UP |
| SEQ ID NO: 408 | PAG1304RP |
| SEQ ID NO: 409 | PAG1305RP |
| SEQ ID NO: 410 | PAG1305UP |
| SEQ ID NO: 412 | PAG1306UP |
| SEQ ID NO: 413 | PAG1307RP |
| SEQ ID NO: 414 | PAG1307UP |
| SEQ ID NO: 415 | PAG1308RP |
| SEQ ID NO: 416 | PAG1308UP |
| SEQ ID NO: 417 | PAG1309RP |
| SEQ ID NO: 418 | PAG1309UP |
| SEQ ID NO: 419 | PAG1310UP |
| SEQ ID NO: 420 | PAG1310RP |
| SEQ ID NO: 421 | PAG1311UP |
| SEQ ID NO: 422 | PAG1312RP |
| SEQ ID NO: 423 | PAG1312UP |
| SEQ ID NO: 424 | PAG1313RP |
| SEQ ID NO: 425 | PAG1313UP |
| SEQ ID NO: 426 | PAG1314RP |
| SEQ ID NO: 427 | PAG1314UP |
| SEQ ID NO: 428 | PAG1315RP |
| SEQ ID NO: 429 | PAG1315UP |
| SEQ ID NO: 430 | PAG1316RP |
| SEQ ID NO: 431 | PAG1316UP |
| SEQ ID NO: 432 | PAG1317RP |
| SEQ ID NO: 433 | PAG1317UP |
| SEQ ID NO: 434 | PAG1318RP |
| SEQ ID NO: 435 | PAG1318UP |
| SEQ ID NO: 436 | PAG1319RP |
| SEQ ID NO: 437 | PAG1319UP |
| SEQ ID NO: 438 | PAG1320RP |
| SEQ ID NO: 439 | PAG1320UP |
| SEQ ID NO: 440 | PAG1321RP |
| SEQ ID NO: 441 | PAG1321UP |
| SEQ ID NO: 442 | PAG1322RP |
| SEQ ID NO: 443 | PAG1322UP |
| SEQ ID NO: 444 | PAG1323RP |
| SEQ ID NO: 445 | PAG1323UP |
| SEQ ID NO: 446 | PAG1324RP |
| SEQ ID NO: 447 | PAG1324UP |
| SEQ ID NO: 448 | PAG1325RP |
| SEQ ID NO: 449 | PAG1325UP |
| SEQ ID NO: 450 | PAG1326RP |
| SEQ ID NO: 451 | PAG1326UP |
| SEQ ID NO: 452 | PAG1327RP |
| SEQ ID NO: 453 | PAG1327UP |
| SEQ ID NO: 454 | PAG1328RP |
| SEQ ID NO: 455 | PAG1328UP |
| SEQ ID NO: 456 | PAG1329RP |
| SEQ ID NO: 457 | PAG1329UP |
| SEQ ID NO: 458 | PAG1330RP |
| SEQ ID NO: 459 | PAG1330UP |
| SEQ ID NO: 460 | PAG1331RP |
| SEQ ID NO: 461 | PAG1331UP |
| SEQ ID NO: 462 | PAG1332RP |
| SEQ ID NO: 463 | PAG1332UP |
| SEQ ID NO: 464 | PAG1333RP |
| SEQ ID NO: 465 | PAG1333UP |
| SEQ ID NO: 466 | PAG1334RP |
| SEQ ID NO: 467 | PAG1334UP |
| SEQ ID NO: 468 | PAG1335RP |
| SEQ ID NO: 469 | PAG1335UP |
| SEQ ID NO: 470 | PAG1336RP |
| SEQ ID NO: 471 | PAG1336UP |
| SEQ ID NO: 472 | PAG1337RP |
| SEQ ID NO: 473 | PAG1337UP |
| SEQ ID NO: 474 | PAG1338RP |
| SEQ ID NO: 475 | PAG1338UP |
| SEQ ID NO: 476 | PAG1339RP |
| SEQ ID NO: 477 | PAG1339UP |
| SEQ ID NO: 478 | PAG1340RP |
| SEQ ID NO: 479 | PAG1340UP |
| SEQ ID NO: 480 | PAG1341RP |
| SEQ ID NO: 481 | PAG1341UP |
| SEQ ID NO: 482 | PAG1342RP |
| SEQ ID NO: 483 | PAG1342UP |
| SEQ ID NO: 484 | PAG1343RP |
| SEQ ID NO: 485 | PAG1343UP |
| SEQ ID NO: 486 | PAG1344RP |
| SEQ ID NO: 487 | PAG1344UP |
| SEQ ID NO: 488 | PAG1345RP |
| SEQ ID NO: 489 | PAG1345UP |
| SEQ ID NO: 490 | PAG1347RP |
| SEQ ID NO: 491 | PAG1347UP |
| SEQ ID NO: 492 | PAG1348RP |
| SEQ ID NO: 493 | PAG1349RP |
| SEQ ID NO: 494 | PAG1349UP |
| SEQ ID NO: 495 | PAG1350RP |
| SEQ ID NO: 496 | PAG1350UP |
| SEQ ID NO: 497 | PAG1351RP |
| SEQ ID NO: 498 | PAG1351UP |
| SEQ ID NO: 499 | PAG1352RP |
| SEQ ID NO: 500 | PAG1353RP |

TABLE 3-continued

| Sequence | Description |
|---|---|
| SEQ ID NO: 501 | PAG1353UP |
| SEQ ID NO: 502 | PAG1354UP |
| SEQ ID NO: 503 | PAG1355RP |
| SEQ ID NO: 504 | PAG1355UP |
| SEQ ID NO: 505 | PAG1356RP |
| SEQ ID NO: 506 | PAG1356UP |
| SEQ ID NO: 507 | PAG1357RP |
| SEQ ID NO: 508 | PAG1357UP |
| SEQ ID NO: 509 | PAG1359RP |
| SEQ ID NO: 510 | PAG1359UP |
| SEQ ID NO: 511 | PAG1360RP |
| SEQ ID NO: 512 | PAG1360UP |
| SEQ ID NO: 513 | PAG1362RP |
| SEQ ID NO: 514 | PAG1362UP |
| SEQ ID NO: 515 | PAG1363RP |
| SEQ ID NO: 516 | PAG1363UP |
| SEQ ID NO: 517 | PAG1364RP |
| SEQ ID NO: 518 | PAG1364UP |
| SEQ ID NO: 519 | PAG1365RP |
| SEQ ID NO: 520 | PAG1365UP |
| SEQ ID NO: 521 | PAG1366RP |
| SEQ ID NO: 522 | PAG1366UP |
| SEQ ID NO: 523 | PAG1367RP |
| SEQ ID NO: 524 | PAG1367UP |
| SEQ ID NO: 525 | PAG1368RP |
| SEQ ID NO: 526 | PAG1368UP |
| SEQ ID NO: 527 | PAG1369RP |
| SEQ ID NO: 528 | PAG1369UP |
| SEQ ID NO: 529 | PAG1370RP |
| SEQ ID NO: 530 | PAG1370UP |
| SEQ ID NO: 531 | PAG1371RP |
| SEQ ID NO: 532 | PAG1371UP |
| SEQ ID NO: 533 | PAG1372RP |
| SEQ ID NO: 534 | PAG1372UP |
| SEQ ID NO: 535 | PAG1373RP |
| SEQ ID NO: 536 | PAG1374RP |
| SEQ ID NO: 537 | PAG1374UP |
| SEQ ID NO: 538 | PAG1375RP |
| SEQ ID NO: 539 | PAG1376RP |
| SEQ ID NO: 540 | PAG1376UP |
| SEQ ID NO: 541 | PAG1378RP |
| SEQ ID NO: 542 | PAG1378UP |
| SEQ ID NO: 543 | PAG1379RP |
| SEQ ID NO: 544 | PAG1379UP |
| SEQ ID NO: 545 | PAG1380RP |
| SEQ ID NO: 546 | PAG1380UP |
| SEQ ID NO: 547 | PAG1381RP |
| SEQ ID NO: 548 | PAG1381UP |
| SEQ ID NO: 549 | PAG1382RP |
| SEQ ID NO: 550 | PAG1382UP |
| SEQ ID NO: 551 | PAG1384RP |
| SEQ ID NO: 552 | PAG1384UP |
| SEQ ID NO: 553 | PAG1385RP |
| SEQ ID NO: 554 | PAG1385UP |
| SEQ ID NO: 555 | PAG1386RP |
| SEQ ID NO: 556 | PAG1386UP |
| SEQ ID NO: 557 | PAG1387RP |
| SEQ ID NO: 558 | PAG1387UP |
| SEQ ID NO: 559 | PAG1388RP |
| SEQ ID NO: 560 | PAG1388UP |
| SEQ ID NO: 561 | PAG1389RP |
| SEQ ID NO: 562 | PAG1389UP |
| SEQ ID NO: 563 | PAG1390RP |
| SEQ ID NO: 564 | PAG1390UP |
| SEQ ID NO: 565 | PAG1391RP |
| SEQ ID NO: 566 | PAG1391UP |
| SEQ ID NO: 567 | PAG1392RP |
| SEQ ID NO: 568 | PAG1393RP |
| SEQ ID NO: 569 | PAG1393UP |
| SEQ ID NO: 570 | PAG1394RP |
| SEQ ID NO: 571 | PAG1394UP |
| SEQ ID NO: 572 | PAG1396RP |
| SEQ ID NO: 573 | PAG1396UP |
| SEQ ID NO: 574 | PAG1397RP |
| SEQ ID NO: 575 | PAG1397UP |
| SEQ ID NO: 576 | PAG1398UP |
| SEQ ID NO: 577 | PAG1399RP |
| SEQ ID NO: 578 | PAG1399UP |
| SEQ ID NO: 579 | PAG1400RP |
| SEQ ID NO: 580 | PAG1400UP |
| SEQ ID NO: 581 | PAG1401RP |
| SEQ ID NO: 582 | PAG1401UP |
| SEQ ID NO: 583 | PAG1402RP |
| SEQ ID NO: 584 | PAG1402UP |
| SEQ ID NO: 585 | PAG1403RP |
| SEQ ID NO: 586 | PAG1403UP |
| SEQ ID NO: 587 | PAG1404RP |
| SEQ ID NO: 588 | PAG1404UP |
| SEQ ID NO: 589 | PAG1405RP |
| SEQ ID NO: 590 | PAG1405UP |
| SEQ ID NO: 591 | PAG1406RP |
| SEQ ID NO: 592 | PAG1406UP |
| SEQ ID NO: 593 | PAG1407RP |
| SEQ ID NO: 594 | PAG1407UP |
| SEQ ID NO: 595 | PAG1408RP |
| SEQ ID NO: 596 | PAG1408UP |
| SEQ ID NO: 597 | PAG1409RP |
| SEQ ID NO: 598 | PAG1409UP |
| SEQ ID NO: 599 | PAG1410RP |
| SEQ ID NO: 600 | PAG1410UP |
| SEQ ID NO: 601 | PAG1411RP |
| SEQ ID NO: 602 | PAG1411UP |
| SEQ ID NO: 603 | PAG1412RP |
| SEQ ID NO: 604 | PAG1412UP |
| SEQ ID NO: 605 | PAG1413RP |
| SEQ ID NO: 606 | PAG1413UP |
| SEQ ID NO: 607 | PAG1414RP |
| SEQ ID NO: 608 | PAG1414UP |
| SEQ ID NO: 609 | PAG1415RP |
| SEQ ID NO: 610 | PAG1415UP |
| SEQ ID NO: 611 | PAG1416RP |
| SEQ ID NO: 612 | PAG1416UP |
| SEQ ID NO: 613 | PAG1417RP |
| SEQ ID NO: 614 | PAG1417UP |
| SEQ ID NO: 615 | PAG1418RP |
| SEQ ID NO: 616 | PAG1418UP |
| SEQ ID NO: 617 | PAG1419RP |
| SEQ ID NO: 618 | PAG1419UP |
| SEQ ID NO: 619 | PAG1420RP |
| SEQ ID NO: 620 | PAG1420UP |
| SEQ ID NO: 621 | PAG1421RP |
| SEQ ID NO: 622 | PAG1421UP |
| SEQ ID NO: 623 | PAG1422RP |
| SEQ ID NO: 624 | PAG1422UP |
| SEQ ID NO: 625 | PAG1423RP |
| SEQ ID NO: 626 | PAG1423UP |
| SEQ ID NO: 627 | PAG1424RP |
| SEQ ID NO: 628 | PAG1424UP |
| SEQ ID NO: 629 | PAG1425RP |
| SEQ ID NO: 630 | PAG1425UP |
| SEQ ID NO: 631 | PAG1426RP |
| SEQ ID NO: 632 | PAG1426UP |
| SEQ ID NO: 633 | PAG1427RP |
| SEQ ID NO: 634 | PAG1427UP |
| SEQ ID NO: 635 | PAG1428RP |
| SEQ ID NO: 636 | PAG1428UP |
| SEQ ID NO: 637 | PAG1429RP |
| SEQ ID NO: 638 | PAG1429UP |
| SEQ ID NO: 639 | PAG1430RP |
| SEQ ID NO: 640 | PAG1430UP |
| SEQ ID NO: 641 | PAG1431RP |
| SEQ ID NO: 642 | PAG1431UP |
| SEQ ID NO: 643 | PAG1432RP |
| SEQ ID NO: 644 | PAG1432UP |
| SEQ ID NO: 645 | PAG1433RP |
| SEQ ID NO: 646 | PAG1433UP |
| SEQ ID NO: 647 | PAG1434RP |
| SEQ ID NO: 648 | PAG1434UP |
| SEQ ID NO: 649 | PAG1435UP |
| SEQ ID NO: 650 | PAG1436RP |
| SEQ ID NO: 651 | PAG1436UP |
| SEQ ID NO: 652 | PAG1437RP |
| SEQ ID NO: 653 | PAG1437UP |
| SEQ ID NO: 654 | PAG1438RP |

TABLE 3-continued

| Sequence | Description |
| --- | --- |
| SEQ ID NO: 655 | PAG1438UP |
| SEQ ID NO: 656 | PAG1439RP |
| SEQ ID NO: 657 | PAG1440RP |
| SEQ ID NO: 658 | PAG1440UP |
| SEQ ID NO: 659 | PAG1441RP |
| SEQ ID NO: 660 | PAG1441UP |
| SEQ ID NO: 661 | PAG1442RP |
| SEQ ID NO: 662 | PAG1442UP |
| SEQ ID NO: 663 | PAG1443RP |
| SEQ ID NO: 664 | PAG1443UP |
| SEQ ID NO: 665 | PAG1444RP |
| SEQ ID NO: 666 | PAG1444UP |
| SEQ ID NO: 667 | PAG1445RP |
| SEQ ID NO: 668 | PAG1445UP |
| SEQ ID NO: 669 | PAG1446RP |
| SEQ ID NO: 670 | PAG1446UP |
| SEQ ID NO: 671 | PAG1447RP |
| SEQ ID NO: 672 | PAG1447UP |
| SEQ ID NO: 673 | PAG1448RP |
| SEQ ID NO: 674 | PAG1448UP |
| SEQ ID NO: 675 | PAG1449RP |
| SEQ ID NO: 676 | PAG1449UP |
| SEQ ID NO: 677 | PAG1450RP |
| SEQ ID NO: 678 | PAG1450UP |
| SEQ ID NO: 679 | PAG1451RP |
| SEQ ID NO: 680 | PAG1451UP |
| SEQ ID NO: 681 | PAG1452RP |
| SEQ ID NO: 682 | PAG1452UP |
| SEQ ID NO: 683 | PAG1453RP |
| SEQ ID NO: 684 | PAG1453UP |
| SEQ ID NO: 685 | PAG1454RP |
| SEQ ID NO: 686 | PAG1454UP |
| SEQ ID NO: 687 | PAG1455RP |
| SEQ ID NO: 688 | PAG1455UP |
| SEQ ID NO: 689 | PAG1456RP |
| SEQ ID NO: 690 | PAG1456UP |
| SEQ ID NO: 691 | PAG1457RP |
| SEQ ID NO: 692 | PAG1457UP |
| SEQ ID NO: 693 | PAG1458RP |
| SEQ ID NO: 694 | PAG1458UP |
| SEQ ID NO: 695 | PAG1459RP |
| SEQ ID NO: 696 | PAG1459UP |
| SEQ ID NO: 697 | PAG1460RP |
| SEQ ID NO: 698 | PAG1460UP |
| SEQ ID NO: 699 | PAG1461RP |
| SEQ ID NO: 700 | PAG1461UP |
| SEQ ID NO: 701 | PAG1462RP |
| SEQ ID NO: 702 | PAG1462UP |
| SEQ ID NO: 703 | PAG1463RP |
| SEQ ID NO: 704 | PAG1463UP |
| SEQ ID NO: 705 | PAG1464RP |
| SEQ ID NO: 706 | PAG1464UP |
| SEQ ID NO: 707 | PAG1465RP |
| SEQ ID NO: 708 | PAG1465UP |
| SEQ ID NO: 709 | PAG1466RP |
| SEQ ID NO: 710 | PAG1466UP |
| SEQ ID NO: 711 | PAG1467RP |
| SEQ ID NO: 712 | PAG1467UP |
| SEQ ID NO: 713 | PAG1468RP |
| SEQ ID NO: 714 | PAG1468UP |
| SEQ ID NO: 715 | PAG1469RP |
| SEQ ID NO: 716 | PAG1469UP |
| SEQ ID NO: 717 | PAG1470RP |
| SEQ ID NO: 718 | PAG1470UP |
| SEQ ID NO: 719 | PAG1471RP |
| SEQ ID NO: 720 | PAG1471UP |
| SEQ ID NO: 721 | PAG1472RP |
| SEQ ID NO: 722 | PAG1472UP |
| SEQ ID NO: 723 | PAG1473RP |
| SEQ ID NO: 724 | PAG1473UP |
| SEQ ID NO: 725 | PAG1474RP |
| SEQ ID NO: 726 | PAG1474UP |
| SEQ ID NO: 727 | PAG1475RP |
| SEQ ID NO: 728 | PAG1475UP |
| SEQ ID NO: 729 | PAG1476RP |
| SEQ ID NO: 730 | PAG1476UP |
| SEQ ID NO: 731 | PAG1477RP |
| SEQ ID NO: 732 | PAG1477UP |
| SEQ ID NO: 733 | PAG1478RP |
| SEQ ID NO: 734 | PAG1478UP |
| SEQ ID NO: 735 | PAG1479RP |
| SEQ ID NO: 736 | PAG1479UP |
| SEQ ID NO: 737 | PAG1480RP |
| SEQ ID NO: 738 | PAG1480UP |
| SEQ ID NO: 739 | PAG1481RP |
| SEQ ID NO: 740 | PAG1481UP |
| SEQ ID NO: 741 | PAG1482RP |
| SEQ ID NO: 742 | PAG1482UP |
| SEQ ID NO: 743 | PAG1483RP |
| SEQ ID NO: 744 | PAG1483UP |
| SEQ ID NO: 745 | PAG1484RP |
| SEQ ID NO: 746 | PAG1484UP |
| SEQ ID NO: 747 | PAG1485RP |
| SEQ ID NO: 748 | PAG1485UP |
| SEQ ID NO: 749 | PAG1486RP |
| SEQ ID NO: 750 | PAG1486UP |
| SEQ ID NO: 751 | PAG1487RP |
| SEQ ID NO: 752 | PAG1487UP |
| SEQ ID NO: 753 | PAG1488RP |
| SEQ ID NO: 754 | PAG1488UP |
| SEQ ID NO: 755 | PAG1489RP |
| SEQ ID NO: 756 | PAG1489UP |
| SEQ ID NO: 757 | PAG1490RP |
| SEQ ID NO: 758 | PAG1490UP |
| SEQ ID NO: 759 | PAG1491RP |
| SEQ ID NO: 760 | PAG1491UP |
| SEQ ID NO: 761 | PAG1492RP |
| SEQ ID NO: 762 | PAG1492UP |
| SEQ ID NO: 763 | PAG1493RP |
| SEQ ID NO: 764 | PAG1493UP |
| SEQ ID NO: 765 | PAG1494RP |
| SEQ ID NO: 766 | PAG1494UP |
| SEQ ID NO: 767 | PAG1495RP |
| SEQ ID NO: 768 | PAG1495UP |
| SEQ ID NO: 769 | PAG1496RP |
| SEQ ID NO: 770 | PAG1496UP |
| SEQ ID NO: 771 | PAG1497RP |
| SEQ ID NO: 772 | PAG1497UP |
| SEQ ID NO: 773 | PAG1498RP |
| SEQ ID NO: 774 | PAG1498UP |
| SEQ ID NO: 775 | PAG1499RP |
| SEQ ID NO: 776 | PAG1499UP |
| SEQ ID NO: 777 | PAG1500RP |
| SEQ ID NO: 778 | PAG1500UP |
| SEQ ID NO: 779 | PAG1501RP |
| SEQ ID NO: 780 | PAG1501UP |
| SEQ ID NO: 781 | PAG1502RP |
| SEQ ID NO: 782 | PAG1502UP |
| SEQ ID NO: 783 | PAG1503RP |
| SEQ ID NO: 784 | PAG1503UP |
| SEQ ID NO: 785 | PAG1504RP |
| SEQ ID NO: 786 | PAG1504UP |
| SEQ ID NO: 787 | PAG1505RP |
| SEQ ID NO: 788 | PAG1505UP |
| SEQ ID NO: 789 | PAG1506RP |
| SEQ ID NO: 790 | PAG1506UP |
| SEQ ID NO: 791 | PAG1507RP |
| SEQ ID NO: 792 | PAG1507UP |
| SEQ ID NO: 793 | PAG1508RP |
| SEQ ID NO: 794 | PAG1508UP |
| SEQ ID NO: 795 | PAG1509RP |
| SEQ ID NO: 796 | PAG1509UP |
| SEQ ID NO: 797 | PAG1510RP |
| SEQ ID NO: 798 | PAG1510UP |
| SEQ ID NO: 799 | PAG1511RP |
| SEQ ID NO: 800 | PAG1511UP |
| SEQ ID NO: 801 | PAG1512RP |
| SEQ ID NO: 802 | PAG1512UP |
| SEQ ID NO: 803 | PAG1513RP |
| SEQ ID NO: 804 | PAG1513UP |
| SEQ ID NO: 805 | PAG1514RP |
| SEQ ID NO: 806 | PAG1514UP |
| SEQ ID NO: 807 | PAG1515RP |
| SEQ ID NO: 808 | PAG1515UP |

TABLE 3-continued

| Sequence | Description |
| --- | --- |
| SEQ ID NO: 809 | PAG1516RP |
| SEQ ID NO: 810 | PAG1516UP |
| SEQ ID NO: 811 | PAG1517RP |
| SEQ ID NO: 812 | PAG1517UP |
| SEQ ID NO: 813 | PAG1518RP |
| SEQ ID NO: 814 | PAG1518UP |
| SEQ ID NO: 815 | PAG1519RP |
| SEQ ID NO: 816 | PAG1519UP |
| SEQ ID NO: 817 | PAG1520RP |
| SEQ ID NO: 818 | PAG1520UP |
| SEQ ID NO: 819 | PAG1521RP |
| SEQ ID NO: 820 | PAG1521UP |
| SEQ ID NO: 821 | PAG1522RP |
| SEQ ID NO: 822 | PAG1522UP |
| SEQ ID NO: 823 | PAG1523RP |
| SEQ ID NO: 824 | PAG1523UP |
| SEQ ID NO: 825 | PAG1524RP |
| SEQ ID NO: 826 | PAG1524UP |
| SEQ ID NO: 827 | PAG1525RP |
| SEQ ID NO: 828 | PAG1525UP |
| SEQ ID NO: 829 | PAG1526RP |
| SEQ ID NO: 830 | PAG1526UP |
| SEQ ID NO: 831 | PAG1527RP |
| SEQ ID NO: 832 | PAG1527UP |
| SEQ ID NO: 833 | PAG1528RP |
| SEQ ID NO: 834 | PAG1528UP |
| SEQ ID NO: 835 | PAG1529RP |
| SEQ ID NO: 836 | PAG1529UP |
| SEQ ID NO: 837 | PAG1530RP |
| SEQ ID NO: 838 | PAG1530UP |
| SEQ ID NO: 839 | PAG1531RP |
| SEQ ID NO: 840 | PAG1531UP |
| SEQ ID NO: 841 | PAG1532RP |
| SEQ ID NO: 842 | PAG1532UP |
| SEQ ID NO: 843 | PAG1533RP |
| SEQ ID NO: 844 | PAG1533UP |
| SEQ ID NO: 845 | PAG1534RP |
| SEQ ID NO: 846 | PAG1534UP |
| SEQ ID NO: 847 | PAG1535RP |
| SEQ ID NO: 848 | PAG1535UP |
| SEQ ID NO: 849 | PAG1536RP |
| SEQ ID NO: 850 | PAG1536UP |
| SEQ ID NO: 851 | PAG1537RP |
| SEQ ID NO: 852 | PAG1537UP |
| SEQ ID NO: 853 | PAG1538RP |
| SEQ ID NO: 854 | PAG1538UP |
| SEQ ID NO: 855 | PAG1539RP |
| SEQ ID NO: 856 | PAG1539UP |
| SEQ ID NO: 857 | PAG1540RP |
| SEQ ID NO: 858 | PAG1540UP |
| SEQ ID NO: 859 | PAG1541RP |
| SEQ ID NO: 860 | PAG1541UP |
| SEQ ID NO: 861 | PAG1542RP |
| SEQ ID NO: 862 | PAG1542UP |
| SEQ ID NO: 863 | PAG1543RP |
| SEQ ID NO: 864 | PAG1543UP |
| SEQ ID NO: 865 | PAG1544RP |
| SEQ ID NO: 866 | PAG1544UP |
| SEQ ID NO: 867 | PAG1545RP |
| SEQ ID NO: 868 | PAG1545UP |
| SEQ ID NO: 869 | PAG1546RP |
| SEQ ID NO: 870 | PAG1546UP |
| SEQ ID NO: 871 | PAG1547RP |
| SEQ ID NO: 872 | PAG1547UP |
| SEQ ID NO: 873 | PAG1548RP |
| SBQ ID NO: 874 | PAG1548UP |
| SEQ ID NO: 875 | PAG1549RP |
| SEQ ID NO: 876 | PAG1549UP |
| SEQ ID NO: 877 | PAG1550RP |
| SEQ ID NO: 878 | PAG1550UP |
| SEQ ID NO: 879 | PAG1551RP |
| SEQ ID NO: 880 | PAG1551UP |
| SEQ ID NO: 881 | PAG1552RP |
| SEQ ID NO: 882 | PAG1552UP |
| SEQ ID NO: 883 | PAG1553RP |
| SEQ ID NO: 884 | PAG1553UP |
| SEQ ID NO: 885 | PAG1554RP |
| SEQ ID NO: 886 | PAG1554UP |
| SEQ ID NO: 887 | PAG1555RP |
| SEQ ID NO: 888 | PAG1555UP |
| SEQ ID NO: 889 | PAG1556RP |
| SEQ ID NO: 890 | PAG1556UP |
| SEQ ID NO: 891 | PAG1557RP |
| SEQ ID NO: 892 | PAG1557UP |
| SEQ ID NO: 893 | PAG1558RP |
| SEQ ID NO: 894 | PAG1558UP |
| SEQ ID NO: 895 | PAG1559RP |
| SEQ ID NO: 896 | PAG1559UP |
| SEQ ID NO: 897 | PAG1560RP |
| SEQ ID NO: 898 | PAG1560UP |
| SEQ ID NO: 899 | PAG1561RP |
| SEQ ID NO: 900 | PAG1561UP |
| SEQ ID NO: 901 | PAG1562RP |
| SEQ ID NO: 902 | PAG1562UP |
| SEQ ID NO: 903 | PAG1563RP |
| SEQ ID NO: 904 | PAG1563UP |
| SEQ ID NO: 905 | PAG1565RP |
| SEQ ID NO: 906 | PAG1565UP |
| SEQ ID NO: 907 | PAG1566RP |
| SEQ ID NO: 908 | PAG1566UP |
| SEQ ID NO: 909 | PAG1567RP |
| SEQ ID NO: 910 | PAG1567UP |
| SEQ ID NO: 911 | PAG1568RP |
| SEQ ID NO: 912 | PAG1568UP |
| SEQ ID NO: 913 | PAG1569RP |
| SEQ ID NO: 914 | PAG1569UP |
| SEQ ID NO: 915 | PAG1570RP |
| SEQ ID NO: 916 | PAG1570UP |
| SEQ ID NO: 917 | PAG1571RP |
| SEQ ID NO: 918 | PAG1571UP |
| SEQ ID NO: 919 | PAG1572RP |
| SEQ ID NO: 920 | PAG1572UP |
| SEQ ID NO: 921 | PAG1573RP |
| SEQ ID NO: 922 | PAG1573UP |
| SEQ ID NO: 923 | PAG1574RP |
| SEQ ID NO: 924 | PAG1574UP |
| SEQ ID NO: 925 | PAG1575RP |
| SEQ ID NO: 926 | PAG1575UP |
| SEQ ID NO: 927 | PAG1576RP |
| SEQ ID NO: 928 | PAG1576UP |
| SEQ ID NO: 929 | PAG1577RP |
| SEQ ID NO: 930 | PAG1577UP |
| SEQ ID NO: 931 | PAG1578RP |
| SEQ ID NO: 932 | PAG1578UP |
| SEQ ID NO: 933 | PAG1579RP |
| SEQ ID NO: 934 | PAG1579UP |
| SEQ ID NO: 935 | PAG1580RP |
| SEQ ID NO: 936 | PAG1580UP |
| SEQ ID NO: 937 | PAG1581RP |
| SEQ ID NO: 938 | PAG1581UP |
| SEQ ID NO: 939 | PAG1582RP |
| SEQ ID NO: 940 | PAG1582UP |
| SEQ ID NO: 941 | PAG1583RP |
| SEQ ID NO: 942 | PAG1583UP |
| SEQ ID NO: 943 | PAG1584RP |
| SEQ ID NO: 944 | PAG1584UP |
| SEQ ID NO: 945 | PAG1585RP |
| SEQ ID NO: 946 | PAG1585UP |
| SEQ ID NO: 947 | PAG1586RP |
| SEQ ID NO: 948 | PAG1586UP |
| SEQ ID NO: 949 | PAG1587RP |
| SEQ ID NO: 950 | PAG1587UP |
| SEQ ID NO: 951 | PAG1588RP |
| SEQ ID NO: 952 | PAG1588UP |
| SEQ ID NO: 953 | PAG1589RP |
| SEQ ID NO: 954 | PAG1589UP |
| SEQ ID NO: 955 | PAG1590RP |
| SEQ ID NO: 956 | PAG1590UP |
| SEQ ID NO: 957 | PAG1591RP |
| SEQ ID NO: 958 | PAG1591UP |
| SEQ ID NO: 959 | PAG1592RP |
| SEQ ID NO: 960 | PAG1592UP |
| SEQ ID NO: 961 | PAG1593RP |
| SEQ ID NO: 962 | PAG1593UP |

TABLE 3-continued

| Sequence | Description |
|---|---|
| SEQ ID NO: 963 | PAG1594RP |
| SEQ ID NO: 964 | PAG1594UP |
| SEQ ID NO: 965 | PAG1595RP |
| SEQ ID NO: 966 | PAG1595UP |
| SEQ ID NO: 967 | PAG1596RP |
| SEQ ID NO: 968 | PAG1596UP |
| SEQ ID NO: 969 | PAG1597RP |
| SEQ ID NO: 970 | PAG1597UP |
| SEQ ID NO: 971 | PAG1598RP |
| SEQ ID NO: 972 | PAG1598UP |
| SEQ ID NO: 973 | PAG1600RP |
| SEQ ID NO: 974 | PAG1600UP |
| SEQ ID NO: 975 | PAG1601RP |
| SEQ ID NO: 976 | PAG1601UP |
| SEQ ID NO: 977 | PAG1602RP |
| SEQ ID NO: 978 | PAG1602UP |
| SEQ ID NO: 979 | PAG1603RP |
| SEQ ID NO: 980 | PAG1603UP |
| SEQ ID NO: 981 | PAG1604RP |
| SEQ ID NO: 982 | PAG1604UP |
| SEQ ID NO: 983 | PAG1605RP |
| SEQ ID NO: 984 | PAG1605UP |
| SEQ ID NO: 985 | PAG1606RP |
| SEQ ID NO: 986 | PAG1606UP |
| SEQ ID NO: 987 | PAG1607RP |
| SEQ ID NO: 988 | PAG1607UP |
| SEQ ID NO: 989 | PAG1608RP |
| SEQ ID NO: 990 | PAG1608UP |
| SEQ ID NO: 991 | PAG1609RP |
| SEQ ID NO: 992 | PAG1609UP |
| SEQ ID NO: 993 | PAG1610RP |
| SEQ ID NO: 994 | PAG1610UP |
| SEQ ID NO: 995 | PAG1611RP |
| SEQ ID NO: 996 | PAG1611UP |
| SEQ ID NO: 997 | PAG1612RP |
| SEQ ID NO: 998 | PAG1613UP |
| SEQ ID NO: 999 | PAG1614RP |
| SEQ ID NO: 1000 | PAG1614UP |
| SEQ ID NO: 1001 | PAG1615RP |
| SEQ ID NO: 1002 | PAG1615UP |
| SEQ ID NO: 1003 | PAG1616RP |
| SEQ ID NO: 1004 | PAG1616UP |
| SEQ ID NO: 1005 | PAG1617RP |
| SEQ ID NO: 1006 | PAG1617UP |
| SEQ ID NO: 1007 | PAG1618RP |
| SEQ ID NO: 1008 | PAG1619RP |
| SEQ ID NO: 1009 | PAG1619UP |
| SEQ ID NO: 1010 | PAG1620RP |
| SEQ ID NO: 1011 | PAG1620UP |
| SEQ ID NO: 1012 | PAG1621RP |
| SEQ ID NO: 1013 | PAG1621UP |
| SEQ ID NO: 1014 | PAG1622RP |
| SEQ ID NO: 1015 | PAG1622UP |
| SEQ ID NO: 1016 | PAG1623RP |
| SEQ ID NO: 1017 | PAG1623UP |
| SEQ ID NO: 1018 | PAG1624RP |
| SEQ ID NO: 1019 | PAG1624UP |
| SEQ ID NO: 1020 | PAG1625RP |
| SEQ ID NO: 1021 | PAG1625UP |
| SEQ ID NO: 1022 | PAG1626RP |
| SEQ ID NO: 1023 | PAG1626UP |
| SEQ ID NO: 1024 | PAG1627RP |
| SEQ ID NO: 1025 | PAG1627UP |
| SEQ ID NO: 1026 | PAG1628RP |
| SEQ ID NO: 1027 | PAG1629RP |
| SEQ ID NO: 1028 | PAG1629UP |
| SEQ ID NO: 1029 | PAG1630RP |
| SEQ ID NO: 1030 | PAG1630UP |
| SEQ ID NO: 1031 | PAG1631RP |
| SEQ ID NO: 1032 | PAG1631UP |
| SEQ ID NO: 1033 | PAG1632RP |
| SEQ ID NO: 1034 | PAG1632UP |
| SEQ ID NO: 1035 | PAG1633RP |
| SEQ ID NO: 1036 | PAG1633UP |
| SEQ ID NO: 1037 | PAG1634RP |
| SEQ ID NO: 1038 | PAG1634UP |
| SEQ ID NO: 1039 | PAG1635RP |
| SEQ ID NO: 1040 | PAG1635UP |
| SEQ ID NO: 1041 | PAG1636RP |
| SEQ ID NO: 1042 | PAG1636UP |
| SEQ ID NO: 1043 | PAG1637RP |
| SEQ ID NO: 1044 | PAG1637UP |
| SEQ ID NO: 1045 | PAG1638RP |
| SEQ ID NO: 1046 | PAG1638UP |
| SEQ ID NO: 1047 | PAG1639RP |
| SEQ ID NO: 1048 | PAG1639UP |
| SEQ ID NO: 1049 | PAG1640RP |
| SEQ ID NO: 1050 | PAG1640UP |
| SEQ ID NO: 1051 | PAG1641RP |
| SEQ ID NO: 1052 | PAG1641UP |
| SEQ ID NO: 1053 | PAG1642RP |
| SEQ ID NO: 1054 | PAG1642UP |
| SEQ ID NO: 1055 | PAG1643RP |
| SEQ ID NO: 1056 | PAG1643UP |
| SEQ ID NO: 1057 | PAG1644RP |
| SEQ ID NO: 1058 | PAG1645RP |
| SEQ ID NO: 1059 | PAG1645UP |
| SEQ ID NO: 1060 | PAG1646RP |
| SEQ ID NO: 1061 | PAG1646UP |
| SEQ ID NO: 1062 | PAG1647RP |
| SEQ ID NO: 1063 | PAG1647UP |
| SEQ ID NO: 1064 | PAG1648RP |
| SEQ ID NO: 1065 | PAG1648UP |
| SEQ ID NO: 1066 | PAG1649RP |
| SEQ ID NO: 1067 | PAG1649UP |
| SEQ ID NO: 1068 | PAG1650RP |
| SEQ ID NO: 1069 | PAG1650UP |
| SEQ ID NO: 1070 | PAG1651RP |
| SEQ ID NO: 1071 | PAG1651UP |
| SEQ ID NO: 1072 | PAG1652RP |
| SEQ ID NO: 1073 | PAG1652UP |
| SEQ ID NO: 1074 | PAG1653RP |
| SEQ ID NO: 1075 | PAG1653UP |
| SEQ ID NO: 1076 | PAG1654RP |
| SEQ ID NO: 1077 | PAG1654UP |
| SEQ ID NO: 1078 | PAG1655RP |
| SEQ ID NO: 1079 | PAG1655UP |
| SEQ ID NO: 1080 | PAG1656RP |
| SEQ ID NO: 1081 | PAG1656UP |
| SEQ ID NO: 1082 | PAG1657RP |
| SEQ ID NO: 1083 | PAG1657JP |
| SEQ ID NO: 1084 | PAG1659RP |
| SEQ ID NO: 1085 | PAG1659UP |
| SEQ ID NO: 1086 | PAG1660RP |
| SEQ ID NO: 1087 | PAG1660UP |
| SEQ ID NO: 1088 | PAG1663RP |
| SEQ ID NO: 1089 | PAG1664RP |
| SEQ ID NO: 1090 | PAG1664UP |
| SEQ ID NO: 1091 | PAG1666RP |
| SEQ ID NO: 1092 | PAG1666UP |
| SEQ ID NO: 1093 | PAG1667RP |
| SEQ ID NO: 1094 | PAG1667UP |
| SEQ ID NO: 1095 | PAG1669RP |
| SEQ ID NO: 1096 | PAG1669UP |
| SEQ ID NO: 1097 | PAG1670RP |
| SEQ ID NO: 1098 | PAG1670UP |
| SEQ ID NO: 1099 | PAG1671RP |
| SEQ ID NO: 1100 | PAG1671UP |
| SEQ ID NO: 1101 | PAG1672RP |
| SEQ ID NO: 1102 | PAG1672UP |
| SEQ ID NO: 1103 | PAG1673RP |
| SEQ ID NO: 1104 | PAG1673UP |
| SEQ ID NO: 1105 | PAG1674RP |
| SEQ ID NO: 1106 | PAG1674UP |
| SEQ ID NO: 1107 | PAG1675RP |
| SEQ ID NO: 1108 | PAG1675UP |
| SEQ ID NO: 1109 | PAG1676RP |
| SEQ ID NO: 1110 | PAG1676UP |
| SEQ ID NO: 1111 | PAG1677RP |
| SEQ ID NO: 1112 | PAG1677UP |
| SEQ ID NO: 1113 | PAG1678RP |
| SEQ ID NO: 1114 | PAG1678UP |
| SEQ ID NO: 1115 | PAG1680RP |
| SEQ ID NO: 1116 | PAG1680UP |

TABLE 3-continued

| Sequence | Description |
| --- | --- |
| SEQ ID NO: 1117 | PAG1681RP |
| SEQ ID NO: 1118 | PAG1681UP |
| SEQ ID NO: 1119 | PAG1682RP |
| SEQ ID NO: 1120 | PAG1682UP |
| SEQ ID NO: 1121 | PAG1683RP |
| SEQ ID NO: 1122 | PAG1683UP |
| SEQ ID NO: 1123 | PAG1684RP |
| SEQ ID NO: 1124 | PAG1684UP |
| SEQ ID NO: 1125 | PAG1685RP |
| SEQ ID NO: 1126 | PAG1686RP |
| SEQ ID NO: 1127 | PAG1687RP |
| SEQ ID NO: 1128 | PAG1687UP |
| SEQ ID NO: 1129 | PAG1688RP |
| SEQ ID NO: 1130 | PAG1688UP |
| SEQ ID NO: 1131 | PAG1689RP |
| SEQ ID NO: 1132 | PAG1689UP |
| SEQ ID NO: 1133 | PAG1690RP |
| SEQ ID NO: 1134 | PAG1690UP |
| SEQ ID NO: 1135 | PAG1691RP |
| SEQ ID NO: 1136 | PAG1691UP |
| SEQ ID NO: 1137 | PAG1692RP |
| SEQ ID NO: 1138 | PAG1692UP |
| SEQ ID NO: 1139 | PAG1693RP |
| SEQ ID NO: 1140 | PAG1693UP |
| SEQ ID NO: 1141 | PAG1694RP |
| SEQ ID NO: 1142 | PAG1694UP |
| SEQ ID NO: 1143 | PAG1695RP |
| SEQ ID NO: 1144 | PAG1695UP |
| SEQ ID NO: 1145 | PAG1696RP |
| SEQ ID NO: 1146 | PAG1696UP |
| SEQ ID NO: 1147 | PAG1698RP |
| SEQ ID NO: 1148 | PAG1698UP |
| SEQ ID NO: 1149 | PAG1699RP |
| SEQ ID NO: 1150 | PAG1699UP |
| SEQ ID NO: 1151 | PAG1700RP |
| SEQ ID NO: 1152 | PAG1700UP |

What is claimed is:

1. An isolated DNA molecule consisting of a nucleotide sequence selected from the group consisting of SEQ ID NOs:58, 59, 80, 120, 158, 321, 329, 749, 1037, and 1061.

2. A cloning vector comprising an *Ashbya gossypii* DNA insert consisting of a nucleotide sequence selected from the group consisting of SEQ ID NOs:58, 59, 80, 120, 158, 321, 329, 749, 1037, and 1061.

* * * * *